US008633245B2

(12) United States Patent
Yamaguchi et al.

(10) Patent No.: US 8,633,245 B2
(45) Date of Patent: Jan. 21, 2014

(54) PAI-1 INHIBITOR

(75) Inventors: Youichi Yamaguchi, Tokyo (JP); Takeshi Yanase, Tokyo (JP); Susumu Muto, Tokyo (JP); Akiko Itai, Tokyo (JP)

(73) Assignee: Institute of Medicinal Molecular Design, Inc., Tokyo (JP)

( * ) Notice: Subject to any disclaimer, the term of this patent is extended or adjusted under 35 U.S.C. 154(b) by 393 days.

(21) Appl. No.: 12/422,099

(22) Filed: Apr. 10, 2009

(65) Prior Publication Data

US 2009/0312315 A1 Dec. 17, 2009

Related U.S. Application Data

(60) Provisional application No. 61/044,108, filed on Apr. 11, 2008.

(51) Int. Cl.
*A61K 31/19* (2006.01)
*C07C 51/00* (2006.01)

(52) U.S. Cl.
USPC .......................................... 514/557; 562/406

(58) Field of Classification Search
USPC .......................................... 514/577; 562/406
See application file for complete search history.

(56) References Cited

U.S. PATENT DOCUMENTS

| | | | |
|---|---|---|---|
| 5,324,743 | A | 6/1994 | Dillard et al. |
| 5,462,954 | A | 10/1995 | Baker et al. |
| 5,552,441 | A | 9/1996 | Dillard et al. |
| 5,750,530 | A | 5/1998 | Bryans et al. |
| 5,817,684 | A | 10/1998 | Fleisch et al. |
| 5,869,501 | A | 2/1999 | Hirayama et al. |
| 5,891,877 | A | 4/1999 | Brocchini et al. |
| 5,910,505 | A | 6/1999 | Fleisch et al. |
| 5,914,340 | A | 6/1999 | Fleisch et al. |
| 5,998,454 | A | 12/1999 | Fleisch et al. |
| 6,333,358 | B1 | 12/2001 | Nakazato et al. |
| 6,476,056 | B2 | 11/2002 | Nakazato et al. |
| 7,074,836 | B1 | 7/2006 | Kawada et al. |
| 7,101,915 | B1 | 9/2006 | Kawada et al. |
| 7,220,783 | B2 | 5/2007 | Kawada et al. |
| 7,491,748 | B2 | 2/2009 | Tani et al. |
| 7,786,161 | B2 | 8/2010 | Tani et al. |
| 2001/0051657 | A1 | 12/2001 | Chiang et al. |
| 2002/0035137 | A1 | 3/2002 | Liu et al. |
| 2003/0013732 | A1 | 1/2003 | Elokdah |
| 2003/0018067 | A1 | 1/2003 | Elokdah et al. |
| 2003/0032626 | A1 | 2/2003 | Mayer et al. |
| 2003/0045560 | A1 | 3/2003 | Commons et al. |
| 2003/0125371 | A1 | 7/2003 | Elokdah et al. |
| 2004/0053962 | A1 | 3/2004 | Adrian |
| 2004/0058965 | A1 | 3/2004 | Momose et al. |
| 2004/0077694 | A1 | 4/2004 | Chiang et al. |
| 2004/0116504 | A1 | 6/2004 | Elokdah et al. |
| 2004/0266733 | A1 | 12/2004 | Mayer et al. |
| 2005/0070584 | A1 | 3/2005 | Havran et al. |

(Continued)

FOREIGN PATENT DOCUMENTS

| | | | |
|---|---|---|---|
| GB | 2 372 740 | A | 9/2002 |
| JP | 5-213930 | A | 8/1993 |

(Continued)

OTHER PUBLICATIONS

Bajou et al, "Absence of Host Plasminogen Activator Inhibitor 1 Prevents Cancer Invasion and Vascularization", *Nature Medicine* 4:923-928 (1998).
Bhattarai et al., "2-*O*-Carboxymethylpyrogallo Derivatives as PTP1B Inhibitors with Antihyperglycemic Activity", *Bioorganic & Medicinal Chemistry Letters*, 17:5357-5360 (2007).
Bjorquist et al, "Identification of the Binding Site for a Low-Molecular-Weight Inhibitor of Plasminogen Activator Inhibitor Type 1 by Site-Directed Mutagenesis", *Biochemistry*, 37:1227-1234 (1998).
Bryant et al, "Host-guest Complexation. 53. Functional Groups Preorganized in Hemispherands for Binding Alkali Metal and Ammonium Cations", *J. Org. Chem.*, 55:4622-4634 (1990).

(Continued)

*Primary Examiner* — Paul Zarek
(74) *Attorney, Agent, or Firm* — Tarolli, Sundheim, Covell & Tummino LLP

(57) ABSTRACT

The compound represented by the following formula (I) and the like have PAI-1 inhibition activity; wherein: $R^1$ represents a $C_{6-10}$ aryl group which may be substituted or the like; T represents a single bond or the like; m represents 0 or 1; when m is 0, G represents —N—C(═O)—$CO_2H$ or the like; when m is 1, G represents an oxygen atom or the like; $R^2$ represents a $C_{6-10}$ aryl group which may be substituted or the like; E represents the following formula (II) wherein one of $R^{31}$, $R^{32}$, $R^{33}$ and $R^{34}$ represents the formula $R^1$-T-, each of the other three independently represents a hydrogen atom or the like, and $R^{35}$ represents the formula —X—Y', a hydrogen atom or the like; X represents —$CH_2$— or the like; Y' represents a carboxy group or the like; M represents a single bond or the like.

[Formula 1]

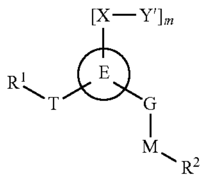

(I)

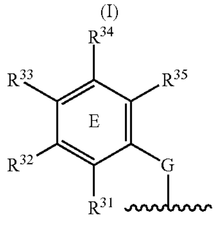

(II)

20 Claims, No Drawings

(56) References Cited

U.S. PATENT DOCUMENTS

| | | | |
|---|---|---|---|
| 2005/0070585 | A1 | 3/2005 | Mahmoud Elokdah et al. |
| 2005/0096377 | A1 | 5/2005 | Hu |
| 2005/0113436 | A1 | 5/2005 | Elokdah et al. |
| 2005/0113439 | A1 | 5/2005 | Hu |
| 2005/0119326 | A1 | 6/2005 | Havran et al. |
| 2005/0119327 | A1 | 6/2005 | Hu |
| 2005/0124656 | A1 | 6/2005 | Swinnen et al. |
| 2005/0124664 | A1 | 6/2005 | Sartori et al. |
| 2005/0124667 | A1 | 6/2005 | Sartori et al. |
| 2005/0143384 | A1 | 6/2005 | Sartori et al. |
| 2005/0209333 | A1 | 9/2005 | Chiang et al. |
| 2005/0215626 | A1 | 9/2005 | Havran et al. |
| 2006/0004012 | A1 | 1/2006 | Akerman et al. |
| 2006/0014725 | A1 | 1/2006 | Mayer et al. |
| 2006/0020003 | A1 | 1/2006 | Commons et al. |
| 2006/0122254 | A1 | 6/2006 | Elokdah et al. |
| 2006/0167059 | A1 | 7/2006 | Elokdah et al. |
| 2006/0173058 | A1 | 8/2006 | Brown et al. |
| 2006/0258728 | A1 * | 11/2006 | Tani et al. ..................... 514/400 |
| 2006/0270728 | A1 | 11/2006 | Elokdah et al. |
| 2007/0142384 | A1 | 6/2007 | Akerman et al. |
| 2007/0173548 | A1 | 7/2007 | Chiang et al. |
| 2007/0185118 | A1 | 8/2007 | Hooft Van Huijsduijnen et al. |
| 2007/0207175 | A1 | 9/2007 | Clary et al. |
| 2007/0213336 | A1 | 9/2007 | Clary et al. |
| 2007/0276011 | A1 | 11/2007 | Muto et al. |
| 2007/0299126 | A1 | 12/2007 | Hu |
| 2008/0182883 | A1 | 7/2008 | Crandall et al. |
| 2008/0214647 | A1 | 9/2008 | Elokdah et al. |
| 2008/0249175 | A1 | 10/2008 | Yamaguchi et al. |
| 2008/0275116 | A1 | 11/2008 | Yamaguchi et al. |
| 2008/0293790 | A1 | 11/2008 | Havran et al. |
| 2008/0319046 | A1 | 12/2008 | Hu |

FOREIGN PATENT DOCUMENTS

| | | | |
|---|---|---|---|
| JP | 10-182551 | A | 7/1998 |
| WO | WO-95/15752 | A1 | 6/1995 |
| WO | WO-96/36347 | A1 | 11/1996 |
| WO | WO-98/25600 | A1 | 6/1998 |
| WO | WO-98/25616 | A1 | 6/1998 |
| WO | WO-98/42334 | A1 | 10/1998 |
| WO | WO-98/42335 | A1 | 10/1998 |
| WO | WO-98/42336 | A1 | 10/1998 |
| WO | WO-98/42345 | A1 | 10/1998 |
| WO | WO-98/42346 | A1 | 10/1998 |
| WO | WO-98/42650 | A1 | 10/1998 |
| WO | WO-01/34135 | A2 | 5/2001 |
| WO | WO-01/34137 | A2 | 5/2001 |
| WO | WO-01/34197 | A2 | 5/2001 |
| WO | WO-01/34198 | A2 | 5/2001 |
| WO | WO-2004/024939 | A2 | 3/2004 |
| WO | WO-2005/097100 | A2 | 10/2005 |

OTHER PUBLICATIONS

Cho et al, "Production of Plasminogen Activator Inhibitor-1 by Human Mast Cells and Its Possible Role in Asthma", *The Journal of Immunology*, 165:3154-3161 (2000).

Elokdah et al, "Tiplaxtinin, a Novel, Orally Efficacious Inhibitor of Plasminogen Activator Inhibitor-1: Design, Synthesis, and Preclinical Characterization", *J. Med Chem.*, 47:3491-3494 (2004).

Erickson et al, "Development of Venous Occlusions in Mice Transgenic for the Plasminogen Activator Inhibitor-1 Gene", *Nature*, 346:74-76 (1990).

Jackson et al, "Comparison of Antagonist and Agonist Binding to the Leukotriene $B_4$ Receptor on Intact Human Polymorphonuclear Neutrophils (PMN)", *The Journal of Pharmacology and Experimental Therapeutics*, 262:80-89 (1992).

Jain et al, "In vitro PAI-1 Inhibitory Activity of Oxalamide Derivatives", *European Journal of Medicinal Chemistry*, xx:1-5, (2007), doi:10.1016/j.ejmech.2007.05.011.

Oh et al, "PAI-1 Promotes Extracellular Matrix Deposition in the Airways of a Murine Asthma Model", *Biochemical Biophysical Research Communications*, 294:1155-1160 (2002).

Paintner et al, "A New Convergent Approach to Biphenomycin Antibiotics", *Synlett*, 4:522-526 (2003).

Samad et al., "Tissue Distribution and Regulation of Plasminogen Activator Inhibitor-1 in Obese Mice", *Molecular Medicine*, 2:568-582 (1996).

Sawyer et al, "Structural Analogues of LY292728, a Highly Potent Xanthone Dicarboxylic Acid Leukotriene $B_4$ Receptor Antagonist: Spatial Positioning of the Secondary Acid Group", *Bioorganic Medicinal Chemistry Letters*, 4:2077-2082 (1994).

Schafer et al, "Disruption of the Plasminogen Activator Inhibitor 1 Gene Reduces the Adiposity and Improves the Metabolic Profile of Genetically Obese and Diabetic OB/OB Mice", *FASEB Journal*, 15:1840-1842 (2001).

Schneiderman et al, "Increased Type 1 Plasminogen Activator Inhibitor Gene Expression in Atherosclerotic Human Arteries", *Proc. Natl. Acad. Sci. USA*, 89:6998-7002 (1992).

Silverman, "Prodrugs" in The Organic Chemistry of Drug Design and Drug Action, Academic Press, Inc., 1992, pp. 352-355.

Stokes et al., "Novel Inhibitors of Bacterial Cytokinesis Indentified by a Cell-Based Antibiotic Screening Assay", *The Journal of Biological Chemistry*, 280:39709-39715 (2005).

Tsuchida et al, "Discovery of Nonpeptidic Small-Molecule AP-1 Inhibitors: Lead Hopping Based on a Three-Dimensional Pharmacophore Model", *J. Med. Chem.*, 49:80-91 (2006).

Tsuchiya et al, "The Antibody to Plasminogen Activator Inhibitor-1 Suppresses Pulmonary Metastases of Human Fibrosarcoma in Athymic Mice", *Gen. Diagn. Pathol.*, 141:41-48 (1995).

* cited by examiner

PAI-1 INHIBITOR

RELATED APPLICATION

This application claims the benefit of U.S. Provisional Patent Application Ser. No. 61/044,108, filed Apr. 11, 2008, which is incorporated by reference in its entirety for all purposes.

FIELD OF THE INVENTION

The present invention relates to compounds that are useful as a plasminogen activator inhibitor-1 (hereinafter referred to as PAI-1) inhibitor and uses thereof.

BACKGROUND ART

It is known that an overexpression of plasminogen activator inhibitor-1 (PAI-1) inhibits the production of plasmin that decomposes fibrin thrombi and tissue proteins and brings a formation of thrombi (for example, refer to the Non-patent Document 2) by inhibiting the activation of plasminogen activator (for example, tissue-type plasminogen activator and urokinase-type plasminogen activator).

Furthermore, the overexpression of PAI-1 is observed in arteriosclerotic lesions, and is known to increase a risk of thrombotic diseases such as cardiac infarction, deep-vein thrombosis (DVT), disseminated intravascular coagulation (DIC) following sepsis and the like (refer to the Non-patent Document 1).

From these facts, compounds that inhibit PAI-1 activity or production are useful for the suppression of forming thrombus, and are expected to be useful drugs to diseases caused by the formation of thrombi such as thrombotic diseases, diseases involving thrombus formation and the like.

Furthermore, it is known that PAI-1 promotes precipitation and accumulation of extracellular matrix and is deeply involved in the development of tissue lesion featuring fibrosis and vascular wall sclerotic lesion. As an extracellular matrix accumulation in the airway of an asthma model mouse is reduced by a PAI-1 knockout (refer to the Non-patent Document 8), it is suggested that PAI-1 is directly involved in the fibrosis. Therefore, compounds that inhibit the activity or production of PAI-1 are useful for the inhibition of fibrosis of tissue, and are expected to be useful drugs to a diseases caused by the fibrosis of tissue.

Besides, PAI-1 is also secreted from mast cells (refer to the Non-patent Document 7), and it is reported that the blood level is high in an obesity model mouse, and is synthesized not only in the endothelial tissue and in the hepatic tissue, but also synthesized in the fatty tissue. Particularly in the visceral fat, PAI-1 synthesis amount is exponentially enhanced together with its deposition (refer to the Non-patent Document 3). Moreover, in the obesity model mouse where PAI-1 gene is knocked out, a decrease of weight and a lowering of blood glucose level and blood insulin level are reported (refer to the Non-patent Document 4), and it shows that PAI-1 has a possibility to aggravate various pathological conditions caused by the fat deposition. Therefore, compounds that inhibit the activity or the production of PAI-1 are useful for the inhibition of visceral fat deposition, and are expected to be useful drugs to diseases caused by the visceral fat deposition.

Furthermore, from the facts that PAI-1 inhibits an adhesion of cell and extracellular matrix by binding to a vitronectin which is a cell adhesion factor, a PAI-1 antibody inhibits a cancer metastasis in a cancer model (refer to the Non-patent Document 5), and the infiltration of cancer and an angiogenesis are inhibited when malignant keratinocytes are transplanted to the PAI-1 knockout mouse (refer to the Non-patent Document 6), compounds that inhibit the activity or the production of PAI-1 are useful for the inhibition of cell migration, cell metastasis, angiogenesis and the like, and are expected to have therapeutic effects to diseases caused by cell migration, cell metastasis, angiogenesis and the like.

Moreover, arterial lesions as an acute rejection and a chronic rejection after heart or kidney transplantation are considered to be caused by the development of tissue fibrosis, the formation of thrombi, and the proliferation and the remodeling of arterial endothelial cell. Since, in the heart transplantation experiment using mise (murine), when a compound having an inhibitory activity to PAI-1 is administered, a graft survival is significantly prolonged compared with the control group and the rate of serious intimal hypertrophy is reduced to one third (refer to the Patent Document 1), compounds that inhibit the activity or the production of PAI-1 are expected as a medicament to inhibit an acute rejection and an arterial lesion after transplantation, after heart or kidney transplantation or transplantation of other organs.

On the other hand, as plasmin which is activated by inhibiting PAI-1 is involved not only in the decomposition of thrombi, but also in the remodeling of tissue, the migration, metastasis and infiltration of cells, the ovulation and implantation, the activation of transforming growth factors which are cytostatic cytokines, and the activation of collagenase, compounds that inhibit the activity or the production of PAI-1 are useful for the inhibition of tissue remodeling, the proliferation, migration, infiltration, and metastasis of cells, angiogenesis and the like, and treatment effects are expected to diseases caused by cell proliferation, angiogenesis, and remodeling of tissues and the like.

In the past, examples of compounds having PAI-1 inhibition activity include, for example, the compounds disclosed in the Patent Documents 1 to 19 and the Non-patent Documents 9 to 11. On the other hand, some compounds have been reported (refer to the Patent Documents 20 to 22) as oxamic acid derivatives, however, it is not known whether they have PAI-1 inhibition activity.

PRIOR ART DOCUMENTS

Patent Documents

[Patent Document 1] European Patent Application Publication No. 1666469 Specification

[Patent Document 2] International Publication No. 95/32190 Pamphlet

[Patent Document 3] International Publication No. 95/21832 Pamphlet

[Patent Document 4] British Patent Application No. 2372740 Specification

[Patent Document 5] International Publication No. 03/000253 Pamphlet

[Patent Document 6] International Publication No. 03/000258 Pamphlet

[Patent Document 7] International Publication No. 03/000649 Pamphlet

[Patent Document 8] International Publication No. 03/000671 Pamphlet

[Patent Document 9] International Publication No. 03/000684 Pamphlet

[Patent Document 10] International Publication No. 2004/052856 Pamphlet

[Patent Document 11] International Publication No. 2004/052893 Pamphlet

[Patent Document 12] International Publication No. 2005/030192 Pamphlet

[Patent Document 13] International Publication No. 2005/030204 Pamphlet

[Patent Document 14] International Publication No. 2005/030715 Pamphlet

[Patent Document 15] International Publication No. 2005/030716 Pamphlet

[Patent Document 16] International Publication No. 2005/030756 Pamphlet

[Patent Document 17] U.S. Patent Application Publication No. 2005/0124664 Specification

[Patent Document 18] U.S. Patent Application Publication No. 2005/0124667 Specification

[Patent Document 19] U.S. Patent Application Publication No. 2005/0143384 Specification

[Patent Document 20] International Publication No. 03/0642376 Pamphlet

[Patent Document 21] International Publication No. 2005/082347 Pamphlet

[Patent Document 22] International Publication No. 02/18323 Pamphlet

Non-Patent Documents

[Non-patent Document 1] Proc. Natl. Acad. Sci. USA, Vol. 89, No. 15, pp. 6998-7002 (1992).

[Non-patent Document 2] Nature, Vol. 346, No. 6279, pp. 74-76 (1990).

[Non-patent Document 3] Mol. Med., Vol. 2, No. 5, pp. 568-582 (1996).

[Non-patent Document 4] FASEB J., Vol. 15, No. 10, pp. 1840-1842 (2001).

[Non-patent Document 5] Gen. Diagn. Pathol., Vol. 141, No. 1, pp. 41-48 (1995).

[Non-patent Document 6] Nat. Med., Vol. 4, No. 8, pp. 923-928 (1998).

[Non-patent Document 7] J. Immunol., Vol. 165, No. 6, pp. 3154-3161 (2000).

[Non-patent Document 8] Biochem. Biophys. Res. Commun., Vol. 294, No. 5, pp. 1155-1160 (2002).

[Non-patent Document 9] Biochemistry, Vol. 37, No. 5, pp. 1227-1234 (1998).

[Non-patent Document 10] J. Med. Chem., Vol. 47, No. 14, pp. 3491-3494 (2004).

[Non-patent Document 11] Mukul R. Jain et al., Eur. J. Med. Chem., Vol. 43 (4), pp. 880-884 (2008), Epub Jun. 3 (2007). [PubMed ID: 17664030]

SUMMARY OF THE INVENTION

Problems to be Solved by the Invention

An object of the present invention is to provide compounds having an inhibitory activity on PAI-1 and uses thereof.

Means to Solve the Problems

The inventors of the present invention conducted various studies to solve the aforementioned problems, and found as a result that the compounds represented by the following formula (I), the salts thereof and the like had inhibitory action on PAI-1, and achieved the present invention:

[Formula 1]

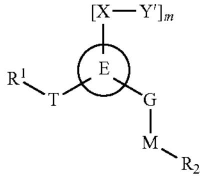

(I)

wherein:

$R^1$ represents a $C_{6-10}$ aryl group or a $C_{6-10}$ aryl group substituted with one to five groups selected from the following substituent group α-1, wherein, when the number of the substituents is two or more, each of the substituents may be the same or different;

T represents a single bond, a 1,4-piperazinylene, —R"—, —N(R')—, the formula —$CH_2$R"—, the formula —C(═O)N(R')—, the formula —N(R')C(═O)— or the formula —$SO_2$N(R')—, wherein the bond at the left-hand end binds to $R^1$, and the bond at the right-hand end binds to E in each of the formulas;

R' represents a hydrogen atom or a $C_{1-6}$ alkyl group;

m represents 0 or 1;

when m is 0, G represents the formula —$(CH_2)_j$—N—C(═O)—$(CH_2)_h$—$CO_2H$ or the formula —$(CH_2)_j$—N—W'—$CO_2H$, wherein the bond at the left-hand end binds to E, and the nitrogen atom binds to M in each of the formulas, wherein j represents 0 or 1;

h represents 0, 1, 2 or 3;

when m is 1, G represents a single bond, an oxygen atom, —C(═O)— or a sulfur atom;

when m is 0, $R^2$ represents a hydrogen atom, a $C_{3-8}$ cycloalkyl group, a $C_{1-6}$ alkyl substituted $C_{3-8}$ cycloalkyl group, a $C_{6-10}$ aryl group or a $C_{6-10}$ aryl group substituted with one to five groups selected from the following substituent group β-1, wherein, when the number of the substituents is two or more, each of the substituents may be the same or different;

when m is 1, $R^2$ represents a hydrogen atom, a $C_{6-10}$ aryl group or a $C_{6-10}$ aryl group substituted with one to five groups selected from the following substituent group β-1, wherein, when the number of the substituents is two or more, each of the substituents may be the same or different;

E represents the following formula (II):

[Formula 2]

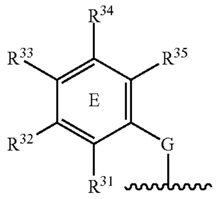

(II)

wherein when m is 1, $R^{34}$ or $R^{35}$ represents the formula —X—Y', wherein when $R^{35}$ represents the formula —X—Y', one of $R^{31}$, $R^{32}$, $R^{33}$ and $R^{34}$ represents the formula $R^1$-T-, and each of the other three independently represents a hydrogen atom or a group selected from the following substituent group γ-1;

when $R^{34}$ represents the formula —X—Y', one of $R^{31}$, $R^{32}$ and $R^{33}$ represents the formula $R^1$-T-, each of the other two independently represents a hydrogen atom or a group selected from the following substituent group γ-1, and $R^{35}$ represents the a hydrogen atom;

when m is 0, one of $R^{31}$, $R^{32}$, $R^{33}$ and $R^{34}$ represents the formula $R^1$-T-, each of the other three independently represents a hydrogen atom or a group selected from the following substituent group γ-1, and $R^{35}$ represents a hydrogen atom or a group selected from the following substituent group γ-1;

X represents a single bond, —CH═CH—, —C(═O)—, the formula —V'—$(V')_k$—, the formula —N($R^4$)—C(═O)—, the formula —N($R^4$)—V'— or the formula —$(V')_k$—R"—W'—, wherein the bond at the left-hand end binds to the benzene ring E and the bond at the right-hand end binds to Y' in each of the formulas;

$R^4$ represents a hydrogen atom or a $C_{1-6}$ alkyl group;

R" represents an oxygen atom or a sulfur atom;

V' represents a methylene group or a methylene group substituted with one or two groups selected from the following substituent group δ-1;

W' represents the formula -$J^1$-$J^2$-$J^3$-, wherein, when G is the formula —$(CH_2)_j$—N—W'—$CO_2H$, $J^1$ binds to the nitrogen atom and $J^3$ binds to the carboxy group; and when X is the formula —$(V')_k$—R"—W'—, $J^1$ binds to R" and $J^3$ binds to Y';

$J^1$ represents a methylene group or a methylene group substituted with one or two groups selected from the following substituent group ϵ-1 wherein, when the number of the substituents is two, each of the substituents may be the same or different;

each of $J^2$ and $J^3$ independently represents a single bond, a methylene group or a methylene group substituted with one or two groups selected from the following substituent group ϵ-1, wherein, when the number of the substituents is two, each of the substituents may be the same or different;

k represents 0, 1 or 2;

Y' represents a carboxy group or a 1H-tetrazol-5-yl group;

M represents a single bond, the formula —C(═O)-$(Q^1)_n$-$(Q^2)_p$-$(Q^3)_r$-, the formula -$(Q^1)_n$-$(Q^2)_p$-$(Q^3)_r$-$(U')_q$—, the formula -$(Q^1)_n$-$(Q^2)_p$-$(U')_q$-$(Q^3)_r$- or the formula -$(Q^1)_n$-$(U')_q$-$(Q^2)_p$-$(Q^3)_r$- wherein, the bond at the left-hand end binds to G, and the bond at the right-hand end binds to $R^2$ in each of the formulas);

each of $Q^1$, $Q^2$ and $Q^3$ independently represents a methylene group or a methylene group substituted with one or two groups selected from the following substituent group ζ-1, wherein, when the number of the substituents is two, each of the substituents may be the same or different;

U' represents an oxygen atom, or a sulfur atom;

n represents an integer of 1 to 10;

p represents an integer of 0 to 10;

q represents 0 or 1;

r represents an integer of 0 to 10;

when M is the formula —C(═O)-$(Q^1)_n$-$(Q^2)_p$-$(Q^3)_r$-, the sum of n, p and r is an integer of 1 to 10;

when M is the formula -$(Q^1)_n$-$(Q^2)_p$-$(Q^3)_r$-$(U')_q$—, the formula -$(Q^1)_n$-$(Q^2)_p$-$(U')_q$-$(Q^3)_r$- or the formula -$(Q^1)_n$-$(U')_q$-$(Q^2)_p$-$(Q^3)_r$-, the sum of n, p, q and r is an integer of 1 to 10,

[Substituent Group α-1]

a halogen atom, a cyano group, a nitro group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group, a carboxy group, an amino group, a $C_{1-6}$ alkylenedioxy group, a $C_{1-6}$ alkylsulfonyl group, a $C_{1-6}$ alkylcarbonyl group, a $C_{1-6}$ alkylsulfonylamino group, a hydroxy group and a carboxy substituted $C_{1-6}$ alkyl group;

[Substituent Group β-1]

a halogen atom, a nitro group, a hydroxy group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group, a phenyl group, a carboxy group, a carboxy substituted $C_{1-6}$ alkyl group, a halogenated $C_{1-6}$ alkoxy substituted phenyl group, a carboxy substituted $C_{1-6}$ alkoxy group, a $C_{1-6}$ alkyl substituted phenyl group and a carboxy substituted $C_{2-6}$ alkenyl group;

[Substituent Group γ-1]

a halogen atom, a $C_{1-10}$ alkyl group, a carboxy substituted $C_{1-10}$ alkyl group, a halogenated $C_{1-10}$ alkyl group, a $C_{1-20}$ alkoxy group, a $C_{3-8}$ cycloalkoxy group, a $C_{3-8}$ cycloalkoxy group substituted with one or two $C_{1-6}$ alkyl groups, a halogenated $C_{1-20}$ alkoxy group, a carboxy substituted $C_{1-20}$ alkoxy group, a hydroxy group, a hydroxy substituted $C_{1-20}$ alkoxy group, a $C_{1-6}$ alkoxy substituted $C_{1-10}$ alkoxy group, a $C_{3-8}$ cycloalkyl substituted $C_{1-20}$ alkoxy group, a phenyl substituted $C_{1-20}$ alkoxy group wherein the phenyl group may be substituted with one to five groups selected from the following substituent group η-1, a phenoxy group wherein the phenyl group may be substituted with one to five groups selected from the following substituent group η-1, a phenoxy substituted $C_{1-20}$ alkoxy group, a di($C_{1-10}$ alkyl)amino group, an adamantyloxy group, a 5 to 7-membered completely saturated heterocyclic group (the heterocyclic group comprises one nitrogen atom as the ring-constituting atom and may further comprise one hetero atom selected from the group consisting of a nitrogen atom, an oxygen atom and a sulfur atom as the ring-constituting atom, and the heterocyclic group binds to E via the nitrogen atom that is the ring-constituting atom), and a 5 to 7-membered completely saturated heterocyclic group substituted with one group selected from the following substituent group θ-1 (the heterocyclic group comprises one nitrogen atom as the ring-constituting atom and may further comprise one hetero atom selected from the group consisting of a nitrogen atom, an oxygen atom and a sulfur atom as the ring-constituting atom, and the heterocyclic group binds to E via the nitrogen atom that is the ring-constituting atom);

[Substituent Group δ-1]

a $C_{1-6}$ alkyl group;

[Substituent Group ϵ-1]

a halogen atom and a $C_{1-10}$ alkyl group;

[Substituent Group ζ-1]

a $C_{1-6}$ alkyl group, a phenyl group and a carboxy group;

[Substituent Group η-1]

a $C_{1-6}$ alkyl group and a halogenated $C_{1-6}$ alkoxy group;

[Substituent Group θ-1]

an oxo group.

The present invention thus provides:

[1] a compound represented by the aforementioned formula (I), a salt thereof, a hydrate of the compound, a hydrate of the salt, a solvate of the compound or a solvate of the salt, provided that:

when G is the formula N—C(═O)—$CO_2H$, E is the following formula:

[Formula 3]

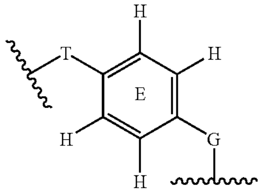

$R^1$ is a phenyl group substituted with one halogenated $C_{1-6}$ alkoxy group, T is a single bond, $R^2$ is a phenyl group or a phenyl group substituted with one or two halogenated $C_{1-6}$ alkyl groups, M is the formula $-(Q^1)_n-(Q^2)_p-(Q^3)_r-(U')_q-$, the formula $-(Q^1)_n-(Q^2)_p-(U')_q-(Q^3)_r-$ or the formula $-(Q^1)_n-(U')_q-(Q^2)_p-(Q^3)_r-$, n is 1, p is 0, q is 0, and r is 0, $Q^1$ is a methylene group substituted with one or two groups selected from the substituent group ζ-1, wherein, when the number of the substituents is two, each of the substituents may be the same or different;

when G is the formula N—C(═O)—$CO_2H$, E is the following formula:

[Formula 4]

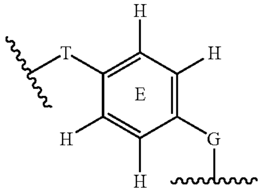

$R^1$ is a phenyl group substituted with one or two substituents selected from a halogen atom, a halogenated $C_{1-6}$ alkyl group, a $C_{1-6}$ alkoxy group and a halogenated $C_{1-6}$ alkoxy group wherein, when the number of the substituents is two, each of the substituents may be the same or different, and $R^2$ is a phenyl group substituted with two halogenated $C_{1-6}$ alkyl groups, T is a single bond, a 1,4-piperazinylene, —R"—, —N(R')—, the formula —$CH_2$R"—, the formula —C(═O)N(R')— or the formula —N(R')C(═O)—;

when G is the formula N—C(═O)—$CO_2H$, E is a benzene ring, $R^1$ is a phenyl group, T is a single bond, and $R^2$ is a 2-carboxyphenyl group, M is the formula $-C(=O)-(Q^1)_n-(Q^2)_p-(Q^3)_r-$, the formula $-(Q^1)_n-(Q^2)_p-(Q^3)_r-(U')_q-$, the formula $-(Q^1)_n-(Q^2)_p-(U')_q-(Q^3)_r-$ or the formula $-(Q^1)_n-(U')_q-(Q^2)_p-(Q^3)_r-$;

[2] a compound represented by the aforementioned formula (I), a salt thereof, a hydrate of the compound, a hydrate of the salt, a solvate of the compound or a solvate of the salt, provided that:

when G is the formula N—C(═O)—$CO_2H$, E is the following formula:

[Formula 5]

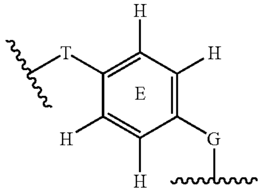

$R^1$ is a phenyl group substituted with one or two substituents selected from a halogen atom, a halogenated $C_{1-6}$ alkyl group, a $C_{1-6}$ alkoxy group and a halogenated $C_{1-6}$ alkoxy group, wherein, when the number of the substituents is two, each of the substituents may be the same or different, and $R^2$ is a phenyl group substituted with two halogenated $C_{1-6}$ alkyl groups, T is a single bond, a 1,4-piperazinylene, —R"—, —N(R')—, the formula —$CH_2$R"—, the formula —C(═O)N(R')— or the formula —N(R')C(═O)—;

when m is 0, G is the formula N—C(═O)—$CO_2H$, E is a benzene ring, $R^1$ is a phenyl group, T is a single bond, and $R^2$ is a 2-carboxyphenyl group, M is the formula $-C(=O)-(Q^1)_n-(Q^2)_p-(Q^3)_r-$, the formula $-(Q^1)_n-(Q^2)_p-(Q^3)_r-(U')_q-$, the formula $-(Q^1)_n-(Q^2)_p-(U')_q-(Q^3)_r-$ or the formula $-(Q^1)_n-(U')_q-(Q^2)_p-(Q^3)_r-$;

when m is 0, one of $R^{31}$, $R^{32}$, $R^{33}$ and $R^{34}$ is the formula $R^1$-T-, each of the other three is independently a hydrogen atom, a halogen atom, a $C_{1-6}$ alkyl group, a halogenated $C_{1-6}$ alkyl group, a carboxy substituted $C_{1-6}$ alkyl group, a $C_{1-6}$ alkoxy group, a halogenated $C_{1-6}$ alkoxy group, a phenyl substituted $C_{1-20}$ alkoxy group, wherein the phenyl group may be substituted with one to five groups selected from the following substituent group η-1 or a di($C_{1-6}$ alkyl)amino group, $R^1$ is a $C_{6-10}$ aryl group or a $C_{6-10}$ aryl group substituted with a group or groups selected from a halogen atom, a cyano group, a nitro group, a $C_{1-6}$ alkyl group, a halogenated $C_{1-6}$ alkyl group, a $C_{1-6}$ alkoxy group, a halogenated $C_{1-6}$ alkoxy group and a $C_{1-6}$ alkylsulfanyl group, G is the formula N—C(═O)—$CO_2H$, $R^2$ is a $C_{6-10}$ aryl group or a $C_{6-10}$ aryl group substituted with a group or groups selected from a halogen atom, a hydroxy group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group and a phenyl group, and T is a single bond or an oxygen atom, M is the formula $-C(=O)-(Q^1)_n-(Q^2)_p-(Q^3)_r-$, the formula $-(Q^1)_n-(Q^2)_p-(Q^3)_r-(U')_q-$, the formula $-(Q^1)_n-(Q^2)_p-(U')_q-(Q^3)_r-$ or the formula $-(Q^1)_n-(U')_q-(Q^2)_p-(Q^3)_r-$, provided that when M is the formula $-(Q^1)_n-(Q^2)_p-(Q^3)_r-(U')_q-$, the formula $-(Q^1)_n-(Q^2)_p-(U')_q-(Q^3)_r-$ or the formula $-(Q^1)_n-(U')_q-(Q^2)_p-(Q^3)_r-$, n is 1, p is 0, q is 0, and r is 0, $Q^1$ is a methylene group substituted with one or two groups selected from the substituent group ζ-1 (when the number of the substituents of the methylene group is two, each of the substituents may be the same or different);

when m is 1, $R^{33}$ is the formula $R^1$-T-, $R^{31}$, $R^{32}$ and $R^{34}$ is a hydrogen atom, $R^{35}$ is the formula —X—Y', T is a single bond, $R^1$ is a $C_{6-10}$ aryl group or a $C_{6-10}$ aryl group substituted with a group or groups selected from a halogen atom, a nitro group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group, a carboxy group, an amino group and a $C_{1-6}$ alkylenedioxy group, $R^2$ is a $C_{6-10}$ aryl group or a $C_{6-10}$ aryl group substituted with a group or groups selected from a halogen atom, a nitro group, a $C_{1-6}$ alkyl group, a halogenated $C_{1-6}$ alkyl group, a $C_{1-6}$ alkoxy group, a halogenated $C_{1-6}$ alkoxy group, a phenyl group, a $C_{1-6}$ alkylsulfanyl group and a phenyl group, G is an oxygen atom, and M is a single bond or —$CH_2$—, X is a single bond, —C(═O)—, the formula —V'—$(V')_k$—, the formula —N($R^4$)—V'— or the formula —$(V')_k$—R"—W'—, provided that when X is —V'—, V' is a methylene group substituted with one or two groups selected from the following substituent group δ-1, and when X is —V'—V'—, one of V' or each of V' is a methylene group substituted with one or two groups selected from the following substituent group δ-1;

when m is 1, $R^{35}$ is the formula —X—Y', X is —$CH_2$—, —$CH_2CH_2$—, —CH═CH— or —N($R^4$)—C(═O)—, T is a single bond, $R^1$ is a $C_{6-10}$ aryl group or a $C_{6-10}$ aryl group substituted with a group or groups selected from a halogen atom, a nitro group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group, a carboxy group, an amino group and a $C_{1-6}$ alkylenedioxy group, $R^2$ is a $C_{6-10}$ aryl group or a $C_{6-10}$ aryl group substituted with a group or groups selected from a halogen atom, a nitro group, a $C_{1-6}$ alkyl group, a halogenated $C_{1-6}$ alkyl group, a $C_{1-6}$ alkoxy group, a halogenated $C_{1-6}$ alkoxy group, a phenyl group and a carboxy group, G is an oxygen atom, and M is a single bond or —$CH_2$—, one of $R^{31}$, $R^{32}$ and $R^{34}$ is the formula $R^1$-T-;

when m is 1, X is —$CH_2$—, —$CH_2CH_2$—, —CH═CH— or —N($R^4$)—C(═O)—, $R^{33}$ is the formula $R^1$-T-, $R^{31}$, $R^{32}$ and $R^{34}$ are hydrogen atoms, $R^{35}$ is the formula —X—Y', $R^1$ is a $C_{6-10}$ aryl group or a $C_{6-10}$ aryl group substituted with a group or groups selected from a halogen atom, a nitro group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group, a carboxy group, an amino group and a $C_{1-6}$ alkylenedioxy group, $R^2$ is a $C_{6-10}$ aryl group or a $C_{6-10}$ aryl group substituted with a group or groups selected from a halogen atom, a nitro group, a $C_{1-6}$ alkyl group, a halogenated $C_{1-6}$ alkyl group, a $C_{1-6}$ alkoxy group, a halogenated $C_{1-6}$ alkoxy group, a phenyl group and a carboxy group, G is an oxygen atom, and M is a single bond or —$CH_2$—, T is a 1,4-piperazinylene, —R"—, —N(R')—, the formula —$CH_2$R"—, the formula —C(═O)N(R')—, the formula —N(R')C(═O)— or the formula —$SO_2$N(R')—;

when m is 1, X is —$CH_2$—, —$CH_2CH_2$—, —CH═CH— or —N($R^4$)—C(═O)—, $R^{33}$ is the formula $R^1$-T-, $R^{35}$ is the formula —X—Y', T is a single bond, $R^1$ is a $C_{6-10}$ aryl group or a $C_{6-10}$ aryl group substituted with a group or groups selected from a halogen atom, a nitro group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group, a carboxy group, an amino group and a $C_{1-6}$ alkylenedioxy group, $R^2$ is a $C_{6-10}$ aryl group or a $C_{6-10}$ aryl group substituted with a group or groups selected from a halogen atom, a nitro group, a $C_{1-6}$ alkyl group, a halogenated $C_{1-6}$ alkyl group, a $C_{1-6}$ alkoxy group, a halogenated $C_{1-6}$ alkoxy group, a phenyl group and a carboxy group, G is an oxygen atom, and M is a single bond or —$CH_2$—, at least one of $R^{31}$, $R^{32}$ and $R^{34}$ is a group selected from the substituent group γ-1; and when m is 1, X is —$CH_2$—, —$CH_2CH_2$—, —CH═CH— or —N($R^4$)—C(═O)—, $R^{33}$ is the formula $R^1$-T-, $R^{31}$, $R^{32}$ and $R^{34}$ are hydrogen atoms, $R^{35}$ is the formula —X—Y', T is a single bond, $R^1$ is a $C_{6-10}$ aryl group or a $C_{6-10}$ aryl group substituted with a group or groups selected from a halogen atom, a nitro group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group, a carboxy group, an amino group and a $C_{1-6}$ alkylenedioxy group, $R^2$ is a $C_{6-10}$ aryl group or a $C_{6-10}$ aryl group substituted with a group or groups selected from a halogen atom, a nitro group, a $C_{1-6}$ alkyl group, a halogenated $C_{1-6}$ alkyl group, a $C_{1-6}$ alkoxy group, a halogenated $C_{1-6}$ alkoxy group, a phenyl group and a carboxy group, and G is an oxygen atom, M is the formula —C(═O)-$(Q^1)_n$-$(Q^2)_p$-$(Q^3)_r$-, the formula -$(Q^1)_n$-$(Q^2)_p$-$(Q^3)_r$-$(U')_q$—, the formula -$(Q^1)_n$-$(Q^2)_p$-$(U')_q$-$(Q^3)_r$- or the formula -$(Q^1)_n$-$(U')_q$-$(Q^2)_p$-$(Q^3)_r$-, provided that when M is the formula -$(Q^1)_n$-$(Q^2)_p$-$(Q^3)_r$-$(U')_q$—, the formula -$(Q^1)_n$-$(Q^2)_p$-$(U')_q$-$(Q^3)_r$- or the formula -$(Q^1)_n$-$(U')_q$-$(Q^2)_p$-$(Q^3)_r$-, n is 1, p is 0, q is 0, and r is 0, $Q^1$ is a methylene group substituted with one or two groups selected from the substituent group ζ-1,

[3] the compound, the salt thereof, the hydrate of the compound, the hydrate of the salt, the solvate of the compound or the solvate of the salt according to the aforementioned [1] or [2], wherein m is 0;

[4] the compound, the salt thereof, the hydrate of the compound, the hydrate of the salt, the solvate of the compound or the solvate of the salt according to the aforementioned [1] or [2], wherein m is 1, provided that:

when X is the formula —N($R^4$)—C(═O)— or the formula —N($R^4$)—V'—, $R^2$ is a hydrogen atom, M is a single bond, the formula -$(Q^1)_n$-$(Q^2)_p$-$(Q^3)_r$-$(U')_q$—, the formula -$(Q^1)_n$-$(Q^2)_p$-$(U')_q$-$(Q^3)_r$- or the formula -$(Q^1)_n$-$(U')_q$-$(Q^2)_p$-$(Q^3)_r$-, and U' is an oxygen atom, or when X is the formula —N($R^4$)—C(═O)— or the formula —N($R^4$)—V'—, $R^2$ is a phenyl group or a phenyl group substituted with one to five substituents selected from the following substituent group η-1, M is a single bond, the formula -$(Q^1)_n$-$(Q^2)_p$-$(Q^3)_r$-$(U')_q$—, the formula -$(Q^1)_n$-$(Q^2)_p$-$(U')_q$-$(Q^3)_r$- or the formula -$(Q^1)_n$-$(U')_q$-$(Q^2)_p$-$(Q^3)_r$-, and q is 0, or when X is the formula —N($R^4$)—C(═O)— or the formula —N($R^4$)—V'—, $R^2$ is a phenyl group, M is the formula -$(Q^1)_n$-$(Q^2)_p$-$(Q^3)_r$-$(U')_q$—, U' is an oxygen atom, and q is 1, G is a single bond, —C(═O)— or a sulfur atom;

[5] a pharmaceutical composition comprising, as an active ingredient, the compound according to any on of the aforementioned [1] to [4], a pharmacologically acceptable salt thereof, a hydrate of the compound, a hydrate of the salt, a solvate of the compound or a solvate of the salt;

[6] a method of inhibiting PAI-1, comprising the step of allowing the compound according to any one of the aforementioned [1] to [4], a pharmacologically acceptable salt thereof, a hydrate of the compound, a hydrate of the salt, a solvate of the compound or a solvate of the salt to act on PAI-1;

[7] a method of inhibiting PAI-1 in a mammal, comprising the step of administering the compound according to any one of the aforementioned [1] to [4], a pharmacologically acceptable salt thereof, a hydrate of the compound, a hydrate of the salt, a solvate of the compound or a solvate of the salt at a dose sufficient to inhibit PAI-1;

[8] a method for prevention and/or therapeutic treatment of a disease caused by an expression of PAI-1 or an enhancement of PAI-1 activity in a mammal, comprising the step of administering the compound according to any one of the aforementioned [1] to [4], a pharmacologically acceptable salt thereof, a hydrate of the compound, a hydrate of the salt, a solvate of the compound or a solvate of the salt at a dose sufficient to prevent and/or treat the disease;

[9] A PAI-1 inhibitor comprising, as an active ingredient, the compound according to any one of the aforementioned [1] to [4], a pharmacologically acceptable salt thereof, a hydrate of the compound, a hydrate of the salt, a solvate of the compound or a solvate of the salt;

[10] a medicament for prevention and/or therapeutic treatment of a disease caused by an expression of PAI-1 or an enhancement of PAI-1 activity, comprising, as an active ingredient, the compound according to any one of the aforementioned [1] to [4], a pharmacologically acceptable salt thereof, a hydrate of the compound, a hydrate of the salt, a solvate of the compound or a solvate of the salt;

[11] use of the compound according to any one of the aforementioned [1] to [4], a pharmacologically acceptable salt thereof, a hydrate of the compound, a hydrate of the salt, a solvate of the compound or a solvate of the salt, for the manufacture of a PAI-1 inhibitor;

[12] use of the compound according to any one of the aforementioned [1] to [4], a pharmacologically acceptable salt thereof, a hydrate of the compound, a hydrate of the salt, a solvate of the compound or a solvate of the salt, for the manufacture of a medicament for prevention and/or therapeutic treatment of a disease caused by an expression of PAI-1 or an enhancement of PAI-1 activity;

[13] the compound according to any one of the aforementioned [1] to [4], a pharmacologically acceptable salt thereof, a hydrate of the salt, a solvate of the compound or a solvate of the salt, for inhibiting PAI-1; and

[14] the compound according to any one of the aforementioned [1] to [4], a pharmacologically acceptable salt thereof, a hydrate of the compound, a hydrate of the salt, a solvate of the compound or a solvate of the salt, for prevention and/or therapeutic treatment of a disease caused by an expression of PAI-1 or an enhancement of PAI-1 activity.

In the present specification, the wording "allow (something) to act" means "allow (something) to exert an inhibitory function on PAI-1 activation" by adding or administering the compound represented by the formula (I), a pharmacologically acceptable salt thereof, a hydrate of the compound, a hydrate of the salt, a solvate of the aforementioned compound, or a solvate of the aforementioned salt. The object to be targeted for the function may be PAI-1, or cultured cells or cells in an individual organism which produce PAI-1. The aforementioned individual organism may be a human or another mammal.

Effects of the Invention

The compounds of the present invention have an inhibitory activity on PAI-1. Therefore, the compounds of the present invention are useful as a medicament for prevention and/or therapeutic treatment of a disease caused by an expression of PAI-1 or an enhancement of PAI-1 activity.

EMBODIMENT TO CARRY OUT INVENTION

Embodiments of the present invention accomplished based on the above-described findings are hereinafter described in detail by giving Examples. When using commercial reagent kits and measuring apparatus, unless otherwise explained, attached protocols to them are used. The objective, characteristics, and advantages of the present invention as well as the idea thereof will be apparent to those skilled in the art from the descriptions given herein. It is to be understood that the embodiments and specific examples of the invention described hereinbelow are to be taken as preferred examples of the present invention. These descriptions are for illustrative and explanatory purposes only and are not intended to limit the invention to these embodiments or examples. It is further apparent to those skilled in the art that various changes and modifications may be made based on the descriptions given herein within the intent and scope of the present invention disclosed herein.

The abbreviations used in the following tables have the following meanings. Me: methyl group, Et: ethyl group, n-Pr: n-propyl group, i-Pr: isopropyl group, n-Bu: n-butyl group, t-Bu: tert-butyl group, n-Pen: n-pentyl group, n-Hex: n-hexyl group, n-Hep: n-heptyl group, n-Oct: n-octyl group, n-Non: n-nonyl group, n-Dec: n-decyl group, Ph: phenyl group, OMe: methoxy group, n-PrO: n-propoxy group, i-PrO: isopropoxy group, n-BuO: n-butoxy group, t-BuO: tert-butoxy group, SMe: methylsulfanyl group, Bn: benzyl group.

In the present invention, $R^1$ in the aforementioned formula (I) represents a $C_{6-10}$ aryl group or a $C_{6-10}$ aryl group substituted with one to five groups selected from the aforementioned substituent group α-1 (when the number of the substituents is two or more, each of the substituents may be the same or different).

$R^1$ is preferably the following formula (III):

[Formula 6]

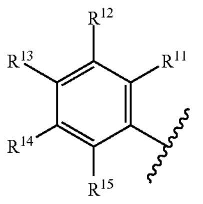

(III)

wherein each of $R^{11}$, $R^{12}$, $R^{13}$, $R^{14}$ and $R^{15}$ independently represents a hydrogen atom or a group selected from the following substituent group α-2, or $R^{11}$ and $R^{12}$, $R^{12}$ and $R^{13}$, $R^{13}$ and $R^{14}$, or $R^{14}$ and $R^{15}$ are taken together to form a ring-constituting $C_{1-6}$ alkylenedioxy group;

[Substituent Group α-2]

a halogen atom, a cyano group, a nitro group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group, a carboxy group, an amino group, a $C_{1-6}$ alkylsulfonyl group, a $C_{1-6}$ alkylcarbonyl group, a $C_{1-6}$ alkylsulfonylamino group, a hydroxy group and a carboxy substituted $C_{1-6}$ alkyl group.

Each of $R^{11}$, $R^{12}$, $R^{13}$, $R^{14}$ and $R^{15}$ is preferably and independently a hydrogen atom or a group selected from the following substituent group α-3, or $R^{11}$ and $R^{12}$, $R^{12}$ and $R^{13}$, $R^{13}$ and $R^{14}$, or $R^{14}$ and $R^{15}$ are taken together to form preferably a ring-constituting methylenedioxy group;

[Substituent Group α-3]

a halogen atom, a cyano group, a nitro group, a methyl group, an isopropyl group, a n-butyl group, a tert-butyl group, a trifluoromethyl group, a methoxy group, an isopropyloxy group, a n-butykoxy group, a tert-butyloxy group, a n-pentyloxy group, a 1-ethylpropoxy group, a trifluoromethoxy group, a methylsulfanyl group, a carboxy group, an amino group, a methysulfonyl group, an acetyl group, a methylsulfonylamino group and a hydroxy group.

$R^{11}$, $R^{12}$, $R^{13}$, $R^{14}$ and $R^{15}$ are preferably any one of the followings:

(1) all of $R^{11}$, $R^{12}$, $R^{13}$, $R^{14}$ and $R^{15}$ is are hydrogen atoms; (2) four of $R^{11}$, $R^{12}$, $R^{13}$, $R^{14}$ and $R^{15}$ are hydrogen atoms and the other one is a group selected from the substituent group α-3; (3) three of $R^{11}$, $R^{12}$, $R^{13}$, $R^{14}$ and $R^{15}$ are hydrogen atoms and the other two are groups selected from the substituent groups α-2 or α-3; or (4) among $R^{11}$, $R^{12}$, $R^{13}$, $R^{14}$ and $R^{15}$, $R^{11}$ and $R^{12}$, $R^{12}$ and $R^{13}$, $R^{13}$ and $R^{14}$, or $R^{14}$ and $R^{15}$ are taken together to form a ring-constituting methylenedioxy group, and all the others are hydrogen atoms.

$R^1$ is preferably a group selected from the following substituent group α-4.

[Substituent Group α-4]

[Formula 7]

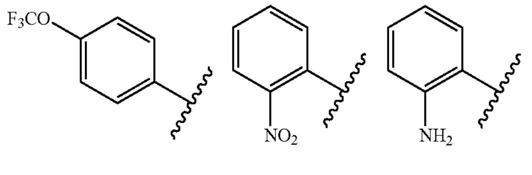

-continued

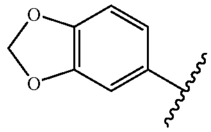
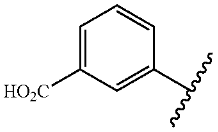
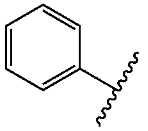
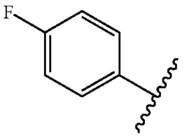
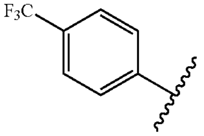
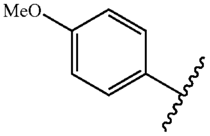
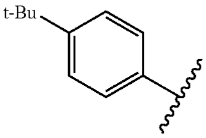
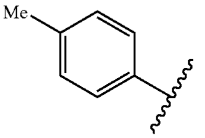
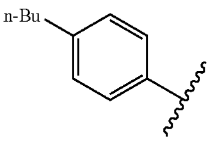
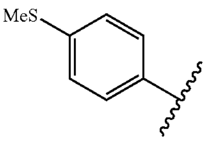
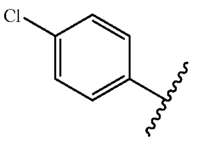
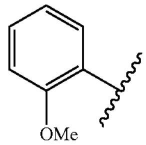
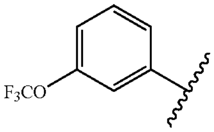
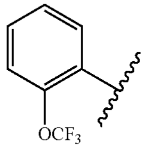
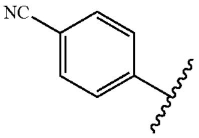
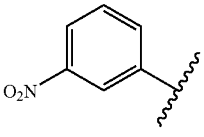
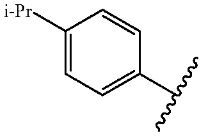
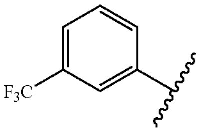
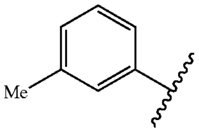
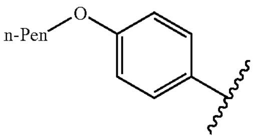
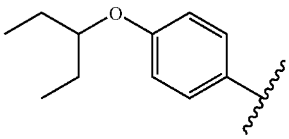
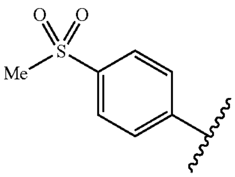
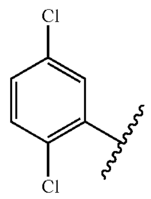

-continued

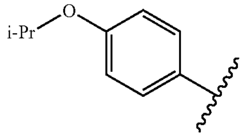
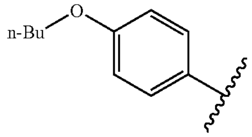
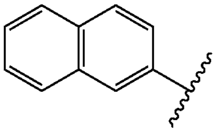
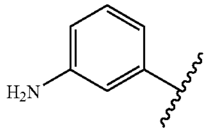
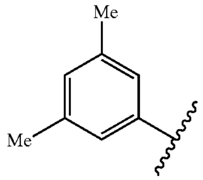
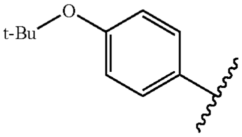
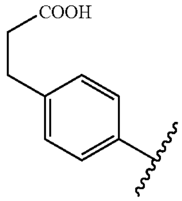
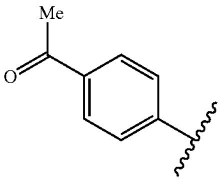
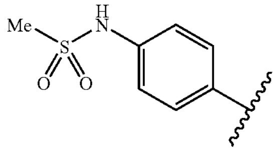
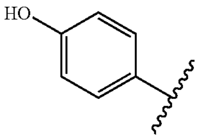

T in the aforementioned formula (I) represents a single bond, a 1,4-piperazinylene, —O—, —S—, —N(R')—, the formula —$CH_2O$ —, the formula —$CH_2S$ —, the formula —C(=O)N(R')—, the formula —N(R')C(=O)— or the formula —$SO_2N(R')$— (in each of the formulas, the bond at the left-hand end binds to $R^1$, and the bond at the right-hand end binds to E). R' represents a hydrogen atom or a $C_{1-6}$ alkyl group. Examples of the aforementioned —N(R')— include —N(H)—, —N(Me)- and the like. Examples of the aforementioned formula —C(=O)N(R')— include —C(=O)N(H)—, —C(=O)N(Me)- and the like. Examples of the aforementioned formula —N(R')C(=O)— include —N(H)C(=O)—, —N(Me)C(=O)— and the like. Examples of the aforementioned formula —$SO_2N(R')$—include —$SO_2N(H)$— and the like. m in the aforementioned formula (I) represents 0 or 1. When m is 0, then G in the aforementioned formula (I) represents the formula —$(CH_2)_j$—N—C(=O)—$(CH_2)_h$—$CO_2H$ or the formula —$(CH_2)_j$—N—W'—$CO_2H$ (in each of the formulas, the bond at the left-hand end binds to E, and the nitrogen atom binds to M). j represents 0 or 1. h represents 0, 1, 2 or 3. Examples of the aforementioned formula —$(CH_2)_j$—N—C(=O)—$(CH_2)_h$—$CO_2H$ include —N—C(=O)—$CO_2H$, —$CH_2$—N—C(=O)—$CO_2H$, —N—C(=O)—$CH_2$—$CO_2H$, —N—C(=O)—$(CH_2)_2$—$CO_2H$, —N—C(=O)—$(CH_2)_3$—$CO_2H$ and the like. Examples of the aforementioned formula —$(CH_2)_j$—N—W'—$CO_2H$ include —N—$CH_2$—$CO_2H$, —N—$(CH_2)_2$—$CO_2H$, —N—CH(n-Bu)-$CO_2H$, —$CH_2$—N—$CH_2$—$CO_2H$ and the like. When m is 1, then G in the aforementioned formula (I) represents a single bond, an oxygen atom, —C(=O)— or a sulfur atom.

$R^2$ in the aforementioned formula (I) represents a hydrogen atom, a $C_{3-8}$ cycloalkyl group, a $C_{1-6}$ alkyl substituted $C_{3-8}$ cycloalkyl group, a $C_{6-10}$ aryl group or a $C_{6-10}$ aryl group substituted with one to five groups selected from the aforementioned substituent group β-1 (when the number of the substituents is two or more, each of the substituents may be the same or different).

When $R^2$ is a $C_{3-8}$ cycloalkyl group or a $C_{1-6}$ alkyl substituted $C_{3-8}$ cycloalkyl group, examples of $R^2$ include any one of the following substituent groups.

[Formula 8]

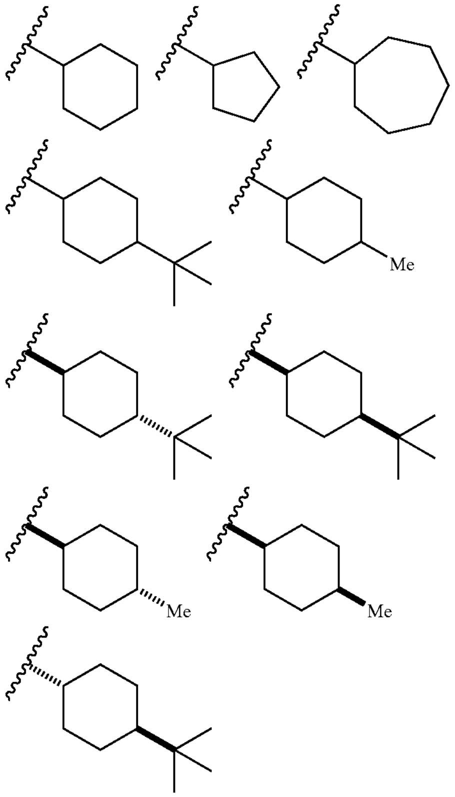

When $R^2$ is a $C_{6-10}$ aryl group or a $C_{6-10}$ aryl group substituted with one to five groups selected from the substituent group β-1 (when the number of the substituents group is two or more, each of the substituents may be the same or different), $R^2$ is preferably the following formula (IV):

[Formula 9]

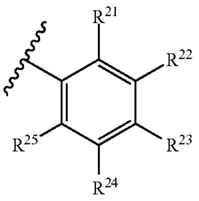

(IV)

wherein each of $R^{21}$, $R^{22}$, $R^{23}$, $R^{24}$ and $R^{25}$ independently represents a hydrogen atom or a group selected from the substituent group β-1.

Each of $R^{21}$, $R^{22}$, $R^{23}$, $R^{24}$ and $R^{25}$ is preferably and independently a hydrogen atom or a group selected from the following substituent group β-2;

[Substituent Group β-2]

a halogen atom, a nitro group, a hydroxy group, a methyl group, a-isopropyl group, a n-butyl group, a tert-butyl group, a 1,1-dimethylpropyl group, a trifluoromethyl group, a methoxy group, a n-butyloxy group, a tert-butyloxy group, a trifluoromethoxy group, a methylsulfanyl group, a phenyl group, a carboxy group, a 2-carboxyethyl group, —CH═CH—COOH, —$OCH_2COOH$, a benzyloxy group, a 4-tert-butylphenyl group and a 4-trifluoromethoxy-phenyl group.

$R^{21}$, $R^{22}$, $R^{23}$, $R^{24}$ and $R^{25}$, are preferably any one of the followings:

(1) all of $R^{21}$, $R^{22}$, $R^{23}$, $R^{24}$ and $R^{25}$ are hydrogen atoms; (2) four of $R^{21}$, $R^{22}$, $R^{23}$, $R^{24}$ and $R^{25}$ are hydrogen atoms and the other one is a group selected from the substituent group β-3; or (3) three of $R^{21}$, $R^{22}$, $R^{23}$, $R^{24}$ and $R^{25}$ are hydrogen atoms and each of the other two is independently a group selected from the substituent groups β-1 or β-2.

When $R^2$ is a $C_{6-10}$ aryl group or a $C_{6-10}$ aryl group substituted with one to five groups selected from the substituent group β-1 (when the number of the substituents is two or more, each of the substituents may be the same or different), $R^2$ is preferably a group selected from the following substituent group β-3.

[Substituent Group β-3]

[Formula 10]

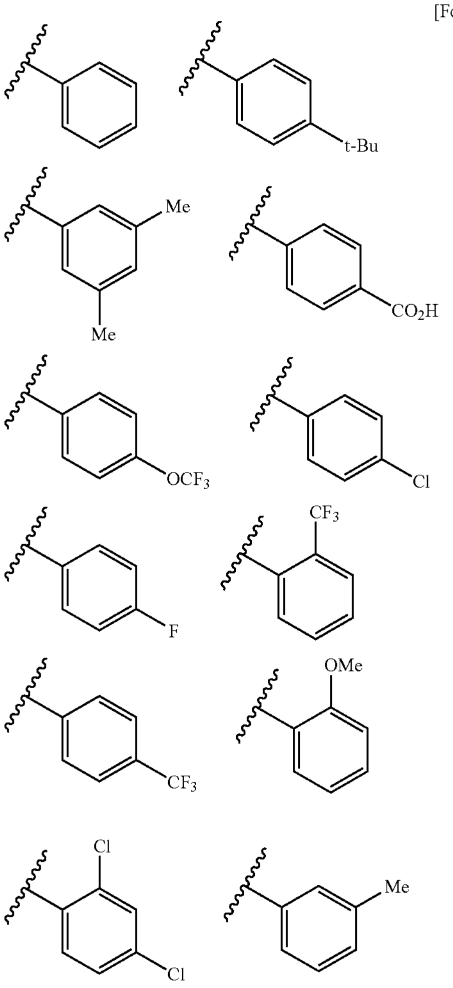

-continued

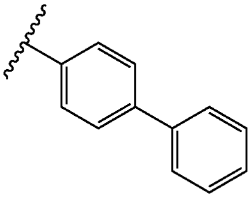
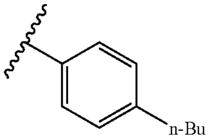
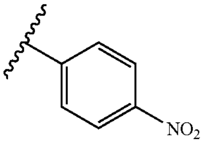
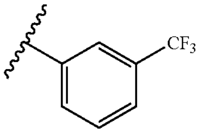
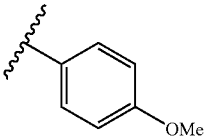
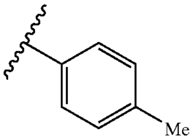
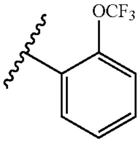
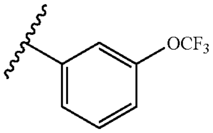
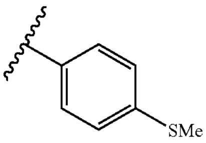
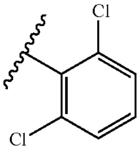
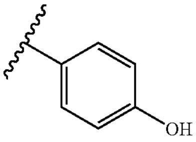
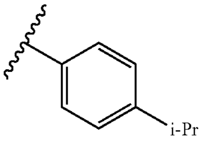
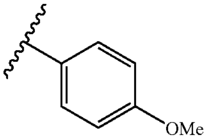
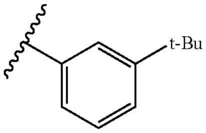
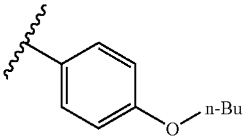
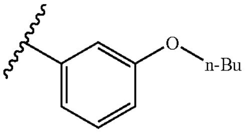
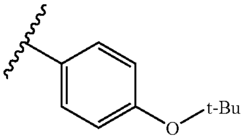
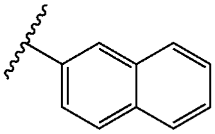
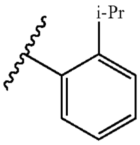
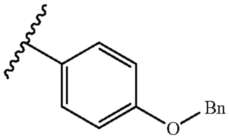
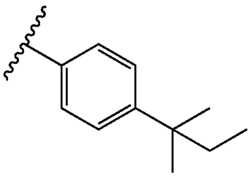
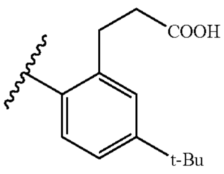

-continued

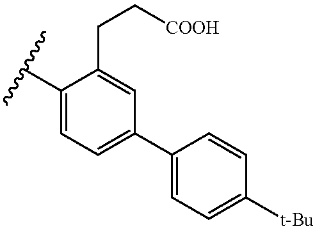
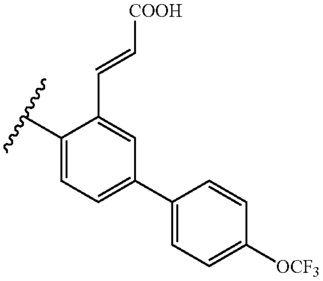
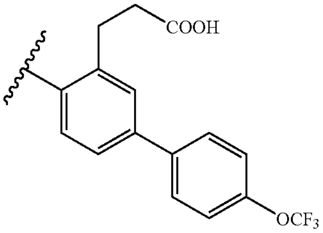
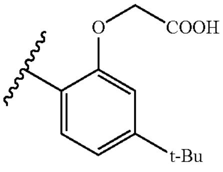
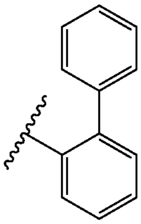
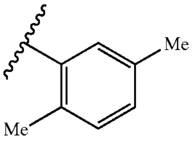

E in the aforementioned formula (I) represents the following formula (II):

[Formula 11]

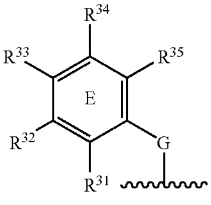

(II)

wherein:

when m is 1, $R^{34}$ or $R^{35}$ represents the formula —X—Y', wherein when $R^{35}$ represents the formula —X—Y', one of $R^{31}$, $R^{32}$, $R^{33}$, and $R^{34}$ represents the formula $R^1$-T-, and each of the other three independently represents a hydrogen atom, or a group selected from the aforementioned substituent group γ-1, when $R^{34}$ represents the formula —X—Y', one of $R^{31}$, $R^{32}$, and $R^{33}$ represents the formula $R^1$-T-, each of the other two independently represents a hydrogen atom or a group selected from the substituent group γ-1, and $R^{35}$ represents a hydrogen atom, when m is 0, one of $R^{31}$, $R^{32}$, $R^{33}$, and $R^{34}$ represents the formula $R^1$-T-, each of the other three independently represents a hydrogen atom or a group selected from the substituent group γ-1, and $R^{35}$ represents a hydrogen atom or a group selected from the substituent group γ-1.

In the aforementioned substituent group γ-1, examples of the $C_{3-8}$ cycloalkoxy group or the $C_{3-8}$ cycloalkoxy group substituted with one or two $C_{1-6}$ alkyl groups selected from the substituent group β-1 include any one of the following substituent groups.

[Formula 12]

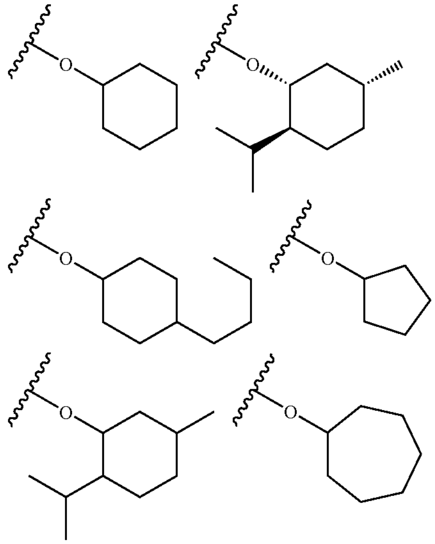

In the aforementioned substituent group γ-1, examples of the $C_{3-8}$ cycloalkyl substituted $C_{1-20}$ alkoxy group include a cyclopentyl substituted $C_{1-20}$ alkoxy group or a cyclohexyl substituted $C_{1-20}$ alkoxy group. In the aforementioned substituent group γ-1, the phenyl group of the phenyl substituted $C_{1-20}$ alkoxy group or of the phenoxy group may optionally be substituted with one to five substituents (when the number of the substituents is two or more, each of the substituents may be the same or different). The substituent is preferably a group selected from the substituent group η-1. The substituent is more preferably a methyl group, a tert-butyl group or a trifluoromethoxy group. In the aforementioned substituent group γ-1, the phenoxy group of the phenoxy substituted $C_{1-20}$ alkoxy group may optionally be substituted with one to five substituents (when the number of the substituents is two or more, each of the substituents may be the same or different) . Examples of the substituent include a group selected from the substituent group η-1.

In the aforementioned substituent group γ-1, the 5 to 7-membered completely saturated heterocyclic group (the heterocyclic group comprises one nitrogen atom as the ring-constituting atom and may further comprise one hetero atom selected from the group consisting of a nitrogen atom, an oxygen atom and a sulfur atom as the ring-constituting atom, and the heterocyclic group binds to E via the nitrogen atom that is the ring-constituting atom) is preferably a pyrrolidin-1-yl group, a hexahydro-1H-azepin-1-yl group, a thiomorpholin-1-yl group, a piperidin-1-yl group and a morpholin-4-yl group. The aforementioned 5 to 7-membered completely saturated heterocyclic group may optionally be substituted with one or two substituents (when the number of the substituents is two or more, each of the substituents may be the same or different). Examples of the aforementioned 5 to 7-membered completely saturated heterocyclic group which is substituted include a 2-piperidon-1-yl group.

When $R^{31}$, $R^{32}$, $R^{33}$; $R^{34}$ or $R^{35}$ is not the formula —X—Y' and the formula $R^1$-T-, $R^{31}$, $R^{32}$, $R^{33}$, $R^{34}$ or $R^{35}$ are preferably a hydrogen atom, or a group selected from the following substituent group γ-2;

[Substituent Group γ-2]

a halogen atom, a methyl group, a n-heptyl group, a 2-carboxyethyl group, a trifluoromethyl group, a methoxy group, a n-propoxy group, an isopropoxy group, a n-butoxy group, a tert-butoxy group, a n-pentyloxy group, a 1-ethylpropoxy group, a n-hexyloxy group, a n-heptyloxy group, a n-octyloxy group, a 2-tert-butoxy-ethoxy group, a n-nonyloxy group, a n-decyloxy group, a n-pentadecyloxy group, a trifluoromethoxy group, $—O(CH_2)_2CF_3$, $—O(CH_2)_4CF_3$, a benzyloxy group, a 4-(tert-butyl)benzyloxy group, a dimethylamino group, a diethylamino group, a piperidin-1-yl group, a 2-oxopiperidin-1-yl group, a morpholin-4-yl group, a pyrrolidin-1-yl group, a azepan-1-yl group, a thiomorpholin-4-yl group, a hydroxy group, $—O(CH_2)_6COOH$, $—O(CH_2)_8COOH$, a 2-adamantyloxy group, $—O(CH_2)_5—OH$, a 4-(tert-butyl)phenoxy group, a phenoxy group, a 3,5-dimethylbenzyloxy group, $—O(CH_2)_4$-Ph, a 4-trifluoromethoxybenzyloxy group, $—O(CH_2)_3$—O-Ph, a 3-cyclopentylpropoxy group, a 3-cyclohexylpropoxy group, a cyclohexyoxy group, a 4-(n-butyl)cyclohexyoxy group, a 2-isopropyl-5-methyl-cyclohexyloxy group, a cyclopentyloxy group and a cycloheptyloxy group.

When m is 1, it is preferable that two or three of $R^{31}$, $R^{32}$, $R^{33}$ and $R^{34}$ are hydrogen atoms. When m is 0, it is preferable that two to four of $R^{31}$, $R^{32}$, $R^{33}$, $R^{34}$ and $R^{35}$ are hydrogen atoms.

X in the aforementioned formula (I) represents a single bond, —CH═CH—, —C(═O)—, the formula $—V'—(V')_k—$, the formula $—N(R^4)—C(═O)—$, the formula $—N(R^4)—V'—$ or the formula $—(V')_k—R''—W'—$ (in each of the formulas, the bond at the left-hand end binds to the benzene ring E, and the bond at the right-hand end binds to Y'). The aforementioned $R^4$ represents a hydrogen atom or a $C_{1-6}$ alkyl group. $R^4$ is preferably a hydrogen atom or a methyl group. The aforementioned R'' represents an oxygen atom or a sulfur atom. The aforementioned V' represents a methylene group or a methylene group substituted with one or two $C_{1-6}$ alkyl groups (when the methylene group is substituted with two $C_{1-6}$ alkyl groups, each of the $C_{1-6}$ alkyl groups may be the same or different). The aforementioned W' represents the formula $-J^1-J^2-J^3-$ (in the formula, when G is the formula $—(CH_2)_j—N—W'—CO_2H$, then $J^1$ binds to the nitrogen atom, and $J^3$ binds to the carboxy group; when X is the formula $—(V')_k—R''—W'—$, $J^1$ binds to R'', and $J^3$ binds to Y'). The aforementioned $J^1$ represents a methylene group or a methylene group substituted with one or two groups selected from the aforementioned substituent group ϵ-1 (when the number of the substituents is two, each of the substituents may be the same or different). Each of the aforementioned $J^2$ and $J^3$ independently represents a single bond, a methylene group or a methylene group substituted with one or two groups selected from the substituent group ϵ-1 (when the number of the substituent is two, each of the substituents may be the same or different).

The aforementioned W' is preferably a $C_{1-3}$ straight chain alkylene group or a $C_{1-3}$ straight chain alkylene group wherein a part or all of the hydrogen atoms are substituted with a group or groups selected from the substituent group ε-1 (when the number of the substituents is two or more, each of the substituents may be the same or different). The aforementioned k represents 0, 1 or 2.

Examples of the aforementioned formula —V'—(V')$_k$— include —$CH_2$—, —$(CH_2)_2$—, —$(CH_2)_3$—, —CH(n-Bu)-$CH_2$— and the like. Examples of the aforementioned formula —N($R^4$)—C(=O)— include —N(H)—C(=O)—, —N(Me)-C(=O)— and the like. Examples of the aforementioned formula —N($R^4$)—V'— include —N(H)—C(Me)$_2$-, —N(H)—CH(n-Bu)-, —N(n-Bu)-$CH_2$—, —N(n-Pr)-$CH_2$—, —N(H)—$CH_2$—, —N(Me)-$CH_2$— and the like. Examples of the aforementioned formula —(V')$_k$—R''—W'— include —$OCH_2$—, —OC(Me)$_2$-, —$CH_2$—O—$CH_2$—, —CH(Me)-O—$CH_2$—, —O$(CH_2)_3$—, —$CH_2$—O—C(Me)$_2$-, —OCH(Et)-, —OCHF—, —$OCF_2$—, —OCH(n-Bu)-, —OCH(n-Hex)-, —O$(CH_2)_2$—CH(Me)- and the like.

Y' in the aforementioned formula (I) represents a carboxy group or a 1H-tetrazol-5-yl group. M in the aforementioned formula (I) represents a single bond, the formula —C(=O)-$(Q^1)_n$-$(Q^2)_p$-$(Q^3)_r$-, the formula -$(Q^1)_n$-$(Q^2)_p$-$(Q^3)_r$-$(U')_q$—, the formula -$(Q^1)_n$-$(Q^2)_p$-$(U')_q$-$(Q^3)_r$-, or the formula -$(Q^1)_n$-$(U')_q$-$(Q^2)_p$-$(Q^3)_r$- (in each of the formulas, the bond at the left-hand end binds to G, and the bond at the right-hand end binds to $R^2$). Each of the aforementioned $Q^1$, $Q^2$ and $Q^3$ independently represents a methylene group or a methylene group substituted with one or two groups selected from the aforementioned substituent group ζ-1 (when the number of the substituents is two, each of the substituents may be the same or different). Each of $Q^1$, $Q^2$ and $Q^3$ is preferably and independently a methylene group or a group selected from the aforementioned substituent group ζ-2.

[Substituent Group ζ-2]

[Formula 13]

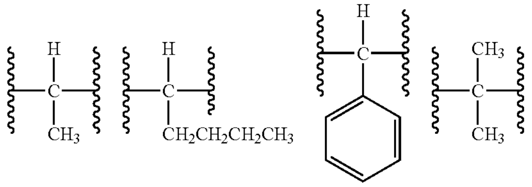

U' represents an oxygen atom or a sulfur atom, n represents an integer of 1 to 10. p represents an integer of 0 to 10. q represents 0 or 1. r represents an integer of 0 to 10. When m is the formula —C(=O)-$(Q^1)_n$-$(Q^2)_p$-$(Q^3)_r$-, then the sum of n, p and r is an integer of 1 to 10. When m is the formula -$(Q^1)_n$-$(Q^2)_p$-$(Q^3)_r$-$(U')_q$—, the formula -$(Q^1)_n$-$(Q^2)_p$-$(U')_q$-$(Q^3)_r$- or the formula -$(Q^1)_n$-$(U')_q$-$(Q^2)_p$-$(Q^3)_r$-, then the sum of n, p, q and r is an integer of 1 to 10. M in the aforementioned formula (I) is preferably a single bond, the formula —C(=O)—$Z^1$—, the formula —$Z^1$—, the formula —$Z^2$—O—, the formula —$Z^2$—S— or the formula —$Z^3$—O—$CH_2$— (in each of the formulas, the bond at the left-hand end binds to G, and the bond at the right-hand end binds to $R^2$). $Z^1$ represents a $C_{1-10}$ straight chain alkylene group or a $C_{1-10}$ straight chain alkylene group wherein a part or all of the hydrogen atoms are substituted with groups selected from the substituent group ζ-1 (when the number of the substituents is two or more, each of the substituents may be the same or different). $Z^2$ represents a $C_{1-9}$ straight chain alkylene group or a $C_{1-9}$ straight chain alkylene group wherein a part or all of the hydrogen atoms are substituted with groups selected from the substituent group ζ-1 (when the number of the substituents is two or more, each of the substituents may be the same or different). $Z^3$ represents a $C_{1-8}$ straight chain alkylene group or a $C_{1-9}$ straight chain alkylene group wherein a part or all of the hydrogen atoms are substituted with groups selected from the substituent group ζ-1 (when the number of the substituents is two or more, each of the substituents may be the same or different). Each of $Z^1$, $Z^2$ and $Z^3$ is preferably and independently a group selected from the following substituent group τ;

[Substituent Group τ]

a methylene group, an ethylene group, a propane-1,3-diyl group, a butane-1,4-diyl group and a pentane-1,5-diyl group.

M is preferably a single bond, —C(=O)—$(CH_2)_3$—, —$CH_2$—, —$(CH_2)_2$—, —$(CH_2)_3$—, —$(CH_2)_4$—, —$(CH_2)_5$—, —$(CH_2)_6$—, —$(CH_2)_7$—, —$(CH_2)_{10}$—, —$(CH_2)_3$O—, —$(CH_2)_4$O—, —$(CH_2)_5$O—, —$(CH_2)_3$S—, —$(CH_2)_3OCH_2$—, —CH(Me)-, —CH(n-Bu)-, —CH(Ph)- or —$CH_2$—C(Me)$_2$-$CH_2$—.

Examples of the "halogen atom" in the aforementioned substituent groups α-1, β-1, γ-1 and ε-1 include a fluorine atom, a chlorine atom, a bromine atom and an iodine atom.

In the present specification, the "alkyl group" or an alkyl moiety of the substituents containing the alkyl moiety may be straight chain, branched chain or any combination of these. Examples of the "$C_{1-6}$ alkyl group" in the aforementioned R', $R^4$ and substituent groups α-1, β-1, δ-1, ζ-1 and η-1 include a n-pentyl group, an isopentyl group, a neopentyl group, a tert-pentyl group, a 1-ethylpropyl group, a n-hexyl group and the like, besides $C_{1-4}$ alkyl groups such as a methyl group, an ethyl group, a n-propyl group, an isopropyl group, a n-butyl group, an isobutyl group, a sec-butyl group, a tert-butyl group and the like. Examples of the "$C_{1-10}$ alkyl group" in the aforementioned substituent groups γ-1 and ε-1 include a n-heptyl group, a n-octyl group, a n-nonyl group, a n-decyl group and the like, besides the aforementioned $C_{1-6}$ alkyl groups. Examples of the "$C_{1-20}$ alkyl group" in the present specification include a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, a n-icosyl group and the like, besides the aforementioned $C_{1-10}$ alkyl groups.

Examples of the "$C_{3-8}$ cycloalkyl group" in the aforementioned $R^2$ include a cyclopropyl group, a cyclobutyl group, a cyclopentyl group, a cyclohexyl group, a cycloheptyl group and a cyclooctyl group. The "$C_{1-6}$ alkyl substituted $C_{3-8}$ cycloalkyl group" means a group in which one or more hydrogen atoms in the $C_{3-8}$ cycloalkyl group are substituted with $C_{1-6}$ alkyl groups. Examples of the "$C_{1-6}$ alkyl substituted $C_{3-8}$ cycloalkyl group" include a 2-methylcyclopropyl group, a 1-methylcyclobutyl group, a 3-cyclopentyl group, a 4-methylcyclohexyl group, a 4-(tert-butyl)cyclohexyl group, a 3,5-dimethylcyclohexyl group, a 4,4-dimethylcyclohexyl group, a 4-methylcycloheptyl group, a 5-methylcyclooctyl group and the like.

The "halogenated $C_{1-6}$ alkyl group" in the aforementioned substituent groups α-1 and β-1 means a group in which one or more hydrogen atoms in the $C_{1-6}$ alkyl group are substituted with halogen atoms. Examples of the halogenated $C_{1-6}$ alkyl group include a chloromethyl group, a bromomethyl group, a fluoromethyl group, a dichloromethyl group, a dibromomethyl group, a difluoromethyl group, a trichloromethyl group, a tribromomethyl group, a trifluoromethyl group, a 2,2,2-trifluoroethyl group, a pentafluoroethyl group, a heptafluoropropyl group, a nonafluorobutyl group, a perfluoropentyl group, a perfluorohexyl group and the like. The halogen atom of the halogenated $C_{1-6}$ alkyl group is preferably a fluorine atom.

The "halogenated $C_{1-10}$ alkyl group" in the aforementioned substituent group γ-1 means a group in which one or more hydrogen atoms in the $C_{1-10}$ alkyl group are substituted with halogen atoms. Examples of the halogenated $C_{1-10}$ alkyl group include a perfluoroheptyl group, a perfluorooctyl group, a perfluorononyl group, a perfluorodecyl group and the like, besides the aforementioned halogenated $C_{1-6}$ alkyl groups. The halogen atom of the halogenated $C_{1-10}$ alkyl group is preferably a fluorine atom.

Examples of the $C_{1-6}$ alkoxy group in the aforementioned substituent groups α-1 and β-1 include a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a neopentyloxy group, a tert-pentyloxy group, a 1-ethylpropoxy group, a n-hexyloxy group and the like.

Examples of the $C_{1-20}$ alkoxy group in the aforementioned substituent group γ-1 include a n-heptyloxy group, a n-octyloxy group, a n-nonyloxy group, a n-decyloxy group, a n-undecyloxy group, a n-dodecyloxy group, a n-tridecyloxy group, a n-tetradecyloxy group, a n-pentadecyloxy group, a n-hexadecyloxy group, a n-heptadecyloxy group, a n-octadecyloxy group, a n-nonadecyloxy group, a n-icosyloxy group and the like, besides the aforementioned $C_{1-6}$ alkoxy groups.

The "$C_{3-8}$ cycloalkoxy group" in the aforementioned substituent group γ-1 means a group in which the hydrogen atom in the hydroxy group is substituted with a $C_{3-8}$ cycloalkyl group. Examples of the $C_{3-8}$ cycloalkoxy group include a cyclopropoxy group, a cyclobutoxy group, a cyclopentyloxy group, a cyclohexyloxy group, a cycloheptyloxy group and a cyclooctyloxy group. The "$C_{3-8}$ cycloalkoxy group substituted with one or two $C_{1-6}$ alkyl groups" in the aforementioned substituent group γ-1 means a group in which one or two hydrogen atoms in the $C_{3-8}$ cycloalkoxy group are substituted with $C_{1-6}$ alkyl groups. When two hydrogen atoms are substituted with $C_{1-6}$ alkyl groups, each of the $C_{1-6}$ alkyl groups may be the same or different. Examples of the $C_{3-8}$ cycloalkoxy group substituted with one or two $C_{1-6}$ alkyl group include a 2-methylcyclopropoxy group, a 1-methylcyclobutoxy group, a 3-cyclopentyloxy group, a 4-methylcyclohexyloxy group, a 4-(n-butyl)cyclohexyloxy group, a 2-isopropyl-5-methyl-cyclohexyloxy group, a 3,5-dimethylcyclohexyloxy group, a 4,4-dimethylcyclohexyloxy group, a 4-methylcycloheptyloxy group, a 5-methylcyclooctyloxy group and the like.

Examples of the halogenated $C_{1-10}$ alkoxy group in the aforementioned substituent groups α-1, β-1 and η-1 include a chloromethoxy group, a bromomethoxy group, a fluoromethoxy group, a dichloromethoxy group, a dibromomethoxy group, a difluoromethoxy group, a trichloromethoxy group, a tribromomethoxy group, a trifluoromethoxy group, a 2,2,2-trifluoroethoxy group, a pentafluoroethoxy group, a heptafluoropropoxy group, a nonafluorobutoxy group, a perfluoropentyloxy group, a perfluorohexyloxy group and the like. Examples of the halogenated $C_{1-20}$ alkoxy group in the aforementioned substituent group γ-1 include a perfluoroheptyloxy group, a perfluorooctyloxy group, a perfluorononyloxy group, a perfluorodecyloxy group, a perfluoroundecyloxy group, a perfluorododecyloxy group, a perfluorotridecyloxy group, a perfluorotetradecyloxy group, a perfluoropentadecyloxy group, a perfluorohexadecyloxy group, a perfluoroheptadecyloxy group, a perfluorooctadecyloxy group, a perfluorononadecyloxy group, a perfluoroicosyloxy group and the like, besides the aforementioned halogenated $C_{1-6}$ alkoxy groups. Each of the halogen atoms of the halogenated $C_{1-10}$ alkoxy group and the halogenated $C_{1-20}$ alkoxy group is preferably a fluorine atom.

The "carboxy substituted $C_{1-6}$ alkoxy group" in the aforementioned substituent group β-1 means a group in which one or more hydrogen atoms in the $C_{1-6}$ alkoxy group are substituted with carboxy groups. Examples of the carboxy substituted $C_{1-6}$ alkoxy group include a carboxymethyloxy group, a carboxyethyloxy group, a carboxypropyloxy group, a carboxybutyloxy group, a carboxypentyloxy group, a carboxyhexyloxy group and the like. The "carboxy substituted $C_{1-20}$ alkoxy group" in the aforementioned substituent group γ-1 means a group in which one or more hydrogen atoms in the $C_{1-20}$ alkoxy group are substituted with carboxy groups. Examples of the carboxy substituted $C_{1-20}$ alkoxy group include a carboxyheptyloxy group, a carboxyoctyloxy group, a carboxynonyloxy group, a carboxydecyloxy group, a carboxyundecyloxy group, a carboxydodecyloxy group, a carboxytridecyloxy group, a carboxytetradecyloxy group, a carboxypentadecyloxy group, a carboxyhexadecyloxy group, a carboxyheptadecyloxy group, a carboxyoctadecyloxy group, a carboxynonadecyloxy group, a carboxylcosadecyloxy group and the like, besides the aforementioned carboxy substituted $C_{1-6}$ alkoxy groups.

Examples of the "$C_{6-10}$ aryl group" in the aforementioned $R^1$ and $R^2$ include a phenyl group, a 1-naphthyl group, a 2-naphthyl group and the like.

Examples of the "$C_{1-6}$ alkylsulfanyl group" in the aforementioned substituent groups α-1 and β-1 include a methylsulfanyl group, an ethylsulfanyl group, a n-propylsulfanyl group, an isopropylsulfanyl group, a n-butylsulfanyl group, an isobutylsulfanyl group, a sec-butylsulfanyl group, a tert-butylsulfanyl group, a n-pentylsulfanyl group, an isopentylsulfanyl group, a neopentylsulfanyl group, a tert-pentylsulfanyl group, a 1-ethylpropylsulfanyl group, a n-hexylsulfanyl group and the like.

The alkylene moiety of the "$C_{1-6}$ alkylenedioxy group" in the aforementioned substituent group α-1 may be straight chain, branched chain, or any combinations of these. Examples of the $C_{1-6}$ alkylenedioxy group include a 1,5-pentylenedioxy group, a 1,6-hexylenedioxy group, a 1,1,2,2-tetramethylethylenedioxy group and the like, besides $C_{1-4}$ alkylenedioxy groups such as a methylenedioxy group, a 1,2-ethylenedioxy group, a 1,3-propylenedioxy group, a 1,4-butylenedioxy group, a 1,1-dimethymethylenedioxy group and the like.

The "carboxy substituted $C_{1-6}$ alkyl group" in the aforementioned substituent groups α-1 and β-1 means a group in which one or more hydrogen atoms of the $C_{1-6}$ alkyl group are substituted with carboxy groups. Examples of the carboxy substituted $C_{1-6}$ alkyl group include a carboxymethyl group, a carboxyethyl group, a carboxypropyl group, a carboxybutyl group, a carboxypentyl group, a carboxyhexyl group and the like. The "carboxy substituted $C_{1-10}$ alkyl group" in the aforementioned substituent group γ-1 means a group in which one or more hydrogen atoms of the $C_{1-10}$ alkyl group are substituted with carboxy groups. Examples of the carboxy substituted $C_{1-10}$ alkyl group include a carboxymethyl group, a 1-carboxyethyl group, a 2-carboxyethyl group, a 3-carboxypropyl group, a 4-carboxybutyl group, a 5-carboxypentyl group, a 6-carboxyhexyl group, a 7-carboxyheptyl group, a 8-carboxyoctyl group, a 9-carboxynonyl group, a 10-carboxydecyl group and the like.

The "$C_{3-8}$ cycloalkyl substituted $C_{1-20}$ alkoxy group" in the aforementioned substituent group γ-1 means a group in which one or more hydrogen atoms of the $C_{1-20}$ alkoxy group are substituted with $C_{3-8}$ cycloalkyl groups. Examples of the $C_{3-8}$ cycloalkyl substituted $C_{1-20}$ alkoxy group include a cyclopropylmethoxy group, a cyclobutylmethoxy group, a cyclopentylmethoxy group, a cyclohexylmethoxy group, a cycloheptylmethoxy group, a cyclooctylmethoxy group, a 1-(cyclohexyl)ethoxy group, a 2-(cyclohexyl)ethoxy group, a 3-(cyclohexyl)propoxy group, a 4-(cyclohexyl)butoxy group, a 5-(cyclohexyl)pentyloxy group, a 6-(cyclohexyl) hexyloxy group, a 7-(cyclohexyl)heptyloxy group, a 8-(cyclohexyl)octyloxy group, a 9-(cyclohexyl)nonyloxy group, a 10-(cyclohexyl)decyloxy group, a 11-(cyclohexyl)undecyloxy group, a 12-(cyclohexyl)dodecyloxy group, a 13-(cyclohexyl)tridecyloxy group, a 14-(cyclohexyl)tetradecyloxy group, a 15-(cyclohexyl)pentadecyloxy group, a 16-(cyclohexyl)hexadecyloxy group, a 17-(cyclohexyl)heptadecyloxy group, a 18-(cyclohexyl)octadecyloxy group, a 19-(cyclohexyl)nonadecyloxy group, a 20-(cyclohexyl)icosyloxy group and the like. The $C_{3-8}$ cycloalkyl substituted $C_{1-20}$ alkoxy group is preferably a $C_{3-8}$ cycloalkyl substituted $C_{1-10}$ alkoxy group, and more preferably a $C_{3-8}$ cycloalkyl substituted $C_{1-6}$ alkoxy group.

The "phenyl substituted $C_{1-20}$ alkoxy group" means a group in which one or more hydrogen atoms of the $C_{1-20}$ alkoxy group are substituted with phenyl groups. Examples of the phenyl substituted $C_{1-20}$ alkoxy group include a benzyloxy group, a 1-phenylethoxy group, a 2-phenylethoxy group, a 3-phenylpropoxy group, a 4-phenylbutoxy group, a 5-phenylpentyloxy group, a 6-phenylhexyloxy group, a 7-phenylheptyloxy group, a 8-phenyloctyloxy group, a 9-phenylnonyloxy group, a 10-phenyldecyloxy group, a 11-phenylundecyloxy group, a 12-phenyldodecyloxy group, a 13-phenyltridecyloxy group, a 14-phenyltetradecyloxy group, a 15-phenylpentadecyloxy group, a 16-phenylhexadecyloxy group, a 17-phenylheptadecyloxy group, a 18-phenyloctadecyloxy group, a 19-phenylnonadecyloxy group, a 20-phenylicosyloxy group and the like. The phenyl substituted $C_{1-20}$ alkoxy group is preferably a phenyl substituted $C_{1-10}$ alkoxy group, and more preferably a phenyl substituted $C_{1-6}$ alkoxy group.

The "hydroxy substituted $C_{1-20}$ alkoxy group" in the aforementioned substituent group γ-1 means a group in which one or more hydrogen atoms of the $C_{1-20}$ alkoxy group are substituted with hydroxy groups. Examples of the hydroxy substituted $C_{1-20}$ alkoxy group include a hydroxymethoxy group, a 1-hydroxyethoxy group, a 2-hydroxyethoxy group, a 3-hydroxypropoxy group, a 4-hydroxybutoxy group, a 5-hydroxypentyloxy group, a 6-hydroxyhexyloxy group, a 7-hydroxyheptyloxy group, a 8-hydroxyoctyloxy group, a 9-hydroxynonyloxy group, a 10-hydroxydecyloxy group, a 11-hydroxyundecyloxy group, a 12-hydroxydodecyloxy group, a 13-hydroxytridecyloxy group, a 14-hydroxytetradecyloxy group, a 15-hydroxypentadecyloxy group, a 16-hydroxyhexadecyloxy group, a 17-hydroxyheptadecyloxy group, a 18-hydroxyoctadecyloxy group, a 19-hydroxynonadecyloxy group, a 20-hydroxyicosyloxy group and the like. The hydroxy substituted $C_{1-20}$ alkoxy group is preferably a hydroxy substituted $C_{1-10}$ alkoxy group, and more preferably a hydroxy substituted $C_{1-6}$ alkoxy group.

The "$C_{1-6}$ alkoxy substituted $C_{1-10}$ alkoxy group" in the aforementioned substituent group γ-1 means a group in which one or more hydrogen atoms of the $C_{1-10}$ alkoxy group are substituted with $C_{1-6}$ alkoxy groups. Examples of the $C_{1-6}$ alkoxy substituted $C_{1-10}$ alkoxy group include a methoxymethoxy group, a 1-methoxyethoxy group, a 2-methoxyethoxy group, a 3-methoxypropoxy group, a 4-methoxybutoxy group, a 5-methoxypentyloxy group, a 6-methoxyhexyloxy group, a 7-methoxyheptyloxy group, a 8-methoxyoctyloxy group, a 9-methoxynonyloxy group, a 10-methoxydecyloxy group, an ethoxymethoxy group, an isopropoxymethoxy group, a tert-butoxymethoxy group and the like. The $C_{1-6}$ alkoxy substituted $C_{1-10}$ alkoxy group is preferably a $C_{1-6}$ alkoxy substituted $C_{1-6}$ alkoxy group.

The "phenoxy substituted $C_{1-20}$ alkoxy group" in the aforementioned substituent group γ-1 means a group in which one or more hydrogen atoms of the $C_{1-20}$ alkoxy group are substituted with phenoxy groups. Examples of the phenoxy substituted $C_{1-20}$ alkoxy group include a phenoxymethoxy group, a 1-phenoxyethoxy group, a 2-phenoxyethoxy group, a 3-phenoxypropoxy group, a 4-phenoxybutoxy group, a 5-phenoxypentyloxy group, a 6-phenoxyhexyloxy group, a 7-phenoxyheptyloxy group, a 8-phenoxyoctyloxy group, a 9-phenoxynonyloxy group, a 10-phenoxydecyloxy group, a 11-phenoxyundecyloxy group, a 12-phenoxydodecyloxy group, a 13-phenoxytridecyloxy group, a 14-phenoxytetradecyloxy group, a 15-phenoxypentadecyloxy group, a 16-phenoxyhexadecyloxy group, a 17-phenoxyheptadecyloxy group, a 18-phenoxyoctadecyloxy group, a 19-phenoxynonadecyloxy group, a 20-phenoxyicosyloxy group and the like. The phenoxy substituted $C_{1-20}$ alkoxy group is preferably a phenoxy substituted $C_{1-10}$ alkoxy group, and more preferably a phenoxy substituted $C_{1-6}$ alkoxy group.

The "di($C_{1-10}$ alkyl)amino group" in the aforementioned substituent group γ-1 means a group in which two hydrogen atoms of the amino group are substituted with $C_{1-10}$ alkyl groups. Each of the two $C_{1-10}$ alkyl groups of the ($C_{1-10}$ alkyl)amino group may be the same or different. Examples of the di($C_{1-6}$ alkyl)amino group include a di(n-pentyl)amino group, a diisopentylamino group, a di(n-hexyl)amino group, a dicyclopentyl amino group, a dicyclohexylamino group, a di(n-heptyl)amino group, a di(n-octyl)amino group, a di(n-nonyl)amino group, a di(n-decyl)amino group and the like, besides di($C_{1-4}$ alkyl)amino groups such as a dimethylamino group, a diethylamino group, a methyl(ethyl)amino group, a di(n-propyl)amino group, a diisopropylamino group, a di(n-butyl)amino group, a diisobutylamino group, a di(sec-butyl) amino group, a dicyclopropylamino group, a dicyclobutylamino group, a di(cyclopropylmethyl)amino group and the like. The di($C_{1-10}$ alkyl)amino group is preferably a di($C_{1-6}$ alkyl)amino group.

Examples of the "5 to 7-membered completely saturated heterocyclic group (the heterocyclic group comprises one nitrogen atom as the ring-constituting atom and may further comprise one hetero atom selected from the group consisting of a nitrogen atom, an oxygen atom and a sulfur atom as the ring-constituting atom, and the heterocyclic group binds to E via the nitrogen atom that is the ring-constituting atom" include a pyrrolidin-1-yl group, a pyrazolidin-1-yl group, an imidazolidin-1-yl group, an oxazolidin-3-yl group, a thiazolidin-3-yl group, a piperidin-1-yl group, a piperazin-1-yl group, a morpholin-4-yl group, a thiomorpholin-4-yl group, a hexahydro-1H-azepin-1-yl group, a hexahydro-1,4-diazepin-1-yl group, a hexahydro-1,4-oxazepin-4-yl group, a hexahydro-1,4-thiazepin-4-yl group and the like.

Examples of the "straight chain alkylene group" in the aforementioned $Z^1$, $Z^2$ and $Z^3$ include a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group and a decane-1,10-diyl group. Examples of the "$C_{1-3}$ straight chain alkylene group" in the aforementioned W' include a methylene group, an ethylene group and a propane-1,3-diyl group.

Examples of the "$C_{1-6}$ alkylsulfonyl group" in the aforementioned substituent group α-1 include a methylsulfonyl group, an ethylsulfonyl group, a n-propylsulfonyl group, an isopropylsulfonyl group, a n-butylsulfonyl group, an isobutylsulfonyl group, a sec-butylsulfonyl group, a tert-butylsulfonyl group, a n-pentylsulfonyl group, an isopentylsulfonyl group, a neopentylsulfonyl group, a tert-pentylsulfonyl group, a 1-ethylpropylsulfonyl group, a n-hexylsulfonyl group and the like. Examples of the "$C_{1-6}$ alkylsulfonylamino group" in the aforementioned substituent group α-1 include a methylsulfonylamino group, an ethylsulfonylamino group, a n-propylsulfonylamino group, an isopropylsulfonylamino group, a n-butylsulfonylamino group, an isobutylsulfonylamino group, a sec-butylsulfonylamino group, a tert-butylsulfonylamino group, a n-pentylsulfonylamino group, an isopentylsulfonylamino group, a neopentylsulfonylamino group, a tert-pentylsulfonylamino group, a 1-ethylpropylsulfonylamino group, a n-hexylsulfonylamino group and the like.

Examples of the "$C_{1-6}$ alkylcarbonyl group" in the aforementioned substituent group α-1 include an acetyl group, an ethylcarbonyl group, a n-propylcarbonyl group, an isopropylcarbonyl group, a n-butylcarbonyl group, an isobutylcarbonyl group, a sec-butylcarbonyl group, a tert-butylcarbonyl group, a n-pentylcarbonyl group, an isopentylcarbonyl group, a neopentylcarbonyl group, a tert-pentylcarbonyl group, a 1-ethylpropylcarbonyl group, a n-hexylcarbonyl group and the like.

The "halogenated $C_{1-6}$ alkoxy substituted phenyl group" in the aforementioned substituent group β-1 means a group in which one or more hydrogen atoms of the phenyl group are substituted with halogenated $C_{1-6}$ alkoxy groups. Examples of the halogenated $C_{1-6}$ alkoxy substituted phenyl group include a chloromethoxyphenyl group, a bromomethoxyphenyl group, a fluoromethoxyphenyl group, a dichloromethoxyphenyl group, a dibromomethoxyphenyl group, a difluoromethoxyphenyl group, a trichloromethoxyphenyl group, a tribromomethoxyphenyl group, a trifluoromethoxyphenyl group, a 3,5-bistrifluoromethoxyphenyl group, a 2,2,2-trifluoroethoxyphenyl group, a pentafluoroethoxyphenyl group, a heptafluoropropoxyphenyl group, a nonafluorobutoxyphenyl group, a perfluoropentyloxyphenyl group, a perfluorohexyloxyphenyl group and the like.

The "$C_{1-6}$ alkyl substituted phenyl group" in the aforementioned substituent group β-1 means a group in which one or more hydrogen atoms of the phenyl group are substituted with $C_{1-6}$ alkyl groups. Examples of the $C_{1-6}$ alkyl substituted phenyl group include a methylphenyl group, a dimethylphenyl group, an ethylphenyl group, a propylphenyl group, a butylphenyl group, a pentylphenyl group, a hexylphenyl group and the like.

The "carboxy substituted $C_{2-6}$ alkenyl group" in the aforementioned substituent group β-1 means a group in which one or more hydrogen atoms of the $C_{2-6}$ alkenyl group are substituted with carboxy groups. Examples of the carboxy substituted $C_{2-6}$ alkenyl group include a carboxyvinyl group, a carboxyallyl group, a carboxypropenyl group, a carboxybutenyl group, a carboxypentenyl group and the like.

The compounds represented by the aforementioned formula (I) may form salts. Examples of pharmacologically acceptable salts include, when the compound has an acidic group, for example, metal salts such as a lithium salt, a sodium salt, a potassium salt, a magnesium salt, a calcium salt and the like, or ammonium salts such as an ammonium salt, a methylammonium salt, a dimethylammonium salt, a trimethylammonium salt, a dicyclohexylammonium and the like, and when the compound has a basic group, for example, mineral acid salts such as a hydrochloride, a hydrobromide, a hydrosulfate, a nitrate, a phosphate and the like, or organic acid salts such as a methane sulfonate, a benzene sulfonate, a para-toluene sulfonate, an acetate, a propionate, a tartrate, a fumarate, a maleate, a malate, an oxalate, a succinate, a citrate, a benzoate, a mandelate, a cinnamate, a lactate and the like. Salts may sometimes form with amino acids such as glycine and the like. As active ingredients of the medicament of the present invention, pharmacologically acceptable salts may also be suitably used.

The compounds represented by the aforementioned formula (I) or the salts thereof may exist as hydrates or solvates. As active ingredients of the medicament of the present invention, any of the aforementioned substances may be used. Furthermore, the compounds represented by the aforementioned formula (I) may sometimes have one or more asymmetric carbons, and may exist as steric isomers such as an optically active substance and a diastereomer. The active ingredients of the medicament of the present invention may be used in pure form of stereoisomers, an arbitrary mixture of enantiomers or diastereomers, and racemate.

Moreover, the compounds represented by the aforementioned formula (I) may exist as tautomers. The active ingredients of the medicament of the present invention may be used in pure form of tautomers or a mixture thereof. Furthermore, when the compounds represented by the formula (I) have olefinic double bonds, the configuration may be either E or Z, and the active ingredients of the medicament of the present invention may be uses in either of geometrical configurations or a mixture thereof.

Examples of the preferred compounds as the active ingredients of the medicaments of the present invention are shown in the following tables. However, the active ingredients of the medicaments of the present invention are not limited to those compounds. In the tables, (a) means that the bond at the left-hand end binds to E, and the bond at the right-hand end binds to the carboxy group. In the tables, (b) means that the bond at the left-hand end binds to G, and the bond at the right-hand end binds to $R^2$. In the tables, (c) means that the compound was obtained as a sodium salt. In the tables, (d) means that the bond at the left-hand end binds to E, and the bond at the right-hand end binds to the 1H-tetrazol-5-yl group. In the tables, (e) means that the bond at the left-hand end binds to the nitrogen atom, and the bond at the right-hand end binds to the carboxy group. In the tables, (f) means that the bond at the left-hand end binds to the nitrogen atom, and the bond at the right-hand end binds to $R^2$.

TABLE 1-1

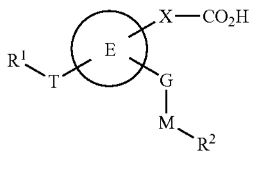

| Compound Number | $R^1$ | $R^2$ | 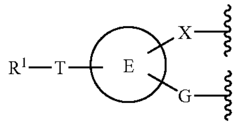 | X[(a)] | M[(b)] |
|---|---|---|---|---|---|
| 1 | 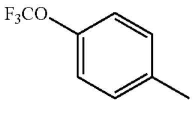 | 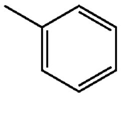 | 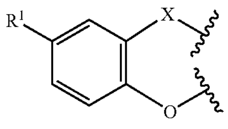 | $-CH_2-$ | $-CH_2-$ |

TABLE 1-1-continued
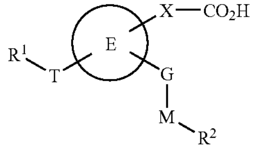
| Compound Number | $R^1$ | $R^2$ | 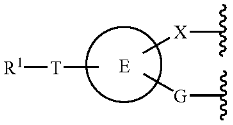 | X[(a)] | M[(b)] |
|---|---|---|---|---|---|
| 2 | 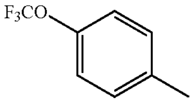 | 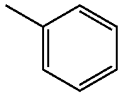 | 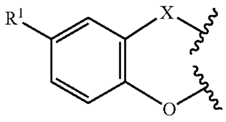 | 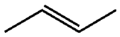 | $—CH_2—$ |
| 3 | 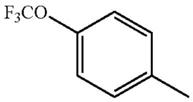 | 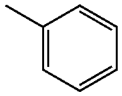 | 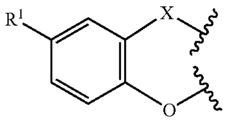 | $—CH_2CH_2—$ | $—CH_2—$ |
| 4 | 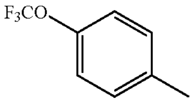 | 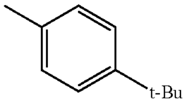 | 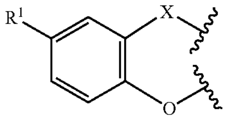 | 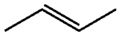 | $—CH_2—$ |
| 5 | 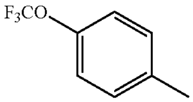 | 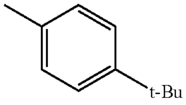 | 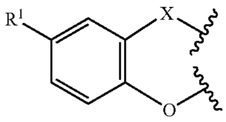 | $—CH_2CH_2—$ | $—CH_2—$ |
| 6[(c)] | 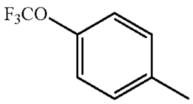 | 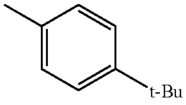 | 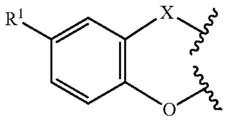 | 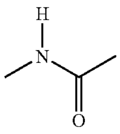 | $—CH_2—$ |
| 7 | 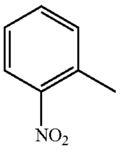 | 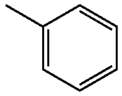 | 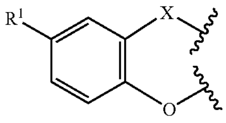 | 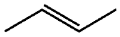 | $—CH_2—$ |
| 8 | 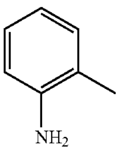 | 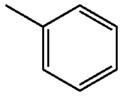 | 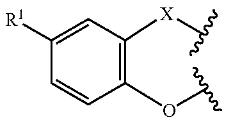 | $—CH_2CH_2—$ | $—CH_2—$ |
| 9 | 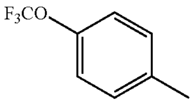 | 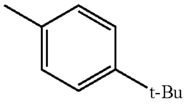 | 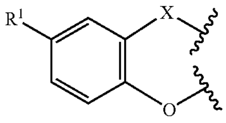 | $—CH_2—$ | $—CH_2—$ |
| 10 | 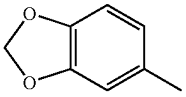 | 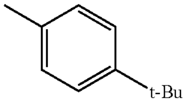 | 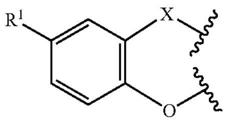 | $—CH_2—$ | $—CH_2—$ |

TABLE 1-2
| | | | | | |
|---|---|---|---|---|---|
| 11 | 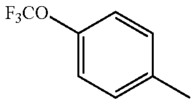 | 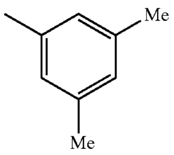 | 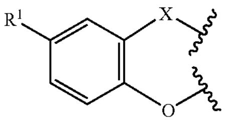 | $—CH_2—$ | $—CH_2—$ |
| 12 | 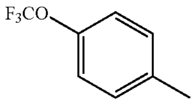 | 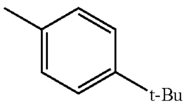 | 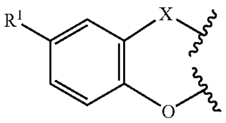 | 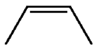 | single bond |
| 13 | 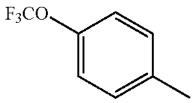 | 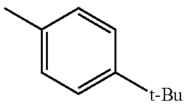 | 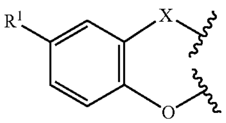 | $—CH_2CH_2—$ | single bond |
| 14 | 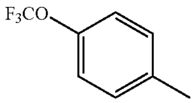 | 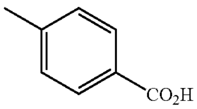 | 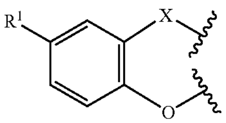 | $—CH_2CH_2—$ | single bond |
| 15 | 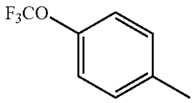 | 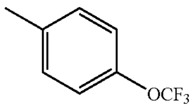 | 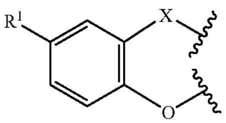 | 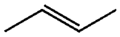 | single bond |
| 16 | 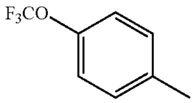 | 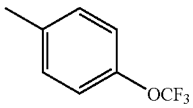 | 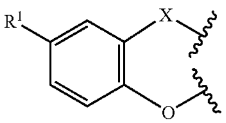 | $—CH_2CH_2—$ | single bond |
| 17 | 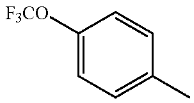 | 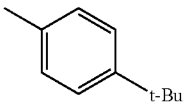 | 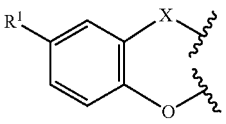 | 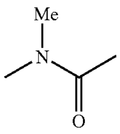 | $—CH_2—$ |
| 18 | 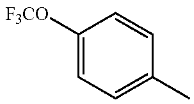 | 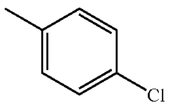 | 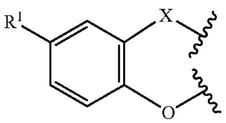 | 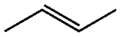 | $—CH_2—$ |
| 19 | 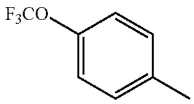 | 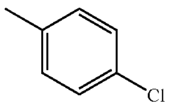 | 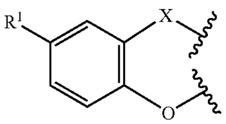 | $—CH_2CH_2—$ | $—CH_2—$ |
| 20 | 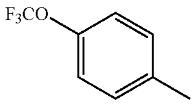 | 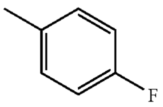 | 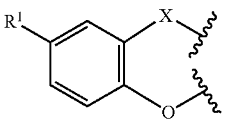 | $—CH_2CH_2—$ | $—CH_2—$ |
| 21 | 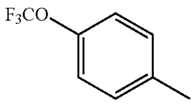 | 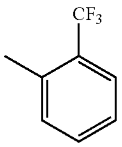 | 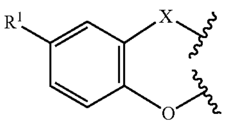 | $—CH_2CH_2—$ | $—CH_2—$ |

TABLE 1-2-continued
| | | | | | |
|---|---|---|---|---|---|
| 22 | 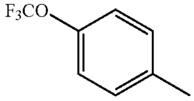 | 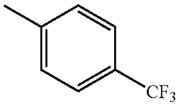 | 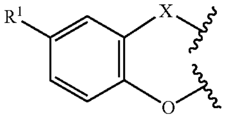 | —$CH_2CH_2$— | —$CH_2$— |
TABLE 1-3
| | | | | | |
|---|---|---|---|---|---|
| 23 | 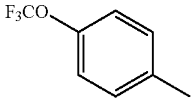 | 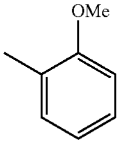 | 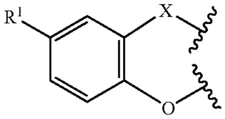 | —$CH_2CH_2$— | —$CH_2$— |
| 24 | 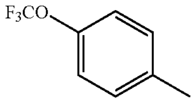 | 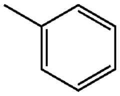 | 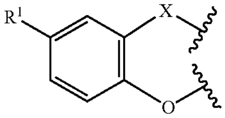 | 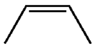 | —$CH_2$— |
| 25 | 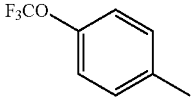 | 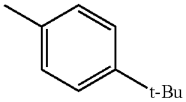 | 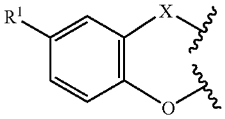 | 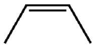 | —$CH_2$— |
| 26 | 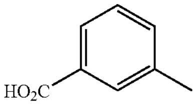 | 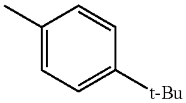 | 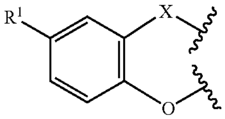 | —$CH_2CH_2$— | —$CH_2$— |
| 27 | 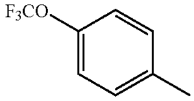 | 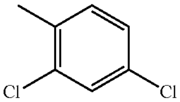 | 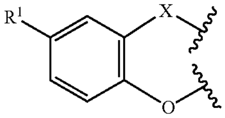 | —$CH_2CH_2$— | —$CH_2$— |
| 28 | 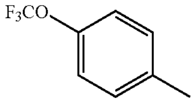 | 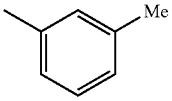 | 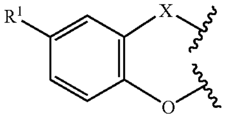 | —$CH_2CH_2$— | —$CH_2$— |
| 29 | 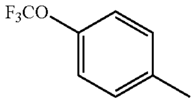 | 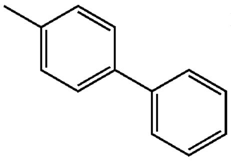 | 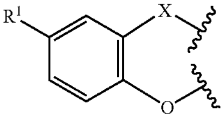 | —$CH_2CH_2$— | —$CH_2$— |
| 30 | 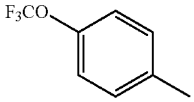 | 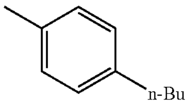 | 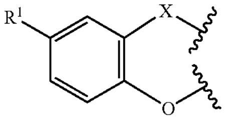 | —$CH_2CH_2$— | —$CH_2$— |
| 31 | 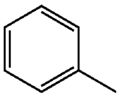 | 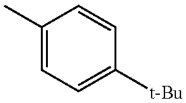 | 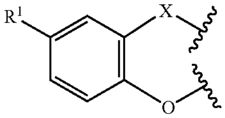 | 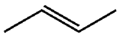 | —$CH_2$— |
| 32 | 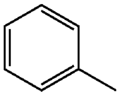 | 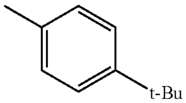 | 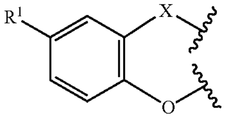 | —$CH_2CH_2$— | —$CH_2$— |

TABLE 1-3-continued
| | | | | | |
|---|---|---|---|---|---|
| 33 | 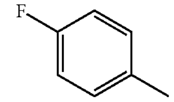 | 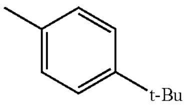 | 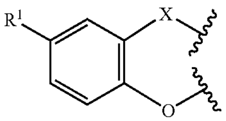 | 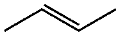 | $-CH_2-$ |
| 34 | 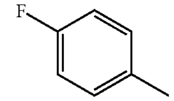 | 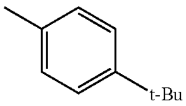 | 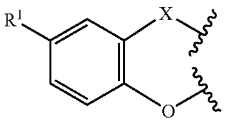 | $-CH_2CH_2-$ | $-CH_2-$ |
TABLE 1-4
| | | | | | |
|---|---|---|---|---|---|
| 35 | 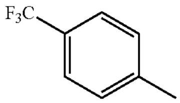 | 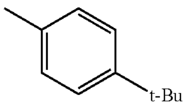 | 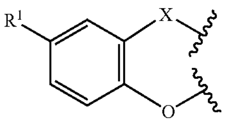 | 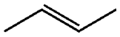 | $-CH_2-$ |
| 36 | 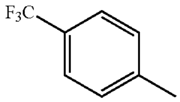 | 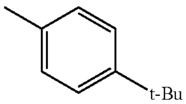 | 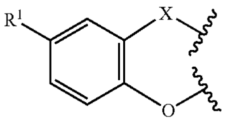 | $-CH_2CH_2-$ | $-CH_2-$ |
| 37 | 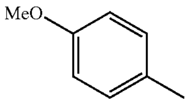 | 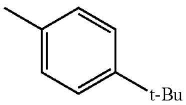 | 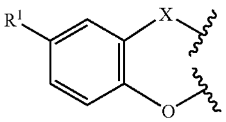 | 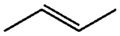 | $-CH_2-$ |
| 38 | 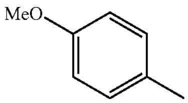 | 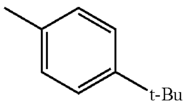 | 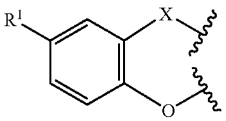 | $-CH_2CH_2-$ | $-CH_2-$ |
| 39 | 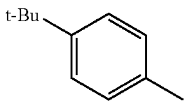 | 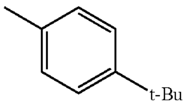 | 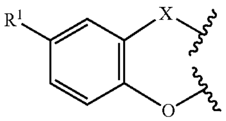 | 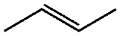 | $-CH_2-$ |
| 40 | 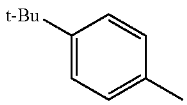 | 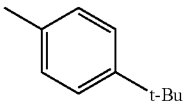 | 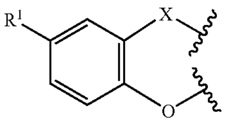 | $-CH_2CH_2-$ | $-CH_2-$ |
| 41 | 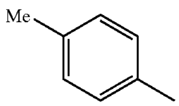 | 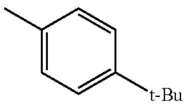 | 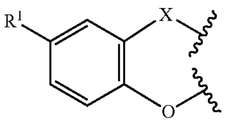 | 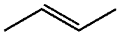 | $-CH_2-$ |
| 42 | 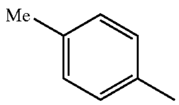 | 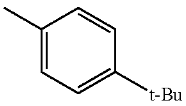 | 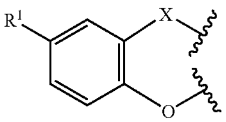 | $-CH_2CH_2-$ | $-CH_2-$ |
| 43 | 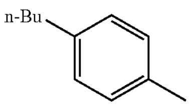 | 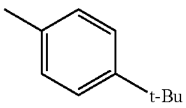 | 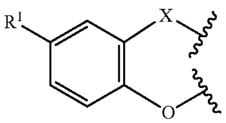 | $-CH_2CH_2-$ | $-CH_2-$ |

TABLE 1-4-continued
| | | | | | |
|---|---|---|---|---|---|
| 44 | 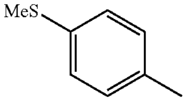 | 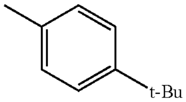 | 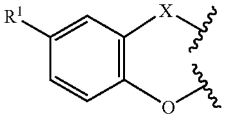 | 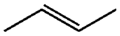 | —$CH_2$— |
| 45 | 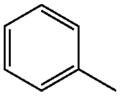 | 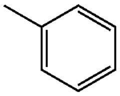 | 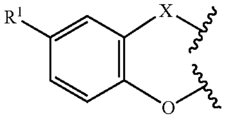 | 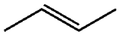 | —$CH_2$— |
| 46 | 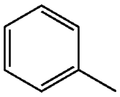 | 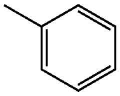 | 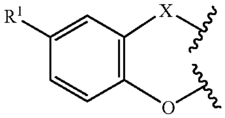 | —$CH_2CH_2$— | —$CH_2$— |
TABLE 1-5
| | | | | | |
|---|---|---|---|---|---|
| 47 | 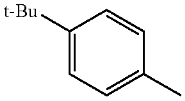 | 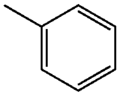 | 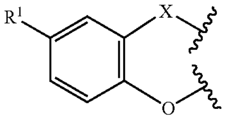 | 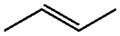 | —$CH_2$— |
| 48 | 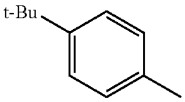 | 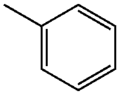 | 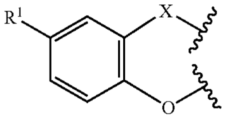 | —$CH_2CH_2$— | —$CH_2$— |
| 49 | 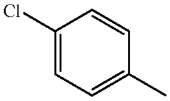 | 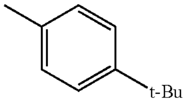 | 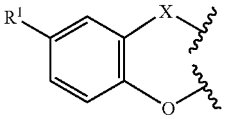 | 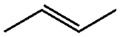 | —$CH_2$— |
| 50 | 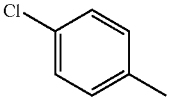 | 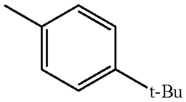 | 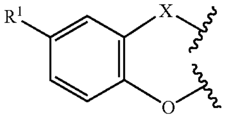 | —$CH_2CH_2$— | —$CH_2$— |
| 51 | 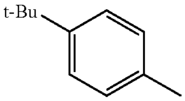 | 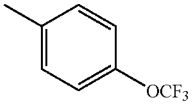 | 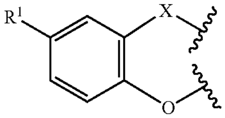 | 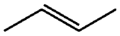 | —$CH_2$— |
| 52 | 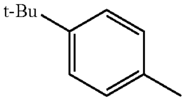 | 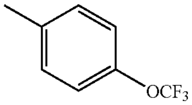 | 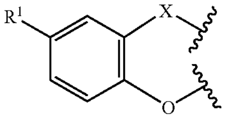 | —$CH_2CH_2$— | —$CH_2$— |
| 53 | 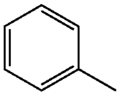 | 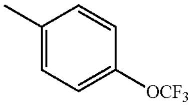 | 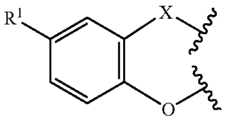 | —$CH_2CH_2$— | —$CH_2$— |
| 54 | 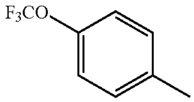 | 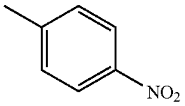 | 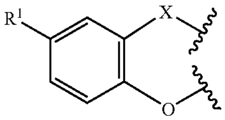 | —$CH_2CH_2$— | —$CH_2$— |

TABLE 1-5-continued
| | | | | | |
|---|---|---|---|---|---|
| 55 | 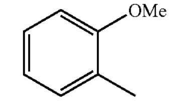 | 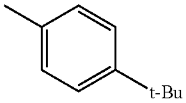 | 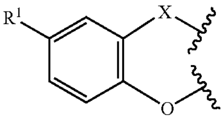 | 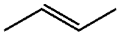 | $—CH_2—$ |
| 56 | 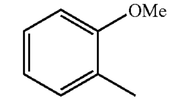 | 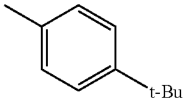 | 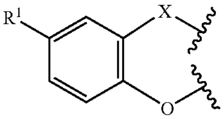 | $—CH_2CH_2—$ | $—CH_2—$ |
| 57 | 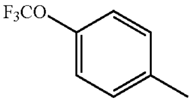 | 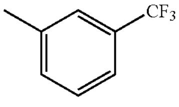 | 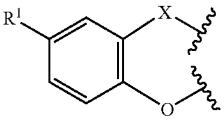 | 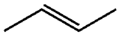 | $—CH_2—$ |
| 58 | 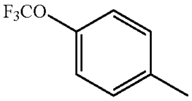 | 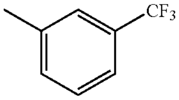 | 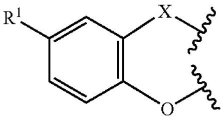 | $—CH_2CH_2—$ | $—CH_2—$ |
TABLE 1-6
| | | | | | |
|---|---|---|---|---|---|
| 59 | 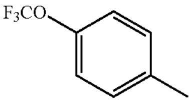 | 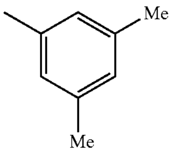 | 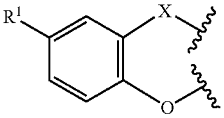 | $—CH_2CH_2—$ | $—CH_2—$ |
| 60 | 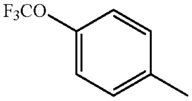 | 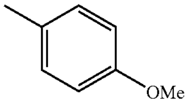 | 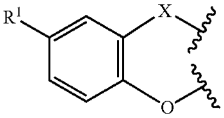 | $—CH_2CH_2—$ | $—CH_2—$ |
| 61 | 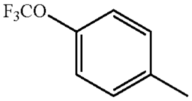 | 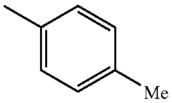 | 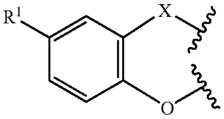 | $—CH_2CH_2—$ | $—CH_2—$ |
| 62 | 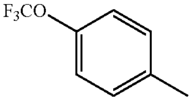 | 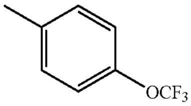 | 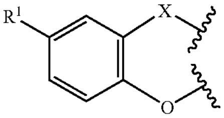 | $—CH_2CH_2—$ | $—CH_2—$ |
| 63 | 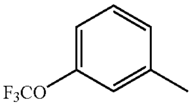 | 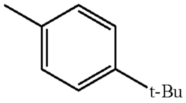 | 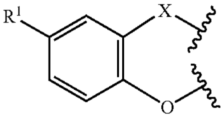 | 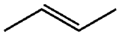 | $—CH_2—$ |
| 64 | 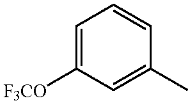 | 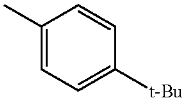 | 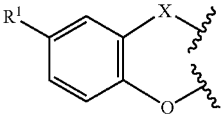 | $—CH_2CH_2—$ | $—CH_2—$ |
| 65 | 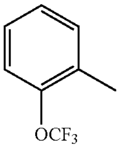 | 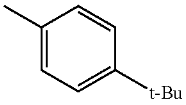 | 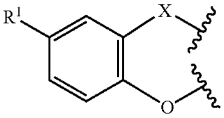 | 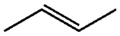 | $—CH_2—$ |

TABLE 1-6-continued
| | | | | | |
|---|---|---|---|---|---|
| 66 | 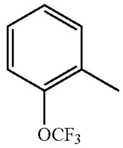 | 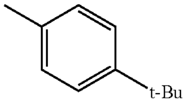 | 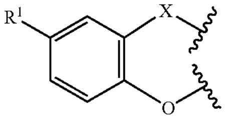 | —$CH_2CH_2$— | —$CH_2$— |
| 67 | 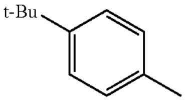 | 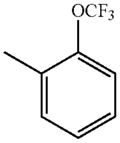 | 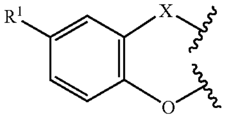 | —$CH_2CH_2$— | —$CH_2$— |
| 68 | 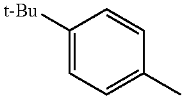 | 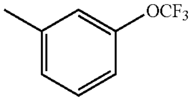 | 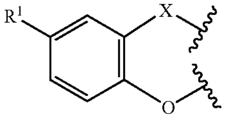 | —$CH_2CH_2$— | —$CH_2$— |
| 69 | 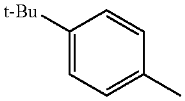 | 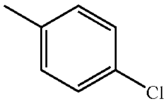 | 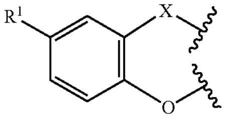 | —$CH_2CH_2$— | —$CH_2$— |
| 70 | 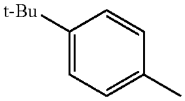 | 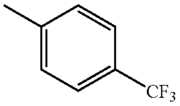 | 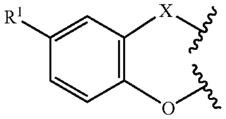 | —$CH_2CH_2$— | —$CH_2$— |
TABLE 1-7
| | | | | | |
|---|---|---|---|---|---|
| 71 | 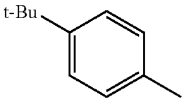 | 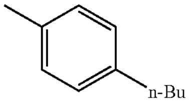 | 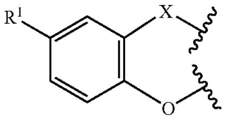 | —$CH_2CH_2$— | —$CH_2$— |
| 72 | 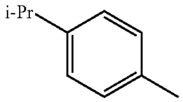 | 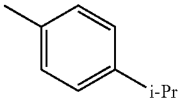 | 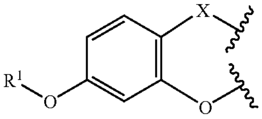 | 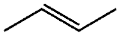 | single bond |
| 73 | 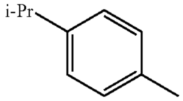 | 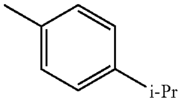 | 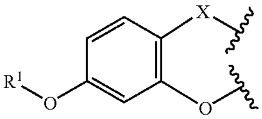 | —$CH_2CH_2$— | single bond |
| 74 | 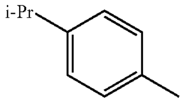 | 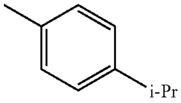 | 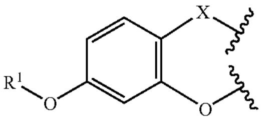 | 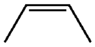 | single bond |
| 75 | 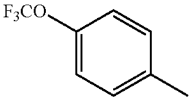 | 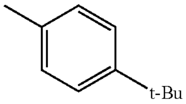 | 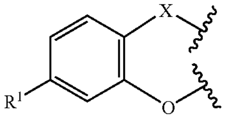 | 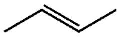 | —$CH_2$— |
| 76 | 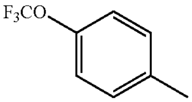 | 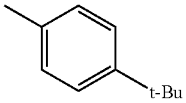 | 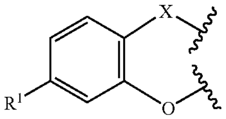 | —$CH_2CH_2$— | —$CH_2$— |

TABLE 1-7-continued
| | | | | | |
|---|---|---|---|---|---|
| 77 | 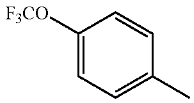 | 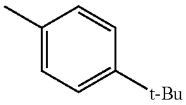 | 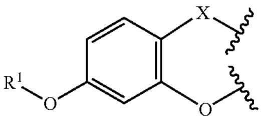 | 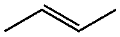 | —$CH_2$— |
| 78 | 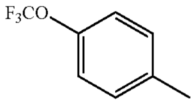 | 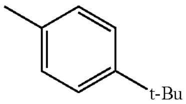 | 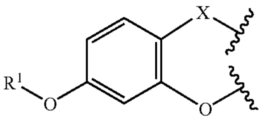 | —$CH_2CH_2$— | —$CH_2$— |
| 79 | 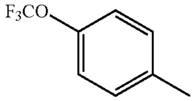 | 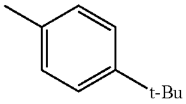 | 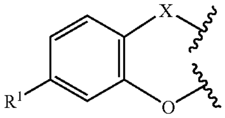 | 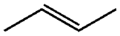 | single bond |
| 80 | 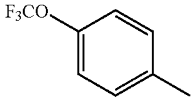 | 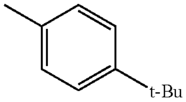 | 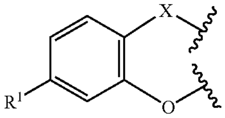 | —$CH_2CH_2$— | single bond |
| 81 | 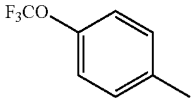 | 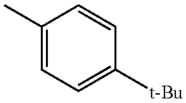 | 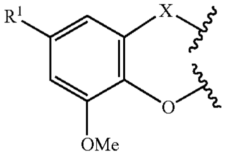 | 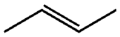 | —$CH_2$— |
| 82 | 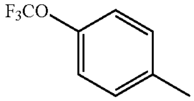 | 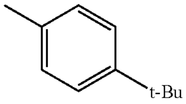 | 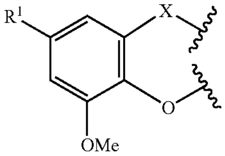 | —$CH_2CH_2$— | —$CH_2$— |
TABLE 1-8
| | | | | | |
|---|---|---|---|---|---|
| 83 | 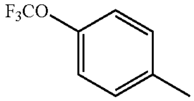 | 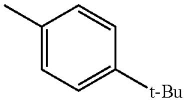 | 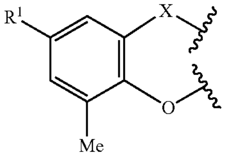 | 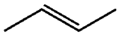 | —$CH_2$— |
| 84 | 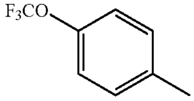 | 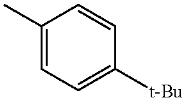 | 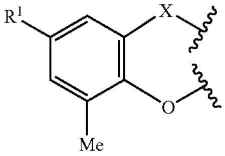 | —$CH_2CH_2$— | —$CH_2$— |
| 85 | 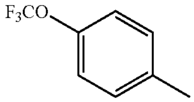 | 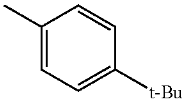 | 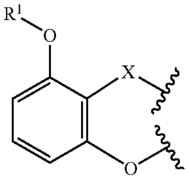 | 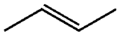 | —$CH_2$— |

TABLE 1-8-continued
| | | | | | |
|---|---|---|---|---|---|
| 86 | 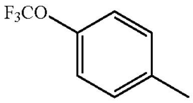 | 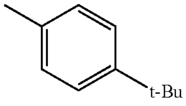 | 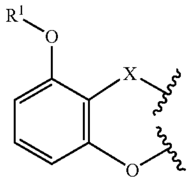 | $—CH_2CH_2—$ | $—CH_2—$ |
| 87 | 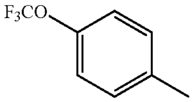 | 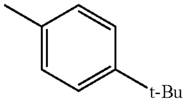 | 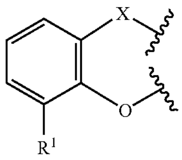 | 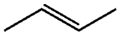 | $—CH_2—$ |
| 88 | 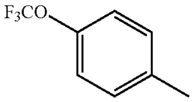 | 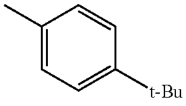 | 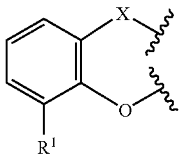 | $—CH_2CH_2—$ | $—CH_2—$ |
| 89 | 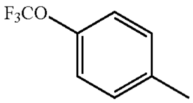 | 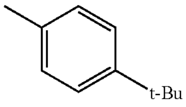 | 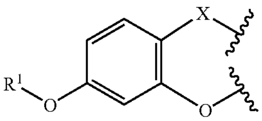 | 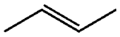 | single bond |
| 90 | 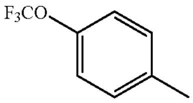 | 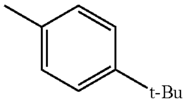 | 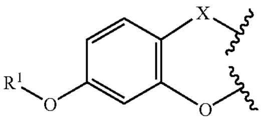 | $—CH_2CH_2—$ | single bond |
| 91 | 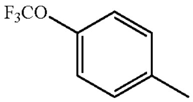 | 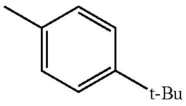 | 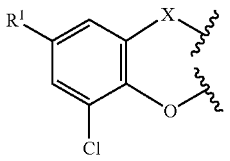 | 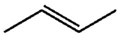 | $—CH_2—$ |
| 92 | 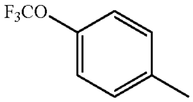 | 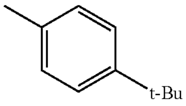 | 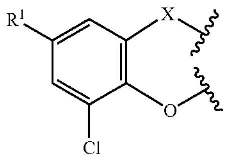 | $—CH_2CH_2—$ | $—CH_2—$ |
| 93 | 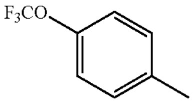 | 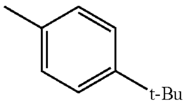 | 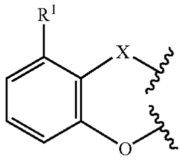 | 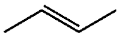 | single bond |
TABLE 1-9
| | | | | | |
|---|---|---|---|---|---|
| 94 | 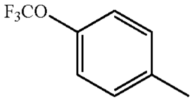 | 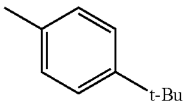 | 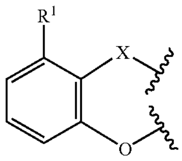 | $—CH_2CH_2—$ | single bond |

TABLE 1-9-continued
| | | | | | |
|---|---|---|---|---|---|
| 95 | 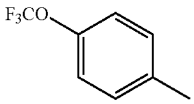 | 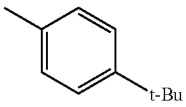 | 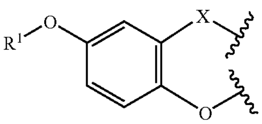 | 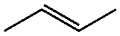 | $—CH_2—$ |
| 96 | 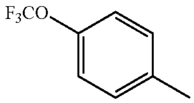 | 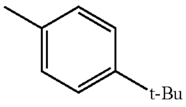 | 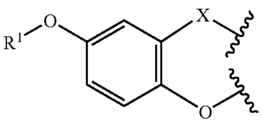 | $—CH_2CH_2—$ | $—CH_2—$ |
| 97 | 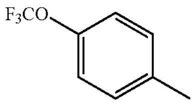 | 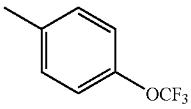 | 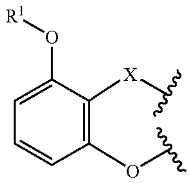 | 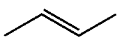 | single bond |
| 98 | 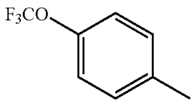 | 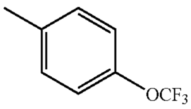 | 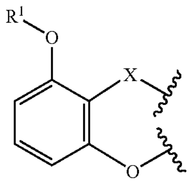 | $—CH_2CH_2—$ | single bond |
| 99 | 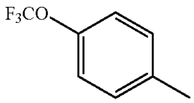 | 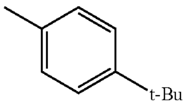 | 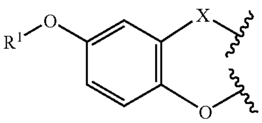 | 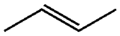 | single bond |
| 100 | 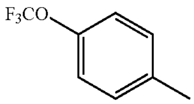 | 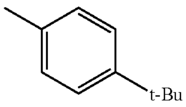 | 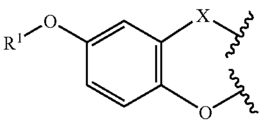 | $—CH_2CH_2—$ | single bond |
| 101 | 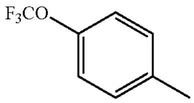 | 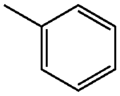 | 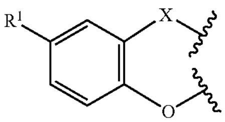 | $—CH_2CH_2—$ | $—(CH_2)_3—$ |
| 102 | 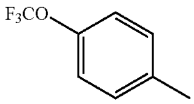 | 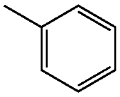 | 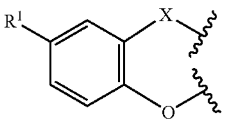 | $—CH_2CH_2—$ | $—(CH_2)_4—$ |
| 103 | 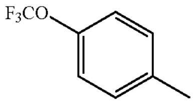 | 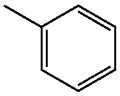 | 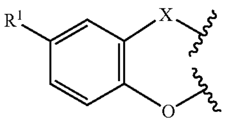 | $—CH_2CH_2—$ | $—(CH_2)_3O—$ |
| 104 | 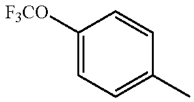 | 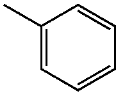 | 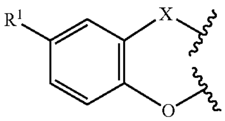 | $—CH_2CH_2—$ | $—(CH_2)_5—$ |

TABLE 1-10
| | | | | | |
|---|---|---|---|---|---|
| 105 | 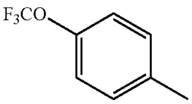 | 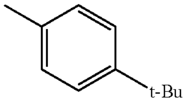 | 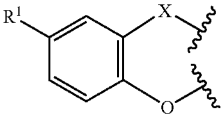 | $-OCH_2-$ | $-CH_2-$ |
| 106 | 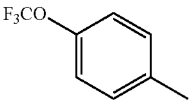 | 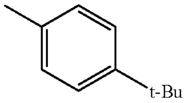 | 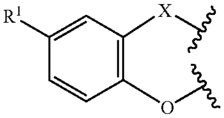 | 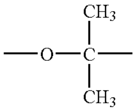 | $-CH_2-$ |
| 107 | 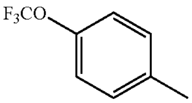 | 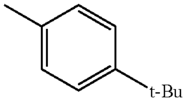 | 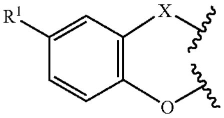 | 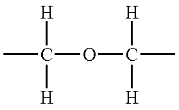 | $-CH_2-$ |
| 108 | 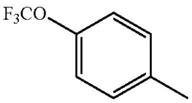 | 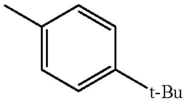 | 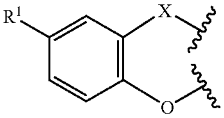 | 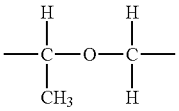 | $-CH_2-$ |
| 109 | 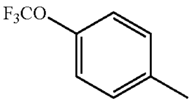 | 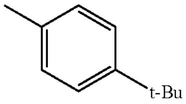 | 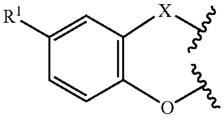 | $-O(CH_2)_3-$ | $-CH_2-$ |
| 110 | 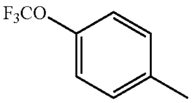 | 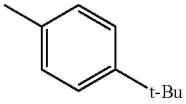 | 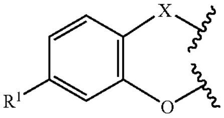 | 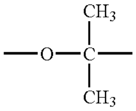 | single bond |
| 111 | 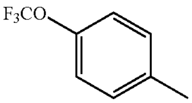 | 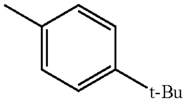 | 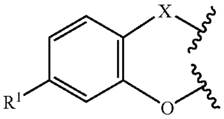 | 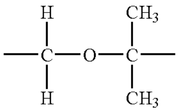 | single bond |
| 112 | 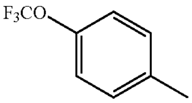 | 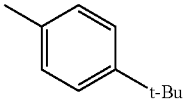 | 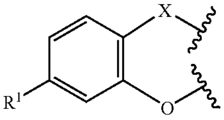 | $-OCH_2-$ | single bond |
| 113 | 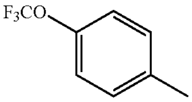 | 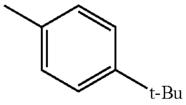 | 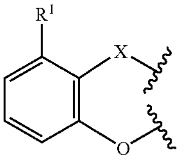 | $-OCH_2-$ | single bond |
| 114 | 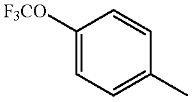 | 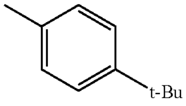 | 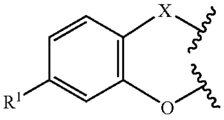 | 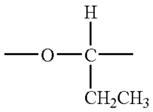 | single bond |
| 115 | 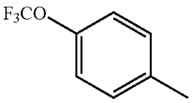 | 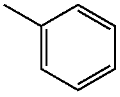 | 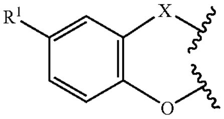 | $-OCH_2-$ | $-(CH_2)_4-$ |

TABLE 1-10-continued
| | | | | | |
|---|---|---|---|---|---|
| 116 | 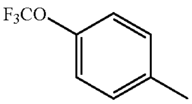 | 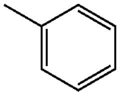 | 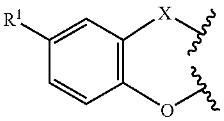 | 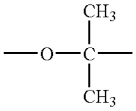 | $—(CH_2)_4—$ |
TABLE 1-11
| | | | | | |
|---|---|---|---|---|---|
| 117 | 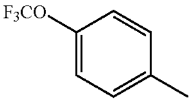 | 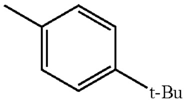 | 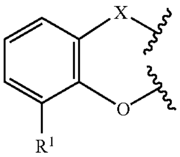 | $—OCH_2—$ | $—CH_2—$ |
| 118 | 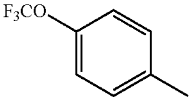 | 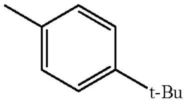 | 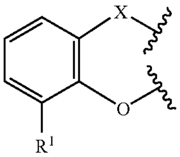 | 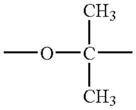 | $—CH_2—$ |
| 119 | 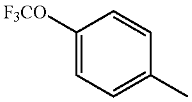 | 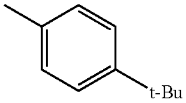 | 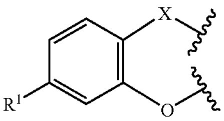 | 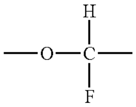 | single bond |
| 120 | 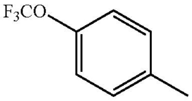 | 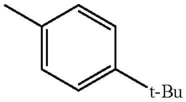 | 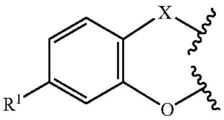 | 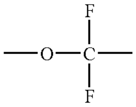 | single bond |
| 251 | 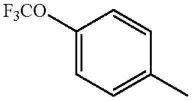 | 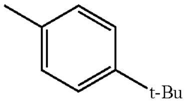 | 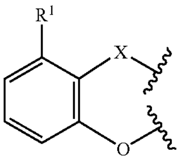 | 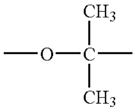 | single bond |
| 301 | 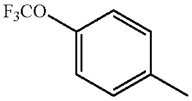 | 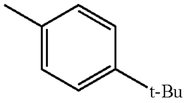 | 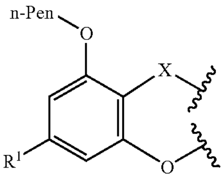 | $—OCH_2—$ | $—CH_2—$ |
| 302 | 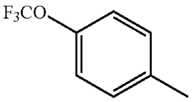 | 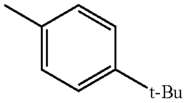 | 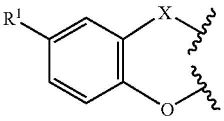 | $—OCH_2—$ | single bond |
| 303 | 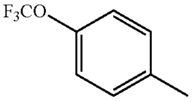 | 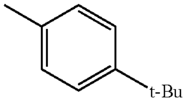 | 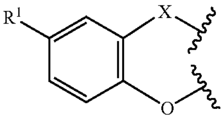 | 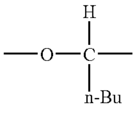 | single bond |
| 304 | 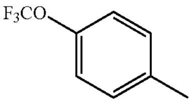 | 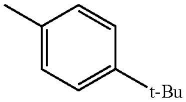 | 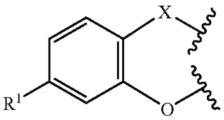 | $—OCH_2—$ | $—CH_2—$ |

TABLE 1-11-continued
| | | | | | |
|---|---|---|---|---|---|
| 305 | 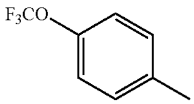 | 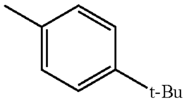 | 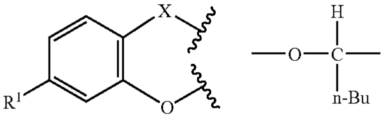 | | single bond |
| 306 | 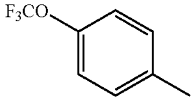 | 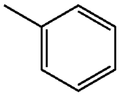 | 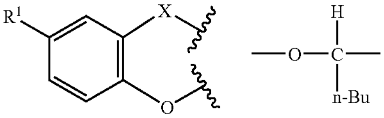 | | $-(CH_2)_4-$ |
TABLE 1-12
| | | | | | |
|---|---|---|---|---|---|
| 307 | 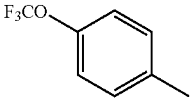 | 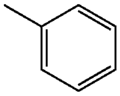 | 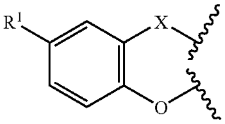 | 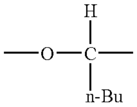 | single bond |
| 308 | 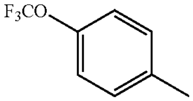 | 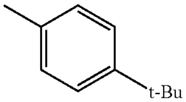 | 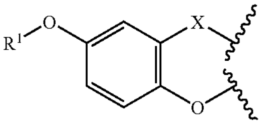 | 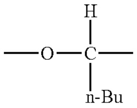 | $-CH_2-$ |
| 309 | 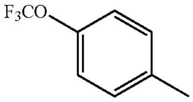 | 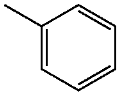 | 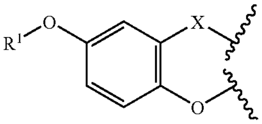 | 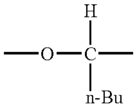 | $-(CH_2)_4-$ |
| 310 | 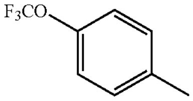 | 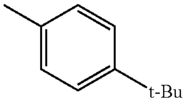 | 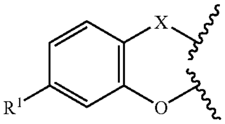 | 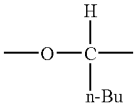 | $-CH_2-$ |
| 311 | 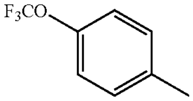 | 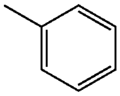 | 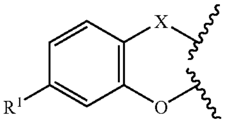 | 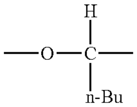 | $-(CH_2)_4-$ |
| 312 | 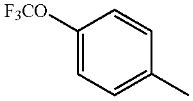 | 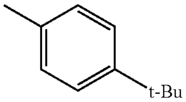 | 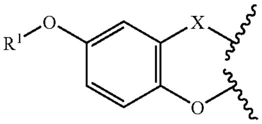 | 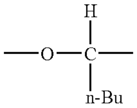 | single bond |
| 313 | 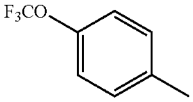 | 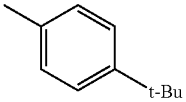 | 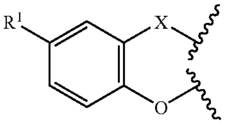 | 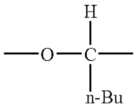 | $-CH_2-$ |
| 314 | 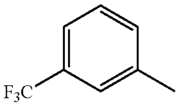 | 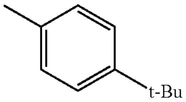 | 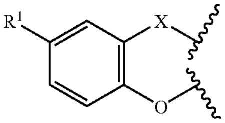 | $-OCH_2-$ | single bond |
| 315 | 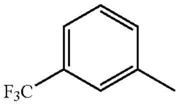 | 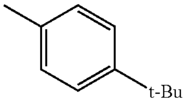 | 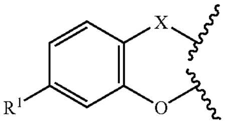 | $-OCH_2-$ | single bond |

TABLE 1-12-continued
| | | | | | |
|---|---|---|---|---|---|
| 316 | 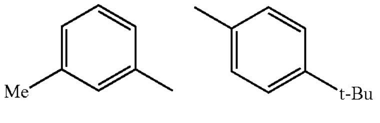 | | 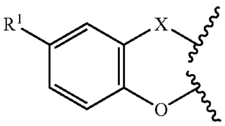 | —$OCH_2$— | single bond |
| 317 | 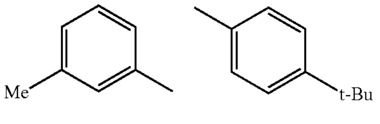 | | 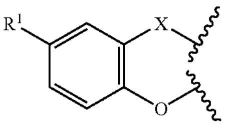 | 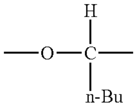 | single bond |
| 318 | 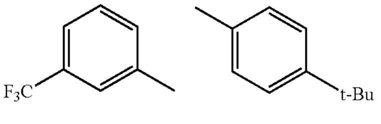 | | 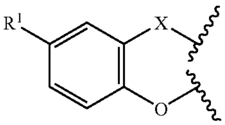 | 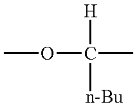 | single bond |
TABLE 1-13
| | | | | | |
|---|---|---|---|---|---|
| 319 | 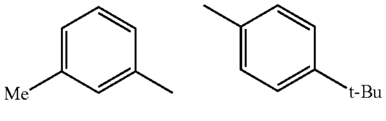 | | 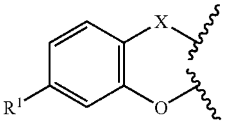 | —$OCH_2$— | single bond |
| 320 | 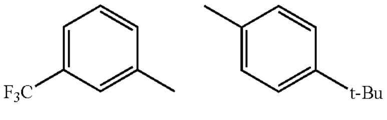 | | 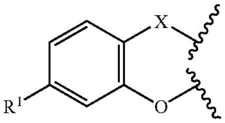 | 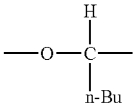 | single bond |
| 321 | 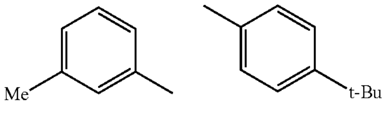 | | 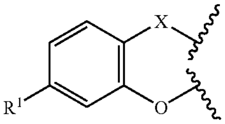 | 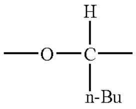 | single bond |
| 322 | 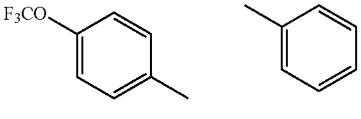 | | 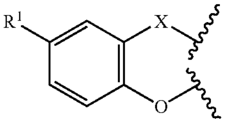 | 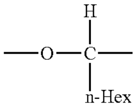 | single bond |
| 323 | 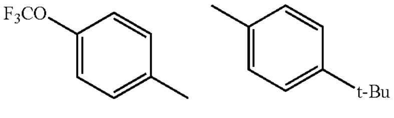 | | 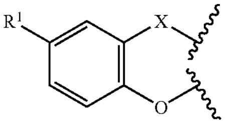 | 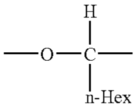 | single bond |
| 324 | 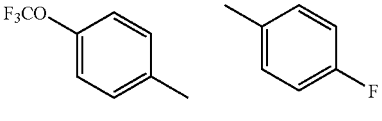 | | 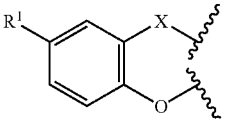 | 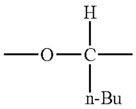 | —$(CH_2)_4$— |
| 325 | 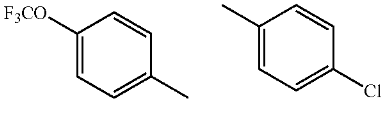 | | 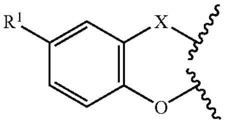 | 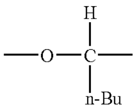 | —$(CH_2)_4$— |
| 326 | 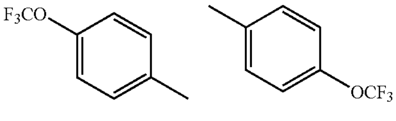 | | 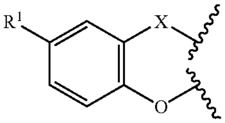 | 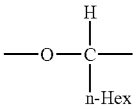 | single bond |

TABLE 1-13-continued
| | | | | | |
|---|---|---|---|---|---|
| 327 | 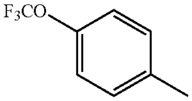 | 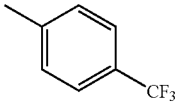 | 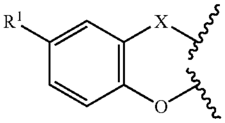 | 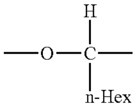 | single bond |
| 328 | 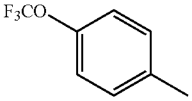 | 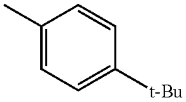 | 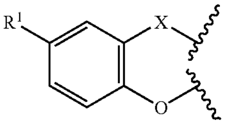 | $—OCH_2—$ | single bond |
| 329 | 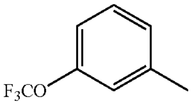 | 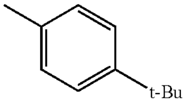 | 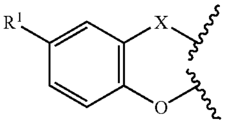 | $—OCH_2—$ | single bond |
| 330 | 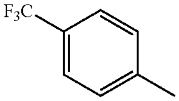 | 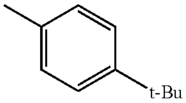 | 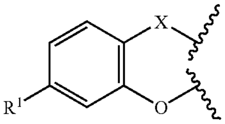 | $—OCH_2—$ | single bond |
TABLE 1-14
| | | | | | |
|---|---|---|---|---|---|
| 331 | 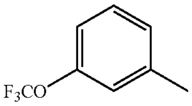 | 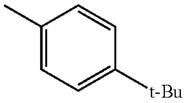 | 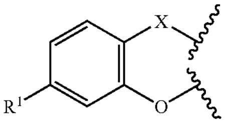 | $—OCH_2—$ | single bond |
| 332 | 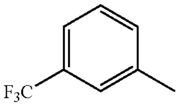 | 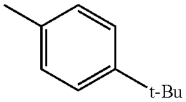 | 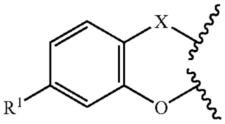 | $—CH_2CH_2—$ | single bond |
| 333 | 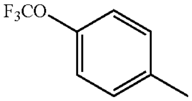 | 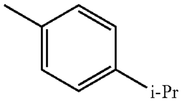 | 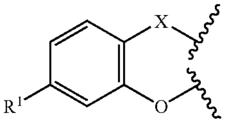 | $—OCH_2—$ | single bond |
| 334 | 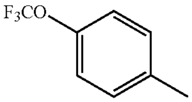 | 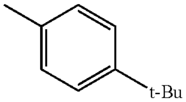 | 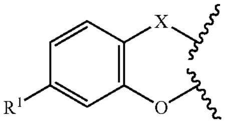 | $—CH_2—$ | single bond |
| 335 | 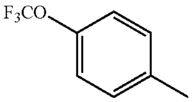 | 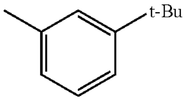 | 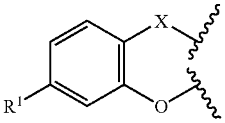 | 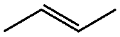 | single bond |
| 336 | 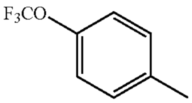 | 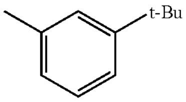 | 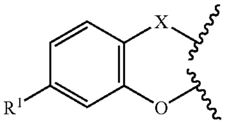 | $—CH_2CH_2—$ | single bond |
| 337 | 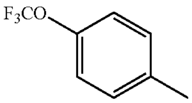 | 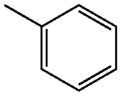 | 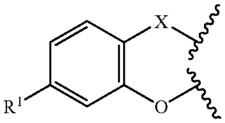 | $—OCH_2—$ | $—(CH_2)_4—$ |

TABLE 1-14-continued
| | | | | | |
|---|---|---|---|---|---|
| 401 | 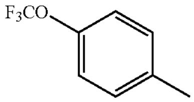 | 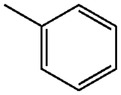 | 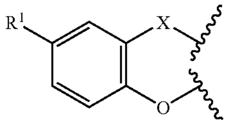 | single bond | $-CH_2-$ |
| 403 | 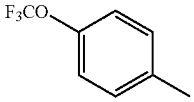 | 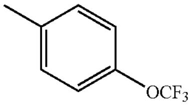 | 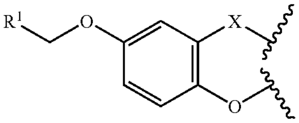 | 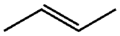 | $-CH_2-$ |
| 404 | 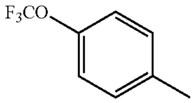 | 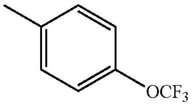 | 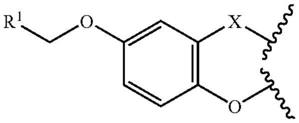 | $-CH_2CH_2-$ | $-CH_2-$ |
| 405 | 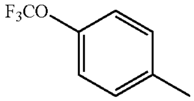 | H | 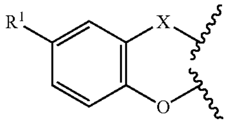 | 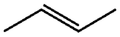 | $-(CH_2)_4-$ |
| 406 | 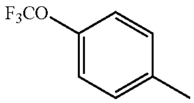 | H | 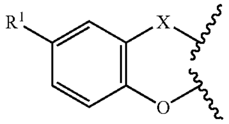 | 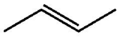 | $-(CH_2)_5-$ |
TABLE 1-15
| | | | | | |
|---|---|---|---|---|---|
| 407 | 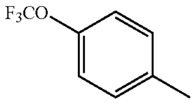 | H | 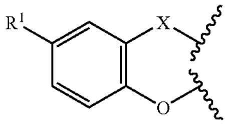 | $-CH_2CH_2-$ | $-(CH_2)_4-$ |
| 408 | 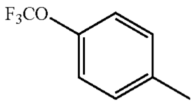 | H | 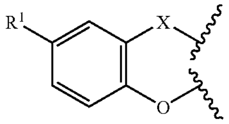 | $-CH_2CH_2-$ | $-(CH_2)_5-$ |
| 409 | 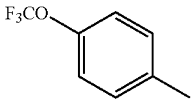 | 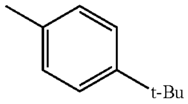 | 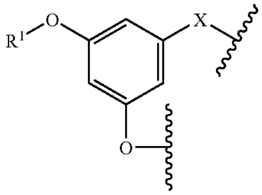 | 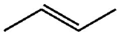 | $-CH_2-$ |
| 410 | 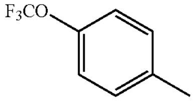 | 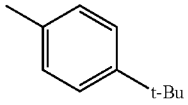 | 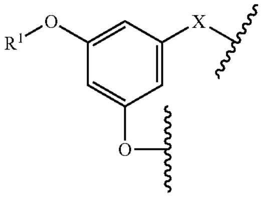 | $-CH_2CH_2-$ | $-CH_2-$ |
| 411 | 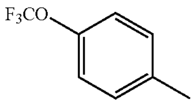 | 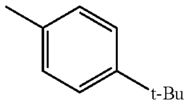 | 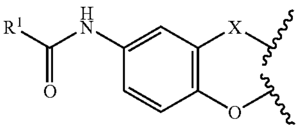 | $-CH_2CH_2-$ | $-CH_2-$ |

TABLE 1-15-continued
| | | | | | |
|---|---|---|---|---|---|
| 412 | 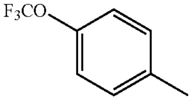 | 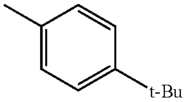 | 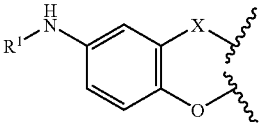 | $—CH_2CH_2—$ | $—CH_2—$ |
| 413 | 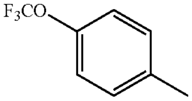 | 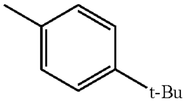 | 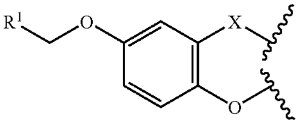 | 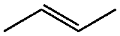 | $—CH_2—$ |
| 414 | 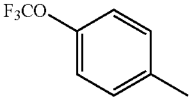 | 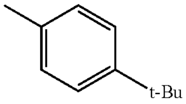 | 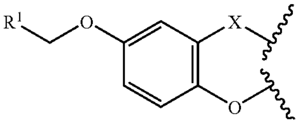 | $—CH_2CH_2—$ | $—CH_2—$ |
| 415 | 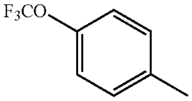 | 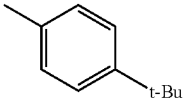 | 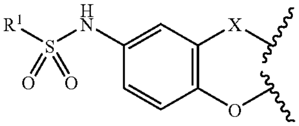 | $—CH_2CH_2—$ | $—CH_2—$ |
| 416 | 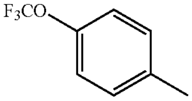 | 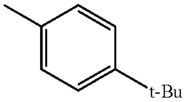 | 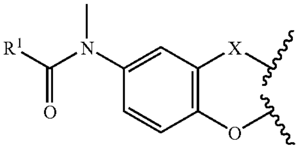 | $—CH_2CH_2—$ | $—CH_2—$ |
| 417 | 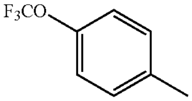 | 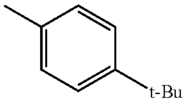 | 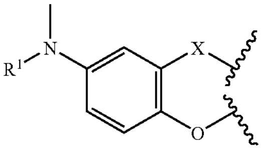 | $—CH_2CH_2—$ | $—CH_2—$ |
TABLE 1-16
| | | | | | |
|---|---|---|---|---|---|
| 418 | 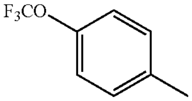 | 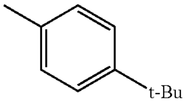 | 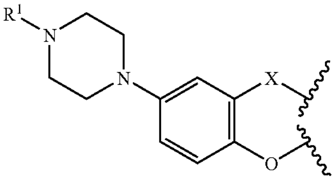 | 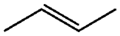 | $—CH_2—$ |
| 419 | 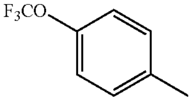 | 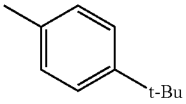 | 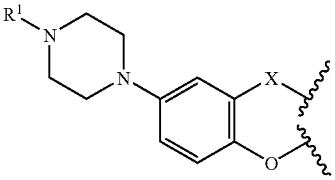 | $—CH_2CH_2—$ | $—CH_2—$ |
| 420 | 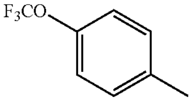 | 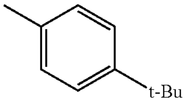 | 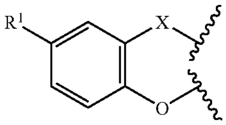 | 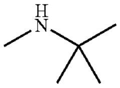 | $—CH_2—$ |
| 421 | 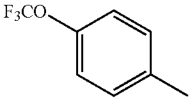 | 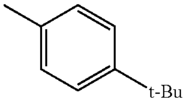 | 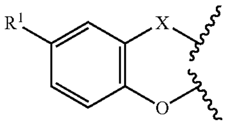 | single bond | $—CH_2—$ |

TABLE 1-16-continued
| | | | | | |
|---|---|---|---|---|---|
| 422 | 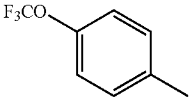 | 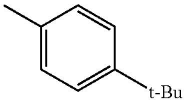 | 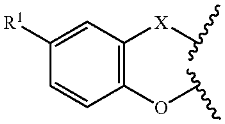 | 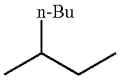 | single bond |
| 423 | 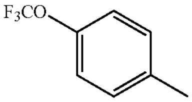 | 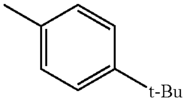 | 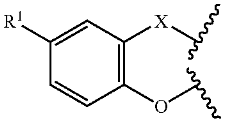 | 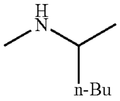 | single bond |
| 424 | 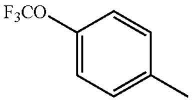 | H | 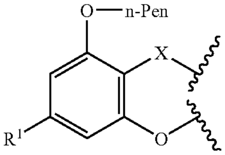 | —$OCH_2$— | —$(CH_2)_5$— |
| 425 | 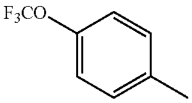 | H | 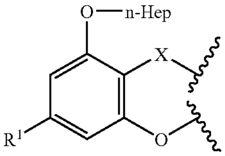 | —$OCH_2$— | —$(CH_2)_7$— |
| 426 | 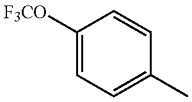 | 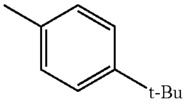 | 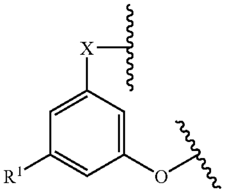 | 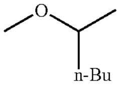 | single bond |
| 427 | 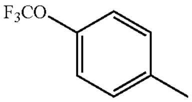 | 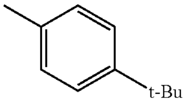 | 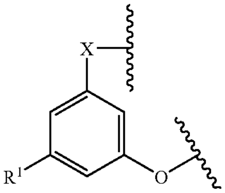 | —$OCH_2$— | single bond |
TABLE 1-17
| | | | | | |
|---|---|---|---|---|---|
| 428 | 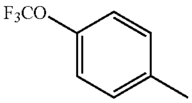 | 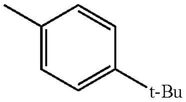 | 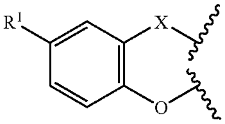 | 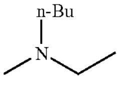 | single bond |
| 429 | 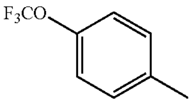 | H | 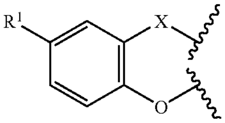 | 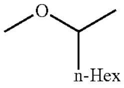 | —$(CH_2)_6$— |
| 430 | 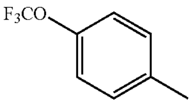 | H | 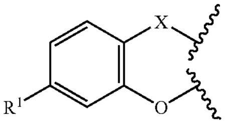 | 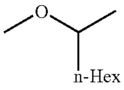 | —$(CH_2)_6$— |

TABLE 1-17-continued
| | | | | | |
|---|---|---|---|---|---|
| 431 | 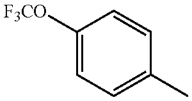 | 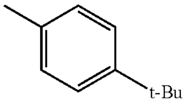 | 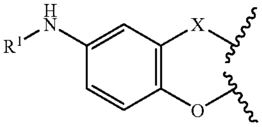 | 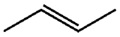 | single bond |
| 432 | 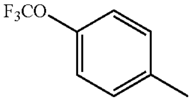 | 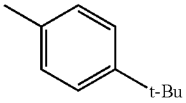 | 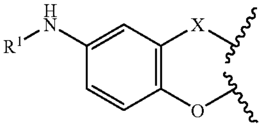 | $—CH_2CH_2—$ | single bond |
| 433 | 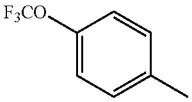 | 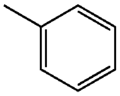 | 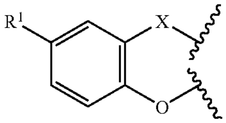 | 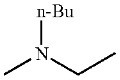 | $—(CH_2)_4—$ |
| 434 | 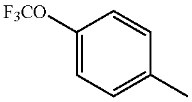 | 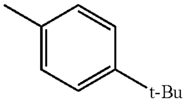 | 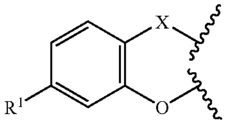 | single bond | single bond |
| 435 | 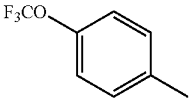 | 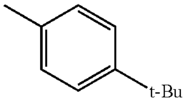 | 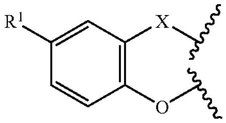 | 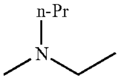 | single bond |
| 436 | 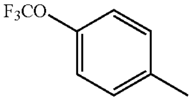 | 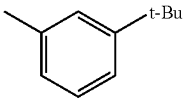 | 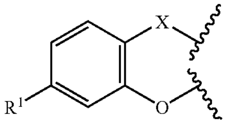 | $—OCH_2—$ | single bond |
| 437 | 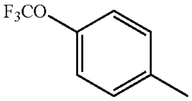 | 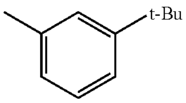 | 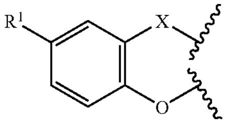 | 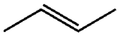 | single bond |
| 438 | 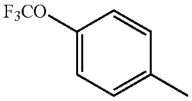 | 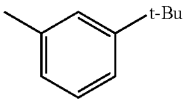 | 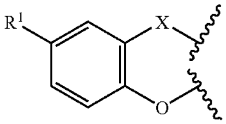 | $—CH_2CH_2—$ | single bond |
| 439 | 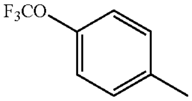 | 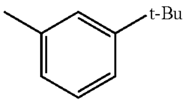 | 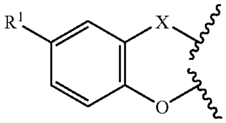 | $—OCH_2—$ | single bond |
TABLE 1-18
| | | | | | |
|---|---|---|---|---|---|
| 440 | 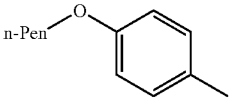 | 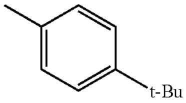 | 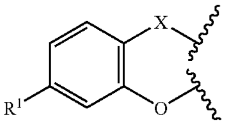 | $—OCH_2—$ | single bond |
| 441 | 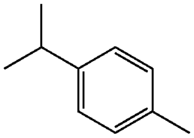 | 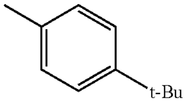 | 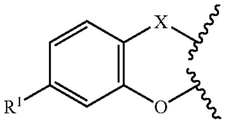 | $—OCH_2—$ | single bond |

TABLE 1-18-continued
| | | | | | |
|---|---|---|---|---|---|
| 442 | 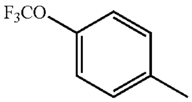 | 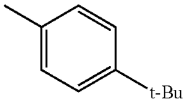 | 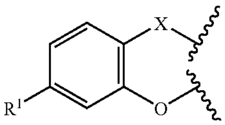 | 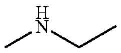 | single bond |
| 443 | 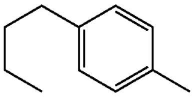 | 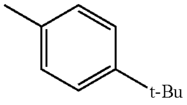 | 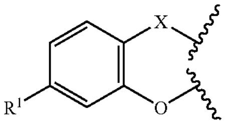 | —$OCH_2$— | single bond |
| 444 | 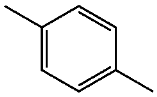 | 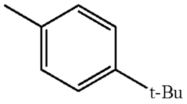 | 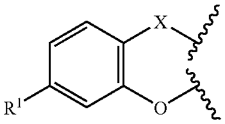 | —$OCH_2$— | single bond |
| 445 | 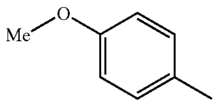 | 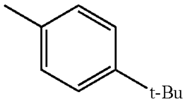 | 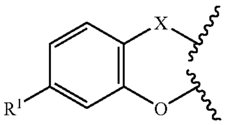 | —$OCH_2$— | single bond |
| 446 | 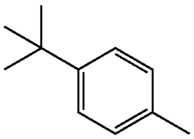 | 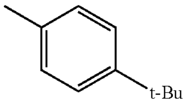 | 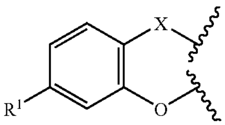 | —$OCH_2$— | single bond |
| 447 | 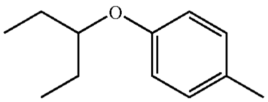 | 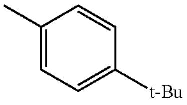 | 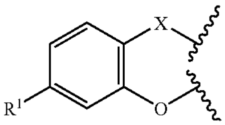 | —$OCH_2$— | single bond |
| 448 | 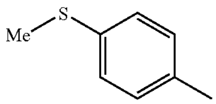 | 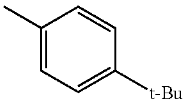 | 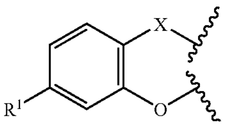 | —$OCH_2$— | single bond |
| 449 | 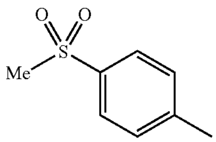 | 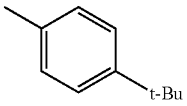 | 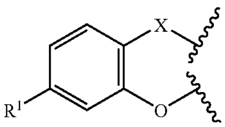 | —$OCH_2$— | single bond |
| 450 | 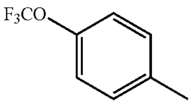 | 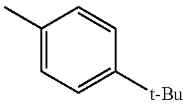 | 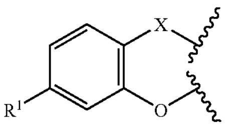 | 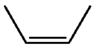 | single bond |
| 451 | 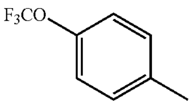 | 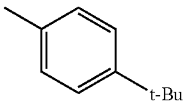 | 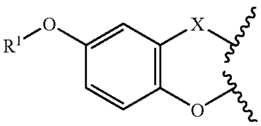 | —$OCH_2$— | —$CH_2$— |

TABLE 1-19
| | | | | | |
|---|---|---|---|---|---|
| 452 | 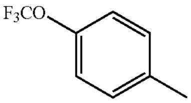 | 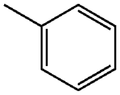 | 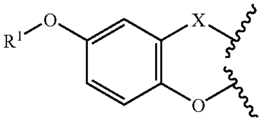 | $—OCH_2—$ | $—(CH_2)_4—$ |
| 453 | 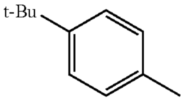 | 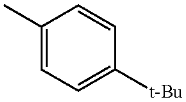 | 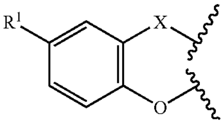 | $—OCH_2—$ | single bond |
| 454 | 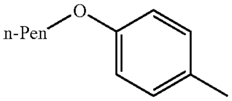 | 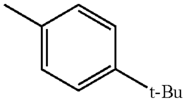 | 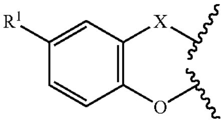 | $—OCH_2—$ | single bond |
| 455 | 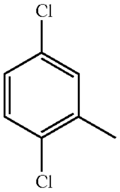 | 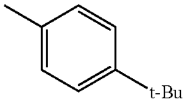 | 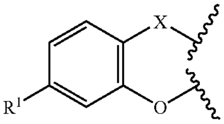 | $—OCH_2—$ | single bond |
| 456 | 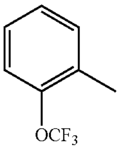 | 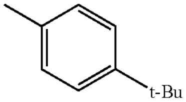 | 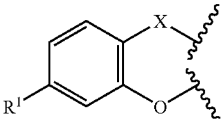 | $—OCH_2—$ | single bond |
| 457 | 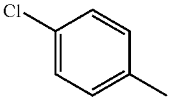 | 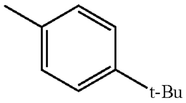 | 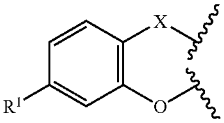 | $—OCH_2—$ | single bond |
| 458 | 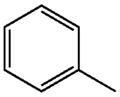 | 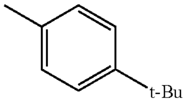 | 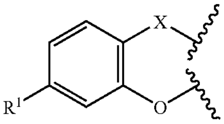 | $—OCH_2—$ | single bond |
| 459 | 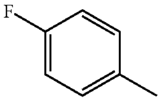 | 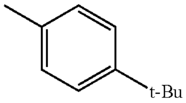 | 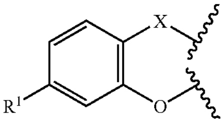 | $—OCH_2—$ | single bond |
| 460 | 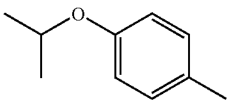 | 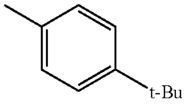 | 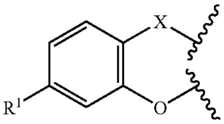 | $—OCH_2—$ | single bond |
| 461 | 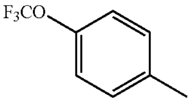 | 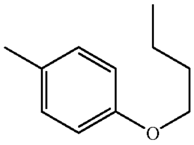 | 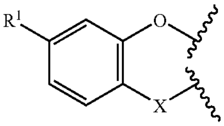 | $—CH_2CH_2—$ | single bond |

TABLE 1-19-continued
| | | | | | |
|---|---|---|---|---|---|
| 462 | 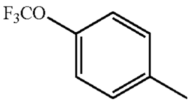 | 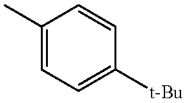 | 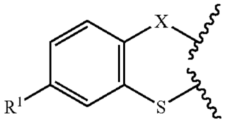 | 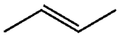 | single bond |
TABLE 1-20
| | | | | | |
|---|---|---|---|---|---|
| 463 | 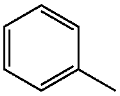 | 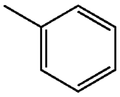 | 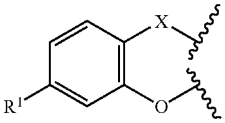 | 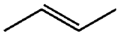 | single bond |
| 464 | 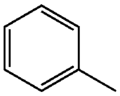 | 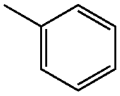 | 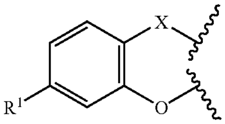 | $—CH_2CH_2—$ | single bond |
| 465 | 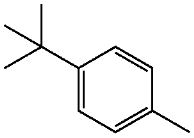 | 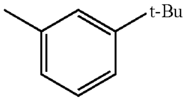 | 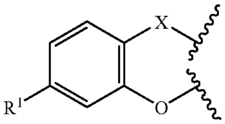 | $—OCH_2—$ | single bond |
| 466 | 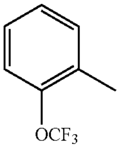 | 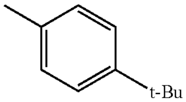 | 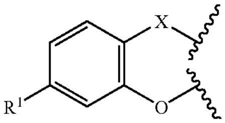 | 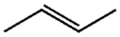 | single bond |
| 467 | 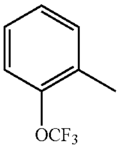 | 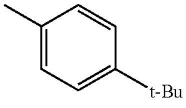 | 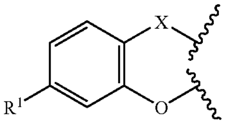 | $—CH_2CH_2—$ | single bond |
| 468 | 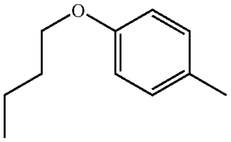 | 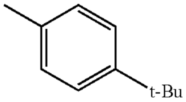 | 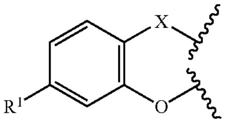 | $—OCH_2—$ | single bond |
| 469 | 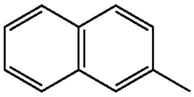 | 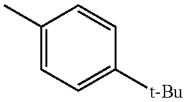 | 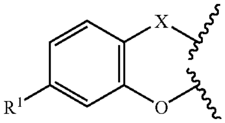 | 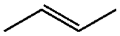 | single bond |
| 470 | 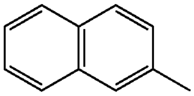 | 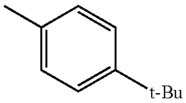 | 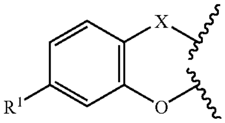 | $—CH_2CH_2—$ | single bond |
| 471 | 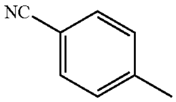 | 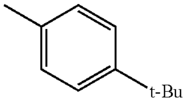 | 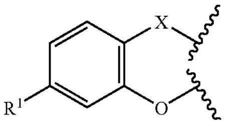 | $—OCH_2—$ | single bond |

TABLE 1-20-continued
| | | | | | |
|---|---|---|---|---|---|
| 472 | 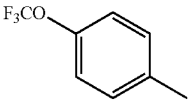 | 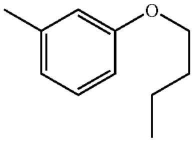 | 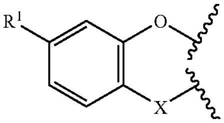 | $-CH_2CH_2-$ | single bond |
| 473 | 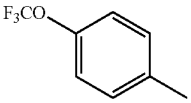 | 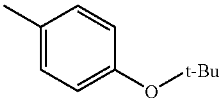 | 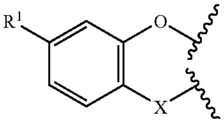 | $-CH_2CH_2-$ | single bond |
TABLE 1-21
| | | | | | |
|---|---|---|---|---|---|
| 474 | 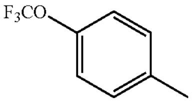 | 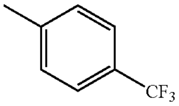 | 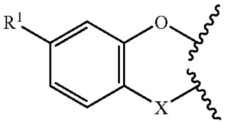 | $-CH_2CH_2-$ | single bond |
| 475 | 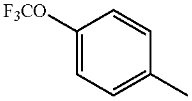 | 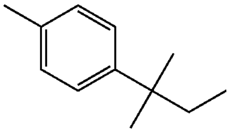 | 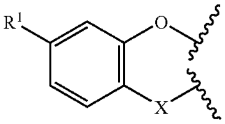 | $-CH_2CH_2-$ | single bond |
| 476 | 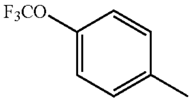 | 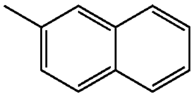 | 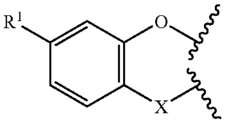 | $-CH_2CH_2-$ | single bond |
| 477 | 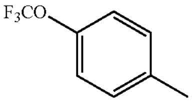 | 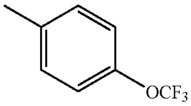 | 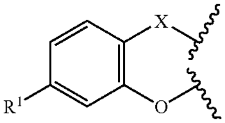 | 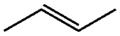 | single bond |
| 478 | 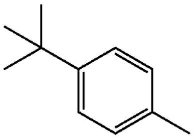 | 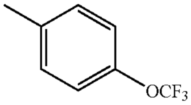 | 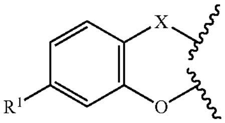 | 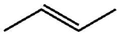 | single bond |
| 479 | 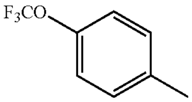 | 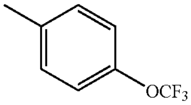 | 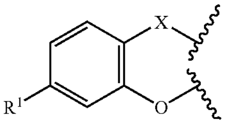 | $-CH_2CH_2-$ | single bond |
| 480 | 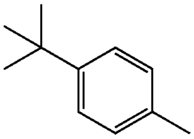 | 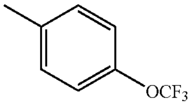 | 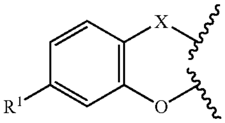 | $-CH_2CH_2-$ | single bond |
| 481 | 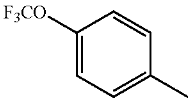 | 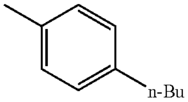 | 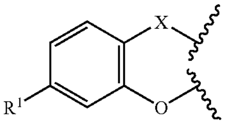 | $-OCH_2-$ | single bond |

TABLE 1-21-continued
| | | | | | |
|---|---|---|---|---|---|
| 482 | 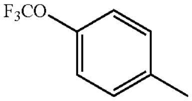 | 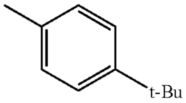 | 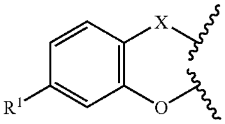 | 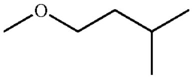 | —$CH_2$— |
| 483 | 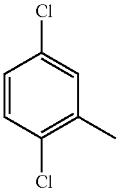 | 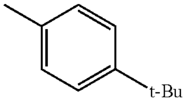 | 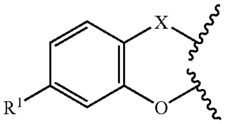 | 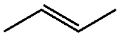 | single bond |
| 484 | 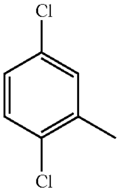 | 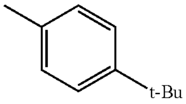 | 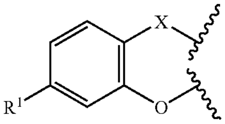 | —$CH_2CH_2$— | single bond |
TABLE 1-22
| | | | | | |
|---|---|---|---|---|---|
| 485 | 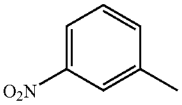 | 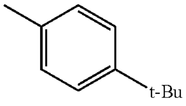 | 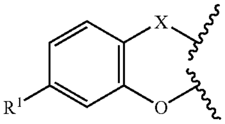 | —$OCH_2$— | single bond |
| 486 | 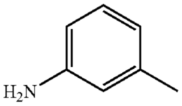 | 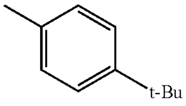 | 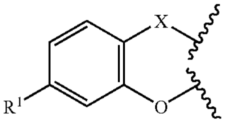 | —$OCH_2$— | single bond |
| 487 | 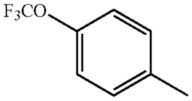 | 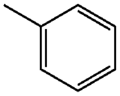 | 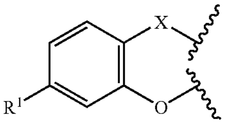 | 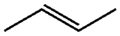 | 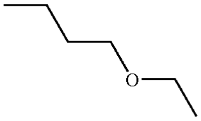 |
| 488 | 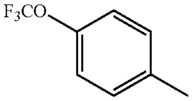 | 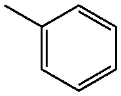 | 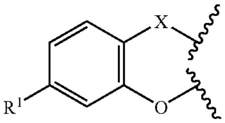 | —$CH_2CH_2$— | 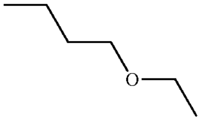 |
| 489 | 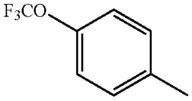 | 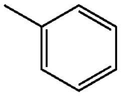 | 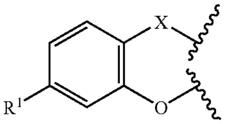 | 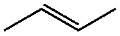 | 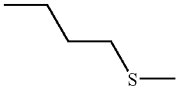 |
| 490 | 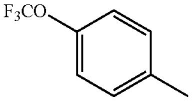 | 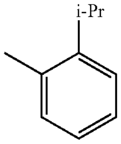 | 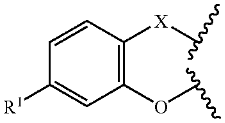 | 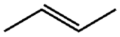 | single bond |
| 491 | 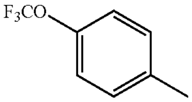 | 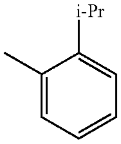 | 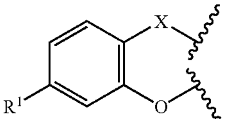 | —$CH_2CH_2$— | single bond |

TABLE 1-22-continued
| | | | | | |
|---|---|---|---|---|---|
| 492 | 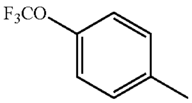 | 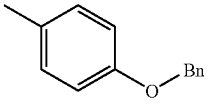 | 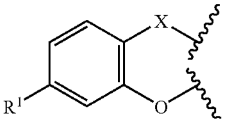 | —$OCH_2$— | single bond |
| 493 | 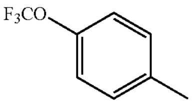 | 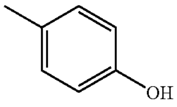 | 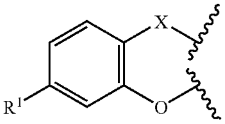 | —$OCH_2$— | single bond |
| 494 | 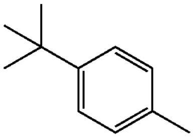 | 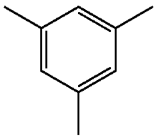 | 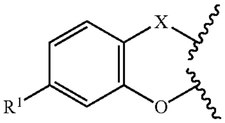 | 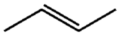 | single bond |
| 495 | 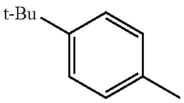 | 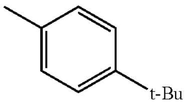 | 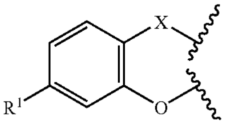 | 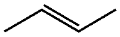 | single bond |
| 496 | 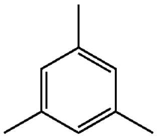 | 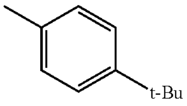 | 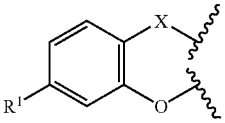 | 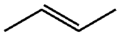 | single bond |
TABLE 1-23
| | | | | | |
|---|---|---|---|---|---|
| 497 | 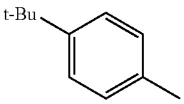 | 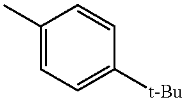 | 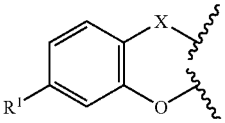 | —$CH_2CH_2$— | single bond |
| 498 | 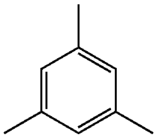 | 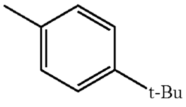 | 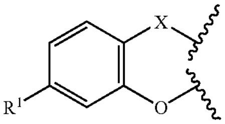 | —$CH_2CH_2$— | single bond |
| 499 | 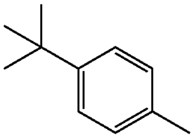 | 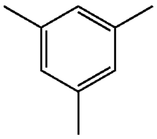 | 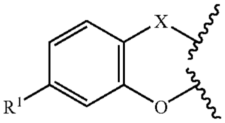 | —$CH_2CH_2$— | single bond |
| 500 | 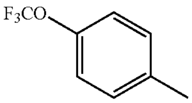 | 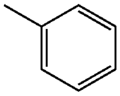 | 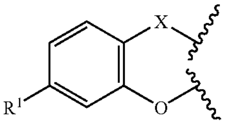 | 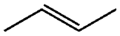 | 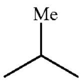 |
| 501 | 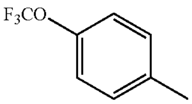 | 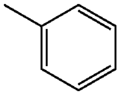 | 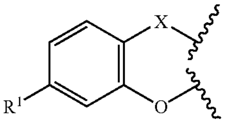 | —$CH_2CH_2$— | 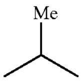 |

TABLE 1-23-continued
| | | | | | |
|---|---|---|---|---|---|
| 502 | 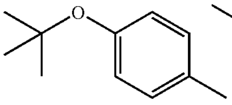 | 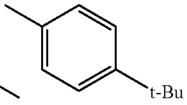 | 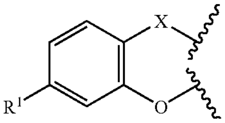 | —$OCH_2$— | single bond |
| 503 | 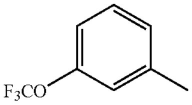 | 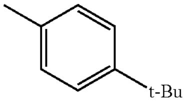 | 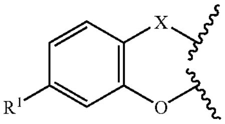 | 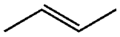 | single bond |
| 504 | 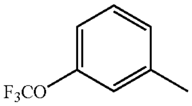 | 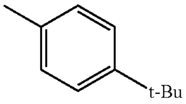 | 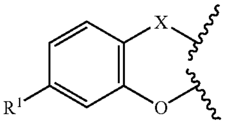 | —$CH_2CH_2$— | single bond |
| 505 | 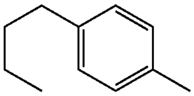 | 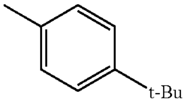 | 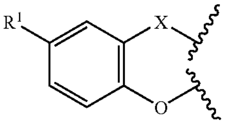 | —$OCH_2$— | single bond |
| 506 | 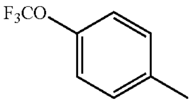 | 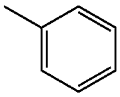 | 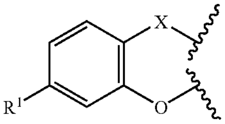 | 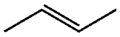 | 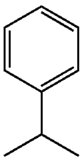 |
| 507 | 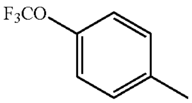 | 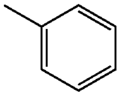 | 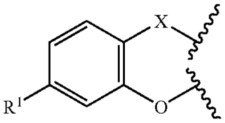 | —$CH_2CH_2$— | 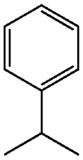 |
TABLE 1-24
| | | | | | |
|---|---|---|---|---|---|
| 508 | 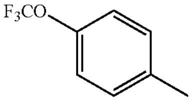 | 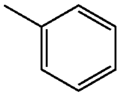 | 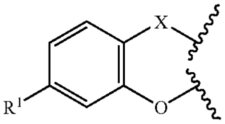 | —$CH_2CH_2$— | 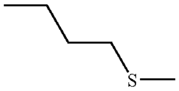 |
| 509 | 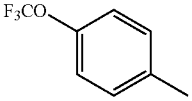 | 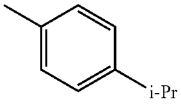 | 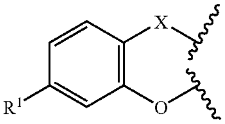 | 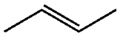 | single bond |
| 510 | 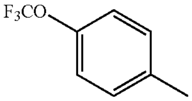 | 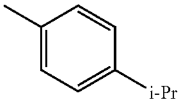 | 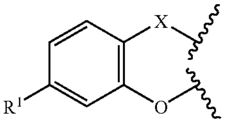 | —$CH_2CH_2$— | single bond |
| 511 | 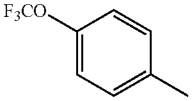 | 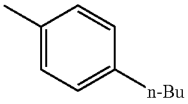 | 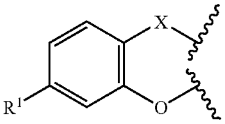 | 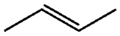 | single bond |

TABLE 1-24-continued
| | | | | | |
|---|---|---|---|---|---|
| 512 | 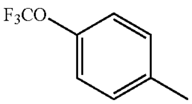 | 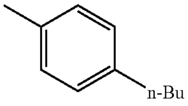 | 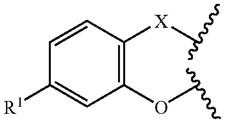 | $-CH_2CH_2-$ | single bond |
| 513 | 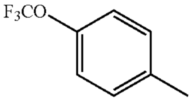 | 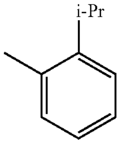 | 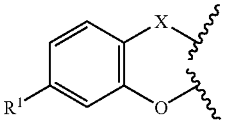 | $-OCH_2-$ | single bond |
| 514 | 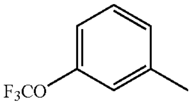 | 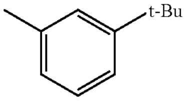 | 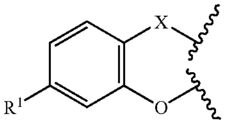 | 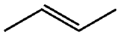 | single bond |
| 515 | 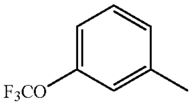 | 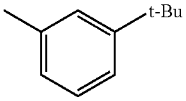 | 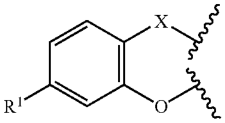 | $-CH_2CH_2-$ | single bond |
| 516 | 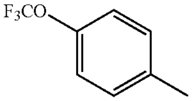 | 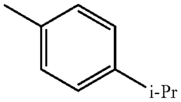 | 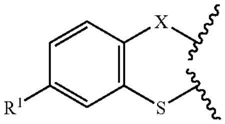 | 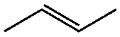 | single bond |
| 517 | 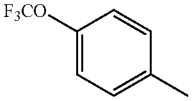 | 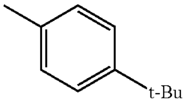 | 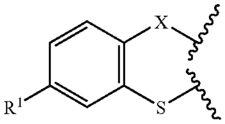 | $-CH_2CH_2-$ | single bond |
| 518 | 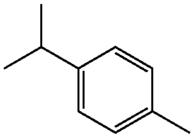 | 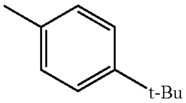 | 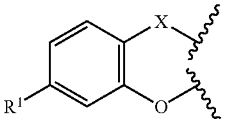 | 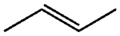 | single bond |
| 519 | 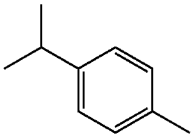 | 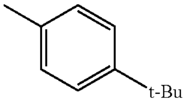 | 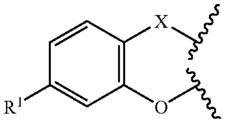 | $-CH_2CH_2-$ | single bond |
TABLE 1-25
| | | | | | |
|---|---|---|---|---|---|
| 520 | 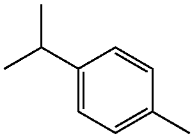 | 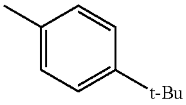 | 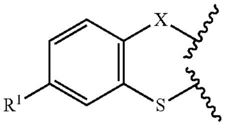 | 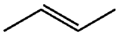 | single bond |
| 521 | 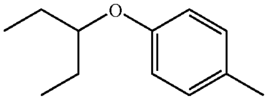 | 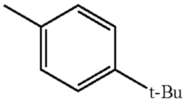 | 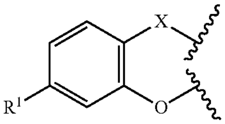 | 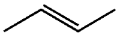 | single bond |

TABLE 1-25-continued
| | | | | | |
|---|---|---|---|---|---|
| 522 | 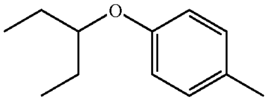 | 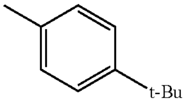 | 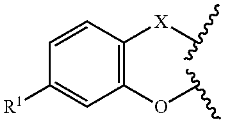 | —$CH_2CH_2$— | single bond |
| 523 | 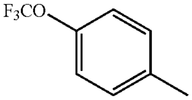 | 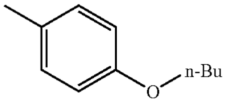 | 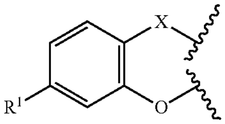 | —$OCH_2$— | single bond |
| 524 | 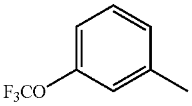 | 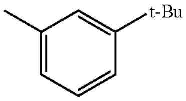 | 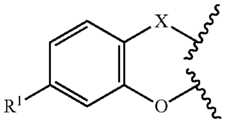 | —$OCH_2$— | single bond |
| 525 | 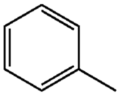 | 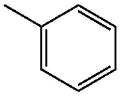 | 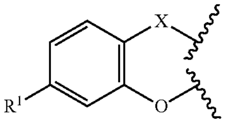 | —$OCH_2$— | single bond |
| 526 | 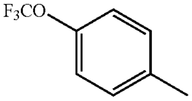 | 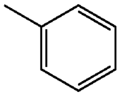 | 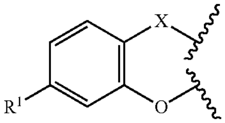 | —$OCH_2$— | single bond |
| 527 | 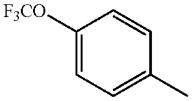 | 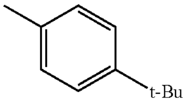 | 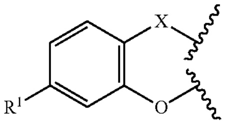 | —$(CH_2)_3$— | single bond |
| 528 | 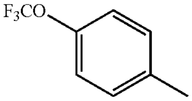 | 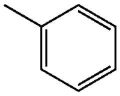 | 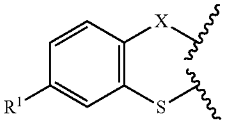 | 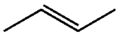 | single bond |
| 529 | 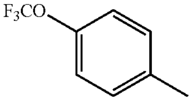 | 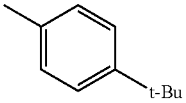 | 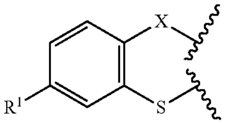 | 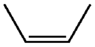 | single bond |
| 530 | 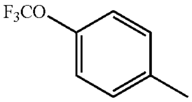 | 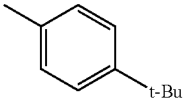 | 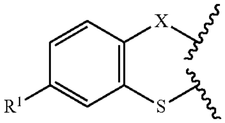 | —$CH_2$— | single bond |
| 531 | 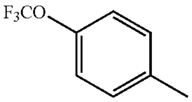 | 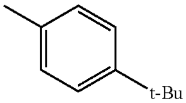 | 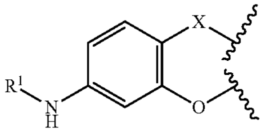 | 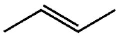 | single bond |

TABLE 1-26
| | | | | | |
|---|---|---|---|---|---|
| 532 | 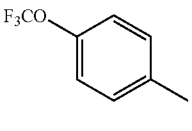 | 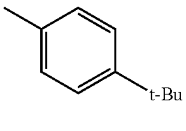 | 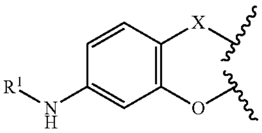 | —$CH_2CH_2$— | single bond |
| 533 | 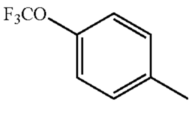 | 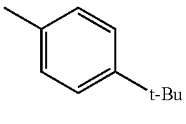 | 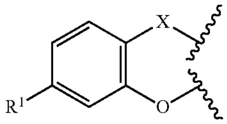 | 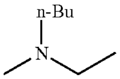 | single bond |
| 534 | 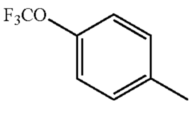 | 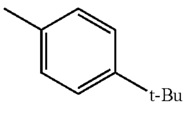 | 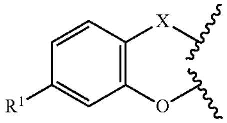 | 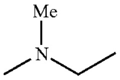 | single bond |
| 535 | 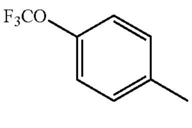 | 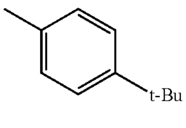 | 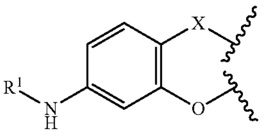 | 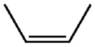 | single bond |
| 536 | 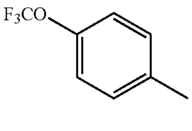 | 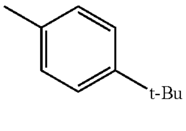 | 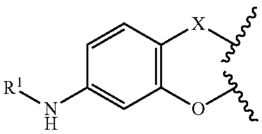 | —$OCH_2$— | single bond |
| 537 | 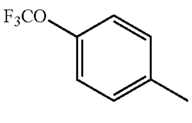 | 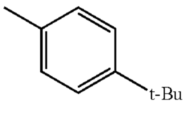 | 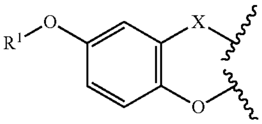 | —$OCH_2$— | single bond |
| 538 | 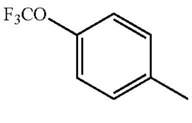 | 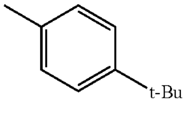 | 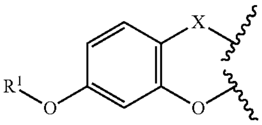 | —$OCH_2$— | single bond |
| 539 | 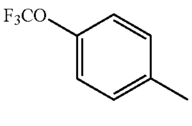 | 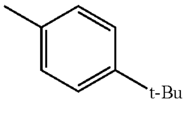 | 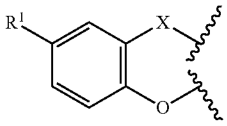 | 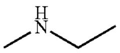 | —$CH_2$— |
| 540 | 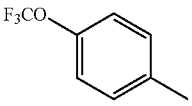 | 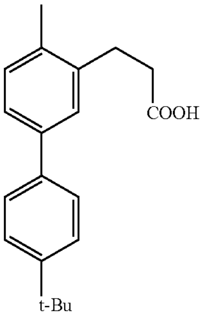 [SMILES: Cc1ccc(-c2ccc(C(C)(C)C)cc2)cc1CCC(=O)O] | 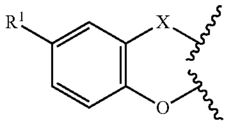 | 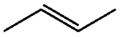 | single bond |

TABLE 1-26-continued
| | | | | | |
|---|---|---|---|---|---|
| 541 | 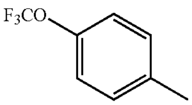 | 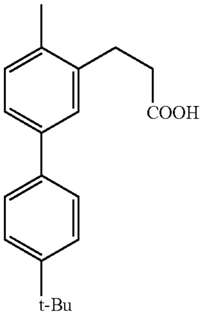 [SMILES: Cc1ccc(-c2ccc(C(C)(C)C)cc2)cc1CCC(=O)O] | 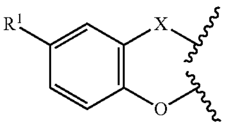 | $—CH_2CH_2—$ | single bond |
TABLE 1-27
| | | | | | |
|---|---|---|---|---|---|
| 542 | 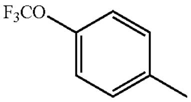 | 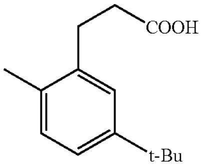 [SMILES: Cc1ccc(C(C)(C)C)cc1CCC(=O)O] | 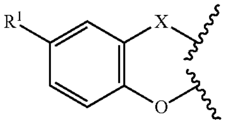 | $—CH_2CH_2—$ | single bond |
| 543 | 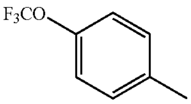 | 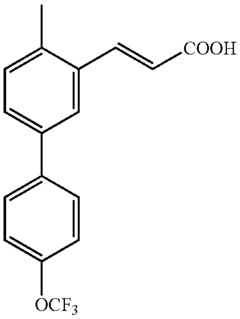 [SMILES: Cc1ccc(-c2ccc(OC(F)(F)F)cc2)cc1/C=C/C(=O)O] | 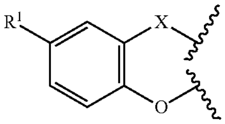 | 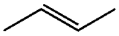 | 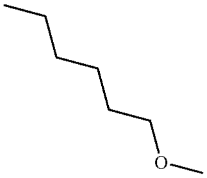 |
| 544 | 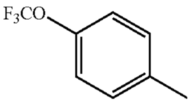 | 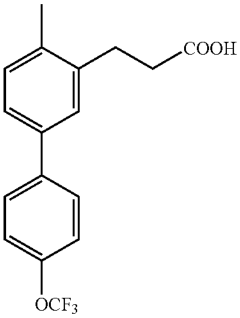 [SMILES: Cc1ccc(-c2ccc(OC(F)(F)F)cc2)cc1CCC(=O)O] | 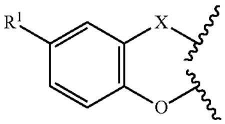 | $—CH_2CH_2—$ | 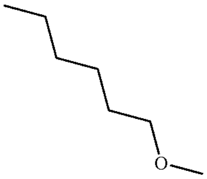 |
| 545 | 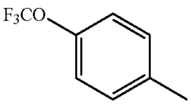 | 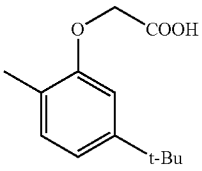 [SMILES: Cc1ccc(C(C)(C)C)cc1OCC(=O)O] | 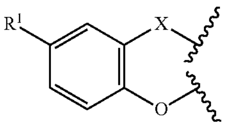 | $—OCH_2—$ | single bond |
| 546 | 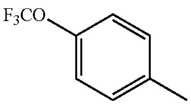 | 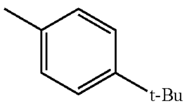 | 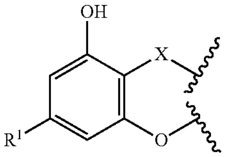 | $—OCH_2—$ | $—CH_2—$ |

TABLE 1-27-continued
| | | | | | |
|---|---|---|---|---|---|
| 547 | 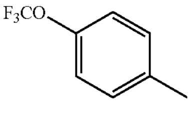 | 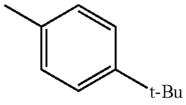 | 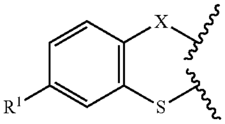 | single bond | single bond |
| 548 | 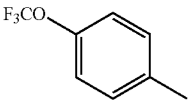 | 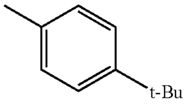 | 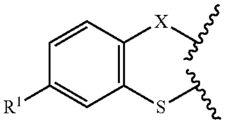 | —C(=O)— | single bond |
| 549 | 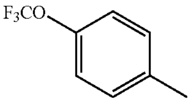 | 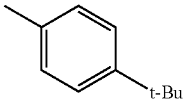 | 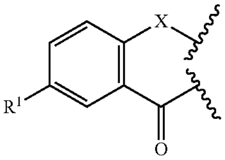 | $—OCH_2—$ | single bond |
| 550 | 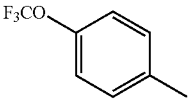 | 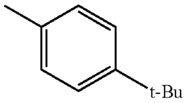 | 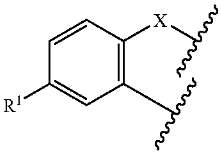 | $—OCH_2—$ | $—CH_2—$ |
| 551 | 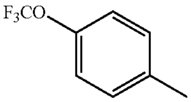 | 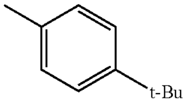 | 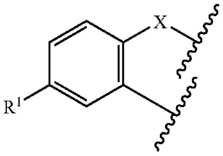 | $—OCH_2—$ | $—(CH_2)_2—$ |
TABLE 2
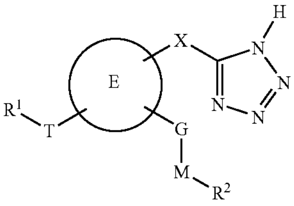
| Compound Number | $R^1$ | $R^2$ | 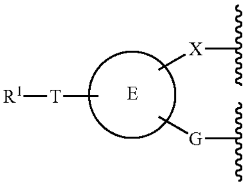 | $X^{(d)}$ | M |
|---|---|---|---|---|---|
| 121 | 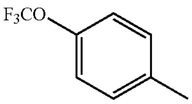 | 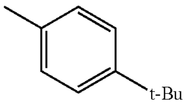 | 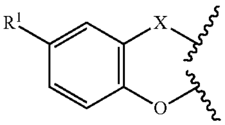 | $—CH_2CH_2—$ | $—CH_2—$ |
| 122 | 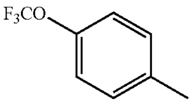 | 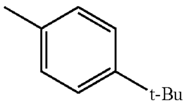 | 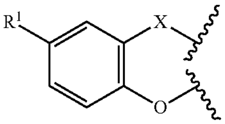 | $—OCH_2—$ | $—CH_2—$ |

TABLE 3-1
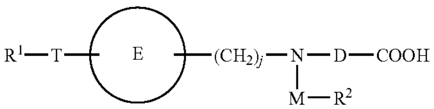
| Compound No. | $R^1$ | 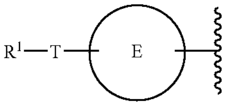 | $R^2$ | M(f) | j | D(e) |
|---|---|---|---|---|---|---|
| 123(c) | 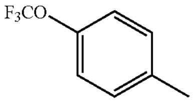 | 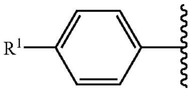 | 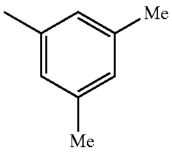 | —$CH_2$— | 0 | —C(═O)— |
| 124(c) | 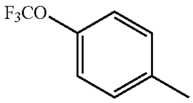 | 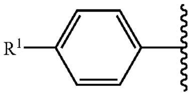 | 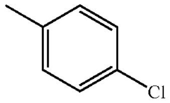 | —$CH_2$— | 0 | —C(═O)— |
| 125(c) | 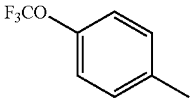 | 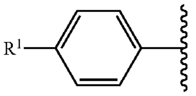 | 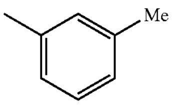 | —$CH_2$— | 0 | —C(═O)— |
| 126 | 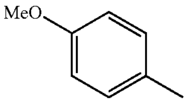 | 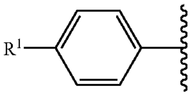 | 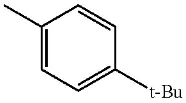 | —$CH_2$— | 0 | —C(═O)— |
| 127 | 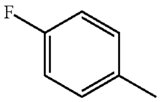 | 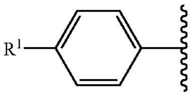 | 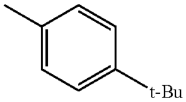 | —$CH_2$— | 0 | —C(═O)— |
| 128 | 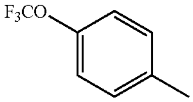 | 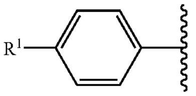 | 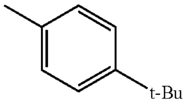 | single bond | 0 | —C(═O)— |
| 129 | 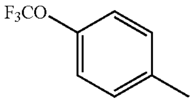 | 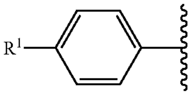 | 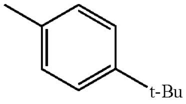 | —$CH_2$— | 0 | —C(═O)— |
| 130 | 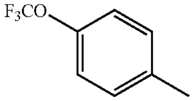 | 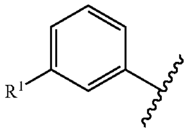 | 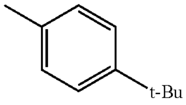 | —$CH_2$— | 0 | —C(═O)— |
| 131 | 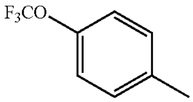 | 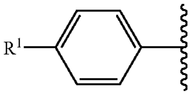 | 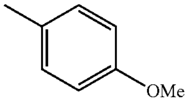 | —$CH_2$— | 0 | —C(═O)— |
| 132 | 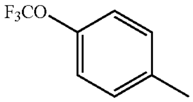 | 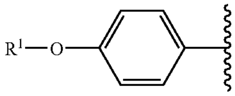 | 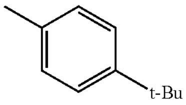 | —$CH_2$— | 0 | —C(═O)— |
| 133(c) | 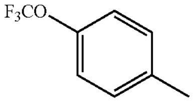 | 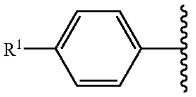 | 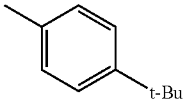 | —$CH_2$— | 0 | —C(═O)— |

TABLE 3-1-continued
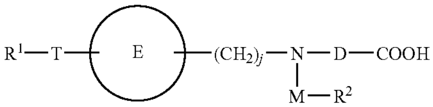
| Compound No. | $R^1$ | 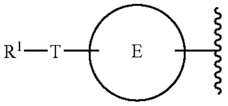 | $R^2$ | $M^{(f)}$ | j | $D^{(e)}$ |
|---|---|---|---|---|---|---|
| 134 | 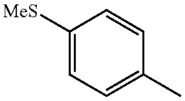 | 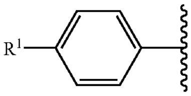 | 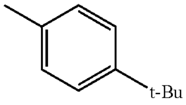 | —$CH_2$— | 0 | —C(═O)— |
TABLE 3-2
| | | | | | | |
|---|---|---|---|---|---|---|
| 135 | 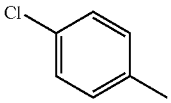 | 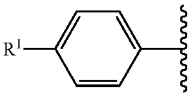 | 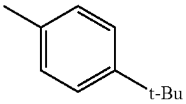 | —$CH_2$— | 0 | —C(═O)— |
| 136 | 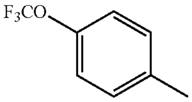 | 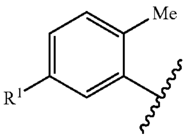 | 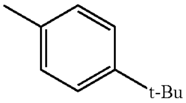 | —$CH_2$— | 0 | —C(═O)— |
| 137 | 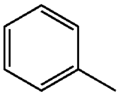 | 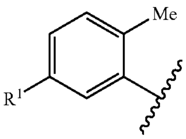 | 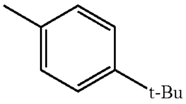 | —$CH_2$— | 0 | —C(═O)— |
| 138 | 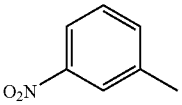 | 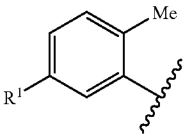 | 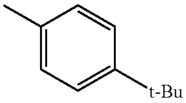 | —$CH_2$— | 0 | —C(═O)— |
| 139 | 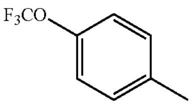 | 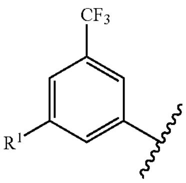 | 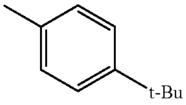 | —$CH_2$— | 0 | —C(═O)— |
| 140 | 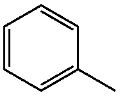 | 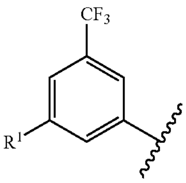 | 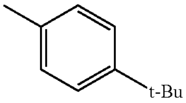 | —$CH_2$— | 0 | —C(═O)— |
| 141 | 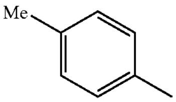 | 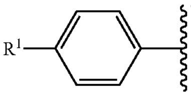 | 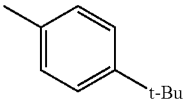 | —$CH_2$— | 0 | —C(═O)— |

TABLE 3-2-continued
| | | | | | | |
|---|---|---|---|---|---|---|
| 142 | 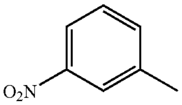 | 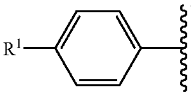 | 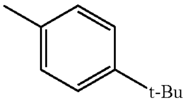 | —$CH_2$— | 0 | —C(=O)— |
| 143 | 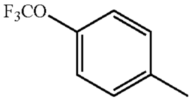 | 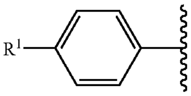 | 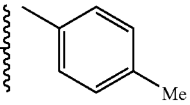 | —$CH_2$— | 0 | —C(=O)— |
| 144 | 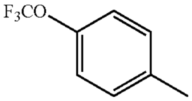 | 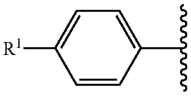 | 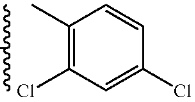 | —$CH_2$— | 0 | —C(=O)— |
| 145 | 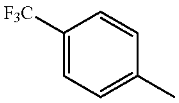 | 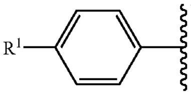 | 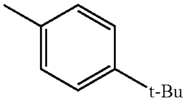 | —$CH_2$— | 0 | —C(=O)— |
| 146 | 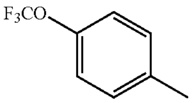 | 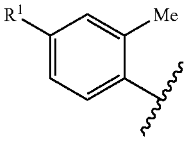 | 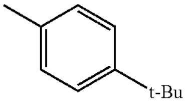 | —$CH_2$— | 0 | —C(=O)— |
| 147 | 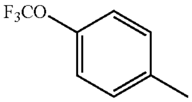 | 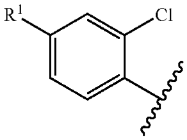 | 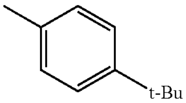 | —$CH_2$— | 0 | —C(=O)— |
TABLE 3-3
| | | | | | | |
|---|---|---|---|---|---|---|
| 148 | 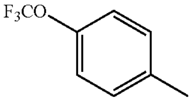 | 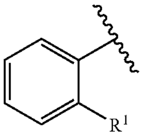 | 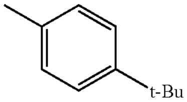 | —$CH_2$— | 0 | —C(=O)— |
| 149 | 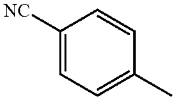 | 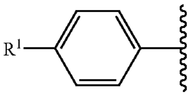 | 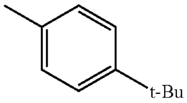 | —$CH_2$— | 0 | —C(=O)— |
| 150 | 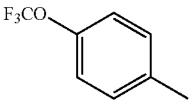 | 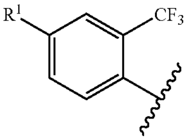 | 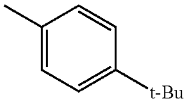 | —$CH_2$— | 0 | —C(=O)— |
| 151 | 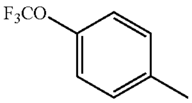 | 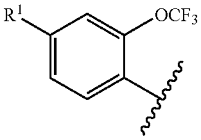 | 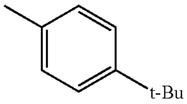 | —$CH_2$— | 0 | —C(=O)— |
| 152 | 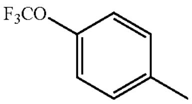 | 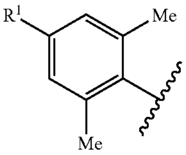 | 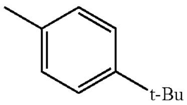 | —$CH_2$— | 0 | —C(=O)— |

TABLE 3-3-continued
| | | | | | | |
|---|---|---|---|---|---|---|
| 153 | 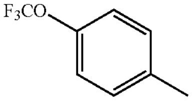 | 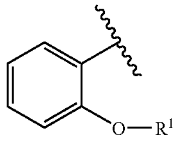 | 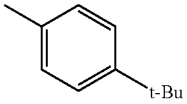 | —$CH_2$— | 0 | —C(═O)— |
| 154 | 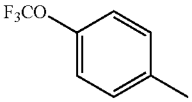 | 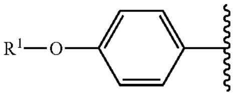 | 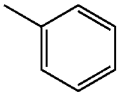 | —$CH_2$— | 0 | —C(═O)— |
| 155 | 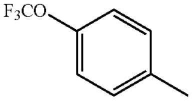 | 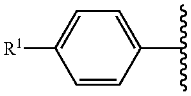 | 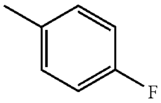 | —$CH_2$— | 0 | —C(═O)— |
| 156 | 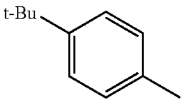 | 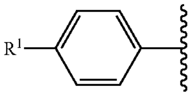 | 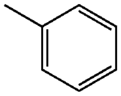 | —$CH_2$— | 0 | —C(═O)— |
| 157 | 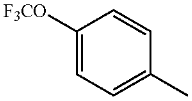 | 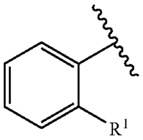 | 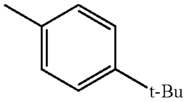 | single bond | 0 | —C(═O)— |
| 158 | 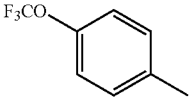 | 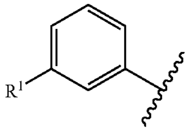 | 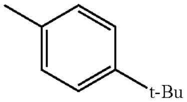 | single bond | 0 | —C(═O)— |
| 159 | 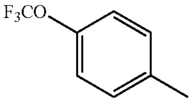 | 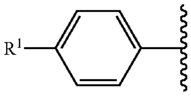 | 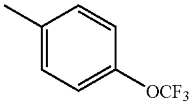 | —$CH_2$— | 0 | —C(═O)— |
| 160 | 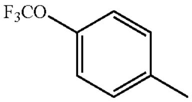 | 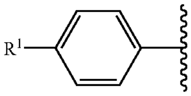 | 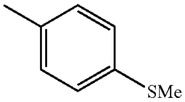 | —$CH_2$— | 0 | —C(═O)— |
TABLE 3-4
| | | | | | | |
|---|---|---|---|---|---|---|
| 161 | 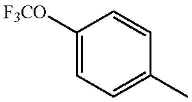 | 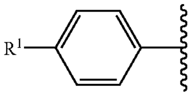 | 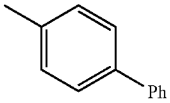 | —$CH_2$— | 0 | —C(═O)— |
| 162 | 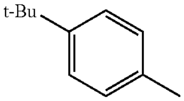 | 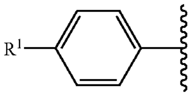 | 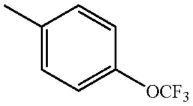 | —$CH_2$— | 0 | —C(═O)— |
| 163 | 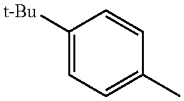 | 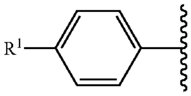 | 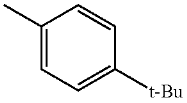 | —$CH_2$— | 0 | —C(═O)— |
| 164 | 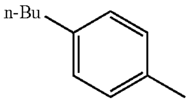 | 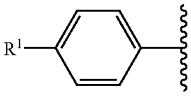 | 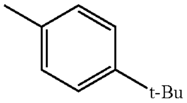 | —$CH_2$— | 0 | —C(═O)— |

TABLE 3-4-continued
| | | | | | | |
|---|---|---|---|---|---|---|
| 165 | 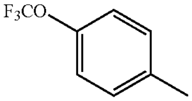 | 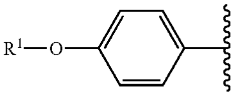 | 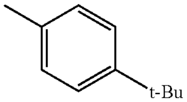 | single bond | 0 | —C(═O)— |
| 166 | 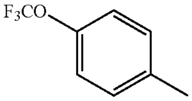 | 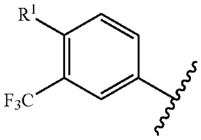 | 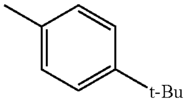 | —$CH_2$— | 0 | —C(═O)— |
| 167 | 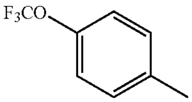 | 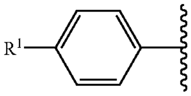 | 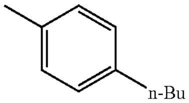 | —$CH_2$— | 0 | —C(═O)— |
| 168 | 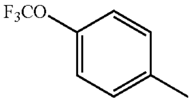 | 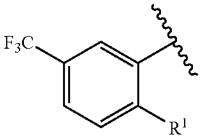 | 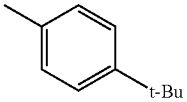 | —$CH_2$— | 0 | —C(═O)— |
| 169 | 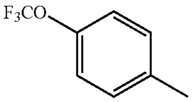 | 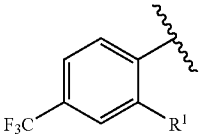 | 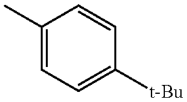 | —$CH_2$— | 0 | —C(═O)— |
| 170 | 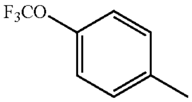 | 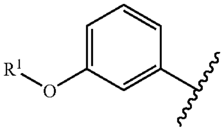 | 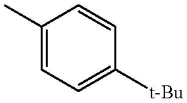 | single bond | 0 | —C(═O)— |
| 171 | 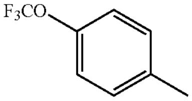 | 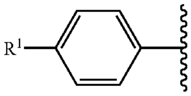 | 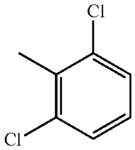 | —$CH_2$— | 0 | —C(═O)— |
| 172 | 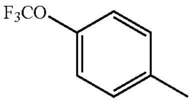 | 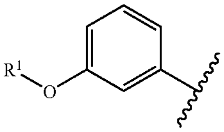 | 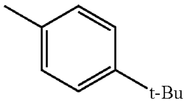 | —$CH_2$— | 0 | —C(═O)— |
| 173 | 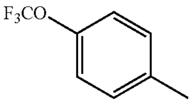 | 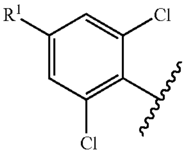 | 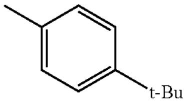 | —$CH_2$— | 0 | —C(═O)— |
TABLE 3-5
| | | | | | | |
|---|---|---|---|---|---|---|
| 174 | 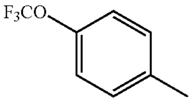 | 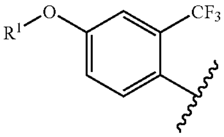 | 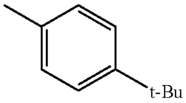 | —$CH_2$— | 0 | —C(═O)— |

TABLE 3-5-continued
| | | | | | | |
|---|---|---|---|---|---|---|
| 175 | 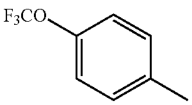 | 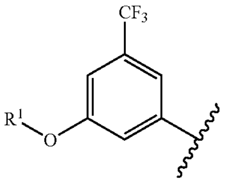 | 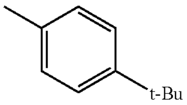 | —$CH_2$— | 0 | —C(═O)— |
| 176 | 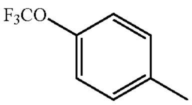 | 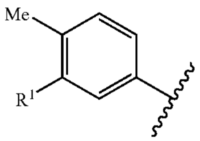 | 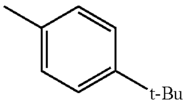 | —$CH_2$— | 0 | —C(═O)— |
| 177 | 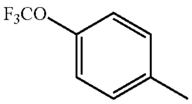 | 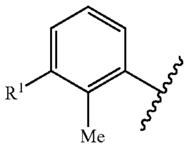 | 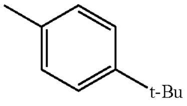 | —$CH_2$— | 0 | —C(═O)— |
| 178 | 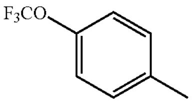 | 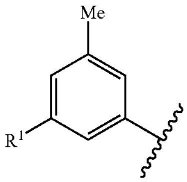 | 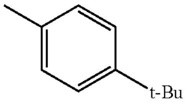 | —$CH_2$— | 0 | —C(═O)— |
| 179 | 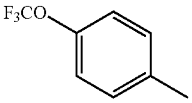 | 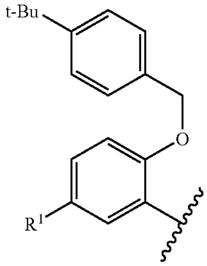 | 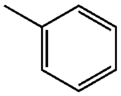 | —$CH_2$— | 0 | —C(═O)— |
| 180 | 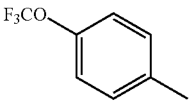 | 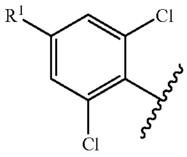 | 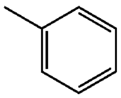 | —$CH_2$— | 0 | —C(═O)— |
| 181 | 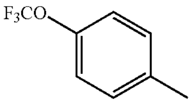 | 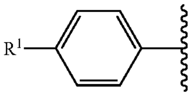 | 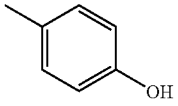 | —$CH_2$— | 0 | —C(═O)— |
| 182 | 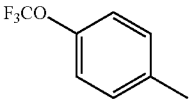 | 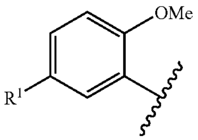 | 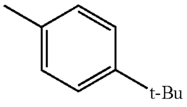 | —$CH_2$— | 0 | —C(═O)— |
| 183 | 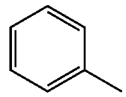 | 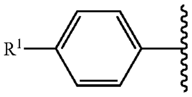 | 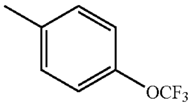 | —$CH_2$— | 0 | —C(═O)— |

TABLE 3-5-continued
| | | | | | | |
|---|---|---|---|---|---|---|
| 184 | 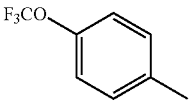 | 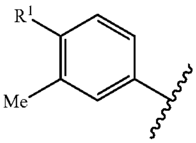 | 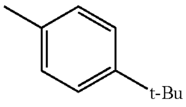 | —$CH_2$— | 0 | —C(═O)— |
TABLE 3-6
| | | | | | | |
|---|---|---|---|---|---|---|
| 185 | 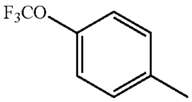 | 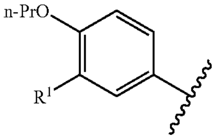 | 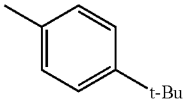 | —$CH_2$— | 0 | —C(═O)— |
| 186 | 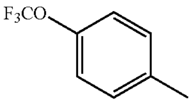 | 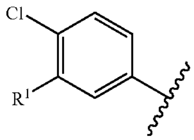 | 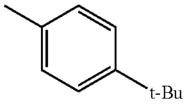 | —$CH_2$— | 0 | —C(═O)— |
| 187 | 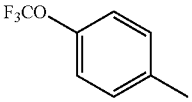 | 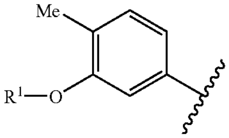 | 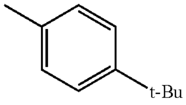 | —$CH_2$— | 0 | —C(═O)— |
| 188 | 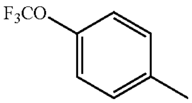 | 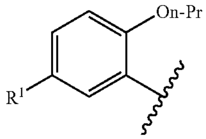 | 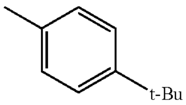 | —$CH_2$— | 0 | —C(═O)— |
| 189 | 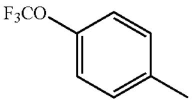 | 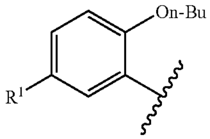 | 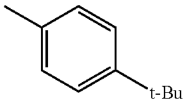 | —$CH_2$— | 0 | —C(═O)— |
| 190 | 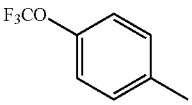 | 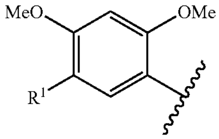 | 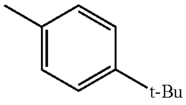 | —$CH_2$— | 0 | —C(═O)— |
| 191 | 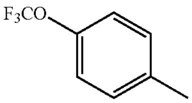 | 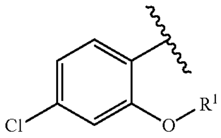 | 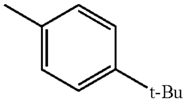 | —$CH_2$— | 0 | —C(═O)— |
| 192 | 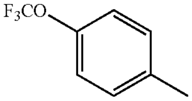 | 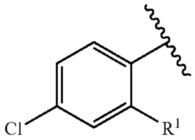 | 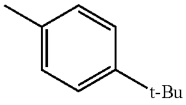 | —$CH_2$— | 0 | —C(═O)— |
| 193 | 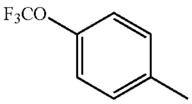 | 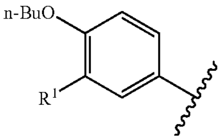 | 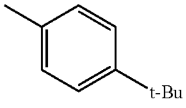 | —$CH_2$— | 0 | —C(═O)— |

TABLE 3-6-continued
| | | | | | | |
|---|---|---|---|---|---|---|
| 194 | 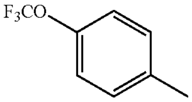 | 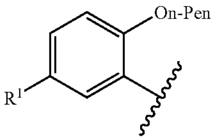 | 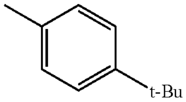 | —CH2— | 0 | —C(═O)— |
| 195 | 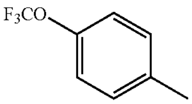 | 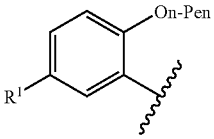 | 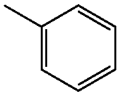 | —CH2— | 0 | —C(═O)— |
| 196 | 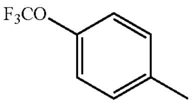 | 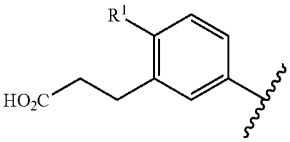 | 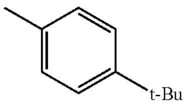 | —CH2— | 0 | —C(═O)— |
| 197 | 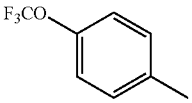 | 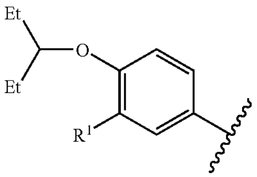 | 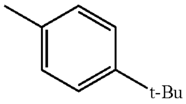 | —CH2— | 0 | —C(═O)— |
TABLE 3-7
| | | | | | | |
|---|---|---|---|---|---|---|
| 198 | 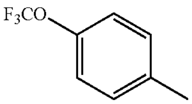 | 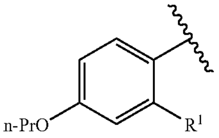 | 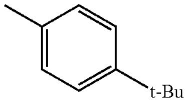 | —CH2— | 0 | —C(═O)— |
| 199 | 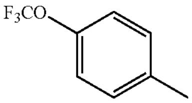 | 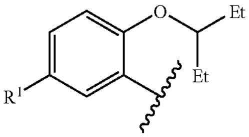 | 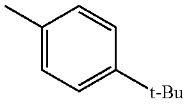 | —CH2— | 0 | —C(═O)— |
| 200 | 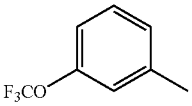 | 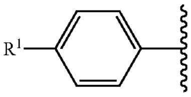 | 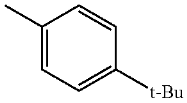 | —CH2— | 0 | —C(═O)— |
| 201 | 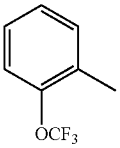 | 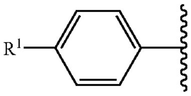 | 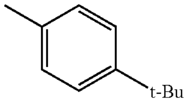 | —CH2— | 0 | —C(═O)— |
| 202 | 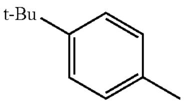 | 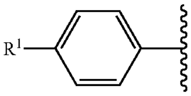 | 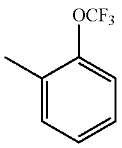 | —CH2— | 0 | —C(═O)— |
| 203 | 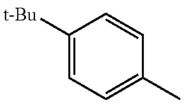 | 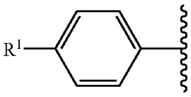 | 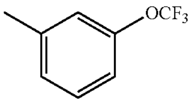 | —CH2— | 0 | —C(═O)— |

TABLE 3-7-continued
| | | | | | | |
|---|---|---|---|---|---|---|
| 204 | 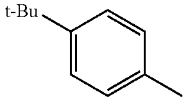 | 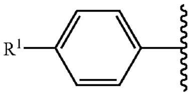 | 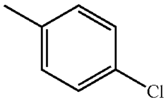 | —$CH_2$— | 0 | —C(=O)— |
| 205 | 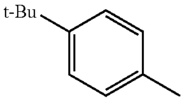 | 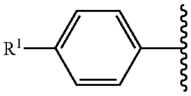 | 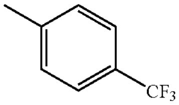 | —$CH_2$— | 0 | —C(=O)— |
| 206 | 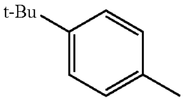 | 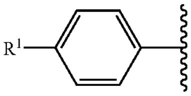 | 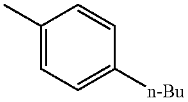 | —$CH_2$— | 0 | —C(=O)— |
| 207 | 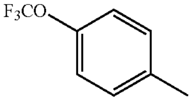 | 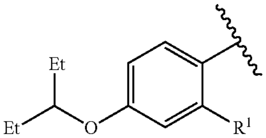 | 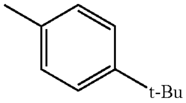 | —$CH_2$— | 0 | —C(=O)— |
| 208 | 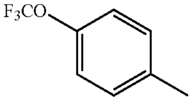 | 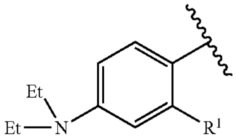 | 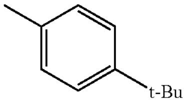 | —$CH_2$— | 0 | —C(=O)— |
| 209 | 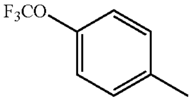 | 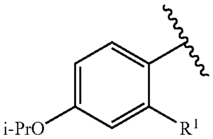 | 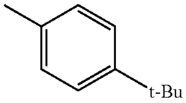 | —$CH_2$— | 0 | —C(=O)— |
| 210 | 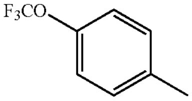 | 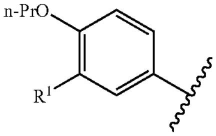 | 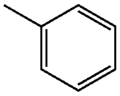 | —$CH_2$— | 0 | —C(=O)— |
TABLE 3-8
| | | | | | | |
|---|---|---|---|---|---|---|
| 211 | 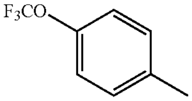 | 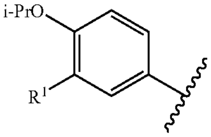 | 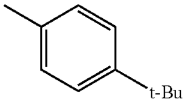 | —$CH_2$— | 0 | —C(=O)— |
| 212 | 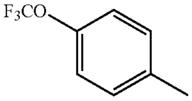 | 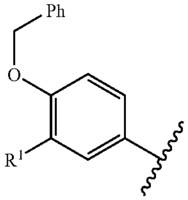 | 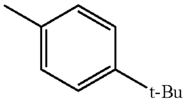 | —$CH_2$— | 0 | —C(=O)— |
| 213 | 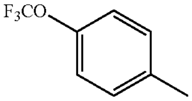 | 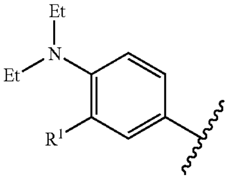 | 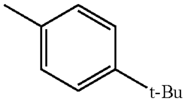 | —$CH_2$— | 0 | —C(=O)— |

TABLE 3-8-continued
| | | | | | | |
|---|---|---|---|---|---|---|
| 214 | 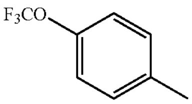 | 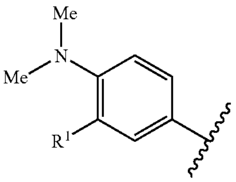 | 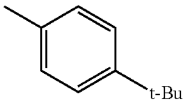 | —CH₂— | 0 | —C(═O)— |
| 215 | 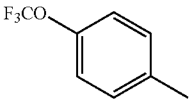 | 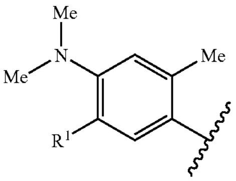 | 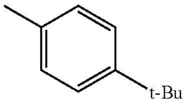 | —CH₂— | 0 | —C(═O)— |
| 216 | 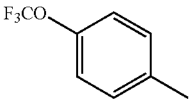 | 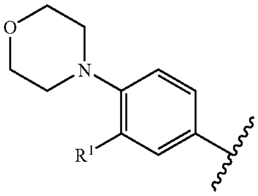 | 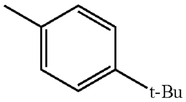 | —CH₂— | 0 | —C(═O)— |
| 217 | 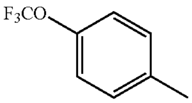 | 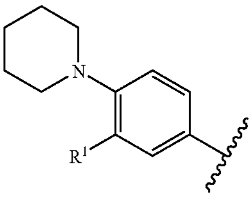 | 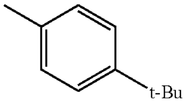 | —CH₂— | 0 | —C(═O)— |
| 218 | 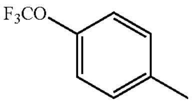 | 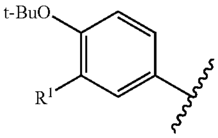 | 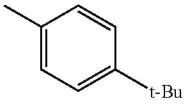 | —CH₂— | 0 | —C(═O)— |
| 219 | 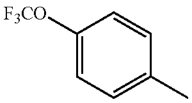 | 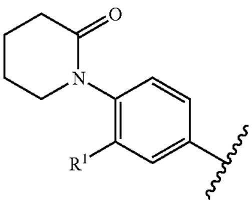 | 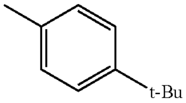 | —CH₂— | 0 | —C(═O)— |
| 220 | 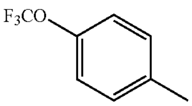 | 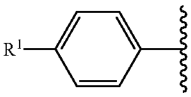 | 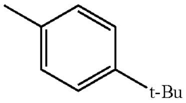 | 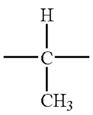 | 0 | —C(═O)— |
| 221 | 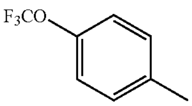 | 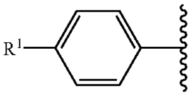 | 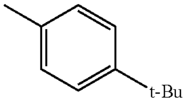 | 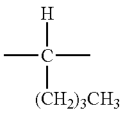 | 0 | —C(═O)— |

TABLE 3-9
| | | | | | | |
|---|---|---|---|---|---|---|
| 222 | 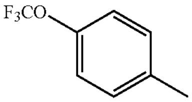 | 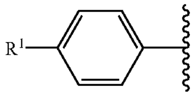 | 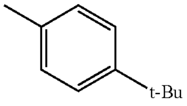 | 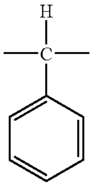 | 0 | —C(═O)— |
| 223[c] | 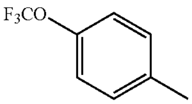 | 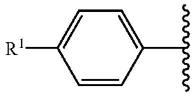 | 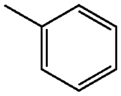 | $-(CH_2)_2-$ | 0 | —C(═O)— |
| 224 | 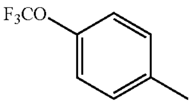 | 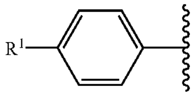 | 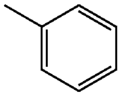 | $-(CH_2)_3-$ | 0 | —C(═O)— |
| 225 | 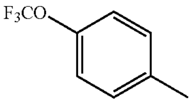 | 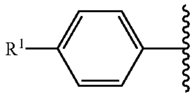 | 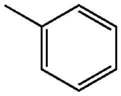 | $-(CH_2)_4-$ | 0 | —C(═O)— |
| 226 | 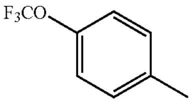 | 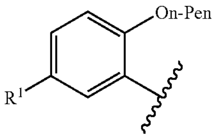 | 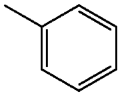 | $-(CH_2)_4-$ | 0 | —C(═O)— |
| 227 | 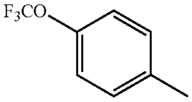 | 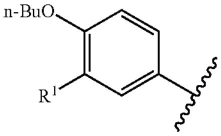 | 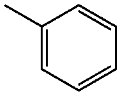 | $-(CH_2)_4-$ | 0 | —C(═O)— |
| 228 | 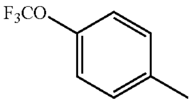 | 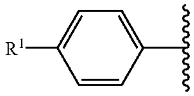 | 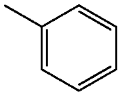 | $-(CH_2)_5-$ | 0 | —C(═O)— |
| 229 | 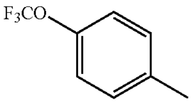 | 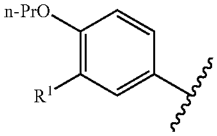 | 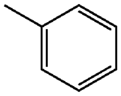 | $-(CH_2)_3-$ | 0 | —C(═O)— |
| 230 | 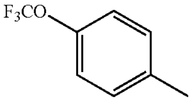 | 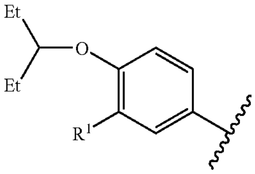 | 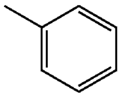 | $-(CH_2)_3-$ | 0 | —C(═O)— |
| 231 | 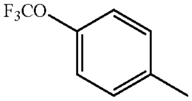 | 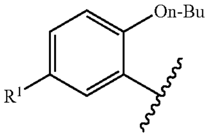 | 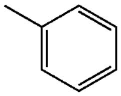 | $-(CH_2)_4-$ | 0 | —C(═O)— |
| 232 | 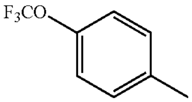 | 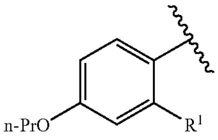 | 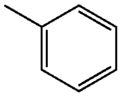 | $-(CH_2)_3-$ | 0 | —C(═O)— |

TABLE 3-9-continued
| | | | | | | |
|---|---|---|---|---|---|---|
| 233 | 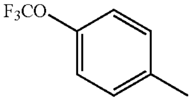 | 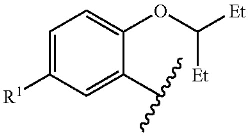 | 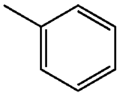 | $—(CH_2)_3—$ | 0 | —C(═O)— |
TABLE 3-10
| | | | | | | |
|---|---|---|---|---|---|---|
| 234 | 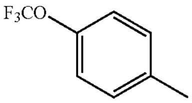 | 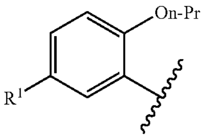 | 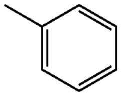 | $—(CH_2)_3—$ | 0 | —C(═O)— |
| 235 | 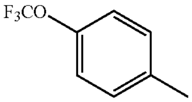 | 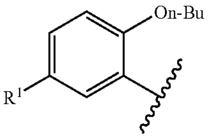 | 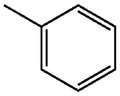 | $—(CH_2)_3—$ | 0 | —C(═O)— |
| 236 | 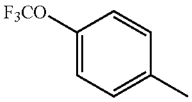 | 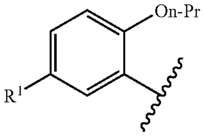 | 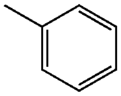 | $—(CH_2)_4—$ | 0 | —C(═O)— |
| 237 | 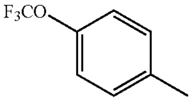 | 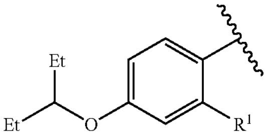 | 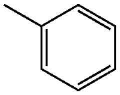 | $—(CH_2)_3—$ | 0 | —C(═O)— |
| 238 | 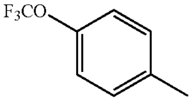 | 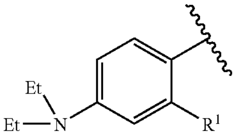 | 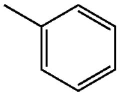 | $—(CH_2)_3—$ | 0 | —C(═O)— |
| 239 | 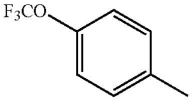 | 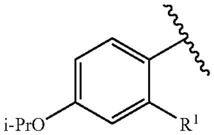 | 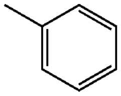 | $—(CH_2)_3—$ | 0 | —C(═O)— |
| 240 | 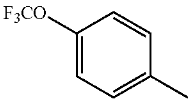 | 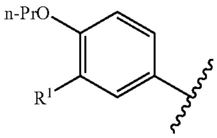 | 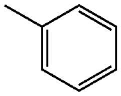 | $—(CH_2)_4—$ | 0 | —C(═O)— |
| 241 | 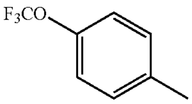 | 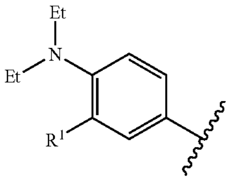 | 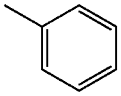 | $—(CH_2)_4—$ | 0 | —C(═O)— |
| 242 | 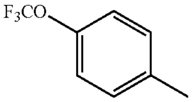 | 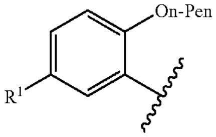 | 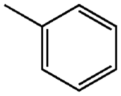 | $—(CH_2)_5—$ | 0 | —C(═O)— |

TABLE 3-10-continued
| | | | | | | |
|---|---|---|---|---|---|---|
| 243 | 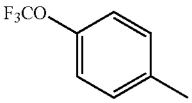 | 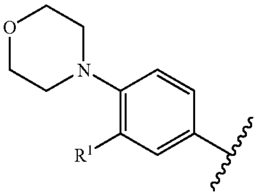 | 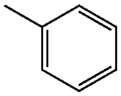 | $-(CH_2)_4-$ | 0 | —C(=O)— |
| 244 | 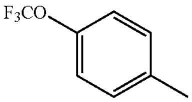 | 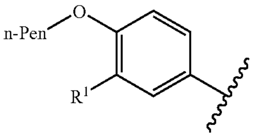 | 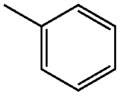 | $-(CH_2)_4-$ | 0 | —C(=O)— |
| 245 | 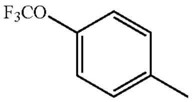 | 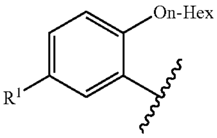 | 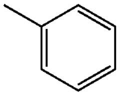 | $-(CH_2)_4-$ | 0 | —C(=O)— |
TABLE 3-11
| | | | | | | |
|---|---|---|---|---|---|---|
| 246 | 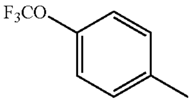 | 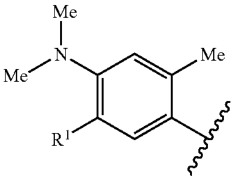 | 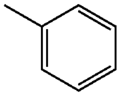 | $-(CH_2)_4-$ | 0 | —C(=O)— |
| 247 | 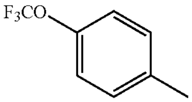 | 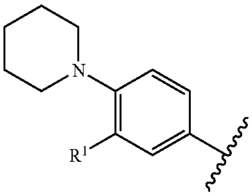 | 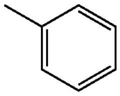 | $-(CH_2)_4-$ | 0 | —C(=O)— |
| 248 | 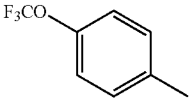 | 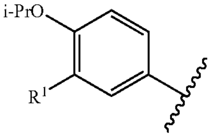 | 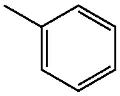 | $-(CH_2)_4-$ | 0 | —C(=O)— |
| 249 | 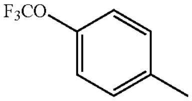 | 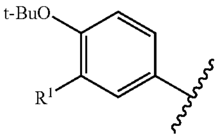 | 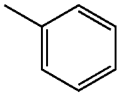 | $-(CH_2)_4-$ | 0 | —C(=O)— |
| 250 | 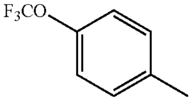 | 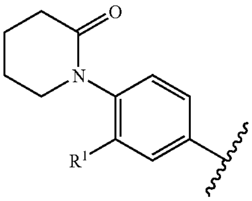 | 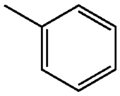 | $-(CH_2)_4-$ | 0 | —C(=O)— |
| 252 | 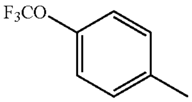 | 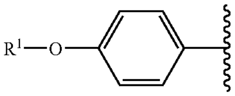 | H | $-(CH_2)_6-$ | 0 | —C(=O)— |

TABLE 3-11-continued
| | | | | | | |
|---|---|---|---|---|---|---|
| 253 | 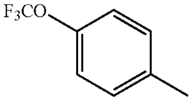 | 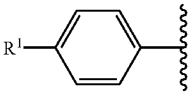 | 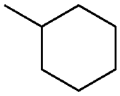 | single bond | 0 | —C(=O)— |
| 254 | 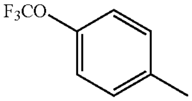 | 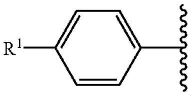 | H | —$(CH_2)_5$— | 0 | —C(=O)— |
| 255 | 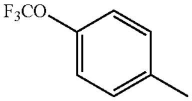 | 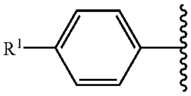 | H | 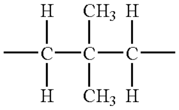 | 0 | —C(=O)— |
| 351 | 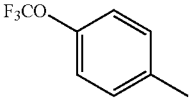 | 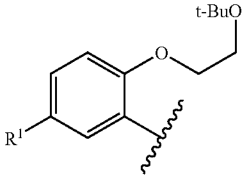 | 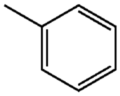 | —$(CH_2)_4$— | 0 | —C(=O)— |
| 352 | 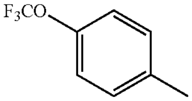 | 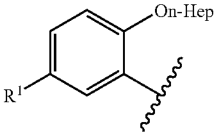 | 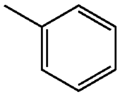 | —$(CH_2)_4$— | 0 | —C(=O)— |
| 353 | 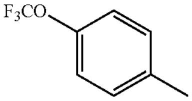 | 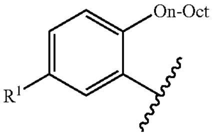 | 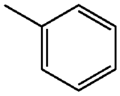 | —$(CH_2)_4$— | 0 | —C(=O)— |
TABLE 3-12
| | | | | | | |
|---|---|---|---|---|---|---|
| 354 | 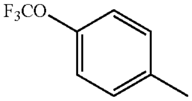 | 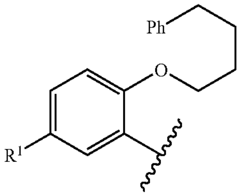 | 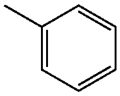 | —$(CH_2)_4$— | 0 | —C(=O)— |
| 355 | 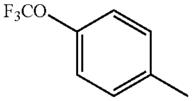 | 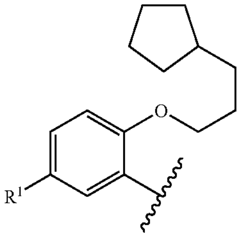 | 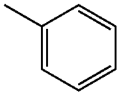 | —$(CH_2)_4$— | 0 | —C(=O)— |
| 356 | 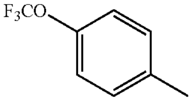 | 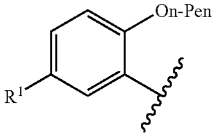 | 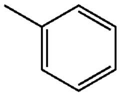 | —$(CH_2)_3O$— | 0 | —C(=O)— |

TABLE 3-12-continued
| | | | | | | |
|---|---|---|---|---|---|---|
| 357 | 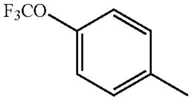 | 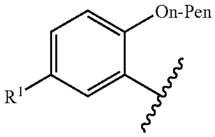 | 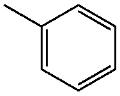 | —$(CH_2)_3$S— | 0 | —C(═O)— |
| 358 | 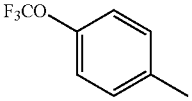 | 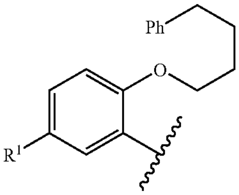 | H | —$(CH_2)_5$— | 0 | —C(═O)— |
| 359 | 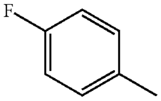 | 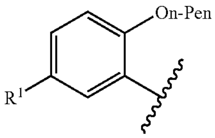 | 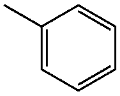 | —$(CH_2)_4$— | 0 | —C(═O)— |
| 360 | 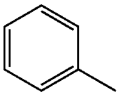 | 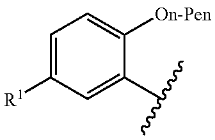 | 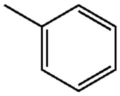 | —$(CH_2)_4$— | 0 | —C(═O)— |
| 361 | 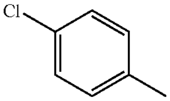 | 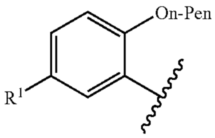 | 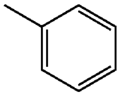 | —$(CH_2)_4$— | 0 | —C(═O)— |
| 362 | 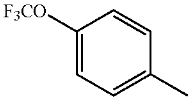 | 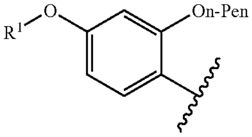 | 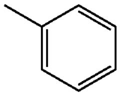 | —$(CH_2)_4$— | 0 | —C(═O)— |
| 363 | 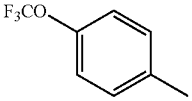 | 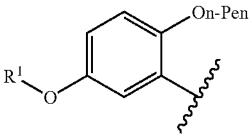 | 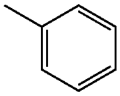 | —$(CH_2)_4$— | 0 | —C(═O)— |
| 364 | 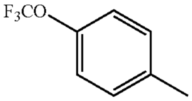 | 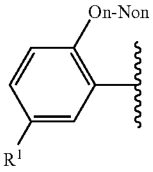 | 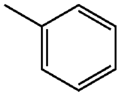 | —$(CH_2)_4$— | 0 | —C(═O)— |
| 365 | 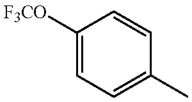 | 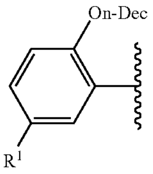 | 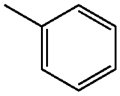 | —$(CH_2)_4$— | 0 | —C(═O)— |

TABLE 3-13
| | | | | | | |
|---|---|---|---|---|---|---|
| 366 | 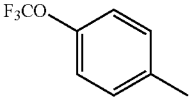 | 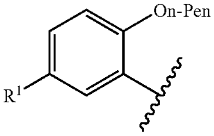 | H | $—(CH_2)_5—$ | 0 | —C(═O)— |
| 367 | 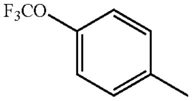 | 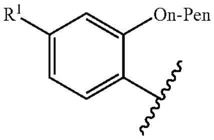 | 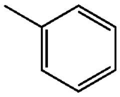 | $—(CH_2)_4—$ | 0 | —C(═O)— |
| 368 | 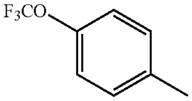 | 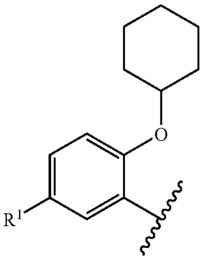 | 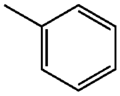 | $—(CH_2)_4—$ | 0 | —C(═O)— |
| 369 | 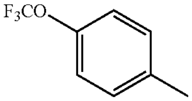 | 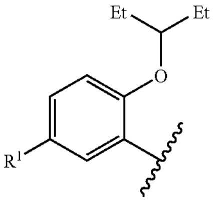 | 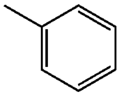 | $—(CH_2)_4—$ | 0 | —C(═O)— |
| 370 | 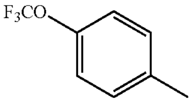 | 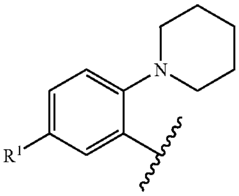 | 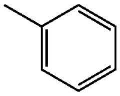 | $—(CH_2)_4—$ | 0 | —C(═O)— |
| 371 | 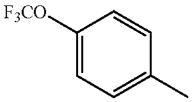 | 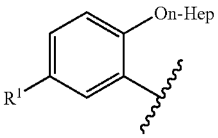 | 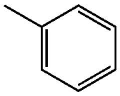 | $—(CH_2)_4—$ | 0 | —C(═O)— |
| 372 | 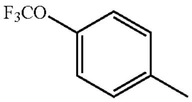 | 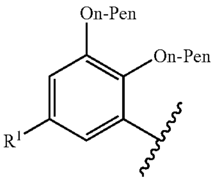 | 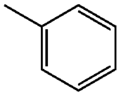 | $—(CH_2)_4—$ | 0 | —C(═O)— |
| 373 | 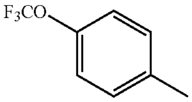 | 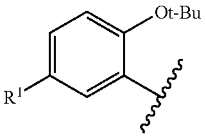 | 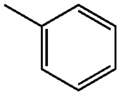 | $—(CH_2)_4—$ | 0 | —C(═O)— |
| 374 | 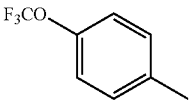 | 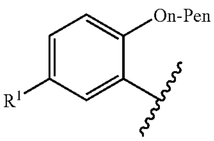 | 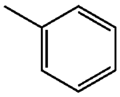 | $—(CH_2)_4O—$ | 0 | —C(═O)— |

TABLE 3-13-continued
| | | | | | | |
|---|---|---|---|---|---|---|
| 375 | 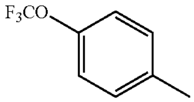 | 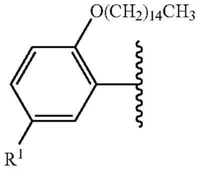 | 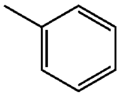 | $—(CH_2)_4—$ | 0 | —C(=O)— |
| 376 | 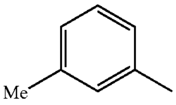 | 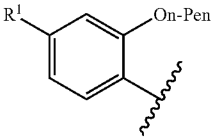 | 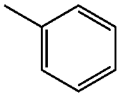 | $—(CH_2)_4—$ | 0 | —C(=O)— |
TABLE 3-14
| | | | | | | |
|---|---|---|---|---|---|---|
| 377 | 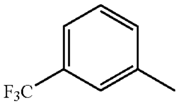 | 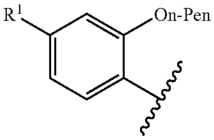 | 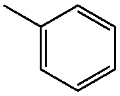 | $—(CH_2)_4—$ | 0 | —C(=O)— |
| 378 | 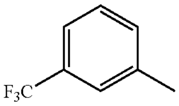 | 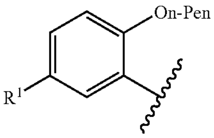 | 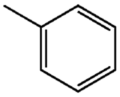 | $—(CH_2)_4—$ | 0 | —C(=O)— |
| 379 | 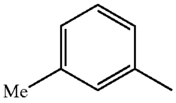 | 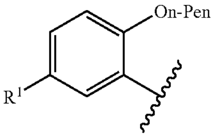 | 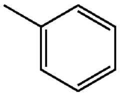 | $—(CH_2)_4—$ | 0 | —C(=O)— |
| 380 | 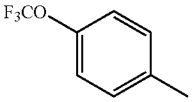 | 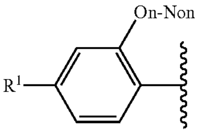 | 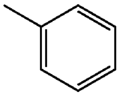 | $—(CH_2)_4—$ | 0 | —C(=O)— |
| 381 | 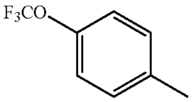 | 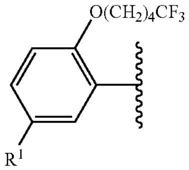 | 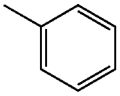 | $—(CH_2)_4—$ | 0 | —C(=O)— |
| 382 | 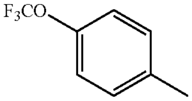 | 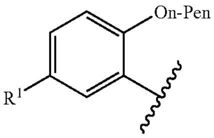 | 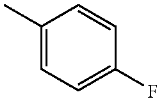 | $—(CH_2)_4—$ | 0 | —C(=O)— |
| 383 | 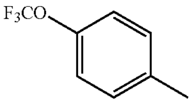 | 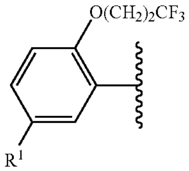 | 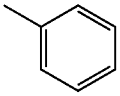 | $—(CH_2)_4—$ | 0 | —C(=O)— |

TABLE 3-14-continued
| | | | | | | |
|---|---|---|---|---|---|---|
| 384 | 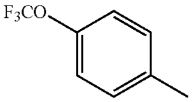 | 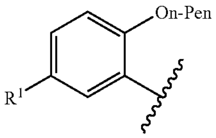 | 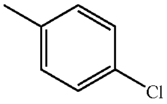 | $-(CH_2)_4-$ | 0 | —C(=O)— |
| 385 | 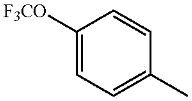 | 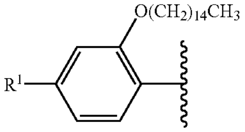 | 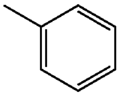 | $-(CH_2)_4-$ | 0 | —C(=O)— |
| 386 | 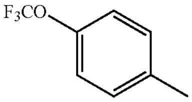 | 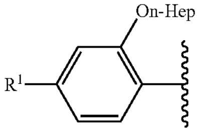 | 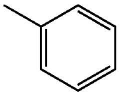 | $-(CH_2)_4-$ | 0 | —C(=O)— |
| 387 | 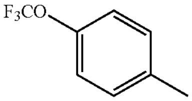 | 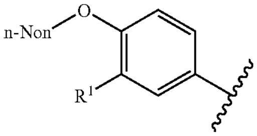 | 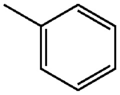 | $-(CH_2)_4-$ | 0 | —C(=O)— |
| 388 | 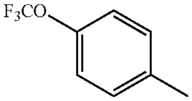 | 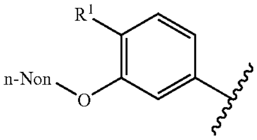 | 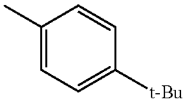 | $-CH_2-$ | 0 | —C(=O)— |
| 389 | 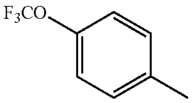 | 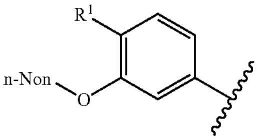 | 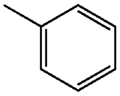 | $-(CH_2)_4-$ | 0 | —C(=O)— |
TABLE 3-15
| | | | | | | |
|---|---|---|---|---|---|---|
| 390 | 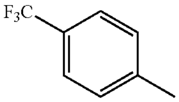 | 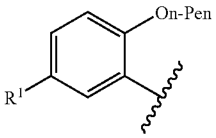 | 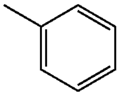 | $-(CH_2)_4-$ | 0 | —C(=O)— |
| 391 | 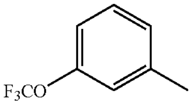 | 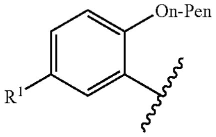 | 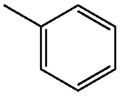 | $-(CH_2)_4-$ | 0 | —C(=O)— |
| 392 | 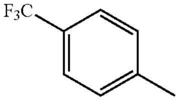 | 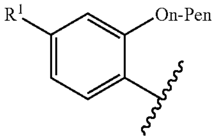 | 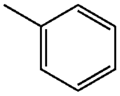 | $-(CH_2)_4-$ | 0 | —C(=O)— |
| 393 | 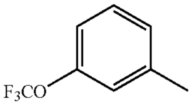 | 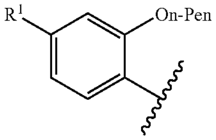 | 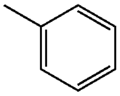 | $-(CH_2)_4-$ | 0 | —C(=O)— |

TABLE 3-15-continued
| | | | | | | |
|---|---|---|---|---|---|---|
| 394 | 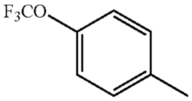 | 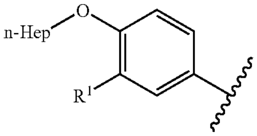 | 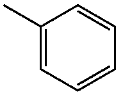 | $—(CH_2)_4—$ | 0 | —C(═O)— |
| 601 | 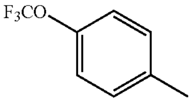 | 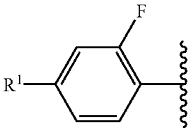 | 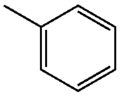 | $—CH_2—$ | 0 | 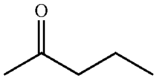 |
| 602 | 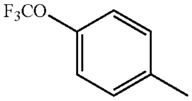 | 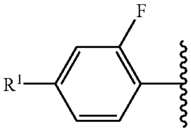 | 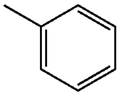 | $—CH_2—$ | 0 | 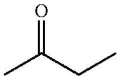 |
| 603 | 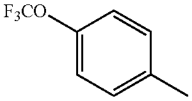 | 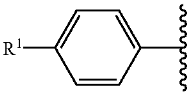 | 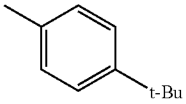 | $—CH_2—$ | 1 | —C(═O)— |
| 604 | 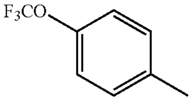 | 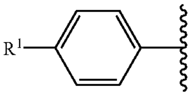 | 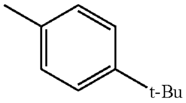 | $—CH_2—$ | 0 | 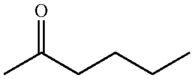 |
| 605 | 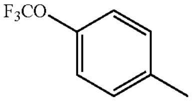 | 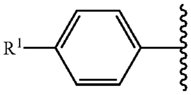 | 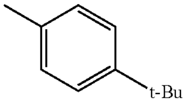 | $—CH_2—$ | 0 | $—CH_2—$ |
| 606 | 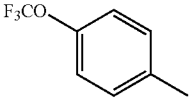 | 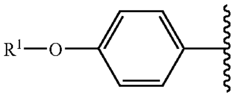 | 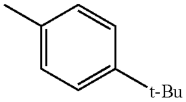 | $—CH_2—$ | 0 | $—CH_2—$ |
| 607 | 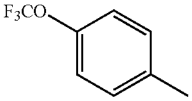 | 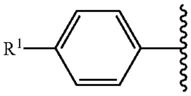 | 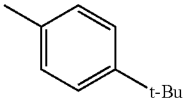 | $—CH_2—$ | 0 | $—(CH_2)_2—$ |
| 608 | 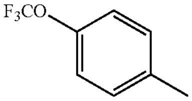 | 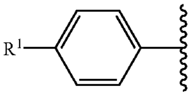 | 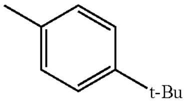 | $—CH_2—$ | 0 | 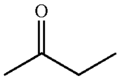 |
| 609 | 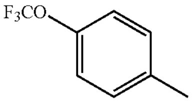 | 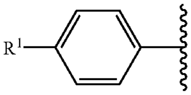 | 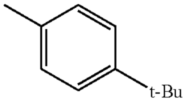 | $—CH_2—$ | 0 | 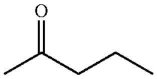 |
TABLE 3-16
| | | | | | | |
|---|---|---|---|---|---|---|
| 610 | 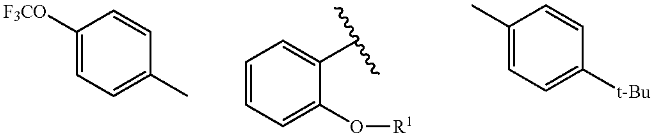 | | | single bond | 0 | $—CH_2—$ |
| 611 | 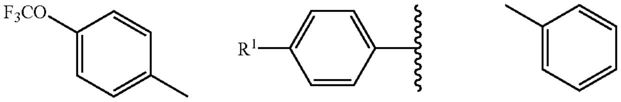 | | | single bond | 1 | —C(═O)— |

TABLE 3-16-continued
| | | | | | | |
|---|---|---|---|---|---|---|
| 612 | 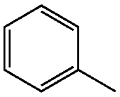 | 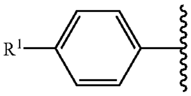 | 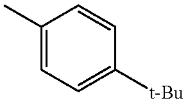 | single bond | 1 | —C(═O)— |
| 613 | 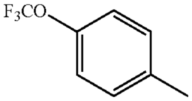 | 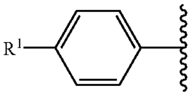 | 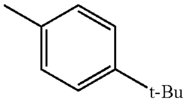 | single bond | 1 | —C(═O)— |
| 614 | 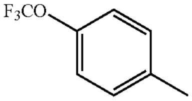 | 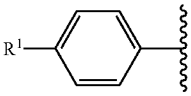 | 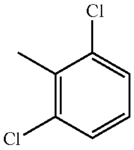 | single bond | 1 | —C(═O)— |
| 615 | 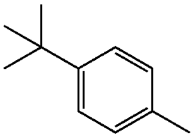 | 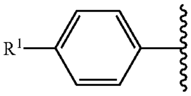 | 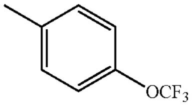 | single bond | 1 | —C(═O)— |
| 616 | 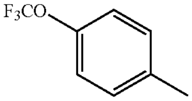 | 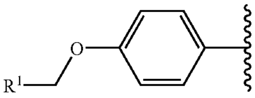 | 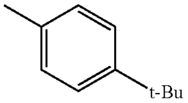 | —$CH_2$— | 0 | —C(═O)— |
| 617 | 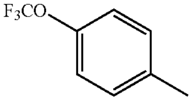 | 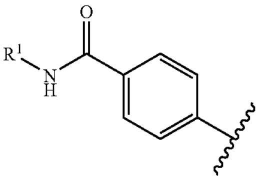 | 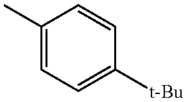 | —$CH_2$— | 0 | —C(═O)— |
| 618 | 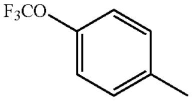 | 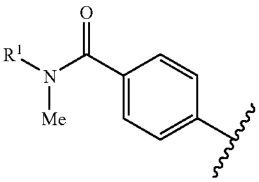 | 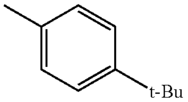 | —$CH_2$— | 0 | —C(═O)— |
| 619 | 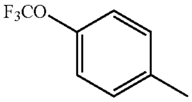 | 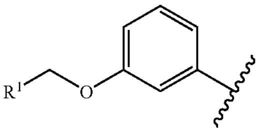 | 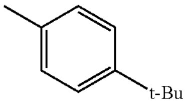 | —$CH_2$— | 0 | —C(═O)— |
| 620 | 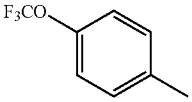 | 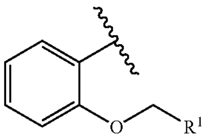 | 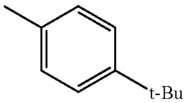 | —$CH_2$— | 0 | —C(═O)— |
| 621 | 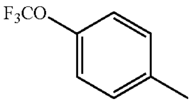 | 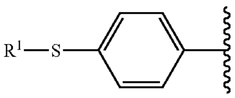 | 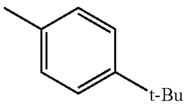 | —$CH_2$— | 0 | —C(═O)— |

TABLE 3-17
| | | | | | | |
|---|---|---|---|---|---|---|
| 622 | 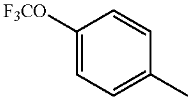 | 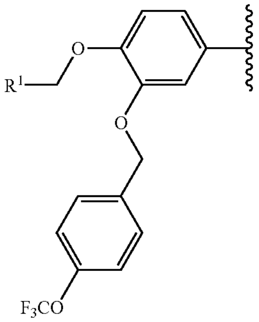 | 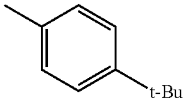 | —CH$_2$— | 0 | —C(═O)— |
| 623 | 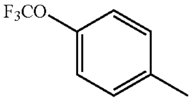 | 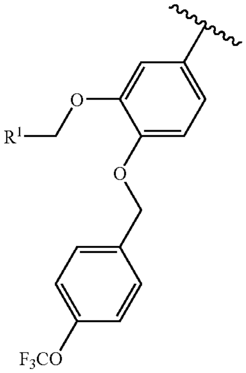 | H | —CH$_2$— | 0 | —C(═O)— |
| 624 | 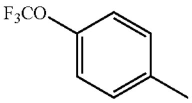 | 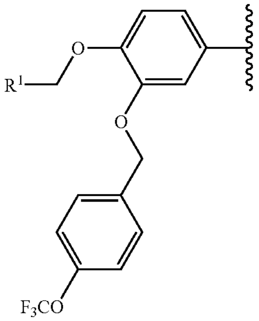 | H | single bond | 0 | —C(═O)— |
| 625 | 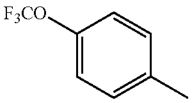 | 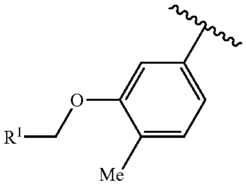 | 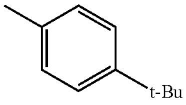 | —CH$_2$— | 0 | —C(═O)— |
| 626 | 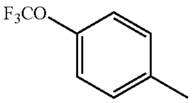 | 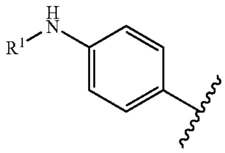 | 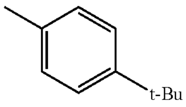 | —CH$_2$— | 0 | —C(═O)— |
| 627 | 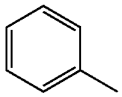 | 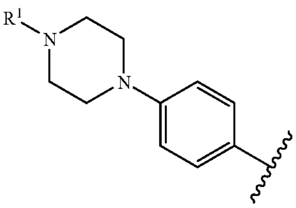 | 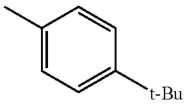 | —CH$_2$— | 0 | —C(═O)— |

TABLE 3-17-continued
| | | | | | | |
|---|---|---|---|---|---|---|
| 628 | 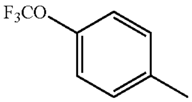 | 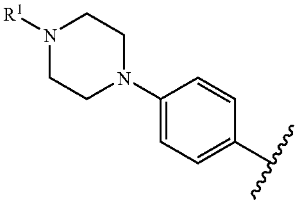 | 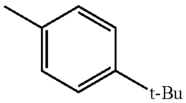 | —$CH_2$— | 0 | —C(═O)— |
| 629 | 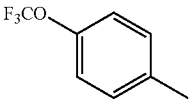 | 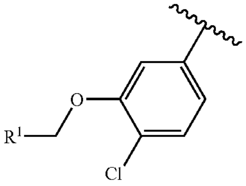 | 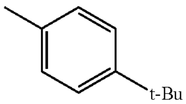 | —$CH_2$— | 0 | —C(═O)— |
TABLE 3-18
| | | | | | | |
|---|---|---|---|---|---|---|
| 630 | 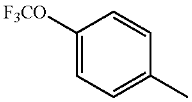 | 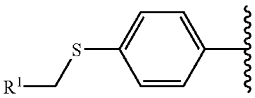 | 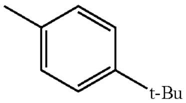 | —$CH_2$— | 0 | —C═O)— |
| 631 | 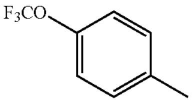 | 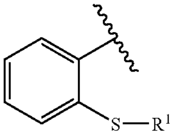 | 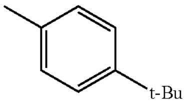 | —$CH_2$— | 0 | —C(═O)— |
| 632 | 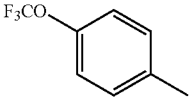 | 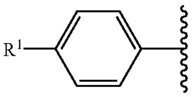 | 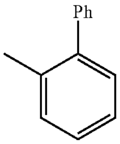 | single bond | 1 | —C(═O)— |
| 633 | 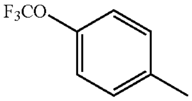 | 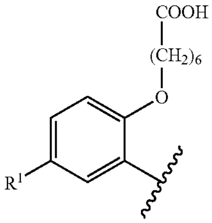 | 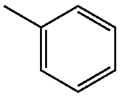 | —$(CH_2)_4$— | 0 | —C(═O)— |
| 634 | 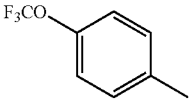 | 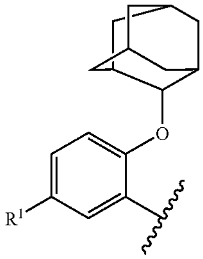 | 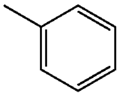 | —$(CH_2)_4$— | 0 | —C(═O)— |

TABLE 3-18-continued
| | | | | | | |
|---|---|---|---|---|---|---|
| 635 | 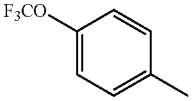 | 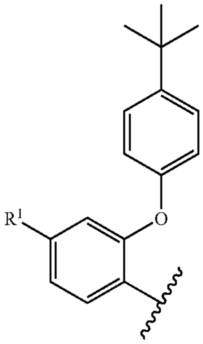 | 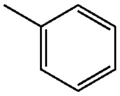 | $-(CH_2)_4-$ | 0 | —C(=O)— |
| 636 | 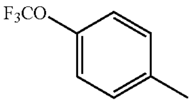 | 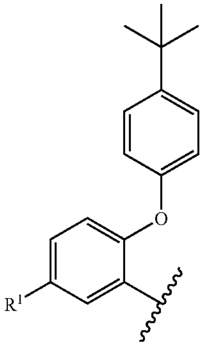 | 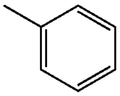 | $-(CH_2)_4-$ | 0 | —C(=O)— |
| 637 | 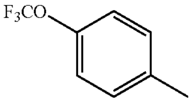 | 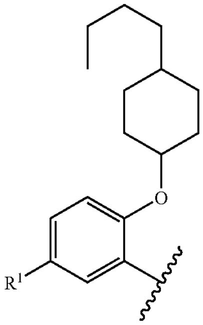 | 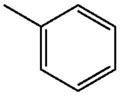 | $-(CH_2)_4-$ | 0 | —C(=O)— |
TABLE 3-19
| | | | | | | |
|---|---|---|---|---|---|---|
| 638 | 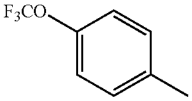 | 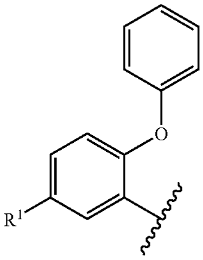 | 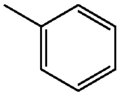 | $-(CH_2)_4-$ | 0 | —C(=O)— |
| 639 | 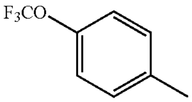 | 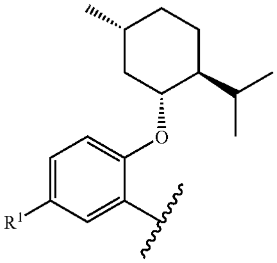 | 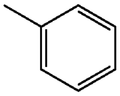 | $-(CH_2)_4-$ | 0 | —C(=O)— |

TABLE 3-19-continued
| | | | | | | |
|---|---|---|---|---|---|---|
| 640 | 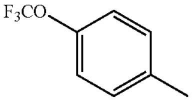 | 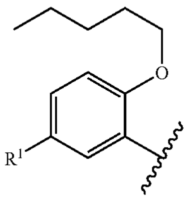 | 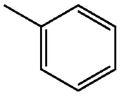 | —$(CH_2)_4$— | 0 | —$CH_2$— |
| 641 | 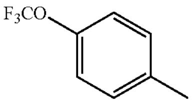 | 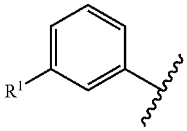 | 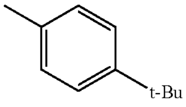 | —$CH_2$— | 0 | 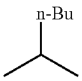 |
| 642 | 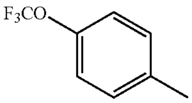 | 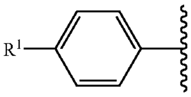 | 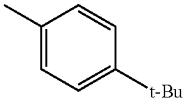 | —$CH_2$— | 0 | 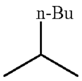 |
| 643 | 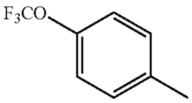 | 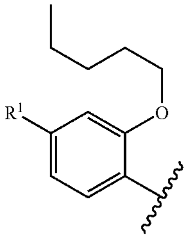 | 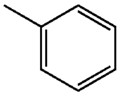 | —$(CH_2)_4$— | 0 | —$CH_2$— |
| 644 | 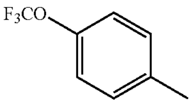 | 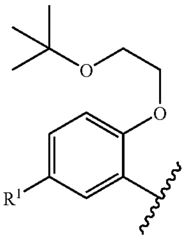 | 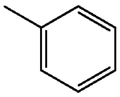 | —$(CH_2)_4$— | 0 | —$CH_2$— |
| 645 | 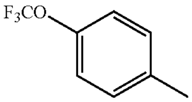 | 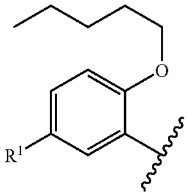 | 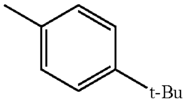 | single bond | 1 | —C(=O)— |
| 646 | 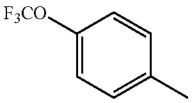 | 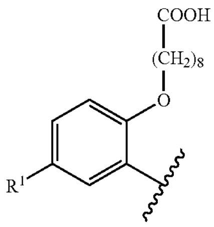 | 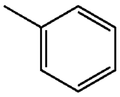 | —$(CH_2)_4$— | 0 | —C(=O)— |

TABLE 3-20
| | | | | | | |
|---|---|---|---|---|---|---|
| 647 | 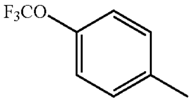 | 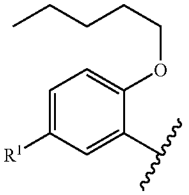 | 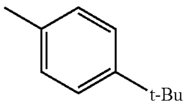 | single bond | 1 | —$CH_2$— |
| 648 | 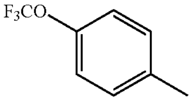 | 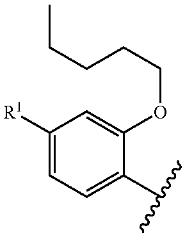 | 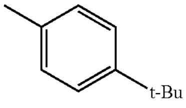 | single bond | 1 | —C(═O)— |
| 649 | 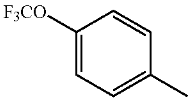 | 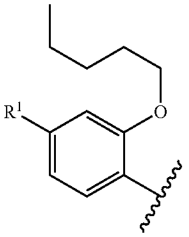 | 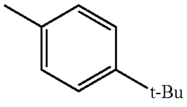 | single bond | 1 | —$CH_2$— |
| 650 | 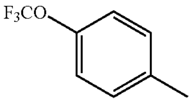 | 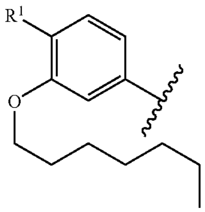 | 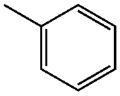 | —$(CH_2)_4$— | 0 | —C(═O)— |
| 651 | 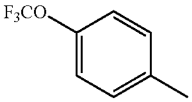 | 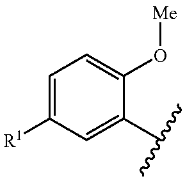 | 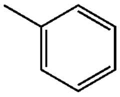 | —$(CH_2)_4$— | 0 | —C(═O)— |
| 652 | 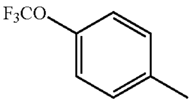 | 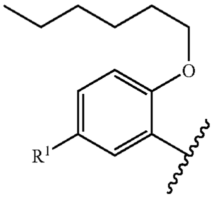 | 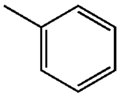 | —$(CH_2)_4$— | 0 | —C(═O)— |
| 653 | 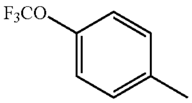 | 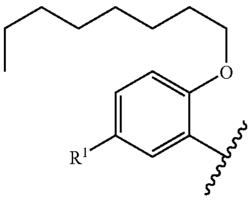 | 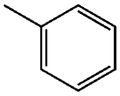 | —$(CH_2)_4$— | 0 | —C(═O)— |

TABLE 3-20-continued
| | | | | | | |
|---|---|---|---|---|---|---|
| 654 | 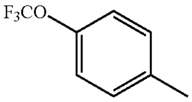 | 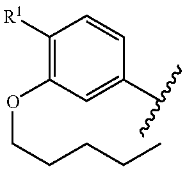 | 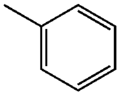 | $-(CH_2)_4-$ | 0 | —C(═O)— |
| 655 | 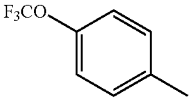 | 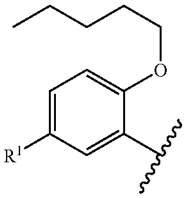 | 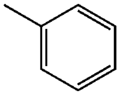 | 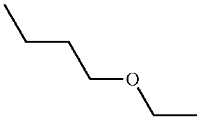 | 0 | —C(═O)— |
TABLE 3-21
| | | | | | | |
|---|---|---|---|---|---|---|
| 656 | 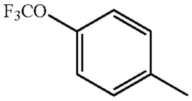 | 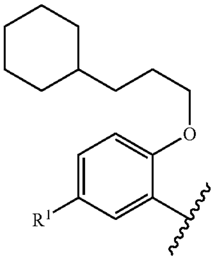 | 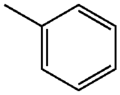 | $-(CH_2)_4-$ | 0 | —C(═O)— |
| 657 | 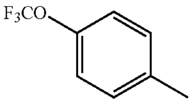 | 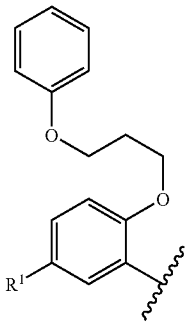 | H | $-(CH_2)_5-$ | 0 | —C(═O)— |
| 658 | 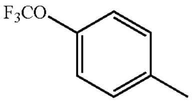 | 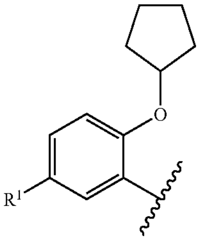 | 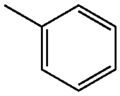 | $-(CH_2)_4-$ | 0 | —C(═O)— |
| 659 | 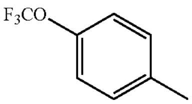 | 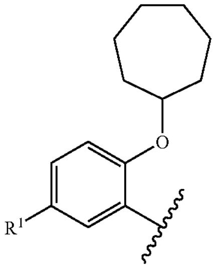 | 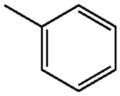 | $-(CH_2)_4-$ | 0 | —C(═O)— |

TABLE 3-21-continued
| | | | | | | |
|---|---|---|---|---|---|---|
| 660 | 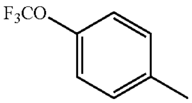 | 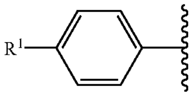 | 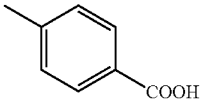 | —$CH_2$— | 0 | —C(=O)— |
| 661 | 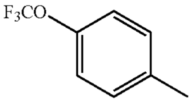 | 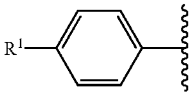 | 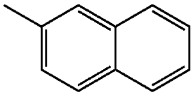 | —$CH_2$— | 0 | —C(=O)— |
| 662 | 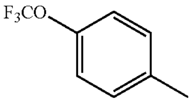 | 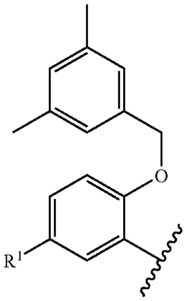 | 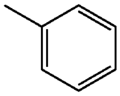 | —$(CH_2)_4$— | 0 | —C(=O)— |
| 663 | 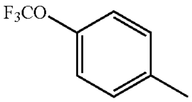 | 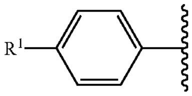 | 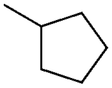 | single bond | 0 | —C(=O)— |
TABLE 3-22
| | | | | | | |
|---|---|---|---|---|---|---|
| 664 | 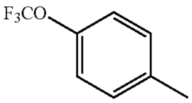 | 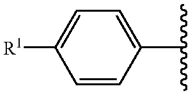 | 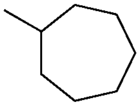 | single bond | 0 | —C(=O)— |
| 665 | 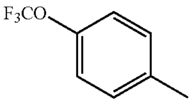 | 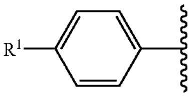 | 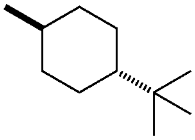 | single bond | 0 | —C(=O)— |
| 666 | 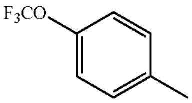 | 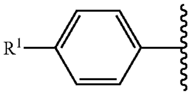 | 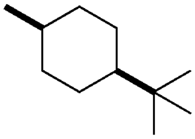 | single bond | 0 | —C(=O)— |
| 667 | 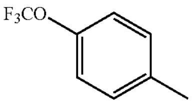 | 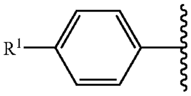 | 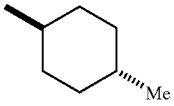 | single bond | 0 | —C(=O)— |
| 668 | 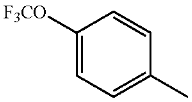 | 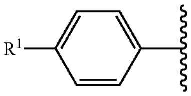 | 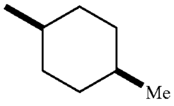 | single bond | 0 | —C(=O)— |
| 669 | 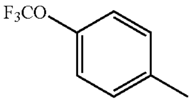 | 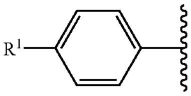 | H | —$(CH_2)_{10}$— | 0 | —C(=O)— |

TABLE 3-22-continued
| | | | | | | |
|---|---|---|---|---|---|---|
| 670 | 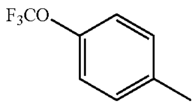 | 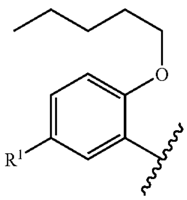 | 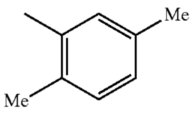 | $-(CH_2)_4-$ | 0 | $-C(=O)-$ |
| 671 | 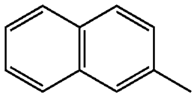 | 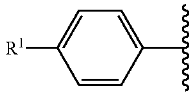 | 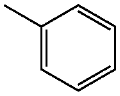 | $-(CH_2)_4-$ | 0 | $-C(=O)-$ |
| 672 | 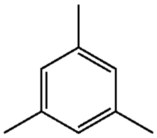 | 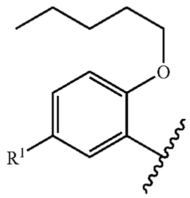 | 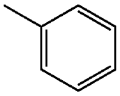 | $-(CH_2)_4-$ | 0 | $-C(=O)-$ |
| 673 | 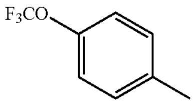 | 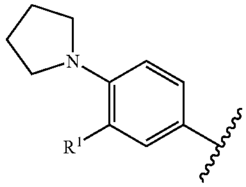 | 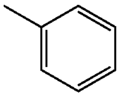 | $-(CH_2)_4-$ | 0 | $-C(=O)-$ |
| 674 | 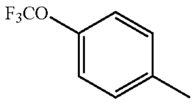 | 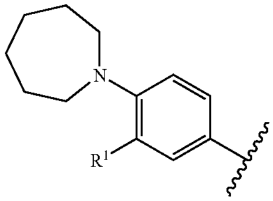 | 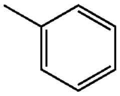 | $-(CH_2)_4-$ | 0 | $-C(=O)-$ |
| 675 | 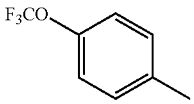 | 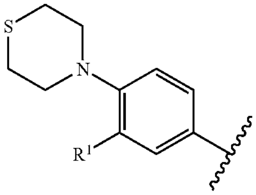 | 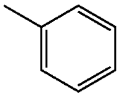 | $-(CH_2)_4-$ | 0 | $-C(=O)-$ |
TABLE 3-23
| | | | | | | |
|---|---|---|---|---|---|---|
| 676 | 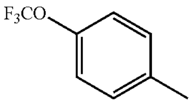 | 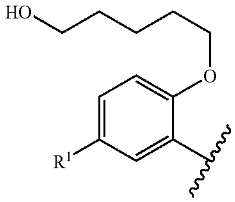 | 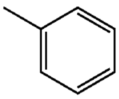 | $-(CH_2)_4-$ | 0 | $-C(=O)-$ |

TABLE 3-23-continued
| | | | | | | |
|---|---|---|---|---|---|---|
| 677 | 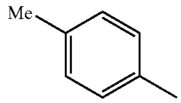 | 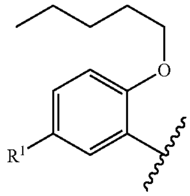 | 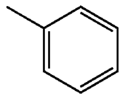 | $-(CH_2)_4-$ | 0 | $-C(=O)-$ |
| 678 | 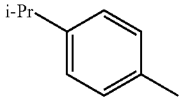 | 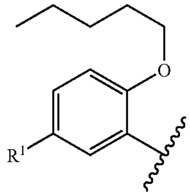 | 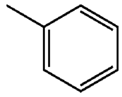 | $-(CH_2)_4-$ | 0 | $-C(=O)-$ |
| 679 | 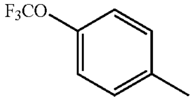 | 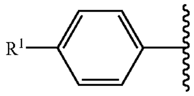 | 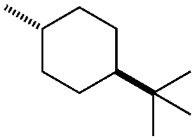 | $-CH_2-$ | 0 | $-C(=O)-$ |
| 680 | 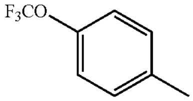 | 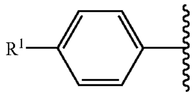 | 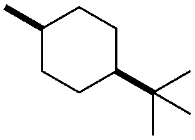 | $-CH_2-$ | 0 | $-C(=O)-$ |
| 681 | 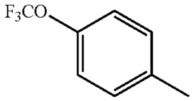 | 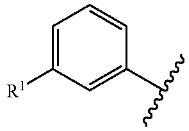 | 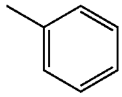 | 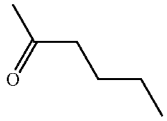 | 0 | $-CH_2-$ |
| 682 | 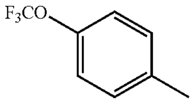 | 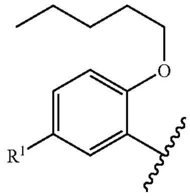 | 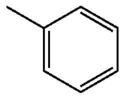 | 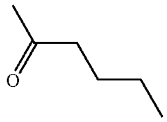 | 0 | $-CH_2-$ |
| 683 | 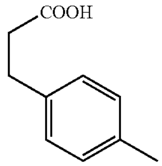 | 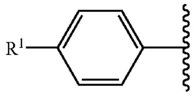 | 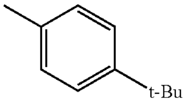 | $-CH_2-$ | 0 | $-C(=O)-$ |
| 684 | 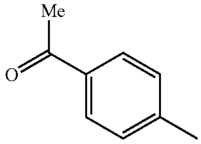 | 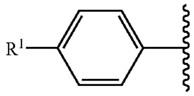 | 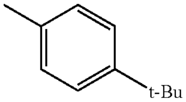 | $-CH_2-$ | 0 | $-C(=O)-$ |
| 685 | 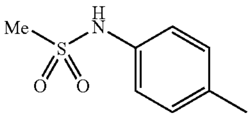 | 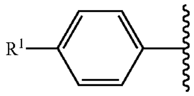 | 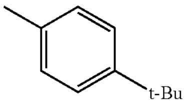 | $-CH_2-$ | 0 | $-C(=O)-$ |

TABLE 3-23-continued

| | | | | | | |
|---|---|---|---|---|---|---|
| 686 | 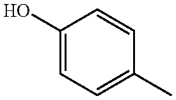 | 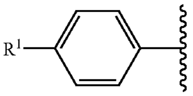 | 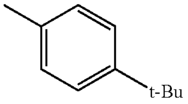 | —$CH_2$— | 0 | —C(═O)— |

The compounds represented by the formula (I) can be prepared, for example, by the following methods.

The compounds represented by the formula (I), wherein m is 1, T is a single bond, X is the formula —V'—(V')$_k$—, and Y' is a carboxy group, can be prepared by the following method:

<Scheme 1>

[Formula 14]

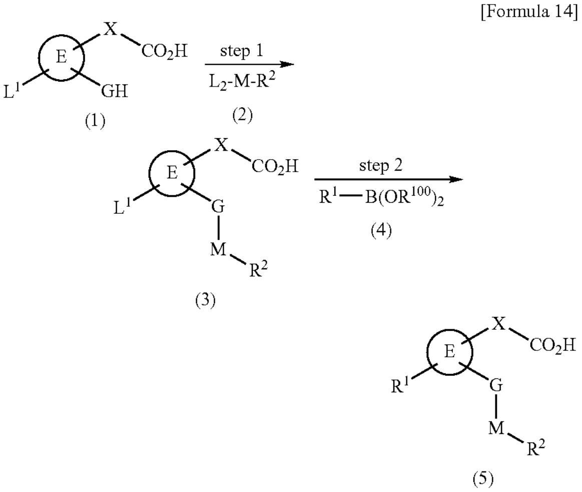

wherein $L^1$ represents a halogen atom or the like; $L^2$ represents a halogen atom or the like; $R^{100}$ represents a hydrogen atom, a $C_{1-6}$ alkyl group or the like; X represents the formula —V'—(V')$_k$—; $R^1$, $R^2$, E, G, V', k and M have the same meanings as the aforementioned definitions.

<Step 1>

The compound represented by the general formula (3) can be prepared by reacting the compound represented by the general formula (1) with the compound represented by the general formula (2). This reaction is carried out, for example, in the presence of a base, in a solvent. Crown ether may be added. Examples of the base include inorganic bases, organic bases and organometallic bases. Excessive amounts of base may preferably be used. Examples of the solvent include halogenated solvents, ether type solvents, amide type solvents, aromatic solvents, ketone type solvents, acetonitrile, or a mixed solvent thereof.

<Step 2>

The final target compound represented by the general formula (5) can be prepared by reacting the compound represented by the general formula (3) with the compound represented by the general formula (4). This reaction is carried out, for example, in the presence of a catalytic amount of a transition metal complex, in the presence or absence of a phosphine ligand, in the presence or absence of a base, in a solvent. Examples of the transition metal complex include [1,1-bis(diphenylphosphino)ferrocene]dichloropalladium(II), tetrakis(triphenylphosphine)palladium, palladium(II) acetate and tris(dibenzylideneacetone)dipalladium. Examples of the phosphine ligand include 2-(di-tert-butylphosphino)biphenyl and 2-dicyclohexylphoshino)biphenyl. Examples of the base include inorganic bases and organic bases. Examples of the solvent include ether type solvents, amide type solvents, aromatic solvents, alcohol type solvents, water, or a mixed solvent thereof.

The compounds represented by the formula (I), wherein m is 1, T is —R''—, X is the formula —V'—(V')$_k$—, and Y' is a carboxy group, can be prepared, for example, by the following method:

<Scheme 2>

[Formula 15]

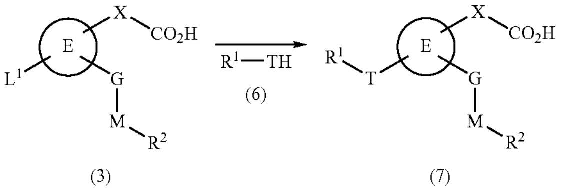

wherein $L^1$ represents a halogen atom or the like; X represents the formula —V'—(V')$_k$—; T represents —R''—; $R^1$, $R^2$, E, G, V', k and M have the same meanings as the aforementioned definitions.

The final target compound represented by the general formula (7) can be prepared by reacting the compound represented by the general formula (3) with the compound represented by the general formula (6). This reaction is carried out, for example, in the presence of copper(II) oxide, in the presence of a base, in a solvent. Examples of the base include inorganic bases. Examples of the solvent include halogenated solvents, pyridine, or a mixed solvent thereof.

The compounds represented by the formula (I), wherein m is 1, T is a single bond, X is the formula —V'—(V')$_k$—, and Y' is a 1H-tetrazol-5-yl group, can be prepared, for example, by the following method:

<Scheme 3>

[Formula 16]

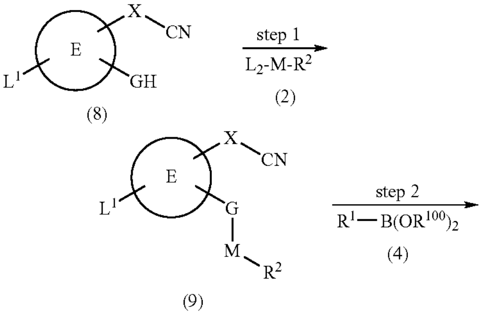

-continued

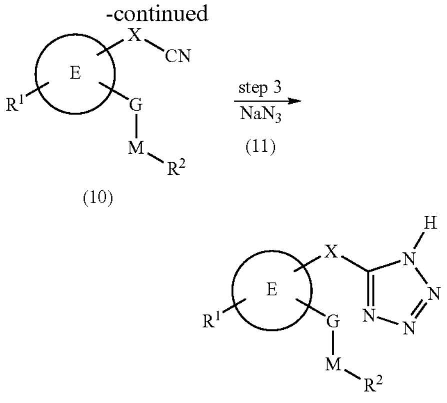

(10) (11) (12)

wherein $L^1$ represents a halogen atom or the like; $L^2$ represents a halogen atom or the like; $R^{100}$ represents a hydrogen atom, a $C_{1-6}$ alkyl group or the like; X represents the formula —V'—(V')$_k$—; $R^1$, $R^2$, E, G, V', k and M have the same meanings as the aforementioned definitions.

<Step 1>

The compound represented by the general formula (9) can be prepared by reacting the compound represented by the general formula (8) with the compound represented by the general formula (2). This reaction is carried out, for example, in the presence of a base, in a solvent. Crown ether may be added. Examples of the base include inorganic bases, organic bases and organometallic bases. Examples of the solvent include halogenated solvents, ether type solvents, amide type solvents, aromatic solvents, ketone type solvents, acetonitrile, or a mixed solvent thereof.

<Step 2>

The compound represented by the general formula (10) can be prepared by reacting the compound represented by the general formula (9) with the compound represented by the general formula (4). This reaction is carried out, for example, in the presence of a catalytic amount of a transition metal complex, in the presence or absence of a phosphine ligand, in the presence or absence of a base, in a solvent. Examples of the transition metal complex include [1,1-bis(diphenylphosphino)ferrocene]dichloropalladium(II), tetrakis(triphenylphosphine)palladium, palladium(II) acetate and tris (dibenzylideneacetone)dipalladium. Examples of the phosphine ligand include 2-(di-tert-butylphosphino)biphenyl and 2-dicyclohexylphoshino)biphenyl. Examples of the base include inorganic bases and organic bases. Examples of the solvent include ether type solvents, amide type solvents, aromatic solvents, alcohol type solvents, water, or a mixed solvent thereof.

<Step 3>

The final target compound represented by the general formula (12) can be prepared by reacting the compound represented by the general formula (10) with the compound represented by the general formula (11). This reaction is carried out, for example, in the presence of an ammonium salt, in a solvent. Examples of the ammonium salt include ammonium chloride and triethylamine hydrochloride.

Examples of the solvent include amide type solvents.

The compounds represented by the formula (I), wherein m is 1, T is —R"—, X is the formula —V'—(V')$_k$—, and Y' is a 1H-tetrazol-5-yl group, can be prepared, for example, by the following method:

<Scheme 4>

[Formula 17]

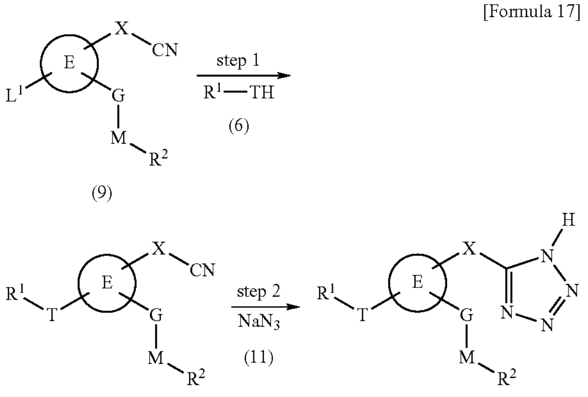

(9) (6) (13) (11) (14)

wherein $L^1$ represents a halogen atom or the like; X represents the formula —V'—(V')$_k$—; T is —R"—; $R^1$, $R^2$, E, G, V', k and M have the same meanings as the aforementioned definitions.

<Step 1>

The compound represented by the general formula (13) can be prepared by reacting the compound represented by the general formula (9) with the compound represented by the general formula (6). This reaction is carried out, for example, in the presence of copper(II) oxide, in the presence of a base, in a solvent. Examples of the base include inorganic bases. Examples of the solvent include halogenated solvents, pyridine, or a mixed solvent thereof.

<Step 2>

The final target compound represented by the general formula (14) can be prepared in the same manner as the aforementioned Step 3 in the Scheme 3 except using the compound represented by the general formula (13) in place of the compound represented by the general formula (10).

The compounds represented by the formula (I), wherein m is 1, T is a single bond, X is —CH═CH—, and Y' is a carboxy group, can be prepared, for example, by the following method:

<Scheme 5>

[Formula 18]

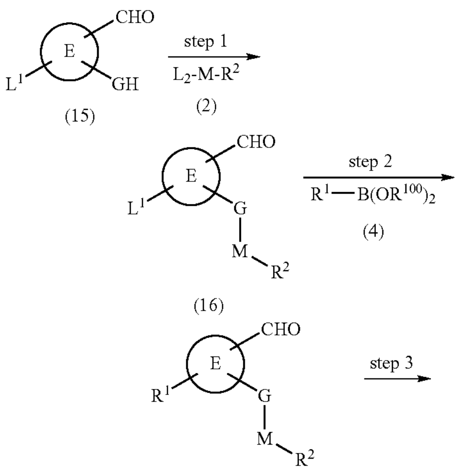

(15) (2) (16) (4) (17)

-continued

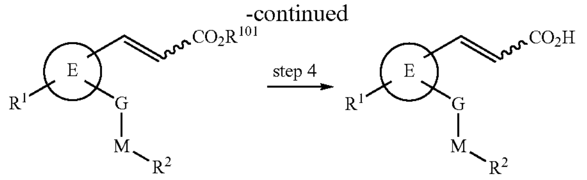

(18) (19)

wherein $L^1$ represents a halogen atom or the like; $L^2$ represents a halogen atom or the like; $R^{100}$ represents a hydrogen atom, a $C_{1-6}$ alkyl group or the like; $R^{101}$ represents a $C_{1-6}$ alkyl group or the like; $R^1$, $R^2$, E, G and M have the same meanings as the aforementioned definitions.

<Step 1>

The compound represented by the general formula (16) can be prepared by reacting the compound represented by the general formula (15) with the compound represented by the general formula (2). This reaction is carried out, for example, in the presence of a base, in a solvent. Crown ether may be added. Examples of the base include inorganic bases, organic bases and organometallic bases. Examples of the solvent include halogenated solvents, ether type solvents, amide type solvents, aromatic solvents, ketone type solvents, acetonitrile, or a mixed solvent thereof.

<Step 2>

The compound represented by the general formula (17) can be prepared by reacting the compound represented by the general formula (16) with the compound represented by the general formula (4). This reaction is carried out, for example, in the presence of a catalytic amount of a transition metal complex, in the presence or absence of a phosphine ligand, in the presence or absence of a base. Examples of the transition metal complex include [1,1-bis(diphenylphosphino)ferrocene]dichloropalladium(II), tetrakis(triphenylphosphine) palladium, palladium(II) acetate and tris(dibenzylideneacetone)dipalladium. Examples of the phosphine ligand include 2-(di-tert-butylphosphino)biphenyl and 2-dicyclohexylphoshino)biphenyl. Examples of the base include inorganic bases and organic bases. Examples of the solvent include ethers, amide type solvents, aromatic solvents, alcohol type solvents, water, or a mixed solvent thereof.

<Step 3>

The compound represented by the general formula (18) can be prepared by reacting the compound represented by the general formula (17) with phosphonoacetic acid triester. This reaction is known as "Horner-Wadsworth-Emmons reaction," and is carried out, for example, in the presence of a base, in a solvent. Crown ether may be added. Examples of the phosphonoacetic acid trimester include triethyl phosphonoacetate and bis(2,2,2-trifluoroethyl)(methoxycarbonylmethyl)phosphonate. Examples of the base include inorganic bases, organic bases and organometallic bases. Examples of the solvent include ether type solvents, aromatic solvents, or a mixed solvent thereof. When this preparation method is carried out, the compounds wherein the double bond is in the E form are mainly obtained. If it is necessary to prepare the compounds wherein the double bond is in the Z form, it is preferable to use bis(2,2,2-trifluoroethyl)(methoxycarbonylmethyl)phosphonate, potassium bis(trimethylsilyl)amide and 18-Crown-6.

In the aforementioned Scheme 5, even if the order of the Steps 2 and 3 in the process are reversed, the compounds represented by the general formula (18) can be prepared.

<Step 4>

The final target compound represented by the general formula (19) can be prepared by the hydrolysis of the compound represented by the general formula (18). This reaction is carried out, for example, in the presence of a base, in a solvent. The reaction may be carried out under ultrasonic irradiation. Examples of the base include inorganic bases. Examples of the solvent include ether type solvents, alcohol type solvents, water, or a mixed solvent thereof. When the aftertreatment is carried out under acidic condition, the free form of the carboxylic acid can be obtained. When the aftertreatment is carried out under basic condition, the salt of the carboxylic acid can be obtained.

The compounds represented by the aforementioned general formula (17) can also be prepared, for example, by the following method:

<Scheme 6>

[Formula 19]

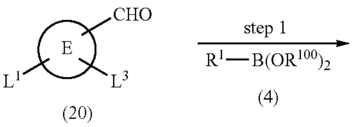

(20) (4)

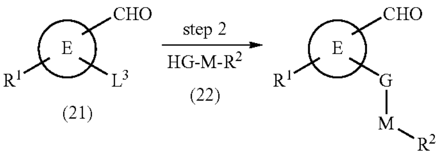

(21) (22) (17)

wherein $L^1$ represents a halogen atom or the like; $L^3$ represents a halogen atom or the like; $R^{100}$ represents a hydrogen atom, a $C_{1-6}$ alkyl group or the like; $R^1$, $R^2$, E, G and M have the same meanings as the aforementioned definitions.

<Step 1>

The compound represented by the general formula (21) can be prepared in the same manner as the aforementioned Step 2 in the Scheme 5 except using the compound represented by the general formula (20) in place of the compound represented by the general formula (16).

<Step 2>

The compound represented by the general formula (17) can be prepared by reacting the compound represented by the general formula (21) with the compound represented by the general formula (22). This reaction is carried out, for example, in the presence of a base, in a solvent. Examples of the base include inorganic bases, organic bases and organometallic bases. Examples of the solvent include ether type solvents, amide type solvents, aromatic solvents, or a mixed solvent thereof.

In the aforementioned Scheme 6, even if the order of the Steps 1 and 2 in the process are reversed, the compounds represented by the general formula (17) can be prepared.

The compounds represented by the aforementioned general formula (19) can also be prepared, for example, by the following method:

<Scheme 7>

[Formula 20]

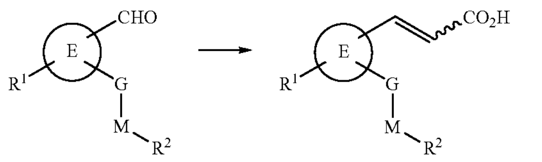

(17) (19)

wherein $R^1$, $R^2$, E, G and M have the same meanings as the aforementioned definitions.

The final target compound represented by the general formula (19) can be prepared by reacting the compound represented by the general formula (17) with malonic acid. This reaction is carried out, for example, in the presence of a catalytic amount of an amine, in the presence or absence of a base, without a solvent or in a solvent. Examples of the amine include pyrrolidine, piperidine and the like. Examples of the base include organic bases. Examples of the solvent include alcohol type solvents, or a mixed solvent thereof. When this preparation method is carried out, the compounds wherein the double bond is in the E form are mainly obtained.

The compounds represented by the formula (I), wherein m is 1, T is —R''—, X is —CH═CH—, and Y' is a carboxy group, can be prepared, for example, by the following method:

<Scheme 8>

[Formula 21]

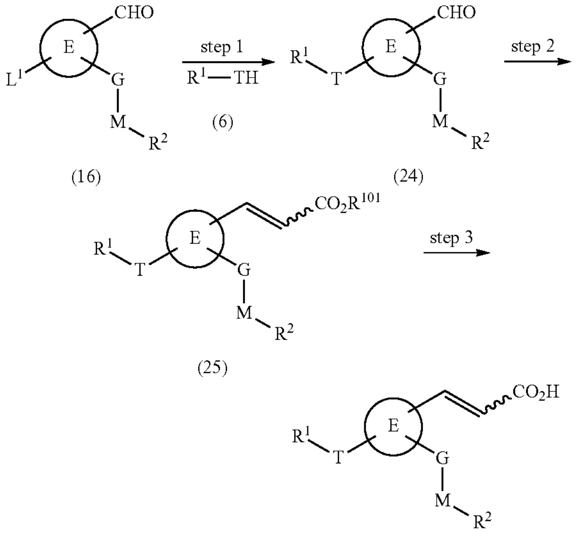

(16) (24) (25) (26)

wherein $L^1$ represents a halogen atom or the like; $R^{101}$ represents a $C_{1-6}$ alkyl group or the like; T represents —R''—; $R^1$, $R^2$, E, G and M have the same meanings as the aforementioned definitions.

<Step 1>

The compound represented by the general formula (24) can be prepared by reacting the compound represented by the general formula (16) with the compound represented by the general formula (6). This reaction is carried out, for example, in the presence of copper(II) oxide, in the presence of a base, in a solvent. Examples of the base include inorganic bases. As the solvent, any solvent can be used as long as it does not inhibit the reaction, and examples include halogenated solvents, pyridine, or or a mixed solvent thereof.

<Step 2>

The compound represented by the general formula (25) can be prepared in the same manner as the aforementioned Step 3 in the Scheme 5 except using the compound represented by the general formula (24) in place of the compound represented by the general formula (17).

In the aforementioned Scheme 8, even if the order of the Steps 1 and 2 in the process are reversed, the compounds represented by the general formula (25) can be prepared.

<Step 3>

The final target compound represented by the general formula (26) can be prepared in the same manner as the aforementioned Step 4 in the Scheme 5 except using the compound represented by the general formula (25) in place of the compound represented by the general formula (18). In the aforementioned Scheme 8, the compound represented by the general formula (26) can also be prepared by converting the formyl group of the compound represented by the general formula (16) into the corresponding acetal group, carrying out the reaction of the obtained acetal derivative in the same manner as the aforementioned Step 1, and then converting the acetal group into the corresponding formyl group.

The compounds represented by the aforementioned general formula (24), wherein -T-$R^1$ exists in the ortho or para position with respect to the formyl group can also be prepared, for example, by the following method:

<Scheme 9>

[Formula 22]

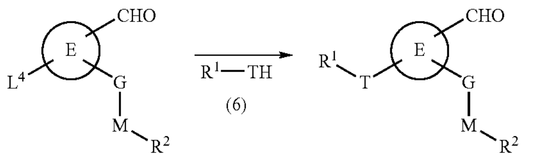

(27) (24)

wherein $L^4$ represents a halogen atom (preferably, a fluorine atom) or the like; $R^1$, $R^2$, T, E, G and M have the same meanings as the aforementioned definitions.

The compound represented by the general formula (24) can be prepared by reacting the compound represented by the general formula (27) with the compound represented by the general formula (6). This reaction is carried out, for example, in the presence of a base, in a solvent, at a reaction temperature of 0° C. to 180° C. (preferably, at a temperature of 0° C. to the boiling point of the solvent). Examples of the base include inorganic bases, organic bases and organometallic bases. Examples of the solvent include ether type solvents, amide type solvents, aromatic solvents, or a mixed solvent thereof.

The compound represented by the aforementioned general formula (24) can also be prepared, for example, by the following method:

<Scheme 10>

[Formula 23]

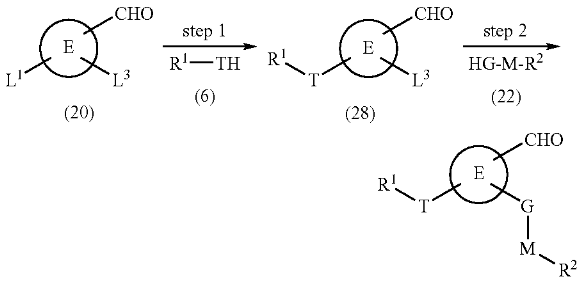

(20) (28) (24)

wherein $L^1$ represents a halogen atom or the like; $L^3$ represents a halogen atom or the like; $R^1$, $R^2$, T, E, G and M have the same meanings as the aforementioned definitions.

<Step 1>

The compound represented by the general formula (28) can be prepared in the same manner as the aforementioned Step 1 in the Scheme 8 except using the compound represented by the general formula (20) in place of the compound represented by the general formula (16).

<Step 2>

The compound represented by the general formula (24) can be prepared in the same manner as the aforementioned Step 2 in the Scheme 6 except using the compound represented by the general formula (28) in place of the compound represented by the general formula (21).

In the aforementioned Scheme 10, even if the order of the Steps 1 and 2 in the process are reversed, the compounds represented by the general formula (24) can be prepared.

The compounds represented by the aforementioned general formula (28) can also be prepared, for example, by the following method:

<Scheme 11>

[Formula 24]

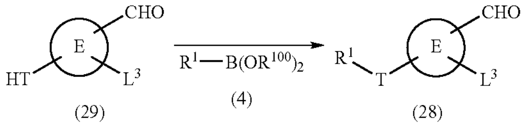

(29) (28)

wherein $L^3$ represents a halogen atom or the like; $R^{100}$ represents a hydrogen atom, a $C_{1-6}$ alkyl group or the like; $R^1$, T and E has the same meaning as the aforementioned definition.

The compound represented by the general formula (28) can be prepared by reacting the compound represented by the general formula (29) with the compound represented by the general formula (4). This reaction is carried out, for example, in the presence of copper(II) acetate, in the presence of a base, in a solvent. Molecular Sieves may be added. Examples of the base include organic bases.

Examples of the solvent include halogenated solvents, pyridine, or a mixed solvent thereof.

The compound represented by the aforementioned general formula (26) can also be prepared, for example, by the following method:

<Scheme 12>

[Formula 25]

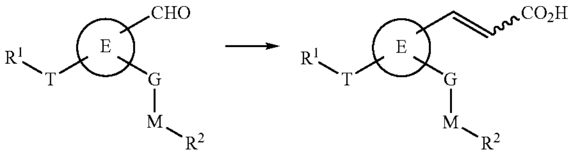

(24) (26)

wherein $R^1$, $R^2$, T, E, G and M have the same meanings as the aforementioned definitions.

The compound represented by the general formula (26) can be prepared in the same manner as the aforementioned Scheme 7 except using the compound represented by the general formula (24) in place of the compound represented by the general formula (17).

The compounds represented by the formula (I), wherein m is 1, T is a single bond, X is —CH═CH—, and Y' is a 1H-tetrazol-5-yl group, can be prepared, for example, by the following method:

<Scheme 13>

[Formula 26]

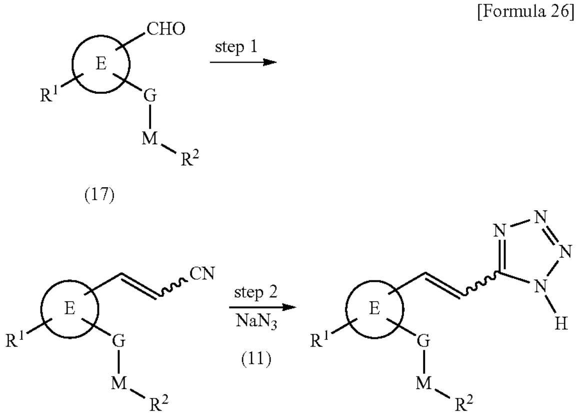

(17) (30) (31)

wherein $R^1$, $R^2$, E, G and M have the same meanings as the aforementioned definitions.

<Step 1>

The compound represented by the general formula (30) can be prepared in the same manner as the aforementioned Step 3 in the Scheme 5 except using cyanomethylphosphonic acid diester in place of phosphonoacetic acid triester. Examples of the cyanomethylphosphonic acid diester include diethyl cyanomethylphosphonate.

<Step 2>

The final target compound represented by the general formula (31) can be prepared in the same manner as the aforementioned Step 3 in the Scheme 3 except using the compound represented by the general formula (30) in place of the compound represented by the general formula (10).

The compounds represented by the formula (I), wherein m is 1, T is —R"—, X is —CH═CH—, and Y' is a 1H-tetrazol-5-yl group, can be prepared, for example, by the following method:

<Scheme 14>

[Formula 27]

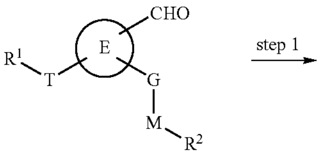

(24)

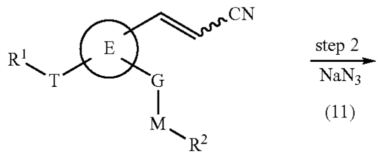

(32)

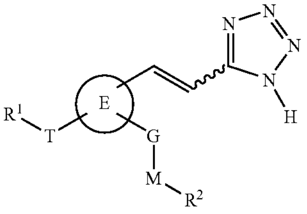

(33)

wherein T represents —R"—; $R^1$, $R^2$, E, G and M have the same meanings as the aforementioned definitions.

<Step 1>

The compound represented by the general formula (32) can be prepared in the same manner as the aforementioned Step 3 in the Scheme 5 except using the compound represented by the general formula (24) in place of the compound represented by the general formula (17) and using cyanomethylphosphonic acid diester in place of phosphonoacetic acid triester. Examples of the cyanomethylphosphonic acid diester include diethyl cyanomethylphosphonate.

<Step 2>

The final target compound represented by the general formula (33) can be prepared in the same manner as the aforementioned Step 3 in the Scheme 3 except using the compound represented by the general formula (32) in place of the compound represented by the general formula (10).

The compounds represented by the formula (I), wherein m is 1, T is a single bond, X is the formula —V'—(V')$_k$—, V' is a methylene group, k is 1, and Y' is a carboxy group, can be prepared, for example, by the following method:

<Scheme 15>

[Formula 28]

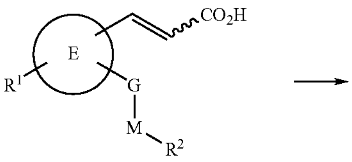

(19)

-continued

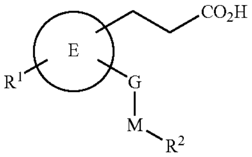

(34)

wherein $R^1$, $R^2$, E, G and M have the same meanings as the aforementioned definitions.

The final target compound represented by the general formula (34) can be prepared by the reduction of the double bond of the compound represented by the general formula (19). This reaction is carried out, for example, in the presence of a catalytic amount of a transition metal, under hydrogen atmosphere, in a solvent. Examples of the transition metal include palladium on activated carbon and platinum dioxide. When M is the formula $-(Q^1)_n-(Q^2)_p-(Q^3)_r-(U')_q-$, the formula $-(Q^1)_n-(Q^2)_p-(U')_q-(Q^3)_r-$ or the formula $-(Q^1)_n-(U')_q-(Q^2)_p-(Q^3)_r-$, n is 1, p is 0, q is 0, and r is 0, it is preferable to use platinum dioxide. Examples of the solvent include ether type solvents, alcohol type solvents, water, or a mixed solvent thereof. As it is obvious from the present preparation method, the compounds represented by the formula (I), wherein X is —CH═CH—, are useful as the synthetic intermediates for the compounds wherein X is the formula —V'—(V')$_k$—, V' is a methylene group, and k is 1.

The compounds represented by the formula (I), wherein m is 1, T is —R"—, X is the formula —V'—(V')$_k$—, V' is a methylene group, k is 1, and Y' is a carboxy group, can be prepared, for example, by the following method:

<Scheme 16>

[Formula 29]

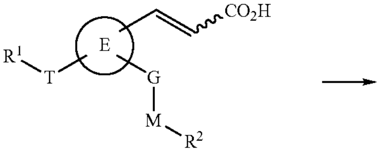

(26)

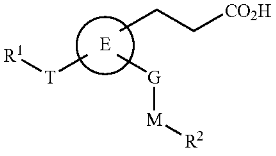

(35)

wherein T represents —R"—; $R^1$, $R^2$, E, G and M have the same meanings as the aforementioned definitions.

The final target compound represented by the general formula (35) can be prepared in the same manner as the aforementioned Scheme 15 except using the compound represented by the general formula (26) in place of the compound represented by the general formula (19).

The compounds represented by the formula (I), wherein m is 1, T is a single bond, X is the formula —V'—(V')$_k$—, V' is a methylene group, k is 1, and Y' is a 1H-tetrazol-5-yl group, can be prepared, for example, by the following method:

<Scheme 17>

[Formula 30]

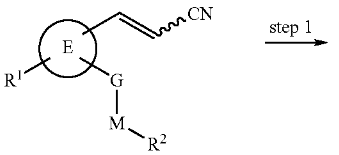

(30)

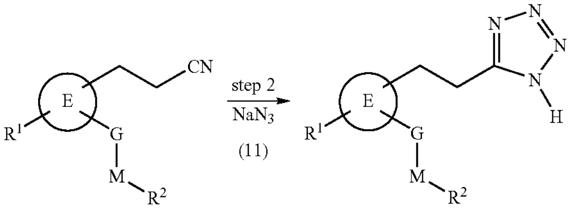

(36) (37)

wherein $R^1$, $R^2$, E, G and M have the same meanings as the aforementioned definitions.

<Step 1>

The compound represented by the general formula (36) can be prepared in the same manner as the aforementioned Scheme 15 except using the compound represented by the general formula (30) in place of the compound represented by the general formula (19).

<Step 2>

The final target compound represented by the general formula (37) can be prepared in the same manner as the aforementioned Step 3 in the Scheme 3 except using the compound represented by the general formula (36) in place of the compound represented by the general formula (10).

The compounds represented by the formula (I), wherein m is 1, T is —R''—, X is the formula —V'—(V')$_k$—, V' is a methylene group, k is 1, and Y' is a 1H-tetrazol-5-yl group, can be prepared, for example, by the following method:

<Scheme 18>

[Formula 31]

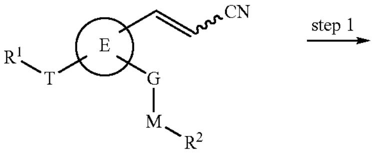

(32)

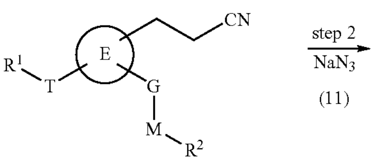

(38)

-continued

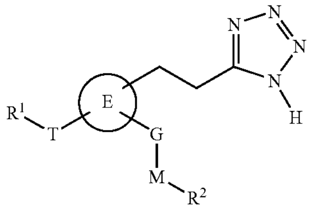

(39)

wherein T represents —R''—; $R^1$, $R^2$, E, G and M have the same meanings as the aforementioned definitions.

<Step 1>

The compound represented by the general formula (38) can be prepared in the same manner as the aforementioned Scheme 15 except using the compound represented by the general formula (32) in place of the compound represented by the general formula (19).

<Step 2>

The final target compound represented by the general formula (39) can be prepared in the same manner as the aforementioned Step 3 in the Scheme 3 except using the compound represented by the general formula (38) in place of the compound represented by the general formula (10).

The compounds represented by the formula (I), wherein m is 1, T is a single bond, X is the formula —N($R^4$)—C(=O)—, $R^4$ is a hydrogen atom, and Y' is a carboxy group, can be prepared, for example, by the following method:

<Scheme 19>

[Formula 32]

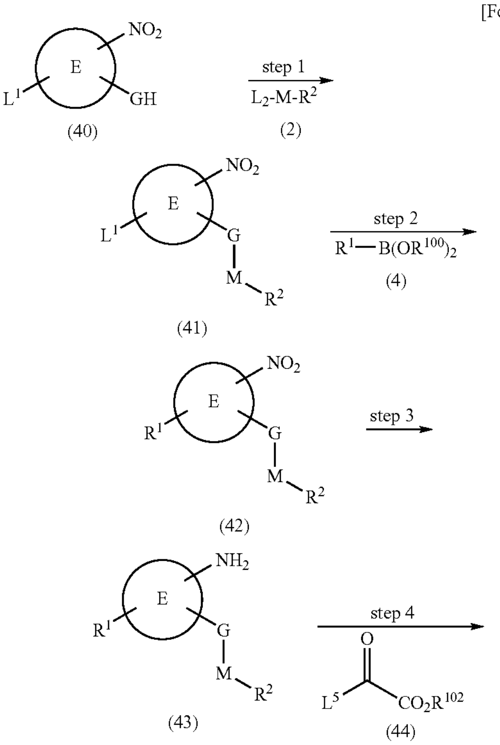

-continued

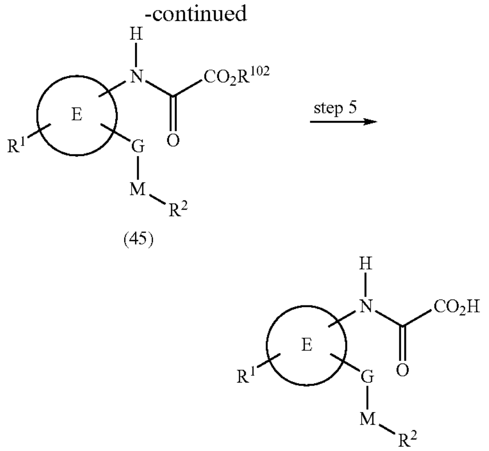

(45)

(46)

wherein $L^1$ represents a halogen atom or the like; $L^2$ represents a halogen atom or the like; $L^5$ represents a halogen atom or the like; $R^{100}$ represents a hydrogen atom, a $C_{1-6}$ alkyl group or the like; $R^{102}$ represents a $C_{1-6}$ alkyl group or the like; $R^1$, $R^2$, E, G and M have the same meanings as the aforementioned definitions.

<Step 1>

The compound represented by the general formula (41) can be prepared in the same manner as the aforementioned Step 1 in the Scheme 5 except using the compound represented by the general formula (40) in place of the compound represented by the general formula (15).

<Step 2>

The compound represented by the general formula (42) can be prepared in the same manner as the aforementioned Step 2 in the Scheme 5 except using the compound represented by the general formula (41) in place of the compound represented by the general formula (16).

<Step 3>

The compound represented by the general formula (43) can be prepared by the reduction of the nitro group of the compound represented by the general formula (42). This reaction is carried out, for example, in the presence of a catalytic amount of a transition metal, under hydrogen atmosphere, in a solvent. Examples of the transition metal include palladium on activated carbon, platinum dioxide and Raney nickel. When M is the formula $-(Q^1)_n-(Q^2)_p-(Q^3)_r-(U')_q-$, the formula $-(Q^1)_n-(Q^2)_p-(U')_q-(Q^3)_r-$ or the formula $-(Q^1)_n-(U')_q-(Q^2)_p-(Q^3)_r-$, n is 1, p is 0, q is 0, and r is 0, it is preferable to use platinum dioxide. Examples of the solvent include ether type solvents, alcohol type solvents, water, or a mixed solvent thereof.

The aforementioned reductive reduction of the nitro group can also be carried out in the presence of a metal or a metal halide, in the presence or absence of an acid, in a solvent. Examples of the metal include iron, tin and zinc. Examples of the metal halide include tin(II) chloride. Examples of the acid include inorganic acids and organic acids. Examples of the solvent include alcohol type solvents, water, or a mixed solvent thereof.

<Step 4>

The compound represented by the general formula (45) can be prepared by reacting the compound represented by the general formula (43) with the compound represented by the general formula (44). This reaction is carried out, for example, in the presence of a base, in a solvent. Examples of the base include inorganic bases and organic bases. Examples of the solvent include halogenated solvents, ether type solvents, or a mixed solvent thereof.

<Step 5>

The final target compound represented by the general formula (46) can be prepared by the hydrolysis of the compound represented by the general formula (45). This reaction is carried out, for example, in the presence of a base, in a solvent. The reaction may be carried out under ultrasonic irradiation. Examples of the base include inorganic bases. Examples of the solvent include ether type solvents, alcohol type solvents, water, or a mixed solvent thereof. When the aftertreatment is carried out under acidic condition, the free form of the oxamic acid can be obtained. When the aftertreatment is carried out under basic condition, the salt of the oxamic acid can be obtained. The compounds represented by the formula (I), wherein m is 1, T is a single bond, X is the formula $—N(R^4)—V'—$, $R^4$ is a hydrogen atom, and Y' is a carboxy group, can be prepared in the same manner as the aforementioned Steps 1 to 5 in the Scheme 19 except using the compound represented by the formula $L^5$-V'—$CO_2R^{102}$ in place of the compound represented by the general formula (44).

The compounds represented by the formula (I), wherein m is 1, T is a single bond, X is $—N(R^4)—C(=O)—$, $R^4$ is a $C_{1-6}$ alkyl group, and Y' is a carboxy group, can be prepared, for example, by the following method:

<Scheme 20>

[Formula 33]

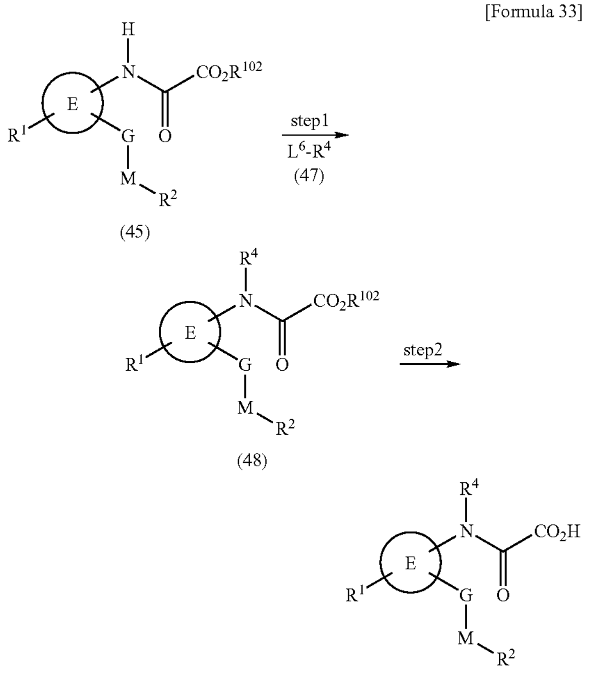

(45)

(48)

(49)

wherein $R^4$ represents a $C_{1-6}$ alkyl group; $L^6$ represents a halogen atom or the like; $R^{102}$ represents a $C_{1-6}$ alkyl group or the like; $R^1$, $R^2$, E, G and M have the same meanings as the aforementioned definitions.

<Step 1>

The compound represented by the general formula (48) can be prepared by reacting the compound represented by the general formula (45) with the compound represented by the general formula (47). This reaction is carried out, for example, in the presence of a base, in a solvent. Crown ether may be added. Examples of the base include inorganic bases, organic bases and organometallic bases. Examples of the solvent include halogenated solvents, ether type solvents, amide type solvents, aromatic solvents, ketone type solvents, acetonitrile, or a mixed solvent thereof.

<Step 2>

The final target compound represented by the general formula (49) can be prepared in the same manner as the aforementioned Step 5 in the Scheme 19 except using the compound represented by the general formula (48) in place of the compound represented by the general formula (45). The compounds represented by the formula (I), wherein m is 1, T is a single bond, X is the formula —N($R^4$)—V'—, $R^4$ is a $C_{1-6}$ alkyl group, and Y' is a carboxy group, can be prepared in the same manner as the aforementioned Steps 1 to 4 in the Scheme 19 and Steps 1 to 2 in the Scheme 20, except using the compound represented by the formula $L^5$-V'—$CO_2R^{102}$ in place of the compound represented by the general formula (44).

The compounds represented by the formula (I), wherein m is 1, T is —R"—, X is —N($R^4$)—C(═O)—, $R^4$ is a hydrogen atom, and Y' is a carboxy group, can be prepared, for example, by the following method:

<Scheme 21>

[Formula 34]

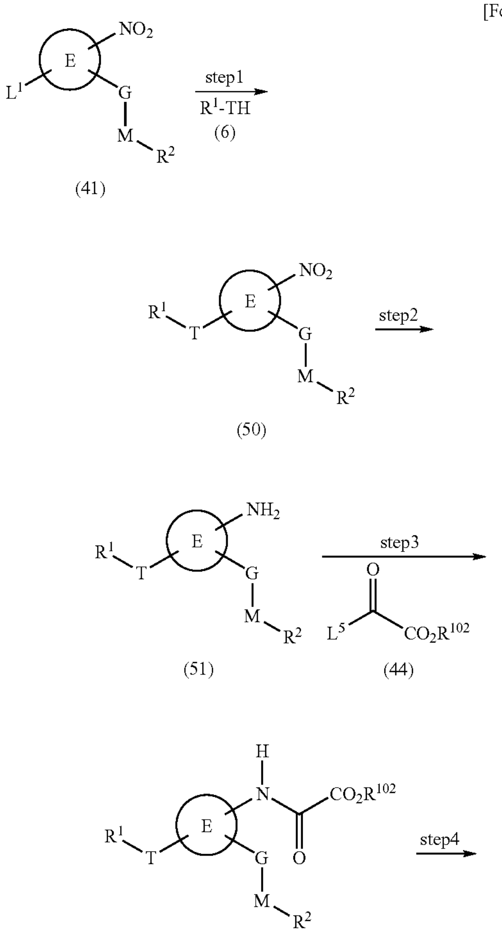

(41) (50) (51) (44) (52)

-continued

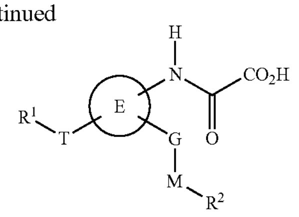

(53)

wherein $L^1$ represents a halogen atom or the like; $L^5$ represents a halogen atom; $R^{102}$ represents a $C_{1-6}$ alkyl group or the like; T represents —R"—; $R^1$, $R^2$, E, G and M have the same meanings as the aforementioned definitions.

<Step 1>

The compound represented by the general formula (50) can be prepared in the same manner as the aforementioned Step 1 in the Scheme 8 except using the compound represented by the general formula (41) in place of the compound represented by the general formula (16).

<Step 2>

The compound represented by the general formula (51) can be prepared in the same manner as the aforementioned Step 3 in the Scheme 19 except using the compound represented by the general formula (50) in place of the compound represented by the general formula (42).

<Step 3>

The compound represented by the general formula (52) can be prepared in the same manner as the aforementioned Step 4 in the Scheme 19 except using the compound represented by the general formula (51) in place of the compound represented by the general formula (43).

<Step 4>

The final target compound represented by the general formula (53) can be prepared in the same manner as the aforementioned Step 5 in the Scheme 19 except using the compound represented by the general formula (52) in place of the compound represented by the general formula (45). The compounds represented by the formula (I), wherein m is 1, T is —R"—, X is the formula —N($R^4$)—V'—, $R^4$ is a hydrogen atom, and Y' is a carboxy group, can be prepared in the same manner as the aforementioned Steps 1 to 4 in the Scheme 21 except using the compound represented by the formula $L^5$-V'—$CO_2R^{102}$ in place of the compound represented by the general formula (44).

The compounds represented by the formula (I), wherein m is 1, T is —R"—, X is —N($R^4$)—C(═O)—, $R^4$ is a $C_{1-6}$ alkyl group, and Y' is a carboxy group, can be prepared, for example, by the following method:

<Scheme 22>

[Formula 35]

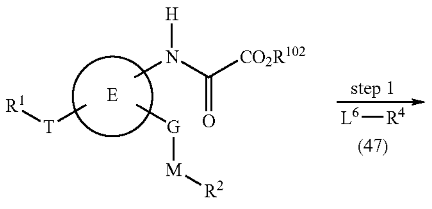

(52)

-continued

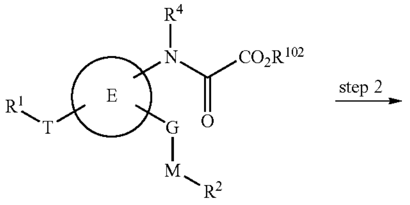

(54)

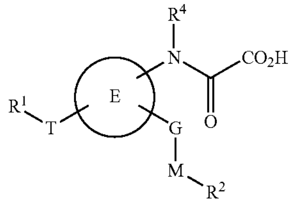

(55)

wherein $R^4$ represents a $C_{1-6}$ alkyl group; $L^6$ represents a halogen atom or the like; $R^{102}$ represents a $C_{1-6}$ alkyl group or the like; T represents —R"—; $R^1$, $R^2$, E, G and M have the same meanings as the aforementioned definitions.

<Step 1>

The compound represented by the general formula (54) can be prepared in the same manner as the aforementioned Step 1 in the Scheme 20 except using the compound represented by the general formula (52) in place of the compound represented by the general formula (45).

<Step 2>

The final target compound represented by the general formula (55) can be prepared in the same manner as the aforementioned Step 5 in the Scheme 19 except using the compound represented by the general formula (54) in place of the compound represented by the general formula (45). The compounds represented by the formula (I), wherein m is 1, T is —R"—, X is the formula —N($R^4$)—V'—, $R^4$ is a $C_{1-6}$ alkyl group, and Y' is a carboxy group, can be prepared in the same manner as the aforementioned Steps 1 to 3 in the Scheme 21 and Steps 1 to 2 in the Scheme 22, except using the compound represented by the formula $L^5$-V'—$CO_2R^{102}$ in place of the compound represented by the general formula (44).

The compounds represented by the formula (I), wherein m is 1, T is a single bond, X is the formula —$(V')_k$—R"—W'—, k is 1, and Y' is a carboxy group, can be prepared, for example, by the following method:

<Scheme 23>

[Formula 36]

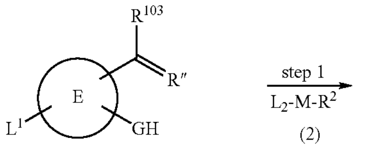

(56)

-continued

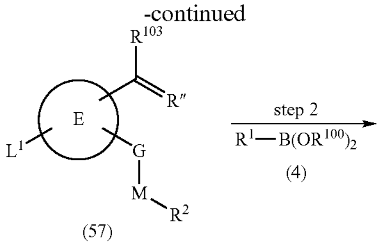

(57)

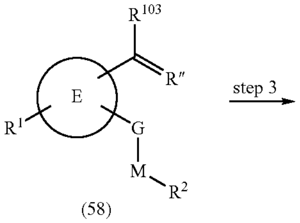

(58)

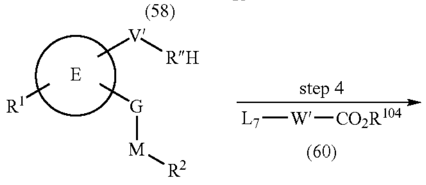

(59)

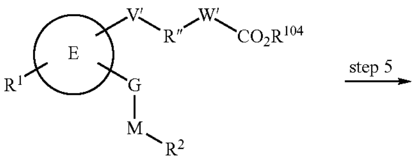

(61)

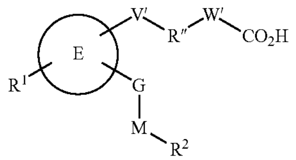

(62)

wherein $L^1$ represents a halogen atom or the like; $L^2$ represents a halogen atom or the like; $L^7$ represents a halogen atom or the like; $R^{100}$ represents a hydrogen atom, a $C_{1-6}$ alkyl group or the like; $R^{103}$ represents a hydrogen atom, or a $C_{1-6}$ alkyl group; $R^{104}$ represents a $C_{1-6}$ alkyl group or the like; $R^1$, $R^2$, E, G, M, R", V' and W' have the same meanings as the aforementioned definitions.

<Step 1>

The compound represented by the general formula (57) can be prepared in the same manner as the aforementioned Step 1 in the Scheme 5 except using the compound represented by the general formula (56) in place of the compound represented by the general formula (15).

<Step 2>

The compound represented by the general formula (58) can be prepared in the same manner as the aforementioned Step 2 in the Scheme 5 except using the compound represented by the general formula (57) in place of the compound represented by the general formula (16).

In the aforementioned Scheme 23, even if the order of the Steps 1 and 2 in the process are reversed, the compounds represented by the general formula (58) can be prepared.

<Step 3>

The compound represented by the general formula (59) can be prepared by the reduction of the carbonyl group of the compound represented by the general formula (58). This reaction is carried out, for example, in the presence of a reducing agent, in a solvent. Examples of the reducing agent include sodium borohydride, lithium borohydride, lithium aluminium hydride and diisobutylaluminium hydride. Examples of the solvent include ether type solvents, alcohol type solvents, water, or a mixed solvent thereof.

<Step 4>

The compound represented by the general formula (61) can be prepared by reacting the compound represented by the general formula (59) with the compound represented by the general formula (60). This reaction is carried out, for example, in the presence of a base, in a solvent. Crown ether may be added. Examples of the base include inorganic bases, organic bases and organometallic bases. Examples of the solvent include halogenated solvents, ether type solvents, amide type solvents, aromatic solvents, ketone type solvents, acetonitrile, or a mixed solvent thereof.

<Step 5>

The final target compound represented by the general formula (62) can be prepared in the same manner as the aforementioned Step 4 in the Scheme 5 except using the a compound represented by the general formula (61) in place of the compound represented by the general formula (18).

The compounds represented by the aforementioned general formula (58) can also be prepared, for example, by the following method:

<Scheme 24>

[Formula 37]

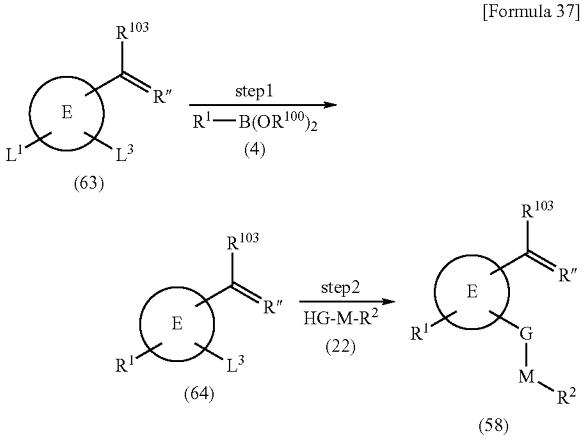

(63) (64) (58)

wherein $L^1$ represents a halogen atom or the like; $L^3$ represents a halogen atom or the like; $R^{100}$ represents a hydrogen atom, a $C_{1-6}$ alkyl group or the like; $R^{103}$ represents a hydrogen atom, or a $C_{1-6}$ alkyl group; $R^1$, $R^2$, E, G, R" and M have the same meanings as the aforementioned definitions.

<Step 1>

The compound represented by the general formula (64) can be prepared in the same manner as the aforementioned Step 2 in the Scheme 5 except using the compound represented by the general formula (63) in place of the compound represented by the general formula (16).

<Step 2>

The compound represented by the general formula (58) can be prepared in the same manner as the aforementioned Step 2 in the Scheme 6 except using the compound represented by the general formula (64) in place of the compound represented by the general formula (21).

In the aforementioned Scheme 24, even if the order of the Steps 1 and 2 in the process are reversed, the compounds represented by the general formula (58) can be prepared.

The compounds represented by the formula (I), wherein m is 1, T is —R"—X is the formula —$(V')_k$—R"—W'—, k is 1, and Y' is a carboxy group, can be prepared, for example, by the following method:

<Scheme 25>

[Formula 38]

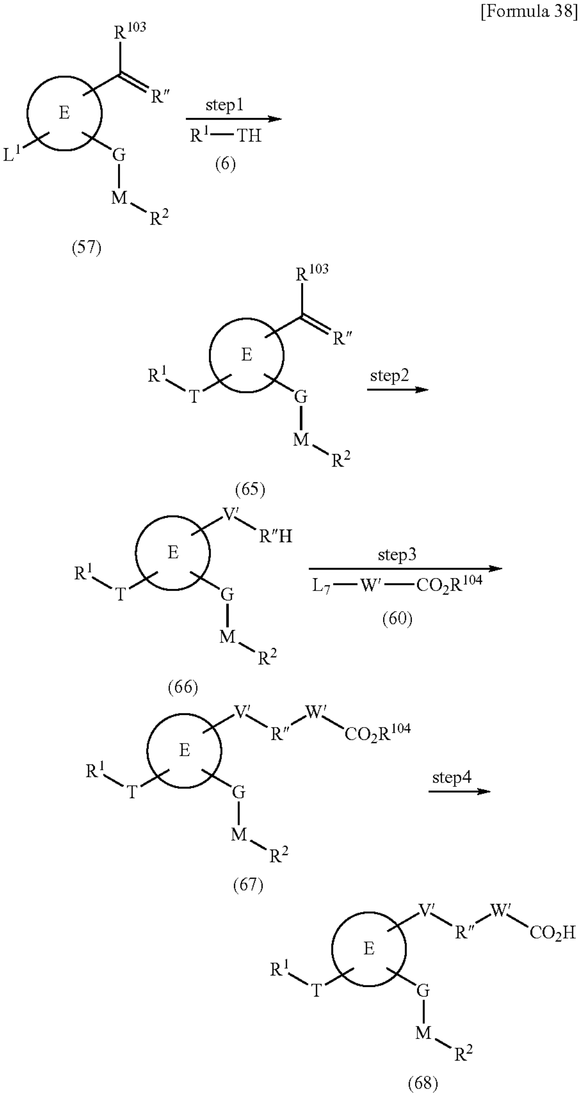

(57) (65) (66) (67) (68)

wherein $L^1$ represents a halogen atom or the like; $L^7$ represents a halogen atom or the like; $R^{103}$ represents a hydrogen atom, or a $C_{1-6}$ alkyl group; $R^{104}$ represents a $C_{1-6}$ alkyl group or the like; T represents —R"—; $R^1$, $R^2$, E, G, M, R", V' and W' have the same meanings as the aforementioned definitions.

<Step 1>

The compound represented by the general formula (65) can be prepared in the same manner as the aforementioned Step 1 in the Scheme 8 except using the compound represented by the general formula (57) in place of the compound represented by the general formula (16).

<Step 2>

The compound represented by the general formula (66) can be prepared in the same manner as the aforementioned Step 3 in the Scheme 23 except using the compound represented by the general formula (65) in place of the compound represented by the general formula (58).

<Step 3>

The compound represented by the general formula (67) can be prepared in the same manner as the aforementioned Step 4 in the Scheme 23 except using the compound represented by the general formula (66) in place of the compound represented by the general formula (59).

<Step 4>

The final target compound represented by the general formula (68) can be prepared in the same manner as the aforementioned Step 4 in the Scheme 5 except using the compound represented by the general formula (67) in place of the compound represented by the general formula (18).

The compounds represented by the aforementioned general formula (65), wherein -T-$R^1$ exist in the ortho or para position with respect to —C(═R")—$R^{103}$ can also be prepared, for example, by the following method:

<Scheme 26>

[Formula 39]

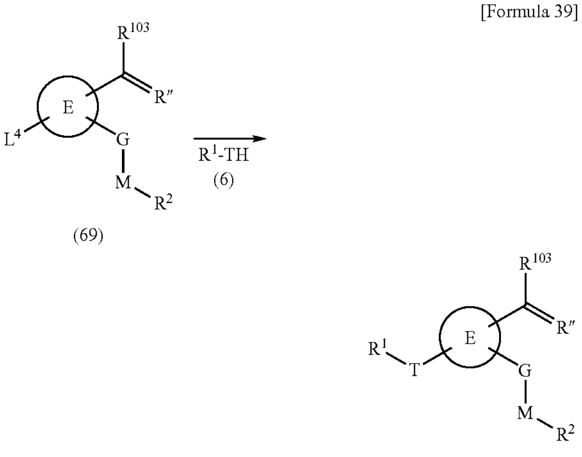

(69)

(65)

wherein $L^4$ represents a halogen atom (preferably, a fluorine atom) or the like; $R^{103}$ represents a hydrogen atom, or a $C_{1-6}$ alkyl group; $R^1$, $R^2$, T, E, G, R" and M have the same meanings as the aforementioned definitions.

The compound represented by the general formula (65) can be prepared in the same manner as the aforementioned Scheme 9 except using the compound represented by the general formula (69) in place of the compound represented by the general formula (27).

The compounds represented by the aforementioned general formula (65) can also be prepared, for example, by the following method:

<Scheme 27>

[Formula 40]

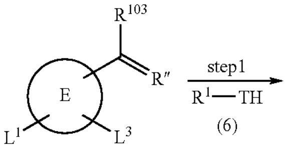

(63)

-continued

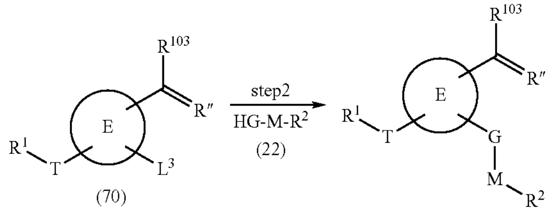

(70)

(65)

wherein $L^1$ represents a halogen atom or the like; $L^3$ represents a halogen atom or the like; $R^{103}$ represents a hydrogen atom, or a $C_{1-6}$ alkyl group; $R^1$, $R^2$, T, E, G, R" and M have the same meanings as the aforementioned definitions.

<Step 1>

The compound represented by the general formula (70) can be prepared in the same manner as to the aforementioned Step 1 in the Scheme 8 except using the compound represented by the general formula (63) in place of the compound represented by the general formula (16).

<Step 2>

The compound represented by the general formula (65) can be prepared in the same manner as the aforementioned Step 2 in the Scheme 6 except using the compound represented by the general formula (70) in place of the compound represented by the general formula (21).

In the aforementioned Scheme 27, even if the order of the Steps 1 and 2 in the processes are reversed, the compounds represented by the general formula (65) can be prepared.

The compounds represented by the aforementioned general formula (70) can also be prepared, for example, by the following method:

<Scheme 28>

[Formula 41]

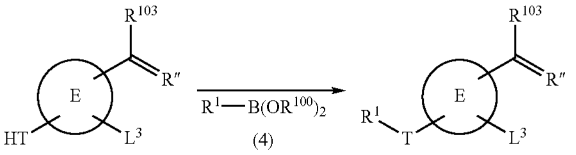

(71)

(70)

Wherein $L^3$ represents a halogen atom or the like; $R^{100}$ represents a hydrogen atom, a $C_{1-6}$ alkyl group or the like; $R^{103}$ represents a hydrogen atom, or a $C_{1-6}$ alkyl group; $R^1$, T, R" and E have the same meanings as the aforementioned definitions.

The compound represented by the general formula (70) can be prepared in the same manner as the aforementioned Scheme 11 except using the compound represented by the general formula (71) in place of the compound represented by the general formula (29).

The compounds represented by the formula (I), wherein m is 1, T is a single bond, X is the formula —$(V')_k$—R"—W'—, k is 1, and Y' is a 1H-tetrazol-5-yl group, can be prepared, for example, by the following method:

<Scheme 29>

[Formula 42]

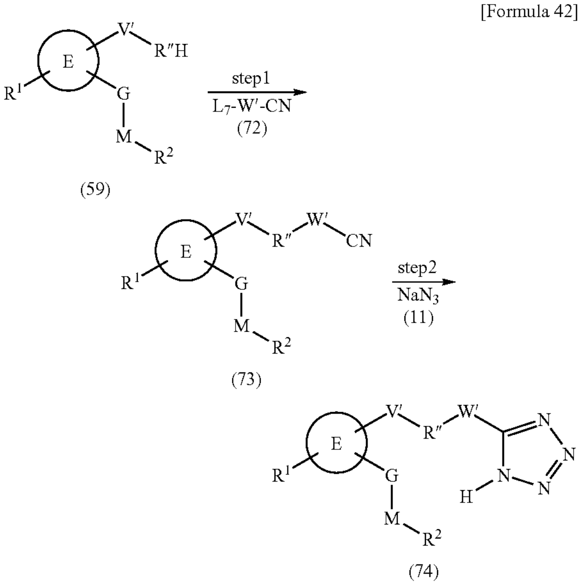

wherein $L^7$ represents a halogen atom or the like; $R^1$, $R^2$, E, M, G, R", V' and W' have the same meanings as the aforementioned definitions.

<Step 1>

The compound represented by the general formula (73) can be prepared in the same manner as the aforementioned Step 4 in the Scheme 23 except using the compound represented by the general formula (72) in place of the compound represented by the general formula (60).

<Step 2>

The final target compound represented by the general formula (74) can be prepared in the same manner as the aforementioned Step 3 in the Scheme 3 except using the compound represented by the general formula (73) in place of the compound represented by the general formula (10).

The compounds represented by the formula (I), wherein m is 1, T is —R"—, X is the formula —$(V')_k$—R"—W'—, k is 1, and Y' is a 1H-tetrazol-5-yl group, can be prepared, for example, by the following method:

<Scheme 30>

[Formula 43]

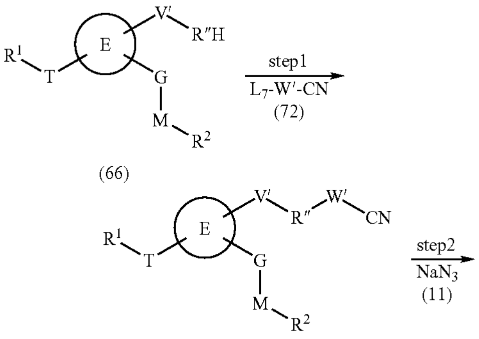

(75)

-continued

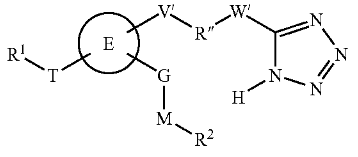

(76)

wherein $L^7$ represents a halogen atom or the like; T represents —R"—; $R^1$, $R^2$, E, M, G, R", V' and W' have the same meanings as the aforementioned definitions.

<Step 1>

The compound represented by the general formula (75) can be prepared in the same manner as the aforementioned Step 4 in the Scheme 23 except using the compound represented by the general formula (66) in place of the compound represented by the general formula (59) and using the compound represented by the general formula (72) in place of the compound represented by the general formula (60).

<Step 2>

The final target compound represented by the general formula (76) can be prepared in the same manner as the aforementioned Step 3 in the Scheme 3 except using the compound represented by the general formula (75) in place of the compound represented by the general formula (10).

The compounds represented by the formula (I), wherein m is 1, T is a single bond, X is the formula —$(V')_k$—R"—W'—, R" is an oxygen atom, k is 0, and Y' is a carboxy group, can be prepared, for example, by the following method:

<Scheme 31>

[Formula 44]

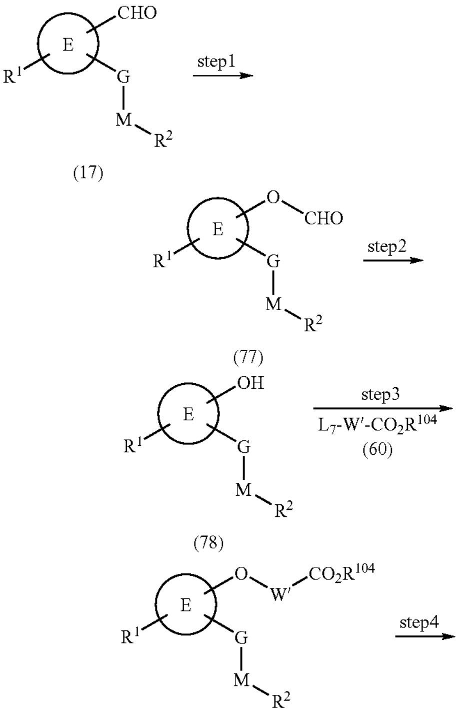

(79)

-continued

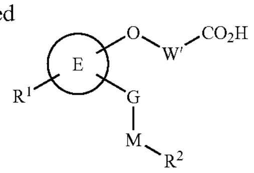

(80)

wherein $L^7$ represents a halogen atom or the like; $R^{104}$ represents a $C_{1-6}$ alkyl group or the like; $R^1$, $R^2$, E, M, G and W' have the same meanings as the aforementioned definitions.

<Step 1>

The compound represented by the general formula (77) can be prepared by reacting the compound represented by the general formula (17) with percarboxylic acid. This reaction is known as "Baeyer-Villiger oxidation," and is carried out, for example, in a solvent. Examples of the percarboxylic acid include peracetic acid, m-chloroperbenzoic acid and the like. Examples of the solvent include halogenated solvents.

<Step 2>

The compound represented by the general formula (78) can be prepared by the hydrolysis of the compound represented by the general formula (77). This reaction is carried out, for example, in the presence of an acid or a base, in a solvent. Examples of the acid include for example, inorganic acids and organic acids. Examples of the base include inorganic bases. Examples of the solvent include ether type solvents, alcohol type solvents, water, or a mixed solvent thereof.

<Step 3>

The compound represented by the general formula (79) can be prepared by reacting the compound represented by the general formula (78) with the compound represented by the general formula (60). This reaction is carried out, for example, in the presence of a base, in a solvent. Crown ether may be added. Examples of the base include inorganic bases, organic bases and organometallic bases. Examples of the solvent include halogenated solvents, ether type solvents, amide type solvents, aromatic solvents, ketone type solvents, acetonitrile, or a mixed solvent thereof.

<Step 4>

The final target compound represented by the general formula (80) can be prepared in the same manner as the aforementioned Step 4 in the Scheme 5 except using the compound represented by the general formula (79) in place of the compound represented by the general formula (18).

The compounds represented by the formula (I), wherein m is 1, T is —R"—, X is the formula —$(V')_k$—R"—W'—, R" is an oxygen atom, k is 0, and Y' is a carboxy group, can be prepared, for example, by the following method:

<Scheme 32>

[Formula 45]

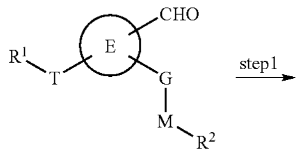

(24)

-continued

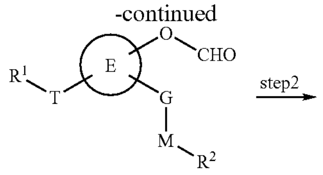

(81)

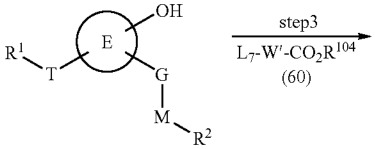

(82)

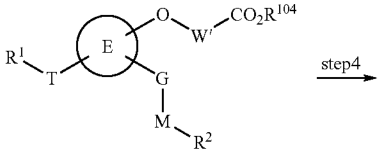

(83)

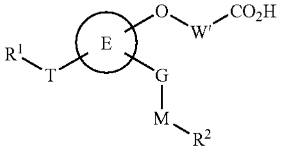

(84)

wherein $L^7$ represents a halogen atom or the like; $R^{104}$ represents a $C_{1-6}$ alkyl group or the like; T represents —R"—; $R^1$, $R^2$, E, M, G and W' have the same meanings as the aforementioned definitions.

<Step 1>

The compound represented by the general formula (81) can be prepared in the same manner as the aforementioned Step 1 in the Scheme 31 except using the compound represented by the general formula (24) in place of the compound represented by the general formula (17).

<Step 2>

The compound represented by the general formula (82) can be prepared in the same manner as the aforementioned Step 2 in the Scheme 31 except using the compound represented by the general formula (81) in place of the compound represented by the general formula (77).

<Step 3>

The compound represented by the general formula (83) can be prepared in the same manner as to the aforementioned Step 3 in the Scheme 31 except using the compound represented by the general formula (82) in place of the compound represented by the general formula (78).

<Step 4>

The final target compound represented by the general formula (84) can be prepared in the same manner as the aforementioned Step 4 in the Scheme 5 except using the compound represented by the general formula (83) in place of the compound represented by the general formula (18).

The compounds represented by the formula (I), wherein m is 1, T is a single bond, X is the formula —$(V')_k$—R"—W'—, R" is an oxygen atom, k is 0, and Y' is a 1H-tetrazol-5-yl group, can be prepared, for example, by the following method:

<Scheme 33>

[Formula 46]

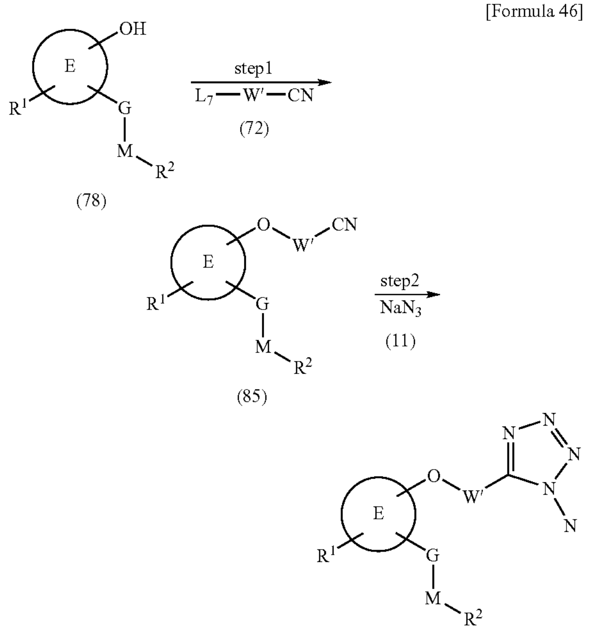

(78) (85) (86)

wherein $L^7$ represents a halogen atom or the like; $R^1$, $R^2$, E, M, G and W' have the same meanings as the aforementioned definitions.

<Step 1>

The compound represented by the general formula (85) can be prepared in the same manner as the aforementioned Step 3 in the Scheme 31 except using the compound represented by the general formula (72) in place of the compound represented by the general formula (60).

<Step 2>

The final target compound represented by the general formula (86) can be prepared in the same manner as the aforementioned Step 3 in the Scheme 3 except using the compound represented by the general formula (85) in place of the compound represented by the general formula (10).

The compounds represented by the formula (I), wherein m is 1, T is —R"—, X is the formula —$(V')_k$—R"—W'—, R" is an oxygen atom, k is 0, and Y' is a 1H-tetrazol-5-yl group, can be prepared, for example, by the following method:

<Scheme 34>

[Formula 47]

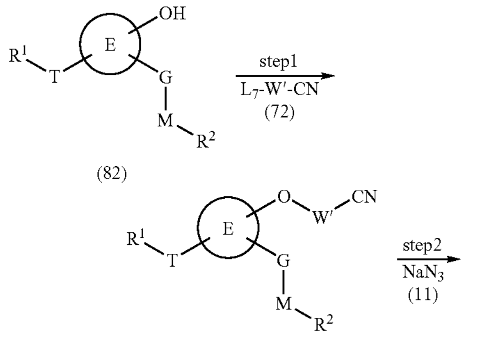

(82) (87)

-continued

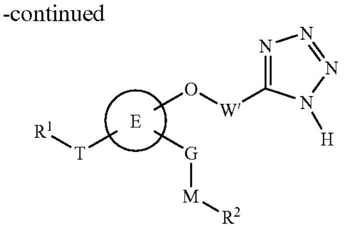

(88)

wherein $L^7$ represents a halogen atom or the like; T represents —R"—; $R^1$, $R^2$, E, M, G and W' have the same meanings as the aforementioned definitions.

<Step 1>

The compound represented by the general formula (87) can be prepared in the same manner as the aforementioned Step 3 in the Scheme 31 except using the compound represented by the general formula (82) in place of the compound represented by the general formula (78) and using the compound represented by the general formula (72) in place of the compound represented by the general formula (60).

<Step 2>

The final target compound represented by the general formula (88) can be prepared in the same manner as the aforementioned Step 3 in the Scheme 3 except using the compound represented by the general formula (87) in place of the compound represented by the general formula (10).

The compounds represented by the formula (I), wherein m is 0, G is the formula —$(CH_2)_j$—N—C(=O)—$(CH_2)_h$—$CO_2H$, and T is a single bond, can be prepared, for example, by the following method:

<Scheme 35>

[Formula 48]

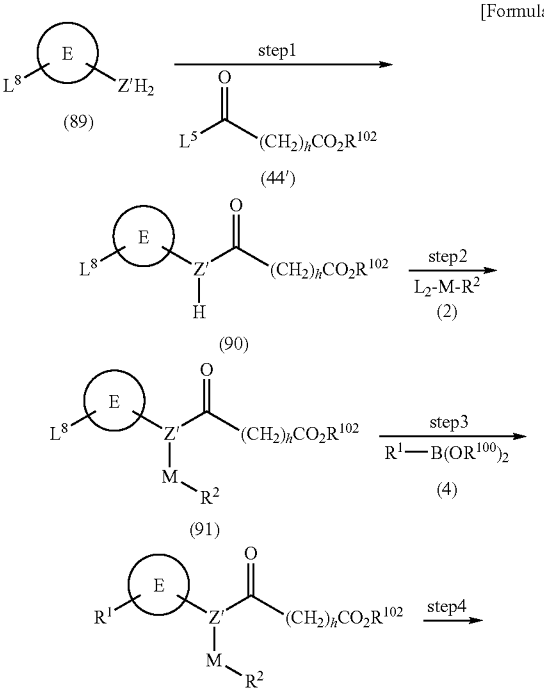

(89) (44') (90) (91) (92)

-continued

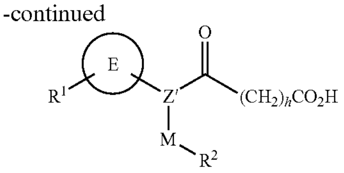

(93)

wherein $L^2$ represents a halogen atom or the like; $L^5$ represents a halogen atom; $L^8$ represents a halogen atom or the like; Z' represents $—(CH_2)_j—N$; $R^{100}$ represents a hydrogen atom, a $C_{1-6}$ alkyl group or the like; $R^{102}$ represents a $C_{1-6}$ alkyl group or the like; $R^1$, $R^2$, E, j, h and M have the same meanings as the aforementioned definitions.

<Step 1>

The compound represented by the general formula (90) can be prepared by reacting the compound represented by the general formula (89) with the compound represented by the general formula (44'). This reaction is carried out, for example, in the presence of a base, in a solvent. Examples of the base include inorganic bases and organic bases. Examples of the solvent include halogenated solvents, ether type solvents, or a mixed solvent thereof.

<Step 2>

The compound represented by the general formula (91) can be prepared by reacting the compound represented by the general formula (90) with the compound represented by the general formula (2). This reaction is carried out, for example, in the presence of a base, in a solvent. Crown ether may be added. Examples of the base include inorganic bases, organic bases and organometallic bases. Examples of the solvent include halogenated solvents, ether type solvents, amide type solvents, aromatic solvents, ketone type solvents, acetonitrile, or a mixed solvent thereof.

In the aforementioned Scheme 35, even if the order of the Steps 1 and 2 in the process are reversed, the compounds represented by the general formula (91) can be prepared.

<Step 3>

The compound represented by the general formula (92) can be prepared by reacting the compound represented by the general formula (91) with the compound represented by the general formula (4). This reaction is carried out, for example, in the presence of a catalytic amount of a transition metal complex, in the presence or absence of a phosphine ligand, in the presence or absence of a base, in a solvent. Examples of the transition metal complex include [1,1-bis(diphenylphosphino)ferrocene]dichloropalladium(II), tetrakis(triphenylphosphine)palladium, palladium(II) acetate and tris(dibenzylideneacetone)dipalladium. Examples of the phosphine ligand include 2-(di-tert-butylphosphino)biphenyl and 2-dicyclohexylphoshino)biphenyl. Examples of the base include inorganic bases and organic bases. Examples of the solvent include ether type solvents, amide type solvents, aromatic solvents, alcohol type solvents, water, or a mixed solvent thereof.

In the aforementioned Scheme 35, even if the order of the Steps 2 and 3 in the process are reversed, the compounds represented by the general formula (92) can be prepared.

<Step 4>

The final target compound represented by the general formula (93) can be prepared by the hydrolysis of the compound represented by the general formula (92). This reaction is carried out, for example, in the presence of a base, in a solvent. The reaction may be carried out under ultrasonic irradiation. Examples of the base include inorganic bases.

Examples of the solvent include ether type solvents, alcohol type solvents, water, or a mixed solvent thereof. When the aftertreatment is carried out under acidic condition, the free form of the oxamic acid can be obtained. When the aftertreatment is carried out under basic condition, the salt of the oxamic acid can be obtained. The compounds represented by the formula (I), wherein m is 0, G is $—(CH_2)_j—N—W'—CO_2H$, and T is a single bond, can be prepared in the same manner as the aforementioned Steps 1 to 4 in the Scheme 35 except using the compound represented by the formula $L^5$-W'—$CO_2R^{102}$ in place of the compound represented by the general formula (44').

The compounds represented by the aforementioned general formula (92) can also be prepared by, for example, the following method:

<Scheme 36>

[Formula 49]

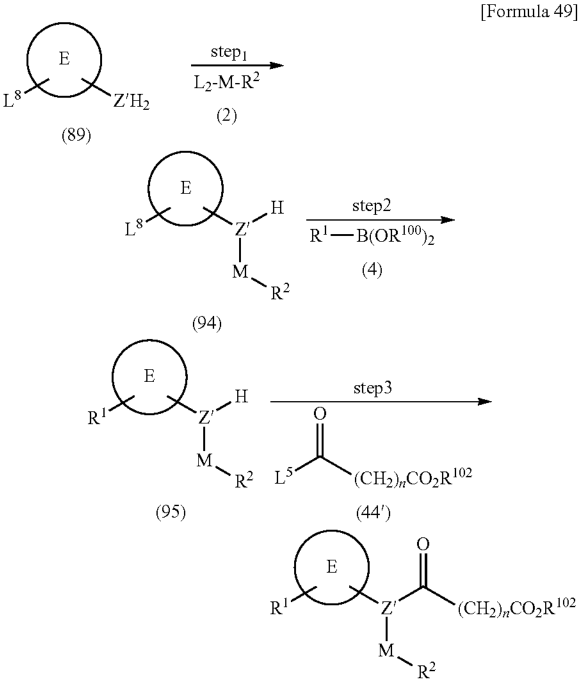

(89) (2) (94) (4) (95) (44') (92)

wherein $L^2$ represents a halogen atom or the like; $L^5$ represents a halogen atom; $L^8$ represents a halogen atom or the like; Z' represents $—(CH_2)_j—N$; $R^{100}$ represents a hydrogen atom, a $C_{1-6}$ alkyl group or the like; $R^{102}$ represents a $C_{1-6}$ alkyl group or the like; $R^1$, $R^2$, E, j, h and M have the same meanings as the aforementioned definitions.

<Step 1>

The compound represented by the general formula (94) can be prepared in the same manner as the aforementioned Step 2 in the Scheme 35 except using the compound represented by the general formula (89) in place of the compound represented by the general formula (90).

<Step 2>

The compound represented by the general formula (95) can be prepared in the same manner as the aforementioned Step 3 in the Scheme 35 except using the compound represented by the general formula (94) in place of the compound represented by the general formula (91).

<Step 3>

The compound represented by the general formula (92) can be prepared in the same manner as the aforementioned Step 1 in the Scheme 35 except using the compound represented by the general formula (95) in place of the compound represented by the general formula (89).

In the aforementioned Scheme 36, even if the order of the Steps 2 and 3 in the process are reversed, the compounds represented by the general formula (92) can be prepared. In the compound (92), the compound wherein the formula $—C(=O)—(CH_2)_h—CO_2R^{102}$ is substituted with the formula $—W'—CO_2R^{102}$ can be prepared can be prepared in the same manner as the aforementioned Steps 1 to 3 in the Scheme 36 except using the compound represented by the formula $L^5$-W'$—CO_2R^{102}$ in place of the compound represented by the general formula (44').

The compounds represented by the aforementioned general formula (92) can also be prepared, for example, by the following method:

<Scheme 37>

[Formula 50]

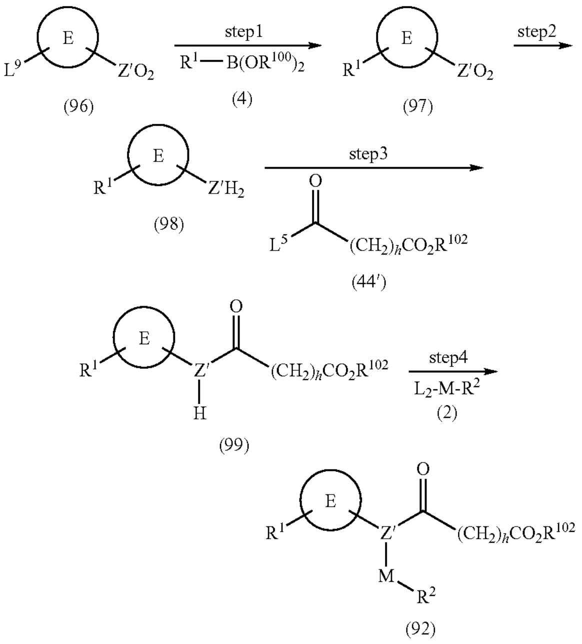

wherein $L^2$ represents a halogen atom or the like; $L^5$ represents a halogen atom; $L^9$ represents a halogen atom or the like; Z' represents $—(CH_2)_j—N$; $R^{100}$ represents a hydrogen atom, a $C_{1-6}$ alkyl group or the like; $R^{102}$ represents a $C_{1-6}$ alkyl group or the like; $R^1$, $R^2$, E, j, h and M have the same meanings as the aforementioned definitions.

<Step 1>

The compound represented by the general formula (97) can be prepared in the same manner as the aforementioned Step 3 in the Scheme 35 except using the compound represented by the general formula (96) in place of the compound represented by the general formula (91).

<Step 2>

The compound represented by the general formula (98) can be prepared by the reduction of the nitro group of the compound represented by the general formula (97). This reaction is carried out, for example, in the presence of a catalytic amount of a transition metal, under hydrogen atmosphere, in a solvent. Examples of the transition metal include palladium on activated carbon, platinum dioxide and Raney nickel. Examples of the solvent include ether type solvents, alcohol type solvents, water, or a mixed solvent thereof.

The aforementioned reductive reaction of the nitro group can also be carried out in the presence of a metal or a metal halide, in the presence or absence of an acid, in a solvent. Examples of the metal include iron, tin and zinc. Examples of the metal halide include tin(II) chloride. Examples of the acid include inorganic acids and organic acids. Examples of the solvent include alcohol type solvents, water, or a mixed solvent thereof.

<Step 3>

The compound represented by the general formula (99) can be prepared in the same manner as the aforementioned Step 1 in the Scheme 35 except using the compound represented by the general formula (98) in place of the compound represented by the general formula (89).

<Step 4>

The compound represented by the general formula (92) can be prepared in the same manner as the aforementioned Step 2 in the Scheme 35 except using the compound represented by the general formula (99) in place of the compound represented by the general formula (90).

In the aforementioned Scheme 37, even if the order of the Steps 3 and 4 in the process are reversed, the compound represented by the general formula (92) can be prepared. In the compound (92), the compound wherein the formula $—C(=O)—(CH_2)_h—CO_2R^{102}$ is substituted with the formula $—W'—CO_2R^{102}$ can be prepared can be prepared in the same manner as the aforementioned Steps 1 to 4 in the Scheme 37 except using the compound represented by the formula $L^5$-W'$—CO_2R^{102}$ in place of the compound represented by the general formula (44').

The compounds represented by the formula (I), wherein m is 0, G is the formula $—(CH_2)_j—N—C(=O)—(CH_2)_h—CO_2H$, T is a single bond, and M is a single bond, can also be prepared, for example, by the following method:

<Scheme 38>

[Formula 51]

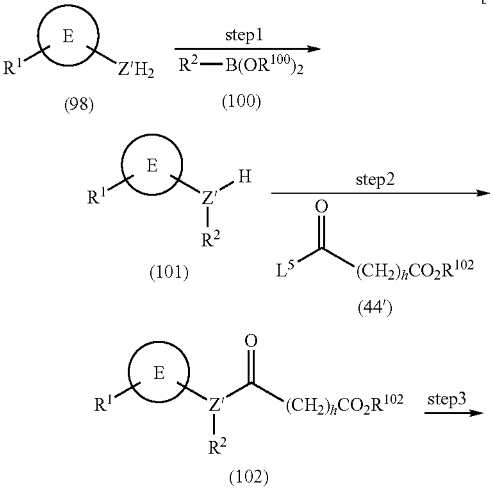

-continued

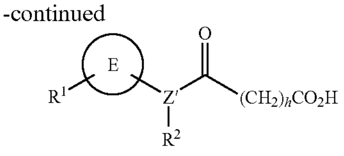

(103)

wherein $L^5$ represents a halogen atom; Z' represents —$(CH_2)_j$—N; $R^{100}$ represents a hydrogen atom, a $C_{1-6}$ alkyl group or the like; $R^{102}$ represents a $C_{1-6}$ alkyl group or the like; $R^1$, $R^2$, j, h and E have the same meanings as the aforementioned definitions.

<Step 1>

The compound represented by the general formula (101) can be prepared by reacting the compound represented by the general formula (98) with the compound represented by the general formula (100). This reaction is carried out, for example, in the presence of copper(II) acetate, in the presence of a base, in a solvent. Molecular Sieves may be added. Examples of the base include organic bases. Examples of the solvent include halogenated solvents, pyridine, or a mixed solvent thereof.

<Step 2>

The compound represented by the general formula (102) can be prepared in the same manner as the aforementioned Step 1 the Scheme 35 except using the compound represented by the general formula (101) in place of the compound represented by the general formula (89).

<Step 3>

The final target compound represented by the general formula (103) can be prepared in the same manner as the aforementioned Step 4 in the Scheme 35 except using the compound represented by the general formula (102) in place of the compound represented by the general formula (92). In the compound (92), the compound wherein the formula —C(═O)—$(CH_2)_h$—$CO_2R^{102}$ is substituted with the formula —W'—$CO_2R^{102}$ can be prepared can be prepared in the same manner as the aforementioned Steps 1 to 3 in the Scheme 38 except using the compound represented by the formula $L^5$-W'—$CO_2R^{102}$ in place of the compound represented by the general formula (44').

The compounds represented by the formula (I), wherein m is 0, G is the formula —$(CH_2)_j$—N—C(═O)—$(CH_2)_h$—$CO_2H$, and T is —R"—, can be prepared, for example, by the following method:

<Scheme 39>

[Formula 52]

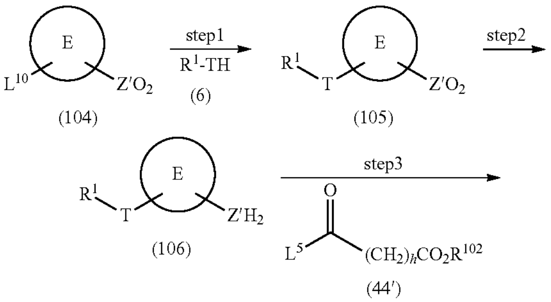

-continued

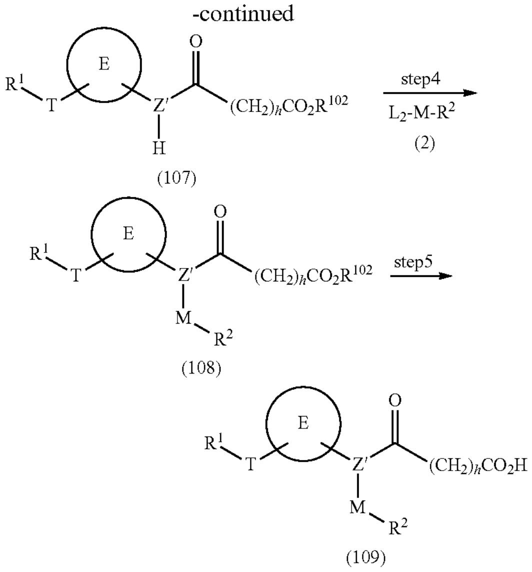

wherein $L^2$ represents a halogen atom or the like; $L^5$ represents a halogen atom; $L^{10}$ represents a halogen atom or the like; Z' represents —$(CH_2)_j$—N; $R^{102}$ represents a $C_{1-6}$ alkyl group or the like; T represents —R"—; $R^1$, $R^2$, E, j, h and M have the same meanings as the aforementioned definitions.

<Step 1>

The compound represented by the general formula (105) can be prepared by reacting the compound represented by the general formula (104) with the compound represented by the general formula (6). This reaction is carried out, for example, in the presence of copper(II) oxide, in the presence of a base, in a solvent. Examples of the base include inorganic bases (for example, potassium carbonate, sodium carbonate and sodium hydrogen carbonate). Examples of the solvent include halogenated solvents, pyridine, or a mixed solvent thereof.

<Step 2>

The compound represented by the general formula (106) can be prepared in the same manner as the aforementioned Step 2 in the Scheme 37 except using the compound represented by the general formula (105) in place of the compound represented by the general formula (97).

<Step 3>

The compound represented by the general formula (107) can be prepared in the same manner as the aforementioned Step 1 in the Scheme 35 except using the compound represented by the general formula (106) in place of the compound represented by the general formula (89).

<Step 4>

The compound represented by the general formula (108) can be prepared in the same manner as the aforementioned Step 2 in the Scheme 35 except using the compound represented by the general formula (107) in place of the compound represented by the general formula (90).

<Step 5>

The final target compound represented by the general formula (109) can be prepared in the same manner as the aforementioned Step 4 in the Scheme 35 except using the compound represented by the general formula (108) in place of the compound represented by the general formula (92).

In the aforementioned Scheme 39, even if the order of the Steps 3 and 4 in the process are reversed, the compound represented by the general formula (108) can be prepared. The compounds represented by the formula (I), wherein m is 0, G is $—(CH_2)_j—N—W'—CO_2H$, T is —R"—, can be prepared in the same manner as the aforementioned Steps 1 to 5 in the Scheme 39 except using the compound represented by the formula $L^5$-W'$—CO_2R^{102}$ in place of the compound represented by the general formula (44').

The compounds represented by the aforementioned general formula (105) can also be prepared, for example, by the following method:

<Scheme 40>

[Formula 53]

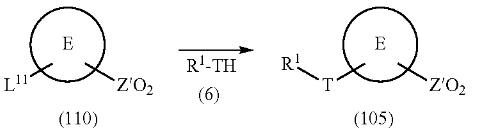

(110) (105)

wherein $L^{11}$ represents a halogen atom, a nitro group or the like; Z' represents $—(CH_2)_j—N$; $R^1$, T and j has the same meaning as the aforementioned definition.

The compound represented by the general formula (105) can be prepared by reacting the compound represented by the general formula (110) with the compound represented by the general formula (6). This reaction is carried out, for example, in the presence of a base, in a solvent. Examples of the base include inorganic bases, organic bases and organometallic bases. Examples of the solvent include ether type solvents, amide type solvents, aromatic solvents, or a mixed solvent thereof.

The compounds represented by the aforementioned general formula (105) can also be prepared, for example, by the following method:

<Scheme 41>

[Chemical Formula 54]

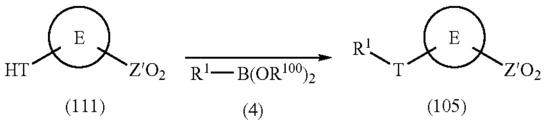

(111) (105)

wherein Z' represents $—(CH_2)_j—N$; $R^{100}$ represents a hydrogen atom, a $C_{1-6}$ alkyl group or the like; $R^1$, T and j has the same meaning as the aforementioned definition.

The compound represented by the general formula (105) can be prepared by reacting the compound represented by the general formula (111) with the compound represented by the general formula (4). This reaction is carried out, for example, in the presence of copper(II) acetate, in the presence of a base, in a solvent. Molecular Sieves may be added. Examples of the base include organic bases. Examples of the solvent include halogenated solvents, pyridine, or a mixed solvent thereof.

The compounds represented by the formula (I), wherein m is 0, G is the formula $—(CH_2)_j—N—C(=O)—(CH_2)_h—CO_2H$, T is —R"—, and M is a single bond, can be prepared, for example, by the following method:

<Scheme 42>

[Formula 55]

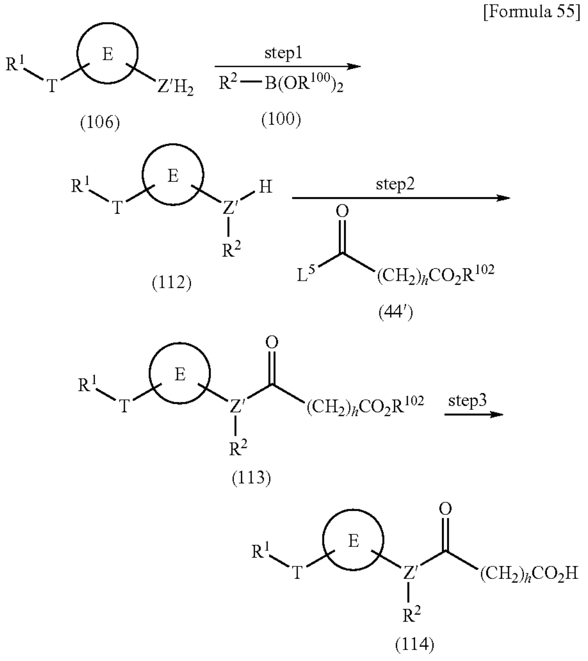

(106) (100) (112) (44') (113) (114)

wherein $L^5$ represents a halogen atom; Z' represents $—(CH_2)_j—N$; $R^{100}$ represents a hydrogen atom, a $C_{1-6}$ alkyl group or the like; $R^{102}$ represents a $C_{1-6}$ alkyl group or the like; T represents —R"—; $R^1$, $R^2$, j, h and E have the same meanings as the aforementioned definitions.

<Step 1>

The compound represented by the general formula (112) can be prepared in the same manner as the aforementioned Step 1 in the Scheme 38 except using the compound represented by the general formula (106) in place of the compound represented by the general formula (98).

<Step 2>

The compound represented by the general formula (113) can be prepared in the same manner as the aforementioned Step 1 in the Scheme 35 except using the compound represented by the general formula (112) in place of the compound represented by the general formula (89).

<Step 3>

The final target compound represented by the general formula (114) can be prepared in the same manner as the aforementioned Step 4 in the Scheme 35 except using the compound represented by the general formula (113) in place of the compound represented by the general formula (92). The compounds represented by the formula (I), wherein m is 0, G is $—(CH_2)_j—N—CO_2H$, T is —R"—, M is a single bond, can be prepared in the same manner as the aforementioned Steps 1 to 3 in the Scheme 42 except using the compound represented by the formula $L^5$-W'$—CO_2R^{102}$ in place of the compound represented by the general formula (44').

The compound represented by the following general formula (59a), which is the compound represented by the aforementioned general formula (59) wherein V' is a methylene group substituted with one $C_{1-6}$ alkyl group, can also be prepared, for example, by the following method:

<Scheme 43>

[Formula 56]

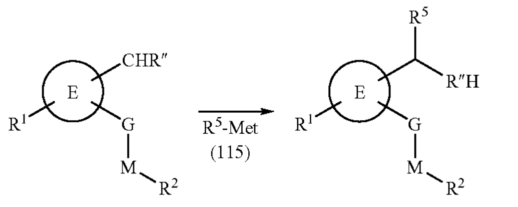

(17) (59a)

wherein $R^5$ represents a $C_{1-6}$ alkyl group; Met represents lithium, —MgBr or the like; $R^1$, $R^2$, M, G, R" and E have the same meanings as the aforementioned definitions.

The compound represented by the general formula (59a) can be prepared by reacting the compound represented by the general formula (17) with the compound represented by the general formula (115). This reaction is carried out, for example, in a solvent. Examples of the $R^5$-Met include a $C_{1-6}$ alkyllithium and a $C_{1-6}$ alkylmagnesium bromide. Examples of the solvent include ether type solvents, or a mixed solvent thereof.

The compound represented by the following general formula (66a), which is the compound represented by the aforementioned general formula (66) wherein V' is a methylene group substituted with one $C_{1-6}$ alkyl group, can also be prepared, for example, by the following method:

<Scheme 44>

[Formula 57]

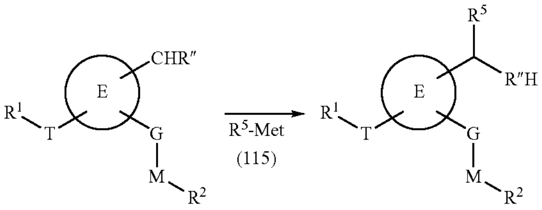

(24) (66a)

wherein $R^5$ represents a $C_{1-6}$ alkyl group; Met represents lithium, —MgBr or the like; $R^1$, $R^2$, T, M, G, R" and E have the same meanings as the aforementioned definitions.

The compound represented by the general formula (66a) can be prepared in the same manner as the aforementioned Scheme 43 except using the compound represented by the general formula (24) in place of the compound represented by the general formula (17).

The compound represented by the following general formula (94a), which is the compound represented by the aforementioned general formula (94) wherein M is the formula $-(Q^1)_n-(Q^2)_p-(Q^3)_r-(U')_q-$, the formula $-(Q^1)_n-(Q^2)_p-(U')_q-(Q^3)_r-$ or the formula $-(Q^1)_n-(U')_q-(Q^2)_p-(Q^3)_r-$, $Q^1$ is a methylene group substituted with one group selected from the group consisting of a $C_{1-6}$ alkyl group and a phenyl group, and n is 1 can also be prepared, for example, by the following method:

<Scheme 45>

[Formula 58]

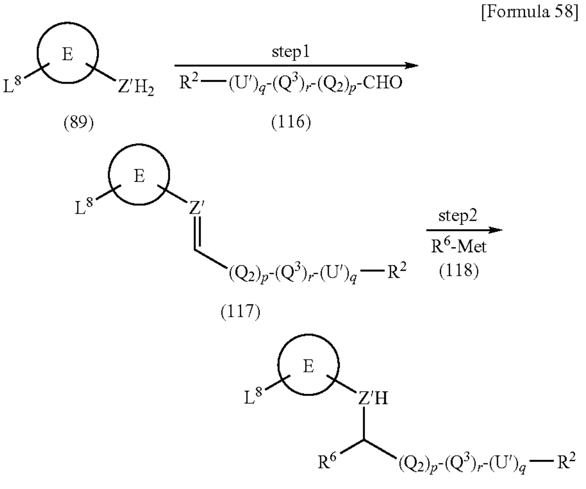

(89) (116) (117) (94a)

wherein $L^8$ represents a halogen atom or the like; Z' represents $—(CH_2)_j—N$; $R^5$ represents a $C_{1-6}$ alkyl group, or a phenyl group; Met represents lithium, —MgBr or the like; $R^2$, j, $Q^2$, $Q^3$, U', p, q, r and E have the same meanings as the aforementioned definitions.

<Step 1>

The compound represented by the general formula (117) can be prepared by reacting the compound represented by the general formula (89) with the compound represented by the general formula (116). This reaction is carried out, for example, in a solvent. Examples of the solvent include alcohol type solvents, or a mixed solvent thereof.

<Step 2>

The compound represented by the general formula (94a) can be prepared by reacting the compound represented by the general formula (117) with the compound represented by the general formula (118). This reaction is carried out, for example, in a solvent. Examples of the $R^6$-Met include a $C_{1-6}$ alkyllithium, a phenyllithium, a $C_{1-6}$ alkylmagnesium bromide and a phenylmagnesium bromide. Examples of the solvent include ether type solvents, or a mixed solvent thereof.

The compound represented by the following general formula (94b), which is the compound represented by the aforementioned general formula (94) wherein M is the formula $-(Q^1)_n-(Q^2)_p-(Q^3)_r-(U')_q-$, the formula $-(Q^1)_n-(Q^2)_p-(U')_q-(Q^3)_r-$ or the formula $-(Q^1)_n-(U')_q-(Q^2)_p-(Q^3)_r-$, $Q^1$ is a methylene group, and n is 1, can also be prepared, for example, by the following method:

<Scheme 46>

[Formula 59]

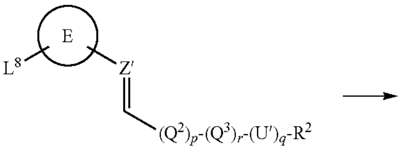

(117)

-continued

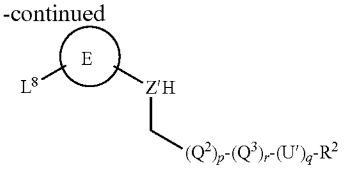

(94b)

wherein $L^8$ represents a halogen atom or the like; Z' represents —$(CH_2)_j$—N; $R^2$, j, $Q^2$, $Q^3$, U', p, q, r and E have the same meanings as the aforementioned definitions.

The compound represented by the general formula (94b) can be prepared by the reduction of the imine of the compound represented by the general formula (117). This reaction is carried out, for example, in the presence of a reducing agent, in a solvent. Examples of the reducing agent include sodium borohydride, and lithium borohydride. Examples of the solvent include ether type solvents, alcohol type solvents, water, or a mixed solvent thereof.

The compounds represented by the general formula (42) can also be prepared, for example, by the following method:

<Scheme 47>

[Formula 60]

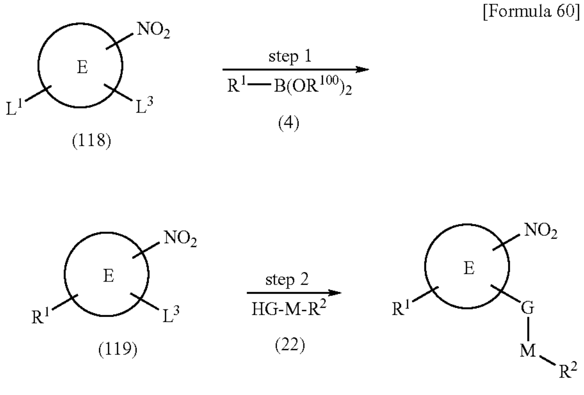

(118) (119) (42)

wherein $L^1$ represents a halogen atom or the like; $L^3$ represents a halogen atom or the like; $R^1$, $R^2$, E, G and M have the same meanings as the aforementioned definitions.

<Step 1>

The compound represented by the general formula (119) can be prepared in the same manner as the aforementioned Step 2 in the Scheme 5 except using the compound represented by the general formula (118) in place of the compound represented by the general formula (16).

<Step 2>

The compound represented by the general formula (42) can be prepared in the same manner as the aforementioned Step 1 in the Scheme 5 except using the compound represented by the general formula (119) in place of the compound represented by the general formula (22).

The compounds represented by the following general formula (98a), which is the compound represented by the aforementioned general formula (98) wherein Z' is —$(CH_2)_j$—N, and j is 1, can also be prepared, for example, by the following method:

<Scheme 48>

[Formula 61]

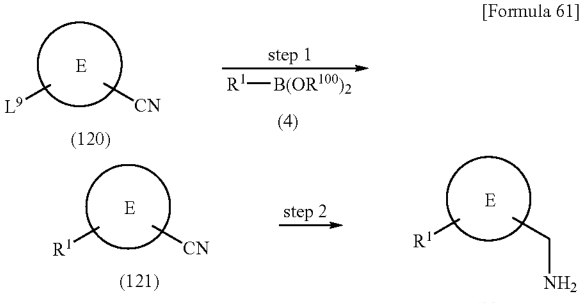

(120) (121) (98a)

wherein $L^9$ represents a halogen atom or the like; $R^{100}$ represents a hydrogen atom, a $C_{1-6}$ alkyl group or the like; $R^1$ and E have the same meanings as the aforementioned definitions.

<Step 1>

The compound represented by the general formula (121) can be prepared in the same manner as the aforementioned Step 3 in the Scheme 35 except using the compound represented by the general formula (120) in place of the compound represented by the general formula (91).

<Step 2>

The compound represented by the general formula (98a) can be prepared by the reduction of the nitrile group of the compound represented by the general formula (121). This reaction is carried out, for example, in the presence of a reducing agent, in a solvent. Examples of the reducing agent include sodium borohydride, lithium borohydride and lithium aluminium hydride. Examples of the solvent include ether type solvents, alcohol type solvents, or a mixed solvent thereof.

The compounds represented by the following general formula (106a), which is the compound represented by the aforementioned general formula (106) wherein Z' is —$(CH_2)_j$—N, and j is 1, can also be prepared, for example, by the following method:

<Scheme 49>

[Formula 62]

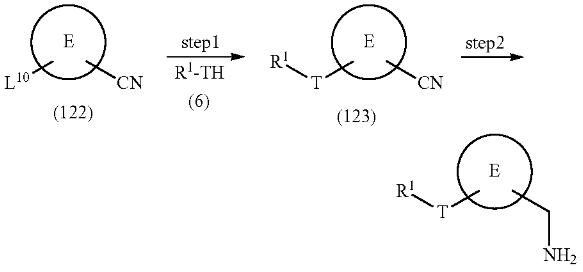

(122) (123) (106a)

wherein $L^{10}$ represents a halogen atom or the like; $R^2$, T and E have the same meanings as the aforementioned definitions.

<Step 1>

The compound represented by the general formula (123) can be prepared in the same manner as the aforementioned Step 1 in the Scheme 39 except using the compound represented by the general formula (122) in place of the compound represented by the general formula (104).

<Step 2>

The compound represented by the general formula (106a) can be prepared in the same manner as the aforementioned Step 2 in the Scheme 48 except using the compound represented by the general formula (123) in place of the compound represented by the general formula (121).

The compounds represented by the following general formula (24a), which is the compound represented by the aforementioned general formula (24) wherein G is an oxygen atom, and M is a single bond, can also be prepared, for example, by the following method:

<Scheme 50>

[Formula 63]

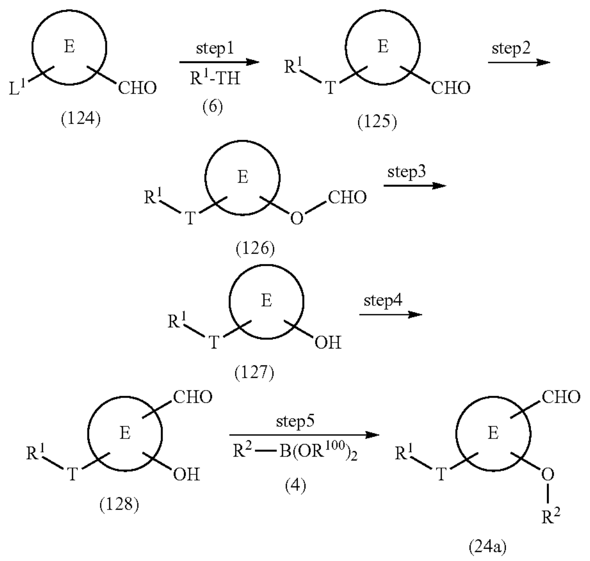

wherein $L^1$ represents a halogen atom or the like; $R^{100}$ represents a hydrogen atom, a $C_{1-6}$ alkyl group or the like; $R^1$, $R^2$, T and E have the same meanings as the aforementioned definitions.

<Step 1>

The compound represented by the general formula (125) can be prepared in the same manner as the aforementioned Step 2 in the Scheme 6 except using the compound represented by the general formula (6) in place of the compound represented by the general formula (22) and using the compound represented by the general formula (124) in place of the compound represented by the general formula (21).

<Step 2>

The compound represented by the general formula (126) can be prepared in the same manner as the aforementioned Step 1 in the Scheme 31 except using the compound represented by the general formula (125) in place of the compound represented by the general formula (17).

<Step 3>

The compound represented by the general formula (127) can be prepared in the same manner as the aforementioned Step 1 in the Scheme 31 except using the compound represented by the general formula (126) in place of the compound represented by the general formula (77).

<Step 4>

The compound represented by the general formula (128) can be prepared by reacting the compound represented by the general formula (127) with hexamethylenetetramine. This reaction is known as "Duff reaction," and is carried out in an organic acid (for example, acetic acid, trifluoroacetic acid and methanesulfonic acid) or an inorganic acid (for example, sulfuric acid. Furthermore, the compound represented by the general formula (128) can also be prepared, for example, by reactions such as Gatterman reaction, Reimee-Tiemann reaction and the like, that are known to those skilled in the art.

<Step 5>

The compound represented by the general formula (24a) can be prepared in the same manner as the aforementioned Scheme 11 except using the compound represented by the general formula (128) in place of the compound represented by the general formula (29).

The compounds represented by the following general formula (82a), which is the compound represented by the aforementioned general formula (82) wherein G is an oxygen atom, and M is a single bond, can also be prepared, for example, by the following method:

<Scheme 51>

[Formula 64]

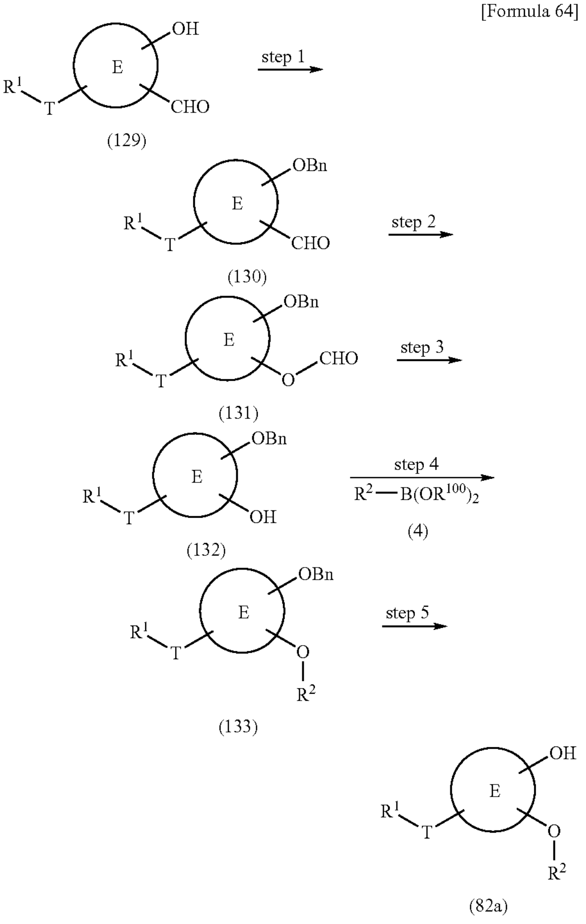

wherein $R^{100}$ represents a hydrogen atom, a $C_{1-6}$ alkyl group or the like; $R^1$, $R^2$, T and E have the same meanings as the aforementioned definitions.

<Step 1>

The compound represented by the general formula (130) can be prepared in the same manner as the aforementioned Step 1 in the Scheme 5 except using benzyl halide in place of the compound represented by the general formula (2) and using the compound represented by the general formula (129) in place of the compound represented by the general formula (15).

<Step 2>

The compound represented by the general formula (131) can be prepared in the same manner as the aforementioned Step 1 in the Scheme 31 except using the compound represented by the general formula (130) in place of the compound represented by the general formula (17).

<Step 3>

The compound represented by the general formula (132) can be prepared in the same manner as the aforementioned Step 2 in the Scheme 31 except using the compound represented by the general formula (131) in place of the compound represented by the general formula (77).

<Step 4>

The compound represented by the general formula (133) can be prepared in the same manner as the aforementioned Scheme 11 except using the compound represented by the general formula (132) in place of the compound represented by the general formula (29).

<Step 5>

The compound represented by the general formula (82a) can be prepared by the deprotection of the benzyl group of the compound represented by the general formula (133). This reaction is carried out, for example, in the presence of a catalytic amount of a transition metal, under hydrogen atmosphere, in a solvent. Examples of the transition metal include palladium on activated carbon, platinum dioxide and Raney nickel. Examples of the solvent include ether type solvents, alcohol type solvents, water, or a mixed solvent thereof.

In each of the aforementioned preparation methods, the compounds in the aforementioned formula (I) wherein T is a 1,4-piperazinylene, —N(R')—, the formula —$CH_2R''$—, the formula —C(═O)N(R')—, the formula —N(R')C(═O)—, or the formula $SO_2N(R')$— can be prepared except using the compound wherein T is a 1,4-piperazinylene, —N(R')—, the formula —$CH_2R''$—, the formula —C(═O)N(R')—, the formula —N(R')C(═O)—, or the formula —$SO_2N(R')$— in place of the compound wherein T is —R''—.

The compounds represented by the following general formula (105a), which is the compound represented by the aforementioned general formula (105) wherein T is —$CH_2R''$—, can be prepared, for example, by the following method:

<Scheme 52>

[Formula 65]

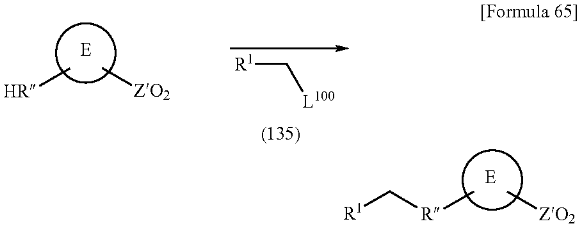

(135)

(105a)

wherein $L^{100}$ represents a halogen atom or the like; $R^1$, R'', Z' and E have the same meanings as the aforementioned definitions.

The compound represented by the general formula (105a) can be prepared by reacting the compound represented by the general formula (134) with the compound represented by the general formula (135). This reaction is carried out, for example, in the presence of a base, in a solvent. Crown ether may be added in the reaction. Examples of the base include inorganic bases, organic bases and organometallic bases. Examples of the solvent include halogenated solvents, ether type solvents, amide type solvents, aromatic solvents, ketone type solvents, acetonitrile, or a mixed solvent thereof.

In each of the aforementioned preparation methods, the compounds in the aforementioned formula (I) wherein X is a single bond or —C(═O)— can be prepared except using the compound wherein X is a single bond or —C(═O)— in place of the compound wherein X is —CH═CH—, the formula —V'—$(V')_k$—, the formula —N($R^4$)—C(═O)—, the formula —N($R^4$)—V'—, or the formula —$(V')_k$—R''—W'—.

The compounds represented by the formula (I), wherein T is the formula —N(R')C(═O)—, and Y' is a carboxy group, can be prepared, by the following method:

<Scheme 53>

[Formula 66]

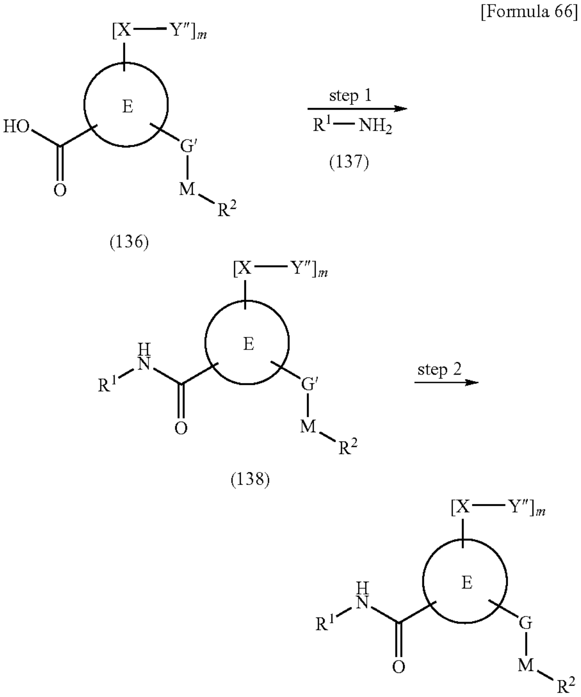

(136)

(138)

(139)

in the formula, when m is 1, G' represents a single bond, an oxygen atom, —C(═O)—, or a sulfur atom; when m is 0, G' represents the formula —$(CH_2)_j$—N—C(═O)—$(CH_2)_h$—$CO_2R^{105}$, or the formula —$(CH_2)_j$—N—W'—$CO_2R^{105}$; Y'' represents the formula —$CO_2R^{105}$; $R^{105}$ represents an alkyl group or the like; $R^1$, $R^2$, X, Y', W', E, h, j and M have the same meanings as the aforementioned definitions.

<Step 1>

The compound represented by the general formula (138) can be prepared by reacting the compound represented by the general formula (136) with the compound represented by the general formula (137). This reaction is carried out in the presence of a condensing agent, in the presence or absence of a base, in a solvent. Examples of the condensing agent include phosphorus oxychloride, 1-ethyl-3-(3-dimethylaminopropyl)carbodiimide hydrochloride, dicyclohexylcarbodiimide. Examples of the base include organic bases. Examples of the solvent include halogenated solvents, ether type solvents, aromatic solvents, or a mixed solvent thereof.

<Step 2>

The final target compound represented by the general formula (139) can be prepared by the hydrolysis of the ester group (the formula $—CO_2R^{105}$) of the compound represented by the general formula (138). This reaction is carried out in the presence of a inorganic acid or a inorganic base, in a solvent. Examples of the solvent include ether type solvents, alcohol type solvents, water, or a mixed solvent thereof.

The compounds represented by the formula (I), wherein T is the formula —C(═O)—N(R')— or the formula $—SO_2N$(R')—, and Y' is a carboxy group, can be prepared, by the following method:

<Scheme 54>

[Formula 67]

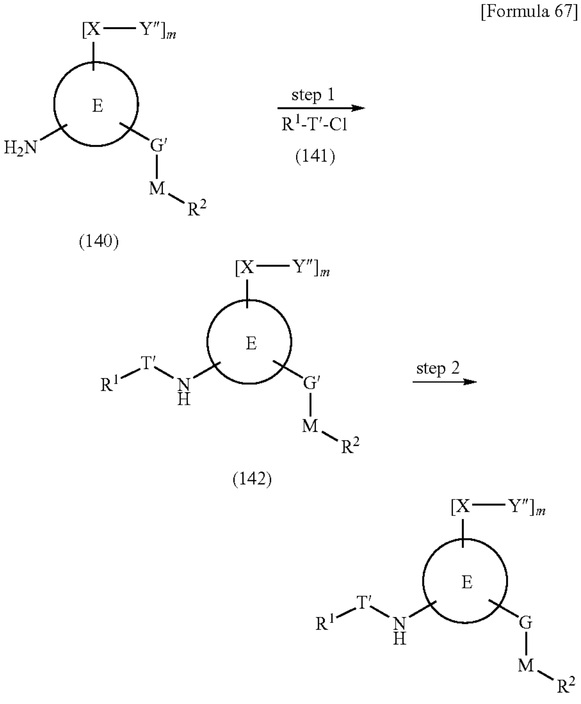

(140) (142) (143)

wherein T' represents —C(═O)— or $—SO_2—$, in the formula; when m is 1, G' represents a single bond, an oxygen atom, —C(═O)—, or a sulfur atom; when m is 0, G' represents the formula $—(CH_2)_j—N—C(═O)—(CH_2)_h—CO_2R^{105}$, or the formula $—(CH_2)_j—N—W'—CO_2R^{105}$; Y" represents the formula $—CO_2R^{105}$; $R^{105}$ represents an alkyl group or the like; $R^1$, $R^2$, X, Y', W', E, h, j and M have the same meanings as the aforementioned definitions.

<Step 1>

The compound represented by the general formula (142) can be prepared by reacting the compound represented by the general formula (140) with the compound represented by the general formula (141). This reaction is carried out in the presence of a base, in a solvent. Examples of the condensing agent include phosphorus oxychloride, 1-ethyl-3-(3-dimethylaminopropyl)carbodiimide hydrochloride, dicyclohexylcarbodiimide. Examples of the base include inorganic bases and organic bases. Examples of the solvent include halogenated solvents, ether type solvents, amide type solvents, aromatic solvents, ketone type solvents, acetonitrile, water, or a mixed solvent thereof.

<Step 2>

The final target compound represented by the general formula (143) can be prepared in the same manner as the aforementioned Scheme 53 except using the compound represented by the general formula (142) in place of the compound represented by the general formula (138).

The compounds represented by the formula (I), wherein m is 1, and Y' is a carboxy group, can also be prepared, by the following method:

<Scheme 55>

[Formula 68]

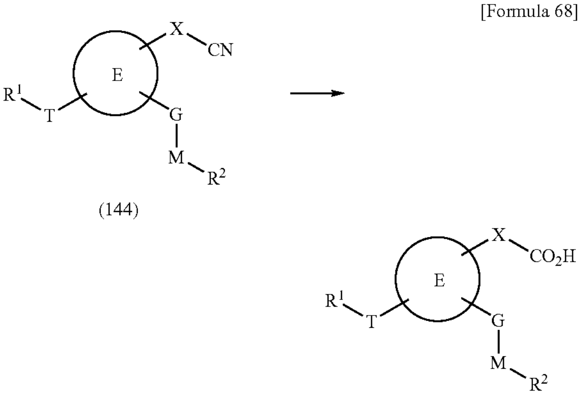

(144) (145)

wherein $R^1$, $R^2$, M, G, T, X and E have the same meanings as the aforementioned definitions.

The compound represented by the general formula (145) can be prepared by the hydrolysis of the cyano group of the compound represented by the general formula (144). This reaction is carried out in the presence of an acid or a base, without a solvent or in a solvent. Examples of the acid include inorganic acids. Examples of the base include inorganic bases. Examples of the solvent include ether type solvents, alcohol type solvents, water, or a mixed solvent thereof.

The compounds represented by the formula (I), wherein m is 1, X is the formula $—V'—(V')_k—$, —V'— is a methylene group substituted with one group selected from the substituent group δ-1, k is 1, and Y' is a carboxy group, can also be prepared, by the following method:

<Scheme 56>

[Formula 69]

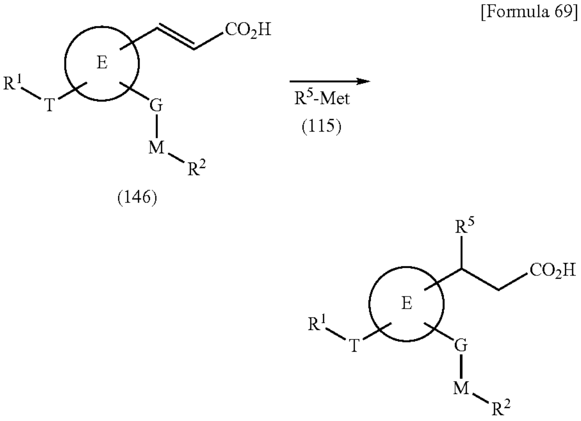

(146) (147)

wherein $R^5$ represents a $C_{1-6}$ alkyl group; Met represents lithium, —MgBr or the like; $R^1$, $R^2$, M, G, T and E have the same meanings as the aforementioned definitions.

The final target compound represented by the general formula (147) can be prepared by reacting the compound represented by the general formula (146) with the compound represented by the general formula (115). This reaction is known as "Michael addition reaction," and is carried out in a solvent. Examples of the $R^5$-Met include a $C_{1-6}$ alkyllithium and a $C_{1-6}$ alkylmagnesium bromide. Examples of the solvent include ether type solvents. The compound represented by $(R^5)_2CuLi$ (Gilman reagent) may be used in place of the compound represented by the general formula (115).

The compounds represented by the formula (I), wherein m is 1, X is a single bond, and Y' is a carboxy group, can also be prepared, by the following method:

<Scheme 57>

[Formula 70]

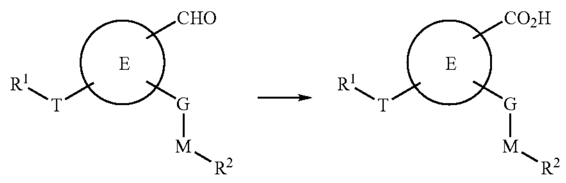

(148) (149)

wherein $R^1$, $R^2$, M, G, T and E have the same meanings as the aforementioned definitions.

The final target compound represented by the general formula (149) can be prepared by the oxidation of the formyl group of the compound represented by the general formula (148). This reaction is carried out, for example, in the presence of an oxidation agent, in a solvent. Examples of the oxidation agent include chlorous acid and potassium permaganate. Examples of the solvent include halogenated solvents, ether type solvents, amide type solvents, aromatic solvents, ketone type solvents, acetonitrile, or a mixed solvent thereof.

The compounds represented by the following general formula (154), which is the compound represented by the aforementioned general formulas (78) or (82) wherein G is —C(=O)—, and M is a single bond, can also be prepared, by the following method:

<Scheme 58>

[Formula 71]

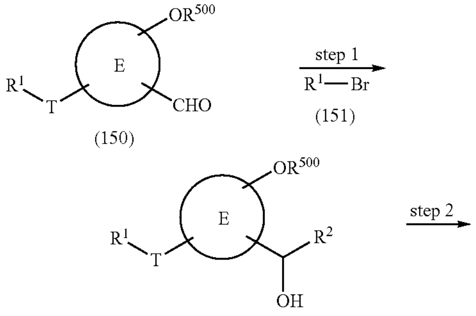

(150) (151) (152)

-continued

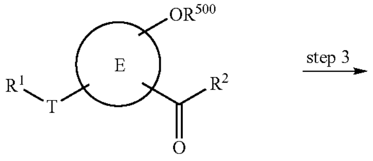

(153)

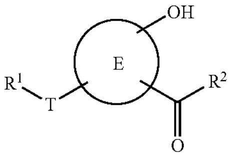

(154)

wherein $R^{500}$ represents a protecting group of the hydroxy group (for example, a tri($C_{1-6}$ alkyl)silyl group, a benzyl group or the like); T represents a single bond or R"; $R^1$, $R^2$, R" and E have the same meanings as the aforementioned definitions.

<Step 1>

The compound represented by the general formula (152) can be prepared by reacting the compound represented by the general formula (150) with the compound represented by the general formula (151). This reaction is carried out, for example, in the presence of a base, in a solvent. Examples of the base include organometallic bases. Examples of the solvent include halogenated solvents, ether type solvents, or a mixed solvent thereof.

<Step 2>

The compound represented by the general formula (153) can be prepared by the oxidation of the compound represented by the general formula (152). This reaction is carried out, for example, in the presence of an oxidation agent, in a solvent. Examples of the oxidation agent include pyridinium dichromate, pyridinium chlorochromate, manganese dioxide and potassium permanganate. Examples of the solvent include halogenated solvents, ether type solvents, amide type solvents, aromatic solvents, ketone type solvents, acetonitrile, or a mixed solvent thereof.

<Step 3>

The compound represented by the general formula (154) can be prepared by the deprotection of the protecting group of the hydroxy group of the compound represented by the general formula (153). Examples of the deprotection reaction include methods described in T. W. Greene and P. G. M. Wuts; Protective Groups in Organic Synthesis, 3rd Ed., 1999.

The compounds represented by the following general formula (154), which is the compound represented by the aforementioned general formulas (78) or (82) wherein G is a single bond, and M is the formula $-(Q^1)_n-(Q^2)_p-(Q^3)_r-(U')_q-$, the formula $-(Q^1)_n-(Q^2)_p-(U')_q-(Q^3)_r-$ or the formula $-(Q^1)_n-(U')_q-(Q^2)_p-(Q^3)_r-$, each of $Q^1$, $Q^2$ and $Q^3$ is a methylene group, the sum of n, p, q and r is 1, and q is 0, can also be prepared, by the following method:

<Scheme 59>

[Formula 72]

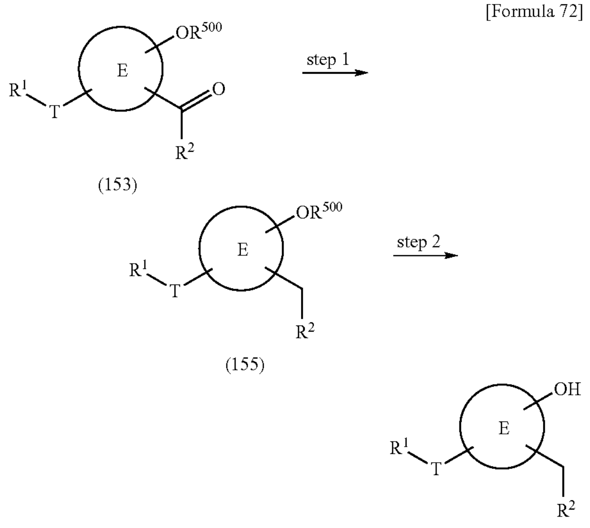

(153)

(155)

(156)

wherein $R^{500}$ represents a protecting group of the hydroxy group (for example, a tri($C_{1-6}$ alkyl)silyl group, a benzyl group or the like); T represents a single bond or R"; $R^1$, $R^2$, R" and E have the same meanings as the aforementioned definitions.

<Step 1>

The compound represented by the general formula (155) can be prepared by the reduction of the carbonyl group of the compound represented by the general formula (153) to the methylene group. This reaction is carried out, for example, in the presence of a catalytic amount of a transition metal, in the presence or absence of an acid, under hydrogen atmosphere, in a solvent. Examples of the transition metal complex include inorganic acids and organic acids. Examples of the acid include palladium on activated carbon and platinum dioxide. Examples of the solvent include ether type solvents, alcohol type solvents, water, or a mixed solvent thereof.

<Step 3>

The compound represented by the general formula (156) can be prepared in the same manner as the aforementioned Step 3 in the Scheme 58 except using the compound represented by the general formula (155) in place of the compound represented by the general formula (153).

The compounds represented by the following general formula (159), which is the compound represented by the aforementioned general formulas (95) or (112) wherein Z' is $—(CH_2)_j—N$, and j is 1, can also be prepared, by the following method:

<Scheme 60>

[Formula 73]

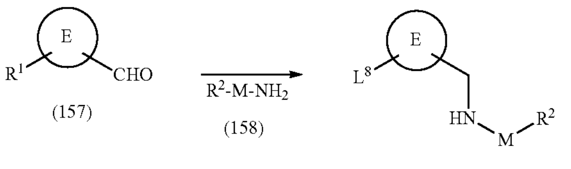

(157)

(158)

(159)

wherein $R^1$, $R^2$, M' and E have the same meanings as the aforementioned definitions.

The compound represented by the general formula (159) can be prepared by reacting the compound represented by the general formula (157) with the compound represented by the general formula (158). This reaction is carried out, for example, in the presence of a reducing agent, in a solvent. An acid may be added. Examples of the reducing agent include sodium triacetoxyborohydride. Examples of the solvent include halogenated solvents, ether type solvents, or a mixed solvent thereof. In the Scheme 60, the reaction can also be carried out for the compound wherein $R^1$ is substituted with $R^1$-T-.

The compounds represented by the formula (I), wherein m is 1, X is the formula $—V'—(V')_k—$, V' is a methylene group, k is 0, and Y' is a carboxy group, can also be prepared, by the following method:

<Scheme 61>

[Formula 74]

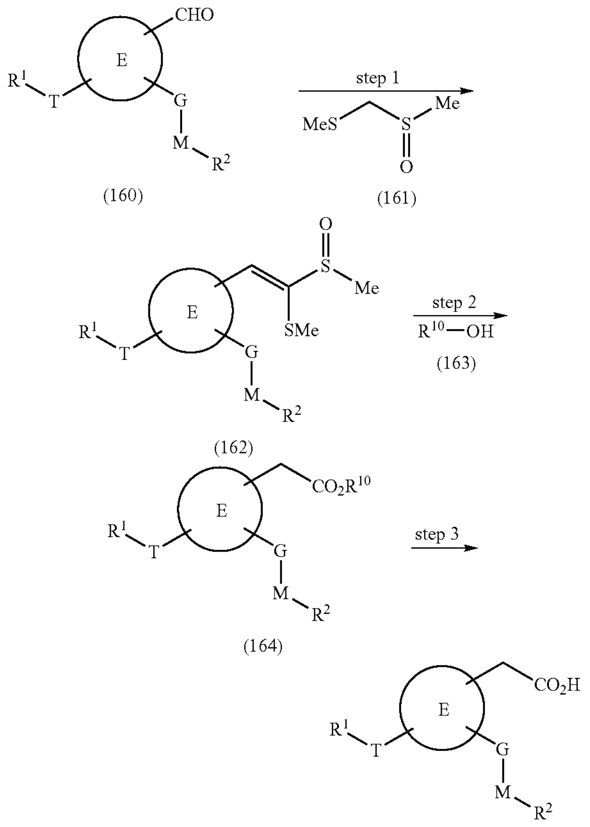

(160)

(161)

(162)

(164)

(165)

wherein $R^{10}$ represents a $C_{1-6}$ alkyl group or the like; T represents a single bond or R"; $R^1$, $R^2$, M, G and E have the same meanings as the aforementioned definitions.

<Step 1>

The compound represented by the general formula (162) can be prepared by reacting the compound represented by the general formula (160) with the compound represented by the general formula (161). This reaction is carried out, for example, in the presence of a base, in a solvent. An organic salt may also be used in place of the base. Examples of the base include inorganic bases. Examples of the organic salt include benzyltrimethylammonium hydroxide. Examples of the solvent include ether type solvents, alcohol type solvents, or a mixed solvent thereof.

<Step 2>

The compound represented by the general formula (164) can be prepared by reacting the compound represented by the general formula (162) with the compound represented by the general formula (163). This reaction is carried out, for example, in the presence of an acid, in a solvent. Examples of the acid include inorganic acids. Examples of the solvent include alcohol type solvents, water, or a mixed solvent thereof.

<Step 3>

The final target compound represented by the general formula (165) can be prepared in the same manner as the aforementioned Step 4 in the Scheme 5 except using the compound represented by the general formula (164) in place of the compound represented by the general formula (18).

The compounds represented by the formula (I), wherein m is 1, X is —C(═O)—, and Y' is a carboxy group, can be prepared, by the following method:

<Scheme 62>

[Formula 75]

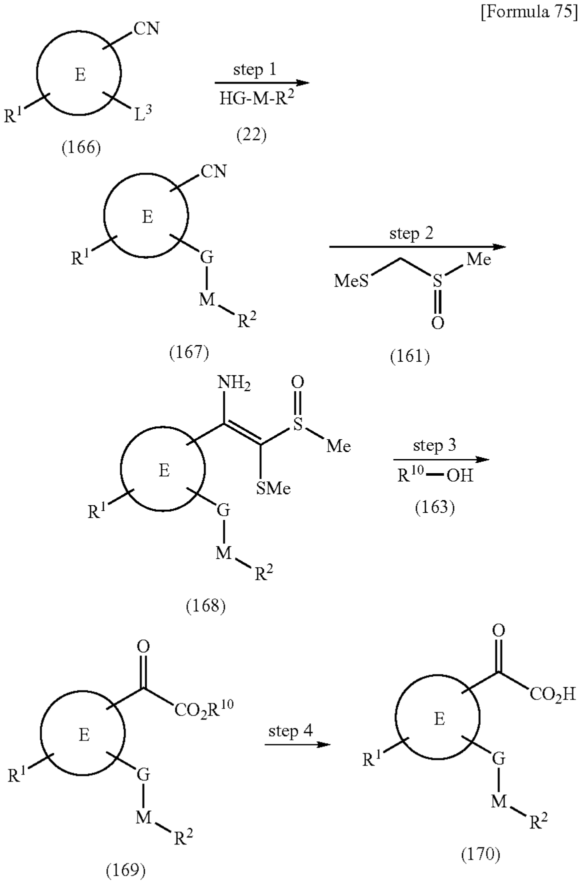

wherein $L^3$ represents a halogen atom or the like; $R^{10}$ represents a $C_{1-6}$ alkyl group or the like; T represents a single bond or R''; $R^1$, $R^2$, M, G and E have the same meanings as the aforementioned definitions.

<Step 1>

The compound represented by the general formula (167) can be prepared in the same manner as the aforementioned Step 2 in the Scheme 10 except using the compound represented by the general formula (166) in place of the compound represented by the general formula (28).

<Step 2>

The compound represented by the general formula (168) can be prepared in the same manner as the aforementioned Step 1 in the Scheme 61 except using the compound represented by the general formula (167) in place of the compound represented by the general formula (160).

<Step 3>

The compound represented by the general formula (169) can be prepared by reacting the compound represented by the general formula (168) with the compound represented by the general formula (163). This reaction is carried out, for example, in the presence of copper(II) chloride dihydrate, in a solvent. Examples of the solvent include alcohol type solvents, water, or a mixed solvent thereof.

<Step 4>

The final target compound represented by the general formula (170) can be prepared in the same manner as the aforementioned Step 4 in the Scheme 5 except using the compound represented by the general formula (169) in place of the compound represented by the general formula (18). In the Scheme 62, the reaction can also be carried out for the compound wherein $R^1$ is substituted with $R^1$-T-.

The compounds represented by the formula (I), wherein m is 1, X is the formula —V'—(V')$_k$—, V' is a methylene group, k is 2, and Y' is a carboxy group, can also be prepared, by the following method:

<Scheme 63>

[Formula 76]

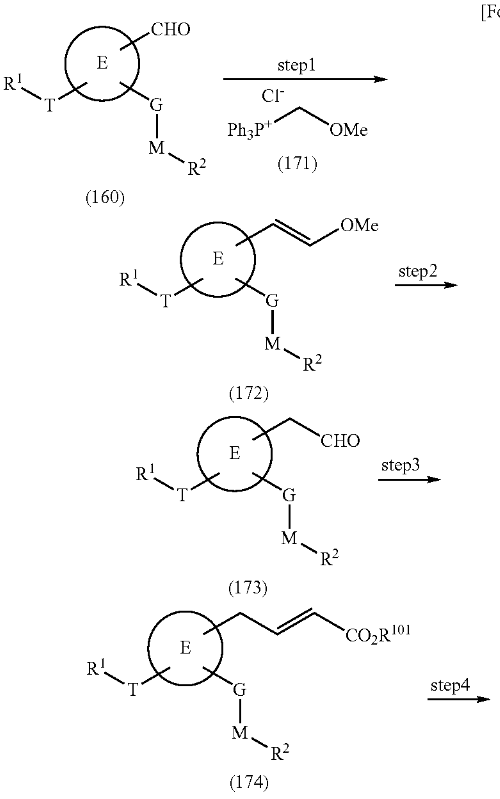

-continued

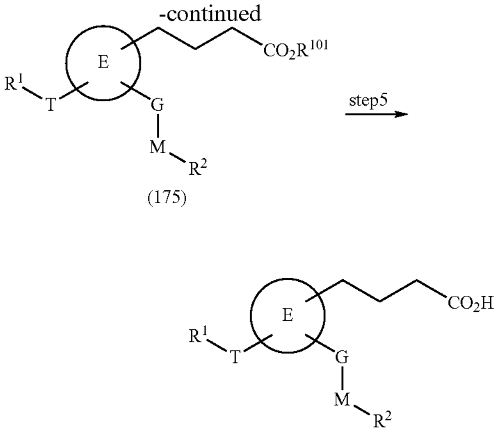

(175)

(176)

wherein $R^{101}$ represents a $C_{1-6}$ alkyl group or the like; T represents a single bond or R"; $R^1$, $R^2$, R", M, G and E have the same meanings as the aforementioned definitions.

<Step 1>

The compound represented by the general formula (172) can be prepared by reacting the compound represented by the general formula (160) with the compound represented by the general formula (171). This reaction is known as "Wittig reaction," and is carried out in the presence of a base, in a solvent. Examples of the base include inorganic bases, organic bases and organometallic bases. Examples of the solvent include ether type solvents, amide type solvents, aromatic solvents, or a mixed solvent thereof.

<Step 2>

The compound represented by the general formula (173) can be prepared by the hydrolysis of the compound represented by the general formula (172). This reaction is carried out, for example, in the presence of an acid, in a solvent. Examples of the acid include inorganic acids and organic acids. Examples of the solvent include alcohol type solvents, water, or a mixed solvent thereof.

<Step 3>

The compound represented by the general formula (174) can be prepared in the same manner as the aforementioned Step 3 in the Scheme 5 except using the compound represented by the general formula (173) in place of the compound represented by the general formula (17).

<Step 4>

The compound represented by the general formula (175) can be prepared in the same manner as the aforementioned Scheme 15 except using the compound represented by the general formula (174) in place of the compound represented by the general formula (19).

<Step 5>

The final target compound represented by the general formula (176) can be prepared in the same manner as the aforementioned Step 4 in the Scheme 5 except using the compound represented by the general formula (175) in place of the compound represented by the general formula (18).

The compounds represented by the general formula (4), wherein $R^{100}$ is a hydrogen atom, can be prepared, for example, by the method described in J. Org. Chem., vol. 55, No. 15, pp. 4622-4634 (1990).

The compounds represented by the general formula (144) can also be prepared by the following method:

<Scheme 64>

[Formula 77]

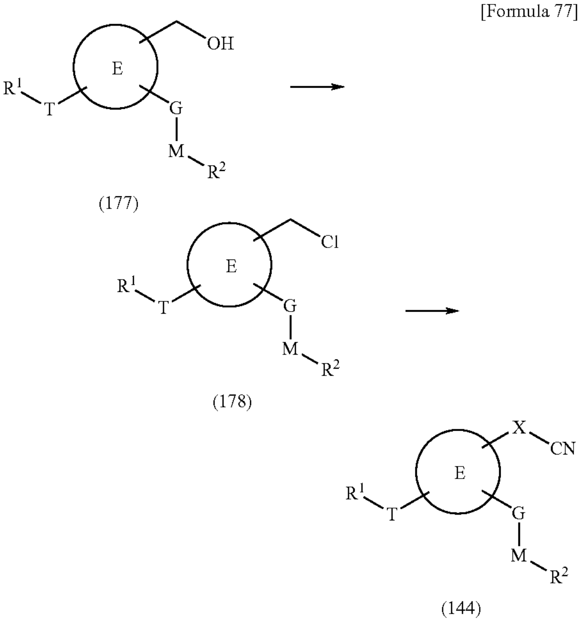

(177)

(178)

(144)

wherein T represents a single bond or R"; $R^1$, $R^2$, R", M, G and E have the same meanings as the aforementioned definitions.

<Step 1>

The compound represented by the general formula (178) can be prepared by the substitution of the hydroxy group of the compound represented by the general formula (177) with the halogen atom. This reaction is carried out, for example, in the presence of thionyl chloride, without a solvent or in a solvent. Examples of the solvent include halogenated solvents, ether type solvents, aromatic solvents, or a mixed solvent thereof.

<Step 2>

The compound represented by the general formula (144) can be prepared by reacting the compound represented by the general formula (178) with a cyanide. This reaction is carried out in a solvent. Examples of the cyanide include sodium cyanide and potassium cyanide. Examples of the solvent include ether type solvents, amide type solvents, aromatic solvents, ketone type solvents, acetonitrile, or a mixed solvent thereof.

In each of the aforementioned preparation methods, examples of the inorganic base include lithium hydride, sodium hydride, potassium hydride, cesium carbonate, potassium carbonate, sodium carbonate, sodium hydrogen carbonate, sodium hydroxide, potassium hydroxide, potassium carbonate, sodium carbonate and potassium fluoride. Examples of the organic base include pyridine, triethylamine and diisopropylethylamine. Examples of the organometallic base include potassium tert-butoxide, lithium diisopropylamide and n-butyllithium. Examples of the inorganic acid include hydrochloric acid and sulfuric acid. Examples of the organic acid include acetic acid, trifluoroacetic acid and methanesulfonic acid. Examples of the crown ether include 18-crown-6. Examples of the Molecular Sieves include Molecular Sieves 4A. Examples of the halogenated solvent include dichloromethane, dichloroethane and chloroform. Examples of the ether type solvent include tetrahydrofuran, 1,2-dimethoxyethane and 1,4-dioxane. Examples of the amide type solvent include dimethylformamide and N-methylpyrrolidone. Examples of the aromatic solvent include benzene and toluene. Examples of the ketone type solvent include acetone and 2-butanone. Examples of the alcohol type solvent include methanol and ethanol.

The compound in the formula (I), in which m is 0, and G is the formula $-(CH_2)_j-N-C(=O)-(CH_2)_h-CO_2H$ or the formula $-(CH_2)_j-N-W'-CO_2H$, can be prepared from the compound in the formula (I), in which m is 0, and G is the formula $-(CH_2)_j-N-C(=O)-(CH_2)_h$-A or the formula $-(CH_2)_j-N-W'$-A (in each of the formulas, A represents a protecting group of the carboxylic acid). Therefore, the compound in the formula (I), in which m is 0, and G is the formula $-(CH_2)_j-N-C(=O)-(CH_2)_h$-A or the formula $-(CH_2)_j-N-W'$-A, is useful as a synthetic intermediate of the compound in the general formula (I), in which m is 0, and G is the formula $-(CH_2)_j-N-C(=O)-(CH_2)_h-CO_2H$ or the formula $-(CH_2)_jN-W'-CO_2-H$.

Furthermore, the compound in the formula (I), in which m is 1, and Y' is a carboxy group, can be prepared from the compound in the formula (I), in which m is 1, and Y' is a protecting group of the carboxy group. Therefore, the compound in the general formula (I), in which m is 1, and Y' is a carboxy group, is useful as a synthetic intermediate of the compound in the general formula (I), in which m is 1, and Y' is a carboxy group.

In the formula (I), when m is 0, and G is the formula $-(CH_2)_j-N-C(=O)-(CH_2)_h$-A or the formula $-(CH_2)_j-N-W'$-A, then examples of A include, more specifically, ester groups such as the formula $-CO_2R^{105}$ and the like.

In the formula (I), when m is 1, and Y' is a protecting group of the carboxy group, then examples of Y' include, more specifically, a cyano group, ester groups such as the formula $-CO_2R^{105}$ and the like, and amide groups such as the formula $-C(=O)-N(R^{106})(R^{107})$ and the like.

$R^{105}$ represents an alkyl group (preferably a $C_{1-10}$ alkyl group, further preferably a $C_{1-6}$ alkyl group), a $C_{6-10}$ aryl group, a $C_{6-10}$ aryl substituted alkyl group (preferably a $C_{6-10}$ aryl substituted $C_{1-10}$ alkyl group, further preferably a phenyl substituted $C_{1-6}$ alkyl group) or the like.

Each of $R^{106}$ and $R^{107}$ independently represents a hydrogen atom, an alkyl group (preferably a $C_{1-10}$ alkyl group, further preferably a $C_{1-6}$ alkyl group), a $C_{6-10}$ aryl group, a $C_{6-10}$ aryl substituted alkyl group (preferably a $C_{6-10}$ aryl substituted $C_{1-10}$ alkyl group, further preferably a phenyl substituted $C_{1-6}$ alkyl group) or the like.

The compound represented by the formula (I) which is an active ingredient of the present invention, a salt thereof, a hydrate of the compound, a hydrate of the salt, a solvate of the compound, or a solvate of the salt can be prepared by using various known synthetic methods, taking advantage of the characteristics based on their basic structure or on the type of their substituent. Depending on the type of the functional group, it can be effective for the production technique for the compounds to protect it with a suitable protective group, or substitute it with a group readily convertible into the functional group, in the starting material or in the intermediate. The functional group includes, for example, amino group, hydroxyl group, and carboxyl group; and their protective groups are described, for example, in T. W. Greene and P. G. M. Wuts; Protective Groups in Organic Synthesis, 3rd Ed., 1999. Depending on the reaction condition, they may be suitably selected and used. Specifically the reaction is conducted after a protective group is introduced into the starting compound, and then optionally the protective group may be removed or may be converted into a desired group to thereby obtain the intended compound.

In the examples of the specification, methods for preparing typical compounds included in the formula (I) are explained in details. Therefore, those skilled in the art can prepare any compound included in the formula (I) by referring to the explanations of the aforementioned general preparation methods and of the specific preparation methods of the examples, selecting appropriate reaction starting materials, reaction reagents, and reaction conditions, and, if necessary, by adding appropriate modification and alteration of these methods.

The medicament of the present invention can be used for prevention and/or therapeutic treatment of a disease caused by an expression of PAI-1 or an enhancement of PAI-1 activity. The term "therapeutic treatment" used in the present specification includes prevention of progression of disease and the term "prevention" includes prevention of reoccurrence. The medicament of the present invention can be used as a medicament for prevention and/or therapeutic treatment of a disease caused by, for example, thrombus formation, fibrosis, visceral fat deposition, angiogenesis, deposition and remodeling of extracellular matrix, diseases caused by the proliferation, migration, infiltration and metastasis of cells (for example, tumor cells, vascular endothelial cells and the like), and the remodeling of tissues (for example, heart remodeling, vascular remodeling and the like).

More specifically, the medicament of the present invention can be used as a medicament for prevention and/or therapeutic treatment of one or more diseases selected from ischemic cerebrovascular diseases such as cerebral thrombosis, cerebral embolism, cerebral infarction, transient ischemic attack, cerebral stroke, cerebrovascular dementia and the like; Alzheimer's disease; Parkinson's disease; Huntington's disease; dementias such as cerebrovascular dementia, senile dementia and the like; ischemic heart diseases such as angina, myocardial infarction, intra-atrial thrombosis caused by atrial fibrillation, heart failure and the like; thrombotic pulmonary diseases such as pulmonary thrombosis, pulmonary embolism and the like; occlusive venous diseases such as deep-vein thrombosis (DVT), thrombophlebitis and the like; occlusive peripheral arterial diseases such as acute arterial occlusion, chronic arterial occlusion and the like; thrombus after bypass vascular transplantation; disseminated intravascular coagulation (DIC); acute coronary occlusion and restenosis after percutaneous transluminal coronary angioplasty (PTCA); angiopathy and thrombus caused by immune disorders such as antiphospholipid antibody syndrome and the like; angiopathy and thrombus caused by congenital thrombotic tendency such as genetic abnormality; thrombotic renal diseases such as renal thrombosis, renal embolism and the like; nephropathy caused by metabolic diseases; arteriosclerosis; thrombotic diseases, thrombosis, fibrosis, blood coagulation, ischemic diseases, heart attack, profound thrombosis, pulmonary thromboembolism, venous thromboembolism, nephrosclerosis, metabolic syndrome, aldosterone tissue disorder, organ failure, economy-class syndrome, endotoxic shock, allergic diseases, vascular events of the brain, the heart and the like, vasculitis, nonbacterial thrombotic endocarditis; severe infections such as sepsis and the like; fibrin-dependent pain in arthritis; diabetic complications such as retinopathy, nephropathy, neurosis, peripheral circulatory disturbance and the like; hypertension; diabetes; hyperinsulinemia; hypercholesterolemia; insulin-resistant disorder; hyperlipidemia; obesity; aging; polycystic ovarian syndrome; autoimmune diseases such as multiple sclerosis and the like; tumors including solid cancers such as lung cancer, pancreatic cancer, colon cancer, gastric cancer, prostate cancer, breast cancer, cervical cancer, ovarian cancer and the like; tumor invasion; tumor metastasis; asthma; endometriosis; age-related macular degeneration; fibrosis of tissues and the corresponding diseases such as prostatic hyperplasia, liver cirrhosis, pulmonary fibrosis, renal fibrosis, interstitial cystitis and the like; atherosclerosis; prevention of restenosis after placement of stent(s); prevention of thrombus formation and thrombosis after implantation of medical device(s) such as artificial joint, artificial blood vessel, artificial heart-lung machine, artificial heart and the like; scar after surgery; prevention of an adhesion of tissues; and acute rejections and arterial lesions after transplantation of the tissue(s) such as heart, kidney or (and) the like. Moreover, since the medicament of the present invention can prevent and improve thrombus formation, it is effective for wound healing and decubitus healing.

As the active ingredient of the medicament on the present invention, one or more kinds of substances selected from the group consisting of the compound represented by the formula (I) and a pharmacologically acceptable salt thereof, and a hydrate thereof and a solvate thereof may be used. As the medicament of the present invention, the aforementioned substance, per se, may be used. However, preferably, the medicament of the present invention is provided in the form of a pharmaceutical composition comprising the aforementioned substance which is an active ingredient together with one or more pharmacologically acceptable pharmaceutical additives. In the aforementioned pharmaceutical compositions, a ratio of the active ingredient to the pharmaceutical additives is approximately 1 weight % to 90 weight %.

The medicament of the present invention may be administered as pharmaceutical compositions for oral administration, for example, granules, subtilized granules, powders, hard capsules, soft capsules, syrup, emulsion, suspension, or solution, or may be administered as pharmaceutical compositions for parenteral administration, for example, injections for intravenous administration, intramuscular administration or subcutaneous administration, drops, suppositories, percutaneous absorbent, transmucosal absorption preparations, nasal drops, ear drops, eye drops, and inhalations. Preparations made as pharmaceutical compositions in a form of powder may be dissolved when necessary and used as injections or drip infusions.

For preparation of pharmaceutical compositions, solid or liquid pharmaceutical additives may be used. Pharmaceutical additives may either be organic or inorganic. When an oral solid preparation is prepared, an excipient is added to the principal agent, and further binders, disintegrator, lubricant, colorant, flavoring agent are added if necessary, preparations in the forms of tablets, coating tablets, granules, powders, capsules and the like may be manufactured by common procedures. Examples of the excipient include lactose, sucrose, saccharose, glucose, corn starch, starch, talc, sorbit, crystal cellulose, dextrin, kaolin, calcium carbonate, and silicon dioxide. Examples of the binder include, for example, polyvinyl alcohol, polyvinyl ether, ethyl cellulose, methyl cellulose, gum Arabic, tragacanth, gelatine, shellac, hydroxypropyl cellulose, hydroxypropyl methyl cellulose, calcium citrate, dextrin, and pectin. Examples of the lubricant include, for example, magnesium stearate, talc, polyethylene glycol, silica, and hydrogenated vegetable oil. As the coloring agent, any material can be used that are approved to be added to ordinary pharmaceuticals. As the flavoring agent, cocoa powder, menthol, aromatic acid, mint oil, borneol, cinnamon powder and the like can be used. These tables and granules may be applied with sugarcoating, gelatine coating, or an appropriate coating, if necessary. Preservatives, antioxidant and the like may be added, if required.

For the preparation of liquid preparations for oral administration such as emulsions, syrups, suspensions, and solutions, commonly used inactive diluents, for example, water or vegetable oil may be used. For these preparations, besides inactive diluents, adjuvants such as wetting agents, suspending aids, sweeting agents, flavoring agents, coloring agents or preservatives may be blended. After a liquid preparation is manufactured, the preparation may be filled in capsules made of a absorbable substance such as gelatin. Examples of solvents or suspending agents used for the preparations of parenteral administration such as injections or suppositories include, for example, water, propylene glycol, polyethylene glycol, benzyl alcohol, ethyl oleate, and lecithin. Examples of base materials used for preparation of suppositories include, for example, cacao butter, emulsified cacao butter, lauric fat, and witepsol. Methods for preparation of the aforementioned preparations are not limited, and any method ordinarily used in the art may be used.

When the preparations are prepared in the form of injections, carriers such as, for example, diluents including water, ethanol, macrogol, propyleneglycol, citric acid, acetic acid, phosphoric acid, lactic acid, sodium lactate, sulfuric acid and sodium hydroxide, pH modifiers and buffer solutions including sodium citrate, sodium acetate and sodium phosphate, stabilizers such as sodium pyrosulfite, ethylenediaminetetraacetic acid, thioglycolic acid and thiolactate may be used. For the preparation, a sufficient amount of a salt, glucose, mannitol or glycerin may be blended in the preparation to manufacture an isotonic solution, and an ordinary solubilizer, a soothing agent, or a topical anesthetic may be used.

When the preparation in the form of an ointment such as a paste, a cream, and a gel is manufactured, an ordinarily used base material, a stabilizer, a wetting agent, and a preservative may be blended, if necessary, and may be prepared by mixing the components by a common method. As the base material, for example, white petrolatum, polyethylene, paraffin, glycerin, cellulose derivatives, polyethylene glycol, silicon, and bentonite may be used. As the preservative, paraoxy methyl benzoate, paraoxy ethyl benzoate, paraoxy propyl benzoate and the like may be used. When the preparation in the form of a patch is manufactured, the aforementioned ointment, cream, gel, or paste and the like may be applied by a common method to an ordinary support. As the support, fabric or nonwoven fabric made of cotton, span rayon, synthetic fibers or and the like; and a film or a foam sheet such as made of soft vinyl chloride, polyethylene, and polyurethane and the like may be preferably used.

A dose of the medicament of the present invention is not particularly limited. For oral administration, a dose may generally be 0.01 to 5,000 mg per day for an adult as the weight of the compound of the present invention. It is preferred to increase or decrease the aforementioned dose appropriately depending on the age, pathological conditions, and symptoms of a patient. The aforementioned dose may be administered once a day or 2 to 3 times a day as divided portions with proper intervals, or intermittent administration for every several days may be acceptable. When the medicament is used as an injection, the dose may be 0.001 to 100 mg per day for an adult as the weight of the compound of the present invention.

Oral or parenteral administration of the medicament of the present invention may be carried out preoperatively, when the medicament of the present invention is used for prophylactic and/or therapeutic treatment of intravascular lesions after vascular transplantation or organ transplantation or after blood circulation restoration, whose examples include, for example, thrombus after bypass vascular transplantation, acute coronary occlusion and restenosis after PTCA, arterial lesions after organ transplantation such as cardiac transplantation and renal transplantation and the like. Furthermore, oral or parenteral administration of the medicament of the present invention may be carried out intraoperatively and/or postoperatively in addition to the aforementioned preoperative administration, if necessary.

EXAMPLES

The present invention will be explained more specifically with reference to the following examples. However the scope of the present invention is not limited to the following examples. In the present examples, when 1 is selected as m, and the carboxy group is selected as Y' of the compound represented by the formula (I), the compounds are prepared, in which each of the partial structures including E and the substituent groups is selected from those shown in the Tables 1-1 to 1-27. Furthermore, when 1 is selected as m and the 1H-tetrazol-5-yl group is selected as Y in the compound represented by the formula (I), the compounds wherein each of the partial structures including E and the substituent groups shown on the Table 2 is respectively selected as the partial structure and the groups are prepared. Furthermore, when 0 is selected as m of the compound represented by the formula (I), the compounds wherein each of the partial structures, the groups and numeric values shown on the Tables 3-1 to 3-12 is respectively selected as the partial structure including E, the substituent groups and j are prepared.

In the following, the number and the structure formula of the intermediate prepared in each example are shown, respectively.

TABLE 4-1

| Number | Structural formula |
|---|---|
| 1<br>(1) | 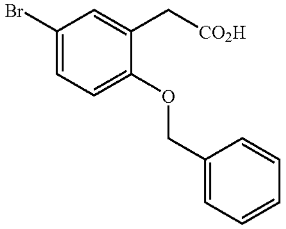 [SMILES: O=C(O)Cc1cc(Br)ccc1OCc1ccccc1] |
| 2<br>(1) | 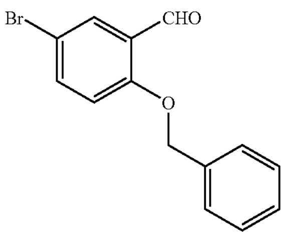 [SMILES: O=Cc1cc(Br)ccc1OCc1ccccc1] |

TABLE 4-1-continued

| Number | Structural formula |
|---|---|
| 2<br>(2) | 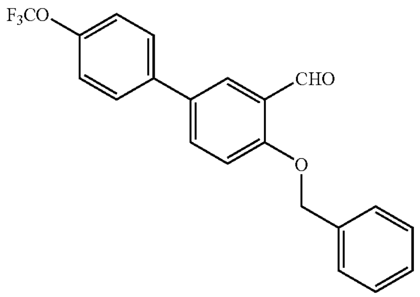 [SMILES: O=Cc1cc(-c2ccc(OC(F)(F)F)cc2)ccc1OCc1ccccc1] |
| 4<br>(1) | 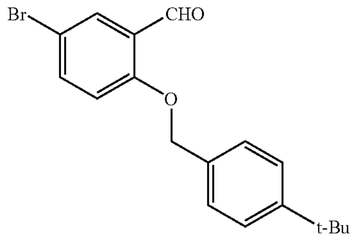 |
| 4<br>(2) | 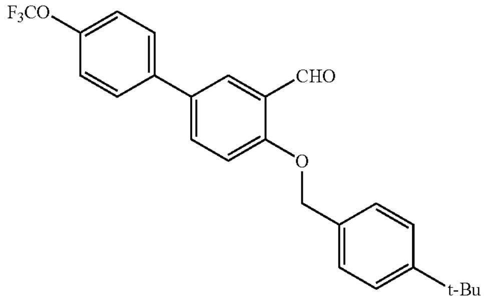 [SMILES: CC(C)(C)c1ccc(COc2ccc(-c3ccc(OC(F)(F)F)cc3)cc2C=O)cc1] |
| 6<br>(1) | 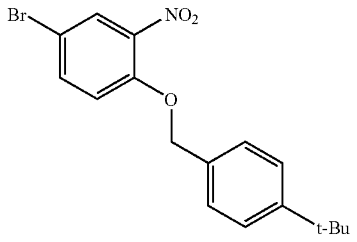 [SMILES: CC(C)(C)c1ccc(COc2ccc(Br)cc2[N+](=O)[O-])cc1] |
| 6<br>(2) | 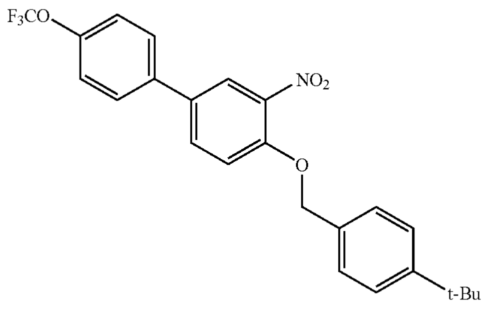 |

TABLE 4-1-continued
| Number | Structural formula |
|---|---|
| 6 (3) | 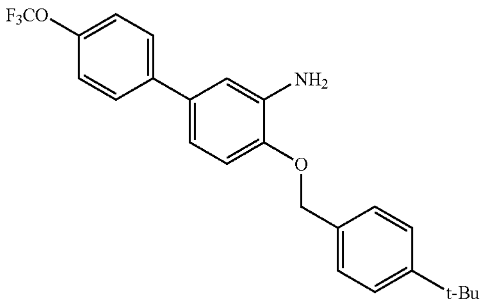 [SMILES: CC(C)(C)c1ccc(COc2ccc(-c3ccc(OC(F)(F)F)cc3)cc2N)cc1] |
| 6 (4) | 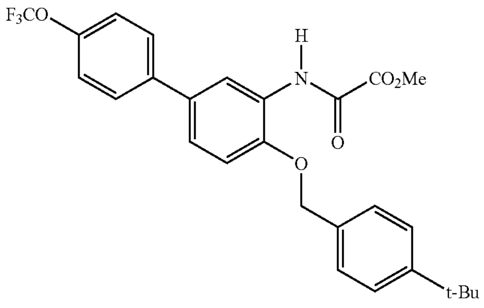 [SMILES: COC(=O)C(=O)Nc1cc(-c2ccc(OC(F)(F)F)cc2)ccc1OCc1ccc(C(C)(C)C)cc1] |
| 7 (1) | 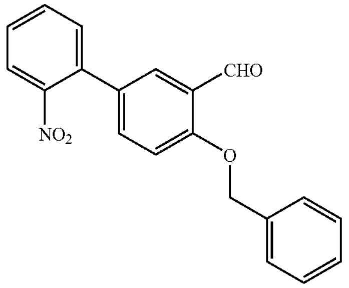 [SMILES: O=Cc1cc(-c2ccccc2[N+](=O)[O-])ccc1OCc1ccccc1] |
| 9 (1) | 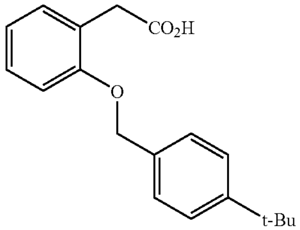 [SMILES: CC(C)(C)c1ccc(COc2ccccc2CC(=O)O)cc1] |
| 9 (2) | 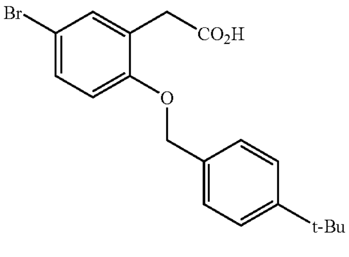 [SMILES: CC(C)(C)c1ccc(COc2ccc(Br)cc2CC(=O)O)cc1] |
TABLE 4-2
| | |
|---|---|
| 11 (1) | 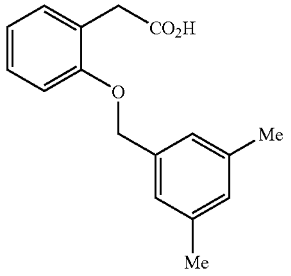 [SMILES: Cc1cc(C)cc(COc2ccccc2CC(=O)O)c1] |
| 11 (2) | 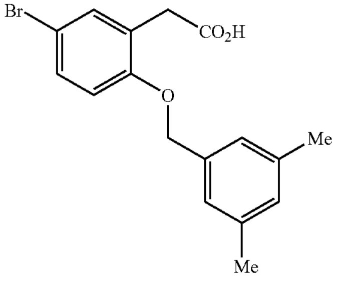 [SMILES: Cc1cc(C)cc(COc2ccc(Br)cc2CC(=O)O)c1] |
| 12 (1) | 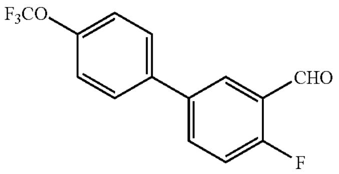 [SMILES: O=Cc1cc(-c2ccc(OC(F)(F)F)cc2)ccc1F] |
| 12 (2) | 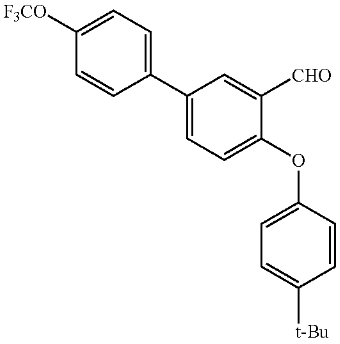 [SMILES: CC(C)(C)c1ccc(Oc2ccc(-c3ccc(OC(F)(F)F)cc3)cc2C=O)cc1] |
| 12 (3) | 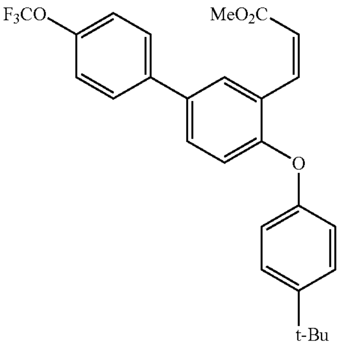 [SMILES: COC(=O)/C=C\c1cc(-c2ccc(OC(F)(F)F)cc2)ccc1Oc1ccc(C(C)(C)C)cc1] |

TABLE 4-2-continued
| | |
|---|---|
| 14 (1) | 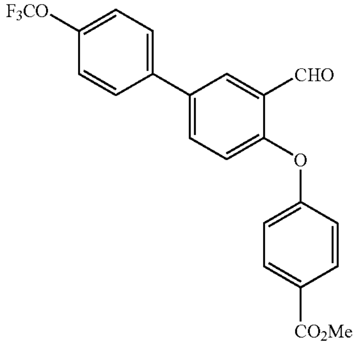 [SMILES: COC(=O)c1ccc(Oc2ccc(-c3ccc(OC(F)(F)F)cc3)cc2C=O)cc1] |
| 14 (2) | 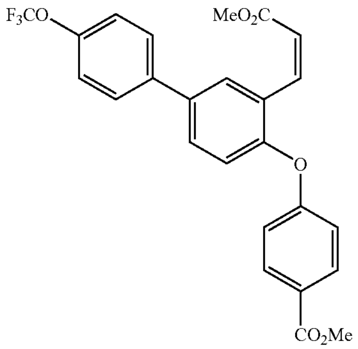 [SMILES: COC(=O)/C=C\c1cc(-c2ccc(OC(F)(F)F)cc2)ccc1Oc1ccc(C(=O)OC)cc1] |
| 14 (3) | 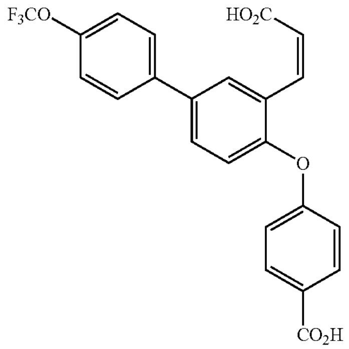 [SMILES: O=C(O)/C=C\c1cc(-c2ccc(OC(F)(F)F)cc2)ccc1Oc1ccc(C(=O)O)cc1] |
| 15 (1) | 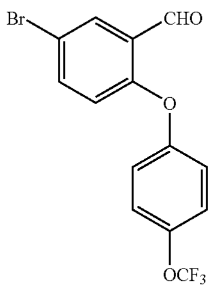 [SMILES: O=Cc1cc(Br)ccc1Oc1ccc(OC(F)(F)F)cc1] |
| 15 (2) | 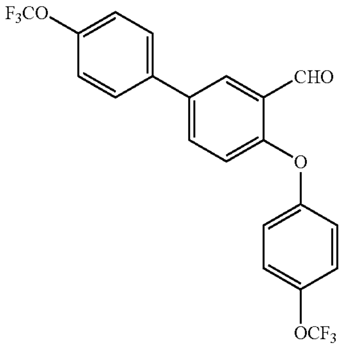 |
| 17 (1) | 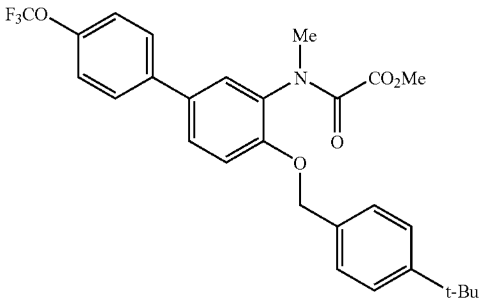 [SMILES: COC(=O)C(=O)N(C)c1cc(-c2ccc(OC(F)(F)F)cc2)ccc1OCc1ccc(C(C)(C)C)cc1] |
| 18 (1) | 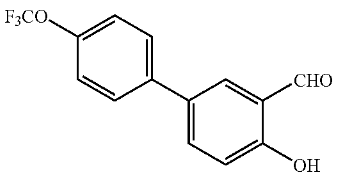 [SMILES: O=Cc1cc(-c2ccc(OC(F)(F)F)cc2)ccc1O] |
TABLE 4-3
| | |
|---|---|
| 18 (2) | 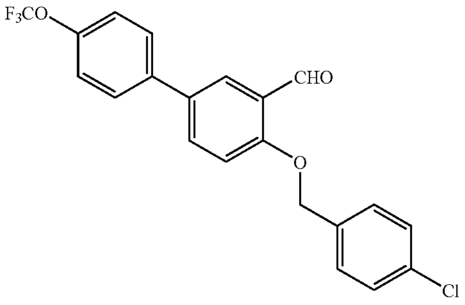 [SMILES: O=Cc1cc(-c2ccc(OC(F)(F)F)cc2)ccc1OCc1ccc(Cl)cc1] |
| 20 (1) | 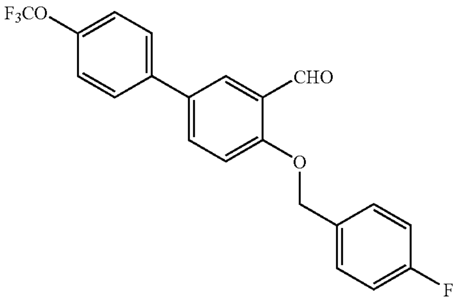 [SMILES: O=Cc1cc(-c2ccc(OC(F)(F)F)cc2)ccc1OCc1ccc(F)cc1] |

TABLE 4-3-continued
20 (2)
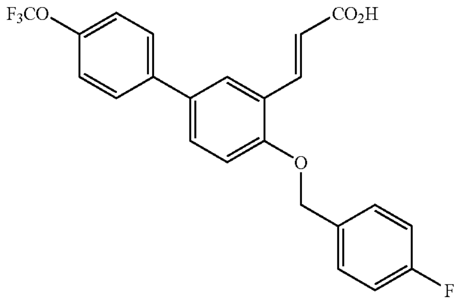 [SMILES: O=C(O)/C=C/c1cc(-c2ccc(OC(F)(F)F)cc2)ccc1OCc1ccc(F)cc1]
21 (1)
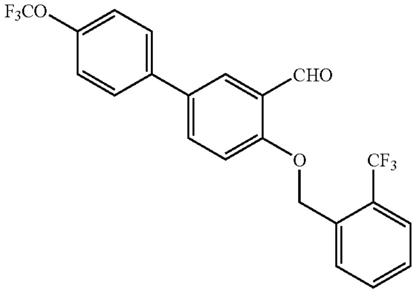 [SMILES: O=Cc1cc(-c2ccc(OC(F)(F)F)cc2)ccc1OCc1ccccc1C(F)(F)F]
21 (2)
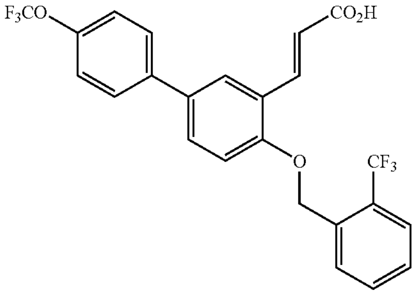 [SMILES: O=C(O)/C=C/c1cc(-c2ccc(OC(F)(F)F)cc2)ccc1OCc1ccccc1C(F)(F)F]
22 (1)
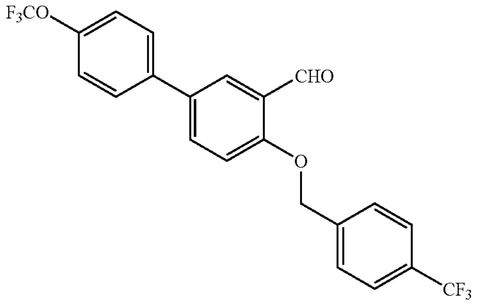 [SMILES: O=Cc1cc(-c2ccc(OC(F)(F)F)cc2)ccc1OCc1ccc(C(F)(F)F)cc1]
22 (2)
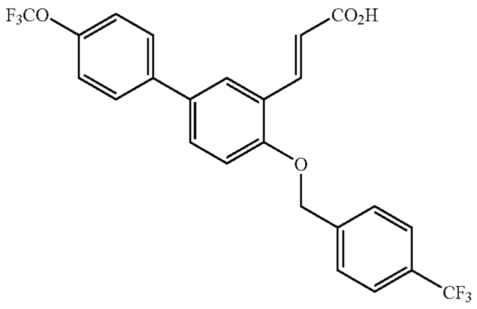 [SMILES: O=C(O)/C=C/c1cc(-c2ccc(OC(F)(F)F)cc2)ccc1OCc1ccc(C(F)(F)F)cc1]
TABLE 4-3-continued
23 (1)
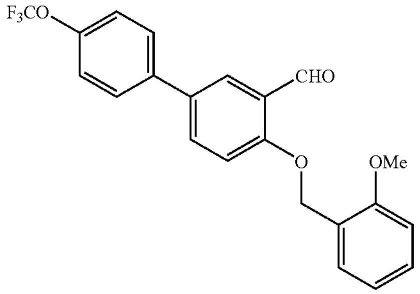 [SMILES: COc1ccccc1COc1ccc(-c2ccc(OC(F)(F)F)cc2)cc1C=O]
23 (2)
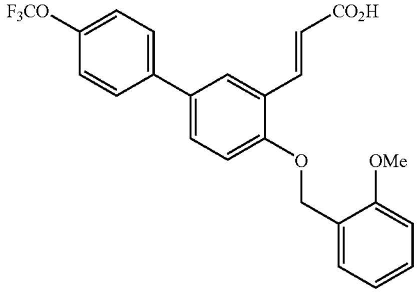 [SMILES: COc1ccccc1COc1ccc(-c2ccc(OC(F)(F)F)cc2)cc1/C=C/C(=O)O]
24 (1)
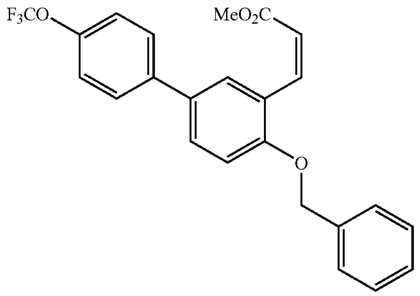 [SMILES: COC(=O)/C=C\c1cc(-c2ccc(OC(F)(F)F)cc2)ccc1OCc1ccccc1]
25 (1)
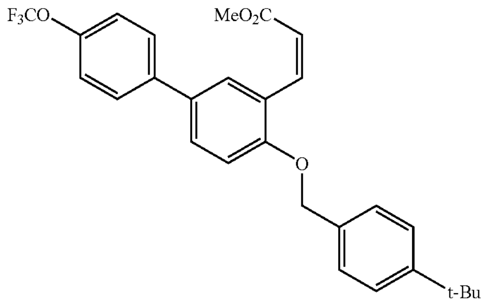 [SMILES: COC(=O)/C=C\c1cc(-c2ccc(OC(F)(F)F)cc2)ccc1OCc1ccc(C(C)(C)C)cc1]
26 (1)
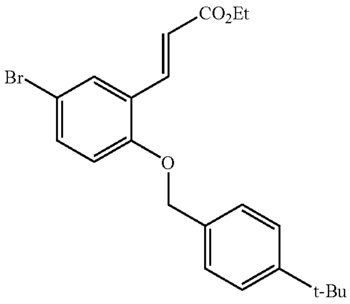 [SMILES: CCOC(=O)/C=C/c1cc(Br)ccc1OCc1ccc(C(C)(C)C)cc1]

TABLE 4-4
26
(2)
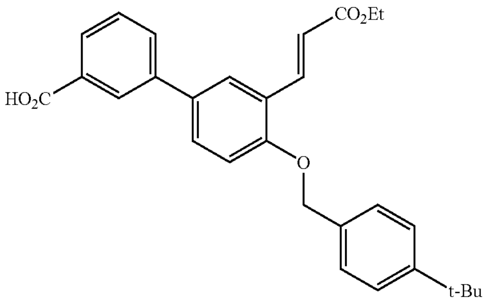 [SMILES: CCOC(=O)/C=C/c1cc(-c2cccc(C(=O)O)c2)ccc1OCc1ccc(C(C)(C)C)cc1]
26
(3)
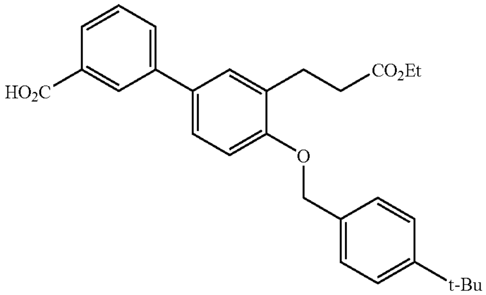 [SMILES: CCOC(=O)CCc1cc(-c2cccc(C(=O)O)c2)ccc1OCc1ccc(C(C)(C)C)cc1]
27
(1)
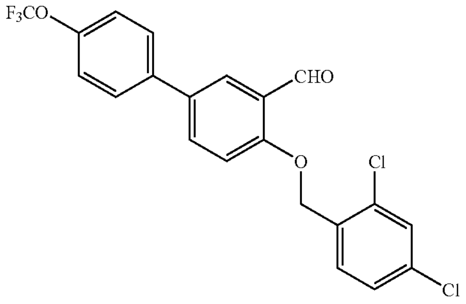 [SMILES: O=Cc1cc(-c2ccc(OC(F)(F)F)cc2)ccc1OCc1ccc(Cl)cc1Cl]
27
(2)
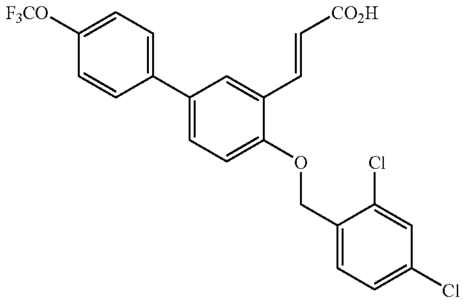 [SMILES: O=C(O)/C=C/c1cc(-c2ccc(OC(F)(F)F)cc2)ccc1OCc1ccc(Cl)cc1Cl]
28
(1)
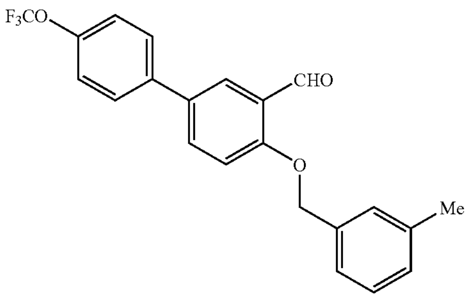 [SMILES: Cc1cccc(COc2ccc(-c3ccc(OC(F)(F)F)cc3)cc2C=O)c1]
TABLE 4-4-continued
28
(2)
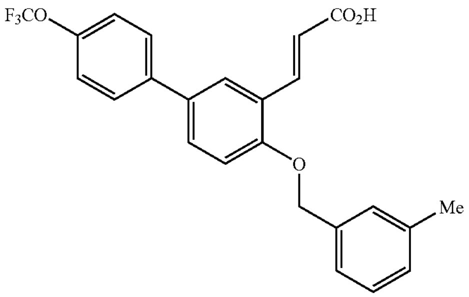 [SMILES: Cc1cccc(COc2ccc(-c3ccc(OC(F)(F)F)cc3)cc2/C=C/C(=O)O)c1]
29
(1)
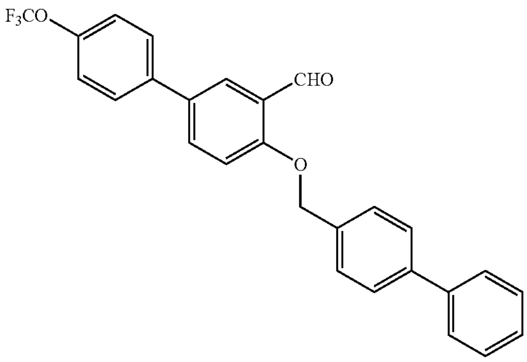 [SMILES: O=Cc1cc(-c2ccc(OC(F)(F)F)cc2)ccc1OCc1ccc(-c2ccccc2)cc1]
29
(2)
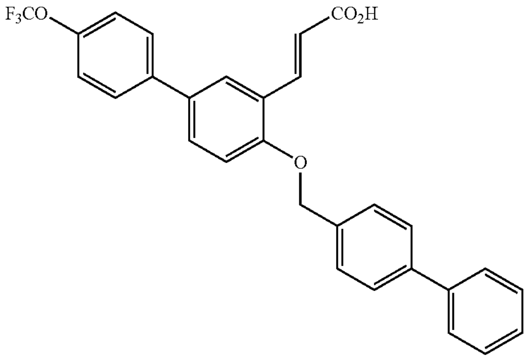 [SMILES: O=C(O)/C=C/c1cc(-c2ccc(OC(F)(F)F)cc2)ccc1OCc1ccc(-c2ccccc2)cc1]
30
(1)
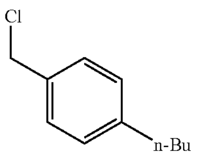
30
(2)
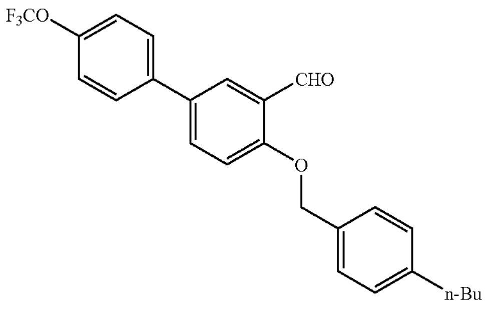

TABLE 4-4-continued
30
(3)
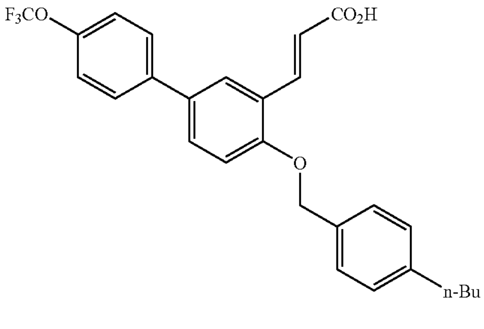
31
(1)
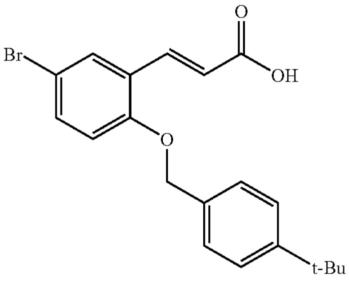 [SMILES: CC(C)(C)c1ccc(COc2ccc(Br)cc2/C=C/C(=O)O)cc1]
TABLE 4-5
43
(1)
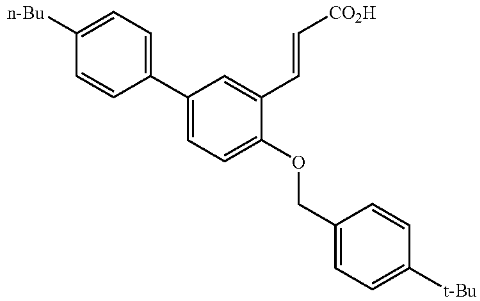
45
(1)
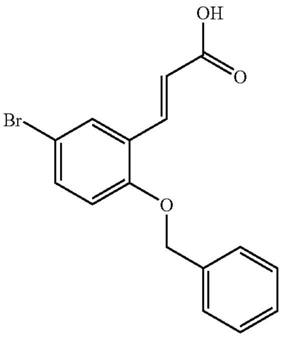 [SMILES: O=C(O)/C=C/c1cc(Br)ccc1OCc1ccccc1]
46
(1)
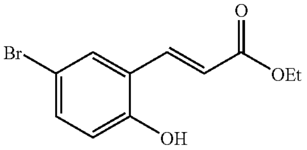 [SMILES: CCOC(=O)/C=C/c1cc(Br)ccc1O]
TABLE 4-5-continued
46
(2)
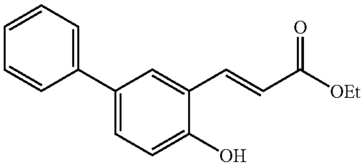 [SMILES: CCOC(=O)/C=C/c1cc(-c2ccccc2)ccc1O]
46
(3)
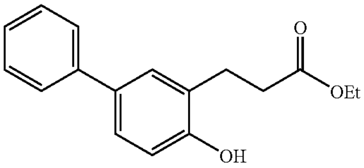 [SMILES: CCOC(=O)CCc1cc(-c2ccccc2)ccc1O]
46
(4)
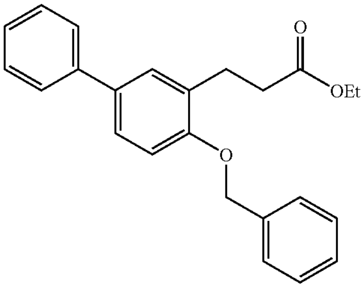 [SMILES: CCOC(=O)CCc1cc(-c2ccccc2)ccc1OCc1ccccc1]
51
(1)
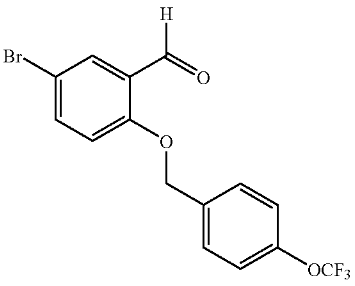 [SMILES: O=Cc1cc(Br)ccc1OCc1ccc(OC(F)(F)F)cc1]
51
(2)
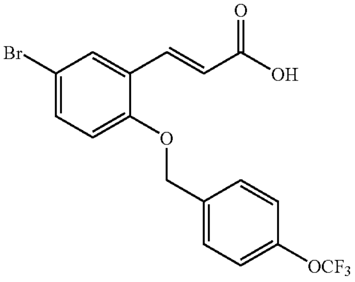 [SMILES: O=C(O)/C=C/c1cc(Br)ccc1OCc1ccc(OC(F)(F)F)cc1]
53
(1)
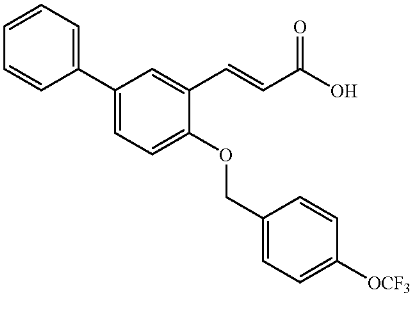 [SMILES: O=C(O)/C=C/c1cc(-c2ccccc2)ccc1OCc1ccc(OC(F)(F)F)cc1]

TABLE 4-5-continued
| | |
|---|---|
| 54 (1) | 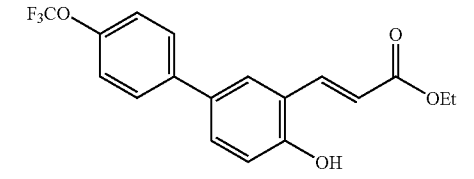 [SMILES: CCOC(=O)/C=C/c1cc(-c2ccc(OC(F)(F)F)cc2)ccc1O] |
| 54 (2) | 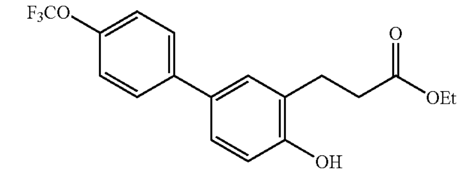 [SMILES: CCOC(=O)CCc1cc(-c2ccc(OC(F)(F)F)cc2)ccc1O] |
| 54 (3) | 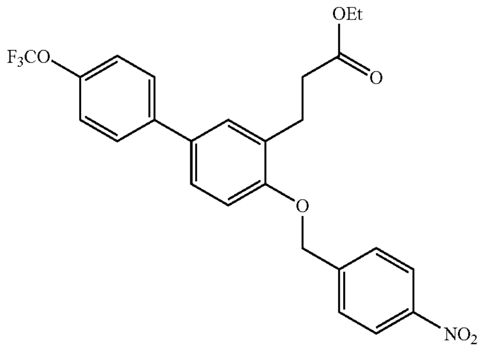 [SMILES: CCOC(=O)CCc1cc(-c2ccc(OC(F)(F)F)cc2)ccc1OCc1ccc([N+](=O)[O-])cc1] |
TABLE 4-6
| | |
|---|---|
| 57 (1) | 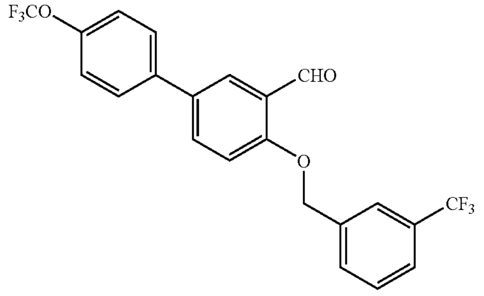 [SMILES: O=Cc1cc(-c2ccc(OC(F)(F)F)cc2)ccc1OCc1cccc(C(F)(F)F)c1] |
| 59 (1) | 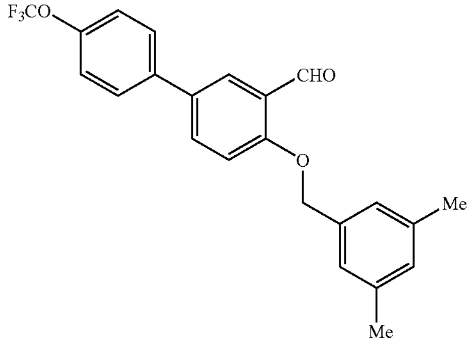 [SMILES: Cc1cc(C)cc(COc2ccc(-c3ccc(OC(F)(F)F)cc3)cc2C=O)c1] |
TABLE 4-6-continued
| | |
|---|---|
| 59 (2) | 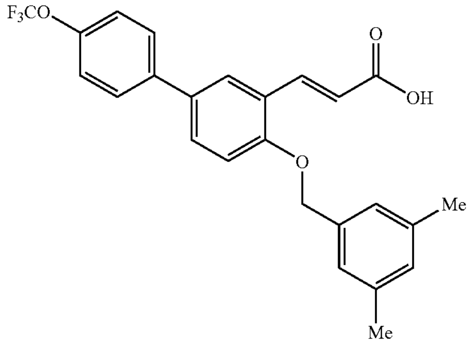 [SMILES: Cc1cc(C)cc(COc2ccc(-c3ccc(OC(F)(F)F)cc3)cc2/C=C/C(=O)O)c1] |
| 60 (1) | 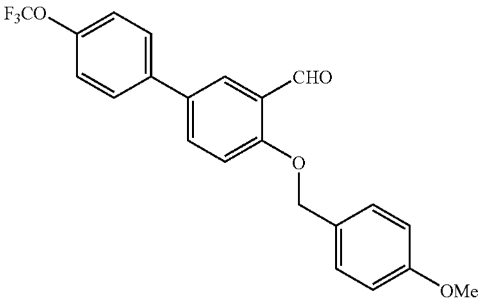 [SMILES: COc1ccc(COc2ccc(-c3ccc(OC(F)(F)F)cc3)cc2C=O)cc1] |
| 60 (2) | 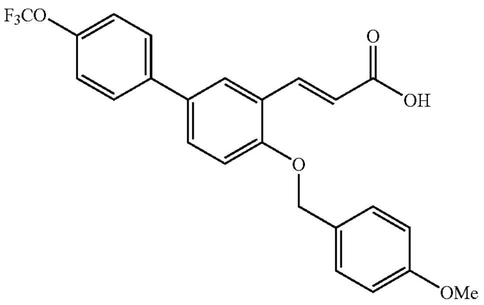 [SMILES: COc1ccc(COc2ccc(-c3ccc(OC(F)(F)F)cc3)cc2/C=C/C(=O)O)cc1] |
| 61 (1) | 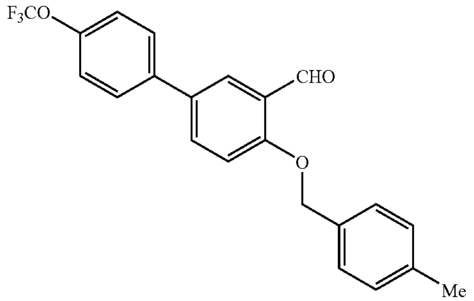 [SMILES: Cc1ccc(COc2ccc(-c3ccc(OC(F)(F)F)cc3)cc2C=O)cc1] |
| 61 (2) | 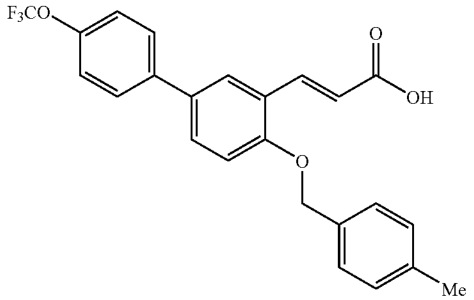 [SMILES: Cc1ccc(COc2ccc(-c3ccc(OC(F)(F)F)cc3)cc2/C=C/C(=O)O)cc1] |

TABLE 4-6-continued
62 (1)
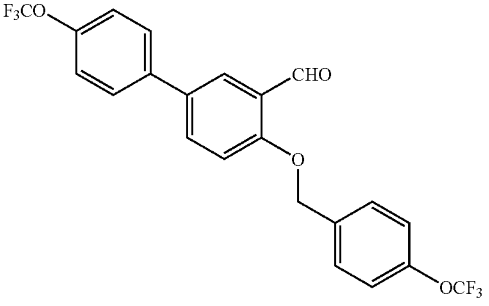 [SMILES: O=Cc1cc(-c2ccc(OC(F)(F)F)cc2)ccc1OCc1ccc(OC(F)(F)F)cc1]
62 (2)
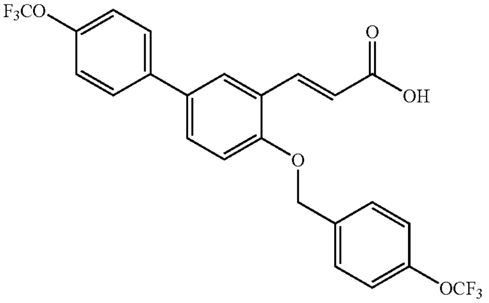 [SMILES: O=C(O)/C=C/c1cc(-c2ccc(OC(F)(F)F)cc2)ccc1OCc1ccc(OC(F)(F)F)cc1]
67 (1)
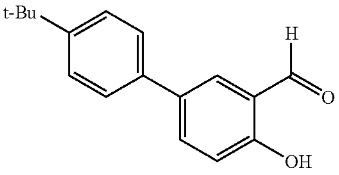 [SMILES: CC(C)(C)c1ccc(-c2ccc(O)c(C=O)c2)cc1]
67 (2)
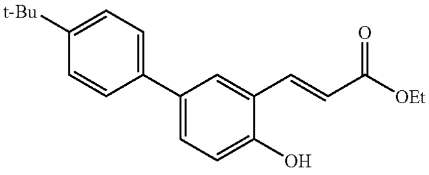 [SMILES: CCOC(=O)/C=C/c1cc(-c2ccc(C(C)(C)C)cc2)ccc1O]
67 (3)
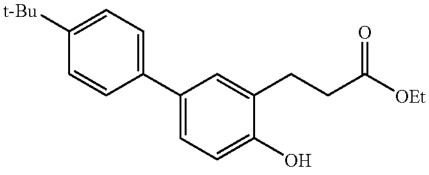 [SMILES: CCOC(=O)CCc1cc(-c2ccc(C(C)(C)C)cc2)ccc1O]
TABLE 4-7
67 (4)
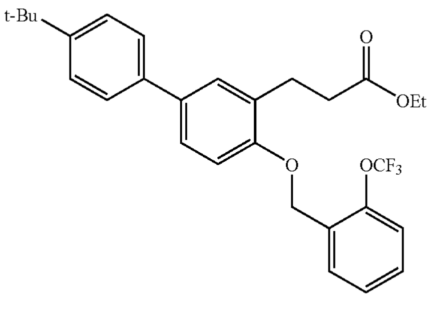 [SMILES: CCOC(=O)CCc1cc(-c2ccc(C(C)(C)C)cc2)ccc1OCc1ccccc1OC(F)(F)F]
TABLE 4-7-continued
68 (1)
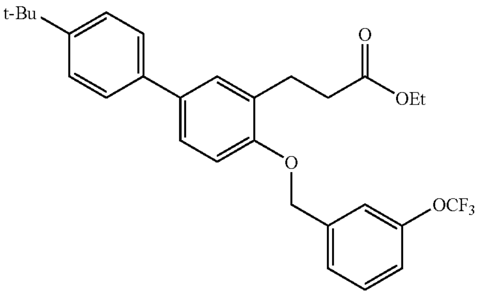 [SMILES: CCOC(=O)CCc1cc(-c2ccc(C(C)(C)C)cc2)ccc1OCc1cccc(OC(F)(F)F)c1]
69 (1)
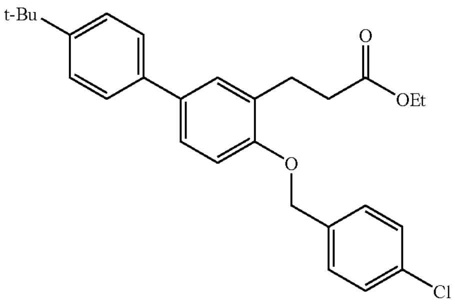 [SMILES: CCOC(=O)CCc1cc(-c2ccc(C(C)(C)C)cc2)ccc1OCc1ccc(Cl)cc1]
70 (1)
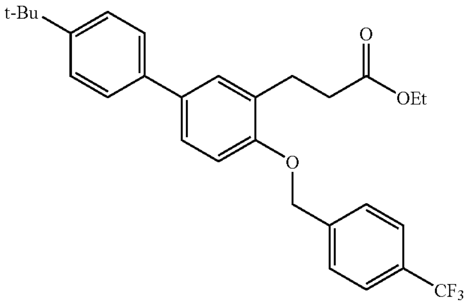 [SMILES: CCOC(=O)CCc1cc(-c2ccc(C(C)(C)C)cc2)ccc1OCc1ccc(C(F)(F)F)cc1]
71 (1)
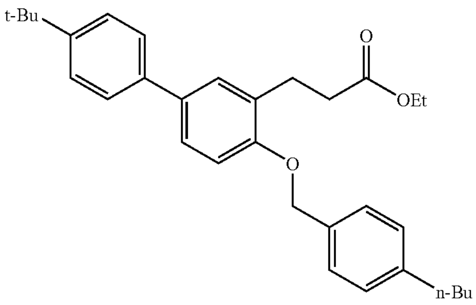
72 (1)
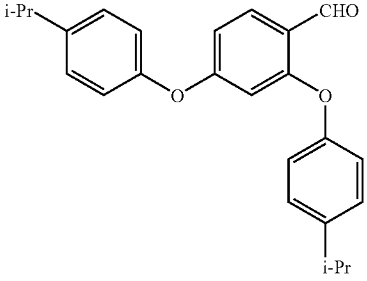 [SMILES: CC(C)c1ccc(Oc2ccc(C=O)c(Oc3ccc(C(C)C)cc3)c2)cc1]

TABLE 4-7-continued
| | |
|---|---|
| 74 (1) | 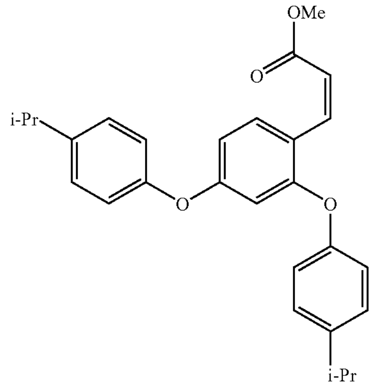 [SMILES: COC(=O)/C=C\c1ccc(Oc2ccc(C(C)C)cc2)cc1Oc1ccc(C(C)C)cc1] |
| 75 (1) | 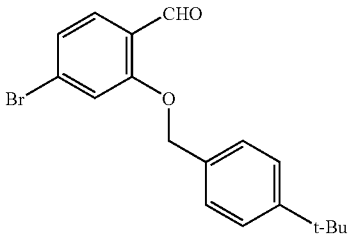 [SMILES: CC(C)(C)c1ccc(COc2cc(Br)ccc2C=O)cc1] |
| 75 (2) | 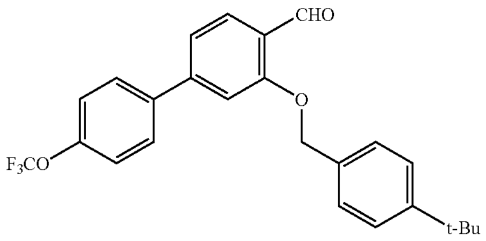 [SMILES: CC(C)(C)c1ccc(COc2cc(-c3ccc(OC(F)(F)F)cc3)ccc2C=O)cc1] |
| 77 (1) | 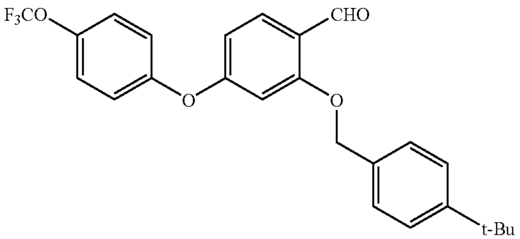 [SMILES: CC(C)(C)c1ccc(COc2cc(Oc3ccc(OC(F)(F)F)cc3)ccc2C=O)cc1] |
| 79 (1) | 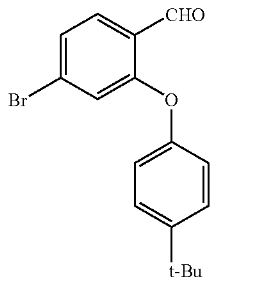 [SMILES: CC(C)(C)c1ccc(Oc2cc(Br)ccc2C=O)cc1] |
TABLE 4-7-continued
| | |
|---|---|
| 79 (2) | 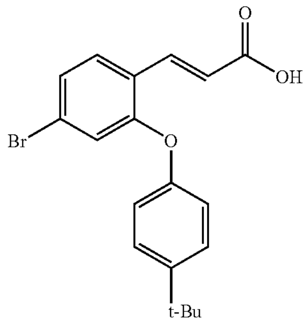 [SMILES: CC(C)(C)c1ccc(Oc2cc(Br)ccc2/C=C/C(=O)O)cc1] |
TABLE 4-8
| | |
|---|---|
| 81 (1) | 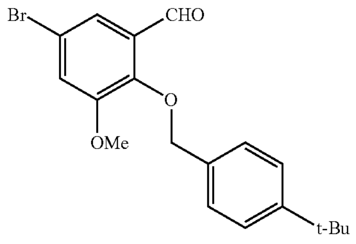 [SMILES: COc1cc(Br)cc(C=O)c1OCc1ccc(C(C)(C)C)cc1] |
| 81 (2) | 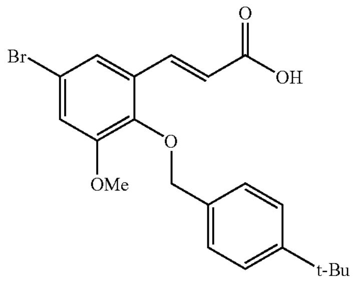 |
| 83 (1) | 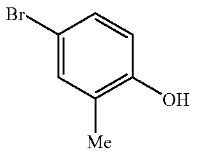 |
| 83 (2) | 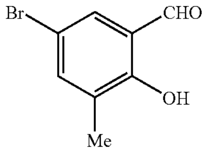 [SMILES: Cc1cc(Br)cc(C=O)c1O] |
| 83 (3) | 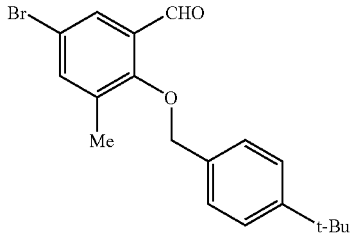 |

TABLE 4-8-continued
| | |
|---|---|
| 83 (4) | 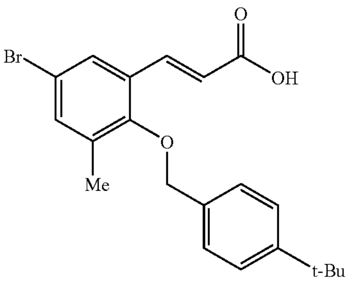 |
| 85 (1) | 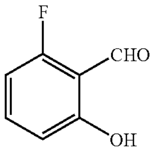 |
| 85 (2) | 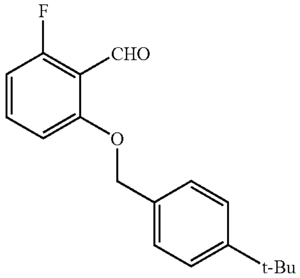 [SMILES: CC(C)(C)c1ccc(COc2cccc(F)c2C=O)cc1] |
| 85 (3) | 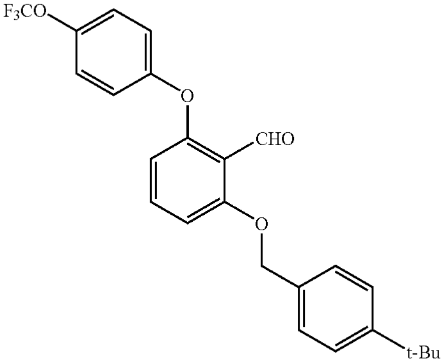 [SMILES: CC(C)(C)c1ccc(COc2cccc(Oc3ccc(OC(F)(F)F)cc3)c2C=O)cc1] |
| 87 (1) | 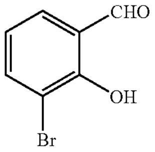 |
| 87 (2) | 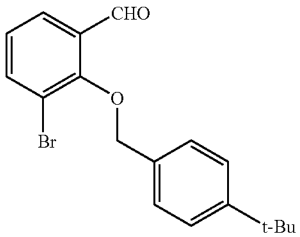 [SMILES: CC(C)(C)c1ccc(COc2c(Br)cccc2C=O)cc1] |
TABLE 4-8-continued
| | |
|---|---|
| 87 (3) | 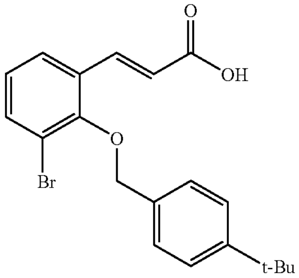 [SMILES: CC(C)(C)c1ccc(COc2c(Br)cccc2/C=C/C(=O)O)cc1] |
| 89 (1) | 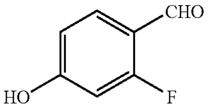 |
| 89 (2) | 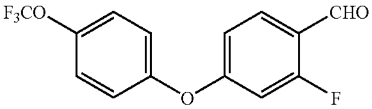 [SMILES: O=Cc1ccc(Oc2ccc(OC(F)(F)F)cc2)cc1F] |
TABLE 4-9
| | |
|---|---|
| 89 (3) | 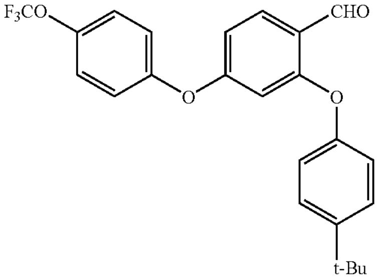 [SMILES: CC(C)(C)c1ccc(Oc2cc(Oc3ccc(OC(F)(F)F)cc3)ccc2C=O)cc1] |
| 91 (1) | 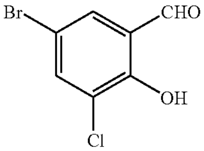 [SMILES: O=Cc1cc(Br)cc(Cl)c1O] |
| 91 (2) | 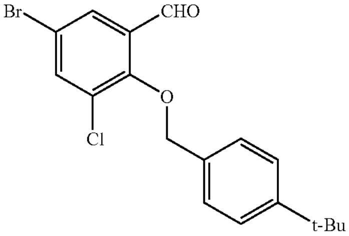 [SMILES: CC(C)(C)c1ccc(COc2c(Cl)cc(Br)cc2C=O)cc1] |
| 91 (3) | 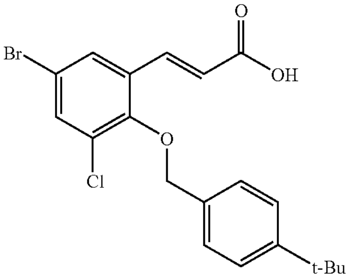 [SMILES: CC(C)(C)c1ccc(COc2c(Cl)cc(Br)cc2/C=C/C(=O)O)cc1] |

TABLE 4-9-continued
| | |
|---|---|
| 93 (1) | 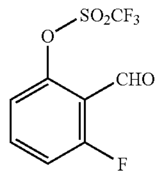 |
| 93 (2) | 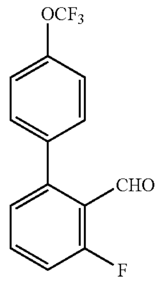 [SMILES: O=Cc1c(F)cccc1-c1ccc(OC(F)(F)F)cc1] |
| 93 (3) | 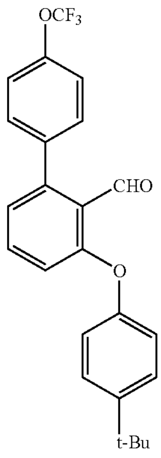 [SMILES: CC(C)(C)c1ccc(Oc2cccc(-c3ccc(OC(F)(F)F)cc3)c2C=O)cc1] |
| 95 (1) | 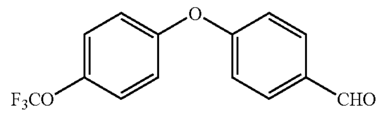 [SMILES: O=Cc1ccc(Oc2ccc(OC(F)(F)F)cc2)cc1] |
| 95 (2) | 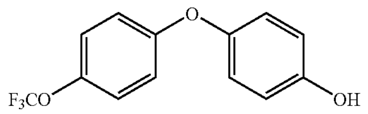 [SMILES: Oc1ccc(Oc2ccc(OC(F)(F)F)cc2)cc1] |
| 95 (3) | 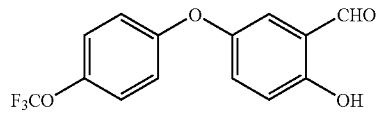 [SMILES: O=Cc1cc(Oc2ccc(OC(F)(F)F)cc2)ccc1O] |
| 95 (4) | 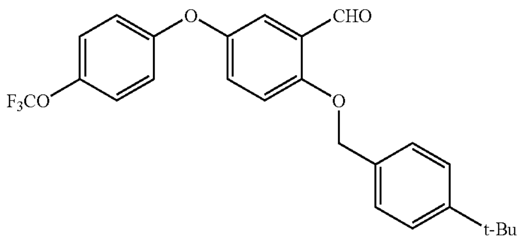 [SMILES: CC(C)(C)c1ccc(COc2ccc(Oc3ccc(OC(F)(F)F)cc3)cc2C=O)cc1] |
| 97 (1) | 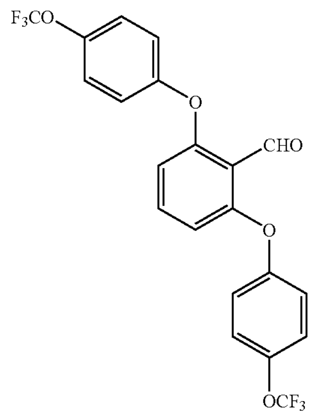 [SMILES: O=Cc1c(Oc2ccc(OC(F)(F)F)cc2)cccc1Oc1ccc(OC(F)(F)F)cc1] |
TABLE 4-10
| | |
|---|---|
| 99 (1) | 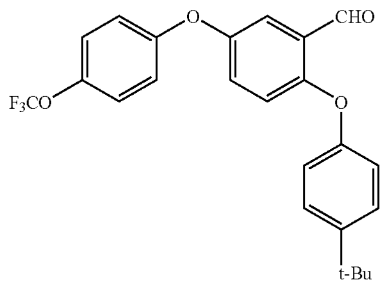 [SMILES: CC(C)(C)c1ccc(Oc2ccc(Oc3ccc(OC(F)(F)F)cc3)cc2C=O)cc1] |
| 101 (1) | 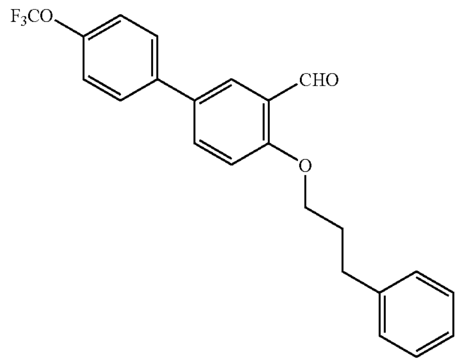 [SMILES: O=Cc1cc(-c2ccc(OC(F)(F)F)cc2)ccc1OCCCc1ccccc1] |
| 101 (2) | 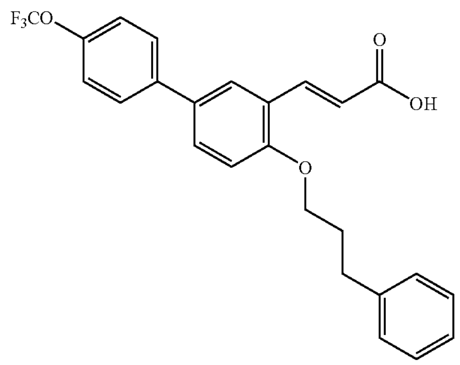 [SMILES: O=C(O)/C=C/c1cc(-c2ccc(OC(F)(F)F)cc2)ccc1OCCCc1ccccc1] |

TABLE 4-10-continued
102 (1)
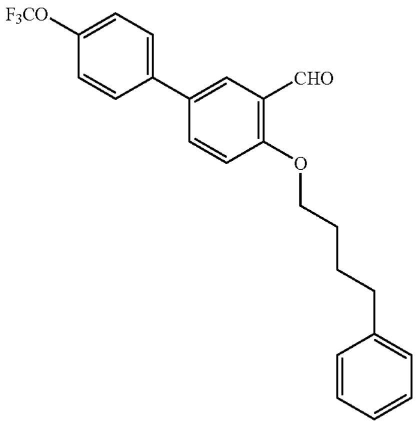 [SMILES: O=Cc1cc(-c2ccc(OC(F)(F)F)cc2)ccc1OCCCCc1ccccc1]
102 (2)
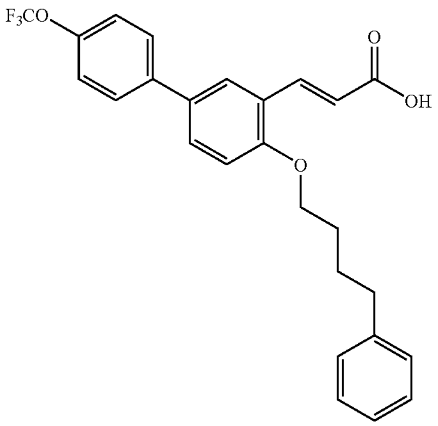 [SMILES: O=C(O)/C=C/c1cc(-c2ccc(OC(F)(F)F)cc2)ccc1OCCCCc1ccccc1]
103 (1)
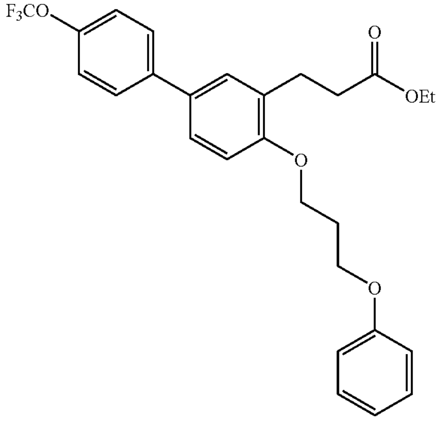 [SMILES: CCOC(=O)CCc1cc(-c2ccc(OC(F)(F)F)cc2)ccc1OCCCOc1ccccc1]
TABLE 4-10-continued
104 (1)
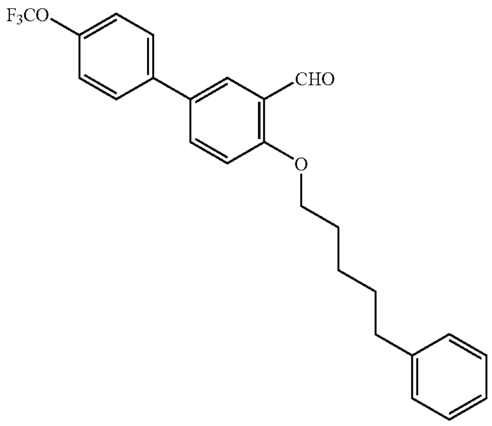 [SMILES: O=Cc1cc(-c2ccc(OC(F)(F)F)cc2)ccc1OCCCCCc1ccccc1]
104 (2)
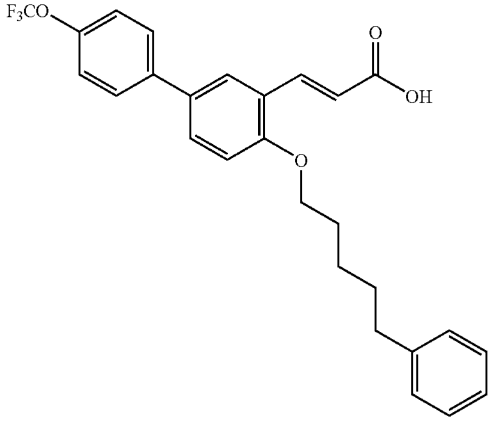 [SMILES: O=C(O)/C=C/c1cc(-c2ccc(OC(F)(F)F)cc2)ccc1OCCCCCc1ccccc1]
105 (1)
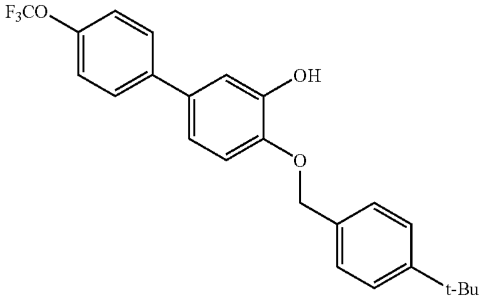 [SMILES: CC(C)(C)c1ccc(COc2ccc(-c3ccc(OC(F)(F)F)cc3)cc2O)cc1]
105 (2)
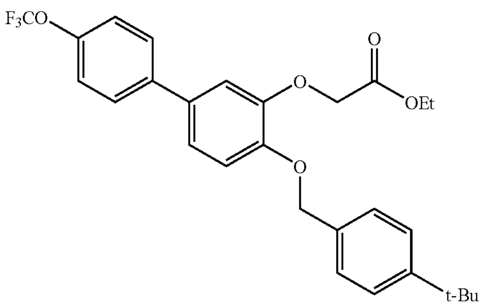 [SMILES: CCOC(=O)COc1cc(-c2ccc(OC(F)(F)F)cc2)ccc1OCc1ccc(C(C)(C)C)cc1]

TABLE 4-11
106 (1)
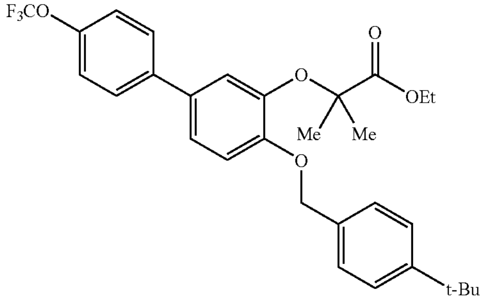 [SMILES: CCOC(=O)C(C)(C)Oc1cc(-c2ccc(OC(F)(F)F)cc2)ccc1OCc1ccc(C(C)(C)C)cc1]
107 (1)
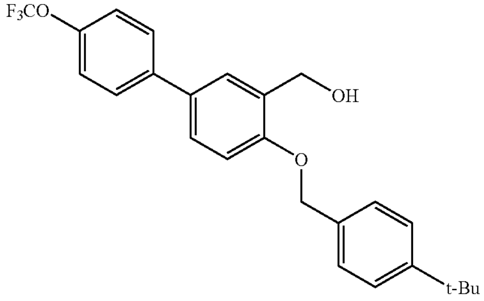 [SMILES: CC(C)(C)c1ccc(COc2ccc(-c3ccc(OC(F)(F)F)cc3)cc2CO)cc1]
107 (2)
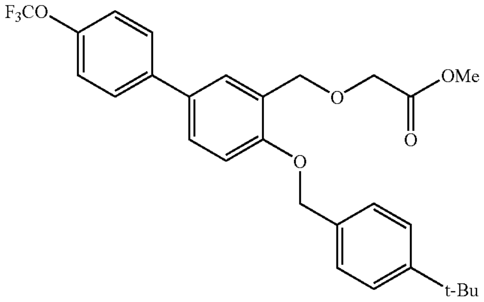 [SMILES: COC(=O)COCc1cc(-c2ccc(OC(F)(F)F)cc2)ccc1OCc1ccc(C(C)(C)C)cc1]
108 (1)
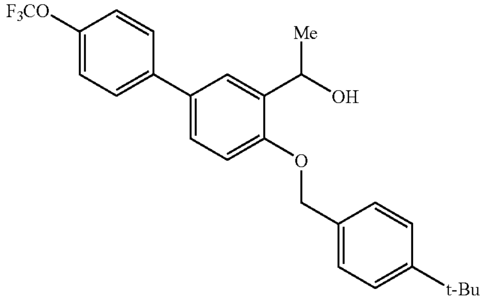 [SMILES: CC(O)c1cc(-c2ccc(OC(F)(F)F)cc2)ccc1OCc1ccc(C(C)(C)C)cc1]
108 (2)
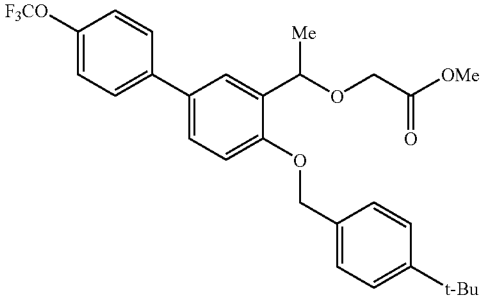 [SMILES: COC(=O)COC(C)c1cc(-c2ccc(OC(F)(F)F)cc2)ccc1OCc1ccc(C(C)(C)C)cc1]
TABLE 4-11-continued
109 (1)
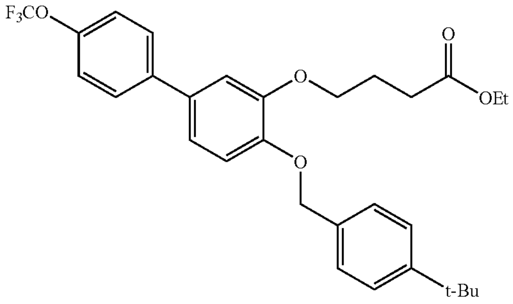 [SMILES: CCOC(=O)CCCOc1cc(-c2ccc(OC(F)(F)F)cc2)ccc1OCc1ccc(C(C)(C)C)cc1]
110 (1)
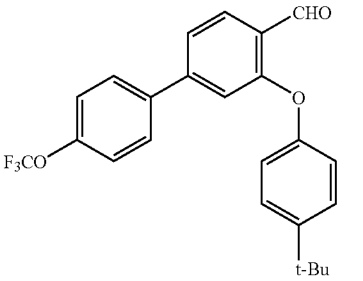
110 (2)
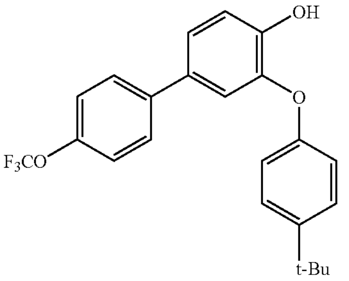 [SMILES: CC(C)(C)c1ccc(Oc2cc(-c3ccc(OC(F)(F)F)cc3)ccc2O)cc1]
111 (1)
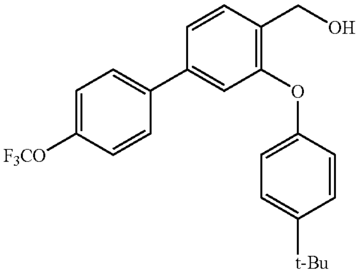 [SMILES: CC(C)(C)c1ccc(Oc2cc(-c3ccc(OC(F)(F)F)cc3)ccc2CO)cc1]
112 (1)
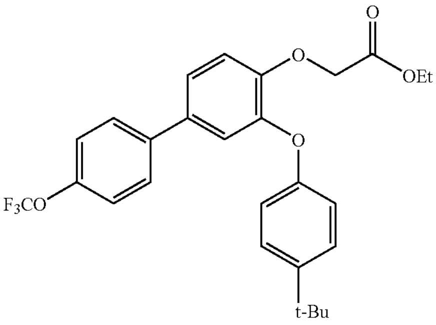 [SMILES: CCOC(=O)COc1ccc(-c2ccc(OC(F)(F)F)cc2)cc1Oc1ccc(C(C)(C)C)cc1]

TABLE 4-12
| | |
|---|---|
| 113 (1) | 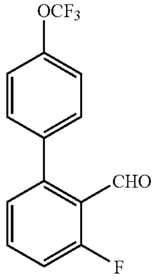 [SMILES: O=Cc1c(F)cccc1-c1ccc(OC(F)(F)F)cc1] |
| 113 (2) | 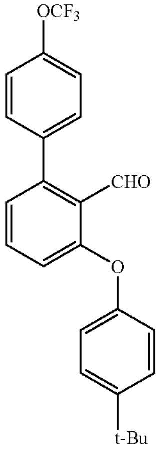 [SMILES: CC(C)(C)c1ccc(Oc2cccc(-c3ccc(OC(F)(F)F)cc3)c2C=O)cc1] |
| 113 (3) | 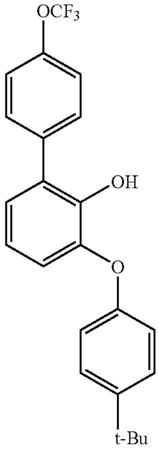 |
| 113 (4) | 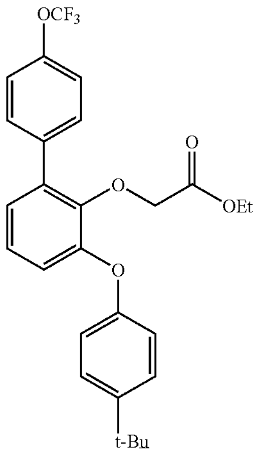 [SMILES: CCOC(=O)COc1c(Oc2ccc(C(C)(C)C)cc2)cccc1-c1ccc(OC(F)(F)F)cc1] |
TABLE 4-12-continued
| | |
|---|---|
| 114 (1) | 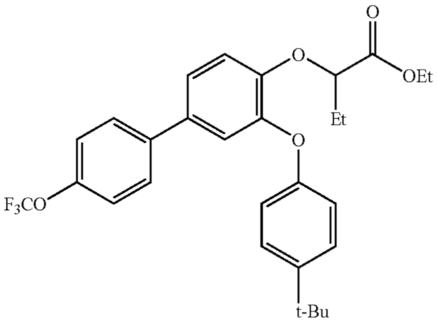 [SMILES: CCOC(=O)C(CC)Oc1ccc(-c2ccc(OC(F)(F)F)cc2)cc1Oc1ccc(C(C)(C)C)cc1] |
| 115 (1) | 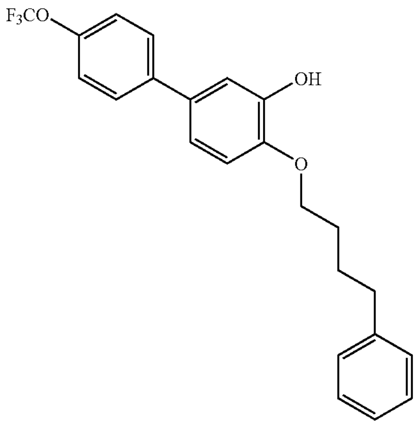 [SMILES: Oc1cc(-c2ccc(OC(F)(F)F)cc2)ccc1OCCCCc1ccccc1] |
| 115 (2) | 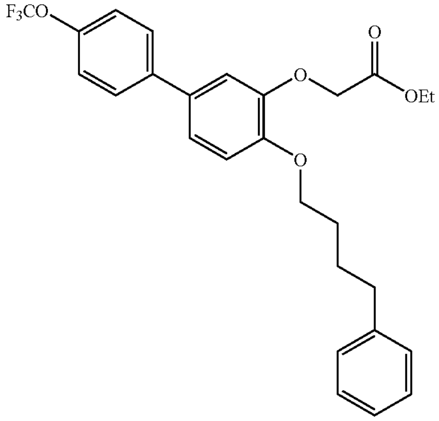 |
| 116 (1) | 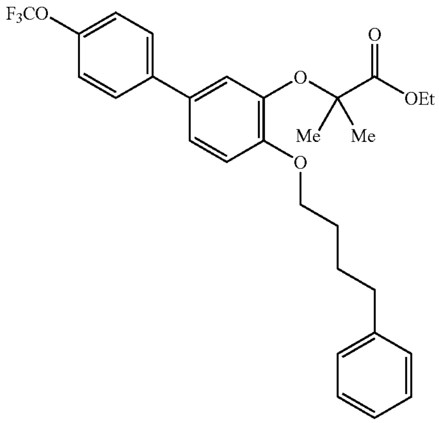 [SMILES: CCOC(=O)C(C)(C)Oc1cc(-c2ccc(OC(F)(F)F)cc2)ccc1OCCCCc1ccccc1] |

TABLE 4-13
117
(1)
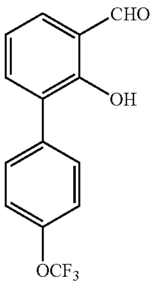 [SMILES: O=Cc1cccc(-c2ccc(OC(F)(F)F)cc2)c1O]
117
(2)
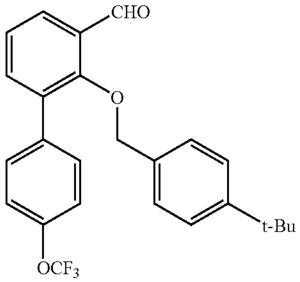 [SMILES: CC(C)(C)c1ccc(COc2c(C=O)cccc2-c2ccc(OC(F)(F)F)cc2)cc1]
117
(3)
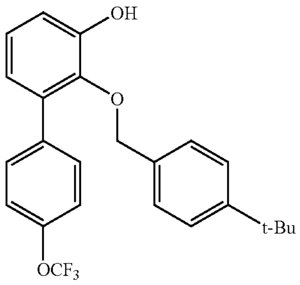 [SMILES: CC(C)(C)c1ccc(COc2c(O)cccc2-c2ccc(OC(F)(F)F)cc2)cc1]
117
(4)
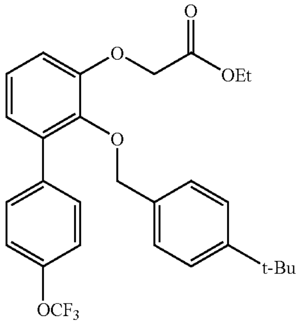 [SMILES: CCOC(=O)COc1cccc(-c2ccc(OC(F)(F)F)cc2)c1OCc1ccc(C(C)(C)C)cc1]
118
(1)
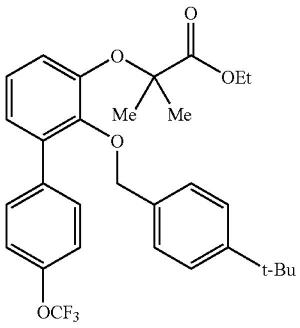 [SMILES: CCOC(=O)C(C)(C)Oc1cccc(-c2ccc(OC(F)(F)F)cc2)c1OCc1ccc(C(C)(C)C)cc1]
TABLE 4-13-continued
119
(1)
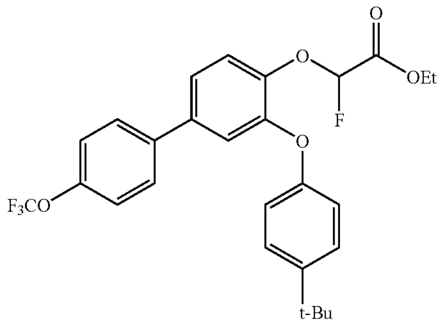 [SMILES: CCOC(=O)C(F)Oc1ccc(-c2ccc(OC(F)(F)F)cc2)cc1Oc1ccc(C(C)(C)C)cc1]
121
(1)
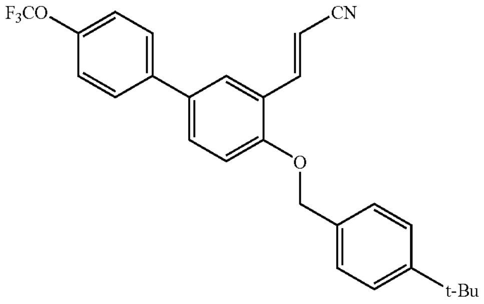 [SMILES: CC(C)(C)c1ccc(COc2ccc(-c3ccc(OC(F)(F)F)cc3)cc2/C=C/C#N)cc1]
121
(2)
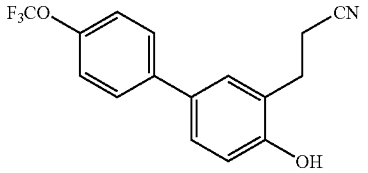 [SMILES: N#CCCc1cc(-c2ccc(OC(F)(F)F)cc2)ccc1O]
121
(3)
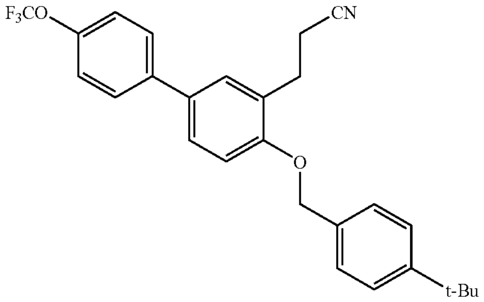 [SMILES: CC(C)(C)c1ccc(COc2ccc(-c3ccc(OC(F)(F)F)cc3)cc2CCC#N)cc1]
122
(1)
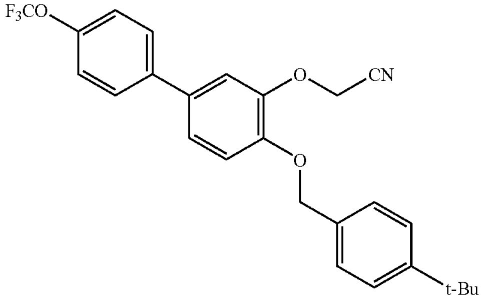 [SMILES: CC(C)(C)c1ccc(COc2ccc(-c3ccc(OC(F)(F)F)cc3)cc2OCC#N)cc1]

TABLE 4-13-continued
| | |
|---|---|
| 123 (1) | 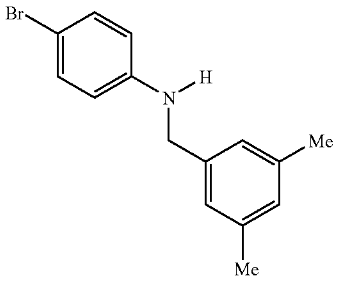 [SMILES: Cc1cc(C)cc(CNc2ccc(Br)cc2)c1] |
| 123 (2) | 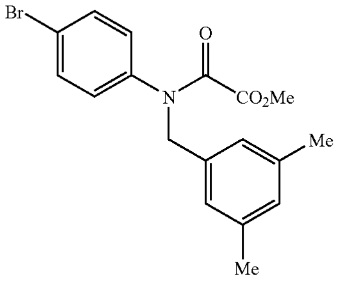 [SMILES: COC(=O)C(=O)N(Cc1cc(C)cc(C)c1)c1ccc(Br)cc1] |
TABLE 4-14
| | |
|---|---|
| 123(3) | 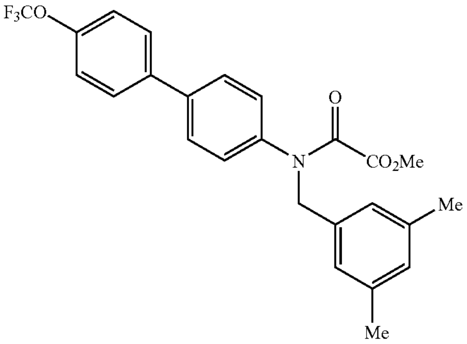 [SMILES: COC(=O)C(=O)N(Cc1cc(C)cc(C)c1)c1ccc(-c2ccc(OC(F)(F)F)cc2)cc1] |
| 124(1) | 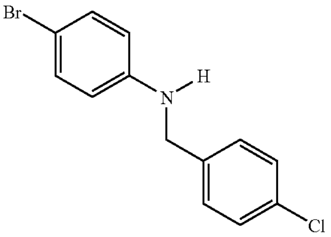 [SMILES: Clc1ccc(CNc2ccc(Br)cc2)cc1] |
| 124(2) | 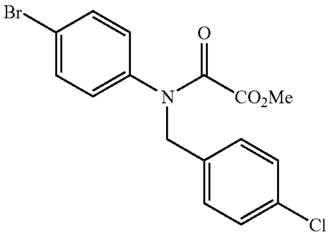 [SMILES: COC(=O)C(=O)N(Cc1ccc(Cl)cc1)c1ccc(Br)cc1] |
TABLE 4-14-continued
| | |
|---|---|
| 124(3) | 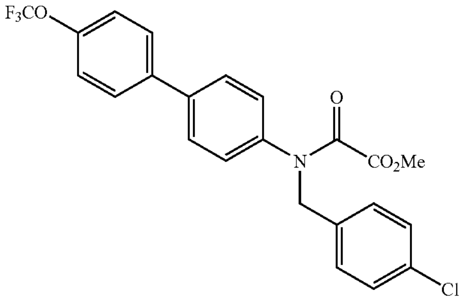 [SMILES: COC(=O)C(=O)N(Cc1ccc(Cl)cc1)c1ccc(-c2ccc(OC(F)(F)F)cc2)cc1] |
| 125(1) | 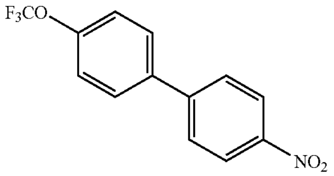 [SMILES: O=[N+]([O-])c1ccc(-c2ccc(OC(F)(F)F)cc2)cc1] |
| 125(2) | 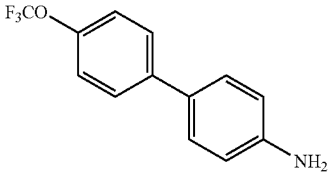 |
| 125(3) | 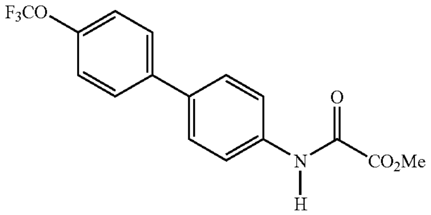 [SMILES: COC(=O)C(=O)Nc1ccc(-c2ccc(OC(F)(F)F)cc2)cc1] |
| 125(4) | 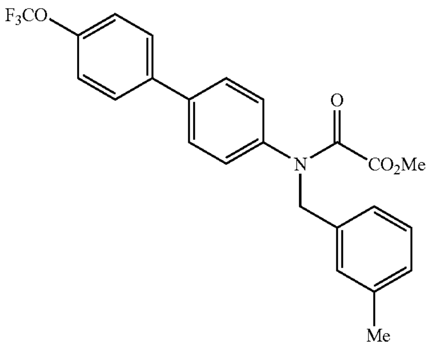 [SMILES: COC(=O)C(=O)N(Cc1cccc(C)c1)c1ccc(-c2ccc(OC(F)(F)F)cc2)cc1] |

TABLE 4-14-continued
126(1)
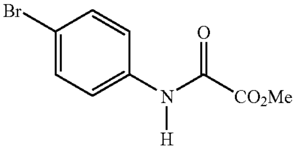 [SMILES: COC(=O)C(=O)Nc1ccc(Br)cc1]
126(2)
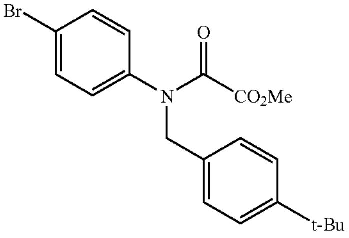 [SMILES: COC(=O)C(=O)N(Cc1ccc(C(C)(C)C)cc1)c1ccc(Br)cc1]
TABLE 4-14-continued
126(3)
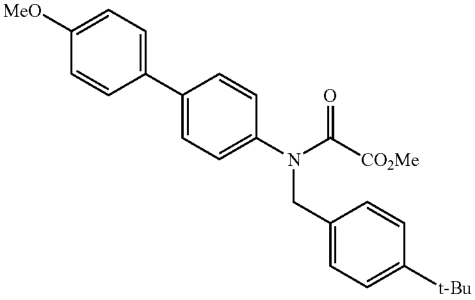 [SMILES: COC(=O)C(=O)N(Cc1ccc(C(C)(C)C)cc1)c1ccc(-c2ccc(OC)cc2)cc1]
127(1)
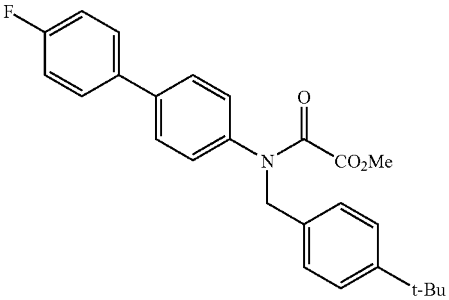 [SMILES: COC(=O)C(=O)N(Cc1ccc(C(C)(C)C)cc1)c1ccc(-c2ccc(F)cc2)cc1]
TABLE 4-15
128(1)
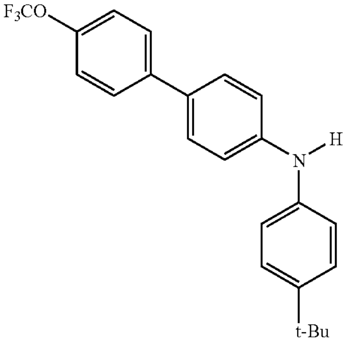 [SMILES: CC(C)(C)c1ccc(Nc2ccc(-c3ccc(OC(F)(F)F)cc3)cc2)cc1]
128(2)
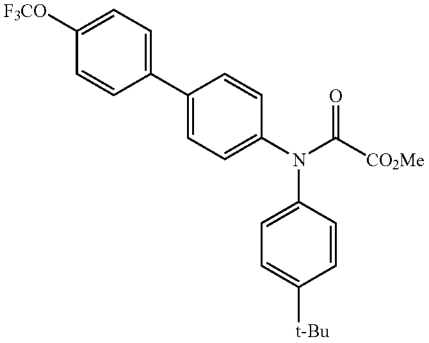 [SMILES: COC(=O)C(=O)N(c1ccc(-c2ccc(OC(F)(F)F)cc2)cc1)c1ccc(C(C)(C)C)cc1]

TABLE 4-15-continued
129(1)
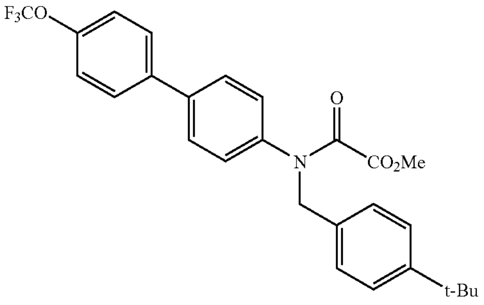 [SMILES: COC(=O)C(=O)N(Cc1ccc(C(C)(C)C)cc1)c1ccc(-c2ccc(OC(F)(F)F)cc2)cc1]
130(1)
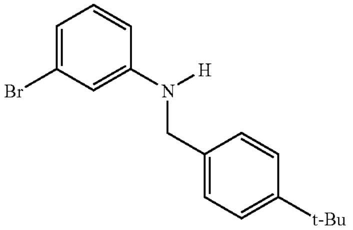 [SMILES: CC(C)(C)c1ccc(CNc2cccc(Br)c2)cc1]
130(2)
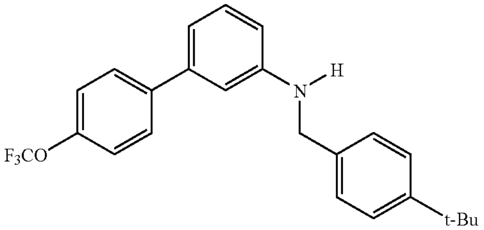 [SMILES: CC(C)(C)c1ccc(CNc2cccc(-c3ccc(OC(F)(F)F)cc3)c2)cc1]
130(3)
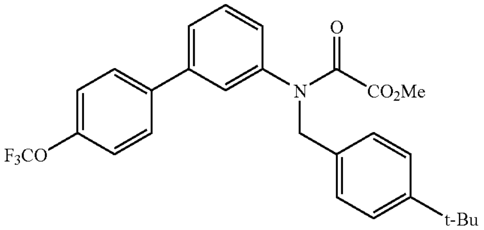 [SMILES: COC(=O)C(=O)N(Cc1ccc(C(C)(C)C)cc1)c1cccc(-c2ccc(OC(F)(F)F)cc2)c1]
131(1)
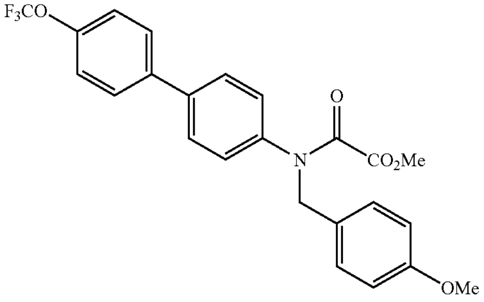 [SMILES: COC(=O)C(=O)N(Cc1ccc(OC)cc1)c1ccc(-c2ccc(OC(F)(F)F)cc2)cc1]
132(1)
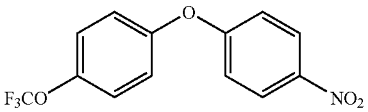
132(2)
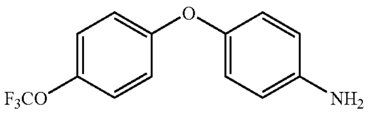 [SMILES: O=[N+]([O-])c1ccc(Oc2ccc(OC(F)(F)F)cc2)cc1]

TABLE 4-15-continued
132(3)
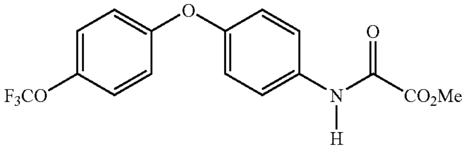 [SMILES: COC(=O)C(=O)Nc1ccc(Oc2ccc(OC(F)(F)F)cc2)cc1]
132(4)
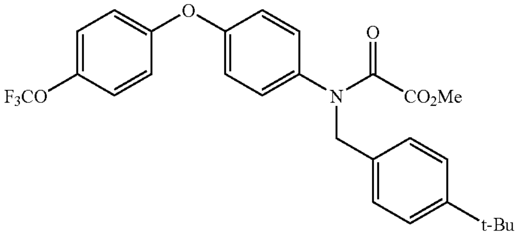 [SMILES: COC(=O)C(=O)N(Cc1ccc(C(C)(C)C)cc1)c1ccc(Oc2ccc(OC(F)(F)F)cc2)cc1]
134(1)
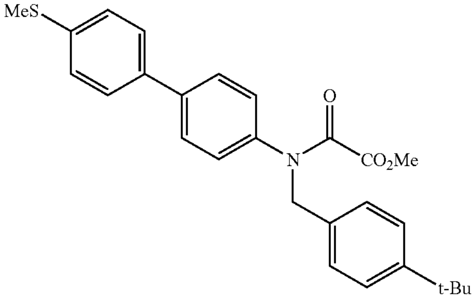
TABLE 4-16
135(1)
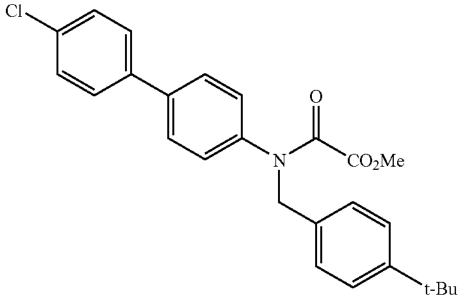 [SMILES: COC(=O)C(=O)N(Cc1ccc(C(C)(C)C)cc1)c1ccc(-c2ccc(Cl)cc2)cc1]
136(1)
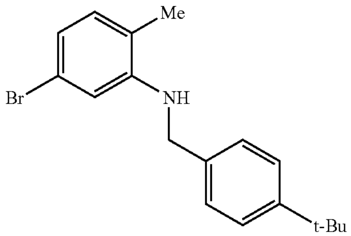 [SMILES: Cc1ccc(Br)cc1NCc1ccc(C(C)(C)C)cc1]
136(2)
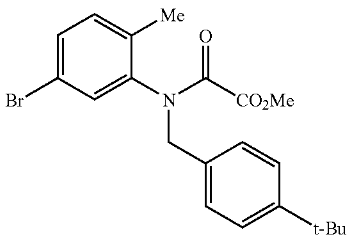 [SMILES: COC(=O)C(=O)N(Cc1ccc(C(C)(C)C)cc1)c1cc(Br)ccc1C]
TABLE 4-16-continued
136(3)
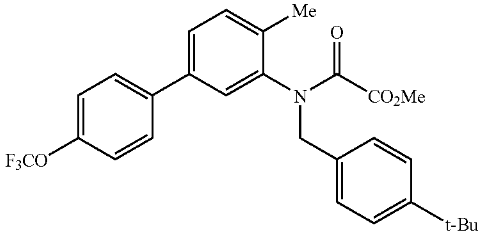 [SMILES: COC(=O)C(=O)N(Cc1ccc(C(C)(C)C)cc1)c1cc(-c2ccc(OC(F)(F)F)cc2)ccc1C]
137(1)
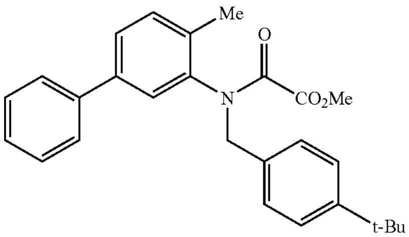 [SMILES: COC(=O)C(=O)N(Cc1ccc(C(C)(C)C)cc1)c1cc(-c2ccccc2)ccc1C]
138(1)
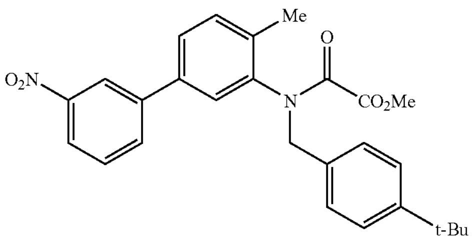 [SMILES: COC(=O)C(=O)N(Cc1ccc(C(C)(C)C)cc1)c1cc(-c2cccc([N+](=O)[O-])c2)ccc1C]

TABLE 4-16-continued
139(1)
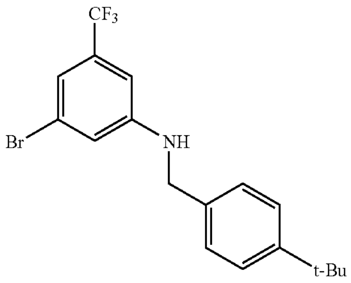 [SMILES: CC(C)(C)c1ccc(CNc2cc(Br)cc(C(F)(F)F)c2)cc1]
139(2)
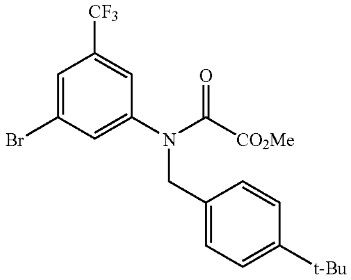 [SMILES: COC(=O)C(=O)N(Cc1ccc(C(C)(C)C)cc1)c1cc(Br)cc(C(F)(F)F)c1]
139(3)
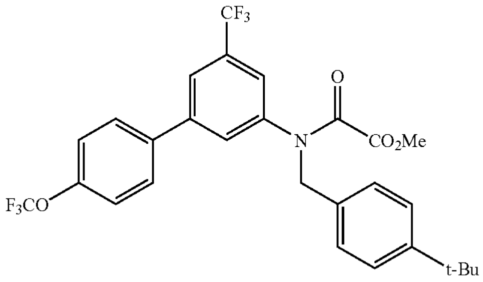 [SMILES: COC(=O)C(=O)N(Cc1ccc(C(C)(C)C)cc1)c1cc(-c2ccc(OC(F)(F)F)cc2)cc(C(F)(F)F)c1]
140(1)
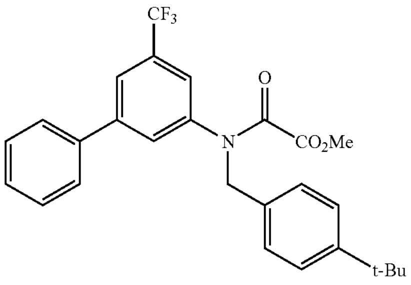 [SMILES: COC(=O)C(=O)N(Cc1ccc(C(C)(C)C)cc1)c1cc(-c2ccccc2)cc(C(F)(F)F)c1]
141(1)
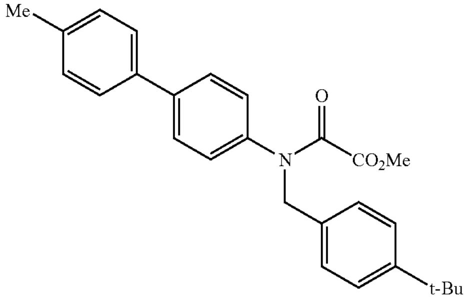 [SMILES: COC(=O)C(=O)N(Cc1ccc(C(C)(C)C)cc1)c1ccc(-c2ccc(C)cc2)cc1]
TABLE 4-16-continued
142(1)
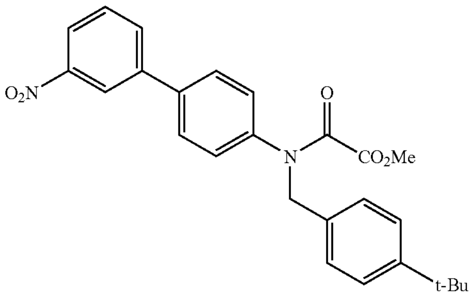 [SMILES: COC(=O)C(=O)N(Cc1ccc(C(C)(C)C)cc1)c1ccc(-c2cccc([N+](=O)[O-])c2)cc1]
TABLE 4-17
143(1)
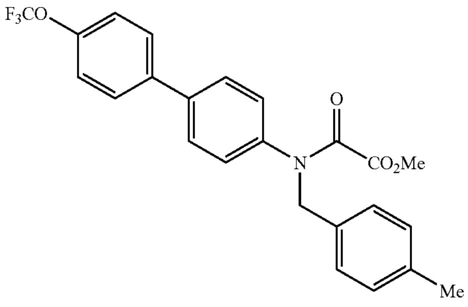 [SMILES: COC(=O)C(=O)N(Cc1ccc(C)cc1)c1ccc(-c2ccc(OC(F)(F)F)cc2)cc1]
144(1)
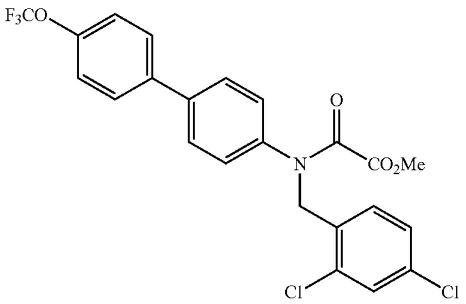 [SMILES: COC(=O)C(=O)N(Cc1ccc(Cl)cc1Cl)c1ccc(-c2ccc(OC(F)(F)F)cc2)cc1]
145(1)
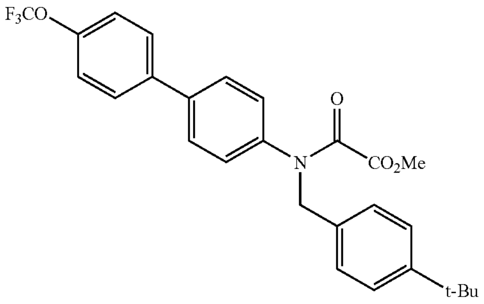 [SMILES: COC(=O)C(=O)N(Cc1ccc(C(C)(C)C)cc1)c1ccc(-c2ccc(OC(F)(F)F)cc2)cc1]
146(1)
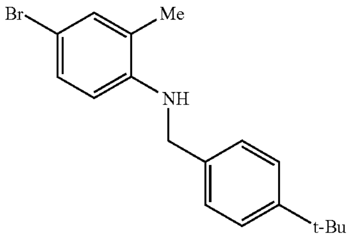 [SMILES: Cc1cc(Br)ccc1NCc1ccc(C(C)(C)C)cc1]

TABLE 4-17-continued
146(2) 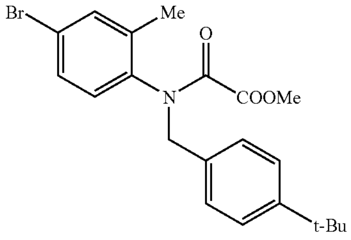 [SMILES: COC(=O)C(=O)N(Cc1ccc(C(C)(C)C)cc1)c1ccc(Br)cc1C]
146(3) 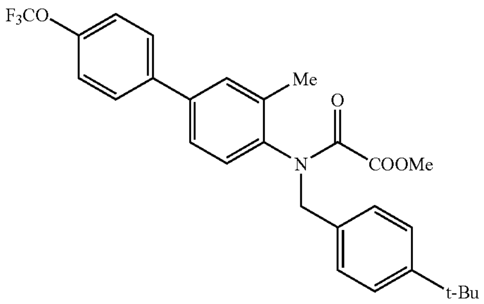 [SMILES: COC(=O)C(=O)N(Cc1ccc(C(C)(C)C)cc1)c1ccc(-c2ccc(OC(F)(F)F)cc2)cc1C]
147(1) 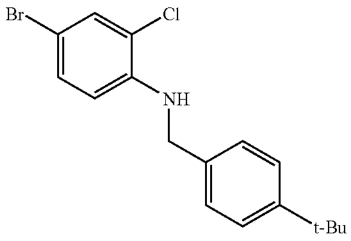 [SMILES: CC(C)(C)c1ccc(CNc2ccc(Br)cc2Cl)cc1]
147(2) 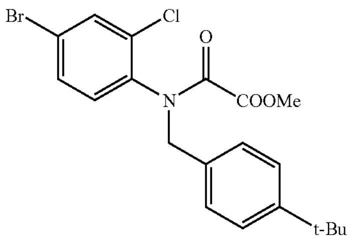 [SMILES: COC(=O)C(=O)N(Cc1ccc(C(C)(C)C)cc1)c1ccc(Br)cc1Cl]
147(3) 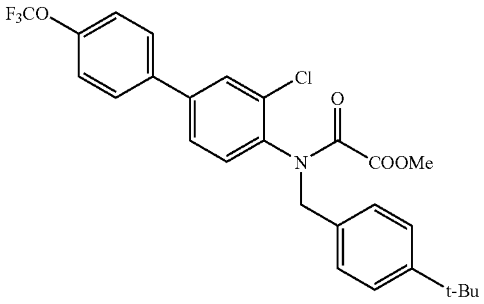 [SMILES: COC(=O)C(=O)N(Cc1ccc(C(C)(C)C)cc1)c1ccc(-c2ccc(OC(F)(F)F)cc2)cc1Cl]
148(1) 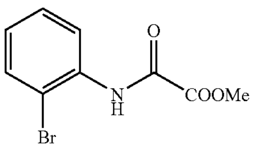 [SMILES: COC(=O)C(=O)Nc1ccccc1Br]
148(2) 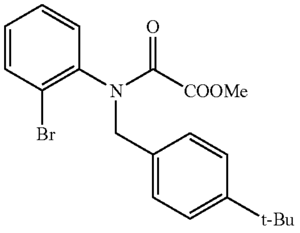 [SMILES: COC(=O)C(=O)N(Cc1ccc(C(C)(C)C)cc1)c1ccccc1Br]
148(3) 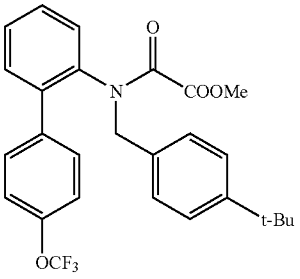 [SMILES: COC(=O)C(=O)N(Cc1ccc(C(C)(C)C)cc1)c1ccccc1-c1ccc(OC(F)(F)F)cc1]
TABLE 4-18
149(1) 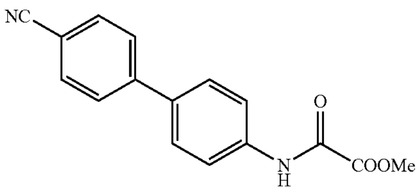
149(2) 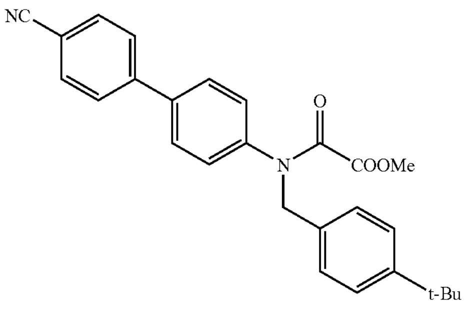
150(1) 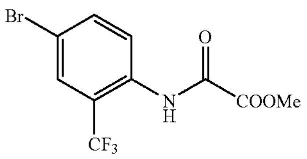 [SMILES: COC(=O)C(=O)Nc1ccc(Br)cc1C(F)(F)F]
150(2) 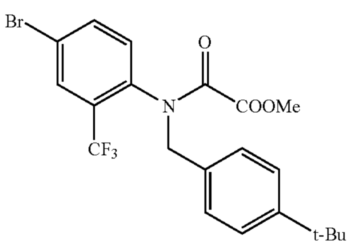 [SMILES: COC(=O)C(=O)N(Cc1ccc(C(C)(C)C)cc1)c1ccc(Br)cc1C(F)(F)F]

TABLE 4-18-continued
150(3) 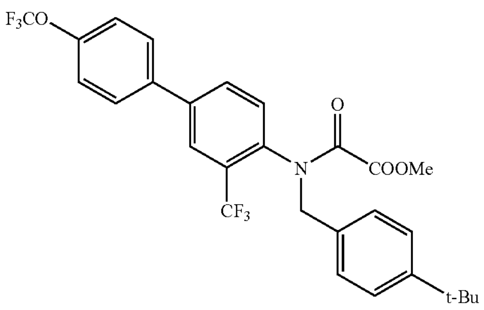 [SMILES: COC(=O)C(=O)N(Cc1ccc(C(C)(C)C)cc1)c1ccc(-c2ccc(OC(F)(F)F)cc2)cc1C(F)(F)F]
151(1) 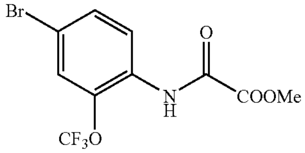
151(2) 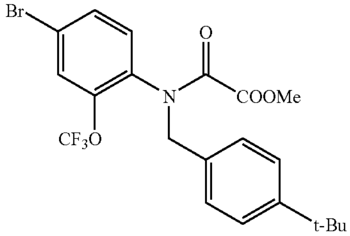
151(3) 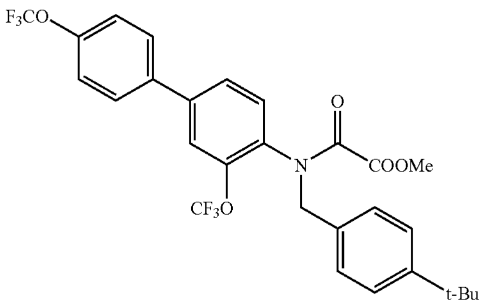
152(1) 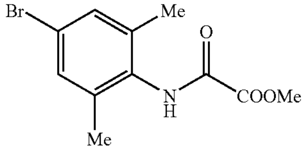 [SMILES: COC(=O)C(=O)Nc1c(C)cc(Br)cc1C]
152(2) 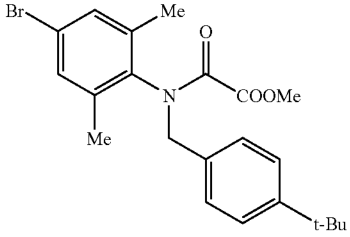 [SMILES: COC(=O)C(=O)N(Cc1ccc(C(C)(C)C)cc1)c1c(C)cc(Br)cc1C]
TABLE 4-18-continued
152(3) 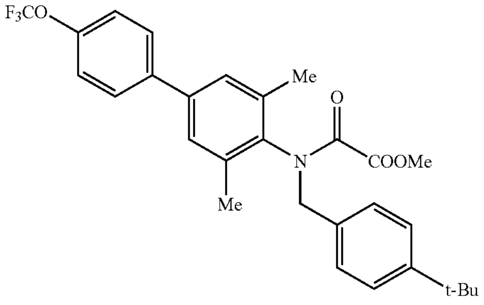
153(1) 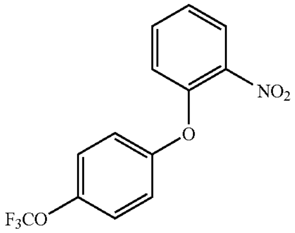 [SMILES: O=[N+]([O-])c1ccccc1Oc1ccc(OC(F)(F)F)cc1]
153(2) 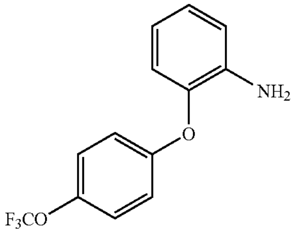
153(3) 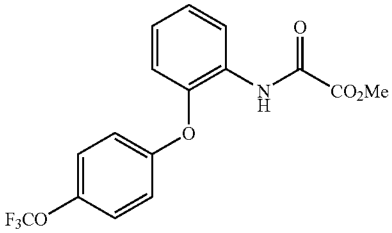 [SMILES: COC(=O)C(=O)Nc1ccccc1Oc1ccc(OC(F)(F)F)cc1]
TABLE 4-19
153(4) 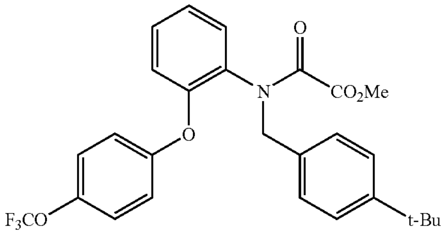 [SMILES: COC(=O)C(=O)N(Cc1ccc(C(C)(C)C)cc1)c1ccccc1Oc1ccc(OC(F)(F)F)cc1]
154(1) 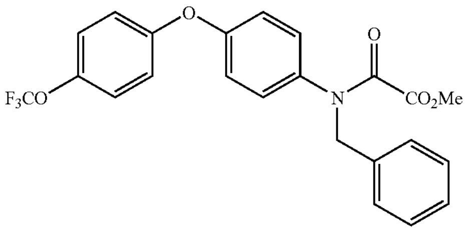 [SMILES: COC(=O)C(=O)N(Cc1ccccc1)c1ccc(Oc2ccc(OC(F)(F)F)cc2)cc1]

TABLE 4-19-continued
155(1)
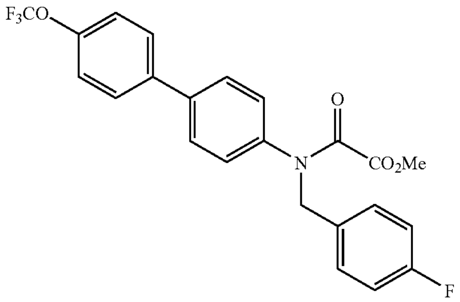 [SMILES: COC(=O)C(=O)N(Cc1ccc(F)cc1)c1ccc(-c2ccc(OC(F)(F)F)cc2)cc1]
156(1)
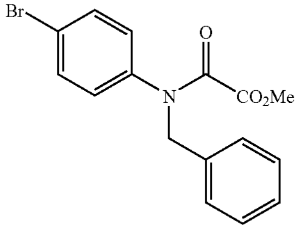 [SMILES: COC(=O)C(=O)N(Cc1ccccc1)c1ccc(Br)cc1]
156(2)
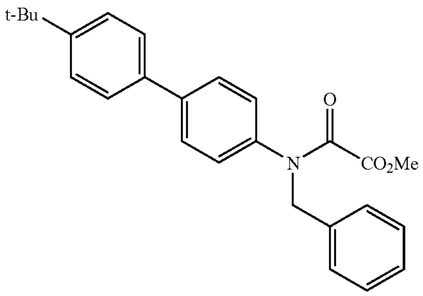 [SMILES: COC(=O)C(=O)N(Cc1ccccc1)c1ccc(-c2ccc(C(C)(C)C)cc2)cc1]
157(1)
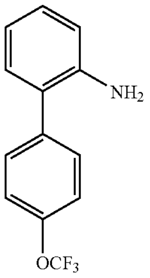 [SMILES: Nc1ccccc1-c1ccc(OC(F)(F)F)cc1]
157(2)
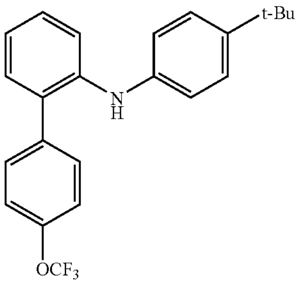 [SMILES: CC(C)(C)c1ccc(Nc2ccccc2-c2ccc(OC(F)(F)F)cc2)cc1]
TABLE 4-19-continued
157(3)
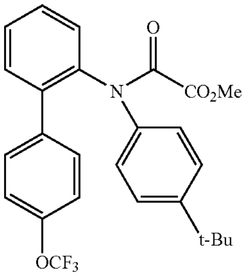 [SMILES: COC(=O)C(=O)N(c1ccc(C(C)(C)C)cc1)c1ccccc1-c1ccc(OC(F)(F)F)cc1]
158(1)
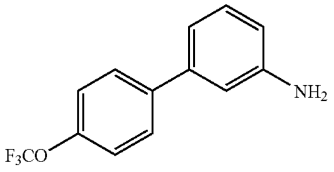 [SMILES: Nc1cccc(-c2ccc(OC(F)(F)F)cc2)c1]
158(2)
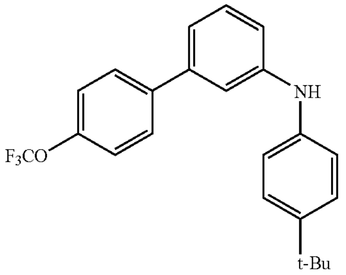 [SMILES: CC(C)(C)c1ccc(Nc2cccc(-c3ccc(OC(F)(F)F)cc3)c2)cc1]
158(3)
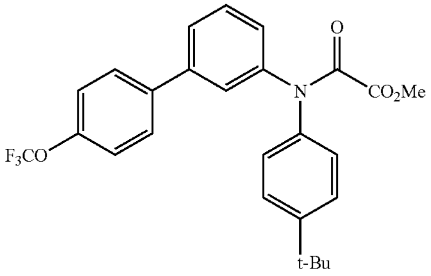 [SMILES: COC(=O)C(=O)N(c1ccc(C(C)(C)C)cc1)c1cccc(-c2ccc(OC(F)(F)F)cc2)c1]
159(1)
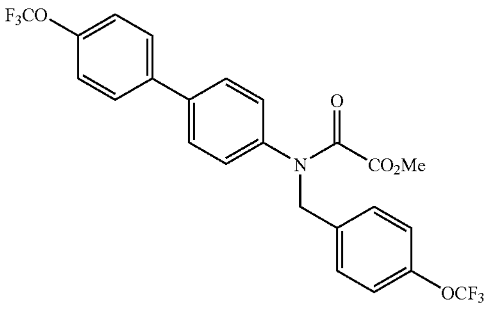 [SMILES: COC(=O)C(=O)N(Cc1ccc(OC(F)(F)F)cc1)c1ccc(-c2ccc(OC(F)(F)F)cc2)cc1]

TABLE 4-20
160(1) 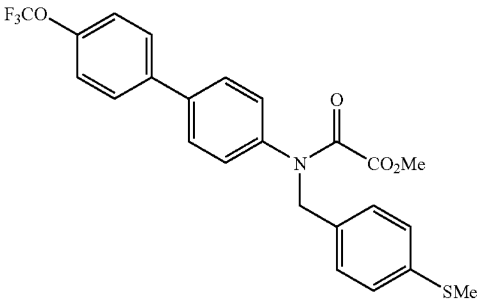
161(1) 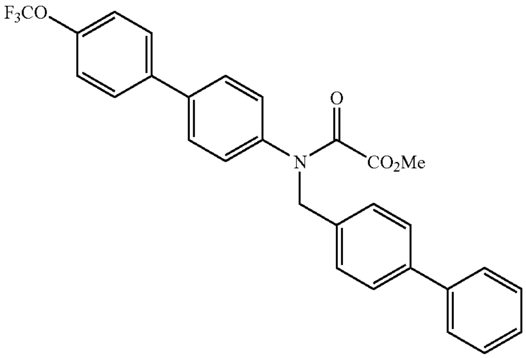 [SMILES: COC(=O)C(=O)N(Cc1ccc(-c2ccccc2)cc1)c1ccc(-c2ccc(OC(F)(F)F)cc2)cc1]
162(1) 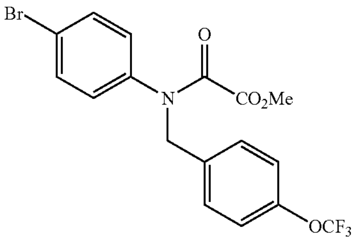 [SMILES: COC(=O)C(=O)N(Cc1ccc(OC(F)(F)F)cc1)c1ccc(Br)cc1]
162(2) 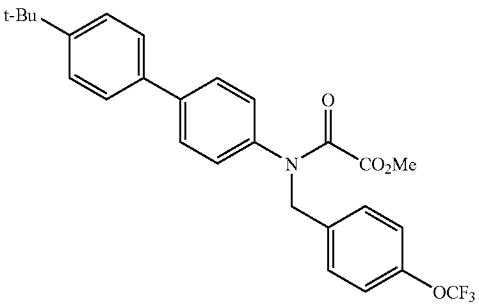 [SMILES: COC(=O)C(=O)N(Cc1ccc(OC(F)(F)F)cc1)c1ccc(-c2ccc(C(C)(C)C)cc2)cc1]
163(1) 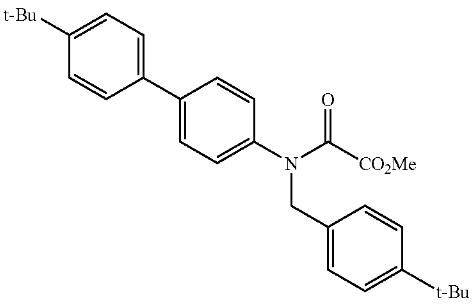 [SMILES: COC(=O)C(=O)N(Cc1ccc(C(C)(C)C)cc1)c1ccc(-c2ccc(C(C)(C)C)cc2)cc1]

TABLE 4-20-continued
164(1)
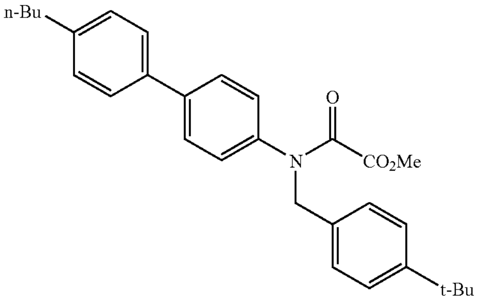
165(1)
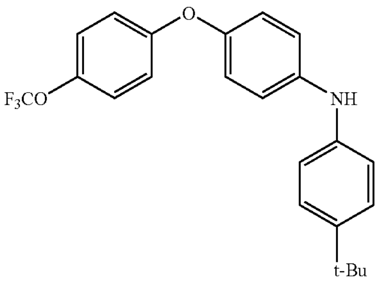 [SMILES: CC(C)(C)c1ccc(Nc2ccc(Oc3ccc(OC(F)(F)F)cc3)cc2)cc1]
165(2)
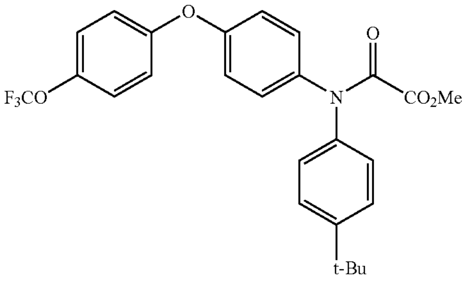 [SMILES: COC(=O)C(=O)N(c1ccc(Oc2ccc(OC(F)(F)F)cc2)cc1)c1ccc(C(C)(C)C)cc1]
166(1)
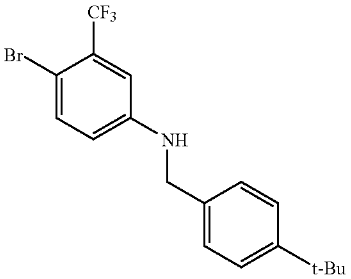 [SMILES: CC(C)(C)c1ccc(CNc2ccc(Br)c(C(F)(F)F)c2)cc1]
166(2)
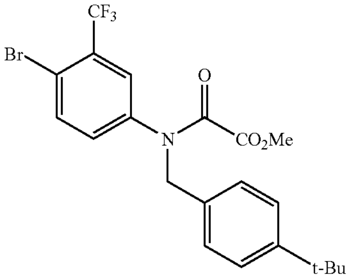 [SMILES: COC(=O)C(=O)N(Cc1ccc(C(C)(C)C)cc1)c1ccc(Br)c(C(F)(F)F)c1]

TABLE 4-20-continued
166(3)
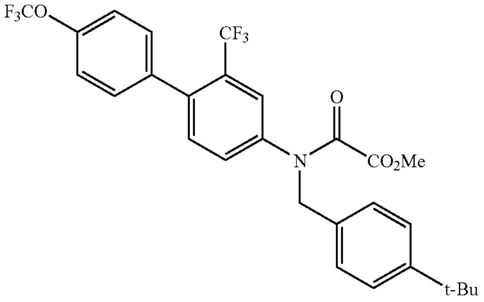 [SMILES: COC(=O)C(=O)N(Cc1ccc(C(C)(C)C)cc1)c1ccc(-c2ccc(OC(F)(F)F)cc2)c(C(F)(F)F)c1]
167(1)
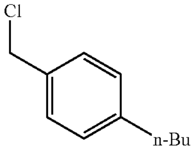
TABLE 4-21
167(2)
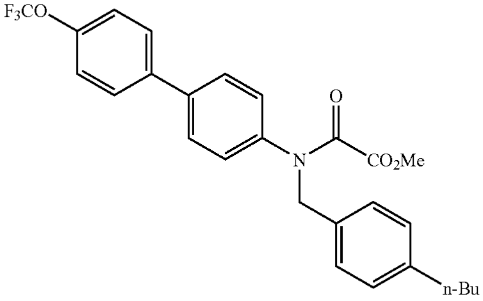
168(1)
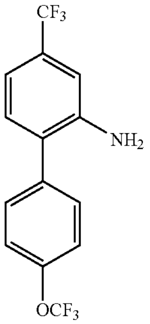 [SMILES: Nc1cc(C(F)(F)F)ccc1-c1ccc(OC(F)(F)F)cc1]
168(2)
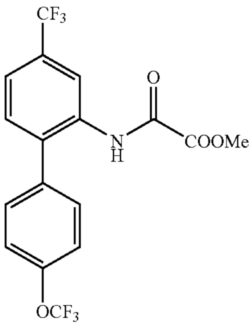 [SMILES: COC(=O)C(=O)Nc1cc(C(F)(F)F)ccc1-c1ccc(OC(F)(F)F)cc1]
TABLE 4-21-continued
168(3)
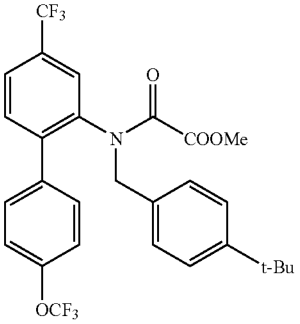 [SMILES: COC(=O)C(=O)N(Cc1ccc(C(C)(C)C)cc1)c1cc(C(F)(F)F)ccc1-c1ccc(OC(F)(F)F)cc1]
169(1)
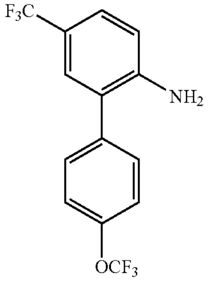 [SMILES: Nc1ccc(C(F)(F)F)cc1-c1ccc(OC(F)(F)F)cc1]
169(2)
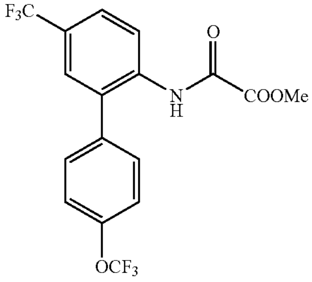 [SMILES: COC(=O)C(=O)Nc1ccc(C(F)(F)F)cc1-c1ccc(OC(F)(F)F)cc1]

TABLE 4-21-continued
169(3)
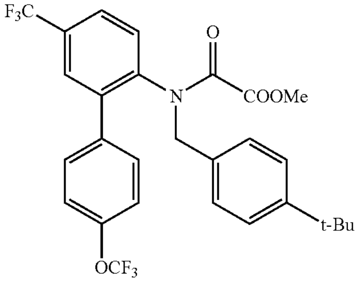 [SMILES: COC(=O)C(=O)N(Cc1ccc(C(C)(C)C)cc1)c1ccc(C(F)(F)F)cc1-c1ccc(OC(F)(F)F)cc1]
170(1)
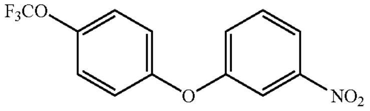
170(2)
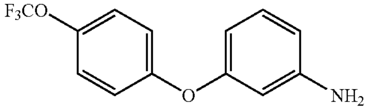 [SMILES: O=[N+]([O-])c1cccc(Oc2ccc(OC(F)(F)F)cc2)c1]
170(3)
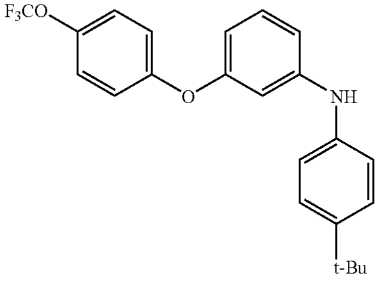 [SMILES: CC(C)(C)c1ccc(Nc2cccc(Oc3ccc(OC(F)(F)F)cc3)c2)cc1]
170(4)
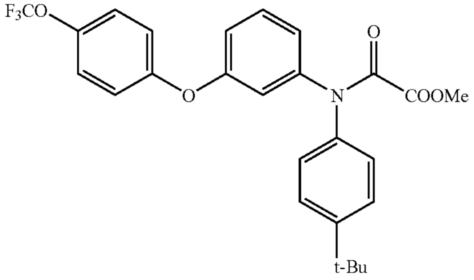 [SMILES: COC(=O)C(=O)N(c1ccc(C(C)(C)C)cc1)c1cccc(Oc2ccc(OC(F)(F)F)cc2)c1]
171(1)
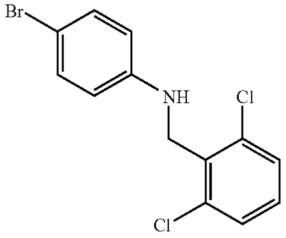 [SMILES: Clc1cccc(Cl)c1CNc1ccc(Br)cc1]
TABLE 4-22
171(2)
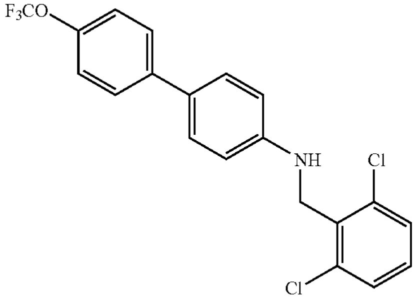 [SMILES: FC(F)(F)Oc1ccc(-c2ccc(NCc3c(Cl)cccc3Cl)cc2)cc1]
171(3)
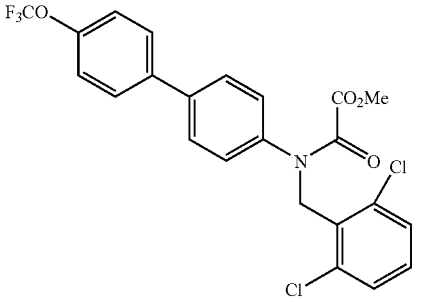 [SMILES: COC(=O)C(=O)N(Cc1c(Cl)cccc1Cl)c1ccc(-c2ccc(OC(F)(F)F)cc2)cc1]
172(1)
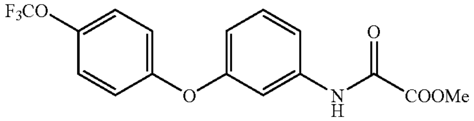 [SMILES: COC(=O)C(=O)Nc1cccc(Oc2ccc(OC(F)(F)F)cc2)c1]

TABLE 4-22-continued
172(2)
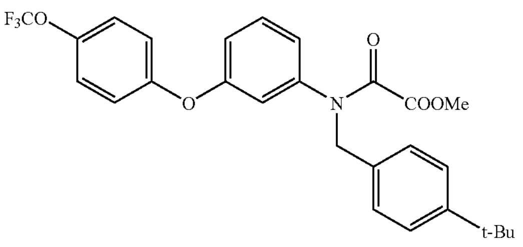 [SMILES: COC(=O)C(=O)N(Cc1ccc(C(C)(C)C)cc1)c1cccc(Oc2ccc(OC(F)(F)F)cc2)c1]
173(1)
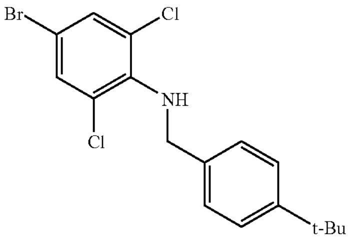 [SMILES: CC(C)(C)c1ccc(CNc2c(Cl)cc(Br)cc2Cl)cc1]
173(2)
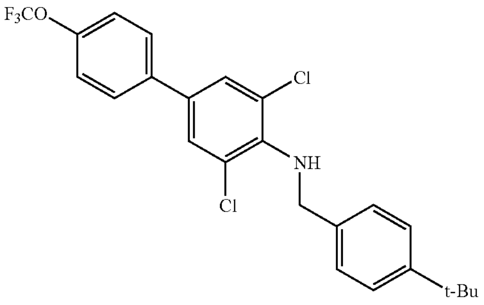 [SMILES: CC(C)(C)c1ccc(CNc2c(Cl)cc(-c3ccc(OC(F)(F)F)cc3)cc2Cl)cc1]
173(3)
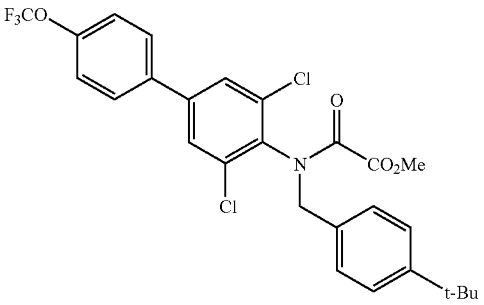 [SMILES: COC(=O)C(=O)N(Cc1ccc(C(C)(C)C)cc1)c1c(Cl)cc(-c2ccc(OC(F)(F)F)cc2)cc1Cl]
174(1)
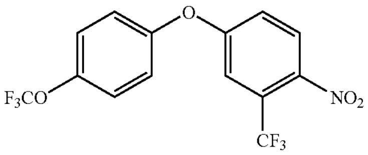
174(2)
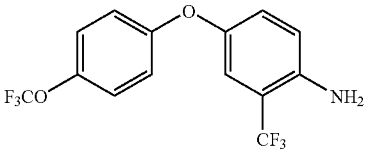 [SMILES: O=[N+]([O-])c1ccc(Oc2ccc(OC(F)(F)F)cc2)cc1C(F)(F)F]
174(3)
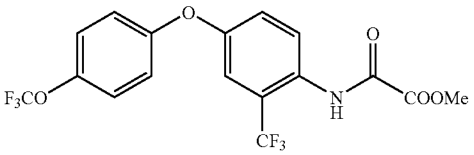 [SMILES: COC(=O)C(=O)Nc1ccc(Oc2ccc(OC(F)(F)F)cc2)cc1C(F)(F)F]

TABLE 4-22-continued
174(4)
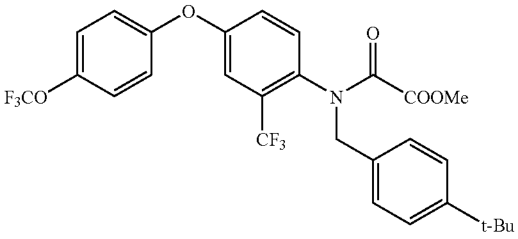 [SMILES: COC(=O)C(=O)N(Cc1ccc(C(C)(C)C)cc1)c1ccc(Oc2ccc(OC(F)(F)F)cc2)cc1C(F)(F)F]
175(1)
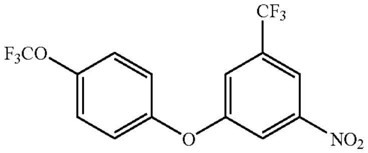
175(2)
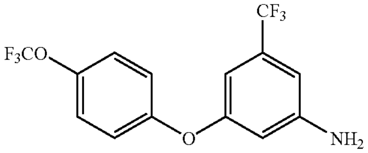 [SMILES: O=[N+]([O-])c1cc(Oc2ccc(OC(F)(F)F)cc2)cc(C(F)(F)F)c1]
175(3)
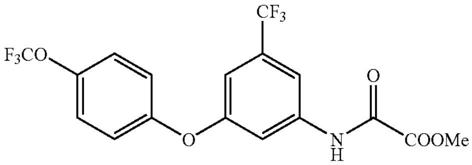 [SMILES: COC(=O)C(=O)Nc1cc(Oc2ccc(OC(F)(F)F)cc2)cc(C(F)(F)F)c1]
TABLE 4-23
175(4)
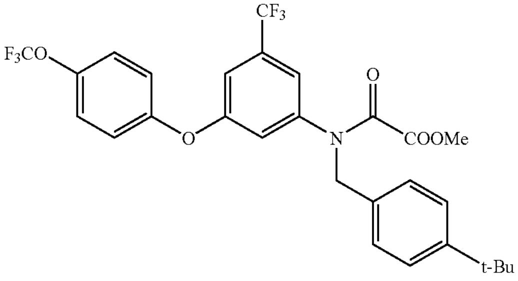 [SMILES: COC(=O)C(=O)N(Cc1ccc(C(C)(C)C)cc1)c1cc(Oc2ccc(OC(F)(F)F)cc2)cc(C(F)(F)F)c1]
176(1)
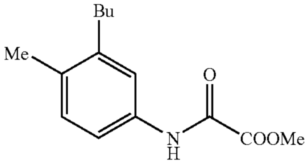
176(2)
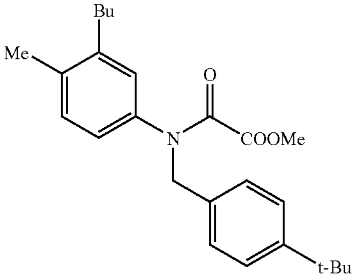

TABLE 4-23-continued
176(3)
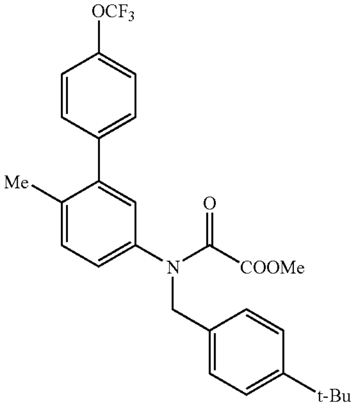 [SMILES: COC(=O)C(=O)N(Cc1ccc(C(C)(C)C)cc1)c1ccc(C)c(-c2ccc(OC(F)(F)F)cc2)c1]
177(1)
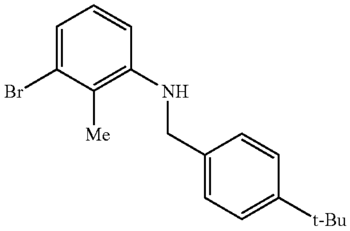 [SMILES: Cc1c(Br)cccc1NCc1ccc(C(C)(C)C)cc1]
177(2)
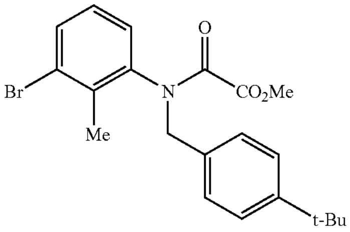 [SMILES: COC(=O)C(=O)N(Cc1ccc(C(C)(C)C)cc1)c1cccc(Br)c1C]
177(3)
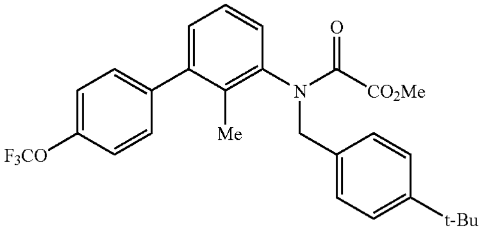 [SMILES: COC(=O)C(=O)N(Cc1ccc(C(C)(C)C)cc1)c1cccc(-c2ccc(OC(F)(F)F)cc2)c1C]
178(1)
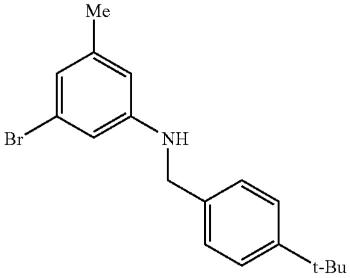

TABLE 4-23-continued
| | |
|---|---|
| 178(2) | 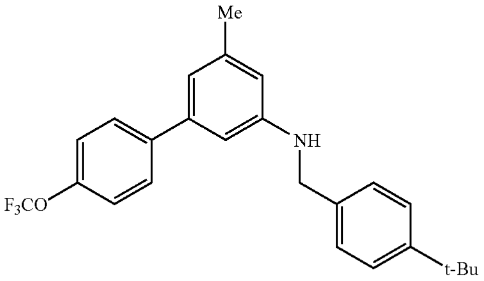 [SMILES: Cc1cc(NCc2ccc(C(C)(C)C)cc2)cc(-c2ccc(OC(F)(F)F)cc2)c1] |
| 178(3) | 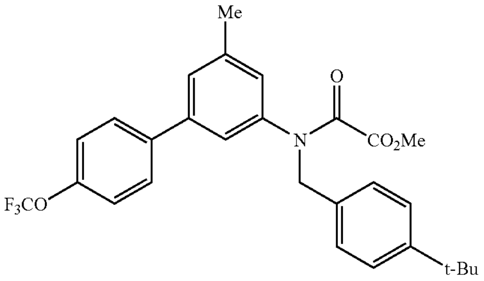 [SMILES: COC(=O)C(=O)N(Cc1ccc(C(C)(C)C)cc1)c1cc(C)cc(-c2ccc(OC(F)(F)F)cc2)c1] |
| 179(1) | 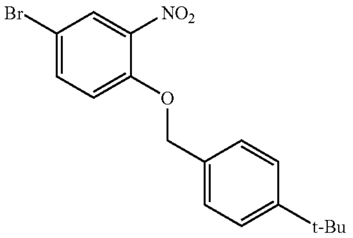 [SMILES: CC(C)(C)c1ccc(COc2ccc(Br)cc2[N+](=O)[O-])cc1] |
| 179(2) | 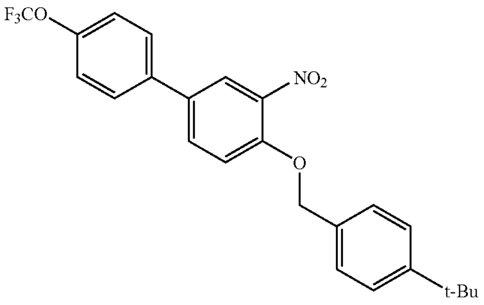 |
TABLE 4-24
| | |
|---|---|
| 179(3) | 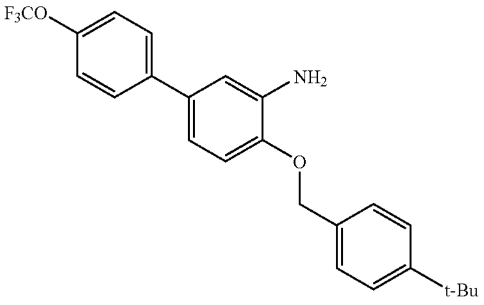 [SMILES: CC(C)(C)c1ccc(COc2ccc(-c3ccc(OC(F)(F)F)cc3)cc2[N+](=O)[O-])cc1] |

TABLE 4-24-continued
179(4)
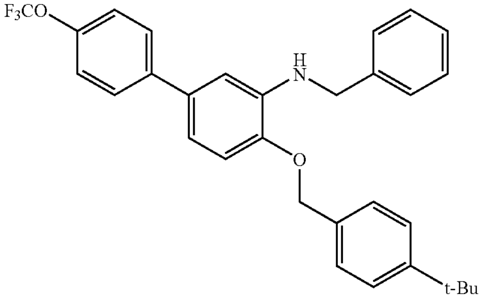 [SMILES: CC(C)(C)c1ccc(COc2ccc(-c3ccc(OC(F)(F)F)cc3)cc2NCc2ccccc2)cc1]
179(5)
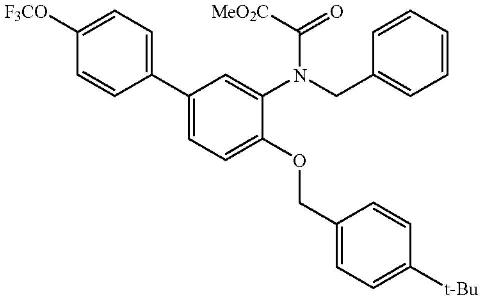 [SMILES: COC(=O)C(=O)N(Cc1ccccc1)c1cc(-c2ccc(OC(F)(F)F)cc2)ccc1OCc1ccc(C(C)(C)C)cc1]
180(1)
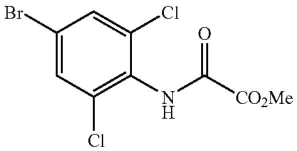
180(2)
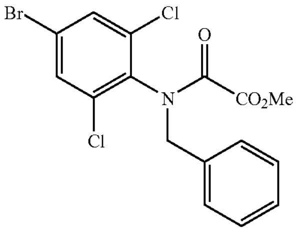 [SMILES: COC(=O)C(=O)N(Cc1ccccc1)c1c(Cl)cc(Br)cc1Cl]
180(3)
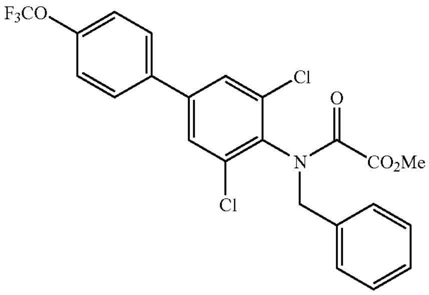 [SMILES: COC(=O)C(=O)N(Cc1ccccc1)c1c(Cl)cc(-c2ccc(OC(F)(F)F)cc2)cc1Cl]
181(1)
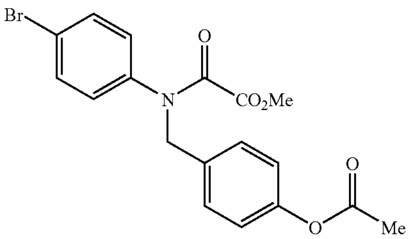 [SMILES: COC(=O)C(=O)N(Cc1ccc(OC(C)=O)cc1)c1ccc(Br)cc1]

TABLE 4-24-continued
181(2)
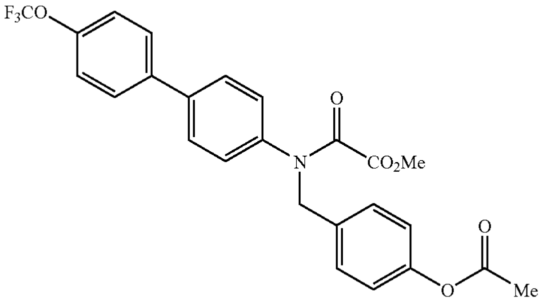 [SMILES: COC(=O)C(=O)N(Cc1ccc(OC(C)=O)cc1)c1ccc(-c2ccc(OC(F)(F)F)cc2)cc1]
182(1)
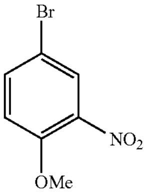 [SMILES: COc1ccc(Br)cc1[N+](=O)[O-]]
182(2)
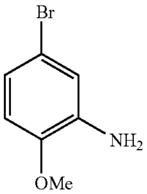
182(3)
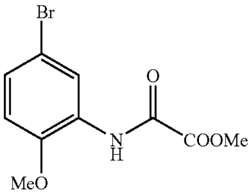 [SMILES: COC(=O)C(=O)Nc1cc(Br)ccc1OC]
182(4)
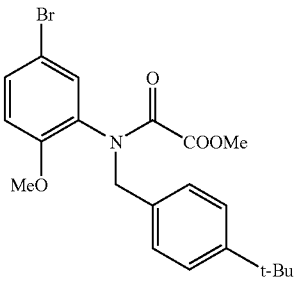 [SMILES: COC(=O)C(=O)N(Cc1ccc(C(C)(C)C)cc1)c1cc(Br)ccc1OC]

TABLE 4-25
182(5)
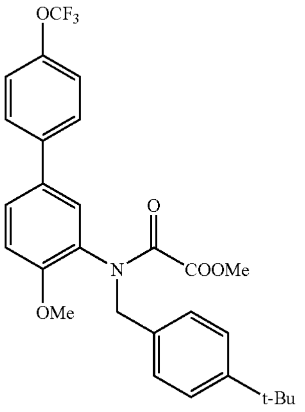 [SMILES: COC(=O)C(=O)N(Cc1ccc(C(C)(C)C)cc1)c1cc(-c2ccc(OC(F)(F)F)cc2)ccc1OC]
183(1)
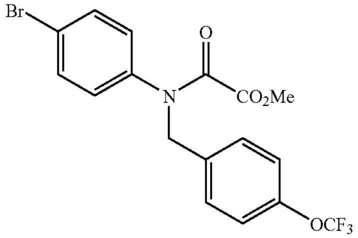 [SMILES: COC(=O)C(=O)N(Cc1ccc(OC(F)(F)F)cc1)c1ccc(Br)cc1]
183(2)
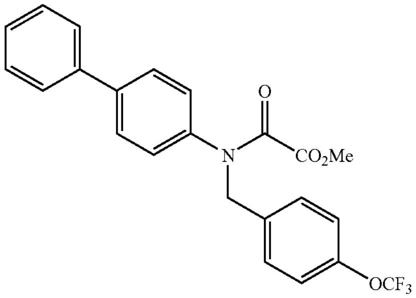 [SMILES: COC(=O)C(=O)N(Cc1ccc(OC(F)(F)F)cc1)c1ccc(-c2ccccc2)cc1]
184(1)
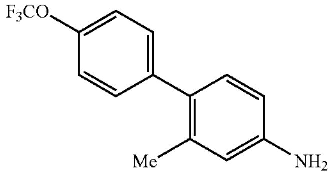 [SMILES: Cc1cc(N)ccc1-c1ccc(OC(F)(F)F)cc1]
184(2)
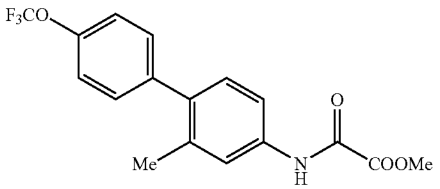 [SMILES: COC(=O)C(=O)Nc1ccc(-c2ccc(OC(F)(F)F)cc2)c(C)c1]
TABLE 4-25-continued
184(3)
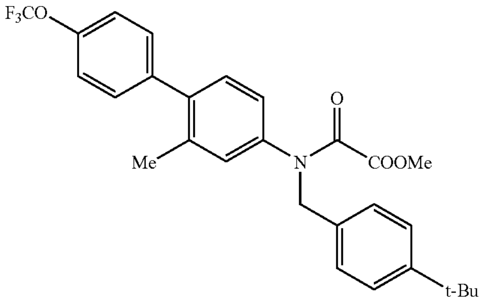 [SMILES: COC(=O)C(=O)N(Cc1ccc(C(C)(C)C)cc1)c1ccc(-c2ccc(OC(F)(F)F)cc2)c(C)c1]
185(1)
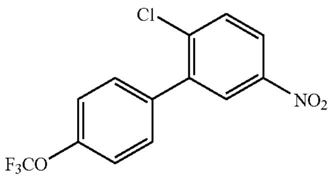 [SMILES: O=[N+]([O-])c1ccc(Cl)c(-c2ccc(OC(F)(F)F)cc2)c1]
185(2)
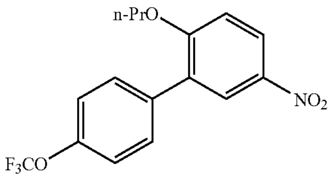
185(3)
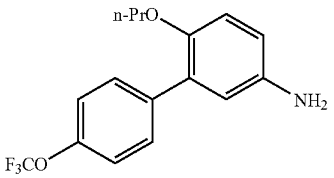
185(4)
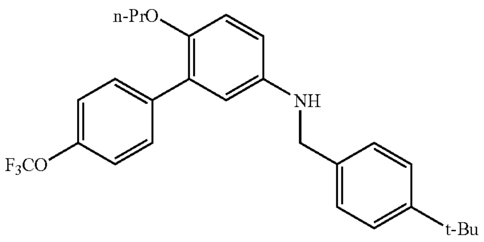
185(5)
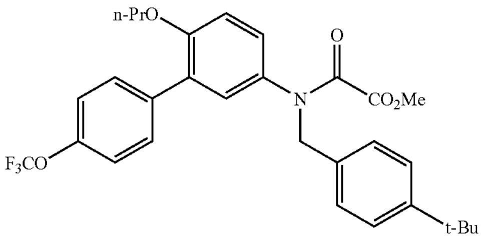
186(1)
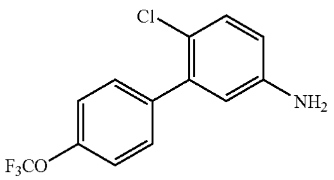

TABLE 4-25-continued
| | |
|---|---|
| 186(2) | 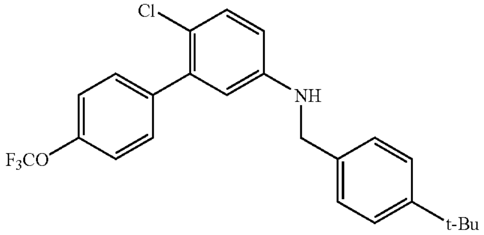 [SMILES: CC(C)(C)c1ccc(CNc2ccc(Cl)c(-c3ccc(OC(F)(F)F)cc3)c2)cc1] |
TABLE 4-25-continued
| | |
|---|---|
| 186(3) | 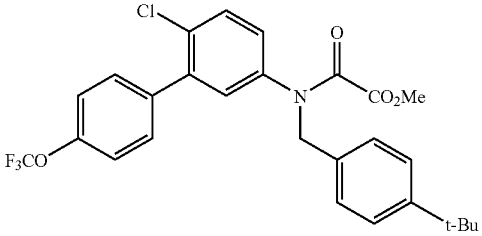 [SMILES: COC(=O)C(=O)N(Cc1ccc(C(C)(C)C)cc1)c1ccc(Cl)c(-c2ccc(OC(F)(F)F)cc2)c1] |
TABLE 4-26
| | |
|---|---|
| 187(1) | 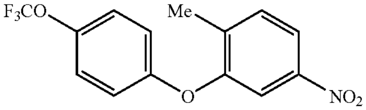 |
| 187(2) | 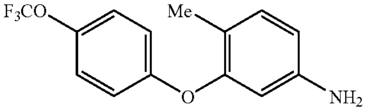 [SMILES: Cc1ccc(N)cc1Oc1ccc(OC(F)(F)F)cc1] |
| 187(3) | 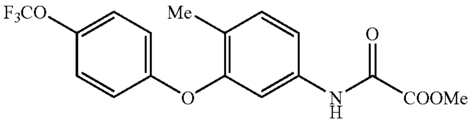 [SMILES: COC(=O)C(=O)Nc1ccc(C)c(Oc2ccc(OC(F)(F)F)cc2)c1] |
| 187(4) | 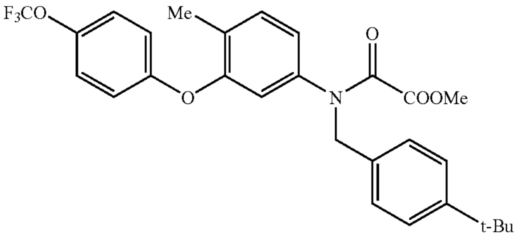 [SMILES: COC(=O)C(=O)N(Cc1ccc(C(C)(C)C)cc1)c1ccc(C)c(Oc2ccc(OC(F)(F)F)cc2)c1] |
| 188(1) | 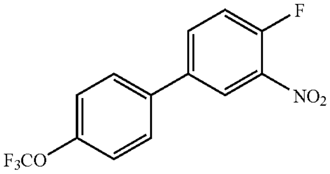 [SMILES: O=[N+]([O-])c1cc(-c2ccc(OC(F)(F)F)cc2)ccc1F] |
| 188(2) | 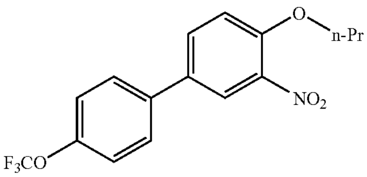 |
| 188(3) | 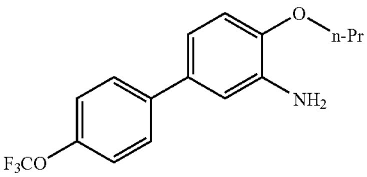 |

TABLE 4-26-continued
188(4)
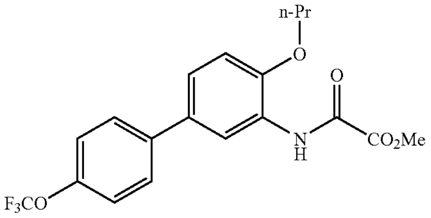
188(5)
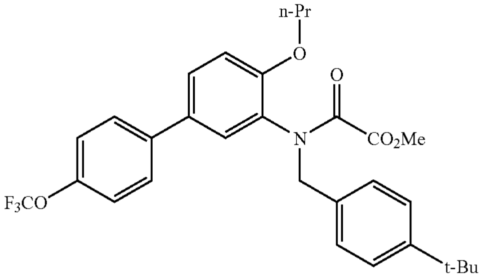
189(1)
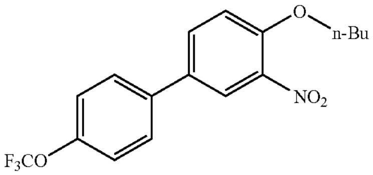
189(2)
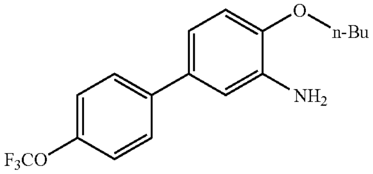
189(3)
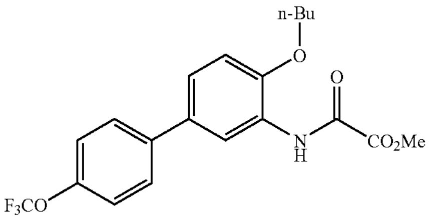
189(4)
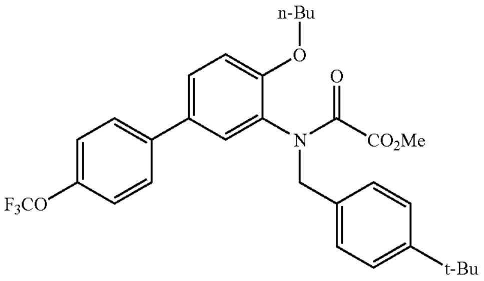
190(1)
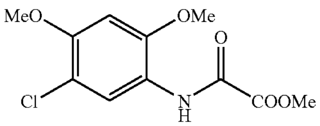 [SMILES: COC(=O)C(=O)Nc1cc(Cl)c(OC)cc1OC]

TABLE 4-26-continued
| | |
|---|---|
| 190(2) | 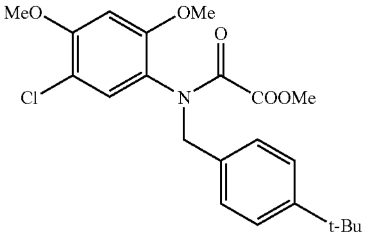 [SMILES: COC(=O)C(=O)N(Cc1ccc(C(C)(C)C)cc1)c1cc(Cl)c(OC)cc1OC] |
| 190(3) | 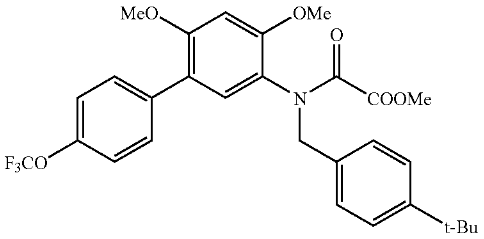 [SMILES: COC(=O)C(=O)N(Cc1ccc(C(C)(C)C)cc1)c1cc(-c2ccc(OC(F)(F)F)cc2)c(OC)cc1OC] |
TABLE 4-27
| | |
|---|---|
| 191 (1) | 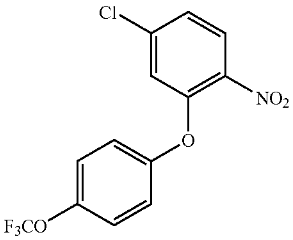 [SMILES: O=[N+]([O-])c1ccc(Cl)cc1Oc1ccc(OC(F)(F)F)cc1] |
| 191 (2) | 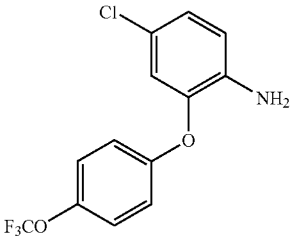 [SMILES: Nc1ccc(Cl)cc1Oc1ccc(OC(F)(F)F)cc1] |
| 191 (3) | 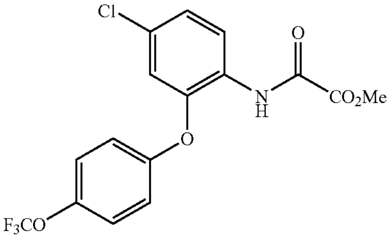 [SMILES: COC(=O)C(=O)Nc1ccc(Cl)cc1Oc1ccc(OC(F)(F)F)cc1] |
| 191 (4) | 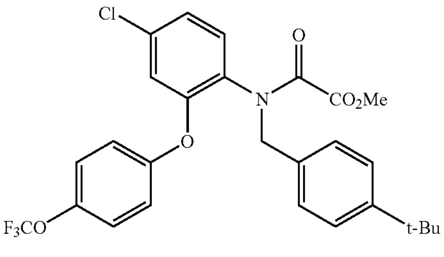 [SMILES: COC(=O)C(=O)N(Cc1ccc(C(C)(C)C)cc1)c1ccc(Cl)cc1Oc1ccc(OC(F)(F)F)cc1] |
TABLE 4-27-continued
| | |
|---|---|
| 192 (1) | 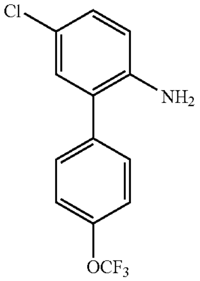 [SMILES: Nc1ccc(Cl)cc1-c1ccc(OC(F)(F)F)cc1] |
| 192 (2) | 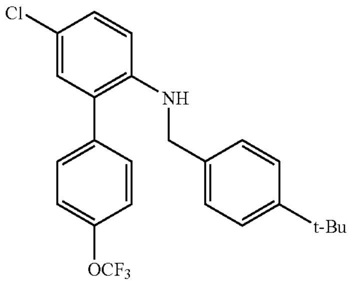 [SMILES: CC(C)(C)c1ccc(CNc2ccc(Cl)cc2-c2ccc(OC(F)(F)F)cc2)cc1] |
| 192 (3) | 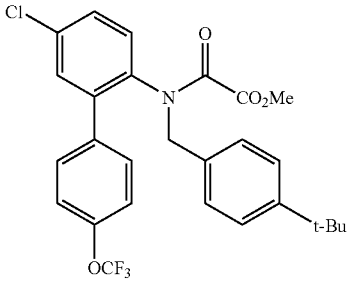 [SMILES: COC(=O)C(=O)N(Cc1ccc(C(C)(C)C)cc1)c1ccc(Cl)cc1-c1ccc(OC(F)(F)F)cc1] |
| 193 (1) | 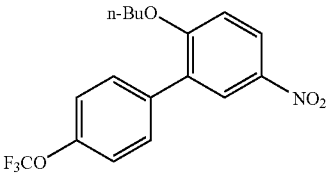 |

TABLE 4-27-continued
| | |
|---|---|
| 193 (2) | 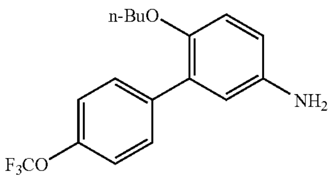 |
| 193 (3) | 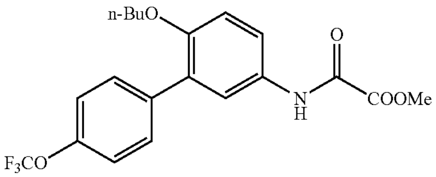 |
| 193 (4) | 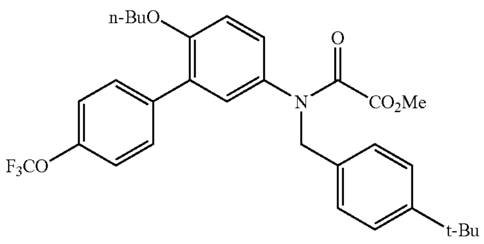 |
| 194 (1) | 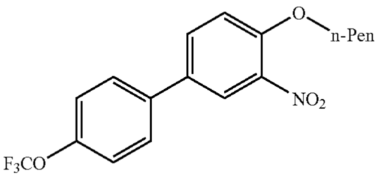 |
| 194 (2) | 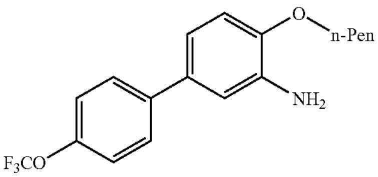 |
| 194 (3) | 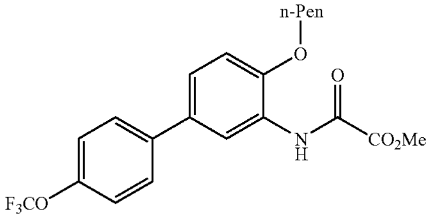 |
TABLE 4-28
| | |
|---|---|
| 194 (4) | 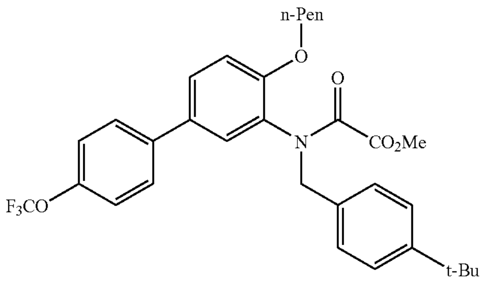 |
TABLE 4-28-continued
| | |
|---|---|
| 195 (1) | 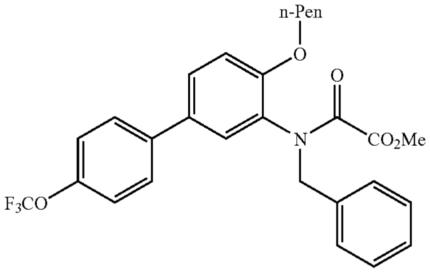 |
| 196 (1) | 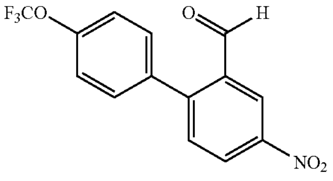 [SMILES: O=Cc1cc([N+](=O)[O-])ccc1-c1ccc(OC(F)(F)F)cc1] |
| 196 (2) | 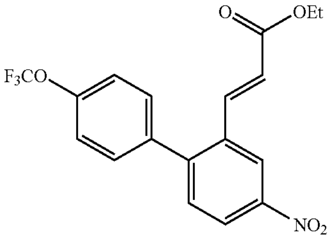 [SMILES: CCOC(=O)/C=C/c1cc([N+](=O)[O-])ccc1-c1ccc(OC(F)(F)F)cc1] |
| 196 (3) | 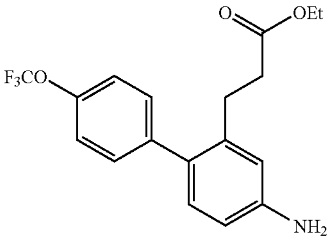 [SMILES: CCOC(=O)CCc1cc(N)ccc1-c1ccc(OC(F)(F)F)cc1] |
| 196 (4) | 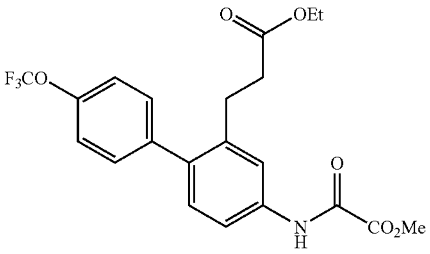 [SMILES: CCOC(=O)CCc1cc(NC(=O)C(=O)OC)ccc1-c1ccc(OC(F)(F)F)cc1] |
| 196 (5) | 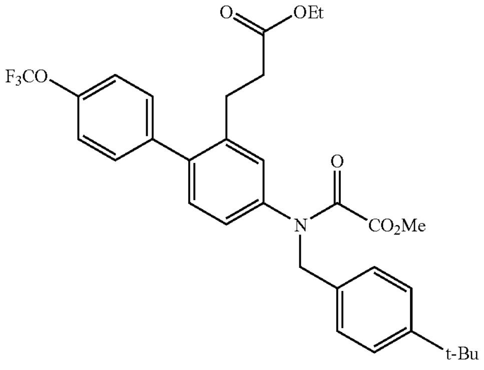 [SMILES: CCOC(=O)CCc1cc(N(Cc2ccc(C(C)(C)C)cc2)C(=O)C(=O)OC)ccc1-c1ccc(OC(F)(F)F)cc1] |

TABLE 4-28-continued
197
(1)
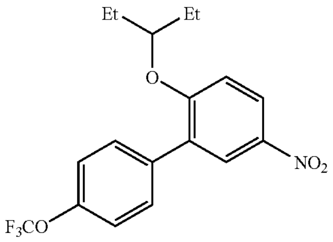 [SMILES: CCC(CC)Oc1ccc(N)cc1-c1ccc(OC(F)(F)F)cc1]
197
(2)
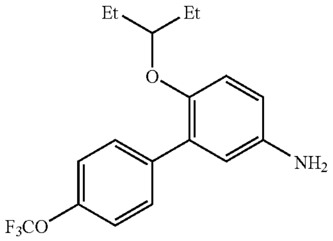
197
(3)
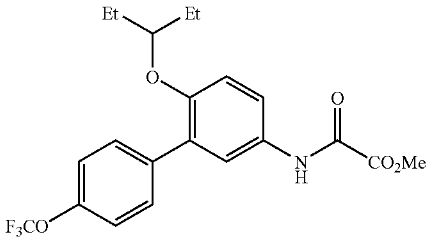 [SMILES: CCC(CC)Oc1ccc(NC(=O)C(=O)OC)cc1-c1ccc(OC(F)(F)F)cc1]
197
(4)
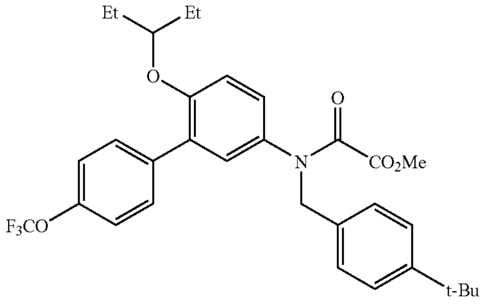 [SMILES: CCC(CC)Oc1ccc(N(Cc2ccc(C(C)(C)C)cc2)C(=O)C(=O)OC)cc1-c1ccc(OC(F)(F)F)cc1]
198
(1)
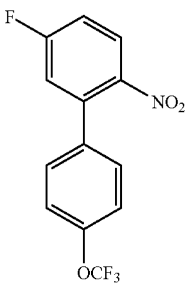 [SMILES: O=[N+]([O-])c1ccc(F)cc1-c1ccc(OC(F)(F)F)cc1]
TABLE 4-29
198
(2)
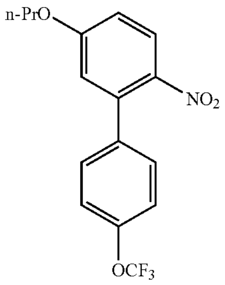
198
(3)
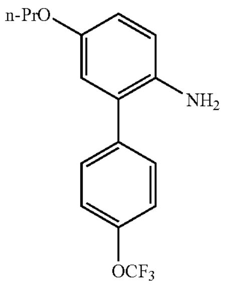
198
(4)
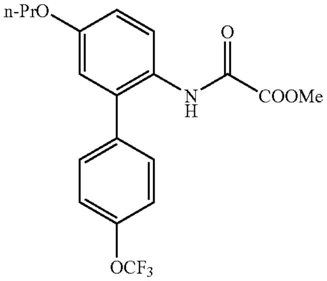
198
(5)
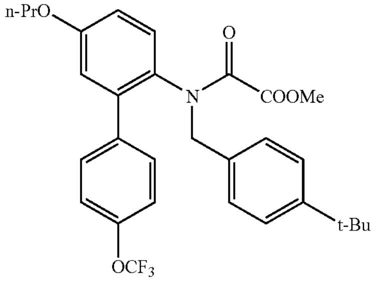
199
(1)
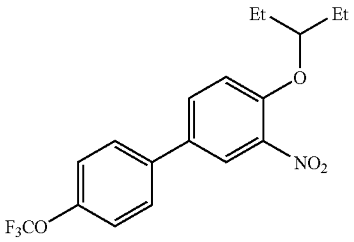

TABLE 4-29-continued
199 (2)
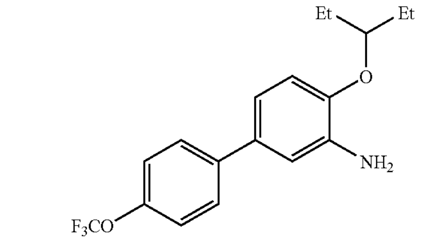 [SMILES: CCC(CC)Oc1ccc(-c2ccc(OC(F)(F)F)cc2)cc1[N+](=O)[O-]]
199 (3)
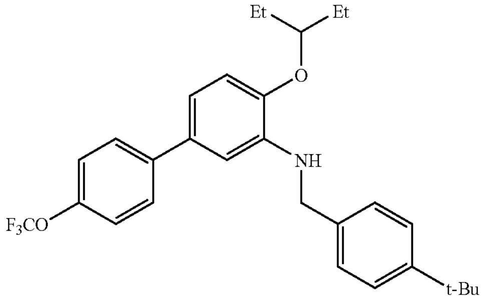 [SMILES: CCC(CC)Oc1ccc(-c2ccc(OC(F)(F)F)cc2)cc1NCc1ccc(C(C)(C)C)cc1]
199 (4)
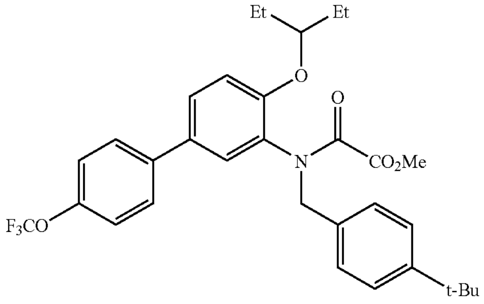 [SMILES: CCC(CC)Oc1ccc(-c2ccc(OC(F)(F)F)cc2)cc1N(Cc1ccc(C(C)(C)C)cc1)C(=O)C(=O)OC]
200 (1)
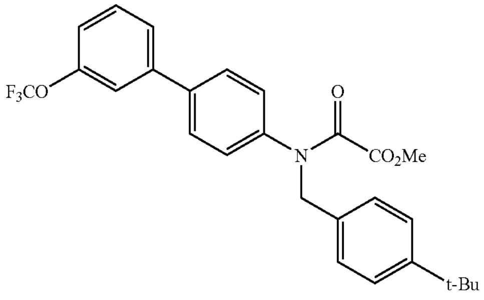 [SMILES: COC(=O)C(=O)N(Cc1ccc(C(C)(C)C)cc1)c1ccc(-c2cccc(OC(F)(F)F)c2)cc1]
201 (1)
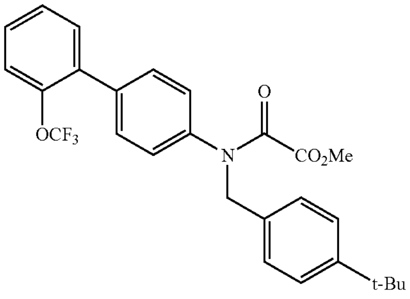 [SMILES: COC(=O)C(=O)N(Cc1ccc(C(C)(C)C)cc1)c1ccc(-c2ccccc2OC(F)(F)F)cc1]
TABLE 4-29-continued
202 (1)
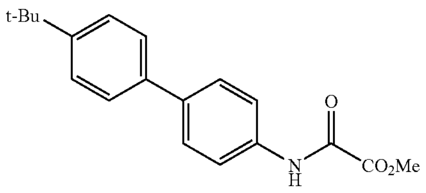 [SMILES: COC(=O)C(=O)Nc1ccc(-c2ccc(C(C)(C)C)cc2)cc1]
202 (2)
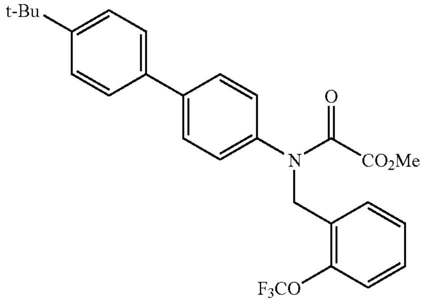 [SMILES: COC(=O)C(=O)N(Cc1ccccc1OC(F)(F)F)c1ccc(-c2ccc(C(C)(C)C)cc2)cc1]
TABLE 4-30
203 (1)
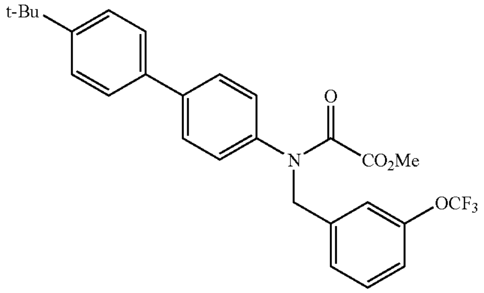 [SMILES: COC(=O)C(=O)N(Cc1cccc(OC(F)(F)F)c1)c1ccc(-c2ccc(C(C)(C)C)cc2)cc1]
204 (1)
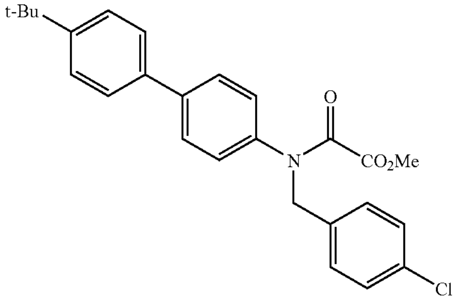 [SMILES: COC(=O)C(=O)N(Cc1ccc(Cl)cc1)c1ccc(-c2ccc(C(C)(C)C)cc2)cc1]
205 (1)
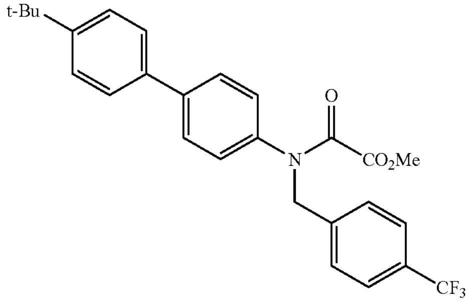 [SMILES: COC(=O)C(=O)N(Cc1ccc(C(F)(F)F)cc1)c1ccc(-c2ccc(C(C)(C)C)cc2)cc1]

TABLE 4-30-continued
206 (1)
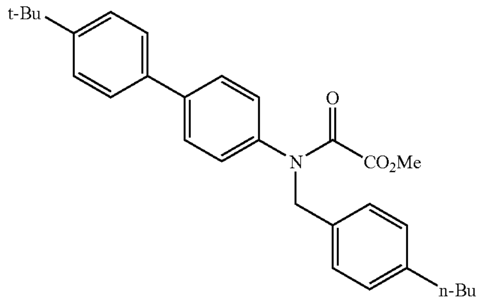
207 (1)
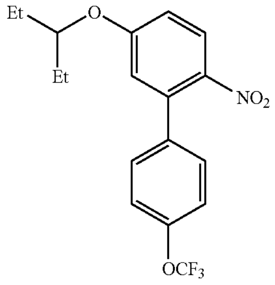
207 (2)
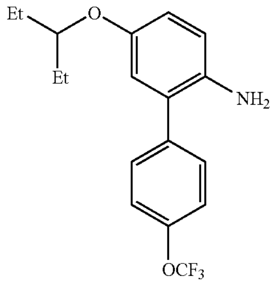 [SMILES: CCC(CC)Oc1ccc([N+](=O)[O-])c(-c2ccc(OC(F)(F)F)cc2)c1]
207 (3)
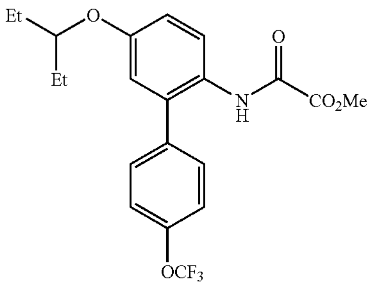 [SMILES: CCC(CC)Oc1ccc(NC(=O)C(=O)OC)c(-c2ccc(OC(F)(F)F)cc2)c1]
207 (4)
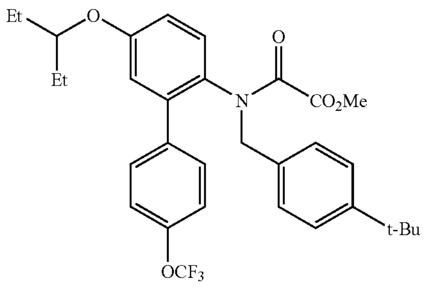 [SMILES: CCC(CC)Oc1ccc(N(Cc2ccc(C(C)(C)C)cc2)C(=O)C(=O)OC)c(-c2ccc(OC(F)(F)F)cc2)c1]
TABLE 4-30-continued
208 (1)
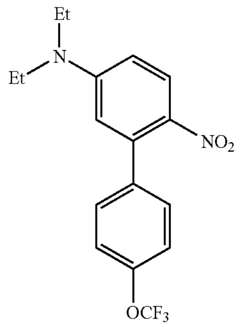 [SMILES: CCN(CC)c1ccc([N+](=O)[O-])c(-c2ccc(OC(F)(F)F)cc2)c1]
208 (2)
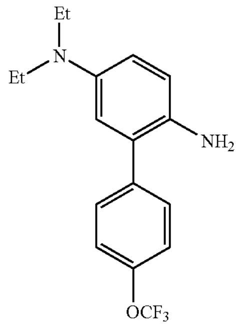
208 (3)
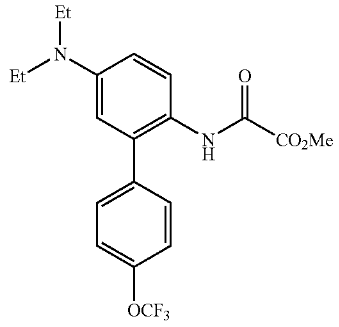 [SMILES: CCN(CC)c1ccc(NC(=O)C(=O)OC)c(-c2ccc(OC(F)(F)F)cc2)c1]
208 (4)
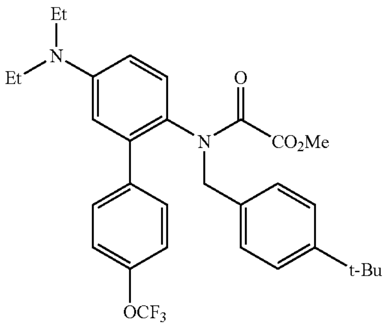 [SMILES: CCN(CC)c1ccc(N(Cc2ccc(C(C)(C)C)cc2)C(=O)C(=O)OC)c(-c2ccc(OC(F)(F)F)cc2)c1]

TABLE 4-31
209 (1)
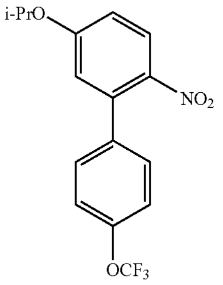
209 (2)
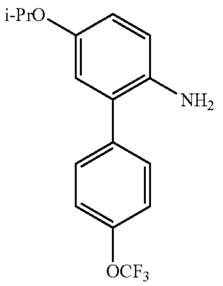
209 (3)
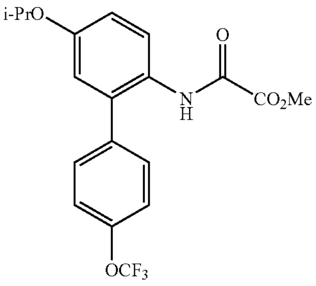
209 (4)
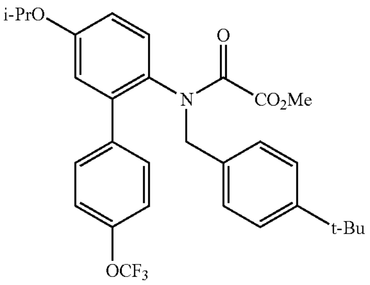
210 (1)
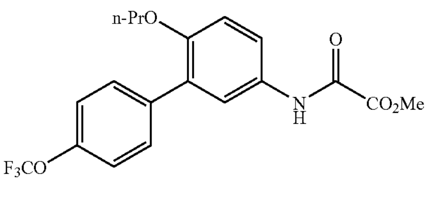
210 (2)
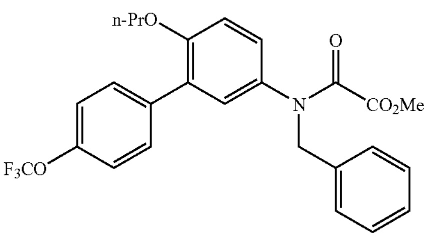
TABLE 4-31-continued
211 (1)
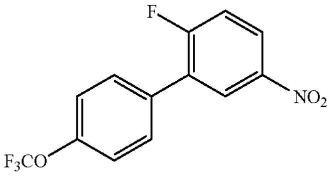
211 (2)
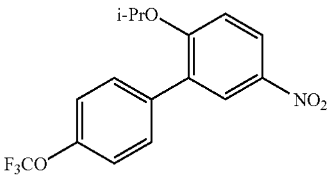
211 (3)
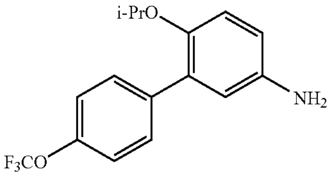
211 (4)
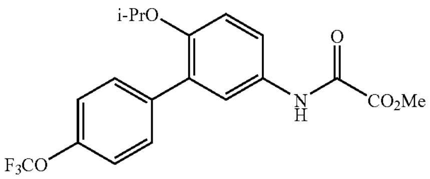
211 (5)
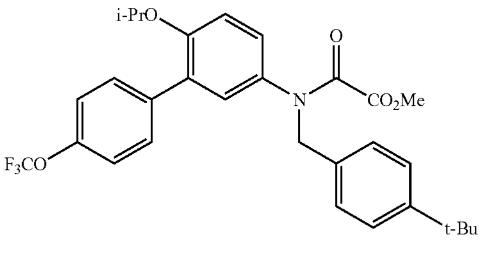
212 (1)
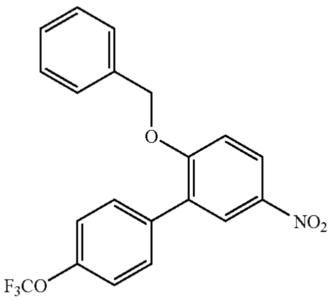
212 (2)
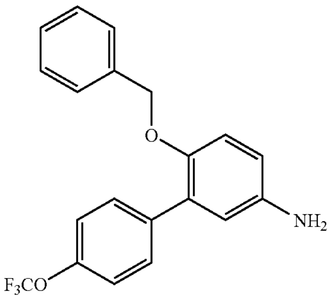 [SMILES: O=[N+]([O-])c1ccc(OCc2ccccc2)c(-c2ccc(OC(F)(F)F)cc2)c1]

TABLE 4-31-continued
212 (3)
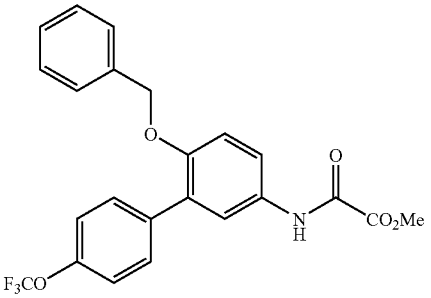 [SMILES: COC(=O)C(=O)Nc1ccc(OCc2ccccc2)c(-c2ccc(OC(F)(F)F)cc2)c1]
TABLE 4-32
212 (4)
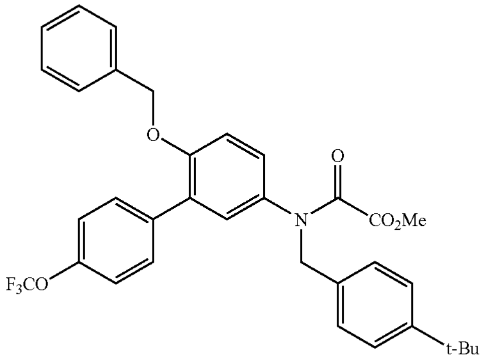 [SMILES: COC(=O)C(=O)N(Cc1ccc(C(C)(C)C)cc1)c1ccc(OCc2ccccc2)c(-c2ccc(OC(F)(F)F)cc2)c1]
213 (1)
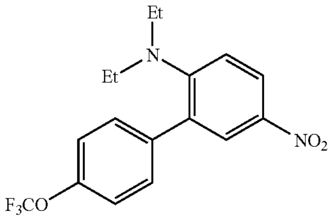 [SMILES: CCN(CC)c1ccc([N+](=O)[O-])cc1-c1ccc(OC(F)(F)F)cc1]
213 (2)
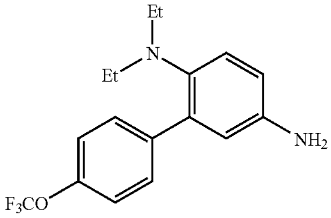
213 (3)
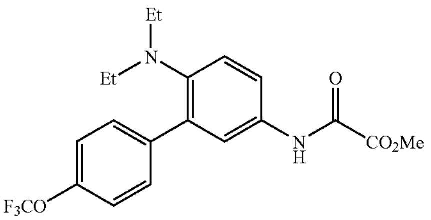 [SMILES: CCN(CC)c1ccc(NC(=O)C(=O)OC)cc1-c1ccc(OC(F)(F)F)cc1]
TABLE 4-32-continued
213 (4)
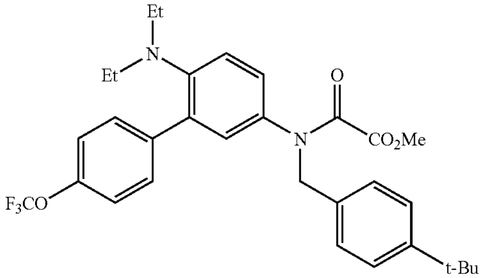 [SMILES: CCN(CC)c1ccc(N(Cc2ccc(C(C)(C)C)cc2)C(=O)C(=O)OC)cc1-c1ccc(OC(F)(F)F)cc1]
214 (1)
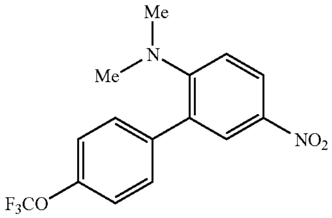 [SMILES: CN(C)c1ccc([N+](=O)[O-])cc1-c1ccc(OC(F)(F)F)cc1]
214 (2)
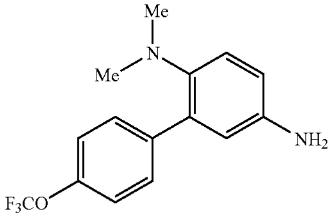
214 (3)
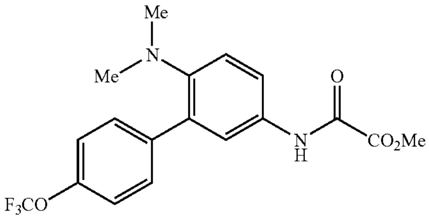
214 (4)
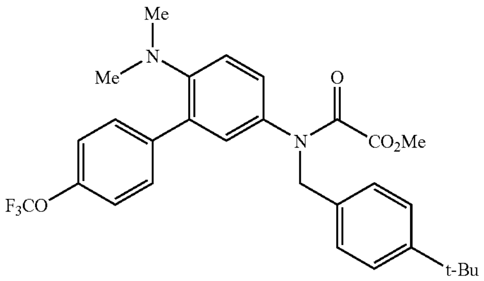
215 (1)
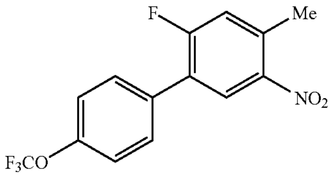 [SMILES: Cc1cc(F)c(-c2ccc(OC(F)(F)F)cc2)cc1[N+](=O)[O-]]

TABLE 4-32-continued
215
(2)
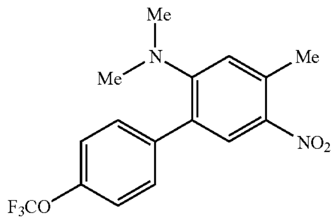
215
(3)
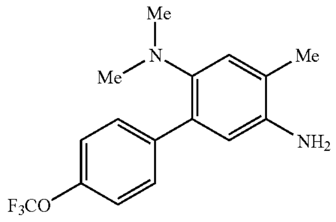 [SMILES: Cc1cc(N(C)C)c(-c2ccc(OC(F)(F)F)cc2)cc1[N+](=O)[O-]]
TABLE 4-33
215
(4)
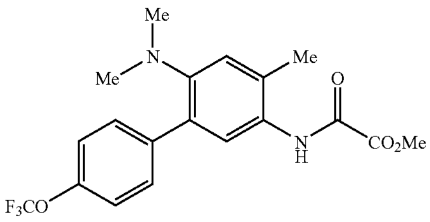 [SMILES: COC(=O)C(=O)Nc1cc(-c2ccc(OC(F)(F)F)cc2)c(N(C)C)cc1C]
215
(5)
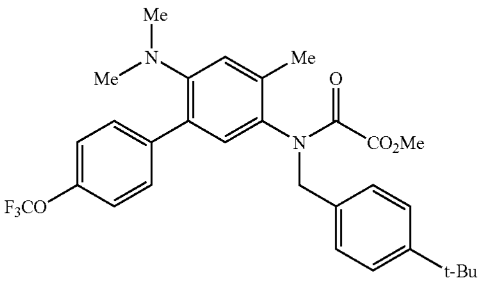 [SMILES: COC(=O)C(=O)N(Cc1ccc(C(C)(C)C)cc1)c1cc(-c2ccc(OC(F)(F)F)cc2)c(N(C)C)cc1C]
216
(1)
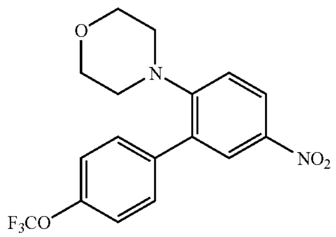
216
(2)
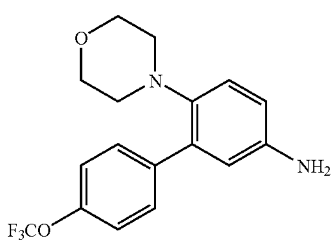
TABLE 4-33-continued
216
(3)
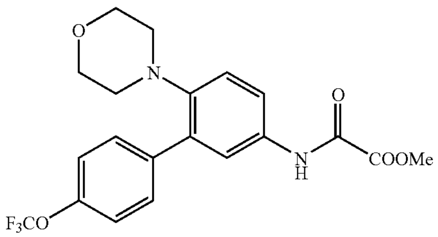 [SMILES: COC(=O)C(=O)Nc1ccc(N2CCOCC2)c(-c2ccc(OC(F)(F)F)cc2)c1]
216
(4)
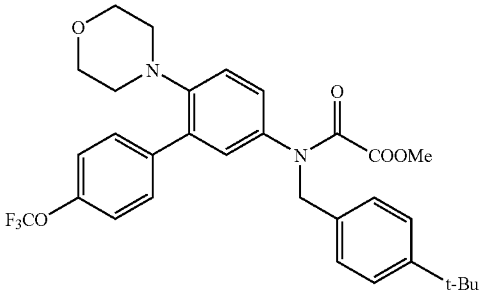
217
(1)
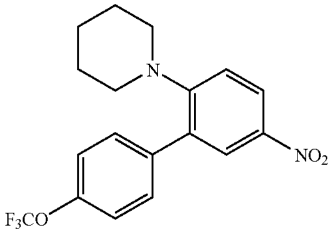 [SMILES: O=[N+]([O-])c1ccc(N2CCCCC2)c(-c2ccc(OC(F)(F)F)cc2)c1]
217
(2)
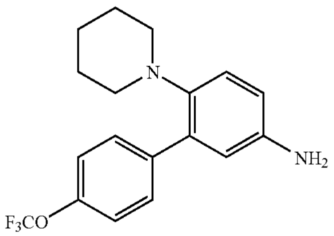
217
(3)
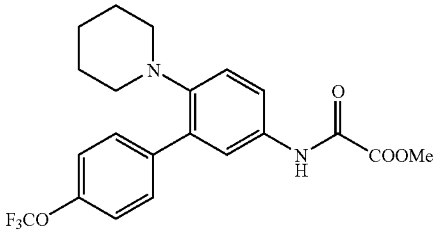 [SMILES: COC(=O)C(=O)Nc1ccc(N2CCCCC2)c(-c2ccc(OC(F)(F)F)cc2)c1]
217
(4)
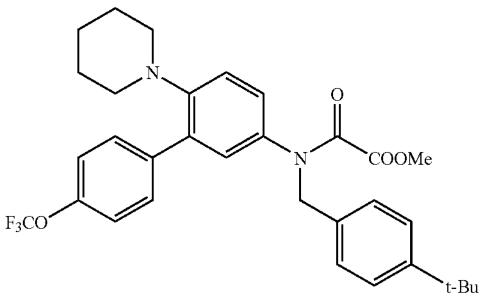

TABLE 4-33-continued
| | |
|---|---|
| 218 (1) | 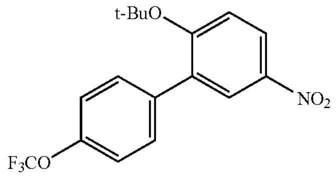 |
| 218 (2) | 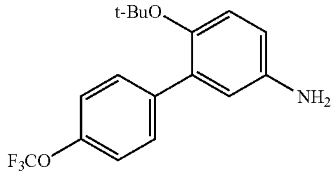 [SMILES: CC(C)(C)Oc1ccc(N)cc1-c1ccc(OC(F)(F)F)cc1] |
| 218 (3) | 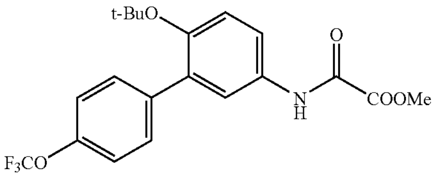 [SMILES: COC(=O)C(=O)Nc1ccc(OC(C)(C)C)c(-c2ccc(OC(F)(F)F)cc2)c1] |
| 218 (4) | 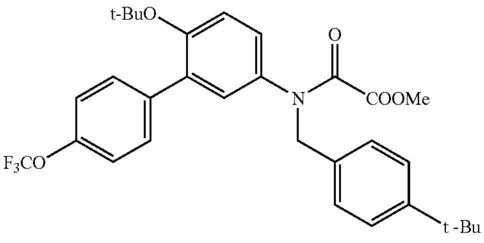 |
TABLE 4-34
| | |
|---|---|
| 219 (1) | 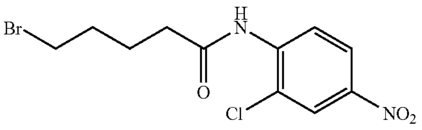 [SMILES: O=C(CCCCBr)Nc1ccc([N+](=O)[O-])cc1Cl] |
| 219 (2) | 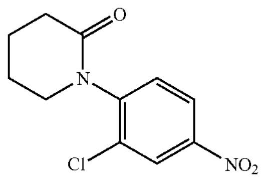 [SMILES: O=C1CCCCN1c1ccc([N+](=O)[O-])cc1Cl] |
| 219 (3) | 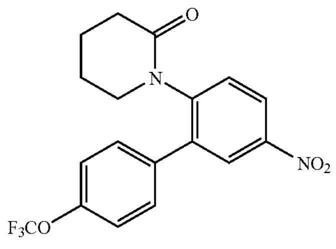 [SMILES: O=C1CCCCN1c1ccc([N+](=O)[O-])cc1-c1ccc(OC(F)(F)F)cc1] |
TABLE 4-34-continued
| | |
|---|---|
| 219 (4) | 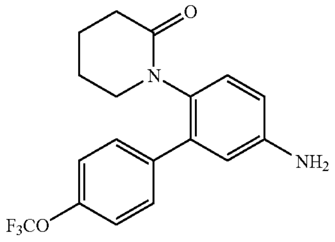 |
| 219 (5) | 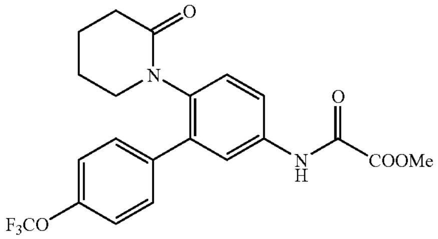 [SMILES: COC(=O)C(=O)Nc1ccc(N2CCCCC2=O)c(-c2ccc(OC(F)(F)F)cc2)c1] |
| 219 (6) | 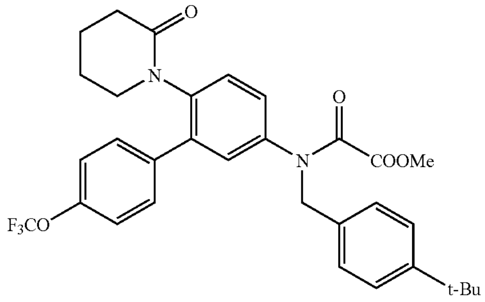 [SMILES: COC(=O)C(=O)N(Cc1ccc(C(C)(C)C)cc1)c1ccc(N2CCCCC2=O)c(-c2ccc(OC(F)(F)F)cc2)c1] |
| 220 (1) | 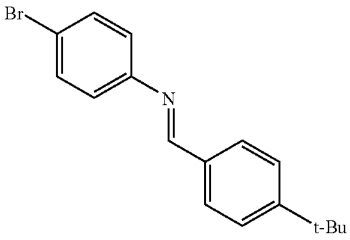 [SMILES: CC(C)(C)c1ccc(/C=N/c2ccc(Br)cc2)cc1] |
| 220 (2) | 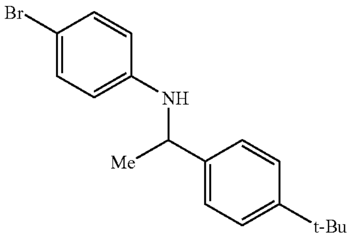 [SMILES: CC(Nc1ccc(Br)cc1)c1ccc(C(C)(C)C)cc1] |
| 220 (3) | 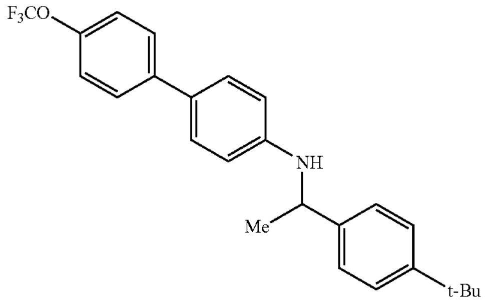 [SMILES: CC(Nc1ccc(-c2ccc(OC(F)(F)F)cc2)cc1)c1ccc(C(C)(C)C)cc1] |

TABLE 4-34-continued
220 (4)
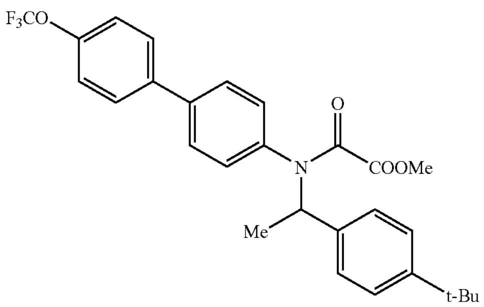 [SMILES: COC(=O)C(=O)N(c1ccc(-c2ccc(OC(F)(F)F)cc2)cc1)C(C)c1ccc(C(C)(C)C)cc1]
221 (1)
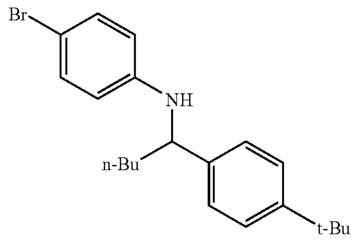
221 (2)
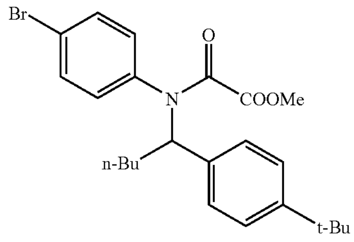
221 (3)
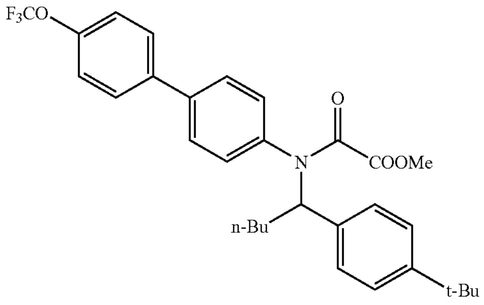
222 (1)
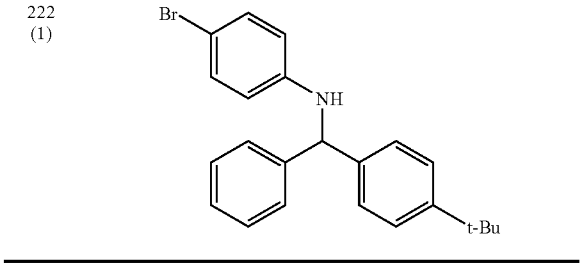
TABLE 4-35
222 (2)
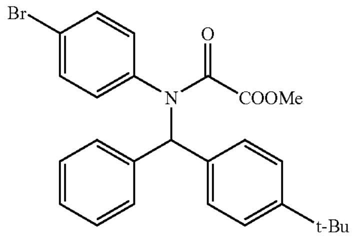 [SMILES: COC(=O)C(=O)N(c1ccc(Br)cc1)C(c1ccccc1)c1ccc(C(C)(C)C)cc1]
222 (3)
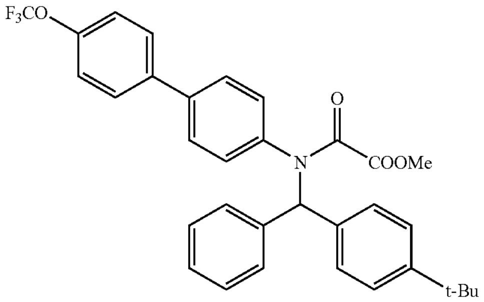 [SMILES: COC(=O)C(=O)N(c1ccc(-c2ccc(OC(F)(F)F)cc2)cc1)C(c1ccccc1)c1ccc(C(C)(C)C)cc1]
223 (1)
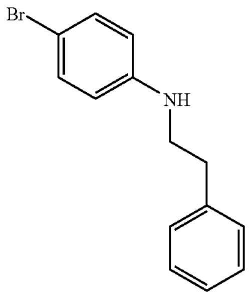 [SMILES: Brc1ccc(NCCc2ccccc2)cc1]
223 (2)
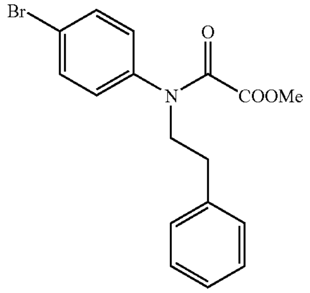 [SMILES: COC(=O)C(=O)N(CCc1ccccc1)c1ccc(Br)cc1]
223 (3)
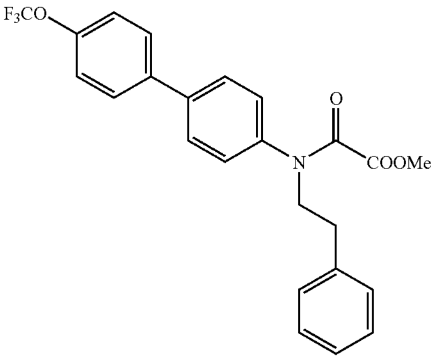 [SMILES: COC(=O)C(=O)N(CCc1ccccc1)c1ccc(-c2ccc(OC(F)(F)F)cc2)cc1]

TABLE 4-35-continued
224 (1)
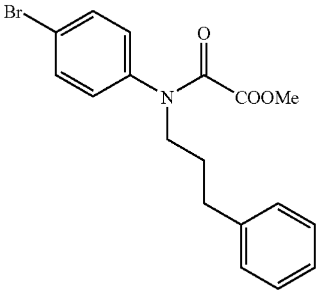 [SMILES: COC(=O)C(=O)N(CCCc1ccccc1)c1ccc(Br)cc1]
224 (2)
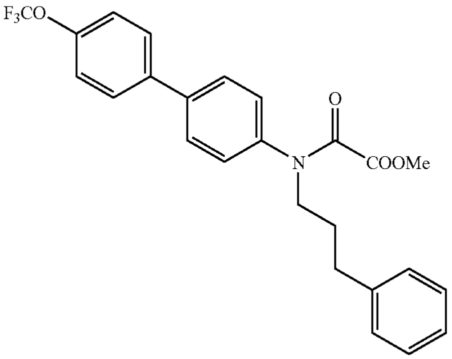 [SMILES: COC(=O)C(=O)N(CCCc1ccccc1)c1ccc(-c2ccc(OC(F)(F)F)cc2)cc1]
225 (1)
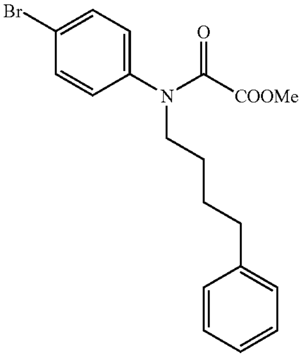 [SMILES: COC(=O)C(=O)N(CCCCc1ccccc1)c1ccc(Br)cc1]
225 (2)
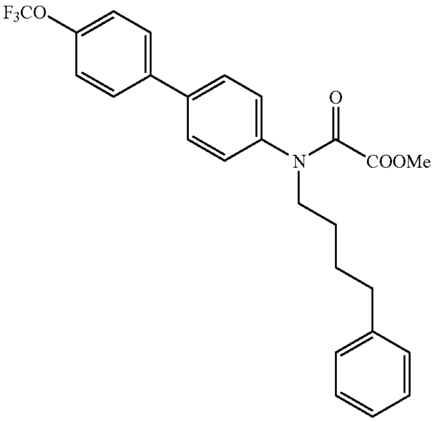 [SMILES: COC(=O)C(=O)N(CCCCc1ccccc1)c1ccc(-c2ccc(OC(F)(F)F)cc2)cc1]
TABLE 4-35-continued
226 (1)
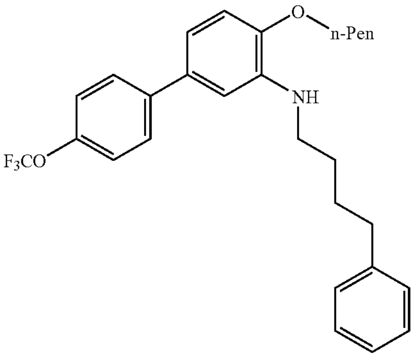
TABLE 4-36
226 (2)
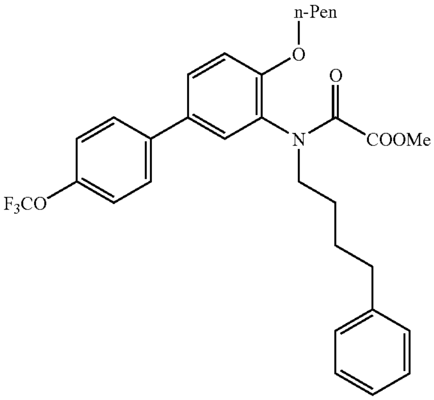
227 (1)
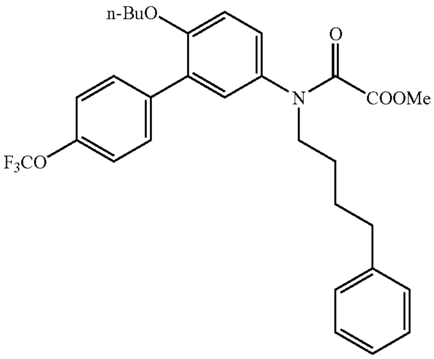
228 (1)
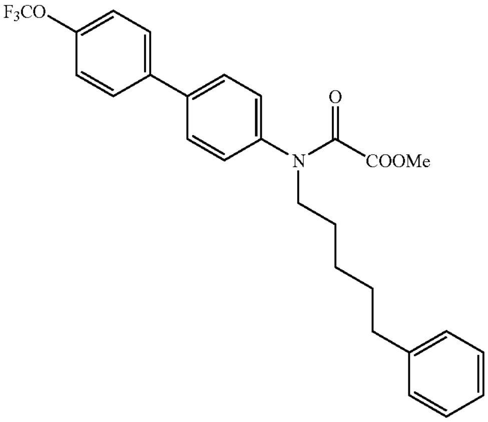 [SMILES: COC(=O)C(=O)N(CCCCCc1ccccc1)c1ccc(-c2ccc(OC(F)(F)F)cc2)cc1]

TABLE 4-36-continued
229
(1)
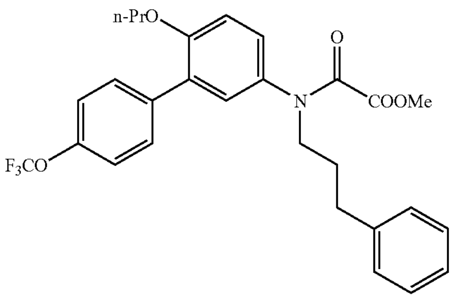
230
(1)
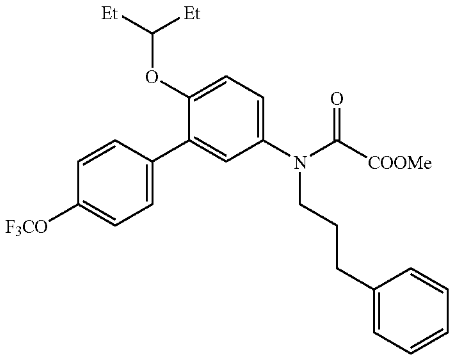 [SMILES: CCC(CC)Oc1ccc(N(CCCc2ccccc2)C(=O)C(=O)OC)cc1-c1ccc(OC(F)(F)F)cc1]
231
(1)
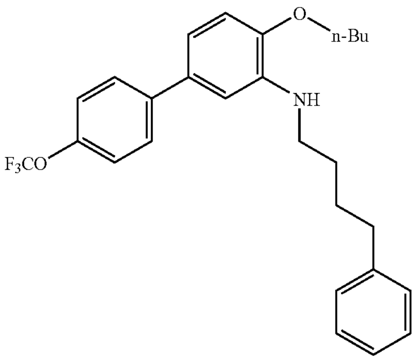
231
(2)
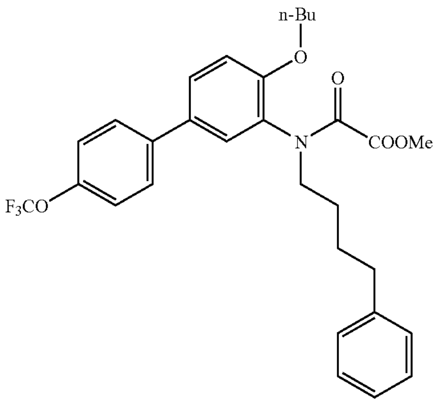
TABLE 4-36-continued
232
(1)
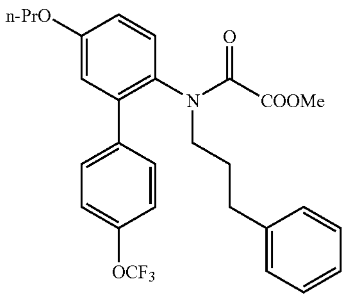
233
(1)
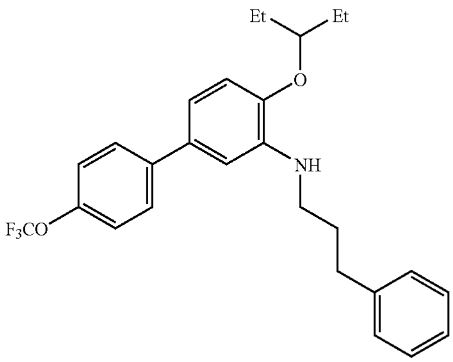 [SMILES: CCC(CC)Oc1ccc(-c2ccc(OC(F)(F)F)cc2)cc1NCCCc1ccccc1]
233
(2)
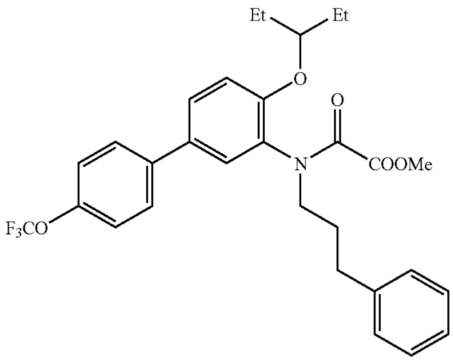 [SMILES: CCC(CC)Oc1ccc(-c2ccc(OC(F)(F)F)cc2)cc1N(CCCc1ccccc1)C(=O)C(=O)OC]
TABLE 4-37
234
(1)
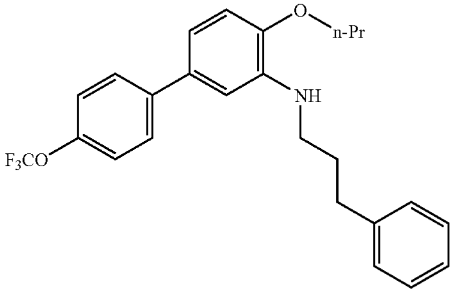

TABLE 4-37-continued
234
(2)
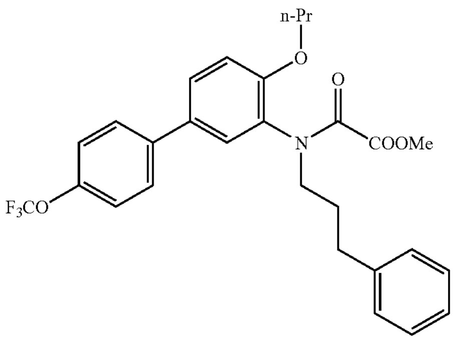
235
(1)
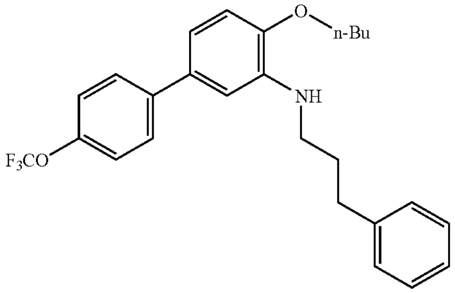
235
(2)
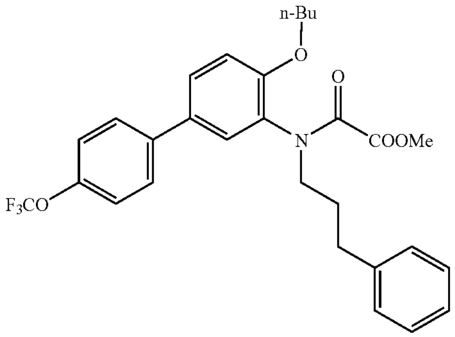
236
(1)
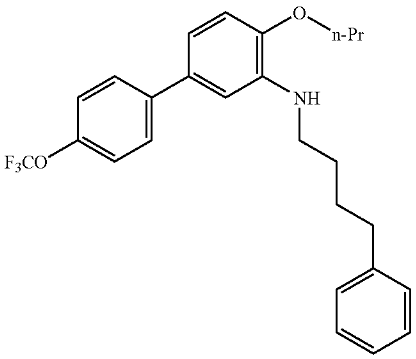
236
(2)
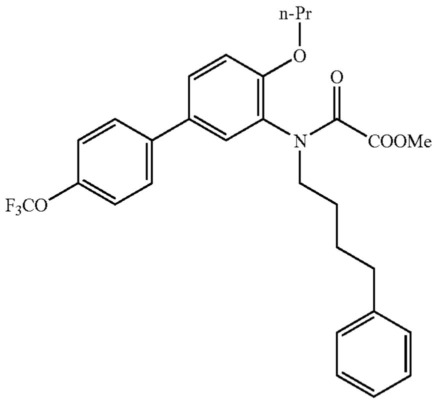
237
(1)
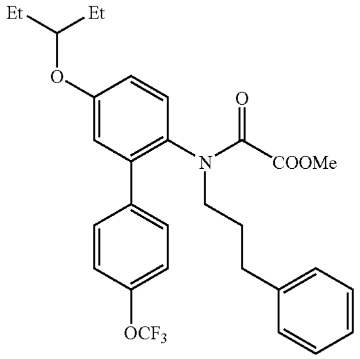 [SMILES: CCC(CC)Oc1ccc(N(CCCc2ccccc2)C(=O)C(=O)OC)c(-c2ccc(OC(F)(F)F)cc2)c1]
238
(1)
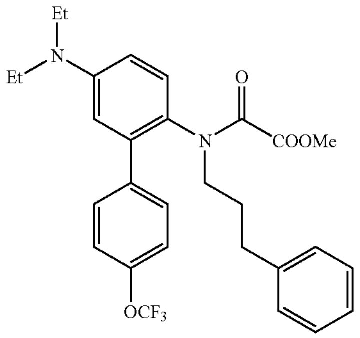 [SMILES: CCN(CC)c1ccc(N(CCCc2ccccc2)C(=O)C(=O)OC)c(-c2ccc(OC(F)(F)F)cc2)c1]
239
(1)
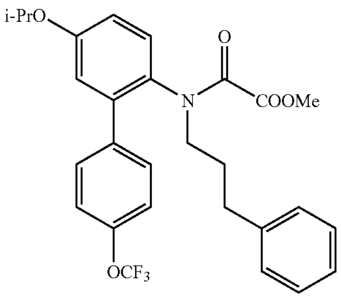

TABLE 4-37-continued
240
(1)
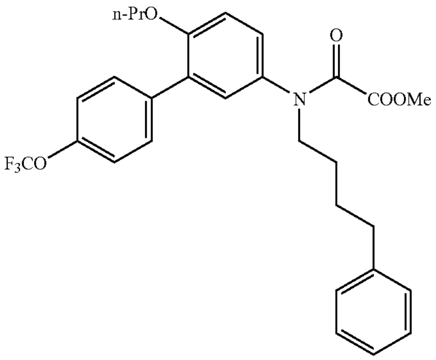
TABLE 4-38
241
(1)
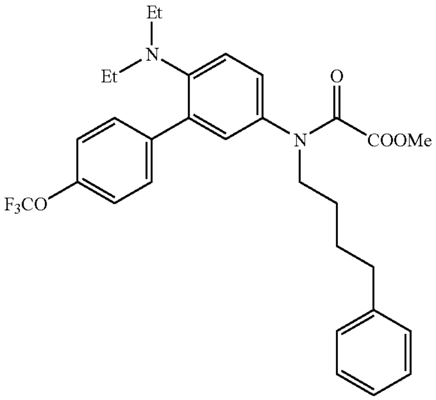 [SMILES: CCN(CC)c1ccc(N(CCCCc2ccccc2)C(=O)C(=O)OC)cc1-c1ccc(OC(F)(F)F)cc1]
242
(1)
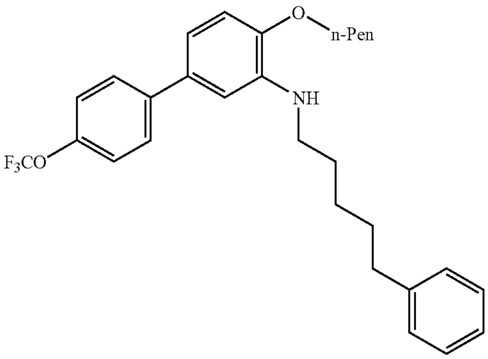
242
(2)
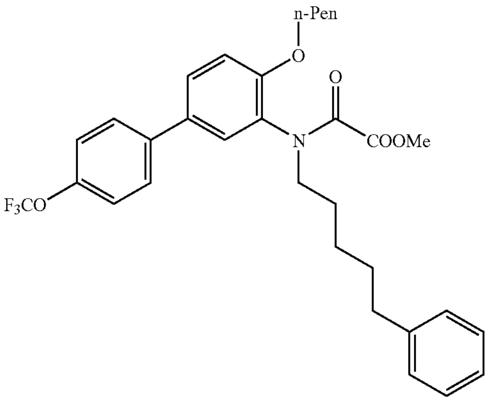
TABLE 4-38-continued
243
(1)
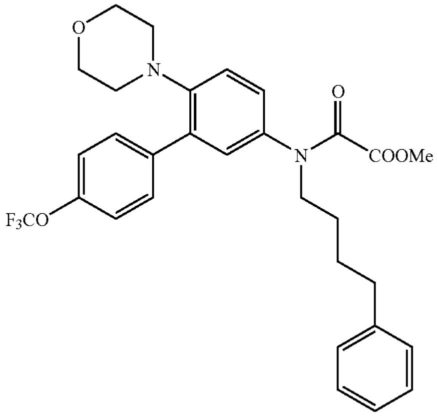 [SMILES: COC(=O)C(=O)N(CCCCc1ccccc1)c1ccc(N2CCOCC2)c(-c2ccc(OC(F)(F)F)cc2)c1]
244
(1)
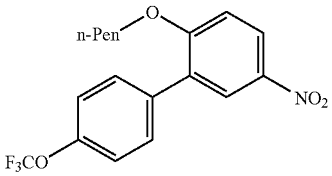
244
(2)
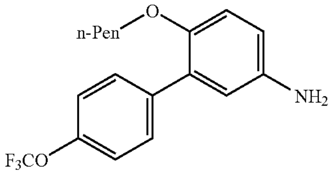
244
(3)
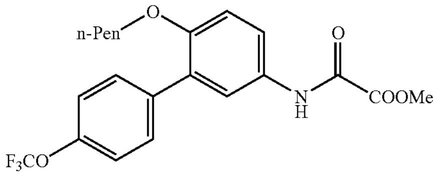
244
(4)
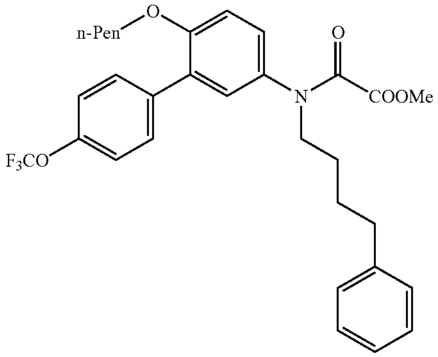
245
(1)
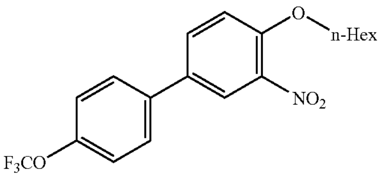

TABLE 4-38-continued
| | |
|---|---|
| 245 (2) | 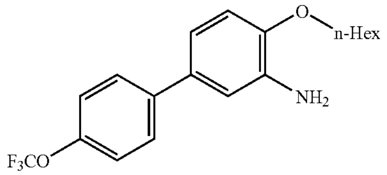 |
| 245 (3) | 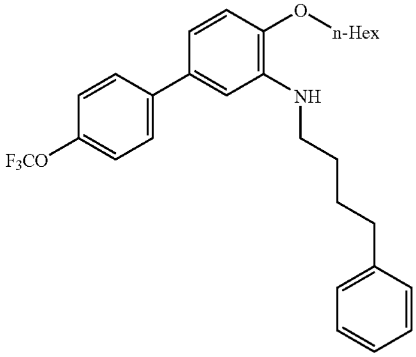 |
| 245 (4) | 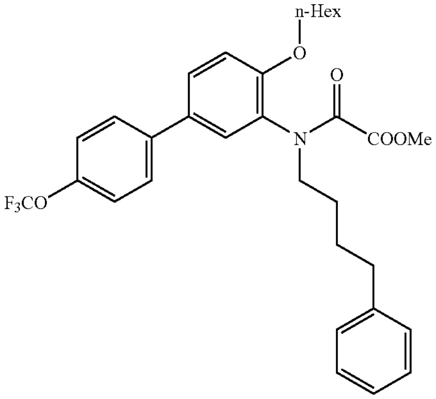 |
TABLE 4-39
| | |
|---|---|
| 246 (1) | 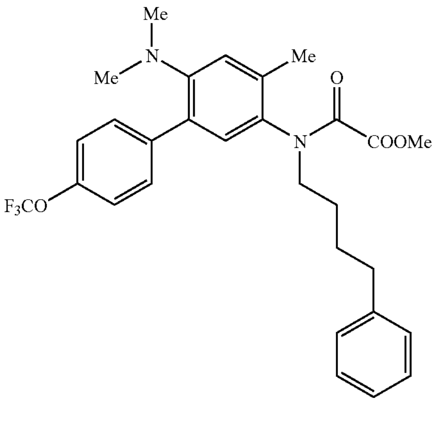 [SMILES: COC(=O)C(=O)N(CCCCc1ccccc1)c1cc(-c2ccc(OC(F)(F)F)cc2)c(N(C)C)cc1C] |
TABLE 4-39-continued
| | |
|---|---|
| 247 (1) | 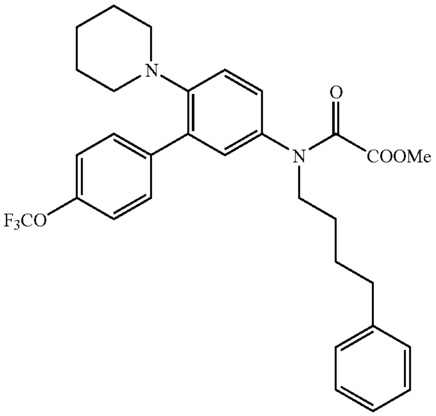 |
| 248 (1) | 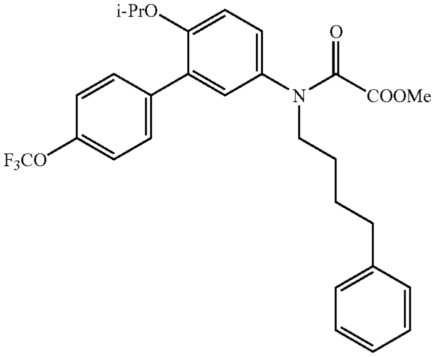 |
| 249 (1) | 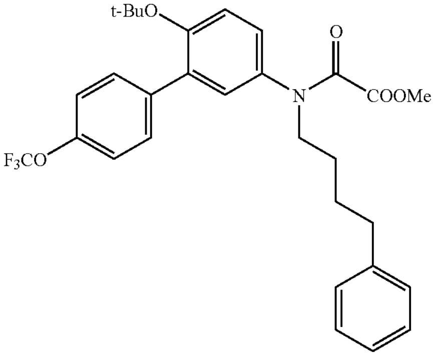 [SMILES: COC(=O)C(=O)N(CCCCc1ccccc1)c1ccc(OC(C)(C)C)c(-c2ccc(OC(F)(F)F)cc2)c1] |
| 250 (1) | 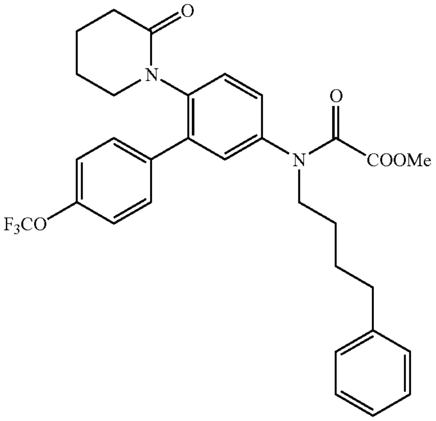 [SMILES: COC(=O)C(=O)N(CCCCc1ccccc1)c1ccc(N2CCCCC2=O)c(-c2ccc(OC(F)(F)F)cc2)c1] |

TABLE 4-39-continued
251 (1)
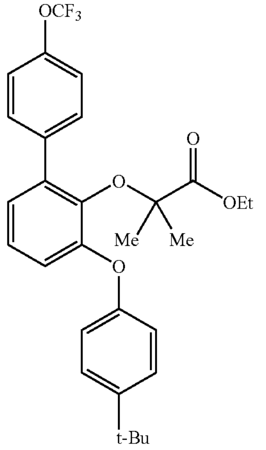 [SMILES: CCOC(=O)C(C)(C)Oc1c(Oc2ccc(C(C)(C)C)cc2)cccc1-c1ccc(OC(F)(F)F)cc1]
252 (1)
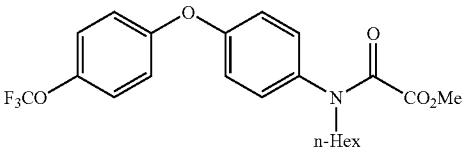
253 (1)
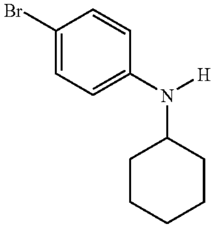 [SMILES: Brc1ccc(NC2CCCCC2)cc1]
253 (2)
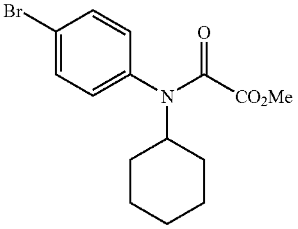 [SMILES: COC(=O)C(=O)N(c1ccc(Br)cc1)C1CCCCC1]
253 (3)
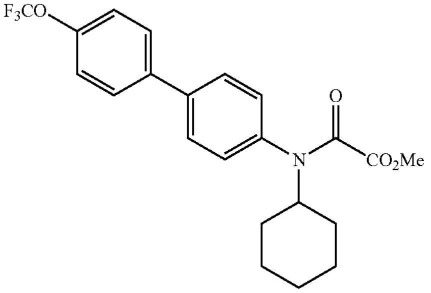 [SMILES: COC(=O)C(=O)N(c1ccc(-c2ccc(OC(F)(F)F)cc2)cc1)C1CCCCC1]
TABLE 4-40
254(1)
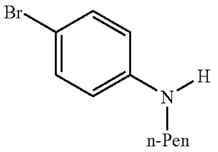
TABLE 4-40-continued
254(2)
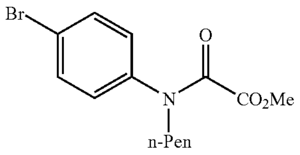
254(3)
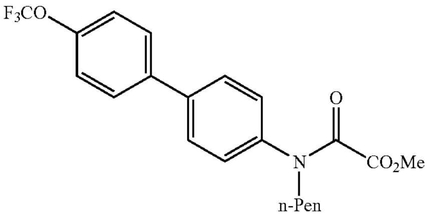
255(1)
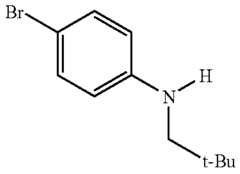 [SMILES: CC(C)(C)CNc1ccc(Br)cc1]
255(2)
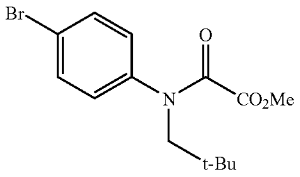 [SMILES: COC(=O)C(=O)N(CC(C)(C)C)c1ccc(Br)cc1]
255(3)
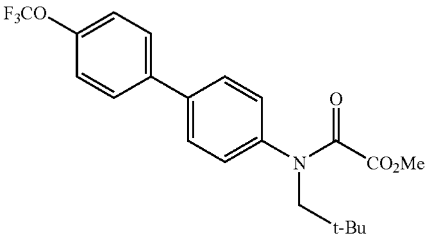 [SMILES: COC(=O)C(=O)N(CC(C)(C)C)c1ccc(-c2ccc(OC(F)(F)F)cc2)cc1]
301(1)
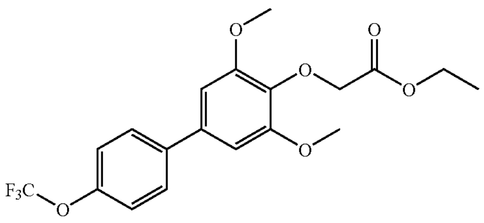 [SMILES: CCOC(=O)COc1c(OC)cc(-c2ccc(OC(F)(F)F)cc2)cc1OC]
301(2)
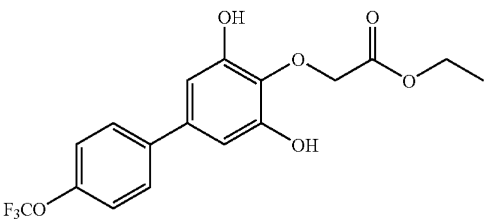 [SMILES: CCOC(=O)COc1c(O)cc(-c2ccc(OC(F)(F)F)cc2)cc1O]

TABLE 4-40-continued
| | |
|---|---|
| 301(3) | 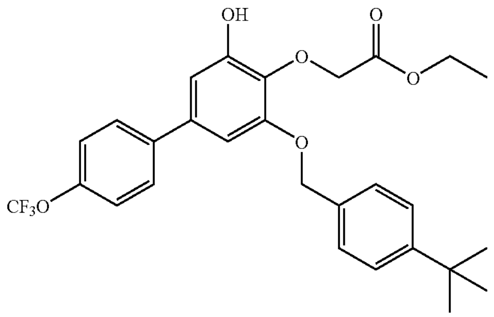 |
| 301(4) | 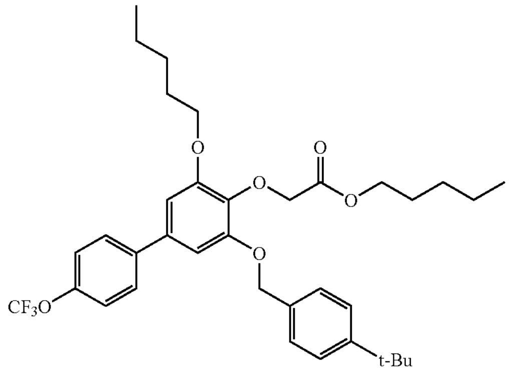 |
| 302(1) | 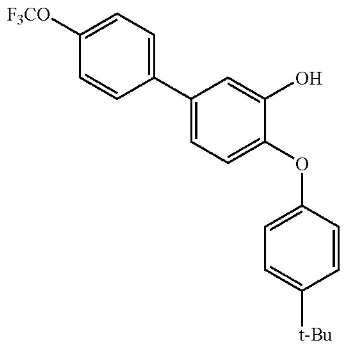 [SMILES: CC(C)(C)c1ccc(Oc2ccc(-c3ccc(OC(F)(F)F)cc3)cc2O)cc1] |
| 302(2) | 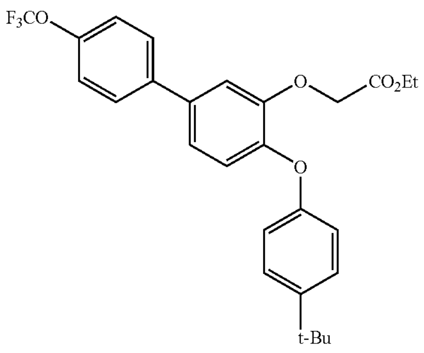 [SMILES: CCOC(=O)COc1cc(-c2ccc(OC(F)(F)F)cc2)ccc1Oc1ccc(C(C)(C)C)cc1] |
TABLE 4-41
| | |
|---|---|
| 303(1) | 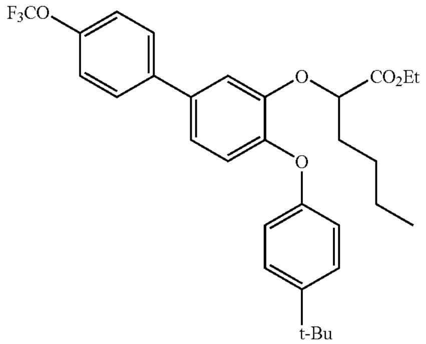 [SMILES: CCCCC(Oc1cc(-c2ccc(OC(F)(F)F)cc2)ccc1Oc1ccc(C(C)(C)C)cc1)C(=O)OCC] |
| 304(1) | 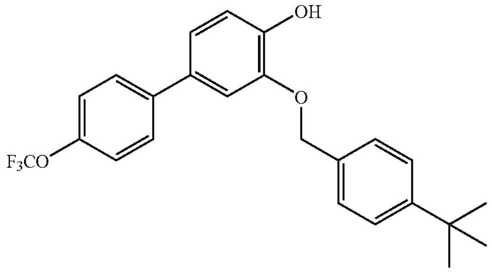 [SMILES: CC(C)(C)c1ccc(COc2cc(-c3ccc(OC(F)(F)F)cc3)ccc2O)cc1] |
| 304(2) | 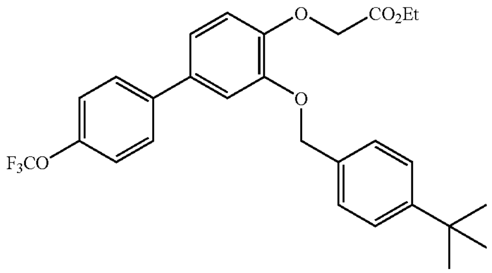 [SMILES: CCOC(=O)COc1ccc(-c2ccc(OC(F)(F)F)cc2)cc1OCc1ccc(C(C)(C)C)cc1] |
| 305(1) | 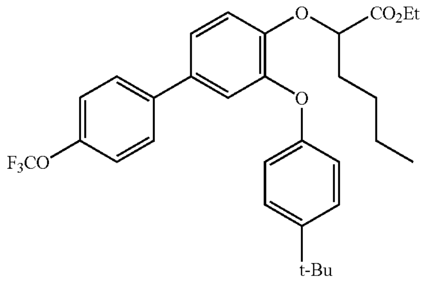 [SMILES: CCCCC(Oc1ccc(-c2ccc(OC(F)(F)F)cc2)cc1Oc1ccc(C(C)(C)C)cc1)C(=O)OCC] |
| 306(1) | 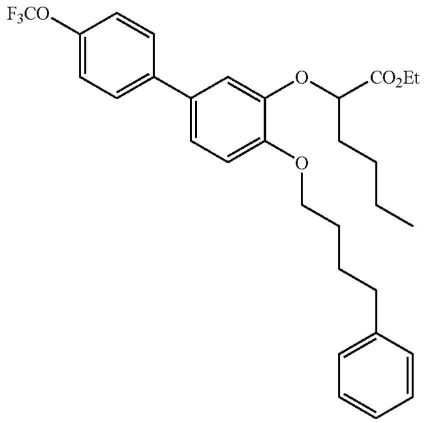 [SMILES: CCCCC(Oc1cc(-c2ccc(OC(F)(F)F)cc2)ccc1OCCCCc1ccccc1)C(=O)OCC] |

TABLE 4-41-continued
307(1)
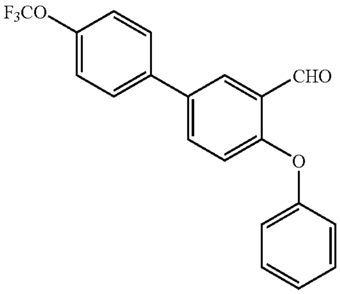
307(2)
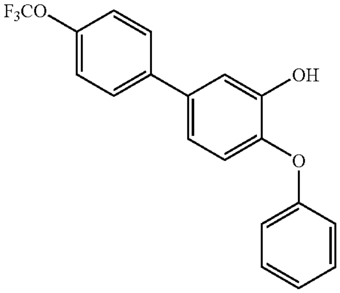 [SMILES: Oc1cc(-c2ccc(OC(F)(F)F)cc2)ccc1Oc1ccccc1]
307(3)
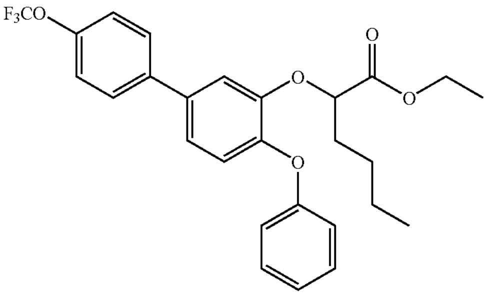 [SMILES: CCCCC(Oc1cc(-c2ccc(OC(F)(F)F)cc2)ccc1Oc1ccccc1)C(=O)OCC]
308(1)
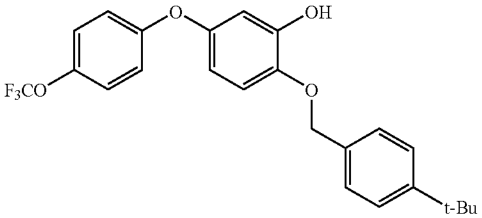
308(2)
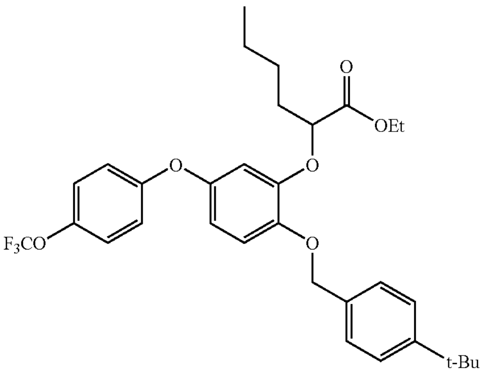
TABLE 4-42
309(1)
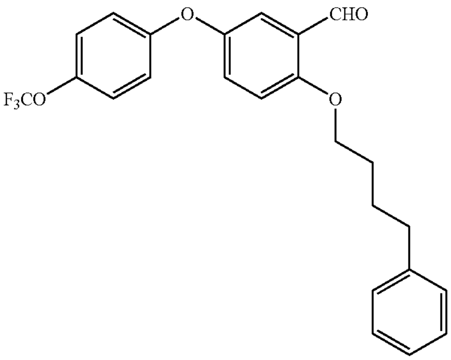
309(2)
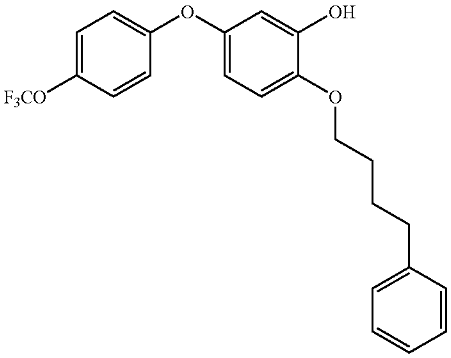 [SMILES: Oc1cc(Oc2ccc(OC(F)(F)F)cc2)ccc1OCCCCc1ccccc1]
309(3)
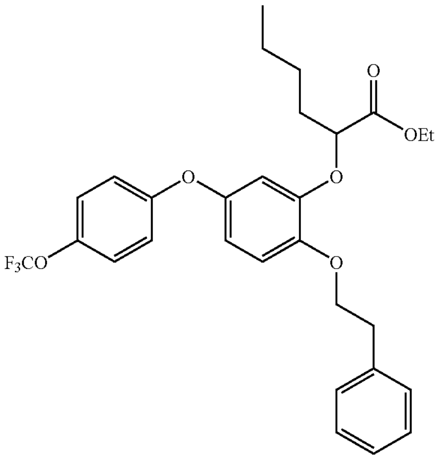 [SMILES: CCCCC(Oc1cc(Oc2ccc(OC(F)(F)F)cc2)ccc1OCCc1ccccc1)C(=O)OCC]
310(1)
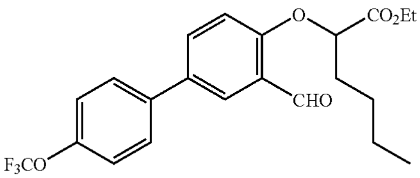
310(2)
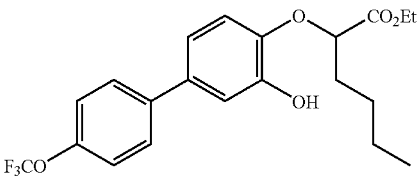 [SMILES: CCCCC(Oc1ccc(-c2ccc(OC(F)(F)F)cc2)cc1O)C(=O)OCC]

TABLE 4-42-continued
| | |
|---|---|
| 310(3) | 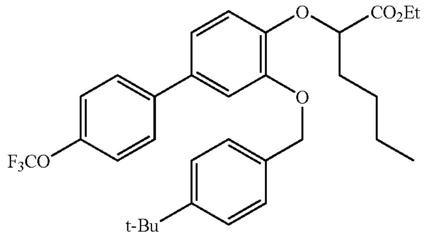 [SMILES: CCCCC(Oc1ccc(-c2ccc(OC(F)(F)F)cc2)cc1OCc1ccc(C(C)(C)C)cc1)C(=O)OCC] |
| 311(1) | 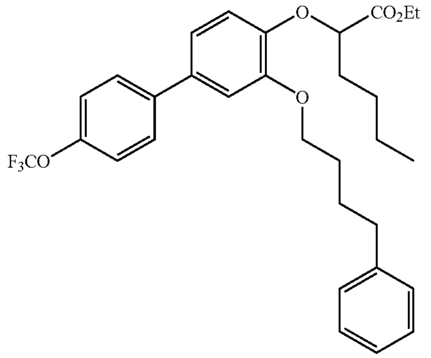 [SMILES: CCCCC(Oc1ccc(-c2ccc(OC(F)(F)F)cc2)cc1OCCCCc1ccccc1)C(=O)OCC] |
| 312(1) | 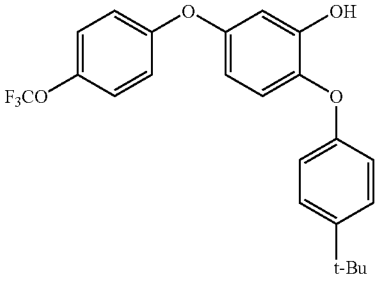 [SMILES: CC(C)(C)c1ccc(Oc2ccc(Oc3ccc(OC(F)(F)F)cc3)cc2O)cc1] |
TABLE 4-43
| | |
|---|---|
| 312(2) | 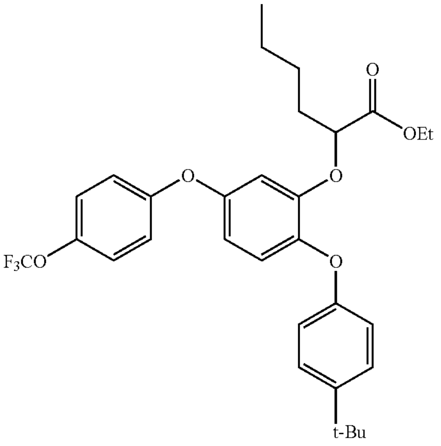 [SMILES: CCCCC(Oc1cc(Oc2ccc(OC(F)(F)F)cc2)ccc1Oc1ccc(C(C)(C)C)cc1)C(=O)OCC] |
TABLE 4-43-continued
| | |
|---|---|
| 313(1) | 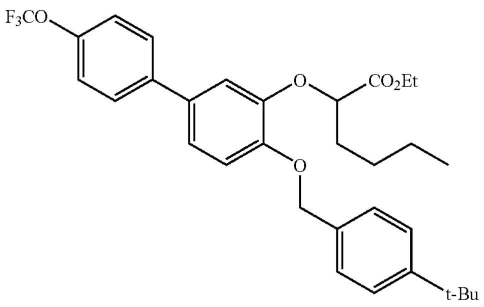 [SMILES: CCCCC(Oc1cc(-c2ccc(OC(F)(F)F)cc2)ccc1OCc1ccc(C(C)(C)C)cc1)C(=O)OCC] |
| 314(1) | 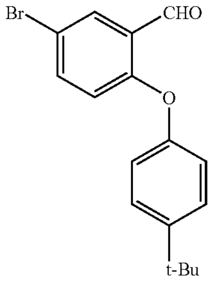 [SMILES: CC(C)(C)c1ccc(Oc2ccc(Br)cc2C=O)cc1] |
| 314(2) | 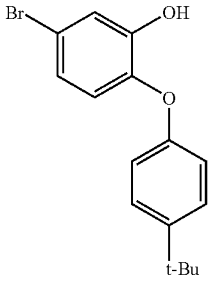 [SMILES: CC(C)(C)c1ccc(Oc2ccc(Br)cc2O)cc1] |
| 314(3) | 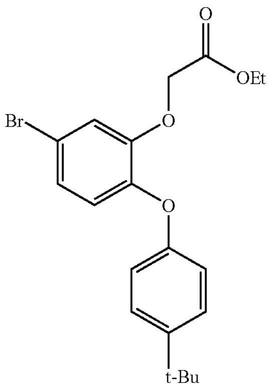 [SMILES: CCOC(=O)COc1cc(Br)ccc1Oc1ccc(C(C)(C)C)cc1] |

TABLE 4-43-continued
314(4)
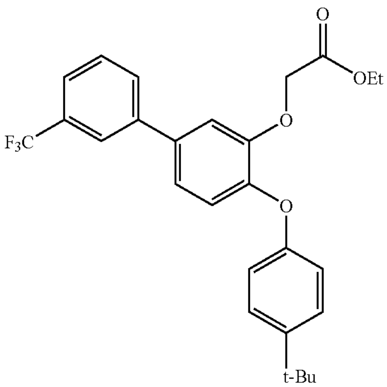 [SMILES: CCOC(=O)COc1cc(-c2cccc(C(F)(F)F)c2)ccc1Oc1ccc(C(C)(C)C)cc1]
315(1)
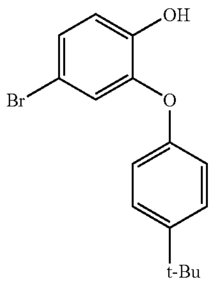 [SMILES: CC(C)(C)c1ccc(Oc2cc(Br)ccc2O)cc1]
315(2)
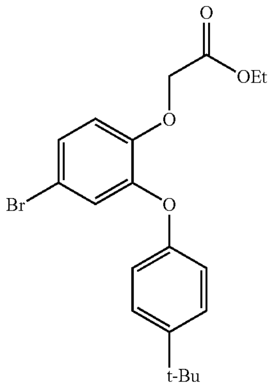 [SMILES: CCOC(=O)COc1ccc(Br)cc1Oc1ccc(C(C)(C)C)cc1]
TABLE 4-44
315(3)
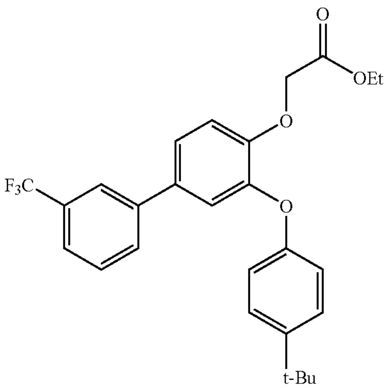 [SMILES: CCOC(=O)COc1ccc(-c2cccc(C(F)(F)F)c2)cc1Oc1ccc(C(C)(C)C)cc1]
TABLE 4-44-continued
316(1)
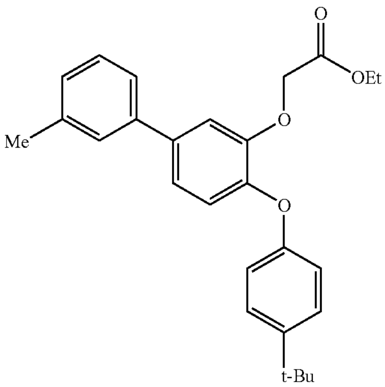 [SMILES: CCOC(=O)COc1cc(-c2cccc(C)c2)ccc1Oc1ccc(C(C)(C)C)cc1]
317(1)
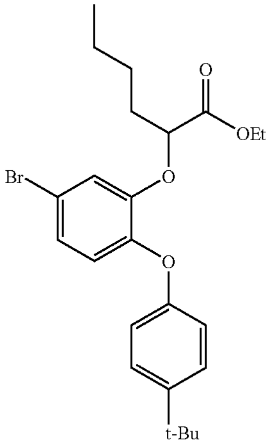 [SMILES: CCCCC(Oc1cc(Br)ccc1Oc1ccc(C(C)(C)C)cc1)C(=O)OCC]
317(2)
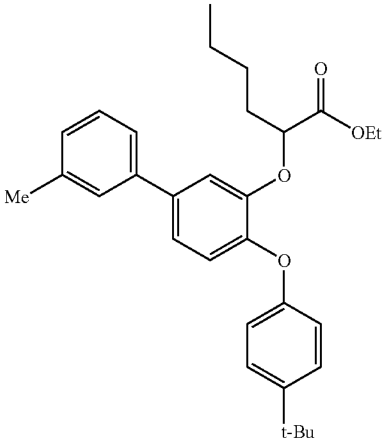 [SMILES: CCCCC(Oc1cc(-c2cccc(C)c2)ccc1Oc1ccc(C(C)(C)C)cc1)C(=O)OCC]

TABLE 4-44-continued
318(1)
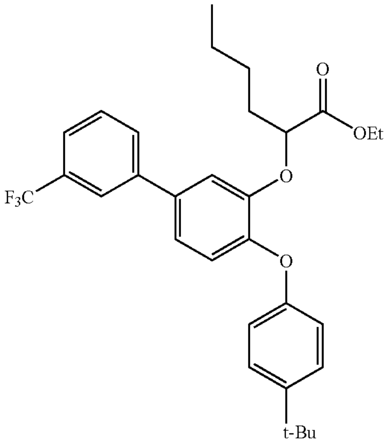 [SMILES: CCCCC(Oc1cc(-c2cccc(C(F)(F)F)c2)ccc1Oc1ccc(C(C)(C)C)cc1)C(=O)OCC]
319(1)
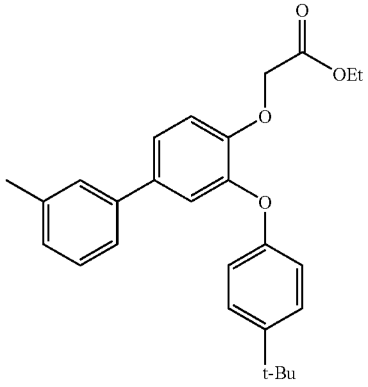 [SMILES: CCOC(=O)COc1ccc(-c2cccc(C)c2)cc1Oc1ccc(C(C)(C)C)cc1]
TABLE 4-45
320(1)
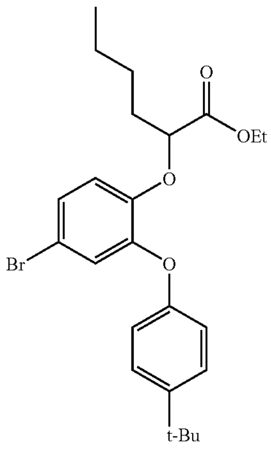 [SMILES: CCCCC(Oc1ccc(Br)cc1Oc1ccc(C(C)(C)C)cc1)C(=O)OCC]
TABLE 4-45-continued
320(2)
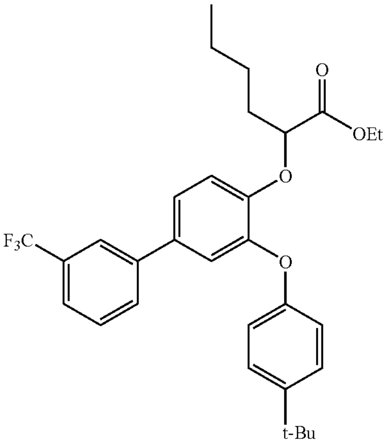 [SMILES: CCCCC(Oc1ccc(-c2cccc(C(F)(F)F)c2)cc1Oc1ccc(C(C)(C)C)cc1)C(=O)OCC]
321(1)
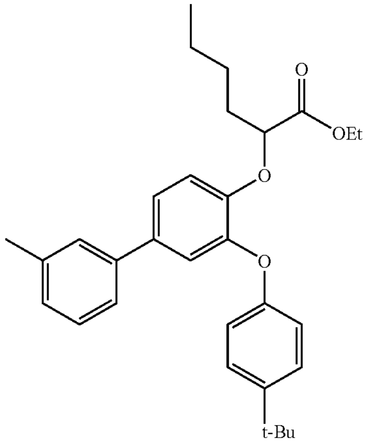 [SMILES: CCCCC(Oc1ccc(-c2cccc(C)c2)cc1Oc1ccc(C(C)(C)C)cc1)C(=O)OCC]
322(1)
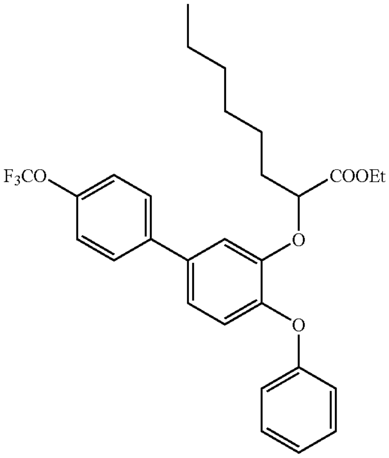 [SMILES: CCCCCCC(Oc1cc(-c2ccc(OC(F)(F)F)cc2)ccc1Oc1ccccc1)C(=O)OCC]

TABLE 4-45-continued
323(1)
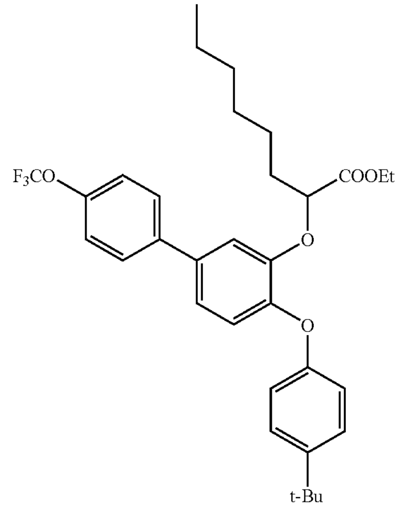 [SMILES: CCCCCCC(Oc1cc(-c2ccc(OC(F)(F)F)cc2)ccc1Oc1ccc(C(C)(C)C)cc1)C(=O)OCC]
324(1)
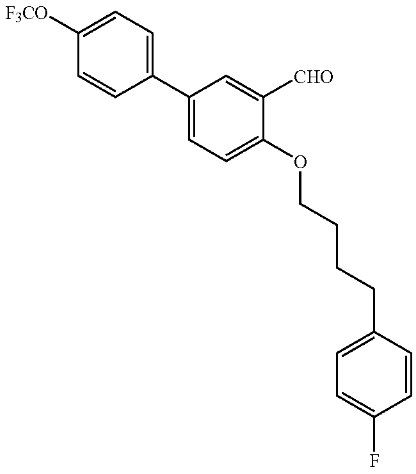
TABLE 4-46
324(2)
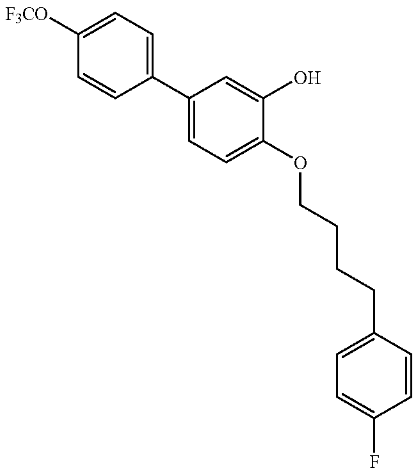 [SMILES: Oc1cc(-c2ccc(OC(F)(F)F)cc2)ccc1OCCCCc1ccc(F)cc1]
TABLE 4-46-continued
324(3)
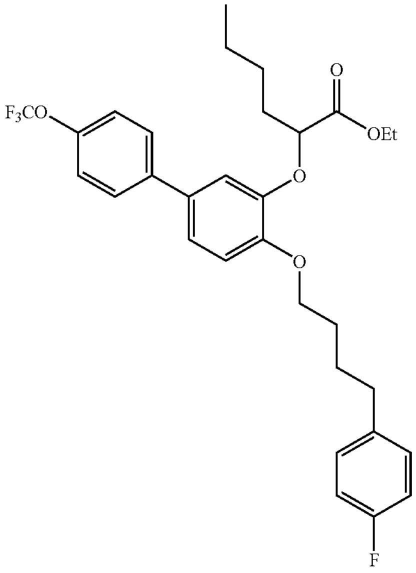 [SMILES: CCCCC(Oc1cc(-c2ccc(OC(F)(F)F)cc2)ccc1OCCCCc1ccc(F)cc1)C(=O)OCC]
325(1)
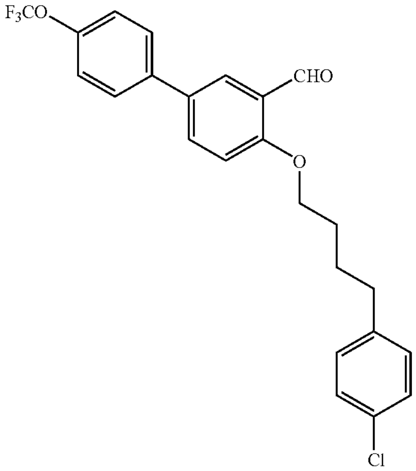 [SMILES: O=Cc1cc(-c2ccc(OC(F)(F)F)cc2)ccc1OCCCCc1ccc(Cl)cc1]
325(2)
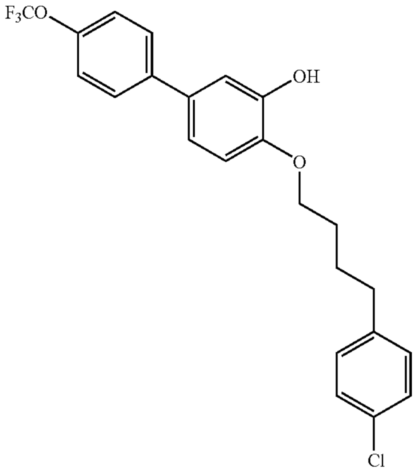 [SMILES: Oc1cc(-c2ccc(OC(F)(F)F)cc2)ccc1OCCCCc1ccc(Cl)cc1]

TABLE 4-46-continued
325(3)
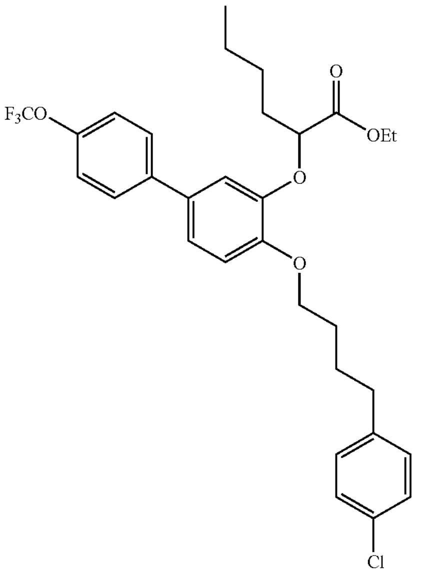
326(1)
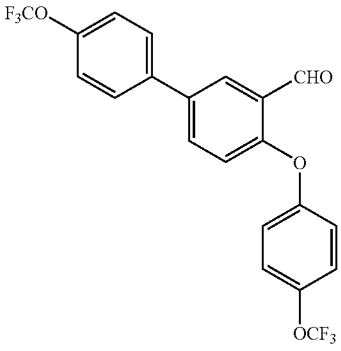
TABLE 4-47
326(2)
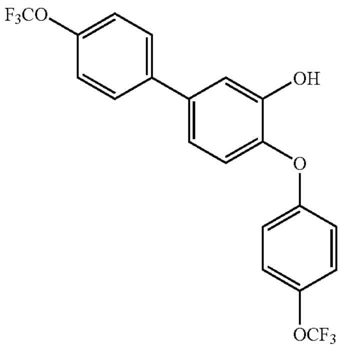 [SMILES: Oc1cc(-c2ccc(OC(F)(F)F)cc2)ccc1Oc1ccc(OC(F)(F)F)cc1]
TABLE 4-47-continued
326(3)
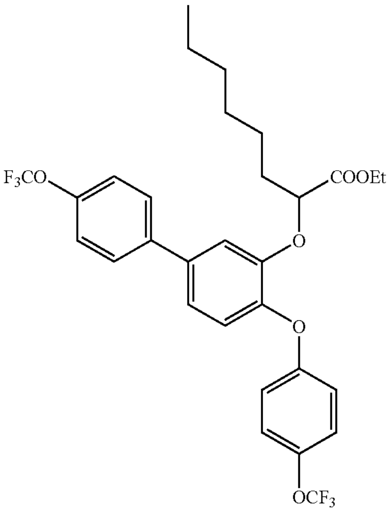
327(1)
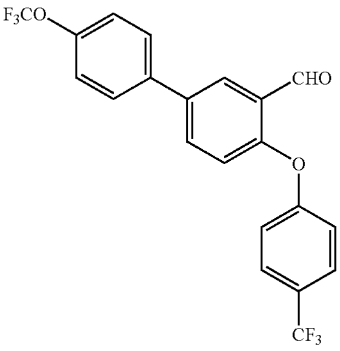 [SMILES: O=Cc1cc(-c2ccc(OC(F)(F)F)cc2)ccc1Oc1ccc(C(F)(F)F)cc1]
327(2)
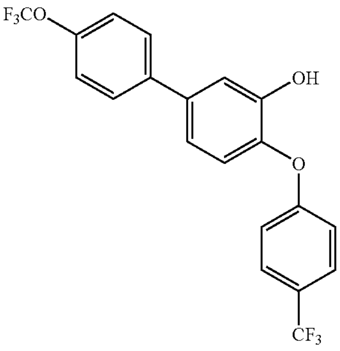

TABLE 4-47-continued
327(3)
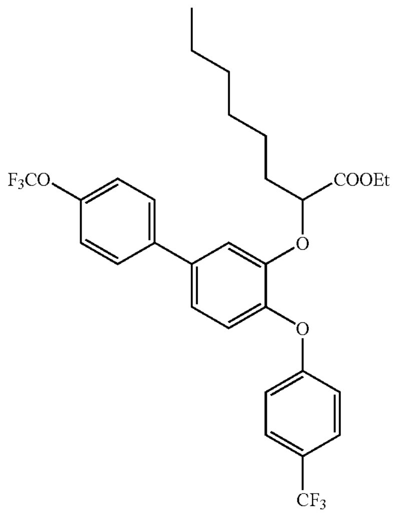 [SMILES: CCCCCCC(Oc1cc(-c2ccc(OC(F)(F)F)cc2)ccc1Oc1ccc(C(F)(F)F)cc1)C(=O)OCC]
328(1)
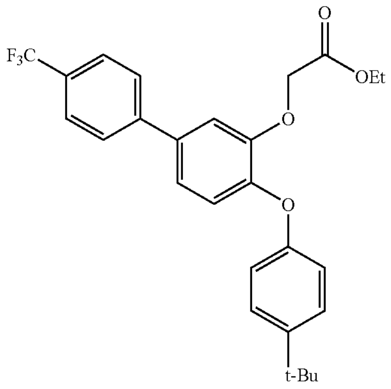 [SMILES: CCOC(=O)COc1cc(-c2ccc(C(F)(F)F)cc2)ccc1Oc1ccc(C(C)(C)C)cc1]
TABLE 4-48
329(1)
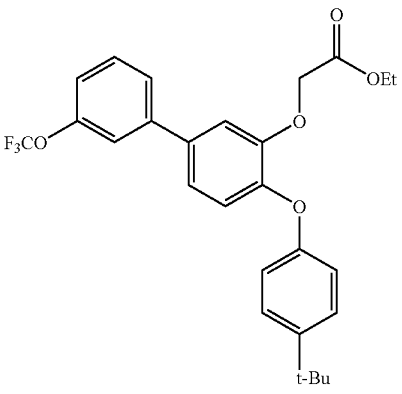 [SMILES: CCOC(=O)COc1cc(-c2cccc(OC(F)(F)F)c2)ccc1Oc1ccc(C(C)(C)C)cc1]
TABLE 4-48-continued
330(1)
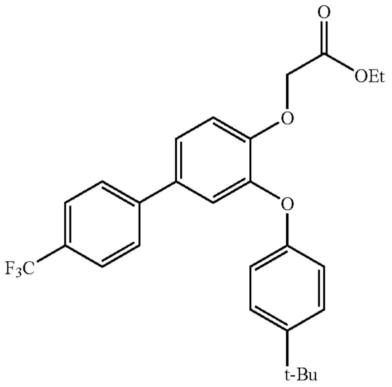 [SMILES: CCOC(=O)COc1ccc(-c2ccc(C(F)(F)F)cc2)cc1Oc1ccc(C(C)(C)C)cc1]
331(1)
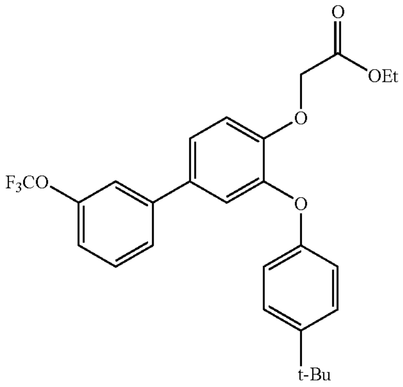 [SMILES: CCOC(=O)COc1ccc(-c2cccc(OC(F)(F)F)c2)cc1Oc1ccc(C(C)(C)C)cc1]
332(1)
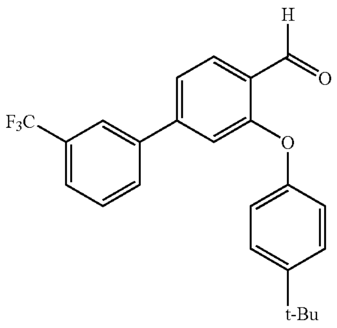 [SMILES: CC(C)(C)c1ccc(Oc2cc(-c3cccc(C(F)(F)F)c3)ccc2C=O)cc1]
332(2)
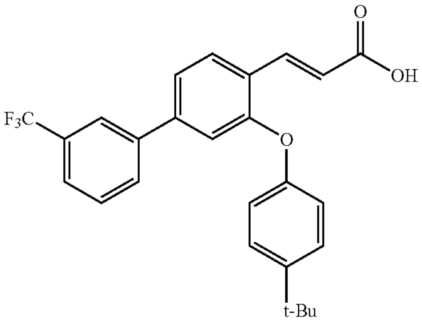 [SMILES: CC(C)(C)c1ccc(Oc2cc(-c3cccc(C(F)(F)F)c3)ccc2/C=C/C(=O)O)cc1]
333(1)
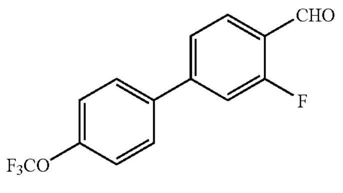 [SMILES: O=Cc1ccc(-c2ccc(OC(F)(F)F)cc2)cc1F]

TABLE 4-48-continued
| | |
|---|---|
| 333(2) | 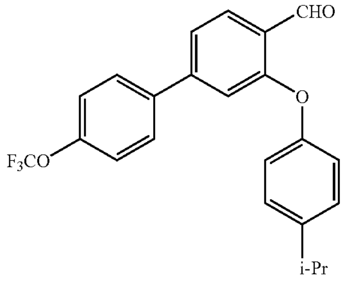 [SMILES: CC(C)c1ccc(Oc2cc(-c3ccc(OC(F)(F)F)cc3)ccc2C=O)cc1] |
| 333(3) | 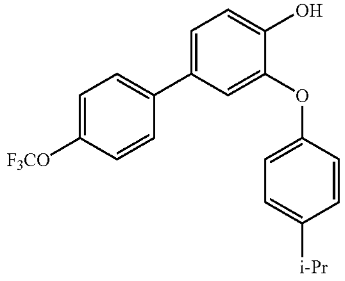 [SMILES: CC(C)c1ccc(Oc2cc(-c3ccc(OC(F)(F)F)cc3)ccc2O)cc1] |
TABLE 4-49
| | |
|---|---|
| 333(4) | 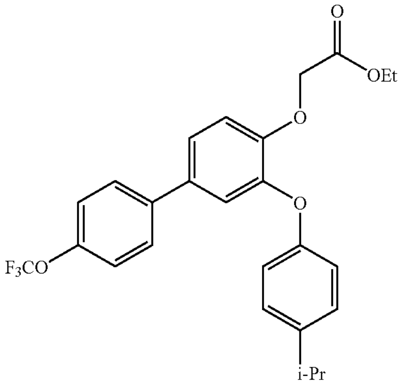 [SMILES: CCOC(=O)COc1ccc(-c2ccc(OC(F)(F)F)cc2)cc1Oc1ccc(C(C)C)cc1] |
| 334(1) | 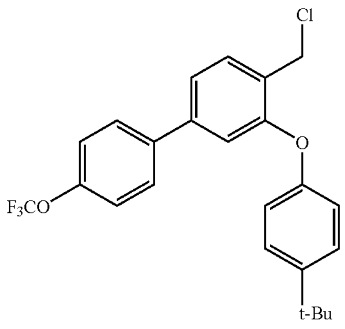 [SMILES: CC(C)(C)c1ccc(Oc2cc(-c3ccc(OC(F)(F)F)cc3)ccc2CCl)cc1] |
TABLE 4-49-continued
| | |
|---|---|
| 334(2) | 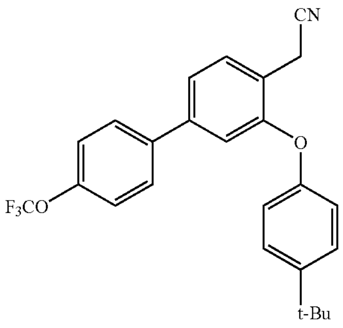 |
| 335(1) | 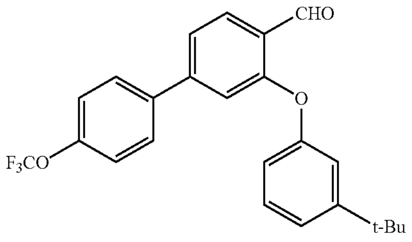 [SMILES: CC(C)(C)c1cccc(Oc2cc(-c3ccc(OC(F)(F)F)cc3)ccc2C=O)c1] |
| 337(1) | 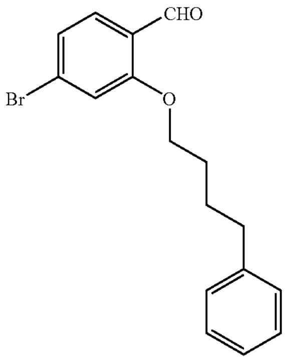 [SMILES: O=Cc1ccc(Br)cc1OCCCCc1ccccc1] |
| 337(2) | 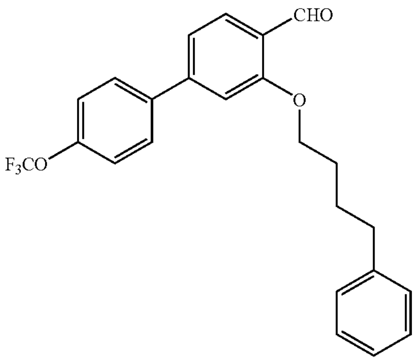 |

TABLE 4-49-continued
337(3)
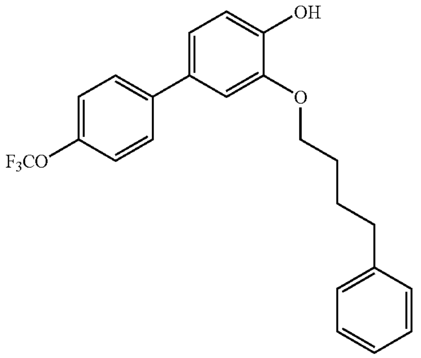 [SMILES: O=Cc1ccc(-c2ccc(OC(F)(F)F)cc2)cc1OCCCCc1ccccc1]
337(4)
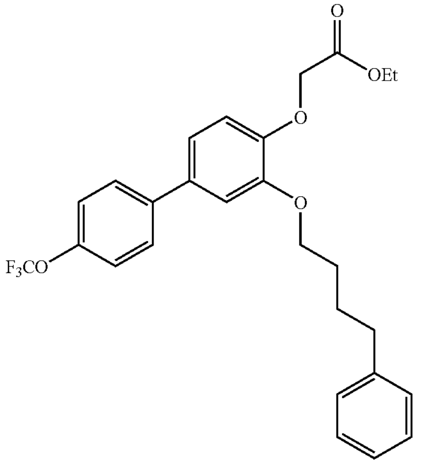 [SMILES: CCOC(=O)COc1ccc(-c2ccc(OC(F)(F)F)cc2)cc1OCCCCc1ccccc1]
TABLE 4-50
351(1)
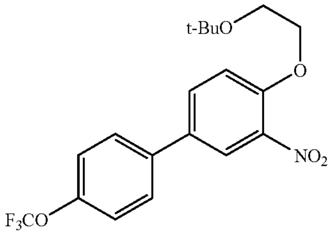
351(2)
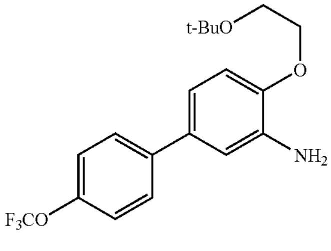 [SMILES: CC(C)(C)OCCOc1ccc(-c2ccc(OC(F)(F)F)cc2)cc1N]
TABLE 4-50-continued
351(3)
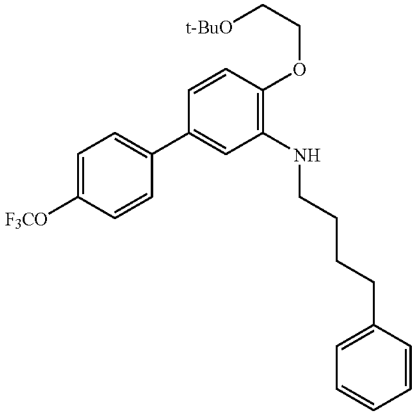 [SMILES: CC(C)(C)OCCOc1ccc(-c2ccc(OC(F)(F)F)cc2)cc1NCCCCc1ccccc1]
351(4)
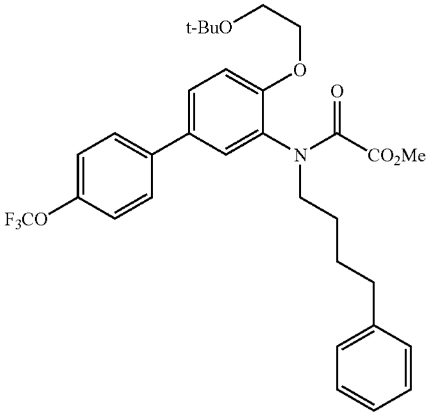 [SMILES: COC(=O)C(=O)N(CCCCc1ccccc1)c1cc(-c2ccc(OC(F)(F)F)cc2)ccc1OCCOC(C)(C)C]
352(1)
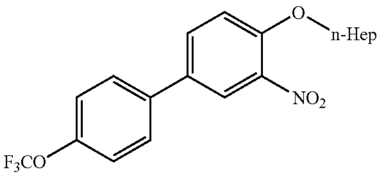
352(2)
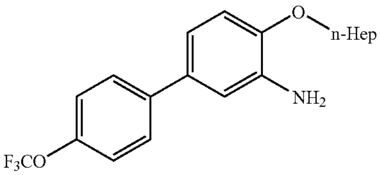
352(3)
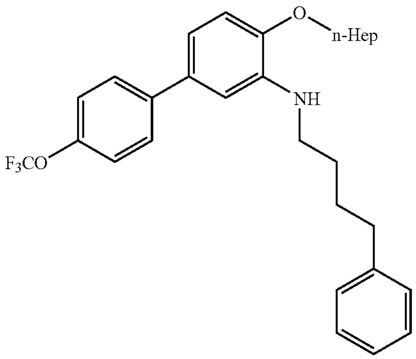

TABLE 4-50-continued
352(4)
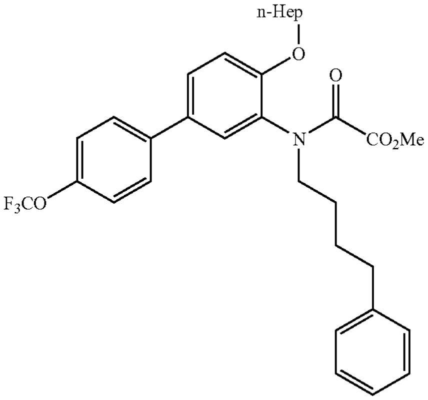
353(1)
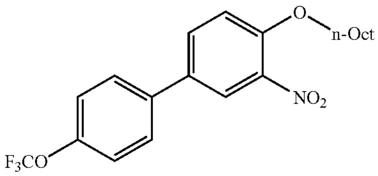
353(2)
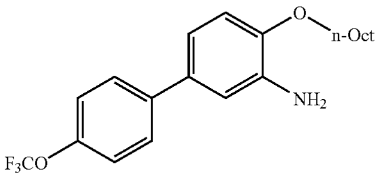
TABLE 4-51
353(3)
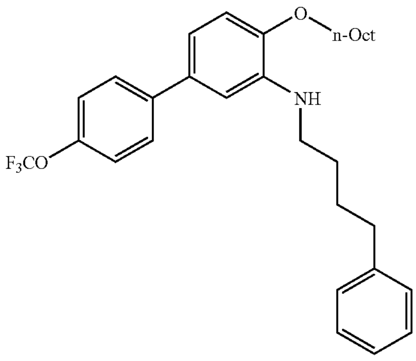
353(4)
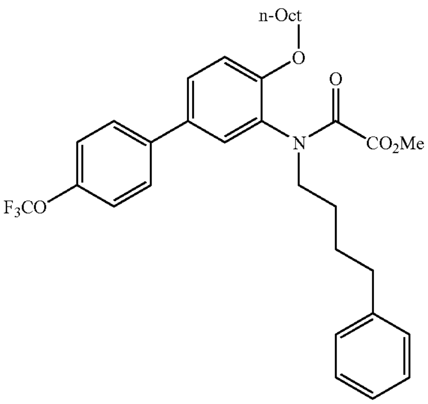
TABLE 4-51-continued
354(1)
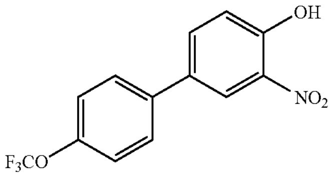 [SMILES: O=[N+]([O-])c1cc(-c2ccc(OC(F)(F)F)cc2)ccc1O]
354(2)
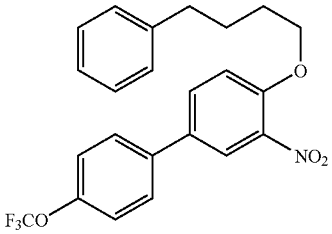 [SMILES: O=[N+]([O-])c1cc(-c2ccc(OC(F)(F)F)cc2)ccc1OCCCCc1ccccc1]
354(3)
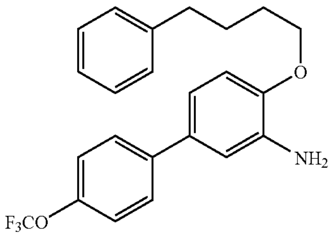
354(4)
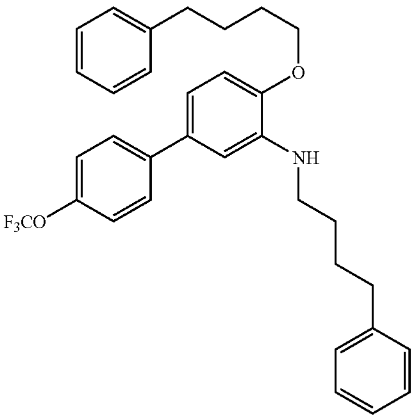 [SMILES: FC(F)(F)Oc1ccc(-c2ccc(OCCCCc3ccccc3)c(NCCCCc3ccccc3)c2)cc1]
354(5)
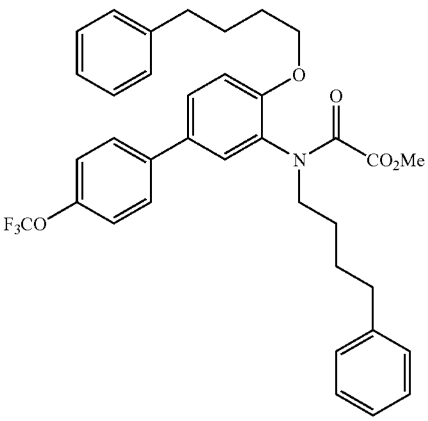 [SMILES: COC(=O)C(=O)N(CCCCc1ccccc1)c1cc(-c2ccc(OC(F)(F)F)cc2)ccc1OCCCCc1ccccc1]

TABLE 4-51-continued
355(1)
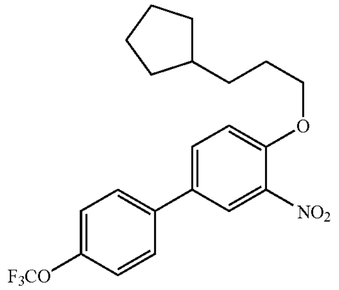 [SMILES: Nc1cc(-c2ccc(OC(F)(F)F)cc2)ccc1OCCCC1CCCC1]
TABLE 4-52
355(2)
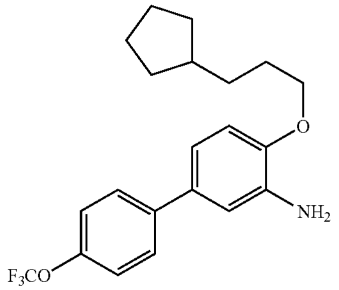
355(3)
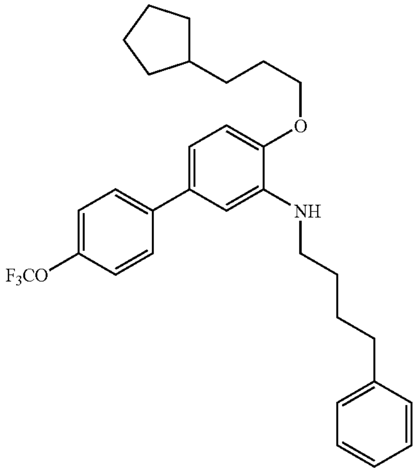 [SMILES: FC(F)(F)Oc1ccc(-c2ccc(OCCCC3CCCC3)c(NCCCCc3ccccc3)c2)cc1]
355(4)
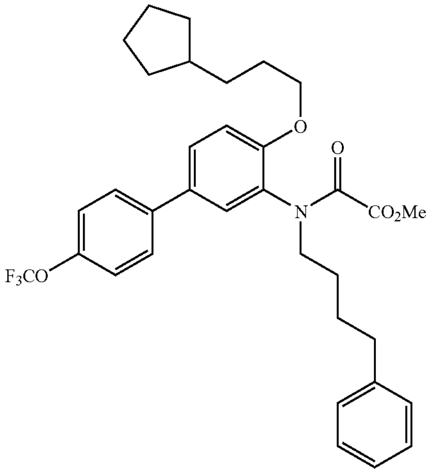 [SMILES: COC(=O)C(=O)N(CCCCc1ccccc1)c1cc(-c2ccc(OC(F)(F)F)cc2)ccc1OCCCC1CCCC1]
TABLE 4-52-continued
356(1)
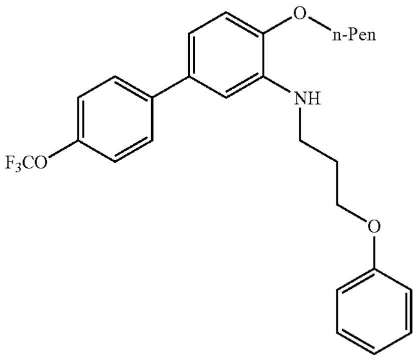
356(2)
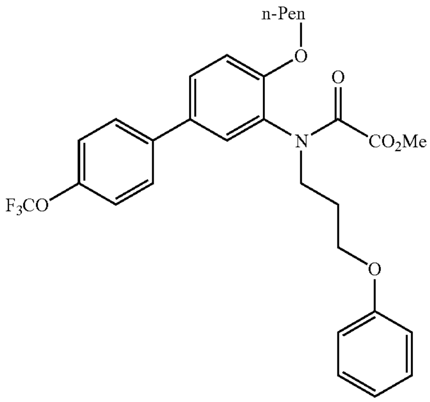
357(1)
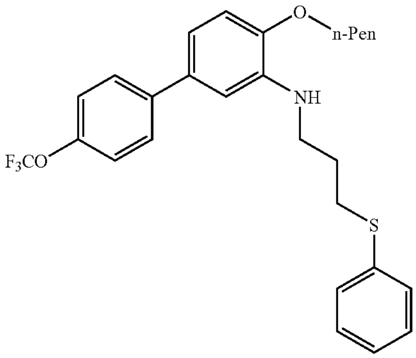
357(2)
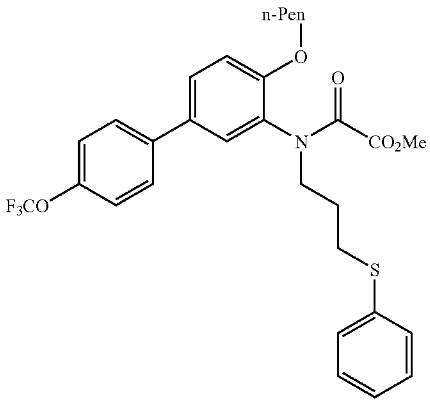

TABLE 4-52-continued
| | |
|---|---|
| 358(1) | 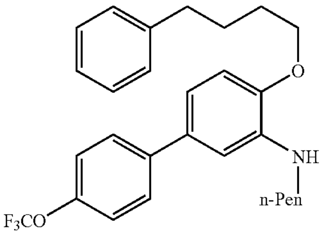 |
TABLE 4-53
| | |
|---|---|
| 358(2) | 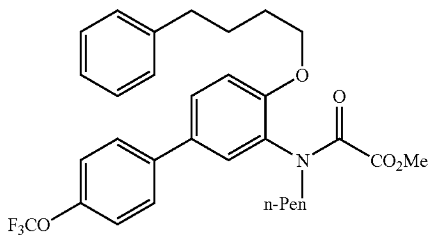 |
| 359(1) | 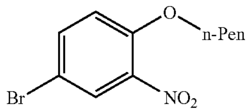 |
| 359(2) | 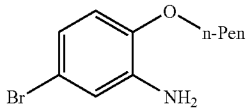 |
| 359(3) | 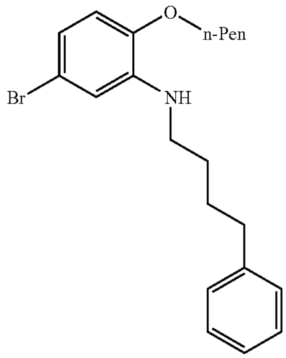 |
| 359(4) | 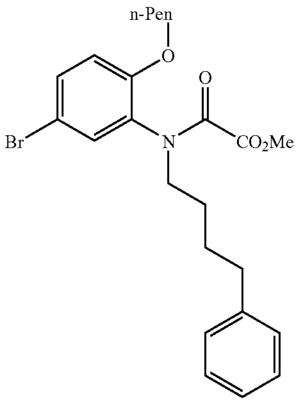 |
TABLE 4-53-continued
| | |
|---|---|
| 359(5) | 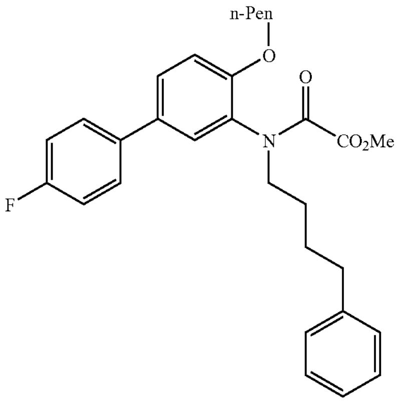 |
| 360(1) | 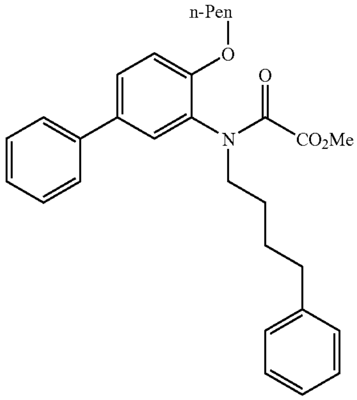 |
| 361(1) | 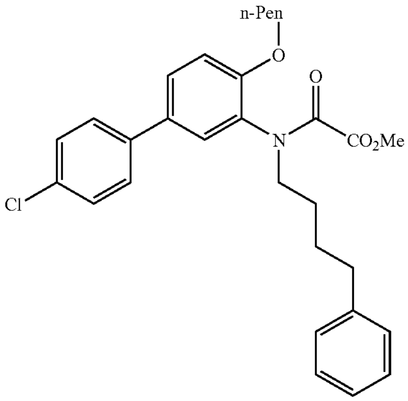 |
| 362(1) | 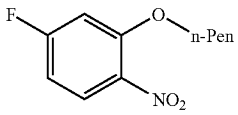 |
| 362(2) | 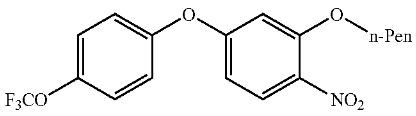 |

TABLE 4-54
362(3)
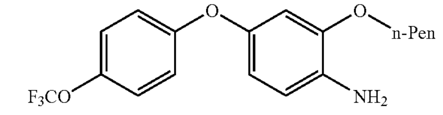
362(4)
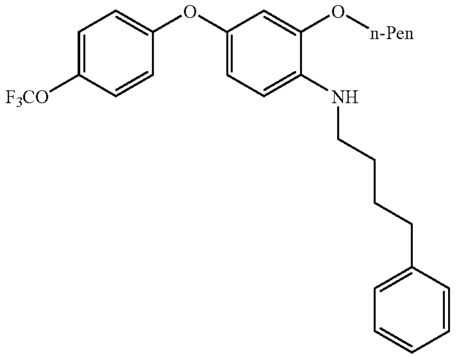
362(5)
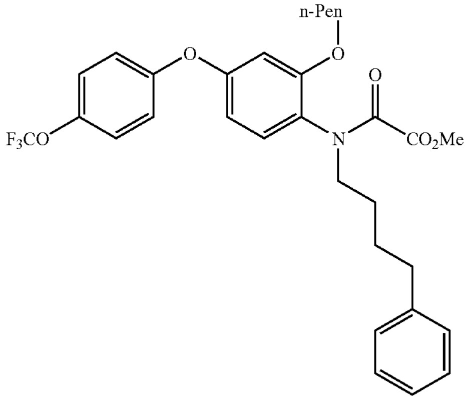
363(1)
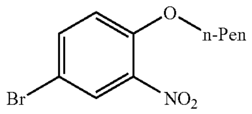
363(2)
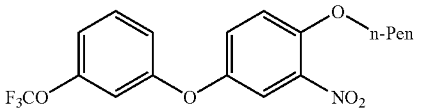
363(3)
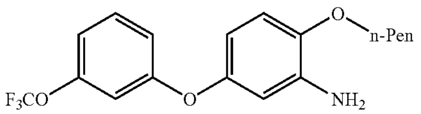
363(4)
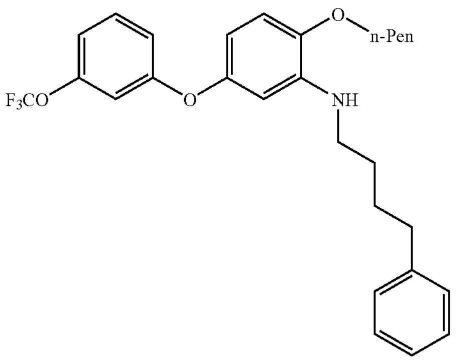
TABLE 4-54-continued
363(5)
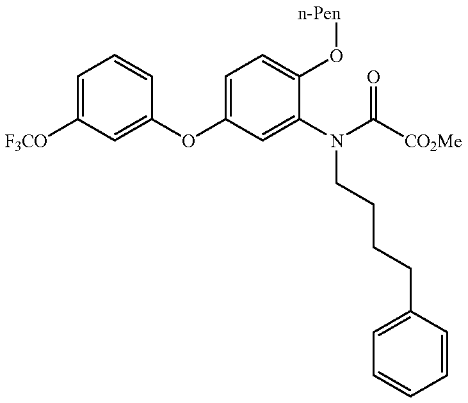
364(1)
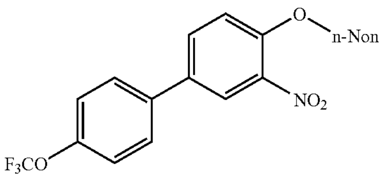
364(2)
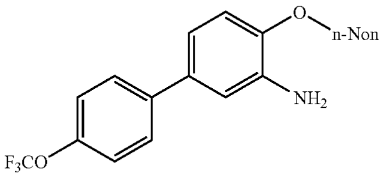
364(3)
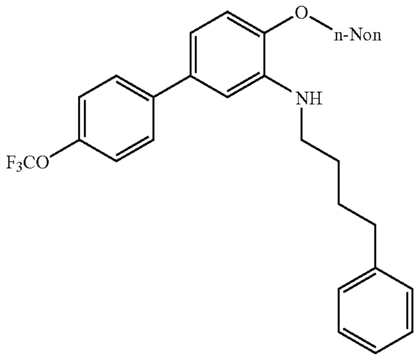
364(4)
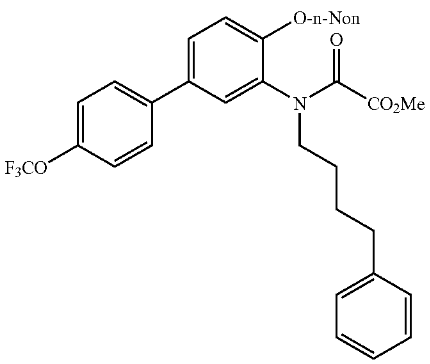

TABLE 4-55
| | |
|---|---|
| 365(1) | 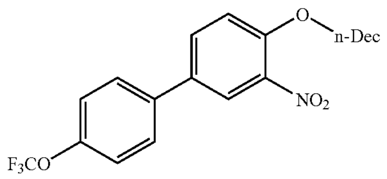 |
| 365(2) | 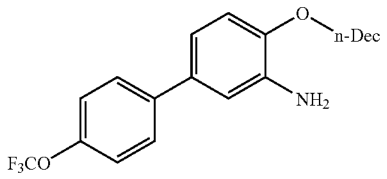 |
| 365(3) | 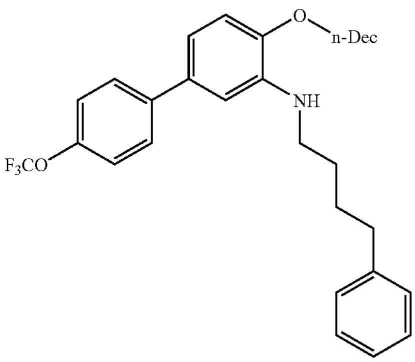 |
| 365(4) | 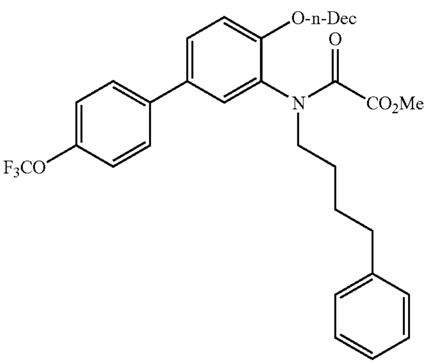 |
| 366(1) | 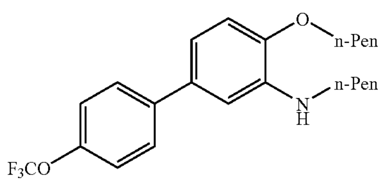 |
| 366(2) | 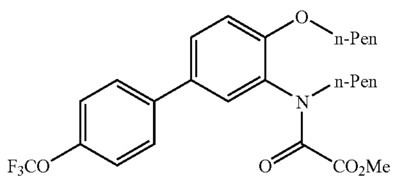 |
TABLE 4-55-continued
| | |
|---|---|
| 367(1) | 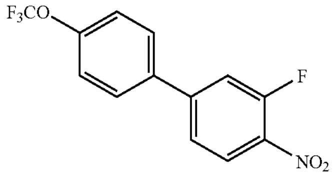 [SMILES: O=[N+]([O-])c1ccc(-c2ccc(OC(F)(F)F)cc2)cc1F] |
| 367(2) | 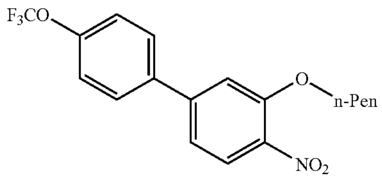 |
| 367(3) | 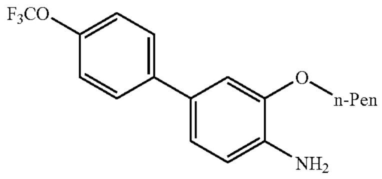 |
| 367(4) | 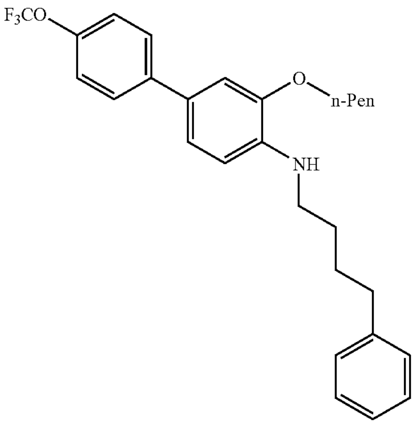 |
TABLE 4-56
| | |
|---|---|
| 367(5) | 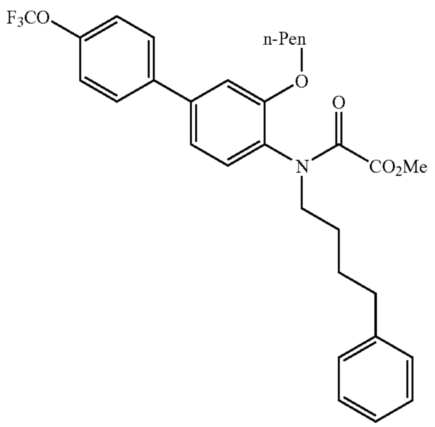 |

TABLE 4-56-continued
368(1)
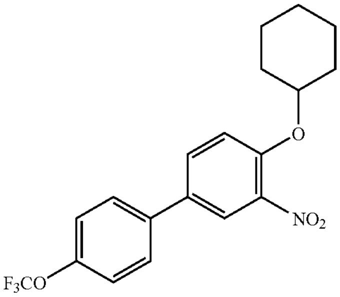
368(2)
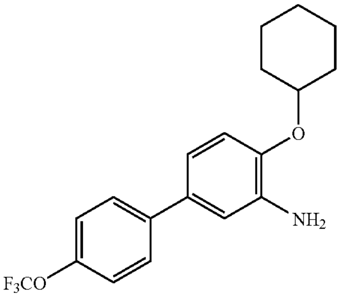 [SMILES: Nc1cc(-c2ccc(OC(F)(F)F)cc2)ccc1OC1CCCCC1]
368(3)
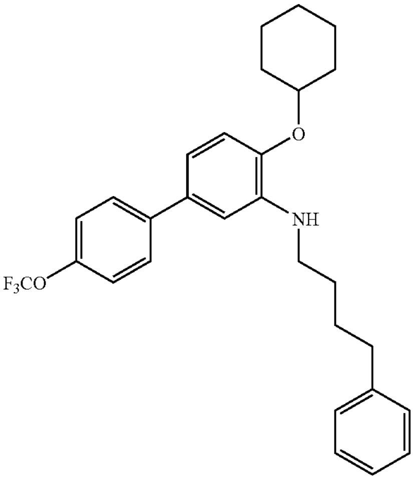 [SMILES: FC(F)(F)Oc1ccc(-c2ccc(OC3CCCCC3)c(NCCCCc3ccccc3)c2)cc1]
368(4)
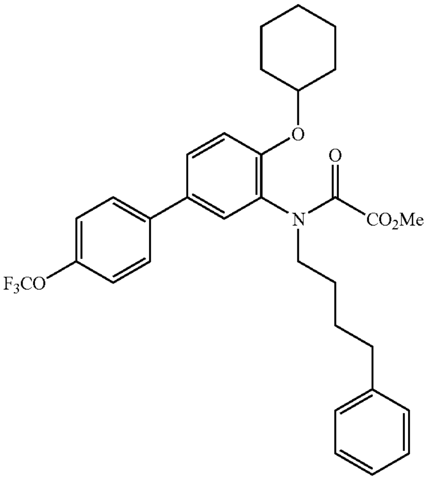 [SMILES: COC(=O)C(=O)N(CCCCc1ccccc1)c1cc(-c2ccc(OC(F)(F)F)cc2)ccc1OC1CCCCC1]
TABLE 4-56-continued
369(1)
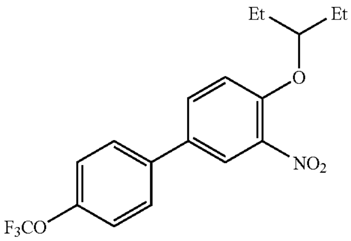 [SMILES: CCC(CC)Oc1ccc(-c2ccc(OC(F)(F)F)cc2)cc1[N+](=O)[O-]]
369(2)
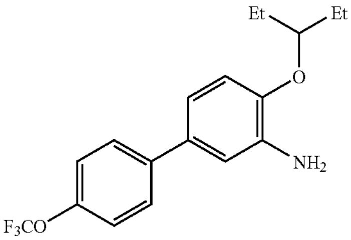
369(3)
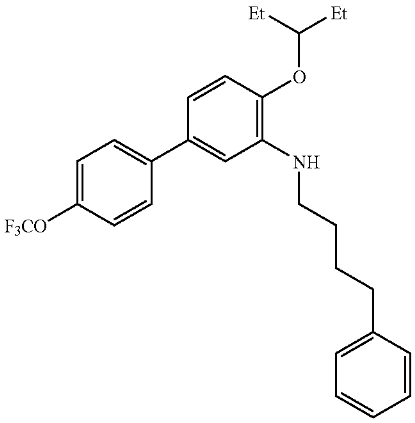 [SMILES: CCC(CC)Oc1ccc(-c2ccc(OC(F)(F)F)cc2)cc1NCCCCc1ccccc1]
TABLE 4-57
369(4)
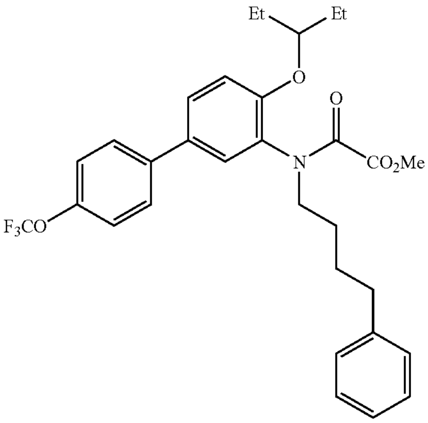 [SMILES: CCC(CC)Oc1ccc(-c2ccc(OC(F)(F)F)cc2)cc1N(CCCCc1ccccc1)C(=O)C(=O)OC]

TABLE 4-57-continued
370(1)
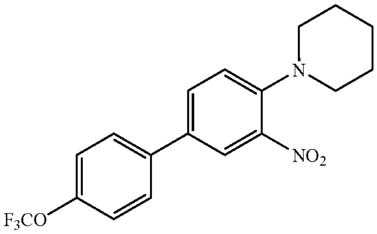 [SMILES: Nc1cc(-c2ccc(OC(F)(F)F)cc2)ccc1N1CCCCC1]
370(2)
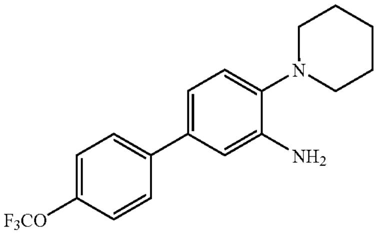
370(3)
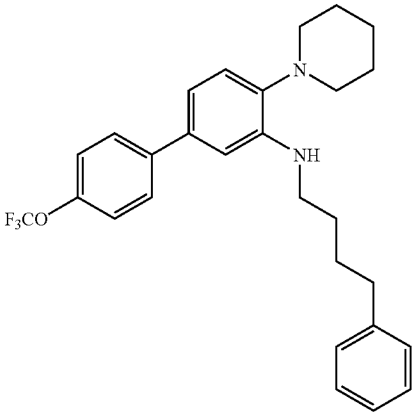 [SMILES: FC(F)(F)Oc1ccc(-c2ccc(N3CCCCC3)c(NCCCCc3ccccc3)c2)cc1]
370(4)
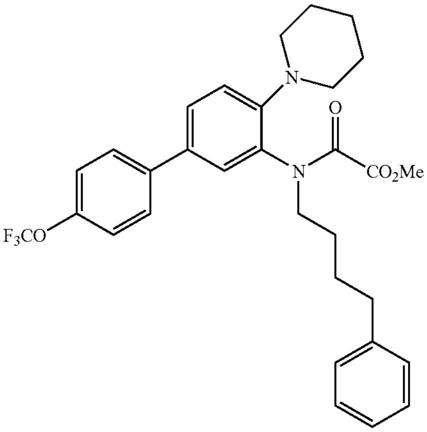 [SMILES: COC(=O)C(=O)N(CCCCc1ccccc1)c1cc(-c2ccc(OC(F)(F)F)cc2)ccc1N1CCCCC1]
371(1)
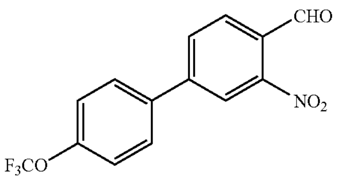 [SMILES: O=Cc1ccc(-c2ccc(OC(F)(F)F)cc2)cc1[N+](=O)[O-]]
TABLE 4-57-continued
371(2)
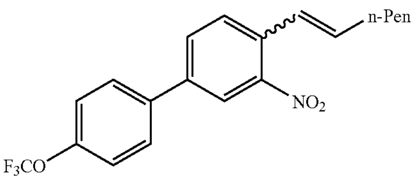
371(3)
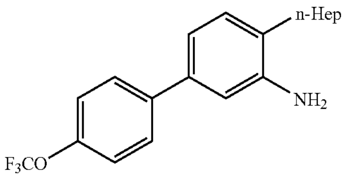
371(4)
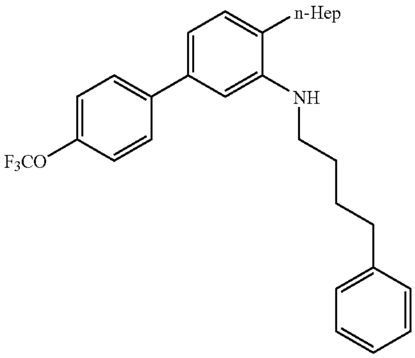
371(5)
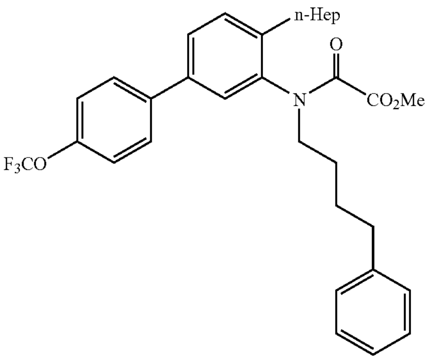
TABLE 4-58
372(1)
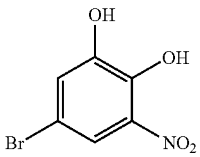 [SMILES: O=[N+]([O-])c1cc(Br)cc(O)c1O]
372(2)
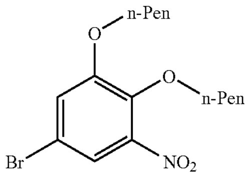

TABLE 4-58-continued
372(3)
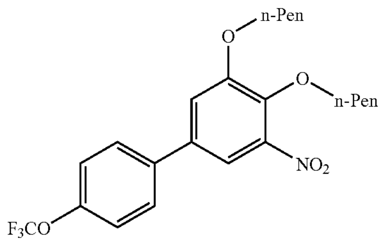
372(4)
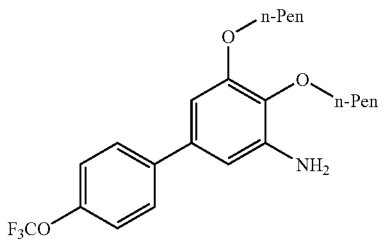
372(5)
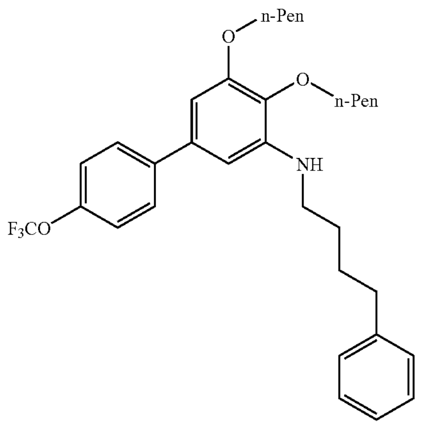
372(6)
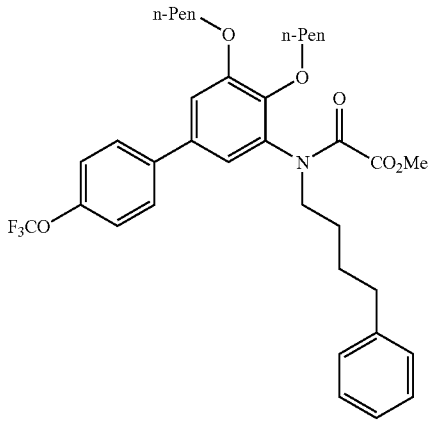
373(1)
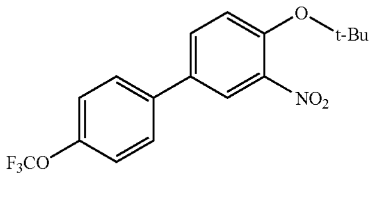 [SMILES: CC(C)(C)Oc1ccc(-c2ccc(OC(F)(F)F)cc2)cc1N]
TABLE 4-58-continued
373(2)
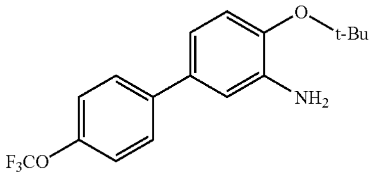
373(3)
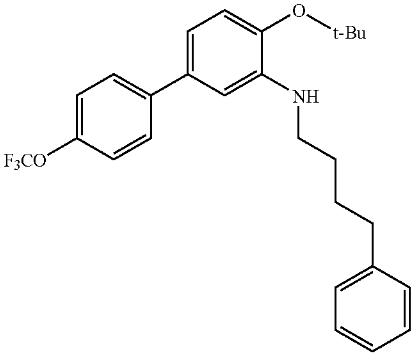 [SMILES: CC(C)(C)Oc1ccc(-c2ccc(OC(F)(F)F)cc2)cc1NCCCCc1ccccc1]
373(4)
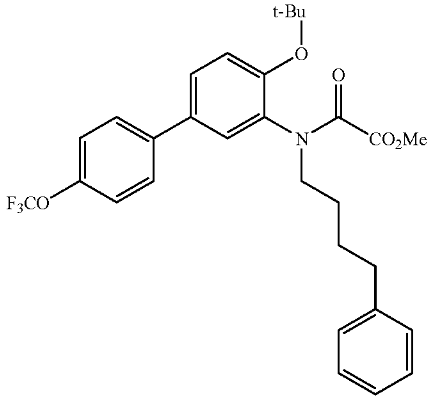 [SMILES: COC(=O)C(=O)N(CCCCc1ccccc1)c1cc(-c2ccc(OC(F)(F)F)cc2)ccc1OC(C)(C)C]
TABLE 4-59
374(1)
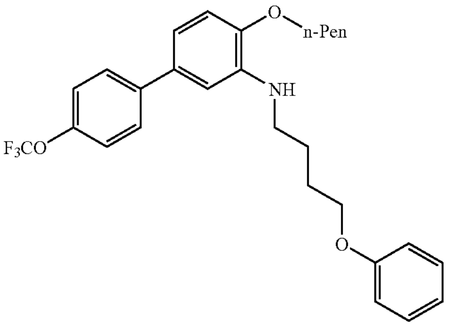

TABLE 4-59-continued
374(2)
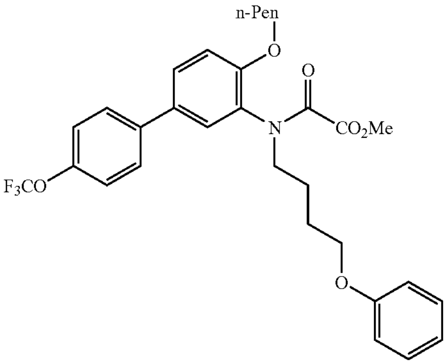
375(1)
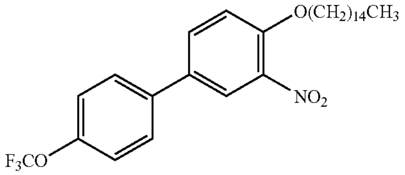
375(2)
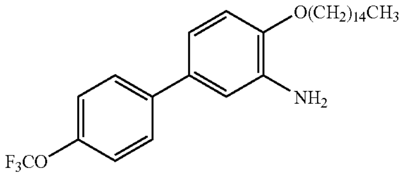
375(3)
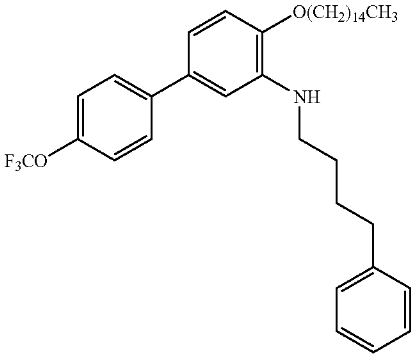
375(4)
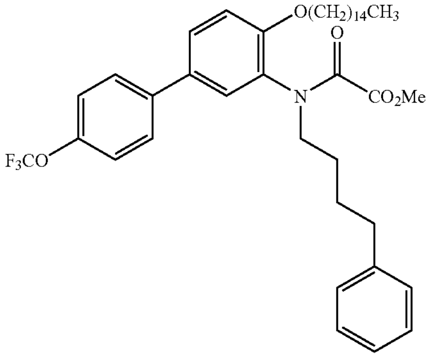
376(1)
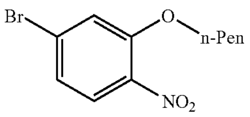
TABLE 4-59-continued
376(2)
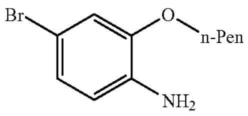
376(3)
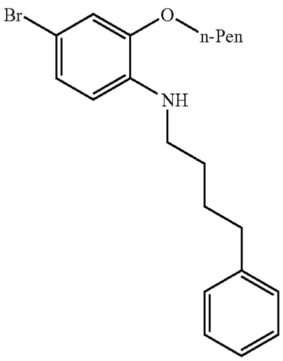
376(4)
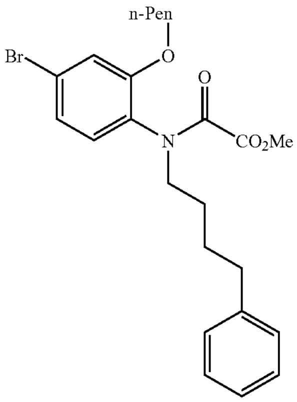
TABLE 4-60
376(5)
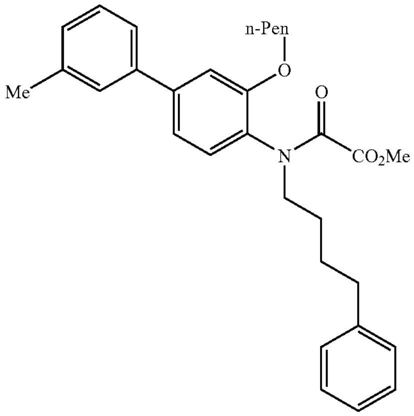

TABLE 4-60-continued
377(1)
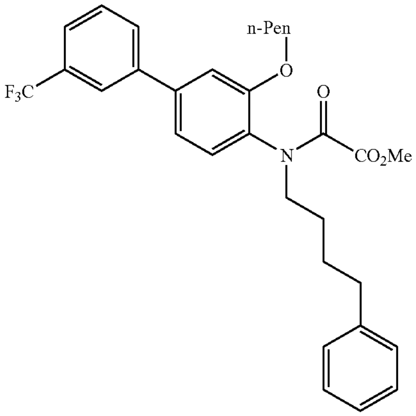
378(1)
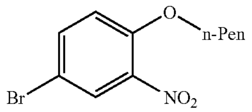
378(2)
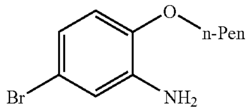
378(3)
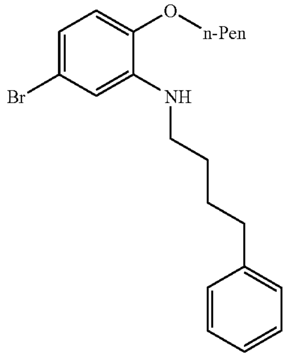
378(4)
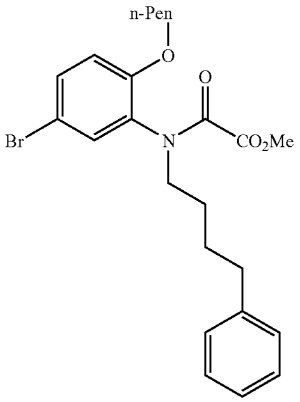
TABLE 4-60-continued
378(5)
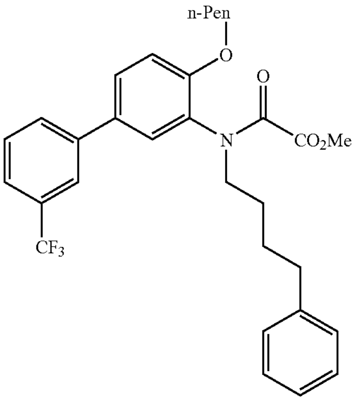
379(1)
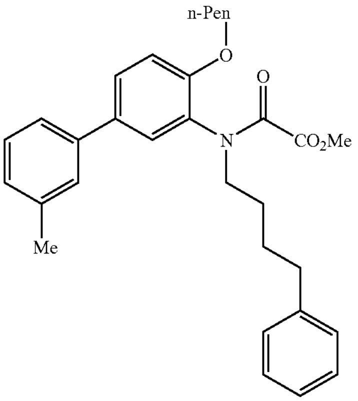
380(1)
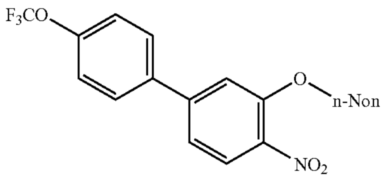
380(2)
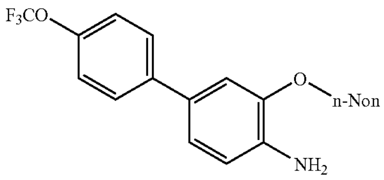

TABLE 4-61
380(3)
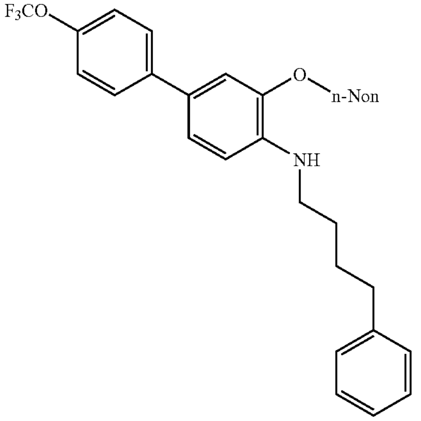
380(4)
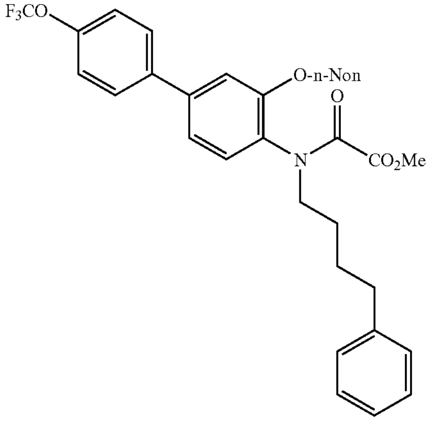
381(1)
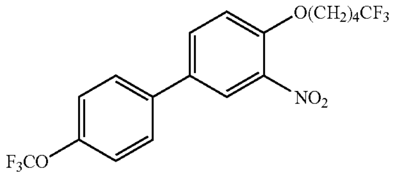
381(2)
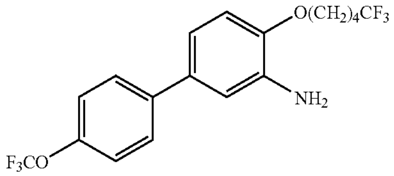
381(3)
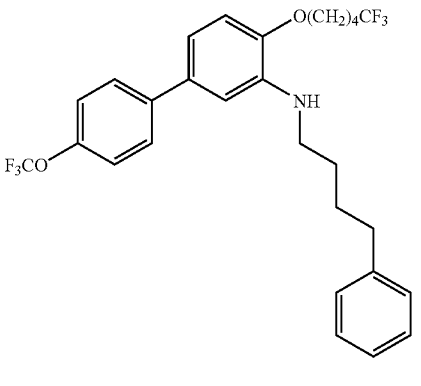
TABLE 4-61-continued
381(4)
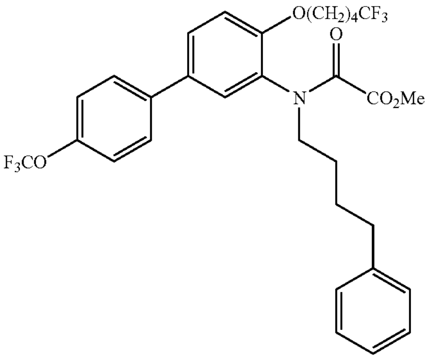
382(1)
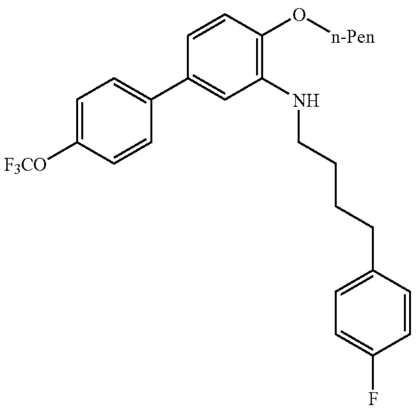
382(2)
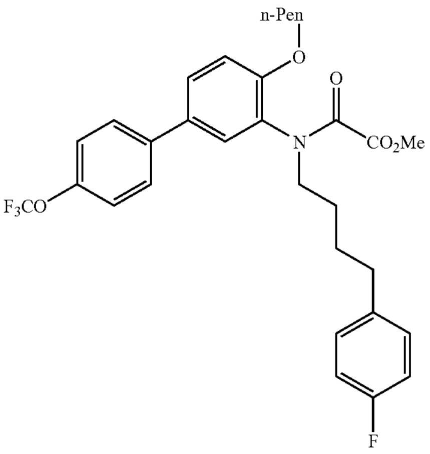
383(1)
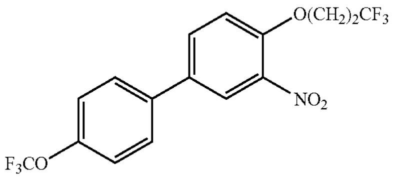
383(2)
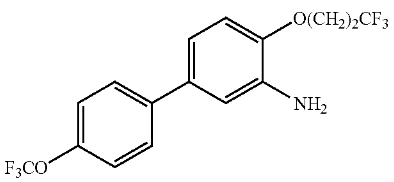

TABLE 4-62
| | |
|---|---|
| 383(3) | 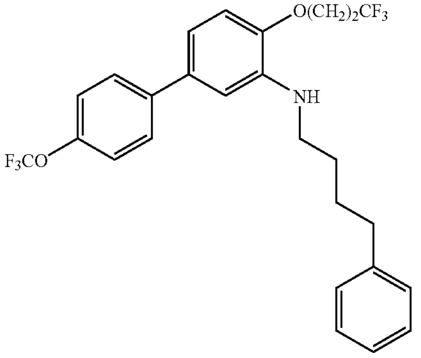 |
| 383(4) | 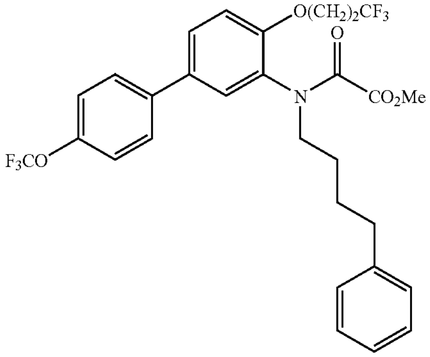 |
| 384(1) | 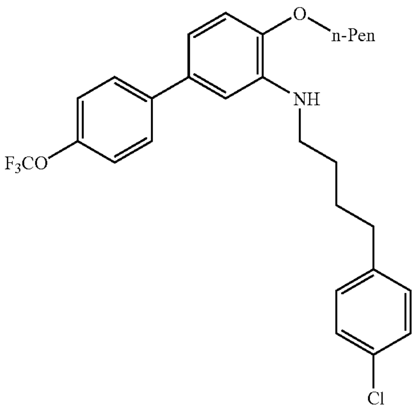 |
| 384(2) | 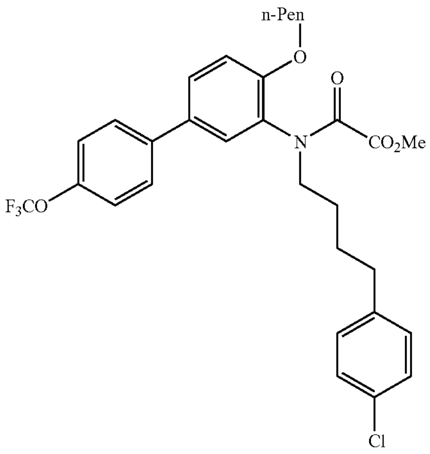 |
TABLE 4-62-continued
| | |
|---|---|
| 385(1) | 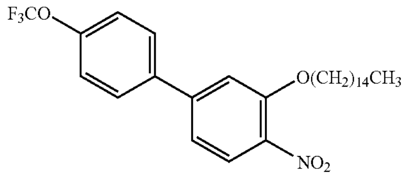 |
| 385(2) | 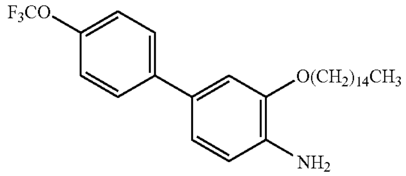 |
| 385(3) | 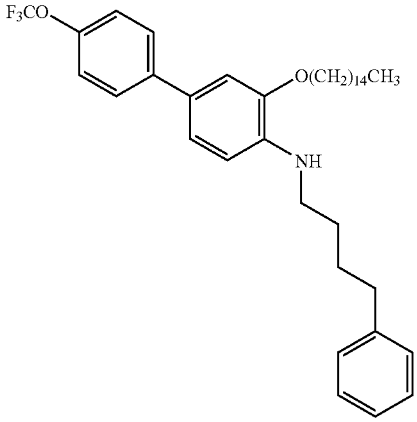 |
| 385(4) | 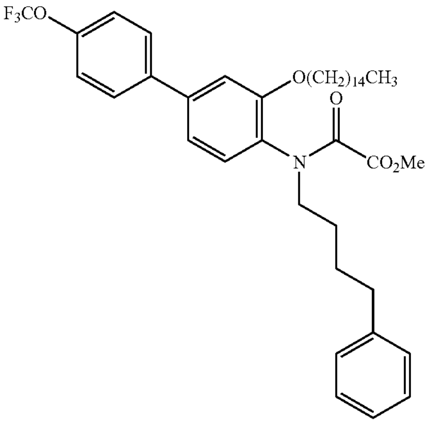 |
| 386(1) | 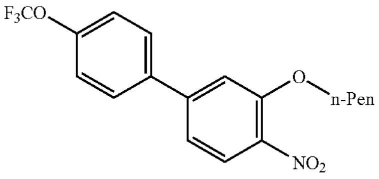 |
| 386(2) | 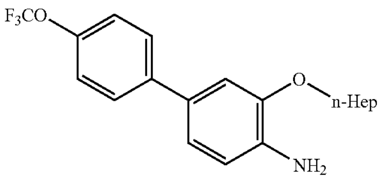 |

TABLE 4-63
386(3)
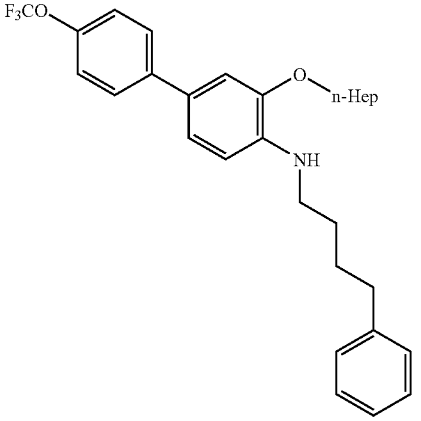
386(4)
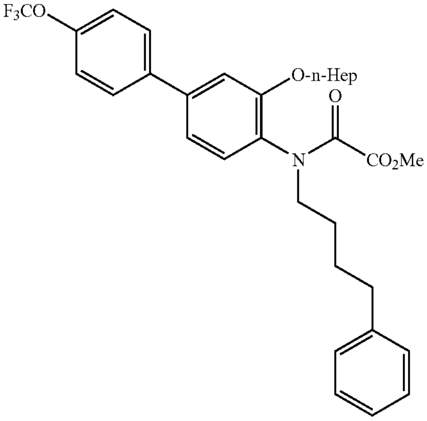
387(1)
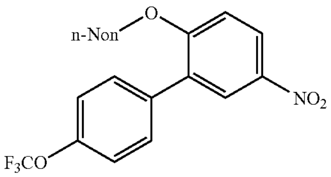
387(2)
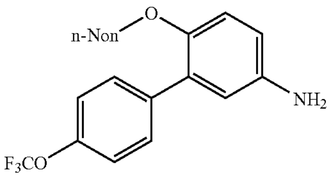
387(3)
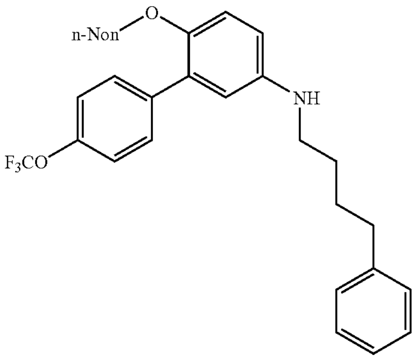
TABLE 4-63-continued
387(4)
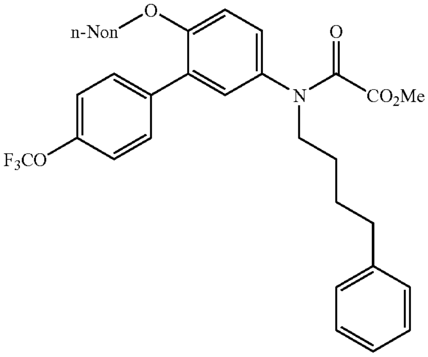
388(1)
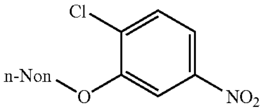
388(2)
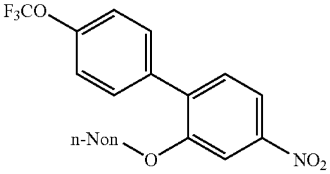
388(3)
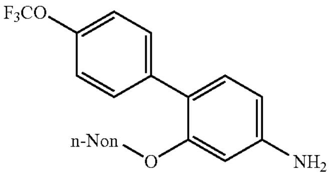
388(4)
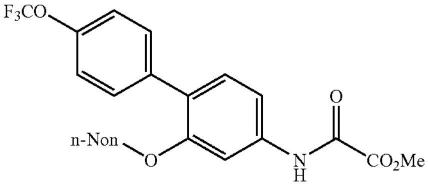
TABLE 4-64
388(5)
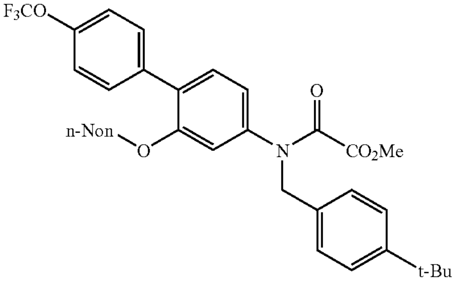

TABLE 4-64-continued
389(1)
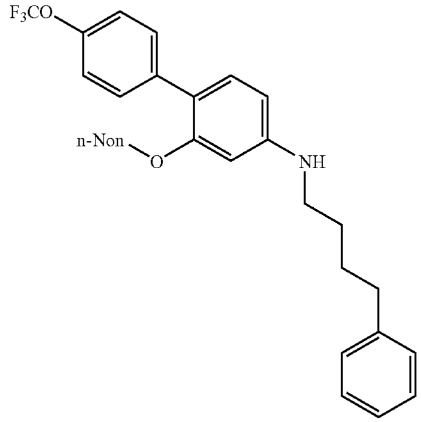
389(2)
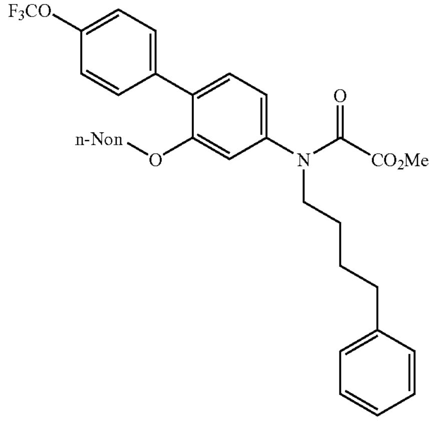
390(1)
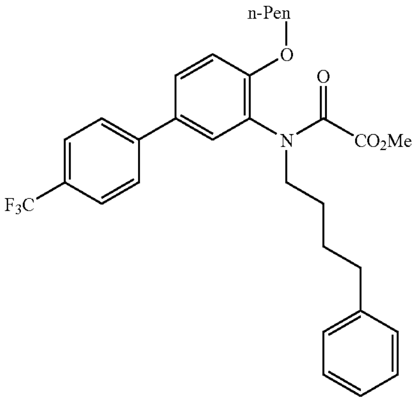
391(1)
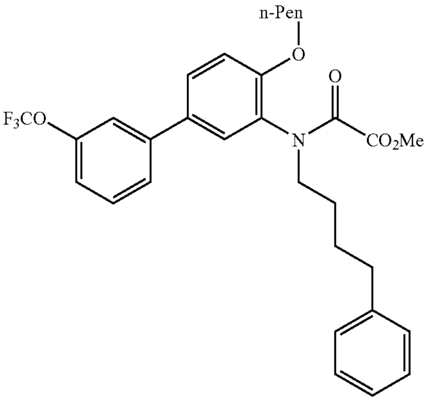
TABLE 4-64-continued
392(1)
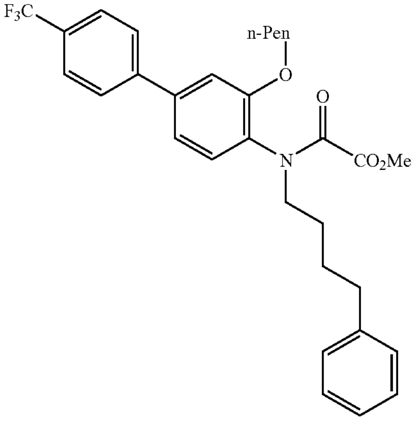
393(1)
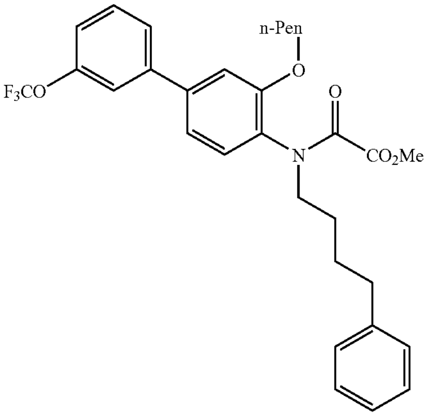
394(1)
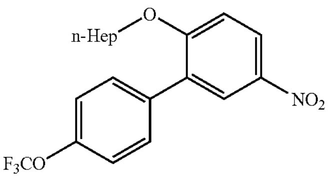

TABLE 4-65
| | |
|---|---|
| 394(2) | 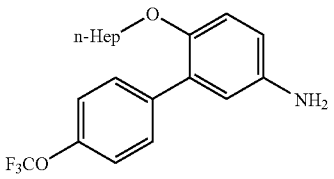 |
| 394(3) | 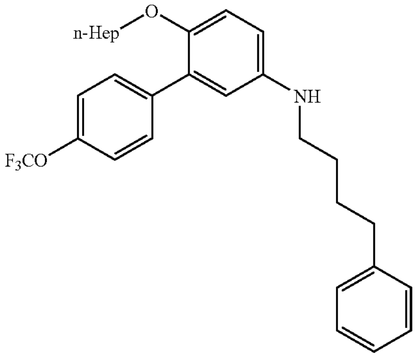 |
| 394(4) | 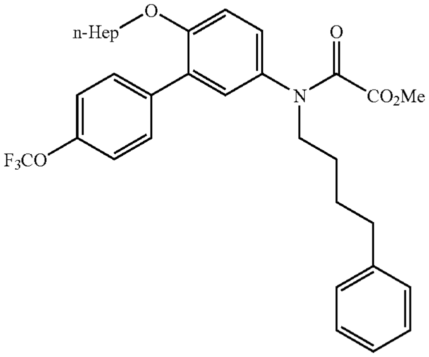 |
| 401(1) | 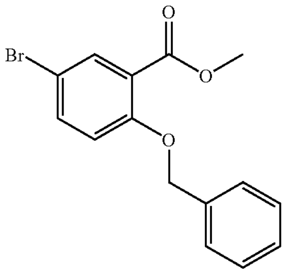 [SMILES: COC(=O)c1cc(Br)ccc1OCc1ccccc1] |
| 401(2) | 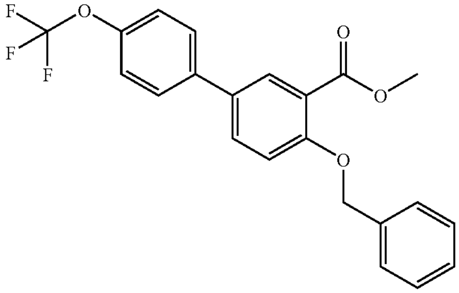 [SMILES: COC(=O)c1cc(-c2ccc(OC(F)(F)F)cc2)ccc1OCc1ccccc1] |

TABLE 4-65-continued
| | |
|---|---|
| 403(1) | 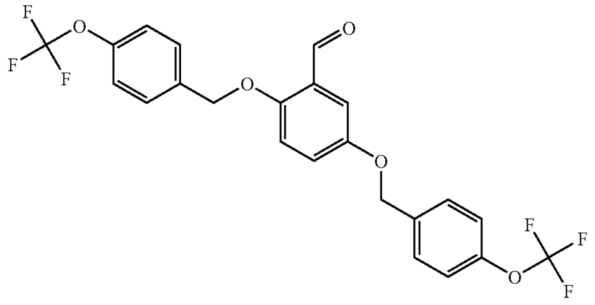 [SMILES: O=Cc1cc(OCc2ccc(OC(F)(F)F)cc2)ccc1OCc1ccc(OC(F)(F)F)cc1] |
| 405(1) | 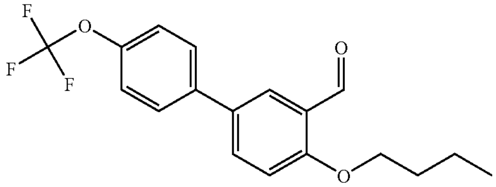 [SMILES: CCCCOc1ccc(-c2ccc(OC(F)(F)F)cc2)cc1C=O] |
| 406(1) | 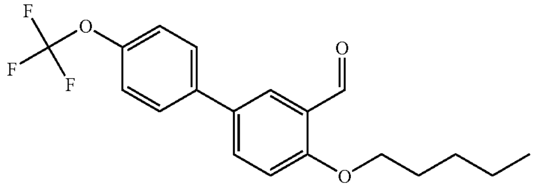 [SMILES: CCCCCOc1ccc(-c2ccc(OC(F)(F)F)cc2)cc1C=O] |
| 409(1) | 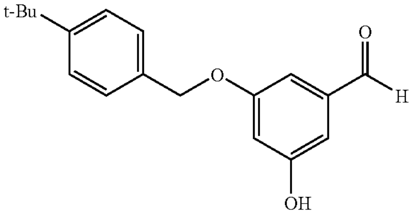 [SMILES: CC(C)(C)c1ccc(COc2cc(O)cc(C=O)c2)cc1] |
| 409(2) | 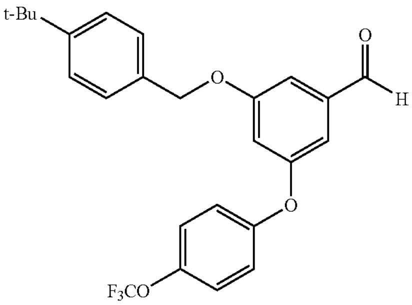 [SMILES: CC(C)(C)c1ccc(COc2cc(C=O)cc(Oc3ccc(OC(F)(F)F)cc3)c2)cc1] |
TABLE 4-66
| | |
|---|---|
| 411(1) | 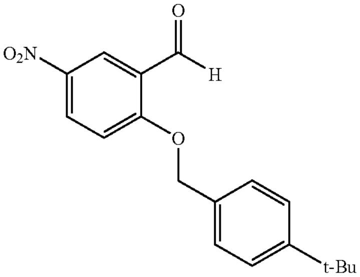 [SMILES: CC(C)(C)c1ccc(COc2ccc([N+](=O)[O-])cc2C=O)cc1] |
TABLE 4-66-continued
| | |
|---|---|
| 411(2) | 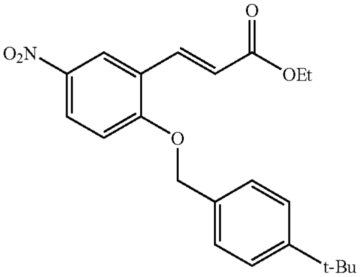 [SMILES: CCOC(=O)/C=C/c1cc([N+](=O)[O-])ccc1OCc1ccc(C(C)(C)C)cc1] |

TABLE 4-66-continued
411(3)
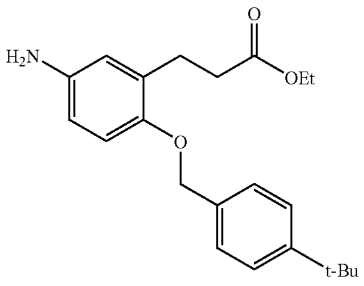 [SMILES: CCOC(=O)CCc1cc(N)ccc1OCc1ccc(C(C)(C)C)cc1]
411(4)
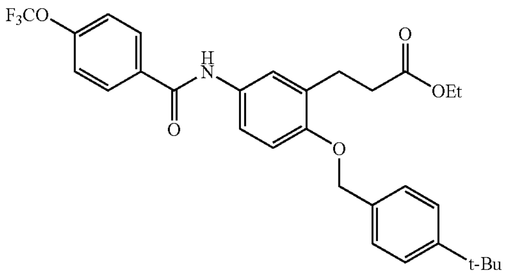
412(1)
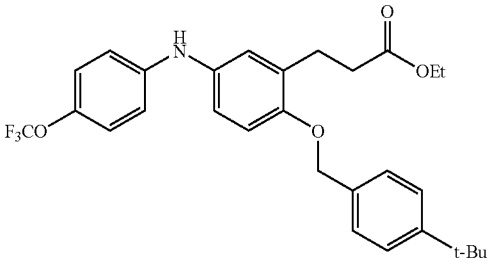
413(1)
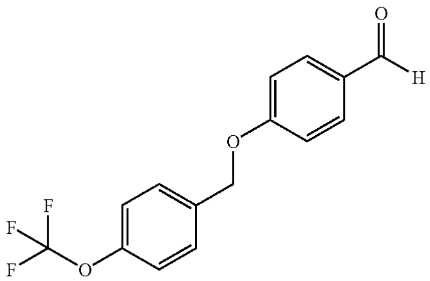 [SMILES: O=Cc1ccc(OCc2ccc(OC(F)(F)F)cc2)cc1]
TABLE 4-66-continued
413(2)
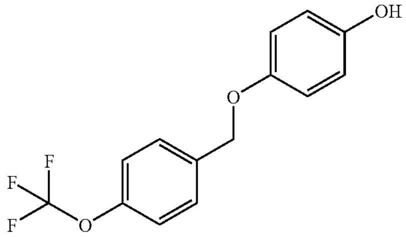 [SMILES: Oc1ccc(OCc2ccc(OC(F)(F)F)cc2)cc1]
413(3)
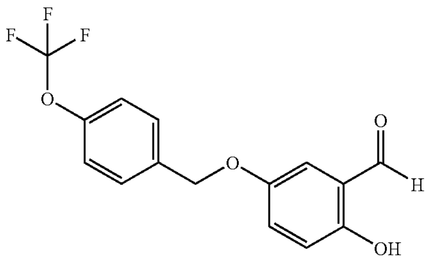 [SMILES: O=Cc1cc(OCc2ccc(OC(F)(F)F)cc2)ccc1O]
413(4)
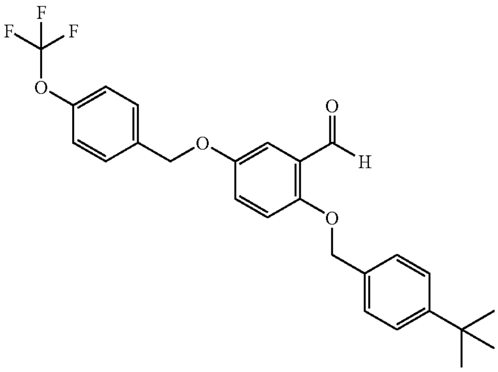 [SMILES: CC(C)(C)c1ccc(COc2ccc(OCc3ccc(OC(F)(F)F)cc3)cc2C=O)cc1]
415(1)
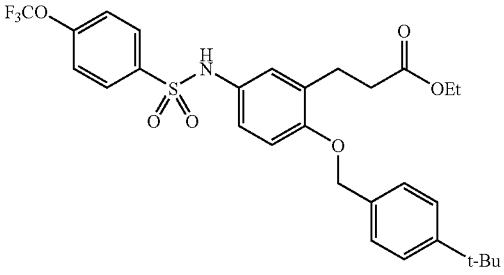
TABLE 4-67
416(1)
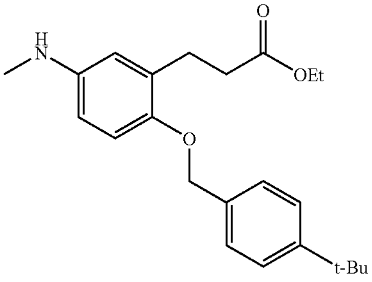 [SMILES: CCOC(=O)CCc1cc(NC)ccc1OCc1ccc(C(C)(C)C)cc1]

TABLE 4-67-continued
416(2)
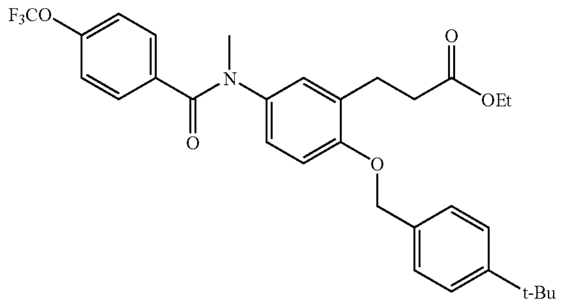 [SMILES: CCOC(=O)CCc1cc(N(C)C(=O)c2ccc(OC(F)(F)F)cc2)ccc1OCc1ccc(C(C)(C)C)cc1]
417(1)
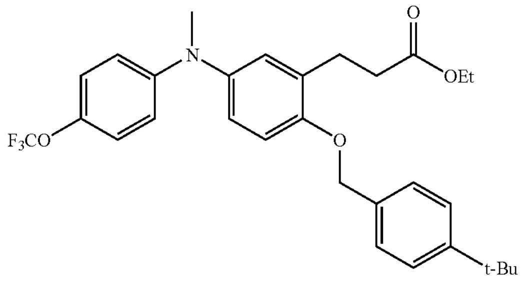 [SMILES: CCOC(=O)CCc1cc(N(C)c2ccc(OC(F)(F)F)cc2)ccc1OCc1ccc(C(C)(C)C)cc1]
418(1)
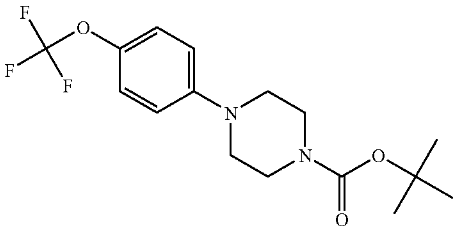 [SMILES: CC(C)(C)OC(=O)N1CCN(c2ccc(OC(F)(F)F)cc2)CC1]
418(2)
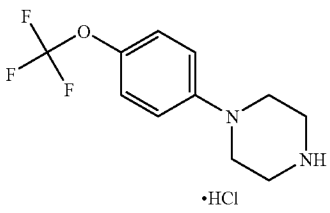 [SMILES: FC(F)(F)Oc1ccc(N2CCNCC2)cc1 ; Cl]
418(3)
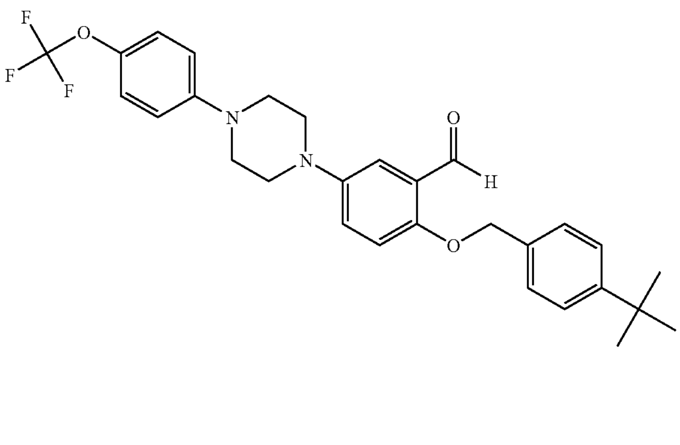 [SMILES: CC(C)(C)c1ccc(COc2ccc(N3CCN(c4ccc(OC(F)(F)F)cc4)CC3)cc2C=O)cc1]

TABLE 4-67-continued
| | |
|---|---|
| 421(1) | 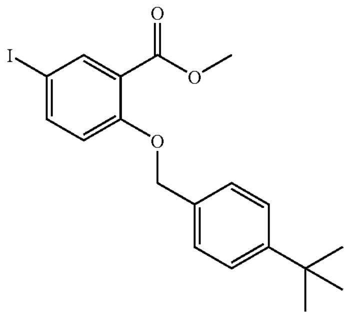 [SMILES: COC(=O)c1cc(I)ccc1OCc1ccc(C(C)(C)C)cc1] |
| 421(2) | 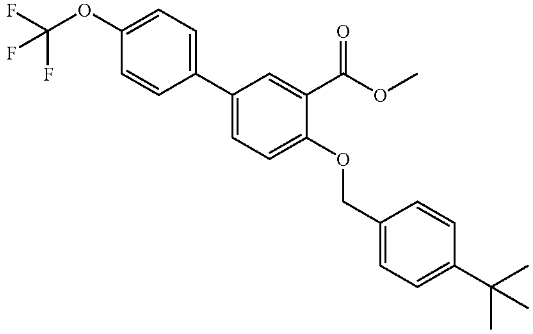 [SMILES: COC(=O)c1cc(-c2ccc(OC(F)(F)F)cc2)ccc1OCc1ccc(C(C)(C)C)cc1] |
| 423(1) | 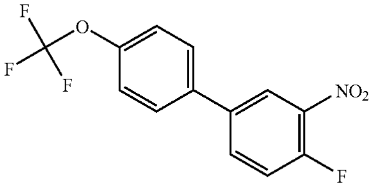 [SMILES: O=[N+]([O-])c1cc(-c2ccc(OC(F)(F)F)cc2)ccc1F] |
TABLE 4-68
| | |
|---|---|
| 423(2) | 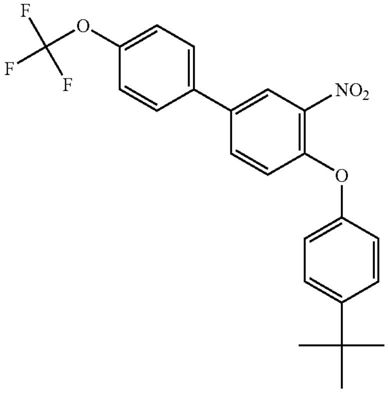 |

TABLE 4-68-continued
423(3)
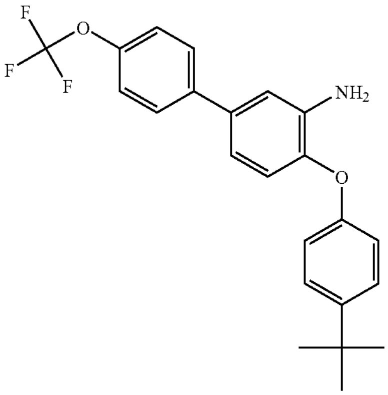
423(4)
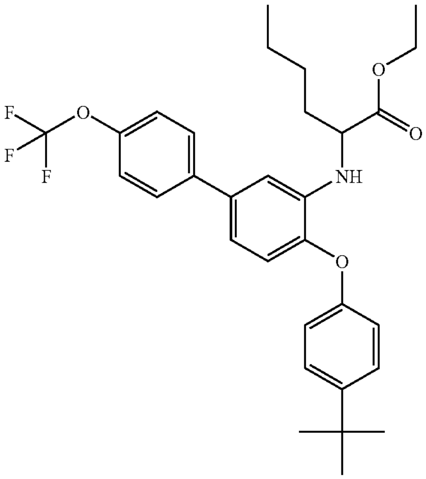 [SMILES: CCCCC(Nc1cc(-c2ccc(OC(F)(F)F)cc2)ccc1Oc1ccc(C(C)(C)C)cc1)C(=O)OCC]
424(1)
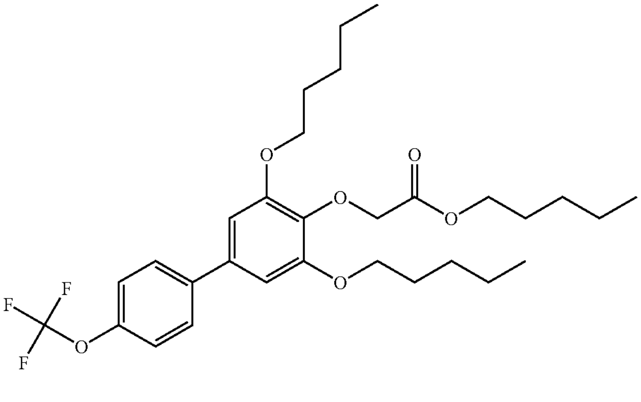 [SMILES: CCCCCOC(=O)COc1c(OCCCCC)cc(-c2ccc(OC(F)(F)F)cc2)cc1OCCCCC]

TABLE 4-68-continued
425(1)
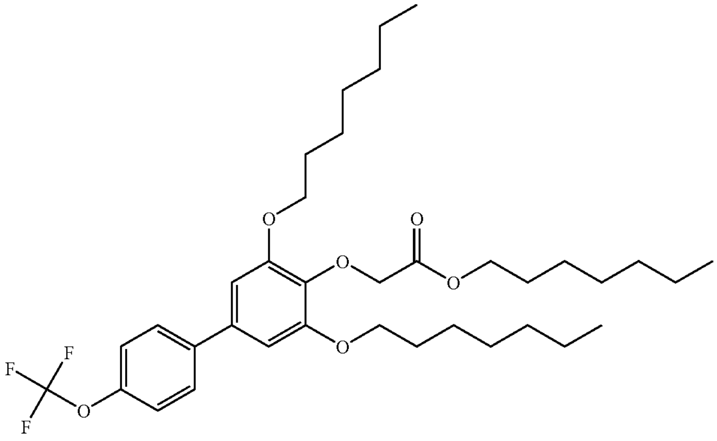 [SMILES: CCCCCCCOC(=O)COc1c(OCCCCCCC)cc(-c2ccc(OC(F)(F)F)cc2)cc1OCCCCCCC]
426(1)
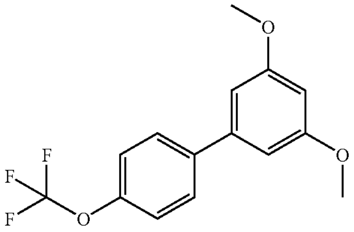 [SMILES: COc1cc(OC)cc(-c2ccc(OC(F)(F)F)cc2)c1]
426(2)
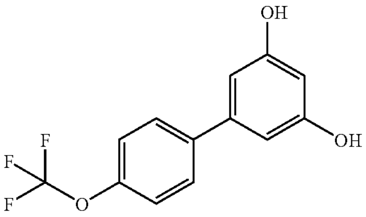 [SMILES: Oc1cc(O)cc(-c2ccc(OC(F)(F)F)cc2)c1]
426(3)
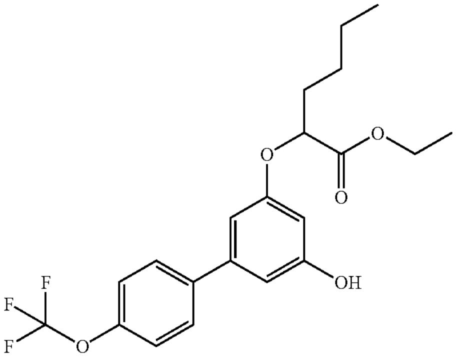 [SMILES: CCCCC(Oc1cc(O)cc(-c2ccc(OC(F)(F)F)cc2)c1)C(=O)OCC]

TABLE 4-69
426(4)
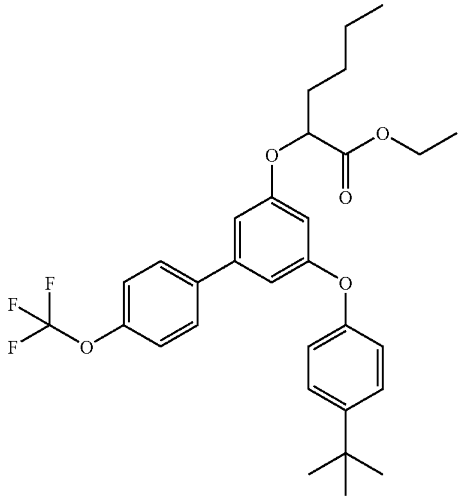 [SMILES: CCCCC(Oc1cc(Oc2ccc(C(C)(C)C)cc2)cc(-c2ccc(OC(F)(F)F)cc2)c1)C(=O)OCC]
427(1)
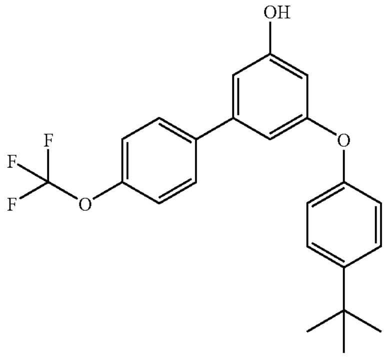 [SMILES: CC(C)(C)c1ccc(Oc2cc(O)cc(-c3ccc(OC(F)(F)F)cc3)c2)cc1]
427(2)
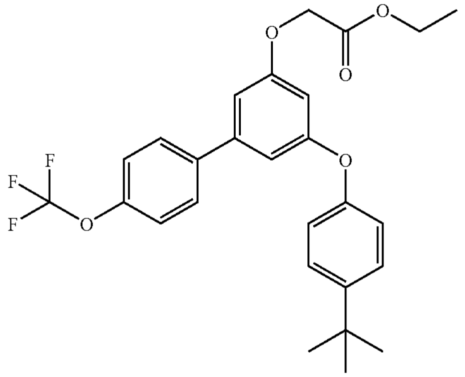 [SMILES: CCOC(=O)COc1cc(Oc2ccc(C(C)(C)C)cc2)cc(-c2ccc(OC(F)(F)F)cc2)c1]
428(1)
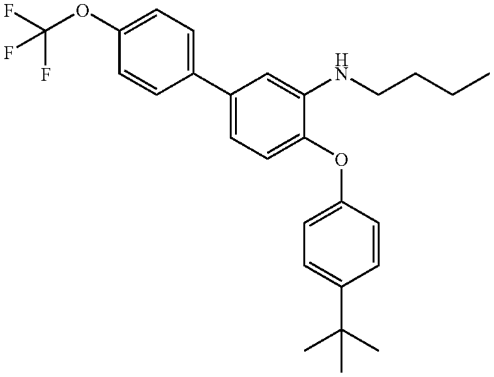 [SMILES: CCCCNc1cc(-c2ccc(OC(F)(F)F)cc2)ccc1Oc1ccc(C(C)(C)C)cc1]
TABLE 4-69-continued
428(2)
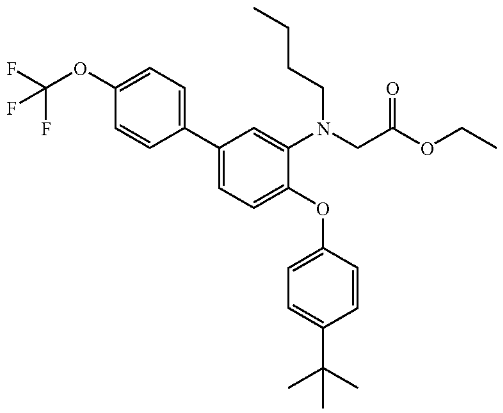 [SMILES: CCCCN(CC(=O)OCC)c1cc(-c2ccc(OC(F)(F)F)cc2)ccc1Oc1ccc(C(C)(C)C)cc1]
429(1)
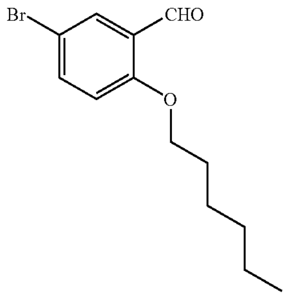 [SMILES: CCCCCCOc1ccc(Br)cc1C=O]
429(2)
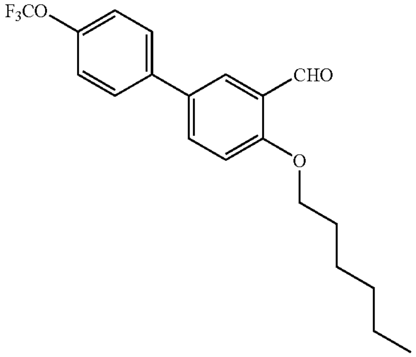 [SMILES: CCCCCCOc1ccc(-c2ccc(OC(F)(F)F)cc2)cc1C=O]
429(3)
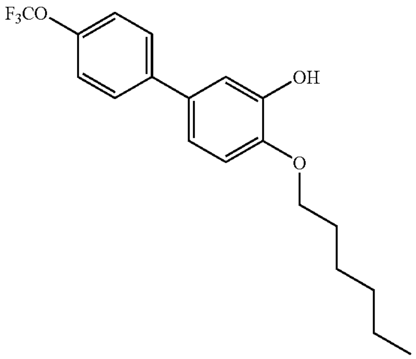 [SMILES: CCCCCCOc1ccc(-c2ccc(OC(F)(F)F)cc2)cc1O]

TABLE 4-70
429(4)
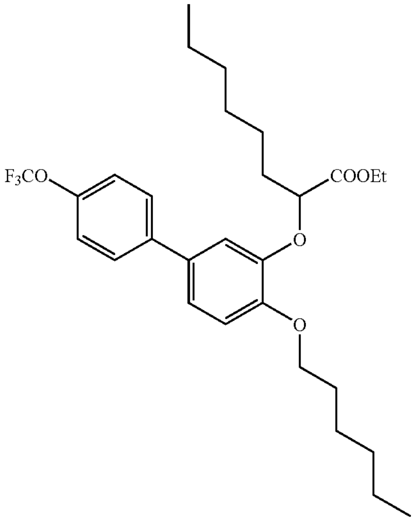 [SMILES: CCCCCCOc1ccc(-c2ccc(OC(F)(F)F)cc2)cc1OC(CCCCCC)C(=O)OCC]
430(1)
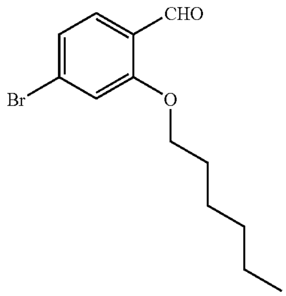 [SMILES: CCCCCCOc1cc(Br)ccc1C=O]
430(2)
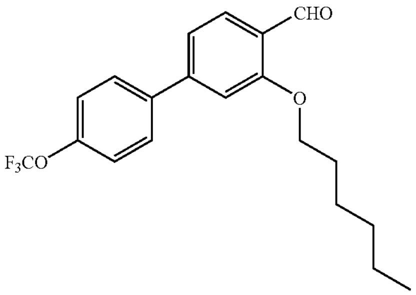 [SMILES: CCCCCCOc1cc(-c2ccc(OC(F)(F)F)cc2)ccc1C=O]
430(3)
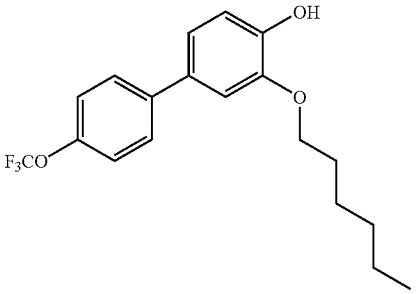 [SMILES: CCCCCCOc1cc(-c2ccc(OC(F)(F)F)cc2)ccc1O]
TABLE 4-70-continued
430(4)
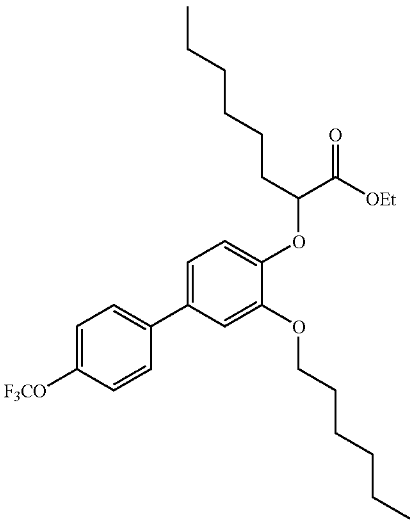 [SMILES: CCCCCCOc1cc(-c2ccc(OC(F)(F)F)cc2)ccc1OC(CCCCCC)C(=O)OCC]
431(1)
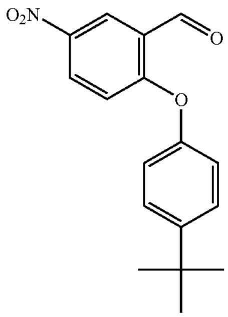 [SMILES: CC(C)(C)c1ccc(Oc2ccc([N+](=O)[O-])cc2C=O)cc1]
431(2)
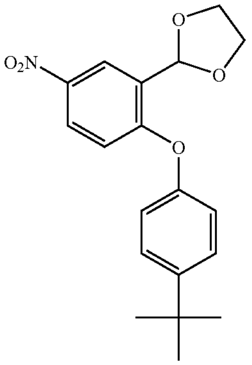
431(3)
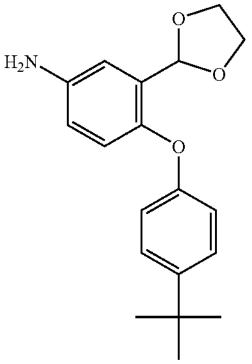 [SMILES: CC(C)(C)c1ccc(Oc2ccc(N)cc2C2OCCO2)cc1]

TABLE 4-71
431(4)
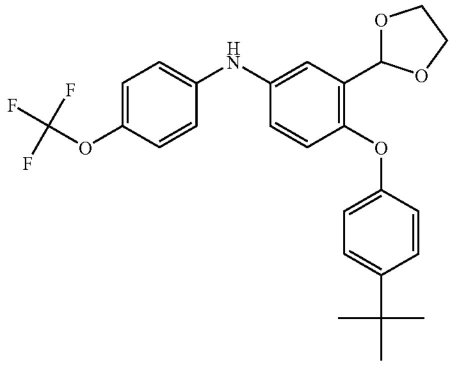 [SMILES: CC(C)(C)c1ccc(Oc2ccc(Nc3ccc(OC(F)(F)F)cc3)cc2C2OCCO2)cc1]
431(5)
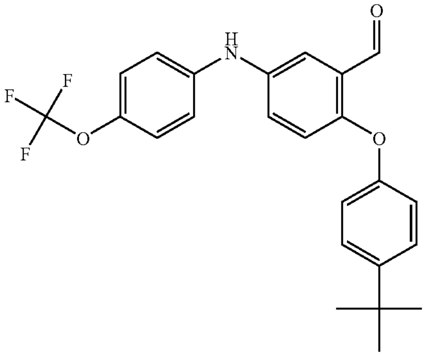 [SMILES: CC(C)(C)c1ccc(Oc2ccc(Nc3ccc(OC(F)(F)F)cc3)cc2C=O)cc1]
433(1)
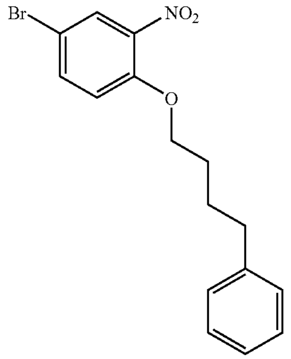 [SMILES: O=[N+]([O-])c1cc(Br)ccc1OCCCCc1ccccc1]
433(2)
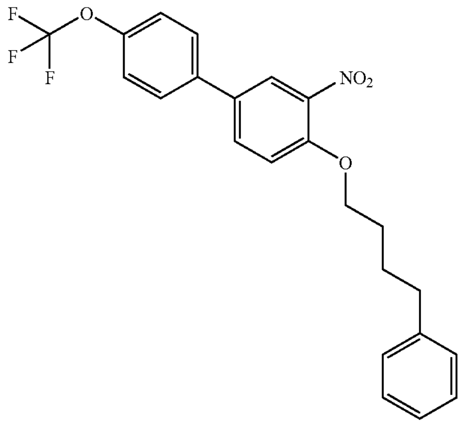 [SMILES: O=[N+]([O-])c1cc(-c2ccc(OC(F)(F)F)cc2)ccc1OCCCCc1ccccc1]
TABLE 4-71-continued
433(3)
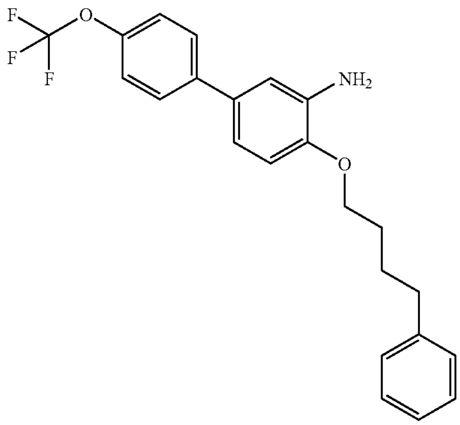
433(4)
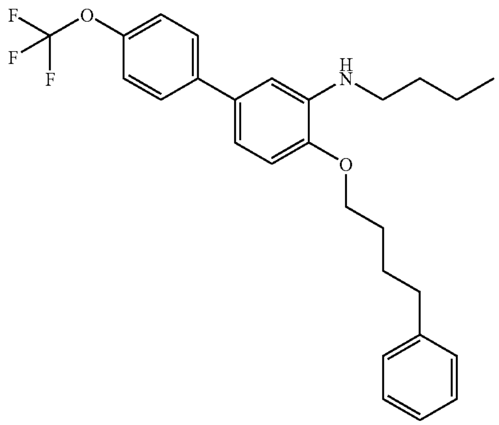 [SMILES: CCCCNc1cc(-c2ccc(OC(F)(F)F)cc2)ccc1OCCCCc1ccccc1]
433(5)
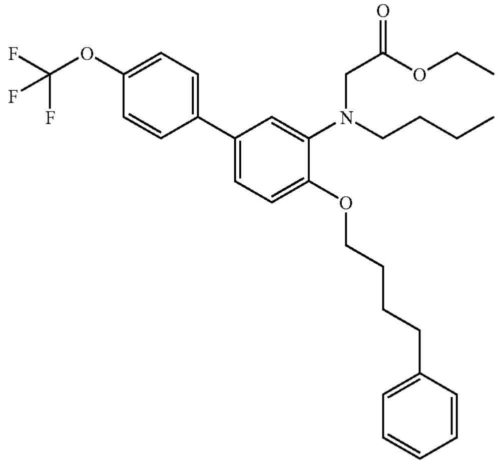 [SMILES: CCCCN(CC(=O)OCC)c1cc(-c2ccc(OC(F)(F)F)cc2)ccc1OCCCCc1ccccc1]

TABLE 4-71-continued
435(1)
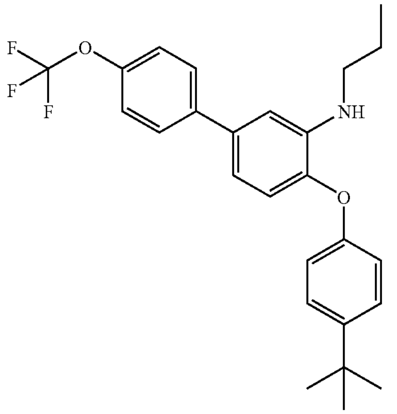 [SMILES: CCCNc1cc(-c2ccc(OC(F)(F)F)cc2)ccc1Oc1ccc(C(C)(C)C)cc1]
TABLE 4-72
435(2)
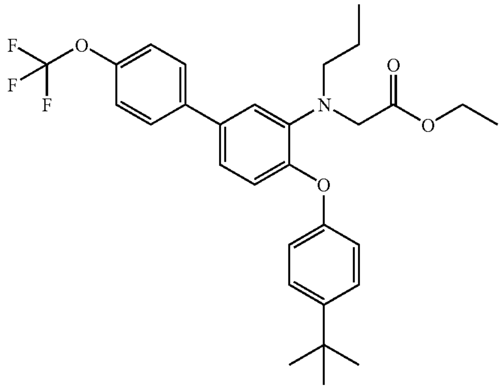 [SMILES: CCCN(CC(=O)OCC)c1cc(-c2ccc(OC(F)(F)F)cc2)ccc1Oc1ccc(C(C)(C)C)cc1]
436(1)
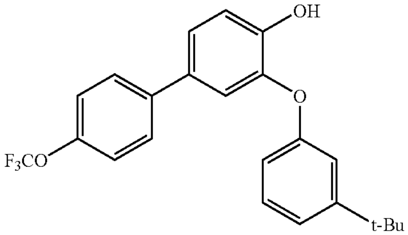 [SMILES: CC(C)(C)c1cccc(Oc2cc(-c3ccc(OC(F)(F)F)cc3)ccc2O)c1]
436(2)
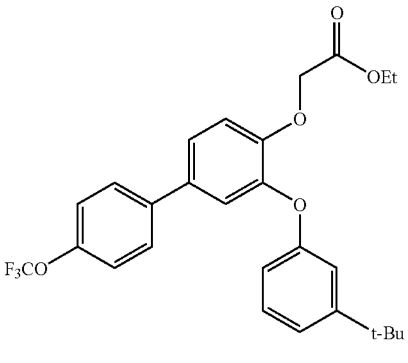 [SMILES: CCOC(=O)COc1ccc(-c2ccc(OC(F)(F)F)cc2)cc1Oc1cccc(C(C)(C)C)c1]
TABLE 4-72-continued
437(1)
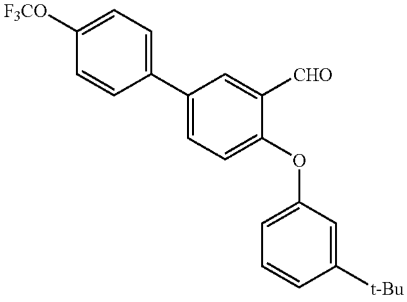 [SMILES: CC(C)(C)c1cccc(Oc2ccc(-c3ccc(OC(F)(F)F)cc3)cc2C=O)c1]
439(1)
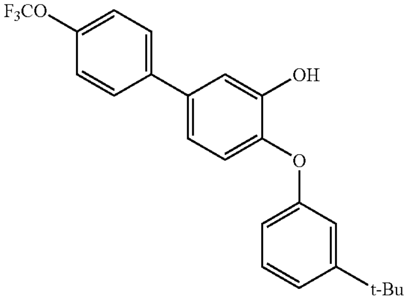 [SMILES: CC(C)(C)c1cccc(Oc2ccc(-c3ccc(OC(F)(F)F)cc3)cc2O)c1]
439(2)
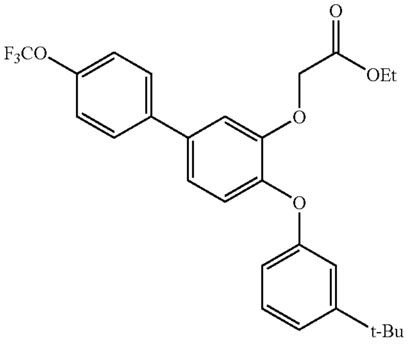 [SMILES: CCOC(=O)COc1cc(-c2ccc(OC(F)(F)F)cc2)ccc1Oc1cccc(C(C)(C)C)c1]
440(1)
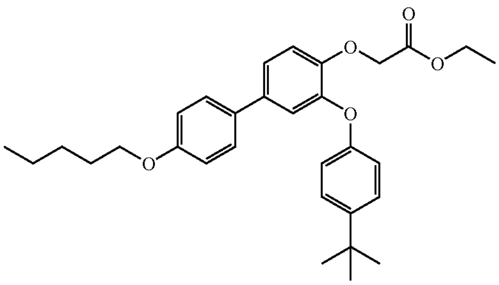 [SMILES: CCCCCOc1ccc(-c2ccc(OCC(=O)OCC)c(Oc3ccc(C(C)(C)C)cc3)c2)cc1]
441(1)
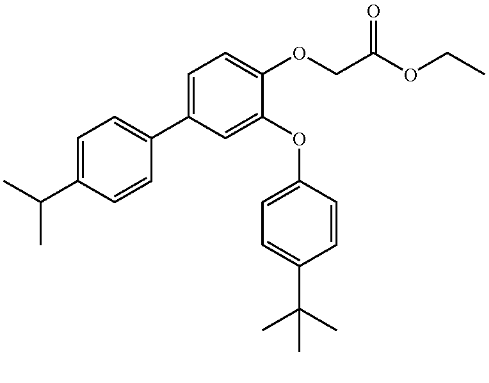 [SMILES: CCOC(=O)COc1ccc(-c2ccc(C(C)C)cc2)cc1Oc1ccc(C(C)(C)C)cc1]

TABLE 4-72-continued
| | |
|---|---|
| 442(1) | 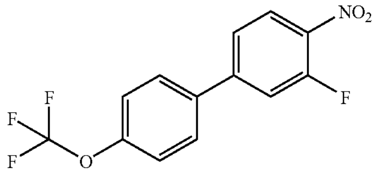 [SMILES: O=[N+]([O-])c1ccc(-c2ccc(OC(F)(F)F)cc2)cc1F] |
| 442(2) | 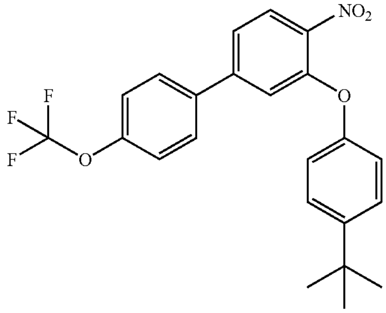 [SMILES: CC(C)(C)c1ccc(Oc2cc(-c3ccc(OC(F)(F)F)cc3)ccc2[N+](=O)[O-])cc1] |
TABLE 4-73
| | |
|---|---|
| 442(3) | 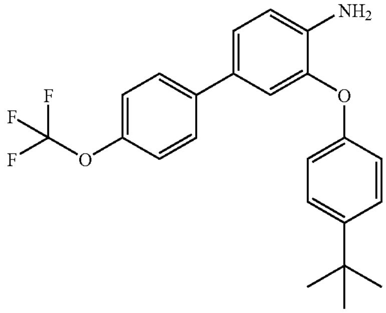 |
| 442(4) | 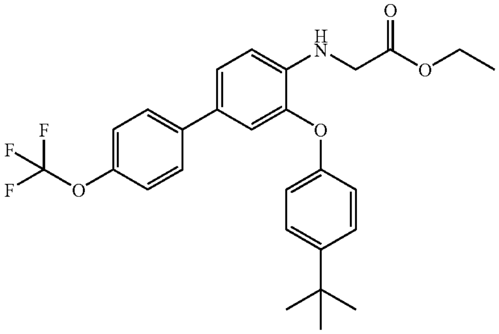 |
| 443(1) | 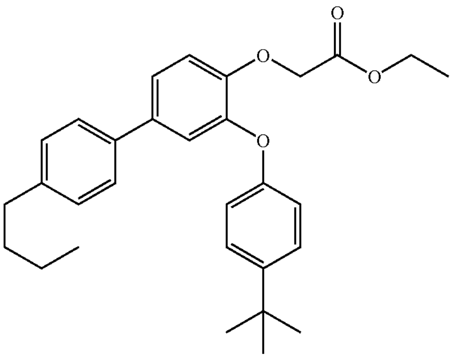 [SMILES: CCCCc1ccc(-c2ccc(OCC(=O)OCC)c(Oc3ccc(C(C)(C)C)cc3)c2)cc1] |
TABLE 4-73-continued
| | |
|---|---|
| 444(1) | 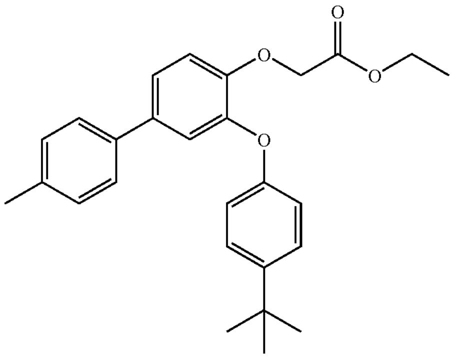 [SMILES: CCOC(=O)COc1ccc(-c2ccc(C)cc2)cc1Oc1ccc(C(C)(C)C)cc1] |
| 445(1) | 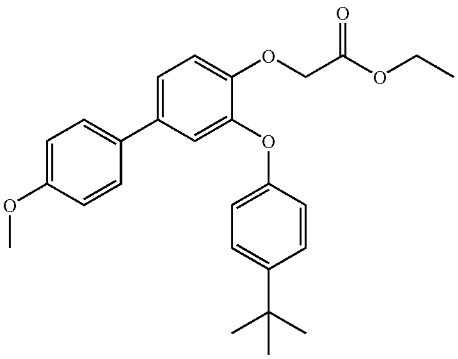 [SMILES: CCOC(=O)COc1ccc(-c2ccc(OC)cc2)cc1Oc1ccc(C(C)(C)C)cc1] |
| 446(1) | 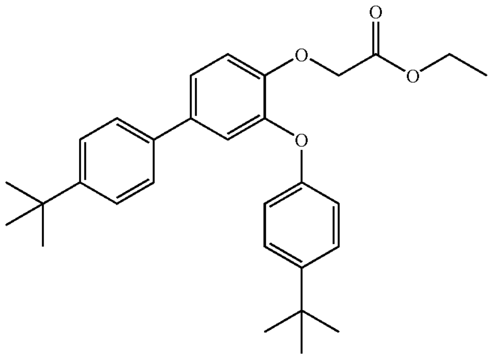 [SMILES: CCOC(=O)COc1ccc(-c2ccc(C(C)(C)C)cc2)cc1Oc1ccc(C(C)(C)C)cc1] |
| 447(1) | 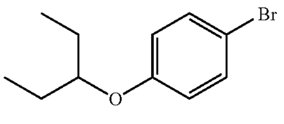 |
| 447(2) | 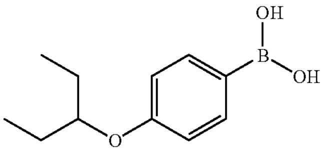 |

TABLE 4-73-continued
447(3)
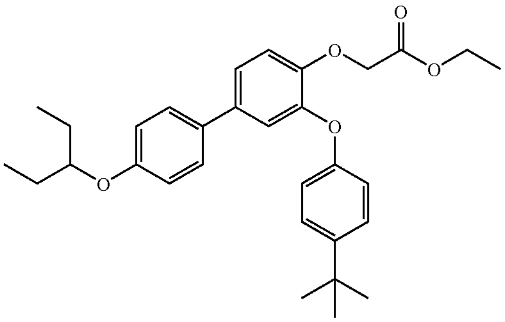 [SMILES: CCOC(=O)COc1ccc(-c2ccc(OC(CC)CC)cc2)cc1Oc1ccc(C(C)(C)C)cc1]
448(1)
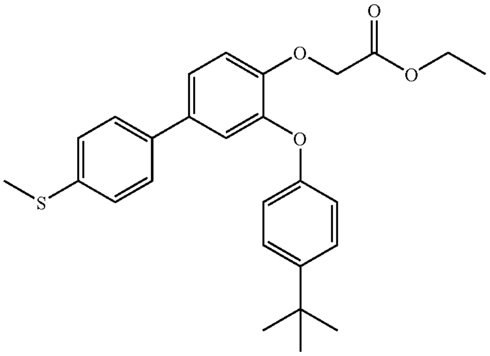 [SMILES: CCOC(=O)COc1ccc(-c2ccc(SC)cc2)cc1Oc1ccc(C(C)(C)C)cc1]
TABLE 4-74
449(1)
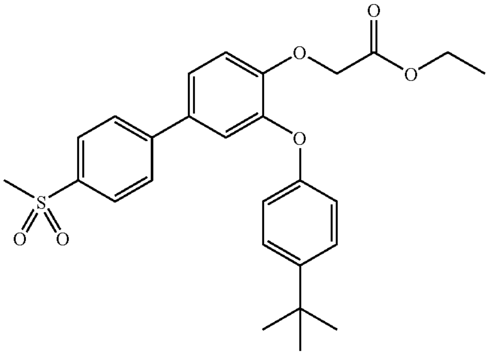 [SMILES: CCOC(=O)COc1ccc(-c2ccc(S(C)(=O)=O)cc2)cc1Oc1ccc(C(C)(C)C)cc1]
450(1)
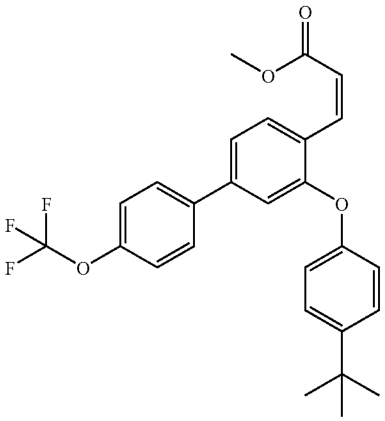 [SMILES: COC(=O)/C=C\c1ccc(-c2ccc(OC(F)(F)F)cc2)cc1Oc1ccc(C(C)(C)C)cc1]
TABLE 4-74-continued
451(1)
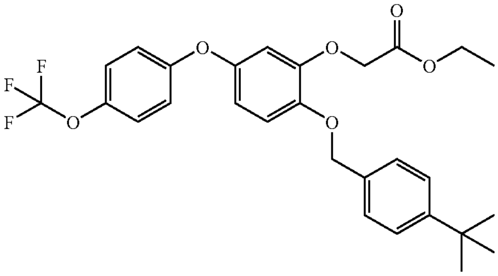 [SMILES: CCOC(=O)COc1cc(Oc2ccc(OC(F)(F)F)cc2)ccc1OCc1ccc(C(C)(C)C)cc1]
452(1)
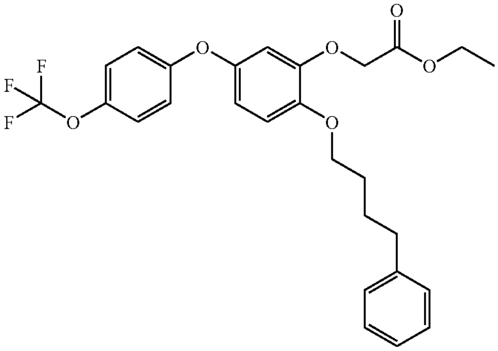 [SMILES: CCOC(=O)COc1cc(Oc2ccc(OC(F)(F)F)cc2)ccc1OCCCCc1ccccc1]
453(1)
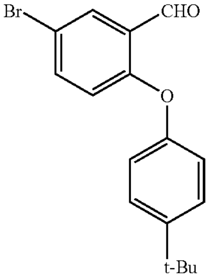 [SMILES: CC(C)(C)c1ccc(Oc2ccc(Br)cc2C=O)cc1]
453(2)
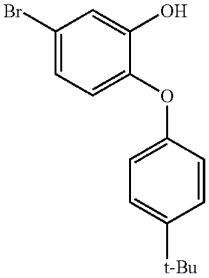
453(3)
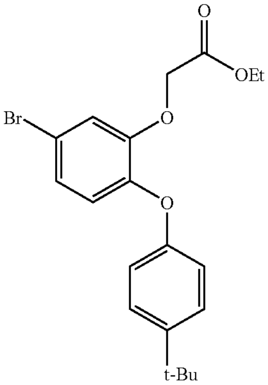 [SMILES: CCOC(=O)COc1cc(Br)ccc1Oc1ccc(C(C)(C)C)cc1]

TABLE 4-74-continued
453(4)
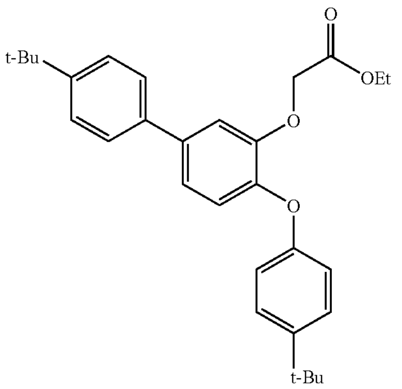 [SMILES: CCOC(=O)COc1cc(-c2ccc(C(C)(C)C)cc2)ccc1Oc1ccc(C(C)(C)C)cc1]
TABLE 4-75
454(1)
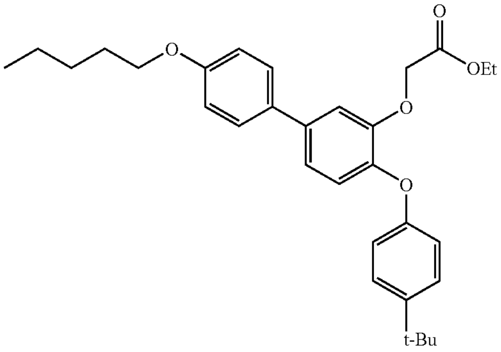 [SMILES: CCCCCOc1ccc(-c2ccc(Oc3ccc(C(C)(C)C)cc3)c(OCC(=O)OCC)c2)cc1]
455(1)
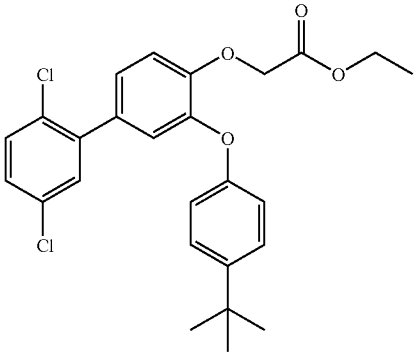 [SMILES: CCOC(=O)COc1ccc(-c2cc(Cl)ccc2Cl)cc1Oc1ccc(C(C)(C)C)cc1]
456(1)
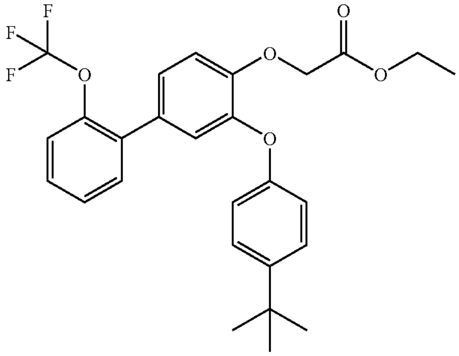 [SMILES: CCOC(=O)COc1ccc(-c2ccccc2OC(F)(F)F)cc1Oc1ccc(C(C)(C)C)cc1]
TABLE 4-75-continued
457(1)
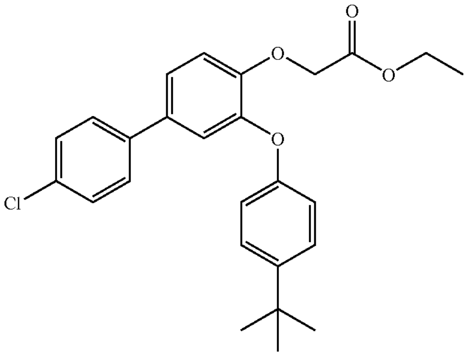 [SMILES: CCOC(=O)COc1ccc(-c2ccc(Cl)cc2)cc1Oc1ccc(C(C)(C)C)cc1]
458(1)
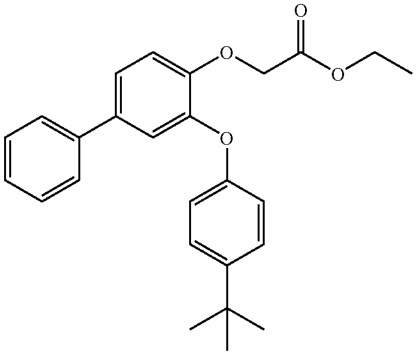 [SMILES: CCOC(=O)COc1ccc(-c2ccccc2)cc1Oc1ccc(C(C)(C)C)cc1]
459(1)
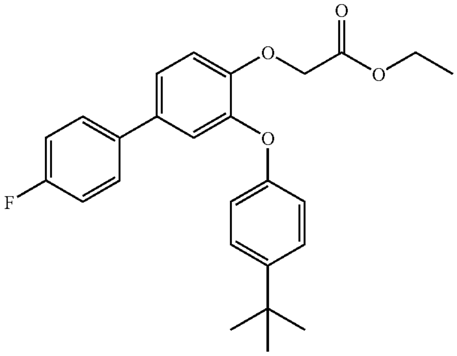 [SMILES: CCOC(=O)COc1ccc(-c2ccc(F)cc2)cc1Oc1ccc(C(C)(C)C)cc1]
460(1)
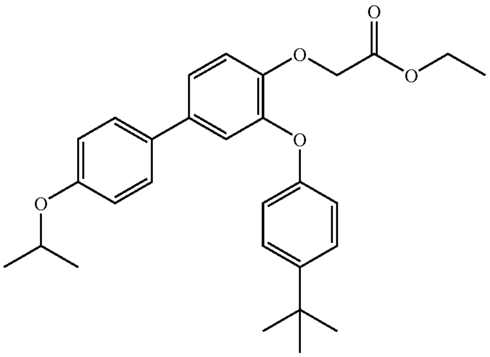 [SMILES: CCOC(=O)COc1ccc(-c2ccc(OC(C)C)cc2)cc1Oc1ccc(C(C)(C)C)cc1]
461(1)
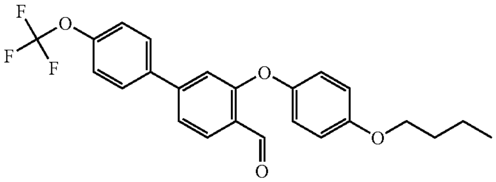 [SMILES: CCCCOc1ccc(Oc2cc(-c3ccc(OC(F)(F)F)cc3)ccc2C=O)cc1]

TABLE 4-75-continued
| |
|---|
TABLE 4-76
| | |
|---|---|
| 461(2) | 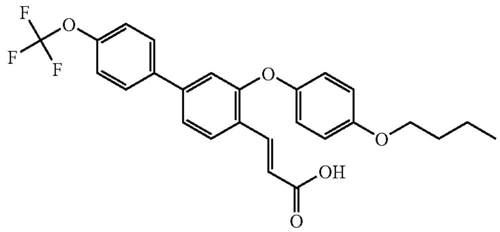 [SMILES: CCCCOc1ccc(Oc2cc(-c3ccc(OC(F)(F)F)cc3)ccc2/C=C/C(=O)O)cc1] |
| 462(1) | 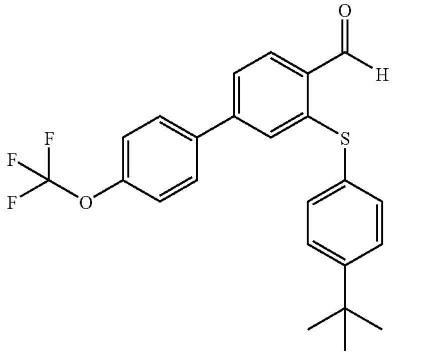 [SMILES: CC(C)(C)c1ccc(Sc2cc(-c3ccc(OC(F)(F)F)cc3)ccc2C=O)cc1] |
| 463(1) | 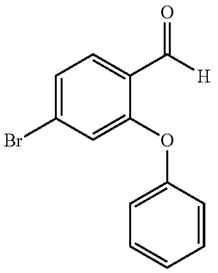 [SMILES: O=Cc1ccc(Br)cc1Oc1ccccc1] |
| 463(2) | 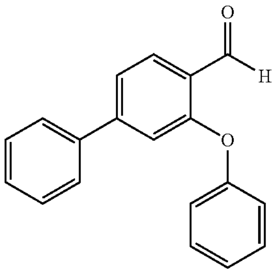 [SMILES: O=Cc1ccc(-c2ccccc2)cc1Oc1ccccc1] |
| 465(1) | 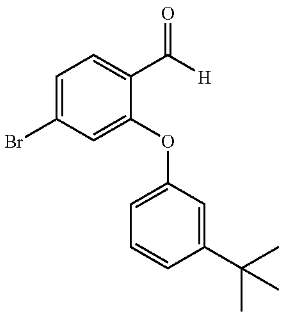 [SMILES: CC(C)(C)c1cccc(Oc2cc(Br)ccc2C=O)c1] |
TABLE 4-76-continued
| | |
|---|---|
| 465(2) | 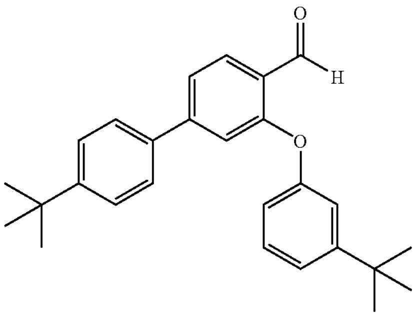 [SMILES: CC(C)(C)c1ccc(-c2ccc(C=O)c(Oc3cccc(C(C)(C)C)c3)c2)cc1] |
| 465(3) | 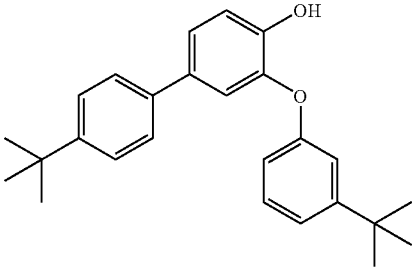 [SMILES: CC(C)(C)c1ccc(-c2ccc(O)c(Oc3cccc(C(C)(C)C)c3)c2)cc1] |
| 465(4) | 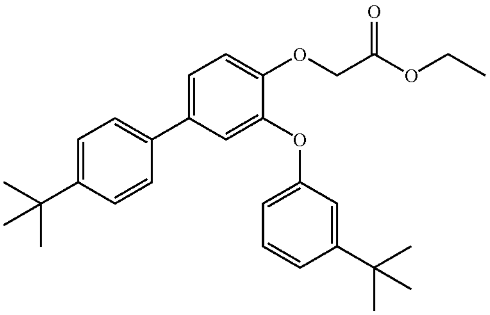 [SMILES: CCOC(=O)COc1ccc(-c2ccc(C(C)(C)C)cc2)cc1Oc1cccc(C(C)(C)C)c1] |
| 466(1) | 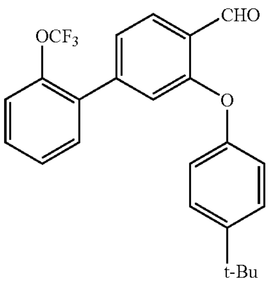 [SMILES: CC(C)(C)c1ccc(Oc2cc(-c3ccccc3OC(F)(F)F)ccc2C=O)cc1] |
| 468(1) | 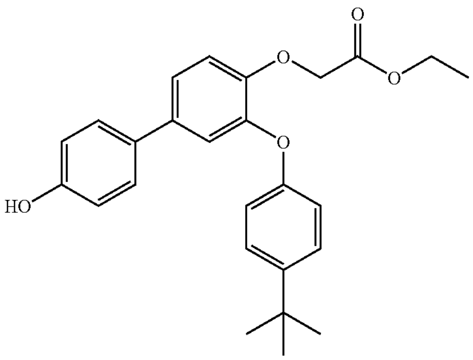 |

TABLE 4-77
468(2)
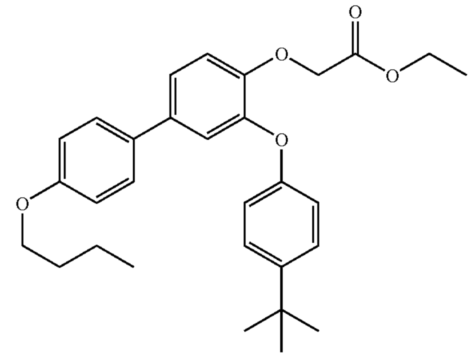 [SMILES: CCCCOc1ccc(-c2ccc(OCC(=O)OCC)c(Oc3ccc(C(C)(C)C)cc3)c2)cc1]
469(1)
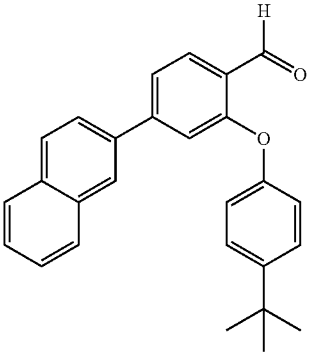 [SMILES: CC(C)(C)c1ccc(Oc2cc(-c3ccc4ccccc4c3)ccc2C=O)cc1]
471(1)
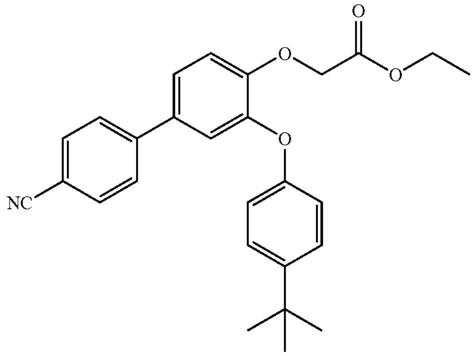
472(1)
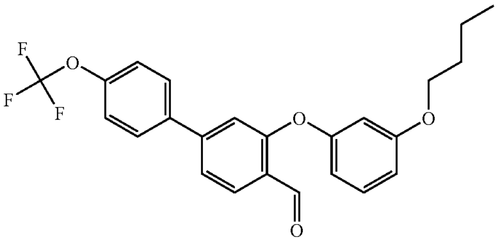 [SMILES: CCCCOc1cccc(Oc2cc(-c3ccc(OC(F)(F)F)cc3)ccc2C=O)c1]
472(2)
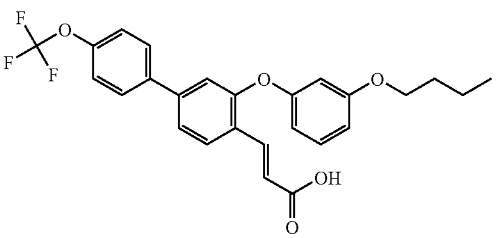 [SMILES: CCCCOc1cccc(Oc2cc(-c3ccc(OC(F)(F)F)cc3)ccc2/C=C/C(=O)O)c1]
TABLE 4-77-continued
473(1)
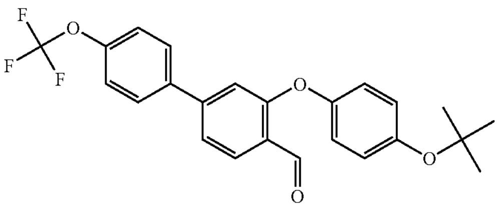 [SMILES: CC(C)(C)Oc1ccc(Oc2cc(-c3ccc(OC(F)(F)F)cc3)ccc2C=O)cc1]
473(2)
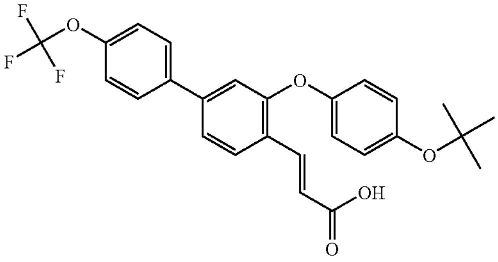 [SMILES: CC(C)(C)Oc1ccc(Oc2cc(-c3ccc(OC(F)(F)F)cc3)ccc2/C=C/C(=O)O)cc1]
474(1)
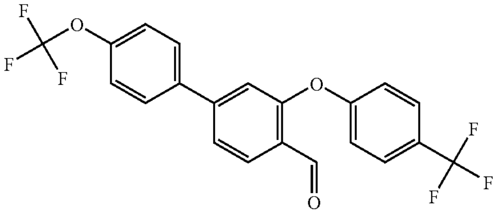 [SMILES: O=Cc1ccc(-c2ccc(OC(F)(F)F)cc2)cc1Oc1ccc(C(F)(F)F)cc1]
474(2)
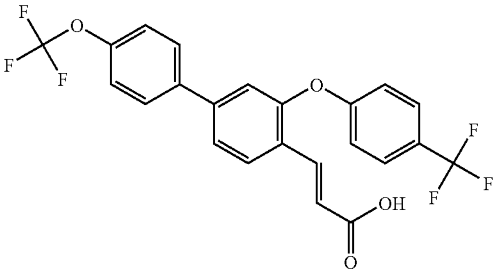 [SMILES: O=C(O)/C=C/c1ccc(-c2ccc(OC(F)(F)F)cc2)cc1Oc1ccc(C(F)(F)F)cc1]
475(1)
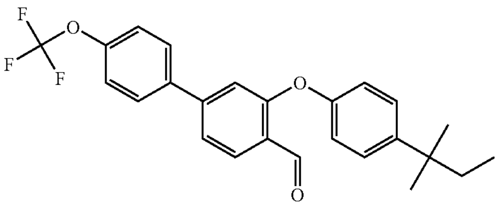 [SMILES: CCC(C)(C)c1ccc(Oc2cc(-c3ccc(OC(F)(F)F)cc3)ccc2C=O)cc1]
475(2)
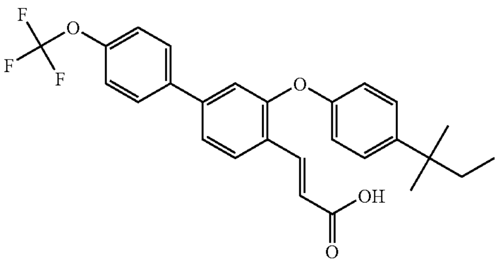 [SMILES: CCC(C)(C)c1ccc(Oc2cc(-c3ccc(OC(F)(F)F)cc3)ccc2/C=C/C(=O)O)cc1]

TABLE 4-77-continued
476(1) 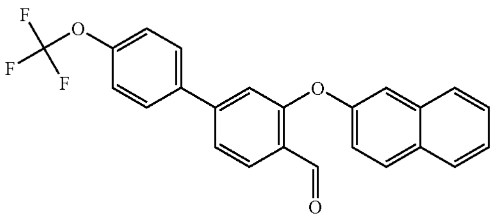 [SMILES: O=Cc1ccc(-c2ccc(OC(F)(F)F)cc2)cc1Oc1ccc2ccccc2c1]
TABLE 4-78
476(2) 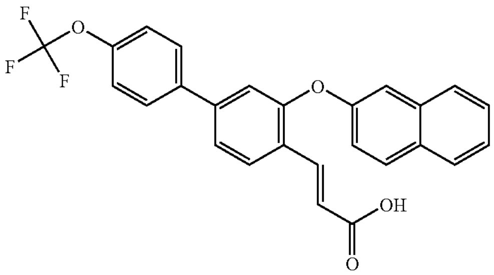 [SMILES: O=C(O)/C=C/c1ccc(-c2ccc(OC(F)(F)F)cc2)cc1Oc1ccc2ccccc2c1]
477(1) 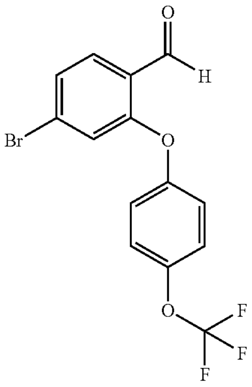 [SMILES: O=Cc1ccc(Br)cc1Oc1ccc(OC(F)(F)F)cc1]
477(2) 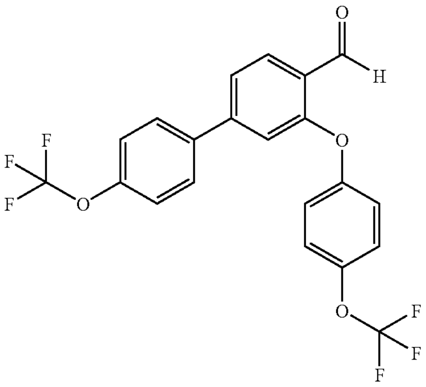 [SMILES: O=Cc1ccc(-c2ccc(OC(F)(F)F)cc2)cc1Oc1ccc(OC(F)(F)F)cc1]
TABLE 4-78-continued
478(1) 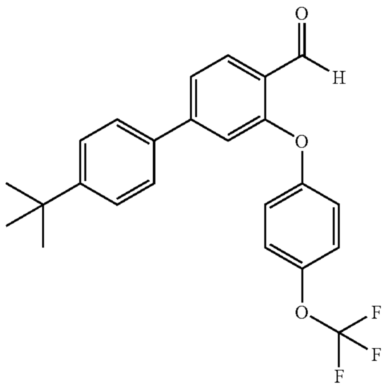 [SMILES: CC(C)(C)c1ccc(-c2ccc(C=O)c(Oc3ccc(OC(F)(F)F)cc3)c2)cc1]
481(1) 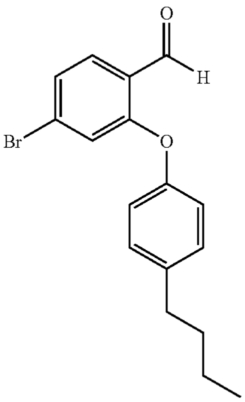 [SMILES: CCCCc1ccc(Oc2cc(Br)ccc2C=O)cc1]
481(2) 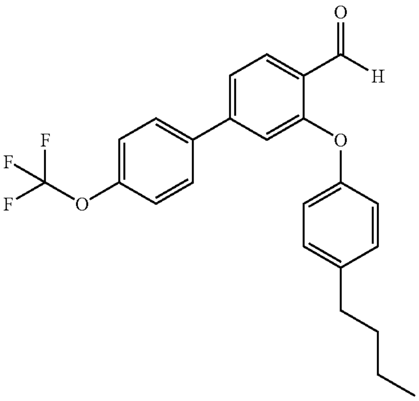 [SMILES: CCCCc1ccc(Oc2cc(-c3ccc(OC(F)(F)F)cc3)ccc2C=O)cc1]

TABLE 4-78-continued
| | |
|---|---|
| 481(3) | 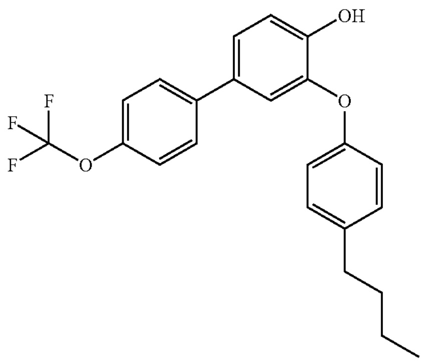 [SMILES: CCCCc1ccc(Oc2cc(-c3ccc(OC(F)(F)F)cc3)ccc2O)cc1] |
| 481(4) | 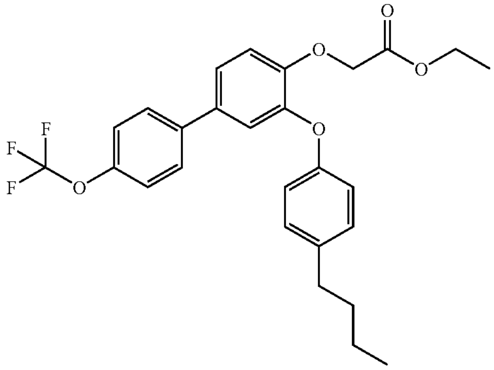 [SMILES: CCCCc1ccc(Oc2cc(-c3ccc(OC(F)(F)F)cc3)ccc2OCC(=O)OCC)cc1] |
TABLE 4-79
| | |
|---|---|
| 482(1) | 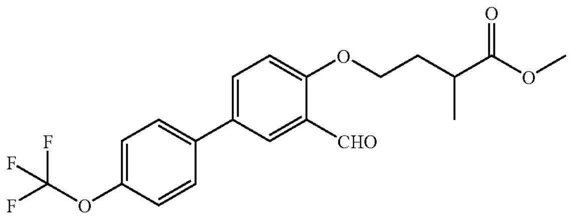 [SMILES: COC(=O)C(C)CCOc1ccc(-c2ccc(OC(F)(F)F)cc2)cc1C=O] |
| 482(2) | 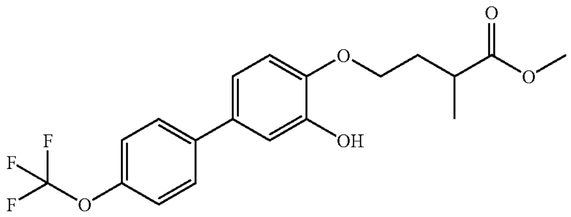 [SMILES: COC(=O)C(C)CCOc1ccc(-c2ccc(OC(F)(F)F)cc2)cc1O] |
| 482(3) | 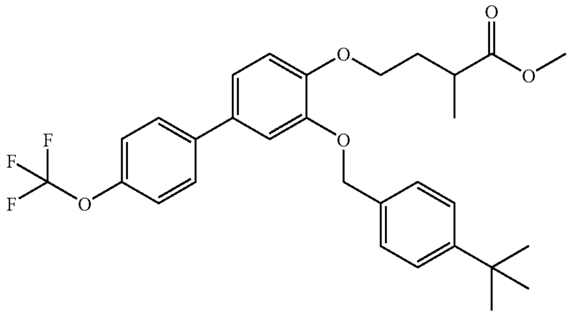 [SMILES: COC(=O)C(C)CCOc1ccc(-c2ccc(OC(F)(F)F)cc2)cc1OCc1ccc(C(C)(C)C)cc1] |
| 483(1) | 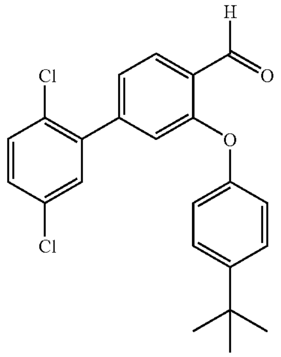 [SMILES: CC(C)(C)c1ccc(Oc2cc(-c3cc(Cl)ccc3Cl)ccc2C=O)cc1] |

TABLE 4-79-continued
485(1)
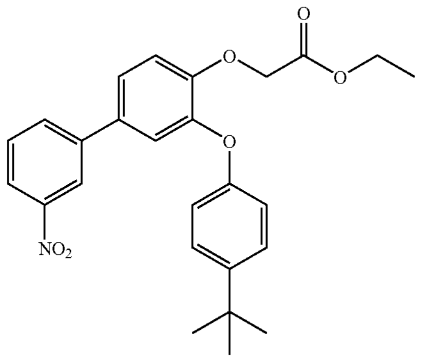 [SMILES: CCOC(=O)COc1ccc(-c2cccc([N+](=O)[O-])c2)cc1Oc1ccc(C(C)(C)C)cc1]
486(1)
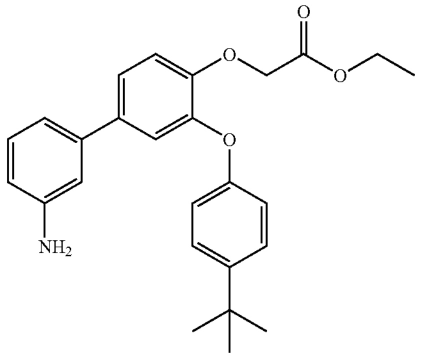 [SMILES: CCOC(=O)COc1ccc(-c2cccc(N)c2)cc1Oc1ccc(C(C)(C)C)cc1]
487(1)
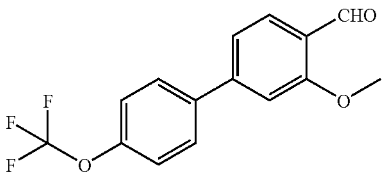 [SMILES: COc1cc(-c2ccc(OC(F)(F)F)cc2)ccc1C=O]
487(2)
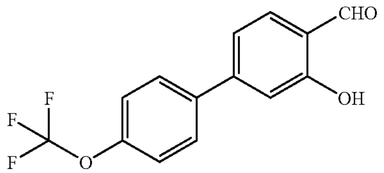 [SMILES: O=Cc1ccc(-c2ccc(OC(F)(F)F)cc2)cc1O]
487(3)
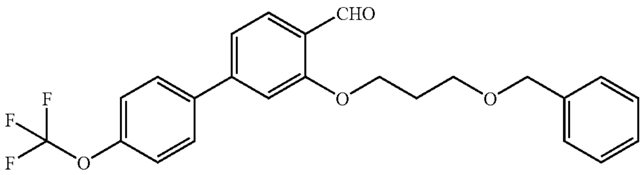 [SMILES: O=Cc1ccc(-c2ccc(OC(F)(F)F)cc2)cc1OCCCOCc1ccccc1]
489(1)
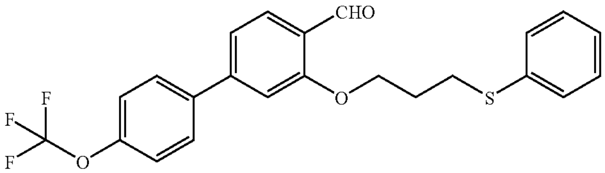 [SMILES: O=Cc1ccc(-c2ccc(OC(F)(F)F)cc2)cc1OCCCSc1ccccc1]

TABLE 4-79-continued
490(1)
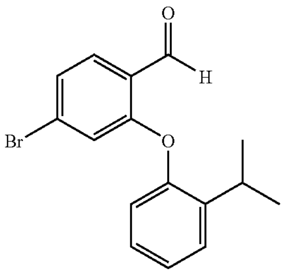 [SMILES: CC(C)c1ccccc1Oc1cc(Br)ccc1C=O]
490(2)
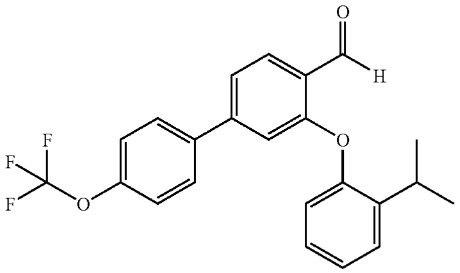 [SMILES: CC(C)c1ccccc1Oc1cc(-c2ccc(OC(F)(F)F)cc2)ccc1C=O]
TABLE 4-80
492(1)
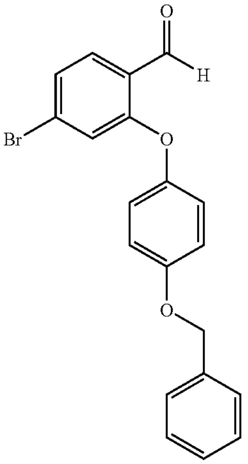 [SMILES: O=Cc1ccc(Br)cc1Oc1ccc(OCc2ccccc2)cc1]
492(2)
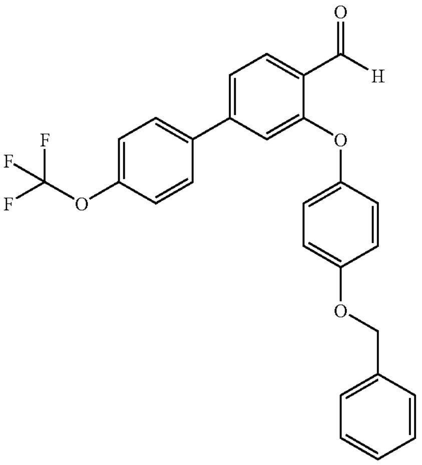 [SMILES: O=Cc1ccc(-c2ccc(OC(F)(F)F)cc2)cc1Oc1ccc(OCc2ccccc2)cc1]
TABLE 4-80-continued
492(3)
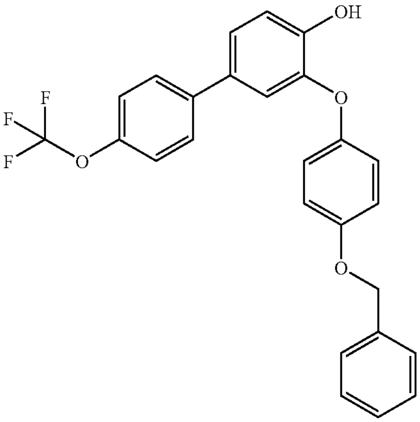 [SMILES: Oc1ccc(-c2ccc(OC(F)(F)F)cc2)cc1Oc1ccc(OCc2ccccc2)cc1]
492(4)
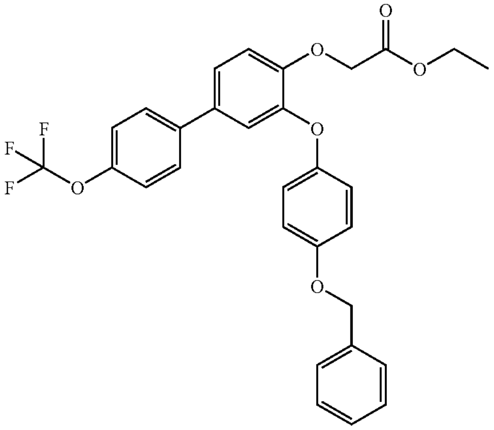 [SMILES: CCOC(=O)COc1ccc(-c2ccc(OC(F)(F)F)cc2)cc1Oc1ccc(OCc2ccccc2)cc1]

TABLE 4-80-continued
494(1)
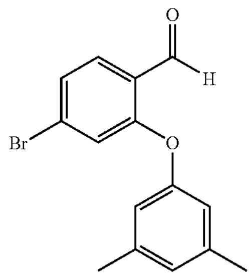 [SMILES: Cc1cc(C)cc(Oc2cc(Br)ccc2C=O)c1]
494(2)
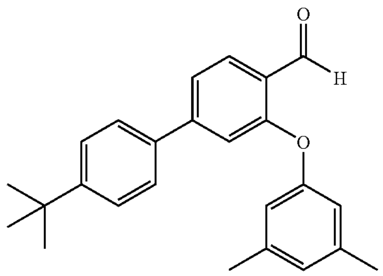 [SMILES: Cc1cc(C)cc(Oc2cc(-c3ccc(C(C)(C)C)cc3)ccc2C=O)c1]
495(1)
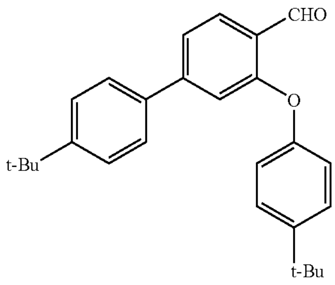 [SMILES: CC(C)(C)c1ccc(Oc2cc(-c3ccc(C(C)(C)C)cc3)ccc2C=O)cc1]
496(1)
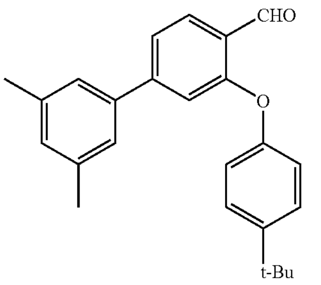 [SMILES: Cc1cc(C)cc(-c2ccc(C=O)c(Oc3ccc(C(C)(C)C)cc3)c2)c1]
TABLE 4-81
500(1)
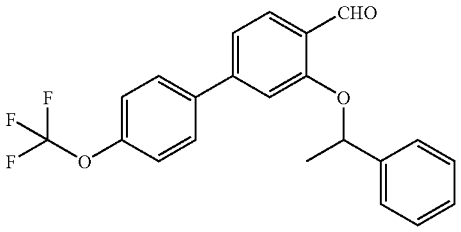 [SMILES: CC(Oc1cc(-c2ccc(OC(F)(F)F)cc2)ccc1C=O)c1ccccc1]
502(1)
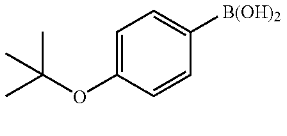
TABLE 4-81-continued
502(2)
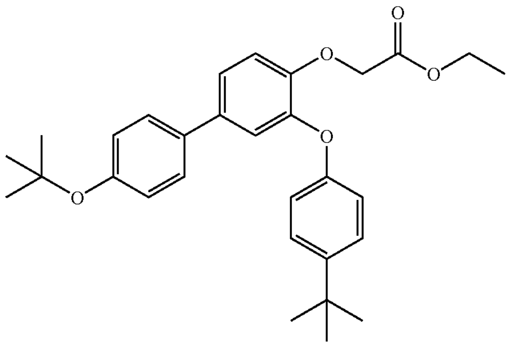 [SMILES: CCOC(=O)COc1ccc(-c2ccc(OC(C)(C)C)cc2)cc1Oc1ccc(C(C)(C)C)cc1]
503(1)
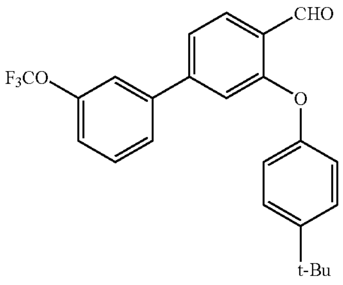 [SMILES: CC(C)(C)c1ccc(Oc2cc(-c3cccc(OC(F)(F)F)c3)ccc2C=O)cc1]
505(1)
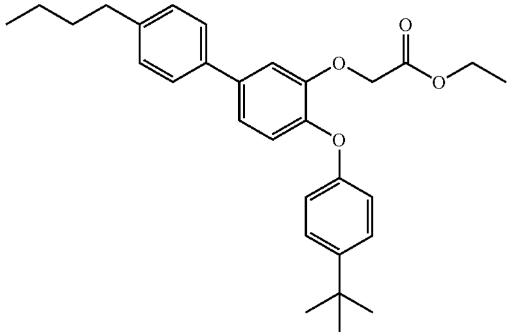 [SMILES: CCCCc1ccc(-c2ccc(Oc3ccc(C(C)(C)C)cc3)c(OCC(=O)OCC)c2)cc1]
506(1)
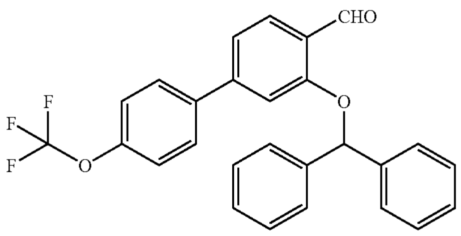 [SMILES: O=Cc1ccc(-c2ccc(OC(F)(F)F)cc2)cc1OC(c1ccccc1)c1ccccc1]
509(1)
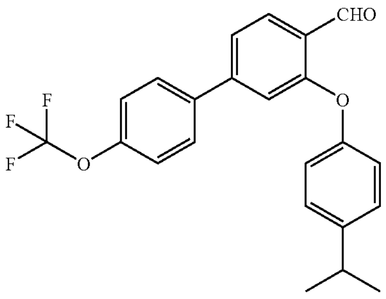 [SMILES: CC(C)c1ccc(Oc2cc(-c3ccc(OC(F)(F)F)cc3)ccc2C=O)cc1]

TABLE 4-81-continued
511(1)
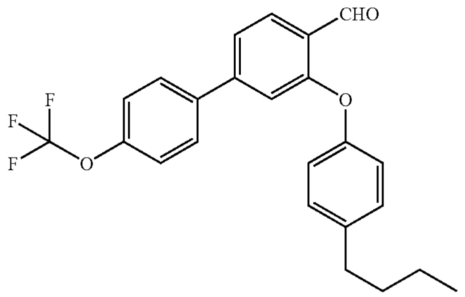 [SMILES: CCCCc1ccc(Oc2cc(-c3ccc(OC(F)(F)F)cc3)ccc2C=O)cc1]
513(1)
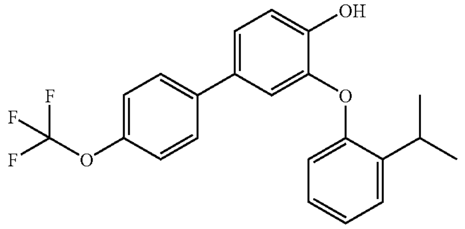 [SMILES: CC(C)c1ccccc1Oc1cc(-c2ccc(OC(F)(F)F)cc2)ccc1O]
TABLE 4-82
513(2)
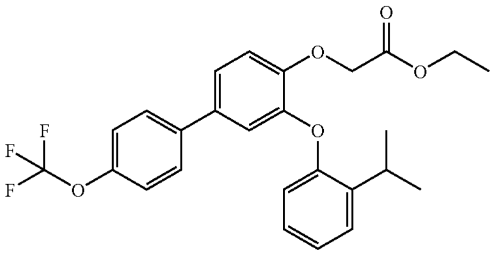 [SMILES: CCOC(=O)COc1ccc(-c2ccc(OC(F)(F)F)cc2)cc1Oc1ccccc1C(C)C]
514(1)
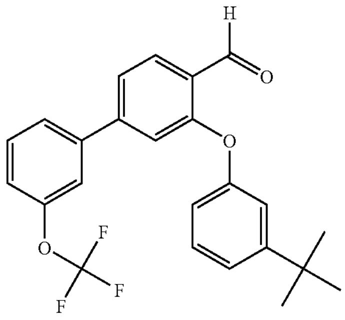 [SMILES: CC(C)(C)c1cccc(Oc2cc(-c3cccc(OC(F)(F)F)c3)ccc2C=O)c1]
516(1)
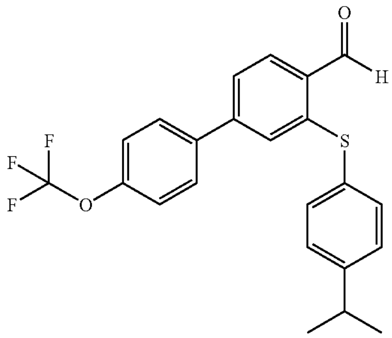 [SMILES: CC(C)c1ccc(Sc2cc(-c3ccc(OC(F)(F)F)cc3)ccc2C=O)cc1]
TABLE 4-82-continued
518(1)
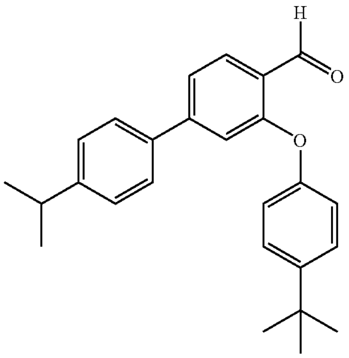 [SMILES: CC(C)c1ccc(-c2ccc(C=O)c(Oc3ccc(C(C)(C)C)cc3)c2)cc1]
520(1)
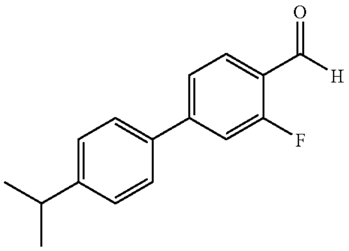 [SMILES: CC(C)c1ccc(-c2ccc(C=O)c(F)c2)cc1]
520(2)
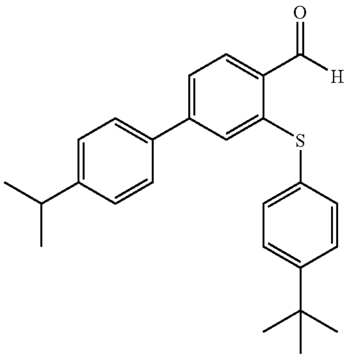 [SMILES: CC(C)c1ccc(-c2ccc(C=O)c(Sc3ccc(C(C)(C)C)cc3)c2)cc1]
521(1)
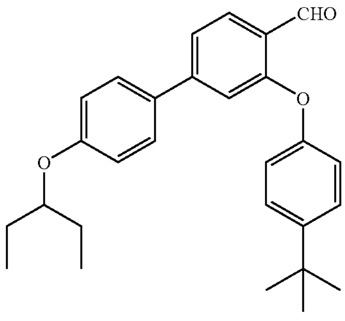 [SMILES: CCC(CC)Oc1ccc(-c2ccc(C=O)c(Oc3ccc(C(C)(C)C)cc3)c2)cc1]
523(1)
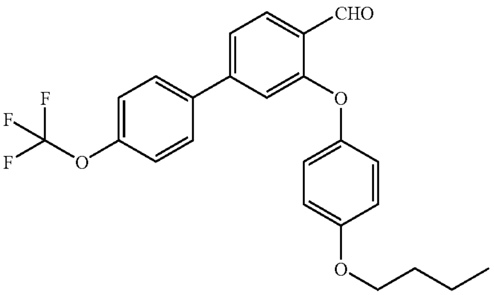

TABLE 4-83
523(2)
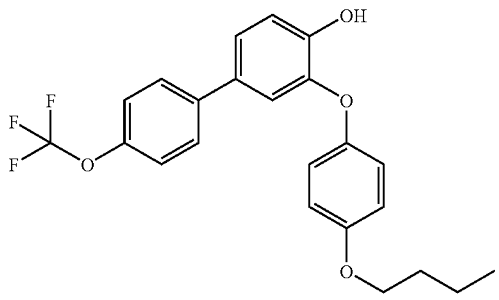 [SMILES: CCCCOc1ccc(Oc2cc(-c3ccc(OC(F)(F)F)cc3)ccc2O)cc1]
523(3)
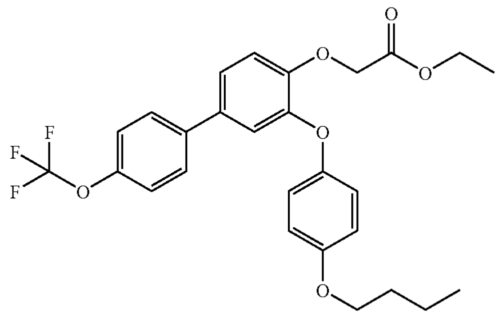 [SMILES: CCCCOc1ccc(Oc2cc(-c3ccc(OC(F)(F)F)cc3)ccc2OCC(=O)OCC)cc1]
524(1)
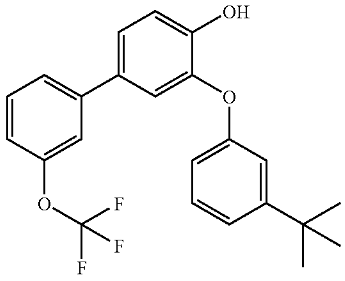 [SMILES: CC(C)(C)c1cccc(Oc2cc(-c3cccc(OC(F)(F)F)c3)ccc2O)c1]
524(2)
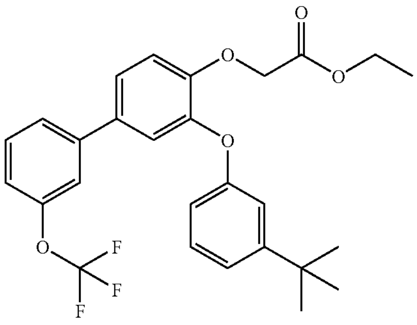 [SMILES: CCOC(=O)COc1ccc(-c2cccc(OC(F)(F)F)c2)cc1Oc1cccc(C(C)(C)C)c1]
525(1)
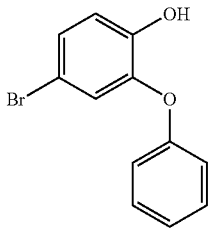 [SMILES: Oc1ccc(Br)cc1Oc1ccccc1]
TABLE 4-83-continued
525(2)
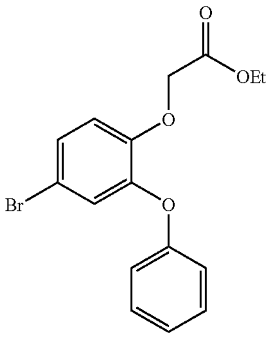 [SMILES: CCOC(=O)COc1ccc(Br)cc1Oc1ccccc1]
525(3)
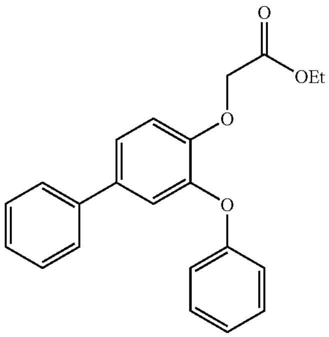 [SMILES: CCOC(=O)COc1ccc(-c2ccccc2)cc1Oc1ccccc1]
526(1)
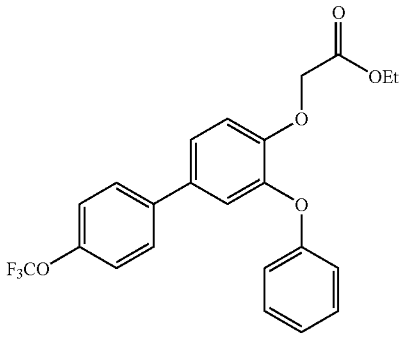 [SMILES: CCOC(=O)COc1ccc(-c2ccc(OC(F)(F)F)cc2)cc1Oc1ccccc1]
527(1)
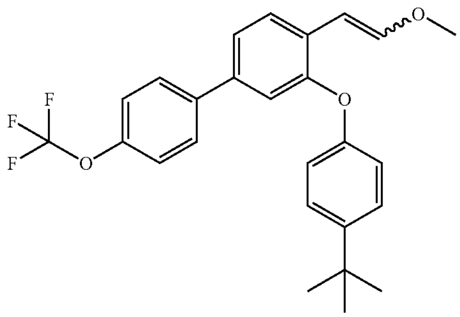 [SMILES: COC=Cc1ccc(-c2ccc(OC(F)(F)F)cc2)cc1Oc1ccc(C(C)(C)C)cc1]

TABLE 4-83-continued
527(2)
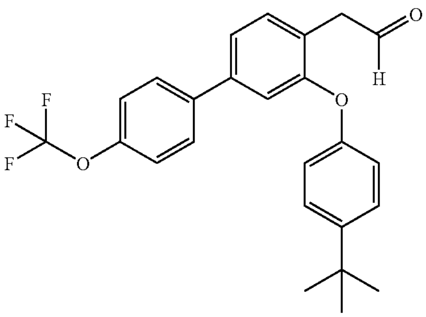 [SMILES: CC(C)(C)c1ccc(Oc2cc(-c3ccc(OC(F)(F)F)cc3)ccc2CC=O)cc1]
TABLE 4-84
527(3)
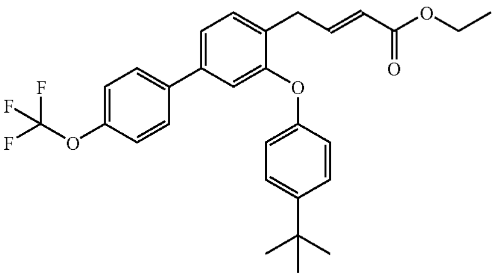 [SMILES: CCOC(=O)/C=C/Cc1ccc(-c2ccc(OC(F)(F)F)cc2)cc1Oc1ccc(C(C)(C)C)cc1]
527(4)
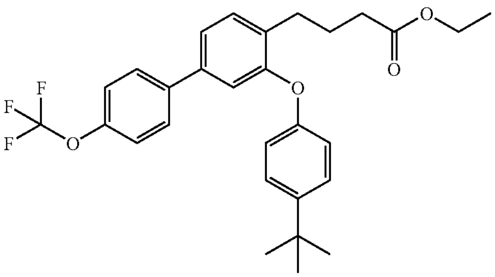 [SMILES: CCOC(=O)CCCc1ccc(-c2ccc(OC(F)(F)F)cc2)cc1Oc1ccc(C(C)(C)C)cc1]
528(1)
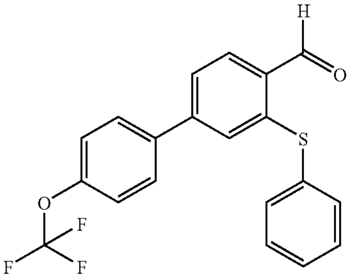 [SMILES: O=Cc1ccc(-c2ccc(OC(F)(F)F)cc2)cc1Sc1ccccc1]
TABLE 4-84-continued
529(1)
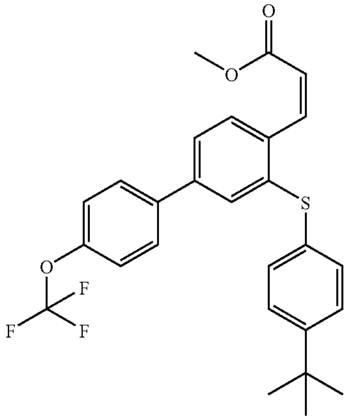 [SMILES: COC(=O)/C=C\c1ccc(-c2ccc(OC(F)(F)F)cc2)cc1Sc1ccc(C(C)(C)C)cc1]
530(1)
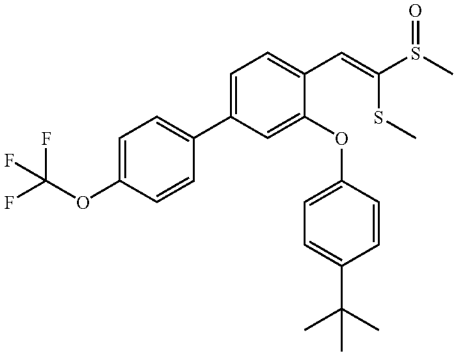 [SMILES: CS/C(=C\c1ccc(-c2ccc(OC(F)(F)F)cc2)cc1Oc1ccc(C(C)(C)C)cc1)S(C)=O]
530(2)
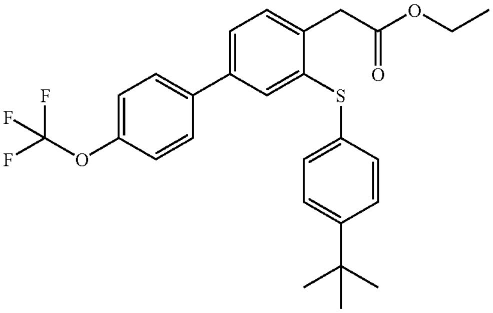 [SMILES: CCOC(=O)Cc1ccc(-c2ccc(OC(F)(F)F)cc2)cc1Sc1ccc(C(C)(C)C)cc1]
531(1)
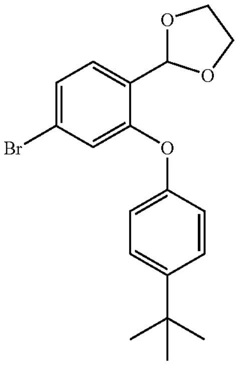 [SMILES: CC(C)(C)c1ccc(Oc2cc(Br)ccc2C2OCCO2)cc1]

TABLE 4-84-continued
531(2)
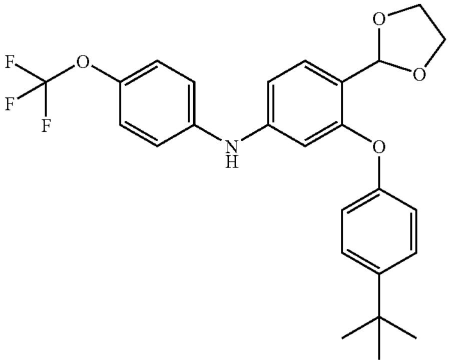 [SMILES: CC(C)(C)c1ccc(Oc2cc(Nc3ccc(OC(F)(F)F)cc3)ccc2C2OCCO2)cc1]
TABLE 4-85
531(3)
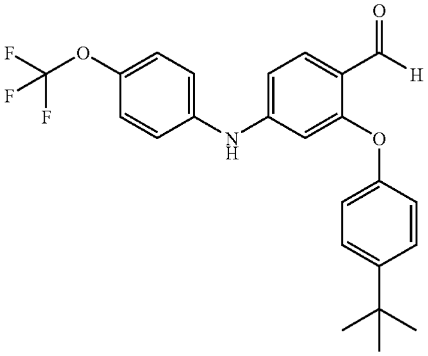 [SMILES: CC(C)(C)c1ccc(Oc2cc(Nc3ccc(OC(F)(F)F)cc3)ccc2C=O)cc1]
533(1)
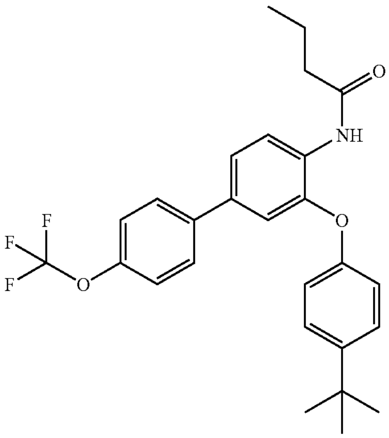 [SMILES: CCCC(=O)Nc1ccc(-c2ccc(OC(F)(F)F)cc2)cc1Oc1ccc(C(C)(C)C)cc1]
533(2)
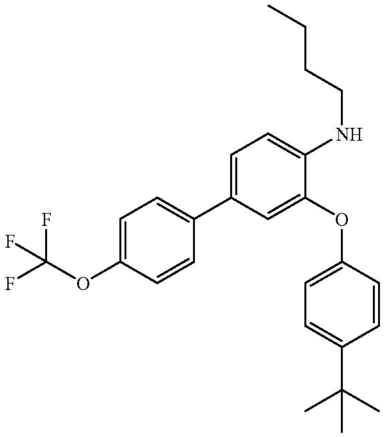 [SMILES: CCCCNc1ccc(-c2ccc(OC(F)(F)F)cc2)cc1Oc1ccc(C(C)(C)C)cc1]
TABLE 4-85-continued
533(3)
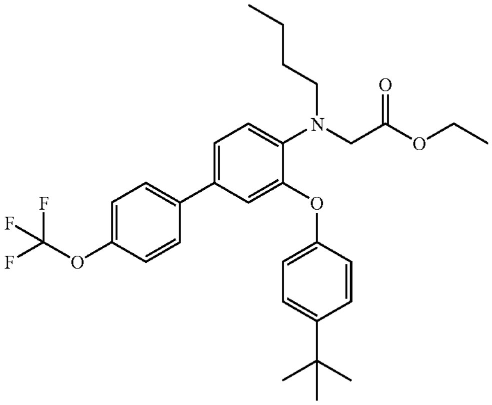 [SMILES: CCCCN(CC(=O)OCC)c1ccc(-c2ccc(OC(F)(F)F)cc2)cc1Oc1ccc(C(C)(C)C)cc1]
534(1)
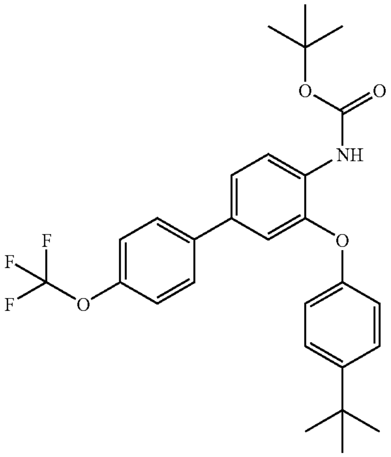 [SMILES: CC(C)(C)OC(=O)Nc1ccc(-c2ccc(OC(F)(F)F)cc2)cc1Oc1ccc(C(C)(C)C)cc1]
534(2)
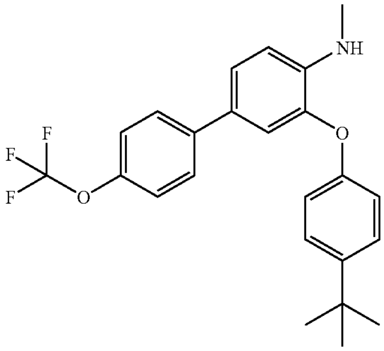 [SMILES: CNc1ccc(-c2ccc(OC(F)(F)F)cc2)cc1Oc1ccc(C(C)(C)C)cc1]

TABLE 4-86
534(3)
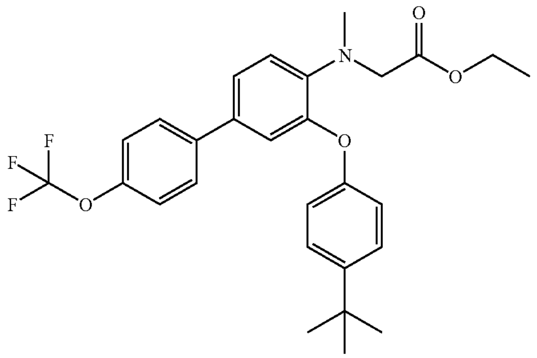 [SMILES: CCOC(=O)CN(C)c1ccc(-c2ccc(OC(F)(F)F)cc2)cc1Oc1ccc(C(C)(C)C)cc1]
535(1)
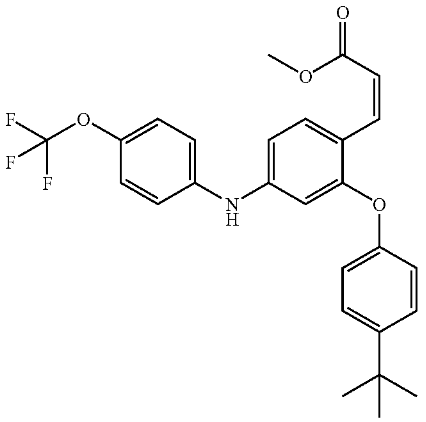 [SMILES: COC(=O)/C=C\c1ccc(Nc2ccc(OC(F)(F)F)cc2)cc1Oc1ccc(C(C)(C)C)cc1]
536(1)
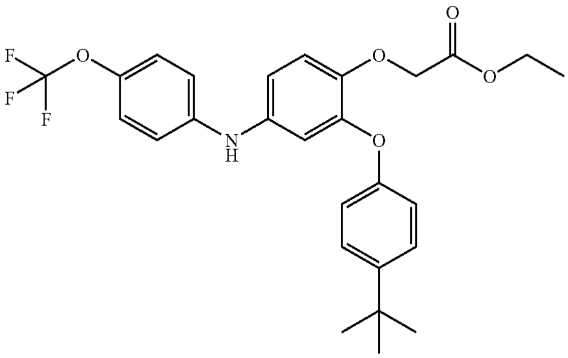 [SMILES: CCOC(=O)COc1ccc(Nc2ccc(OC(F)(F)F)cc2)cc1Oc1ccc(C(C)(C)C)cc1]
537(1)
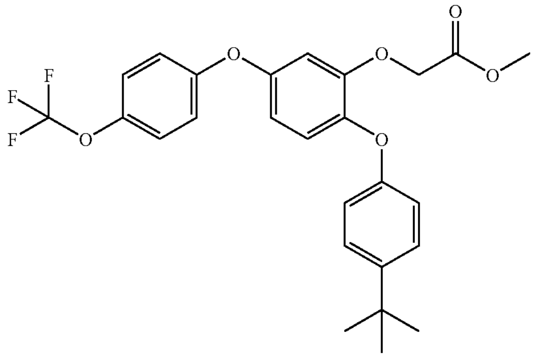 [SMILES: COC(=O)COc1cc(Oc2ccc(OC(F)(F)F)cc2)ccc1Oc1ccc(C(C)(C)C)cc1]

TABLE 4-86-continued
538(1)
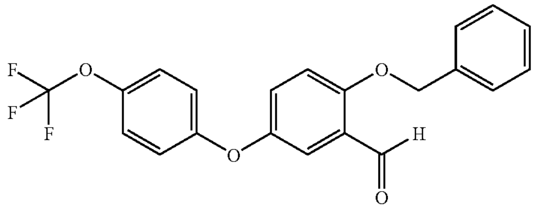 [SMILES: O=Cc1cc(Oc2ccc(OC(F)(F)F)cc2)ccc1OCc1ccccc1]
538(2)
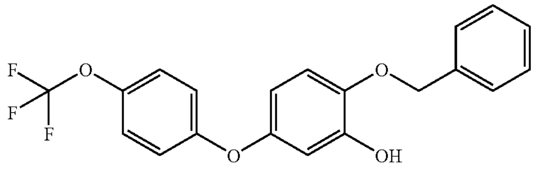 [SMILES: Oc1cc(Oc2ccc(OC(F)(F)F)cc2)ccc1OCc1ccccc1]
538(3)
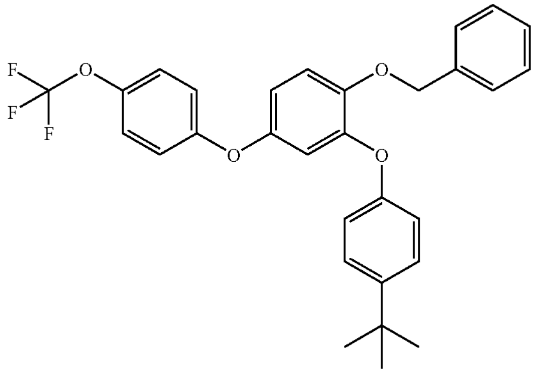 [SMILES: CC(C)(C)c1ccc(Oc2cc(Oc3ccc(OC(F)(F)F)cc3)ccc2OCc2ccccc2)cc1]
538(4)
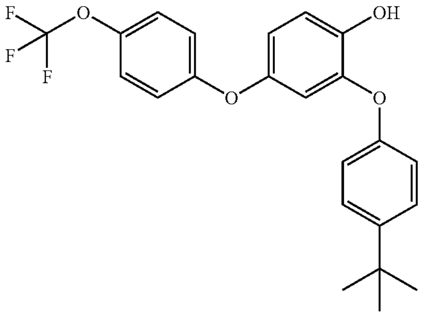 [SMILES: CC(C)(C)c1ccc(Oc2cc(Oc3ccc(OC(F)(F)F)cc3)ccc2O)cc1]
538(5)
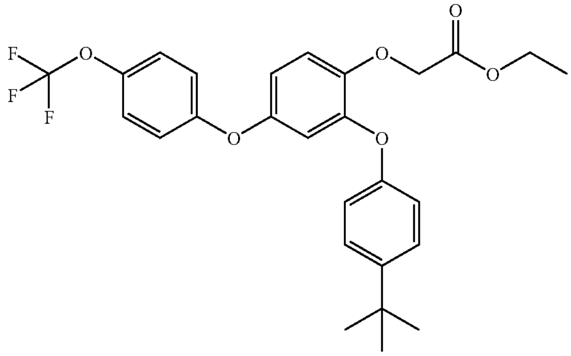 [SMILES: CCOC(=O)COc1ccc(Oc2ccc(OC(F)(F)F)cc2)cc1Oc1ccc(C(C)(C)C)cc1]

TABLE 4-86-continued
540(1)
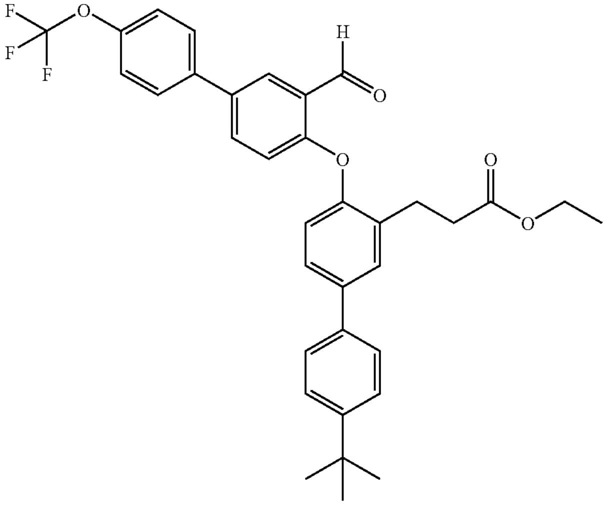 [SMILES: CCOC(=O)CCc1cc(-c2ccc(C(C)(C)C)cc2)ccc1Oc1ccc(-c2ccc(OC(F)(F)F)cc2)cc1C=O]
TABLE 4-87
540(2)
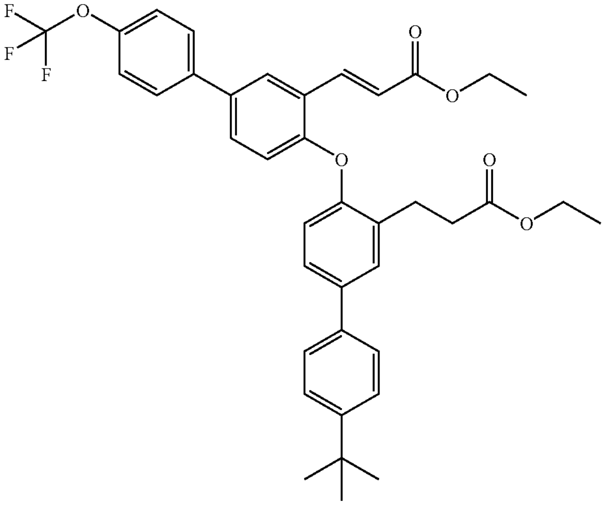 [SMILES: CCOC(=O)/C=C/c1cc(-c2ccc(OC(F)(F)F)cc2)ccc1Oc1ccc(-c2ccc(C(C)(C)C)cc2)cc1CCC(=O)OCC]
542(1)
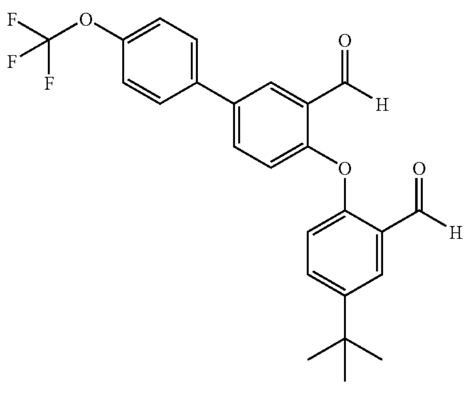 [SMILES: CC(C)(C)c1ccc(Oc2ccc(-c3ccc(OC(F)(F)F)cc3)cc2C=O)c(C=O)c1]

TABLE 4-87-continued
542(2)
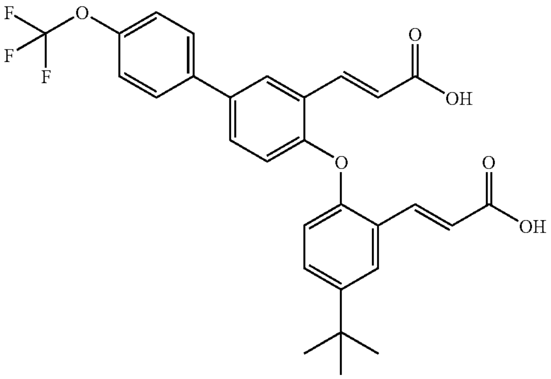 [SMILES: CC(C)(C)c1ccc(Oc2ccc(-c3ccc(OC(F)(F)F)cc3)cc2/C=C/C(=O)O)c(/C=C/C(=O)O)c1]
543(1)
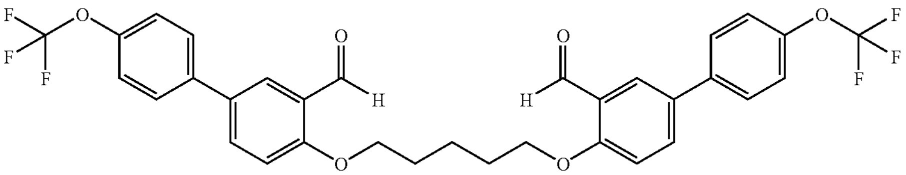 [SMILES: O=Cc1cc(-c2ccc(OC(F)(F)F)cc2)ccc1OCCCCCOc1ccc(-c2ccc(OC(F)(F)F)cc2)cc1C=O]
545(1)
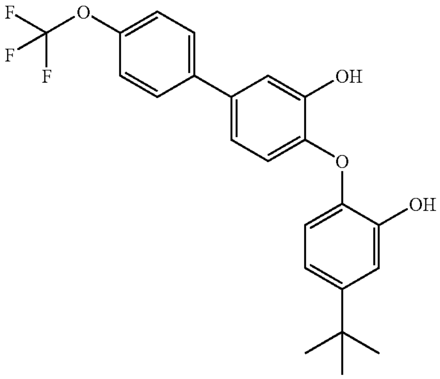 [SMILES: CC(C)(C)c1ccc(Oc2ccc(-c3ccc(OC(F)(F)F)cc3)cc2O)c(O)c1]
545(2)
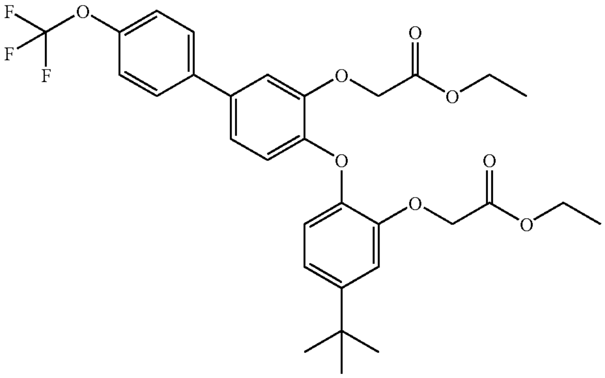 [SMILES: CCOC(=O)COc1cc(-c2ccc(OC(F)(F)F)cc2)ccc1Oc1ccc(C(C)(C)C)cc1OCC(=O)OCC]
547(1)
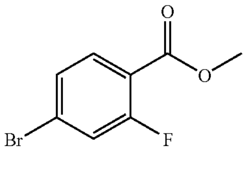

TABLE 4-87-continued
547(2)
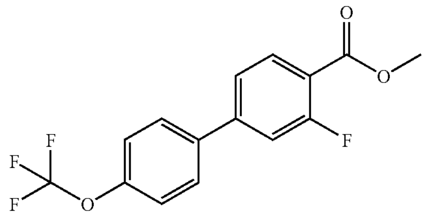 [SMILES: COC(=O)c1ccc(-c2ccc(OC(F)(F)F)cc2)cc1F]
TABLE 4-88
547(3)
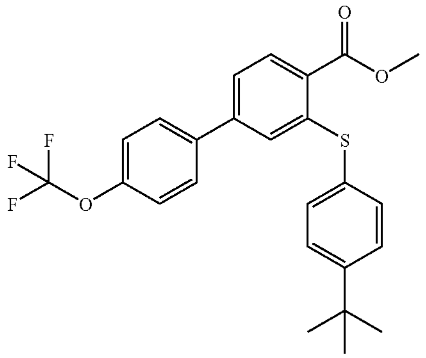 [SMILES: COC(=O)c1ccc(-c2ccc(OC(F)(F)F)cc2)cc1Sc1ccc(C(C)(C)C)cc1]
548(1)
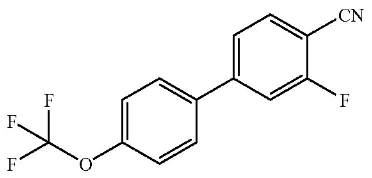 [SMILES: N#Cc1ccc(-c2ccc(OC(F)(F)F)cc2)cc1F]
548(2)
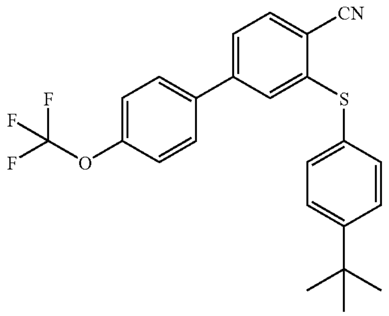 [SMILES: CC(C)(C)c1ccc(Sc2cc(-c3ccc(OC(F)(F)F)cc3)ccc2C#N)cc1]
548(3)
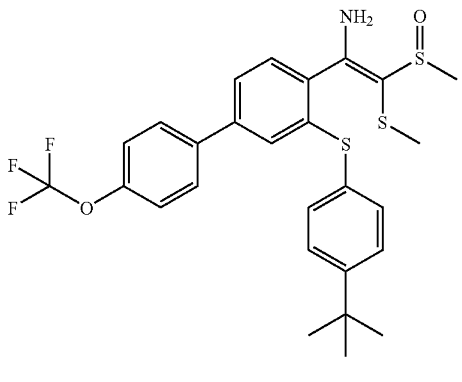 [SMILES: CS/C(=C(/N)c1ccc(-c2ccc(OC(F)(F)F)cc2)cc1Sc1ccc(C(C)(C)C)cc1)S(C)=O]
TABLE 4-88-continued
548(4)
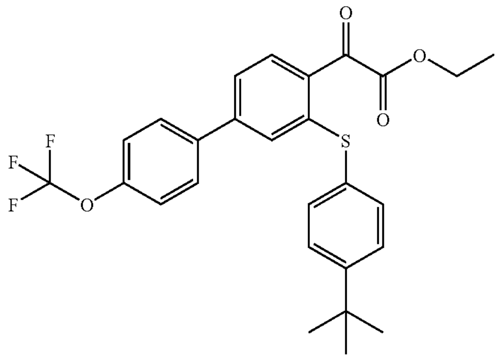 [SMILES: CCOC(=O)C(=O)c1ccc(-c2ccc(OC(F)(F)F)cc2)cc1Sc1ccc(C(C)(C)C)cc1]
549(1)
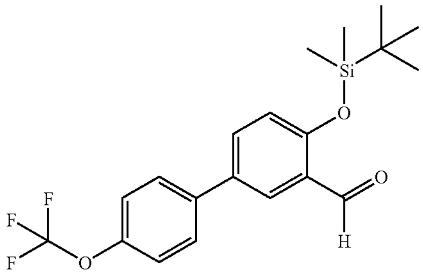 [SMILES: CC(C)(C)[Si](C)(C)Oc1ccc(-c2ccc(OC(F)(F)F)cc2)cc1C=O]
549(2)
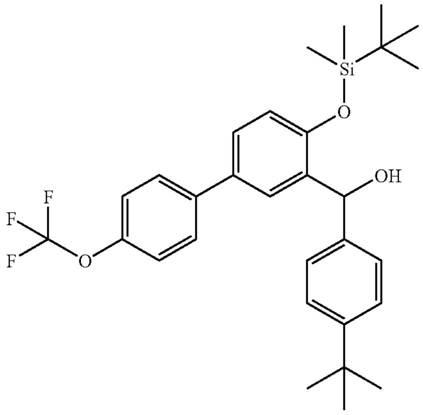 [SMILES: CC(C)(C)c1ccc(C(O)c2cc(-c3ccc(OC(F)(F)F)cc3)ccc2O[Si](C)(C)C(C)(C)C)cc1]

TABLE 4-88-continued
| | |
|---|---|
| 549(3) | 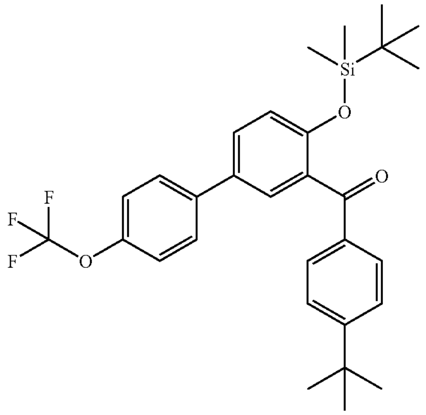 [SMILES: CC(C)(C)c1ccc(C(=O)c2cc(-c3ccc(OC(F)(F)F)cc3)ccc2O[Si](C)(C)C(C)(C)C)cc1] |
TABLE 4-89
| | |
|---|---|
| 549(4) | 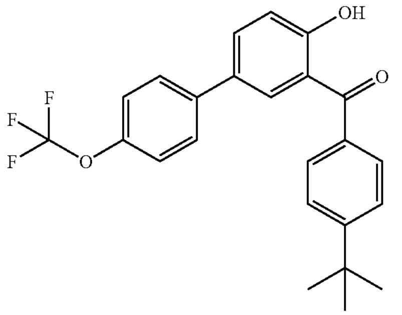 [SMILES: CC(C)(C)c1ccc(C(=O)c2cc(-c3ccc(OC(F)(F)F)cc3)ccc2O)cc1] |
| 549(5) | 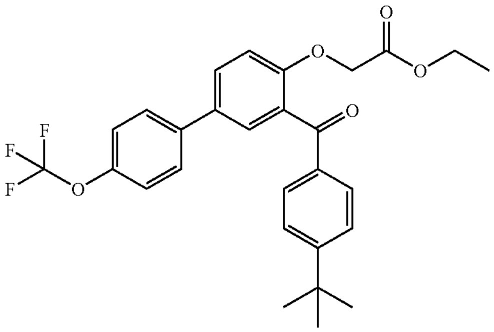 [SMILES: CCOC(=O)COc1ccc(-c2ccc(OC(F)(F)F)cc2)cc1C(=O)c1ccc(C(C)(C)C)cc1] |
TABLE 4-89-continued
| | |
|---|---|
| 551(1) | 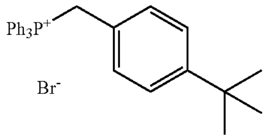 |
| 551(2) | 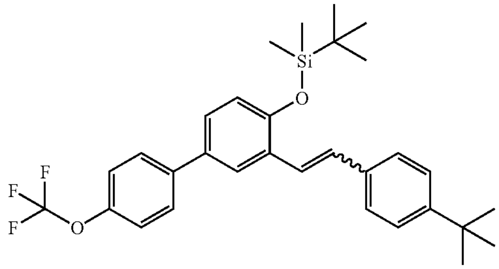 [SMILES: CC(C)(C)c1ccc(C=Cc2cc(-c3ccc(OC(F)(F)F)cc3)ccc2O[Si](C)(C)C(C)(C)C)cc1] |
| 551(3) | 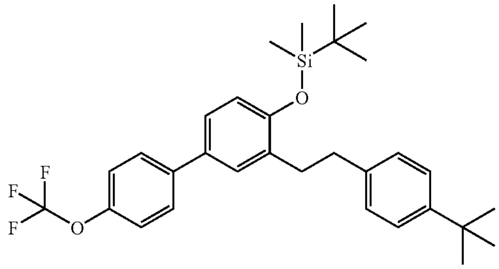 [SMILES: CC(C)(C)c1ccc(CCc2cc(-c3ccc(OC(F)(F)F)cc3)ccc2O[Si](C)(C)C(C)(C)C)cc1] |
| 551(4) | 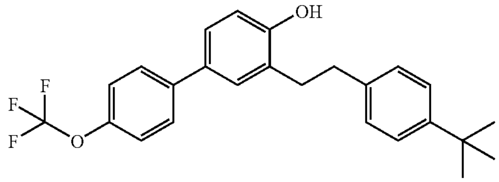 [SMILES: CC(C)(C)c1ccc(CCc2cc(-c3ccc(OC(F)(F)F)cc3)ccc2O)cc1] |
| 551(5) | 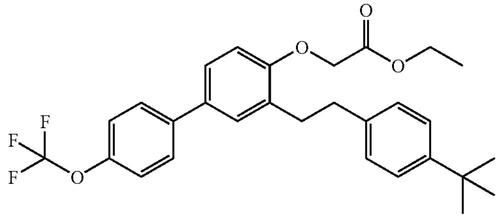 [SMILES: CCOC(=O)COc1ccc(-c2ccc(OC(F)(F)F)cc2)cc1CCc1ccc(C(C)(C)C)cc1] |
TABLE 4-90
| | |
|---|---|
| 601(1) | 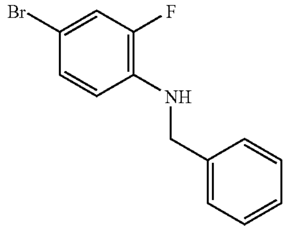 [SMILES: Fc1cc(Br)ccc1NCc1ccccc1] |

TABLE 4-90-continued
601(2)
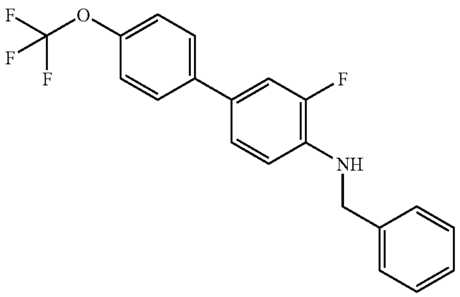 [SMILES: Fc1cc(-c2ccc(OC(F)(F)F)cc2)ccc1NCc1ccccc1]
601(3)
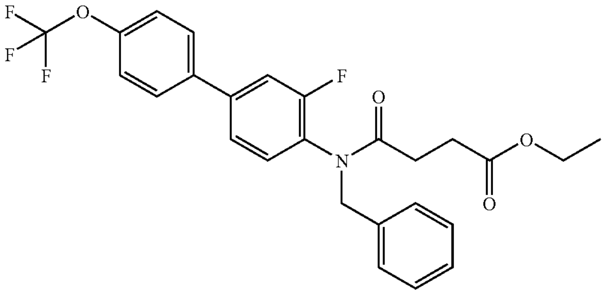 [SMILES: CCOC(=O)CCC(=O)N(Cc1ccccc1)c1ccc(-c2ccc(OC(F)(F)F)cc2)cc1F]
602(1)
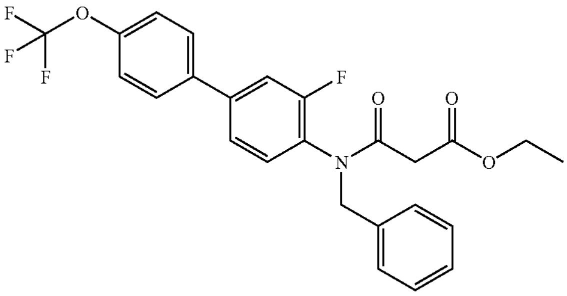 [SMILES: CCOC(=O)CC(=O)N(Cc1ccccc1)c1ccc(-c2ccc(OC(F)(F)F)cc2)cc1F]
603(1)
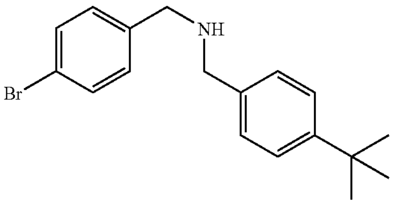 [SMILES: CC(C)(C)c1ccc(CNCc2ccc(Br)cc2)cc1]
603(2)
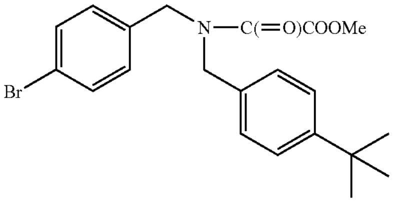
603(3)
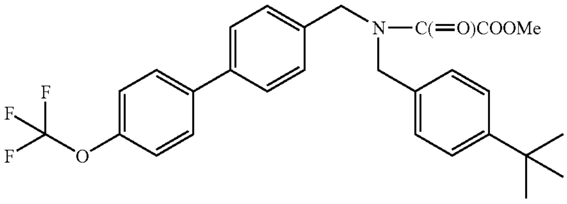

TABLE 4-90-continued
| | |
|---|---|
| 604(1) | 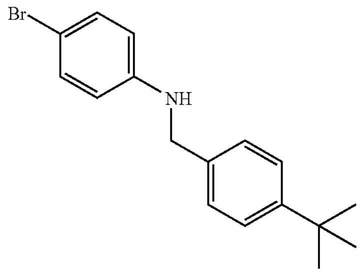 [SMILES: CC(C)(C)c1ccc(CNc2ccc(Br)cc2)cc1] |
| 604(2) | 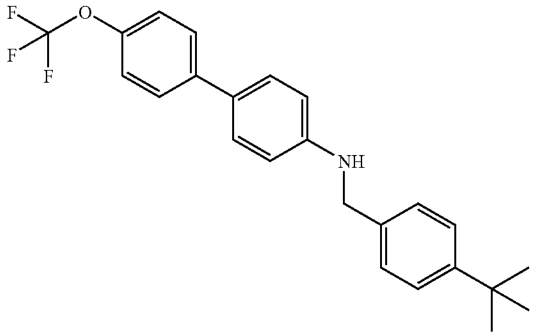 [SMILES: CC(C)(C)c1ccc(CNc2ccc(-c3ccc(OC(F)(F)F)cc3)cc2)cc1] |
| 604(3) | 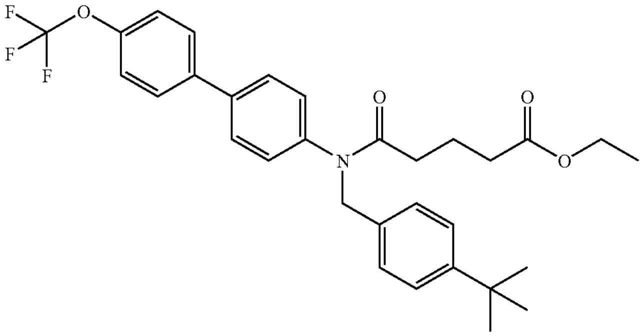 [SMILES: CCOC(=O)CCCC(=O)N(Cc1ccc(C(C)(C)C)cc1)c1ccc(-c2ccc(OC(F)(F)F)cc2)cc1] |
| 605(1) | 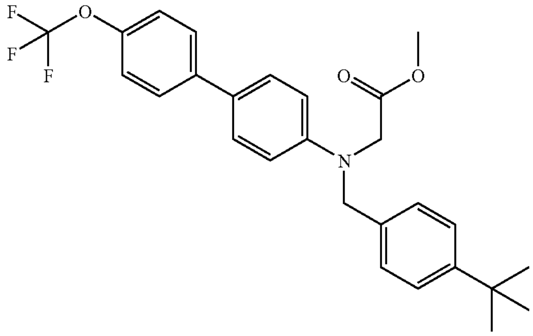 [SMILES: COC(=O)CN(Cc1ccc(C(C)(C)C)cc1)c1ccc(-c2ccc(OC(F)(F)F)cc2)cc1] |
| 606(1) | 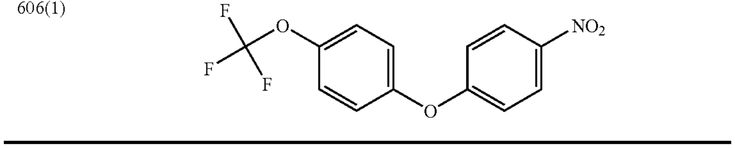 |

TABLE 4-91
606(2)
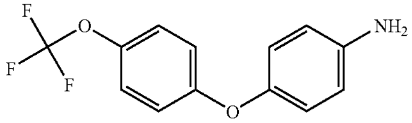 [SMILES: Nc1ccc(Oc2ccc(OC(F)(F)F)cc2)cc1]
606(3)
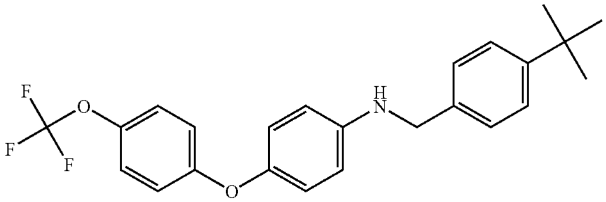 [SMILES: CC(C)(C)c1ccc(CNc2ccc(Oc3ccc(OC(F)(F)F)cc3)cc2)cc1]
606(4)
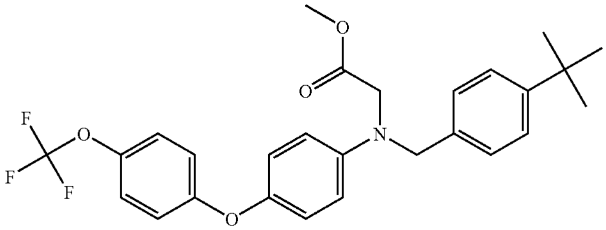 [SMILES: COC(=O)CN(Cc1ccc(C(C)(C)C)cc1)c1ccc(Oc2ccc(OC(F)(F)F)cc2)cc1]
607(1)
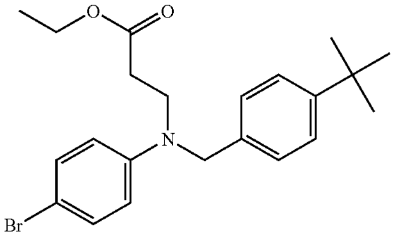 [SMILES: CCOC(=O)CCN(Cc1ccc(C(C)(C)C)cc1)c1ccc(Br)cc1]
607(2)
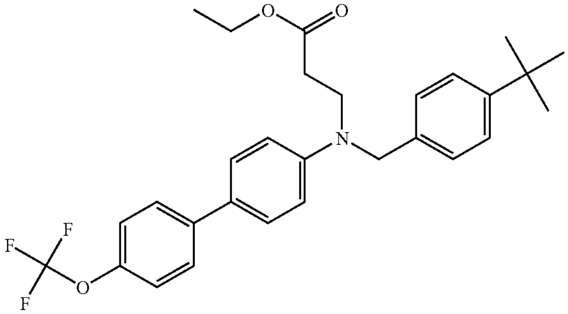 [SMILES: CCOC(=O)CCN(Cc1ccc(C(C)(C)C)cc1)c1ccc(-c2ccc(OC(F)(F)F)cc2)cc1]
608(1)
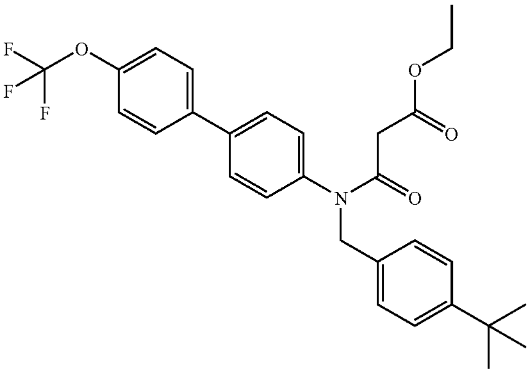 [SMILES: CCOC(=O)CC(=O)N(Cc1ccc(C(C)(C)C)cc1)c1ccc(-c2ccc(OC(F)(F)F)cc2)cc1]

TABLE 4-91-continued
| | |
|---|---|
| 609(1) | 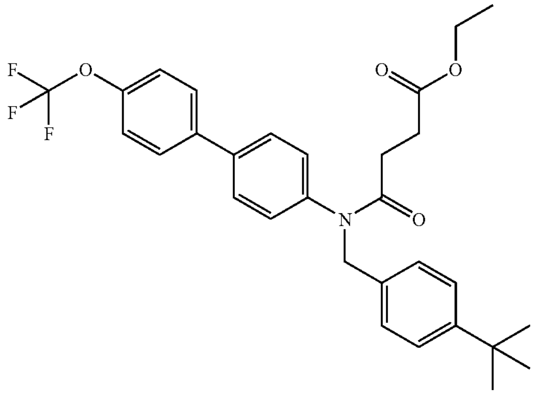 [SMILES: CCOC(=O)CCC(=O)N(Cc1ccc(C(C)(C)C)cc1)c1ccc(-c2ccc(OC(F)(F)F)cc2)cc1] |
| 610(1) | 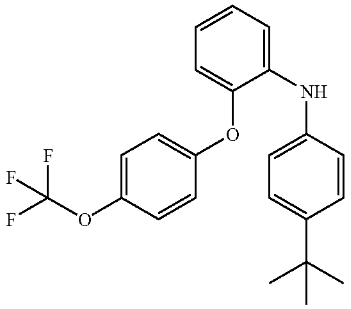 [SMILES: CC(C)(C)c1ccc(Nc2ccccc2Oc2ccc(OC(F)(F)F)cc2)cc1] |
| 610(2) | 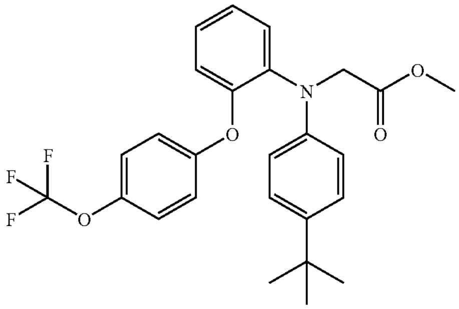 [SMILES: COC(=O)CN(c1ccc(C(C)(C)C)cc1)c1ccccc1Oc1ccc(OC(F)(F)F)cc1] |
| 611(1) | 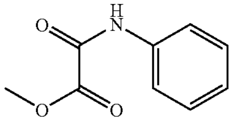 |
TABLE 4-92
| | |
|---|---|
| 611(2) | 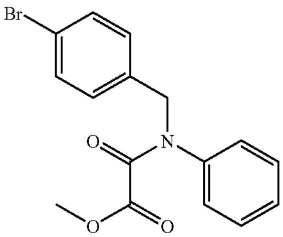 [SMILES: COC(=O)C(=O)N(Cc1ccc(Br)cc1)c1ccccc1] |
TABLE 4-92-continued
| | |
|---|---|
| 611(3) | 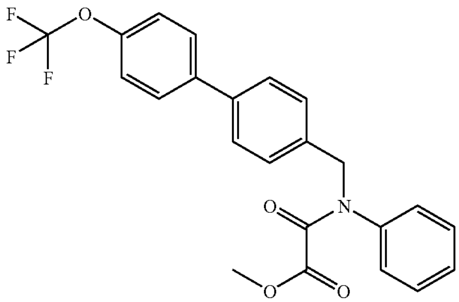 [SMILES: COC(=O)C(=O)N(Cc1ccc(-c2ccc(OC(F)(F)F)cc2)cc1)c1ccccc1] |

TABLE 4-92-continued
612(1)
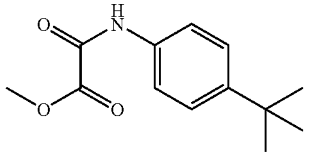 [SMILES: COC(=O)C(=O)Nc1ccc(C(C)(C)C)cc1]
612(2)
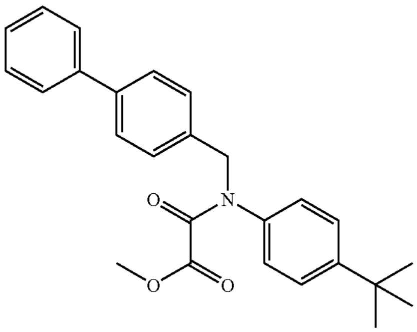 [SMILES: COC(=O)C(=O)N(Cc1ccc(-c2ccccc2)cc1)c1ccc(C(C)(C)C)cc1]
613(1)
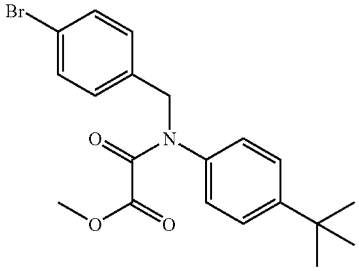 [SMILES: COC(=O)C(=O)N(Cc1ccc(Br)cc1)c1ccc(C(C)(C)C)cc1]
613(2)
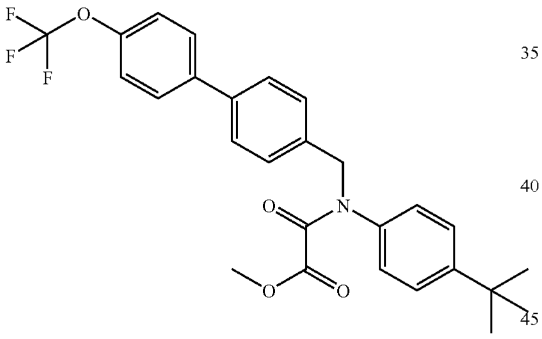
TABLE 4-92-continued
614(1)
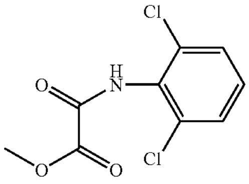
614(2)
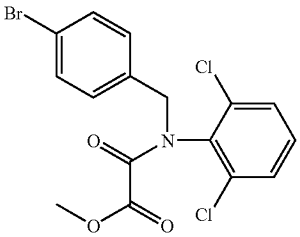 [SMILES: COC(=O)C(=O)N(Cc1ccc(Br)cc1)c1c(Cl)cccc1Cl]
614(3)
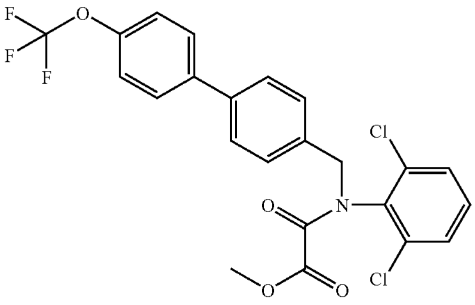 [SMILES: COC(=O)C(=O)N(Cc1ccc(-c2ccc(OC(F)(F)F)cc2)cc1)c1c(Cl)cccc1Cl]
615(1)
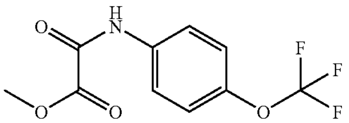 [SMILES: COC(=O)C(=O)Nc1ccc(OC(F)(F)F)cc1]
TABLE 4-93
615(2)
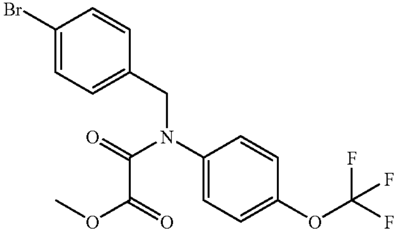 [SMILES: COC(=O)C(=O)N(Cc1ccc(Br)cc1)c1ccc(OC(F)(F)F)cc1]

TABLE 4-93-continued
615(3)
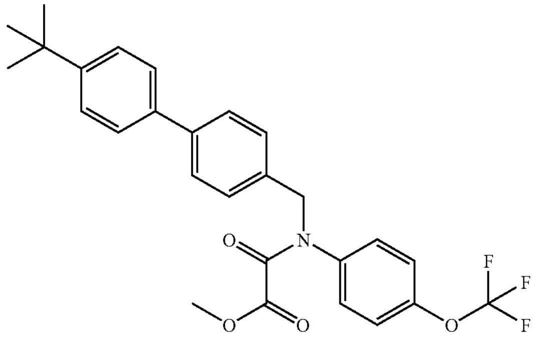 [SMILES: COC(=O)C(=O)N(Cc1ccc(-c2ccc(C(C)(C)C)cc2)cc1)c1ccc(OC(F)(F)F)cc1]
616(1)
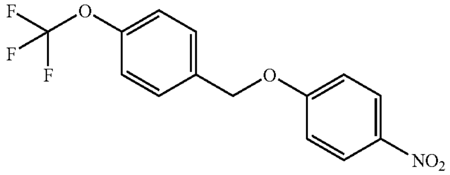 [SMILES: O=[N+]([O-])c1ccc(OCc2ccc(OC(F)(F)F)cc2)cc1]
616(2)
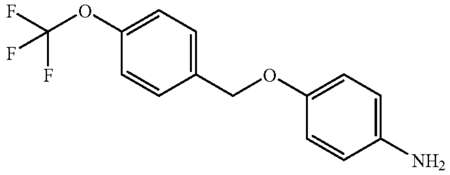
616(3)
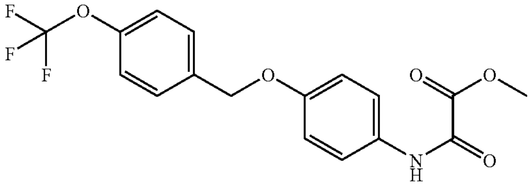 [SMILES: COC(=O)C(=O)Nc1ccc(OCc2ccc(OC(F)(F)F)cc2)cc1]
616(4)
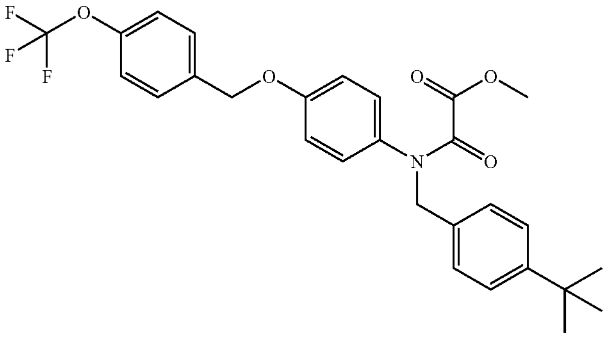 [SMILES: COC(=O)C(=O)N(Cc1ccc(C(C)(C)C)cc1)c1ccc(OCc2ccc(OC(F)(F)F)cc2)cc1]
617(1)
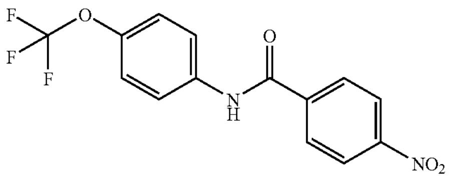 [SMILES: O=C(Nc1ccc(OC(F)(F)F)cc1)c1ccc([N+](=O)[O-])cc1]
617(2)
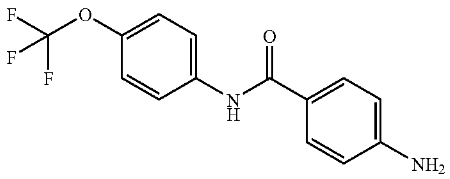 [SMILES: Nc1ccc(C(=O)Nc2ccc(OC(F)(F)F)cc2)cc1]

TABLE 4-93-continued
| | |
|---|---|
| 617(3) | 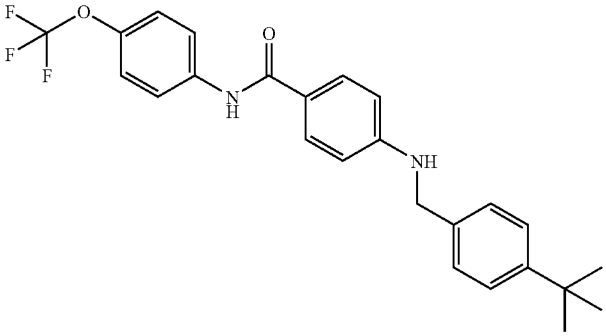 [SMILES: CC(C)(C)c1ccc(CNc2ccc(C(=O)Nc3ccc(OC(F)(F)F)cc3)cc2)cc1] |
| 617(4) | 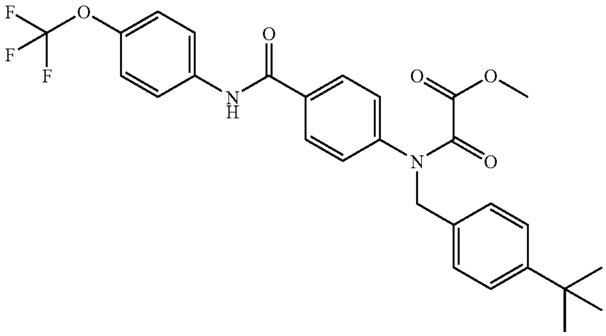 [SMILES: COC(=O)C(=O)N(Cc1ccc(C(C)(C)C)cc1)c1ccc(C(=O)Nc2ccc(OC(F)(F)F)cc2)cc1] |
| 618(1) | 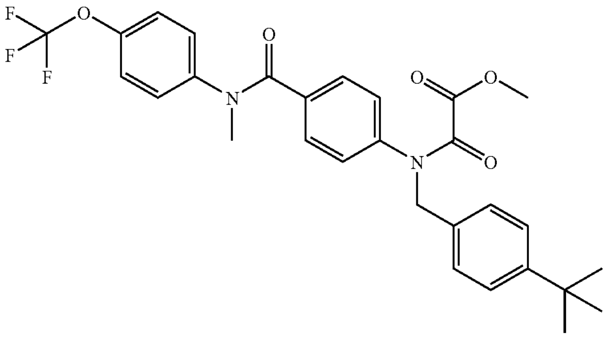 [SMILES: COC(=O)C(=O)N(Cc1ccc(C(C)(C)C)cc1)c1ccc(C(=O)N(C)c2ccc(OC(F)(F)F)cc2)cc1] |
| 619(1) | 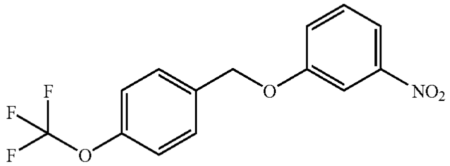 [SMILES: O=[N+]([O-])c1cccc(OCc2ccc(OC(F)(F)F)cc2)c1] |
TABLE 4-94
| | |
|---|---|
| 619(2) | 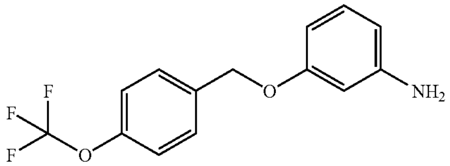 |
| 619(3) | 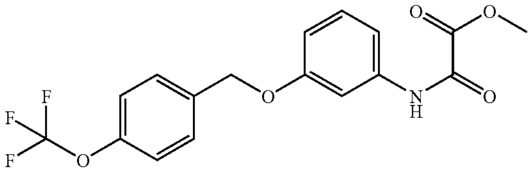 [SMILES: COC(=O)C(=O)Nc1cccc(OCc2ccc(OC(F)(F)F)cc2)c1] |

TABLE 4-94-continued
619(4)
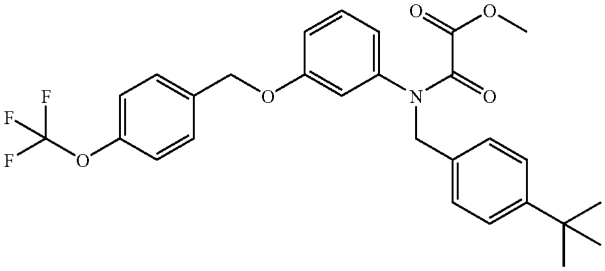 [SMILES: COC(=O)C(=O)N(Cc1ccc(C(C)(C)C)cc1)c1cccc(OCc2ccc(OC(F)(F)F)cc2)c1]
620(1)
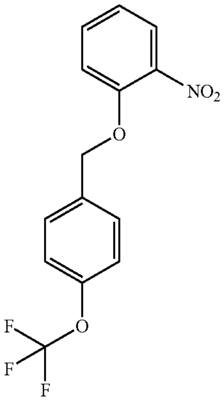
620(2)
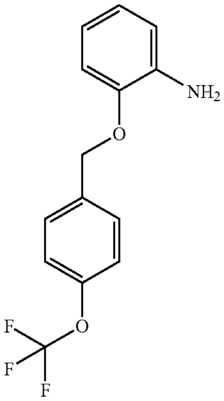 [SMILES: Nc1ccccc1OCc1ccc(OC(F)(F)F)cc1]
620(3)
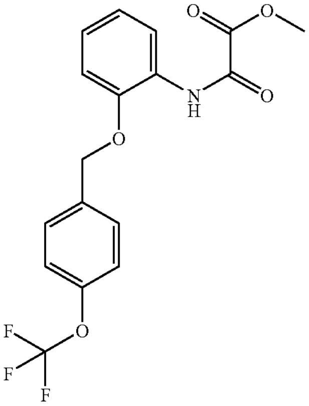 [SMILES: COC(=O)C(=O)Nc1ccccc1OCc1ccc(OC(F)(F)F)cc1]

TABLE 4-94-continued
| | |
|---|---|
| 620(4) | 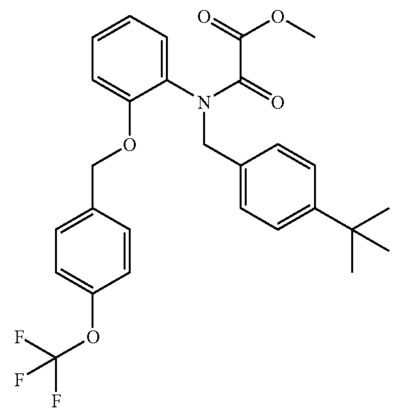 [SMILES: COC(=O)C(=O)N(Cc1ccc(C(C)(C)C)cc1)c1ccccc1OCc1ccc(OC(F)(F)F)cc1] |
| 621(1) | 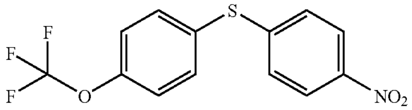 |
TABLE 4-95
| | |
|---|---|
| 621(2) | 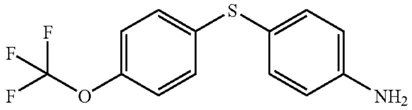 [SMILES: O=[N+]([O-])c1ccc(Sc2ccc(OC(F)(F)F)cc2)cc1] |
| 621(3) | 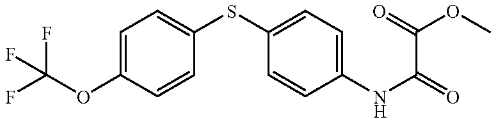 [SMILES: COC(=O)C(=O)Nc1ccc(Sc2ccc(OC(F)(F)F)cc2)cc1] |
| 621(4) | 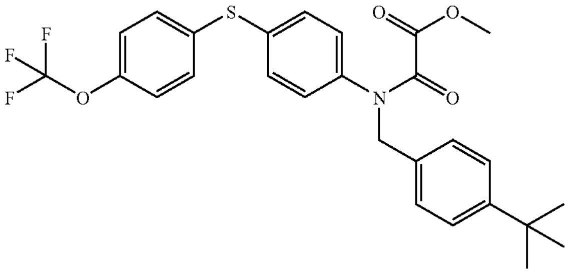 [SMILES: COC(=O)C(=O)N(Cc1ccc(C(C)(C)C)cc1)c1ccc(Sc2ccc(OC(F)(F)F)cc2)cc1] |
| 622(1) | 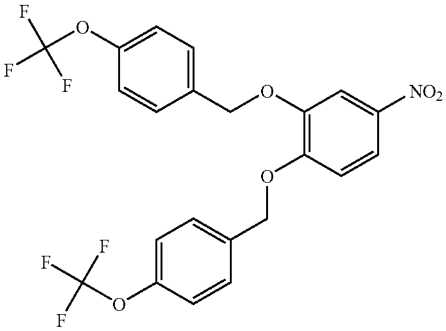 |

TABLE 4-95-continued
622(2)
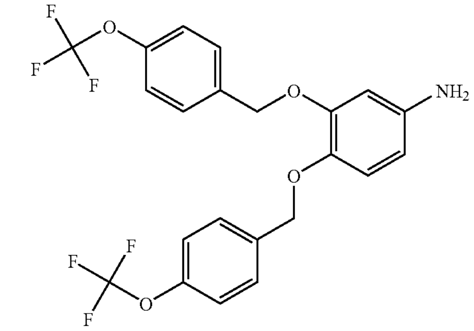 [SMILES: O=[N+]([O-])c1ccc(OCc2ccc(OC(F)(F)F)cc2)c(OCc2ccc(OC(F)(F)F)cc2)c1]
622(3)
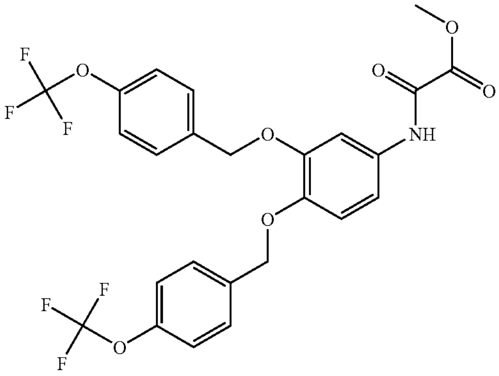 [SMILES: COC(=O)C(=O)Nc1ccc(OCc2ccc(OC(F)(F)F)cc2)c(OCc2ccc(OC(F)(F)F)cc2)c1]
622(4)
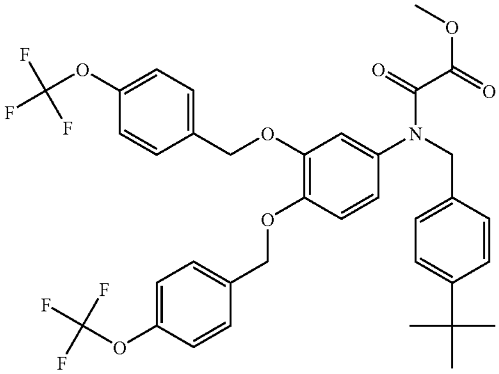 [SMILES: COC(=O)C(=O)N(Cc1ccc(C(C)(C)C)cc1)c1ccc(OCc2ccc(OC(F)(F)F)cc2)c(OCc2ccc(OC(F)(F)F)cc2)c1]
623(1)
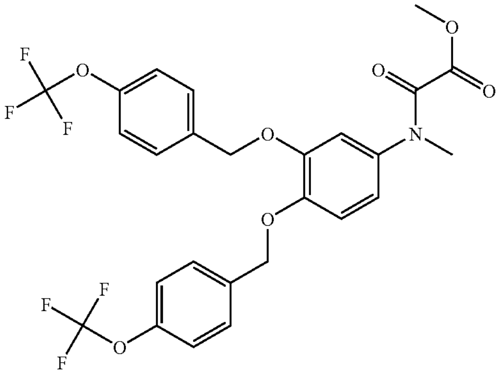 [SMILES: COC(=O)C(=O)N(C)c1ccc(OCc2ccc(OC(F)(F)F)cc2)c(OCc2ccc(OC(F)(F)F)cc2)c1]
625(1)
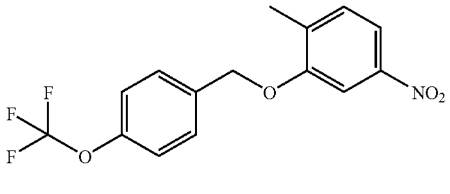 [SMILES: Cc1ccc([N+](=O)[O-])cc1OCc1ccc(OC(F)(F)F)cc1]

TABLE 4-95-continued
625(2)
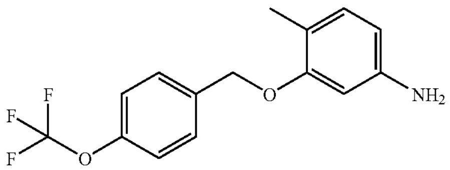 [SMILES: Cc1ccc(N)cc1OCc1ccc(OC(F)(F)F)cc1]
625(3)
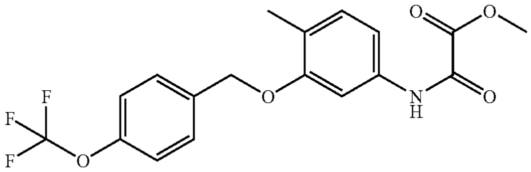
625(4)
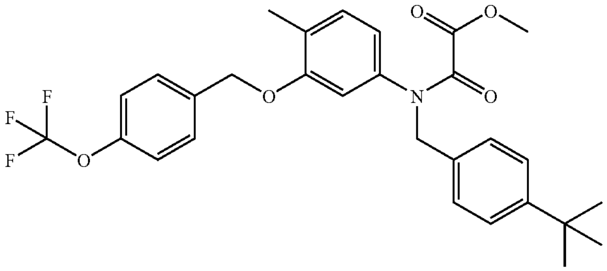 [SMILES: COC(=O)C(=O)N(Cc1ccc(C(C)(C)C)cc1)c1ccc(C)c(OCc2ccc(OC(F)(F)F)cc2)c1]
TABLE 4-96
626(1)
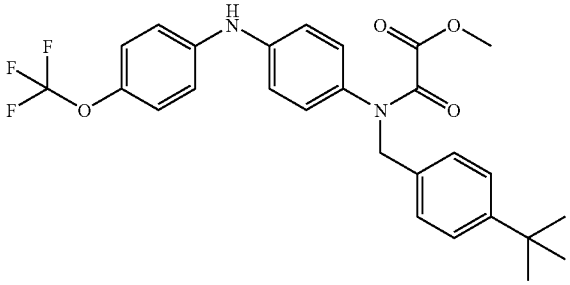 [SMILES: COC(=O)C(=O)N(Cc1ccc(C(C)(C)C)cc1)c1ccc(Nc2ccc(OC(F)(F)F)cc2)cc1]
627(1)
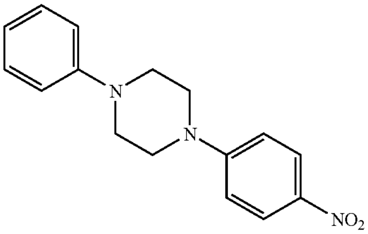 [SMILES: O=[N+]([O-])c1ccc(N2CCN(c3ccccc3)CC2)cc1]
627(2)
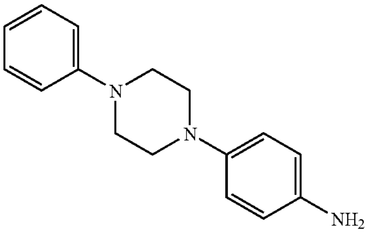

TABLE 4-96-continued
627(3)
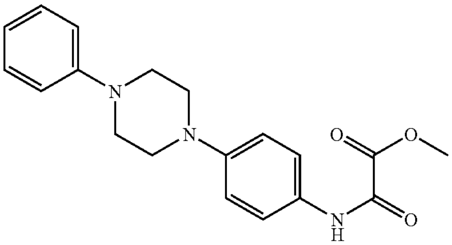 [SMILES: COC(=O)C(=O)Nc1ccc(N2CCN(c3ccccc3)CC2)cc1]
627(4)
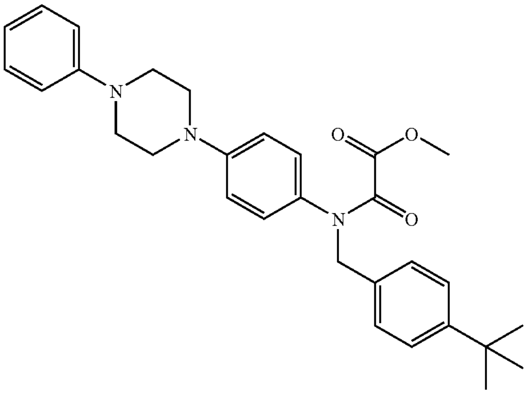 [SMILES: COC(=O)C(=O)N(Cc1ccc(C(C)(C)C)cc1)c1ccc(N2CCN(c3ccccc3)CC2)cc1]
628(1)
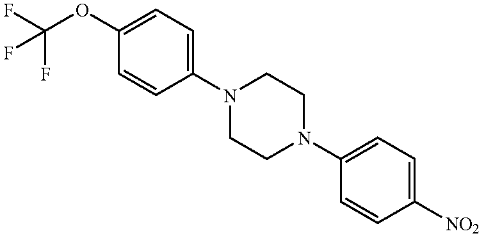
628(2)
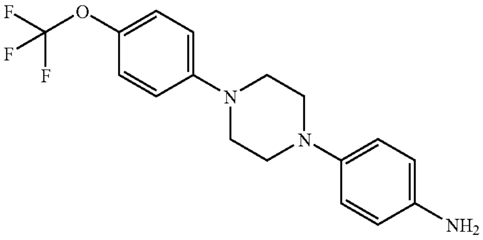 [SMILES: O=[N+]([O-])c1ccc(N2CCN(c3ccc(OC(F)(F)F)cc3)CC2)cc1]
628(3)
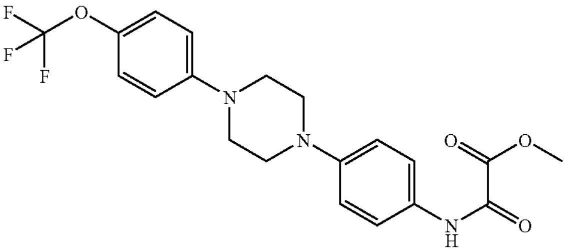 [SMILES: COC(=O)C(=O)Nc1ccc(N2CCN(c3ccc(OC(F)(F)F)cc3)CC2)cc1]

TABLE 4-96-continued
628(4)
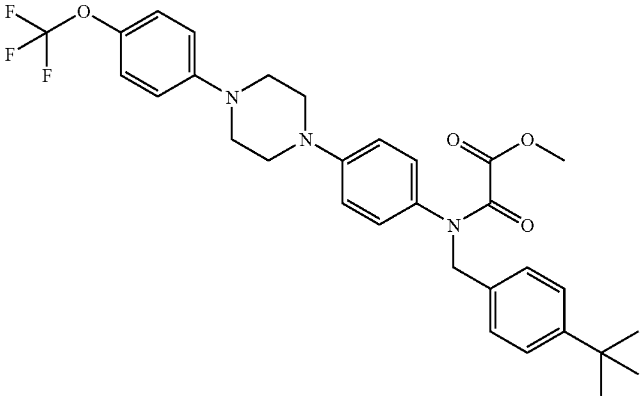 [SMILES: COC(=O)C(=O)N(Cc1ccc(C(C)(C)C)cc1)c1ccc(N2CCN(c3ccc(OC(F)(F)F)cc3)CC2)cc1]
629(1)
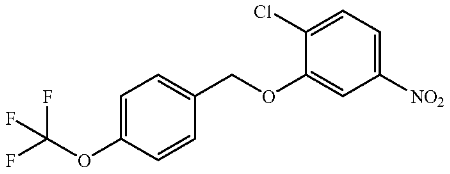
629(2)
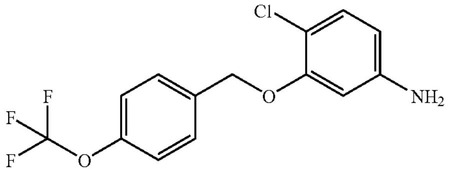 [SMILES: Nc1ccc(Cl)c(OCc2ccc(OC(F)(F)F)cc2)c1]
629(3)
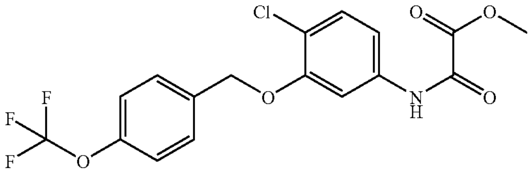 [SMILES: COC(=O)C(=O)Nc1ccc(Cl)c(OCc2ccc(OC(F)(F)F)cc2)c1]
TABLE 4-97
629(4)
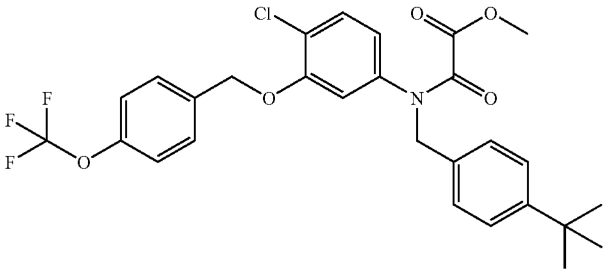 [SMILES: COC(=O)C(=O)N(Cc1ccc(C(C)(C)C)cc1)c1ccc(Cl)c(OCc2ccc(OC(F)(F)F)cc2)c1]
630(1)
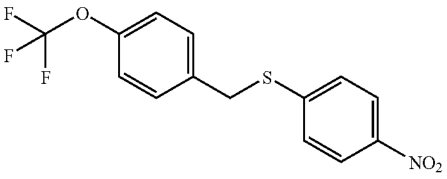

TABLE 4-97-continued
630(2)
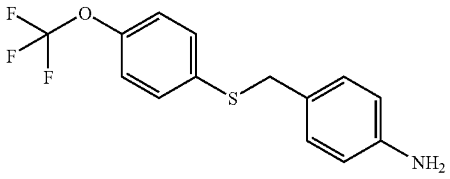
630(3)
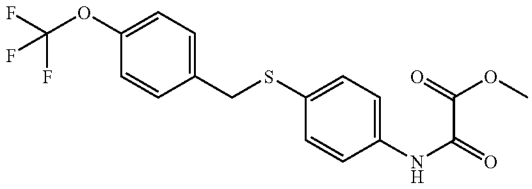
630(4)
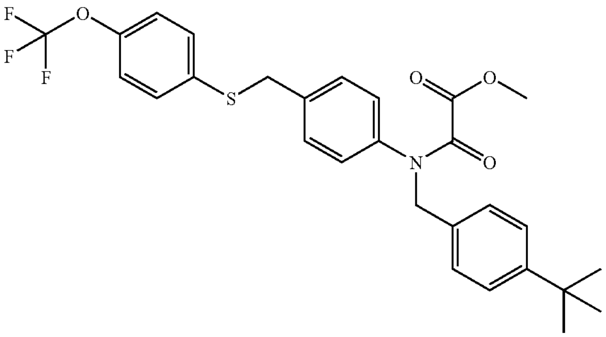
631(1)
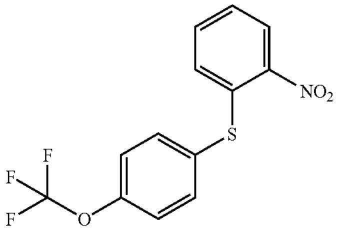
631(2)
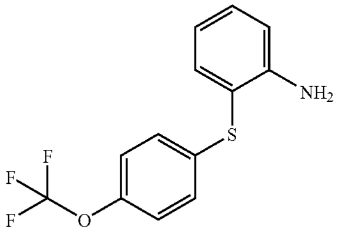 [SMILES: O=[N+]([O-])c1ccccc1Sc1ccc(OC(F)(F)F)cc1]
631(3)
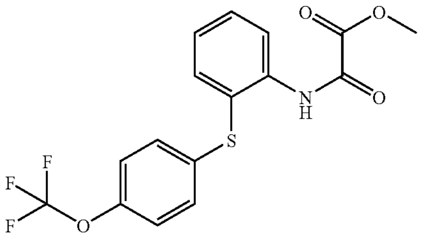 [SMILES: COC(=O)C(=O)Nc1ccccc1Sc1ccc(OC(F)(F)F)cc1]

TABLE 4-97-continued
631(4)
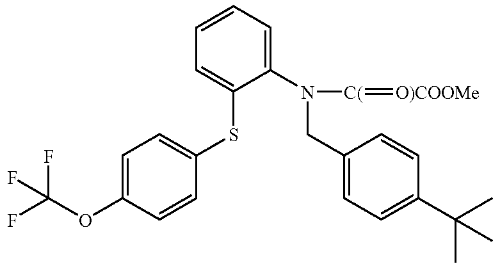
632(1)
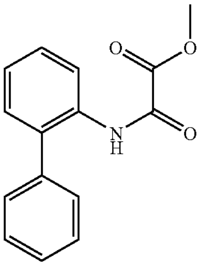 [SMILES: COC(=O)C(=O)Nc1ccccc1-c1ccccc1]
632(2)
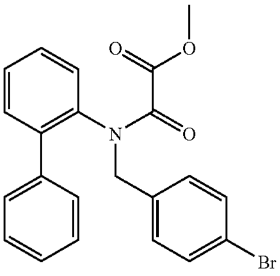 [SMILES: COC(=O)C(=O)N(Cc1ccc(Br)cc1)c1ccccc1-c1ccccc1]
632(3)
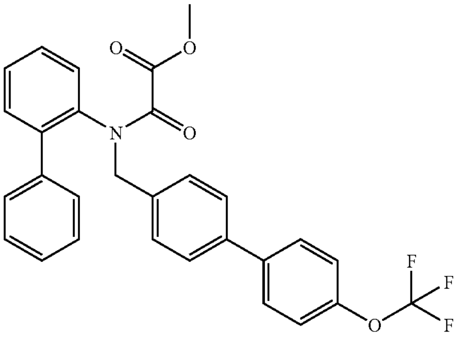 [SMILES: COC(=O)C(=O)N(Cc1ccc(-c2ccc(OC(F)(F)F)cc2)cc1)c1ccccc1-c1ccccc1]
TABLE 4-98
633(1)
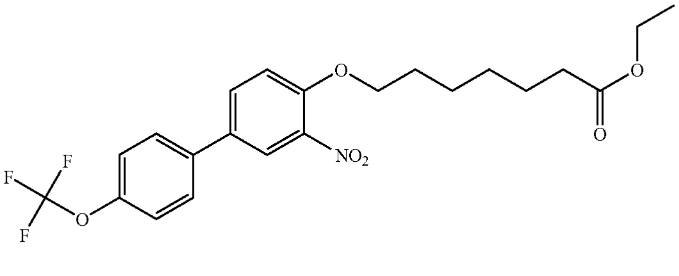 [SMILES: CCOC(=O)CCCCCCOc1ccc(-c2ccc(OC(F)(F)F)cc2)cc1[N+](=O)[O-]]

TABLE 4-98-continued
633(2)
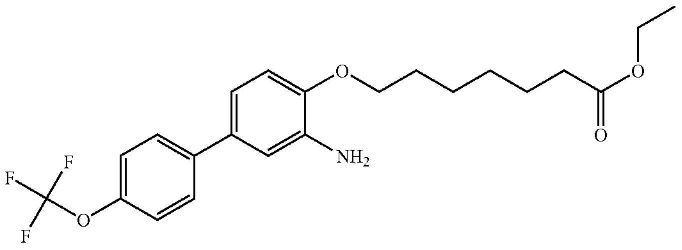
633(3)
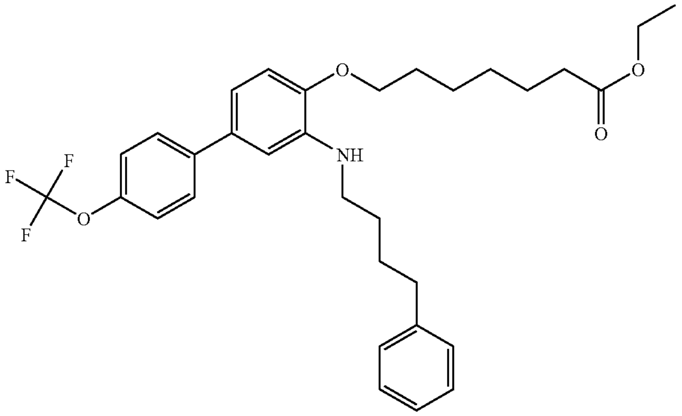 [SMILES: CCOC(=O)CCCCCCOc1ccc(-c2ccc(OC(F)(F)F)cc2)cc1NCCCCc1ccccc1]
633(4)
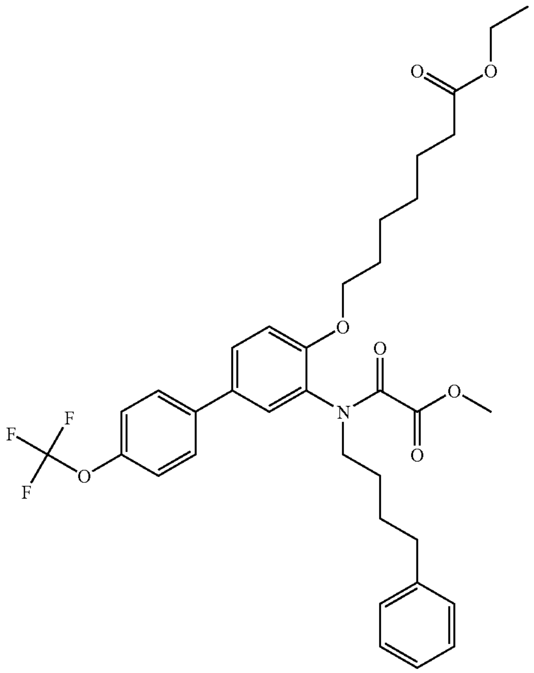 [SMILES: CCOC(=O)CCCCCCOc1ccc(-c2ccc(OC(F)(F)F)cc2)cc1N(CCCCc1ccccc1)C(=O)C(=O)OC]
634(1)
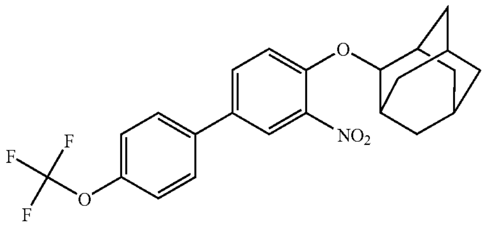 [SMILES: O=[N+]([O-])c1cc(-c2ccc(OC(F)(F)F)cc2)ccc1OC1C2CC3CC(C2)CC1C3]

TABLE 4-98-continued
| | |
|---|---|
| 634(2) | 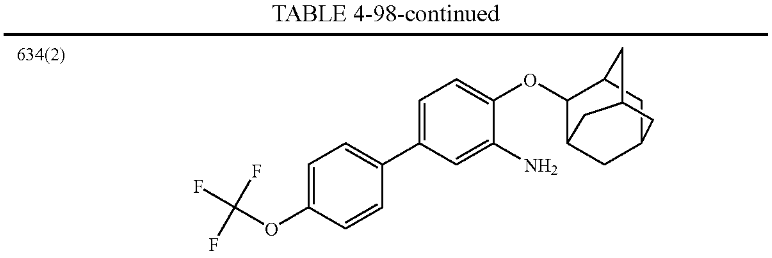 |
| 634(3) | 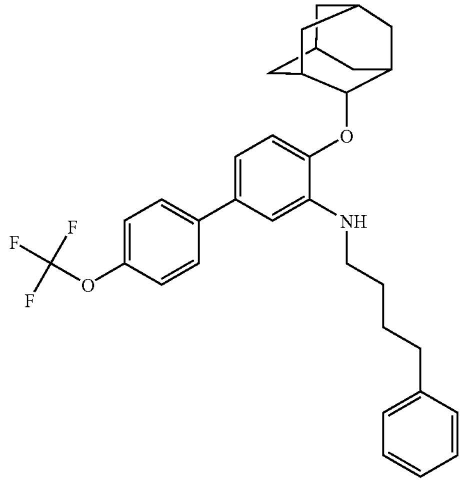 [SMILES: FC(F)(F)Oc1ccc(-c2ccc(OC3C4CC5CC(C4)CC3C5)c(NCCCCc3ccccc3)c2)cc1] |
| 634(4) | 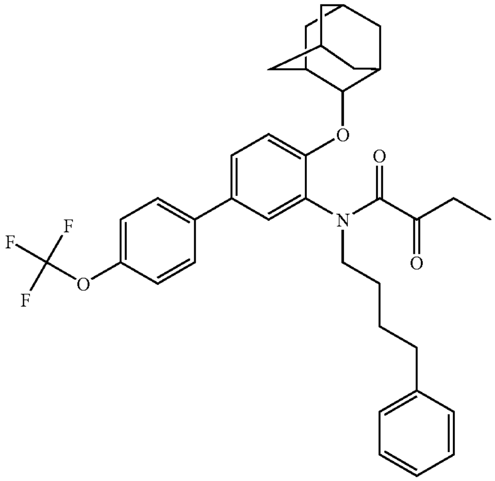 [SMILES: CCC(=O)C(=O)N(CCCCc1ccccc1)c1cc(-c2ccc(OC(F)(F)F)cc2)ccc1OC1C2CC3CC(C2)CC1C3] |
TABLE 4-99
| | |
|---|---|
| 635 (1) | 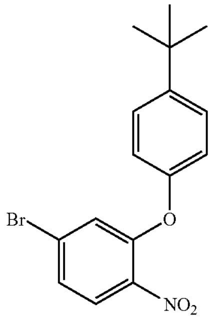 [SMILES: CC(C)(C)c1ccc(Oc2cc(Br)ccc2[N+](=O)[O-])cc1] |
TABLE 4-99-continued
| | |
|---|---|
| 635 (2) | 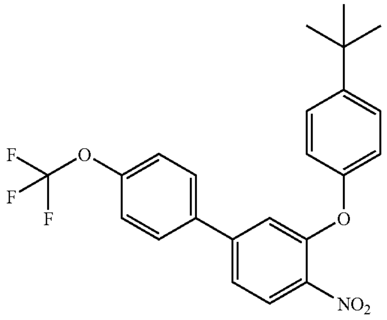 [SMILES: CC(C)(C)c1ccc(Oc2cc(-c3ccc(OC(F)(F)F)cc3)ccc2N)cc1] |

TABLE 4-99-continued
| | |
|---|---|
| 635 (3) | 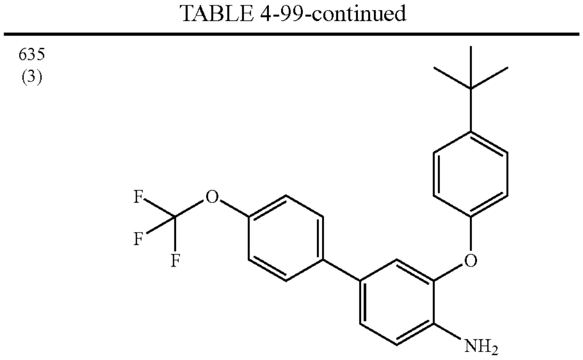 |
| 635 (4) | 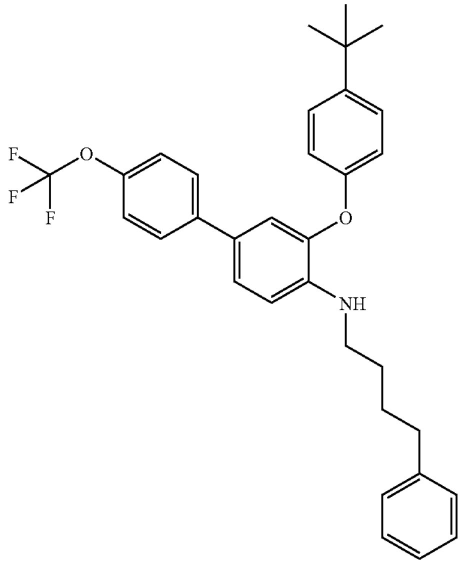 [SMILES: CC(C)(C)c1ccc(Oc2cc(-c3ccc(OC(F)(F)F)cc3)ccc2NCCCCc2ccccc2)cc1] |
| 635 (5) | 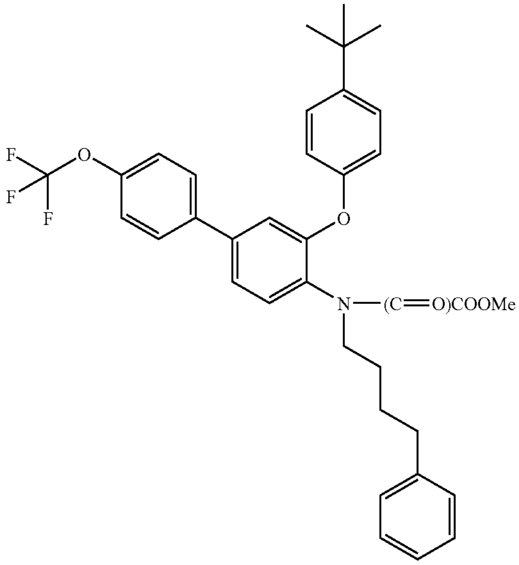 |
TABLE 4-100
| | |
|---|---|
| 636(1) | 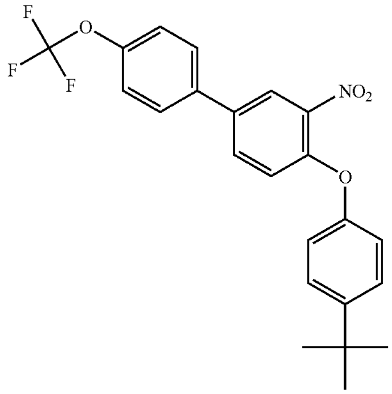 [SMILES: CC(C)(C)c1ccc(Oc2ccc(-c3ccc(OC(F)(F)F)cc3)cc2[N+](=O)[O-])cc1] |

TABLE 4-100-continued
636(2)
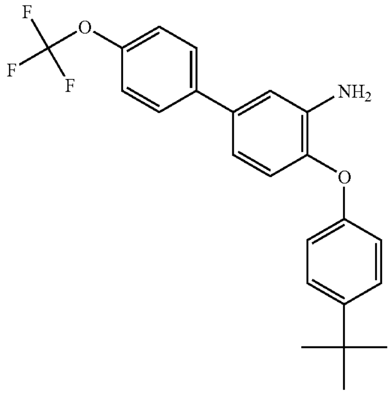
636(3)
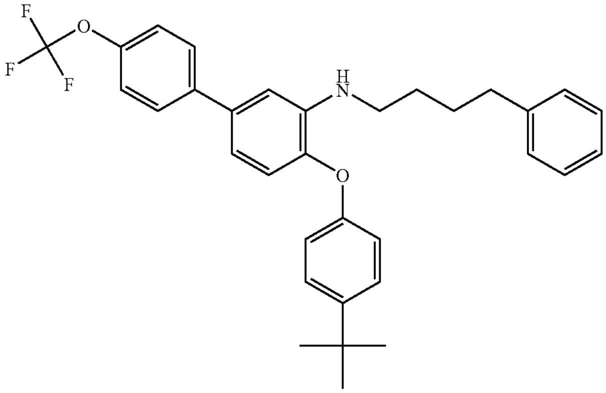 [SMILES: CC(C)(C)c1ccc(Oc2ccc(-c3ccc(OC(F)(F)F)cc3)cc2NCCCCc2ccccc2)cc1]
636(4)
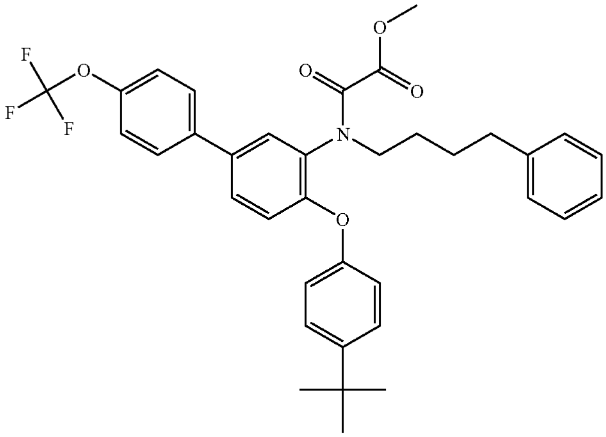 [SMILES: COC(=O)C(=O)N(CCCCc1ccccc1)c1cc(-c2ccc(OC(F)(F)F)cc2)ccc1Oc1ccc(C(C)(C)C)cc1]
637(1)
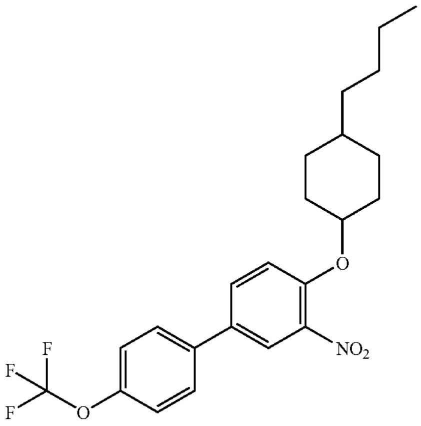 [SMILES: CCCCC1CCC(Oc2ccc(-c3ccc(OC(F)(F)F)cc3)cc2[N+](=O)[O-])CC1]

TABLE 4-100-continued
637(2)
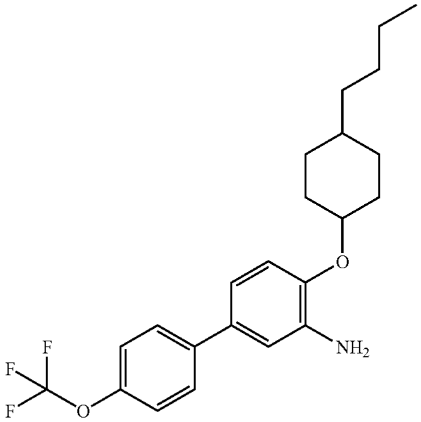
TABLE 4-101
637(3)
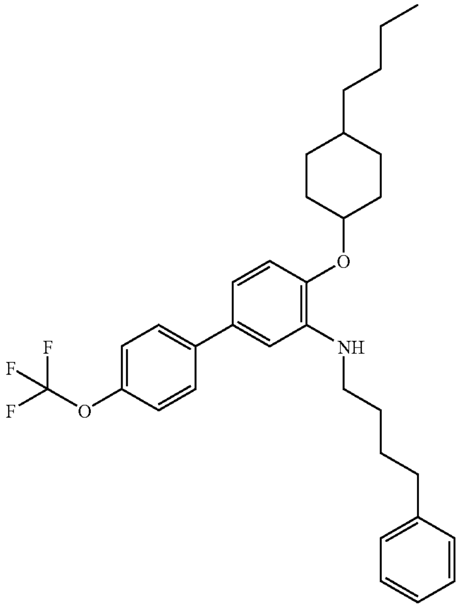 [SMILES: CCCCC1CCC(Oc2ccc(-c3ccc(OC(F)(F)F)cc3)cc2NCCCCc2ccccc2)CC1]
TABLE 4-101-continued
637(4)
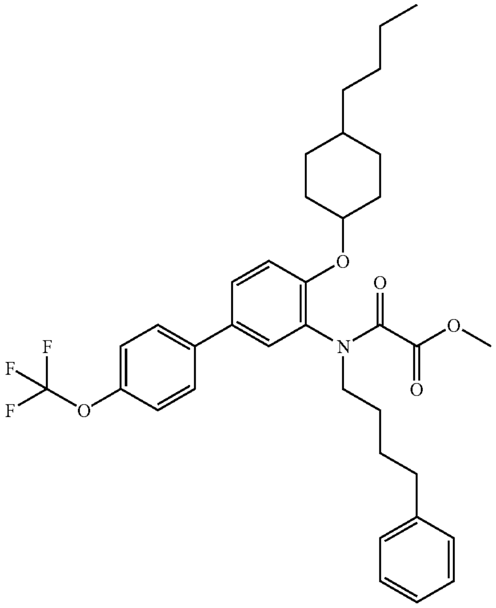 [SMILES: CCCCC1CCC(Oc2ccc(-c3ccc(OC(F)(F)F)cc3)cc2N(CCCCc2ccccc2)C(=O)C(=O)OC)CC1]
638(1)
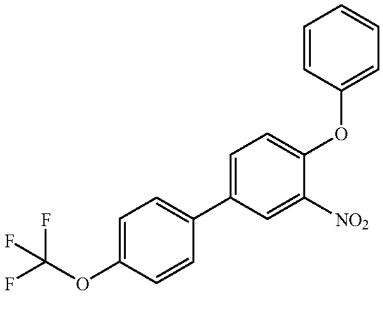 [SMILES: O=[N+]([O-])c1cc(-c2ccc(OC(F)(F)F)cc2)ccc1Oc1ccccc1]

TABLE 4-101-continued
| | |
|---|---|
| 638(2) | 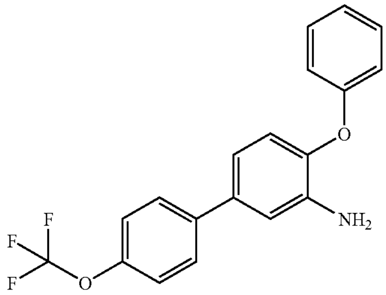 |
| 638(3) | 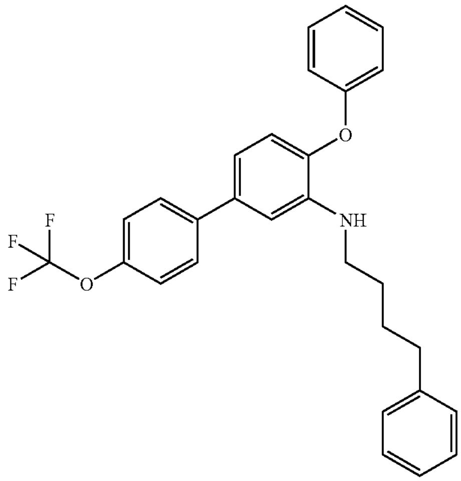 [SMILES: FC(F)(F)Oc1ccc(-c2ccc(Oc3ccccc3)c(NCCCCc3ccccc3)c2)cc1] |
| 638(4) | 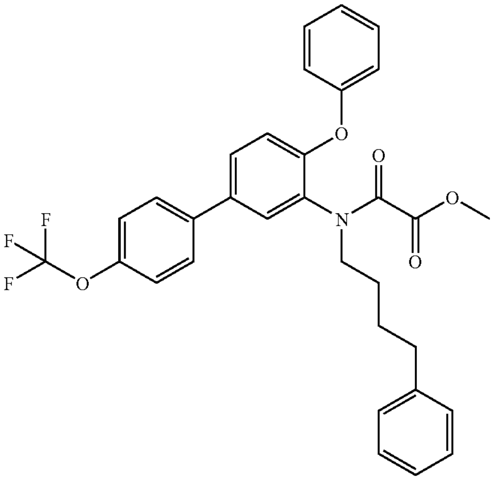 [SMILES: COC(=O)C(=O)N(CCCCc1ccccc1)c1cc(-c2ccc(OC(F)(F)F)cc2)ccc1Oc1ccccc1] |
| 639(1) | 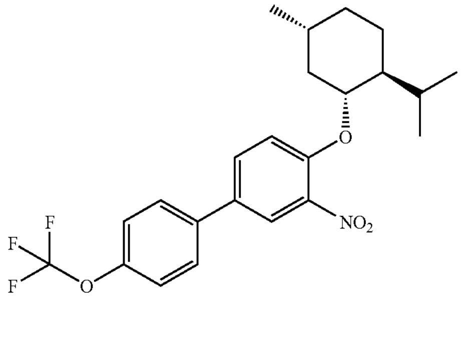 [SMILES: CC(C)[C@@H]1CC[C@@H](C)C[C@H]1Oc1ccc(-c2ccc(OC(F)(F)F)cc2)cc1[N+](=O)[O-]] |
TABLE 4-101-continued
| | |
|---|---|
| 639(2) | 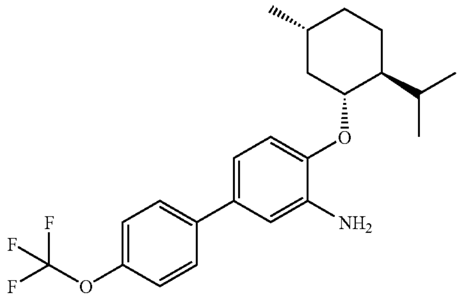 |
TABLE 4-102
| | |
|---|---|
| 639 (3) | 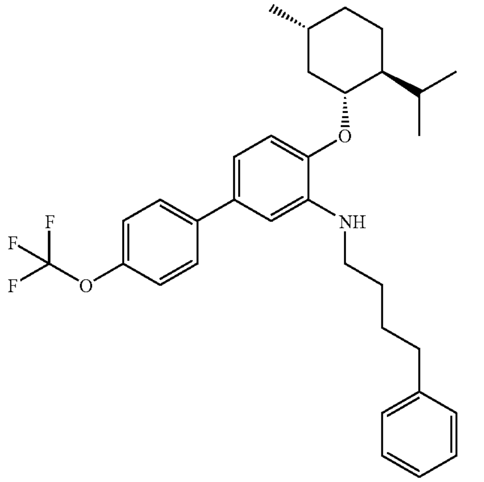 [SMILES: CC(C)[C@@H]1CC[C@@H](C)C[C@H]1Oc1ccc(-c2ccc(OC(F)(F)F)cc2)cc1NCCCCc1ccccc1] |
| 639 (4) | 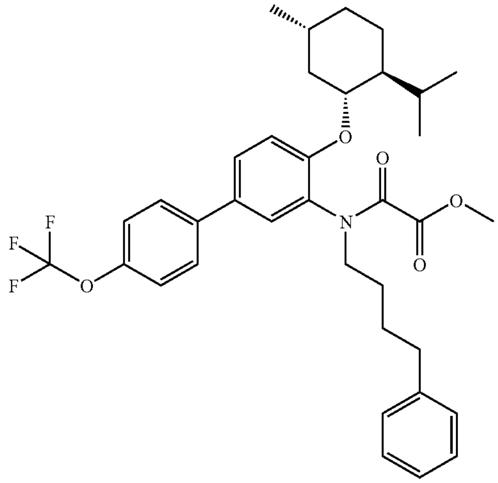 [SMILES: COC(=O)C(=O)N(CCCCc1ccccc1)c1cc(-c2ccc(OC(F)(F)F)cc2)ccc1O[C@@H]1C[C@H](C)CC[C@H]1C(C)C] |

TABLE 4-102-continued
640
(1)
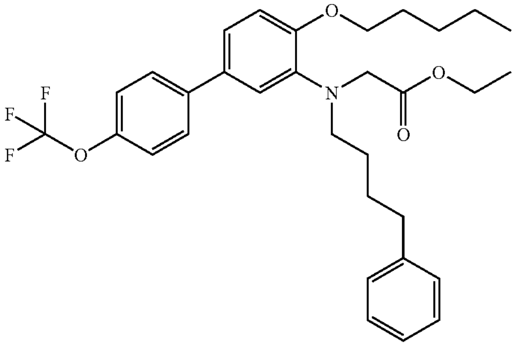 [SMILES: CCCCCOc1ccc(-c2ccc(OC(F)(F)F)cc2)cc1N(CCCCc1ccccc1)CC(=O)OCC]
641
(1)
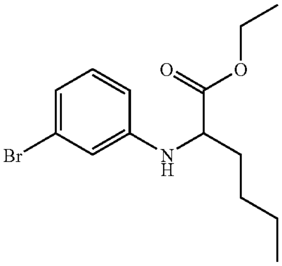 [SMILES: CCCCC(Nc1cccc(Br)c1)C(=O)OCC]
641
(2)
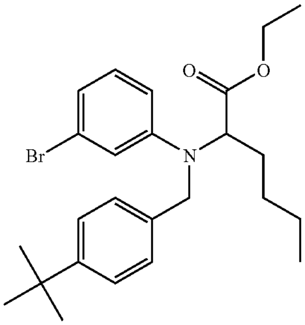 [SMILES: CCCCC(C(=O)OCC)N(Cc1ccc(C(C)(C)C)cc1)c1cccc(Br)c1]
641
(3)
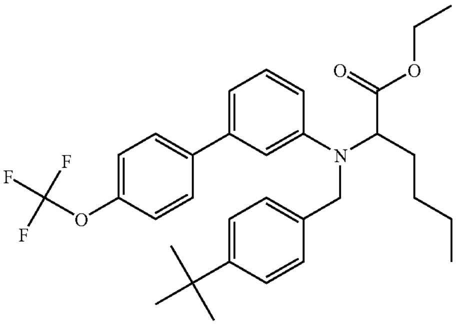 [SMILES: CCCCC(C(=O)OCC)N(Cc1ccc(C(C)(C)C)cc1)c1cccc(-c2ccc(OC(F)(F)F)cc2)c1]
642
(1)
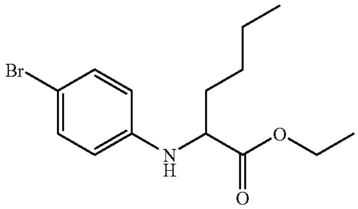 [SMILES: CCCCC(Nc1ccc(Br)cc1)C(=O)OCC]
642
(2)
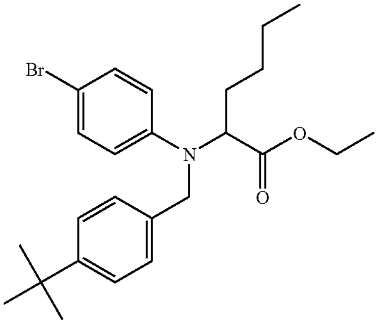 [SMILES: CCCCC(C(=O)OCC)N(Cc1ccc(C(C)(C)C)cc1)c1ccc(Br)cc1]
TABLE 4-103
642(3)
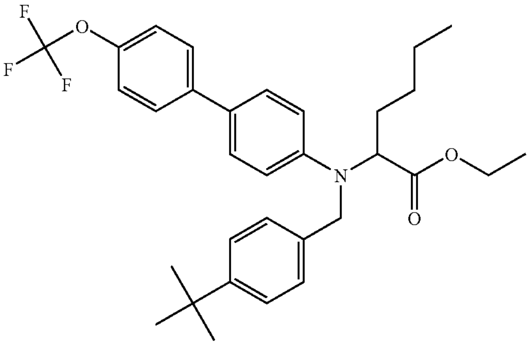 [SMILES: CCCCC(C(=O)OCC)N(Cc1ccc(C(C)(C)C)cc1)c1ccc(-c2ccc(OC(F)(F)F)cc2)cc1]

TABLE 4-103-continued
643(1)
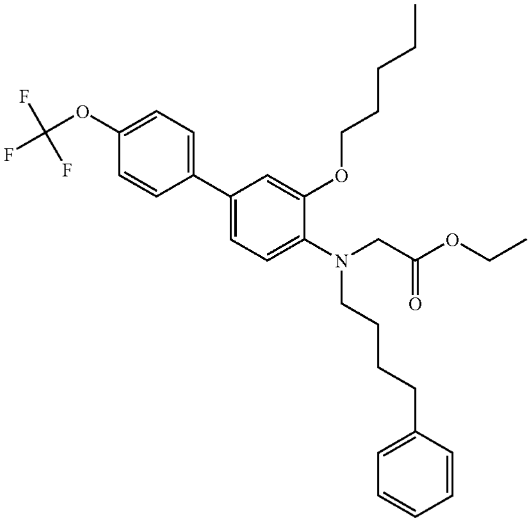 [SMILES: CCCCCOc1cc(-c2ccc(OC(F)(F)F)cc2)ccc1N(CCCCc1ccccc1)CC(=O)OCC]
644(1)
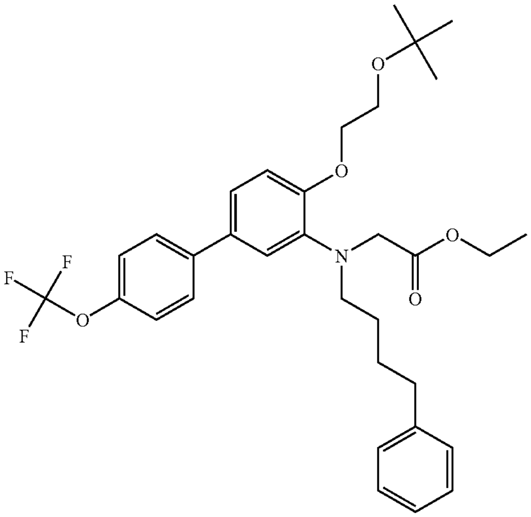 [SMILES: CCOC(=O)CN(CCCCc1ccccc1)c1cc(-c2ccc(OC(F)(F)F)cc2)ccc1OCCOC(C)(C)C]
645(1)
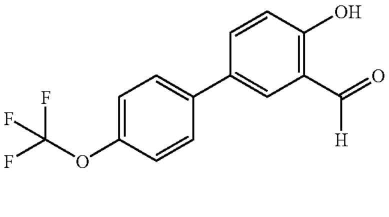 [SMILES: O=Cc1cc(-c2ccc(OC(F)(F)F)cc2)ccc1O]
645(2)
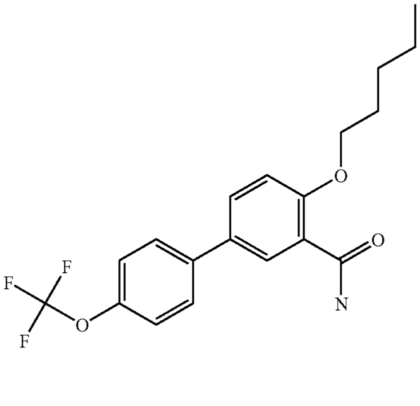 [SMILES: CCCCCOc1ccc(-c2ccc(OC(F)(F)F)cc2)cc1C(N)=O]

TABLE 4-103-continued
645(3)
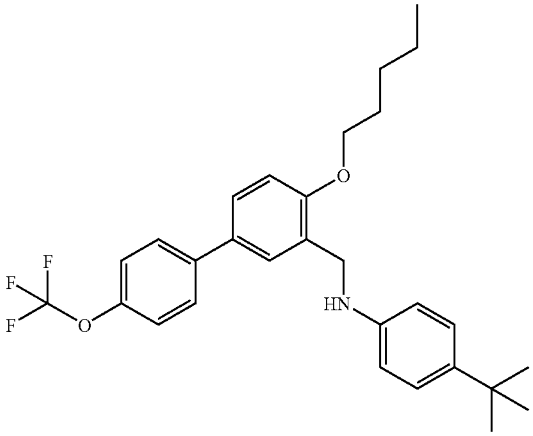 [SMILES: CCCCCOc1ccc(-c2ccc(OC(F)(F)F)cc2)cc1CNc1ccc(C(C)(C)C)cc1]
645(4)
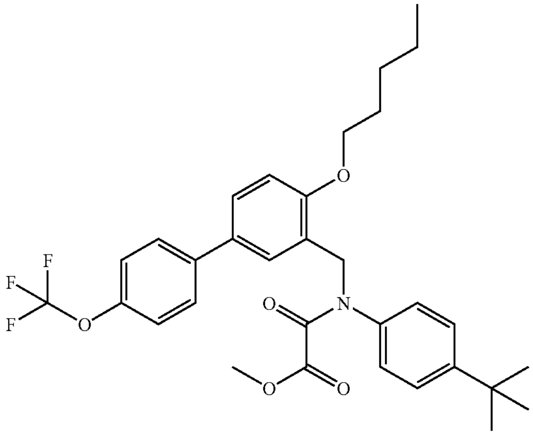 [SMILES: CCCCCOc1ccc(-c2ccc(OC(F)(F)F)cc2)cc1CN(C(=O)C(=O)OC)c1ccc(C(C)(C)C)cc1]
646(1)
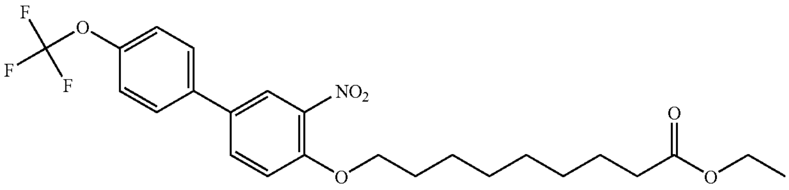
TABLE 4-104
646(2)
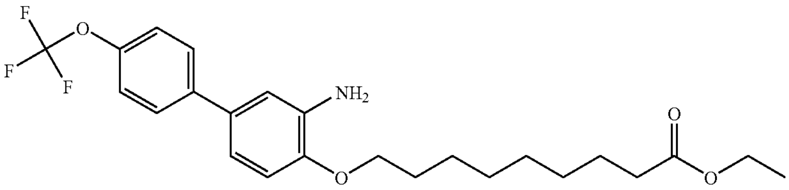 [SMILES: CCOC(=O)CCCCCCCCOc1ccc(-c2ccc(OC(F)(F)F)cc2)cc1[N+](=O)[O-]]

TABLE 4-104-continued
646(3)
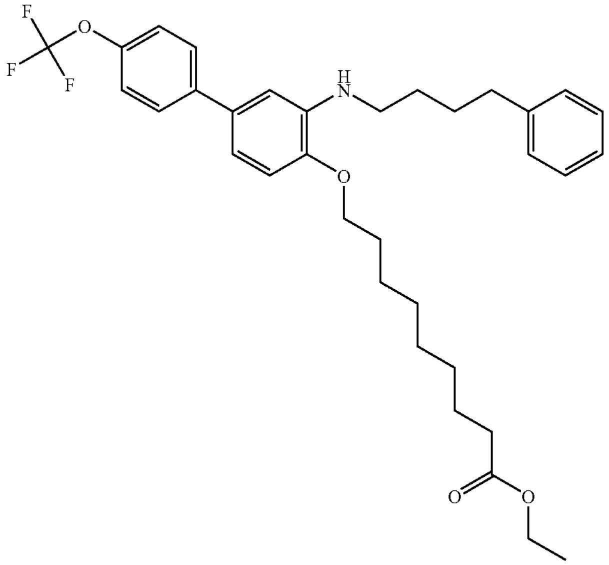 [SMILES: CCOC(=O)CCCCCCCCOc1ccc(-c2ccc(OC(F)(F)F)cc2)cc1NCCCCc1ccccc1]
646(4)
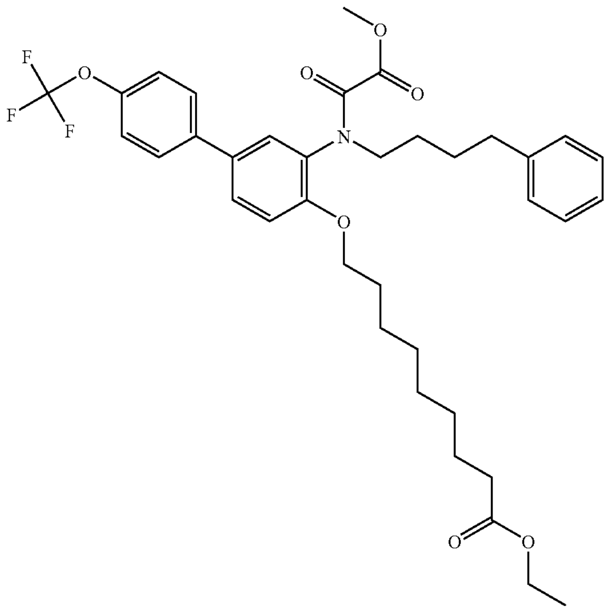 [SMILES: CCOC(=O)CCCCCCCCOc1ccc(-c2ccc(OC(F)(F)F)cc2)cc1N(CCCCc1ccccc1)C(=O)C(=O)OC]
647(1)
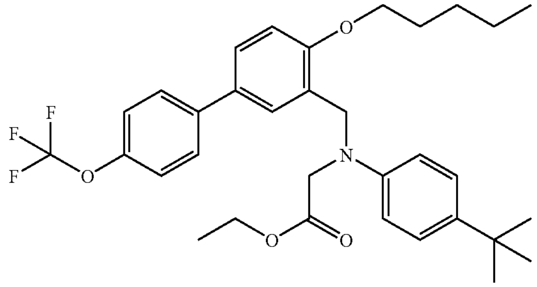 [SMILES: CCCCCOc1ccc(-c2ccc(OC(F)(F)F)cc2)cc1CN(CC(=O)OCC)c1ccc(C(C)(C)C)cc1]
648(1)
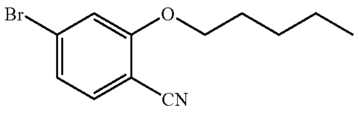

TABLE 4-104-continued
| | |
|---|---|
| 648(2) | 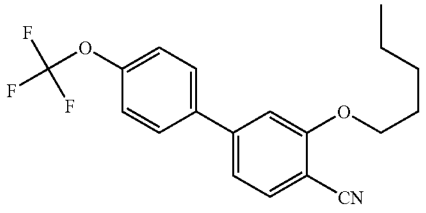 [SMILES: CCCCCOc1cc(-c2ccc(OC(F)(F)F)cc2)ccc1C#N] |
| 648(3) | 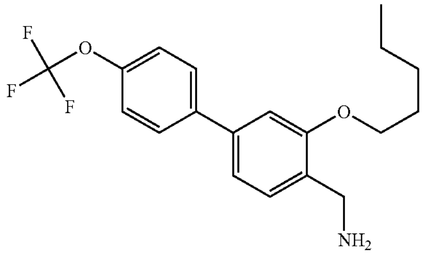 [SMILES: CCCCCOc1cc(-c2ccc(OC(F)(F)F)cc2)ccc1CN] |
| 648(4) | 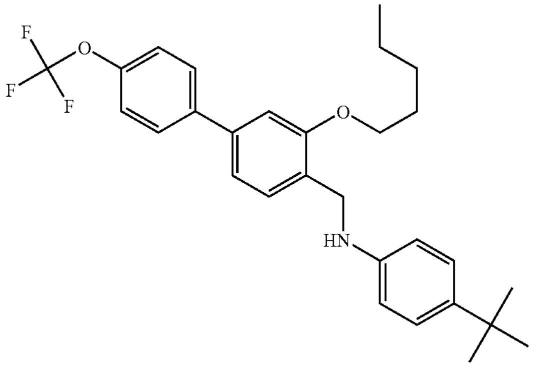 [SMILES: CCCCCOc1cc(-c2ccc(OC(F)(F)F)cc2)ccc1CNc1ccc(C(C)(C)C)cc1] |
TABLE 4-105
| | |
|---|---|
| 648(5) | 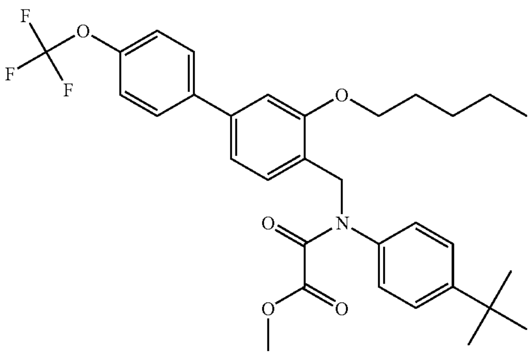 [SMILES: CCCCCOc1cc(-c2ccc(OC(F)(F)F)cc2)ccc1CN(C(=O)C(=O)OC)c1ccc(C(C)(C)C)cc1] |

TABLE 4-105-continued
649(1)
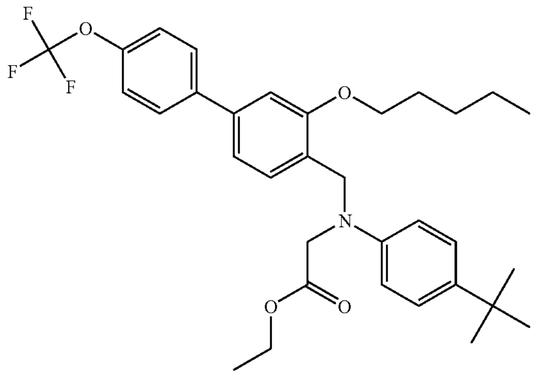 [SMILES: CCCCCOc1cc(-c2ccc(OC(F)(F)F)cc2)ccc1CN(CC(=O)OCC)c1ccc(C(C)(C)C)cc1]
650(1)
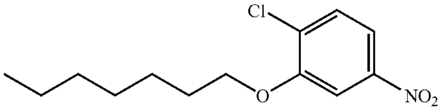 [SMILES: CCCCCCCOc1cc([N+](=O)[O-])ccc1Cl]
650(2)
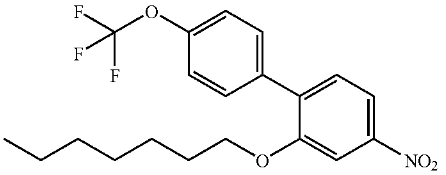
650(3)
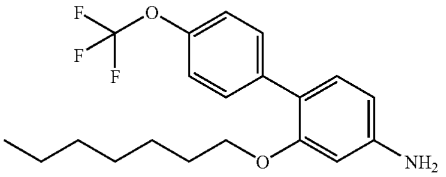 [SMILES: CCCCCCCOc1cc([N+](=O)[O-])ccc1-c1ccc(OC(F)(F)F)cc1]
650(4)
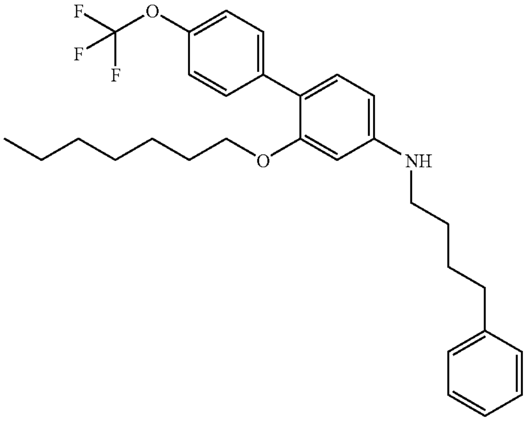 [SMILES: CCCCCCCOc1cc(NCCCCc2ccccc2)ccc1-c1ccc(OC(F)(F)F)cc1]

TABLE 4-105-continued
650(5)
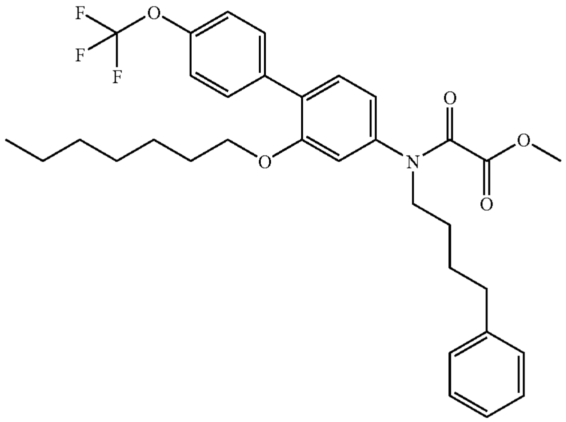 [SMILES: CCCCCCCOc1cc(N(CCCCc2ccccc2)C(=O)C(=O)OC)ccc1-c1ccc(OC(F)(F)F)cc1]
651(1)
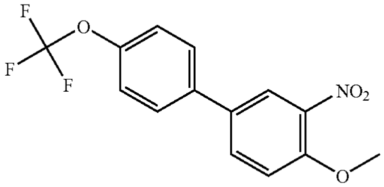 [SMILES: COc1ccc(-c2ccc(OC(F)(F)F)cc2)cc1[N+](=O)[O-]]
651(2)
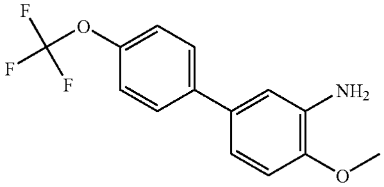
651(3)
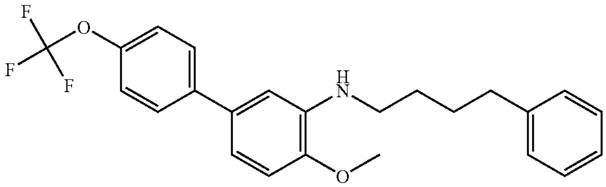 [SMILES: COc1ccc(-c2ccc(OC(F)(F)F)cc2)cc1NCCCCc1ccccc1]
651(4)
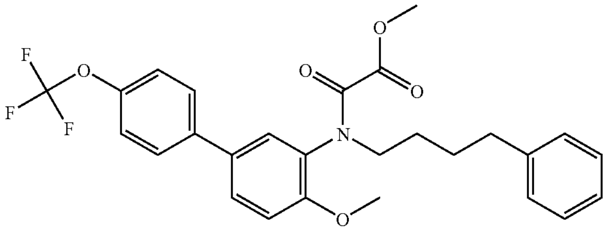 [SMILES: COC(=O)C(=O)N(CCCCc1ccccc1)c1cc(-c2ccc(OC(F)(F)F)cc2)ccc1OC]
652(1)
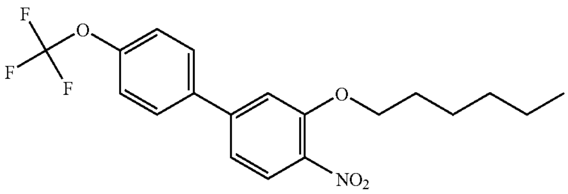

TABLE 4-106
652(2)
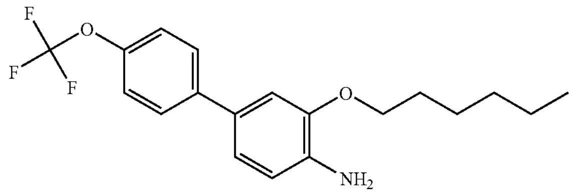 [SMILES: CCCCCCOc1cc(-c2ccc(OC(F)(F)F)cc2)ccc1N]
652(3)
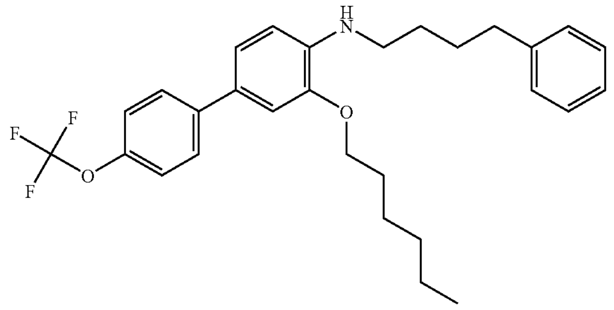 [SMILES: CCCCCCOc1cc(-c2ccc(OC(F)(F)F)cc2)ccc1NCCCCc1ccccc1]
652(4)
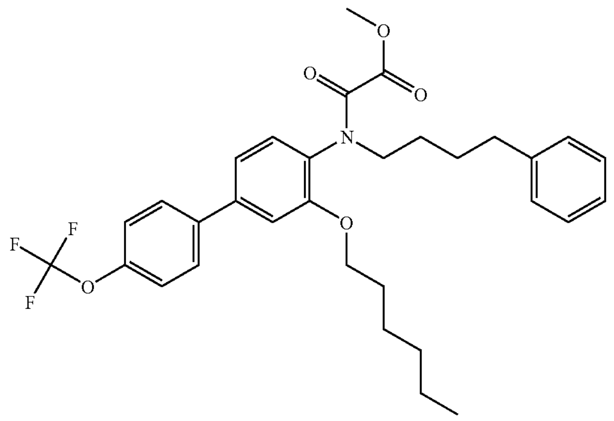 [SMILES: CCCCCCOc1cc(-c2ccc(OC(F)(F)F)cc2)ccc1N(CCCCc1ccccc1)C(=O)C(=O)OC]
653(1)
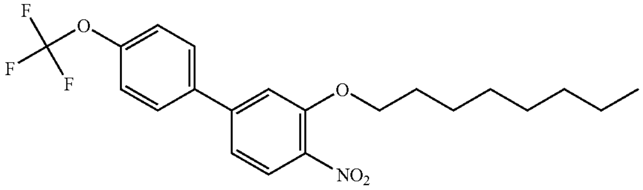 [SMILES: CCCCCCCCOc1cc(-c2ccc(OC(F)(F)F)cc2)ccc1[N+](=O)[O-]]
653(2)
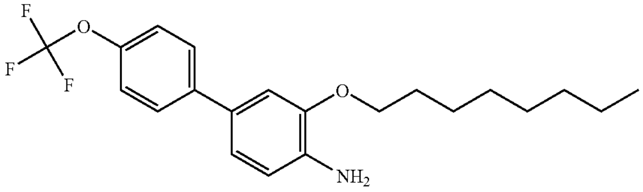

TABLE 4-106-continued
653(3)
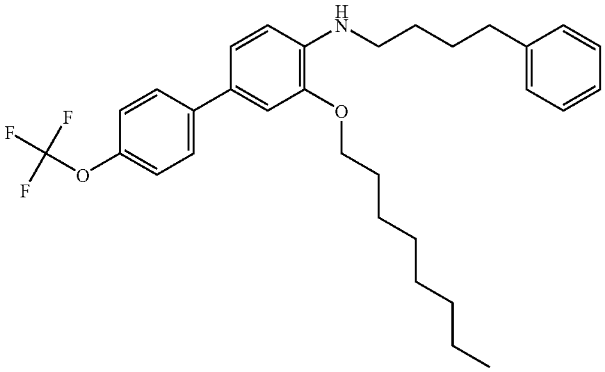 [SMILES: CCCCCCCCOc1cc(-c2ccc(OC(F)(F)F)cc2)ccc1NCCCCc1ccccc1]
653(4)
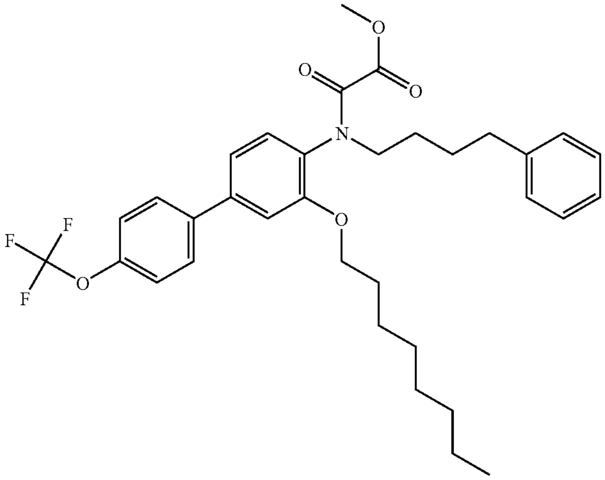 [SMILES: CCCCCCCCOc1cc(-c2ccc(OC(F)(F)F)cc2)ccc1N(CCCCc1ccccc1)C(=O)C(=O)OC]
654(1)
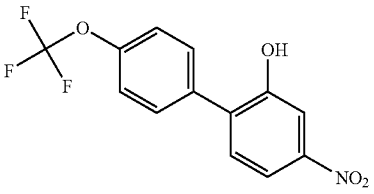 [SMILES: O=[N+]([O-])c1ccc(-c2ccc(OC(F)(F)F)cc2)c(O)c1]
654(2)
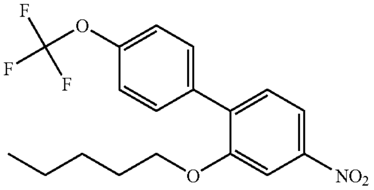
654(3)
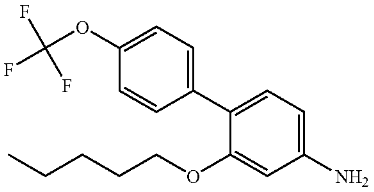 [SMILES: CCCCCOc1cc([N+](=O)[O-])ccc1-c1ccc(OC(F)(F)F)cc1]

TABLE 4-107
654(4)
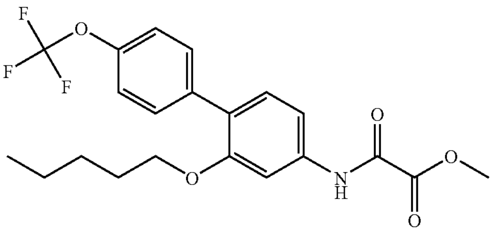 [SMILES: CCCCCOc1cc(NC(=O)C(=O)OC)ccc1-c1ccc(OC(F)(F)F)cc1]
654(5)
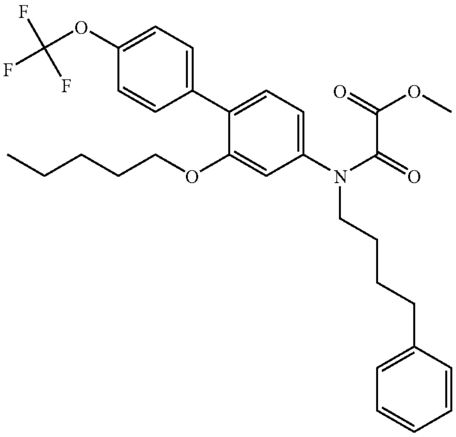 [SMILES: CCCCCOc1cc(N(CCCCc2ccccc2)C(=O)C(=O)OC)ccc1-c1ccc(OC(F)(F)F)cc1]
655(1)
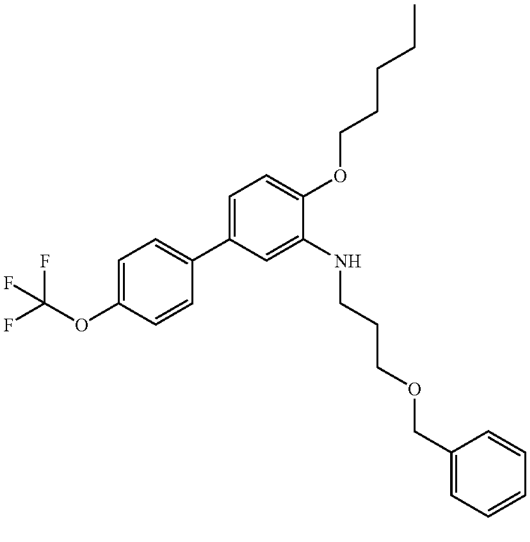 [SMILES: CCCCCOc1ccc(-c2ccc(OC(F)(F)F)cc2)cc1NCCCOCc1ccccc1]

TABLE 4-107-continued
655(2)
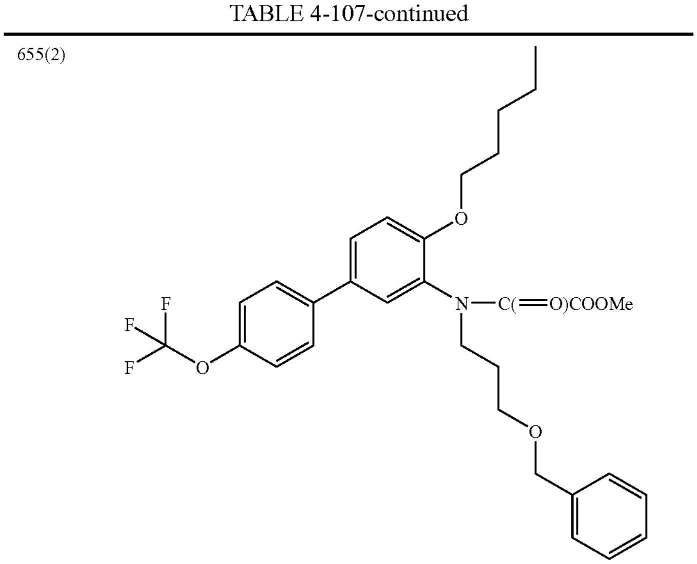
656(1)
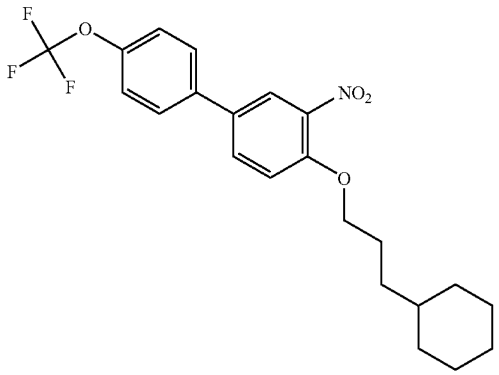 [SMILES: O=[N+]([O-])c1cc(-c2ccc(OC(F)(F)F)cc2)ccc1OCCCC1CCCCC1]
656(2)
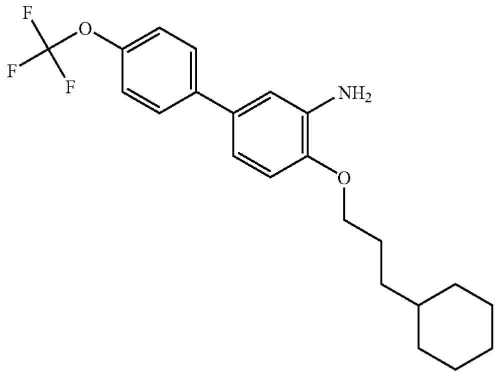
656(3)
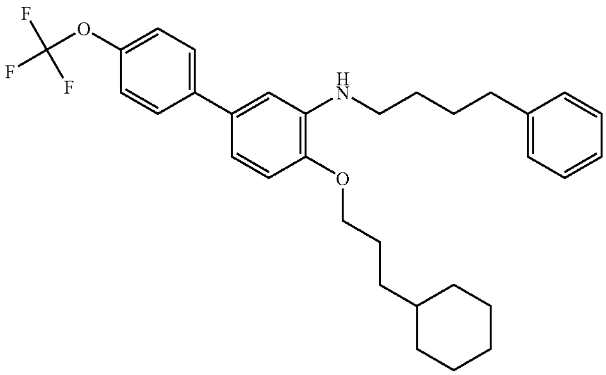 [SMILES: FC(F)(F)Oc1ccc(-c2ccc(OCCCC3CCCCC3)c(NCCCCc3ccccc3)c2)cc1]

TABLE 4-107-continued
656(4)
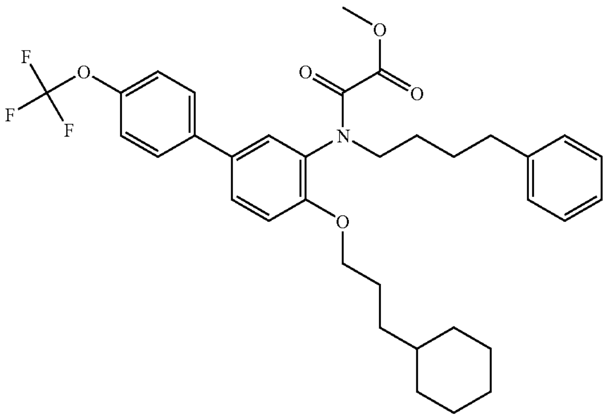 [SMILES: COC(=O)C(=O)N(CCCCc1ccccc1)c1cc(-c2ccc(OC(F)(F)F)cc2)ccc1OCCCC1CCCCC1]
TABLE 4-108
657(1)
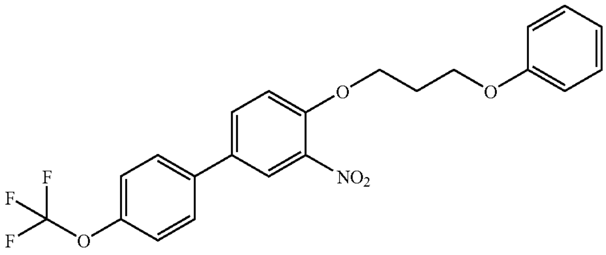 [SMILES: O=[N+]([O-])c1cc(-c2ccc(OC(F)(F)F)cc2)ccc1OCCCOc1ccccc1]
657(2)
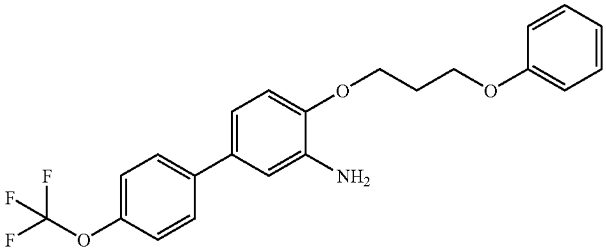 [SMILES: Nc1cc(-c2ccc(OC(F)(F)F)cc2)ccc1OCCCOc1ccccc1]
657(3)
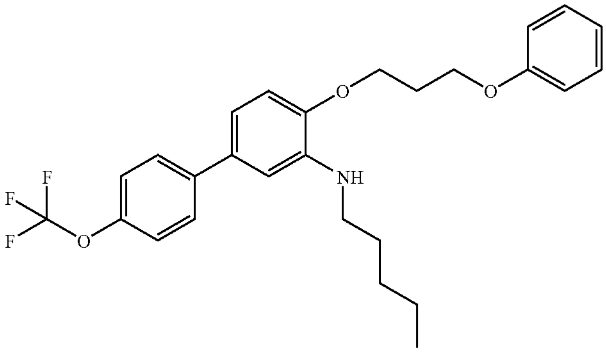 [SMILES: CCCCCNc1cc(-c2ccc(OC(F)(F)F)cc2)ccc1OCCCOc1ccccc1]

TABLE 4-108-continued
657(4)
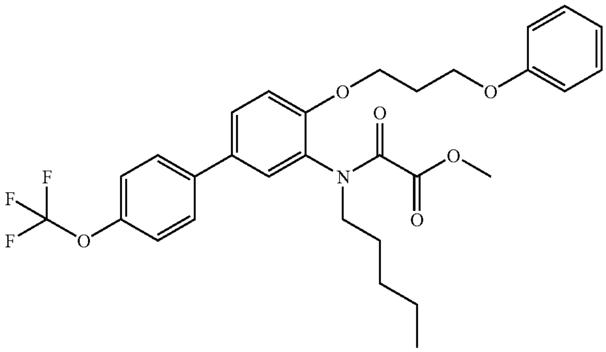 [SMILES: CCCCCN(C(=O)C(=O)OC)c1cc(-c2ccc(OC(F)(F)F)cc2)ccc1OCCCOc1ccccc1]
658(1)
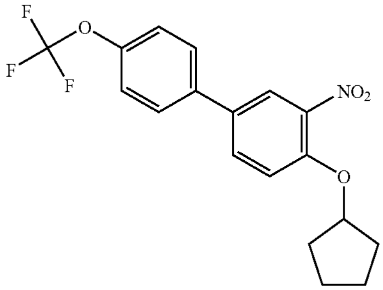
658(2)
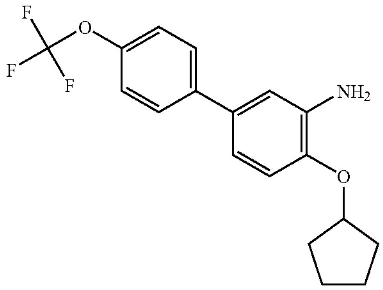 [SMILES: Nc1cc(-c2ccc(OC(F)(F)F)cc2)ccc1OC1CCCC1]
658(3)
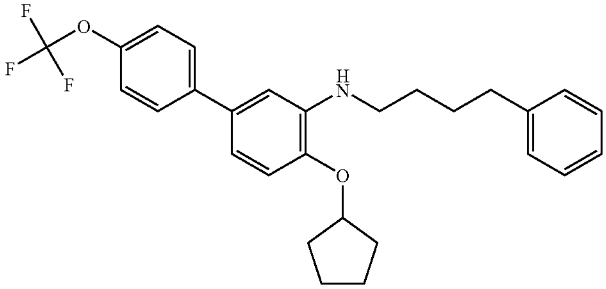 [SMILES: FC(F)(F)Oc1ccc(-c2ccc(OC3CCCC3)c(NCCCCc3ccccc3)c2)cc1]
658(4)
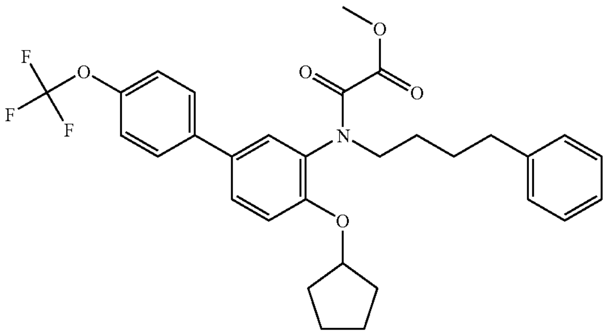 [SMILES: COC(=O)C(=O)N(CCCCc1ccccc1)c1cc(-c2ccc(OC(F)(F)F)cc2)ccc1OC1CCCC1]

TABLE 4-108-continued
659(1)
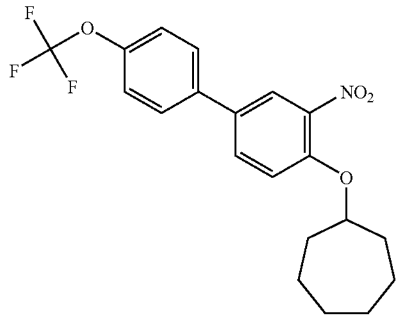
659(2)
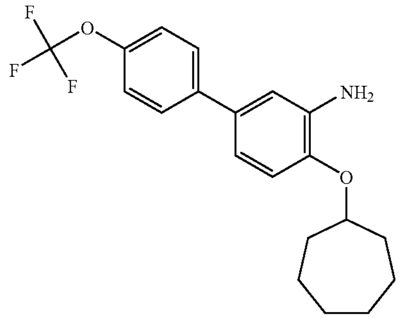 [SMILES: Nc1cc(-c2ccc(OC(F)(F)F)cc2)ccc1OC1CCCCCC1]
659(3)
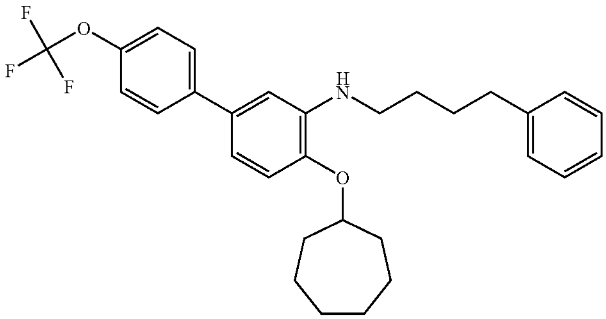 [SMILES: FC(F)(F)Oc1ccc(-c2ccc(OC3CCCCCC3)c(NCCCCc3ccccc3)c2)cc1]
659(4)
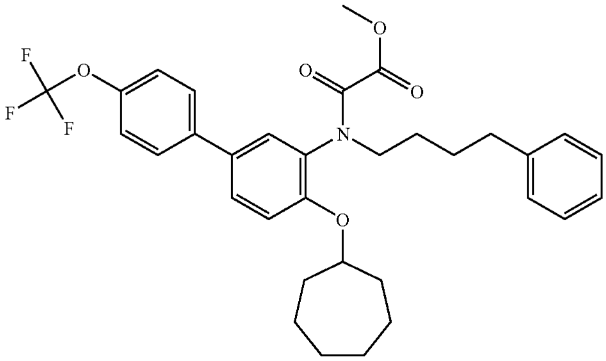 [SMILES: COC(=O)C(=O)N(CCCCc1ccccc1)c1cc(-c2ccc(OC(F)(F)F)cc2)ccc1OC1CCCCCC1]

TABLE 4-109
| | |
|---|---|
| 660(1) | 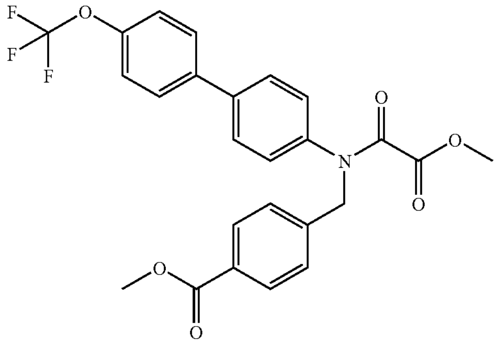 [SMILES: COC(=O)C(=O)N(Cc1ccc(C(=O)OC)cc1)c1ccc(-c2ccc(OC(F)(F)F)cc2)cc1] |
| 661(1) | 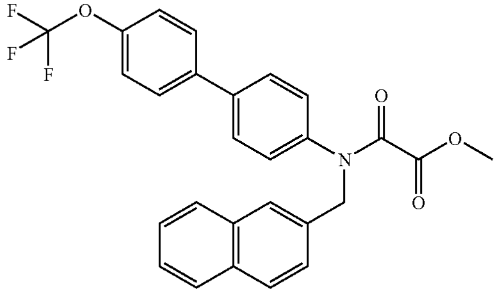 [SMILES: COC(=O)C(=O)N(Cc1ccc2ccccc2c1)c1ccc(-c2ccc(OC(F)(F)F)cc2)cc1] |
| 662(1) | 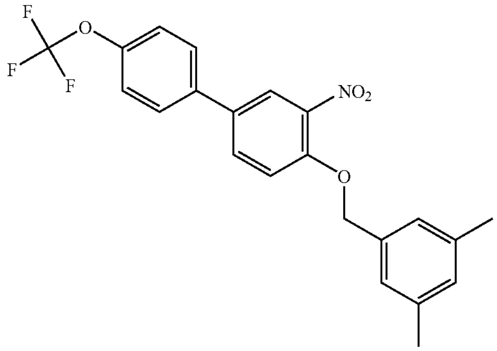 [SMILES: Cc1cc(C)cc(COc2ccc(-c3ccc(OC(F)(F)F)cc3)cc2[N+](=O)[O-])c1] |
| 662(2) | 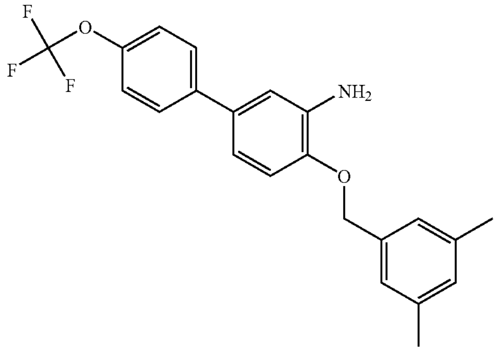 |

TABLE 4-109-continued
662(3)
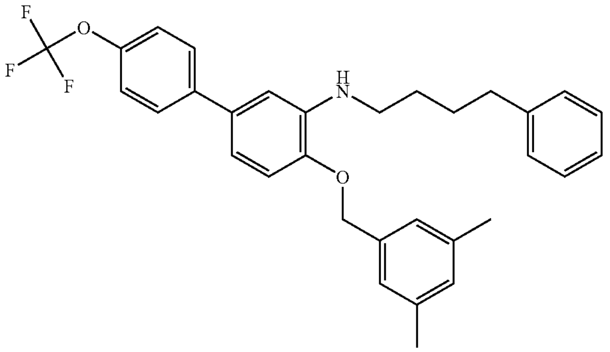 [SMILES: Cc1cc(C)cc(COc2ccc(-c3ccc(OC(F)(F)F)cc3)cc2NCCCCc2ccccc2)c1]
662(4)
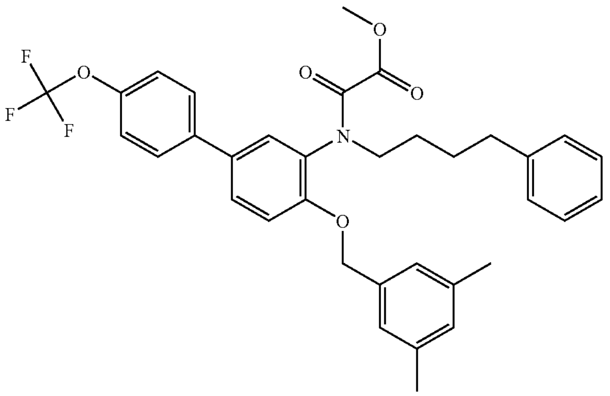 [SMILES: COC(=O)C(=O)N(CCCCc1ccccc1)c1cc(-c2ccc(OC(F)(F)F)cc2)ccc1OCc1cc(C)cc(C)c1]
663(1)
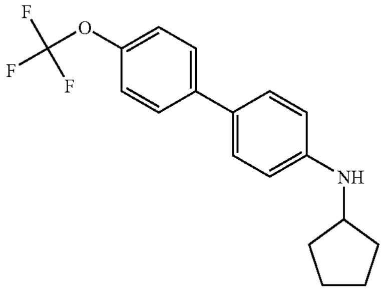 [SMILES: FC(F)(F)Oc1ccc(-c2ccc(NC3CCCC3)cc2)cc1]
663(2)
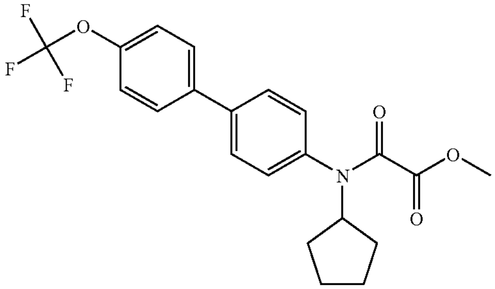 [SMILES: COC(=O)C(=O)N(c1ccc(-c2ccc(OC(F)(F)F)cc2)cc1)C1CCCC1]

TABLE 4-109-continued
| | |
|---|---|
| 664(1) | 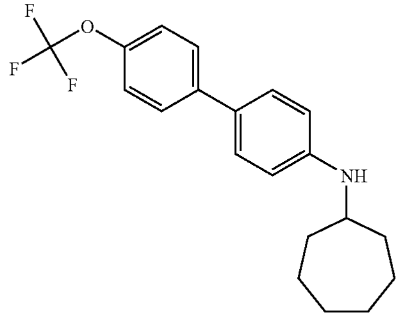 [SMILES: FC(F)(F)Oc1ccc(-c2ccc(NC3CCCCCC3)cc2)cc1] |
| 664(2) | 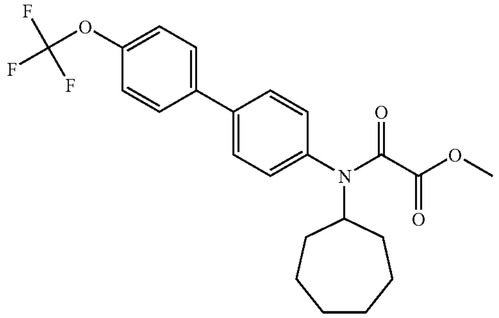 [SMILES: COC(=O)C(=O)N(c1ccc(-c2ccc(OC(F)(F)F)cc2)cc1)C1CCCCCC1] |
TABLE 4-110
| | |
|---|---|
| 665(1) | 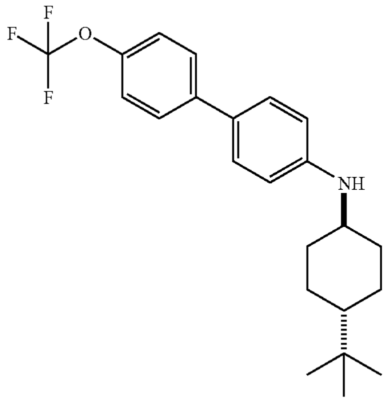 |
| 665(2) | 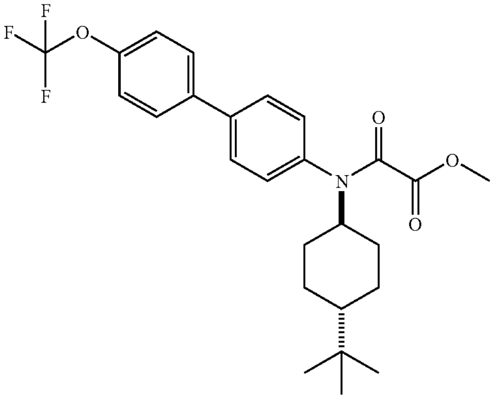 |
TABLE 4-110-continued
| | |
|---|---|
| 666(1) | 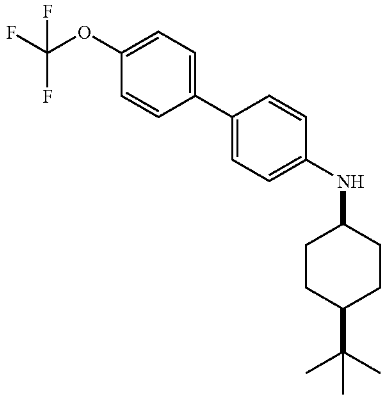 |
| 666(2) | 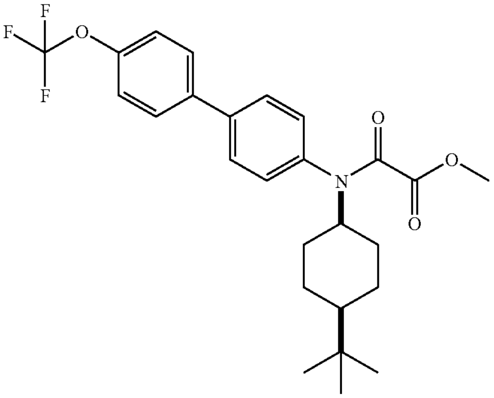 |

TABLE 4-110-continued
667(1)
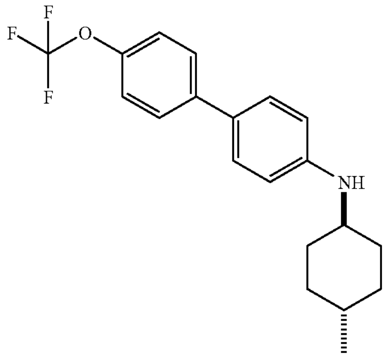
667(2)
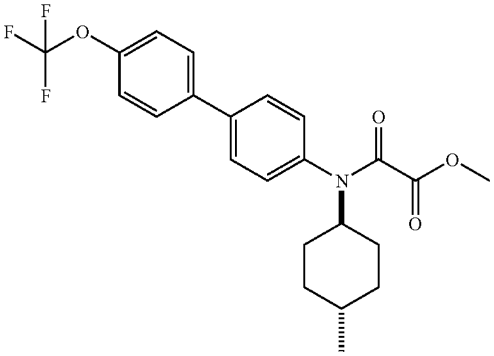
668(1)
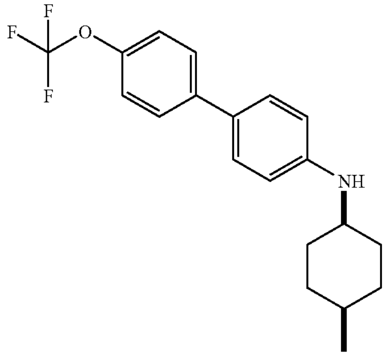
668(2)
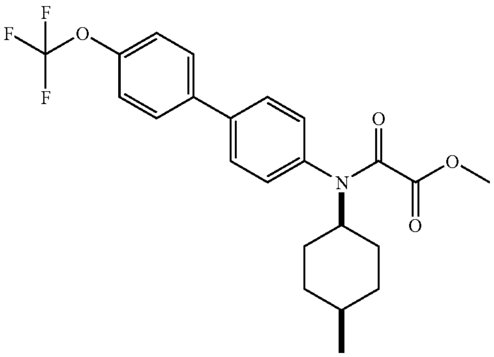
TABLE 4-111
669(1)
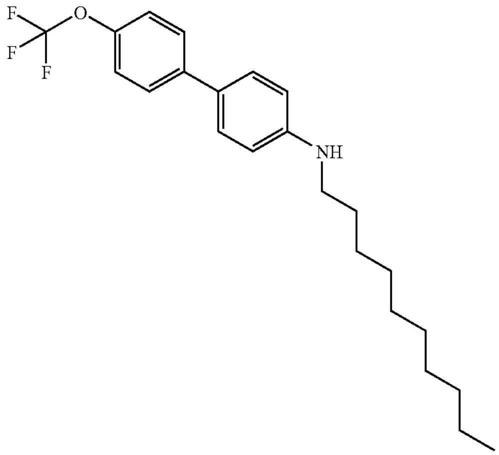 [SMILES: CCCCCCCCCCNc1ccc(-c2ccc(OC(F)(F)F)cc2)cc1]
669(2)
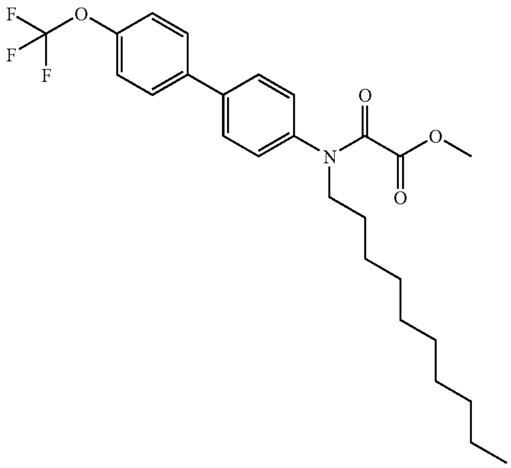 [SMILES: CCCCCCCCCCN(C(=O)C(=O)OC)c1ccc(-c2ccc(OC(F)(F)F)cc2)cc1]
670(1)
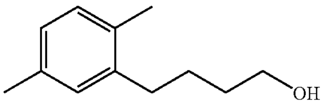
670(2)
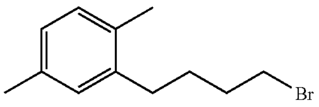

TABLE 4-111-continued
670(3)
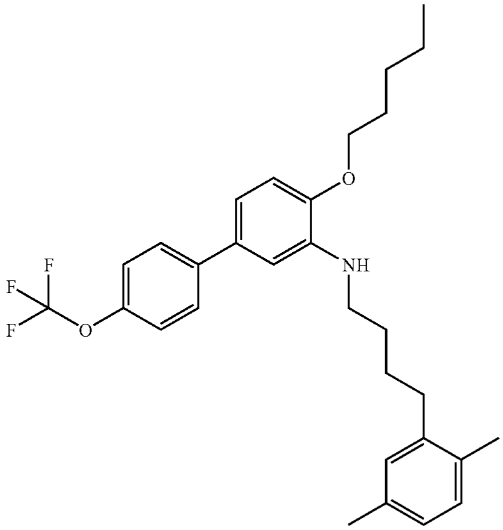 [SMILES: CCCCCOc1ccc(-c2ccc(OC(F)(F)F)cc2)cc1NCCCCc1cc(C)ccc1C]
670(4)
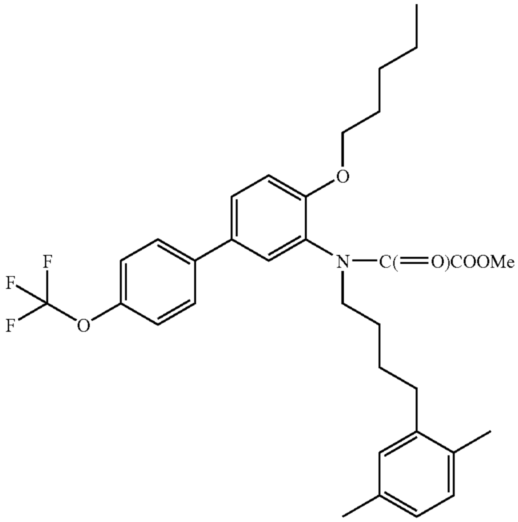
671(1)
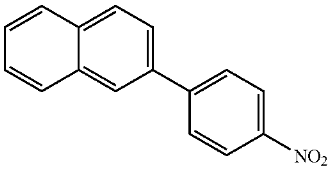 [SMILES: Nc1ccc(-c2ccc3ccccc3c2)cc1]
671(2)
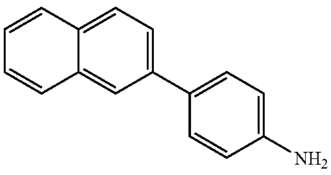
671(3)
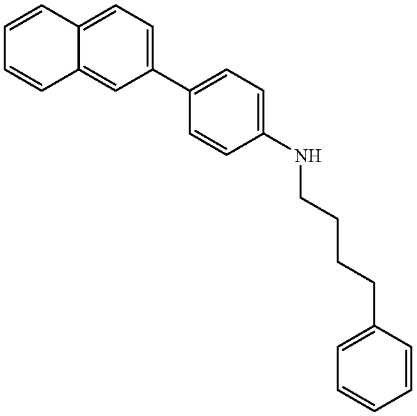 [SMILES: c1ccc(CCCCNc2ccc(-c3ccc4ccccc4c3)cc2)cc1]
671(4)
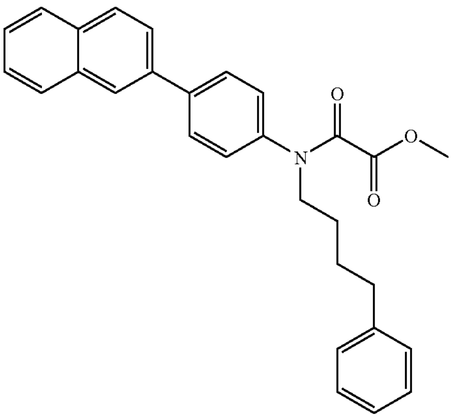 [SMILES: COC(=O)C(=O)N(CCCCc1ccccc1)c1ccc(-c2ccc3ccccc3c2)cc1]
TABLE 4-112
672(1)
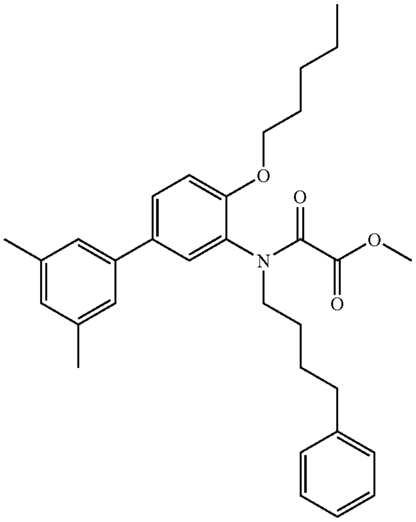

TABLE 4-112-continued
673(1)
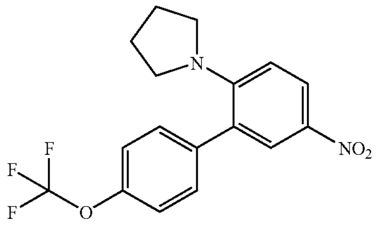 [SMILES: O=[N+]([O-])c1ccc(N2CCCC2)c(-c2ccc(OC(F)(F)F)cc2)c1]
673(2)
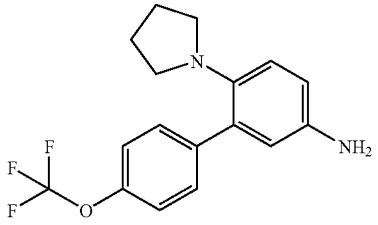
673(3)
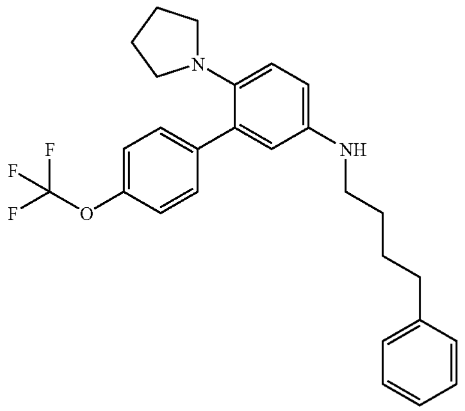 [SMILES: FC(F)(F)Oc1ccc(-c2cc(NCCCCc3ccccc3)ccc2N2CCCC2)cc1]
673(4)
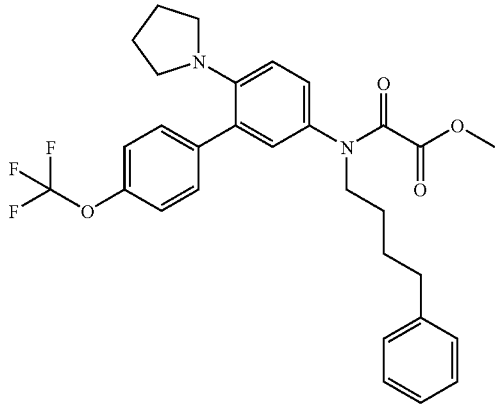 [SMILES: COC(=O)C(=O)N(CCCCc1ccccc1)c1ccc(N2CCCC2)c(-c2ccc(OC(F)(F)F)cc2)c1]
674(1)
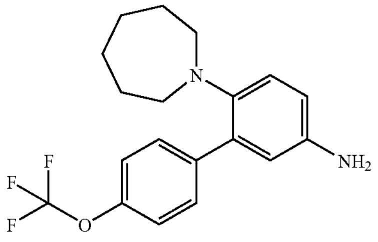 [SMILES: Nc1ccc(N2CCCCCC2)c(-c2ccc(OC(F)(F)F)cc2)c1]
674(2)
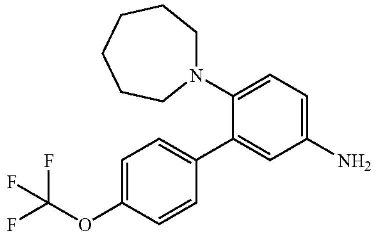 [SMILES: Nc1ccc(N2CCCCCC2)c(-c2ccc(OC(F)(F)F)cc2)c1]
674(3)
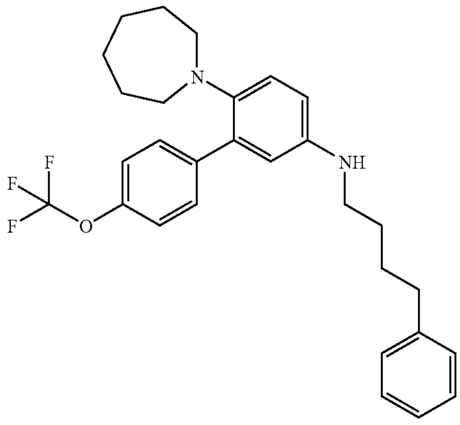 [SMILES: FC(F)(F)Oc1ccc(-c2cc(NCCCCc3ccccc3)ccc2N2CCCCCC2)cc1]

TABLE 4-113
| | |
|---|---|
| 674(4) | 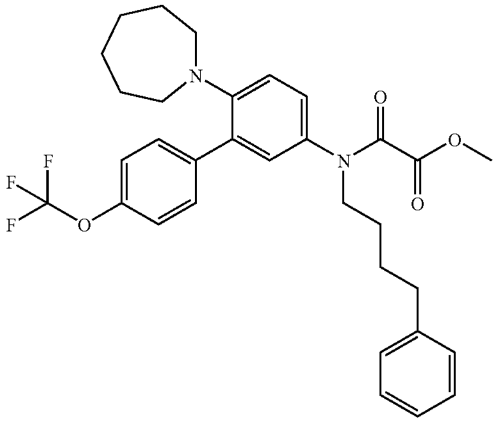 [SMILES: COC(=O)C(=O)N(CCCCc1ccccc1)c1ccc(N2CCCCCC2)c(-c2ccc(OC(F)(F)F)cc2)c1] |
| 675(1) | 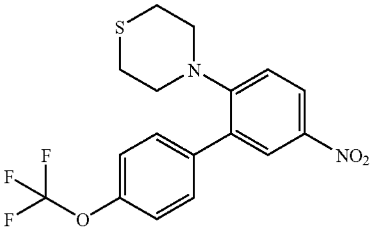 [SMILES: O=[N+]([O-])c1ccc(N2CCSCC2)c(-c2ccc(OC(F)(F)F)cc2)c1] |
| 675(2) | 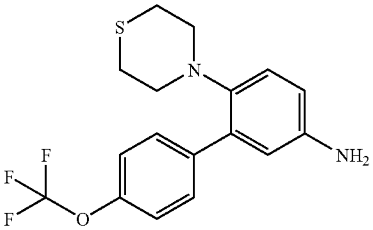 |
| 675(3) | 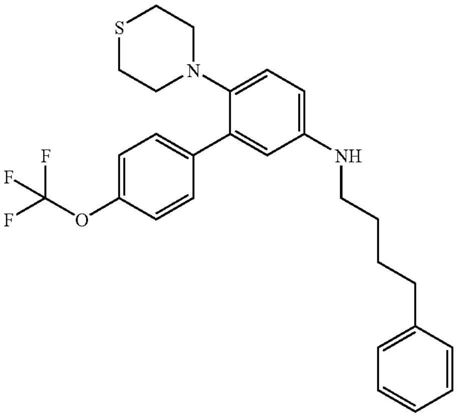 [SMILES: FC(F)(F)Oc1ccc(-c2cc(NCCCCc3ccccc3)ccc2N2CCSCC2)cc1] |

TABLE 4-113-continued
675(4)
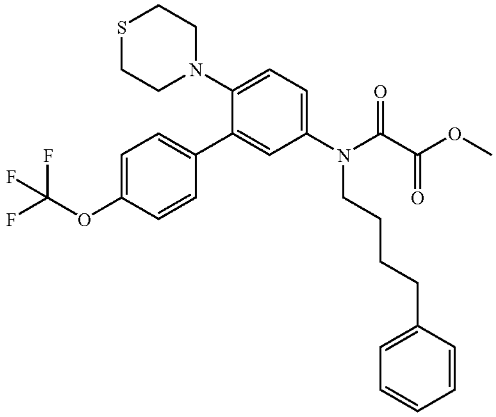 [SMILES: COC(=O)C(=O)N(CCCCc1ccccc1)c1ccc(N2CCSCC2)c(-c2ccc(OC(F)(F)F)cc2)c1]
676(1)
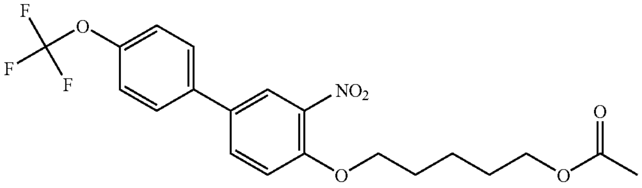 [SMILES: CC(=O)OCCCCCOc1ccc(-c2ccc(OC(F)(F)F)cc2)cc1[N+](=O)[O-]]
676(2)
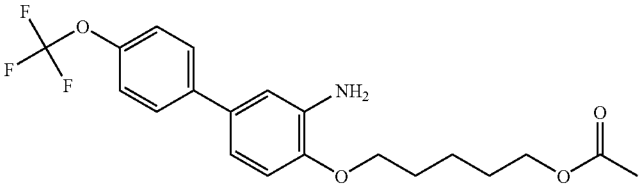
676(3)
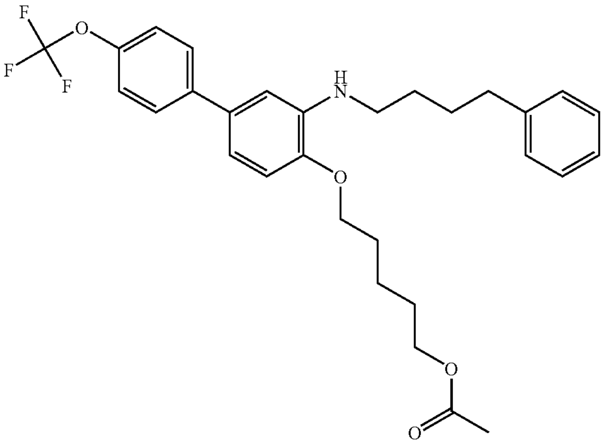 [SMILES: CC(=O)OCCCCCOc1ccc(-c2ccc(OC(F)(F)F)cc2)cc1NCCCCc1ccccc1]

TABLE 4-114
676(4)
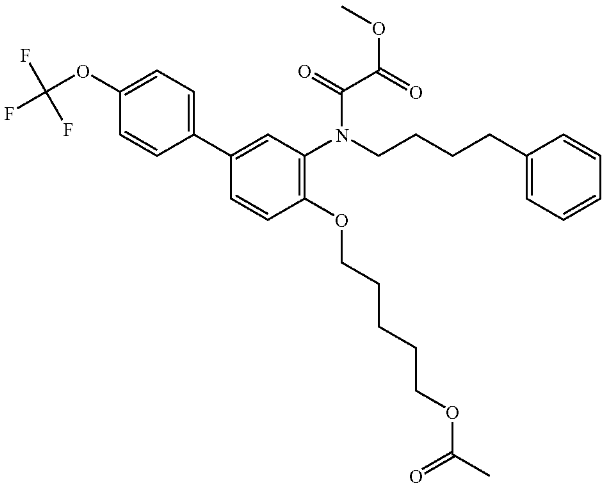 [SMILES: COC(=O)C(=O)N(CCCCc1ccccc1)c1cc(-c2ccc(OC(F)(F)F)cc2)ccc1OCCCCCOC(C)=O]
677(1)
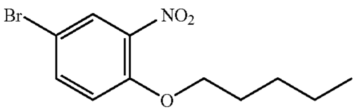 [SMILES: CCCCCOc1ccc(Br)cc1[N+](=O)[O-]]
677(2)
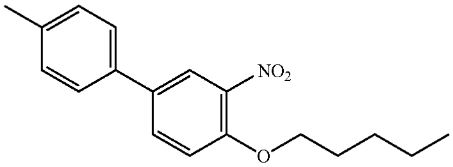 [SMILES: CCCCCOc1ccc(-c2ccc(C)cc2)cc1[N+](=O)[O-]]
677(3)
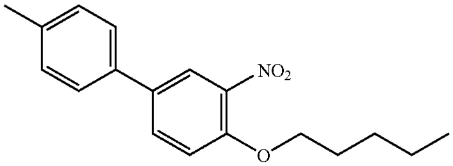 [SMILES: CCCCCOc1ccc(-c2ccc(C)cc2)cc1[N+](=O)[O-]]
677(4)
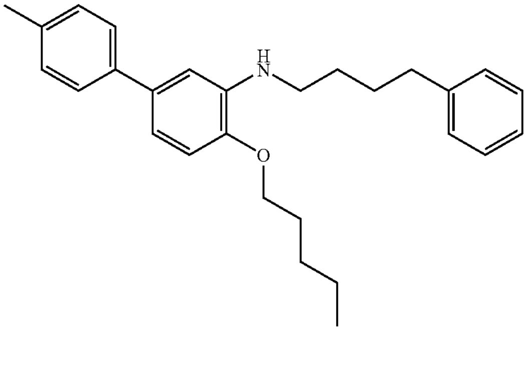 [SMILES: CCCCCOc1ccc(-c2ccc(C)cc2)cc1NCCCCc1ccccc1]

TABLE 4-114-continued
677(5)
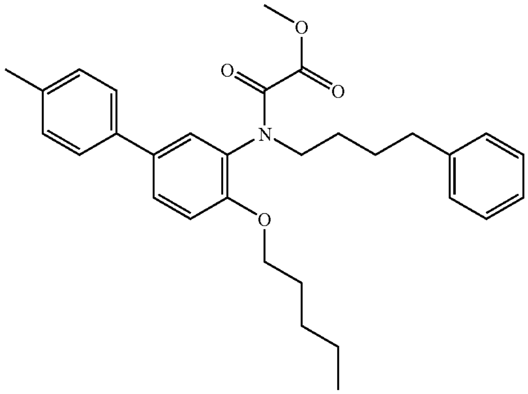 [SMILES: CCCCCOc1ccc(-c2ccc(C)cc2)cc1N(CCCCc1ccccc1)C(=O)C(=O)OC]
678(1)
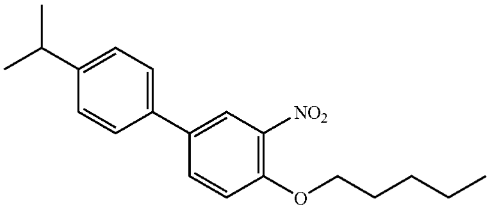
678(2)
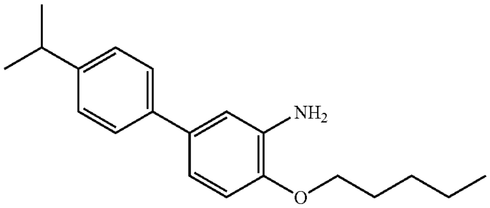 [SMILES: CCCCCOc1ccc(-c2ccc(C(C)C)cc2)cc1[N+](=O)[O-]]
678(3)
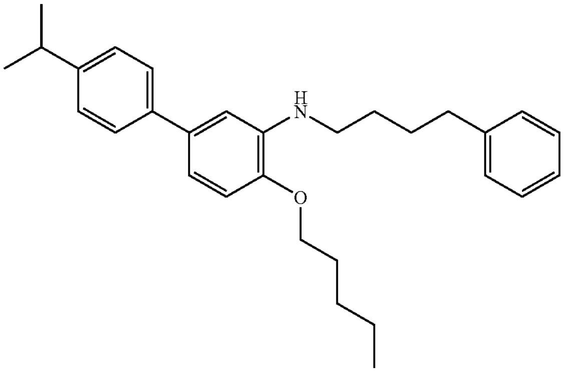 [SMILES: CCCCCOc1ccc(-c2ccc(C(C)C)cc2)cc1NCCCCc1ccccc1]
678(4)
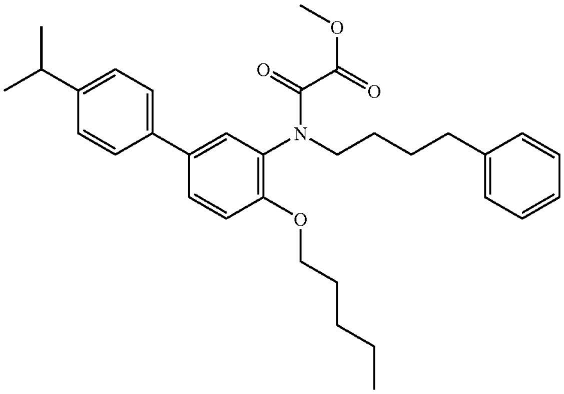 [SMILES: CCCCCOc1ccc(-c2ccc(C(C)C)cc2)cc1N(CCCCc1ccccc1)C(=O)C(=O)OC]

TABLE 4-115
679(1)
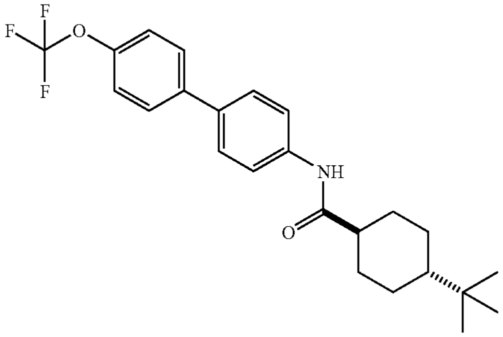
679(2)
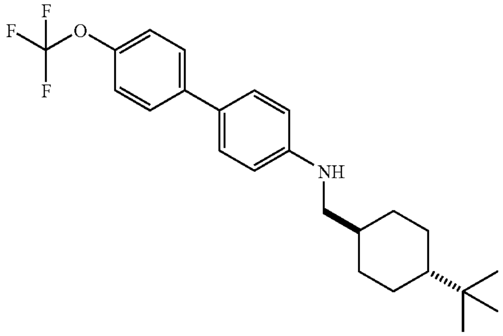
679(3)
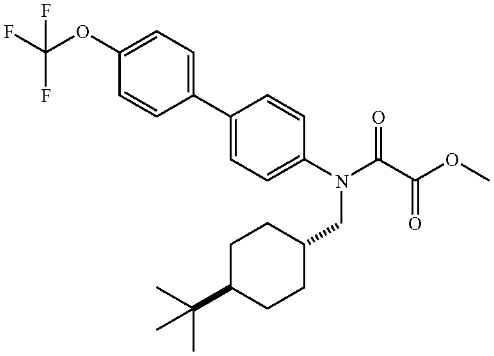
680(1)
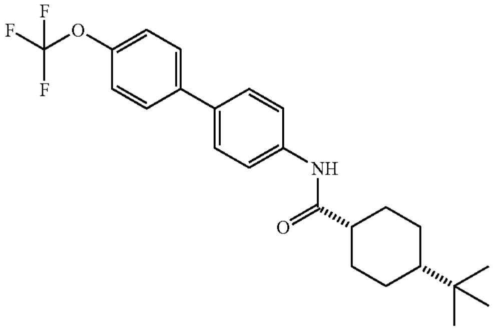
TABLE 4-115-continued
680(2)
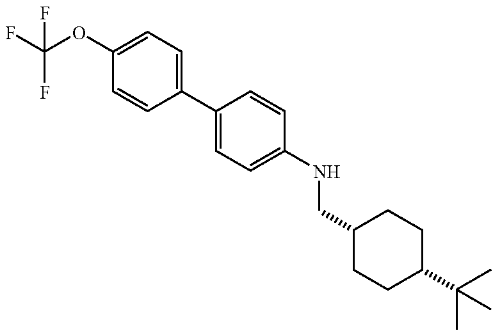
680(3)
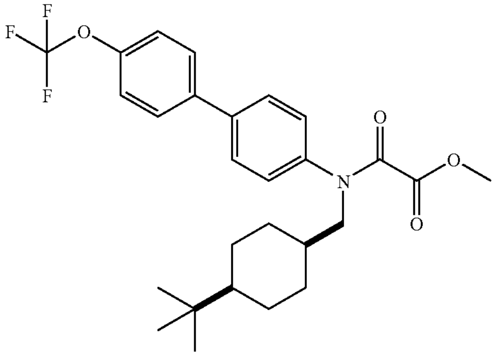
681(1)
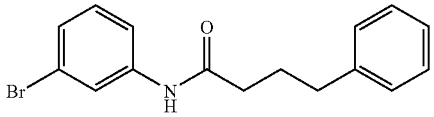 [SMILES: O=C(CCCc1ccccc1)Nc1cccc(Br)c1]
681(2)
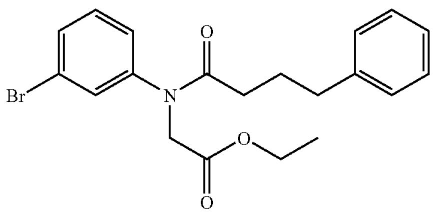 [SMILES: CCOC(=O)CN(C(=O)CCCc1ccccc1)c1cccc(Br)c1]

TABLE 4-115-continued
| | |
|---|---|
| 681(3) | 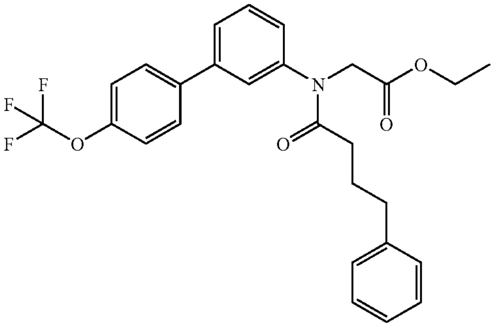 [SMILES: CCOC(=O)CN(C(=O)CCCc1ccccc1)c1cccc(-c2ccc(OC(F)(F)F)cc2)c1] |
| 682(1) | 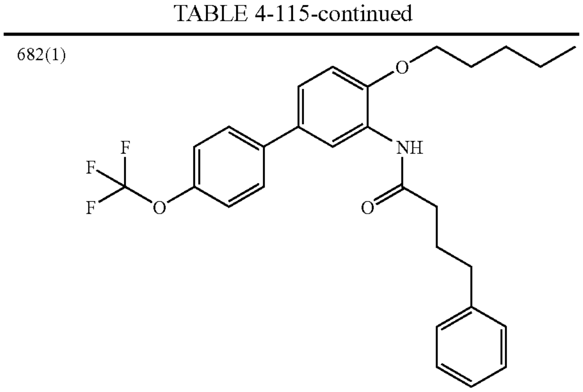 |
TABLE 4-116
| | |
|---|---|
| 682(2) | 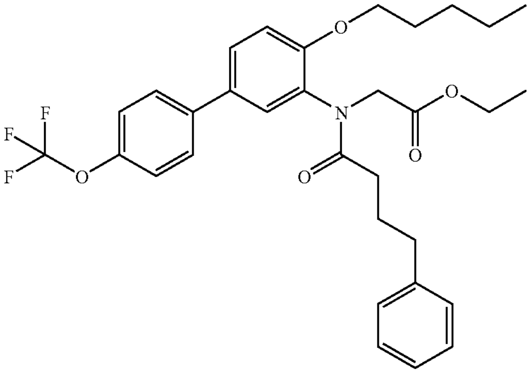 [SMILES: CCCCCOc1ccc(-c2ccc(OC(F)(F)F)cc2)cc1N(CC(=O)OCC)C(=O)CCCc1ccccc1] |
| 683(1) | 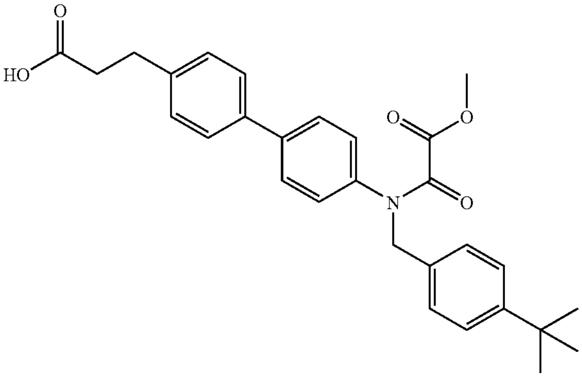 [SMILES: COC(=O)C(=O)N(Cc1ccc(C(C)(C)C)cc1)c1ccc(-c2ccc(CCC(=O)O)cc2)cc1] |
| 684(1) | 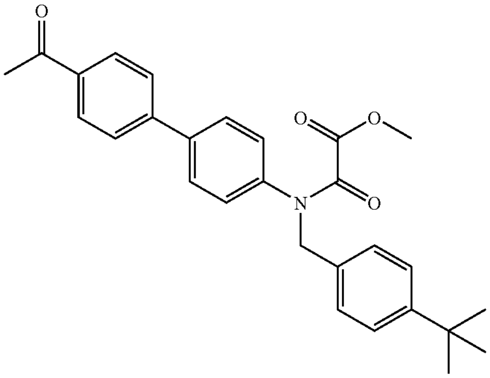 [SMILES: COC(=O)C(=O)N(Cc1ccc(C(C)(C)C)cc1)c1ccc(-c2ccc(C(C)=O)cc2)cc1] |

TABLE 4-116-continued

| | |
|---|---|
| 685(1) | 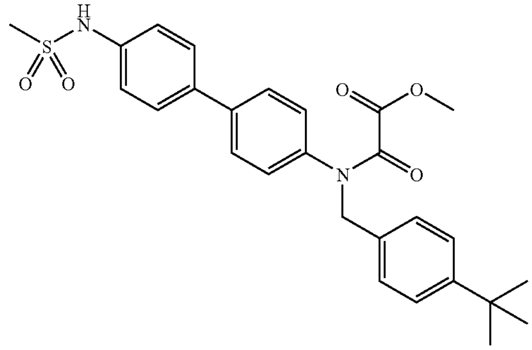 [SMILES: COC(=O)C(=O)N(Cc1ccc(C(C)(C)C)cc1)c1ccc(-c2ccc(NS(C)(=O)=O)cc2)cc1] |
| 686(1) | 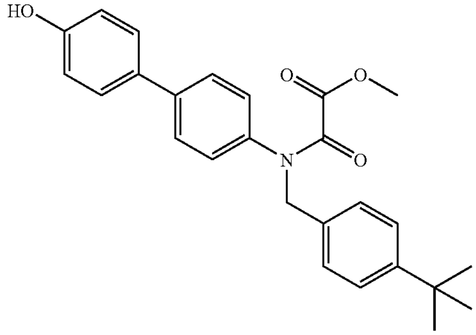 [SMILES: COC(=O)C(=O)N(Cc1ccc(C(C)(C)C)cc1)c1ccc(-c2ccc(O)cc2)cc1] |

Example 1

Preparation of the Compound 1

(1) Preparation of the Intermediate 1(1).

A mixture of 2-benzyloxyphenylacetic acid (242 mg, 1.0 mmol), N-bromosuccinimide (178 mg, 1.9 mmol) and dichloromethane (4 ml) was stirred overnight at room temperature under argon atmosphere. The reaction mixture was diluted with ethyl acetate, washed with saturated brine, and dried over anhydrous sodium sulfate. The solvent was evaporated under reduced pressure to give the title compound (280 mg, 87.2%) as a white solid.

$^1$H-NMR ($CDCl_3$) δ: 3.67 (2H, s), 5.04 (2H, s), 6.78 (1H, d, J=9.6 Hz), 7.25-7.37 (7H, m).

(2) Preparation of the Compound 1.

A mixture of the intermediate 1(1) (261 mg, 0.813 mmol), 4-(trifluoromethoxy)phenylboronic acid (218 mg, 1.056 mmol), [1,1'-bis(diphenylphosphino)ferrocene]dichloropalladium(II) (43 mg, 0.057 mmol), potassium carbonate (169 mg, 1.22 mmol), dioxane (4 ml) and water (0.5 ml) was stirred at 80° C. for 2 hours. The reaction mixture was cooled to room temperature, and the solvent was evaporated under reduced pressure. Ethyl acetate was added to the residue, and the solution was filtered through Celite. The residue obtained by concentration of the filtrate under reduced pressure was purified by column chromatography on silica gel (n-hexane:ethyl acetate=3:2) to give the title compound (160 mg, 48.9%) as a white solid.

$^1$H-NMR ($CDCl_3$) δ: 3.78 (2H, s), 5.11 (2H, s), 6.99 (1H, d, J=8.1 Hz), 7.23-7.45 (9H, m), 7.53 (2H, d, J=9.0 Hz).

Example 2

Preparation of the Compound 2

(1) Preparation of the Intermediate 2(1).

A mixture of benzyl bromide (2.04 g, 11.926 mmol), 5-bromosalicylaldehyde (1.844 g, 9.174 mmol), potassium carbonate (5.07 g, 36.696 mmol) and dimethylformamide (15 ml) was stirred at 50° C. for 2 hours under argon atmosphere. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was washed with methanol to give the title compound (1.2 g, 44.9%) as a white solid.

$^1$H-NMR ($CDCl_3$) δ: 5.10 (2H, s), 6.80 (1H, d, J=9.0 Hz), 7.28-7.44 (6H, m), 7.69 (1H, d, J=2.4 Hz), 10.46 (1H, s).

(2) Preparation of the Intermediate 2(2).

The title compound was obtained in the same manner as the Example 1(2) using the following starting materials.

Starting materials: the intermediate 2(1) and 4-(trifluoromethoxy)phenylboronic acid; Yield: 63.0% (pale yellow solid).

$^1$H-NMR (DMSO-$d_6$) δ: 5.37 (2H, s), 7.32-7.57 (8H, m), 7.75-7.85 (2H, m), 7.96-8.03 (2H, m), 10.47 (1H, s).

(3) Preparation of the Compound 2.

A mixture of the intermediate 2(2) (4.0 g, 9.336 mmol), malonic acid (2.137 g, 20.539 mmol), pyridine (4.3 ml) and piperidine (184 μl, 1.867 mmol) was refluxed for 1 hour under argon atmosphere. The reaction mixture was cooled to room temperature, adjusted to pH 1 by addition of 2 N hydrochloric acid, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=1:1) to give the title compound (4.26 g, 97.0%) as a white solid.

$^1$H-NMR (DMSO-$d_6$) δ: 5.24 (2H, s), 6.63 (1H, d, J=16.2 Hz), 7.04 (1H, d, J=8.7 Hz), 7.23-7.58 (10H, m), 7.73 (1H, d, J=6.9 Hz), 8.20 (1H, d, J=16.2 Hz).

Example 3

Preparation of the Compound 3

A mixture of the compound 2 (100 mg, 0.241 mmol), platinum oxide (5 mg) and ethanol (10 ml) was stirred for 1 hour under hydrogen atmosphere. The reaction mixture was filtered through Celite. The residue obtained by concentration of the filtrate under reduced pressure was washed with methanol under suspension to give the title compound (78 mg, 78.0%) as a white solid.

$^1$H-NMR ($CDCl_3$) δ: 2.74 (2H, t, J=7.5 Hz), 3.06 (2H, t, J=7.8 Hz), 5.14 (2H, s), 6.96 (2H, d, J=8.4 Hz), 7.22-7.54 (11H, m).

Example 4

Preparation of the Compound 4

(1) Preparation of the Intermediate 4(1).

The title compound was obtained in the same manner as the Example 2(1) using the following starting materials.

Starting materials: 4-(tert-butyl)benzyl bromide and 5-bromosalicylaldehyde; Yield: 42.3% (pale yellow oil).

$^1$H-NMR ($CDCl_3$) δ: 1.36 (9H, s), 5.14 (2H, s), 6.97 (1H, d, J=8.7 Hz), 7.35 (2H, d, J=8.7 Hz), 7.43 (2H, d, J=8.7 Hz), 7.60 (1H, dd, J=2.7, 8.7 Hz), 7.94 (1H, d, J=2.7 Hz), 10.45 (1H, s).

(2) Preparation of the Intermediate 4(2).

The title compound was obtained in the same manner as the Example 1(2) using the following starting materials.

Starting materials: the intermediate 4(1) and 4-(trifluoromethoxy)phenylboronic acid; Yield: 47.2% (pale yellow solid).

$^1$H-NMR ($CDCl_3$) δ: 1.34 (9H, s), 5.21 (2H, s), 7.16 (1H, d, J=9.0 Hz), 7.24-7.29 (2H, m), 7.37-7.47 (4H, m), 7.56-7.60 (2H, m), 7.73 (1H, dd, J=2.4, 9.0 Hz), 8.06 (1H, d, J=2.4 Hz), 10.59 (1H, s).

(3) Preparation of the Compound 4.

The title compound was obtained in the same manner as the Example 2(3) using the following starting materials.

Starting materials: the intermediate 4(2) and malonic acid; Yield: 49.1% (white solid).

$^1$H-NMR ($CDCl_3$) δ: 1.35 (9H, s), 5.20 (2H, s), 6.63 (1H, d, J=16.2 Hz), 7.07 (1H, d, J=8.4 Hz), 7.23-7.57 (10H, m), 7.74 (1H, d, J=2.1 Hz), 8.20 (1H, d, J=16.2 Hz).

Example 5

Preparation of the Compound 5

The title compound was obtained in the same manner as the Example 3 using the following starting material.

Starting material: the compound 4; Yield: 54.8% (white solid).

$^1$H-NMR ($CDCl_3$) δ: 1.34 (9H, s), 2.74 (2H, t, J=7.5 Hz), 3.06 (2H, t, J=7.5 Hz), 5.11 (2H, s), 6.97 (1H, d, J=8.1 Hz), 7.22-7.25 (2H, m), 7.35-7.44 (5H, m), 7.53 (2H, d, J=8.7 Hz).

Example 6

Preparation of the Compound 6

(1) Preparation of the Intermediate 6(1).

The title compound was obtained in the same manner as the Example 2(1) using the following starting materials.

Starting materials: 4-(tert-butyl)benzyl bromide and 4-bromo-2-nitrophenol; Yield: 77.1% (white solid).

$^1$H-NMR ($CDCl_3$) δ: 1.32 (9H, s), 5.19 (2H, s), 7.02 (1H, d, J=8.7 Hz), 7.34-7.43 (4H, m), 7.58 (1H, dd, J=2.7, 8.7 Hz), 7.97 (1H, d, J=2.7 Hz).

(2) Preparation of the Intermediate 6(2).

The title compound was obtained in the same manner as the Example 1(2) using the following starting materials.

Starting materials: the intermediate 6(1) and 4-(trifluoromethoxy)phenylboronic acid; Yield: 74.6% (pale yellow solid).

$^1$H-NMR ($CDCl_3$) δ: 1.33 (9H, s), 5.26 (2H, s), 7.22 (1H, d, J=8.7 Hz), 7.28-7.58 (8H, m), 7.68 (1H, dd, J=2.4, 8.7 Hz), 8.05 (1H, d, J=2.4 Hz).

(3) Preparation of the Intermediate 6(3)

The title compound was obtained in the same manner as the Example 3 using the following starting material.

Starting material: the intermediate 6(2); Yield: 83.5% (pale yellow solid).

$^1$H-NMR ($CDCl_3$) δ: 1.34 (9H, s), 3.93 (2H, brs), 5.09 (2H, s), 6.87-6.97 (3H, m), 7.22-7.57 (8H, m).

(4) Preparation of Methyl the Intermediate 6(4).

A solution of methyl chloroglyoxylate (184 μl, 2.0 mmol) in dichloromethane (1.5 ml) was added dropwise at a slow speed to a mixture of the intermediate 6(3) (415 mg, 1.0 mmol), sodium hydrogen carbonate (168 mg, 2.0 mmol), water (5 ml) and dichloromethane (7 ml), and the mixture was stirred at 0° C. for 2 hours. The reaction mixture was diluted with water, and extracted with ethyl acetate. The organic layer was washed with saturated brine, and dried over anhydrous sodium sulfate. The solvent was evaporated under reduced pressure to give the title compound (456 mg, 90.9%) as a white solid.

$^1$H-NMR ($CDCl_3$) δ: 1.34 (9H, s), 3.97 (3H, s), 5.20 (2H, s), 7.07 (1H, d, J=8.4 Hz), 7.22-7.62 (9H, m), 8.70 (1H, d, J=2.4 Hz), 9.62 (1H, brs).

(5) Preparation of the Compound 6.

A mixture of the intermediate 6(4) (436 mg, 0.869 mmol), methanol (2 ml), tetrahydrofuran (2 ml) and a 2 N aqueous solution of sodium hydroxide (1.3 ml) was stirred at room temperature for 30 minutes. The precipitated solid was collected by filtration, and washed with methanol to give the title compound (390 mg, 88.1%) as a white solid.

$^1$H-NMR (DMSO-$d_6$) δ: 1.29 (9H, s), 5.25 (2H, s), 7.26 (1H, s), 7.26 (1H, d, J=8.4 Hz), 7.34 (1H, dd, J=2.4, 8.4 Hz), 7.67 (1H, d, J=8.7 Hz), 8.68 (2H, d, J=2.4 Hz), 10.38 (1H, brs).

Example 7

Preparation of the Compound 7

(1) Preparation of the Intermediate 7(1).

The title compound was obtained in the same manner as the Example 1(2) using the following starting materials.

Starting materials: the intermediate 2(1) and 2-nitrophenylboronic acid; Yield: 29.1% (pale yellow solid).

$^1$H-NMR ($CDCl_3$) δ: 5.17 (2H, s), 6.99 (1H, d, J=8.7 Hz), 7.24 (1H, dd, J=8.7, 2.1 Hz), 7.30-7.51 (7H, m), 7.53-7.61 (2H, m), 7.82 (1H, dd, J=8.7, 1.2 Hz).

(2) Preparation of the Compound 7.

The title compound was obtained in the same manner as the Example 2(3) using the following starting materials.

Starting materials: the intermediate 7(1) and malonic acid; Yield: 42.4% (yellow solid).

$^1$H-NMR (DMSO-$d_6$) δ: 5.27 (2H, s), 6.59 (1H, d, J=16.2 Hz), 7.26 (1H, d, J=8.4 Hz), 7.32-7.52 (6H, m), 7.59-7.64 (2H, m), 7.72-7.78 (2H, m), 7.86 (1H, d, J=16.2 Hz), 7.96-8.00 (1H, m), 12.36 (1H, s).

Example 8

Preparation of the Compound 8

The title compound was obtained in the same manner as the Example 3 using the following starting material.

Starting material: the compound 7; Yield: 39.1% (pink solid).

$^1$H-NMR (DMSO-$d_6$) δ: 2.56 (2H, t, J=7.8 Hz), 2.87 (2H, t, J=7.8 Hz), 4.71 (2H, brs), 5.17 (2H, s), 6.55-6.63 (1H, m), 6.73 (1H, d, J=8.4 Hz), 6.93-7.03 (2H, m), 7.10 (1H, d, J=8.4 Hz), 7.19-7.23 (2H, m), 7.31-7.36 (1H, m), 7.39-7.44 (2H, m), 7.48-7.50 (2H, m), 12.08 (1H, brs).

Example 9

Preparation of the Compound 9

(1) Preparation of the Intermediate 9(1).

A mixture of 4-(tert-butyl)benzyl bromide (2.240 g, 9.861 mmol), 2-hydroxyphenylacetic acid (1.00 g, 6.572 mmol), potassium carbonate (3.996 g, 28.918 mmol), chloroform (6 ml) and methanol (6 ml) was refluxed for 2 hours. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=4:1) to give the title compound (1.007 g, 51.4%) as a white solid.

$^1$H-NMR ($CDCl_3$) δ: 1.32 (9H, s), 3.73 (2H, s), 5.06 (2H, s), 6.92-6.97 (2H, m), 7.21-7.41 (6H, m).

(2) Preparation of the Intermediate 9(2).

The title compound was obtained in the same manner as the Example 1(1) using the following starting material.

Starting material: the intermediate 9(1); Yield: 49.9% (white solid).

$^1$H-NMR ($CDCl_3$) δ: 1.31 (9H, s), 3.68 (3H, s), 5.02 (2H, s), 6.81 (2H, d, J=9.6 Hz), 7.26-7.39 (6H, m).

(3) Preparation of the Compound 9.

The title compound was obtained in the same manner as the Example 1(2) using the following starting materials.

Starting materials: the intermediate 9(2) and 4-(trifluoromethoxy)phenylboronic acid; Yield: 19.9% (white solid).

$^1$H-NMR (DMSO-$d_6$) δ: 1.29 (9H, s), 3.64 (2H, s), 5.14 (2H, s), 7.13 (1H, d, J=8.7 Hz), 7.36-7.43 (6H, m), 7.54-7.57 (2H, m), 7.72 (2H, d, J=8.1 Hz), 12.28 (1H, brs).

Example 10

Preparation of the Compound 10

The title compound was obtained in the same manner as the Example 1(2) using the following starting materials.

Starting materials: the intermediate 9(2) and 3,4-(methylenedioxy)phenylboronic acid; Yield: 30.3% (white solid).

$^1$H-NMR (DMSO-$d_6$) δ: 1.28 (9H, s), 3.62 (2H, s), 5.11 (2H, s), 6.04 (2H, s), 6.96 (2H, d, J=8.1 Hz), 7.05-7.09 (2H, m), 7.17 (2H, d, J=1.5 Hz), 7.35-7.48 (6H, m), 12.23 (1H, s).

Example 11

Preparation of the Compound 11

(1) Preparation of the Intermediate 11(1).

The title compound was obtained in the same manner as the Example 9(1) using the following starting materials.

Starting materials: 2-hydroxyphenylacetic acid and 3,5-dimethylbenzyl bromide; Yield: 33.9% (white solid).

$^1$H-NMR ($CDCl_3$) δ: 2.29 (6H, s), 3.72 (2H, s), 5.00 (2H, s), 6.91-6.96 (3H, m), 7.00 (2H, s), 7.19-7.23 (1H, m), 7.24-7.28 (1H, m).

(2) Preparation of the Intermediate 11(2).

The title compound was obtained in the same manner as the Example 1(1) using the following starting material.

Starting material: the intermediate 11(1); Yield: 38.5% (white solid).

$^1$H-NMR ($CDCl_3$) δ: 2.29 (6H, s), 3.72 (2H, s), 5.00 (2H, s), 6.91-6.96 (3H, m), 7.00 (2H, s), 7.19-7.23 (1H, m), 7.24-7.28 (1H, m).

(3) Preparation of the Compound 11.

The title compound was obtained in the same manner as the Example 1(2) using the following starting materials.

Starting materials: the intermediate 11(2) and 4-(trifluoromethoxy)phenylboronic acid; Yield: 7.2% (white solid).

$^1$H-NMR ($CDCl_3$) δ: 2.30 (6H, s), 3.78 (2H, s), 5.05 (2H, s), 6.93-7.02 (4H, m), 7.23-7.27 (2H, m), 7.40-7.45 (2H, m), 7.53 (2H, d, J=8.7 Hz).

Example 12

Preparation of the Compound 12

(1) Preparation of the Intermediate 12(1).

The title compound was obtained in the same manner as the Example 1(2) using the following starting materials.

Starting materials: 5-bromo-2-fluorobenzaldehyde and 4-(trifluoromethoxy)phenylboronic acid; Yield: 91.6% (pale yellow oil).

$^1$H-NMR ($CDCl_3$) δ: 7.24-7.33 (3H, m), 7.55-7.61 (2H, m), 7.76-7.82 (1H, m), 8.05 (1H, dd, J=2.4, 6.3 Hz), 10.42 (1H, s).

(2) Preparation of the Intermediate 12(2).

A mixture of the intermediate 12(1) (750 mg, 2.639 mmol), 4-(tert-butyl)phenol (436 mg, 2.903 mmol), potassium carbonate (547 mg, 3.958 mmol) and dimethylacetamide (4 ml) was stirred at 160° C. for 1 hour. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=15:1) to give the title compound (598 mg, 54.7%) as a pale yellow solid.

$^1$H-NMR ($CDCl_3$) δ: 1.35 (9H, s), 1.27 (1H, d, J=8.7 Hz), 6.98 (2H, d, J=8.7 Hz), 7.28 (2H, d, J=8.4 Hz), 7.43 (2H, d, J=8.7 Hz), 7.59 (2H, d, J=8.4 Hz), 7.68 (1H, dd, J=2.7, 8.7 Hz), 8.12 (1H, d, J=2.7 Hz), 10.58 (1H, t, J=8.1 Hz).

(3) Preparation of the Intermediate 12(3).

A solution of potassium bis(trimethylsilyl)amide (414 mg, 1.973 mmol) in tetrahydrofuran (3 ml) was added dropwise at a slow speed to a mixture of bis(2,2,2-trifluoroethyl)(methoxycarbonylmethyl)phosphonate (627 mg, 1.973 mmol), 18-crown-6 (2.048 g, 7.750 mmol) and tetrahydrofuran (20 ml) at −78° C. under argon atmosphere. A solution of the intermediate 12(2) (584 mg, 1.409 mmol) in tetrahydrofuran (3 ml) was added dropwise at a slow speed to the mixture at −78° C. under argon atmosphere, and the mixture was stirred at −78° C. for 30 minutes. A saturated aqueous solution of ammonium chloride was added to the reaction mixture. The residue obtained by evaporation of the solvent under reduced pressure was diluted with ethyl acetate, washed with water, and dried over anhydrous sodium sulfate. The residue obtained by evaporation of the solvent under reduced pressure was purified by column chromatography on silica gel (n-hexane:ethyl acetate=15:1) to give the title compound (597 mg, 90.1%) as a pale yellow oil.

$^1$H-NMR ($CDCl_3$) δ: 1.32 (9H, s), 3.71 (3H, s), 6.04 (1H, d, J=12.6 Hz), 6.90-6.98 (3H, m), 7.20-7.31 (3H, m), 7.36 (2H, d, J=9.6 Hz), 7.44 (1H, dd, J=2.4, 8.4 Hz), 7.59 (2H, d, J=8.7 Hz), 7.95 (1H, d, J=2.4 Hz).

(4) Preparation of the Compound 12.

A mixture of the intermediate 12(3) (590 mg, 1.293 mmol), methanol (1 ml), tetrahydrofuran (4 ml) and a 2 N aqueous solution of sodium hydroxide (1.94 ml) was stirred at 60° C. for 1 hour. The reaction mixture was cooled to room temperature, acidified by addition of 2 N hydrochloric acid, and extracted with ethyl acetate. The organic layer was washed with saturated brine, and dried over anhydrous sodium sulfate. The solvent was evaporated under reduced pressure to give the title compound (550 mg, 93.2%) as a pale yellow oil.

$^1$H-NMR ($CDCl_3$) δ: 1.32 (9H, s), 3.49 (2H, s), 6.06 (1H, d, J=12.6 Hz), 6.91 (1H, d, J=8.4 Hz), 6.95 (2H, d, J=8.7 Hz), 7.20-7.24 (2H, m), 7.30-7.36 (3H, m), 7.43 (1H, dd, J=2.1, 8.4 Hz), 7.50-7.54 (2H, m), 7.90 (1H, d, J=2.1 Hz).

Example 13

Preparation of the Compound 13

The title compound was obtained in the same manner as the Example 3 using the following starting material.

Starting material: the compound 12; Yield: 75.4% (clear colorless oil).

$^1$H-NMR ($CDCl_3$) δ: 1.33 (9H, s), 2.76 (2H, t, J=7.5 Hz), 3.06 (2H, t, J=7.5 Hz), 6.89 (1H, d, J=6.9 Hz), 6.93 (2H, d, J=8.7 Hz), 7.24-7.39 (5H, m), 7.46 (1H, d, J=2.1 Hz), 7.55 (2H, d, J=8.7 Hz).

Example 14

Preparation of the Compound 14

(1) Preparation of the Intermediate 14(1).

The title compound was obtained in the same manner as the Example 12(2) using the following starting materials.

Starting materials: the intermediate 12(1) and methyl 4-hydroxybenzoate; Yield: 40.5% (pale yellow solid).

$^1$H-NMR ($CDCl_3$) δ: 3.93 (3H, s), 7.09 (1H, d, J=8.7 Hz), 7.12 (2H, d, J=8.4 Hz), 7.32 (2H, d, J=8.4 Hz), 7.62 (2H, d, J=8.4 Hz), 7.77 (1H, dd, J=2.4, 8.7 Hz), 8.10 (2H, d, J=8.4 Hz), 8.16 (1H, d, J=2.4 Hz), 10.47 (1H, s).

(2) Preparation of Methyl the Intermediate 14(2).

The title compound was obtained in the same manner as the Example 12(3) using the following starting materials.

Starting materials: the intermediate 14(1) and bis(2,2,2-trifluoroethyl)(methoxycarbonylmethyl)phosphonate; Yield: 84.3% (pale yellow oil).

$^1$H-NMR ($CDCl_3$) δ: 3.69 (3H, s), 3.90 (3H, s), 5.01 (1H, d, J=12.3 Hz), 6.99 (2H, d, J=9.3 Hz), 7.06 (1H, d, J=8.7 Hz), 7.09 (1H, d, J=12.3 Hz), 7.29 (2H, d, J=8.4 Hz), 7.54 (1H, dd, J=2.4, 8.7 Hz), 7.61 (2H, d, J=8.4 Hz), 7.92 (1H, d, J=2.4 Hz), 8.00 (2H, d, J=9.3 Hz).

(3) Preparation of the Intermediate 14(3).

The title compound was obtained in the same manner as the Example 12(4) using the following starting material.

Starting material: the intermediate 14(2); Yield: 58.5% (white solid).

$^1$H-NMR (DMSO-$d_6$) δ: 6.05 (1H, d, J=12.6 Hz), 6.97-7.06 (3H, m), 7.15 (1H, d, J=9.0 Hz), 7.45-7.50 (2H, m), 7.71 (1H, dd, J=2.1, 9.0 Hz), 7.78 (2H, d, J=8.7 Hz), 7.92-7.97 (3H, m), 12.69 (1H, brs).

(4) Preparation of the Compound 14.

The title compound was obtained in the same manner as the Example 3 using the following starting material.

Starting material: the intermediate 14(3); Yield: 100% (white solid).

$^1$H-NMR (DMSO-$d_6$) δ: 2.57 (2H, t, J=7.5 Hz), 2.85 (2H, t, J=7.5 Hz), 7.03 (2H, d, J=8.7 Hz), 7.10 (1H, d, J=8.4 Hz), 7.46 (2H, d, J=8.7 Hz), 7.60 (1H, dd, J=2.4, 8.4 Hz), 7.72 (1H, d, J=2.4 Hz), 7.81 (2H, d, J=8.7 Hz), 7.96 (2H, d, J=8.7 Hz).

Example 15

Preparation of the Compound 15

(1) Preparation of the Intermediate 15(1).

A mixture of 5-bromo-2-fluorobenzaldehyde (1.07 g, 5.280 mmol), 4-(trifluoromethoxy)phenol (940 mg, 5.280 mmol), potassium carbonate (1.46 g, 10.560 mmol), copper (II) oxide (420 mg, 5.280 mmol) and pyridine (10 ml) was stirred at 180° C. for 6 hours. The reaction mixture was cooled to room temperature and filtered through Celite. The filtrate was diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=6:1) to give the title compound (1.58 g, 83.1%) as a brown oil.

$^1$H-NMR ($CDCl_3$) δ: 6.18 (1H, d, J=8.7 Hz), 7.09 (2H, d, J=8.7 Hz), 7.25-7.28 (2H, m), 7.61-7.65 (1H, m), 8.05 (1H, d, J=2.4 Hz), 10.41 (1H, s).

(2) Preparation of the Intermediate 15(2).

The title compound was obtained in the same manner as the Example 1(2) using the following starting materials.

Starting materials: the intermediate 15(1) and 4-(trifluoromethoxy)phenylboronic acid; Yield: 94.3% (clear yellow oil).

$^1$H-NMR ($CDCl_3$) δ: 7.00 (1H, d, J=8.4 Hz), 7.12-7.15 (2H, m), 7.26-7.32 (4H, m), 7.59-7.62 (2H, m), 7.73 (1H, dd, J=8.4, 2.4 Hz), 8.15 (1H, d, J=2.4 Hz), 10.54 (1H, s).

(3) Preparation of the Compound 15.

The title compound was obtained in the same manner as the Example 2(3) using the following starting materials.

Starting materials: the intermediate 15(2) and malonic acid; Yield: 64.5% (white solid).

$^1$H-NMR ($CDCl_3$) δ: 6.64 (1H, d, J=16.2 Hz), 6.96 (1H, d, J=8.7 Hz), 7.05-7.08 (2H, m), 7.23-7.33 (4H, m), 7.53 (1H, dd, J=8.7, 2.4 Hz), 7.57-7.60 (2H, m), 7.82 (1H, d, J=2.4 Hz), 8.12 (1H, d, J=16.2 Hz).

Example 16

Preparation of the Compound 16

The title compound was obtained in the same manner as the Example 3 using the following starting material.

Starting material: the compound 15; Yield: 87.8% (clear colorless oil).

$^1$H-NMR ($CDCl_3$) δ: 2.74 (2H, t, J=7.5 Hz), 3.03 (2H, t, J=7.5 Hz), 6.92 (1H, d, J=8.7 Hz), 6.98-7.02 (2H, m), 7.20 (2H, d, J=8.1 Hz), 7.26-7.29 (2H, m), 7.38 (1H, dd, J=8.7, 2.1 Hz), 7.48 (1H, d, J=2.1 Hz), 7.53-7.58 (2H, m).

Example 17

Preparation of the Compound 17

(1) Preparation of the Intermediate 17(1).

A mixture of the intermediate 6(4) (3.0 g, 5.982 mmol), methyl iodide (9.387 g, 66.180 mmol), potassium carbonate (2.480 g, 17.946 mmol), 18-crown-6 (158 mg, 0.598 mmol) and acetonitrile (50 ml) was stirred at 85° C. for 3 hours. The reaction mixture was cooled to room temperature, diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=5:1) to give the title compound (3.066 g, 99.4%) as a colorless oil.

$^1$H-NMR ($CDCl_3$) δ: 1.33 (9H, s), 3.12 (3H, s), 3.55 (3H, s), 5.15 (2H, s), 7.08 (1H, d, J=8.4 Hz), 7.24-7.29 (2H, m), 7.34-7.53 (8H, m).

(2) Preparation of the Compound 17.

The title compound was obtained in the same manner as the Example 12(4) using the following starting material.

Starting material: the intermediate 17(1); Yield: 90.1% (white solid).

$^1$H-NMR (DMSO-$d_6$) δ: 1.29 (9H, s), 3.18 (3H, s), 5.13-5.26 (2H, m), 7.28 (2H, d, J=8.7 Hz), 7.39-7.46 (6H, m), 7.62 (1H, d, J=2.1 Hz), 7.69 (1H, dd, J=2.1, 8.7 Hz), 7.73 (2H, d, J=9.0 Hz).

Example 18

Preparation of the Compound 18

(1) Preparation of the Intermediate 18(1).

The title compound was obtained in the same manner as the Example 1(2) using the following starting materials.

Starting materials: 5-bromosalicylaldehyde and 4-(trifluoromethoxy)phenylboronic acid; Yield: 78.1% (yellow solid).

$^1$H-NMR ($CDCl_3$) δ: 7.09 (1H, d, J=8.1 Hz), 7.30 (2H, d, J=7.8 Hz), 7.54-7.59 (2H, m), 7.72-7.76 (2H, m), 9.98 (1H, s), 11.03 (1H, s).

(2) Preparation of the Intermediate 18(2).

The title compound was obtained in the same manner as the Example 2(1) using the following starting materials.

Starting materials: the intermediate 18(1) and 4-chlorobenzyl chloride; Yield: 73.1% (white solid).

$^1$H-NMR ($CDCl_3$) δ: 5.22 (2H, s), 7.11 (1H, d, J=8.7 Hz), 7.26-7.29 (2H, m), 7.39-7.41 (4H, m), 7.56-7.59 (2H, m), 7.74 (1H, dd, J=8.7, 2.4 Hz), 8.07 (1H, d, J=2.4 Hz), 10.58 (1H, s).

(3) Preparation of the Compound 18.

The title compound was obtained in the same manner as the Example 2(3) using the following starting materials.

Starting materials: the intermediate 18(2) and malonic acid; Yield: 84.2% (white solid).

$^1$H-NMR ($CDCl_3$) δ: 5.20 (2H, s), 6.62 (1H, d, J=16.2 Hz), 7.01 (1H, d, J=8.4 Hz), 7.29 (2H, d, J=8.7 Hz), 7.38-7.39 (4H, m), 7.50-7.57 (3H, m), 7.74 (1H, d, J=2.4 Hz), 8.18 (1H, d, J=16.2 Hz).

Example 19

Preparation of the Compound 19

The title compound was obtained in the same manner as the Example 3 using the following starting material.

Starting material: the compound 18; Yield: 50.0% (white solid).

$^1$H-NMR ($CDCl_3$) δ: 2.72 (2H, t, J=7.2 Hz), 3.05 (2H, t, J=7.2 Hz), 5.10 (2H, s), 6.93 (1H, d, J=8.4 Hz), 7.22-7.26 (2H, m), 7.35-7.40 (6H, m), 7.51-7.54 (2H, m).

Example 20

Preparation of the Compound 20

(1) Preparation of the Intermediate 20(1).

The title compound was obtained in the same manner as the Example 2(1) using the following starting materials.

Starting materials: the intermediate 18(1) and 4-fluorobenzyl chloride; Yield: 96.8% (brown solid).

$^1$H-NMR ($CDCl_3$) δ: 5.21 (2H, s), 7.09-7.15 (3H, m), 7.26-7.30 (2H, m), 7.42-7.47 (2H, m), 7.56-7.59 (2H, m), 7.75 (1H, dd, J=8.7, 2.4 Hz), 8.07 (1H, d, J=2.4 Hz), 10.57 (1H, s).

(2) Preparation of the Intermediate 20(2).

The title compound was obtained in the same manner as the Example 2(3) using the following starting materials.

Starting materials: the intermediate 20(1) and malonic acid; Yield: 62.5% (white solid).

$^1$H-NMR ($CDCl_3$) δ: 5.19 (2H, s), 6.61 (1H, d, J=16.2 Hz), 7.03 (1H, d, J=8.7 Hz), 7.07-7.15 (2H, m), 7.29 (2H, d, J=8.4 Hz), 7.41-7.46 (2H, m), 7.51-7.57 (3H, m), 7.74 (1H, d, J=2.1 Hz), 8.18 (1H, d, J=16.2 Hz).

(3) Preparation of the Compound 20.

The title compound was obtained in the same manner as the Example 3 using the following starting material.

Starting material: the intermediate 20(2); Yield: 55.9% (white solid).

$^1$H-NMR ($CDCl_3$) δ: 2.72 (2H, t, J=7.5 Hz), 3.05 (2H, t, J=7.5 Hz), 5.10 (2H, s), 6.96 (1H, d, J=8.4 Hz), 7.01 (2H, t, J=8.7 Hz), 7.25 (2H, d, J=8.1 Hz), 7.36-7.44 (4H, m), 7.51-7.54 (2H, m).

Example 21

Preparation of the Compound 21

(1) Preparation of the Intermediate 21(1).

The title compound was obtained in the same manner as the Example 2(1) using the following starting materials.

Starting materials: the intermediate 18(1) and 2-(trifluoromethyl)benzyl chloride; Yield: 72.9% (pale pink solid).

$^1$H-NMR ($CDCl_3$) δ: 5.45 (2H, s), 7.11 (1H, d, J=8.7 Hz), 7.29 (2H, d, J=8.7 Hz), 7.49 (1H, t, J=7.2 Hz), 7.56-7.65 (3H, m), 7.73-7.77 (3H, m), 8.09 (1H, d, J=2.4 Hz), 10.62 (1H, s).

(2) Preparation of the Intermediate 21(2).

The title compound was obtained in the same manner as the Example 2(3) using the following starting materials.

Starting materials: the intermediate 21(1) and malonic acid; Yield: 89.7% (white solid).

$^1$H-NMR ($CDCl_3$) δ: 5.43 (2H, s), 6.63 (1H, d, J=16.2 Hz), 6.98 (1H, d, J=8.4 Hz), 7.29 (2H, d, J=8.1 Hz), 7.44-7.63 (5H, m), 7.71-7.77 (3H, m), 8.25 (1H, d, J=16.2 Hz).

(3) Preparation of the Compound.

The title compound was obtained in the same manner as the Example 3 using the following starting material.

Starting material: the intermediate 21(2); Yield: 79.1% (white solid).

$^1$H-NMR ($CDCl_3$) δ: 2.76 (2H, t, J=7.5 Hz), 3.10 (2H, t, J=7.5 Hz), 5.34 (2H, s), 6.92 (1H, d, J=8.4 Hz), 7.25 (2H, t, J=7.8 Hz), 7.37 (1H, dd, J=8.4, 2.4 Hz), 7.41 (1H, d, J=2.4 Hz), 7.44 (1H, d, J=7.8 Hz), 7.50-7.61 (3H, m), 7.70-7.75 (2H, m).

Example 22

Preparation of the Compound 22

(1) Preparation of the Intermediate 22(1).

The title compound was obtained in the same manner as the Example 2(1) using the following starting materials.

Starting materials: the intermediate 18(1) and 4-(trifluoromethyl)benzyl chloride; Yield: 100.0% (clear brown oil).

$^1$H-NMR ($CDCl_3$) δ: 5.32 (2H, s), 7.11 (1H, d, J=8.7 Hz), 7.29 (2H, d, J=8.7 Hz), 7.65-7.61 (4H, m), 7.70 (2H, d, J=8.4 Hz), 7.75 (1H, dd, J=8.7, 2.7 Hz), 8.09 (1H, d, J=2.7 Hz).

(2) Preparation of the Intermediate 22(2).

The title compound was obtained in the same manner as the Example 2(3) using the following starting materials.

Starting materials: the intermediate 22(1) and malonic acid; Yield: 53.4% (white solid).

$^1$H-NMR ($CDCl_3$) δ: 5.29 (2H, s), 6.63 (1H, d, J=16.2 Hz), 7.00 (1H, d, J=8.7 Hz), 7.29 (2H, d, J=8.1 Hz), 7.51-7.59 (5H, m), 7.69 (2H, d, J=8.7 Hz), 7.76 (1H, d, J=2.1 Hz), 8.21 (1H, d, J=16.2 Hz).

(3) Preparation of the Compound.

The title compound was obtained in the same manner as the Example 3 using the following starting material.

Starting material: the intermediate 22(2); Yield: 67.3% (white solid).

$^1$H-NMR ($CDCl_3$) δ: 2.74 (2H, t, J=7.5 Hz), 3.08 (2H, t, J=7.5 Hz), 5.19 (2H, s), 6.92 (1H, d, J=8.1 Hz), 7.23-7.26 (2H, m), 7.35-7.41 (2H, m), 7.50-7.57 (4H, m), 7.66 (2H, d, J=7.8 Hz).

Example 23

Preparation of the Compound 23

(1) Preparation of the Intermediate 23(1).

The title compound was obtained in the same manner as the Example 2(1) using the following starting materials.

Starting materials: the intermediate 18(1) and 2-methoxybenzyl chloride; Yield: 77.0% (white solid).

$^1$H-NMR ($CDCl_3$) δ: 3.89 (3H, s), 5.29 (2H, s), 6.95 (1H, d, J=8.4 Hz), 6.98-7.03 (1H, m), 7.19 (1H, d, J=8.4 Hz), 7.26-7.29 (2H, m), 7.32-7.38 (1H, m), 7.45-7.48 (1H, m), 7.56-7.61 (2H, m), 7.74 (1H, dd, J=8.4 Hz, J=2.4 Hz), 8.06 (1H, d, J=2.4 Hz).

(2) Preparation of the Intermediate 23(2).

The title compound was obtained in the same manner as the Example 2(3) using the following starting materials.

Starting materials: the intermediate 23(1) and malonic acid; Yield: 65.4% (white solid).

$^1$H-NMR ($CDCl_3$) δ: 3.90 (3H, s), 5.28 (2H, s), 6.65 (1H, d, J=16.2 Hz), 6.94 (1H, d, J=8.1 Hz), 6.97-7.02 (1H, m), 7.09 (1H, d, J=8.7 Hz), 7.26-7.36 (3H, m), 7.44 (1H, dd, J=8.1, 1.5 Hz), 7.50-7.57 (3H, m), 7.72 (1H, d, J=2.1 Hz), 8.21 (1H, d, J=16.2 Hz).

(3) Preparation of the Compound 23.

The title compound was obtained in the same manner as the Example 3 using the following starting material.

Starting material: the intermediate 23(2); Yield: 74.8% (white solid).

$^1$H-NMR ($CDCl_3$) δ: 2.76 (2H, t, J=7.2 Hz), 3.06 (2H, t, J=7.2 Hz), 3.87 (3H, s), 5.17 (2H, s), 6.91-7.03 (3H, m), 7.23-7.57 (8H, m).

Example 24

Preparation of the Compound 24

(1) Preparation of the Intermediate 24(1).

The title compound was obtained in the same manner as the Example 12(3) using the following starting materials.

Starting materials: the intermediate 2(2) and bis(2,2,2-trifluoroethyl)(methoxycarbonylmethyl)phosphonate; Yield: 66.1% (clear colorless oil).

$^1$H-NMR ($CDCl_3$) δ: 3.68 (3H, s), 5.14 (2H, s), 7.01 (1H, d, J=8.7 Hz), 7.24-7.50 (9H, m), 7.54-7.59 (3H, m), 7.91 (1H, d, J=2.1 Hz).

(2) Preparation of the Compound 24.

The title compound was obtained in the same manner as the Example 12(4) using the following starting material.

Starting material: the intermediate 24(1); Yield: 55.3% (white solid).

$^1$H-NMR ($CDCl_3$) δ: 5.14 (2H, s), 6.04 (1H, d, J=12.9 Hz), 7.01 (1H, d, J=8.7 Hz), 7.19 (2H, d, J=8.1 Hz), 7.32-7.51 (9H, m), 7.86 (1H, d, J=2.4 Hz).

Example 25

Preparation of the Compound 25

(1) Preparation of the Intermediate 25(1).

The title compound was obtained in the same manner as the Example 12(3) using the following starting materials.

Starting materials: the intermediate 4(2) and bis(2,2,2-trifluoroethyl)(methoxycarbonylmethyl)phosphonate; Yield: 64.2% (white solid).

$^1$H-NMR ($CDCl_3$) δ: 1.36 (9H, s), 3.69 (3H, s), 5.11 (2H, s), 7.02 (1H, d, J=8.4 Hz), 7.23-7.45 (7H, m), 7.49 (1H, dd, J=2.4, 8.4 Hz), 7.54-7.60 (2H, m), 7.92 (1H, d, J=2.4 Hz).

(2) Preparation of the Compound 25.

The title compound was obtained in the same manner as the Example 12(4) using the following starting material.

Starting material: the intermediate 25(1); Yield: 83.4% (white solid).

$^1$H-NMR ($CDCl_3$) δ: 1.33 (9H, s), 5.10 (2H, s), 6.02 (1H, d, J=12.3 Hz), 7.01 (1H, d, J=8.7 Hz), 7.17 (2H, d, J=8.7 Hz), 7.34-7.50 (8H, m), 7.87 (1H, d, J=2.4 Hz).

Example 26

Preparation of the Compound 26

(1) Preparation of the Intermediate 26(1).

A solution of triethyl phosphonoacetate (1.356 g, 6.048 mmol) in tetrahydrofuran (45 ml) was added dropwise at a slow speed to sodium hydride (264 mg, 6.048 mmol) at room temperature under argon atmosphere, and the mixture was stirred at room temperature for 30 minutes. A solution of the intermediate 4(1) (1.5 g, 4.319 mmol) in tetrahydrofuran (25 ml) was added dropwise at a slow speed to the mixture at 0° C. under argon atmosphere, and the mixture was stirred at room temperature overnight. A small portion of saturated aqueous solution of ammonium chloride was added to the reaction mixture. The residue obtained by evaporation of tetrahydrofuran under reduced pressure was extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=10:1) to give the title compound (1.59 g, 88.2%) as a colorless oil.

$^1$H-NMR ($CDCl_3$) δ: 1.24-1.43 (12H, m), 4.25 (2H, q, J=7.2 Hz), 5.10 (2H, s), 6.49 (1H, d, J=16.2 Hz), 6.84 (1H, d, J=8.7 Hz), 7.32-7.43 (5H, m), 7.63 (1H, d, J=2.7 Hz), 7.98 (1H, d, J=16.2 Hz).

(2) Preparation of the Intermediate 26(2).

The title compound was obtained in the same manner as the Example 1(2) using the following starting materials.

Starting materials: the intermediate 26(1) and 3-carboxyphenylboronic acid; Yield: 49.3% (white solid).

$^1$H-NMR ($CDCl_3$) δ: 1.28-1.37 (12H, m), 4.27 (2H, q, J=7.2 Hz), 5.20 (2H, s), 6.63 (1H, d, J=16.2 Hz), 7.07 (1H, d, J=9.0 Hz), 7.36-7.45 (4H, m), 7.52-7.60 (2H, m), 7.78-7.82 (2H, m), 8.06-8.11 (1H, m), 8.14 (1H, d, J=16.2 Hz), 8.31 (1H, t, J=1.8 Hz).

(3) Preparation of the Intermediate 26(3).

The title compound was obtained in the same manner as the Example 3 using the following starting material.

Starting material: the intermediate 26(2); Yield: 86.5% (white solid).

$^1$H-NMR ($CDCl_3$) δ: 1.21-1.34 (12H, m), 2.70 (2H, d, J=7.5 Hz), 3.09 (2H, d, J=7.5 Hz), 4.13 (2H, q, J=7.2 Hz), 5.13 (2H, s), 7.10 (1H, d, J=8.4 Hz), 7.37-7.54 (7H, m), 7.76-7.81 (1H, m), 8.02-8.07 (1H, m), 8.30 (1H, t, J=1.8 Hz).

(4) Preparation of the Compound 26.

The title compound was obtained in the same manner as the Example 12(4) using the following starting material.

Starting material: the intermediate 26(3); Yield: 59.1% (white solid).

$^1$H-NMR ($CDCl_3$) δ: 1.29 (9H, s), 2.58 (2H, d, J=7.8 Hz), 2.91 (2H, d, J=7.8 Hz), 5.16 (2H, s), 7.15 (1H, d, J=9.0 Hz), 7.38-7.57 (7H, m), 7.83-7.89 (1H, m), 8.13 (1H, t, J=1.5 Hz), 12.58 (1H, brs).

Example 27

Preparation of the Compound 27

(1) Preparation of the Intermediate 27(1).

The title compound was obtained in the same manner as the Example 2(1) using the following starting materials.

Starting materials: the intermediate 18(1) and 2,4-dichlorobenzyl chloride; Yield: 78% (white solid).

$^1$H-NMR ($CDCl_3$) δ: 5.30 (2H, s), 7.13 (1H, d, J=8.7 Hz), 7.25-7.35 (3H, m), 7.47 (1H, d, J=2.1 Hz), 7.52 (1H, d, J=8.1 Hz), 7.55-7.61 (2H, m), 7.75 (1H, dd, J=2.7, 8.7 Hz), 8.08 (1H, d, J=2.7 Hz), 10.59 (1H, s).

(2) Preparation of the Intermediate 27(2).

The title compound was obtained in the same manner as the Example 2(3) using the following starting materials.

Starting materials: the intermediate 27(1) and malonic acid; Yield: 75% (white solid).

$^1$H-NMR ($CDCl_3$) δ: 5.28 (2H, s), 6.61 (1H, d, J=15.9 Hz), 7.00 (1H, d, J=8.4 Hz), 7.25-7.36 (3H, m), 7.46-7.58 (5H, m), 7.75 (1H, d, J=2.4 Hz), 8.21 (1H, d, J=15.9 Hz).

(3) Preparation of the Compound 27.

The title compound was obtained in the same manner as the Example 3 using the following starting materials.

Starting material: the intermediate 27(2); Yield: 30% (white solid).

$^1$H-NMR ($CDCl_3$) δ: 2.74 (2H, t, J=7.5 Hz), 3.08 (2H, t, J=7.5 Hz), 5.18 (2H, s), 6.94 (1H, d, J=8.4 Hz), 7.23-7.32 (3H, m), 7.36-7.45 (3H, m), 7.48-7.56 (3H, m).

Example 28

Preparation of the Compound 28

(1) Preparation of the Intermediate 28(1).

The title compound was obtained in the same manner as the Example 2(1) using the following starting materials.

Starting materials: the intermediate 18(1) and 3-methylbenzyl bromide; Yield: 50% (white solid).

$^1$H-NMR ($CDCl_3$) δ: δ 2.39 (3H, s), 5.21 (2H, s), 7.14 (1H, d, J=8.5 Hz), 7.18 (1H, d, J=7.0 Hz), 7.23-7.33 (5H, m), 7.55-7.60 (2H, m), 7.73 (1H, dd, J=8.5, 2.5 Hz), 8.06 (1H, d, J=2.5 Hz), 10.60 (1H, s).

(2) Preparation of the Intermediate 28(2).

The title compound was obtained in the same manner as the Example 2(3) using the following starting materials.

Starting materials: the intermediate 28(1) and malonic acid; Yield: 92% (white solid).

$^1$H-NMR (DMSO-$d_6$) δ: 2.33 (3H, s), 5.23 (2H, s), 6.74 (1H, d, J=16.0 Hz), 7.17 (1H, d, J=7.0 Hz), 7.25-7.34 (4H, m), 7.41-7.48 (2H, m), 7.72 (1H, dd, J=8.5, 2.0 Hz), 7.82-7.87 (2H, m), 7.91 (1H, d, J=16.0 Hz), 8.04 (1H, d, J=2.0 Hz), 12.37 (1H, s).

(3) Preparation of the Compound 28.

The title compound was obtained in the same manner as the Example 3 using the following starting materials.

Starting material: the intermediate 28(2); Yield: 66% (white solid).

$^1$H-NMR (DMSO-$d_6$) δ: 2.33 (3H, s), 2.57 (2H, t, J=8.0 Hz), 2.90 (2H, t, J=8.0 Hz), 5.15 (2H, s), 7.10-7.15 (2H, m), 7.25-7.32 (3H, m), 7.41 (2H, d, J=9.0 Hz), 7.47-7.51 (2H, m), 7.72 (2H, d, J=9.0 Hz), 12.13 (1H, s).

Example 29

Preparation of the Compound 29

(1) Preparation of the Intermediate 29(1).

The title compound was obtained in the same manner as the Example 2(1) using the following starting materials.

Starting materials: the intermediate 18(1) and 4-phenylbenzyl bromide; Yield: 99% (white solid).

$^1$H-NMR (DMSO-$d_6$) δ: 5.29 (2H, s), 7.17 (1H, d, J=8.5 Hz), 7.28 (2H, d, J=8.5 Hz), 7.34-7.39 (2H, m), 7.43-7.48 (2H, m), 7.52-7.66 (7H, m), 7.75 (1H, dd, J=8.5, 2.5 Hz), 8.08 (1H, d, J=2.5 Hz), 10.62 (1H, s).

(2) Preparation of the Intermediate 29(2).

The title compound was obtained in the same manner as the Example 2(3) using the following starting materials.

Starting materials: the intermediate 29(1) and malonic acid; Yield: 81% (white solid).

$^1$H-NMR (DMSO-$d_6$) δ: 5.33 (2H, s), 6.76 (1H, d, J=16.0 Hz), 7.29-7.50 (6H, m), 7.58 (2H, d, J=8.5 Hz), 7.68-7.74 (5H, m), 7.85 (2H, d, J=8.5 Hz), 7.95 (1H, d, J=16.0 Hz), 8.06 (1H, d, J=2.0 Hz), 12.37 (1H, s).

(3) Preparation of the Compound 29.

The title compound was obtained in the same manner as the Example 3 using the following starting material.

Starting material: the intermediate 29(2); Yield: 20% (white solid).

$^1$H-NMR (DMSO-$d_6$) δ: 2.59 (2H, t, J=8.0 Hz), 2.93 (2H, t, J=8.0 Hz), 5.25 (2H, s), 7.16 (1H, d, J=9.5 Hz), 7.34-7.52 (7H, m), 7.57 (2H, d, J=8.5 Hz), 7.67-7.74 (6H, m), 12.13 (1H, s).

Example 30

Preparation of the Compound 30

(1) Preparation of the Intermediate 30(1).

Methanesulfonyl chloride (3.069 g, 26.791 mmol) was added to a solution of 4-butylbenzyl alcohol (4.000 g, 24.355 mmol) in dichloromethane (120 ml) at 0° C. under argon atmosphere. Then triethylamine (2.711 g, 26.791 mmol) was added dropwise at a slow speed to this mixture at 0° C., and the mixture was stirred at room temperature overnight. The solvent was evaporated under reduced pressure and the residue was diluted with ethyl acetate. The organic layer was washed with saturated brine, and dried over anhydrous sodium sulfate. The residue obtained by evaporation of the solvent under reduced pressure was purified by column chromatography on silica gel (n-hexane) to give the title compound (3.64 g, 82%) as a colorless oil.

$^1$H-NMR ($CDCl_3$) δ: 0.92 (3H, t, J=7.5 Hz), 1.35 (2H, sext, J=7.5 Hz), 1.52-1.64 (2H, m), 2.60 (2H, t, J=7.5 Hz), 4.57 (2H, s), 7.15-7.18 (2H, m), 7.25-7.30 (2H, m).

(2) Preparation of the Intermediate 30(2).

The title compound was obtained in the same manner as the Example 2(1) using the following starting materials.

Starting materials: the intermediate 18(1) and the intermediate 30(1); Yield: 43% (yellowish-white solid).

$^1$H-NMR (DMSO-$d_6$) δ: 0.89 (3H, t, J=7.0 Hz), 1.30 (2H, sext, J=7.0 Hz), 1.55 (2H, quint, J=7.0 Hz), 2.58 (2H, t, J=7.0 Hz), 5.31 (2H, s), 7.23 (2H, d, J=8.0 Hz), 7.44 (5H, d, J=8.0 Hz), 7.79 (2H, d, J=8.0 Hz), 7.95-8.00 (2H, m), 10.45 (1H, s).

(3) Preparation of the Intermediate 30(3).

The title compound was obtained in the same manner as the Example 2(3) using the following starting materials.

Starting materials: the intermediate 30(2) and malonic acid; Yield: 58% (white solid).

$^1$H-NMR (DMSO-$d_6$) δ: 0.89 (3H, t, J=7.5 Hz), 1.31 (2H, sext, J=7.5 Hz), 1.51-1.61 (2H, m), 2.59 (2H, t, J=7.5 Hz), 5.23 (2H, s), 6.72 (1H, d, J=16.0 Hz), 7.23-7.29 (3H, m), 7.37-7.43 (4H, m), 7.72 (1H, dd, J=9.0, 2.0 Hz), 7.82-7.86 (2H, m), 7.90 (1H, d, J=16.0 Hz), 8.04 (1H, d, J=2.0 Hz), 12.34 (1H, s).

(4) Preparation of the Compound 30.

The title compound was obtained in the same manner as the Example 3 using the following starting material.

Starting material: the intermediate 30(3); Yield: 33% (white solid).

$^1$H-NMR (DMSO-$d_6$) δ: 0.89 (3H, t, J=7.5 Hz), 1.31 (2H, sext, J=7.5 Hz), 1.55 (2H, quint, J=7.5 Hz), 2.56 (2H, t, J=7.5 Hz), 2.58 (2H, t, J=7.5 Hz), 2.89 (2H, t, J=7.5 Hz), 5.15 (2H, s), 7.13 (1H, d, J=9.0 Hz), 7.21-7.23 (2H, m), 7.36-7.42 (4H, m), 7.47-7.50 (2H, m), 7.69-7.73 (2H, m), 12.12 (1H, s).

Example 31

Preparation of the Compound 31

(1) Preparation of the Intermediate 31(1).

The title compound was obtained in the same manner as the Example 2(3) using the following starting materials.

Starting materials: the intermediate 4(1) and malonic acid; Yield: 84% (white solid).

$^1$H-NMR (DMSO-$d_6$) δ: 1.28 (9H, s), 5.17 (2H, s), 6.61 (1H, d, J=16.1 Hz), 7.13-7.17 (1H, m), 7.36-7.44 (4H, m), 7.52-7.55 (1H, m), 7.77 (1H, d, J=16.1 Hz), 7.90 (1H, s), 12.43 (1H, s).

(2) Preparation of the Compound 31.

The title compound was obtained in the same manner as the Example 1(2) using the following starting materials.

Starting materials: the intermediate 31(1) and phenylboronic acid; Yield: 58% (pale yellow solid).

$^1$H-NMR ($CDCl_3$) δ: 1.34 (9H, s), 5.19 (2H, s), 6.63 (1H, d, J=16.1 Hz), 7.06 (1H, d, J=8.8 Hz), 7.33-7.46 (7H, m), 7.54-7.58 (3H, m), 7.78 (1H, d, J=2.4 Hz), 8.22 (1H, d, J=16.1 Hz).

Example 32

Preparation of the Compound 32

The title compound was obtained in the same manner as the Example 3 using the following starting material.

Starting material: the compound 31; Yield: 33% (white solid).

$^1$H-NMR ($CDCl_3$) δ: 1.33 (9H, s), 2.74 (2H, t, J=7.6 Hz), 3.07 (2H, t, J=7.6 Hz), 5.11 (2H, s), 6.98 (1H, d, J=8.1 Hz), 7.29-7.44 (9H, m), 7.52-7.55 (2H, m).

Example 33

Preparation of the Compound 33

The title compound was obtained in the same manner as the Example 1(2) using the following starting materials.

Starting materials: the intermediate 31(1) and 4-fluorophenylboronic acid; Yield: 52% (pale yellow solid).

$^1$H-NMR ($CDCl_3$) δ: 1.34 (9H, s), 5.20 (2H, s), 6.63 (1H, d, J=16.1 Hz), 7.04-7.15 (2H, m), 7.37-7.53 (8H, m), 7.72 (1H, d, J=2.2 Hz), 8.20 (1H, d, J=16.1 Hz).

Example 34

Preparation of the Compound 34

The title compound was obtained in the same manner as the Example 3 using the following starting material Starting material: the compound 33; Yield: 22% (white solid).

$^1$H-NMR ($CDCl_3$) δ: 1.34 (9H, s), 2.74 (2H, t, J=7.6 Hz), 3.06 (2H, t, J=7.6 Hz), 5.10 (2H, s), 6.97 (1H, d, J=8.2 Hz), 7.08 (2H, t, J=8.6 Hz), 7.33-7.49 (8H, m).

Example 35

Preparation of the Compound 35

The title compound was obtained in the same manner as the Example 1(2) using the following starting materials.

Starting materials: the intermediate 31(1) and 4-(trifluoromethyl)phenylboronic acid; Yield: 49% (pale orange solid).

$^1$H-NMR ($CDCl_3$) δ: 1.34 (9H, s), 5.21 (2H, s), 6.64 (1H, d, J=16.0 Hz), 7.09 (1H, d, J=8.6 Hz), 7.37-7.46 (4H, m), 7.57 (1H, dd, J=2.2, 8.6 Hz), 7.63-7.71 (4H, m), 7.77 (1H, d, J=2.2 Hz), 8.21 (1H, d, J=16.0 Hz).

Example 36

Preparation of the Compound 36

The title compound was obtained in the same manner as the Example 3 using the following starting material.

Starting material: the compound 35; Yield: 79% (white solid).

$^1$H-NMR ($CDCl_3$) δ: 1.34 (9H, m), 2.75 (2H, t, J=7.6 Hz), 3.07 (2H, t, J=7.6 Hz), 5.12 (2H, s), 7.01 (1H, d, J=8.2 Hz), 7.35-7.44 (6H, m), 7.60-7.67 (4H, m).

Example 37

Preparation of the Compound 37

The title compound was obtained in the same manner as the Example 1(2) using the following starting materials.

Starting materials: the intermediate 31(1) and 4-methoxyphenylboronic acid; Yield: 43% (pale yellow solid).

$^1$H-NMR ($CDCl_3$) δ: 1.34 (9H, s), 3.85 (3H, s), 5.18 (2H, s), 6.62 (1H, d, J=16.1 Hz), 6.96-7.05 (3H, m), 7.37-7.53 (7H, m), 7.73 (1H, d, J=2.2 Hz), 8.22 (1H, d, J=16.1 Hz).

Example 38

Preparation of the Compound 38

The title compound was obtained in the same manner as the Example 3 using the following starting material.

Starting material: the compound 37; Yield: 74% (white solid).

$^1$H-NMR (DMSO-$d_6$) δ: 1.29 (9H, s), 2.51 (2H, t, J=7.6 Hz), 2.89 (2H, t, J=7.6 Hz), 3.78 (3H, s), 5.13 (2H, s), 6.96-6.99 (2H, m), 7.06-7.09 (1H, d, J=8.2 Hz), 7.38-7.45 (6H, m), 7.51-7.54 (2H, m), 12.10 (1H, bs).

Example 39

Preparation of the Compound 39

The title compound was obtained in the same manner as the Example 1(2) using the following starting materials.

Starting materials: the intermediate 31(1) and 4-(tert-butyl)phenylboronic acid; Yield: 58% (pale orange solid).

$^1$H-NMR ($CDCl_3$) δ: 1.34 (9H, s), 1.36 (9H, s), 5.18 (2H, s), 6.62 (1H, d, J=16.1 Hz), 7.05 (1H, d, J=8.6 Hz), 7.37-7.51 (8H, m), 7.58 (1H, dd, J=2.0, 8.6 Hz), 7.77 (1H, d, J=2.0 Hz), 8.21 (1H, d, J=16.1 Hz).

Example 40

Preparation of the Compound 40

The title compound was obtained in the same manner as the Example 3 using the following starting material.

Starting material: the compound 39; Yield: 50% (white solid).

$^1$H-NMR ($CDCl_3$) δ: 1.34 (9H, s), 1.35 (9H, s), 2.72-2.77 (2H, m), 3.04-3.09 (2H, m), 5.10 (2H, s), 6.97 (1H, d, J=8.4 Hz), 7.36-7.49 (10H, m).

Example 41

Preparation of the Compound 41

The title compound was obtained in the same manner as the Example 1(2) using the following starting materials.

Starting materials: the intermediate 31(1) and 4-methylphenylboronic acid; Yield: 51% (yellow solid).

$^1$H-NMR ($CDCl_3$) δ: 1.34 (9H, s), 2.39 (3H, s), 5.18 (2H, s), 6.62 (1H, d, J=16.1 Hz), 7.04 (1H, d, J=8.6 Hz), 7.23-7.26 (2H, m), 7.37-7.46 (6H, m), 7.54 (1H, dd, J=2.2, 8.6 Hz), 7.76 (1H, d, J=2.2 Hz), 8.21 (1H, d, J=16.1 Hz).

Example 42

Preparation of the Compound 42

The title compound was obtained in the same manner as the Example 3 using the following starting material.

Starting material: the compound 41; Yield: 95% (white solid).

$^1$H-NMR ($CDCl_3$) δ: 1.34 (9H, s), 2.37 (3H, s), 2.72-2.77 (2H, m), 3.04-3.09 (2H, m), 5.10 (2H, s), 6.97 (1H, d, J=8.2 Hz), 7.19-7.26 (2H, m), 7.36-7.45 (8H, m).

Example 43

Preparation of the Compound 43

(1) Preparation of the Intermediate 43(1).

The title compound was obtained in the same manner as the Example 1(2) using the following starting materials.

Starting materials: the intermediate 31(1) and 4-butylphenylboronic acid; Yield: 49% (pale yellow solid).

$^1$H-NMR ($CDCl_3$) δ: 0.95 (3H, t, J=7.3 Hz), 1.30-1.42 (11H, m), 1.63 (2H, quint, J=7.8 Hz), 2.65 (2H, t, J=7.8 Hz), 5.18 (2H, s), 6.62 (1H, d, J=16.1 Hz), 7.04 (1H, d, J=8.8 Hz), 7.23-7.26 (3H, m), 7.37-7.47 (5H, m), 7.55 (1H, dd, J=2.4, 8.8 Hz), 7.76 (1H, d, J=2.4 Hz), 8.21 (1H, d, J=16.1 Hz).

(2) Preparation of the Compound 43.

The title compound was obtained in the same manner as the Example 3 using the following starting material.

Starting material: the intermediate 43(1); Yield: 49% (white solid).

$^1$H-NMR ($CDCl_3$) δ: 0.94 (3H, t, J=7.3 Hz), 1.31-1.41 (11H, m), 1.62 (2H, quint, J=7.6 Hz), 2.63 (2H, t, J=7.7 Hz), 2.74 (2H, t, J=7.7 Hz), 3.06 (2H, t, J=7.6 Hz), 5.10 (2H, s), 6.97 (1H, d, J=8.2 Hz), 7.20-7.25 (2H, m), 7.35-7.46 (8H, m).

Example 44

Preparation of the Compound 44

The title compound was obtained in the same manner as the Example 1(2) using the following starting materials.

Starting materials: the intermediate 31(1) and 4-(methylsulfanyl)phenylboronic acid; Yield: 38% (pale yellow solid).

$^1$H-NMR ($CDCl_3$) δ: 1.34 (9H, s), 2.52 (3H, s), 5.19 (2H, s), 6.63 (1H, d, J=16.1 Hz), 7.05 (1H, d, J=8.8 Hz), 7.31-7.49 (8H, m), 7.53 (1H, dd, J=2.4, 8.8 Hz), 7.75 (1H, d, J=2.4 Hz), 8.21 (1H, d, J=16.1 Hz).

Example 45

Preparation of the Compound 45

(1) Preparation of the Intermediate 45(1).

The title compound was obtained in the same manner as the Example 2(3) using the following starting materials.

Starting materials: the intermediate 2(1) and malonic acid; Yield: 44% (white solid).

$^1$H-NMR (DMSO-$d_6$) δ: 5.21 (2H, s), 6.61 (1H, d, J=16.0 Hz), 7.15 (1H, d, J=8.5 Hz), 7.32-7.47 (5H, m), 7.54 (1H, dd, J=8.5, 2.5 Hz), 7.77 (1H, d, J=16.0 Hz), 7.91 (1H, d, J=2.5 Hz), 12.42 (1H, s).

(2) Preparation of the Compound 45.

The title compound was obtained in the same manner as the Example 1(2) using the following starting materials.

Starting materials: the intermediate 45(1) and phenylboronic acid; Yield: 31% (yellow solid).

$^1$H-NMR (DMSO-$d_6$) δ: 5.27 (2H, s), 6.71 (1H, d, J=16.0 Hz), 7.27 (1H, d, J=8.5 Hz), 7.30-7.50 (8H, m), 7.68-7.72 (2H, m), 7.76-7.78 (1H, m), 7.91 (1H, d, J=16.0 Hz), 7.99-8.02 (1H, m), 12.33 (1H, s).

Example 46

Preparation of the Compound 46

(1) Preparation of the Intermediate 46(1).

The title compound was obtained in the same manner as the Example 26(1) using the following starting materials.

Starting materials: 5-bromosalicylaldehyde and triethyl phosphonoacetate; Yield: 47% (pale yellow solid).

$^1$H-NMR ($CDCl_3$) δ: 1.35 (3H, t, J=7.0 Hz), 4.30 (2H, q, J=7.0 Hz), 6.64 (1H, d, J=16.0 Hz), 6.78 (1H, d, J=8.5 Hz), 7.31 (1H, dd, J=8.5, 2.5 Hz), 7.36 (1H, brs), 7.58 (1H, d, J=2.5 Hz), 7.98 (1H, d, J=16.0 Hz).

(2) Preparation of the Intermediate 46(2).

The title compound was obtained in the same manner as the Example 1(2) using the following starting materials.

Starting materials: the intermediate 46(1) and phenylboronic acid; Yield: 44% (white solid).

$^1$H-NMR ($CDCl_3$) δ: 1.36 (3H, t, J=7.0 Hz), 4.31 (2H, q, J=7.0 Hz), 6.45 (1H, s), 6.71 (1H, d, J=16.0 Hz), 6.93 (1H, d, J=8.0 Hz), 7.31-7.35 (1H, m), 7.39-7.44 (2H, m), 7.47 (1H, dd, J=8.0, 2.5 Hz), 7.52-7.55 (2H, m), 7.69 (1H, d, J=2.5 Hz), 8.08 (1H, d, J=16.0 Hz).

(3) Preparation of the Intermediate 46(3).

The title compound was obtained in the same manner as the Example 3 using the following starting material.

Starting material: the intermediate 46(2); Yield: 99% (colorless oil).

$^1$H-NMR (DMSO-$d_6$) δ: 1.14 (3H, t, J=7.0 Hz), 2.60 (2H, t, J=7.5 Hz), 2.84 (2H, t, J=7.5 Hz), 4.04 (2H, q, J=7.0 Hz), 6.87 (1H, d, J=8.5 Hz), 7.26 (1H, tt, J=7.0, 2.0 Hz), 7.32 (1H, dd, J=8.5, 2.0 Hz), 7.37 (1H, d, J=2.0 Hz), 7.39-7.42 (2H, m), 7.53-7.57 (2H, m), 9.57 (1H, s).

(4) Preparation of the Intermediate 46(4).

The title compound was obtained in the same manner as the Example 2(1) using the following starting materials.

Starting materials: the intermediate 46(3) and benzyl bromide; Yield: 99% (white solid).

$^1$H-NMR (DMSO-$d_6$) δ: 1.13 (3H, t, J=7.0 Hz), 2.64 (2H, t, J=7.5 Hz), 2.94 (2H, t, J=7.5 Hz), 4.03 (2H, q, J=7.0 Hz), 5.19 (2H, s), 7.12 (1H, d, J=9.0 Hz), 7.27-7.48 (10H, m), 7.60 (2H, d, J=7.5 Hz).

(5) Preparation of the Compound 46.

The title compound was obtained in the same manner as the Example 12(4) using the following starting material.

Starting material: the intermediate 46(4); Yield: 81% (white solid).

$^1$H-NMR (DMSO-$d_6$) δ: 2.58 (2H, t, J=7.5 Hz), 2.91 (2H, t, J=7.5 Hz), 5.19 (2H, s), 7.11 (1H, d, J=8.0 Hz), 7.27-7.48 (10H, m), 7.60 (2H, d, J=8.0 Hz), 12.12 (1H, s).

Example 47

Preparation of the Compound 47

The title compound was obtained in the same manner as the Example 2(1) using the following starting materials.

Starting materials: the intermediate 45(1) and 4-(tert-butyl)phenylboronic acid; Yield: 40% (yellow solid).

$^1$H-NMR (DMSO-$d_6$) δ: 1.30 (9H, s), 5.24 (2H, s), 6.64 (1H, d, J=16.0 Hz), 7.22 (1H, d, J=9.0 Hz), 7.34-7.49 (7H, m), 7.59-7.61 (3H, m), 7.80 (1H, d, J=16.0 Hz), 7.89-7.90 (1H, m).

Example 48

Preparation of the Compound 48

The title compound was obtained in the same manner as the Example 3 using the following starting material.

Starting material: the compound 47; Yield: 18% (white solid).

$^1$H-NMR (DMSO-$d_6$) δ: 1.30 (9H, s), 2.56 (2H, t, J=7.5 Hz), 2.90 (2H, t, J=7.5 Hz), 5.22 (2H, s), 7.09 (1H, d, J=9.0 Hz), 7.40-7.46 (6H, m), 7.52 (2H, d, J=9.0 Hz), 7.62 (2H, d, J=9.0 Hz), 12.14 (1H, s).

Example 49

Preparation of the Compound 49

The title compound was obtained in the same manner as the Example 1(2) using the following starting materials.

Starting materials: the intermediate 31(1) and 4-chlorophenylboronic acid; Yield: 29% (pale yellow solid).

$^1$H-NMR ($CDCl_3$) δ: 1.34 (9H, s), 5.19 (2H, s), 6.63 (1H, d, J=16.1 Hz), 7.05 (1H, d, J=8.6 Hz), 7.36-7.49 (8H, m), 7.51 (1H, dd, J=2.2, 8.6 Hz), 7.73 (1H, d, J=2.2 Hz), 8.20 (1H, d, J=16.1 Hz).

Example 50

Preparation of the Compound 50

The title compound was obtained in the same manner as the Example 3 using the following starting material.

Starting material: the compound 49; Yield: 90% (white solid).

$^1$H-NMR ($CDCl_3$) δ: 1.34 (9H, s), 2.74 (2H, t, J=7.5 Hz), 3.06 (2H, t, J=7.5 Hz), 5.11 (2H, s), 6.97 (1H, d, J=8.2 Hz), 7.34-7.47 (10H, m).

Example 51

Preparation of the Compound 51

(1) Preparation of the Intermediate 51(1).

The title compound was obtained in the same manner as the Example 2(1) using the following starting materials.

Starting materials: 4-(trifluoromethoxy)benzyl bromide and 5-bromosalicylaldehyde; Yield: 66% (white solid).

$^1$H-NMR (DMSO-$d_6$) δ: 5.34 (2H, s), 7.32 (1H, d, J=9.0 Hz), 7.39-7.42 (2H, m), 7.66 (2H, d, J=8.5 Hz), 7.78 (1H, d, J=2.5 Hz), 7.84 (1H, dd, J=9.0, 2.5 Hz), 10.33 (1H, s).

(2) Preparation of the Intermediate 51(2).

The title compound was obtained in the same manner as the Example 2(3) using the following starting materials.

Starting materials: the intermediate 51(1) and malonic acid; Yield: 92% (white solid).

$^1$H-NMR (DMSO-$d_6$) δ: 5.26 (2H, s), 6.61 (1H, d, J=16.0 Hz), 7.14 (1H, d, J=9.0 Hz), 7.40-7.43 (2H, m), 7.55 (1H, dd, J=9.0, 2.5 Hz), 7.57-7.60 (2H, m), 7.77 (1H, d, J=16.0 Hz), 7.92 (1H, d, J=2.5 Hz), 12.43 (1H, s).

(3) Preparation of the Compound 51.

The title compound was obtained in the same manner as the Example 1(2) using the following starting materials.

Starting materials: the intermediate 51(2) and 4-(tert-butyl)phenylboronic acid; Yield: 35% (white solid).

$^1$H-NMR (DMSO-$d_6$) δ: 1.31 (9H, s), 5.31 (2H, s), 6.69 (1H, d, J=16.0 Hz), 7.24 (1H, d, J=8.5 Hz), 7.42-7.46 (4H, m), 7.61-7.64 (4H, m), 7.67 (1H, dd, J=8.5, 2.0 Hz), 7.91 (1H, d, J=16.0 Hz), 7.97 (1H, d, J=2.0 Hz), 12.36 (1H, s).

Example 52

Preparation of the Compound 52

The title compound was obtained in the same manner as the Example 3 using the following starting material.

Starting material: the compound 51; Yield: 47% (white solid).

$^1$H-NMR (DMSO-$d_6$) δ: 1.30 (9H, s), 2.56 (2H, t, J=7.5 Hz), 2.90 (2H, t, J=7.5 Hz), 5.22 (2H, s), 7.09 (1H, d, J=9.0 Hz), 7.40-7.46 (6H, m), 7.52 (2H, d, J=9.0 Hz), 7.62 (2H, d, J=9.0 Hz), 12.14 (1H, s).

Example 53

Preparation of the Compound 53

(1) Preparation of the Intermediate 53(1).

The title compound was obtained in the same manner as the Example 1(2) using the following starting materials.

Starting materials: the intermediate 51(2) and phenylboronic acid; Yield: 46% (white solid).

$^1$H-NMR ($CDCl_3$) δ: 5.21 (2H, s), 6.62 (1H, d, J=16.0 Hz), 7.02 (1H, d, J=8.5 Hz), 7.27 (2H, d, J=8.0 Hz), 7.34 (1H, tt, J=8.0, 1.5 Hz), 7.42-7.50 (4H, m), 7.56 (2H, d, J=8.5 Hz), 7.57 (1H, dd, J=8.5, 2.5 Hz), 7.79 (1H, d, J=2.5 Hz), 8.20 (1H, d, J=16.0 Hz).

(2) Preparation of the Compound 53.

The title compound was obtained in the same manner as the Example 3 using the following starting material.

Starting material: the intermediate 53(1); Yield: 83% (white solid).

$^1$H-NMR ($CDCl_3$) δ: 2.73 (2H, t, J=7.5 Hz), 3.07 (2H, t, J=7.5 Hz), 5.13 (2H, s), 6.95 (1H, d, J=8.0 Hz), 7.23-7.25 (2H, m), 7.27-7.33 (1H, m), 7.38-7.55 (8H, m).

Example 54

Preparation of the Compound 54

(1) Preparation of the Intermediate 54(1).

The title compound was obtained in the same manner as the Example 1(2) using the following starting materials.

Starting materials: the intermediate 46(1) and 4-(trifluoromethoxy)phenylboronic acid; Yield: 37% (yellow solid).

$^1$H-NMR ($CDCl_3$) δ: 1.37 (3H, t, J=7.0 Hz), 4.32 (2H, q, J=7.0 Hz), 6.74 (1H, d, J=16.0 Hz), 6.95 (1H, d, J=8.5 Hz), 6.98 (1H, s), 7.26 (2H, d, J=8.0 Hz), 7.43 (1H, dd, J=2.0, 8.5 Hz), 7.52-7.55 (2H, m), 7.65 (1H, d, J=2.0 Hz), 8.09 (1H, d, J=16.0 Hz).

(2) Preparation of the Intermediate 54(2).

The title compound was obtained in the same manner as the Example 3 using the following starting material.

Starting materials: the intermediate 54(1); Yield: 92% (white solid).

$^1$H-NMR ($CDCl_3$) δ: 1.24 (3H, t, J=7.0 Hz), 2.76 (2H, t, J=6.0 Hz), 2.95 (2H, t, J=6.0 Hz), 4.16 (2H, q, J=7.0 Hz), 6.97 (1H, d, J=8.5 Hz), 7.24 (2H, d, J=9.0 Hz), 7.28 (1H, d, J=2.5 Hz), 7.32 (1H, dd, J=2.5, 8.5 Hz), 7.47 (1H, s), 7.50-7.54 (2H, m).

(3) Preparation of the Intermediate 54(3).

The title compound was obtained in the same manner as the Example 2(1) using the following starting materials.

Starting materials: the intermediate 54(2) and 4-nitrobenzyl bromide; Yield: 66% (white solid).

$^1$H-NMR ($CDCl_3$) δ: 1.22 (3H, t, J=7.0 Hz), 2.69 (2H, t, J=7.5 Hz), 3.09 (2H, t, J=7.5 Hz), 4.13 (2H, q, J=7.0 Hz), 5.25 (2H, s), 6.91 (1H, d, J=8.5 Hz), 7.26 (2H, d, J=8.0 Hz), 7.37 (1H, dd, J=8.5, 2.5 Hz), 7.42 (1H, d, J=2.5 Hz), 7.52-7.55 (2H, m), 7.64 (2H, d, J=8.5 Hz), 8.26-8.29 (2H, m).

(4) Preparation of the Compound 54.

The title compound was obtained in the same manner as the Example 12(4) using the following starting material.

Starting material: the intermediate 54(3); Yield: 42% (white solid).

$^1$H-NMR (DMSO-$d_6$) δ: 2.60 (2H, t, J=7.5 Hz), 2.95 (2H, t, J=7.5 Hz), 5.38 (2H, s), 7.11 (1H, d, J=8.5 Hz), 7.42 (2H, d, J=9.0 Hz), 7.50 (1H, dd, J=8.5, 2.0 Hz), 7.54 (1H, d, J=2.0 Hz), 7.71-7.77 (4H, m), 8.27-8.29 (2H, m), 12.14 (1H, s).

Example 55

Preparation of the Compound 55

The title compound was obtained in the same manner as the Example 1(2) using the following starting materials.

Starting materials: the intermediate 31(1) and 2-methoxyphenylboronic acid; Yield: 54% (pale yellow solid).

$^1$H-NMR ($CDCl_3$) δ: 1.34 (9H, s), 3.82 (3H, s), 5.18 (2H, s), 6.58 (1H, d, J=16.1 Hz), 6.97-7.04 (3H, m), 7.28-7.32 (2H, m), 7.38-7.45 (4H, m), 7.51 (1H, dd, J=2.0, 8.4 Hz), 7.74 (1H, d, J=2.0 Hz), 8.21 (1H, d, J=16.1 Hz).

Example 56

Preparation of the Compound 56

The title compound was obtained in the same manner as the Example 3 using the following starting material.

Starting material: the compound 55; Yield: 92% (white solid).

$^1$H-NMR ($CDCl_3$) δ: 1.33 (9H, m), 2.74 (2H, t, J=7.8 Hz), 3.05 (2H, t, J=7.8 Hz), 3.80 (3H, s), 5.10 (2H, s), 6.94-7.03 (3H, m), 7.24-7.30 (2H, m), 7.34-7.44 (6H, m).

Example 57

Preparation of the Compound 57

(1) Preparation of the Intermediate 57(1).

The title compound was obtained in the same manner as the Example 2(1) using the following starting materials.

Starting materials: the intermediate 18(1) and 3-(trifluoromethyl)benzyl bromide; Yield: 71% (white solid).

$^1$H-NMR ($CDCl_3$) δ: 5.29 (2H, s), 7.13 (1H, d, J=9.0 Hz), 7.29 (2H, d, J=8.5 Hz), 7.56-7.60 (2H, m), 7.63-7.73 (4H, m), 7.76 (1H, dd, J=9.0, 2.5 Hz), 8.09 (1H, d, J=2.5 Hz), 10.59 (1H, s).

(2) Preparation of the Compound 57.

The title compound was obtained in the same manner as the Example 2(3) using the following starting materials.

Starting materials: the intermediate 57(1) and malonic acid; Yield: 82% (white solid).

$^1$H-NMR ($CDCl_3$) δ: 5.27 (2H, s), 6.62 (1H, d, J=16.0 Hz), 7.02 (1H, d, J=9.0 Hz), 7.29 (2H, d, J=8.0 Hz), 7.52-7.71 (7H, m), 7.76 (1H, d, J=2.5 Hz), 8.20 (1H, d, J=16.0 Hz).

Example 58

Preparation of the Compound 58

The title compound was obtained in the same manner as the Example 3 using the following starting material.

Starting material: the compound 57; Yield: 33% (white solid).

$^1$H-NMR ($CDCl_3$) δ: 2.74 (2H, t, J=7.5 Hz), 3.07 (2H, t, J=7.5 Hz), 5.18 (2H, s), 6.95 (1H, d, J=8.0 Hz), 7.23-7.25 (2H, m), 7.38 (1H, dd, J=8.0, 2.0 Hz), 7.41 (1H, d, J=2.0 Hz), 7.50-7.54 (3H, m), 7.59-7.65 (2H, m), 7.71 (1H, s).

Example 59

Preparation of the Compound 59

(1) Preparation of the Intermediate 59(1)

The title compound was obtained in the same manner as the Example 2(1) using the following starting materials.

Starting materials: the intermediate 18(1) and 3,5-dimethylbenzyl bromide; Yield: 51% (white solid).

$^1$H-NMR ($CDCl_3$) δ: 2.35 (6H, s), 5.17 (2H, s), 7.00 (1H, s), 7.06 (2H, s), 7.14 (1H, d, J=9.0 Hz), 7.25-7.29 (2H, m), 7.55-7.60 (2H, m), 7.73 (1H, dd, J=9.0, 2.5 Hz), 8.07 (1H, d, J=2.5 Hz), 10.60 (1H, s).

(2) Preparation of the Intermediate 59(2).

The title compound was obtained in the same manner as the Example 2(3) using the following starting materials.

Starting materials: the intermediate 59(1) and malonic acid; Yield: 64% (white solid).

$^1$H-NMR ($CDCl_3$) δ: 2.34 (6H, s), 5.16 (2H, s), 6.66 (1H, d, J=16.0 Hz), 6.98 (1H, s), 7.04 (1H, d, J=8.5 Hz), 7.06 (2H, s), 7.26-7.29 (2H, m), 7.51 (1H, dd, J=8.5, 2.5 Hz), 7.53-7.56 (2H, m), 7.73 (1H, d, J=2.5 Hz), 8.19 (1H, d, J=16.0 Hz).

(3) Preparation of the Compound 59.

The title compound was obtained in the same manner as the Example 3 using the following starting material.

Starting material: the intermediate 59(2); Yield: 59% (white solid).

$^1$H-NMR ($CDCl_3$) δ: 2.33 (6H, s), 2.74 (2H, t, J=7.5 Hz), 3.06 (2H, t, J=7.5 Hz), 5.06 (2H, s), 6.96 (1H, s), 6.96 (1H, d, J=8.5 Hz), 7.05 (2H, s), 7.22-7.25 (2H, m), 7.36 (1H, dd, J=8.5, 2.5 Hz), 7.39 (1H, d, J=2.5 Hz), 7.51-7.54 (2H, m).

Example 60

Preparation of the Compound 60

(1) Preparation of the Intermediate 60(1).

The title compound was obtained in the same manner as the Example 2(1) using the following starting materials.

Starting materials: the intermediate 18(1) and 4-methoxybenzyl bromide; Yield: 84% (white solid).

$^1$H-NMR ($CDCl_3$) δ: 3.83 (3H, s), 5.17 (2H, s), 6.93-6.96 (2H, m), 7.16 (1H, d, J=8.5 Hz), 7.26-7.29 (2H, m), 7.37-7.40 (2H, m), 7.56-7.60 (2H, m), 7.73 (1H, dd, J=8.5, 2.5 Hz), 8.06 (1H, d, J=2.5 Hz), 10.55 (1H, s).

(2) Preparation of the Intermediate 60(2).

The title compound was obtained in the same manner as the Example 2(3) using the following starting materials.

Starting materials: the intermediate 60(1) and malonic acid; Yield: 78% (white solid).

$^1$H-NMR ($CDCl_3$) δ: 3.83 (3H, s), 5.15 (2H, s), 6.62 (1H, d, J=16.0 Hz), 6.93-6.96 (2H, m), 7.06 (1H, d, J=9.0 Hz), 7.26-7.29 (2H, m), 7.38 (2H, d, J=8.5 Hz), 7.52 (1H, dd, J=9.0, 2.0 Hz), 7.55 (2H, d, J=8.5 Hz), 7.72 (1H, d, J=2.0 Hz), 8.16 (1H, d, J=16.0 Hz).

(3) Preparation of the Compound 60.

The title compound was obtained in the same manner as the Example 3 using the following starting material.

Starting material: the intermediate 60(2); Yield: 62% (white solid).

$^1$H-NMR ($CDCl_3$) δ: 2.72 (2H, t, J=7.5 Hz), 3.03 (2H, t, J=7.5 Hz), 3.82 (3H, s), 5.06 (2H, s), 6.91-6.95 (2H, m), 6.98 (1H, d, J=8.5 Hz), 7.23-7.26 (2H, m), 7.34-7.38 (4H, m), 7.51-7.54 (2H, m).

Example 61

Preparation of the Compound 61

(1) Preparation of the Intermediate 61(1).

The title compound was obtained in the same manner as the Example 2(1) using the following starting materials.

Starting materials: the intermediate 18(1) and 4-methylbenzyl bromide; Yield: 65% (white solid).

$^1$H-NMR ($CDCl_3$) δ: 2.38 (3H, s), 5.20 (2H, s), 7.14 (1H, d, J=8.5 Hz), 7.23 (2H, d, J=8.0 Hz), 7.27 (2H, d, J=8.5 Hz), 7.35 (2H, d, J=8.0 Hz), 7.55-7.59 (2H, m), 7.73 (1H, dd, J=8.5, 2.5 Hz), 8.06 (1H, d, J=2.5 Hz), 10.58 (1H, s).

(2) Preparation of the Intermediate 61(2).

The title compound was obtained in the same manner as the Example 2(3) using the following starting materials.

Starting materials: the intermediate 61(1) and malonic acid; Yield: 82% (white solid).

$^1$H-NMR ($CDCl_3$) δ: 2.37 (3H, s), 5.19 (2H, s), 6.64 (1H, d, J=16.0 Hz), 7.05 (1H, d, J=8.5 Hz), 7.22 (2H, d, J=8.0 Hz), 7.28 (2H, d, J=8.0 Hz), 7.34 (2H, d, J=8.0 Hz), 7.51 (1H, dd, J=8.5, 2.5 Hz), 7.52-7.56 (2H, m), 7.72 (1H, d, J=2.5 Hz), 8.17 (1H, d, J=16.0 Hz).

(3) Preparation of the Compound 61.

The title compound was obtained in the same manner as the Example 3 using the following starting material.

Starting material: the intermediate 61(2); Yield: 39% (white solid).

$^1$H-NMR ($CDCl_3$) δ: 2.36 (3H, s), 2.73 (2H, t, J=7.5 Hz), 3.04 (2H, t, J=7.5 Hz), 5.09 (2H, s), 6.97 (1H, d, J=8.0 Hz), 7.19-7.25 (4H, m), 7.33 (2H, d, J=8.5 Hz), 7.36 (1H, dd, J=8.0, 2.5 Hz), 7.39 (1H, d, J=2.5 Hz), 7.50-7.53 (2H, m).

Example 62

Preparation of the Compound 62

(1) Preparation of the Intermediate 62(1).

The title compound was obtained in the same manner as the Example 2(1) using the following starting materials.

Starting materials: the intermediate 18(1) and 4-(trifluoromethoxy)benzyl bromide; Yield: 99% (white solid).

$^1$H-NMR ($CDCl_3$) δ: 5.24 (2H, s), 7.13 (1H, d, J=8.5 Hz), 7.28 (4H, d, J=9.0 Hz), 7.47-7.52 (2H, m), 7.57-7.59 (2H, m), 7.75 (1H, dd, J=8.5, 2.5 Hz), 8.08 (1H, d, J=2.5 Hz), 10.58 (1H, s).

(2) Preparation of the Intermediate 62(2).

The title compound was obtained in the same manner as the Example 2(3) using the following starting materials.

Starting materials: the intermediate 62(1) and malonic acid; Yield: 81% (white solid).

$^1$H-NMR ($CDCl_3$) δ: 5.22 (2H, s), 6.62 (1H, d, J=16.0 Hz), 7.03 (1H, d, J=8.5 Hz), 7.27-7.30 (4H, m), 7.47-7.58 (5H, m), 7.75 (1H, d, J=2.5 Hz), 8.20 (1H, d, J=16.0 Hz).

(3) Preparation of the Compound 62.

The title compound was obtained in the same manner as the Example 3 using the following starting material.

Starting material: the intermediate 62(2); Yield: 36% (white solid).

$^1$H-NMR ($CDCl_3$) δ: 2.73 (2H, t, J=7.5 Hz), 3.06 (2H, t, J=7.5 Hz), 5.13 (2H, s), 6.95 (1H, d, J=8.5 Hz), 7.23-7.26 (4H, m), 7.37 (1H, dd, J=8.5, 2.5 Hz), 7.41 (1H, d, J=2.5 Hz), 7.45-7.48 (2H, m), 7.50-7.55 (2H, m).

Example 63

Preparation of the Compound 63

The title compound was obtained in the same manner as the Example 1(2) using the following starting materials.

Starting materials: the intermediate 31(1) and 3-(trifluoromethoxy)phenylboronic acid; Yield: 28% (white solid).

$^1$H-NMR ($CDCl_3$) δ: 1.34 (9H, s), 5.20 (2H, s), 6.64 (1H, d, J=15.9 Hz), 7.07 (1H, d, J=8.7 Hz), 7.17-7.24 (1H, m), 7.26-7.50 (7H, m), 7.54 (1H, dd, J=2.4, 8.7 Hz), 7.75 (1H, d, J=2.4 Hz), 8.20 (1H, d, J=15.9 Hz).

Example 64

Preparation of the Compound 64

The title compound was obtained in the same manner as the Example 3 using the following starting material.

Starting material: the compound 63; Yield: 92% (colorless oil).

$^1$H-NMR ($CDCl_3$) δ: 1.34 (9H, s), 2.75 (2H, t, J=7.5 Hz), 3.07 (2H, t, J=7.5 Hz), 5.12 (2H, s), 6.99 (1H, d, J=8.4 Hz), 7.11-7.16 (1H, m), 7.34-7.48 (9H, m).

Example 65

Preparation of the Compound 65

The title compound was obtained in the same manner as the Example 1(2) using the following starting materials.

Starting materials: the intermediate 31(1) and 2-(trifluoromethoxy)phenylboronic acid; Yield: 24% (pale yellow solid).

$^1$H-NMR ($CDCl_3$) δ: 1.34 (9H, s), 5.19 (2H, s), 6.58 (1H, d, J=16.2 Hz), 7.06 (1H, d, J=8.7 Hz), 7.33-7.48 (9H, m), 7.66 (1H, d, J=2.1 Hz), 8.19 (1H, d, J=16.2 Hz).

Example 66

Preparation of the Compound 66

The title compound was obtained in the same manner as the Example 3 using the following starting material.

Starting material: the compound 65; Yield: 71% (colorless oil).

$^1$H-NMR ($CDCl_3$) δ: 1.34 (9H, s), 2.73 (2H, t, J=7.5 Hz), 3.05 (2H, t, J=7.5 Hz), 5.11 (2H, s), 6.98 (1H, d, J=9.3 Hz), 7.27-7.45 (10H, m).

Example 67

Preparation of the Compound 67

(1) Preparation of the Intermediate 67(1).

The title compound was obtained in the same manner as the Example 1(2) using the following starting materials.

Starting materials: 5-bromosalicylaldehyde and 4-(tert-butyl)phenylboronic acid; Yield: 64% (white solid).

$^1$H-NMR ($CDCl_3$) δ: 1.37 (9H, s), 7.06 (1H, d, J=8.7 Hz), 7.45-7.52 (4H, m), 7.74-7.79 (2H, m), 9.97 (1H, s), 10.98 (1H, s).

(2) Preparation of the Intermediate 67(2).

The title compound was obtained in the same manner as the Example 31(1) using the following starting materials.

Starting materials: the intermediate 67(1) and triethyl phosphonoacetate; Yield: 70% (pale yellow solid).

$^1$H-NMR ($CDCl_3$) δ: 1.36 (9H, s), 1.36 (3H, t, J=7.2 Hz), 4.30 (2H, q, J=7.2 Hz), 6.26 (1H, s), 6.69 (1H, d, J=16.2 Hz), 6.90 (1H, d, J=8.1 Hz), 7.42-7.50 (5H, m), 7.68 (1H, d, J=2.1 Hz), 8.06 (1H, d, J=16.2 Hz).

(3) Preparation of the Intermediate 67(3).

The title compound was obtained in the same manner as the Example 3 using the following starting material.

Starting material: the intermediate 67(2); Yield: 96% (white solid).

$^1$H-NMR ($CDCl_3$) δ: 1.24 (3H, t, J=7.2 Hz), 1.35 (9H, s), 2.75 (2H, t, J=5.7 Hz), 2.95 (2H, t, J=5.7 Hz), 4.15 (2H, q, J=7.2 Hz), 6.94 (1H, d, J=8.4 Hz), 7.29-7.37 (3H, m), 7.40-7.49 (4H, m).

(4) Preparation of the Intermediate 67(4).

The title compound was obtained in the same manner as the Example 2(1) using the following starting materials.

Starting materials: the intermediate 67(3) and 2-(trifluoromethoxy)benzyl bromide; Yield: 99% (colorless oil).

$^1$H-NMR ($CDCl_3$) δ: 1.22 (3H, t, J=7.2 Hz), 1.36 (9H, s), 2.68 (2H, t, J=7.5 Hz), 3.07 (2H, t, J=7.5 Hz), 4.12 (2H, q, J=7.2 Hz), 5.22 (2H, s), 6.94 (1H, d, J=8.4 Hz), 7.30-7.50 (9H, m), 7.63-7.66 (1H, m).

(5) Preparation of the Compound 67.

The title compound was obtained in the same manner as the Example 12(4) using the following starting material.

Starting material: the intermediate 67(4); Yield: 99% (white solid).

$^1$H-NMR (DMSO-$d_6$) δ: 1.31 (9H, s), 2.49-2.56 (2H, m), 2.87 (2H, t, J=7.8 Hz), 5.21 (2H, s), 7.13 (1H, d, J=9.0 Hz), 7.42-7.53 (9H, m), 7.66-7.72 (1H, m), 12.06 (1H, brs).

Example 68

Preparation of the Compound 68

(1) Preparation of the Intermediate 68(1).

The title compound was obtained in the same manner as the Example 2(1) using the following starting materials.

Starting materials: the intermediate 67(3) and 3-(trifluoromethoxy)benzyl bromide; Yield: 99% (colorless oil).

$^1$H-NMR ($CDCl_3$) δ: 1.22 (3H, t, J=7.2 Hz), 1.36 (9H, s), 2.67 (2H, t, J=7.5 Hz), 3.07 (2H, t, J=7.5 Hz), 4.12 (2H, q, J=7.2 Hz), 5.14 (2H, s), 6.92 (1H, d, J=8.7 Hz), 7.15-7.19 (1H, m), 7.33-7.50 (9H, m).

(2) Preparation of the Compound 68.

The title compound was obtained in the same manner as the Example 12(4) using the following starting material.

Starting material: the intermediate 68(1); Yield: 81% (white solid).

$^1$H-NMR (DMSO-$d_6$) δ: 1.31 (9H, s), 2.56 (2H, t, J=7.8 Hz), 2.92 (2H, t, J=7.8 Hz), 5.25 (2H, s), 7.09 (1H, d, J=8.7 Hz), 7.32-7.35 (1H, m), 7.42-7.58 (9H, m), 12.09 (1H, brs).

Example 69

Preparation of the Compound 69

(1) Preparation of the Intermediate 69(1).

The title compound was obtained in the same manner as the Example 2(1) using the following starting materials.

Starting materials: the intermediate 67(3) and 4-chlorobenzyl bromide; Yield: 99% (white solid).

$^1$H-NMR ($CDCl_3$) δ: 1.22 (3H, t, J=7.2 Hz), 1.35 (9H, s), 2.66 (2H, t, J=7.5 Hz), 3.05 (2H, t, J=7.5 Hz), 4.12 (2H, q, J=7.2 Hz), 5.09 (2H, s), 6.91 (1H, d, J=8.1 Hz), 7.32-7.49 (10H, m).

(2) Preparation of the Compound 69.

The title compound was obtained in the same manner as the Example 12(4) using the following starting material.

Starting material: the intermediate 69(1); Yield: 66% (white solid).

$^1$H-NMR (DMSO-$d_6$) δ: 1.30 (9H, s), 2.56 (2H, t, J=7.8 Hz), 2.89 (2H, t, J=7.8 Hz), 5.18 (2H, s), 7.03-7.09 (1H, m), 7.40-7.53 (10H, m), 12.09 (1H, brs).

Example 70

Preparation of the Compound 70

(1) Preparation of the Intermediate 70(1).

The title compound was obtained in the same manner as the Example 2(1) using the following starting materials.

Starting materials: the intermediate 67(3) and 4-(trifluoromethyl)benzyl bromide; Yield: 99% (white solid).

$^1$H-NMR ($CDCl_3$) δ: 1.22 (3H, t, J=7.2 Hz), 1.35 (9H, s), 2.68 (2H, t, J=7.5 Hz), 3.08 (2H, t, J=7.5 Hz), 4.12 (2H, q, J=7.2 Hz), 5.18 (2H, s), 6.91 (1H, d, J=8.1 Hz), 7.38-7.49 (6H, m), 7.56-7.58 (2H, m), 7.65-7.67 (2H, m).

(2) Preparation of the Compound 70.

The title compound was obtained in the same manner as the Example 12(4) using the following starting material.

Starting material: the intermediate 70(1); Yield: 78% (white solid).

$^1$H-NMR (DMSO-$d_6$) δ: 1.30 (9H, s), 2.58 (2H, t, J=7.8 Hz), 2.93 (2H, t, J=7.8 Hz), 5.30 (2H, s), 7.08 (1H, d, J=8.4 Hz), 7.41-7.47 (4H, m), 7.51-7.53 (2H, m), 7.69-7.72 (2H, m), 7.77-7.79 (2H, m), 12.10 (1H, brs).

Example 71

Preparation of the Compound 71

(1) Preparation of the Intermediate 71(1).

The title compound was obtained in the same manner as the Example 2(1) using the following starting materials.

Starting materials: the intermediate 67(3) and 4-butylbenzyl chloride; Yield: 99% (yellow oil).

$^1$H-NMR ($CDCl_3$) δ: 0.93 (3H, t, J=7.2 Hz), 1.22 (3H, t, J=7.2 Hz), 1.32-1.39 (11H, m), 1.54-1.66 (2H, m), 2.59-2.70 (4H, m), 3.02-3.10 (2H, m), 4.10-4.17 (2H, m), 5.09 (2H, s), 6.96 (1H, d, J=8.1 Hz), 7.19-7.22 (2H, m), 7.34-7.49 (8H, m).

(2) Preparation of the Compound 71.

The title compound was obtained in the same manner as the Example 12(4) using the following starting material.

Starting material: the intermediate 71(1); Yield: 92% (white solid).

$^1$H-NMR (DMSO-$d_6$) δ: 0.90 (3H, t, J=7.2 Hz), 1.25-1.37 (11H, m), 1.51-1.61 (2H, m), 2.50-2.61 (4H, m), 2.89 (2H, t, J=7.8 Hz), 5.13 (2H, s), 7.09 (1H, d, J=9.0 Hz), 7.21-7.23 (2H, m), 7.36-7.45 (6H, m), 7.50-7.52 (2H, m), 12.09 (1H, brs).

Example 72

Preparation of the Compound 72

(1) Preparation of the Intermediate 72(1).

The title compound was obtained in the same manner as the Example 12(2) using the following starting materials.

Starting materials: 2,4-difluorobenzaldehyde and 4-isopropylphenol; Yield: 97.6% (brown oil).

$^1$H-NMR ($CDCl_3$) δ: 1.24 (6H, d, J=6.9 Hz), 1.25 (6H, d, J=6.9 Hz), 2.85-2.96 (2H, m), 6.44 (1H, d, J=2.4 Hz), 6.11 (1H, dd, J=2.4, 9.0 Hz), 6.92-6.96 (2H, m), 6.98-7.02 (2H, m), 7.19-7.26 (4H, m), 7.86 (1H, d, J=9.0 Hz), 10.40 (1H, s).

(2) Preparation of the Compound 72.

The title compound was obtained in the same manner as the Example 2(3) using the following starting materials.

Starting materials: the intermediate 72(1) and malonic acid; Yield: 100% (white solid).

$^1$H-NMR ($CDCl_3$) δ: 1.22 (6H, d, J=2.7 Hz), 1.25 (6H, d, J=2.4 Hz), 2.84-2.94 (2H, m), 6.47 (1H, d, J=2.1 Hz), 6.50

(1H, d, J=16.2 Hz), 6.60 (1H, dd, J=2.1, 8.7 Hz), 6.89-6.98 (4H, m), 7.15-7.22 (4H, m), 7.53 (1H, d, J=8.7 Hz), 8.07 (1H, d, J=16.2 Hz).

Example 73

Preparation of the Compound 73

The title compound was obtained in the same manner as the Example 3 using the following starting material.

Starting material: the compound 72; Yield: 74.0% (white solid).

$^1$H-NMR ($CDCl_3$) δ: 1.21 (6H, d, J=2.4 Hz), 1.24 (6H, d, J=2.4 Hz), 2.70 (2H, t, J=7.5 Hz), 2.82-2.94 (2H, m), 2.96 (2H, t, J=7.5 Hz), 6.53 (1H, d, J=2.1 Hz), 6.61 (1H, dd, J=2.1, 8.4 Hz), 6.86-6.92 (4H, m), 7.12-7.18 (5H, m).

Example 74

Preparation of the Compound 74

(1) Preparation of the Intermediate 74(1).

The title compound was obtained in the same manner as the Example 12(3) using the following starting materials.

Starting materials: the intermediate 72(1) and bis(2,2,2-trifluoroethyl)(methoxycarbonylmethyl)phosphonate; Yield: 95.4% (yellow oil).

$^1$H-NMR ($CDCl_3$) δ: 1.22 (6H, s), 1.24 (6H, s), 2.81-2.96 (2H, m), 3.70 (3H, s), 5.91 (1H, d, J=12.6 Hz), 6.50 (1H, d, J=2.4 Hz), 6.63 (1H, dd, J=2.4, 8.4 Hz), 6.89-6.95 (4H, m), 7.14-7.18 (5H, m), 7.77 (1H, d, J=8.4 Hz).

(2) Preparation of the Compound 74.

The title compound was obtained in the same manner as the Example 12(4) using the following starting material.

Starting material: the intermediate 74(1); Yield: 74.3% (white solid).

$^1$H-NMR ($CDCl_3$) δ: 1.22 (6H, s), 1.24 (6H, s), 2.83-2.93 (2H, m), 5.92 (1H, d, J=12.6 Hz), 6.48 (1H, d, J=2.4 Hz), 6.60 (1H, dd, J=2.4, 8.7 Hz), 6.90-6.95 (4H, m), 7.15-7.19 (4H, m), 7.26 (1H, d, J=12.6 Hz), 7.77 (1H, d, J=8.7 Hz).

Example 75

Preparation of the Compound 75

(1) Preparation of the Intermediate 75(1).

A mixture of 4-bromo-2-fluorobenzaldehyde (2.00 g, 9.85 mmol), 4-(tert-butyl)benzyl alcohol (1.78 g, 10.84 mmol), potassium carbonate (2.04 g, 14.78 mmol) and dimethylformamide (4 ml) was stirred at 120° C. for 8 hours. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=20:1) to give the title compound (893 mg, 17.4%) as a yellow oil.

$^1$H-NMR ($CDCl_3$) δ: 1.33 (9H, s), 5.14 (2H, s), 7.18-7.22 (1H, m), 7.26-7.34 (1H, m), 7.37 (2H, d, J=8.4 Hz), 7.45 (2H, d, J=8.4 Hz), 7.72 (1H, d, J=8.1 Hz), 10.46 (1H, s).

(2) Preparation of the Intermediate 75(2).

The title compound was obtained in the same manner as the Example 1(2) using the following starting materials.

Starting materials: the intermediate 75(1) and 4-(trifluoromethoxy)phenylboronic acid; Yield: 61.5% (white solid).

$^1$H-NMR ($CDCl_3$) δ: 1.35 (9H, s), 5.23 (2H, s), 7.22 (1H, s), 7.24-7.26 (1H, m), 7.31-7.34 (1H, m), 7.39-7.48 (4H, m), 7.59-7.62 (2H, m), 7.92-7.95 (2H, m), 10.57 (1H, s).

(3) Preparation of the Compound 75.

The title compound was obtained in the same manner as the Example 2(3) using the following starting materials.

Starting materials: the intermediate 75(2) and malonic acid; Yield: 93.6% (white solid).

$^1$H-NMR ($CDCl_3$) δ: 1.35 (9H, s), 5.23 (2H, s), 6.60 (1H, d, J=16.2 Hz), 7.15-7.20 (2H, m), 7.29 (2H, d, J=8.1 Hz), 7.39-7.47 (4H, m), 7.55-7.58 (2H, m), 7.64 (1H, d, J=8.1 Hz), 8.18 (1H, d, J=16.2 Hz).

Example 76

Preparation of the Compound 76

The title compound was obtained in the same manner as the Example 3 using the following starting material.

Starting material: the compound 75; Yield: 78.3% (white solid).

$^1$H-NMR ($CDCl_3$) δ: 1.32 (9H, s), 2.74 (2H, t, J=7.2 Hz), 3.05 (2H, t, J=7.2 Hz), 5.13 (2H, s), 7.06-7.09 (2H, m), 7.25-7.28 (3H, m), 7.37-7.45 (4H, m), 7.52-7.56 (2H, m).

Example 77

Preparation of the Compound 77

(1) Preparation of the Intermediate 77(1).

The title compound was obtained in the same manner as the Example 15(1) using the following starting materials.

Starting materials: the intermediate 75(1) and 4-(trifluoromethoxy)phenol; Yield: 21.7% (white solid).

$^1$H-NMR ($CDCl_3$) δ: 1.34 (9H, s), 5.09 (2H, s), 6.56 (1H, dd, J=2.1, 8.4 Hz), 6.62 (1H, d, J=2.1 Hz), 7.04-7.08 (1H, m), 7.25 (2H, d, J=8.4 Hz), 7.31 (2H, d, J=8.4 Hz), 7.42 (2H, d, J=8.4 Hz), 7.84 (2H, d, J=8.4 Hz), 10.43 (1H, s).

(2) Preparation of the Compound 77.

The title compound was obtained in the same manner as the Example 2(3) using the following starting materials.

Starting materials: the intermediate 77(1) and malonic acid; Yield: 92.6% (white solid).

$^1$H-NMR ($CDCl_3$) δ: 1.34 (9H, s), 5.09 (2H, s), 6.49 (1H, d, J=16.2 Hz), 6.55 (1H, dd, J=2.1, 8.4 Hz), 6.61 (1H, d, J=2.1 Hz), 6.99-7.03 (2H, m), 7.20 (2H, d, J=8.7 Hz), 7.26-7.31 (2H, m), 7.39-7.42 (2H, m), 7.51 (1H, d, J=8.4 Hz), 8.09 (1H, d, J=16.2 Hz).

Example 78

Preparation of the Compound 78

The title compound was obtained in the same manner as the Example 3 using the following starting material.

Starting material: the compound 77; Yield: 80.0% (colorless oil).

$^1$H-NMR ($CDCl_3$) δ: 1.33 (9H, s), 2.69 (2H, t, J=7.8 Hz), 2.97 (2H, t, J=7.8 Hz), 5.00 (2H, s), 6.50 (1H, dd, J=2.4, 8.1 Hz), 6.62 (1H, d, J=2.4 Hz), 6.94-6.97 (2H, m), 7.11-7.16 (3H, m), 7.30 (2H, d, J=8.1 Hz), 7.38-7.41 (2H, m).

Example 79

Preparation of the Compound 79

(1) Preparation of the Intermediate 79(1).

The title compound was obtained in the same manner as the Example 12(2) using the following starting materials.

Starting materials: 4-bromo-2-fluorobenzaldehyde and 4-(tert-butyl)phenol; Yield: 75.9% (white solid).

$^1$H-NMR ($CDCl_3$) δ: 1.35 (9H, s), 6.99-7.05 (3H, m), 7.27-7.31 (1H, m), 7.41-7.47 (2H, m), 7.78 (1H, d, J=8.1 Hz), 10.49 (1H, d, J=0.9 Hz).

(2) Preparation of the Intermediate 79(2).

The title compound was obtained in the same manner as the Example 2(3) using the following starting materials.

Starting materials: the intermediate 79(1) and malonic acid; Yield: 65% (white solid).

$^1$H-NMR (DMSO-$d_6$) δ: 1.29 (9H, s), 6.64 (1H, d, J=16.0 Hz), 6.96-7.01 (3H, m), 7.39 (1H, dd, J=2.0, 8.5 Hz), 7.43-7.46 (2H, m), 7.74 (1H, d, J=16.0 Hz), 7.85 (1H, d, J=8.5 Hz), 12.51 (1H, s).

(3) Preparation of the Compound 79.

The title compound was obtained in the same manner as the Example 1(2) using the following starting materials.

Starting materials: the intermediate 79(2) and 4-(trifluoromethoxy)phenylboronic acid; Yield: 96% (white solid).

$^1$H-NMR (DMSO-$d_6$) δ: 1.25 (9H, s), 6.65 (1H, d, J=16.0 Hz), 6.91-6.96 (2H, m), 7.25 (1H, d, J=2.0 Hz), 7.37-7.43 (4H, m), 7.55 (1H, dd, J=2.0, 8.5 Hz), 7.74-7.77 (2H, m), 7.77 (1H, d, J=16.0 Hz), 8.01 (1H, d, J=8.0 Hz), 12.48 (1H, s).

Example 80

Preparation of the Compound 80

The title compound was obtained in the same manner as the Example 3 using the following starting material.

Starting material: the compound 79; Yield: 93% (white solid).

$^1$H-NMR (DMSO-$d_6$) δ: 1.26 (9H, s), 2.55 (2H, t, J=7.5 Hz), 2.84 (2H, t, J=7.5 Hz), 6.87-6.92 (2H, m), 7.15 (1H, s), 7.34-7.47 (6H, m), 7.68-7.72 (2H, m), 12.18 (1H, s).

Example 81

Preparation of the Compound 81

(1) Preparation of the Intermediate 81(1).

The title compound was obtained in the same manner as the Example 2(1) using the following starting materials.

Starting materials: 5-bromo-2-hydroxy-3-methoxybenzaldehyde and 4-(tert-butyl)benzyl bromide; Yield: 96% (colorless oil).

$^1$H-NMR (DMSO-$d_6$) δ: 1.26 (9H, s), 3.95 (3H, s), 5.11 (2H, s), 7.30 (1H, d, J=2.5 Hz), 7.32 (2H, d, J=8.0 Hz), 7.39 (2H, d, J=8.0 Hz), 7.58 (1H, d, J=2.5 Hz), 9.98 (1H, s).

(2) Preparation of the Intermediate 81(2).

The title compound was obtained in the same manner as the Example 2(3) using the following starting materials.

Starting materials: the intermediate 81(1) and malonic acid; Yield: 76% (white solid).

$^1$H-NMR (DMSO-$d_6$) δ: 1.27 (9H, s), 3.88 (3H, s), 4.92 (2H, s), 6.48 (1H, d, J=16.0 Hz), 7.29-7.31 (2H, m), 7.30 (1H, d, J=2.0 Hz), 7.36-7.39 (2H, m), 7.51 (1H, d, J=2.0 Hz), 7.64 (1H, d, J=16.0 Hz), 12.38 (1H, s).

(3) Preparation of the Compound 81.

The title compound was obtained in the same manner as the Example 1(2) using the following starting materials.

Starting materials: the intermediate 81(2) and 4-(trifluoromethoxy)phenylboronic acid; Yield: 31% (white solid).

$^1$H-NMR (DMSO-$d_6$) δ: 1.28 (9H, s), 3.97 (3H, s), 4.97 (2H, s), 6.64 (1H, d, J=16.0 Hz), 7.34-7.46 (7H, m), 7.62 (1H, d, J=2.0 Hz), 7.81 (1H, d, J=16.0 Hz), 7.91 (2H, d, J=8.5 Hz), 12.34 (1H, s).

Example 82

Preparation of the Compound 82

The title compound was obtained in the same manner as the Example 3 using the following starting material.

Starting material: the compound 81; Yield: 63% (white solid).

$^1$H-NMR (DMSO-$d_6$) δ: 1.29 (9H, s), 2.44 (2H, t, J=7.5 Hz), 2.83 (2H, t, J=7.5 Hz), 3.93 (3H, s), 4.95 (2H, s), 7.11 (1H, d, J=2.0 Hz), 7.21 (1H, d, J=2.0 Hz), 7.36-7.45 (6H, m), 7.77-7.80 (2H, m), 12.09 (1H, s).

Example 83

Preparation of the Compound 83

(1) Preparation of the Intermediate 83(1).

Boron tribromide (2.0 ml, 21.116 mmol) was added dropwise to a solution of 5-bromo-2-methoxytoluene (2.108 g, 10.486 mmol) in dichloromethane (20 ml) at −78° C., and the mixture was stirred at 0° C. for 6 hours. A saturated aqueous solution of sodium hydrogen carbonate was added to the reaction mixture, and the mixture was extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=15:1) to give the title compound (1.942 g, 99%) as a white solid.

$^1$H-NMR ($CDCl_3$) δ: 2.22 (3H, s), 4.83 (1H, s), 6.65 (1H, d, J=8.4 Hz), 7.16 (1H, dd, J=2.4, 8.4 Hz), 7.23 (1H, d, J=2.4 Hz).

(2) Preparation of the Intermediate 83(2).

Triethylamine (2.5 ml, 17.94 mmol) was added to a mixture of paraformaldehyde (811 mg, 27.00 mmol), magnesium chloride (1.714 g, 18.00 mmol) and tetrahydrofuran (45 ml), and the mixture was stirred at room temperature for 20 minutes. The intermediate 83(1) (1.683 g, 9.00 mmol) was added to the reaction mixture, and the mixture was refluxed for 8 hours. The reaction mixture was cooled to room temperature, and diluted with ethyl acetate. The organic layer was washed with 1 N hydrochloric acid, water and saturated brine, and dried over anhydrous sodium sulfate. The residue obtained by evaporation of the solvent under reduced pressure was washed with n-hexane to give the title compound (714 mg, 36.9%) as a yellowish-orange solid.

$^1$H-NMR ($CDCl_3$) δ: 2.26 (3H, s), 7.49-7.52 (2H, m), 9.82 (1H, s), 11.19 (1H, s).

(3) Preparation of the Intermediate 83(3).

The title compound was obtained in the same manner as the Example 2(1) using the following starting materials.

Starting materials: the intermediate 83(2) and 4-(tert-butyl)benzyl bromide; Yield: 53% (colorless oil).

$^1$H-NMR ($CDCl_3$) δ: 1.33 (9H, s), 2.34 (3H, s), 4.92 (2H, s), 7.30-7.33 (2H, m), 7.41-7.44 (2H, m), 7.58-7.59 (1H, m), 7.78-7.89 (1H, m), 10.13 (1H, s).

(4) Preparation of the Intermediate 83(4).

The title compound was obtained in the same manner as the Example 2(3) using the following starting materials.

Starting materials: the intermediate 83(3) and malonic acid; Yield: 76% (white solid).

$^1$H-NMR ($CDCl_3$) δ: 1.33 (9H, s), 2.30 (3H, s), 4.77 (2H, s), 6.38 (1H, d, J=16.1 Hz), 7.34-7.44 (5H, m), 7.54-7.55 (1H, m), 7.97 (1H, d, J=16.1 Hz).

(5) Preparation of the Compound 83.

The title compound was obtained in the same manner as the Example 1(2) using the following starting materials.

Starting materials: the intermediate 83(4) and 4-(trifluoromethoxy)phenylboronic acid; Yield: 41% (white solid).

$^1$H-NMR ($CDCl_3$) δ: 1.34 (9H, s), 2.40 (3H, s), 4.84 (2H, s), 6.51 (1H, d, J=16.1 Hz), 7.26-7.31 (2H, m), 7.40-7.46 (5H, m), 7.57-7.60 (3H, m), 8.14 (1H, d, J=16.1 Hz).

Example 84

Preparation of the Compound 84

The title compound was obtained in the same manner as the Example 3 using the following starting material.

Starting material: the compound 83; Yield: 91% (white solid).

$^1$H-NMR ($CDCl_3$) δ: 1.34 (9H, s), 2.40 (3H, s), 2.71 (2H, t, J=7.8 Hz), 3.04 (2H, t, J=7.8 Hz), 4.84 (2H, s), 7.24-7.27 (4H, m), 7.44 (4H, s), 7.53-7.56 (2H, m).

Example 85

Preparation of the Compound 85

(1) Preparation of the Intermediate 85(1).

The title compound was obtained in the same manner as the Example 83(1) using the following starting material.

Starting material: 2-fluoro-6-methoxybenzaldehyde; Yield: 82% (reddish purple solid).

$^1$H-NMR ($CDCl_3$) δ: 6.60-6.67 (1H, m), 6.75-6.78 (1H, m), 7.43-7.51 (1H, m), 10.27 (1H, s), 11.43 (1H, s).

(2) Preparation of the Intermediate 85(2).

The title compound was obtained in the same manner as the Example 2(1) using the following starting materials.

Starting materials: the intermediate 85(1) and 4-(tert-butyl)benzyl bromide; Yield: 91% (white solid).

$^1$H-NMR ($CDCl_3$) δ: 1.33 (9H, s), 5.16 (2H, s), 6.71-6.77 (1H, m), 6.85 (1H, d, J=8.4 Hz), 7.35-7.50 (5H, m), 10.50 (1H, s).

(3) Preparation of the Intermediate 85(3).

The title compound was obtained in the same manner as the Example 12(2) using the following starting materials.

Starting materials: the intermediate 85(2) and 4-(trifluoromethoxy)phenol; Yield: 85% (brown solid).

$^1$H-NMR ($CDCl_3$) δ: 1.34 (9H, s), 5.18 (2H, s), 6.49 (1H, d, J=8.4 Hz), 6.83 (1H, d, J=8.6 Hz), 7.01-7.04 (2H, m), 7.18-7.21 (2H, m), 7.38-7.45 (5H, m), 10.57 (1H, s).

(4) Preparation of the Compound 85.

The title compound was obtained in the same manner as the Example 2(3) using the following starting materials.

Starting materials: the intermediate 85(3) and malonic acid; Yield: 82% (flesh-colored solid).

$^1$H-NMR ($CDCl_3$) δ: 1.33 (9H, s), 5.19 (2H, s), 6.46 (1H, d, J=8.4 Hz), 6.77 (1H, d, J=8.4 Hz), 6.94 (1H, d, J=16.3 Hz), 6.99-7.03 (2H, m), 7.18-7.27 (3H, m), 7.36-7.44 (4H, m), 8.20 (1H, d, J=16.3 Hz).

Example 86

Preparation of the Compound 86

The title compound was obtained in the same manner as the Example 3 using the following starting material.

Starting material: the compound 85; Yield: 96% (pale yellow solid).

$^1$H-NMR ($CDCl_3$) δ: 1.32 (9H, s), 2.59 (2H, t, J=7.9 Hz), 3.05 (2H, t, J=7.9 Hz), 5.09 (2H, s), 6.50 (1H, d, J=8.2 Hz), 6.75 (1H, d, J=8.2 Hz), 6.92-6.95 (2H, m), 7.10-7.16 (3H, m), 7.34-7.43 (4H, m).

Example 87

Preparation of the Compound 87

(1) Preparation of the Intermediate 87(1).

The title compound was obtained in the same manner as the Example 83(2) using the following starting materials.

Starting materials: 2-bromophenol and paraformaldehyde; Yield: 33% (yellow solid).

$^1$H-NMR ($CDCl_3$) δ: 6.93-6.98 (1H, m), 7.54-7.57 (1H, m), 7.78-7.81 (1H, m), 9.87 (1H, s), 11.62 (1H, s).

(2) Preparation of the Intermediate 87(2).

The title compound was obtained in the same manner as the Example 2(1) using the following starting materials.

Starting materials: the intermediate 87(1) and 4-(tert-butyl)benzyl bromide; Yield: 97% (colorless oil).

$^1$H-NMR ($CDCl_3$) δ: 1.33 (9H, s), 5.09 (2H, s), 7.15 (1H, t, J=7.7 Hz), 7.37-7.45 (4H, m), 7.78 (1H, dd, J=1.6, 7.7 Hz), 7.85 (1H, dd, J=1.6, 7.7 Hz), 10.14 (1H, s).

(3) Preparation of the Intermediate 87(3).

The title compound was obtained in the same manner as the Example 2(3) using the following starting materials.

Starting materials: the intermediate 87(2) and malonic acid; Yield: 89% (white solid).

$^1$H-NMR ($CDCl_3$) δ: 1.33 (9H, s), 4.94 (2H, s), 6.40 (1H, d, J=16.1 Hz), 7.04-7.09 (1H, m), 7.42-7.47 (4H, m), 7.51-7.54 (1H, m), 7.64-7.67 (1H, m), 8.00 (1H, d, J=16.1 Hz).

(4) Preparation of the Compound 87.

The title compound was obtained in the same manner as the Example 1(2) using the following starting materials.

Starting materials: the intermediate 87(3) and 4-(trifluoromethoxy)phenylboronic acid; Yield: 43% (pale yellow solid).

$^1$H-NMR ($CDCl_3$) δ: 1.29 (9H, s), 4.23 (2H, s), 6.51 (1H, d, J=16.1 Hz), 6.93-6.96 (2H, m), 7.23-7.29 (5H, m), 7.39-7.42 (1H, m), 7.56-7.64 (3H, m), 8.18 (1H, d, J=16.1 Hz).

Example 88

Preparation of the Compound 88

The title compound was obtained in the same manner as the Example 3 using the following starting material.

Starting material: the compound 87; Yield: 85% (white solid).

$^1$H-NMR ($CDCl_3$) δ: 1.29 (9H, s), 2.73 (2H, t, J=7.8 Hz), 3.06 (2H, t, J=7.8 Hz), 4.37 (2H, s), 2.97-7.00 (2H, m), 7.12-7.31 (7H, m), 7.59-7.63 (2H, m).

Example 89

Preparation of the Compound (1) Preparation of the Intermediate 89(1).

The title compound was obtained in the same manner as the Example 83(1) using the following starting material.

Starting material: 2-fluoro-4-methoxybenzaldehyde; Yield: 68% (white solid).

$^1$H-NMR (DMSO-$d_6$) δ: 6.68 (1H, dd, J=2.0, 13.0 Hz), 6.76 (1H, dd, J=2.0, 8.5 Hz), 7.07 (1H, t, J=8.5 Hz), 10.01 (1H, s), 11.13 (1H, s).

(2) Preparation of the Intermediate 89(2).

A mixture of the intermediate 89(1) (500 mg, 3.563 mmol), 4-(trifluoromethoxy)phenylboronic acid (1.46 g, 7.136 mmol), copper(II) acetate (648 mg, 3.568 mmol), triethylamine (2.5 ml, 17.84 mmol), molecular sieves 4A and dichloromethane (35 ml) was stirred at room temperature for 2 hours. The reaction mixture was filtered through Celite. The residue obtained by concentration of the filtrate under reduced pressure was diluted with ethyl acetate. The organic layer was washed with water and saturated brine, and dried over anhydrous sodium sulfate. The residue obtained by concentration of the filtrate under reduced pressure was purified by column chromatography on silica gel (n-hexane:ethyl acetate=10:1) to give the title compound (132 mg, 12%) as a yellow oil.

$^1$H-NMR ($CDCl_3$) δ: 6.69 (1H, dd, J=2.5, 11.5 Hz), 6.82-6.86 (1H, m), 7.11-7.15 (2H, m), 7.30 (2H, d, J=9.0 Hz), 7.86 (1H, t, J=8.5 Hz), 10.25 (1H, s).

(3) Preparation of the Intermediate 89(3).

The title compound was obtained in the same manner as the Example 12(2) using the following starting materials.

Starting materials: the intermediate 89(2) and 4-(tert-butyl)phenol; Yield: 54% (yellow oil).

$^1$H-NMR ($CDCl_3$) δ: 1.32 (9H, s), 6.45 (1H, d, J=2.0 Hz), 6.63 (1H, dd, J=2.0, 8.5 Hz), 6.99-7.04 (4H, m), 7.19-7.22 (2H, m), 7.38-7.41 (2H, m), 7.90 (1H, d, J=8.5 Hz), 10.42 (1H, s).

(4) Preparation of the Compound 89.

The title compound was obtained in the same manner as the Example 2(3) using the following starting materials.

Starting materials: the intermediate 89(3) and malonic acid; Yield: 95% (white solid).

$^1$H-NMR ($CDCl_3$) δ: 1.31 (9H, s), 6.49 (1H, d, J=2.5 Hz), 6.52 (1H, d, J=16.0 Hz), 6.54 (1H, dd, J=2.5, 8.5 Hz), 6.94-7.01 (4H, m), 7.16-7.19 (2H, m), 7.35-7.38 (2H, m), 7.58 (1H, d, J=8.5 Hz), 8.08 (1H, d, J=16.0 Hz).

Example 90

Preparation of the Compound 90

The title compound was obtained in the same manner as the Example 3 using the following starting material.

Starting material: the compound 89; Yield: 87% (colorless oil).

$^1$H-NMR ($CDCl_3$) δ: 1.30 (9H, s), 2.72 (2H, t, J=7.5 Hz), 2.98 (2H, t, J=7.5 Hz), 6.53 (1H, d, J=2.5 Hz), 6.63 (1H, dd, J=2.5, 8.5 Hz), 6.88-6.96 (4H, m), 7.12-7.15 (2H, m), 7.22 (1H, d, J=8.5 Hz), 7.31-7.34 (2H, m).

Example 91

Preparation of the Compound 91

(1) Preparation of the Intermediate 91(1).

The title compound was obtained in the same manner as the Example 83(2) using the following starting materials.

Starting materials: 4-bromo-2-chlorophenol and paraformaldehyde; Yield: 13% (yellow solid).

$^1$H-NMR ($CDCl_3$) δ: 7.63 (1H, d, J=2.5 Hz), 7.75 (1H, d, J=2.5 Hz), 9.85 (1H, s), 11.39 (1H, s).

(2) Preparation of the Intermediate 91(2).

The title compound was obtained in the same manner as the Example 2(1) using the following starting materials.

Starting materials: the intermediate 91(1) and 4-(tert-butyl)benzyl bromide; Yield: 94% (colorless oil).

$^1$H-NMR ($CDCl_3$) δ: 1.32 (9H, s), 5.10 (2H, s), 7.29-7.32 (2H, m), 7.39-7.42 (2H, m), 7.80-7.81 (2H, m), 9.97 (1H, s).

(3) Preparation of the Intermediate 91(3).

The title compound was obtained in the same manner as the Example 2(3) using the following starting materials.

Starting materials: the intermediate 91(2) and malonic acid; Yield: 30% (white solid).

$^1$H-NMR ($CDCl_3$) δ: 1.32 (9H, s), 4.95 (2H, s), 6.34 (1H, d, J=16.0 Hz), 7.37 (2H, dd, J=2.5, 8.5 Hz), 7.42 (2H, dd, J=2.5, 8.5 Hz), 7.58 (1H, d, J=2.5 Hz), 7.62 (1H, d, J=2.5 Hz), 7.84 (1H, d, J=16.0 Hz).

(4) Preparation of the Compound 91.

The title compound was obtained in the same manner as the Example 1(2) using the following starting materials.

Starting materials: the intermediate 91(3) and 4-(trifluoromethoxy)phenylboronic acid; Yield: 39% (white solid).

$^1$H-NMR ($CDCl_3$) δ: 1.33 (9H, s), 5.00 (2H, s), 6.46 (1H, d, J=16.0 Hz), 7.32 (2H, d, J=8.5 Hz), 7.43 (4H, s), 7.56-7.59 (2H, m), 7.62 (1H, d, J=2.0 Hz), 7.67 (1H, d, J=2.0 Hz), 7.99 (1H, d, J=16.0 Hz).

Example 92

Preparation of the Compound 92

The title compound was obtained in the same manner as the Example 3 using the following starting material.

Starting material: the compound 91; Yield: 73% (white solid).

$^1$H-NMR (DMSO-$d_6$) δ: 1.30 (9H, s), 2.56 (2H, t, J=7.5 Hz), 2.93 (2H, t, J=7.5 Hz), 4.95 (2H, s), 7.44-7.46 (6H, m), 7.58 (1H, d, J=2.0 Hz), 7.70 (1H, d, J=2.0 Hz), 7.81 (2H, d, J=8.5 Hz), 12.17 (1H, s).

Example 93

Preparation of the Compound 93

(1) Preparation of the Intermediate 93(1).

Trifluoromethanesulfonic anhydride (672 mg, 2.381 mmol), 4-dimethylaminopyridine (23 mg, 0.189 mmol) and triethylamine (0.32 ml, 2.296 mmol) were added to a solution of the intermediate 85(1) (266 mg, 1.899 mmol) in dichloromethane (4 ml) at 0° C. under argon atmosphere, and the mixture was stirred at room temperature for 20 hours. A saturated aqueous solution of ammonium chloride was added to the reaction mixture, and the mixture was extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=5:1) to give the title compound (384 mg, 74.2%) as a white solid.

$^1$H-NMR ($CDCl_3$) δ: 7.18-7.33 (2H, m), 7.65-7.73 (1H, m), 10.38 (1H, s).

(2) Preparation of the Intermediate 93(2).

The title compound was obtained in the same manner as the Example 1(2) using the following starting materials.

Starting materials: the intermediate 93(1) and 4-(trifluoromethoxy)phenylboronic acid; Yield: 78% (colorless oil).

$^1$H-NMR ($CDCl_3$) δ: 7.17-7.38 (6H, m), 7.56-7.63 (1H, m), 10.04 (1H, s).

(3) Preparation of the Intermediate 93(3).

The title compound was obtained in the same manner as the Example 12(2) using the following starting materials.

Starting materials: the intermediate 93(2) and 4-(tert-butyl)phenol; Yield: 43% (yellow solid).

$^1$H-NMR ($CDCl_3$) δ: 1.36 (9H, s), 6.92-6.95 (1H, m), 6.98-7.04 (3H, m), 7.26-7.28 (2H, m), 7.34-7.49 (5H, m), 10.33 (1H, s).

(4) Preparation of the Compound 93.

The title compound was obtained in the same manner as the Example 2(3) using the following starting materials.

Starting materials: the intermediate 93(3) and malonic acid; Yield: 68% (flesh-colored solid).

$^1$H-NMR ($CDCl_3$) δ: 1.34 (9H, s), 6.64 (1H, d, J=16.3 Hz), 6.87-7.04 (4H, m), 7.26-7.40 (7H, m), 7.65 (1H, d, J=16.3 Hz).

Example 94

Preparation of the Compound 94

The title compound was obtained in the same manner as the Example 3 using the following starting material.

Starting material: the compound 93; Yield: 47% (white solid).

$^1$H-NMR ($CDCl_3$) δ: 1.32 (9H, s), 2.53-2.59 (2H, m), 2.90-2.96 (2H, m), 6.83-6.95 (4H, m), 7.14-7.20 (1H, m), 7.24-7.26 (2H, m), 7.31-7.37 (4H, m).

Example 95

Preparation of the Compound 95

(1) Preparation of the Intermediate 95(1).

The title compound was obtained in the same manner as the Example 89(2) using the following starting materials.

Starting materials: 4-(trifluoromethoxy)phenylboronic acid and 4-hydroxybenzaldehyde; Yield: 49% (yellow solid).

$^1$H-NMR ($CDCl_3$) δ: 7.07-7.12 (4H, m), 7.25-7.28 (2H, m), 7.85-7.90 (2H, m), 9.95 (1H, s).

(2) Preparation of the Intermediate 95(2).

m-Chloroperbenzoic acid (690 mg, 3.079 mmol) was added to a solution of the intermediate 95(1) (695 mg, 2.463 mmol) in chloroform (6.8 ml), and the mixture was stirred at room temperature for 2 hours. A saturated aqueous solution of sodium hydrogen sulfite was added to the reaction mixture, and the mixture was extracted with ethyl acetate. The organic layer was washed with a saturated aqueous solution of sodium hydrogen carbonate and saturated brine, and dried over anhydrous sodium sulfate. Methanol (20 ml) and catalytic amount of concentrated hydrochloric acid were added to the residue obtained by evaporation of the solvent under reduced pressure, and the mixture was stirred at room temperature for 30 minutes. The residue obtained by evaporation of the solvent under reduced pressure was purified by column chromatography on silica gel (n-hexane:ethyl acetate=3:1) to give the title compound (561 mg, 84.3%) as a colorless oil.

$^1$H-NMR ($CDCl_3$) δ: 4.64 (1H, s), 6.81-6.86 (2H, m), 6.90-6.96 (4H, m), 7.12-7.16 (2H, m).

(3) Preparation of the Intermediate 95(3).

The title compound was obtained in the same manner as the Example 83(2) using the following starting materials.

Starting materials: the intermediate 95(2) and paraformaldehyde; Yield: 39% (colorless oil).

$^1$H-NMR ($CDCl_3$) δ: 6.93-7.04 (3H, m), 7.17-7.29 (4H, m), 9.84 (1H, s), 10.85 (1H, s).

(4) Preparation of the Intermediate 95(4).

The title compound was obtained in the same manner as the Example 2(1) using the following starting materials.

Starting materials: the intermediate 95(3) and 4-(tert-butyl)benzyl bromide; Yield: 94% (colorless oil).

$^1$H-NMR ($CDCl_3$) δ: 1.34 (9H, s), 5.16 (2H, s), 6.93-6.97 (2H, m), 7.07-7.24 (4H, m), 7.36-7.50 (5H, m), 10.51 (1H, s).

(5) Preparation of the Compound 95.

The title compound was obtained in the same manner as the Example 2(3) using the following starting materials.

Starting materials: the intermediate 95(4) and malonic acid; Yield: 68% (pale yellow solid).

$^1$H-NMR ($CDCl_3$) δ: 1.34 (9H, s), 5.13 (2H, s), 6.47 (1H, d, J=16.1 Hz), 6.92-7.05 (4H, m), 7.15-7.26 (3H, m), 7.35-7.45 (4H, m), 8.11 (1H, d, J=16.1 Hz).

Example 96

Preparation of the Compound 96

The title compound was obtained in the same manner as the Example 3 using the following starting material.

Starting material: the compound 95; Yield: 94% (white oil).

$^1$H-NMR ($CDCl_3$) δ: 1.34 (9H, s), 2.69 (2H, t, J=7.5 Hz), 2.97 (2H, t, J=7.5 Hz), 5.05 (2H, s), 6.83-6.94 (5H, m), 7.11-7.14 (2H, m), 7.34-7.43 (4H, m).

Example 97

Preparation of the Compound 97

(1) Preparation of the Intermediate 97(1).

The title compound was obtained in the same manner as the Example 12(2) using the following starting materials.

Starting materials: 2,6-difluorobenzaldehyde and 4-(trifluoromethoxy)phenol; Yield: 11% (white solid).

$^1$H-NMR ($CDCl_3$) δ: 6.64 (2H, d, J=8.5 Hz), 7.07-7.10 (4H, m), 7.23-7.26 (4H, m), 7.40 (1H, t, J=8.5 Hz), 10.55 (1H, s).

(2) Preparation of the Compound 97.

The title compound was obtained in the same manner as the Example 2(3) using the following starting materials.

Starting materials: the intermediate 97(1) and malonic acid; Yield: 83% (white solid).

$^1$H-NMR ($CDCl_3$) δ: 6.60 (2H, d, J=8.5 Hz), 6.92 (1H, d, J=16.5 Hz), 7.04-7.09 (4H, m), 7.21 (1H, t, J=8.5 Hz), 7.22-7.26 (4H, m), 8.13 (1H, d, J=16.5 Hz).

Example 98

Preparation of the Compound 98

The title compound was obtained in the same manner as the Example 3 using the following starting material.

Starting material: the compound 97; Yield: 92% (colorless oil).

$^1$H-NMR ($CDCl_3$) δ: 2.60-2.65 (2H, m), 3.02-3.07 (2H, m), 6.64 (2H, d, J=8.0 Hz), 6.98-7.02 (4H, m), 7.13 (1H, t, J=8.0 Hz), 7.18-7.21 (4H, m).

Example 99

Preparation of the Compound 99

(1) Preparation of the Intermediate 99(1).

The title compound was obtained in the same manner as the Example 89(2) using the following starting materials.

Starting materials: the intermediate 95(3) and 4-(tert-butyl)phenylboronic acid; Yield: 94% (colorless oil).

$^1$H-NMR ($CDCl_3$) δ: 1.34 (9H, s), 6.93-6.97 (2H, m), 7.07-7.24 (4H, m), 7.36-7.50 (5H, m), 10.51 (1H, s).

(2) Preparation of the Compound 99.

The title compound was obtained in the same manner as the Example 2(3) using the following starting materials.

Starting materials: the intermediate 99(1) and malonic acid; Yield: 98% (ocherous solid).

$^1$H-NMR ($CDCl_3$) δ: 1.32 (9H, s), 6.49 (1H, d=16.1 Hz), 6.88-7.02 (6H, m), 7.18-7.21 (2H, m), 7.28-7.29 (1H, m), 7.35-7.38 (2H, m), 8.04 (1H, d, J=16.1 Hz).

Example 100

Preparation of the Compound 100

The title compound was obtained in the same manner as the Example 3 using the following starting material.

Starting material: the compound 99; Yield: 92% (yellow oil).

$^1$H-NMR ($CDCl_3$) δ: 1.31 (9H, s), 2.69 (2H, t, J=7.6 Hz), 2.94 (2H, t, J=7.6 Hz), 6.80-6.90 (4H, m), 6.95-6.99 (3H, m), 7.15-7.18 (2H, m), 7.31-7.34 (2H, m).

Example 101

Preparation of the Compound 101

(1) Preparation of the Intermediate 101(1).

The title compound was obtained in the same manner as the Example 2(1) using the following starting materials.

Starting materials: the intermediate 18(1) and 3-phenylpropyl bromide; Yield: 74.3% (yellow solid).

$^1$H-NMR ($CDCl_3$) δ: 2.18-2.27 (2H, m), 2.87 (2H, t, J=7.5 Hz), 4.14 (2H, t, J=6.3 Hz), 7.02 (1H, d, J=8.4 Hz), 7.20-7.34 (7H, m), 7.56-7.59 (2H, m), 7.72 (1H, dd, J=2.4, 8.4 Hz), 8.05 (1H, d, J=2.4 Hz), 10.53 (1H, s).

(2) Preparation of the Intermediate 101(2).

The title compound was obtained in the same manner as the Example 2(3) using the following starting materials.

Starting materials: the intermediate 101(1) and malonic acid; Yield: 62.8% (white solid).

$^1$H-NMR ($CDCl_3$) δ: 2.18-2.27 (2H, m), 2.88 (2H, t, J=7.5 Hz), 4.10 (2H, t, J=6.3 Hz), 6.68 (1H, d, J=16.2 Hz), 6.96 (1H, d, J=8.4 Hz), 7.19-7.33 (7H, m), 7.51-7.58 (3H, m), 7.72 (1H, d, J=2.1 Hz), 8.16 (1H, d, J=16.2 Hz).

(3) Preparation of the Compound 101.

The title compound was obtained in the same manner as the Example 3 using the following starting material.

Starting material: the intermediate 101(2); Yield: 79.7% (white solid).

$^1$H-NMR (DMSO-$d_6$) δ: 2.03-2.09 (2H, m), 2.57 (2H, t, J=7.8 Hz), 2.79 (2H, t, J=7.8 Hz), 2.89 (2H, t, J=7.8 Hz), 4.02 (2H, t, J=6.0 Hz), 7.01 (1H, d, J=9.3 Hz), 7.16-7.32 (5H, m), 7.39-7.42 (2H, m), 7.46-7.49 (2H, m), 7.70-7.73 (2H, m), 12.13 (1H, brs).

Example 102

Preparation of the Compound 102

(1) Preparation of the Intermediate 102(1).

The title compound was obtained in the same manner as the Example 2(1) using the following starting materials.

Starting materials: the intermediate 18(1) and 4-phenylbutyl bromide; Yield: 74.3% (yellow solid).

$^1$H-NMR ($CDCl_3$) δ: 1.82-1.94 (4H, m), 2.71-2.76 (2H, m), 4.12-4.18 (2H, m), 7.04 (1H, d, J=8.7 Hz), 7.19-7.30 (7H, m), 7.56-7.59 (2H, m), 7.73 (1H, dd, J=2.4, 8.7 Hz), 8.04 (1H, d, J=2.4 Hz), 10.54 (1H, s).

(2) Preparation of the Intermediate 102(2).

The title compound was obtained in the same manner as the Example 2(3) using the following starting materials.

Starting materials: the intermediate 102(1) and malonic acid; Yield: 82.9% (white solid).

$^1$H-NMR (DMSO-$d_6$) δ: 1.85-1.91 (4H, m), 2.73 (2H, t, J=7.2 Hz), 4.11 (2H, t, J=6.0 Hz), 6.64 (1H, d, J=16.2 Hz), 6.98 (1H, d, J=8.4 Hz), 7.19-7.33 (7H, m), 7.52-7.57 (3H, m), 7.71 (1H, d, J=2.1 Hz), 8.14 (1H, d, J=16.2 Hz).

(3) Preparation of the Compound 102.

The title compound was obtained in the same manner as the Example 3 using the following starting material.

Starting material: the intermediate 102(2); Yield: 57.8% (white solid).

$^1$H-NMR (DMSO-$d_6$) δ: 1.76-1.80 (4H, m), 2.53 (2H, t, J=7.8 Hz), 2.64-2.68 (2H, m), 2.85 (2H, t, J=7.8 Hz), 4.03-4.08 (2H, m), 7.03 (1H, d, J=9.0 Hz), 7.14-7.31 (5H, m), 7.38-7.42 (2H, m), 7.46-7.50 (2H, m), 7.68-7.73 (2H, m), 12.10 (1H, brs).

Example 103

Preparation of the Compound 103

(1) Preparation of the Intermediate 103(1).

The title compound was obtained in the same manner as the Example 2(1) using the following starting materials.

Starting materials: the intermediate 54(2) and 3-phenoxypropyl bromide; Yield: 100% (colorless oil).

$^1$H-NMR ($CDCl_3$) δ: 1.21 (3H, t, J=7.2 Hz), 2.27-2.36 (2H, m), 2.62 (2H, t, J=7.8 Hz), 3.00 (2H, t, J=7.5 Hz), 4.07-4.25 (6H, m), 6.88-6.98 (4H, m), 7.22-7.32 (4H, m), 7.34-7.39 (2H, m), 7.50-7.55 (2H, m).

(2) Preparation of the Compound 103.

The title compound was obtained in the same manner as the Example 12(4) using the following starting material.

Starting material: the intermediate 103(1); Yield: 58.5% (white solid).

$^1$H-NMR ($CDCl_3$) δ: 2.31 (2H, quintet, J=7.5 Hz), 2.69 (2H, t, J=7.5 Hz), 3.01 (2H, t, J=7.5 Hz), 4.19 (2H, t, J=6.0 Hz), 4.23 (2H, t, J=6.0 Hz), 6.90-6.97 (4H, m), 7.22-7.31 (4H, m), 7.36-7.40 (2H, m), 7.50-7.55 (2H, m).

Example 104

Preparation of the Compound 104

(1) Preparation of the Intermediate 104(1).

The title compound was obtained in the same manner as the Example 2(1) using the following starting materials.

Starting materials: the intermediate 18(1) and 5-phenylpentyl chloride; Yield: 100% (brown oil).

$^1$H-NMR ($CDCl_3$) δ: 1.52-1.58 (2H, m), 1.68-1.74 (2H, m), 1.88-1.94 (2H, m), 2.64-2.69 (2H, m), 4.10-4.14 (2H, m), 7.05 (1H, d, J=8.7 Hz), 7.16-7.21 (3H, m), 7.26-7.31 (4H, m), 7.56-7.59 (2H, m), 7.73 (1H, dd, J=2.7, 8.7 Hz), 8.04 (1H, d, J=2.7 Hz), 10.53 (1H, s).

(2) Preparation of the Intermediate 104(2).

The title compound was obtained in the same manner as the Example 2(3) using the following starting materials.

Starting materials: the intermediate 104(1) and malonic acid; Yield: 97.3% (white solid).

$^1$H-NMR ($CDCl_3$) δ: 1.51-1.61 (2H, m), 1.68-1.79 (2H, m), 1.88-1.97 (2H, m), 2.65-2.70 (2H, m), 4.07-4.11 (2H, m), 6.64 (1H, d, J=16.2 Hz), 6.98 (1H, d, J=8.7 Hz), 7.18-7.21 (2H, m), 7.25-7.31 (5H, m), 7.51-7.57 (3H, m), 7.71 (1H, d, J=2.4 Hz), 8.12 (1H, d, J=16.2 Hz).

(3) Preparation of the Compound 104.

The title compound was obtained in the same manner as the Example 3 using the following starting material.

Starting material: the intermediate 104(2); Yield: 40.2% (white solid).

$^1$H-NMR (DMSO-$d_6$) δ: 1.44-1.53 (2H, m), 1.60-1.70 (2H, m), 1.74-1.83 (2H, m), 2.49-2.51 (2H, m), 2.58-2.63 (2H, m), 2.81-2.86 (2H, m), 4.00-4.04 (2H, m), 7.01-7.04 (1H, m), 7.15-7.29 (5H, m), 7.39-7.41 (2H, m), 7.46-7.50 (2H, m), 7.69-7.72 (2H, m), 12.09 (1H, brs).

Example 105

Preparation of the Compound 105

(1) Preparation of the Intermediate 105(1).

The title compound was obtained in the same manner as the Example 95(2) using the following starting material.

Starting material: the intermediate 4(2); Yield: 95.0% (milky white solid).

$^1$H-NMR ($CDCl_3$) δ: 1.35 (9H, s), 5.12 (2H, s), 5.72 (1H, s), 6.99-7.04 (2H, m), 7.16-7.17 (1H, m), 7.23-7.26 (2H, m), 7.36-7.46 (4H, m), 7.52-7.56 (2H, m).

(2) Preparation of the Intermediate 105(2).

A mixture of the intermediate 105(1) (158 mg, 0.379 mmol), ethyl bromoacetate (75 mg, 0.451 mmol), potassium carbonate (210 mg, 1.517 mmol) and dimethylformamide (0.75 ml) was stirred at 50° C. for 2 hours. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=3:1) to give the title compound (185 mg, 97.2%) as a white solid.

$^1$H-NMR ($CDCl_3$) δ: 1.27 (3H, t, J=7.1 Hz), 1.33 (9H, s), 4.24 (2H, q, J=7.1 Hz), 4.75 (2H, s), 5.16 (2H, s), 7.00-7.03 (1H, m), 7.13-7.16 (2H, m), 7.23-7.26 (2H, m), 7.41 (4H, s), 7.49-7.52 (2H, m).

(3) Preparation of the Compound 105.

The title compound was obtained in the same manner as the Example 12(4) using the following starting material.

Starting material: the intermediate 105(2); Yield: 94.0% (white solid).

$^1$H-NMR ($CDCl_3$) δ: 1.33 (9H, m), 4.73 (2H, s), 5.16 (2H, s), 7.07-7.10 (1H, m), 7.19-7.28 (4H, m), 7.36-7.45 (4H, m), 7.50-7.53 (2H, m).

Example 106

Preparation of the Compound 106

(1) Preparation of the Intermediate 106(1).

The title compound was obtained in the same manner as the Example 105(2) using the following starting materials.

Starting materials: the intermediate 105(1) and ethyl 2-bromoisobutyrate; Yield: 100% (white solid).

$^1$H-NMR ($CDCl_3$) δ: 1.23 (3H, t, J=7.1 Hz), 1.33 (9H, s), 1.59 (6H, s), 4.16 (2H, q, J=7.1 Hz), 5.09 (2H, s), 6.98-7.01 (1H, m), 7.15-7.22 (4H, m), 7.37-7.43 (4H, m), 7.48-7.52 (2H, m).

(2) Preparation of the Compound 106.

The title compound was obtained in the same manner as the Example 12(4) using the following starting material.

Starting material: the intermediate 106(1); Yield: 99.0% (white solid).

$^1$H-NMR ($CDCl_3$) δ: 1.33 (9H, s), 1.57 (6H, s), 5.17 (2H, s), 7.08-7.11 (1H, m), 7.22-7.37 (6H, m), 7.41-7.44 (2H, m), 7.50-7.53 (2H, m).

Example 107

Preparation of the Compound 107

(1) Preparation of the Intermediate 107(1).

Sodium borohydride (35 mg, 0.934 mmol) was added to a solution of the intermediate 4(2) (400 mg, 0.934 mmol) in methanol (10 ml) at 0° C., and the mixture was stirred at room temperature for 1 hour. The reaction mixture was neutralized by addition of 2 N hydrochloric acid, and extracted with ethyl acetate. The organic layer was washed with water and saturated brine, and dried over anhydrous sodium sulfate. The residue was evaporated under reduced pressure to give the title compound (394 mg, 98%) as a white solid.

$^1$H-NMR ($CDCl_3$) δ: 1.34 (9H, s), 2.35 (1H, brs), 4.79 (2H, s), 5.14 (2H, s), 7.05 (1H, d, J=8.4 Hz), 7.23-7.29 (2H, m), 7.35-7.49 (5H, m), 7.51-7.59 (3H, m).

(2) Preparation of the Intermediate 107(2).

A solution of intermediate 107(2) (129 mg, 0.30 mmol) in tetrahydrofuran (1 ml) was added dropwise to a mixture of sodium hydride (26 mg, 0.60 mmol) and tetrahydrofuran (2 ml) at 0° C. under argon atmosphere, and the mixture was stirred at room temperature for 30 minutes. Methyl bromoacetate (46 mg, 0.30 mmol) was added to the mixture, and the mixture was stirred at 80° C. for 6 hours. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=6:1) to give the title compound (42 mg, 28.0%) as a colorless oil.

$^1$H-NMR ($CDCl_3$) δ: 1.34 (9H, s), 3.73 (3H, s), 4.19 (2H, s), 4.78 (2H, s), 5.10 (2H, s), 7.00-7.03 (1H, m), 7.24-7.27 (2H, m), 7.35-7.47 (5H, m), 7.55-7.58 (2H, m), 7.65-7.67 (1H, m).

(3) Preparation of the Compound 107.

The title compound was obtained in the same manner as the Example 12(4) using the following starting material.

Starting material: the intermediate 107(2); Yield: 58.9% (whitish-brown solid).

$^1$H-NMR (DMSO-$d_6$) δ: 1.28 (9H, s), 4.14 (2H, s), 4.66 (2H, s), 5.16 (2H, s), 7.18 (1H, d, J=8.7 Hz), 7.38-7.43 (6H, m), 7.58 (1H, dd, J=2.1, 8.7 Hz), 7.67 (1H, d, J=2.1 Hz), 7.70-7.74 (2H, m), 12.67 (1H, brs).

Example 108

Preparation of the Compound 108

(1) Preparation of the Intermediate 108(1).

Methylmagnesium bromide (0.96 M solution in tetrahydrofuran; 1.46 ml, 1.401 mmol) was added to a solution of the intermediate 4(2) (400 mg, 0.934 mmol) in tetrahydrofuran (10 ml) at 0° C. under argon atmosphere, and the mixture was stirred at room temperature for 1 hour. The reaction mixture was diluted with water, and extracted with ethyl acetate. The organic layer was washed with water and saturated brine, and dried over anhydrous sodium sulfate. The residue obtained by evaporation of the solvent under reduced pressure was washed with n-hexane to give the title compound (411 mg, 99%) as a white solid.

$^1$H-NMR ($CDCl_3$) δ: 1.34 (9H, s), 1.57 (3H, d, J=6.6 Hz), 2.59 (1H, brs), 5.13 (2H, s), 5.21 (1H, q, J=6.6 Hz), 7.04 (1H, d, J=8.4 Hz), 7.23-7.29 (2H, m), 7.34-7.47 (5H, m), 7.54-7.61 (3H, m).

(2) Preparation of the Intermediate 108(2).

The title compound was obtained in the same manner as the Example 107(2) using the following starting materials.

Starting materials: the intermediate 108(1) and methyl bromoacetate; Yield: 14.4% (colorless oil).

$^1$H-NMR ($CDCl_3$) δ: 1.34 (9H, s), 1.52-1.62 (3H, m), 3.70 (3H, s), 3.99-4.10 (2H, m), 5.09-5.13 (3H, m), 7.00-7.03 (1H, m), 7.24-7.29 (2H, m), 7.33-7.45 (5H, m), 7.52-7.60 (3H, m).

(3) Preparation of the Compound 108.

The title compound was obtained in the same manner as the Example 12(4) using the following starting material.

Starting material: the intermediate 108(2); Yield: 50.0% (whitish-brown solid).

$^1$H-NMR (DMSO-$d_6$) δ: 1.29 (9H, s), 1.39 (3H, d, J=6.6 Hz), 3.83 (1H, d, J=16.5 Hz), 3.98 (1H, d, J=16.5 Hz), 5.00 (1H, q, J=6.6 Hz), 5.16 (2H, s), 7.19 (1H, d, J=8.4 Hz), 7.36-7.44 (6H, m), 7.56 (1H, dd, J=2.7, 8.4 Hz), 7.63 (1H, d, J=2.7 Hz), 7.71-7.75 (2H, m), 12.60 (1H, brs).

Example 109

Preparation of the Compound 109

(1) Preparation of the Intermediate 109(1).

The title compound was obtained in the same manner as the Example 105(2) using the following starting materials.

Starting materials: the intermediate 105(1) and ethyl 4-bromobutyrate; Yield: 49% (pale yellow solid).

$^1$H-NMR ($CDCl_3$) δ: 1.25 (3H, t, J=7.1 Hz), 1.33 (9H, s), 2.13-2.22 (2H, m), 2.54-2.59 (2H, m), 4.10-4.17 (4H, m), 5.13 (2H, s), 6.98-7.11 (3H, m), 7.23-7.26 (2H, m), 7.40 (4H, s), 7.52-7.55 (2H, m).

(2) Preparation of the Compound 109.

The title compound was obtained in the same manner as the Example 12(4) using the following starting material.

Starting material: the intermediate 109(1); Yield: 88% (pale yellow solid).

$^1$H-NMR ($CDCl_3$) δ: 1.32 (9H, s), 2.15-2.21 (2H, m), 2.60-2.65 (2H, m), 4.13-4.17 (2H, m), 5.13 (2H, s), 6.98-7.11 (3H, m), 7.20-7.26 (2H, m), 7.34-7.40 (4H, m), 7.52-7.55 (2H, m).

Example 110

Preparation of the Compound 110

(1) Preparation of the Intermediate 110(1).

The title compound was obtained in the same manner as the Example 1(2) using the following starting materials.

Starting materials: the intermediate 79(1) and 4-(trifluoromethoxy)phenylboronic acid; Yield: 100% (pale yellow oil).

$^1$H-NMR ($CDCl_3$) δ: 1.34 (9H, s), 7.01-7.07 (2H, m), 7.08-7.10 (1H, m), 7.25-7.29 (2H, m), 7.34-7.39 (1H, m), 7.39-7.45 (2H, m), 7.50-7.55 (2H, m), 8.01 (1H, d, J=8.1 Hz), 10.53-10.54 (1H, m).

(2) Preparation of the Intermediate 110(2).

The title compound was obtained in the same manner as the Example 95(2) using the following starting material.

Starting material: the intermediate 110(1); Yield: 100% (white solid).

$^1$H-NMR ($CDCl_3$) δ: 1.33 (9H, s), 5.61 (1H, s), 6.96-7.02 (2H, m), 7.08-7.13 (2H, m), 7.18-7.26 (3H, m), 7.34-7.39 (2H, m), 7.43-7.49 (2H, m).

(3) Preparation of the Compound 110.

Sodium hydroxide (239 mg, 5.968 mmol) was added to a mixture of the intermediate 110(2) (300 mg, 0.746 mmol), 1,1,1-trichloro-2-methyl-2-propanol (chloretone, 256 mg, 1.491 mmol) and acetone (3 ml) at 0° C., and the mixture was refluxed for 4 hours. The reaction mixture was cooled to 0° C., diluted with water, acidified by addition of 2 N hydrochloric acid, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=1:1) to give the title compound (139 mg, 38.1%) as a pale yellow solid.

$^1$H-NMR ($CDCl_3$) δ: 1.32 (9H, s), 1.61 (6H, s), 6.92-6.98 (2H, m), 7.15-7.20 (2H, m), 7.22-7.28 (3H, m), 7.33-7.39 (2H, m), 7.46-7.51 (2H, m).

Example 111

Preparation of the Compound 111

(1) Preparation of the Intermediate 111(1).

The title compound was obtained in the same manner as the Example 107(1) using the following starting material.

Starting material: the intermediate 110(1); Yield: 92.5% (white solid).

$^1$H-NMR ($CDCl_3$) δ: 1.30 (9H, s), 2.11 (1H, brs), 4.79 (2H, s), 6.93-6.98 (2H, m), 7.06-7.08 (1H, m), 7.22-7.26 (2H, m), 7.31 (1H, dd, J=1.8, 7.8 Hz), 7.33-7.38 (2H, m), 7.47-7.54 (3H, m).

(2) Preparation of the Compound 111.

The title compound was obtained in the same manner as the Example 110(3) using the following starting materials.

Starting materials: the intermediate 111(1) and 1,1,1-trichloro-2-methyl-2-propanol (chloretone); Yield: 9.9% (colorless oil).

$^1$H-NMR ($CDCl_3$) δ: 1.32 (9H, s), 1.55 (6H, s), 4.63 (2H, s), 6.94-6.98 (2H, m), 7.08 (1H, d, J=2.1 Hz), 7.22-7.27 (2H, m), 7.31 (1H, dd, J=2.1, 8.1 Hz), 7.33-7.38 (2H, m), 7.47-7.53 (3H, m).

Example 112

Preparation of the Compound 112

(1) Preparation of the Intermediate 112(1).

The title compound was obtained in the same manner as the Example 105(2) using the following starting materials.

Starting materials: the intermediate 110(2) and ethyl bromoacetate; Yield: 100% (colorless oil).

$^1$H-NMR ($CDCl_3$) δ: 1.22-1.37 (12H, m), 4.23 (2H, q, J=7.2 Hz), 4.72 (2H, s), 6.92-6.98 (2H, m), 7.01-7.05 (1H, m), 7.18-7.29 (4H, m), 7.29-7.35 (2H, m), 7.45-7.51 (2H, m).

(2) Preparation of the Compound 112.

The title compound was obtained in the same manner as the Example 12(4) using the following starting material.

Starting material: the intermediate 112(1); Yield: 72.6% (white solid).

$^1$H-NMR (DMSO-$d_6$) δ: 1.26 (9H, s), 4.77 (2H, s), 6.84-6.92 (2H, m), 7.14 (1H, d, J=8.7 Hz), 7.29-7.43 (5H, m), 7.49 (1H, dd, J=2.4, 8.7 Hz), 7.68-7.77 (2H, m), 13.05 (1H, s).

Example 113

Preparation of the Compound 113

(1) Preparation of the Intermediate 113(1).

A mixture of 2-chloro-6-fluorobenzaldehyde (634 mg, 4.00 mmol), 4-(trifluoromethoxy)phenylboronic acid (1.23 g, 6.00 mmol), palladium(II) acetate (9 mg, 0.04 mmol), 2-(di-tert-butylphosphino)biphenyl (23 mg, 0.08 mmol), potassium fluoride (697 mg, 12.00 mmol) and tetrahydrofuran (5 ml) was stirred at 80° C. for 5 hours. The reaction mixture was cooled to room temperature, and the solvent was evaporated under reduced pressure. The residue was diluted with ethyl acetate, and filtered through Celite. The residue obtained by concentration of the filtrate under reduced pressure was purified by column chromatography on silica gel (n-hexane:ethyl acetate=6:1) to give the title compound (893 mg, 79.0%) as a yellow oil.

$^1$H-NMR ($CDCl_3$) δ: 7.18-7.25 (2H, m), 7.29-7.32 (2H, m), 7.35-7.38 (2H, m), 7.56-7.64 (1H, m), 10.04 (1H, s).

(2) Preparation of the Intermediate 113(2).

The title compound was obtained in the same manner as the Example 12(2) using the following starting materials.

Starting materials: the intermediate 113(1) and 4-(tert-butyl)phenol; Yield: 73.5% (white solid).

$^1$H-NMR ($CDCl_3$) δ: 1.34 (9H, s), 6.94 (1H, dd, J=0.9, 8.4 Hz), 7.00-7.04 (3H, m), 7.24-7.28 (2H, m), 7.34-7.38 (2H, m), 7.39-7.42 (2H, m), 7.44-7.49 (1H, m), 10.34 (1H, s).

(3) Preparation of the Intermediate 113(3).

The title compound was obtained in the same manner as the Example 95(2) using the following starting material.

Starting material: the intermediate 113(2); Yield: 91.8% (white solid).

$^1$H-NMR ($CDCl_3$) δ: 1.33 (9H, s), 6.87-6.89 (2H, m), 7.00-7.03 (2H, m), 7.06-7.10 (1H, m), 7.27-7.30 (2H, m), 7.37-7.40 (2H, m), 7.66-7.69 (2H, m).

(4) Preparation of the Intermediate 113(4).

The title compound was obtained in the same manner as the Example 105(2) using the following starting materials.

Starting materials: the intermediate 113(3) and ethyl bromoacetate; Yield: 100.0% (yellow oil).

$^1$H-NMR ($CDCl_3$) δ: 1.11 (3H, t, J=7.2 Hz), 1.32 (9H, s), 4.03 (2H, q, J=7.2 Hz), 4.50 (2H, s), 6.92-6.97 (3H, m), 7.08-7.10 (2H, m), 7.25-7.28 (2H, m), 7.34-7.36 (2H, m), 7.62-7.65 (2H, m).

(5) Preparation of the Compound 113.

The title compound was obtained in the same manner as the Example 12(4) using the following starting material.

Starting material: the intermediate 113(4); Yield: 81.9% (white solid).

$^1$H-NMR (DMSO-$d_6$) δ: 1.28 (9H, s), 4.50 (2H, s), 6.93-6.97 (3H, m), 7.15-7.17 (2H, m), 7.39-7.43 (4H, m), 7.65-7.70 (2H, m), 12.70 (1H, brs).

Example 114

Preparation of the Compound 114

(1) Preparation of the Intermediate 114(1).

The title compound was obtained in the same manner as the Example 105(2) using the following starting materials.

Starting materials: the intermediate 110(2) and ethyl 2-bromobutyrate; Yield: 100% (pale yellow oil).

$^1$H-NMR ($CDCl_3$) δ: 1.03 (3H, t, J=7.5 Hz), 1.20-1.33 (12H, m), 1.82-1.95 (2H, m), 4.10-4.26 (2H, m), 4.93 (1H, t, J=6.0 Hz), 6.90-6.95 (2H, m), 6.98 (1H, d, J=8.1 Hz), 7.20-7.26 (4H, m), 7.27-7.32 (2H, m), 7.46-7.51 (2H, m).

(2) Preparation of the Compound 114.

The title compound was obtained in the same manner as the Example 12(4) using the following starting material.

Starting material: the intermediate 114(1); Yield: 19.5% (white solid).

$^1$H-NMR ($CDCl_3$) δ: 0.99 (3H, t, J=7.5 Hz), 1.31 (9H, s), 1.95-2.04 (2H, m), 4.69 (1H, t, J=5.7 Hz), 6.95 (2H, d, J=8.4 Hz), 7.08 (1H, d, J=8.1 Hz), 7.18-7.29 (4H, m), 7.31-7.37 (2H, m), 7.48 (2H, d, J=8.7 Hz).

Example 115

Preparation of the Compound 115

(1) Preparation of the Intermediate 115(1).

The title compound was obtained in the same manner as the Example 95(2) using the following starting material.

Starting material: the intermediate 102(1); Yield: 87.7% (colorless oil).

$^1$H-NMR ($CDCl_3$) δ: 1.77-2.04 (4H, m), 2.69-2.74 (2H, m), 4.05-4.13 (2H, m), 5.65 (1H, brs), 6.88 (1H, d, J=8.1 Hz), 7.02 (1H, dd, J=2.1, 8.1 Hz), 7.15 (1H, d, J=2.1 Hz), 7.19-7.33 (7H, m), 7.52-7.55 (2H, m).

(2) Preparation of the Intermediate 115(2).

The title compound was obtained in the same manner as the Example 105(2) using the following starting materials.

Starting materials: the intermediate 115(1) and ethyl bromoacetate; Yield: 97.1% (white solid).

$^1$H-NMR ($CDCl_3$) δ: 1.28 (3H, t, J=7.2 Hz), 1.82-1.90 (4H, m), 2.69-2.74 (2H, m), 4.05-4.09 (2H, m), 4.25 (2H, q, J=7.2 Hz), 4.71 (2H, s), 6.95 (1H, d, J=8.1 Hz), 7.11-7.32 (9H, m), 7.50-7.53 (2H, m).

(3) Preparation of the Compound 115.

The title compound was obtained in the same manner as the Example 12(4) using the following starting material.

Starting material: the intermediate 115(2); Yield: 78.7% (white solid).

$^1$H-NMR (DMSO-$d_6$) δ: 1.73-1.76 (4H, m), 2.64-2.69 (2H, m), 4.01-4.08 (2H, m), 4.72 (2H, s), 7.06 (1H, d, J=8.4 Hz), 7.14-7.30 (7H, m), 7.39-7.42 (2H, m), 7.70-7.73 (2H, m), 12.93 (1H, brs).

Example 116

Preparation of the Compound 116

(1) Preparation of the Intermediate 116(1).

The title compound was obtained in the same manner as the Example 105(2) using the following starting materials.

Starting materials: the intermediate 115(1) and ethyl 2-bromoisobutyrate; Yield: 59.3% (yellow oil).

$^1$H-NMR ($CDCl_3$) δ: 1.26 (3H, t, J=7.2 Hz), 1.56 (6H, s), 1.81-1.88 (4H, m), 2.70-2.76 (2H, m), 4.00-4.07 (2H, m), 4.23 (2H, q, J=7.2 Hz), 7.14-7.29 (8H, m), 7.48-7.51 (2H, m), 7.52-7.55 (2H, m).

(2) Preparation of the Compound 116.

The title compound was obtained in the same manner as the Example 12(4) using the following starting material.

Starting material: the intermediate 116(1); Yield: 26.5% (brown solid).

$^1$H-NMR (DMSO-$d_6$) δ: 1.38 (6H, s), 1.72-1.79 (4H, m), 2.67 (2H, t, J=6.9 Hz), 3.96 (2H, t, J=6.9 Hz), 6.92 (1H, d, J=8.1 Hz), 7.01 (1H, dd, J=2.1, 8.1 Hz), 7.15-7.31 (5H, m), 7.34 (1H, d, J=2.1 Hz), 7.37-7.40 (2H, m), 7.56-7.59 (2H, m).

Example 117

Preparation of the Compound 117

(1) Preparation of the Intermediate 117(1).

The title compound was obtained in the same manner as the Example 1(2) using the following starting materials.

Starting materials: the intermediate 87(1) and 4-(trifluoromethoxy)phenylboronic acid; Yield: 73.0% (brown oil).

$^1$H-NMR ($CDCl_3$) δ: 7.10-7.15 (1H, m), 7.25-7.31 (2H, m), 7.58-7.64 (4H, m), 9.96 (1H, s), 11.59 (1H, s).

(2) Preparation of the Intermediate 117(2).

The title compound was obtained in the same manner as the Example 2(1) using the following starting materials.

Starting materials: the intermediate 117(1) and 4-(tert-butyl)benzyl bromide; Yield: 100.0% (yellow solid).

$^1$H-NMR ($CDCl_3$) δ: 1.30 (9H, s), 4.54 (2H, s), 6.93-7.01 (2H, m), 7.24-7.36 (5H, m), 7.59-7.63 (3H, m), 7.87 (1H, dd, J=2.1, 7.5 Hz), 10.39 (1H, s).

(3) Preparation of the Intermediate 117(3).

The title compound was obtained in the same manner as the Example 95(2) using the following starting material.

Starting material: the intermediate 117(2); Yield: 95.7% (yellow oil).

$^1$H-NMR ($CDCl_3$) δ: 1.30 (9H, s), 4.43 (2H, s), 6.88 (1H, dd, J=2.1, 7.8 Hz), 6.98 (1H, dd, J=2.1, 7.8 Hz), 7.04-7.12 (3H, m), 7.28-7.35 (4H, m), 7.63-7.66 (2H, m).

(4) Preparation of the Intermediate 117(4).

The title compound was obtained in the same manner as the Example 105(2) using the following starting materials.

Starting materials: the intermediate 117(3) and ethyl bromoacetate; Yield: 74.4% (colorless oil).

$^1$H-NMR ($CDCl_3$) δ: 1.26-1.33 (12H, m), 4.29 (2H, q, J=7.2 Hz), 4.74 (2H, s), 4.79 (2H, s), 6.90 (1H, dd, J=1.8, 7.8 Hz), 6.93-7.00 (3H, m), 7.07-7.12 (1H, m), 7.17-7.23 (4H, m), 7.44-7.46 (2H, m).

(5) Preparation of the Compound 117.

The title compound was obtained in the same manner as the Example 12(4) using the following starting material.

Starting material: the intermediate 117(4); Yield: 87.7% (white solid).

$^1$H-NMR (DMSO-$d_6$) δ: 1.27 (9H, s), 4.80 (2H, s), 4.83 (2H, s), 6.92 (1H, dd, J=1.5, 7.8 Hz), 6.95-6.98 (2H, m), 7.03 (1H, dd, J=1.5, 7.8 Hz), 7.10-7.14 (1H, m), 7.18-7.20 (2H, m), 7.33-7.36 (2H, m), 7.46-7.49 (2H, m), 13.90 (1H, brs).

Example 118

Preparation of the Compound 118

(1) Preparation of the Intermediate 118(1).

The title compound was obtained in the same manner as the Example 105(2) using the following starting materials.

Starting materials: the intermediate 117(3) and ethyl 2-bromoisobutyrate; Yield: 44.9% (yellow oil).

$^1$H-NMR ($CDCl_3$) δ: 1.25-1.33 (12H, m), 1.67 (6H, s), 4.26 (2H, q, J=7.2 Hz), 4.73 (2H, s), 6.88 (1H, dd, J=1.8, 7.8 Hz), 6.92-6.99 (3H, m), 7.00-7.12 (1H, m), 7.16-7.24 (4H, m), 7.44-7.46 (2H, m).

(2) Preparation of the Compound 118.

The title compound was obtained in the same manner as the Example 12(4) using the following starting material.

Starting material: the intermediate 118(1); Yield: 12.3% (yellow solid).

$^1$H-NMR ($CDCl_3$) δ: 1.28 (9H, s), 1.65 (6H, s), 4.61 (2H, s), 6.88-6.92 (2H, m), 7.03-7.16 (3H, m), 7.22-7.26 (4H, m), 7.49-7.52 (2H, m).

Example 119

Preparation of the Compound 119

(1) Preparation of the Intermediate 119(1).

The title compound was obtained in the same manner as the Example 105(2) using the following starting materials.

Starting materials: the intermediate 110(2) and ethyl bromofluoroacetate; Yield: 98.0% (colorless oil).

$^1$H-NMR ($CDCl_3$) δ: 1.22-1.28 (3H, m), 1.31 (9H, s), 4.25 (2H, q, J=7.2 Hz), 5.98 (1H, d, J=59.1 Hz), 6.92-6.96 (2H, m), 7.20-7.37 (7H, m), 7.46-7.51 (2H, m).

(2) Preparation of the Compound 119.

The title compound was obtained in the same manner as the Example 12(4) using the following starting material.

Starting material: the intermediate 119(1); Yield: 90.7% (yellow oil).

$^1$H-NMR (DMSO-$d_6$) δ: 1.26 (9H, s), 6.36 (1H, d, J=59.1 Hz), 6.90-6.93 (2H, m), 7.35-7.47 (6H, m), 7.54 (1H, dd, J=1.8, 8.4 Hz), 7.71-7.74 (2H, m), 14.09 (1H, brs).

Example 120

Preparation of the Compound 120

Sodium hydride (65 mg, 1.490 mmol) was added to a mixture of the intermediate 110(2) (300 mg, 0.745 mmol), chlorodifluoroacetic acid (117 mg, 0.894 mmol) and dioxane (10 ml) at 0° C., and the mixture was refluxed for 10 hours. The reaction mixture was cooled to room temperature, diluted with water, acidified by addition of 2 N hydrochloric acid, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=1:1) to give the title compound (95 mg, 25.7%) as a white solid.

$^1$H-NMR (DMSO-$d_6$) δ: 1.27 (9H, s), 6.91-6.95 (2H, m), 7.26 (1H, d, J=1.5 Hz), 7.34-7.46 (6H, m), 7.69-7.71 (2H, m).

Example 121

Preparation of the Compound 121

(1) Preparation of the Intermediate 121(1).

A mixture of lithium hydroxide (101 mg, 2.40 mmol), diethyl cyanomethylphosphonate (390 mg, 2.20 mmol) and tetrahydrofuran (20 ml) was stirred at 70° C. for 30 minutes under argon atmosphere. After the reaction mixture was cooled to room temperature, the intermediate 4(2) (857 mg, 2.00 mmol) was added, and the mixture was stirred at room temperature for 4 hours. 1 N Hydrochloric acid was added to the reaction mixture, and the mixture was extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=10:1) to give the title compound (631 mg, 70.0%) as a colorless oil.

This compound was obtained as a mixture of the rotational isomers.

Major isomer (E form): $^1$H-NMR ($CDCl_3$) δ: 1.35 (9H, s), 5.14 (2H, s), 6.13 (1H, d, J=16.8 Hz), 7.07-7.76 (12H, m).

Minor isomer (Z form): $^1$H-NMR ($CDCl_3$) δ: 1.34 (9H, s), 5.12 (2H, s), 5.46 (1H, d, J=12.0 Hz), 7.06-7.75 (11H, m), 8.34 (1H, d, J=2.4 Hz).

(2) Preparation of the Intermediate 121(2).

The title compound was obtained in the same manner as the Example 3 using the following starting material.

Starting material: the intermediate 121(1); Yield: 46% (white solid).

$^1$H-NMR ($CDCl_3$) δ: 2.72 (2H, t, J=7.5 Hz), 3.03 (2H, t, J=7.5 Hz), 5.23 (1H, s), 6.82 (1H, d, J=8.1 Hz), 7.22-7.28 (2H, m), 7.32 (1H, dd, J=2.1, 8.1 Hz), 7.36 (1H, d, J=2.1 Hz), 7.50-7.55 (2H, m).

(3) Preparation of the Intermediate 121(3).

The title compound was obtained in the same manner as the Example 2(1) using the following starting materials.

Starting materials: the intermediate 121(2) and 4-(tert-butyl)benzyl bromide; Yield: 98% (colorless oil).

$^1$H-NMR ($CDCl_3$) δ: 1.35 (9H, s), 2.68 (2H, t, J=7.2 Hz), 3.06 (2H, t, J=7.2 Hz), 5.10 (2H, s), 7.03 (1H, d, J=8.4 Hz), 7.24-7.28 (2H, m), 7.33-7.38 (2H, m), 7.39-7.46 (4H, m), 7.52-7.57 (2H, m).

(4) Preparation of the Compound 121.

A mixture of the intermediate 121(3) (227 mg, 0.5 mmol), sodium azide (98 mg, 1.5 mmol), triethylamine hydrochloride (103 mg, 0.75 mol) and 1-methyl-2-pyrrolidone (5 mL) was stirred at 150° C. for 4 hours under argon atmosphere. The reaction mixture was cooled to room temperature, diluted with water and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=1:1) to give the title compound (45 mg, 18%) as a white solid.

$^1$H-NMR (DMSO-$d_6$) δ: 1.29 (9H, s), 3.10-3.27 (4H, m), 5.16 (2H, s), 7.15 (1H, d, J=8.7 Hz), 7.39-7.45 (6H, m), 7.44 (1H, d, J=2.4 Hz), 7.50 (1H, dd, J=2.4, 8.7 Hz), 7.65-7.70 (2H, m).

Example 122

Preparation of the Compound 122

(1) Preparation of the Intermediate 122(1).

A mixture of the intermediate 105(1) (110 mg, 0.264 mmol), bromoacetonitrile (34 mg, 0.291 mmol), cesium carbonate (95 mg, 0.291 mmol) and acetone (2 ml) was stirred at room temperature for 2 hours. Water was added to the residue obtained by evaporation of the solvent under reduced pressure, and the residue was extracted with ethyl acetate. The organic layer was washed with saturated brine, and dried over anhydrous sodium sulfate. The residue obtained by evaporation of the solvent under reduced pressure was washed with n-hexane to give the title compound (90 mg, 74.8%) as a white solid.

$^1$H-NMR ($CDCl_3$) δ: 1.34 (9H, s), 4.88 (2H, s), 5.14 (2H, s), 7.09 (1H, d, J=7.8 Hz), 7.25-7.30 (4H, m), 7.36-7.45 (4H, m), 7.51-7.57 (2H, m).

(2) Preparation of the Compound 122.

The title compound was obtained in the same manner as the Example 121(4) using the following starting material.

Starting material: the intermediate 122(1); Yield: 81.9% (white solid).

$^1$H-NMR (DMSO-$d_6$) δ: 1.27 (9H, s), 5.13 (2H, s), 5.59 (2H, s), 7.15-7.20 (1H, m), 7.26-7.31 (1H, m), 7.34-7.47 (7H, m), 7.72-7.77 (2H, m).

Example 123

Preparation of the Compound 123

(1) Preparation of the Intermediate 123(1).

A mixture of 3,5-dimethylbenzyl bromide (1.59 g, 7.986 mmol), 4-bromoaniline (1.374 g, 7.986 mmol), potassium carbonate (5.519 g, 39.93 mmol) and N,N-dimethylformamide (6.5 ml) was stirred at 80° C. for 2 hours under argon atmosphere. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=15) to give the title compound (2.106 g, 57.2%) as a pale yellow oil.

$^1$H-NMR ($CDCl_3$) δ: 2.30 (6H, s), 4.00 (1H, brs), 4.20 (2H, s), 6.47-6.53 (2H, m), 6.90-6.98 (3H, m), 7.21-7.26 (2H, m).

(2) Preparation of the Intermediate 123(2).

Methyl chloroglyoxylate (0.566 ml, 6.16 mmol) was added dropwise to a mixture of the intermediate 123(1) (1.49 g, 5.13 mmol), triethylamine (1.08 ml, 7.70 mmol) and dichloromethane (20 ml) at 0° C., and the mixture was stirred at room temperature for 1 hour. The reaction mixture was diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=3:1) to give the title compound (1.66 g, 86%) as a pale yellow oil.

$^1$H-NMR ($CDCl_3$) δ: 2.26 (6H, s), 3.59 (3H, s), 4.84 (2H, s), 6.80 (2H, s), 6.90 (1H, s), 6.70-6.92 (2H, m), 7.40-7.46 (2H, m).

(3) Preparation of the Intermediate 123(3).

A mixture of the intermediate 123(2) (707 mg, 1.88 mmol), 4-(trifluoromethoxy)phenylboronic acid (500 mg, 2.44 mmol), [1,1'-bis(diphenylphosphino)ferrocene]dichloropalladium(II) (300 mg, 0.357 mmol), potassium carbonate (389 mg, 2.82 mmol), dioxane (10 ml) and water (1 ml) was stirred at 80° C. for 4 hours. The reaction mixture was cooled to room temperature, and filtered through Celite. The residue obtained by concentration of the filtrate under reduced pressure was purified by column chromatography on silica gel (n-hexane: ethyl acetate=10:1) to give the title compound (630 mg, 73%) as a pale brown oil.

$^1$H-NMR ($CDCl_3$) δ: 2.26 (6H, s), 3.59 (3H, s), 4.90 (2H, s), 6.85 (2H, s), 6.91 (1H, s), 7.12-7.17 (2H, m), 7.25-7.31 (2H, m), 7.46-7.52 (2H, m), 7.53-7.59 (2H, m).

(4) Preparation of the Compound 123.

A mixture of the intermediate 123(3) (200 mg, 0.437 mmol), a 2 N aqueous solution of sodium hydroxide (2 ml) and water (1 ml) was irradiated with ultrasound for 5 minutes. The reaction mixture was diluted with water, and extracted with ethyl acetate. The organic layer was washed with saturated brine, and dried over anhydrous sodium sulfate. The solvent was evaporated under reduced pressure to give the title compound (130 mg, 66%) as a white solid.

$^1$H-NMR (DMSO-$d_6$) δ: 2.20 (6H, s), 4.87 (2H, s), 6.78-7.00 (3H, m), 7.30-7.37 (2H, m), 7.39-7.45 (2H, m), 7.51-7.59 (2H, m), 7.70-7.77 (2H, m).

Example 124

Preparation of the Compound 124

(1) Preparation of the Intermediate 124(1).

The title compound was obtained in the same manner as the Example 123(1) using the following starting materials.

Starting materials: 4-chlorobenzyl chloride and 4-bromoaniline; Yield: 21% (white solid).

$^1$H-NMR ($CDCl_3$) δ: 4.10 (1H, brs), 4.25-4.31 (2H, m), 6.44-6.51 (2H, m), 7.20-7.34 (6H, m).

(2) Preparation of the Intermediate 124(2).

The title compound was obtained in the same manner as the Example 123(2) using the following starting materials.

Starting materials: the intermediate 124(1) and methyl chloroglyoxylate; Yield: 96% (colorless oil).

$^1$H-NMR ($CDCl_3$) δ: 3.59 (3H, s), 4.88 (2H, s), 6.88-6.94 (2H, m), 7.12-7.17 (2H, m), 7.24-7.30 (2H, m), 7.42-7.48 (2H, m).

(3) Preparation of the Intermediate 124(3).

The title compound was obtained in the same manner as the Example 123(3) using the following starting materials.

Starting materials: the intermediate 124(2) and 4-(trifluoromethoxy)phenylboronic acid; Yield: 28% (pale brown oil).

$^1$H-NMR ($CDCl_3$) δ: 3.59 (3H, s), 4.94 (2H, s), 7.09-7.22 (4H, m), 7.24-7.32 (4H, m), 7.47-7.59 (4H, m).

(4) Preparation of the Compound 124.

The title compound was obtained in the same manner as the Example 123(4) using the following starting material.

Starting material: the intermediate 124(3); Yield: 93% (white solid).

$^1$H-NMR (DMSO-$d_6$) δ: 4.91 (2H, s), 7.20-7.38 (6H, m), 7.38-7.48 (2H, m), 7.52-7.63 (2H, m), 7.71-7.82 (2H, m).

Example 125

Preparation of the Compound 125

(1) Preparation of the Intermediate 125(1).

The title compound was obtained in the same manner as the Example 123(3) using the following starting materials.

Starting materials: 4-bromonitrobenzene and 4-(trifluoromethoxy)phenylboronic acid; Yield: 98% (white solid).

$^1$H-NMR ($CDCl_3$) δ: 7.32-7.38 (2H, m), 7.62-7.68 (2H, m), 7.69-7.75 (2H, m), 8.29-8.35 (2H, m).

(2) Preparation of the Intermediate 125(2).

A mixture of the intermediate 125(1) (6.41 g, 22.6 mmol), 10% platinum on activated carbon (150 mg) and methanol (50 ml) was stirred for 16 hours under hydrogen atmosphere. The reaction mixture was filtered through Celite. The filtrate was concentrated under reduced pressure to give the title compound (5.48 g, 96%) as a white solid.

$^1$H-NMR ($CDCl_3$) δ: 3.75 (2H, brs), 6.73-6.78 (2H, m), 7.23 (2H, d, J=8.4 Hz), 7.35-7.40 (2H, m), 7.50-7.55 (2H, m).

(3) Preparation of the Intermediate 125(3).

A solution of methyl chloroglyoxylate (2.98 ml, 32.4 mmol) in dichloromethane (10 ml) was added dropwise at a slow speed to a mixture of the intermediate 125(2) (5.476 g, 21.6 mmol), sodium hydrogen carbonate (3.62 g, 43.2 mmol), dichloromethane (40 ml) and water (40 ml), and stirred at 0° C. for 2 hours. The reaction mixture was diluted with water, and extracted with ethyl acetate. The organic layer was washed with saturated brine, and dried over anhydrous sodium sulfate. The solvent was evaporated under reduced pressure to give the title compound (6.71 g, 91.5%) as a white solid.

$^1$H-NMR (DMSO-$d_6$) δ: 3.87 (3H, s), 7.41-7.48 (2H, m), 7.67-7.73 (2H, m), 7.76-7.82 (2H, m), 7.84-7.91 (2H, m), 10.94 (1H, s).

(4) Preparation of the Intermediate 125(4).

A mixture of the intermediate 125(3) (250 mg, 0.737 mmol), 3-methylbenzyl bromide (0.299 ml, 2.21 mmol), potassium carbonate (306 mg, 2.21 mmol), 18-crown-6 (20 mg, 0.074 mmol) and acetonitrile (10 ml) was stirred at 50° C. for 3 hours under argon atmosphere. The reaction mixture was cooled to room temperature, diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=2:1) to give the title compound (320 mg, 98%) as a colorless oil.

$^1$H-NMR ($CDCl_3$) δ: 2.32 (3H, s), 3.59 (3H, s), 4.95 (2H, s), 7.02-7.32 (8H, m), 7.46-7.52 (2H, m), 7.52-7.59 (2H, m).

(5) Preparation of the Compound 125.

The title compound was obtained in the same manner as the Example 123(4) using the following starting material.

Starting material: the intermediate 125(4); Yield: 93% (white solid).

$^1$H-NMR (DMSO-$d_6$) δ: 2.25 (3H, s), 4.92 (2H, s), 6.95-7.23 (4H, m), 7.30-7.38 (2H, m), 7.39-7.44 (2H, m), 7.52-7.60 (2H, m), 7.70-7.77 (2H, m).

Example 126

Preparation of the Compound 126

(1) Preparation of the Intermediate 126(1).

The title compound was obtained in the same manner as the Example 123(2) using the following starting materials.

Starting materials: 4-bromoaniline and methyl chloroglyoxylate; Yield: 68.9% (white solid).

$^1$H-NMR ($CDCl_3$) δ: 3.98 (3H, s), 7.47-7.57 (4H, m), 8.85 (1H, brs).

(2) Preparation of the Intermediate 126(2).

The title compound was obtained in the same manner as the Example 125(4) using the following starting materials.

Starting materials: the intermediate 126(1) and 4-(tert-butyl)benzyl bromide; Yield: 99.0% (colorless oil).

$^1$H-NMR ($CDCl_3$) δ: 1.28 (9H, s), 3.58 (3H, s), 4.88 (2H, s), 6.93 (2H, d, J=8.1 Hz), 7.12 (2H, d, J=8.1 Hz), 7.30 (2H, d, J=8.1 Hz), 7.43 (2H, d, J=8.1 Hz).

(3) Preparation of the Intermediate 126(3).

The title compound was obtained in the same manner as the Example 123(3) using the following starting materials.

Starting materials: the intermediate 126(2) and 4-methoxyphenylboronic acid; Yield: 100% (colorless oil).

$^1$H-NMR ($CDCl_3$) δ: 1.32 (9H, m), 3.57 (3H, s), 3.84 (3H, s), 4.93 (2H, s), 6.96 (2H, d, J=9.0 Hz), 7.01 (2H, d, J=8.4 Hz), 7.18 (2H, d, J=8.7 Hz), 7.31 (2H, d, J=8.4 Hz), 7.46-7.52 (4H, m).

(4) Preparation of the Compound 126.

A mixture of the intermediate 126(3) (230 mg, 0.533 mmol), methanol (1.5 ml), a 2 N aqueous solution of sodium hydroxide (0.8 ml) and tetrahydrofuran (1.5 ml) was stirred at room temperature for 10 minutes. The reaction mixture was adjusted to pH 5-6 by addition of 2 N hydrochloric acid, and extracted with ethyl acetate. The organic layer was washed with saturated brine, and dried over anhydrous sodium sulfate. The solvent was evaporated under reduced pressure to give the title compound (160 mg, 71.9%) as a white solid.

$^1$H-NMR (DMSO-$d_6$) δ: 1.25 (9H, s), 3.79 (3H, s), 4.93 (2H, s), 7.01 (2H, d, J=8.7 Hz), 7.16 (2H, d, J=8.4 Hz), 7.27 (2H, d, J=8.7 Hz), 7.35 (2H, d, J=8.4 Hz), 7.59-7.65 (4H, m).

Example 127

Preparation of the Compound 127

(1) Preparation of the Intermediate 127(1).

The title compound was obtained in the same manner as the Example 123(3) using the following starting materials.

Starting materials: the intermediate 126(2) and 4-fluorophenylboronic acid. Yield: 100% (colorless oil).

$^1$H-NMR ($CDCl_3$) δ: 1.30 (9H, s), 3.58 (3H, s), 4.94 (2H, s), 7.09-7.19 (6H, m), 7.31 (2H, d, J=7.8 Hz), 7.47-7.54 (4H, m).

(2) Preparation of the Compound 127.

The title compound was obtained in the same manner as the Example 126(4) using the following starting material.

Starting material: the intermediate 127(1); Yield: 71.6% (white solid).

$^1$H-NMR (DMSO-$d_6$) δ: 1.25 (9H, s), 4.95 (2H, s), 7.16 (2H, d, J=8.4 Hz), 7.25-7.36 (6H, m), 7.66-7.73 (4H, m).

Example 128

Preparation of the Compound 128

(1) Preparation of the Intermediate 128(1).

A mixture of the intermediate 125(2) (112 mg, 0.442 mmol), 4-(tert-butyl)phenylboronic acid (87 mg, 0.486 mmol), copper(II) acetate (40 mg, 0.221 mmol), triethylamine (0.061 ml, 0.884 mmol) and pyridine (3.0 ml) was stirred at 50° C. for 2 hours. The reaction mixture was cooled to room temperature and filtered through Celite. The filtrate was diluted with 1 N hydrochloric acid (10 ml), and extracted with ethyl acetate. The organic layer was dried over anhydrous sodium sulfate. The residue obtained by evaporation of the solvent under reduced pressure was purified by column chromatography on silica gel (n-hexane:ethyl acetate=1:1) to give the title compound (50 mg, 29%) as a pale yellow solid.

$^1$H-NMR ($CDCl_3$) δ: 1.32 (9H, s), 5.73 (1H, s), 7.05-7.12 (4H, m), 7.22-7.27 (2H, m), 7.29-7.36 (2H, m), 7.41-7.47 (2H, m), 7.52-7.58 (2H, m).

(2) Preparation of the Intermediate 128(2).

The title compound was obtained in the same manner as the Example 123(2) using the following starting materials.

Starting materials: the intermediate 128(1) and methyl chloroglyoxylate; Yield: 88% (pale yellow oil).

This compound was obtained as a mixture of the rotational isomers (3:2).

Major isomer: $^1$H-NMR ($CDCl_3$) δ: 1.33 (9H, s), 3.60 (3H, s), 7.20-7.46 (8H, m), 7.51-7.62 (4H, m).

Minor isomer: $^1$H-NMR ($CDCl_3$) δ: 1.31 (9H, s), 3.65 (3H, s), 7.20-7.46 (8H, m), 7.51-7.62 (4H, m).

(3) Preparation of the Compound 128.

The title compound was obtained in the same manner as the Example 126(4) using the following starting material.

Starting material: the intermediate 128(2); Yield: 96% (pale brown solid).

This compound was obtained as a mixture of the rotational isomers.

$^1$H-NMR (DMSO-$d_6$) δ: 1.25-1.31 (9H, m), 7.06-7.55 (8H, m), 7.66-7.86 (4H, m).

Example 129

Preparation of the Compound 129

(1) Preparation of the Intermediate 129(1).

The title compound was obtained in the same manner as the Example 125(4) using the following starting materials.

Starting materials: the intermediate 125(3) and 4-(tert-butyl)benzyl bromide; Yield: 100% (colorless oil).

$^1$H-NMR ($CDCl_3$) δ: 1.30 (9H, s), 3.58 (3H, s), 4.95 (2H, s), 7.14-7.20 (4H, m), 7.25-7.34 (4H, m), 7.48-7.59 (4H, m).

(2) Preparation of the Compound 129.

The title compound was obtained in the same manner as the Example 126(4) using the following starting material.

Starting material: the intermediate 129(1); Yield: 86.7% (white solid).

$^1$H-NMR (DMSO-$d_6$) δ: 1.23 (9H, s), 4.91 (2H, s), 7.15-7.60 (8H, m), 7.57 (2H, d, J=8.4 Hz), 7.73 (2H, d, J=9.0 Hz).

Example 130

Preparation of the Compound 130

(1) Preparation of the Intermediate 130(1).

The title compound was obtained in the same manner as the Example 123(1) using the following starting materials.

Starting materials: 3-bromoaniline and 4-(tert-butyl)benzyl bromide; Yield: 66.4% (pale yellow oil).

$^1$H-NMR ($CDCl_3$) δ: 1.32 (9H, s), 4.04 (1H, brs), 4.25 (2H, d, J=4.8 Hz), 6.51-6.55 (1H, m), 6.78 (1H, t, J=1.8 Hz), 6.80-6.83 (1H, m), 7.00 (1H, t, J=8.1 Hz), 7.28 (2H, d, J=8.4 Hz), 7.36-7.39 (2H, m).

(2) Preparation of the Intermediate 130(2).

The title compound was obtained in the same manner as the Example 123(3) using the following starting materials.

Starting materials: the intermediate 130(1) and 4-(trifluoromethoxy)phenylboronic acid; Yield: 86.7% (yellow solid).

$^1$H-NMR ($CDCl_3$) δ: 1.33 (9H, s), 4.12 (2H, d, J=7.2 Hz), 4.34 (1H, s), 6.63-6.67 (1H, m), 6.80-6.81 (1H, m), 6.87-6.91 (1H, m), 7.22-7.29 (3H, m), 7.33 (2H, d, J=8.1 Hz), 7.39 (2H, d, J=8.1 Hz), 7.52-7.57 (2H, m).

(3) Preparation of the Intermediate 130(3).

The title compound was obtained in the same manner as the Example 123(2) using the following starting materials.

Starting materials: the intermediate 130(2) and methyl chloroglyoxylate; Yield: 87.5% (white solid).

$^1$H-NMR ($CDCl_3$) δ: 1.30 (9H, s), 3.55 (3H, s), 4.95 (2H, s), 7.11-7.13 (2H, m), 7.17 (2H, d, J=8.1 Hz), 7.25 (2H, d, J=8.1 Hz), 7.31-7.34 (2H, m), 7.38-7.44 (3H, m), 7.48-7.52 (1H, m).

(4) Preparation of the Compound 130.

The title compound was obtained in the same manner as the Example 126(4) using the following starting material.

Starting material: methyl the intermediate 130(3); Yield: 32.3% (white solid).

$^1$H-NMR (DMSO-$d_6$) δ: 1.22 (9H, s), 4.95 (2H, s), 7.16 (2H, d, J=7.8 Hz), 7.26-7.33 (3H, m), 7.38-7.43 (3H, m), 7.51-7.53 (2H, m), 7.68 (2H, d, J=8.4 Hz).

Example 131

Preparation of the Compound 131

(1) Preparation of the Intermediate 131(1).

The title compound was obtained in the same manner as the Example 125(4) using the following starting materials.

Starting materials: the intermediate 125(3) and 4-methoxybenzyl bromide; Yield: 82.7% (colorless oil).

$^1$H-NMR ($CDCl_3$) δ: 3.57 (3H, s), 3.79 (3H, s), 4.91 (2H, s), 6.82 (2H, d, J=8.4 Hz), 7.11 (2H, d, J=8.4 Hz), 7.16 (2H, d, J=8.7 Hz), 7.28 (2H, d, J=8.4 Hz), 7.49 (2H, d, J=8.4 Hz), 7.56 (2H, d, J=8.7 Hz).

(2) Preparation of the Compound 131.

The title compound was obtained in the same manner as the Example 126(4) using the following starting material.

Starting material: the intermediate 131(1); Yield: 55.8% (white solid).

$^1$H-NMR (DMSO-$d_6$) δ: 3.69 (3H, s), 4.87 (2H, s), 6.80-6.89 (2H, m), 7.10-7.38 (4H, m), 7.42 (2H, d, J=8.4 Hz), 7.55 (2H, d, J=8.4 Hz), 7.74 (2H, d, J=8.4 Hz).

Example 132

Preparation of the Compound 132

(1) Preparation of the Intermediate 132(1).

A mixture of 4-(trifluoromethoxy)phenol (2.50 g, 14.036 mmol), 4-fluoro-1-nitrobenzene (1.98 g, 14.036 mmol), potassium carbonate (2.90 g, 20.982 mmol) and N,N-dimethylacetamide (15 ml) was stirred at 160° C. for 2 hours under argon atmosphere. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=10:1) to give the title compound (4.18 g, 100%) as a pale yellow solid.

$^1$H-NMR ($CDCl_3$) δ: 7.02-7.06 (2H, m), 7.10-7.14 (2H, m), 7.26-7.31 (2H, m), 8.21-8.25 (2H, m).

(2) Preparation of the Intermediate 132(2).

A mixture of the intermediate 132(1) (4.18 g, 13.970 mmol), 10% platinum on activated carbon (270 mg) and ethanol (40 ml) was stirred for 3 hours under hydrogen atmosphere. The reaction mixture was filtered through Celite. The residue obtained by concentration of the filtrate under reduced pressure was purified by column chromatography on silica gel (n-hexane:ethyl acetate=3:1) to give the title compound (3.54 g, 93.9%) as a yellow oil.

$^1$H-NMR ($CDCl_3$) δ: 3.61 (2H, s), 6.67-6.70 (2H, m), 6.85-6.88 (2H, m), 6.89-6.92 (2H, m), 7.12 (2H, t, J=9.0 Hz).

(3) Preparation of the Intermediate 132(3).

The title compound was obtained in the same manner as the Example 125(3) using the following starting materials.

Starting materials: the intermediate 132(2) and methyl chloroglyoxylate; Yield: 96.9% (white solid).

$^1$H-NMR ($CDCl_3$) δ: 3.98 (3H, s), 6.97-7.05 (4H, m), 7.16-7.22 (2H, m), 7.62-7.65 (2H, m), 8.85 (1H, brs).

(4) Preparation of the Intermediate 132(4).

The title compound was obtained in the same manner as the Example 125(4) using the following starting materials.

Starting materials: the intermediate 132(3) and 4-(tert-butyl)benzyl bromide; Yield: 92.0% (colorless oil).

$^1$H-NMR ($CDCl_3$) δ: 1.30 (9H, s), 3.59 (3H, s), 4.88 (2H, s), 6.88-6.91 (2H, m), 6.98-7.01 (2H, m), 7.03-7.06 (2H, m), 7.16 (2H, d, J=8.4 Hz), 7.20 (2H, d, J=8.4 Hz), 7.30-7.33 (2H, m).

(5) Preparation of the Compound 132.

The title compound was obtained in the same manner as the Example 126(4) using the following starting material.

Starting material: the intermediate 132(4); Yield: 78.5% (yellow solid).

$^1$H-NMR ($CDCl_3$) δ: 1.23 (9H, s), 4.80 (2H, s), 5.83 (1H, brs), 6.75 (2H, d, J=8.4 Hz), 6.89-6.97 (4H, m), 7.08-7.13 (4H, m), 7.23 (2H, d, J=7.2 Hz).

Example 133

Preparation of the Compound 133

The title compound was obtained in the same manner as the Example 123(4) using the following starting material.

Starting material: the intermediate 129(1); Yield: 56.5% (white solid).

$^1$H-NMR (DMSO-$d_6$) δ: 1.24 (9H, s), 4.89 (2H, s), 7.18-7.43 (8H, m), 7.54-7.57 (2H, m), 7.72-7.77 (2H, m).

Example 134

Preparation of the Compound 134

(1) Preparation of the Intermediate 134(1).

The title compound was obtained in the same manner as the Example 123(3) using the following starting materials.

Starting materials: the intermediate 126(2) and 4-(methylsulfanyl)phenylboronic acid; Yield: 81.2% (colorless oil).

$^1$H-NMR ($CDCl_3$) δ: 1.30 (9H, s), 2.52 (3H, s), 3.58 (3H, s), 4.94 (2H, s), 7.11-7.38 (4H, m), 7.28-7.36 (4H, m), 7.45-7.54 (4H, m).

(2) Preparation of the Compound 134.

The title compound was obtained in the same manner as the Example 126(4) using the following starting material.

Starting material: the intermediate 134(1); Yield: 94.2% (white solid).

$^1$H-NMR (DMSO-$d_6$) δ: 1.24 (9H, s), 2.51 (3H, s), 4.93 (2H, s), 7.13-7.18 (2H, m), 7.28-7.36 (6H, m), 7.58-7.66 (4H, m).

Example 135

Preparation of the Compound 135

(1) Preparation of the Intermediate 135(1).

The title compound was obtained in the same manner as the Example 123(3) using the following starting materials.

Starting materials: the intermediate 126(2) and 4-chlorophenylboronic acid; Yield: 88.0% (pale brown oil).

$^1$H-NMR (DMSO-$d_6$) δ: 1.30 (9H, s), 3.59 (2H, s), 4.94 (2H, s), 7.09-7.54 (12H, m).

(2) Preparation of the Compound 135.

The title compound was obtained in the same manner as the Example 126(4) using the following starting material.

Starting material: the intermediate 135(1); Yield: 44.0% (white solid).

$^1$H-NMR (DMSO-$d_6$) δ: 1.24 (9H, s), 4.89 (2H, s), 7.02-7.74 (12H, m).

Example 136

Preparation of the Compound 136

(1) Preparation of the Intermediate 136(1).

The title compound was obtained in the same manner as the Example 123(1) using the following starting materials.

Starting materials: 5-bromo-2-methylaniline and 4-(tert-butyl)benzyl bromide; Yield: 71.8% (colorless oil).

$^1$H-NMR ($CDCl_3$) δ: 1.33 (9H, s), 2.08 (3H, s), 3.81 (1H, brs), 4.28 (2H, d, J=4.8 Hz), 6.75-6.92 (2H, m), 6.88-6.92 (1H, m), 7.28-7.32 (2H, m), 4.28 (2H, d, J=4.8 Hz).

(2) Preparation of the Intermediate 136(2).

The title compound was obtained in the same manner as the Example 125(3) using the following starting materials.

Starting materials: the intermediate 136(1) and methyl chloroglyoxylate; Yield: 94.8% (colorless oil).

$^1$H-NMR ($CDCl_3$) δ: 1.30 (9H, s), 2.07 (3H, s), 3.54 (3H, s), 4.35 (1H, d, J=13.8 Hz), 5.20 (1H, d, J=13.8 Hz), 6.91 (1H, d, J=2.1 Hz), 7.07-7.13 (3H, m), 7.28-7.33 (2H, m), 7.35 (1H, dd, J=2.1, 8.4 Hz).

(3) Preparation of the Intermediate 136(3).

The title compound was obtained in the same manner as the Example 123(3) using the following starting materials.

Starting materials: the intermediate 136(2) and 4-(trifluoromethoxy)phenylboronic acid; Yield: 80.0% (colorless oil).

$^1$H-NMR ($CDCl_3$) δ: 1.30 (9H, s), 2.27 (3H, s), 3.48 (3H, s), 4.14 (1H, d, J=13.5 Hz), 5.51 (1H, d, J=13.5 Hz), 6.75 (1H, d, J=1.8 Hz), 7.11-7.20 (4H, m), 7.24-7.34 (5H, m), 7.42 (1H, dd, J=1.8, 7.8 Hz).

(4) Preparation of the Compound 136.

The title compound was obtained in the same manner as the Example 126(4) using the following starting material.

Starting material: the intermediate 136(3); Yield: 37.0% (white solid).

This compound was obtained as a mixture of the rotational isomers.

Major isomer: $^1$H-NMR (DMSO-$d_6$) δ: 1.24 (9H, s), 2.19 (3H, s), 4.32 (1H, d, J=14.1 Hz), 5.26 (1H, d, J=14.1 Hz), 6.93 (1H, d, J=1.8 Hz), 7.07-7.20 (2H, m), 7.29-7.50 (7H, m), 6.93 (1H, dd, J=1.8, 10.2 Hz).

Minor isomer: $^1$H-NMR (DMSO-$d_6$) δ: 1.23 (9H, s), 1.97 (3H, s), 4.60 (1H, d, J=14.1 Hz), 4.96 (1H, d, J=14.1 Hz), 6.80-7.60 (11H, m).

Example 137

Preparation of the Compound 137

(1) Preparation of the Intermediate 137(1).

The title compound was obtained in the same manner as the Example 123(3) using the following starting materials.

Starting materials: the intermediate 136(2) and phenylboronic acid; Yield: 98.3% (pale yellow oil).

$^1$H-NMR ($CDCl_3$) δ: 1.31 (9H, s), 2.26 (3H, s), 3.47 (3H, s), 4.17 (1H, d, J=13.8 Hz), 5.49 (1H, d, J=13.8 Hz), 6.81 (1H, d, J=1.8 Hz), 7.13-7.17 (2H, m), 7.23-7.38 (8H, m), 7.45 (1H, dd, J=1.8, 7.5 Hz).

(2) Preparation of the Compound 137.

The title compound was obtained in the same manner as the Example 126(4) using the following starting material.

Starting material: the intermediate 137(1); Yield: 44.3% (white solid).

This compound was obtained as a mixture of the rotational isomers.

Major isomer: $^1$H-NMR (DMSO-$d_6$) δ: 1.27 (9H, s), 2.22 (3H, s), 4.23 (1H, d, J=14.4 Hz), 5.33 (1H, d, J=14.4 Hz), 6.85 (1H, d, J=1.8 Hz), 7.12-7.16 (2H, m), 7.28-7.41 (8H, m), 7.54 (1H, dd, J=1.8, 8.1 Hz).

Minor isomer: $^1$H-NMR (DMSO-$d_6$) δ: 1.26 (9H, s), 2.00 (3H, s), 4.55 (1H, d, J=15.0 Hz), 4.97 (1H, d, J=15.0 Hz), 6.73-7.60 (12H, m).

Example 138

Preparation of the Compound 138

(1) Preparation of the Intermediate 138(1).

The title compound was obtained in the same manner as the Example 123(3) using the following starting materials.

Starting materials: the intermediate 136(2) and 3-nitrophenylboronic acid; Yield: 52.1% (colorless oil).

$^1$H-NMR ($CDCl_3$) δ: 1.30 (9H, s), 2.28 (3H, s), 3.51 (3H, s), 4.20 (1H, d, J=14.1 Hz), 5.49 (1H, d, J=14.1 Hz), 6.89 (1H, d, J=2.1 Hz), 7.11-7.21 (2H, m), 7.29-7.42 (3H, m), 7.45-7.55 (3H, m), 8.13-8.26 (2H, m).

(2) Preparation of the Compound 138.

The title compound was obtained in the same manner as the Example 126(4) using the following starting material.

Starting material: the intermediate 138(1); Yield: 96.5% (pale white solid).

This compound was obtained as a mixture of the rotational isomers.

Major isomer: $^1$H-NMR (DMSO-$d_6$) δ: 1.24 (9H, s), 2.26 (3H, s), 3.99 (1H, d, J=13.8 Hz), 5.29 (1H, d, J=13.8 Hz), 7.01 (1H, d, J=1.8 Hz), 7.12-8.24 (10H, m).

Minor isomer: $^1$H-NMR (DMSO-$d_6$) δ: 1.23 (9H, s), 3.31 (3H, s), 4.54 (1H, d, J=15.3 Hz), 4.98 (1H, d, J=15.3 Hz), 7.08 (1H, d, J=1.8 Hz), 7.10-8.24 (10H, m).

Example 139

Preparation of the Compound 139

(1) Preparation of the Intermediate 139(1).

The title compound was obtained in the same manner as the Example 123(1) using the following starting materials.

Starting materials: 3-bromo-5-(trifluoromethyl)aniline and 4-(tert-butyl)benzyl bromide; Yield: 99.9% (colorless oil).

$^1$H-NMR ($CDCl_3$) δ: 1.33 (9H, s), 4.27 (2H, s), 4.59 (1H, s), 6.73-6.75 (1H, m), 6.87-6.89 (1H, m), 7.03-7.05 (1H, m), 7.23-7.28 (2H, m), 7.36-7.41 (2H, m).

(2) Preparation of the Intermediate 139(2).

The title compound was obtained in the same manner as the Example 125(3) using the following starting materials.

Starting materials: the intermediate 139(1) and methyl chloroglyoxylate; Yield: 65.5% (colorless oil).

$^1$H-NMR ($CDCl_3$) δ: 1.30 (9H, s), 3.63 (3H, s), 4.92 (2H, s), 7.09-7.18 (3H, m), 7.30-7.36 (2H, m), 7.39-7.42 (1H, m), 7.69-7.71 (1H, m).

(3) Preparation of the Intermediate 139(3).

The title compound was obtained in the same manner as the Example 123(3) using the following starting materials.

Starting materials: the intermediate 139(2) and 4-(trifluoromethoxy)phenylboronic acid; Yield: 75.7% (colorless oil).

$^1$H-NMR ($CDCl_3$) δ: 1.30 (9H, s), 3.59 (3H, s), 4.97 (2H, s), 7.13-7.17 (2H, m), 7.26-7.45 (8H, m), 7.72-7.74 (1H, m).

(4) Preparation of the Compound 139.

The title compound was obtained in the same manner as the Example 126(4) using the following starting material.

Starting material: the intermediate 139(3); Yield: 43.5% (white solid).

$^1$H-NMR (DMSO-$d_6$) δ: 1.22 (9H, s), 4.97 (2H, s), 7.10-7.22 (2H, m), 7.29 (1H, d, J=8.4 Hz), 7.46 (2H, d, J=8.7 Hz), 7.57-7.61 (2H, m), 7.72-7.90 (4H, m).

Example 140

Preparation of the Compound 140

(1) Preparation of the Intermediate 140(1).

The title compound was obtained in the same manner as the Example 123(3) using the following starting materials.

Starting materials: the intermediate 139(2) and phenylboronic acid; Yield: 91.1% (white solid).

$^1$H-NMR ($CDCl_3$) δ: 1.30 (9H, s), 3.58 (3H, s), 4.97 (2H, s), 7.13-7.18 (2H, m), 7.26-7.46 (9H, m), 7.75-7.77 (1H, m).

(2) Preparation of the Compound 140.

The title compound was obtained in the same manner as the Example 126(4) using the following starting material.

Starting material: the intermediate 140(1); Yield: 24.9% (white solid).

$^1$H-NMR (DMSO-$d_6$) δ: 1.23 (9H, s), 4.97 (2H, s), 7.10-7.24 (2H, m), 7.30 (2H, d, J=7.8 Hz), 7.38-7.51 (3H, m), 7.53-7.64 (3H, m), 7.69-7.73 (1H, m), 7.74-7.82 (1H, m).

Example 141

Preparation of the Compound 141

(1) Preparation of the Intermediate 141(1).

The title compound was obtained in the same manner as the Example 123(3) using the following starting materials.

Starting materials: the intermediate 126(2) and 4-methylphenylboronic acid; Yield: 91.3% (colorless oil).

$^1$H-NMR ($CDCl_3$) δ: 1.30 (9H, s), 2.39 (3H, s), 3.57 (3H, s), 4.93 (2H, s), 7.05-7.38 (8H, m), 7.38-7.60 (4H, m).

(2) Preparation of the Compound 141.

The title compound was obtained in the same manner as the Example 126(4) using the following starting material.

Starting material: the intermediate 141(1); Yield: 99.9% (white solid).

$^1$H-NMR (DMSO-$d_6$) δ: 1.24 (9H, s), 2.32 (3H, s), 4.87 (2H, s), 7.06-7.45 (8H, m), 7.51 (4H, d, J=8.0 Hz).

Example 142

Preparation of the Compound 142

(1) Preparation of the Intermediate 142(1).

The title compound was obtained in the same manner as the Example 123(3) using the following starting materials.

Starting materials: the intermediate 126(2) and 3-nitrophenylboronic acid; Yield: 59.3% (white solid).

$^1$H-NMR ($CDCl_3$) δ: 1.30 (9H, s), 3.61 (3H, s), 4.96 (2H, s), 7.13-7.25 (4H, m), 7.29-7.39 (2H, m), 7.54-7.68 (3H, m), 7.84-7.94 (1H, m), 8.18-8.27 (1H, m), 8.38-8.46 (1H, m).

(2) Preparation of the Compound 142.

The title compound was obtained in the same manner as the Example 126(4) using the following starting material.

Starting material: the intermediate 142(1); Yield: 99.9% (yellow solid).

$^1$H-NMR (DMSO-$d_6$) δ: 1.24 (9H, s), 4.91 (2H, s), 7.09-7.27 (2H, m), 7.29 (2H, d, J=8.2 Hz), 7.43 (2H, d, J=8.5 Hz), 7.67 (2H, d, J=8.5 Hz), 7.73 (1H, t, J=8.2 Hz), 8.06-8.22 (2H, m) 8.36-8.44 (1H, m).

Example 143

Preparation of the Compound 143

(1) Preparation of the Intermediate 143(1).

The title compound was obtained in the same manner as the Example 125(4) using the following starting materials.

Starting materials: the intermediate 125(3) and 4-methylbenzyl chloride; Yield: 24.1% (white solid).

$^1$H-NMR ($CDCl_3$) δ: 2.31 (3H, s), 3.57 (3H, s), 4.94 (2H, s), 7.06-7.17 (6H, m), 7.27 (2H, d, J=8.8 Hz), 7.49 (2H, d, J=8.8 Hz), 7.55 (2H, d, J=8.8 Hz).

(2) Preparation of the Compound 143.

The title compound was obtained in the same manner as the Example 126(4) using the following starting material.

Starting material: the intermediate 143(1): Yield: 86.9% (white solid).

$^1$H-NMR (DMSO-$d_6$) δ: 2.23 (3H, s), 4.88 (2H, s), 6.98-7.48 (8H, m), 7.48-7.63 (2H, m) 7.73 (2H, d, J=8.5 Hz).

Example 144

Preparation of the Compound 144

(1) Preparation of the Intermediate 144(1).

The title compound was obtained in the same manner as the Example 125(4) using the following starting materials.

Starting materials: the intermediate 125(3) and 2,4-dichlorobenzyl chloride; Yield: 59.5% (colorless oil).

$^1$H-NMR ($CDCl_3$) δ: 3.61 (3H, s), 5.11 (2H, s), 7.14-7.42 (7H, m), 7.51 (2H, d, J=8.8 Hz), 7.56 (2H, d, J=8.8 Hz).

(2) Preparation of the Compound 144.

The title compound was obtained in the same manner as the Example 126(4) using the following starting material.

Starting material: the intermediate 144(1); Yield: 98.8% (white solid).

$^1$H-NMR (DMSO-$d_6$) δ: 4.94 (2H, s), 7.33-7.48 (6H, m), 7.53-7.63 (3H, m), 7.75 (2H, d, J=8.8 Hz).

Example 145

Preparation of the Compound 145

(1) Preparation of the Intermediate 145(1).

The title compound was obtained in the same manner as the Example 123(3) using the following starting materials.

Starting materials: the intermediate 126(2) and 4-(trifluoromethyl)phenylboronic acid; Yield: 55.7% (white solid).

$^1$H-NMR ($CDCl_3$) δ: 1.30 (9H, s), 3.60 (3H, s), 4.95 (2H, s), 7.18 (4H, d, J=8.1 Hz), 7.32 (2H, d, J=8.1 Hz), 7.55 (2H, d, J=8.7 Hz), 7.62-7.76 (4H, m).

(2) Preparation of the Compound 145.

The title compound was obtained in the same manner as the Example 126(4) using the following starting material.

Starting material: the intermediate 145(1); Yield: 99.5% (white solid).

$^1$H-NMR (DMSO-$d_6$) δ: 1.23 (9H, s), 4.90 (2H, s), 7.09-7.36 (4H, m), 7.41 (2H, d, J=8.5 Hz), 7.63 (2H, d, J=8.5 Hz), 7.78 (2H, d, J=8.5 Hz), 7.85 (2H, d, J=8.5 Hz).

Example 146

Preparation of the Compound 146

(1) Preparation of the Intermediate 146(1).

The title compound was obtained in the same manner as the Example 123(1) using the following starting materials.

Starting materials: 4-bromo-2-methylaniline and 4-(tert-butyl)benzyl bromide; Yield: 55.8% (white solid).

$^1$H-NMR (DMSO-$d_6$) δ: 1.33 (9H, s), 2.12 (3H, s), 3.82 (1H, brs), 4.30 (2H, s), 6.49 (1H, d, J=9.3 Hz), 7.12-7.21 (2H, m), 7.23-7.33 (2H, m), 7.34-7.43 (2H, m).

(2) Preparation of the Intermediate 146(2).

The title compound was obtained in the same manner as the Example 125(3) using the following starting materials.

Starting materials: the intermediate 146(1) and methyl chloroglyoxylate; Yield: 80.2% (colorless oil).

$^1$H-NMR ($CDCl_3$) δ: 1.29 (9H, s), 2.13 (3H, s), 3.52 (3H, s), 4.26 (1H, d, J=14.0 Hz), 5.24 (1H, d, J=14.0 Hz), 6.64 (1H, d, J=8.5 Hz), 7.04-7.15 (2H, m), 7.15-7.23 (1H, m), 7.23-7.34 (2H, m), 7.34-7.44 (1H, m).

(3) Preparation of the Intermediate 146(3).

The title compound was obtained in the same manner as the Example 123(3) using the following starting materials.

Starting materials: the intermediate 146(2) and 4-(trifluoromethoxy)phenylboronic acid; Yield: 66.9% (white solid).

$^1$H-NMR ($CDCl_3$) δ: 1.30 (9H, s), 2.23 (3H, s), 3.52 (3H, s), 4.33 (1H, d, J=14.1 Hz), 5.29 (1H, d, J=14.1 Hz), 6.78-6.86 (1H, m), 6.88 (1H, d, J=8.2 Hz), 7.09 (1H, d, J=8.8 Hz), 7.16 (2H, d, J=8.2 Hz), 7.20-7.36 (3H, m), 7.42 (1H, s), 7.52-7.61 (2H, m).

(4) Preparation of the Compound 146.

The title compound was obtained in the same manner as the Example 126(4) using the following starting material.

Starting material: the intermediate 146(3); Yield: 41.1% (white solid).

This compound was obtained as a mixture of the rotational isomers.

Major isomer: $^1$H-NMR (DMSO-$d_6$) δ: 1.26 (9H, s), 2.24 (3H, s), 4.10 (1H, d, J=13.8 Hz), 5.13 (1H, d, J=13.8 Hz), 6.94 (1H, d, J=8.2 Hz), 7.14 (1H, d, J=8.0 Hz), 7.21-7.56 (7H, m), 7.75 (2H, d, J=8.8 Hz).

Minor isomer: $^1$H-NMR (DMSO-$d_6$) δ: 1.23 (9H, s), 1.98 (3H, s), 4.48-4.74 (1H, m), 4.74-4.98 (1H, m), 6.90-7.86 (11H, m).

Example 147

Preparation of the Compound 147

(1) Preparation of the Intermediate 147(1).

The title compound was obtained in the same manner as the Example 123(1) using the following starting materials.

Starting materials: 4-bromo-2-chloroaniline and 4-(tert-butyl)benzyl bromide; Yield: 43.7% (white solid).

$^1$H-NMR ($CDCl_3$) δ: 1.32 (9H, s), 4.33 (2H, s), 4.70 (1H, brs), 6.52 (1H, d, J=8.8 Hz), 7.18 (1H, d, J=2.2, 8.8 Hz), 7.27 (2H, d, J=8.0 Hz), 7.34-7.43 (3H, m).

(2) Preparation of the Intermediate 147(2).

The title compound was obtained in the same manner as the Example 125(3) using the following starting materials.

Starting materials: the intermediate 147(1) and methyl chloroglyoxylate; Yield: 88.3% (colorless oil).

$^1$H-NMR ($CDCl_3$) δ: 1.29 (9H, s), 3.59 (3H, s), 4.17 (1H, d, J=14.4 Hz), 5.51 (1H, d, J=14.4 Hz), 6.71 (1H, d, J=8.5 Hz), 7.06-7.18 (2H, m), 7.21-7.36 (3H, m), 7.63 (1H, d, J=2.2 Hz).

(3) Preparation of the Intermediate 147(3).

The title compound was obtained in the same manner as the Example 123(3) using the following starting materials.

Starting materials: the intermediate 147(2) and 4-(trifluoromethoxy)phenylboronic acid; Yield: 43.9% (white solid).

$^1$H-NMR ($CDCl_3$) δ: 1.29 (9H, s), 3.59 (3H, s), 4.25 (1H, d, J=14.4 Hz), 5.56 (1H, d, J=14.4 Hz), 6.95 (1H, d, J=7.8 Hz), 7.17 (2H, d, J=8.1 Hz), 7.24-7.37 (5H, m), 7.51-7.60 (2H, m), 7.66 (1H, d, J=1.8 Hz).

(4) Preparation of the Compound 147.

The title compound was obtained in the same manner as the Example 126(4) using the following starting material.

Starting material: the intermediate 147(3); Yield: 92.1% (white solid).

This compound was obtained as a mixture of the rotational isomers.

Major isomer: $^1$H-NMR (DMSO-$d_6$) δ: 1.24 (9H, s), 4.06 (1H, d, J=14.7 Hz), 5.39 (1H, d, J=14.7 Hz), 7.08-7.22 (2H, m), 7.22-7.39 (3H, m), 7.39-7.58 (3H, m), 7.74-7.88 (3H, m).

Minor isomer: $^1$H-NMR (DMSO-$d_6$) δ: 1.23 (9H, s), 4.38-4.84 (1H, m), 4.84-5.28 (1H, m), 7.02-7.88 (11H, m).

Example 148

Preparation of the Compound 148

(1) Preparation of the Intermediate 148(1).

The title compound was obtained in the same manner as the Example 125(3) using the following starting materials.

Starting materials: 2-bromoaniline and methyl chloroglyoxylate; Yield: 98.5% (white solid).

$^1$H-NMR ($CDCl_3$) δ: 4.00 (3H, s), 7.04-7.61 (3H, m), 8.41-8.44 (1H, m), 9.48 (1H, brs).

(2) Preparation of the Intermediate 148(2).

The title compound was obtained in the same manner as the Example 123(1) using the following starting materials.

Starting materials: methyl N-(2-bromophenyl)oxamate and 4-(tert-butyl)benzyl bromide; Yield: 25.6% (colorless oil).

$^1$H-NMR ($CDCl_3$) δ: 1.29 (9H, s), 3.55 (3H, s), 4.18 (1H, d, J=14.1 Hz), 5.56 (1H, d, J=14.1 Hz), 6.82-6.86 (1H, m), 7.11-7.30 (6H, m), 7.63-7.67 (1H, m).

(3) Preparation of the Intermediate 148(3).

The title compound was obtained in the same manner as the Example 123(3) using the following starting materials.

Starting materials: the intermediate 148(2) and 4-(trifluoromethoxy)phenylboronic acid; Yield: 80.0% (colorless oil).

$^1$H-NMR ($CDCl_3$) δ: 1.25 (9H, s), 3.47 (1H, d, J=14.1 Hz), 3.63 (3H, s), 5.10 (1H, d, J=14.1 Hz), 6.82-6.86 (1H, m), 6.91-6.95 (2H, m), 7.17-7.42 (7H, m), 7.59-7.65 (2H, m).

(4) Preparation of the Compound 148.

The title compound was obtained in the same manner as the Example 126(4) using the following starting material.

Starting material: the intermediate 148(3); Yield: 66.9% (white solid).

$^1$H-NMR (DMSO-$d_6$) δ: 1.20 (9H, s), 3.14 (1H, d, J=14.7 Hz), 4.82 (1H, d, J=14.7 Hz), 6.86 (2H, d, J=8.1 Hz), 7.05-7.36 (6H, m), 7.43 (2H, d, J=8.4 Hz), 8.05 (2H, d, J=8.7 Hz).

Example 149

Preparation of the Compound 149

(1) Preparation of the Intermediate 149(1).

The title compound was obtained in the same manner as the Example 125(3) using the following starting materials.

Starting materials: 4-(4-aminophenyl)benzonitrile and methyl chloroglyoxylate; Yield: 80.9% (white solid).

$^1$H-NMR (DMSO-$d_6$) δ: 3.87 (3H, s), 7.77-7.94 (8H, m), 10.98 (1H, brs).

(2) Preparation of the Intermediate 149(2).

The title compound was obtained in the same manner as the Example 123(1) using the following starting materials.

Starting materials: the intermediate 149(1) and 4-(tert-butyl)benzyl bromide; Yield: 77.7% (pale yellow oil).

$^1$H-NMR ($CDCl_3$) δ: 1.30 (9H, s), 3.60 (3H, s), 4.95 (2H, s), 7.15-7.22 (4H, m), 7.32 (2H, d, J=8.4 Hz), 7.54 (2H, d, J=8.1 Hz), 7.65 (2H, d, J=7.8 Hz), 7.73 (2H, d, J=7.8 Hz).

(3) Preparation of the Compound 149.

The title compound was obtained in the same manner as the Example 126(4) using the following starting material.

Starting material: the intermediate 149(2); Yield: 48.7% (white solid).

$^1$H-NMR (DMSO-$d_6$) δ: 1.23 (9H, s), 4.91 (2H, s), 7.12-7.34 (4H, m), 7.42 (2H, d, J=8.7 Hz), 7.64 (2H, d, J=8.7 Hz), 7.82-7.92 (4H, m).

Example 150

Preparation of the Compound 150

(1) Preparation of the Intermediate 150(1).

The title compound was obtained in the same manner as the Example 125(3) using the following starting materials.

Starting materials: 4-bromo-2-(trifluoromethyl)aniline and methyl chloroglyoxylate; Yield: 71.9% (white solid).

$^1$H-NMR ($CDCl_3$) δ: 4.00 (3H, s), 7.73 (1H, dd, J=2.1, 8.7 Hz), 7.79 (1H, d, J=2.1 Hz), 8.29 (1H, d, J=8.7 Hz), 9.30 (1H, brs).

(2) Preparation of the Intermediate 150(2).

The title compound was obtained in the same manner as the Example 123(1) using the following starting materials.

Starting materials: the intermediate 150(1) and 4-(tert-butyl)benzyl bromide; Yield: 70.2% (colorless oil).

$^1$H-NMR ($CDCl_3$) δ: 1.31 (9H, s), 3.61 (3H, s), 3.91 (1H, d, J=14.7 Hz), 5.76 (1H, d, J=14.7 Hz), 6.66 (1H, d, J=8.7 Hz), 7.12-7.17 (2H, m), 7.29-7.36 (2H, m), 7.52 (1H, dd, J=2.4, 8.7 Hz), 7.86 (1H, d, J=2.4 Hz).

(3) Preparation of the Intermediate 150(3).

The title compound was obtained in the same manner as the Example 123(3) using the following starting materials.

Starting materials: the intermediate 150(2) and 4-(trifluoromethoxy)phenylboronic acid; Yield: 44.6% (colorless oil).

$^1$H-NMR ($CDCl_3$) δ: 1.31 (9H, s), 3.60 (3H, s), 3.99 (1H, d, J=14.4 Hz), 5.79 (1H, d, J=14.4 Hz), 6.91 (1H, d, J=8.4 Hz), 7.16-7.21 (2H, m), 7.27-7.36 (4H, m), 7.54-7.63 (3H, m), 7.90 (1H, d, J=2.1 Hz).

(4) Preparation of the Compound 150.

The title compound was obtained in the same manner as the Example 126(4) using the following starting material.

Starting material: the intermediate 150(3); Yield: 66.7% (white solid).

This compound was obtained as a mixture of the rotational isomers.

Major isomer: $^1$H-NMR (DMSO-$d_6$) δ: 1.26 (9H, s), 3.86 (1H, d, J=14.7 Hz), 5.51 (1H, d, J=14.7 Hz), 7.08-7.80 (11H, m).

Minor isomer: $^1$H-NMR (DMSO-$d_6$) δ: 1.25 (9H, s), 4.26 (1H, d, J=15.3 Hz), 5.33 (1H, d, J=15.3 Hz), 6.79 (1H, d, J=8.4 Hz), 7.08-7.80 (10H, m).

Example 151

Preparation of the Compound 151

(1) Preparation of the Intermediate 151(1).

The title compound was obtained in the same manner as the Example 125(3) using the following starting materials.

Starting materials: 4-bromo-2-(trifluoromethoxy)aniline and methyl chloroglyoxylate; Yield: 80.7% (white solid).

$^1$H-NMR ($CDCl_3$) δ: 4.00 (3H, s), 7.47-7.50 (2H, m), 8.36-8.41 (1H, m), 9.21 (1H, brs).

(2) Preparation of the Intermediate 151(2).

The title compound was obtained in the same manner as the Example 123(1) using the following starting materials.

Starting materials: the intermediate 151(1) and 4-(tert-butyl)benzyl bromide; Yield: 89.9% (colorless oil).

$^1$H-NMR ($CDCl_3$) δ: 1.29 (9H, s), 3.61 (3H, s), 4.31 (1H, d, J=14.7 Hz), 5.37 (1H, d, J=14.7 Hz), 6.84 (1H, d, J=8.7 Hz), 7.08-7.13 (2H, m), 7.25-7.32 (3H, m), 7.43-7.46 (1H, m).

(3) Preparation of the Intermediate 151(3).

The title compound was obtained in the same manner as the Example 123(3) using the following starting materials.

Starting materials: the intermediate 151(2) and 4-(trifluoromethoxy)phenylboronic acid; Yield: 44.7% (colorless oil).

$^1$H-NMR ($CDCl_3$) δ: 1.29 (9H, s), 3.61 (3H, s), 4.37 (1H, d, J=14.4 Hz), 5.44 (1H, d, J=14.4 Hz), 7.06 (1H, d, J=8.1 Hz), 7.14-7.17 (2H, m), 7.26-7.35 (5H, m), 7.43-7.48 (1H, m), 7.53-7.58 (2H, m).

(4) Preparation of the Compound 151.

The title compound was obtained in the same manner as the Example 126(4) using the following starting material.

Starting material: the intermediate 151(3); Yield: 47.6% (white solid).

This compound was obtained as a mixture of the rotational isomers.

Major isomer: $^1$H-NMR (DMSO-$d_6$) δ: 1.24 (9H, s), 4.84 (2H, s), 7.07-7.80 (11H, m).

Minor isomer: $^1$H-NMR (DMSO-$d_6$) δ: 1.22 (9H, s), 4.77 (2H, s), 7.07-7.80 (11H, m).

Example 152

Preparation of the Compound 152

(1) Preparation of the Intermediate 152(1).

The title compound was obtained in the same manner as the Example 125(3) using the following starting materials.

Starting materials: 4-bromo-2,6-dimethylaniline and methyl chloroglyoxylate; Yield: 73.0% (white solid).

$^1$H-NMR ($CDCl_3$) δ: 2.22 (6H, s), 3.99 (3H, s), 7.26 (2H, d, J=1.5 Hz), 8.32 (1H, brs).

(2) Preparation of the Intermediate 152(2).

The title compound was obtained in the same manner as the Example 123(1) using the following starting materials.

Starting materials: the intermediate 152(1) and 4-(tert-butyl)benzyl bromide; Yield: 89.1% (colorless oil).

$^1$H-NMR ($CDCl_3$) δ: 1.29 (9H, s), 1.88 (6H, s), 3.51 (3H, s), 4.72 (2H, s), 7.11-7.15 (2H, m), 7.16-7.18 (2H, m), 7.25-7.30 (2H, m).

(3) Preparation of the Intermediate 152(3).

The title compound was obtained in the same manner as the Example 123(3) using the following starting materials.

Starting materials: the intermediate 152(2) and 4-(trifluoromethoxy)phenylboronic acid; Yield: 79.4% (colorless oil).

$^1$H-NMR ($CDCl_3$) δ: 1.29 (9H, s), 1.97 (6H, s), 3.51 (3H, s), 4.78 (2H, s), 7.16-7.22 (4H, m), 7.25-7.30 (4H, m), 7.55-7.61 (2H, m).

(4) Preparation of the Compound 152.

The title compound was obtained in the same manner as the Example 126(4) using the following starting material.

Starting material: the intermediate 152(3); Yield: 51.7% (white solid).

This compound was obtained as a mixture of the rotational isomers.

Major isomer: $^1$H-NMR (DMSO-$d_6$) δ: 1.25 (9H, s), 1.99 (6H, s), 4.55 (2H, s), 7.13-7.77 (10H, m).

Minor isomer: $^1$H-NMR (DMSO-$d_6$) δ: 1.23 (9H, s), 1.85 (6H, s), 4.62 (2H, s), 7.13-7.77 (10H, m).

Example 153

Preparation of the Compound 153

(1) Preparation of the Intermediate 153(1).

The title compound was obtained in the same manner as the Example 132(1) using the following starting materials.

Starting materials: 2-fluoro-1-nitrobenzene and 4-(trifluoromethoxy)phenol; Yield: 94% (yellow oil).

$^1$H-NMR ($CDCl_3$) δ: 7.02-7.09 (3H, m), 7.20-7.30 (3H, m), 7.52-7.60 (1H, m), 7.98 (1H, dd, J=1.5, 8.1 Hz).

(2) Preparation of the Intermediate 153(2).

The title compound was obtained in the same manner as the Example 125(2) using the following starting material.

Starting material: the intermediate 153(1); Yield: 98% (colorless oil).

$^1$H-NMR ($CDCl_3$) δ: 3.78 (2H, brs), 6.70-6.78 (1H, m), 6.84 (1H, dd, J=1.8, 8.1 Hz), 6.88 (1H, dd, J=1.5, 8.1 Hz), 6.93-6.99 (2H, m), 7.01 (1H, dt, J=1.5, 8.1 Hz), 7.12-7.18 (2H, m).

(3) Preparation of the Intermediate 153(3).

The title compound was obtained in the same manner as the Example 125(3) using the following starting materials.

Starting materials: the intermediate 153(2) and methyl chloroglyoxylate; Yield: 96% (white solid).

$^1$H-NMR ($CDCl_3$) δ: 3.96 (3H, s), 6.89 (1H, dd, J=1.8, 8.1 Hz), 7.03-7.26 (6H, m), 8.79 (1H, dd, J=1.8, 7.8 Hz), 9.43 (1H, brs).

(4) Preparation of the Intermediate 153(4).

The title compound was obtained in the same manner as the Example 125(4) using the following starting materials.

Starting materials: the intermediate 153(3) and 4-(tert-butyl)benzyl bromide; Yield: 93% (colorless oil).

$^1$H-NMR ($CDCl_3$) δ: 1.28 (9H, s), 3.62 (3H, s), 4.72 (1H, d, J=14.4 Hz), 5.13 (1H, d, J=14.4 Hz), 6.78 (1H, dd, J=1.5, 8.4 Hz), 6.85-6.93 (2H, m), 6.97-7.10 (2H, m), 7.12-7.28 (7H, m).

(5) Preparation of the Compound 153.

The title compound was obtained in the same manner as the Example 126(4) using the following starting material.

Starting material: the intermediate 153(4); Yield: 84% (white solid).

$^1$H-NMR (DMSO-$d_6$) δ: 1.24 (9H, s), 4.64 (1H, d, J=15.0 Hz), 5.03 (1H, d, J=15.0 Hz), 6.80-6.86 (1H, m), 6.98-7.04 (2H, m), 7.06-7.36 (7H, m), 7.37-7.44 (2H, m), 13.95 (1H, brs).

Example 154

Preparation of the Compound 154

(1) Preparation of the Intermediate 154(1).

The title compound was obtained in the same manner as the Example 125(4) using the following starting materials.

Starting materials: the intermediate 132(3) and benzyl bromide; Yield: 92% (colorless oil).

$^1$H-NMR ($CDCl_3$) δ: 3.60 (3H, s), 4.92 (2H, s), 6.85-6.92 (2H, m), 6.96-7.05 (4H, m), 7.17-7.35 (7H, m).

(2) Preparation of the Compound 154.

The title compound was obtained in the same manner as the Example 126(4) using the following starting material.

Starting material: the intermediate 154(1); Yield: 93% (white solid).

$^1$H-NMR ($CDCl_3$) δ: 4.89 (2H, s), 5.71 (1H, brs), 6.82-7.02 (6H, m), 7.14-7.23 (4H, m), 7.24-7.31 (3H, m).

Example 155

Preparation of the Compound 155

(1) Preparation of the Intermediate 155(1).

The title compound was obtained in the same manner as the Example 123(1) using the following starting materials.

Starting materials: the intermediate 125(3) and 4-fluorobenzyl chloride; Yield: 67.6% (colorless oil).

$^1$H-NMR ($CDCl_3$) δ: 3.59 (3H, s), 4.94 (2H, s), 6.96-7.02 (2H, m), 7.10-7.13 (2H, m), 7.20-7.25 (2H, m), 7.26-7.33 (2H, m), 7.48-7.53 (2H, m), 7.54-7.58 (2H, m).

(2) Preparation of the Compound 155.

The title compound was obtained in the same manner as the Example 126(4) using the following starting material.

Starting material: the intermediate 155(1); Yield: 64.5% (white solid).

$^1$H-NMR (DMSO-$d_6$) δ: 4.89 (2H, s), 7.06-7.12 (2H, m), 7.24-7.34 (4H, m), 7.42 (2H, d, J=8.7 Hz), 7.55 (2H, d, J=8.1 Hz), 7.74 (2H, d, J=8.7 Hz).

Example 156

Preparation of the Compound 156

(1) Preparation of the Intermediate 156(1).

The title compound was obtained in the same manner as the Example 123(1) using the following starting materials.

Starting materials: the intermediate 126(1) and benzyl chloride; Yield: 60.2% (colorless oil).

$^1$H-NMR ($CDCl_3$) δ: 3.59 (3H, s), 4.92 (2H, s), 6.89-6.94 (2H, m), 7.18-7.23 (2H, m), 7.26-7.30 (3H, m), 7.40-7.45 (2H, m).

(2) Preparation of the Intermediate 156(2).

The title compound was obtained in the same manner as the Example 123(3) using the following starting materials.

Starting materials: the intermediate 156(1) and 4-(tert-butyl)phenylboronic acid; Yield: 86.5% (yellow oil).

$^1$H-NMR ($CDCl_3$) δ: 1.35 (9H, s), 3.56 (3H, s), 4.97 (2H, s), 7.09-7.12 (2H, m), 7.23-7.31 (4H, m), 7.43-7.54 (7H, m).

(3) Preparation of the Compound 156.

The title compound was obtained in the same manner as the Example 126(4) using the following starting material.

Starting material: the intermediate 156(2); Yield: 65.9% (white solid).

$^1$H-NMR (DMSO-$d_6$) δ: 1.30 (9H, s), 4.95 (2H, s), 7.22-7.36 (7H, m), 7.45 (2H, d, J=8.4 Hz), 7.53-7.56 (4H, m).

Example 157

Preparation of the Compound 157

(1) Preparation of the Intermediate 157(1).

The title compound was obtained in the same manner as the Example 123(3) using the following starting materials.

Starting materials: 2-bromoaniline and 4-(trifluoromethoxy)phenylboronic acid; Yield: 83% (reddish brown solid).

$^1$H-NMR ($CDCl_3$) δ: 3.77 (2H, brs), 6.78 (1H, dd, J=1.2, 9.0 Hz), 6.84 (1H, dt, J=1.2, 7.5 Hz), 7.10 (1H, dd, J=1.5, 7.5 Hz), 7.15-7.21 (1H, m), 7.27-7.32 (2H, m), 7.45-7.52 (2H, m).

(2) Preparation of the Intermediate 157(2).

A mixture of the intermediate 157(1) (633 mg, 2.50 mmol), 1-bromo-4-(tert-butyl)benzene (533 mg, 2.50 mmol), rac-2,2'-bis(diphenylphosphino)-1,1'-binaphthyl (124 mg, 0.2 mmol), bis(dibenzylideneacetone)palladium(0) (72 mg, 0.125 mmol), potassium tert-butoxide (1.68 g, 15.0 mmol) and toluene (10 ml) was stirred at 60° C. for 5 hours under argon atmosphere. After the reaction mixture was cooled to room temperature, a saturated aqueous solution of ammonium chloride was added. The mixture was filtered through Celite, and the filtrate was extracted with ethyl acetate. The residue obtained by evaporation of the solvent under reduced pressure was purified by column chromatography on silica gel (n-hexane:ethyl acetate=5:1) to give the title compound (857 mg, 89%) as a brown oil.

$^1$H-NMR ($CDCl_3$) δ: 1.31 (9H, s), 5.44 (1H, s), 6.93-7.04 (3H, m), 7.18-7.38 (7H, m), 7.46-7.52 (2H, m).

(3) Preparation of the Intermediate 157(3).

The title compound was obtained in the same manner as the Example 125(3) using the following starting materials.

Starting materials: the intermediate 157(2) and methyl chloroglyoxylate; Yield: 44% (white solid).

This compound was obtained as a mixture of the rotational isomers.

Major isomer: $^1$H-NMR ($CDCl_3$) δ: 1.19 (9H, s), 3.71 (3H, s), 6.53-6.59 (2H, m), 7.00-7.11 (3H, m), 7.13-7.24 (3H, m), 7.29-7.36 (1H, m), 7.39-7.51 (3H, m).

Minor isomer: $^1$H-NMR ($CDCl_3$) δ: 1.21 (9H, s), 3.58 (3H, s), 6.58-6.65 (2H, m), 7.00-7.11 (3H, m), 7.13-7.24 (3H, m), 7.29-7.36 (1H, m), 7.39-7.51 (3H, m).

(4) Preparation of the Compound 157.

The title compound was obtained in the same manner as the Example 126(4) using the following starting material.

Starting material: the intermediate 157(3); Yield: 94% (pale brown solid).

This compound was obtained as a mixture of the rotational isomers.

Major isomer: $^1$H-NMR (DMSO-$d_6$) δ: 1.15 (9H, s), 6.48-6.56 (2H, m), 7.00-7.62 (10H, m), 14.21 (1H, brs).

Minor isomer: $^1$H-NMR (DMSO-$d_6$) δ: 1.18 (9H, s), 6.67-6.73 (2H, m), 7.00-7.62 (10H, m), 14.21 (1H, brs).

Example 158

Preparation of the Compound 158

(1) Preparation of the Intermediate 158(1).

The title compound was obtained in the same manner as the Example 123(3) using the following starting materials.

Starting materials: 3-bromoaniline and 4-(trifluoromethoxy)phenylboronic acid; Yield: 83% (pale yellow oil).

$^1H$-NMR ($CDCl_3$) δ: 3.76 (2H, brs), 6.70 (1H, ddd, J=1.8, 2.1, 8.1 Hz), 6.86 (1H, dd, J=1.8, 2.1 Hz), 6.94 (1H, ddd, J=0.9, 1.8, 7.5 Hz), 7.20-7.29 (3H, m), 7.53-7.59 (2H, m).

(2) Preparation of the Intermediate 158(2).

The title compound was obtained in the same manner as the Example 157(2) using the following starting materials.

Starting materials: the intermediate 158(1) and 1-bromo-4-(tert-butyl)benzene; Yield: 90% (brown oil).

$^1H$-NMR ($CDCl_3$) δ: 1.32 (9H, s), 5.73 (1H, s), 7.00-7.11 (3H, m), 7.17-7.35 (7H, m), 7.54-7.60 (2H, m).

(3) Preparation of the Intermediate 158(3).

The title compound was obtained in the same manner as the Example 125(3) using the following starting materials.

Starting materials: the intermediate 158(2) and methyl chloroglyoxylate; Yield: 73% (pale brown solid).

This compound was obtained as a mixture of the rotational isomers.

Major isomer: $^1H$-NMR ($CDCl_3$) δ: 1.31 (9H, s), 3.61 (3H, s), 7.20-7.34 (5H, m), 7.36-7.62 (7H, m).

Minor isomer: $^1H$-NMR ($CDCl_3$) δ: 1.30 (9H, s), 3.62 (3H, s), 7.20-7.34 (5H, m), 7.36-7.62 (7H, m).

(4) Preparation of the Compound 158.

The title compound was obtained in the same manner as the Example 126(4) using the following starting material.

Starting material: the intermediate 158(3); Yield: 71% (white solid).

This compound was obtained as a mixture of the rotational isomers.

$^1H$-NMR (DMSO-$d_6$) δ: 1.27 (9H, s), 7.17-7.31 (7H, m), 7.35-7.58 (5H, m), 14.17 (1H, brs).

Example 159

Preparation of the Compound 159

(1) Preparation of the Intermediate 159(1).

The title compound was obtained in the same manner as the Example 125(4) using the following starting materials.

Starting materials: the intermediate 125(3) and 4-(trifluoromethoxy)benzyl bromide; Yield: 81.5% (colorless oil).

$^1H$-NMR ($CDCl_3$) δ: 3.60 (3H, s), 4.98 (2H, s), 7.10-7.21 (4H, m), 7.24-7.35 (4H, m), 7.48-7.62 (4H, m).

(2) Preparation of the Compound 159.

The title compound was obtained in the same manner as the Example 126(4) using the following starting material.

Starting material: the intermediate 159(1); Yield: 72.6% (white solid).

$^1H$-NMR (DMSO-$d_6$) δ: 4.98 (2H, s), 7.20-7.67 (10H, m), 7.67-7.81 (2H, m).

Example 160

Preparation of the Compound 160

(1) Preparation of the Intermediate 160(1).

The title compound was obtained in the same manner as the Example 125(4) using the following starting materials.

Starting materials: the intermediate 125(3) and 4-(methylsulfanyl)benzyl chloride; Yield: 34.3% (colorless oil).

$^1H$-NMR ($CDCl_3$) δ: 2.64 (3H, s), 3.58 (3H, s), 4.93 (2H, s), 7.09-7.21 (6H, m), 7.24-7.33 (2H, m), 7.46-7.61 (4H, m).

(2) Preparation of the Compound 160.

The title compound was obtained in the same manner as the Example 126(4) using the following starting material.

Starting material: the intermediate 160(1); Yield: 97.9% (white solid).

$^1H$-NMR (DMSO-$d_6$) δ: 2.42 (3H, m), 4.90 (2H, s), 7.06-7.50 (8H, m), 7.57 (2H, d, J=8.5 Hz), 7.74 (2H, d, J=8.5 Hz).

Example 161

Preparation of the Compound 161

(1) Preparation of the Intermediate 161(1).

The title compound was obtained in the same manner as the Example 125(4) using the following starting materials.

Starting materials: the intermediate 125(3) and 4-phenylbenzyl bromide; Yield: 45.6% (white solid).

$^1H$-NMR ($CDCl_3$) δ: 3.60 (3H, s), 5.02 (2H, s), 7.13-7.22 (2H, m), 7.22-7.64 (15H, m).

(2) Preparation of the Compound 161.

The title compound was obtained in the same manner as the Example 126(4) using the following starting material.

Starting material: the intermediate 161(1); Yield: 87.9% (white solid).

$^1H$-NMR (DMSO-$d_6$) δ: 5.00 (2H, s), 7.26-7.52 (9H, m), 7.52-7.70 (6H, m), 7.75 (2H, d, J=9.0 Hz).

Example 162

Preparation of the Compound 162

(1) Preparation of the Intermediate 162(1).

The title compound was obtained in the same manner as the Example 125(4) using the following starting materials.

Starting materials: the intermediate 126(1) and 4-(trifluoromethoxy)benzyl bromide; Yield: 91.8% (colorless oil).

$^1H$-NMR ($CDCl_3$) δ: 3.60 (3H, s), 4.91 (2H, s), 6.87-6.97 (2H, m), 7.08-7.19 (2H, m), 7.19-7.32 (2H, m), 7.40-7.53 (2H, m).

(2) Preparation of the Intermediate 162(2).

The title compound was obtained in the same manner as the Example 123(3) using the following starting materials.

Starting materials: the intermediate 162(1) and 4-(tert-butyl)phenylboronic acid; Yield: 28.5% (white solid).

$^1H$-NMR ($CDCl_3$) δ: 1.35 (9H, s), 3.57 (3H, s), 4.97 (2H, s), 7.01-7.20 (4H, m), 7.22-7.35 (2H, m), 7.38-7.60 (6H, m).

(3) Preparation of the Compound 162.

The title compound was obtained in the same manner as the Example 126(4) using the following starting material.

Starting material: the intermediate 162(2); Yield: 93.5% (white solid).

$^1H$-NMR (DMSO-$d_6$) δ: 1.30 (9H, s), 4.94 (2H, s), 7.20-7.66 (12H, m).

Example 163

Preparation of the Compound 163

(1) Preparation of the Intermediate 163(1).

The title compound was obtained in the same manner as the Example 123(3) using the following starting materials.

Starting materials: the intermediate 126(2) and 4-(tert-butyl)phenylboronic acid; Yield: 99.9% (yellow oil).

$^1H$-NMR ($CDCl_3$) δ: 1.30 (9H, s), 1.35 (9H, s), 3.56 (3H, s), 4.94 (2H, s), 7.13 (2H, d, J=8.7 Hz), 7.18 (2H, d, J=8.1 Hz), 7.30-7.33 (2H, m), 7.42-7.54 (6H, m).

(2) Preparation of the Compound 163.

The title compound was obtained in the same manner as the Example 126(4) using the following starting material.

Starting material: the intermediate 163(1); Yield: 62.8% (white solid).

$^1H$-NMR (DMSO-$d_6$) δ: 1.23 (9H, s), 1.30 (9H, s), 4.89 (2H, s), 7.14-7.37 (6H, m), 7.42-7.55 (6H, m).

Example 164

Preparation of the Compound 164

(1) Preparation of the Intermediate 164(1).

The title compound was obtained in the same manner as the Example 123(3) using the following starting materials.

Starting materials: the intermediate 126(2) and 4-butylphenylboronic acid; Yield: 99.9% (yellow oil).

$^1$H-NMR ($CDCl_3$) δ: 0.93 (3H, t, J=7.2 Hz), 1.30 (9H, s), 1.54-1.62 (4H, m), 2.65 (2H, t, J=8.1 Hz), 3.57 (3H, s), 4.94 (2H, s), 7.11-7.14 (2H, m), 7.17-7.20 (2H, m), 7.23-7.27 (2H, m), 7.29-7.33 (2H, m), 7.42-7.49 (2H, m), 7.50-7.73 (2H, m).

(2) Preparation of the Compound 164.

The title compound was obtained in the same manner as the Example 126(4) using the following starting material.

Starting material: the intermediate 164(1); Yield: 56.7% (white solid).

$^1$H-NMR (DMSO-$d_6$) δ: 0.90 (3H, t, J=7.2 Hz), 1.24-1.37 (11H, m), 1.52-1.62 (2H, m), 2.59 (2H, d, J=2.7 Hz), 4.90 (2H, s), 7.15-7.35 (8H, m), 7.51-7.57 (4H, m).

Example 165

Preparation of the Compound 165

(1) Preparation of the Intermediate 165(1).

The title compound was obtained in the same manner as the Example 157(2) using the following starting materials.

Starting materials: the intermediate 132(1) and 1-bromo-4-(tert-butyl)benzene; Yield: 69% (brown solid).

$^1$H-NMR ($CDCl_3$) δ: 1.31 (9H, s), 5.59 (1H, brs), 6.91-7.08 (8H, m), 7.12-7.19 (2H, m), 7.27-7.33 (2H, m).

(2) Preparation of the Intermediate 165(2).

The title compound was obtained in the same manner as the Example 125(3) using the following starting materials.

Starting materials: the intermediate 165(1) and methyl chloroglyoxylate; Yield: 90% (pale brown oil).

This compound was obtained as a mixture of the rotational isomers.

Major isomer: $^1$H-NMR ($CDCl_3$) δ: 1.32 (9H, s), 3.60 (3H, s), 6.96-7.07 (4H, m), 7.16-7.32 (6H, m), 7.36-7.44 (2H, m).

Minor isomer: $^1$H-NMR ($CDCl_3$) δ: 1.30 (9H, s), 3.66 (3H, s), 6.96-7.07 (4H, m), 7.16-7.32 (6H, m), 7.36-7.44 (2H, m).

(3) Preparation of the Compound 165.

The title compound was obtained in the same manner as the Example 126(4) using the following starting material.

Starting material: the intermediate 165(2); Yield: 83% (white solid).

This compound was obtained as a mixture of the rotational isomers.

Major isomer: $^1$H-NMR (DMSO-$d_6$) δ: 1.28 (9H, s), 7.05-7.19 (4H, m), 7.19-7.50 (8H, m), 14.15 (1H, brs).

Minor isomer: $^1$H-NMR (DMSO-$d_6$) δ: 1.26 (9H, s), 6.93-7.06 (4H, m), 7.19-7.50 (8H, m), 14.15 (1H, brs).

Example 166

Preparation of the Compound 166

(1) Preparation of the Intermediate 166(1).

The title compound was obtained in the same manner as the Example 123(1) using the following starting materials.

Starting materials: 4-bromo-3-(trifluoromethyl)aniline and 4-(tert-butyl)benzyl bromide; Yield: 64.3% (yellow oil).

$^1$H-NMR ($CDCl_3$) δ: 1.31 (9H, s), 4.28 (2H, s), 4.59 (1H, brs), 6.61 (1H, dd, J=2.7, 9.0 Hz), 6.95 (1H, d, J=2.7 Hz), 7.26-7.28 (2H, m), 7.34-7.43 (3H, m).

(2) Preparation of the Intermediate 166(2).

The title compound was obtained in the same manner as the Example 125(3) using the following starting materials.

Starting materials: the intermediate 166(1) and methyl chloroglyoxylate; Yield: 76.5% (colorless oil).

$^1$H-NMR ($CDCl_3$) δ: 1.29 (9H, s), 3.60 (3H, s), 4.91 (2H, s), 7.08-7.13 (3H, m), 7.31-7.34 (3H, m), 7.65 (1H, d, J=8.7 Hz).

(3) Preparation of the Intermediate 166(3).

The title compound was obtained in the same manner as the Example 123(3) using the following starting materials.

Starting materials: the intermediate 166(2) and 4-(trifluoromethoxy)phenylboronic acid; Yield: 8.8% (colorless oil).

$^1$H-NMR ($CDCl_3$) δ: 1.30 (9H, s), 3.65 (3H, s), 4.98 (2H, s), 6.81-6.84 (2H, m), 7.05-7.11 (2H, m), 7.16-7.41 (7H, m).

(4) Preparation of the Compound 166.

The title compound was obtained in the same manner as the Example 126(4) using the following starting material.

Starting material: the intermediate 166(3); Yield: 62.7% (white solid).

$^1$H-NMR (DMSO-$d_6$) δ: 1.24 (9H, s), 4.93 (2H, s), 7.18-7.24 (2H, m), 7.30-7.35 (3H, m), 7.40-7.44 (4H, m), 7.58-7.61 (1H, m), 7.73 (1H, brs).

Example 167

Preparation of the Compound 167

(1) Preparation of the Intermediate 167(1).

Methanesulfonyl chloride (3.069 g, 26.791 mmol) was added to a solution of 4-butylbenzyl alcohol (4.000 g, 24.355 mmol) in dichloromethane (120 mL) at 0° C. under argon atmosphere. Triethylamine (2.711 g, 26.791 mmol) was added dropwise at a slow speed to this mixture, and the mixture was stirred at room temperature overnight. The solvent was evaporated under reduced pressure, and the residue was diluted with ethyl acetate. The organic layer was washed with saturated brine, and dried over anhydrous sodium sulfate. The residue obtained by evaporation of the solvent under reduced pressure was purified by column chromatography on silica gel (n-hexane) to give the title compound (3.64 g, 82%) as a colorless oil.

$^1$H-NMR ($CDCl_3$) δ: 0.92 (3H, t, J=7.5 Hz), 1.35 (2H, sext, J=7.5 Hz), 1.52-1.64 (2H, m), 2.60 (2H, t, J=7.5 Hz), 4.57 (2H, s), 7.15-7.18 (2H, m), 7.25-7.30 (2H, m).

(2) Preparation of the Intermediate 167(2).

The title compound was obtained in the same manner as the Example 123(1) using the following starting materials.

Starting materials: the intermediate 125(3) and the intermediate 167(1); Yield: 83.6% (colorless oil).

$^1$H-NMR ($CDCl_3$) δ: 0.89-0.95 (3H, m), 1.30-1.39 (2H, m), 1.52-1.57 (2H, m), 2.58 (2H, t, J=7.8 Hz), 3.58 (3H, s), 4.94 (2H, s), 7.09-7.16 (6H, m), 7.26-7.30 (2H, m), 7.47-7.51 (2H, m), 7.54-7.60 (2H, m).

(3) Preparation of the Compound 167.

The title compound was obtained in the same manner as the Example 126(4) using the following starting material.

Starting material: the intermediate 167(2); Yield: 84.2% (pale pink solid).

$^1$H-NMR (DMSO-$d_6$) δ: 0.87 (3H, t, J=4.5 Hz), 1.20-1.33 (2H, m), 1.45-1.50 (2H, m), 3.30-3.37 (2H, m), 4.87 (2H, s), 7.06-7.22 (4H, m), 7.34 (2H, d, J=8.1 Hz), 7.41 (2H, d, J=8.1 Hz), 7.54 (2H, d, J=8.4 Hz), 7.71-7.76 (2H, m).

Example 168

Preparation of the Compound 168

(1) Preparation of the Intermediate 168(1).

The title compound was obtained in the same manner as the Example 123(3) using the following starting materials.

Starting materials: 2-bromo-5-(trifluoromethyl)aniline and 4-(trifluoromethoxy)phenylboronic acid; Yield: 99% (white solid).

$^1$H-NMR ($CDCl_3$) δ: 4.02 (2H, brs), 6.78 (1H, d, J=8.7 Hz), 7.29-7.36 (3H, m), 7.37-7.44 (1H, m), 7.44-7.51 (2H, m).

(2) Preparation of the Intermediate 168(2).

The title compound was obtained in the same manner as the Example 125(3) using the following starting materials.

Starting materials: the intermediate 168(1) and methyl chloroglyoxylate; Yield: 99% (white solid).

$^1$H-NMR ($CDCl_3$) δ: 3.92 (3H, s), 7.38-7.47 (5H, m), 7.50-7.56 (1H, m), 8.76-8.79 (1H, m), 9.02 (1H, brs).

(3) Preparation of the Intermediate 168(3).

The title compound was obtained in the same manner as the Example 125(4) using the following starting materials.

Starting materials: the intermediate 168(2) and 4-(tert-butyl)benzyl bromide; Yield: 73% (white solid).

This compound was obtained as a mixture of the rotational isomers.

Major isomer: $^1$H-NMR ($CDCl_3$) δ: 1.25 (9H, s), 3.43 (1H, d, J=14.4 Hz), 3.66 (3H, s), 5.20 (1H, d, J=14.4 Hz), 6.82-6.98 (3H, m), 7.16-7.58 (2H, m), 7.32-7.40 (2H, m), 7.51 (1H, d, J=7.8 Hz), 7.60-7.69 (3H, m).

Minor isomer: $^1$H-NMR ($CDCl_3$) δ: 1.27 (9H, s), 3.43 (1H, d, J=14.4 Hz), 3.90 (3H, s), 5.20 (1H, d, J=14.4 Hz), 6.82-7.69 (11H, m).

(4) Preparation of the Compound 168.

The title compound was obtained in the same manner as the Example 126(4) using the following starting material.

Starting material: the intermediate 168(3); Yield: 93% (white solid).

This compound was obtained as a mixture of the rotational isomers.

Major isomer: $^1$H-NMR (DMSO-$d_6$) δ: 1.21 (9H, s), 3.42 (1H, d, J=14.4 Hz), 5.03 (1H, d, J=14.4 Hz), 6.83-6.94 (2H, m), 7.00-7.09 (1H, m), 7.15-7.44 (3H, m), 7.60-7.87 (5H, m), 14.67 (1H, brs).

Minor isomer: $^1$H-NMR (DMSO-$d_6$) δ: 1.22 (9H, s), 4.01-4.18 (1H, m), 4.57-4.70 (1H, m), 6.84-7.87 (11H, m), 14.67 (1H, brs).

Example 169

Preparation of the Compound 169

(1) Preparation of the Intermediate 169(1).

The title compound was obtained in the same manner as the Example 123(3) using the following starting materials.

Starting materials: 2-bromo-4-(trifluoromethyl)aniline and 4-(trifluoromethoxy)phenylboronic acid; Yield: 98% (pale brown oil).

$^1$H-NMR ($CDCl_3$) δ: 4.02 (2H, brs), 6.78 (1H, d, J=8.7 Hz), 7.29-7.36 (3H, m), 7.37-7.44 (1H, m), 7.44-7.51 (2H, m).

(2) Preparation of the Intermediate 169(2).

The title compound was obtained in the same manner as the Example 125(3) using the following starting materials.

Starting materials: the intermediate 169(1) and methyl chloroglyoxylate; Yield: 94% (white solid).

$^1$H-NMR ($CDCl_3$) δ: 3.92 (3H, s), 7.38-7.50 (4H, m), 7.54-7.58 (1H, m), 7.67-7.75 (1H, m), 8.63 (1H, d, J=8.4 Hz), 9.08 (1H, brs).

(3) Preparation of the Intermediate 169(3).

The title compound was obtained in the same manner as the Example 125(4) using the following starting materials.

Starting materials: the intermediate 169(2) and 4-(tert-butyl)benzyl bromide; Yield: 84% (white solid).

This compound was obtained as a mixture of the rotational isomers.

Major isomer: $^1$H-NMR ($CDCl_3$) δ: 1.26 (9H, s), 3.50 (1H, d, J=14.4 Hz), 3.67 (3H, s), 5.14 (1H, d, J=14.4 Hz), 6.85-7.00 (3H, m), 7.15-7.51 (5H, m), 7.55-7.67 (3H, m).

Minor isomer: $^1$H-NMR ($CDCl_3$) δ: 1.28 (9H, s), 3.50 (1H, d, J=14.4 Hz), 3.88 (3H, s), 5.14 (1H, d, J=14.4 Hz), 6.85-7.67 (11H, m).

(4) Preparation of the Compound 169.

The title compound was obtained in the same manner as the Example 126(4) using the following starting material.

Starting material: the intermediate 169(3); Yield: 94% (white solid).

This compound was obtained as a mixture of the rotational isomers.

Major isomer: $^1$H-NMR (DMSO-$d_6$) δ: 1.22 (9H, s), 3.42 (1H, d, J=14.7 Hz), 4.91 (1H, d, J=14.7 Hz), 6.89-6.98 (2H, m), 7.17-7.42 (3H, m), 7.51-7.59 (2H, m), 7.70-7.86 (4H, m), 14.48 (1H, brs).

Minor isomer: $^1$H-NMR (DMSO-$d_6$) δ: 1.23 (9H, s), 4.12-4.30 (1H, m), 4.47-4.70 (1H, m), 6.89-7.86 (11H, m), 14.48 (1H, brs).

Example 170

Preparation of the Compound 170

(1) Preparation of the Intermediate 170(1).

The title compound was obtained in the same manner as the Example 132(1) using the following starting materials.

Starting materials: 1,3-dinitrobenzene and 4-(trifluoromethoxy)phenol; Yield: 74% (pale yellow oil).

$^1$H-NMR ($CDCl_3$) δ: 7.05-7.11 (2H, m), 7.23-7.30 (2H, m), 7.33 (1H, ddd, J=0.9, 2.4, 8.4 Hz), 7.52 (1H, t, J=8.4 Hz), 7.82 (1H, t, J=2.4 Hz), 7.98 (1H, ddd, J=0.9, 2.4, 8.4 Hz).

(2) Preparation of the Intermediate 170(2).

The title compound was obtained in the same manner as the Example 125(2) using the following starting material.

Starting material: the intermediate 170(1); Yield: 98% (colorless oil).

$^1$H-NMR ($CDCl_3$) δ: 3.73 (2H, brs), 6.33 (1H, t, J=2.4 Hz), 6.39 (1H, ddd, J=0.9, 2.4, 8.1 Hz), 6.45 (1H, ddd, J=0.9, 2.4, 8.1 Hz), 6.98-7.04 (2H, m), 7.11 (1H, t, J=8.1 Hz), 7.13-7.20 (2H, m).

(3) Preparation of the Intermediate 170(3).

The title compound was obtained in the same manner as the Example 157(2) using the following starting materials.

Starting materials: the intermediate 170(2) and 1-bromo-4-(tert-butyl)benzene; Yield: 69% (orange oil).

$^1$H-NMR ($CDCl_3$) δ: 1.30 (9H, s), 5.69 (1H, brs), 6.48 (1H, ddd, J=0.9, 2.1, 8.4 Hz), 6.69 (1H, t, J=2.4 Hz), 6.76 (1H, ddd, J=0.9, 2.4, 8.4 Hz), 6.98-7.06 (4H, m), 7.13-7.22 (3H, m), 7.27-7.32 (2H, m).

(4) Preparation of the Intermediate 170(4).

The title compound was obtained in the same manner as the Example 125(3) using the following starting materials.

Starting materials: the intermediate 170(3) and methyl chloroglyoxylate; Yield: 84% (pale yellow solid).

This compound was obtained as a mixture of the rotational isomers.

Major isomer: $^1$H-NMR ($CDCl_3$) δ: 1.31 (9H, m), 3.58 (3H, s), 6.87-7.25 (9H, m), 7.29-7.44 (3H, m).

Minor isomer: $^1$H-NMR ($CDCl_3$) δ: 1.31 (9H, m), 3.66 (3H, s), 6.87-7.25 (9H, m), 7.29-7.44 (3H, m).

(5) Preparation of the Compound 170.

The title compound was obtained in the same manner as the Example 126(4) using the following starting material.

Starting material: the intermediate 170(4); Yield: 94% (white solid).

This compound was obtained as a mixture of the rotational isomers.

$^1$H-NMR (DMSO-$d_6$) δ: 1.27 (9H, s), 6.90-7.35 (6H, m), 7.36-7.50 (6H, m), 14.24 (1H, brs).

Example 171

Preparation of the Compound 171

(1) Preparation of the Intermediate 171(1).

The title compound was obtained in the same manner as the Example 123(1) using the following starting materials.

Starting materials: 4-bromoaniline and 2,6-dichlorobenzyl chloride; Yield: 41.0% (white solid).

$^1$H-NMR ($CDCl_3$) δ: 4.02 (1H, brs), 4.55 (2H, s), 6.62-6.67 (2H, m), 7.15-7.21 (1H, m), 7.24-7.29 (2H, m), 7.33 (2H, d, J=7.8 Hz).

(2) Preparation of the Intermediate 171(2).

The title compound was obtained in the same manner as the Example 123(3) using the following starting materials.

Starting materials: the intermediate 171(1) and 4-(trifluoromethoxy)phenylboronic acid; Yield: 36.3% (white solid).

$^1$H-NMR ($CDCl_3$) δ: 4.13 (1H, brs), 4.64 (2H, s), 6.82-6.86 (2H, m), 7.16-7.25 (3H, m), 7.34 (2H, d, J=7.8 Hz), 7.40-7.45 (2H, m), 7.50-7.55 (2H, m).

(3) Preparation of the Intermediate 171(3).

The title compound was obtained in the same manner as the Example 125(3) using the following starting materials.

Starting materials: the intermediate 171(2) and methyl chloroglyoxylate; Yield: 99.9% (colorless oil).

$^1$H-NMR ($CDCl_3$) δ: 3.56 (3H, s), 5.38 (2H, s), 7.06-7.12 (1H, m), 7.15-7.22 (4H, m), 7.25-7.27 (2H, m), 7.38-7.42 (2H, m), 7.51-7.55 (2H, m).

(4) Preparation of the Compound 171.

The title compound was obtained in the same manner as the Example 126(4) using the following starting material.

Starting material: the intermediate 171(3); Yield: 67.8% (white solid).

$^1$H-NMR (DMSO-$d_6$) δ: 5.24 (2H, s), 7.23-7.27 (3H, m), 7.35-7.42 (4H, m), 7.57 (2H, d, J=8.1 Hz), 7.72 (2H, d, J=8.4 Hz).

Example 172

Preparation of the Compound 172

(1) Preparation of the Intermediate 172(1).

The title compound was obtained in the same manner as the Example 125(3) using the following starting materials.

Starting materials: the intermediate 170(2) and methyl chloroglyoxylate; Yield: 71% (white solid).

$^1$H-NMR ($CDCl_3$) δ: 3.97 (3H, s), 6.80-6.88 (1H, m), 7.00-7.07 (2H, m), 7.17-7.24 (2H, m), 7.33-7.42 (3H, m), 8.84 (1H, brs).

(2) Preparation of the Intermediate 172(2).

The title compound was obtained in the same manner as the Example 125(4) using the following starting materials.

Starting materials: the intermediate 172(1) and 4-(tert-butyl)benzyl bromide; Yield: 93% (colorless oil).

$^1$H-NMR ($CDCl_3$) δ: 1.29 (9H, s), 3.60 (3H, s), 4.90 (2H, s), 6.73 (1H, t, J=2.4 Hz), 6.84-6.98 (4H, m), 7.11-7.23 (4H, m), 7.25-7.32 (3H, m).

(3) Preparation of the Compound 172.

The title compound was obtained in the same manner as the Example 126(4) using the following starting material.

Starting material: the intermediate 172(2); Yield: 90.8% (colorless oil).

$^1$H-NMR (DMSO-$d_6$) δ: 1.23 (9H, s), 4.88 (2H, s), 6.88 (1H, brs), 6.95-7.12 (6H, m), 7.30 (2H, d, J=7.8 Hz), 7.35-7.40 (3H, m).

Example 173

Preparation of the Compound 173

(1) Preparation of the Intermediate 173(1).

The title compound was obtained in the same manner as the Example 123(1) using the following starting materials.

Starting materials: 4-bromo-2,6-dichloroaniline and 4-(tert-butyl)benzyl bromide; Yield: 20.2% (red oil).

$^1$H-NMR ($CDCl_3$) δ: 1.31 (9H, s), 4.23 (1H, brs), 4.44 (2H, s), 7.29-7.38 (6H, m).

(2) Preparation of the Intermediate 173(2).

The title compound was obtained in the same manner as the Example 123(3) using the following starting materials.

Starting materials: the intermediate 173(1) and 4-(trifluoromethoxy)phenylboronic acid; Yield: 42.3% (white solid).

$^1$H-NMR ($CDCl_3$) δ: 1.33 (9H, s), 4.34 (1H, brs), 4.52 (2H, s), 7.25-7.29 (2H, m), 7.34-7.41 (4H, m), 7.45 (2H, s), 7.50-7.53 (2H, m).

(3) Preparation of the Intermediate 173(3).

The title compound was obtained in the same manner as the Example 125(3) using the following starting materials.

Starting materials: the intermediate 173(2) and methyl chloroglyoxylate; Yield: 99.9% (colorless oil).

$^1$H-NMR ($CDCl_3$) δ: 1.27 (9H, s), 3.68 (3H, s), 4.93 (2H, s), 7.16-7.20 (2H, m), 7.22-7.26 (2H, m), 7.29-7.33 (2H, m), 7.49 (2H, s), 7.55-7.58 (2H, m).

(4) Preparation of the Compound 173.

The title compound was obtained in the same manner as the Example 126(4) using the following starting material.

Starting material: the intermediate 173(3); Yield: 31.3% (pale orange solid).

This compound was obtained as a mixture of the rotational isomers.

Major isomer: $^1$H-NMR (DMSO-$d_6$) δ: 1.22 (9H, s), 4.80 (2H, s), 7.17-7.29 (4H, m), 7.44-7.47 (2H, m), 7.76-7.77 (2H, m), 7.86 (2H, d, J=8.4 Hz).

Minor isomer: $^1$H-NMR (DMSO-$d_6$) δ: 1.22 (9H, s), 4.73 (2H, s), 7.17-7.29 (4H, m), 7.44-7.47 (2H, m), 7.76-7.77 (2H, m), 7.86 (2H, d, J=8.4 Hz).

Example 174

Preparation of the Compound 174

(1) Preparation of the Intermediate 174(1).

The title compound was obtained in the same manner as the Example 132(1) using the following starting materials.

Starting materials: 4-fluoro-1-nitro-2-(trifluoromethyl) benzene and 4-(trifluoromethoxy)phenol; Yield: 88% (pale yellow oil).

$^1$H-NMR ($CDCl_3$) δ: 7.10-7.19 (3H, m), 7.29-7.36 (2H, m), 7.41 (1H, d, J=3.0 Hz), 7.98 (1H, d, J=9.0 Hz).

(2) Preparation of the Intermediate 174(2).

The title compound was obtained in the same manner as the Example 125(2) using the following starting material.

Starting material: the intermediate 174(1); Yield: 99% (gray oil).

$^1$H-NMR ($CDCl_3$) δ: 4.10 (2H, brs), 6.76 (1H, d, J=9.0 Hz), 6.88-6.94 (2H, m), 7.03 (1H, dd, J=2.7, 8.7 Hz), 7.12-7.19 (3H, m).

(3) Preparation of the Intermediate 174(3).

The title compound was obtained in the same manner as the Example 125(3) using the following starting materials.

Starting materials: the intermediate 174(2) and methyl chloroglyoxylate; Yield: 95% (white solid).

$^1$H-NMR ($CDCl_3$) δ: 4.01 (3H, s), 7.01-7.07 (2H, m), 7.18-7.27 (3H, m), 7.32 (1H, d, J=2.7 Hz), 8.26 (1H, d, J=9.0 Hz), 9.22 (1H, brs).

(4) Preparation of the Intermediate 174(4).

The title compound was obtained in the same manner as the Example 125(4) using the following starting materials.

Starting materials: the intermediate 174(3) and 4-(tert-butyl)benzyl bromide; Yield: 94% (colorless oil).

This compound was obtained as a mixture of the rotational isomers.

Major isomer: $^1$H-NMR ($CDCl_3$) δ: 1.30 (9H, s), 3.62 (3H, s), 3.65 (1H, d, J=14.4 Hz), 5.75 (1H, d, J=14.4 Hz), 6.78 (1H, d, J=9.0 Hz), 6.92 (1H, dd, J=3.0, 9.0 Hz), 7.02-7.08 (2H, m), 7.13-7.20 (2H, m), 7.21-7.37 (5H, m).

Minor isomer: $^1$H-NMR ($CDCl_3$) δ: 1.30 (9H, s), 3.94 (3H, s), 4.36 (1H, d, J=14.4 Hz), 5.11 (1H, d, J=14.4 Hz), 6.72 (1H, d, J=9.0 Hz), 6.89-6.96 (1H, m), 7.02-7.08 (2H, m), 7.13-7.20 (2H, m), 7.21-7.37 (5H, m).

(5) Preparation of the Compound 174.

The title compound was obtained in the same manner as the Example 126(4) using the following starting material.

Starting material: the intermediate 174(4); Yield: 91% (white solid).

This compound was obtained as a mixture of the rotational isomers.

Major isomer: $^1$H-NMR ($CDCl_3$) δ: 1.24 (9H, s), 4.05 (1H, d, J=14.4 Hz), 5.39 (1H, d, J=14.4 Hz), 6.99 (1H, d, J=8.4 Hz), 7.12-7.23 (5H, m), 7.30-7.36 (2H, m), 7.40-7.48 (3H, m), 14.00 (1H, brs).

Minor isomer: $^1$H-NMR ($CDCl_3$) δ: 1.23 (9H, s), 4.42 (1H, d, J=15.6 Hz), 5.03 (1H, d, J=15.6 Hz), 6.90 (1H, d, J=8.4 Hz), 7.12-7.23 (5H, m), 7.30-7.36 (2H, m), 7.40-7.48 (3H, m), 14.00 (1H, brs).

Example 175

Preparation of the Compound 175

(1) Preparation of the Intermediate 175(1).

The title compound was obtained in the same manner as the Example 132(1) using the following starting materials.

Starting materials: 1,3-dinitro-5-(trifluoromethyl)benzene and 4-(trifluoromethoxy)phenol; Yield: 75% (orange oil).

$^1$H-NMR ($CDCl_3$) δ: 7.09-7.16 (2H, m), 7.30-7.36 (2H, m), 7.57 (1H, brs), 7.95 (1H, t, J=2.1 Hz), 8.22 (1H, brs).

(2) Preparation of the Intermediate 175(2).

The title compound was obtained in the same manner as the Example 125(2) using the following starting material.

Starting material: the intermediate 175(1); Yield: 99% (pale yellow oil).

$^1$H-NMR ($CDCl_3$) δ: 3.90 (2H, brs), 6.42 (1H, t, J=2.4 Hz), 6.61 (1H, brs), 6.65 (1H, brs), 7.00-7.05 (2H, m), 7.18-7.24 (2H, m).

(3) Preparation of the Intermediate 175(3).

The title compound was obtained in the same manner as the Example 125(3) using the following starting materials.

Starting materials: the intermediate 175(2) and methyl chloroglyoxylate; Yield: 7% (pale yellow oil).

$^1$H-NMR ($CDCl_3$) δ: 3.98 (3H, s), 7.04-7.10 (3H, m), 7.22-7.29 (2H, m), 7.57-7.63 (2H, m), 8.96 (1H, brs).

(4) Preparation of the Intermediate 175(4).

The title compound was obtained in the same manner as the Example 125(4) using the following starting materials.

Starting materials: the intermediate 175(3) and 4-(tert-butyl)benzyl bromide; Yield: 85% (colorless oil).

$^1$H-NMR ($CDCl_3$) δ: 1.29 (9H, s), 3.64 (3H, s), 4.90 (2H, s), 6.86 (1H, t, J=2.1 Hz), 6.92-7.00 (2H, m), 7.02 (1H, brs), 7.07-7.14 (2H, m), 7.12 (1H, brs), 7.20-7.26 (2H, m), 7.27-7.33 (2H, m).

(5) Preparation of the Compound 175.

The title compound was obtained in the same manner as the Example 126(4) using the following starting material.

Starting material: the intermediate 175(4); Yield: 71% (white solid).

$^1$H-NMR (DMSO-$d_6$) δ: 1.23 (9H, s), 4.92 (2H, s), 7.04-7.17 (5H, m), 7.26-7.47 (6H, m), 14.45 (1H, brs).

Example 176

Preparation of the Compound 176

(1) Preparation of the Intermediate 176(1).

The title compound was obtained in the same manner as the Example 125(3) using the following starting materials.

Starting materials: 3-bromo-4-methylaniline and methyl chloroglyoxylate; Yield: 92.5% (white solid).

$^1$H-NMR ($CDCl_3$) δ: 2.38 (3H, s), 3.98 (3H, s), 7.23 (1H, d, J=8.2 Hz), 7.49 (1H, dd, J=2.2, 8.2 Hz), 7.87 (1H, d, J=2.2 Hz), 8.79 (1H, brs).

(2) Preparation of the Intermediate 176(2).

The title compound was obtained in the same manner as the Example 125(4) using the following starting materials.

Starting materials: the intermediate 176(1) and 4-(tert-butyl)benzyl bromide; Yield: 83.3% (colorless oil).

$^1$H-NMR ($CDCl_3$) δ: 1.30 (9H, s), 2.37 (3H, s), 3.61 (3H, s), 4.87 (2H, s), 6.90 (1H, dd, J=2.2, 8.2 Hz), 7.07-7.21 (3H, m), 7.27 (1H, d, J=2.2 Hz), 7.28-7.38 (2H, m).

(3) Preparation of the Intermediate 176(3).

The title compound was obtained in the same manner as the Example 123(3) using the following starting materials.

Starting materials: the intermediate 176(2) and 4-(trifluoromethoxy)phenylboronic acid; Yield: 73.9% (white solid).

$^1$H-NMR ($CDCl_3$) δ: 1.29 (9H, s), 2.23 (3H, s), 3.58 (3H, s), 4.91 (2H, s), 6.79 (1H, d, J=2.2 Hz), 7.01 (1H, dd, J=2.2, 8.0 Hz), 7.08-7.27 (7H, m), 7.27-7.37 (2H, m).

(4) Preparation of the Compound 176.

The title compound was obtained in the same manner as the Example 126(4) using the following starting material.

Starting material: the intermediate 176(3); Yield: 56.7% (white solid).

$^1$H-NMR (DMSO-$d_6$) δ: 1.23 (9H, s), 2.17 (3H, s), 4.84 (2H, s), 6.90-7.22 (4H, m), 7.22-7.33 (3H, m), 7.33-7.50 (4H, m).

Example 177

Preparation of the Compound 177

(1) Preparation of the Intermediate 177(1).

The title compound was obtained in the same manner as the Example 123(1) using the following starting materials.

Starting materials: 3-bromo-2-methylaniline and 4-(tert-butyl)benzyl bromide; Yield: 45.5% (white solid).

$^1$H-NMR ($CDCl_3$) δ: 1.32 (9H, s), 1.55 (1H, brs), 2.27 (3H, s), 4.32 (2H, s), 6.61-6.64 (1H, m), 6.94 (1H, t, J=7.8 Hz), 6.98-7.00 (1H, m), 7.28-7.31 (2H, m), 7.37-7.40 (2H, m).

(2) Preparation of the Intermediate 177(2).

The title compound was obtained in the same manner as the Example 125(3) using the following starting materials.

Starting materials: the intermediate 177(1) and methyl chloroglyoxylate; Yield: 95.2% (colorless oil).

$^1$H-NMR ($CDCl_3$) δ: 1.29 (9H, s), 2.24 (3H, s), 3.52 (3H, s), 4.24 (1H, d, J=14.1 Hz), 5.30 (1H, d, J=14.1 Hz), 6.73-6.76 (1H, m), 6.94 (1H, t, J=8.1 Hz), 7.10-7.12 (2H, m), 7.27-7.30 (2H, m), 7.52-7.55 (1H, m).

(3) Preparation of the Intermediate 177(3).

The title compound was obtained in the same manner as the Example 123(3) using the following starting materials.

Starting materials: the intermediate 177(2) and 4-(trifluoromethoxy)phenylboronic acid; Yield: 81.0% (brown oil).

This compound was obtained as a mixture of the rotational isomers.

Major isomer: $^1$H-NMR ($CDCl_3$) δ: 1.31 (9H, s), 2.02 (3H, s), 3.53 (3H, s), 4.34 (1H, d, J=13.8 Hz), 5.30 (1H, d, J=13.8 Hz), 6.85 (1H, dd, J=1.8, 8.1 Hz), 7.10-7.33 (10H, m).

Minor isomer: $^1$H-NMR ($CDCl_3$) δ: 1.29 (9H, s), 2.05 (3H, s), 3.52 (3H, s), 4.60 (1H, d, J=13.8 Hz), 4.84 (1H, d, J=13.8 Hz), 6.74 (1H, dd, J=1.8, 8.1 Hz), 6.81-6.84 (2H, m), 7.08-7.23 (7H, m), 7.54 (1H, dd, J=1.8, 8.1 Hz).

(4) Preparation of the Compound 177.

The title compound was obtained in the same manner as the Example 126(4) using the following starting material.

Starting material: the intermediate 177(3); Yield: 23.8% (white solid).

This compound was obtained as a mixture of the rotational isomers.

Major isomer: $^1$H-NMR (DMSO-$d_6$) δ: 1.26 (9H, s), 2.07 (3H, s), 4.11 (1H, d, J=14.7 Hz), 5.17 (1H, d, J=14.7 Hz), 6.89-6.93 (1H, m), 7.08-7.18 (3H, m), 7.25-7.43 (7H, m).

Minor isomer: $^1$H-NMR (DMSO-$d_6$) δ: 1.24 (9H, s), 1.73 (3H, s), 4.64 (1H, d, J=14.7 Hz), 4.90 (1H, d, J=14.7 Hz), 6.89-6.93 (1H, m), 7.08-7.18 (3H, m), 7.25-7.43 (7H, m).

Example 178

Preparation of the Compound 178

(1) Preparation of the Intermediate 178(1).

The title compound was obtained in the same manner as the Example 157(2) using the following starting materials.

Starting materials: 1,3-dibromo-5-methylbenzene and 4-(tert-butyl)benzylamine; Yield: 84.2% (yellow oil).

$^1$H-NMR ($CDCl_3$) δ: 1.32 (9H, s), 2.23 (3H, s), 3.95 (1H, brs), 4.24 (2H, s), 6.36 (1H, s), 6.60 (1H, s), 6.68 (1H, s), 7.25-7.29 (2H, m), 7.37-7.39 (2H, m).

(2) Preparation of the Intermediate 178(2).

The title compound was obtained in the same manner as the Example 123(3) using the following starting materials.

Starting materials: the intermediate 178(1) and 4-(trifluoromethoxy)phenylboronic acid; Yield: 90.9% (brown oil).

$^1$H-NMR ($CDCl_3$) δ: 1.33 (9H, s), 2.33 (3H, s), 4.03 (1H, brs), 4.33 (2H, s), 6.49 (1H, s), 6.62 (1H, s), 6.72 (1H, s), 7.22-7.25 (2H, m), 7.32 (2H, d, J=8.4 Hz), 7.39 (2H, d, J=8.4 Hz), 7.51-7.58 (2H, m).

(3) Preparation of the Intermediate 178(3).

The title compound was obtained in the same manner as the Example 125(3) using the following starting materials.

Starting materials: the intermediate 178(2) and methyl chloroglyoxylate; Yield: 89.3% (brown oil).

$^1$H-NMR ($CDCl_3$) δ: 1.30 (9H, s), 2.37 (3H, s), 3.56 (3H, s), 4.94 (2H, s), 6.90-6.95 (2H, m), 7.16-7.19 (2H, m), 7.21-7.26 (2H, m), 7.30 (1H, brs), 7.32-7.34 (2H, m), 7.38-7.41 (2H, m).

(4) Preparation of the Compound 178.

The title compound was obtained in the same manner as the Example 126(4) using the following starting material.

Starting material: the intermediate 178(3); Yield: 19.6% (white solid).

$^1$H-NMR (DMSO-$d_6$) δ: 1.27 (9H, s), 2.29 (3H, s), 4.90 (2H, s), 7.11-7.48 (3H, m), 7.26-7.43 (6H, m), 7.63-7.67 (2H, m).

Example 179

Preparation of the Compound 179

(1) Preparation of the Intermediate 179(1).

A mixture of 4-(tert-butyl)benzyl bromide (6.252 g, 27.522 mmol), 4-bromo-2-nitrophenol (5.0 g, 22.934 mmol), potassium carbonate (12.679 g, 91.736 mmol) and dimethylformamide (40 ml) was stirred at 50° C. for 3 hours under argon atmosphere. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was washed with n-hexane to give the title compound (8.1 g, 97.0%) as a white solid.

$^1$H-NMR ($CDCl_3$) δ: 1.32 (9H, s), 5.19 (2H, s), 7.02 (1H, d, J=8.7 Hz), 7.34-7.43 (4H, m), 7.58 (1H, dd, J=2.7, 8.7 Hz), 7.97 (1H, d, J=2.7 Hz).

(2) Preparation of the Intermediate 179(2).

The title compound was obtained in the same manner as the Example 123(3) using the following starting materials.

Starting materials: the intermediate 179(1) and 4-(trifluoromethoxy)phenylboronic acid; Yield: 74.6% (pale yellow oil).

$^1$H-NMR ($CDCl_3$) δ: 1.33 (9H, s), 5.26 (2H, s), 7.22 (1H, d, J=8.7 Hz), 7.28-7.58 (8H, m), 7.68 (1H, dd, J=2.4, 8.7 Hz), 8.05 (1H, d, J=2.4 Hz).

(3) Preparation of the Intermediate 179(3).

The title compound was obtained in the same manner as the Example 125(2) using the following starting material.

Starting material: the intermediate 179(2); Yield: 83.5% (pale yellow solid).

$^1$H-NMR ($CDCl_3$) δ: 1.34 (9H, s), 3.93 (2H, brs), 5.09 (2H, s), 6.87-6.97 (3H, m), 7.22-7.57 (8H, m).

(4) Preparation of the Intermediate 179(4).

The title compound was obtained in the same manner as the Example 123(1) using the following starting materials.

Starting materials: the intermediate 179(3) and benzyl bromide; Yield: 93% (yellow oil).

$^1$H-NMR ($CDCl_3$) δ: 1.41 (9H, s), 4.65-4.72 (2H, m), 4.96 (1H, brs), 5.25 (2H, s), 7.02-7.06 (1H, m), 7.15-7.25 (4H, m), 7.26-7.40 (2H, m), 7.56-7.61 (4H, m), 7.64-7.67 (4H, m), 7.89-7.91 (1H, m).

(5) Preparation of the Intermediate 179(5).

The title compound was obtained in the same manner as the Example 125(3) using the following starting materials.

Starting materials: the intermediate 179(4) and methyl chloroglyoxylate; Yield: 31% (white solid).

$^1$H-NMR ($CDCl_3$) δ: 1.35 (9H, s), 3.53 (3H, s), 4.44 (1H, d, J=14.4 Hz), 5.10 (2H, s), 5.43 (1H, d, J=14.4 Hz), 7.01-7.05 (2H, m), 7.19-7.26 (7H, m), 7.30-7.36 (4H, m), 7.41-7.45 (3H, m).

(6) Preparation of the Compound 179.

The title compound was obtained in the same manner as the Example 126(4) using the following starting material.

Starting material: the intermediate 179(5); Yield: 67% (white solid).

This compound was obtained as a mixture of the rotational isomers.

Major isomer: $^1$H-NMR (DMSO-$d_6$) δ: 1.30 (9H, s), 4.19-4.25 (1H, m), 5.21 (2H, s), 5.38-5.44 (1H, m), 7.13-7.26 (6H, m), 7.35-7.53 (10H, m).

Minor isomer: $^1$H-NMR (DMSO-$d_6$) δ: 1.30 (9H, s), 4.90-5.21 (2H, m), 5.15 (2H, s), 7.13-7.26 (6H, m), 7.35-7.53 (10H, m).

Example 180

Preparation of the Compound 180

(1) Preparation of the Intermediate 180(1).

The title compound was obtained in the same manner as the Example 125(3) using the following starting materials.

Starting materials: 2,6-dichloro-4-bromoaniline and methyl chloroglyoxylate; Yield: 93.0% (pink solid).

$^1$H-NMR ($CDCl_3$) δ: 4.01 (3H, s), 7.58 (2H, s), 8.51 (1H, brs).

(2) Preparation of the Intermediate 180(2).

The title compound was obtained in the same manner as the Example 123(1) using the following starting materials.

Starting materials: the intermediate 180(1) and benzyl bromide; Yield: 99.9% (red oil).

$^1$H-NMR ($CDCl_3$) δ: 3.69 (3H, s), 4.92 (2H, s), 7.21-7.29 (5H, m), 7.47 (2H, s).

(3) Preparation of the Intermediate 180(3).

The title compound was obtained in the same manner as the Example 123(3) using the following starting materials.

Starting materials: the intermediate 180(2) and 4-(trifluoromethoxy)phenylboronic acid; Yield: 91.6% (red oil).

$^1$H-NMR ($CDCl_3$) δ: 3.69 (3H, s), 4.98 (2H, s), 7.22-7.32 (7H, m), 7.49 (2H, s), 7.54-7.58 (2H, m).

(4) Preparation of the Compound 180.

The title compound was obtained in the same manner as the Example 126(4) using the following starting material.

Starting material: the intermediate 180(3); Yield: 94.5% (white solid).

This compound was obtained as a mixture of the rotational isomers.

Major isomer: $^1$H-NMR (DMSO-$d_6$) δ: 4.76 (2H, s), 7.17-7.22 (4H, m), 7.34-7.37 (1H, m), 7.44 (2H, d, J=8.4 Hz), 7.70-7.75 (2H, m), 7.84-7.88 (2H, m).

Minor isomer: $^1$H-NMR (DMSO-$d_6$) δ: 4.72 (2H, s), 7.17-7.22 (4H, m), 7.34-7.37 (1H, m), 7.44 (2H, d, J=8.4 Hz), 7.70-7.75 (2H, m), 7.84-7.88 (2H, m).

Example 181

Preparation of the Compound 181

(1) Preparation of the Intermediate 181(1).

The title compound was obtained in the same manner as the Example 125(4) using the following starting materials.

Starting materials: the intermediate 126(1) and 4-(chloromethyl)phenyl acetate; Yield: 43.9% (colorless oil).

$^1$H-NMR ($CDCl_3$) δ: 2.29 (3H, s), 3.59 (3H, s), 4.90 (2H, s), 6.89-6.98 (2H, m), 6.98-7.08 (2H, m), 7.18-7.26 (2H, m), 7.40-7.50 (2H, m).

(2) Preparation of the Intermediate 181(2).

The title compound was obtained in the same manner as the Example 123(3) using the following starting materials.

Starting materials: the intermediate 181(1) and 4-(trifluoromethoxy)phenylboronic acid; Yield: 26.3% (pale brown oil).

$^1$H-NMR ($CDCl_3$) δ: 2.59 (3H, s), 3.59 (3H, s), 4.96 (2H, s), 6.95-7.10 (2H, m), 7.10-7.20 (2H, m), 7.20-7.38 (4H, m), 7.42-7.67 (4H, m).

(3) Preparation of the Compound 181.

The title compound was obtained in the same manner as the Example 126(4) using the following starting material.

Starting material: the intermediate 181(2); Yield: 90.6% (white solid).

$^1$H-NMR (DMSO-$d_6$) δ: 4.79 (2H, s), 6.54-6.74 (2H, m), 6.90-7.36 (4H, m), 7.36-7.48 (2H, m), 7.48-7.65 (2H, m), 7.68-7.84 (2H, m), 9.31 (1H, s).

Example 182

Preparation of the Compound 182

(1) Preparation of the Intermediate 182(1).

4-Bromo-2-nitrophenol (1.00 g, 4.59 mmol) was added by small portions to a suspension of sodium hydride (400 mg, 9.17 mmol) in dimethylformamide (12 ml) at room temperature under argon atmosphere, and the mixture was stirred at room temperature for 30 minutes. A solution of methyl iodide (1.30 g, 9.174 mmol) in dimethylformamide (4 ml) was added to this mixture, and the mixture was stirred at room temperature for 6 hours. The reaction mixture was diluted with water and extracted with diisopropyl ether. The organic layer was washed with water and saturated brine, and dried over anhydrous sodium sulfate. The solvent was evaporated under reduced pressure to give the title compound (658 mg, 61.8%) as a pale yellow solid.

$^1$H-NMR ($CDCl_3$) δ: 3.96 (3H, s), 6.99 (1H, d, J=9.1 Hz), 7.65 (1H, dd, J=2.5, 9.1 Hz), 7.98 (1H, d, J=2.5 Hz).

(2) Preparation of the Intermediate 182(2).

The title compound was obtained in the same manner as the Example 125(2) using the following starting material.

Starting material: the intermediate 182(1); Yield: 52.1% (brown solid).

$^1$H-NMR (DMSO-$d_6$) δ: 3.74 (3H, s), 5.01 (2H, s), 6.61 (1H, dd, J=2.5, 8.5 Hz), 6.71 (1H, d, J=8.5 Hz), 6.75 (1H, d, J=2.5 Hz).

(3) Preparation of the Intermediate 182(3).

The title compound was obtained in the same manner as the Example 125(3) using the following starting materials.

Starting materials: the intermediate 182(2) and methyl chloroglyoxylate; Yield: 91.0% (pale brown solid).

$^1$H-NMR ($CDCl_3$) δ: 3.91 (3H, s), 3.98 (3H, s), 6.79 (1H, d, J=8.5 Hz), 7.25 (1H, d, J=2.5, 8.5 Hz), 8.58 (1H, d, J=2.5 Hz), 9.44 (1H, brs).

(4) Preparation of the Intermediate 182(4).

The title compound was obtained in the same manner as the Example 125(4) using the following starting materials.

Starting materials: the intermediate 182(3) and 4-(tert-butyl)benzyl bromide; Yield: 77.8% (pale yellow oil).

$^1$H-NMR ($CDCl_3$) δ: 1.29 (9H, s), 3.60 (3H, s), 3.73 (3H, s), 4.46 (1H, d, J=14.1 Hz), 5.19 (1H, d, J=14.1 Hz), 6.76 (1H, d, J=8.8 Hz), 7.01 (1H, d, J=2.5 Hz), 7.08-7.17 (2H, m), 7.25-7.33 (2H, m), 7.37 (1H, dd, J=2.5, 8.8 Hz).

(5) Preparation of the Intermediate 182(5).

The title compound was obtained in the same manner as the Example 123(3) using the following starting materials.

Starting materials: the intermediate 182(4) and 4-(trifluoromethoxy)phenylboronic acid; Yield: 36.5% (pale yellow solid).

$^1$H-NMR ($CDCl_3$) δ: 1.29 (9H, s), 3.54 (3H, s), 3.85 (3H, s), 4.30 (1H, d, J=14.1 Hz), 5.45 (1H, d, J=14.1 Hz), 6.91 (1H, d, J=2.5 Hz), 6.98 (1H, d, J=8.5 Hz), 7.08-7.22 (4H, m), 7.22-7.40 (4H, m), 7.46 (1H, dd, J=2.5, 8.5 Hz).

(6) Preparation of the Compound 182.

The title compound was obtained in the same manner as the Example 126(4) using the following starting material.

Starting material: the intermediate 182(5); Yield: 74.3% (pale orange solid).

This compound was obtained as a mixture of the rotational isomers.

Major isomer: $^1$H-NMR (DMSO-$d_6$) δ: 1.22 (9H, s), 3.83 (3H, s), 4.14-4.50 (1H, m), 5.06-5.42 (1H, m), 7.08-7.15 (2H, m), 7.15-7.22 (2H, m), 7.26-7.33 (2H, m), 7.33-7.42 (2H, m), 7.46-7.56 (2H, m), 7.59 (1H, dd, J=2.5, 8.5 Hz).

Minor isomer: $^1$H-NMR (DMSO-$d_6$) δ: 1.21 (9H, s), 3.76 (3H, s), 4.56-4.88 (2H, m), 6.90-7.64 (11H, m).

Example 183

Preparation of the Compound 183

(1) Preparation of the Intermediate 183(1).

The title compound was obtained in the same manner as the Example 123(1) using the following starting materials.

Starting materials: the intermediate 126(1) and 4-(trifluoromethoxy)benzyl chloride; Yield: 99.9% (colorless oil).

$^1$H-NMR ($CDCl_3$) δ: 3.60 (3H, s), 4.91 (2H, s), 6.90-6.95 (2H, m), 7.13-7.16 (2H, m), 7.22-7.27 (2H, m), 7.43-7.50 (2H, m).

(2) Preparation of the Intermediate 183(2).

The title compound was obtained in the same manner as the Example 123(3) using the following starting materials.

Starting materials: the intermediate 183(1) and phenylboronic acid; Yield: 80.7% (yellow oil).

$^1$H-NMR ($CDCl_3$) δ: 3.59 (3H, s), 4.97 (2H, s), 7.10-7.17 (4H, m), 7.28-7.31 (2H, m), 7.37-7.47 (3H, m), 7.54-7.58 (4H, m).

(3) Preparation of the Compound 183.

The title compound was obtained in the same manner as the Example 126(4) using the following starting material.

Starting material: the intermediate 183(2); Yield: 66.3% (white solid).

$^1$H-NMR (DMSO-$d_6$) δ: 4.93 (2H, s), 7.30-7.35 (6H, m), 7.41-7.46 (3H, m), 7.53-7.56 (2H, m), 7.60-7.63 (2H, m).

Example 184

Preparation of the Compound 184

(1) Preparation of the Intermediate 184(1).

The title compound was obtained in the same manner as the Example 123(3) using the following starting materials.

Starting materials: 4-bromo-3-methylaniline and 4-(trifluoromethoxy)phenylboronic acid; Yield: 92% (brown oil).

$^1$H-NMR ($CDCl_3$) δ: 2.20 (3H, s), 3.68 (2H, brs), 6.56-6.63 (2H, m), 7.01 (1H, d, J=8.1 Hz), 7.18-7.32 (4H, m).

(2) Preparation of the Intermediate 184(2).

The title compound was obtained in the same manner as the Example 125(3) using the following starting materials.

Starting materials: the intermediate 184(1) and methyl chloroglyoxylate; Yield: 95% (pale orange solid).

$^1$H-NMR ($CDCl_3$) δ: 2.28 (3H, s), 3.99 (3H, s), 7.20-7.36 (5H, m), 7.52-7.57 (2H, m), 8.86 (1H, brs).

(3) Preparation of the Intermediate 184(3).

The title compound was obtained in the same manner as the Example 125(4) using the following starting materials.

Starting materials: the intermediate 184(2) and 4-(tert-butyl)benzyl bromide; Yield: 93% (colorless oil).

$^1$H-NMR ($CDCl_3$) δ: 1.30 (9H, s), 2.19 (3H, s), 3.62 (3H, s), 4.94 (2H, s), 6.95 (1H, dd, J=1.8, 8.1 Hz), 7.01 (1H, d, J=1.8 Hz), 7.13 (1H, d, J=8.1 Hz), 7.17-7.36 (8H, m).

(4) Preparation of the Compound 184.

The title compound was obtained in the same manner as the Example 126(4) using the following starting material.

Starting material: the intermediate 184(3); Yield: 94% (white solid).

$^1$H-NMR (DMSO-$d_6$) δ: 1.23 (9H, s), 2.12 (3H, s), 4.92 (2H, s), 7.06-7.27 (5H, m), 7.29-7.48 (6H, m), 14.08 (1H, brs).

Example 185

Preparation of the Compound 185

(1) Preparation of the Intermediate 185(1).

The title compound was obtained in the same manner as the Example 123(3) using the following starting materials.

Starting materials: 3-bromo-4-chloro-1-nitrobenzene and 4-(trifluoromethoxy)phenylboronic acid; Yield: 99.9% (brown oil).

$^1$H-NMR ($CDCl_3$) δ: 7.33-7.36 (2H, m), 7.48-7.52 (2H, m), 7.67 (1H, d, J=8.7 Hz), 8.18 (1H, dd, J=2.7, 8.7 Hz), 8.23 (1H, d, J=2.7 Hz).

(2) Preparation of the Intermediate 185(2).

1-Propanol (284 mg, 4.72 mmol) was added dropwise at a slow speed to a suspension of sodium hydride (206 mg, 4.72 mmol) in dimethylformamide (4 ml) at 0° C. under argon atmosphere, and the mixture was stirred at room temperature for 30 minutes. A solution of the intermediate 185(1) (1.00 g, 3.15 mmol) in dimethylformamide (2 ml) was added dropwise at a slow speed to this mixture at 0° C., and the mixture was stirred at room temperature for 2 hours. The reaction mixture was diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=6:1) to give the title compound (586 mg, 54.5%) as a pale yellow solid.

$^1$H-NMR ($CDCl_3$) δ: 0.99 (3H, t, J=7.5 Hz), 1.75-1.85 (2H, m), 4.07 (2H, t, J=6.6 Hz), 7.01-7.04 (1H, m), 7.26-7.30 (2H, m), 7.55-7.60 (2H, m), 8.22-8.26 (2H, m).

(3) Preparation of the Intermediate 185(3).

The title compound was obtained in the same manner as the Example 125(2) using the following starting material.

Starting material: the intermediate 185(2); Yield: 97.7% (black oil).

$^1$H-NMR ($CDCl_3$) δ: 0.91 (3H, t, J=7.2 Hz), 1.61-1.70 (2H, m), 3.49 (2H, brs), 3.80 (2H, t, J=6.6 Hz), 6.64-6.69 (2H, m), 6.83 (1H, d, J=8.1 Hz), 7.20-7.23 (2H, m), 7.53-7.58 (2H, m).

(4) Preparation of the Intermediate 185(4).

The title compound was obtained in the same manner as the Example 123(1) using the following starting materials.

Starting materials: the intermediate 185(3) and 4-(tert-butyl)benzyl bromide; Yield: 12.0% (yellow oil).

$^1$H-NMR ($CDCl_3$) δ: 0.90 (3H, t, J=7.5 Hz), 1.32 (9H, s), 1.60-1.71 (2H, m), 3.79 (2H, t, J=6.3 Hz), 4.09-4.16 (1H, m), 4.27 (2H, s), 6.60-6.63 (2H, m), 6.86 (1H, d, J=8.7 Hz), 7.20-7.23 (2H, m), 7.30-7.33 (2H, m), 7.37-7.40 (2H, m), 7.53-7.56 (2H, m).

(5) Preparation of the Intermediate 185(5).

The title compound was obtained in the same manner as the Example 123(2) using the following starting materials.

Starting materials: the intermediate 185(4) and methyl chloroglyoxylate; Yield: 99.9% (colorless oil).

$^1$H-NMR ($CDCl_3$) δ: 0.96 (3H, t, J=7.5 Hz), 1.30 (9H, s), 1.70-1.79 (2H, m), 3.57 (3H, s), 3.89-3.94 (2H, m), 4.88 (2H, s), 6.84-6.87 (2H, m), 7.04 (1H, dd, J=2.4, 8.4 Hz), 7.15-7.19 (4H, m), 7.31-7.39 (4H, m).

(6) Preparation of the Compound 185.

The title compound was obtained in the same manner as the Example 126(4) using the following starting material.

Starting material: the intermediate 185(5); Yield: 69.8% (white solid).

$^1$H-NMR (DMSO-$d_6$) δ: 0.89 (3H, t, J=7.2 Hz), 1.24 (9H, s), 1.61-1.68 (2H, m), 3.90 (2H, t, J=6.0 Hz), 4.81 (2H, s), 6.96-7.13 (4H, m), 7.19-7.22 (1H, m), 7.28-7.37 (4H, m), 7.44-7.54 (2H, m).

Example 186

Preparation of the Compound 186

(1) Preparation of the Intermediate 186(1).

The title compound was obtained in the same manner as the Example 125(2) using the following starting material.

Starting material: the intermediate 185(1); Yield: 94.5% (yellow oil).

$^1$H-NMR ($CDCl_3$) δ: 3.89 (2H, brs), 6.61-6.65 (2H, m), 7.21-7.27 (3H, m), 7.43-7.46 (2H, m).

(2) Preparation of the Intermediate 186(2).

The title compound was obtained in the same manner as the Example 123(1) using the following starting materials.

Starting materials: the intermediate 186(1) and 4-(tert-butyl)benzyl bromide; Yield: 24.5% (brown oil).

$^1$H-NMR ($CDCl_3$) δ: 1.32 (9H, s), 4.07 (1H, brs), 4.28 (2H, s), 6.55-6.58 (2H, m), 7.22-7.30 (5H, m), 7.37-7.40 (2H, m), 7.42-7.45 (2H, m).

(3) Preparation of the Intermediate 186(3).

The title compound was obtained in the same manner as the Example 123(2) using the following starting materials.

Starting materials: the intermediate 186(2) and methyl chloroglyoxylate; Yield: 76.2% (yellow oil).

$^1$H-NMR ($CDCl_3$) δ: 1.30 (9H, s), 3.61 (3H, s), 4.91 (2H, s), 6.89 (1H, d, J=2.7 Hz), 7.05 (1H, dd, J=2.7, 8.4 Hz), 7.13-7.16 (2H, m), 7.21-7.34 (6H, m), 7.43 (1H, d, J=8.4 Hz).

(4) Preparation of the Compound 186.

The title compound was obtained in the same manner as the Example 126(4) using the following starting material.

Starting material: the intermediate 186(3); Yield: 76.5% (white solid).

$^1$H-NMR (DMSO-$d_6$) δ: 1.23 (9H, s), 4.91 (2H, s), 7.10-7.18 (2H, m), 7.22-7.33 (4H, m), 7.43-7.54 (5H, m).

Example 187

Preparation of the Compound 187

(1) Preparation of the Intermediate 187(1).

A mixture of 2-methyl-5-nitrophenol (765 mg, 5.00 mmol), 4-(trifluoromethoxy)phenylboronic acid (1.24 g, 6.00 mmol), copper(II) acetate (999 mg, 5.50 mmol), triethylamine (3.48 ml, 25.0 mmol), molecular sieves 4A and dichloromethane (20.0 ml) was stirred at room temperature overnight under argon atmosphere. The reaction mixture was filtered through Celite. The residue obtained by evaporation of the solvent of the filtrate under reduced pressure was purified by column chromatography on silica gel (n-hexane:ethyl acetate=20:1) to give the title compound (323 mg, 20.6%) as a colorless oil.

$^1$H-NMR ($CDCl_3$) δ: 2.39 (3H, s), 6.96-7.03 (2H, m), 7.22-7.26 (2H, m), 7.42 (1H, d, J=8.4 Hz), 7.68 (1H, d, J=2.1 Hz), 7.94 (1H, dd, J=2.1, 8.4 Hz).

(2) Preparation of the Intermediate 187(2).

The title compound was obtained in the same manner as the Example 125(2) using the following starting material.

Starting material: the intermediate 187(1); Yield: 99.9% (colorless oil).

$^1$H-NMR ($CDCl_3$) δ: 2.09 (3H, s), 3.58 (2H, brs), 6.26 (1H, d, J=2.1 Hz), 6.44 (1H, dd, J=2.1, 8.1 Hz), 6.86-6.92 (2H, m), 7.02 (1H, d, J=8.1 Hz), 7.10-7.13 (2H, m).

(3) Preparation of the Intermediate 187(3).

The title compound was obtained in the same manner as the Example 125(3) using the following starting materials.

Starting materials: the intermediate 187(2) and methyl chloroglyoxylate; Yield: 98.7% (white solid).

$^1$H-NMR ($CDCl_3$) δ: 2.22 (3H, s), 3.95 (3H, s), 6.89-6.96 (2H, m), 7.14-7.20 (2H, m), 7.23-7.28 (2H, m), 7.34 (1H, dd, J=2.1, 8.4 Hz), 8.78 (1H, brs).

(4) Preparation of the Intermediate 187(4).

The title compound was obtained in the same manner as the Example 123(1) using the following starting materials.

Starting materials: the intermediate 187(3) and 4-(tert-butyl)benzyl bromide; Yield: 37.5% (colorless oil).

$^1$H-NMR ($CDCl_3$) δ: 1.27 (9H, s), 2.19 (3H, s), 3.58 (3H, s), 4.86 (2H, s), 6.60 (1H, d, J=2.1 Hz), 6.75-6.80 (2H, m), 6.84 (1H, dd, J=2.1, 8.1 Hz), 7.09-7.16 (4H, m), 7.20 (1H, d, J=8.1 Hz), 7.24-7.29 (2H, m).

(5) Preparation of the Compound 187.

The title compound was obtained in the same manner as the Example 126(4) using the following starting material.

Starting material: the intermediate 187(4); Yield: 27.2% (white solid).

$^1$H-NMR (DMSO-$d_6$) δ: 1.22 (9H, s), 2.12 (3H, s), 4.84 (2H, s), 6.69 (1H, d, J=2.1 Hz), 6.85-6.91 (2H, m), 7.03 (1H, dd, J=2.1, 8.1 Hz), 7.08 (2H, d, J=8.4 Hz), 7.30 (2H, d, J=8.4 Hz), 7.31-7.37 (3H, m).

Example 188

Preparation of the Compound 188

(1) Preparation of the Intermediate 188(1).

The title compound was obtained in the same manner as the Example 123(3) using the following starting materials.

Starting materials: 5-bromo-2-fluoro-1-nitrobenzene and 4-(trifluoromethoxy)phenylboronic acid; Yield: 99.9% (brown oil).

$^1$H-NMR ($CDCl_3$) δ: 7.33-7.43 (3H, m), 7.57-7.62 (2H, m), 7.79-7.84 (1H, m), 8.23 (1H, dd, J=2.4, 6.9 Hz).

(2) Preparation of the Intermediate 188(2).

The title compound was obtained in the same manner as the Example 185(2) using the following starting materials.

Starting materials: the intermediate 188(1) and 1-propanol; Yield: 64.4% (yellow oil).

$^1$H-NMR ($CDCl_3$) δ: 1.09 (3H, t, J=7.2 Hz), 1.83-1.96 (2H, m), 4.12 (2H, t, J=6.3 Hz), 7.15 (1H, d, J=8.7 Hz), 7.29-7.32 (2H, m), 7.54-7.59 (2H, m), 7.69 (1H, dd, J=2.4, 8.7 Hz), 8.03 (1H, d, J=2.4 Hz).

(3) Preparation of the Intermediate 188(3).

The title compound was obtained in the same manner as the Example 125(2) using the following starting material.

Starting material: the intermediate 188(2); Yield: 95.5% (white solid).

$^1$H-NMR ($CDCl_3$) δ: 1.07 (3H, t, J=7.5 Hz), 1.81-1.89 (2H, m), 3.90 (2H, brs), 4.00 (2H, t, J=6.0 Hz), 6.83 (1H, d, J=8.4 Hz), 6.88-6.93 (2H, m), 7.22-7.24 (2H, m), 7.51-7.54 (2H, m).

(4) Preparation of the Intermediate 188(4).

The title compound was obtained in the same manner as the Example 123(2) using the following starting materials.

Starting materials: the intermediate 188(3) and methyl chloroglyoxylate; Yield: 97.0% (pale yellow solid).

$^1$H-NMR ($CDCl_3$) δ: 1.12 (3H, t, J=7.5 Hz), 1.89-1.96 (2H, m), 3.99 (3H, s), 4.09 (2H, t, J=6.6 Hz), 6.98 (1H, d, J=8.4 Hz), 7.25-7.33 (3H, m), 7.57-7.62 (2H, m), 8.68 (1H, d, J=2.1 Hz), 9.62 (1H, brs).

(5) Preparation of the Intermediate 188(5).

The title compound was obtained in the same manner as the Example 123(1) using the following starting materials.

Starting materials: the intermediate 188(4) and 4-(tert-butyl)benzyl bromide; Yield: 88.7% (brown oil).

$^1$H-NMR ($CDCl_3$) δ: 1.06 (3H, t, J=7.5 Hz), 1.28 (9H, s), 1.76-1.83 (2H, m), 3.53 (3H, s), 3.89-3.99 (2H, m), 4.39 (1H, d, J=14.4 Hz), 5.38 (1H, d, J=14.4 Hz), 6.94-6.97 (2H, m), 7.13-7.20 (4H, m), 7.26-7.33 (4H, m), 7.41-7.45 (1H, m).

(6) Preparation of the Compound 188.

The title compound was obtained in the same manner as the Example 126(4) using the following starting material.

Starting material: the intermediate 188(5); Yield: 55.6% (white solid).

This compound was obtained as a mixture of the rotational isomers.

Major isomer: $^1$H-NMR (DMSO-$d_6$) δ: 0.99 (3H, t, J=7.2 Hz), 1.21 (9H, s), 1.69-1.76 (2H, m), 3.90-3.99 (2H, m), 4.40-4.44 (1H, m), 5.18-5.23 (1H, m), 7.09-7.14 (2H, m), 7.25-7.38 (6H, m), 7.46-7.55 (3H, m).

Minor isomer: $^1$H-NMR (DMSO-$d_6$) δ: 0.97-1.04 (3H, m), 1.27 (9H, s), 1.69-1.76 (2H, m), 3.90-3.99 (2H, m), 4.75-4.82 (1H, m), 5.18-5.23 (1H, m), 7.00-7.14 (2H, m), 7.25-7.38 (6H, m), 7.46-7.55 (3H, m).

Example 189

Preparation of the Compound 189

(1) Preparation of the Intermediate 189(1).

The title compound was obtained in the same manner as the Example 185(2) using the following starting materials.

Starting materials: the intermediate 188(1) and 1-butanol; Yield: 30.9% (yellow solid).

$^1$H-NMR ($CDCl_3$) δ: 0.99 (3H, t, J=7.5 Hz), 1.50-1.58 (2H, m), 1.80-1.88 (2H, m), 4.15 (2H, t, J=6.3 Hz), 7.15 (1H, d, J=8.7 Hz), 7.29-7.32 (2H, m), 7.54-7.59 (2H, m), 7.69 (1H, dd, J=2.4, 6.3 Hz), 8.02 (1H, d, J=2.4 Hz).

(2) Preparation of the Intermediate 189(2).

The title compound was obtained in the same manner as the Example 125(2) using the following starting material.

Starting material: the intermediate 189(1); Yield: 98.1% (white solid).

$^1$H-NMR ($CDCl_3$) δ: 1.00 (3H, t, J=7.5 Hz), 1.47-1.59 (2H, m), 1.78-1.87 (2H, m), 3.90 (2H, brs), 4.04 (2H, t, J=6.3 Hz), 6.83 (1H, d, J=8.4 Hz), 6.88-6.93 (2H, m), 7.21-7.25 (2H, m), 7.50-7.56 (2H, m).

(3) Preparation of the Intermediate 189(3).

The title compound was obtained in the same manner as the Example 123(2) using the following starting materials.

Starting materials: the intermediate 189(2) and methyl chloroglyoxylate; Yield: 94.0% (pale yellow solid).

$^1$H-NMR ($CDCl_3$) δ: 1.03 (3H, t, J=7.2 Hz), 1.53-1.61 (2H, m), 1.84-1.91 (2H, m), 3.99 (3H, s), 4.13 (2H, t, J=6.6 Hz), 6.98 (1H, d, J=8.7 Hz), 7.25-7.33 (3H, m), 7.57-7.62 (2H, m), 8.68 (1H, d, J=2.1 Hz), 9.61 (1H, brs).

(4) Preparation of the Intermediate 189(4).

The title compound was obtained in the same manner as the Example 123(1) using the following starting materials.

Starting materials: the intermediate 189(3) and 4-(tert-butyl)benzyl bromide; Yield: 86.6% (colorless oil).

$^1$H-NMR ($CDCl_3$) δ: 0.99 (3H, t, J=7.5 Hz), 1.28 (9H, s), 1.45-1.55 (2H, m), 1.73-1.79 (2H, m), 3.53 (3H, s), 3.95-3.99 (2H, m), 4.38 (1H, d, J=14.4 Hz), 5.38 (1H, d, J=14.4 Hz), 6.94-6.97 (2H, m), 7.13-7.20 (4H, m), 7.26-7.33 (4H, m), 7.41-7.45 (1H, m).

(5) Preparation of the Compound 189.

The title compound was obtained in the same manner as the Example 126(4) using the following starting material.

Starting material: the intermediate 189(4); Yield: 80.4% (white solid).

This compound was obtained as a mixture of the rotational isomers.

Major isomer: $^1$H-NMR (DMSO-$d_6$) δ: 0.95 (3H, t, J=7.2 Hz), 1.24 (9H, s), 1.40-1.48 (2H, m), 1.69-1.74 (2H, m), 3.90-3.99 (2H, m), 4.40-4.44 (1H, m), 5.18-5.23 (1H, m), 7.09-7.14 (2H, m), 7.25-7.38 (6H, m), 7.46-7.55 (3H, m).

Minor isomer: $^1$H-NMR (DMSO-$d_6$) δ: 0.95 (3H, t, J=7.2 Hz), 1.26 (9H, s), 1.40-1.48 (2H, m), 1.69-1.74 (2H, m), 3.90-3.99 (2H, m), 4.78-4.84 (1H, m), 5.18-5.23 (1H, m), 7.00-7.14 (2H, m), 7.25-7.38 (6H, m), 7.46-7.55 (3H, m).

Example 190

Preparation of the Compound 190

(1) Preparation of the Intermediate 190(1).

The title compound was obtained in the same manner as the Example 125(3) using the following starting materials.

Starting materials: 5-chloro-2,4-dimethoxyaniline and methyl chloroglyoxylate; Yield: 52.4% (pale purple solid).

$^1$H-NMR ($CDCl_3$) δ: 3.91 (3H, s), 3.94 (3H, s), 3.97 (3H, s), 6.54 (1H, s), 8.46 (1H, s), 9.26 (1H, brs).

(2) Preparation of the Intermediate 190(2).

The title compound was obtained in the same manner as the Example 123(1) using the following starting materials.

Starting materials: the intermediate 190(1) and 4-(tert-butyl)benzyl bromide; Yield: 87.8% (pale purple oil).

$^1$H-NMR ($CDCl_3$) δ: 1.29 (9H, s), 3.59 (3H, s), 3.76 (3H, s), 3.90 (3H, s), 4.36 (1H, d, J=14.1 Hz), 5.19 (1H, d, J=14.1 Hz), 6.45 (1H, s), 6.86 (1H, s), 7.11 (2H, d, J=8.1 Hz), 7.28 (2H, d, J=8.1 Hz).

(3) Preparation of the Intermediate 190(3).

A mixture of the intermediate 190(2) (800 mg, 1.91 mmol), 4-(trifluoromethoxy)phenylboronic acid (549 mg, 2.67 mmol), palladium(II) acetate (21 mg, 0.095 mmol), potassium fluoride (332 mg, 5.72 mmol), 2-(di-tert-butylphosphino)biphenyl (57 mg, 0.191 mmol) and tetrahydrofuran (3.0 ml) was refluxed for 5 hours under argon atmosphere. The reaction mixture was cooled to room temperature, diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=2:1) to give the title compound (140 mg, 14%) as a pale yellow oil.

$^1$H-NMR ($CDCl_3$) δ: 1.29 (9H, s), 3.55 (3H, s), 3.84 (3H, s), 3.87 (3H, s), 4.20 (1H, d, J=13.8 Hz), 5.43 (1H, d, J=13.8 Hz), 6.51 (1H, s), 6.62 (1H, s), 7.09-7.15 (4H, m), 7.19-7.24 (2H, m), 7.27-7.32 (2H, m).

(4) Preparation of the Compound 190.

The title compound was obtained in the same manner as the Example 126(4) using the following starting material.

Starting material: the intermediate 190(3); Yield: 69.5% (white solid).

This compound was obtained as a mixture of the rotational isomers.

Major isomer: $^1$H-NMR (DMSO-$d_6$) δ: 1.23 (9H, s), 3.83 (3H, s), 3.88 (3H, s), 4.18 (1H, d, J=14.7 Hz), 5.25 (1H, d, J=14.7 Hz), 6.66 (1H, s), 6.82 (1H, s), 7.11 (2H, d, J=8.4 Hz), 7.28-7.35 (6H, m).

Minor isomer: $^1$H-NMR (DMSO-$d_6$) δ: 1.25 (9H, s), 3.80 (3H, s), 3.82 (3H, s), 4.28-4.38 (1H, m), 5.05-5.11 (1H, m), 6.61-7.34 (10H, m).

Example 191

Preparation of the Compound 191

(1) Preparation of the Intermediate 191(1).

The title compound was obtained in the same manner as the Example 132(1) using the following starting materials.

Starting materials: 4-chloro-2-fluoro-1-nitrobenzene and 4-(trifluoromethoxy)phenol; Yield: 99.9% (yellow oil).

$^1$H-NMR ($CDCl_3$) δ: 6.83-6.87 (2H, m), 6.99 (1H, d, J=2.1 Hz), 7.05-7.12 (2H, m), 7.21 (1H, dd, J=2.1, 9.0 Hz), 7.96 (1H, d, J=9.0 Hz).

(2) Preparation of the Intermediate 191(2).

The title compound was obtained in the same manner as the Example 125(2) using the following starting material.

Starting material: the intermediate 191(1); Yield: 99.9% (yellow oil).

$^1$H-NMR ($CDCl_3$) δ: 3.81 (2H, brs), 6.80-6.84 (2H, m), 6.94-7.01 (3H, m), 7.17-7.20 (2H, m).

(3) Preparation of the Intermediate 191(3).

The title compound was obtained in the same manner as the Example 123(2) using the following starting materials.

Starting materials: the intermediate 191(2) and methyl chloroglyoxylate; Yield: 64.1% (yellow oil).

$^1$H-NMR ($CDCl_3$) δ: 3.96 (3H, s), 6.83 (1H, d, J=2.1 Hz), 7.05-7.13 (2H, m), 7.15 (1H, dd, J=2.1, 9.0 Hz), 7.22-7.26 (2H, m), 8.45 (1H, d, J=9.0 Hz), 9.40 (1H, brs).

(4) Preparation of the Intermediate 191(4).

The title compound was obtained in the same manner as the Example 123(1) using the following starting materials.

Starting materials: the intermediate 191(3) and 4-(tert-butyl)benzyl bromide; Yield: 99.9% (brown oil).

$^1$H-NMR ($CDCl_3$) δ: 1.27 (9H, s), 3.66 (3H, s), 4.72 (1H, d, J=14.1 Hz), 5.08 (1H, d, J=14.1 Hz), 6.70 (1H, d, J=2.1 Hz), 6.87-6.90 (2H, m), 6.95-7.01 (2H, m), 7.13-7.16 (2H, m), 7.19-7.24 (2H, m), 7.26-7.28 (2H, m).

(5) Preparation of the Compound 191.

The title compound was obtained in the same manner as the Example 126(4) using the following starting material.

Starting material: the intermediate 191(4); Yield: 21.3% (pale orange solid).

This compound was obtained as a mixture of the rotational isomers.

Major isomer: $^1$H-NMR (DMSO-$d_6$) δ: 1.23 (9H, s), 3.33 (2H, s), 6.18-6.82 (1H, m), 6.96-6.99 (1H, m), 7.03-7.14 (3H, m), 7.20-7.40 (6H, m).

Minor isomer: $^1$H-NMR (DMSO-$d_6$) δ: 1.24 (9H, s), 4.75 (2H, s), 6.18-6.82 (1H, m), 6.96-6.99 (1H, m), 7.03-7.14 (3H, m), 7.20-7.40 (6H, m).

Example 192

Preparation of the Compound 192

(1) Preparation of the Intermediate 192(1).

The title compound was obtained in the same manner as the Example 123(3) using the following starting materials.

Starting materials: 2-bromo-4-chloroaniline and 4-(trifluoromethoxy)phenylboronic acid; Yield: 95.3% (brown oil).

$^1$H-NMR ($CDCl_3$) δ: 3.71 (2H, brs), 6.70 (1H, d, J=8.4 Hz), 7.08 (1H, d, J=2.4 Hz), 7.12 (1H, dd, J=2.4, 8.4 Hz), 7.27-7.31 (2H, m), 7.44-7.48 (2H, m).

(2) Preparation of the Intermediate 192(2).

The title compound was obtained in the same manner as the Example 123(1) using the following starting materials.

Starting materials: the intermediate 192(1) and 4-(tert-butyl)benzyl bromide; Yield: 94.3% (brown oil).

$^1$H-NMR ($CDCl_3$) δ: 1.31 (9H, s), 3.84 (1H, brs), 4.28 (2H, s), 6.93-6.95 (1H, m), 7.05 (1H, d, J=2.7 Hz), 7.15 (1H, dd, J=2.7, 8.7 Hz), 7.19-7.25 (2H, m), 7.27-7.31 (2H, m), 7.34-7.36 (2H, m), 7.44-7.47 (2H, m).

(3) Preparation of the Intermediate 192(3).

The title compound was obtained in the same manner as the Example 123(2) using the following starting materials.

Starting materials: the intermediate 192(2) and methyl chloroglyoxylate; Yield: 95.6% (yellow oil).

$^1$H-NMR ($CDCl_3$) δ: 1.28 (9H, s), 3.42 (1H, d, J=14.4 Hz), 3.67 (3H, s), 5.11 (1H, d, J=14.4 Hz), 6.76 (1H, d, J=8.4 Hz), 6.90-6.95 (2H, m), 7.17 (1H, dd, J=2.4, 8.4 Hz), 7.20-7.24 (2H, m), 7.31-7.34 (2H, m), 7.39 (1H, d, J=2.4 Hz), 7.59-7.62 (2H, m).

(4) Preparation of the Compound 192.

The title compound was obtained in the same manner as the Example 126(4) using the following starting material.

Starting material: the intermediate 192(3); Yield: 61.5% (white solid).

This compound was obtained as a mixture of the rotational isomers.

Major isomer: $^1$H-NMR (DMSO-$d_6$) δ: 1.21 (9H, s), 3.09 (1H, d, J=14.7 Hz), 4.81 (1H, d, J=14.7 Hz), 6.85-6.88 (2H, m), 7.03 (1H, d, J=8.4 Hz), 7.19-7.21 (2H, m), 7.27 (1H, dd, J=2.7, 8.4 Hz), 7.40 (1H, d, J=2.7 Hz), 7.43-7.46 (2H, m), 8.05-8.08 (2H, m).

Minor isomer: $^1$H-NMR (DMSO-$d_6$) δ: 1.21 (9H, s), 3.89-3.94 (1H, m), 4.55-4.61 (1H, m), 6.93-6.97 (2H, m), 7.09-7.12 (2H, m), 7.19-7.46 (5H, m), 8.05-8.08 (2H, m).

Example 193

Preparation of the Compound 193

(1) Preparation of the Intermediate 193(1).

The title compound was obtained in the same manner as the Example 185(2) using the following starting materials.

Starting materials: the intermediate 185(1) and 1-butanol; Yield: 87.6% (yellow solid).

$^1$H-NMR ($CDCl_3$) δ: 0.94 (3H, t, J=7.2 Hz), 1.39-1.46 (2H, m), 1.72-1.81 (2H, m), 4.10 (2H, t, J=6.6 Hz), 7.03 (1H, dd, J=1.5, 7.8 Hz), 7.26-7.30 (2H, m), 7.55-7.58 (2H, m), 8.22-8.26 (2H, m).

(2) Preparation of the Intermediate 193(2).

The title compound was obtained in the same manner as the Example 125(2) using the following starting material.

Starting material: the intermediate 193(1); Yield: 91.9% (brown oil).

$^1$H-NMR ($CDCl_3$) δ: 0.87 (3H, t, J=7.2 Hz), 1.31-1.41 (2H, m) 1.58-1.67 (2H, m), 3.48 (2H, brs), 3.83 (2H, t, J=6.3 Hz), 6.64-6.68 (2H, m), 6.82 (1H, d, J=8.4 Hz), 7.20-7.23 (2H, m), 7.53-7.55 (2H, m).

(3) Preparation of the Intermediate 193(3).

The title compound was obtained in the same manner as the Example 123(2) using the following starting materials.

Starting materials: the intermediate 193(2) and methyl chloroglyoxylate; Yield: 78.7% (white solid).

$^1$H-NMR ($CDCl_3$) δ: 0.91 (3H, t, J=7.5 Hz), 1.36-1.43 (2H, m), 1.66-1.73 (2H, m), 3.95-3.99 (5H, m), 6.98 (1H, d, J=8.7 Hz), 7.23-7.27 (2H, m), 7.52 (1H, d, J=2.7 Hz), 7.54-7.57 (2H, m), 7.65 (1H, dd, J=3.0, 8.7 Hz), 8.80 (1H, brs).

(4) Preparation of the Intermediate 193(4).

The title compound was obtained in the same manner as the Example 123(1) using the following starting materials.

Starting materials: the intermediate 193(3) and 4-(tert-butyl)benzyl bromide; Yield: 76.9% (colorless oil).

$^1$H-NMR ($CDCl_3$) δ: 0.92 (3H, t, J=7.2 Hz), 1.30 (9H, s), 1.36-1.44 (2H, m), 1.66-4.73 (2H, m), 3.57 (3H, s), 3.95 (2H, t, J=6.3 Hz), 4.88 (2H, s), 6.85-6.88 (2H, m), 7.04 (1H, dd, J=2.7, 9.0 Hz), 7.15-7.20 (4H, m), 7.30-7.34 (2H, m), 7.35-7.38 (2H, m).

(5) Preparation of the Compound 193.

The title compound was obtained in the same manner as the Example 126(4) using the following starting material.

Starting material: the intermediate 193(4); Yield: 75.9% (white solid).

$^1$H-NMR (DMSO-$d_6$) δ: 0.85 (3H, t, J=7.2 Hz), 1.24 (9H, s), 1.29-1.36 (2H, m), 1.56-1.65 (2H, m), 3.95 (2H, t, J=6.3 Hz), 4.84 (2H, s), 7.02 (1H, d, J=8.7 Hz), 7.09 (1H, d, J=2.4 Hz), 7.12-7.14 (2H, m), 7.19 (1H, dd, J=2.4, 8.7 Hz), 7.28-7.37 (4H, m), 7.48-7.51 (2H, m).

Example 194

Preparation of the Compound 194

(1) Preparation of the Intermediate 194(1).

The title compound was obtained in the same manner as the Example 185(2) using the following starting materials.

Starting materials: the intermediate 188(1) and 1-pentanol; Yield: 74.9% (brown solid).

$^1$H-NMR ($CDCl_3$) δ: 0.95 (3H, t, J=7.2 Hz), 1.39-1.54 (4H, m), 1.82-1.91 (2H, m), 4.11-4.17 (2H, m), 7.15 (1H, d, J=9.0 Hz), 7.29-7.32 (2H, m), 7.55-7.58 (2H, m), 7.70 (1H, dd, J=2.7, 9.0 Hz), 8.02 (1H, d, J=2.7 Hz).

(2) Preparation of the Intermediate 194(2).

The title compound was obtained in the same manner as the Example 125(2) using the following starting material.

Starting material: the intermediate 194(1); Yield: 76.8% (yellow solid).

$^1$H-NMR ($CDCl_3$) δ: 0.95 (3H, t, J=7.2 Hz), 1.37-1.55 (4H, m), 1.80-1.87 (2H, m), 3.89 (2H, brs), 4.01-4.05 (2H, m), 6.82-6.93 (3H, m), 7.21-7.25 (2H, m), 7.50-7.55 (2H, m).

(3) Preparation of the Intermediate 194(3).

The title compound was obtained in the same manner as the Example 125(3) using the following starting materials.

Starting materials: the intermediate 194(2) and methyl chloroglyoxylate; Yield: 84.8% (white solid).

$^1$H-NMR ($CDCl_3$) δ: 0.97 (3H, t, J=7.2 Hz), 1.40-1.52 (4H, m), 1.86-1.95 (2H, m), 3.99 (3H, s), 4.11 (2H, t, J=6.6 Hz), 6.98 (1H, d, J=8.4 Hz), 7.25-7.33 (3H, m), 7.58-7.61 (2H, m), 8.68 (1H, d, J=2.1 Hz), 9.60 (1H, brs).

(4) Preparation of the Intermediate 194(4).

The title compound was obtained in the same manner as the Example 123(1) using the following starting materials.

Starting materials: the intermediate 194(3) and 4-(tert-butyl)benzyl bromide; Yield: 50.0% (colorless oil).

$^1$H-NMR ($CDCl_3$) δ: 0.95 (3H, t, J=7.2 Hz), 1.28 (9H, s), 1.40-1.49 (4H, m), 1.74-1.81 (2H, m), 3.53 (3H, s), 3.93-3.99 (2H, m), 4.37 (1H, d, J=13.8 Hz), 5.40 (1H, d, J=13.8 Hz), 6.94-6.97 (2H, m), 7.13-7.20 (4H, m), 7.27-7.31 (4H, m), 7.43 (1H, dd, J=2.4, 8.7 Hz).

(5) Preparation of the Compound 194.

The title compound was obtained in the same manner as the Example 126(4) using the following starting material.

Starting material: the intermediate 194(4); Yield: 80.4% (white solid).

This compound was obtained as a mixture of the rotational isomers.

Major isomer: $^1$H-NMR (DMSO-$d_6$) δ: 0.90-0.99 (3H, m), 1.21 (9H, s), 1.32-1.50 (4H, m), 1.72-1.78 (2H, m), 3.32-3.40 (1H, m), 4.03-4.07 (2H, m), 4.73-4.78 (1H, m), 7.05-7.09 (3H, m), 7.24-7.27 (2H, m), 7.35-7.38 (3H, m), 7.43-7.46 (1H, m), 7.51-7.54 (2H, m).

Minor isomer: $^1$H-NMR (DMSO-$d_6$) δ: 0.90-0.99 (3H, m), 1.21 (9H, s), 1.32-1.50 (4H, m), 1.72-1.78 (2H, m), 3.96 (2H, t, J=6.3 Hz), 4.21-4.26 (1H, m), 5.22-5.26 (1H, m), 6.94-6.95 (1H, m), 7.05-7.54 (10H, m).

Example 195

Preparation of the Compound 195

(1) Preparation of the Intermediate 195(1).

The title compound was obtained in the same manner as the Example 123(1) using the following starting materials.

Starting materials: the intermediate 194(3) and benzyl bromide; Yield: 30.3% (colorless oil).

$^1$H-NMR ($CDCl_3$) δ: 0.95 (3H, t, J=7.2 Hz), 1.34-1.50 (4H, m), 1.75-1.84 (2H, m), 3.54 (3H, s), 3.95-4.00 (2H, m), 4.48 (1H, d, J=14.4 Hz), 5.38 (1H, d, J=14.4 Hz), 6.95 (1H, d, J=8.7 Hz), 7.03 (1H, d, J=2.7 Hz), 7.19-7.29 (7H, m), 7.32-7.35 (2H, m), 7.43 (1H, dd, J=2.7, 8.7 Hz).

(2) Preparation of the Compound 195.

The title compound was obtained in the same manner as the Example 126(4) using the following starting material.

Starting material: the intermediate 195(1); Yield: 43.4% (white solid).

This compound was obtained as a mixture of the rotational isomers.

Major isomer: $^1$H-NMR (DMSO-$d_6$) δ: 0.90-0.95 (3H, m), 1.32-1.50 (4H, m), 1.72-1.79 (2H, m), 3.28-3.30 (1H, m), 4.03-4.07 (2H, m), 4.83-4.88 (1H, m), 7.05-7.26 (6H, m), 7.35-7.39 (3H, m), 7.44-7.55 (3H, m).

Minor isomer: $^1$H-NMR (DMSO-$d_6$) δ: 0.90-0.95 (3H, m), 1.32-1.50 (4H, m), 1.72-1.79 (2H, m), 3.97 (2H, t, J=6.3 Hz), 4.21-4.26 (1H, m), 5.22-5.26 (1H, m), 7.02-7.26 (6H, m), 7.35-7.55 (6H, m).

Example 196

Preparation of the Compound 196

(1) Preparation of the Intermediate 196(1).

The title compound was obtained in the same manner as the Example 190(3) using the following starting materials.

Starting materials: 2-chloro-5-nitrobenzaldehyde and 4-(trifluoromethoxy)phenylboronic acid;

Yield: 39.3% (yellow oil).

$^1$H-NMR ($CDCl_3$) δ: 7.39-7.48 (4H, m), 7.65 (1H, d, J=8.1 Hz), 8.49 (1H, dd, J=2.4, 8.1 Hz), 8.86 (1H, d, J=2.4 Hz), 10.00 (1H, s).

(2) Preparation of the Intermediate 196(2).

A solution of triethyl phosphonoacetate (492 mg, 2.19 mmol) in tetrahydrofuran (5 ml) was added dropwise at a slow speed to sodium hydride (95 mg, 2.19 mmol) at room temperature under argon atmosphere, and the mixture was stirred at room temperature for 30 minutes. A solution of the intermediate 196(1) (488 mg, 1.56 mmol) in tetrahydrofuran (3 ml) was added dropwise at a slow speed to this mixture at 0° C., and the mixture was stirred at room temperature for 3 hours. A small amount of saturated aqueous solution of ammonium chloride was added to the reaction mixture. The residue obtained by evaporation of the tetrahydrofuran under reduced pressure was extracted with ethyl acetate. The organic layer was washed with saturated brine, and dried over anhydrous sodium sulfate. The residue obtained by evaporation of the solvent under reduced pressure was washed with methanol to give the title compound (176 mg, 29.6%) as a white solid.

$^1$H-NMR ($CDCl_3$) δ: 1.31 (3H, t, J=7.2 Hz), 4.24 (2H, q, J=7.2 Hz), 6.57 (1H, d, J=16.2 Hz), 7.33-7.38 (4H, m), 7.53 (1H, d, J=8.1 Hz), 7.63 (1H, d, J=16.2 Hz), 8.28 (1H, dd, J=2.4, 8.1 Hz), 8.56 (1H, d, J=2.4 Hz).

(3) Preparation of the Intermediate 196(3).

The title compound was obtained in the same manner as the Example 125(2) using the following starting material.

Starting material: the intermediate 196(2); Yield: 96.8% (black oil).

$^1$H-NMR ($CDCl_3$) δ: 1.19 (3H, t, J=7.2 Hz), 2.37-2.42 (2H, m), 2.84 (2H, t, J=8.4 Hz), 3.35 (2H, brs), 4.02-4.10 (2H, m), 6.59 (1H, dd, J=2.4, 8.1 Hz), 6.62 (1H, d, J=2.4 Hz), 6.98 (1H, d, J=8.1 Hz), 7.20-7.23 (2H, m), 7.27-7.31 (2H, m).

(4) Preparation of the Intermediate 196(4).

The title compound was obtained in the same manner as the Example 123(2) using the following starting materials.

Starting materials: the intermediate 196(3) and methyl chloroglyoxylate; Yield: 80.1% (white solid).

$^1$H-NMR ($CDCl_3$) δ: 1.16-1.25 (3H, m), 2.43 (2H, t, J=7.2 Hz), 2.92 (2H, t, J=7.2 Hz), 3.96-4.10 (5H, m), 7.20 (1H, d, J=8.4 Hz), 7.25-7.33 (4H, m), 7.55-7.61 (2H, m), 8.90 (1H, brs).

(5) Preparation of the Intermediate 196(5).

The title compound was obtained in the same manner as the Example 123(1) using the following starting materials.

Starting materials: the intermediate 196(4) and 4-(tert-butyl)benzyl bromide; Yield: 72.7% (colorless oil).

$^1$H-NMR ($CDCl_3$) δ: 1.18 (3H, t, J=7.2 Hz), 1.30 (9H, s), 2.28 (2H, t, J=7.5 Hz), 2.81 (2H, t, J=7.5 Hz), 3.61 (3H, s), 4.04 (2H, q, J=7.2 Hz), 4.93 (2H, s), 6.93 (1H, d, J=2.1 Hz), 7.00 (1H, dd, J=2.1, 8.1 Hz), 7.13 (1H, d, J=8.1 Hz), 7.17-7.19 (2H, m), 7.27-7.35 (6H, m).

(6) Preparation of the Compound 196.

The title compound was obtained in the same manner as the Example 126(4) using the following starting material.

Starting material: the intermediate 196(5); Yield: 80.4% (white solid).

$^1$H-NMR (DMSO-$d_6$) δ: 1.25 (9H, s), 2.30 (2H, t, J=7.2 Hz), 2.70 (2H, t, J=7.2 Hz), 4.93 (2H, s), 7.11-7.23 (5H, m), 7.34-7.37 (2H, m), 7.40-7.44 (4H, m), 12.12 (1H, brs).

Example 197

Preparation of the Compound 197

(1) Preparation of the Intermediate 197(1).

The title compound was obtained in the same manner as the Example 185(2) using the following starting materials.

Starting materials: the intermediate 185(1) and 3-pentanol; Yield: 43.4% (yellow oil).

$^1$H-NMR ($CDCl_3$) δ: 0.89 (6H, t, J=7.8 Hz), 1.64-1.70 (4H, m), 4.31-4.35 (1H, m), 6.98-7.01 (1H, m), 7.26-7.29 (2H, m), 7.53-7.56 (2H, m), 8.19-8.23 (2H, m).

(2) Preparation of the Intermediate 197(2).

The title compound was obtained in the same manner as the Example 125(2) using the following starting material.

Starting material: the intermediate 197(1); Yield: 99.9% (black oil).

$^1$H-NMR ($CDCl_3$) δ: 0.78 (6H, t, J=7.2 Hz), 1.44-1.54 (4H, m), 3.48 (2H, brs), 3.81-3.88 (1H, m), 6.62-6.67 (2H, m), 6.80-6.84 (1H, m), 7.19-7.22 (2H, m), 7.51-7.55 (2H, m).

(3) Preparation of the Intermediate 197(3).

The title compound was obtained in the same manner as the Example 123(2) using the following starting materials.

Starting materials: the intermediate 197(2) and methyl chloroglyoxylate; Yield: 99.3% (brown oil).

$^1$H-NMR ($CDCl_3$) δ: 0.84 (6H, t, J=7.5 Hz), 1.55-1.61 (4H, m), 3.97 (3H, s), 4.09-4.13 (1H, m), 6.96 (1H, d, J=9.0 Hz), 7.21-7.27 (2H, m), 7.49 (1H, d, J=2.7 Hz), 7.53-7.67 (2H, m), 7.63 (1H, dd, J=2.7, 9.0 Hz), 8.79 (1H, brs).

(4) Preparation of the Intermediate 197(4).

The title compound was obtained in the same manner as the Example 123(1) using the following starting materials.

Starting materials: the intermediate 197(3) and 4-(tert-butyl)benzyl bromide; Yield: 84.0% (colorless oil).

$^1$H-NMR ($CDCl_3$) δ: 0.84 (6H, t, J=7.5 Hz), 1.30 (9H, s), 1.55-1.61 (4H, m), 3.56 (3H, s), 4.10-4.14 (1H, m), 4.88 (2H, s), 6.82-6.86 (2H, m), 7.02 (1H, dd, J=2.7, 8.7 Hz), 7.15-7.19 (4H, m), 7.31-7.38 (4H, m).

(5) Preparation of the Compound 197.

The title compound was obtained in the same manner as the Example 126(4) using the following starting material.

Starting material: the intermediate 197(4); Yield: 81.2% (white solid).

$^1$H-NMR (DMSO-$d_6$) δ: 0.80 (6H, t, J=7.5 Hz), 1.24 (9H, s), 1.50-1.56 (4H, m), 4.17-4.22 (1H, m), 4.78 (2H, s), 6.93-6.97 (1H, m), 7.11-7.19 (4H, m), 7.28-7.36 (4H, m), 7.51-7.54 (2H, m).

Example 198

Preparation of the Compound 198

(1) Preparation of the Intermediate 198(1).

The title compound was obtained in the same manner as the Example 123(3) using the following starting materials.

Starting materials: 2-bromo-4-fluoro-1-nitrobenzene and 4-(trifluoromethoxy)phenylboronic acid; Yield: 37.4% (colorless oil).

$^1$H-NMR ($CDCl_3$) δ: 7.10-8.01 (7H, m).

(2) Preparation of the Intermediate 198(2).

The title compound was obtained in the same manner as the Example 185(2) using the following starting materials.

Starting materials: the intermediate 198(1) and 1-propanol; Yield: 88.2% (yellow oil).

$^1$H-NMR ($CDCl_3$) δ: 1.05 (3H, t, J=7.5 Hz), 1.78-1.92 (2H, m), 4.01 (2H, t, J=6.6 Hz), 6.81 (1H, d, J=2.7 Hz), 6.94 (1H, dd, J=2.7, 9.3 Hz), 7.21-7.35 (4H, m), 8.02 (1H, d, J=9.3 Hz).

(3) Preparation of the Intermediate 198(3).

The title compound was obtained in the same manner as the Example 125(2) using the following starting material.

Starting material: the intermediate 198(2); Yield: 99.9% (yellow oil).

$^1$H-NMR ($CDCl_3$) δ: 1.02 (3H, t, J=7.5 Hz), 1.71-1.84 (2H, m), 3.45 (2H, brs), 3.87 (2H, t, J=6.6 Hz), 6.71 (1H, d, J=2.7 Hz), 6.72 (1H, d, J=8.7 Hz), 6.79 (1H, dd, J=2.7, 8.7 Hz), 7.26-7.31 (2H, m), 7.46-7.52 (2H, m).

(4) Preparation of the Intermediate 198(4).

The title compound was obtained in the same manner as the Example 125(3) using the following starting materials.

Starting materials: the intermediate 198(3) and methyl chloroglyoxylate; Yield: 41.0% (white solid).

$^1$H-NMR ($CDCl_3$) δ: 1.04 (3H, t, J=7.5 Hz), 1.75-1.88 (2H, m), 3.89 (3H, s), 3.94 (2H, t, J=6.6 Hz), 6.83 (1H, d, J=3.0 Hz), 6.96 (1H, dd, J=3.0, 9.0 Hz), 7.34 (2H, d, J=8.7 Hz), 7.42 (2H, d, J=8.7 Hz), 8.22 (1H, d, J=9.0 Hz), 8.74 (1H, brs).

(5) Preparation of the Intermediate 198(5).

The title compound was obtained in the same manner as the Example 123(1) using the following starting materials.

Starting materials: the intermediate 198(4) and 4-(tert-butyl)benzyl bromide; Yield: 91.3% (colorless oil).

$^1$H-NMR ($CDCl_3$) δ: 1.03 (3H, t, J=6.9 Hz), 1.27 (9H, s), 1.77-2.04 (2H, m), 3.40 (1H, d, J=14.4 Hz), 3.65 (3H, s), 3.91 (2H, t, J=6.6 Hz), 5.07 (1H, d, J=14.4 Hz), 6.67 (1H, dd, J=2.7, 8.4 Hz), 6.74 (1H, d, J=8.4 Hz), 6.89 (1H, d, J=2.7 Hz), 6.90-6.96 (2H, m), 7.18-7.23 (2H, m), 7.26-7.32 (2H, m), 7.59-7.65 (2H, m).

(6) Preparation of the Compound 198.

The title compound was obtained in the same manner as the Example 126(4) using the following starting material.

Starting material: the intermediate 198(5); Yield: 43.5% (white solid).

This compound was obtained as a mixture of the rotational isomers.

Major isomer: $^1$H-NMR (DMSO-$d_6$) δ: 0.95 (3H, t, J=7.5 Hz), 1.21 (9H, s), 1.64-1.76 (2H, m), 3.05 (1H, d, J=14.7 Hz), 3.91 (2H, t, J=6.3 Hz), 4.78 (1H, d, J=14.7 Hz), 6.72 (1H, dd, J=3.0, 8.4 Hz), 6.82 (1H, d, J=3.0 Hz), 6.86 (2H, d, J=8.4 Hz), 6.94 (1H, d, J=8.4 Hz), 7.17-7.21 (2H, m), 7.37-7.42 (2H, m), 8.04-8.08 (2H, m).

Minor isomer: $^1$H-NMR (DMSO-$d_6$) δ: 0.93-4.55 (18H, m), 6.78-6.91 (5H, m), 7.06-7.10 (2H, m), 7.25-7.29 (2H, m), 7.32-7.36 (2H, m).

Example 199

Preparation of the Compound 199

(1) Preparation of the Intermediate 199(1).

The title compound was obtained in the same manner as the Example 185(2) using the following starting materials.

Starting materials: the intermediate 188(1) and 3-pentanol; Yield: 85.0% (yellow oil).

$^1$H-NMR ($CDCl_3$) δ: 1.00 (6H, t, J=7.5 Hz), 1.72-1.81 (4H, m), 4.31-4.35 (1H, m), 7.12 (1H, d, J=8.7 Hz), 7.27-7.31 (2H, m), 7.53-7.58 (2H, m), 7.66 (1H, dd, J=2.1, 8.7 Hz), 7.97 (1H, d, J=2.1 Hz).

(2) Preparation of the Intermediate 199(2).

The title compound was obtained in the same manner as the Example 125(2) using the following starting material.

Starting material: the intermediate 199(1); Yield: 84.8% (brown solid).

$^1$H-NMR ($CDCl_3$) δ: 0.99 (6H, t, J=7.5 Hz), 1.68-1.77 (4H, m), 3.89 (2H, brs), 4.16-4.20 (1H, m), 6.81-6.92 (3H, m), 7.21-7.25 (2H, m), 7.50-7.53 (2H, m).

(3) Preparation of the Intermediate 199(3).

The title compound was obtained in the same manner as the Example 123(1) using the following starting materials.

Starting materials: the intermediate 199(2) and 4-(tert-butyl)benzyl bromide; Yield: 74.5% (colorless oil).

$^1$H-NMR ($CDCl_3$) δ: 0.95-1.04 (6H, m), 1.29 (9H, s), 1.67-1.81 (4H, m), 4.18-4.40 (3H, m), 4.74-4.79 (1H, m), 6.77-6.81 (2H, m), 6.89-6.94 (2H, m), 7.04 (1H, dd, J=2.4, 8.1 Hz), 7.17-7.50 (6H, m).

(4) Preparation of the Intermediate 199(4).

The title compound was obtained in the same manner as the Example 123(2) using the following starting materials.

Starting materials: the intermediate 199(3) and methyl chloroglyoxylate; Yield: 99.9% (brown oil).

$^1$H-NMR ($CDCl_3$) δ: 0.94-1.02 (6H, m), 1.29 (9H, s), 1.57-1.78 (4H, m), 3.52 (3H, s), 4.22-4.32 (2H, m), 5.46-5.51 (1H, m), 6.92-6.95 (2H, m), 7.13-7.21 (4H, m), 7.26-7.31 (4H, m), 7.41 (1H, dd, J=2.4, 9.0 Hz).

(5) Preparation of the Compound 199.

The title compound was obtained in the same manner as the Example 126(4) using the following starting material.

Starting material: the intermediate 199(4); Yield: 45.9% (white solid).

This compound was obtained as a mixture of the rotational isomers.

Major isomer: $^1$H-NMR (DMSO-$d_6$) δ: 0.88-0.96 (6H, m), 1.20 (9H, s), 1.57-1.64 (4H, m), 4.26-5.30 (3H, m), 7.06-7.08 (2H, m), 7.23-7.52 (9H, m).

Minor isomer: $^1$H-NMR (DMSO-$d_6$) δ: 0.88-0.96 (6H, m), 1.20 (9H, s), 1.57-1.64 (4H, m), 4.26-5.30 (3H, m), 6.92-7.08 (2H, m), 7.23-7.52 (9H, m).

Example 200

Preparation of the Compound 200

(1) Preparation of the Intermediate 200(1).

The title compound was obtained in the same manner as the Example 123(3) using the following starting materials.

Starting materials: the intermediate 126(2) and 3-(trifluoromethoxy)phenylboronic acid; Yield: 96.0% (pale yellow oil).

$^1$H-NMR ($CDCl_3$) δ: 1.30 (9H, s), 3.59 (3H, s), 4.95 (2H, s), 7.15-7.25 (5H, m), 7.30-7.34 (2H, m), 7.38-7.55 (5H, m).

(2) Preparation of the Compound 200.

The title compound was obtained in the same manner as the Example 126(4) using the following starting material.

Starting material: the intermediate 200(1); Yield: 58.2% (white solid).

$^1$H-NMR ($CDCl_3$) δ: 1.24 (9H, s), 4.95 (2H, s), 7.17 (2H, d, J=7.8 Hz), 7.31-7.40 (5H, m), 7.58 (1H, t, J=7.8 Hz), 7.60-7.63 (1H, m), 7.68-7.74 (3H, m).

Example 201

Preparation of the Compound 201

(1) Preparation of the Intermediate 201(1).

The title compound was obtained in the same manner as the Example 123(3) using the following starting materials.

Starting materials: the intermediate 126(2) and 2-(trifluoromethoxy)phenylboronic acid; Yield: 88.3% (pale yellow oil).

$^1$H-NMR ($CDCl_3$) δ: 1.30 (9H, s), 3.53 (3H, s), 4.96 (2H, s), 7.11-7.20 (4H, m), 7.29-7.44 (8H, m).

(2) Preparation of the Compound 201.

The title compound was obtained in the same manner as the Example 126(4) using the following starting material.

Starting material: the intermediate 201(1); Yield: 59.5% (white solid).

$^1$H-NMR ($CDCl_3$) δ: 1.24 (9H, s), 4.95 (2H, s), 7.13 (2H, d, J=7.8 Hz), 7.29-7.35 (4H, m), 7.44-7.55 (6H, m).

Example 202

Preparation of the Compound 202

(1) Preparation of the Intermediate 202(1).

The title compound was obtained in the same manner as the Example 190(3) using the following starting materials.

Starting materials: the intermediate 126(1) and 4-(tert-butyl)phenylboronic acid; Yield: 47.5% (gray solid).

$^1$H-NMR ($CDCl_3$) δ: 1.36 (9H, s), 3.99 (3H, s), 7.45-7.54 (4H, m), 7.59-7.72 (4H, m), 8.88 (1H, brs).

(2) Preparation of the Intermediate 202(2).

The title compound was obtained in the same manner as the Example 123(1) using the following starting materials.

Starting materials: the intermediate 202(1) and 2-(trifluoromethoxy)benzyl bromide; Yield: 91.1% (colorless oil).

$^1$H-NMR ($CDCl_3$) δ: 1.35 (9H, s), 3.58 (3H, s), 5.10 (2H, s), 7.11-7.21 (3H, m), 7.27-7.35 (2H, m), 7.43-7.54 (7H, m).

(3) Preparation of the Compound 202.

The title compound was obtained in the same manner as the Example 126(4) using the following starting material.

Starting material: the intermediate 202(2); Yield: 68.7% (white solid).

$^1$H-NMR (DMSO-$d_6$) δ: 1.30 (9H, s), 5.06 (2H, s), 7.27-7.49 (8H, m), 7.54-7.59 (2H, m), 7.62-7.67 (2H, m).

Example 203

Preparation of the Compound 203

(1) Preparation of the Intermediate 203(1).

The title compound was obtained in the same manner as the Example 123(1) using the following starting materials.

Starting materials: the intermediate 202(1) and 3-(trifluoromethoxy)benzyl bromide; Yield: 82.2% (colorless oil).

$^1$H-NMR ($CDCl_3$) δ: 1.35 (9H, s), 3.57 (3H, s), 4.99 (2H, s), 7.07-7.17 (4H, m), 7.22-7.27 (1H, m), 7.35 (1H, t, J=7.8 Hz), 7.44-7.56 (6H, m).

(2) Preparation of the Compound 203.

The title compound was obtained in the same manner as the Example 126(4) using the following starting material.

Starting material: the intermediate 203(1); Yield: 69.6% (white solid).

$^1$H-NMR (DMSO-$d_6$) δ: 1.30 (9H, s), 5.04 (2H, s), 7.18-7.21 (1H, m), 7.24-7.32 (4H, m), 7.45-7.51 (3H, m), 7.54-7.60 (2H, m), 7.63-7.69 (2H, m).

Example 204

Preparation of the Compound 204

(1) Preparation of the Intermediate 204(1).

The title compound was obtained in the same manner as the Example 123(1) using the following starting materials.

Starting materials: the intermediate 202(1) and 4-chlorobenzyl chloride; Yield: 51.9% (colorless oil).

$^1$H-NMR ($CDCl_3$) δ: 1.35 (9H, s), 3.56 (3H, s), 4.93 (2H, s), 7.06-7.11 (2H, m), 7.17-7.22 (2H, m), 7.25-7.29 (2H, m), 7.44-7.55 (6H, m).

(2) Preparation of the Compound 204.

The title compound was obtained in the same manner as the Example 126(4) using the following starting material.

Starting material: the intermediate 204(1); Yield: 71.6% (white solid).

$^1$H-NMR (DMSO-$d_6$) δ: 1.30 (9H, s), 4.97 (2H, s), 7.24-7.29 (4H, m), 7.37-7.43 (2H, m), 7.44-7.49 (2H, m), 7.55-7.60 (2H, m), 7.63-7.69 (2H, m).

Example 205

Preparation of the Compound 205

(1) Preparation of the Intermediate 205(1).

The title compound was obtained in the same manner as the Example 123(1) using the following starting materials.

Starting materials: the intermediate 202(1) and 4-(trifluoromethyl)benzyl chloride; Yield: 52.4% (colorless oil).

$^1$H-NMR ($CDCl_3$) δ: 1.35 (9H, s), 3.58 (3H, s), 5.02 (2H, s), 7.09-7.14 (2H, m), 7.37-7.41 (2H, m), 7.44-7.59 (8H, m).

(2) Preparation of the Compound 205.

The title compound was obtained in the same manner as the Example 126(4) using the following starting material.

Starting material: the intermediate 205(1); Yield: 73.6% (white solid).

$^1$H-NMR (DMSO-$d_6$) δ: 1.30 (9H, s), 5.08 (2H, s), 7.31 (2H, d, J=8.4 Hz), 7.44-7.50 (4H, m), 7.54-7.60 (2H, m), 7.67 (2H, d, J=8.4 Hz), 7.72 (2H, d, J=8.4 Hz).

Example 206

Preparation of the Compound 206

(1) Preparation of the Intermediate 206(1).

The title compound was obtained in the same manner as the Example 123(1) using the following starting materials.

Starting materials: the intermediate 202(1) and the intermediate 167(1); Yield: 32.8% (colorless oil).

$^1$H-NMR ($CDCl_3$) δ: 0.92 (3H, t, J=7.5 Hz), 1.22-1.41 (11H, m), 1.52-1.62 (2H, m), 2.58 (2H, t, J=7.8 Hz), 3.55 (3H, s), 4.93 (2H, s), 7.08-7.17 (6H, m), 7.43-7.53 (6H, m).

(2) Preparation of the Compound 206.

The title compound was obtained in the same manner as the Example 126(4) using the following starting material.

Starting material: the intermediate 206(1); Yield: 58.8% (white solid).

$^1$H-NMR (DMSO-$d_6$) δ: 0.87 (3H, t, J=7.5 Hz), 1.21-1.34 (11H, m), 1.46-1.56 (2H, m), 2.53 (2H, t, J=7.5 Hz), 4.93 (2H, s), 7.09-7.16 (4H, m), 7.23-7.28 (2H, m), 7.43-7.49 (2H, m), 7.54-7.60 (2H, m), 7.61-7.67 (2H, m).

Example 207

Preparation of the Compound 207

(1) Preparation of the Intermediate 207(1).

The title compound was obtained in the same manner as the Example 185(2) using the following starting materials.

Starting materials: the intermediate 198(1) and 3-pentanol; Yield: 91.4% (brown oil).

$^1$H-NMR ($CDCl_3$) δ: 0.96 (6H, t, J=7.2 Hz), 1.68-1.77 (4H, m), 4.24-4.27 (1H, m), 6.80 (1H, d, J=2.7 Hz), 6.92 (1H, dd, J=2.7, 9.0 Hz), 7.24-7.35 (4H, m), 8.01 (1H, d, J=9.0 Hz).

(2) Preparation of the Intermediate 207(2).

The title compound was obtained in the same manner as the Example 125(2) using the following starting material.

Starting material: the intermediate 207(1); Yield: 96.3% (brown oil).

$^1$H-NMR ($CDCl_3$) δ: 0.96 (6H, t, J=7.5 Hz), 1.61-1.70 (4H, m), 3.46 (2H, brs), 3.94-3.99 (1H, m), 6.69-6.72 (2H, m), 6.79 (1H, dd, J=2.7, 8.7 Hz), 7.26-7.30 (2H, m), 7.48-7.51 (2H, m).

(3) Preparation of the Intermediate 207(3).

The title compound was obtained in the same manner as the Example 123(2) using the following starting materials.

Starting materials: the intermediate 207(2) and methyl chloroglyoxylate; Yield: 91.0% (brown oil).

$^1$H-NMR ($CDCl_3$) δ: 0.96 (6H, t, J=7.5 Hz), 1.64-1.71 (4H, m), 3.89 (3H, s), 4.11-4.15 (1H, m), 6.83 (1H, d, J=3.0 Hz), 6.96 (1H, dd, J=3.0, 9.0 Hz), 7.33-7.36 (2H, m), 7.40-7.43 (2H, m), 8.20 (1H, d, J=9.0 Hz), 8.74 (1H, brs).

(4) Preparation of the Intermediate 207(4).

The title compound was obtained in the same manner as the Example 123(1) using the following starting materials.

Starting materials: the intermediate 207(3) and 4-(tert-butyl)benzyl bromide; Yield: 94.9% (colorless oil).

$^1$H-NMR ($CDCl_3$) δ: 0.92-0.97 (6H, m), 1.26 (9H, s), 1.62-1.70 (4H, m), 3.42 (1H, d, J=14.4 Hz), 3.64 (3H, s), 4.08-4.15 (1H, m), 5.05 (1H, d, J=14.4 Hz), 6.66 (1H, dd, J=2.7, 8.7 Hz), 6.75 (1H, d, J=8.7 Hz), 6.88 (1H, d, J=2.7 Hz), 6.93-6.96 (2H, m), 7.18-7.22 (2H, m), 7.25-7.33 (2H, m), 7.60-7.63 (2H, m).

(5) Preparation of the Compound 207.

The title compound was obtained in the same manner as the Example 126(4) using the following starting material.

Starting material: the intermediate 207(4); Yield: 76.1% (white solid).

This compound was obtained as a mixture of the rotational isomers.

Major isomer: $^1$H-NMR (DMSO-$d_6$) δ: 0.85-0.91 (6H, m), 1.18-1.21 (9H, m), 1.55-1.62 (4H, m), 3.07 (1H, d, J=14.7 Hz), 4.17-4.24 (1H, m), 4.76 (1H, d, J=14.7 Hz), 6.72 (1H, dd, J=2.7, 8.7 Hz), 6.80 (1H, d, J=2.7 Hz), 6.86-6.88 (2H, m), 6.96 (1H, d, J=8.7 Hz), 7.17-7.20 (2H, m), 7.39-7.41 (2H, m), 8.04-8.07 (2H, m).

Minor isomer: $^1$H-NMR (DMSO-$d_6$) δ: 0.85-0.91 (6H, m), 1.18-1.21 (9H, m), 1.55-1.62 (4H, m), 3.79-3.86 (1H, m), 4.17-4.24 (1H, m), 4.47-4.44 (1H, m), 6.77-6.98 (3H, m), 7.07-7.41 (6H, m), 8.04-8.07 (2H, m).

Example 208

Preparation of the Compound 208

(1) Preparation of the Intermediate 208(1).

A mixture of the intermediate 198(1) (700 mg, 2.32 mmol), diethylamine (339 mg, 4.64 mmol), potassium carbonate (320 mg, 2.32 mmol) and acetonitrile (5 ml) was stirred at 100° C. for 10 hours under argon atmosphere. The reaction mixture was cooled to room temperature, diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=10:1) to give the title compound (580 mg, 70.5%) as a yellow solid.

$^1$H-NMR ($CDCl_3$) δ: 1.22 (6H, t, J=6.9 Hz), 3.45 (4H, q, J=6.9 Hz), 6.37 (1H, d, J=3.0 Hz), 6.60 (1H, dd, J=3.0, 9.0 Hz), 7.23-7.33 (4H, m), 8.08 (1H, d, J=9.0 Hz).

(2) Preparation of the Intermediate 208(2).

The title compound was obtained in the same manner as the Example 125(2) using the following starting material.

Starting material: the intermediate 208(1); Yield: 87.5% (yellow solid).

$^1$H-NMR ($CDCl_3$) δ: 1.11 (6H, t, J=6.9 Hz), 3.24 (4H, q, J=6.9 Hz), 3.35 (2H, brs), 6.57 (1H, d, J=2.7 Hz), 6.66-6.75 (2H, m), 7.26-7.29 (2H, m), 7.48-7.52 (2H, m).

(3) Preparation of the Intermediate 208(3).

The title compound was obtained in the same manner as the Example 123(2) using the following starting materials.

Starting materials: the intermediate 208(2) and methyl chloroglyoxylate; Yield: 89.5% (colorless oil).

$^1$H-NMR ($CDCl_3$) δ: 1.17 (6H, t, J=6.9 Hz), 3.37 (4H, q, J=6.9 Hz), 3.88 (3H, s), 6.53 (1H, d, J=3.0 Hz), 6.72 (1H, dd, J=3.0, 9.0 Hz), 7.31-7.34 (2H, m), 7.37-7.43 (2H, m), 8.08 (1H, d, J=9.0 Hz), 8.63 (1H, brs).

(4) Preparation of the Intermediate 208(4).

The title compound was obtained in the same manner as the Example 123(1) using the following starting materials.

Starting materials: the intermediate 208(3) and 4-(tert-butyl)benzyl bromide; Yield: 90.7% (yellow oil).

$^1$H-NMR ($CDCl_3$) δ: 1.16 (6H, t, J=7.2 Hz), 1.27 (9H, s), 3.30-3.39 (5H, m), 3.65 (3H, s), 5.00 (1H, d, J=14.4 Hz), 6.40 (1H, dd, J=3.0, 9.0 Hz), 6.54 (1H, d, J=3.0 Hz), 6.68 (1H, d, J=9.0 Hz), 6.96-6.99 (2H, m), 7.19-7.22 (2H, m), 7.25-7.30 (2H, m), 7.60-7.62 (2H, m).

(5) Preparation of the Compound 208.

The title compound was obtained in the same manner as the Example 126(4) using the following starting material.

Starting material: the intermediate 208(4); Yield: 75.7% (white solid).

$^1$H-NMR (DMSO-$d_6$) δ: 1.06 (6H, t, J=7.2 Hz), 1.22 (9H, s), 3.31-3.36 (5H, m), 4.80 (1H, d, J=14.4 Hz), 6.53-6.56 (2H, m), 6.76-6.78 (1H, m), 6.92-6.94 (2H, m), 7.23-7.36 (2H, m), 7.46-7.48 (2H, m), 7.71-7.74 (2H, m).

Example 209

Preparation of the Compound 209

(1) Preparation of the Intermediate 209(1).

The title compound was obtained in the same manner as the Example 185(2) using the following starting materials.

Starting materials: the intermediate 198(1) and 2-propanol; Yield: 99.9% (yellow oil).

$^1$H-NMR ($CDCl_3$) δ: 1.39 (6H, d, J=6.0 Hz), 4.63-4.69 (1H, m), 6.79 (1H, d, J=2.7 Hz), 6.92 (1H, dd, J=2.7, 9.0 Hz), 7.24-7.34 (4H, m), 8.01 (1H, d, J=9.0 Hz).

(2) Preparation of the Intermediate 209(2).

The title compound was obtained in the same manner as the Example 125(2) using the following starting material.

Starting material: the intermediate 209(1); Yield: 92.1% (yellow oil).

$^1$H-NMR ($CDCl_3$) δ: 1.24-1.34 (6H, m), 3.47 (2H, brs), 4.36-4.44 (1H, m), 6.69-6.72 (2H, m), 6.78 (1H, dd, J=2.7, 8.7 Hz), 7.25-7.30 (2H, m), 7.46-7.51 (2H, m).

(3) Preparation of the Intermediate 209(3).

The title compound was obtained in the same manner as the Example 123(2) using the following starting materials.

Starting materials: the intermediate 209(2) and methyl chloroglyoxylate; Yield: 74.0% (yellow solid).

$^1$H-NMR ($CDCl_3$) δ: 1.35 (6H, d, J=6.0 Hz), 3.89 (3H, s), 4.52-4.60 (1H, m), 6.82 (1H, d, J=3.0 Hz), 6.95 (1H, dd, J=3.0, 9.0 Hz), 7.33-7.36 (2H, m), 7.39-7.43 (2H, m), 8.21 (1H, d, J=9.0 Hz), 8.74 (1H, brs).

(4) Preparation of the Intermediate 209(4).

The title compound was obtained in the same manner as the Example 123(1) using the following starting materials.

Starting materials: the intermediate 209(3) and 4-(tert-butyl)benzyl bromide; Yield: 99.9% (colorless oil).

$^1$H-NMR ($CDCl_3$) δ: 1.26 (9H, s), 1.32-1.35 (6H, m), 3.40 (1H, d, J=14.4 Hz), 3.65 (3H, s), 4.50-4.56 (1H, m), 5.06 (1H, d, J=14.4 Hz), 6.65 (1H, dd, J=2.7, 8.7 Hz), 6.74 (1H, d, J=8.7 Hz), 6.86 (1H, d, J=2.7 Hz), 6.92-6.95 (2H, m), 7.19-7.22 (2H, m), 7.28-7.31 (2H, m), 7.60-7.63 (2H, m).

(5) Preparation of the Compound 209.

The title compound was obtained in the same manner as the Example 126(4) using the following starting material.

Starting material: the intermediate 209(4); Yield: 40.1% (white solid).

This compound was obtained as a mixture of the rotational isomers.

Major isomer: $^1$H-NMR (DMSO-$d_6$) δ: 1.15-1.27 (15H, m), 3.03 (1H, d, J=14.7 Hz), 4.56-4.64 (1H, m), 4.76 (1H, d, J=14.7 Hz), 6.70 (1H, dd, J=3.0, 8.7 Hz), 6.78 (1H, d, J=3.0 Hz), 6.84-6.87 (2H, m), 6.94 (1H, d, J=8.7 Hz), 7.17-7.20 (2H, m), 7.38-7.41 (2H, m), 8.05-8.08 (2H, m).

Minor isomer: $^1$H-NMR (DMSO-$d_6$) δ: 1.15-1.27 (15H, m), 3.78-3.82 (1H, m), 4.47-4.51 (1H, m), 4.56-4.64 (1H, m), 6.70 (1H, dd, J=3.0, 8.7 Hz), 6.76-6.78 (1H, m), 6.84-6.87 (2H, m), 6.94 (1H, d, J=8.7 Hz), 7.07-7.41 (4H, m), 8.05-8.08 (2H, m).

Example 210

Preparation of the Compound 210

(1) Preparation of the Intermediate 210(1).

The title compound was obtained in the same manner as the Example 125(3) using the following starting materials.

Starting materials: the intermediate 185(3) and methyl chloroglyoxylate; Yield: 75.3% (white solid).

$^1$H-NMR ($CDCl_3$) δ: 0.96 (3H, t, J=7.5 Hz), 1.68-1.81 (2H, m), 3.93 (2H, t, J=6.3 Hz), 3.97 (3H, s), 6.97 (1H, d, J=9.0 Hz), 7.22-7.27 (2H, m), 7.52 (1H, d, J=2.4 Hz), 7.54-7.59 (2H, m), 7.65 (1H, dd, J=2.4, 9.0 Hz), 8.80 (1H, brs).

(2) Preparation of the Intermediate 210(2).

The title compound was obtained in the same manner as the Example 123(1) using the following starting materials.

Starting materials: the intermediate 210(1) and benzyl bromide; Yield: 80.3% (colorless oil).

$^1$H-NMR ($CDCl_3$) δ: 0.96 (3H, t, J=7.2 Hz), 1.68-1.77 (2H, m), 3.58 (3H, s), 3.90 (2H, t, J=6.3 Hz), 4.92 (2H, s), 6.82-6.85 (1H, m), 6.96-7.00 (2H, m), 7.19-7.33 (7H, m), 7.39-7.42 (2H, m).

(3) Preparation of the Compound 210.

The title compound was obtained in the same manner as the Example 126(4) using the following starting material.

Starting material: the intermediate 210(2); Yield: 57.1% (white solid).

$^1$H-NMR (DMSO-$d_6$) δ: 0.88 (3H, t, J=7.2 Hz), 1.60-1.67 (2H, m), 3.88-3.92 (2H, m), 4.84 (2H, s), 6.93-7.04 (2H, m), 7.15-7.30 (6H, m), 7.36-7.38 (2H, m), 7.54-7.57 (2H, m).

Example 211

Preparation of the Compound 211

(1) Preparation of the Intermediate 211(1).

The title compound was obtained in the same manner as the Example 123(3) using the following starting materials.

Starting materials: 3-bromo-4-fluoro-1-nitrobenzene and 4-(trifluoromethoxy)phenylboronic acid; Yield: 70.8% (white solid).

$^1$H-NMR ($CDCl_3$) δ: 7.30-7.37 (3H, m), 7.60-7.63 (2H, m), 8.23-8.29 (1H, m), 8.36-8.39 (1H, m).

(2) Preparation of the Intermediate 211(2).

The title compound was obtained in the same manner as the Example 185(2) using the following starting materials.

Starting materials: the intermediate 211(1) and 2-propanol; Yield: 99.9% (yellow solid).

$^1$H-NMR ($CDCl_3$) δ: 1.36 (6H, d, J=6.0 Hz), 4.68-4.76 (1H, m), 7.01-7.04 (1H, m), 7.25-7.29 (2H, m), 7.54-7.59 (2H, m), 8.20-8.24 (2H, m).

(3) Preparation of the Intermediate 211(3).

The title compound was obtained in the same manner as the Example 125(2) using the following starting material.

Starting material: the intermediate 211(2); Yield: 99.9% (brown oil).

$^1$H-NMR ($CDCl_3$) δ: 1.13 (6H, d, J=6.0 Hz), 3.50 (2H, brs), 4.06-4.14 (1H, m), 6.62-6.67 (2H, m), 6.85 (1H, d, J=8.7 Hz), 7.20-7.23 (2H, m), 7.53-7.58 (2H, m).

(4) Preparation of the Intermediate 211(4).

The title compound was obtained in the same manner as the Example 125(3) using the following starting materials.

Starting materials: the intermediate 211(3) and methyl chloroglyoxylate; Yield: 73.2% (purple solid).

$^1$H-NMR ($CDCl_3$) δ: 1.25 (6H, d, J=6.0 Hz), 3.97 (3H, s), 4.41-4.49 (1H, m), 6.99 (1H, d, J=8.7 Hz), 7.22-7.27 (2H, m), 7.51 (1H, d, J=2.7 Hz), 7.55-7.59 (2H, m), 7.64 (1H, dd, J=2.7, 8.7 Hz), 8.80 (1H, brs).

(5) Preparation of the Intermediate 211(5).

The title compound was obtained in the same manner as the Example 123(1) using the following starting materials.

Starting materials: the intermediate 211(4) and 4-(tert-butyl)benzyl bromide; Yield: 89.1% (brown solid).

$^1$H-NMR ($CDCl_3$) δ: 1.25-1.33 (15H, m), 3.56 (3H, s), 4.46-4.54 (1H, m), 4.88 (2H, s), 6.86-6.88 (2H, m), 7.03 (1H, dd, J=2.7, 8.7 Hz), 7.16-7.19 (4H, m), 7.31-7.34 (2H, m), 7.35-7.38 (2H, m).

(6) Preparation of the Compound 211.

The title compound was obtained in the same manner as the Example 126(4) using the following starting material.

Starting material: the intermediate 211(5); Yield: 44.1% (white solid).

$^1$H-NMR (DMSO-$d_6$) δ: 1.20-1.24 (15H, m), 4.57-4.65 (1H, m), 4.87 (2H, s), 7.01 (1H, d, J=2.4 Hz), 7.10-7.19 (4H, m), 7.34-7.38 (4H, m), 7.46-7.49 (2H, m).

Example 212

Preparation of the Compound 212

(1) Preparation of the Intermediate 212(1).

The title compound was obtained in the same manner as the Example 185(2) using the following starting materials.

Starting materials: the intermediate 211(1) and benzylalcohol; Yield: 81.4% (white solid).

$^1$H-NMR ($CDCl_3$) δ: 5.23 (2H, s), 7.09 (1H, d, J=9.0 Hz), 7.26-7.37 (7H, m), 7.58-7.61 (2H, m), 8.20-8.25 (2H, m).

(2) Preparation of the Intermediate 212(2).

The title compound was obtained in the same manner as the Example 125(2) using the following starting material.

Starting material: the intermediate 212(1); Yield: 94.1% (yellowish-brown oil).

$^1$H-NMR ($CDCl_3$) δ: 3.51 (2H, brs), 4.91 (2H, s), 6.60-6.69 (2H, m), 6.89 (1H, d, J=8.7 Hz), 7.21-7.32 (7H, m), 7.54-7.57 (2H, m).

(3) Preparation of the Intermediate 212(3).

The title compound was obtained in the same manner as the Example 125(3) using the following starting materials.

Starting materials: the intermediate 212(2) and methyl chloroglyoxylate; Yield: 78.4% (pale orange solid).

$^1$H-NMR ($CDCl_3$) δ: 3.97 (3H, s), 5.08 (2H, s), 7.04 (1H, d, J=9.0 Hz), 7.26-7.36 (7H, m), 7.54-7.66 (4H, m), 8.81 (1H, brs).

(4) Preparation of the Intermediate 212(4).

The title compound was obtained in the same manner as the Example 123(1) using the following starting materials.

Starting materials: the intermediate 212(3) and 4-(tert-butyl)benzyl bromide; Yield: 70.1% (colorless oil).

$^1$H-NMR ($CDCl_3$) δ: 1.30 (9H, s), 3.55 (3H, s), 4.88 (2H, s), 5.07 (2H, s), 6.89 (1H, d, J=3.0 Hz), 6.94 (1H, d, J=8.7 Hz), 7.04 (1H, dd, J=3.0, 8.7 Hz), 7.14-7.19 (4H, m), 7.24-7.41 (9H, m).

(5) Preparation of the Compound 212.

The title compound was obtained in the same manner as the Example 126(4) using the following starting material.

Starting material: the intermediate 212(4); Yield: 47.5% (white solid).

$^1$H-NMR (DMSO-$d_6$) δ: 1.25 (9H, s), 4.89 (2H, s), 5.13 (2H, s), 7.04-7.24 (5H, m), 7.32-7.38 (9H, m), 7.49-7.53 (2H, m).

Example 213

Preparation of the Compound 213

(1) Preparation of the Intermediate 213(1).

The title compound was obtained in the same manner as the Example 208(1) using the following starting materials.

Starting materials: the intermediate 211(1) and diethylamine; Yield: 40.1% (yellow oil).

$^1$H-NMR ($CDCl_3$) δ: 0.97 (6H, t, J=7.2 Hz), 3.04 (4H, q, J=7.2 Hz), 7.02 (1H, d, J=9.0 Hz), 7.26-7.03 (2H, m), 7.51-7.56 (2H, m), 8.03 (1H, d, J=2.7 Hz), 8.12 (1H, dd, J=2.7, 9.0 Hz).

(2) Preparation of the Intermediate 213(2).

The title compound was obtained in the same manner as the Example 125(2) using the following starting material.

Starting material: the intermediate 213(1); Yield: 95.1% (yellowish-green oil).

$^1$H-NMR ($CDCl_3$) δ: 0.85 (6H, t, J=7.2 Hz), 2.76 (4H, q, J=7.2 Hz), 3.53 (2H, brs), 6.60-6.67 (2H, m), 6.97 (1H, d, J=8.4 Hz), 7.17-7.20 (2H, m), 7.51-7.56 (2H, m).

(3) Preparation of the Intermediate 213(3).

The title compound was obtained in the same manner as the Example 125(3) using the following starting materials.

Starting materials: the intermediate 213(2) and methyl chloroglyoxylate; Yield: 85.6% (pale green solid).

$^1$H-NMR ($CDCl_3$) δ: 0.89 (6H, t, J=7.2 Hz), 2.85 (4H, q, J=7.2 Hz), 3.97 (3H, s), 7.09 (1H, d, J=8.7 Hz), 7.21-7.24 (2H, m), 7.41 (1H, d, J=2.7 Hz), 7.56-7.59 (2H, m), 7.62 (1H, dd, J=2.7, 8.7 Hz), 8.79 (1H, brs).

(4) Preparation of the Intermediate 213(4).

The title compound was obtained in the same manner as the Example 123(1) using the following starting materials.

Starting materials: the intermediate 213(3) and 4-(tert-butyl)benzyl bromide; Yield: 88.1% (colorless oil).

$^1$H-NMR ($CDCl_3$) δ: 0.86 (6H, t, J=7.2 Hz), 1.29 (9H, s), 2.83 (4H, q, J=7.2 Hz), 3.54 (3H, s), 4.88 (2H, s), 6.77 (1H, d, J=2.4 Hz), 6.96-6.97 (2H, m), 7.15-7.18 (4H, m), 7.29-7.33 (2H, m), 7.38-7.41 (2H, m).

(5) Preparation of the Compound 213.

The title compound was obtained in the same manner as the Example 126(4) using the following starting material.

Starting material: the intermediate 213(4); Yield: 64.7% (white solid).

$^1$H-NMR (DMSO-$d_6$) δ: 0.79 (6H, t, J=7.2 Hz), 1.23 (9H, s), 2.78 (4H, q, J=7.2 Hz), 4.87 (2H, s), 6.88 (1H, d, J=2.1 Hz), 7.07-7.14 (4H, m), 7.32-7.38 (4H, m), 7.48-7.50 (2H, m), 13.93 (1H, brs).

Example 214

Preparation of the Compound 214

(1) Preparation of the Intermediate 214(1).

The title compound was obtained in the same manner as the Example 208(1) using the following starting materials.

Starting materials: the intermediate 211(1) and dimethylamine hydrochloride; Yield: 99.9% (yellow solid).

$^1$H-NMR ($CDCl_3$) δ: 2.71 (6H, s), 6.95 (1H, d, J=9.0 Hz), 7.26-7.30 (2H, m), 7.50-7.55 (2H, m), 8.06 (1H, d, J=3.0 Hz), 8.13 (1H, dd, J=3.0, 9.0 Hz).

(2) Preparation of the Intermediate 214(2).

The title compound was obtained in the same manner as the Example 125(2) using the following starting material.

Starting material: the intermediate 214(1); Yield: 99.9% (blue oil).

$^1$H-NMR ($CDCl_3$) δ: 2.44 (6H, s), 3.50 (2H, brs), 6.60 (1H, d, J=2.7 Hz), 6.65 (1H, dd, J=2.7, 8.7 Hz), 6.94 (1H, d, J=8.7 Hz), 7.19-7.22 (2H, m), 7.56-7.60 (2H, m).

(3) Preparation of the Intermediate 214(3).

The title compound was obtained in the same manner as the Example 125(3) using the following starting materials.

Starting materials: the intermediate 214(2) and methyl chloroglyoxylate; Yield: 82.1% (green solid).

$^1$H-NMR ($CDCl_3$) δ: 2.54 (6H, s), 3.97 (3H, s), 7.05 (1H, d, J=8.7 Hz), 7.23-7.26 (2H, m), 7.40 (1H, d, J=2.7 Hz), 7.56-7.63 (3H, m), 8.78 (1H, brs).

(4) Preparation of the Intermediate 214(4).

The title compound was obtained in the same manner as the Example 123(1) using the following starting materials.

Starting materials: the intermediate 214(3) and 4-(tert-butyl)benzyl bromide; Yield: 66.8% (brown oil).

$^1$H-NMR ($CDCl_3$) δ: 1.29 (9H, s), 2.51 (6H, s), 3.56 (3H, s), 4.86 (2H, s), 6.74 (1H, d, J=2.7 Hz), 6.89 (1H, d, J=8.4 Hz), 6.98 (1H, dd, J=2.7, 8.4 Hz), 7.16-7.20 (4H, m), 7.30-7.33 (2H, m), 7.40-7.43 (2H, m).

(5) Preparation of the Compound 214.

The title compound was obtained in the same manner as the Example 126(4) using the following starting material.

Starting material: the intermediate 214(4); Yield: 85.5% (white solid).

$^1$H-NMR (DMSO-$d_6$) δ: 1.24 (9H, s), 2.45 (6H, s), 4.85 (2H, s), 6.87 (1H, d, J=2.7 Hz), 7.03 (1H, d, J=8.7 Hz), 7.10-7.15 (3H, m), 7.32-7.35 (2H, m), 7.37-7.40 (2H, m), 7.50-7.53 (2H, m), 13.88 (1H, brs).

Example 215

Preparation of the Compound 215

(1) Preparation of the Intermediate 215(1).

The title compound was obtained in the same manner as the Example 123(3) using the following starting materials.

Starting materials: 5-bromo-4-fluoro-2-methyl-1-nitrobenzene and 4-(trifluoromethoxy)phenylboronic acid; Yield: 97.9% (orange solid).

$^1$H-NMR ($CDCl_3$) δ: 2.67 (3H, s), 7.15 (1H, d, J=10.8 Hz), 7.31-7.35 (2H, m), 7.57-7.61 (2H, m), 8.17 (1H, d, J=7.5 Hz).

(2) Preparation of the Intermediate 215(2).

The title compound was obtained in the same manner as the Example 208(1) using the following starting materials.

Starting materials: the intermediate 215(1) and dimethylamine hydrochloride; Yield: 99.9% (yellow solid).

$^1$H-NMR ($CDCl_3$) δ: 2.68 (9H, s), 6.75 (1H, s), 7.24-7.29 (2H, m), 7.45-7.54 (2H, m), 7.99 (1H, s).

(3) Preparation of the Intermediate 215(3).

The title compound was obtained in the same manner as the Example 125(2) using the following starting material.

Starting material: the intermediate 215(2); Yield: 93.5% (pale yellow oil).

$^1$H-NMR ($CDCl_3$) δ: 2.21 (3H, s), 2.48 (6H, s), 3.55 (2H, brs), 6.58 (1H, s), 6.89 (1H, s), 7.18-7.29 (2H, m), 7.52-7.59 (2H, m).

(4) Preparation of the Intermediate 215(4).

The title compound was obtained in the same manner as the Example 125(3) using the following starting materials.

Starting materials: the intermediate 215(3) and methyl chloroglyoxylate; Yield: 70.2% (white solid).

$^1$H-NMR (DMSO-$d_6$) δ: 2.19 (3H, s), 2.48 (6H, s), 3.84 (3H, s), 6.97 (1H, s), 7.11 (1H, s), 7.37-7.42 (2H, m), 7.60-7.65 (2H, m), 10.26 (1H, brs).

(5) Preparation of the Intermediate 215(5).

The title compound was obtained in the same manner as the Example 123(1) using the following starting materials.

Starting materials: the intermediate 215(4) and 4-(tert-butyl)benzyl bromide; Yield: 77.2% (white solid).

$^1$H-NMR ($CDCl_3$) δ: 1.28 (9H, s), 2.20 (3H, s), 2.50 (6H, s), 3.51 (3H, s), 4.12 (1H, d, J=13.8 Hz), 5.40 (1H, d, J=13.8 Hz), 6.38 (1H, s), 6.78 (1H, s), 7.09-7.16 (4H, m), 7.23-7.31 (4H, m).

(6) Preparation of the Compound 215.

The title compound was obtained in the same manner as the Example 126(4) using the following starting material.

Starting material: the intermediate 215(5); Yield: 52.6% (white solid).

This compound was obtained as a mixture of the rotational isomers.

Major isomer: $^1$H-NMR (DMSO-$d_6$) δ: 1.23 (9H, s), 2.17 (3H, s), 2.45 (6H, s), 4.14 (1H, d, J=13.8 Hz), 5.24 (1H, d, J=13.8 Hz), 6.37 (1H, s), 6.92 (1H, s), 7.08-7.14 (2H, m), 7.27-7.42 (6H, m).

Minor isomer: $^1$H-NMR (DMSO-$d_6$) δ: 1.22 (9H, s), 1.98 (3H, s), 2.44 (6H, s), 4.38-4.47 (1H, m), 4.83-4.92 (1H, m), 6.40 (1H, s), 6.88 (1H, s), 7.08-7.42 (8H, m).

Example 216

Preparation of the Compound 216

(1) Preparation of the Intermediate 216(1).

The title compound was obtained in the same manner as the Example 208(1) using the following starting materials.

Starting materials: the intermediate 211(1) and morpholine; Yield: 67.9% (yellow solid).

$^1$H-NMR ($CDCl_3$) δ: 2.92-2.96 (4H, m), 3.59-3.64 (4H, m), 7.05 (1H, d, J=9.0 Hz), 7.30-7.34 (2H, m), 7.63-7.69 (2H, m), 8.09 (1H, d, J=2.7 Hz), 8.18 (1H, dd, J=2.7, 9.0 Hz).

(2) Preparation of the Intermediate 216(2).

The title compound was obtained in the same manner as the Example 125(2) using the following starting material.

Starting material: the intermediate 216(1); Yield: 100% (yellow solid).

$^1$H-NMR ($CDCl_3$) δ: 2.69-2.73 (4H, m), 3.45-3.60 (6H, m), 6.62 (1H, d, J=2.7 Hz), 6.67 (1H, dd, J=2.7, 8.4 Hz), 6.92 (1H, d, J=8.4 Hz), 7.19-7.25 (2H, m), 7.60-7.65 (2H, m).

(3) Preparation of the Intermediate 216(3).

The title compound was obtained in the same manner as the Example 125(3) using the following starting materials.

Starting materials: the intermediate 216(2) and methyl chloroglyoxylate; Yield: 76.1% (pale yellow solid).

$^1$H-NMR ($CDCl_3$) δ: 2.76-2.81 (4H, m), 3.56-3.61 (4H, m), 3.97 (3H, s), 7.05 (1H, d, J=9.0 Hz), 7.24-7.28 (2H, m), 7.46 (1H, d, J=2.7 Hz), 7.62-7.70 (3H, m), 8.80 (1H, brs).

(4) Preparation of the Intermediate 216(4).

The title compound was obtained in the same manner as the Example 123(1) using the following starting materials.

Starting materials: the intermediate 216(3) and 4-(tert-butyl)benzyl bromide; Yield: 55.8% (white solid).

$^1$H-NMR ($CDCl_3$) δ: 1.30 (9H, s), 2.75-2.79 (4H, m), 3.56-3.60 (7H, m), 4.88 (2H, s), 6.79 (1H, d, J=2.7 Hz), 6.92

(1H, d, J=8.4 Hz), 7.04 (1H, dd, J=2.7, 8.4 Hz), 7.12-7.24 (4H, m), 7.29-7.35 (2H, m), 7.46-7.51 (2H, m).

(5) Preparation of the Compound 216.

The title compound was obtained in the same manner as the Example 126(4) using the following starting material.

Starting material: the intermediate 216(4); Yield: 100% (white solid).

$^1$H-NMR (DMSO-$d_6$) δ: 1.24 (9H, s), 2.66-2.75 (4H, m), 3.45-3.51 (4H, m), 4.88 (2H, s), 6.95 (1H, d, J=2.4 Hz), 7.06 (1H, d, J=8.7 Hz), 7.11-7.21 (3H, m), 7.32-7.44 (4H, m), 7.62-7.67 (2H, m).

Example 217

Preparation of the Compound 217

(1) Preparation of the Intermediate 217(1).

The title compound was obtained in the same manner as the Example 208(1) using the following starting materials.

Starting materials: the intermediate 211(1) and piperidine; Yield: 85.4% (yellow solid).

$^1$H-NMR ($CDCl_3$) δ: 1.43-1.54 (6H, m), 2.85-2.98 (4H, m), 7.02 (1H, d, J=9.0 Hz), 7.27-7.32 (2H, m), 7.61-7.67 (2H, m), 8.05 (1H, d, J=2.7 Hz), 8.15 (1H, dd, J=2.7, 9.0 Hz).

(2) Preparation of the Intermediate 217(2).

The title compound was obtained in the same manner as the Example 125(2) using the following starting material.

Starting material: the intermediate 217(1); Yield: 100% (yellow oil).

$^1$H-NMR ($CDCl_3$) δ: 1.35-1.52 (6H, m), 2.51-2.75 (4H, m), 3.50 (2H, brs), 6.60-6.66 (2H, m), 6.91 (1H, d, J=8.4 Hz), 7.17-7.24 (2H, m), 7.62-7.67 (2H, m).

(3) Preparation of the Intermediate 217(3).

The title compound was obtained in the same manner as the Example 125(3) using the following starting materials.

Starting materials: the intermediate 217(2) and methyl chloroglyoxylate; Yield: 76.5% (pale yellow solid).

$^1$H-NMR ($CDCl_3$) δ: 1.40-1.50 (6H, m), 2.69-2.82 (4H, m), 3.96 (3H, s), 7.04 (1H, d, J=8.7 Hz), 7.22-7.26 (2H, m), 7.41 (1H, d, J=2.4 Hz), 7.61 (1H, dd, J=2.4, 8.7 Hz), 7.64-7.70 (2H, m), 8.78 (1H, brs).

(4) Preparation of the Intermediate 217(4).

The title compound was obtained in the same manner as the Example 123(1) using the following starting materials.

Starting materials: the intermediate 217(3) and 4-(tert-butyl)benzyl bromide; Yield: 56.9% (white solid).

$^1$H-NMR ($CDCl_3$) δ: 1.30 (9H, s), 1.39-1.50 (6H, m), 2.65-2.79 (4H, m), 3.56 (3H, s), 4.87 (2H, s), 6.76 (1H, d, J=2.7 Hz), 6.90 (1H, d, J=8.7 Hz), 6.99 (1H, dd, J=2.7, 8.7 Hz), 7.15-7.20 (4H, m), 7.29-7.34 (2H, m), 7.46-7.52 (2H, m).

(5) Preparation of the Compound 217.

The title compound was obtained in the same manner as the Example 126(4) using the following starting material.

Starting material: the intermediate 217(4); Yield: 100% (white solid).

$^1$H-NMR (DMSO-$d_6$) δ: 1.24 (9H, s), 1.32-1.41 (6H, m), 2.60-2.72 (4H, m), 4.87 (2H, s), 6.91 (1H, d, J=2.4 Hz), 7.03 (1H, d, J=8.7 Hz), 7.11-7.16 (3H, m), 7.31-7.41 (4H, m), 7.58-7.63 (2H, m).

Example 218

Preparation of the Compound 218

(1) Preparation of the Intermediate 218(1).

The title compound was obtained in the same manner as the Example 185(2) using the following starting materials.

Starting materials: the intermediate 211(1) and tert-butanol; Yield: 100.0% (yellow oil).

$^1$H-NMR ($CDCl_3$) δ: 1.30 (9H, s), 7.23 (1H, d, J=9.0 Hz), 7.26-7.30 (2H, m), 7.56-7.59 (2H, m), 8.16 (1H, dd, J=2.7, 9.0 Hz), 8.24 (1H, d, J=2.7 Hz).

(2) Preparation of the Intermediate 218(2).

The title compound was obtained in the same manner as the Example 125(2) using the following starting material.

Starting material: the intermediate 218(1); Yield: 100% (yellow oil).

$^1$H-NMR ($CDCl_3$) δ: 1.02 (9H, s), 3.56 (2H, brs), 6.60 (1H, dd, J=2.7, 8.4 Hz), 6.67 (1H, d, J=2.7 Hz), 6.93 (1H, d, J=8.4 Hz), 7.20-7.23 (2H, m), 7.54-7.57 (2H, m).

(3) Preparation of the Intermediate 218(3).

The title compound was obtained in the same manner as the Example 125(3) using the following starting materials.

Starting materials: the intermediate 218(2) and methyl chloroglyoxylate; Yield: 83.8% (white solid).

$^1$H-NMR ($CDCl_3$) δ: 1.11 (9H, s), 3.98 (3H, s), 7.13-7.16 (1H, m), 7.23-7.27 (2H, m), 7.56-7.61 (4H, m), 8.83 (1H, brs).

(4) Preparation of the Intermediate 218(4).

The title compound was obtained in the same manner as the Example 123(1) using the following starting materials.

Starting materials: the intermediate 218(3) and 4-(tert-butyl)benzyl bromide; Yield: 100% (yellow oil).

$^1$H-NMR ($CDCl_3$) δ: 1.10 (9H, s), 1.29 (9H, s), 3.54 (3H, s), 4.91 (2H, s), 6.90 (1H, d, J=2.7 Hz), 6.99 (1H, dd, J=2.7, 8.7 Hz), 7.05 (1H, d, J=8.7 Hz), 7.14-7.20 (4H, m), 7.29-7.34 (2H, m), 7.36-7.40 (2H, m).

(5) Preparation of the Compound 218.

The title compound was obtained in the same manner as the Example 126(4) using the following starting material.

Starting material: the intermediate 218(4); Yield: 77.8% (white solid).

$^1$H-NMR (DMSO-$d_6$) δ: 1.05 (9H, s), 1.23 (9H, s), 4.81 (2H, s), 7.00-7.03 (2H, m), 7.10-7.29 (5H, m), 7.34-7.36 (2H, m), 7.49-7.52 (2H, m).

Example 219

Preparation of the Compound 219

(1) Preparation of the Intermediate 219(1).

5-Bromovaleryl chloride (3.89 ml, 19.51 mmol) was added to a solution of 2-chloro-4-nitroaniline (2.59 g, 15.00 mmol) in dimethylacetamide (10 ml) at 0° C., and the mixture was stirred at room temperature for 2 hours. The reaction mixture was diluted with ethyl acetate. The organic layer was washed with water, a saturated aqueous solution of sodium hydrogen carbonate and saturated brine, and dried over anhydrous sodium sulfate. The residue obtained by evaporation of the solvent under reduced pressure was washed with n-hexane to give the title compound (4.64 g, 92.2%) as a white solid.

$^1$H-NMR ($CDCl_3$) δ: 1.93-2.00 (4H, m), 2.56 (2H, t, J=7.2 Hz), 3.47 (2H, t, J=6.0 Hz), 7.87 (1H, brs), 8.18 (1H, dd, J=2.7, 9.0 Hz), 8.31 (1H, d, J=2.7 Hz), 8.70 (1H, d, J=9.0 Hz).

(2) Preparation of the Intermediate 219(2).

A mixture of the intermediate 219(1) (4.64 g, 13.82 mmol), potassium carbonate (3.82 g, 27.65 mmol) and dimethylformamide (40 ml) was stirred at room temperature for 2 hours. The reaction mixture was diluted with water, and extracted with ethyl acetate. The organic layer was washed with water and saturated brine, and dried over anhydrous sodium sulfate. The residue obtained by evaporation of the solvent under reduced pressure was washed with n-hexane and diisopropyl ether to give the title compound (3.20 g, 90.9%) as a white solid.

$^1$H-NMR ($CDCl_3$) δ: 1.93-2.02 (4H, m), 2.58-2.63 (2H, m), 3.52-3.63 (2H, m), 7.46 (1H, d, J=8.4 Hz), 8.19 (1H, dd, J=2.7, 8.4 Hz), 8.38 (1H, d, J=2.7 Hz).

(3) Preparation of the Intermediate 219(3).

The title compound was obtained in the same manner as the Example 190(3) using the following starting materials.

Starting materials: the intermediate 219(2) and 4-(trifluoromethoxy)phenylboronic acid; Yield: 62.6% (orange solid).

$^1$H-NMR ($CDCl_3$) δ: 1.74-1.84 (4H, m), 2.34-2.52 (2H, m), 2.98-3.06 (1H, m), 3.34-3.42 (1H, m), 7.29-7.33 (2H, m), 7.41-7.48 (3H, m), 8.27-8.31 (2H, m).

(4) Preparation of the Intermediate 219(4).

The title compound was obtained in the same manner as the Example 125(2) using the following starting material.

Starting material: the intermediate 219(3); Yield: 90.4% (green solid).

$^1$H-NMR ($CDCl_3$) δ: 1.32-1.80 (4H, m), 2.27-2.54 (2H, m), 2.85-2.93 (1H, m), 3.25-3.34 (1H, m), 3.78 (2H, brs), 6.66-6.73 (2H, m), 7.02 (1H, d, J=8.4 Hz), 7.20-7.23 (2H, m), 7.36-7.41 (2H, m).

(5) Preparation of the Intermediate 219(5).

The title compound was obtained in the same manner as the Example 125(3) using the following starting materials.

Starting materials: the intermediate 219(4) and methyl chloroglyoxylate; Yield: 80.3% (white solid).

$^1$H-NMR ($CDCl_3$) δ: 1.37-1.81 (4H, m), 2.30-2.39 (1H, m), 2.47-2.55 (1H, m), 2.90-2.95 (1H, m), 3.29-3.36 (1H, m), 3.98 (3H, s), 7.22-7.27 (3H, m), 7.36-7.41 (2H, m), 7.63 (1H, d, J=2.1 Hz), 7.71 (1H, dd, J=2.1, 8.4 Hz), 9.05 (1H, brs).

(6) Preparation of the Intermediate 219(6).

The title compound was obtained in the same manner as the Example 123(1) using the following starting materials.

Starting materials: the intermediate 219(5) and 4-(tert-butyl)benzyl bromide; Yield: 96.4% (colorless oil).

$^1$H-NMR ($CDCl_3$) δ: 1.25-1.70 (13H, m), 2.30-2.52 (2H, m), 2.90-2.96 (1H, m), 3.27-3.33 (1H, m), 3.60 (3H, s), 4.81-4.86 (1H, m), 5.00-5.05 (1H, m), 7.01 (1H, d, J=2.1 Hz), 7.17-7.27 (8H, m), 7.30-7.34 (2H, m).

(7) Preparation of the Compound 219.

The title compound was obtained in the same manner as the Example 126(4) using the following starting material.

Starting material: the intermediate 219(6); Yield: 78.7% (white solid).

$^1$H-NMR (DMSO-$d_6$) δ: 1.24-1.70 (13H, m), 2.10-2.32 (2H, m), 2.50-2.89 (2H, m), 4.92-4.98 (2H, m), 7.15-7.20 (3H, m), 7.29-7.37 (6H, m), 7.42-7.45 (2H, m), 14.24 (1H, brs).

Example 220

Preparation of the Compound 220

(1) Preparation of the Intermediate 220(1).

A mixture of 4-(tert-butyl)benzaldehyde (811 mg, 5.00 mmol), 4-bromoaniline (860 mg, 5.00 mmol) and ethanol (10 ml) was refluxed for 7 hours. The reaction mixture was cooled to room temperature. The precipitated solid was collected by filtration, and washed with methanol to give the title compound (1.08 g, 68.0%) as a pale yellow solid.

$^1$H-NMR (DMSO-$d_6$) δ: 1.32 (9H, s), 7.19-7.24 (2H, m), 7.55 (2H, d, J=8.4 Hz), 7.58-7.61 (2H, m), 7.86 (2H, d, J=8.4 Hz), 8.59 (1H, s).

(2) Preparation of the Intermediate 220(2).

Methyllithium (1.2 M solution in diethyl ether; 1.98 ml, 2.37 mmol) was added to a solution of the intermediate 220 (1) (500 mg, 1.58 mmol) in diethyl ether (5 ml) at −10° C. under argon atmosphere, and the mixture was stirred at −10° C. for 3 hours. A saturated aqueous solution of ammonium chloride was added to the reaction mixture at room temperature, and the mixture was extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=6:1) to give the title compound (209 mg, 39.8%) as a brown oil.

$^1$H-NMR ($CDCl_3$) δ: 1.30 (9H, s), 1.50 (3H, d, J=6.9 Hz), 4.04 (1H, brs), 4.42 (1H, brs), 6.38-6.41 (2H, m), 7.14-7.17 (2H, m), 7.23-7.26 (2H, m), 7.31-7.34 (2H, m).

(3) Preparation of the Intermediate 220(3).

The title compound was obtained in the same manner as the Example 123(3) using the following starting materials.

Starting materials: the intermediate 220(2) and 4-(trifluoromethoxy)phenylboronic acid; Yield: 67.0% (yellow oil).

$^1$H-NMR ($CDCl_3$) δ: 1.32 (9H, s), 1.53 (3H, d, J=6.9 Hz), 4.14 (1H, brs), 4.52 (1H, q, J=6.9 Hz), 6.58-6.62 (2H, m), 7.18-7.22 (2H, m), 7.27-7.37 (6H, m), 7.45-7.49 (2H, m).

(4) Preparation of the Intermediate 220(4).

The title compound was obtained in the same manner as the Example 123(2) using the following starting materials.

Starting materials: the intermediate 220(3) and methyl chloroglyoxylate; Yield: 78.0% (yellow oil).

$^1$H-NMR ($CDCl_3$) δ: 1.32 (9H, s), 1.52 (3H, d, J=7.2 Hz), 3.50 (3H, s), 6.13 (1H, q, J=7.2 Hz), 6.90-6.91 (2H, m), 7.20 (2H, d, J=8.7 Hz), 7.26-7.34 (4H, m), 7.42 (2H, d, J=8.7 Hz), 7.55-7.78 (2H, m).

(5) Preparation of the Compound 220.

The title compound was obtained in the same manner as the Example 126(4) using the following starting material.

Starting material: the intermediate 220(4); Yield: 50.9% (brown solid).

$^1$H-NMR (DMSO-$d_6$) δ: 1.28 (9H, s), 1.35 (3H, s), 5.59 (1H, brs), 6.99 (2H, brs), 7.25-7.34 (4H, m), 7.42 (2H, d, J=8.4 Hz), 7.50 (2H, d, J=8.4 Hz), 7.75 (2H, d, J=8.4 Hz).

Example 221

Preparation of the Compound 221

(1) Preparation of the Intermediate 221(1).

The title compound was obtained in the same manner as the Example 220(2) using the following starting materials.

Starting materials: the intermediate 220(1) and n-butyllithium; Yield: 100% (yellow oil).

$^1$H-NMR ($CDCl_3$) δ: 0.88 (3H, t, J=6.6 Hz), 1.23-1.42 (13H, m), 1.72-1.80 (2H, m), 4.06 (1H, brs), 4.21 (1H, t, J=6.9 Hz), 6.36-6.41 (2H, m), 7.11-7.17 (2H, m), 7.20 (2H, d, J=8.4 Hz), 7.31 (2H, d, J=8.4 Hz).

(2) Preparation of the Intermediate 221(2).

The title compound was obtained in the same manner as the Example 125(3) using the following starting materials.

Starting materials: the intermediate 221(1) and methyl chloroglyoxylate; Yield: 86.9% (colorless oil).

$^1$H-NMR ($CDCl_3$) δ: 0.88 (3H, t, J=6.9 Hz), 1.22-1.43 (13H, m), 1.80-1.90 (2H, m), 3.49 (3H, s), 5.89 (1H, t, J=8.1 Hz), 6.52-6.68 (2H, m), 7.04-7.08 (2H, m), 7.26-7.30 (2H, m), 7.33 (2H, d, J=8.7 Hz).

(3) Preparation of the Intermediate 221(3).

The title compound was obtained in the same manner as the Example 123(3) using the following starting materials.

Starting materials: the intermediate 221(2) and 4-(trifluoromethoxy)phenylboronic acid; Yield: 77.9% (colorless oil).

$^1$H-NMR ($CDCl_3$) δ: 0.92 (3H, t, J=7.2 Hz), 1.23-1.52 (13H, m), 1.84-1.89 (2H, m), 3.48 (3H, s), 5.93 (1H, t, J=8.1 Hz), 6.79-6.90 (2H, m), 7.09-7.14 (2H, m), 7.24-7.32 (4H, m), 7.41 (2H, d, J=8.7 Hz), 7.54-7.60 (2H, m).

(4) Preparation of the Compound 221.

The title compound was obtained in the same manner as the Example 126(4) using the following starting material.

Starting material: the intermediate 221(3); Yield: 89.6% (white solid).

$^1$H-NMR (DMSO-$d_6$) δ: 0.85-0.87 (3H, t, J=7.2 Hz), 1.21-1.44 (13H, m), 1.80-1.88 (2H, m), 5.71 (1H, t, J=8.1 Hz), 6.89-6.93 (2H, m), 7.13 (2H, d, J=8.4 Hz), 7.35 (2H, d, J=8.4 Hz), 7.44 (2H, d, J=8.1 Hz), 7.64 (2H, d, J=8.7 Hz), 7.76-7.84 (2H, m).

Example 222

Preparation of the Compound 222

(1) Preparation of the Intermediate 222(1).

The title compound was obtained in the same manner as the Example 220(2) using the following starting materials.

Starting materials: the intermediate 220(1) and phenyllithium; Yield: 79.9% (yellow solid).

$^1$H-NMR ($CDCl_3$) δ: 1.29 (9H, s), 4.24-4.29 (1H, m), 5.42 (1H, d, J=3.0 Hz), 6.37-6.45 (2H, m), 7.11-7.43 (11H, m).

(2) Preparation of the Intermediate 222(2).

The title compound was obtained in the same manner as the Example 125(3) using the following starting materials.

Starting materials: the intermediate 222(1) and methyl chloroglyoxylate; Yield: 75.9% (white solid).

$^1$H-NMR ($CDCl_3$) δ: 1.30 (9H, s), 3.56 (3H, s), 6.73-6.78 (2H, m), 7.04-7.35 (12H, m).

(3) Preparation of the Intermediate 222(3).

The title compound was obtained in the same manner as the Example 123(3) using the following starting materials.

Starting materials: the intermediate 222(2) and 4-(trifluoromethoxy)phenylboronic acid; Yield: 72.4% (white solid).

$^1$H-NMR ($CDCl_3$) δ: 1.30 (9H, s), 3.55 (3H, s), 6.96-7.00 (2H, m), 7.07 (1H, s), 7.16 (2H, d, J=8.4 Hz), 7.22-7.34 (11H, m), 7.47-7.53 (2H, m).

(4) Preparation of the Compound 222.

The title compound was obtained in the same manner as the Example 126(4) using the following starting material.

Starting material: the intermediate 222(3); Yield: 42.1% (white solid).

$^1$H-NMR (DMSO-$d_6$) δ: 1.26 (9H, s), 6.78 (1H, s), 7.08-7.44 (13H, m), 7.57 (2H, d, J=8.4 Hz), 7.69-7.75 (2H, m).

Example 223

Preparation of the Compound 223

(1) Preparation of the Intermediate 223(1).

n-Butyllithium (2.5 M solution in hexane; 2.2 ml, 5.5 mmol) was added to a solution of 4-bromoaniline (1.03 g, 6.0 mmol) in tetrahydrofuran at −78° C. under argon atmosphere, and the mixture was stirred for 30 minutes. 2-Phenyethyl bromide (925 mg, 5.0 mmol) was added to the reaction mixture, and the mixture was stirred at room temperature for 1 hour. A saturated aqueous solution of ammonium chloride was added to the reaction mixture. Tetrahydrofuran was evaporated under reduced pressure, and the obtained residue was diluted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=10:1) to give the title compound (126 mg, 9%) as a colorless oil.

$^1$H-NMR ($CDCl_3$) δ: 2.90 (2H, t, J=6.9 Hz), 3.37 (2H, t, J=6.9 Hz), 3.68 (1H, brs), 6.45-6.52 (2H, m), 7.21-7.37 (7H, m).

(2) Preparation of the Intermediate 223(2).

The title compound was obtained in the same manner as the Example 125(3) using the following starting materials.

Starting materials: the intermediate 223(1) and methyl chloroglyoxylate; Yield: 99% (pale brown oil).

$^1$H-NMR ($CDCl_3$) δ: 2.87-2.94 (2H, m), 3.58 (3H, s), 3.94-4.02 (2H, m), 6.91-6.96 (2H, m), 7.13-7.32 (5H, m), 7.44-7.51 (2H, m).

(3) Preparation of the Intermediate 223(3).

The title compound was obtained in the same manner as the Example 123(3) using the following starting materials.

Starting materials: the intermediate 223(2) and 4-(trifluoromethoxy)phenylboronic acid; Yield: 27% (pale brown oil).

$^1$H-NMR ($CDCl_3$) δ: 2.90-3.00 (2H, m), 3.58 (3H, s), 4.00-4.08 (2H, m), 7.16-7.34 (9H, m), 7.51-7.64 (4H, m).

(4) Preparation of the Compound 223.

The title compound was obtained in the same manner as the Example 123(4) using the following starting material.

Starting material: the intermediate 223(3); Yield: 81% (white solid).

$^1$H-NMR (DMSO-$d_6$) δ: 2.77 (2H, brs), 3.80-3.93 (2H, m), 7.14-7.31 (5H, m), 7.36-7.50 (4H, m), 7.63 (2H, brs), 7.75-7.86 (2H, m).

Example 224

Preparation of the Compound 224

(1) Preparation of the Intermediate 224(1).

The title compound was obtained in the same manner as the Example 123(1) using the following starting materials.

Starting materials: the intermediate 126(1) and 3-phenylpropyl bromide; Yield: 57.4% (colorless oil).

$^1$H-NMR ($CDCl_3$) δ: 1.83-1.92 (2H, m), 2.63 (2H, t, J=7.8 Hz), 3.58 (3H, s), 3.81 (2H, t, J=7.5 Hz), 7.05-7.08 (2H, m), 7.10-7.13 (2H, m), 7.18-7.29 (3H, m), 7.50-7.53 (2H, m).

(2) Preparation of the Intermediate 224(2).

The title compound was obtained in the same manner as the Example 123(3) using the following starting materials.

Starting materials: the intermediate 224(1) and 4-(trifluoromethoxy)phenylboronic acid; Yield: 34.8% (colorless oil).

$^1$H-NMR ($CDCl_3$) δ: 1.87-1.97 (2H, m), 2.67 (2H, t, J=7.5 Hz), 3.58 (3H, s), 3.88 (2H, t, J=7.5 Hz), 7.12-7.20 (3H, m), 7.24-7.32 (6H, m), 7.56-7.61 (4H, m).

(3) Preparation of the Compound 224.

The title compound was obtained in the same manner as the Example 126(4) using the following starting material.

Starting material: the intermediate 224(2); Yield: 81.8% (white solid).

$^1$H-NMR (DMSO-d$_6$) δ: 1.70-1.75 (2H, m), 2.49-2.57 (2H, m), 3.72-3.78 (2H, m), 7.11-7.26 (5H, m), 7.40-7.46 (4H, m), 7.62-7.66 (2H, m), 7.77-7.80 (2H, m).

Example 225

Preparation of the Compound 225

(1) Preparation of the Intermediate 225(1).

The title compound was obtained in the same manner as the Example 123(1) using the following starting materials.

Starting materials: the intermediate 126(1) and 4-phenylbutyl bromide; Yield: 77.5% (colorless oil).

$^1$H-NMR (CDCl$_3$) δ: 1.54-1.62 (4H, m), 2.60 (2H, t, J=7.2 Hz), 3.57 (3H, s), 3.77 (2H, t, J=6.9 Hz), 7.02-7.05 (2H, m), 7.10-7.14 (2H, m), 7.18-7.29 (3H, m), 7.48-7.51 (2H, m).

(2) Preparation of the Intermediate 225(2).

The title compound was obtained in the same manner as the Example 123(3) using the following starting materials.

Starting materials: the intermediate 225(1) and 4-(trifluoromethoxy)phenylboronic acid; Yield: 68.6% (brown oil).

$^1$H-NMR (CDCl$_3$) δ: 1.58-1.69 (4H, m), 2.58-2.64 (2H, m), 3.57 (3H, s), 3.81-3.86 (2H, m), 7.11-7.20 (3H, m), 7.23-7.32 (6H, m), 7.54-7.61 (4H, m).

(3) Preparation of the Compound 225.

The title compound was obtained in the same manner as the Example 126(4) using the following starting material.

Starting material: the intermediate 225(2); Yield: 54.9% (flesh-colored solid).

$^1$H-NMR (DMSO-d$_6$) δ: 1.39-1.54 (4H, m), 3.30-3.36 (2H, m), 3.64-3.72 (2H, m), 7.11-7.25 (5H, m), 7.35-7.37 (2H, m), 7.43-7.46 (2H, m), 7.58-7.63 (2H, m), 7.77-7.80 (2H, m).

Example 226

Preparation of the Compound 226

(1) Preparation of the Intermediate 226(1).

The title compound was obtained in the same manner as the Example 123(1) using the following starting materials.

Starting materials: the intermediate 194(2) and 4-phenylbutyl bromide; Yield: 63.3% (white solid).

$^1$H-NMR (CDCl$_3$) δ: 0.91-0.98 (3H, m), 1.38-1.48 (4H, m), 1.71-1.85 (6H, m), 2.67 (2H, t, J=7.2 Hz), 3.19-3.24 (2H, m), 4.02 (2H, t, J=6.6 Hz), 4.27 (1H, brs), 6.74-6.80 (3H, m), 7.18-7.31 (7H, m), 7.52-7.56 (2H, m).

(2) Preparation of the Intermediate 226(2).

The title compound was obtained in the same manner as the Example 125(3) using the following starting materials.

Starting materials: the intermediate 226(1) and methyl chloroglyoxylate; Yield: 63.6% (white solid).

$^1$H-NMR (CDCl$_3$) δ: 0.93 (3H, t, J=7.2 Hz), 1.35-1.44 (4H, m), 1.56-1.66 (4H, m), 1.76-1.82 (2H, m), 2.57-2.62 (2H, m), 3.51-3.60 (4H, m), 3.97-4.03 (3H, m), 6.99 (1H, d, J=8.7 Hz), 7.10-7.32 (8H, m), 7.47-7.51 (3H, m).

(3) Preparation of the Compound 226.

The title compound was obtained in the same manner as the Example 126(4) using the following starting material.

Starting material: the intermediate 226(2); Yield: 76.9% (white solid).

This compound was obtained as a mixture of the rotational isomers.

Major isomer: $^1$H-NMR (DMSO-d$_6$) δ: 0.88 (3H, t, J=6.9 Hz), 1.27-1.60 (8H, m), 1.67-1.74 (2H, m), 2.49-2.55 (2H, m), 3.30-3.40 (1H, m), 3.88-4.17 (3H, m), 7.08-7.21 (6H, m), 7.41-7.48 (3H, m), 7.59-7.70 (3H, m), 13.77 (1H, brs).

Minor isomer: $^1$H-NMR (DMSO-d$_6$) δ: 0.88 (3H, t, J=6.9 Hz), 1.27-1.60 (8H, m), 1.67-1.74 (2H, m), 2.49-2.55 (2H, m), 3.30-4.17 (4H, m), 7.08-7.21 (6H, m), 7.37-7.44 (3H, m), 7.59-7.72 (3H, m), 13.77 (1H, brs).

Example 227

Preparation of the Compound 227

(1) Preparation of the Intermediate 227(1).

The title compound was obtained in the same manner as the Example 123(1) using the following starting materials.

Starting materials: the intermediate 193(3) and 4-phenylbutyl bromide; Yield: 91.1% (yellow oil).

$^1$H-NMR (CDCl$_3$) δ: 0.93 (3H, t, J=7.2 Hz), 1.38-1.45 (2H, m), 1.56-1.75 (6H, m), 2.61 (2H, t, J=7.2 Hz), 3.57 (3H, s), 3.77 (2H, t, J=7.2 Hz), 3.98 (2H, t, J=6.6 Hz), 6.91 (1H, d, J=8.4 Hz), 7.09-7.17 (5H, m), 7.20-7.27 (4H, m), 7.48-7.52 (2H, m).

(2) Preparation of the Compound 227.

The title compound was obtained in the same manner as the Example 126(4) using the following starting material.

Starting material: the intermediate 227(1); Yield: 77.1% (white solid).

$^1$H-NMR (DMSO-d$_6$) δ: 0.87 (3H, t, J=7.2 Hz), 1.32-1.52 (6H, m), 1.60-1.69 (2H, m), 2.51-2.55 (2H, m), 3.63 (2H, t, J=7.2 Hz), 3.98 (2H, t, J=6.3 Hz), 7.02 (1H, d, J=8.7 Hz), 7.10-7.13 (3H, m), 7.18-7.24 (4H, m), 7.40 (2H, d, J=8.1 Hz), 7.59-7.62 (2H, m).

Example 228

Preparation of the Compound 228

(1) Preparation of the Intermediate 228(1).

The title compound was obtained in the same manner as the Example 123(1) using the following starting materials.

Starting materials: the intermediate 125(3) and 5-phenylpentyl chloride; Yield: 14.6% (yellow oil).

$^1$H-NMR (CDCl$_3$) δ: 1.35-1.39 (2H, m), 1.57-1.62 (4H, m), 2.56-2.61 (2H, m), 3.57 (3H, s), 3.77-3.82 (2H, m), 7.12-7.19 (4H, m), 7.24-7.32 (5H, m), 7.52-7.60 (4H, m).

(2) Preparation of the Compound 228.

The title compound was obtained in the same manner as the Example 126(4) using the following starting material.

Starting material: the intermediate 228(1); Yield: 67.5% (yellowish-white solid).

$^1$H-NMR (DMSO-d$_6$) δ: 1.19-1.25 (2H, m), 1.44-1.54 (6H, m), 3.59-3.67 (2H, m), 7.12-7.26 (5H, m), 7.35-7.38 (2H, m), 7.43-7.46 (2H, m), 7.60-7.64 (2H, m), 7.77-7.80 (2H, m).

Example 229

Preparation of the Compound 229

(1) Preparation of the Intermediate 229(1).

The title compound was obtained in the same manner as the Example 123(1) using the following starting materials.

Starting materials: the intermediate 210(1) and 3-phenylpropyl bromide; Yield: 61.3% (colorless oil).

$^1$H-NMR (CDCl$_3$) δ: 0.98 (3H, t, J=7.5 Hz), 1.70-1.83 (2H, m), 1.85-1.96 (2H, m), 2.65 (2H, t, J=8.4 Hz), 3.58 (3H, s), 3.78-3.84 (2H, m), 3.92-3.97 (2H, m), 6.92 (1H, d, J=9.3 Hz), 7.10-7.29 (9H, m), 7.49-7.54 (2H, m).

(2) Preparation of the Compound 229.

The title compound was obtained in the same manner as the Example 126(4) using the following starting material.

Starting material: the intermediate 229(1); Yield: 58.3% (colorless oil).

$^1$H-NMR (DMSO-$d_6$) δ: 0.90 (3H, t, J=7.2 Hz), 1.52-1.56 (4H, m), 2.50-2.57 (2H, m), 3.52-3.57 (2H, m), 3.58-4.01 (2H, m), 7.01-7.31 (8H, m), 7.35-7.45 (2H, m), 7.59-7.68 (2H, m).

Example 230

Preparation of the Compound 230

(1) Preparation of the Intermediate 230(1).

The title compound was obtained in the same manner as the Example 123(1) using the following starting materials.

Starting materials: the intermediate 197(3) and 3-phenylpropyl bromide; Yield: 86.0% (colorless oil).

$^1$H-NMR ($CDCl_3$) δ: 0.82-0.88 (6H, m), 1.56-1.64 (4H, m), 1.90-1.93 (2H, m), 2.63-2.69 (2H, m), 3.57 (3H, s), 3.78-3.83 (2H, m), 4.11-4.15 (1H, m), 6.88-6.92 (1H, m), 7.11-7.27 (9H, m), 7.48-7.50 (2H, m).

(2) Preparation of the Compound 230.

The title compound was obtained in the same manner as the Example 126(4) using the following starting material.

Starting material: the intermediate 230(1); Yield: 60.5% (whitish-pink solid).

$^1$H-NMR (DMSO-$d_6$) δ: 0.79-0.85 (6H, m), 1.49-1.58 (4H, m), 1.65-1.73 (2H, m), 2.49-2.55 (2H, m), 3.60-3.65 (2H, m), 4.22-4.26 (1H, m), 7.00-7.26 (8H, m), 7.37-7.40 (2H, m), 7.58-7.62 (2H, m).

Example 231

Preparation of the Compound 231

(1) Preparation of the Intermediate 231(1).

The title compound was obtained in the same manner as the Example 123(1) using the following starting materials.

Starting materials: the intermediate 189(2) and 4-phenylbutyl bromide; Yield: 55.4% (colorless oil).

$^1$H-NMR ($CDCl_3$) δ: 0.96-1.01 (3H, m), 1.47-1.57 (4H, m), 1.70-1.84 (4H, m), 2.66-2.71 (2H, m), 3.20-3.22 (2H, m), 4.03 (2H, t, J=6.6 Hz), 4.27 (1H, brs), 6.73-6.80 (3H, m), 7.11-7.30 (7H, m), 7.51-7.55 (2H, m).

(2) Preparation of the Intermediate 231(2).

The title compound was obtained in the same manner as the Example 123(2) using the following starting materials.

Starting materials: the intermediate 231(1) and methyl chloroglyoxylate; Yield: 89.1% (yellow oil).

$^1$H-NMR ($CDCl_3$) δ: 0.97 (3H, t, J=7.2 Hz), 1.45-1.52 (2H, m), 1.60-1.68 (4H, m), 1.73-1.80 (2H, m), 2.57-2.63 (2H, m), 3.50-3.57 (5H, m), 3.98-4.05 (2H, m), 6.99 (1H, d, J=8.4 Hz), 7.10-7.32 (8H, m), 7.47-7.51 (3H, m).

(3) Preparation of the Compound 231.

The title compound was obtained in the same manner as the Example 126(4) using the following starting material.

Starting material: the intermediate 231(2); Yield: 73.3% (yellow solid).

$^1$H-NMR (DMSO-$d_6$) δ: 0.92 (3H, t, J=7.5 Hz), 1.40-1.54 (6H, m), 1.62-1.72 (2H, m), 2.46-2.50 (2H, m), 3.66-4.05 (4H, m), 7.06-7.21 (6H, m), 7.40-7.43 (2H, m), 7.48-7.49 (1H, m), 7.56-7.60 (1H, m), 7.66-7.71 (2H, m).

Example 232

Preparation of the Compound 232

(1) Preparation of the Intermediate 232(1).

The title compound was obtained in the same manner as the Example 123(1) using the following starting materials.

Starting materials: the intermediate 198(4) and 3-phenylpropyl bromide; Yield: 54.6% (colorless oil).

$^1$H-NMR ($CDCl_3$) δ: 1.05 (3H, t, J=7.5 Hz), 1.50-1.89 (4H, m), 2.29-2.58 (3H, m), 3.67 (3H, s), 3.77-3.87 (1H, m), 3.94 (2H, t, J=6.6 Hz), 6.82 (1H, dd, J=2.7, 8.7 Hz), 6.87 (1H, d, J=2.7 Hz), 6.95-7.00 (2H, m), 7.06 (1H, d, J=8.7 Hz), 7.11-7.27 (5H, m), 7.47-7.53 (2H, m).

(2) Preparation of the Compound 232.

The title compound was obtained in the same manner as the Example 126(4) using the following starting material.

Starting material: the intermediate 232(1); Yield: 19.8% (white solid).

This compound was obtained as a mixture of the rotational isomers.

Major isomer: $^1$H-NMR ($CDCl_3$) δ: 0.88 (3H, t, J=7.5 Hz), 1.23-1.74 (4H, m), 2.04-2.35 (3H, m), 3.50-3.77 (3H, m), 6.49-6.85 (4H, m), 6.95-7.23 (6H, m), 7.56 (2H, d, J=8.4 Hz).

Minor isomer: $^1$H-NMR ($CDCl_3$) δ: 0.98 (3H, t, J=7.2 Hz), 1.23-1.74 (4H, m), 2.04-2.35 (3H, m), 3.50-3.77 (3H, m), 6.49-6.85 (4H, m), 6.95-7.23 (8H, m).

Example 233

Preparation of the Compound 233

(1) Preparation of the Intermediate 233(1).

The title compound was obtained in the same manner as the Example 123(1) using the following starting materials.

Starting materials: the intermediate 199(2) and 3-phenylpropyl bromide; Yield: 83.3% (colorless oil).

$^1$H-NMR ($CDCl_3$) δ: 0.95-1.01 (6H, m), 1.68-1.77 (4H, m), 1.99-2.04 (2H, m), 2.73-2.78 (2H, m), 3.21-3.24 (2H, m), 4.15-4.19 (1H, m), 4.38 (1H, brs), 6.70-6.79 (3H, m), 7.20-7.31 (7H, m), 7.51-7.53 (2H, m).

(2) Preparation of the Intermediate 232(2).

The title compound was obtained in the same manner as the Example 123(2) using the following starting materials.

Starting materials: the intermediate 233(1) and methyl chloroglyoxylate; Yield: 70.7% (yellow oil).

$^1$H-NMR ($CDCl_3$) δ: 0.90-0.99 (6H, m), 1.66-1.71 (4H, m), 1.86-1.95 (2H, m), 2.61-2.70 (2H, m), 3.43-3.52 (4H, m), 4.10-4.23 (2H, m), 6.95 (1H, d, J=9.0 Hz), 7.10-7.27 (7H, m), 7.33 (1H, d, J=2.4 Hz), 7.46-7.50 (3H, m).

(3) Preparation of the Compound 233.

The title compound was obtained in the same manner as the Example 126(4) using the following starting material.

Starting material: the intermediate 233(2); Yield: 85.7% (white solid).

$^1$H-NMR (DMSO-$d_6$) δ: 0.84-0.88 (6H, m), 1.50-1.59 (6H, m), 3.15-3.21 (2H, m), 3.61-4.34 (3H, m), 7.06-7.22 (6H, m), 7.33-7.42 (2H, m), 7.48-7.57 (2H, m), 7.66-7.71 (2H, m).

Example 234

Preparation of the Compound 234

(1) Preparation of the Intermediate 234(1).

The title compound was obtained in the same manner as the Example 123(1) using the following starting materials.

Starting materials: the intermediate 188(3) and 3-phenylpropyl bromide; Yield: 39.3% (colorless oil).

$^1$H-NMR ($CDCl_3$) δ: 1.06 (3H, t, J=7.2 Hz), 1.82-1.92 (2H, m), 1.97-2.02 (2H, m), 2.70-2.78 (2H, m), 3.20-3.26 (2H, m), 3.97-4.01 (2H, m), 4.34 (1H, brs), 6.70-6.80 (3H, m), 7.17-7.32 (7H, m), 7.50-7.53 (2H, m).

(2) Preparation of the Intermediate 234(2).

The title compound was obtained in the same manner as the Example 123(2) using the following starting materials.

Starting materials: the intermediate 234(1) and methyl chloroglyoxylate; Yield: 90.5% (colorless oil).

$^1$H-NMR ($CDCl_3$) δ: 1.03 (3H, t, J=7.2 Hz), 1.78-1.98 (4H, m), 2.62-2.68 (2H, m), 3.53 (3H, s), 3.55-4.02 (4H, m), 6.99 (1H, d, J=8.7 Hz), 7.10-7.28 (7H, m), 7.34 (1H, d, J=2.4 Hz), 7.48-7.52 (3H, m).

(3) Preparation of the Compound 234.

The title compound was obtained in the same manner as the Example 126(4) using the following starting material.

Starting material: the intermediate 234(2); Yield: 79.5% (white solid).

$^1$H-NMR (DMSO-$d_6$) δ: 0.92-0.98 (3H, m), 1.63-1.73 (4H, m), 3.29-3.96 (6H, m), 7.05-7.23 (6H, m), 7.40-7.42 (2H, m), 7.49-7.60 (2H, m), 7.66-7.72 (2H, m).

Example 235

Preparation of the Compound 235

(1) Preparation of the Intermediate 235(1).

The title compound was obtained in the same manner as the Example 123(1) using the following starting materials.

Starting materials: the intermediate 189(2) and 3-phenylpropyl bromide; Yield: 85.8% (colorless oil).

$^1$H-NMR ($CDCl_3$) δ: 1.00 (3H, t, J=7.2 Hz), 1.51-1.56 (2H, m), 1.79-1.84 (2H, m), 1.99-2.04 (2H, m), 2.73-2.78 (2H, m), 3.21-3.29 (2H, m), 4.01-4.06 (2H, m), 4.32 (1H, brs), 6.70-6.80 (3H, m), 7.20-7.29 (7H, m), 7.50-7.53 (2H, m).

(2) Preparation of the Intermediate 235(2).

The title compound was obtained in the same manner as the Example 123(2) using the following starting materials.

Starting materials: the intermediate 235(1) and methyl chloroglyoxylate; Yield: 72.1% (colorless oil).

$^1$H-NMR ($CDCl_3$) δ: 0.96 (3H, t, J=7.2 Hz), 1.43-1.56 (2H, m), 1.72-1.81 (2H, m), 1.86-1.93 (2H, m), 2.63-2.69 (2H, m), 3.54 (3H, s), 3.57-4.07 (4H, m), 6.99 (1H, d, J=8.7 Hz), 7.10-7.18 (2H, m), 7.21-7.28 (5H, m), 7.34 (1H, d, J=2.4 Hz), 7.48-7.51 (3H, m).

(3) Preparation of the Compound 235.

The title compound was obtained in the same manner as the Example 126(4) using the following starting material.

Starting material: the intermediate 235(2); Yield: 84.7% (white solid).

$^1$H-NMR (DMSO-$d_6$) δ: 0.89-0.94 (3H, m), 1.39-1.41 (2H, m), 1.62-1.69 (4H, m), 3.25-3.35 (2H, m), 3.62-4.61 (4H, m), 7.03-7.21 (6H, m), 7.32-7.72 (6H, m).

Example 236

Preparation of the Compound 236

(1) Preparation of the Intermediate 236(1).

The title compound was obtained in the same manner as the Example 123(1) using the following starting materials.

Starting materials: the intermediate 188(3) and 4-phenylbutyl bromide; Yield: 87.8% (colorless oil).

$^1$H-NMR ($CDCl_3$) δ: 1.02-1.07 (3H, m), 1.54-1.86 (6H, m), 2.66-2.70 (2H, m), 3.12-3.18 (2H, m), 3.96-4.00 (2H, m), 4.38 (1H, brs), 6.74-6.80 (2H, m), 7.12-7.28 (8H, m), 7.52-7.55 (2H, m).

(2) Preparation of the Intermediate 236(2).

The title compound was obtained in the same manner as the Example 123(2) using the following starting materials.

Starting materials: the intermediate 236(1) and methyl chloroglyoxylate; Yield: 73.8% (yellow oil).

$^1$H-NMR ($CDCl_3$) δ: 1.04 (3H, t, J=7.2 Hz), 1.60-1.72 (4H, m), 1.76-1.88 (2H, m), 2.55-2.65 (2H, m), 3.50-3.60 (4H, m), 3.90-4.05 (3H, m), 6.98 (1H, d, J=8.7 Hz), 7.10-7.15 (3H, m), 7.19-7.33 (5H, m), 7.47-7.51 (3H, m).

(3) Preparation of the Compound 236.

The title compound was obtained in the same manner as the Example 126(4) using the following starting material.

Starting material: the intermediate 236(2); Yield: 88.0% (white solid).

$^1$H-NMR (DMSO-$d_6$) δ: 0.99 (3H, t, J=7.2 Hz), 1.35-1.52 (4H, m), 1.67-1.77 (2H, m), 3.30-4.07 (6H, m), 7.06-7.20 (6H, m), 7.41-7.43 (2H, m), 7.48-7.57 (2H, m), 7.64-7.71 (2H, m).

Example 237

Preparation of the Compound 237

(1) Preparation of the Intermediate 237(1).

The title compound was obtained in the same manner as the Example 123(1) using the following starting materials.

Starting materials: the intermediate 207(3) and 3-phenylpropyl bromide; Yield: 68.0% (yellow oil).

$^1$H-NMR ($CDCl_3$) δ: 0.97 (6H, t, J=7.5 Hz), 1.65-1.74 (6H, m), 2.33-2.59 (3H, m), 3.67 (3H, s), 3.76-3.82 (1H, m), 4.10-4.17 (1H, m), 6.80 (1H, dd, J=2.7, 8.4 Hz), 6.86 (1H, d, J=2.7 Hz), 6.97-7.00 (2H, m), 7.05 (1H, d, J=8.4 Hz), 7.15-7.25 (5H, m), 7.48-7.51 (2H, m).

(2) Preparation of the Compound 237.

The title compound was obtained in the same manner as the Example 126(4) using the following starting material.

Starting material: the intermediate 237(1); Yield: 75.8% (white solid).

$^1$H-NMR (DMSO-$d_6$) δ: 0.90 (6H, t, J=7.5 Hz), 1.45-1.64 (6H, m), 2.21-2.45 (3H, m), 3.52-3.62 (1H, m), 4.31-4.35 (1H, m), 6.93-7.05 (4H, m), 7.11-7.22 (4H, m), 7.37-7.44 (2H, m), 7.62-7.64 (2H, m).

Example 238

Preparation of the Compound 238

(1) Preparation of the Intermediate 238(1).

The title compound was obtained in the same manner as the Example 123(1) using the following starting materials.

Starting materials: the intermediate 208(3) and 3-phenylpropyl bromide; Yield: 68.0% (yellow oil).

$^1$H-NMR ($CDCl_3$) δ: 1.16-1.21 (6H, m), 1.57-1.78 (2H, m), 2.28-2.59 (3H, m), 3.33-3.40 (4H, m), 3.67-3.82 (4H, m), 6.50-6.54 (2H, m), 6.98-7.02 (2H, m), 7.14-7.26 (6H, m), 7.50-7.73 (2H, m).

(2) Preparation of the Compound 238.

The title compound was obtained in the same manner as the Example 126(4) using the following starting material.

Starting material: the intermediate 238(1); Yield: 71.1% (white solid).

$^1$H-NMR (DMSO-$d_6$) δ: 1.10 (6H, t, J=7.2 Hz), 1.46-1.53 (2H, m), 2.17-2.50 (5H, m), 3.32-3.38 (2H, m), 3.51-3.58 (1H, m), 6.55 (1H, d, J=2.7 Hz), 6.65 (1H, dd, J=2.7, 8.4 Hz), 6.98-7.06 (3H, m), 7.13-7.23 (3H, m), 7.40-7.43 (2H, m), 7.62-7.65 (2H, m).

Example 239

Preparation of the Compound 239

(1) Preparation of the Intermediate 239(1).

The title compound was obtained in the same manner as the Example 123(1) using the following starting materials.

Starting materials: the intermediate 209(3) and 3-phenylpropyl bromide; Yield: 96.1% (colorless oil).

$^1$H-NMR ($CDCl_3$) δ: 1.35-1.37 (6H, m), 1.56-1.74 (2H, m), 2.30-2.53 (3H, m), 3.67 (3H, s), 3.75-3.86 (1H, m), 4.52-4.60 (1H, m), 6.80 (1H, dd, J=2.7, 8.7 Hz), 6.85 (1H, d, J=2.7 Hz), 6.97-7.00 (2H, m), 7.05 (1H, d, J=8.7 Hz), 7.15-7.26 (5H, m), 7.48-7.51 (2H, m).

(2) Preparation of the Compound 239.

The title compound was obtained in the same manner as the Example 126(4) using the following starting material.

Starting material: the intermediate 239(1); Yield: 69.9% (white solid).

$^1$H-NMR (DMSO-$d_6$) δ: 1.26-1.40 (8H, m), 2.22-2.41 (4H, m), 4.60-4.68 (1H, m), 6.79-6.87 (2H, m), 6.94-6.97 (2H, m), 7.11-7.16 (4H, m), 7.31-7.34 (2H, m), 7.95-7.98 (2H, m).

Example 240

Preparation of the Compound 240

(1) Preparation of the Intermediate 240(1).

The title compound was obtained in the same manner as the Example 123(1) using the following starting materials.

Starting materials: the intermediate 210(1) and 4-phenylbutyl bromide; Yield: 95.7% (yellow oil).

$^1$H-NMR ($CDCl_3$) δ: 0.98 (3H, t, J=7.2 Hz), 1.60-1.78 (6H, m), 2.61 (2H, t, J=6.9 Hz), 3.57 (3H, s), 3.77 (2H, t, J=6.9 Hz), 3.94 (2H, t, J=6.3 Hz), 6.91 (1H, d, J=8.4 Hz), 7.09-7.17 (5H, m), 7.21-7.27 (4H, m), 7.50-7.52 (2H, m).

(2) Preparation of the Compound 240.

The title compound was obtained in the same manner as the Example 126(4) using the following starting material.

Starting material: the intermediate 240(1); Yield: 82.3% (white solid).

$^1$H-NMR (DMSO-$d_6$) δ: 0.92 (3H, t, J=7.2 Hz), 1.36-1.50 (4H, m), 1.62-1.73 (2H, m), 2.49-2.55 (2H, m), 3.60-3.64 (2H, m), 3.93-3.97 (2H, m), 6.99-7.25 (8H, m), 7.39-7.42 (2H, m), 7.60-7.63 (2H, m).

Example 241

Preparation of the Compound 241

(1) Preparation of the Intermediate 241(1).

The title compound was obtained in the same manner as the Example 123(1) using the following starting materials.

Starting materials: the intermediate 213(3) and 4-phenylbutyl bromide; Yield: 83.8% (colorless oil).

$^1$H-NMR ($CDCl_3$) δ: 0.85-0.94 (6H, m), 1.56-1.71 (4H, m), 2.59-2.64 (2H, m), 2.87 (4H, q, J=6.9 Hz), 3.53 (3H, s), 3.75-3.79 (2H, m), 6.99-7.04 (3H, m), 7.11-7.17 (3H, m), 7.20-7.26 (4H, m), 7.50-7.53 (2H, m).

(2) Preparation of the Compound 241.

The title compound was obtained in the same manner as the Example 126(4) using the following starting material.

Starting material: the intermediate 241(1); Yield: 73.0% (white solid).

$^1$H-NMR (DMSO-$d_6$) δ: 0.84 (6H, t, J=6.9 Hz), 1.38-1.50 (4H, m), 2.80 (4H, q, J=6.9 Hz), 3.29-3.33 (2H, m), 3.60-3.64 (2H, m), 7.01-7.22 (8H, m), 7.37-7.39 (2H, m), 7.61-7.64 (2H, m).

Example 242

Preparation of the Compound 242

(1) Preparation of the Intermediate 242(1).

The title compound was obtained in the same manner as the Example 123(1) using the following starting materials.

Starting materials: the intermediate 194(2) and 5-phenylpentyl chloride; Yield: 20.5% (colorless oil).

$^1$H-NMR ($CDCl_3$) δ: 0.81 (3H, t, J=7.2 Hz), 1.25-1.37 (6H, m), 1.51-1.61 (4H, m), 1.67-1.72 (2H, m), 2.50 (2H, t, J=7.5 Hz), 3.01-3.06 (2H, m), 3.88 (2H, t, J=6.6 Hz), 4.13 (1H, brs), 6.60-6.66 (3H, m), 7.02-7.16 (7H, m), 7.39-7.42 (2H, m).

(2) Preparation of the Intermediate 242(2).

The title compound was obtained in the same manner as the Example 125(3) using the following starting materials.

Starting materials: the intermediate 242(1) and methyl chloroglyoxylate; Yield: 90.1% (yellow oil).

$^1$H-NMR ($CDCl_3$) δ: 0.93 (3H, t, J=6.9 Hz), 1.34-1.46 (6H, m), 1.54-1.64 (4H, m), 1.78-1.84 (2H, m), 2.57 (2H, t, J=7.8 Hz), 3.53-3.55 (4H, m), 3.92-4.04 (3H, m), 6.99 (1H, d, J=8.7 Hz), 7.11-7.17 (3H, m), 7.21-7.28 (4H, m), 7.33 (1H, d, J=2.4 Hz), 7.47-7.52 (3H, m).

(3) Preparation of the Compound 242.

The title compound was obtained in the same manner as the Example 126(4) using the following starting material.

Starting material: the intermediate 242(2); Yield: 90.7% (yellow oil).

$^1$H-NMR ($CDCl_3$) δ: 0.91 (3H, t, J=7.2 Hz), 1.32-1.43 (6H, m), 1.58-1.63 (4H, m), 1.72-1.80 (2H, m), 2.57 (2H, t, J=7.5 Hz), 3.70-3.79 (2H, m), 3.96 (2H, t, J=6.6 Hz), 6.96 (1H, d, J=8.4 Hz), 7.10-7.17 (3H, m), 7.21-7.27 (4H, m), 7.32 (1H, d, J=2.1 Hz), 7.45-7.53 (3H, m).

Example 243

Preparation of the Compound 243

(1) Preparation of the Intermediate 243(1).

The title compound was obtained in the same manner as the Example 123(1) using the following starting materials.

Starting materials: the intermediate 216(3) and 4-phenylbutyl bromide; Yield: 47.8% (colorless oil).

$^1$H-NMR ($CDCl_3$) δ: 1.58-1.65 (4H, m), 2.57-2.65 (2H, m), 2.77-2.85 (4H, m), 3.54-3.66 (4H, m), 3.57 (3H, s), 3.74-3.80 (2H, m), 6.97 (1H, d, J=8.7 Hz), 7.04 (1H, d, J=2.4 Hz), 7.08-7.30 (8H, m), 7.58-7.64 (2H, m).

(2) Preparation of the Compound 243.

The title compound was obtained in the same manner as the Example 126(4) using the following starting material.

Starting material: the intermediate 243(1); Yield: 98.7% (white solid).

$^1$H-NMR (DMSO-$d_6$) δ: 1.39-1.59 (4H, m), 2.52-2.58 (2H, m), 2.70-2.80 (4H, m), 3.49-3.59 (4H, m), 3.72 (2H, t, J=6.9 Hz), 7.08-7.26 (8H, m), 7.44-7.48 (2H, m), 7.71-7.76 (2H, m).

Example 244

Preparation of the Compound 244

(1) Preparation of the Intermediate 244(1).

The title compound was obtained in the same manner as the Example 185(2) using the following starting materials.

Starting materials: the intermediate 211(1) and 1-pentanol; Yield: 100.0% (yellow solid).

$^1$H-NMR ($CDCl_3$) δ: 0.89 (3H, t, J=7.5 Hz), 1.30-1.40 (4H, m), 1.73-1.80 (2H, m), 4.09 (2H, t, J=6.6 Hz), 7.01-7.04 (1H, m), 7.26-7.30 (2H, m), 7.54-7.58 (2H, m), 8.22-8.26 (2H, m).

(2) Preparation of the Intermediate 244(2).

The title compound was obtained in the same manner as the Example 125(2) using the following starting material.

Starting material: the intermediate 244(1); Yield: 98.8% (yellow oil).

$^1$H-NMR ($CDCl_3$) δ: 0.83-0.88 (3H, m), 1.24-1.35 (4H, m), 1.59-1.68 (2H, m), 3.48 (2H, brs), 3.82 (2H, t, J=6.6 Hz), 6.63-6.68 (2H, m), 6.81-6.84 (1H, m), 7.20-7.23 (2H, m), 7.51-7.57 (2H, m).

(3) Preparation of the Intermediate 244(3).

The title compound was obtained in the same manner as the Example 125(3) using the following starting materials.

Starting materials: the intermediate 244(2) and methyl chloroglyoxylate; Yield: 86.3% (white solid).

$^1$H-NMR ($CDCl_3$) δ: 0.87 (3H, t, J=7.2 Hz), 1.31-1.34 (4H, m), 1.67-1.74 (2H, m), 3.94-3.97 (5H, m), 6.97 (1H, d, J=9.0 Hz), 7.23-7.29 (2H, m), 7.52 (1H, d, J=2.4 Hz), 7.54-7.57 (2H, m), 7.65 (1H, dd, J=2.4, 9.0 Hz), 8.80 (1H, brs).

(4) Preparation of the Intermediate 244(4).

The title compound was obtained in the same manner as the Example 123(1) using the following starting materials.

Starting materials: the intermediate 244(3) and 4-phenylbutyl bromide; Yield: 65.4% (colorless oil).

$^1$H-NMR ($CDCl_3$) δ: 0.89 (3H, t, J=7.2 Hz), 1.33-1.39 (4H, m), 1.56-1.76 (6H, m), 2.61 (2H, t, J=6.9 Hz), 3.57 (3H, s), 3.77 (2H, t, J=6.9 Hz), 3.97 (2H, t, J=6.3 Hz), 6.91 (1H, d, J=8.4 Hz), 7.09-7.28 (9H, m), 7.48-7.52 (2H, m).

(5) Preparation of the Compound 244.

The title compound was obtained in the same manner as the Example 126(4) using the following starting material.

Starting material: the intermediate 244(4); Yield: 80.0% (white solid).

$^1$H-NMR (DMSO-$d_6$) δ: 0.83 (3H, t, J=6.6 Hz), 1.24-1.51 (8H, m), 1.63-1.68 (2H, m), 2.49-2.54 (2H, m), 3.60-3.65 (2H, m), 3.95-3.99 (2H, m), 6.99-7.02 (1H, m), 7.09-7.12 (3H, m), 7.18-7.24 (4H, m), 7.38-7.40 (2H, m), 7.58-7.61 (2H, m).

Example 245

Preparation of the Compound 245

(1) Preparation of the Intermediate 245(1).

The title compound was obtained in the same manner as the Example 185(2) using the following starting materials.

Starting materials: the intermediate 188(1) and 1-hexanol; Yield: 100.0% (orange solid).

$^1$H-NMR ($CDCl_3$) δ: 0.89-0.94 (3H, m), 1.31-1.38 (4H, m), 1.40-1.57 (2H, m), 1.83-1.90 (2H, m), 4.15 (2H, t, J=6.3 Hz), 7.15 (1H, d, J=9.0 Hz), 7.28-7.32 (2H, m), 7.55-7.58 (2H, m), 7.70 (1H, dd, J=2.4, 9.0 Hz), 8.02 (1H, d, J=2.4 Hz).

(2) Preparation of the Intermediate 245(2).

The title compound was obtained in the same manner as the Example 125(2) using the following starting material.

Starting material: the intermediate 245(1); Yield: 95.0% (yellow solid).

$^1$H-NMR ($CDCl_3$) δ: 0.89-0.94 (3H, m), 1.33-1.39 (4H, m), 1.47-1.52 (2H, m), 1.80-1.86 (2H, m), 3.89 (2H, brs), 4.03 (2H, t, J=6.6 Hz), 6.82-6.92 (3H, m), 7.21-7.25 (2H, m), 7.50-7.54 (2H, m).

(3) Preparation of the Intermediate 245(3).

The title compound was obtained in the same manner as the Example 123(1) using the following starting materials.

Starting materials: the intermediate 245(2) and 4-phenylbutyl bromide; Yield: 26.2% (white solid).

$^1$H-NMR ($CDCl_3$) δ: 0.90-0.92 (3H, m), 1.32-1.86 (12H, m), 2.67 (2H, t, J=7.8 Hz), 3.19-3.26 (2H, m), 4.02 (2H, t, J=6.3 Hz), 4.25-4.31 (1H, m), 6.73-6.80 (3H, m), 7.17-7.30 (7H, m), 7.52-7.55 (2H, m).

(4) Preparation of the Intermediate 245(4).

The title compound was obtained in the same manner as the Example 125(3) using the following starting materials.

Starting materials: the intermediate 245(3) and methyl chloroglyoxylate; Yield: 100.0% (colorless oil).

$^1$H-NMR ($CDCl_3$) δ: 0.91 (3H, t, J=6.9 Hz), 1.32-1.49 (6H, m), 1.60-1.65 (4H, m), 1.73-1.82 (2H, m), 2.58-2.62 (2H, m), 3.51-3.61 (4H, m), 3.97-4.06 (3H, m), 6.90 (1H, d, J=8.7 Hz), 7.10-7.15 (3H, m), 7.19-7.28 (4H, m), 7.32 (1H, d, J=2.4 Hz), 7.46-7.51 (3H, m).

(5) Preparation of the Compound 245.

The title compound was obtained in the same manner as the Example 126(4) using the following starting material.

Starting material: the intermediate 245(4); Yield: 94.8% (flesh-colored solid).

This compound was obtained as a mixture of the rotational isomers.

Major isomer: $^1$H-NMR (DMSO-$d_6$) δ: 0.85-0.89 (3H, m), 1.28-1.52 (10H, m), 1.67-1.75 (2H, m), 2.46-2.52 (2H, m), 3.11-3.62 (2H, m), 3.97-4.02 (2H, m), 7.07-7.20 (6H, m), 7.41-7.43 (2H, m), 7.47-7.52 (2H, m), 7.64-7.67 (2H, m).

Minor isomer: $^1$H-NMR (DMSO-$d_6$) δ: 0.85-0.89 (3H, m), 1.28-1.52 (10H, m), 1.67-1.75 (2H, m), 2.46-2.52 (2H, m), 3.11-3.62 (2H, m), 3.97-4.02 (2H, m), 7.07-7.20 (6H, m), 7.28-7.29 (2H, m), 7.41-7.57 (2H, m), 7.68-7.71 (2H, m).

Example 246

Preparation of the Compound 246

(1) Preparation of the Intermediate 246(1).

The title compound was obtained in the same manner as the Example 123(1) using the following starting materials.

Starting materials: the intermediate 215(4) and 4-phenylbutyl bromide; Yield: 69.8% (colorless oil).

$^1$H-NMR ($CDCl_3$) δ: 1.52-1.73 (4H, m), 2.27 (3H, s), 2.47-2.63 (2H, m), 2.54 (6H, s), 3.01-3.02 (1H, m), 3.52 (3H, s), 4.08-4.20 (1H, m), 6.83 (1H, s), 6.88 (1H, s), 7.09-7.27 (7H, m), 7.45-7.51 (2H, m).

(2) Preparation of the Compound 246.

The title compound was obtained in the same manner as the Example 126(4) using the following starting material.

Starting material: the intermediate 246(1); Yield: 74.1% (white solid).

This compound was obtained as a mixture of the rotational isomers.

Major isomer: $^1$H-NMR (DMSO-$d_6$) δ: 1.40-1.56 (4H, m), 2.21 (3H, s), 2.47 (6H, s), 2.48-2.58 (2H, m), 2.81-2.93 (1H, m), 3.88-3.99 (1H, m), 6.86 (1H, s), 6.87 (1H, s), 7.07-7.23 (5H, m), 7.37-7.43 (2H, m), 7.55-7.60 (2H, m).

Minor isomer: $^1$H-NMR (DMSO-$d_6$) δ: 1.40-1.56 (4H, m), 2.09 (3H, s), 2.48 (6H, s), 2.48-2.58 (2H, m), 3.38-3.52 (1H, m), 3.57-3.70 (1H, m), 6.82 (1H, s), 6.94 (1H, s), 7.07-7.23 (5H, m), 7.37-7.43 (2H, m), 7.60-7.65 (2H, m).

Example 247

Preparation of the Compound 247

(1) Preparation of the Intermediate 247(1).

The title compound was obtained in the same manner as the Example 123(1) using the following starting materials.

Starting materials: the intermediate 217(3) and 4-phenylbutyl bromide; Yield: 67.6% (colorless oil).

$^1$H-NMR ($CDCl_3$) δ: 1.41-1.52 (6H, m), 1.56-1.65 (4H, m), 2.61 (2H, t, J=6.9 Hz), 2.73-2.80 (4H, m), 3.56 (3H, s), 3.73-3.79 (2H, m), 6.94-7.27 (10H, m), 7.58-7.64 (2H, m).

(2) Preparation of the Compound 247.

The title compound was obtained in the same manner as the Example 126(4) using the following starting material.

Starting material: the intermediate 247(1); Yield: 80.7% (white solid).

$^1$H-NMR (DMSO-$d_6$) δ: 1.34-1.57 (10H, m), 2.49-2.55 (2H, m), 2.62-2.78 (4H, m), 3.58-3.67 (2H, m), 6.95-7.23 (8H, m), 7.38-7.44 (2H, m), 7.71-7.76 (2H, m).

Example 248

Preparation of the Compound 248

(1) Preparation of the Intermediate 248(1).

The title compound was obtained in the same manner as the Example 123(1) using the following starting materials.

Starting materials: the intermediate 211(4) and 4-phenylbutyl bromide; Yield: 51.2% (yellow oil).

$^1$H-NMR ($CDCl_3$) δ: 1.29 (6H, d, J=6.0 Hz), 1.61-1.67 (4H, m), 2.61 (2H, t, J=7.2 Hz), 3.56 (3H, s), 3.77 (2H, t, J=7.2 Hz), 4.49-4.56 (1H, m), 6.92 (1H, d, J=9.0 Hz), 7.07-7.26 (9H, m), 7.49-7.52 (2H, m).

(2) Preparation of the Compound 248.

The title compound was obtained in the same manner as the Example 126(4) using the following starting material.

Starting material: the intermediate 248(1); Yield: 78.9% (white solid).

$^1$H-NMR (DMSO-$d_6$) δ: 1.23 (6H, d, J=6.0 Hz), 1.37-1.52 (4H, m), 2.48-2.51 (2H, m), 3.59-3.63 (2H, m), 4.54-4.59 (1H, m), 6.99-7.24 (8H, m), 7.37-7.40 (2H, m), 7.60-7.63 (2H, m).

Example 249

Preparation of the Compound 249

(1) Preparation of the Intermediate 249(1).

The title compound was obtained in the same manner as the Example 123(1) using the following starting materials.

Starting materials: the intermediate 218(3) and 4-phenylbutyl bromide; Yield: 74.0% (colorless oil).

$^1$H-NMR ($CDCl_3$) δ: 1.14 (9H, s), 1.59-1.68 (4H, m), 2.62 (2H, t, J=7.2 Hz), 3.53 (3H, s), 3.79 (2H, t, J=6.9 Hz), 7.05-7.27 (10H, m), 7.50-7.53 (2H, m).

(2) Preparation of the Compound 249.

The title compound was obtained in the same manner as the Example 126(4) using the following starting material.

Starting material: the intermediate 249(1); Yield: 75.0% (white solid).

$^1$H-NMR (DMSO-$d_6$) δ: 1.10 (9H, s), 1.40-1.49 (4H, m), 2.48-2.52 (2H, m), 3.64-3.68 (2H, m), 7.05-7.32 (8H, m), 7.39-7.41 (2H, m), 7.58-7.61 (2H, m).

Example 250

Preparation of the Compound 250

(1) Preparation of the Intermediate 250(1).

The title compound was obtained in the same manner as the Example 123(1) using the following starting materials.

Starting materials: the intermediate 219(5) and 4-phenylbutyl bromide; Yield: 66.4% (white solid).

$^1$H-NMR ($CDCl_3$) δ: 1.40-1.83 (8H, m), 2.32-2.64 (4H, m), 2.92-2.98 (1H, m), 3.28-3.34 (1H, m), 3.59 (3H, s), 3.78-3.82 (2H, m), 7.12-7.36 (12H, m).

(2) Preparation of the Compound of 250.

The title compound was obtained in the same manner as the Example 126(4) using the following starting material.

Starting material: the intermediate 250(1); Yield: 88.0% (white solid).

$^1$H-NMR (DMSO-$d_6$) δ: 1.37-1.78 (6H, m), 2.12-2.36 (2H, m), 2.48-2.56 (3H, m), 2.86-2.94 (1H, m), 3.30-3.46 (2H, m), 3.76-3.81 (2H, m), 7.09-7.24 (5H, m), 7.31-7.48 (7H, m), 13.98 (1H, brs).

Example 251

Preparation of the Compound (1) Preparation of the Intermediate 251(1).

The title compound was obtained in the same manner as the Example 105(2) using the following starting materials.

Starting materials: the intermediate 113(3) and ethyl 2-bromoisobutyrate; Yield: 22.2% (colorless oil).

$^1$H-NMR ($CDCl_3$) δ: 1.03 (3H, t, J=7.2 Hz), 1.24 (6H, s), 1.32 (9H, s), 3.85 (2H, q, J=7.2 Hz), 6.80 (1H, dd, J=2.4, 7.2 Hz), 6.93-6.97 (2H, m), 7.00-7.04 (2H, m), 7.24-7.25 (2H, m), 7.32-7.36 (2H, m), 7.59-7.63 (2H, m).

(2) Preparation of the Compound 251.

The title compound was obtained in the same manner as the Example 12(4) using the following starting material.

Starting material: the intermediate 251(1); Yield: 86.8% (white solid).

$^1$H-NMR (DMSO-$d_6$) δ: 1.12 (6H, s), 1.29 (9H, s), 6.81 (1H, dd, J=2.1, 7.2 Hz), 6.92-6.96 (2H, m), 7.07-7.16 (2H, m), 7.40-7.44 (4H, m), 7.61-7.64 (2H, m).

Example 252

Preparation of the Compound 252

(1) Preparation of the Intermediate 252(1).

The title compound was obtained in the same manner as the Example 125(4) using the following starting materials.

Starting materials: the intermediate 132(3) and 1-chlorohexane; Yield: 10.0% (colorless oil).

$^1$H-NMR ($CDCl_3$) δ: 0.87 (3H, t, J=6.9 Hz), 1.24-1.33 (6H, m), 1.53-1.60 (2H, m), 3.58 (3H, s), 3.74 (2H, t, J=7.5 Hz), 6.97-7.05 (4H, m), 7.18-7.24 (4H, m).

(2) Preparation of the Compound 252.

The title compound was obtained in the same manner as the Example 126(4) using the following starting material.

Starting material: the intermediate 252(1); Yield: 100.0% (white solid).

$^1$H-NMR (DMSO-$d_6$) δ: 0.85 (3H, t, J=6.6 Hz), 1.19-1.25 (6H, m), 1.32-1.42 (2H, m), 3.61 (2H, t, J=7.2 Hz), 6.96-7.13 (4H, m), 7.28-7.42 (4H, m).

Example 253

Preparation of the Compound 253

(1) Preparation of the Intermediate 253(1).

A mixture of 4-bromoaniline (500 mg, 2.907 mmol), cyclohexanone (285 mg, 2.907 mmol), zinc powder (760 mg, 11.627 mmol), acetic acid (2.5 ml) and water (0.25 ml) was stirred at room temperature for 1 hour, then stirred at 60° C. for 4 hours. The reaction mixture was cooled to room temperature, and filtered. The filtrate was adjusted to pH 9 by addition of a 2 N aqueous solution of sodium hydroxide, and extracted with diisopropyl ether. The organic layer was washed with saturated brine, and dried over anhydrous sodium sulfate. The residue obtained by evaporation of the solvent under reduced pressure was purified by column chromatography on silica gel (n-hexane:ethyl acetate=5:1) to give the title compound (229 mg, 31%) as a pale orange solid.

$^1$H-NMR ($CDCl_3$) δ: 1.01-1.46 (5H, m), 1.53-1.84 (3H, m), 1.93-2.12 (2H, m), 3.11-3.28 (1H, m), 3.53 (1H, brs), 6.40-6.52 (2H, m), 7.16-7.26 (2H, m).

(2) Preparation of the Intermediate 253(2).

The title compound was obtained in the same manner as the Example 123(2) using the following starting materials.

Starting materials: the intermediate 253(1) and methyl chloroglyoxylate; Yield: 85.0% (colorless oil).

$^1$H-NMR ($CDCl_3$) δ: 0.80-2.16 (10H, m), 3.51 (3H, s), 4.38-4.64 (1H, m), 6.99-7.15 (2H, m), 7.45-7.60 (2H, m).

(3) Preparation of the Intermediate 253(3).

The title compound was obtained in the same manner as the Example 123(3) using the following starting materials.

Starting materials: the intermediate 253(2) and 4-(trifluoromethoxy)phenylboronic acid; Yield: 60.3% (pale yellow oil).

$^1$H-NMR ($CDCl_3$) δ: 0.82-2.19 (10H, m), 3.50 (3H, s), 4.40-4.70 (1H, m), 7.16-7.40 (4H, m), 7.48-7.70 (4H, m).

(4) Preparation of the Compound 253.

The title compound was obtained in the same manner as the Example 126(4) using the following starting material.

Starting material: the intermediate 253(3); Yield: 90.8% (white solid).

$^1$H-NMR ($CDCl_3$) δ: 0.66-2.10 (10H, m), 4.10-4.44 (1H, s), 7.04-7.34 (2H, m), 7.38-7.53 (2H, m), 7.53-7.74 (2H, m), 7.74-7.90 (2H, m).

Example 254

Preparation of the Compound 254

(1) Preparation of the Intermediate 254(1).

The title compound was obtained in the same manner as the Example 125(4) using the following starting materials.

Starting materials: 4-bromoaniline and 1-iodopentane; Yield: 22.9% (pale yellow oil).

$^1$H-NMR ($CDCl_3$) δ: 0.80-1.04 (3H, m), 1.16-1.73 (6H, m), 3.05 (2H, t, J=7.2 Hz), 3.48-3.78 (1H, m), 6.38-6.54 (2H, m), 7.17-7.30 (2H, m).

(2) Preparation of the Intermediate 254(2).

The title compound was obtained in the same manner as the Example 123(2) using the following starting materials.

Starting materials: the intermediate 254(1) and methyl chloroglyoxylate; Yield: 51.4% (colorless oil).

$^1$H-NMR ($CDCl_3$) δ: 0.79-0.95 (3H, m), 1.20-1.38 (4H, m), 1.42-1.68 (2H, m), 3.58 (3H, s), 3.74 (2H, t, J=7.2 Hz), 7.04-7.16 (2H, m), 7.47-7.60 (2H, m).

(3) Preparation of the Intermediate 254(3).

The title compound was obtained in the same manner as the Example 123(3) using the following starting materials.

Starting materials: the intermediate 254(2) and 4-(trifluoromethoxy)phenylboronic acid; Yield: 77.1% (pale yellow oil).

$^1$H-NMR ($CDCl_3$) δ: 0.80-0.96 (3H, m), 1.20-1.42 (4H, m), 1.48-1.68 (2H, m), 3.58 (3H, s), 3.74-3.87 (2H, m), 7.20-7.39 (4H, m), 7.50-7.68 (4H, m).

(4) Preparation of the Compound 254.

The title compound was obtained in the same manner as the Example 126(4) using the following starting material.

Starting material: the intermediate 254(3); Yield: 83.7% (white solid).

$^1$H-NMR (DMSO-$d_6$) δ: 0.74-0.94 (3H, m), 1.10-1.33 (4H, m), 1.33-1.53 (2H, m), 3.56-3.86 (2H, m), 7.32-7.56 (4H, m), 7.64-7.76 (2H, m), 7.76-7.90 (2H, m).

Example 255

Preparation of the Compound 255

(1) Preparation of the Intermediate 255(1).

The title compound was obtained in the same manner as the Example 123(1) using the following starting materials.

Starting materials: 4-bromoaniline and 1-bromo-2,2-dimethylpropane; Yield: 8.9% (brown solid).

$^1$H-NMR ($CDCl_3$) δ: 0.97 (9H, s), 2.84 (2H, s), 3.64 (1H, brs), 6.40-6.54 (2H, m), 7.14-7.29 (2H, m).

(2) Preparation of the Intermediate 255(2).

The title compound was obtained in the same manner as the Example 123(2) using the following starting materials.

Starting materials: the intermediate 255(1) and methyl chloroglyoxylate; Yield: 97.1% (brown oil).

$^1$H-NMR ($CDCl_3$) δ: 0.86 (9H, s), 3.58 (3H, s), 3.71 (2H, s), 7.11-7.21 (2H, m), 7.46-7.56 (2H, m).

(3) Preparation of the Intermediate 255(3).

The title compound was obtained in the same manner as the Example 123(3) using the following starting materials.

Starting materials: the intermediate 255(2) and 4-(trifluoromethoxy)phenylboronic acid; Yield: 42.0% (brown oil).

$^1$H-NMR ($CDCl_3$) δ: 0.90 (9H, s), 3.58 (3H, s), 3.78 (2H, s), 7.24-7.44 (4H, m), 7.53-7.68 (4H, m).

(4) Preparation of the Compound 255.

The title compound was obtained in the same manner as the Example 126(4) using the following starting material.

Starting material: the intermediate 255(3); Yield: 83.7% (brown solid).

$^1$H-NMR (DMSO-$d_6$) δ: 0.77 (9H, s), 3.69 (2H, s), 7.26-7.57 (4H, m), 7.57-7.74 (2H, m), 7.74-8.04 (2H, m).

Example 301

Preparation of the Compound 301

(1) Preparation of the Intermediate 301(1).

The title compound was obtained in the same manner as the Example 1(2) using the following starting materials.

Starting materials: ethyl 2-(4-bromo-2,6-dimethoxyphenoxy)acetate and 4-(trifluoromethoxy)phenylboronic acid; Yield: 92% (orange oil).

$^1$H-NMR ($CDCl_3$) δ: 1.32 (3H, t, J=7.2 Hz), 3.90 (6H, s), 4.28 (2H, q, J=7.2 Hz), 4.67 (2H, s), 6.72 (2H, s), 7.25-7.29 (2H, m), 7.52-7.58 (2H, m).

(2) Preparation of the Intermediate 301(2).

The title compound was obtained in the same manner as the Example 83(1) using the following starting material.

Starting material: the intermediate 301(1); Yield: 47.2% (white solid).

$^1$H-NMR ($CDCl_3$) δ: 1.33 (3H, t, J=7.2 Hz), 4.32 (2H, q, J=7.2 Hz), 4.65 (2H, s), 6.71 (2H, s), 6.84 (2H, s), 7.23-7.27 (2H, m), 7.50-7.53 (2H, m).

(3) Preparation of the Intermediate 301(3).

The title compound was obtained in the same manner as the Example 2(1) using the following starting materials.

Starting materials: the intermediate 301(2) and 4-(tert-butyl)benzyl bromide; Yield: 17% (colorless oil).

$^1$H-NMR ($CDCl_3$) δ: 1.30 (3H, t, J=6.9 Hz), 1.35 (9H, s), 4.27 (2H, q, J=6.9 Hz), 4.69 (2H, s), 5.11 (2H, s), 6.69 (1H, d, J=1.8 Hz), 6.83 (1H, d, J=1.8 Hz), 7.23-7.31 (2H, m), 7.38-7.53 (6H, m), 8.96 (1H, brs).

(4) Preparation of the Intermediate 301(4).

The title compound was obtained in the same manner as the Example 2(1) using the following starting materials.

Starting materials: the intermediate 301(3) and 1-chloropentane; Yield: 66% (colorless oil).

$^1$H-NMR ($CDCl_3$) δ: 0.86-0.96 (6H, m), 1.23-1.50 (17H, m), 1.60-1.69 (2H, m), 1.78-1.88 (2H, m), 4.03 (2H, t, J=6.6 Hz), 4.15 (2H, t, J=6.9 Hz), 4.67 (2H, s), 5.14 (2H, s), 6.72 (1H, d, J=1.8 Hz), 6.76 (1H, d, J=1.8 Hz), 7.22-7.27 (2H, m), 7.36-7.44 (4H, m), 7.45-7.50 (2H, m).

(5) Preparation of the Compound 301.

The title compound was obtained in the same manner as the Example 12(4) using the following starting material.

Starting material: the intermediate 301(4); Yield: 100% (colorless oil).

$^1$H-NMR ($CDCl_3$) δ: 0.95 (3H, d, J=6.9 Hz), 1.23-1.50 (13H, m), 1.84-1.94 (2H, m), 4.08-4.13 (2H, m), 4.66 (2H, s), 5.15 (2H, s), 6.74-6.76 (1H, m), 6.82-6.84 (1H, m), 7.26-7.52 (8H, m).

Example 302

Preparation of the Compound 302

(1) Preparation of the Intermediate 302(1).

The title compound was obtained in the same manner as the Example 95(2) using the following starting material.

Starting material: the intermediate 12(2); Yield: 96.8% (yellow oil).

$^1$H-NMR ($CDCl_3$) δ: 1.33 (9H, s), 5.69 (1H, s), 6.93 (1H, d, J=8.1 Hz), 6.96-7.05 (3H, m), 7.20-7.31 (3H, m), 7.33-7.42 (2H, m), 7.51-7.60 (2H, m).

(2) Preparation of the Intermediate 302(2).

The title compound was obtained in the same manner as the Example 105(2) using the following starting materials.

Starting materials: the intermediate 302(1) and ethyl bromoacetate; Yield: 74.5% (colorless oil).

$^1$H-NMR ($CDCl_3$) δ: 1.25 (3H, t, J=7.2 Hz), 1.32 (9H, s), 4.23 (2H, q, J=7.2 Hz), 4.74 (2H, s), 6.92-6.99 (2H, m), 7.02 (1H, d, J=8.1 Hz), 7.11-7.19 (2H, m), 7.21-7.30 (2H, m), 7.30-7.38 (2H, m), 7.50-7.57 (2H, m).

(3) Preparation of the Compound 302.

The title compound was obtained in the same manner as the Example 12(4) using the following starting material.

Starting material: the intermediate 302(2); Yield: 86.5% (white solid).

$^1$H-NMR (DMSO-$d_6$) δ: 1.24 (9H, s), 4.34 (2H, s), 6.84-6.92 (2H, m), 6.95 (1H, d, J=8.1 Hz), 7.12 (1H, dd, J=8.1, 2.1 Hz), 7.16 (1H, d, J=2.1 Hz), 7.26-7.35 (2H, m), 7.35-7.44 (2H, m), 7.65-7.75 (2H, m).

Example 303

Preparation of the Compound 303

(1) Preparation of the Intermediate 303(1).

The title compound was obtained in the same manner as the Example 105(2) using the following starting materials.

Starting materials: the intermediate 302(1) and ethyl 2-bromohexanoate; Yield: 98.5% (colorless oil).

$^1$H-NMR ($CDCl_3$) δ: 0.82 (3H, t, J=7.2 Hz), 1.15-1.37 (16H, m), 1.74-1.95 (2H, m), 4.17 (2H, q, J=7.2 Hz), 4.68 (1H, dd, J=5.1, 7.5 Hz), 6.88-6.95 (2H, m), 7.04 (1H, d, J=9.0 Hz), 7.11-7.17 (2H, m), 7.23-7.35 (4H, m), 7.49-7.56 (2H, m).

(2) Preparation of the Compound 303.

The title compound was obtained in the same manner as the Example 12(4) using the following starting material.

Starting material: the intermediate 303(1); Yield: 73.4% (white solid).

$^1$H-NMR (DMSO-$d_6$) δ: 0.73 (3H, t, J=6.6 Hz), 1.02-1.38 (13H, m), 1.60-1.79 (2H, m), 4.86 (1H, t, J=6.3 Hz), 6.78-6.92 (2H, m), 7.12 (1H, d, J=8.1, Hz), 7.21 (1H, d, J=2.1 Hz), 7.27 (1H, dd, J=2.1, 8.1 Hz), 7.29-7.38 (2H, m), 7.40-7.50 (2H, m), 7.70-7.81 (2H, m), 13.08 (1H, brs).

Example 304

Preparation of the Compound 304

(1) Preparation of the Intermediate 304(1).

The title compound was obtained in the same manner as the Example 95(2) using the following starting material.

Starting material: the intermediate 75(2); Yield: 75.3% (pale yellow solid).

$^1$H-NMR ($CDCl_3$) δ: 1.34 (9H, s), 5.11 (2H, s), 5.74 (1H, s), 7.00 (1H, d, J=8.4 Hz), 7.07 (1H, dd, J=2.4, 8.4 Hz), 7.12

(1H, d, J=2.4 Hz), 7.20-7.28 (2H, m), 7.33-7.41 (2H, m), 7.41-7.47 (2H, m), 7.47-7.54 (2H, m).

(2) Preparation of the Intermediate 304(2).

The title compound was obtained in the same manner as the Example 105(2) using the following starting materials.

Starting materials: the intermediate 304(1) and ethyl bromoacetate; Yield: 89.7% (colorless oil).

$^1$H-NMR ($CDCl_3$) δ: 1.29 (3H, t, J=7.2 Hz), 1.33 (9H, s), 4.25 (2H, q, J=7.2 Hz), 4.73 (2H, s), 5.17 (2H, s), 9.95 (1H, d, J=8.4 Hz), 7.08 (1H, dd, J=2.1, 8.4 Hz), 7.13 (1H, d, J=2.1 Hz), 7.20-7.28 (2H, m), 7.41 (4H, s), 7.44-7.51 (2H, m).

(3) Preparation of the Compound 304.

The title compound was obtained in the same manner as the Example 12(4) using the following starting material.

Starting material: the intermediate 304(2); Yield: 66.4% (white solid).

$^1$H-NMR ($CDCl_3$) δ: 1.29 (9H, s), 4.73 (2H, s), 5.18 (2H, s), 6.96 (1H, d, J=8.7 Hz), 7.19 (1H, dd, J=2.1, 8.7 Hz), 7.33-7.50 (7H, m), 7.70-7.80 (2H, m), 12.99 (1H, brs).

Example 305

Preparation of the Compound 305

(1) Preparation of the Intermediate 305(1).

The title compound was obtained in the same manner as the Example 105(2) using the following starting materials.

Starting materials: the intermediate 110(2) and ethyl 2-bromohexanoate; Yield: 97.7% (colorless oil).

$^1$H-NMR ($CDCl_3$) δ: 0.81 (3H, t, J=7.2 Hz), 1.18-1.35 (16H, m), 1.72-1.93 (2H, m), 4.18 (2H, q, J=7.2 Hz), 4.58-4.68 (1H, m), 6.86-6.94 (2H, m), 6.98 (1H, d, J=8.1 Hz), 7.18-7.35 (6H, m), 7.45-7.54 (2H, m).

(3) Preparation of the Compound 305.

The title compound was obtained in the same manner as the Example 12(4) using the following starting material.

Starting material: the intermediate 305(1); Yield: 52.8% (colorless oil).

$^1$H-NMR (DMSO-$d_6$) δ: 0.71 (3H, t, J=6.6 Hz), 1.00-1.18 (4H, m), 1.25 (9H, s), 1.60-1.73 (2H, m), 4.68 (1H, t, J=6.0 Hz), 6.79-6.90 (2H, m), 7.02 (1H, d, J=8.4 Hz), 7.26-7.35 (2H, m), 7.35-7.46 (3H, m), 7.49 (1H, dd, J=2.7, 8.4 Hz), 7.70-7.81 (2H, m), 13.07 (1H, brs).

Example 306

Preparation of the Compound 306

(1) Preparation of the Intermediate 306(1).

The title compound was obtained in the same manner as the Example 105(2) using the following starting materials.

Starting materials: the intermediate 115(1) and ethyl 2-bromohexanoate; Yield: 24.2% (colorless oil).

$^1$H-NMR ($CDCl_3$) δ: 0.91 (3H, t, J=7.2 Hz), 1.22 (3H, t, J=7.2 Hz), 1.30-1.45 (2H, m), 1.45-1.62 (2H, m), 1.76-2.07 (6H, m), 2.66-2.75 (2H, m), 3.95-4.12 (2H, m), 4.12-4.29 (2H, m), 4.62-4.72 (1H, m), 6.89-6.97 (1H, m), 7.08-7.34 (9H, m), 7.45-7.54 (2H, m).

(2) Preparation of the Compound 306.

The title compound was obtained in the same manner as the Example 12(4) using the following starting material.

Starting material: the intermediate 306(1); Yield: 75.1% (white solid).

$^1$H-NMR (DMSO-$d_6$) δ: 0.84 (3H, t, J=7.2 Hz), 1.20-1.38 (2H, m), 1.38-1.53 (2H, m), 1.65-1.92 (6H, m), 2.65-2.76 (2H, m), 3.88-4.16 (2H, m), 4.77 (1H, t, J=6.0 Hz), 7.07 (1H, d, J=8.4 Hz), 7.12 (1H, d, J=2.4 Hz), 7.13-7.33 (6H, m), 7.37-7.47 (2H, m), 7.64-7.74 (2H, m), 12.94 (1H, brs).

Example 307

Preparation of the Compound 307

(1) Preparation of the Intermediate 307(1).

The title compound was obtained in the same manner as the Example 12(2) using the following starting materials.

Starting materials: the intermediate 12(1) and phenol; Yield: 68.8% (-like substance).

$^1$H-NMR ($CDCl_3$) δ: 6.98 (1H, d, J=8.4 Hz), 7.08-7.17 (2H, m), 7.18-7.26 (1H, m), 7.26-7.35 (2H, m), 7.38-7.49 (2H, m), 7.56-7.65 (2H, m), 7.70 (1H, dd, J=2.7, 8.4 Hz), 8.13 (1H, d, J=2.7 Hz), 10.58 (1H, s).

(2) Preparation of the Intermediate 307(2).

The title compound was obtained in the same manner as the Example 95(2) using the following starting material.

Starting material: the intermediate 307(1); Yield: 66.9% (yellow solid).

$^1$H-NMR ($CDCl_3$) δ: 5.74 (1H, s), 6.92 (1H, d, J=8.4 Hz), 7.02 (1H, dd, J=2.4, 8.4 Hz), 7.04-7.10 (2H, m), 7.10-7.18 (1H, m), 7.22-7.30 (3H, m), 7.30-7.41 (2H, m), 7.51-7.60 (2H, m).

(3) Preparation of the Intermediate 307(3).

The title compound was obtained in the same manner as the Example 105(2) using the following starting materials.

Starting materials: the intermediate 307(2) and ethyl 2-bromohexanoate; Yield: 100% (colorless oil).

$^1$H-NMR ($CDCl_3$) δ: 0.76-0.86 (3H, m), 1.14-1.52 (7H, m), 1.72-1.92 (2H, m), 4.17 (2H, q, J=7.2 Hz), 4.02-4.70 (1H, m), 6.94-7.19 (6H, m), 7.23-7.36 (4H, m), 7.49-7.57 (2H, m).

(4) Preparation of the Compound 307.

The title compound was obtained in the same manner as the Example 12(4) using the following starting material.

Starting material: the intermediate 307(3); Yield: 75.3% (white solid).

$^1$H-NMR (DMSO-$d_6$) δ: 0.73 (3H, t, J=6.9 Hz), 0.99-1.24 (4H, m), 1.60-1.78 (2H, m), 4.79-4.96 (1H, m), 6.86-6.99 (2H, m), 6.99-7.10 (1H, m), 7.16 (1H, d, J=8.1 Hz), 7.21 (1H, d, J=2.1 Hz), 7.25-7.39 (3H, m), 7.40-7.53 (2H, m), 7.71-7.83 (2H, m), 13.05 (1H, brs).

Example 308

Preparation of the Compound 308

(1) Preparation of the Intermediate 308(1).

The title compound was obtained in the same manner as the Example 95(2) using the following starting material.

Starting material: the intermediate 95(4); Yield: 92% (colorless oil).

$^1$H-NMR ($CDCl_3$) δ: 1.34 (9H, s), 5.05 (2H, s), 5.76 (1H, s), 6.50 (1H, dd, J=3.0, 8.7 Hz), 6.66 (1H, d, J=3.0 Hz), 6.90 (1H, d, J=8.7 Hz), 6.94-6.99 (2H, m), 7.11-7.18 (2H, m), 7.33-7.39 (2H, m), 7.41-7.47 (2H, m).

(2) Preparation of the Intermediate 308(2).

The title compound was obtained in the same manner as the Example 105(2) using the following starting materials.

Starting materials: the intermediate 308(1) and ethyl 2-bromohexanoate; Yield: 100% (colorless oil).

$^1$H-NMR ($CDCl_3$) δ: 0.87 (3H, t, J=7.2 Hz), 1.17 (3H, t, J=7.2 Hz), 1.31-1.54 (4H, m), 1.33 (9H, s), 1.83-2.02 (2H, m), 4.04-4.19 (2H, m), 4.60 (1H, dd, J=2.7, 4.5 Hz), 5.03 (1H, d, J=11.4 Hz), 5.10 (1H, d, J=11.4 Hz), 6.55-6.63 (2H, m), 6.89-6.96 (3H, m), 7.10-7.17 (2H, m), 7.35-7.43 (4H, m).

(3) Preparation of the Compound 308.

The title compound was obtained in the same manner as the Example 12(4) using the following starting material.

Starting material: the intermediate 308(2); Yield: 47% (white solid).

$^1$H-NMR (DMSO-d$_6$) δ: 0.82 (3H, t, J=7.2 Hz), 1.17-1.48 (4H, m), 1.26 (9H, s), 1.68-1.82 (2H, m), 4.17 (1H, brs), 4.99 (1H, d, J=11.7 Hz), 5.06 (1H, d, J=11.7 Hz), 6.42 (1H, dd, J=2.4, 8.4 Hz), 6.56 (1H, d, J=2.4 Hz), 6.92-7.00 (3H, m), 7.25-7.33 (2H, m), 7.33-7.43 (4H, m).

Example 309

Preparation of the Compound 309

(1) Preparation of the Intermediate 309(1).

The title compound was obtained in the same manner as the Example 2(1) using the following starting materials.

Starting materials: the intermediate 95(3) and 4-phenylbutyl bromide; Yield: 99% (colorless oil).

$^1$H-NMR (CDCl$_3$) δ: 1.77-1.97 (4H, m), 2.71 (2H, t, J=7.2 Hz), 4.09 (2H, t, J=6.0 Hz), 6.90-6.99 (3H, m), 7.12-7.35 (8H, m), 7.47 (1H, d, J=3.3 Hz), 10.46 (1H, s).

(2) Preparation of the Intermediate 309(2).

The title compound was obtained in the same manner as the Example 95(2) using the following starting material.

Starting material: the intermediate 309(1); Yield: 95% (colorless oil).

$^1$H-NMR (CDCl$_3$) δ: 1.74-1.93 (4H, m), 2.70 (2H, t, J=6.9 Hz), 4.04 (2H, t, J=6.0 Hz), 5.69 (1H, s), 6.49 (1H, dd, J=2.7, 9.0 Hz), 6.65 (1H, d, J=2.7 Hz), 6.78 (1H, d, J=9.0 Hz), 6.91-6.98 (2H, m), 7.11-7.17 (2H, m), 7.17-7.34 (5H, m).

(3) Preparation of the Intermediate 309(3).

The title compound was obtained in the same manner as the Example 105(2) using the following starting materials.

Starting materials: the intermediate 309(2) and ethyl 2-bromohexanoate; Yield: 100% (colorless oil).

$^1$H-NMR (CDCl$_3$) δ: 0.89 (3H, t, J=7.2 Hz), 1.18 (3H, t, J=7.2 Hz), 1.27-1.42 (2H, m), 1.43-1.54 (2H, m), 1.76-2.01 (6H, m), 2.64-2.77 (2H, m), 3.94-4.07 (2H, m), 4.08-4.22 (2H, m), 4.57 (1H, dd, J=5.1, 6.9 Hz), 6.58-6.63 (2H, m), 6.82-6.87 (1H, m), 6.88-6.95 (2H, m), 7.10-7.16 (2H, m), 7.17-7.32 (5H, m).

(4) Preparation of the Compound 309.

The title compound was obtained in the same manner as the Example 12(4) using the following starting material.

Starting material: the intermediate 309(3); Yield: 94% (colorless oil).

$^1$H-NMR (DMSO-d$_6$) δ: 0.80 (3H, t, J=7.2 Hz), 1.21-1.45 (4H, m), 1.63-1.86 (6H, m), 2.64 (2H, t, J=7.2 Hz), 3.88-4.06 (2H, m), 4.61 (1H, t, J=6.0 Hz), 6.55-6.61 (2H, m), 6.93-7.02 (3H, m), 7.11-7.36 (7H, m), 12.94 (1H, m).

Example 310

Preparation of the Compound 310

(1) Preparation of the Intermediate 310(1).

The title compound was obtained in the same manner as the Example 105(2) using the following starting materials.

Starting materials: the intermediate 18(1) and ethyl 2-bromohexanoate; Yield: 80.2% (colorless oil).

$^1$H-NMR (CDCl$_3$) δ: 0.95 (3H, t, J=7.2 Hz), 1.26 (3H, t, J=7.2 Hz), 1.34-1.64 (4H, m), 1.98-2.14 (2H, m), 4.24 (2H, q, J=7.2 Hz), 4.79-4.84 (1H, m), 6.91 (1H, d, J=8.7 Hz), 7.23-7.36 (2H, m), 7.53-7.64 (2H, m), 7.70 (1H, dd, J=2.4, 8.7 Hz), 8.07 (1H, d, J=2.4 Hz), 10.63 (1H, s).

(2) Preparation of the Intermediate 310(2).

The title compound was obtained in the same manner as the Example 95(2) using the following starting material.

Starting material: the intermediate 310(1); Yield: 74.9% (yellow oil).

$^1$H-NMR ($^1$H-NMR (CDCl$_3$) δ: 0.97 (3H, t, J=7.2 Hz), 1.27 (3H, t, J=7.2 Hz), 1.35-1.52 (2H, m), 1.52-1.68 (2H, m), 1.92-2.08 (2H, m), 4.10-4.33 (2H, m), 4.48-4.63 (1H, m), 6.92 (1H, d, J=8.1 Hz), 7.00 (1H, dd, J=2.1, 8.1 Hz), 7.12 (1H, s), 7.17 (1H, d, J=2.1 Hz), 7.20-7.32 (2H, m), 7.48-7.60 (2H, m).

(3) Preparation of the Intermediate 310(3).

The title compound was obtained in the same manner as the Example 2(1) using the following starting materials.

Starting materials: the intermediate 310(2) and 4-(tert-butyl)benzyl bromide; Yield: 44.2% (colorless oil).

$^1$H-NMR (CDCl$_3$) δ: 0.89 (3H, t, J=7.5 Hz), 1.18-1.64 (16H, m), 1.85-2.09 (2H, m), 4.08-4.28 (2H, m), 4.62-4.76 (1H, m), 5.11 (1H, d, J=11.7 Hz), 5.17 (1H, d, J=11.7 Hz), 6.96 (1H, d, J=8.4 Hz), 7.06 (1H, dd, J=2.4, 8.4 Hz), 7.12 (1H, d, J=2.4 Hz), 7.19-7.28 (2H, m), 7.36-7.45 (4H, m), 7.45-7.52 (2H, m).

(4) Preparation of the Compound 310.

The title compound was obtained in the same manner as the Example 12(4) using the following starting material.

Starting material: the intermediate 310(3); Yield: 91.2% (white solid).

$^1$H-NMR (DMSO-d$_6$) δ: 0.85 (3H, t, J=7.5 Hz), 1.22-1.51 (13H, m), 1.80-1.92 (2H, m), 4.69 (1H, t, J=6.0 Hz), 5.19 (2H, s), 6.93 (1H, d, J=8.4 Hz), 7.19 (1H, dd, J=2.4, 8.4 Hz), 7.33-7.48 (7H, m), 7.68-7.79 (2H, m), 13.00 (1H, brs).

Example 311

Preparation of the Compound 311

(1) Preparation of the Intermediate 311(1).

The title compound was obtained in the same manner as the Example 2(1) using the following starting materials.

Starting materials: the intermediate 310(2) and 4-phenylbutyl bromide; Yield: 20.6% (colorless oil).

$^1$H-NMR (CDCl$_3$) δ: 0.91 (3H, t, J=7.2 Hz), 1.23 (3H, t, J=7.2 Hz), 1.29-2.08 (9H, m), 2.58 (1H, t, J=7.2 Hz), 2.63-2.77 (2H, m), 3.92-4.32 (4H, m), 4.58-4.73 (1H, m), 6.87-7.38 (10H, m), 7.44-7.58 (2H, m).

(2) Preparation of the Compound 311.

The title compound was obtained in the same manner as the Example 12(4) using the following starting material.

Starting material: the intermediate 311(1); Yield: 56.3% (white solid).

$^1$H-NMR (DMSO-d$_6$) δ: 0.84 (3H, t, J=7.5 Hz), 1.20-1.38 (2H, m), 1.38-1.52 (2H, m), 1.69-1.92 (6H, m), 2.61-2.73 (2H, m), 4.00-4.22 (2H, m), 4.64 (1H, t, J=6.0 Hz), 6.89 (1H, d, J=8.7 Hz), 7.10-7.34 (7H, m), 7.41 (2H, d, J=9.0 Hz), 7.69-7.80 (2H, m), 12.95 (1H, s).

Example 312

Preparation of the Compound 312

(1) Preparation of the Intermediate 312(1).

The title compound was obtained in the same manner as the Example 95(2) using the following starting material.

Starting material: the intermediate 99(1); Yield: 82% (pale yellow solid).

This compound was obtained as a mixture of the rotational isomers.

Major isomer: $^1$H-NMR ($CDCl_3$) δ: 1.32 (9H, s), 5.68 (1H, s), 6.47-6.54 (1H, m), 6.71-6.76 (1H, m), 6.82-6.92 (1H, m), 6.90-7.04 (4H, m), 7.14-7.21 (2H, m), 7.32-7.43 (2H, m).

Minor isomer: $^1$H-NMR ($CDCl_3$) δ: 1.34 (9H, s), 5.72 (1H, s), 6.47-6.54 (1H, m), 6.71-6.76 (1H, m), 6.82-6.92 (1H, m), 6.90-7.04 (4H, m), 7.14-7.21 (2H, m), 7.32-7.43 (2H, m).

(2) Preparation of the Intermediate 312(2).

The title compound was obtained in the same manner as the Example 105(2) using the following starting materials.

Starting materials: the intermediate 312(1) and ethyl 2-bromohexanoate; Yield: 100% (colorless oil).

This compound was obtained as a mixture of the rotational isomers.

Major isomer: $^1$H-NMR ($CDCl_3$) δ: 0.74-0.96 (6H, m), 1.12-1.33 (4H, m), 1.30 (9H, s), 1.65-2.13 (2H, m), 4.02-4.28 (2H, m), 4.48-4.57 (1H, m), 6.58-6.64 (2H, m), 6.84-6.95 (3H, m), 6.96-7.03 (2H, m), 7.13-7.21 (2H, m), 7.25-7.36 (2H, m).

Minor isomer: $^1$H-NMR ($CDCl_3$) δ: 0.74-0.96 (6H, m), 1.12-1.33 (4H, m), 1.31 (9H, s), 1.65-2.13 (2H, m), 4.02-4.28 (2H, m), 4.48-4.57 (1H, m), 6.58-6.64 (2H, m), 6.84-6.95 (3H, m), 6.96-7.03 (2H, m), 7.13-7.21 (2H, m), 7.25-7.36 (2H, m).

(3) Preparation of the Compound 312.

The title compound was obtained in the same manner as the Example 12(4) using the following starting material.

Starting material: the intermediate 312(2); Yield: 84% (colorless oil).

This compound was obtained as a mixture of the rotational isomers.

Major isomer: $^1$H-NMR ($CDCl_3$) δ: 0.81 (3H, t, J=6.9 Hz), 1.18-1.37 (4H, m), 1.30 (9H, s), 1.82-1.94 (2H, m), 4.61 (1H, q, J=6.0 Hz), 6.60-6.73 (2H, m), 6.85-7.08 (5H, m), 7.14-7.22 (2H, m), 7.29-7.37 (2H, m).

Minor isomer: $^1$H-NMR ($CDCl_3$) δ: 0.81 (3H, t, J=6.9 Hz), 1.18-1.37 (4H, m), 1.32 (9H, s), 1.82-1.94 (2H, m), 4.61 (1H, q, J=6.0 Hz), 6.60-6.73 (2H, m), 6.85-7.08 (5H, m), 7.14-7.22 (2H, m), 7.29-7.37 (2H, m).

Example 313

Preparation of the Compound 313

(1) Preparation of the Intermediate 313(1).

The title compound was obtained in the same manner as the Example 105(2) using the following starting materials.

Starting materials: the intermediate 105(1) and ethyl 2-bromohexanoate; Yield: 60.2% (white solid).

$^1$H-NMR ($CDCl_3$) δ: 0.88 (3H, t, J=7.5 Hz), 1.14-1.64 (16H, m), 1.84-2.09 (2H, m), 4.05-4.26 (2H, m), 4.70 (1H, dd, J=5.1, 7.5 Hz), 5.12 (2H, dd, J=11.7, 16.8 Hz), 7.01 (1H, d, J=8.4 Hz), 7.10-7.19 (2H, m), 7.20-7.28 (2H, m), 7.36-7.45 (4H, m), 7.46-7.55 (2H, m).

(2) Preparation of the Compound 313.

The title compound was obtained in the same manner as the Example 12(4) using the following starting material.

Starting material: the intermediate 313(1); Yield: 72.9% (white solid).

$^1$H-NMR (DMSO-$d_6$) δ: 0.85 (3H, t, J=7.2 Hz), 1.18-1.56 (13H, m), 1.78-1.94 (2H, m), 4.84 (1H, t, J=6.3 Hz), 5.12 (1H, d, J=12.3 Hz), 5.16 (1H, d, J=12.3 Hz), 7.12-7.19 (2H, m), 7.23 (1H, dd, J=1.8, 8.7 Hz), 7.37-7.49 (6H, m), 7.65-7.73 (2H, m), 12.95 (1H, s).

Example 314

Preparation of the Compound 314

(1) Preparation of the Intermediate 314(1).

The title compound was obtained in the same manner as the Example 12(2) using the following starting materials.

Starting materials: 5-bromo-2-fluorobenzaldehyde and 4-(tert-butyl)phenol; Yield: 94% (white solid).

$^1$H-NMR ($CDCl_3$) δ: 1.34 (9H, s), 6.79 (1H, d, J=8.7 Hz), 6.96-7.03 (2H, m), 7.38-7.44 (2H, m), 7.56 (1H, dd, J=2.4, 8.7 Hz), 8.02 (1H, d, J=2.4 Hz), 10.45 (1H, s).

(2) Preparation of the Intermediate 314(2).

The title compound was obtained in the same manner as the Example 95(2) using the following starting material.

Starting material: the intermediate 314(1); Yield: 82% (pale yellow solid).

$^1$H-NMR ($CDCl_3$) δ: 1.32 (9H, s), 5.67 (1H, s), 6.72 (1H, d, J=8.7 Hz), 6.90-6.98 (3H, m), 7.19 (1H, d, J=2.4 Hz), 7.32-7.38 (2H, m).

(3) Preparation of the Intermediate 314(3).

The title compound was obtained in the same manner as the Example 105(2) using the following starting materials.

Starting materials: the intermediate 314(2) and ethyl bromoacetate; Yield: quantitative (colorless oil).

$^1$H-NMR ($CDCl_3$) δ: 1.27 (3H, t, J=6.9 Hz), 1.31 (9H, s), 4.22 (2H, q, J=6.9 Hz), 4.66 (2H, s), 6.83 (1H, d, J=9.0 Hz), 6.86-6.93 (2H, m), 7.05-7.11 (2H, m), 7.28-7.25 (2H, m).

(4) Preparation of the Intermediate 314(4).

The title compound was obtained in the same manner as the Example 1(2) using the following starting materials.

Starting materials: the intermediate 314(3) and 3-(trifluoromethyl)phenylboronic acid; Yield: 83% (colorless oil).

$^1$H-NMR ($CDCl_3$) δ: 1.26 (3H, t, J=7.2 Hz), 1.32 (9H, s), 4.23 (2H, q, J=7.2 Hz), 4.76 (2H, s), 6.92-7.10 (3H, m), 7.16-7.22 (2H, m), 7.30-7.39 (2H, m), 7.50-7.63 (2H, m), 7.68-7.74 (1H, m), 7.75-7.79 (1H, m).

(5) Preparation of the Compound 314.

The title compound was obtained in the same manner as the Example 12(4) using the following starting material.

Starting material: the intermediate 314(4); Yield: 87% (colorless oil).

$^1$H-NMR ($CDCl_3$) δ: 1.32 (9H, s), 4.77 (2H, s), 6.94-7.00 (2H, m), 7.03-7.10 (1H, m), 7.20-7.27 (2H, m), 7.34-7.40 (2H, m), 7.52-7.64 (2H, m), 7.68-7.74 (1H, m), 7.75-7.80 (1H, m).

Example 315

Preparation of the Compound 315

(1) Preparation of the Intermediate 315(1).

The title compound was obtained in the same manner as the Example 95(2) using the following starting material.

Starting material: the intermediate 79(1); Yield: 95.5% (yellow oil).

$^1$H-NMR ($CDCl_3$) δ: 1.34 (9H, s), 5.60 (1H, s), 6.91-6.99 (4H, m), 7.12 (1H, dd, J=2.4, 8.6 Hz), 7.36-7.41 (2H, m).

(2) Preparation of the Intermediate 315(2).

The title compound was obtained in the same manner as the Example 105(2) using the following starting materials.

Starting materials: the intermediate 315(1) and ethyl 2-bromoacetate; Yield: 95.2% (colorless oil).

$^1$H-NMR ($CDCl_3$) δ: 1.26 (3H, t, J=7.1 Hz), 1.32 (9H, s), 4.22 (2H, q, J=7.1 Hz), 4.67 (2H, s), 6.85 (1H, d, J=8.6 Hz), 6.91-6.95 (2H, m), 7.05 (1H, d, J=2.4 Hz), 7.16 (1H, dd, J=2.4, 8.6 Hz), 7.32-7.37 (2H, m).

(3) Preparation of the Intermediate 315(3).

The title compound was obtained in the same manner as the Example 1(2) using the following starting materials.

Starting materials: the intermediate 315(2) and 3-(trifluoromethyl)phenylboronic acid; Yield: 48.8% (colorless oil).

$^1$H-NMR ($CDCl_3$) δ: 1.27 (3H, t, J=7.1 Hz), 1.31 (9H, s), 4.24 (2H, q, J=7.1 Hz), 4.73 (2H, s), 6.93-6.98 (2H, m), 7.05 (1H, d, J=8.4 Hz), 7.24 (1H, d, J=2.2 Hz), 7.30-7.34 (3H, m), 7.43-7.57 (2H, m), 7.63-7.67 (1H, m), 7.72 (1H, brs).

(4) Preparation of the Compound 315.

The title compound was obtained in the same manner as the Example 12(4) using the following starting material.

Starting material: the intermediate 315(3); Yield: 81.2% (pale yellow solid).

$^1$H-NMR ($CDCl_3$) δ: 1.31 (9H, s), 4.73 (2H, s), 6.93-6.98 (2H, m), 7.10 (1H, d, J=8.6 Hz), 7.26 (1H, d, J=2.0 Hz), 7.33-7.38 (3H, m), 7.48-7.59 (2H, m), 7.64-7.67 (1H, m), 7.72 (1H, brs).

Example 316

Preparation of the Compound 316

(1) Preparation of the Intermediate 316(1).

The title compound was obtained in the same manner as the Example 1(2) using the following starting materials.

Starting materials: the intermediate 314(3) and 3-methylphenylboronic acid; Yield: 60% (colorless oil).

$^1$H-NMR ($CDCl_3$) δ: 1.23 (3H, t, J=7.2 Hz), 1.31 (9H, s), 2.42 (3H, s), 4.22 (2H, q, J=7.2 Hz), 4.73 (2H, s), 6.91-7.05 (3H, m), 7.13-7.21 (3H, m), 7.29-7.37 (5H, m).

(2) Preparation of the Compound 316.

The title compound was obtained in the same manner as the Example 12(4) using the following starting material.

Starting material: the intermediate 316(1); Yield: 70% (colorless oil).

$^1$H-NMR ($CDCl_3$) δ: 1.32 (9H, s), 2.42 (3H, s), 4.75 (2H, s), 6.91-7.06 (3H, m), 7.15-7.28 (4H, m), 7.30-7.38 (4H, m).

Example 317

Preparation of the Compound 317

(1) Preparation of the Intermediate 317(1).

The title compound was obtained in the same manner as the Example 105(2) using the following starting materials.

Starting materials: the intermediate 314(2) and ethyl 2-bromohexanoate; Yield: quantitative (colorless oil).

$^1$H-NMR ($CDCl_3$) δ: 0.74-0.85 (3H, m), 1.20-1.35 (7H, m), 1.30 (9H, s), 1.71-1.90 (2H, m), 4.13-4.25 (2H, m), 4.57 (1H, dd, J=5.1, 7.2 Hz), 6.83-6.90 (2H, m), 7.00-7.10 (3H, m), 7.26-7.32 (2H, m).

(2) Preparation of the Intermediate 317(2).

The title compound was obtained in the same manner as the Example 1(2) using the following starting materials.

Starting materials: the intermediate 317(1) and 3-methylphenylboronic acid; Yield: 72% (colorless oil).

$^1$H-NMR ($CDCl_3$) δ: 0.81 (3H, t, J=6.9 Hz), 1.21 (3H, t, J=6.9 Hz), 1.22-1.36 (4H, m), 1.36 (9H, s), 1.75-1.90 (2H, m), 2.41 (3H, s), 4.11-4.23 (2H, m), 4.67 (1H, dd, J=5.4, 7.2 Hz), 6.88-6.95 (2H, m), 7.01-7.06 (1H, m), 7.11-7.21 (3H, m), 7.26-7.36 (5H, m).

(3) Preparation of the Compound 317.

The title compound was obtained in the same manner as the Example 12(4) using the following starting material.

Starting material: the intermediate 317(2); Yield: 58% (colorless oil).

$^1$H-NMR ($CDCl_3$) δ: 0.85 (3H, t, J=6.9 Hz), 1.22-1.47 (4H, m), 1.31 (9H, s), 1.89-1.98 (2H, m), 2.41 (3H, s), 4.76 (1H, t, J=6.0 Hz), 6.90-6.97 (2H, m), 7.01-7.05 (1H, m), 7.12-7.24 (3H, m), 7.28-7.36 (5H, m).

Example 318

Preparation of the Compound 318

(1) Preparation of the Intermediate 318(1).

The title compound was obtained in the same manner as the Example 1(2) using the following starting materials.

Starting materials: the intermediate 317(1) and 3-(trifluoromethyl)phenylboronic acid; Yield: 76% (colorless oil).

$^1$H-NMR ($CDCl_3$) δ: 0.82 (3H, t, J=6.9 Hz), 1.22 (3H, t, J=6.9 Hz), 1.22-1.36 (4H, m), 1.31 (9H, s), 1.76-1.92 (2H, m), 4.12-4.23 (2H, m), 4.67 (1H, dd, J=5.4, 7.2 Hz), 6.88-6.96 (2H, m), 7.02-7.09 (1H, m), 7.12-7.22 (2H, m), 7.28-7.35 (2H, m), 7.48-7.63 (2H, m), 7.76-7.79 (2H, m).

(2) Preparation of the Compound 318.

The title compound was obtained in the same manner as the Example 12(4) using the following starting material.

Starting material: the intermediate 318(1); Yield: 96% (colorless oil).

$^1$H-NMR ($CDCl_3$) δ: 0.87 (3H, t, J=6.9 Hz), 1.20-1.50 (4H, m), 1.32 (9H, s), 1.90-2.01 (2H, m), 4.79 (1H, t, J=6.0 Hz), 6.88-6.96 (2H, m), 7.02-7.09 (1H, m), 7.12-7.22 (2H, m), 7.28-7.35 (2H, m), 7.48-7.63 (2H, m), 7.76-7.79 (2H, m).

Example 319

Preparation of the Compound 319

(1) Preparation of the Intermediate 319(1).

The title compound was obtained in the same manner as the Example 1(2) using the following starting materials.

Starting materials: the intermediate 315(2) and 3-methylphenylboronic acid; Yield: 77.8% (colorless oil).

$^1$H-NMR ($CDCl_3$) δ: 1.28 (3H, t, J=7.1 Hz), 1.32 (9H, s), 2.39 (3H, s), 4.24 (2H, q, J=7.1 Hz), 4.72 (2H, s), 6.94-6.99 (2H, m), 7.03 (1H, d, J=8.6 Hz), 7.11-7.16 (1H, m), 7.25 (1H, d, J=2.2 Hz), 7.27-7.34 (6H, m).

(2) Preparation of the Compound 319.

The title compound was obtained in the same manner as the Example 12(4) using the following starting material.

Starting material: the intermediate 319(1); Yield: 81.2% (pale yellow solid).

$^1$H-NMR ($CDCl_3$) δ: 1.33 (9H, s), 2.41 (3H, s), 4.72 (2H, s), 6.95-7.00 (2H, m), 7.09 (1H, d, J=8.4 Hz), 7.14-7.18 (1H, m), 7.25 (1H, d, J=2.2 Hz), 7.27-7.38 (6H, m).

Example 320

Preparation of the Compound 320

(1) Preparation of the Intermediate 320(1).

The title compound was obtained in the same manner as the Example 105(2) using the following starting materials.

Starting materials: the intermediate 315(1) and ethyl 2-bromohexanoate; Yield: 94.1% (colorless oil).

$^1$H-NMR ($CDCl_3$) δ: 0.82 (3H, t, J=7.3 Hz), 1.22 (3H, t, J=7.1 Hz), 1.20-1.26 (4H, m), 1.31 (9H, s), 1.78-1.84 (2H, m), 4.17 (2H, q, J=7.1 Hz), 4.57 (1H, dd, J=5.1, 7.1 Hz), 6.81 (1H, d, J=8.6 Hz), 6.87-6.92 (2H, m), 7.09 (1H, d, J=2.4 Hz), 7.14 (1H, dd, J=2.6, 8.6 Hz), 7.28-7.35 (2H, m).

(2) Preparation of the Intermediate 320(2).

The title compound was obtained in the same manner as the Example 1(2) using the following starting materials.

Starting materials: the intermediate 320(1) and 3-(trifluoromethyl)phenylboronic acid; Yield: 48.8% (colorless oil).

$^1$H-NMR ($CDCl_3$) δ: 0.81 (3H, t, J=7.3 Hz), 1.24-1.34 (4H, m), 1.24 (3H, t, J=7.1 Hz), 1.30 (9H, s), 1.78-1.88 (2H, m), 4.19 (2H, q, J=7.1 Hz), 4.64 (1H, dd, J=5.1, 7.3 Hz), 6.89-6.94 (2H, m), 7.00 (1H, d, J=8.2 Hz), 7.25-7.33 (4H, m), 7.48-7.57 (2H, m), 7.65-7.68 (1H, m), 7.76 (1H, brs).

(3) Preparation of the Compound 320.

The title compound was obtained in the same manner as the Example 12(4) using the following starting material.

Starting material: the intermediate 320(2); Yield: 87.7% (pale yellow solid).

$^1$H-NMR ($CDCl_3$) δ: 0.87 (3H, t, J=7.1 Hz), 1.25-1.34 (4H, m), 1.24 (3H, t, J=7.1 Hz), 1.31 (9H, s), 1.92-1.99 (2H, m), 4.74 (1H, t, J=5.7 Hz), 6.92-6.98 (2H, m), 7.10 (1H, d, J=8.4 Hz), 7.25 (1H, d, J=2.2 Hz), 7.31-7.38 (3H, m), 7.48-7.59 (2H, m), 7.64-7.66 (1H, m), 7.72 (1H, brs).

Example 321

Preparation of the Compound 321

(1) Preparation of the Intermediate 321(1).

The title compound was obtained in the same manner as the Example 1(2) using the following starting materials.

Starting materials: the intermediate 320(1) and 3-methylphenylboronic acid; Yield: 85.7% (colorless oil).

$^1$H-NMR ($CDCl_3$) δ: 0.80 (3H, t, J=7.1 Hz), 1.20-1.31 (4H, m), 1.23 (3H, t, J=7.1 Hz), 1.30 (9H, s), 1.78-1.88 (2H, m), 2.38 (3H, s), 4.18 (2H, q, J=7.1 Hz), 4.62 (1H, dd, J=4.9, 7.3 Hz), 6.88-6.93 (2H, m), 6.98 (1H, d, J=8.6 Hz), 7.08-7.13 (1H, m), 7.31-7.26 (7H, m).

(2) Preparation of the Compound 321.

The title compound was obtained in the same manner as the Example 12(4) using the following starting material.

Starting material: the intermediate 321(1); Yield: 63.6% (colorless solid).

$^1$H-NMR ($CDCl_3$) δ: 0.87 (3H, t, J=7.1 Hz), 1.26-1.46 (4H, m), 1.30 (9H, s), 1.92-1.99 (2H, m), 2.38 (3H, s), 4.71 (1H, t, J=5.7 Hz), 6.92-6.97 (2H, m), 7.07 (1H, d, J=8.4 Hz), 7.12-7.16 (1H, m), 7.23-7.36 (7H, m).

Example 322

Preparation of the Compound 322

(1) Preparation of the Intermediate 322(1).

The title compound was obtained in the same manner as the Example 105(2) using the following starting materials.

Starting materials: the intermediate 307(2) and ethyl 2-bromooctanoate; Yield: 89% (colorless syrup).

$^1$H-NMR ($CDCl_3$) δ: 0.85 (3H, t, J=6.7 Hz), 1.10-1.34 (11H, m), 1.75-1.87 (2H, m), 4.17 (2H, q, J=7.1 Hz), 4.66 (1H, dd, J=5.3, 7.1 Hz), 6.94-7.17 (6H, m), 7.23-7.34 (4H, m), 7.50-7.55 (2H, m).

(2) Preparation of the Compound 322.

The title compound was obtained in the same manner as the Example 12(4) using the following starting material.

Starting material: the intermediate 322(1); Yield: 97% (white solid).

$^1$H-NMR ($CDCl_3$) δ: 0.84 (3H, t, J=6.8 Hz), 1.15-1.31 (6H, m), 1.31-1.43 (2H, m), 1.90 (2H, dd, J=6.0, 15.3 Hz), 4.74 (1H, t, J=6.0 Hz), 6.98 (2H, d, J=8.6 Hz), 7.07 (2H, t, J=9.2 Hz), 7.17-7.21 (2H, m), 7.24-7.34 (4H, m), 7.52 (2H, d, J=8.2 Hz).

Example 323

Preparation of the Compound 323

(1) Preparation of the Intermediate 323(1).

The title compound was obtained in the same manner as the Example 105(2) using the following starting materials.

Starting materials: the intermediate 302(1) and ethyl 2-bromooctanoate; Yield: 91% (colorless syrup).

$^1$H-NMR ($CDCl_3$) δ: 0.84 (3H, t, J=6.8 Hz), 1.16-1.38 (8H, m), 1.20 (3H, t, J=7.2 Hz), 1.31 (9H, s), 1.74-1.93 (2H, m), 4.17 (2H, q, J=7.1 Hz), 4.68 (1H, dd, J=5.1, 7.3 Hz), 6.92 (2H, d, J=8.8 Hz), 7.04 (1H, d, J=9.0 Hz), 7.12-7.16 (2H, m), 7.24-7.34 (4H, m), 7.53 (2H, d, J=8.8 Hz).

(2) Preparation of the Compound 323.

The title compound was obtained in the same manner as the Example 12(4) using the following starting material.

Starting material: the intermediate 323(1); Yield: 98% (white solid).

$^1$H-NMR ($CDCl_3$) δ: 0.85 (3H, t, J=6.7 Hz), 1.17-1.34 (6H, m), 1.31 (9H, s), 1.35-1.48 (2H, m), 1.88-1.97 (2H, m), 4.76 (1H, t, J=5.9 Hz), 6.94 (2H, d, J=8.8 Hz), 7.03 (1H, d, J=7.9 Hz), 7.15-7.20 (2H, m), 7.24-7.29 (2H, m), 7.34 (2H, d, J=8.8 Hz), 7.52 (2H, d, J=8.8 Hz).

Example 324

Preparation of the Compound 324

(1) Preparation of the Intermediate 324(1).

The title compound was obtained in the same manner as the Example 2(1) using the following starting materials.

Starting materials: the intermediate 18(1) and 4-(4-fluorophenyl)butyl bromide; Yield: 87% (pale yellow oil).

$^1$H-NMR ($CDCl_3$) δ: 1.78-1.98 (4H, m), 2.70 (2H, t, J=7.2 Hz), 4.14 (2H, t, J=6.0 Hz), 6.94-7.07 (3H, m), 7.11-7.20 (2H, m), 7.21-7.33 (2H, m), 7.54-7.64 (2H, m), 7.73 (1H, dd, J=2.4, 9.0 Hz), 8.04 (1H, d, J=2.4 Hz), 10.52-10.55 (1H, m).

(2) Preparation of the Intermediate 324(2).

The title compound was obtained in the same manner as the Example 95(2) using the following starting material.

Starting material: the intermediate 324(1); Yield: 39% (pale yellow oil).

$^1$H-NMR ($CDCl_3$) δ: 1.72-1.94 (4H, m), 2.70 (2H, t, J=7.2 Hz), 4.09 (2H, t, J=6.0 Hz), 5.66 (1H, s), 6.89 (1H, d, J=8.1 Hz), 6.94-7.06 (3H, m), 7.11-7.20 (3H, m), 7.21-7.33 (2H, m), 7.51-7.58 (2H, m).

(3) Preparation of the Intermediate 324(3).

The title compound was obtained in the same manner as the Example 105(2) using the following starting materials.

Starting materials: the intermediate 324(2) and ethyl 2-bromohexanoate; Yield: 49% (colorless oil).

$^1$H-NMR ($CDCl_3$) δ: 0.90 (3H, t, J=7.2 Hz), 1.23 (3H, t, J=7.2 Hz), 1.28-1.64 (4H, m), 1.74-2.03 (6H, m), 2.68 (2H, t, J=7.2 Hz), 3.87-4.10 (2H, m), 4.14-4.24 (2H, m), 4.63-4.70 (1H, m), 6.90-7.02 (3H, m), 7.10-7.28 (6H, m), 7.46-7.53 (2H, m).

(4) Preparation of the Compound 324.

The title compound was obtained in the same manner as the Example 12(4) using the following starting material.

Starting material: the intermediate 324(3); Yield: 99% (white solid).

$^1$H-NMR ($CDCl_3$) δ: 0.94 (3H, t, J=7.2 Hz), 1.35-1.48 (2H, m), 1.52-1.68 (2H, m), 1.73-1.92 (4H, m), 2.00-2.10 (2H, m), 2.62 (2H, t, J=7.2 Hz), 4.09 (2H, t, J=6.3 Hz), 4.61 (1H, dd, J=5.4, 6.3 Hz), 6.92-7.03 (3H, m), 7.12-7.19 (3H, m), 7.21-7.30 (3H, m), 7.46-7.54 (2H, m).

Example 325

Preparation of the Compound 325

(1) Preparation of the Intermediate 325(1).

The title compound was obtained in the same manner as the Example 2(1) using the following starting materials.

Starting materials: the intermediate 18(1) and 4-(4-chlorophenyl)butyl bromide; Yield: 67% (pale yellow oil).

$^1$H-NMR ($CDCl_3$) δ: 1.77-1.97 (4H, m), 2.69 (2H, t, J=7.2 Hz), 4.13 (2H, t, J=6.0 Hz), 7.04 (1H, d, J=9.0 Hz), 7.10-7.15 (2H, m), 7.23-7.31 (4H, m), 7.54-7.62 (2H, m), 7.73 (1H, dd, J=2.4, 9.0 Hz), 8.04 (1H, d, J=2.4 Hz), 10.53 (1H, s).

(2) Preparation of the Intermediate 325(2).

The title compound was obtained in the same manner as the Example 95(2) using the following starting material.

Starting material: the intermediate 325(1); Yield: 45% (colorless oil).

$^1$H-NMR ($CDCl_3$) δ: 1.70-1.94 (4H, m), 2.68 (2H, t, J=7.2 Hz), 4.09 (2H, t, J=6.0 Hz), 5.66 (1H, s), 6.89 (1H, d, J=8.1 Hz), 6.94-7.18 (4H, m), 7.21-7.30 (4H, m), 7.50-7.58 (2H, m).

(3) Preparation of the Intermediate 325(3).

The title compound was obtained in the same manner as the Example 105(2) using the following starting materials.

Starting materials: the intermediate 325(2) and ethyl 2-bromohexanoate; Yield: 45% (colorless oil).

$^1$H-NMR ($CDCl_3$) δ: 0.90 (3H, t, J=7.2 Hz), 1.15-1.66 (7H, m), 1.77-2.02 (6H, m), 2.68 (2H, t, J=7.2 Hz), 4.00-4.10 (2H, m), 4.14-4.24 (2H, m), 4.63-4.70 (1H, m), 6.93 (1H, d, J=8.4 Hz), 7.11-7.19 (4H, m), 7.21-7.29 (4H, m), 7.46-7.53 (2H, m).

(4) Preparation of the Compound 325.

The title compound was obtained in the same manner as the Example 12(4) using the following starting material.

Starting material: the intermediate 325(3); Yield: 95% (white solid).

$^1$H-NMR ($CDCl_3$) δ: 0.94 (3H, t, J=7.2 Hz), 1.34-1.49 (2H, m), 1.53-1.66 (2H, m), 1.72-1.96 (4H, m), 2.00-2.11 (2H, m), 2.68 (2H, t, J=7.2 Hz), 4.08 (2H, t, J=6.0 Hz), 4.61 (1H, t, J=6.3 Hz), 6.97 (1H, d, J=8.4 Hz), 7.11-7.19 (3H, m), 7.21-7.30 (5H, m), 7.46-7.53 (2H, m).

Example 326

Preparation of the Compound 326

(1) Preparation of the Intermediate 326(1).

The title compound was obtained in the same manner as the Example 12(2) using the following starting materials.

Starting materials: the intermediate 12(1) and 4-(trifluoromethoxy)phenol; Yield: 75% (pale brown oil).

$^1$H-NMR ($CDCl_3$) δ: 7.00 (1H, d, J=8.6 Hz), 7.14 (2H, d, J=9.2 Hz), 7.25-7.33 (4H, m), 7.60 (2H, d, J=8.8 Hz), 7.73 (1H, dd, J=2.6, 8.6 Hz), 8.15 (1H, d, J=2.4 Hz), 10.54 (1H, s).

(2) Preparation of the Intermediate 326(2).

The title compound was obtained in the same manner as the Example 95(2) using the following starting material.

Starting material: the intermediate 326(1); Yield: 64% (pale yellow syrup).

$^1$H-NMR ($CDCl_3$) δ: 5.60 (1H, s), 6.94 (1H, d, J=8.4 Hz), 7.02-7.11 (3H, m), 7.20-7.30 (5H, m), 7.56 (2H, d, J=8.4 Hz).

(3) Preparation of the Intermediate 326(3).

The title compound was obtained in the same manner as the Example 105(2) using the following starting materials.

Starting materials: the intermediate 326(2) and ethyl 2-bromooctanoate; Yield: 93% (colorless syrup).

$^1$H-NMR ($CDCl_3$) δ: 0.85 (3H, t, J=6.8 Hz), 1.13-1.29 (11H, m), 1.75-1.85 (2H, m), 4.17 (2H, q, J=7.1 Hz), 4.65 (1H, t, J=6.1 Hz), 6.97 (2H, d, J=9.0 Hz), 7.06-7.19 (5H, m), 7.25-7.31 (2H, m), 7.53 (2H, d, J=8.4 Hz).

(4) Preparation of the Compound 326.

The title compound was obtained in the same manner as the Example 12(4) using the following starting material.

Starting material: the intermediate 326(3); Yield: 98% (white solid).

$^1$H-NMR ($CDCl_3$) δ: 0.84 (3H, t, J=6.7 Hz), 1.13-1.38 (8H, m), 1.83-1.92 (2H, m), 4.72 (1H, t, J=6.0 Hz), 6.98 (2H, d, J=9.2 Hz), 7.07-7.29 (7H, m), 7.52 (2H, d, J=8.8 Hz).

Example 327

Preparation of the Compound 327

(1) Preparation of the Intermediate 327(1).

The title compound was obtained in the same manner as the Example 12(2) using the following starting materials.

Starting materials: the intermediate 12(1) and 4-(trifluoromethyl)phenol; Yield: 51% (colorless syrup).

$^1$H-NMR ($CDCl_3$) δ: 7.07 (1H, d, J=8.6 Hz), 7.19 (2H, d, J=8.4 Hz), 7.32 (2H, d, J=7.9 Hz), 7.62 (2H, d, J=8.8 Hz), 7.68 (2H, d, J=8.6 Hz), 7.77 (1H, dd, J=2.4, 8.6 Hz), 8.17 (1H, d, J=2.4 Hz), 10.48 (1H, s).

(2) Preparation of the Intermediate 327(2).

The title compound was obtained in the same manner as the Example 95(2) using the following starting material.

Starting material: the intermediate 327(1); Yield: 82% (pale yellow syrup).

$^1$H-NMR ($CDCl_3$) δ: 5.54 (1H, s), 7.00 (1H, d, J=8.4 Hz), 7.09 (1H, dd, J=2.2, 7.9 Hz), 7.14 (2H, d, J=9.0 Hz), 7.25-7.31 (3H, m), 7.58 (2H, d, J=8.4 Hz), 7.62 (2H, d, J=9.0 Hz).

(3) Preparation of the Intermediate 327(3).

The title compound was obtained in the same manner as the Example 105(2) using the following starting materials.

Starting materials: the intermediate 327(2) and ethyl 2-bromooctanoate; Yield: 91% (colorless syrup).

$^1$H-NMR ($CDCl_3$) δ: 0.83 (3H, t, J=6.9 Hz), 1.09-1.24 (11H, m), 1.72-1.82 (2H, m), 4.18 (2H, q, J=7.1 Hz), 4.63 (1H, t, J=6.0 Hz), 7.00-7.07 (3H, m), 7.17-7.19 (2H, m), 7.29 (2H, d, J=8.8 Hz), 7.52-7.58 (4H, m).

(4) Preparation of the Compound 327.

The title compound was obtained in the same manner as the Example 12(4) using the following starting material.

Starting material: the intermediate 327(3); Yield: 96% (white solid).

$^1$H-NMR ($CDCl_3$) δ: 0.83 (3H, t, J=6.8 Hz), 1.08-1.27 (8H, m), 1.79-1.87 (2H, m), 4.70 (1H, t, J=5.9 Hz), 7.02 (2H, d, J=9.0 Hz), 7.10-7.30 (5H, m), 7.51-7.57 (4H, m).

Example 328

Preparation of the Compound 328

(1) Preparation of the Intermediate 328(1).

The title compound was obtained in the same manner as the Example 1(2) using the following starting materials.

Starting materials: the intermediate 314(3) and 4-(trifluoromethyl)phenylboronic acid; Yield: 69% (colorless oil).

$^1$H-NMR ($CDCl_3$) δ: 1.26 (3H, t, J=7.2 Hz), 1.32 (9H, s), 4.23 (2H, q, J=7.2 Hz), 4.75 (2H, s), 6.93-7.00 (2H, m), 7.03 (1H, d, J=8.1 Hz), 7.16-7.24 (2H, m), 7.32-7.38 (2H, m), 7.60-7.71 (4H, m).

(2) Preparation of the Compound 328.

The title compound was obtained in the same manner as the Example 12(4) using the following starting material.

Starting material: the intermediate 328(1); Yield: 99% (white solid).

$^1$H-NMR ($CDCl_3$) δ: 1.32 (9H, s), 4.77 (2H, s), 6.93-7.01 (2H, m), 7.05 (1H, d, J=8.7 Hz), 7.21-7.26 (2H, m), 7.33-7.40 (2H, m), 7.61-7.72 (4H, m).

Example 329

Preparation of the Compound 329

(1) Preparation of the Intermediate 329(1).

The title compound was obtained in the same manner as the Example 1(2) using the following starting materials.

Starting materials: the intermediate 314(3) and 3-(trifluoromethoxy)phenylboronic acid; Yield: 95% (colorless oil).

$^1$H-NMR ($CDCl_3$) δ: 1.26 (3H, t, J=7.2 Hz), 1.32 (9H, s), 4.23 (2H, q, J=7.2 Hz), 4.75 (2H, s), 6.93-7.00 (2H, m), 7.00-7.05 (1H, m), 7.12-7.23 (3H, m), 7.30-7.39 (3H, m), 7.42-7.50 (2H, m).

(2) Preparation of the Compound 329.

The title compound was obtained in the same manner as the Example 12(4) using the following starting material.

Starting material: the intermediate 329(1); Yield: 83% (white solid).

$^1$H-NMR ($CDCl_3$) δ: 1.32 (9H, s), 4.76 (2H, s), 6.93-7.00 (2H, m), 7.00-7.05 (1H, m), 7.12-7.23 (3H, m), 7.30-7.39 (3H, m), 7.43-7.50 (2H, m).

Example 330

Preparation of the Compound 330

(1) Preparation of the Intermediate 330(1).

The title compound was obtained in the same manner as the Example 1(2) using the following starting materials.

Starting materials: the intermediate 315(2) and 4-(trifluoromethyl)phenylboronic acid; Yield: 64.7% (colorless oil).

$^1$H-NMR ($CDCl_3$) δ: 1.27 (3H, t, J=7.1 Hz), 1.31 (9H, s), 4.24 (2H, q, J=7.1 Hz), 4.73 (2H, s), 6.93-6.98 (2H, m), 7.04 (1H, d, J=8.4 Hz), 7.24 (1H, d, J=2.2 Hz), 7.30-7.34 (3H, m), 7.56-7.65 (4H, m).

(2) Preparation of the Compound 330.

The title compound was obtained in the same manner as the Example 12(4) using the following starting material.

Starting material: the intermediate 330(1); Yield: 80.9% (white solid).

$^1$H-NMR ($CDCl_3$) δ: 1.31 (9H, s), 4.74 (2H, s), 6.93-6.98 (2H, m), 7.09 (1H, d, J=8.4 Hz), 7.25 (1H, d, J=2.2 Hz), 7.31-7.37 (3H, m), 7.56-7.66 (4H, m).

Example 331

Preparation of the Compound 331

(1) Preparation of the Intermediate 331(1).

The title compound was obtained in the same manner as the Example 1(2) using the following starting materials.

Starting materials: the intermediate 315(2) and 3-(trifluoromethoxy)phenylboronic acid; Yield: 75.0% (colorless oil).

$^1$H-NMR ($CDCl_3$) δ: 1.26 (3H, t, J=7.1 Hz), 1.30 (9H, s), 4.23 (2H, q, J=7.1 Hz), 4.72 (2H, s), 6.92-6.97 (2H, m), 7.03 (1H, d, J=8.4 Hz), 7.13-7.17 (1H, m), 7.21 (1H, d, J=2.2 Hz), 7.27-7.35 (4H, m), 7.39-7.41 (2H, m).

(2) Preparation of the Compound 331.

The title compound was obtained in the same manner as the Example 12(4) using the following starting material.

Starting material: the intermediate 331(1); Yield: 81.2% (white solid).

$^1$H-NMR ($CDCl_3$) δ: 1.31 (9H, s), 4.71 (2H, s), 6.93-6.97 (2H, m), 7.09 (1H, d, J=8.4 Hz), 7.15-7.19 (1H, m), 7.23 (1H, d, J=2.0 Hz), 7.30-7.43 (6H, m).

Example 332

Preparation of the Compound 332

(1) Preparation of the Intermediate 332(1).

The title compound was obtained in the same manner as the Example 1(2) using the following starting materials.

Starting materials: the intermediate 79(1) and 3-(trifluoromethyl)phenylboronic acid; Yield: 97.7% (white solid).

$^1$H-NMR ($CDCl_3$) δ: 1.34 (9H, s), 7.01-7.06 (2H, m), 7.12 (1H, d, J=1.5 Hz), 7.39-7.44 (3H, m), 7.52-7.74 (4H, m), 8.03 (1H, d, J=8.1 Hz), 10.54 (1H, s).

(2) Preparation of the Intermediate 332(2).

The title compound was obtained in the same manner as the Example 2(3) using the following starting materials.

Starting materials: the intermediate 332(1) and malonic acid; Yield: 100% (white solid).

$^1$H-NMR (DMSO-$d_6$) δ: 1.27 (9H, s), 6.70 (1H, d, J=16.2 Hz), 6.88-7.00 (2H, m), 7.36-7.42 (3H, m), 7.64-7.81 (4H, m), 7.92-8.00 (2H, m), 8.04 (1H, d, J=8.1 Hz), 12.5 (1H, brs).

(3) Preparation of the Compound 332.

The title compound was obtained in the same manner as the Example 3 using the following starting material.

Starting material: the intermediate 332(2); Yield: 90% (white solid).

$^1$H-NMR (DMSO-$d_6$) δ: 1.27 (9H, s), 2.55 (2H, t, J=7.5 Hz), 2.85 (2H, t, J=7.5 Hz), 6.90 (2H, d, J=8.4 Hz), 7.24 (1H, s), 7.38 (2H, d, J=8.4 Hz), 7.46-7.53 (2H, m), 7.63-7.71 (2H, m), 7.88-7.91 (2H, m), 12.5 (1H, brs).

Example 333

Preparation of the Compound 333

(1) Preparation of the Intermediate 333(1).

The title compound was obtained in the same manner as the Example 1(2) using the following starting materials.

Starting materials: 4-bromo-2-fluorobenzaldehyde and 4-(trifluoromethoxy)phenylboronic acid; Yield: 94.4% (colorless oil).

$^1$H-NMR ($CDCl_3$) δ: 7.32-7.36 (2H, m), 7.44 (1H, d, J=1.7 Hz), 7.46-7.49 (1H, m), 7.61-7.67 (2H, m), 7.96 (1H, dd, J=7.5, 8.1 Hz), 10.40 (1H, d, J=0.6 Hz).

(2) Preparation of the Intermediate 333(2).

The title compound was obtained in the same manner as the Example 12(2) using the following starting materials.

Starting materials: the intermediate 333(1) and 4-(isopropyl)phenol; Yield: 86.3% (pale yellow oil).

$^1$H-NMR ($CDCl_3$) δ: 1.28 (6H, d, J=6.9 Hz), 2.95 (1H, sept, J=6.9 Hz), 7.03-7.08 (3H, m), 7.25-7.31 (4H, m), 7.34-7.41 (1H, m), 7.51-7.56 (2H, m), 8.02 (1H, d, J=8.2 Hz), 10.55 (1H, d, J=0.7 Hz).

(3) Preparation of the Intermediate 333(3).

The title compound was obtained in the same manner as the Example 95(2) using the following starting material.

Starting material: the intermediate 333(2); Yield: 86.3% (pale yellow oil).

$^1$H-NMR ($CDCl_3$) δ: 1.25 (6H, d, J=6.9 Hz), 2.91 (1H, sept, J=6.9 Hz), 5.65 (1H, s), 6.97-7.03 (2H, m), 7.04 (1H, d, J=2.0 Hz), 7.11 (1H, d, J=8.4 Hz), 7.19-7.25 (5H, m), 7.43-7.48 (2H, m).

(4) Preparation of the Intermediate 333(4).

The title compound was obtained in the same manner as the Example 105(2) using the following starting materials.

Starting materials: the intermediate 333(3) and ethyl 2-bromoacetate; Yield: 90.6% (colorless oil).

$^1$H-NMR ($CDCl_3$) δ: 1.24 (6H, d, J=6.9 Hz), 1.27 (3H, t, J=7.1 Hz), 2.89 (1H, sept, J=6.9 Hz), 4.23 (2H, q, J=7.1 Hz), 4.72 (2H, s), 6.93-6.97 (2H, m), 7.02 (1H, d, J=8.4 Hz), 7.14-7.30 (6H, m), 7.45-7.50 (2H, m).

(5) Preparation of the Compound 333.

The title compound was obtained in the same manner as the Example 12(4) using the following starting material.

Starting material: the intermediate 333(4); Yield: 96.3% (white solid).

$^1$H-NMR ($CDCl_3$) δ: 1.24 (6H, d, J=7.0 Hz), 2.90 (1H, sept, J=7.0 Hz), 4.73 (2H, s), 6.93-6.98 (2H, m), 7.08 (1H, d, J=8.4 Hz), 7.18-7.30 (6H, m), 7.46-7.51 (2H, m).

Example 334

Preparation of the Compound 334

(1) Preparation of the Intermediate 334(1).

Thionyl chloride (0.280 ml) was added to the intermediate 111(1) (160 mg, 0.384 mmol) at 0° C., and the mixture was stirred for 3 hours. A saturated aqueous solution of sodium hydrogen carbonate was added to the residue obtained by evaporation of the reaction mixture under reduced pressure, and the mixture was extracted with chloroform. The organic layer was dried over anhydrous sodium sulfate. The solvent was evaporated under reduced pressure to give the title compound (150 mg, 90%) as a colorless oil.

$^1$H-NMR ($CDCl_3$) δ: 1.32 (9H, s), 4.74 (2H, s), 6.91-7.02 (2H, m), 7.06 (1H, d, J=1.5 Hz), 7.18-7.40 (5H, m), 7.41-7.52 (2H, m), 7.55 (1H, d, J=7.8 Hz).

(2) Preparation of the Intermediate 334(2).

Sodium cyanide (36 mg, 0.700 mmol) was added to a mixture of the intermediate 334(1) (150 mg, 0.350 mmol) and N,N-dimethylformamide (10 ml), and the mixture was stirred at room temperature for 16 hours. The reaction mixture was diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=5:1) to give the title compound (118 mg, 79%) as a colorless oil.

$^1$H-NMR ($CDCl_3$) δ: 1.33 (9H, s), 3.83 (2H, s), 6.91-6.99 (2H, m), 7.05 (1H, d, J=1.5 Hz), 7.20-7.28 (2H, m), 7.31 (1H, dd, J=1.5, 7.8 Hz), 7.34-7.41 (2H, m), 7.44-7.52 (2H, m), 7.56 (1H, d, J=7.8 Hz).

(3) Preparation of the Compound 334.

A 2 N aqueous solution of sodium hydroxide (1.0 ml) was added to a mixture of the intermediate 334(2) (118 mg, 0.277 mmol) and ethanol (2 ml), and the mixture was refluxed for 6 hours. The reaction mixture was cooled to room temperature, adjusted to pH 1 by addition of 2 N hydrochloric acid, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=1:1) to give the title compound (44 mg, 35%) as a colorless oil.

$^1$H-NMR ($CDCl_3$) δ: 1.31 (9H, s), 3.78 (2H, s), 6.91-6.98 (2H, m), 7.05 (1H, d, J=1.5 Hz), 7.18-7.29 (3H, m), 7.30-7.40 (3H, m), 7.41-7.51 (2H, m).

Example 335

Preparation of the Compound 335

(1) Preparation of the Intermediate 335(1).

The title compound was obtained in the same manner as the Example 12(2) using the following starting materials.

Starting materials: the intermediate 333(1) and 3-(tert-butyl)phenol; Yield: 95.2% (pale yellow oil).

$^1$H-NMR ($CDCl_3$) δ: 1.34 (9H, s), 6.87-6.91 (1H, m), 7.07 (1H, d, J=1.7 Hz), 7.19-7.28 (4H, m), 7.32 (1H, d, J=7.9 Hz), 7.35-7.39 (1H, m), 7.49-7.56 (2H, m), 8.02 (1H, d, J=8.1 Hz), 10.56 (1H, d, J=0.7 Hz).

(2) Preparation of the Compound 335.

The title compound was obtained in the same manner as the Example 2(3) using the following starting materials.

Starting materials: the intermediate 335(1) and malonic acid; Yield: 90.7% (white solid).

$^1$H-NMR ($CDCl_3$) δ: 1.33 (9H, s), 6.63 (1H, d, J=16.2 Hz), 6.80-6.84 (1H, m), 7.05 (1H, d, J=1.7 Hz), 7.15-7.33 (6H, m), 7.47-7.52 (2H, m), 7.72 (1H, d, J=8.1 Hz), 8.16 (1H, d, J=16.2 Hz).

Example 336

Preparation of the Compound 336

The title compound was obtained in the same manner as the Example 3 using the following starting material.

Starting material: the compound 335; Yield: 84.6% (white solid).

$^1$H-NMR ($CDCl_3$) δ: 1.31 (9H, s), 2.75 (2H, t, J=7.7 Hz), 3.05 (2H, t, J=7.7 Hz), 6.73-6.77 (1H, m), 7.04 (1H, d, J=1.8 Hz), 7.09-7.16 (2H, m), 7.20-7.27 (4H, m), 7.35 (1H, d, J=7.9 Hz), 7.45-7.49 (2H, m).

Example 377

Preparation of the Compound 377

(1) Preparation of the Intermediate 377(1).

The title compound was obtained in the same manner as the Example 2(1) using the following starting materials.

Starting materials: 4-bromo-2-hydroxybenzaldehyde and 4-phenylbutyl bromide; Yield: 75% (white solid).

$^1$H-NMR ($CDCl_3$) δ: 1.76-1.97 (4H, m), 2.66-2.75 (2H, m), 4.02-4.10 (2H, m), 7.11-7.34 (7H, m), 7.68 (1H, d, J=8.1 Hz), 10.41 (1H, s).

(2) Preparation of the Intermediate 337(2).

The title compound was obtained in the same manner as the Example 1(2) using the following starting materials.

Starting materials: the intermediate 337(1) and 4-(trifluoromethoxy)phenylboronic acid; Yield: 79% (white solid).

$^1$H-NMR ($CDCl_3$) δ: 1.81-1.98 (4H, m), 2.67-2.77 (2H, m), 4.12-4.20 (2H, m), 7.05-7.35 (9H, m), 7.55-7.64 (2H, m), 7.90 (1H, d, J=8.1 Hz), 10.51 (1H, s).

(3) Preparation of the Intermediate 337(3).

The title compound was obtained in the same manner as the Example 95(2) using the following starting material.

Starting material: the intermediate 337(2); Yield: 77% (white solid).

$^1$H-NMR ($CDCl_3$) δ: 1.77-1.94 (4H, m), 2.67-2.75 (2H, m), 4.07-4.15 (2H, m), 5.64 (1H, s), 6.96-7.01 (2H, m), 7.05 (1H, dd, J=1.8, 8.4 Hz), 7.15-7.34 (7H, m), 7.47-7.55 (2H, m).

(4) Preparation of the Intermediate 337(4).

The title compound was obtained in the same manner as the Example 105(2) using the following starting materials.

Starting materials: the intermediate 337(3) and ethyl bromoacetate; Yield: 89% (colorless oil).

$^1$H-NMR ($CDCl_3$) δ: 1.29 (3H, t, J=7.2 Hz). 1.80-1.97 (4H, m), 2.67-2.75 (2H, m), 4.06-4.13 (2H, m), 4.26 (2H, q, J=7.2 Hz), 4.70 (2H, s), 6.90-6.97 (1H, m), 7.02-7.09 (2H, m), 7.14-7.33 (7H, m), 7.48-7.55 (2H, m).

(5) Preparation of the Compound 337.

The title compound was obtained in the same manner as the Example 12(4) using the following starting material.

Starting material: the intermediate 337(4); Yield: 51% (white solid).

$^1$H-NMR ($CDCl_3$) δ: 1.77-1.98 (4H, m), 2.67-2.75 (2H, m), 4.07-4.15 (2H, m), 4.71 (2H, s), 7.10-7.12 (3H, m), 7.14-7.33 (7H, m), 7.47-7.56 (2H, m).

Example 351

Preparation of the Compound 351

(1) Preparation of the Intermediate 351(1).

The title compound was obtained in the same manner as the Example 185(2) using the following starting materials.

Starting materials: the intermediate 188(1) and ethylene glycol mono-tert-butyl ether; Yield: 100% (yellow solid).

$^1$H-NMR ($CDCl_3$) δ: 1.24 (9H, s), 3.79 (2H, t, J=5.4 Hz), 4.27 (2H, t, J=5.4 Hz), 7.23 (1H, d, J=8.4 Hz), 7.27-7.32 (2H, m), 7.54-7.59 (2H, m), 7.70 (1H, dd, J=2.1, 8.4 Hz), 8.03 (1H, d, J=2.1 Hz).

(2) Preparation of the Intermediate 351(2).

The title compound was obtained in the same manner as the Example 125(2) using the following starting material.

Starting material: the intermediate 351(1); Yield: 100% (pale yellow oil).

$^1$H-NMR ($CDCl_3$) δ: 1.25 (9H, s), 3.74 (2H, t, J=4.5 Hz), 3.97 (2H, s), 4.14 (2H, t, J=4.5 Hz), 6.88-6.92 (3H, m), 7.21-7.25 (2H, m), 7.50-7.54 (2H, m).

(3) Preparation of the Intermediate 351(3).

The title compound was obtained in the same manner as the Example 123(1) using the following starting materials.

Starting materials: the intermediate 351(2) and 4-phenylbutyl bromide; Yield: 68% (yellow oil).

$^1$H-NMR ($CDCl_3$) δ: 1.23 (9H, s), 1.67-1.92 (4H, m), 2.64-2.70 (2H, m), 3.14-3.22 (2H, m), 3.72 (2H, t, J=5.4 Hz), 4.09-4.13 (2H, m), 4.40 (1H, s), 6.72-7.32 (10H, m), 7.46-7.56 (2H, m).

(4) Preparation of the Intermediate 351(4).

The title compound was obtained in the same manner as the Example 123(2) using the following starting materials.

Starting materials: the intermediate 351(3) and methyl chloroglyoxylate; Yield: 54% (colorless oil).

$^1$H-NMR ($CDCl_3$) δ: 1.22 (9H, s), 1.53-1.72 (4H, m), 2.54-2.65 (2H, m), 3.51 (3H, s), 3.54-4.18 (6H, m), 7.02-7.31 (9H, m), 7.46-7.51 (3H, m).

(5) Preparation of the Compound 351.

The title compound was obtained in the same manner as the Example 126(4) using the following starting material.

Starting material: the intermediate 351(4); Yield: 47% (white solid).

This compound was obtained as a mixture of the rotational isomers.

Major isomer: $^1$H-NMR (DMSO-$d_6$) δ: 1.16 (9H, s), 1.29-1.55 (4H, m), 2.41-2.55 (2H, m), 3.60-3.72 (3H, m), 4.05-4.18 (3H, m), 7.04-7.71 (12H, m).

Minor isomer: $^1$H-NMR (DMSO-$d_6$) δ: 1.15 (9H, s), 1.29-1.55 (4H, m), 2.41-2.55 (2H, m), 3.60-3.72 (3H, m), 4.05-4.18 (3H, m), 7.04-7.71 (12H, m).

Example 352

Preparation of the Compound 352

(1) Preparation of the Intermediate 352(1).

The title compound was obtained in the same manner as the Example 185(2) using the following starting materials.

Starting materials: the intermediate 188(1) and 1-heptanol; Yield: 52.0% (yellow solid).

$^1$H-NMR ($CDCl_3$) δ: 0.90 (3H, t, J=6.9 Hz), 1.29-1.41 (6H, m), 1.45-1.52 (2H, m), 1.82-1.89 (2H, m), 4.15 (2H, t, J=6.6 Hz), 7.15 (1H, d, J=9.0 Hz), 7.29-7.32 (2H, m), 7.54-7.59 (2H, m), 7.70 (1H, dd, J=2.4, 9.0 Hz), 8.03 (1H, d, J=2.4 Hz).

(2) Preparation of the Intermediate 352(2).

The title compound was obtained in the same manner as the Example 125(2) using the following starting material.

Starting material: the intermediate 352(1); Yield: 100% (white solid).

$^1$H-NMR ($CDCl_3$) δ: 0.90 (3H, t, J=6.9 Hz), 1.28-1.50 (8H, m), 1.79-1.88 (2H, m), 3.89 (2H, brs), 4.02 (2H, t, J=6.6 Hz), 6.83 (1H, d, J=8.4 Hz), 6.88-6.93 (2H, m), 7.21-7.24 (2H, m), 7.50-7.55 (2H, m).

(3) Preparation of the Intermediate 352(3).

The title compound was obtained in the same manner as the Example 123(1) using the following starting materials.

Starting materials: the intermediate 352(2) and 4-phenylbutyl bromide; Yield: 65.1% (white solid).

$^1$H-NMR ($CDCl_3$) δ: 0.89-0.93 (3H, m), 1.35-1.89 (12H, m), 2.61-2.71 (4H, m), 3.99-4.32 (5H, m), 6.72-6.79 (1H, m), 7.10-7.32 (10H, m), 7.52-7.60 (1H, m).

(4) Preparation of the Intermediate 352(4).

The title compound was obtained in the same manner as the Example 123(2) using the following starting materials.

Starting materials: the intermediate 352(3) and methyl chloroglyoxylate; Yield: 28.2% (yellow oil).

$^1$H-NMR ($CDCl_3$) δ: 0.88-0.92 (3H, m), 1.25-1.49 (8H, m), 1.57-1.71 (4H, m), 1.77-1.86 (2H, m), 2.57-2.69 (2H, m), 3.48-3.60 (4H, m), 3.98-4.08 (3H, m), 6.99 (1H, d, J=9.0 Hz), 7.08-7.32 (8H, m), 7.47-7.51 (3H, m).

(5) Preparation of the Compound 352.

The title compound was obtained in the same manner as the Example 126(4) using the following starting material.

Starting material: the intermediate 352(4); Yield: 73.4% (yellow solid).

This compound was obtained as a mixture of the rotational isomers.

Major isomer: $^1$H-NMR (DMSO-$d_6$) δ: 0.85 (3H, t, J=7.2 Hz), 1.21-1.48 (12H, m), 1.67-1.74 (2H, m), 2.49-2.53 (2H, m), 3.31-3.35 (1H, m), 3.97-4.02 (3H, m), 7.06-7.20 (6H, m), 7.40-7.43 (2H, m), 7.49-7.51 (2H, m), 7.64-7.67 (2H, m).

Minor isomer: $^1$H-NMR (DMSO-$d_6$) δ: 0.85 (3H, t, J=7.2 Hz), 1.21-1.48 (12H, m), 1.67-1.74 (2H, m), 2.49-2.53 (2H, m), 3.31-3.35 (1H, m), 3.62-3.67 (1H, m), 3.97-4.02 (2H, m), 7.06-7.20 (5H, m), 7.28-7.30 (1H, m), 7.40-7.43 (2H, m), 7.54-7.59 (2H, m), 7.67-7.70 (2H, m).

Example 353

Preparation of the Compound 353

(1) Preparation of the Intermediate 353(1).

The title compound was obtained in the same manner as the Example 185(2) using the following starting materials.

Starting materials: the intermediate 188(1) and 1-octanol; Yield: 89.3% (yellow solid).

$^1$H-NMR ($CDCl_3$) δ: 0.89 (3H, t, J=6.9 Hz), 1.28-1.41 (8H, m), 1.45-1.52 (2H, m), 1.82-1.89 (2H, m), 4.15 (2H, t, J=6.6 Hz), 7.15 (1H, d, J=9.0 Hz), 7.29-7.32 (2H, m), 7.54-7.59 (2H, m), 7.70 (1H, dd, J=2.4, 9.0 Hz), 8.03 (1H, d, J=2.4 Hz).

(2) Preparation of the Intermediate 353(2).

The title compound was obtained in the same manner as the Example 125(2) using the following starting material.

Starting material: the intermediate 353(1); Yield: 93.2% (gray solid).

$^1$H-NMR ($CDCl_3$) δ: 0.89 (3H, t, J=7.2 Hz), 1.30-1.37 (10H, m), 1.79-1.88 (2H, m), 3.89 (2H, brs), 4.02 (2H, t, J=6.6 Hz), 6.83 (1H, d, J=8.4 Hz), 6.88-6.93 (2H, m), 7.21-7.24 (2H, m), 7.50-7.55 (2H, m).

(3) Preparation of the Intermediate 353(3).

The title compound was obtained in the same manner as the Example 123(1) using the following starting materials.

Starting materials: the intermediate 353(2) and 4-phenylbutyl bromide; Yield: 60.5% (colorless oil).

$^1$H-NMR ($CDCl_3$) δ: 0.89 (3H, t, J=6.9 Hz), 1.23-1.50 (10H, m), 1.74-1.82 (6H, m), 2.66-2.69 (2H, m), 3.18-3.22 (2H, m), 4.02 (2H, t, J=6.6 Hz), 4.26 (1H, brs), 6.73-6.78 (3H, m), 7.18-7.31 (7H, m), 7.53-7.55 (2H, m).

(4) Preparation of the Intermediate 353(4).

The title compound was obtained in the same manner as the Example 123(2) using the following starting materials.

Starting materials: the intermediate 353(3) and methyl chloroglyoxylate; Yield: 100% (colorless oil).

$^1$H-NMR ($CDCl_3$) δ: 0.88 (3H, t, J=6.9 Hz), 1.26-1.49 (10H, m), 1.57-1.66 (4H, m), 1.70-1.81 (2H, m), 2.51-2.66 (2H, m), 3.50-3.62 (4H, m), 3.82-4.06 (3H, m), 6.98 (1H, d, J=8.7 Hz), 7.09-7.32 (8H, m), 7.47-7.51 (3H, m).

(5) Preparation of the Compound 353.

The title compound was obtained in the same manner as the Example 126(4) using the following starting material.

Starting material: the intermediate 353(4); Yield: 79.4% (white solid).

This compound was obtained as a mixture of the rotational isomers.

Major isomer: $^1$H-NMR (DMSO-$d_6$) δ: 0.82-0.85 (3H, m), 1.24-1.49 (14H, m), 1.67-1.74 (2H, m), 2.44-2.50 (2H, m), 3.15-3.26 (1H, m), 3.97-4.02 (3H, m), 7.06-7.20 (6H, m), 7.40-7.43 (2H, m), 7.49-7.52 (1H, m), 7.64-7.70 (3H, m).

Minor isomer: $^1$H-NMR (DMSO-$d_6$) δ: 0.82-0.85 (3H, m), 1.24-1.49 (14H, m), 1.67-1.74 (2H, m), 2.44-2.50 (2H, m), 3.15-3.26 (1H, m), 3.61-3.72 (1H, m), 3.97-4.02 (2H, m), 7.06-7.20 (5H, m), 7.29-7.30 (1H, m), 7.40-7.43 (2H, m), 7.49-7.58 (3H, m), 7.64-7.70 (1H, m).

Example 354

Preparation of the Compound 354

(1) Preparation of the Intermediate 354(1).

The title compound was obtained in the same manner as the Example 123(3) using the following starting materials.

Starting materials: 4-bromo-2-nitrophenol and 4-(trifluoromethoxy)phenylboronic acid; Yield: 72.4% (yellow solid).

$^1$H-NMR ($CDCl_3$) δ: 7.27 (1H, d, J=9.0 Hz), 7.30-7.34 (2H, m), 7.56-7.61 (2H, m), 7.80 (1H, dd, J=2.4, 9.0 Hz), 8.31 (1H, d, J=2.4 Hz), 10.61 (1H, s).

(2) Preparation of the Intermediate 354(2).

A mixture of 4-phenylbutyl bromide (277 g, 1.30 mmol), the intermediate 354(1) (299 mg, 1.00 mmol), potassium carbonate (207 mg, 1.50 mmol) and dimethylformamide (6 ml) was stirred at 90° C. for 3 hours under argon atmosphere. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=6:1) to give the title compound (395 mg, 92%) as a pale yellow solid.

$^1$H-NMR ($CDCl_3$) δ: 1.85-2.01 (4H, m), 2.68-2.74 (2H, m), 4.15 (2H, t, J=6.6 Hz), 7.12 (1H, d, J=8.7 Hz), 7.17-7.32 (7H, m), 7.54-7.58 (2H, m), 7.69 (1H, dd, J=2.7, 8.7 Hz), 8.03 (1H, d, J=2.7 Hz).

(3) Preparation of the Intermediate 354(3).

The title compound was obtained in the same manner as the Example 125(2) using the following starting material.

Starting material: the intermediate 354(2); Yield: 86.2% (yellow solid).

$^1$H-NMR ($CDCl_3$) δ: 1.79-1.90 (4H, m), 2.71 (2H, t, J=7.5 Hz), 3.87 (2H, brs), 4.05 (2H, t, J=6.0 Hz), 6.82 (1H, d, J=8.1 Hz), 6.87-6.92 (2H, m), 7.20-7.32 (7H, m), 7.49-7.54 (2H, m).

(4) Preparation of the Intermediate 354(4).

The title compound was obtained in the same manner as the Example 123(1) using the following starting materials.

Starting materials: the intermediate 354(3) and 4-phenylbutyl bromide; Yield: 41.2% (white solid).

$^1$H-NMR ($CDCl_3$) δ: 1.70-1.89 (8H, m), 2.65-2.72 (4H, m), 3.17-3.23 (2H, m), 4.04 (2H, t, J=6.0 Hz), 4.23-4.27 (1H, m), 6.73-6.79 (3H, m), 7.16-7.22 (6H, m), 7.25-7.31 (6H, m), 7.51-7.56 (2H, m).

(5) Preparation of the Intermediate 354(5).

The title compound was obtained in the same manner as the Example 123(2) using the following starting materials.

Starting materials: the intermediate 354(4) and methyl chloroglyoxylate; Yield: 100% (yellow oil).

$^1$H-NMR ($CDCl_3$) δ: 1.56-1.66 (4H, m), 1.79-1.83 (4H, m), 2.56-2.61 (2H, m), 2.68 (2H, t, J=6.9 Hz), 3.50-3.56 (4H, m), 3.97-4.05 (3H, m), 6.96 (1H, d, J=9.0 Hz), 7.08-7.32 (13H, m), 7.46-7.50 (3H, m).

(6) Preparation of the Compound 354.

The title compound was obtained in the same manner as the Example 126(4) using the following starting material.

Starting material: the intermediate 354(5); Yield: 61.9% (white solid).

This compound was obtained as a mixture of the rotational isomers.

Major isomer: $^1$H-NMR (DMSO-$d_6$) δ: 1.36-1.51 (4H, m), 1.72-1.79 (4H, m), 2.44-2.56 (2H, m), 2.62-2.68 (2H, m), 3.16-3.23 (2H, m), 4.00-4.08 (2H, m), 7.03-7.27 (11H, m), 7.37-7.40 (2H, m), 7.46-7.50 (2H, m), 7.62-7.66 (2H, m).

Minor isomer: $^1$H-NMR (DMSO-$d_6$) δ: 1.36-1.51 (4H, m), 1.72-1.79 (4H, m), 2.44-2.56 (2H, m), 2.62-2.68 (2H, m), 3.16-3.23 (2H, m), 3.58-3.66 (1H, m), 4.08-4.16 (1H, m), 7.03-7.27 (11H, m), 7.37-7.40 (2H, m), 7.46-7.50 (2H, m), 7.62-7.66 (2H, m).

Example 355

Preparation of the Compound 355

(1) Preparation of the Intermediate 355(1).

The title compound was obtained in the same manner as the Example 185(2) using the following starting materials.

Starting materials: the intermediate 188(1) and 3-cyclopentyl-1-propanol; Yield: 100% (orange solid).

$^1$H-NMR ($CDCl_3$) δ: 0.86-1.88 (13H, m), 4.14 (2H, t, J=6.3 Hz), 7.15 (1H, d, J=8.7 Hz), 7.28-7.32 (2H, m), 7.54-7.58 (2H, m), 7.70 (1H, dd, J=2.4, 8.7 Hz), 8.03 (1H, d, J=2.4 Hz).

(2) Preparation of the Intermediate 355(2).

The title compound was obtained in the same manner as the Example 125(2) using the following starting material.

Starting material: the intermediate 355(1); Yield: 75% (white solid).

$^1$H-NMR ($CDCl_3$) δ: 0.85-1.88 (13H, m), 3.89 (2H, brs), 4.03 (2H, t, J=6.6 Hz), 6.83 (1H, d, J=8.1 Hz), 6.87-6.93 (2H, m), 7.21-7.25 (2H, m), 7.49-7.54 (2H, m).

(3) Preparation of the Intermediate 355(3).

The title compound was obtained in the same manner as the Example 123(1) using the following starting materials.

Starting materials: the intermediate 355(2) and 4-phenylbutyl bromide; Yield: 100% (brown oil).

$^1$H-NMR ($CDCl_3$) δ: 0.83-1.92 (17H, m), 2.64-2.71 (2H, m), 3.18-3.23 (2H, m), 3.96-4.03 (2H, m), 4.27 (1H, brs), 6.73-7.33 (10H, m), 7.46-7.56 (2H, m).

(4) Preparation of the Intermediate 355(4).

The title compound was obtained in the same manner as the Example 123(2) using the following starting materials.

Starting materials: the intermediate 355(3) and methyl chloroglyoxylate; Yield: 63% (colorless oil).

$^1$H-NMR ($CDCl_3$) δ: 1.05-1.94 (17H, m), 2.57-2.67 (2H, m), 3.53 (3H, s), 3.56-4.05 (4H, m), 6.98 (1H, d, J=8.4 Hz), 7.09-7.33 (8H, m), 7.46-7.52 (3H, m).

(5) Preparation of the Compound 355.

The title compound was obtained in the same manner as the Example 126(4) using the following starting material.

Starting material: the intermediate 355(4); Yield: 36% (white solid).

$^1$H-NMR (DMSO-$d_6$) δ: 1.00-1.86 (17H, m), 2.34-2.61 (2H, m), 3.02-4.15 (4H, m), 7.05-7.30 (6H, m), 7.39-7.45 (2H, m), 7.47-7.58 (2H, m), 7.62-7.71 (2H, m).

Example 356

Preparation of the Compound 356

(1) Preparation of the Intermediate 356(1).

The title compound was obtained in the same manner as the Example 123(1) using the following starting materials.

Starting materials: the intermediate 194(2) and 3-phenoxypropyl bromide; Yield: 54% (white solid).

$^1$H-NMR ($CDCl_3$) δ: 0.93 (3H, t, J=6.9 Hz), 1.32-1.49 (4H, m), 1.78-1.88 (2H, m), 2.16 (2H, quint, J=6.0 Hz), 3.40-3.50 (2H, m), 4.02 (2H, t, J=6.6 Hz), 4.12 (2H, t, J=5.7 Hz), 4.53 (1H, brs), 6.78-6.81 (3H, m), 6.88-6.98 (3H, m), 7.18-7.31 (4H, m), 7.50-7.55 (2H, m).

(2) Preparation of the Intermediate 356(2).

The title compound was obtained in the same manner as the Example 123(2) using the following starting materials.

Starting materials: the intermediate 356(1) and methyl chloroglyoxylate; Yield: 79% (white solid).

$^1$H-NMR ($CDCl_3$) δ: 0.92 (3H, t, J=7.2 Hz), 1.30-1.49 (4H, m), 1.76-1.85 (2H, m), 2.06-2.17 (2H, m), 3.54 (3H, s), 3.79-4.16 (6H, m), 6.81-6.85 (2H, m), 6.88-6.94 (1H, m), 6.98 (1H, t, J=8.7 Hz), 7.19-7.30 (4H, m), 7.37 (1H, t, J=2.7 Hz), 7.42-7.52 (3H, m).

(3) Preparation of the Compound 356.

The title compound was obtained in the same manner as the Example 126(4) using the following starting material.

Starting material: the intermediate 356(2); Yield: 65% (white solid).

$^1$H-NMR ($CDCl_3$) δ: 0.85-0.91 (3H, m), 1.24-1.50 (4H, m), 1.62-1.79 (4H, m), 2.87-2.96 (2H, m), 3.72-4.09 (4H, m), 7.07-7.23 (6H, m), 7.32-7.58 (4H, m), 7.62-7.72 (2H, m).

Example 357

Preparation of the Compound 357

(1) Preparation of the Intermediate 357(1).

The title compound was obtained in the same manner as the Example 123(1) using the following starting materials.

Starting materials: the intermediate 194(2) and 3-chloropropyl phenyl sulfide; Yield: 42% (white solid).

$^1$H-NMR ($CDCl_3$) δ: 0.94 (3H, t, J=7.5 Hz), 1.33-1.50 (4H, m), 1.78-1.88 (2H, m), 1.97-2.07 (2H, m), 3.05 (2H, t, J=7.2 Hz), 3.36 (2H, t, J=6.9 Hz), 4.02 (2H, t, J=6.6 Hz), 4.36 (1H, brs), 6.75-6.81 (3H, m), 7.13-7.36 (7H, m), 7.51-7.55 (2H, m).

(2) Preparation of the Intermediate 357(2).

The title compound was obtained in the same manner as the Example 123(2) using the following starting materials.

Starting materials: the intermediate 357(1) and methyl chloroglyoxylate; Yield: 77% (white solid).

$^1$H-NMR ($CDCl_3$) δ: 0.93 (3H, t, J=7.2 Hz), 1.33-1.47 (4H, m), 1.74-1.96 (4H, m), 2.96 (2H, t, J=7.2 Hz), 3.54 (3H, s), 3.72-4.08 (4H, m), 6.98 (1H, d, J=9.0 Hz), 7.09-7.33 (8H, m), 7.46-7.52 (3H, m).

(3) Preparation of the Compound 357.

The title compound was obtained in the same manner as the Example 126(4) using the following starting material.

Starting material: the intermediate 357(2); Yield: 63% (white solid).

$^1$H-NMR (DMSO-$d_6$) δ: 0.81-0.89 (3H, m), 1.23-1.42 (4H, m), 1.65-1.93 (4H, m), 3.75-4.03 (6H, m), 6.80-6.90 (3H, m), 7.07-7.26 (3H, m), 7.38-7.41 (2H, m), 7.48-7.58 (2H, m), 7.63-7.73 (2H, m).

Example 358

Preparation of the Compound 358

(1) Preparation of the Intermediate 358(1).

The title compound was obtained in the same manner as the Example 123(1) using the following starting materials.

Starting materials: the intermediate 354(3) and 1-chloropentane; Yield: 24.4% (orange oil).

$^1$H-NMR ($CDCl_3$) δ: 0.88-0.94 (3H, m), 1.33-1.42 (4H, m), 1.65-1.71 (2H, m), 1.83-1.88 (2H, m), 2.71 (2H, t, J=7.2 Hz), 3.17 (2H, t, J=7.2 Hz), 4.05 (2H, t, J=6.0 Hz), 4.12 (2H, t, J=6.6 Hz), 4.24 (1H, brs), 6.75-6.79 (3H, m), 7.19-7.29 (7H, m), 7.54-7.57 (2H, m).

(2) Preparation of the Intermediate 358(2).

The title compound was obtained in the same manner as the Example 123(2) using the following starting materials.

Starting materials: the intermediate 358(1) and methyl chloroglyoxylate; Yield: 100% (orange solid).

$^1$H-NMR ($CDCl_3$) δ: 0.82-0.93 (3H, m), 1.26-1.38 (4H, m), 1.51-1.60 (2H, m), 1.81-1.85 (4H, m), 2.67 (2H, t, J=6.6 Hz), 3.48-3.56 (4H, m), 3.89-4.05 (3H, m), 6.98 (1H, d, J=8.7 Hz), 7.19-7.21 (3H, m), 7.26-7.32 (4H, m), 7.36 (1H, d, J=2.4 Hz), 7.47-7.53 (3H, m).

(3) Preparation of the Compound 358.

The title compound was obtained in the same manner as the Example 126(4) using the following starting material.

Starting material: the intermediate 358(2); Yield: 84.9% (white solid).

This compound was obtained as a mixture of the rotational isomers.

Major isomer: $^1$H-NMR (DMSO-$d_6$) δ: 0.77-0.93 (3H, m), 1.15-1.40 (6H, m), 1.69-1.71 (4H, m), 2.61-2.65 (2H, m), 3.22-3.30 (2H, m), 4.03-4.08 (2H, m), 7.06-7.33 (6H, m), 7.37-7.41 (2H, m), 7.49-7.51 (2H, m), 7.66-7.69 (2H, m).

Minor isomer: $^1$H-NMR (DMSO-$d_6$) δ: 0.77-0.93 (3H, m), 1.15-1.40 (6H, m), 1.69-1.71 (4H, m), 2.61-2.65 (2H, m), 3.63-3.69 (1H, m), 4.03-4.12 (3H, m), 7.06-7.33 (6H, m), 7.37-7.41 (2H, m), 7.52-7.57 (2H, m), 7.66-7.71 (2H, m).

Example 359

Preparation of the Compound 359

(1) Preparation of the Intermediate 359(1).

The title compound was obtained in the same manner as the Example 185(2) using the following starting materials.

Starting materials: 4-bromo-1-fluoro-2-nitrobenzene and 1-pentanol; Yield: 68.6% (clear brown oil).

$^1$H-NMR ($CDCl_3$) δ: 0.93 (3H, t, J=7.2 Hz), 1.35-1.55 (4H, m), 1.79-1.86 (2H, m), 4.08 (2H, t, J=6.3 Hz), 6.96 (1H, d, J=9.0 Hz), 7.60 (1H, dd, J=2.4, 9.0 Hz), 7.95 (1H, d, J=2.4 Hz).

(2) Preparation of the Intermediate 359(2).

The title compound was obtained in the same manner as the Example 125(2) using the following starting material.

Starting material: the intermediate 359(1); Yield: 99.5% (brown solid).

$^1$H-NMR ($CDCl_3$) δ: 0.93 (3H, t, J=7.2 Hz), 1.32-1.45 (4H, m), 1.76-1.81 (2H, m), 3.95 (2H, t, J=6.6 Hz), 4.31 (2H, brs), 6.62 (1H, d, J=8.4 Hz), 6.81 (1H, dd, J=2.4, 8.4 Hz), 6.87 (1H, d, J=2.4 Hz).

(3) Preparation of the Intermediate 359(3).

The title compound was obtained in the same manner as the Example 123(1) using the following starting materials.

Starting materials: the intermediate 359(2) and 4-phenylbutyl bromide; Yield: 58.8% (brown oil).

$^1$H-NMR ($CDCl_3$) δ: 0.90-0.94 (3H, m), 1.38-1.45 (4H, m), 1.68-1.81 (6H, m), 2.67 (2H, t, J=7.2 Hz), 3.10 (2H, t, J=6.0 Hz), 3.93 (2H, t, J=6.6 Hz), 4.19-4.27 (1H, m), 6.56 (1H, d, J=8.4 Hz), 6.64 (1H, d, J=2.1 Hz), 6.70 (1H, dd, J=2.1, 8.4 Hz), 7.16-7.31 (5H, m).

(4) Preparation of the Intermediate 359(4).

The title compound was obtained in the same manner as the Example 123(2) using the following starting materials.

Starting materials: the intermediate 359(3) and methyl chloroglyoxylate; Yield: 54.5% (white solid).

$^1$H-NMR ($CDCl_3$) δ: 0.92 (3H, t, J=7.2 Hz), 1.35-1.41 (4H, m), 1.55-1.62 (4H, m), 1.71-1.79 (2H, m), 2.58-2.63 (2H, m), 3.51-3.62 (4H, m), 3.86-3.96 (3H, m), 6.79 (1H, d, J=8.7 Hz), 7.11-7.29 (6H, m), 7.40 (1H, dd, J=2.7, 8.7 Hz).

(5) Preparation of the Intermediate 359(5).

The title compound was obtained in the same manner as the Example 123(3) using the following starting materials.

Starting materials: the intermediate 359(4) and 4-fluorophenylboronic acid; Yield: 85.4% (clear colorless oil).

$^1$H-NMR ($CDCl_3$) δ: 0.93 (3H, t, J=7.2 Hz), 1.35-1.46 (4H, m), 1.58-1.69 (4H, m), 1.75-1.85 (2H, m), 2.57-2.64 (2H, m), 3.50-3.61 (4H, m), 3.97-4.06 (3H, m), 6.96 (1H, d, J=8.4 Hz), 7.08-7.16 (5H, m), 7.18-7.25 (2H, m), 7.30 (1H, d, J=2.4 Hz), 7.40-7.49 (3H, m).

(6) Preparation of the Compound 359.

The title compound was obtained in the same manner as the Example 126(4) using the following starting material.

Starting material: the intermediate 359(5); Yield: 77.6% (white solid).

This compound was obtained as a mixture of the rotational isomers.

Major isomer: $^1$H-NMR (DMSO-$d_6$) δ: 0.88 (3H, t, J=6.6 Hz), 1.24-1.50 (8H, m), 1.64-1.70 (2H, m), 2.46-2.53 (2H, m), 3.20-3.28 (2H, m), 3.96-4.01 (2H, m), 7.03-7.26 (8H, m), 7.43-7.60 (4H, m).

Minor isomer: $^1$H-NMR (DMSO-$d_6$) δ: 0.88 (3H, t, J=6.6 Hz), 1.24-1.50 (8H, m), 1.64-1.70 (2H, m), 2.46-2.53 (2H, m), 3.64-3.72 (1H, m), 3.96-4.01 (3H, m), 6.92-6.97 (2H, m), 7.03-7.26 (8H, m), 7.43-7.60 (2H, m).

Example 360

Preparation of the Compound 360

(1) Preparation of the Intermediate 360(1).

The title compound was obtained in the same manner as the Example 123(3) using the following starting materials.

Starting materials: the intermediate 359(4) and phenylboronic acid; Yield: 60.6% (clear colorless oil).

$^1$H-NMR ($CDCl_3$) δ: 0.93 (3H, t, J=7.2 Hz), 1.35-1.46 (4H, m), 1.58-1.69 (4H, m), 1.75-1.85 (2H, m), 2.57-2.64 (2H, m), 3.50-3.61 (4H, m), 3.97-4.06 (3H, m), 6.98 (1H, d, J=8.4 Hz), 7.10-7.16 (3H, m), 7.18-7.25 (2H, m), 7.33-7.36 (2H, m), 7.40-7.55 (5H, m).

(2) Preparation of the Compound 360.

The title compound was obtained in the same manner as the Example 126(4) using the following starting material.

Starting material: the intermediate 360(1); Yield: 61.5% (white solid).

This compound was obtained as a mixture of the rotational isomers.

Major isomer: $^1$H-NMR (DMSO-$d_6$) δ: 0.89 (3H, t, J=6.6 Hz), 1.24-1.50 (8H, m), 1.68-1.74 (2H, m), 2.46-2.53 (2H, m), 3.20-3.28 (2H, m), 3.97-4.04 (2H, m), 7.03-7.20 (6H, m), 7.24-7.35 (2H, m), 7.38-7.55 (5H, m).

Minor isomer: $^1$H-NMR (DMSO-$d_6$) δ: 0.89 (3H, t, J=6.6 Hz), 1.24-1.50 (8H, m), 1.68-1.74 (2H, m), 2.46-2.53 (2H, m), 3.64-3.72 (1H, m), 3.97-4.04 (3H, m), 6.72-6.78 (2H, m), 7.03-7.20 (6H, m), 7.38-7.55 (5H, m).

Example 361

Preparation of the Compound 361

(1) Preparation of the Intermediate 361(1).

The title compound was obtained in the same manner as the Example 123(3) using the following starting materials.

Starting materials: the intermediate 359(4) and 4-chlorophenylboronic acid; Yield: 72.6% (clear colorless oil).

$^1$H-NMR ($CDCl_3$) δ: 0.93 (3H, t, J=6.9 Hz), 1.35-1.46 (4H, m), 1.58-1.69 (4H, m), 1.75-1.82 (2H, m), 2.57-2.64 (2H, m), 3.50-3.61 (4H, m), 3.97-4.06 (3H, m), 6.97 (1H, d, J=8.7 Hz), 7.10-7.27 (6H, m), 7.31 (1H, d, J=2.4 Hz), 7.38-7.43 (3H, m), 7.48 (1H, dd, J=2.4, 8.7 Hz).

(2) Preparation of the Compound 361.

The title compound was obtained in the same manner as the Example 126(4) using the following starting material.

Starting material: the intermediate SYN361(1); Yield: 31.0% (white solid).

This compound was obtained as a mixture of the rotational isomers.

Major isomer: $^1$H-NMR (DMSO-$d_6$) δ: 0.88 (3H, t, J=6.6 Hz), 1.24-1.50 (8H, m), 1.64-1.73 (2H, m), 2.46-2.53 (2H, m), 3.20-3.28 (2H, m), 3.96-4.03 (2H, m), 7.04-7.21 (7H, m), 7.44-7.60 (5H, m).

Minor isomer: $^1$H-NMR (DMSO-$d_6$) δ: 0.88 (3H, t, J=6.6 Hz), 1.24-1.50 (8H, m), 1.64-1.73 (2H, m), 2.46-2.53 (2H, m), 3.64-3.72 (1H, m), 3.96-4.03 (3H, m), 6.74-6.78 (2H, m), 7.04-7.21 (5H, m), 7.44-7.60 (5H, m).

Example 362

Preparation of the Compound 362

(1) Preparation of the Intermediate 362(1).

The title compound was obtained in the same manner as the Example 354(2) using the following starting materials.

Starting materials: 5-fluoro-2-nitrophenol and 1-chloropentane; Yield: 51.4% (clear yellow oil).

$^1$H-NMR ($CDCl_3$) δ: 0.94 (3H, t, J=7.2 Hz), 1.35-1.53 (4H, m), 1.81-1.90 (2H, m), 4.08 (2H, t, J=6.3 Hz), 6.66-6.78 (2H, m), 7.90-7.95 (1H, m).

(2) Preparation of the Intermediate 362(2).

The title compound was obtained in the same manner as the Example 132(1) using the following starting materials.

Starting materials: the intermediate 362(1) and 4-(trifluoromethoxy)phenol; Yield: 92.2% (clear pale yellow oil).

$^1$H-NMR ($CDCl_3$) δ: 0.93 (3H, t, J=6.9 Hz), 1.36-1.48 (4H, m), 1.79-1.88 (2H, m), 4.02 (2H, t, J=6.3 Hz), 6.48 (1H, dd, J=2.4, 9.0 Hz), 6.65 (1H, d, J=2.4 Hz), 7.08-7.12 (2H, m), 7.25-7.29 (2H, m), 7.92 (1H, d, J=9.0 Hz).

(3) Preparation of the Intermediate 362(3).

The title compound was obtained in the same manner as the Example 125(2) using the following starting material.

Starting material: the intermediate 362(2); Yield: 100% (red oil).

$^1$H-NMR ($CDCl_3$) δ: 0.93 (3H, t, J=6.9 Hz), 1.36-1.48 (4H, m), 1.76-1.83 (2H, m), 3.73 (2H, brs), 3.93 (2H, t, J=6.3 Hz), 6.48 (1H, dd, J=2.4, 8.4 Hz), 6.64 (1H, d, J=2.4 Hz), 6.69 (1H, d, J=8.4 Hz), 6.89-6.94 (2H, m), 7.10-7.14 (2H, m).

(4) Preparation of the Intermediate 362(4).

The title compound was obtained in the same manner as the Example 123(1) using the following starting materials.

Starting materials: the intermediate 362(3) and 4-phenylbutyl bromide; Yield: 74.4% (clear colorless oil).

$^1$H-NMR ($CDCl_3$) δ: 0.92 (3H, t, J=6.9 Hz), 1.36-1.48 (4H, m), 1.72-1.83 (6H, m), 2.67-2.72 (2H, m), 3.13-3.20 (2H, m), 3.89-3.96 (2H, m), 4.07 (1H, brs), 6.51-6.55 (3H, m), 6.89-6.94 (2H, m), 7.10-7.29 (7H, m).

(5) Preparation of the Intermediate 362(5).

The title compound was obtained in the same manner as the Example 123(2) using the following starting materials.

Starting materials: the intermediate 362(4) and methyl chloroglyoxylate; Yield: 77.3% (clear colorless oil).

$^1$H-NMR ($CDCl_3$) δ: 0.91 (3H, t, J=6.9 Hz), 1.32-1.46 (4H, m), 1.55-1.64 (4H, m), 1.66-1.76 (2H, m), 2.59-2.64 (2H, m), 3.40-3.61 (4H, m), 3.85-4.00 (3H, m), 6.43 (1H, dd, J=2.4, 9.0 Hz), 6.58 (1H, d, J=2.4 Hz), 7.01-7.04 (3H, m), 7.12-7.28 (7H, m).

(6) Preparation of the Compound 362.

The title compound was obtained in the same manner as the Example 126(4) using the following starting material.

Starting material: the intermediate 362(5); Yield: 100% (clear pale yellow oil).

This compound was obtained as a mixture of the rotational isomers.

Major isomer: $^1$H-NMR (DMSO-$d_6$) δ: 0.86 (3H, t, J=6.6 Hz), 1.24-1.52 (8H, m), 1.62-1.70 (2H, m), 2.46-2.53 (2H, m), 3.26-3.38 (2H, m), 3.88-3.92 (2H, m), 6.38-6.53 (1H, m), 6.71-6.79 (1H, m), 7.07-7.26 (8H, m), 7.38-7.41 (2H, m).

Minor isomer: $^1$H-NMR (DMSO-$d_6$) δ: 0.86 (3H, t, J=6.6 Hz), 1.24-1.52 (8H, m), 1.62-1.70 (2H, m), 2.46-2.53 (2H, m), 3.19-3.38 (3H, m), 3.50-3.59 (1H, m), 6.38-6.53 (1H, m), 6.71-6.79 (1H, m), 6.96-7.26 (8H, m), 7.38-7.41 (2H, m).

Example 363

Preparation of the Compound 363

(1) Preparation of the Intermediate 363(1).

The title compound was obtained in the same manner as the Example 185(2) using the following starting materials.

Starting materials: 4-bromo-1-fluoro-2-nitrobenzene and 1-pentanol; Yield: 74.1% (brown oil).

$^1$H-NMR ($CDCl_3$) δ: 0.93 (3H, t, J=6.9 Hz), 1.38-1.48 (4H, m), 1.79-1.88 (2H, m), 4.08 (2H, t, J=6.3 Hz), 6.96 (1H, d, J=9.0 Hz), 7.60 (1H, dd, J=2.4, 9.0 Hz), 7.95 (1H, d, J=2.4 Hz).

(2) Preparation of the Intermediate 363(2).

A mixture of the intermediate 363(1) (1.00 g, 3.47 mmol), 4-(trifluoromethoxy)phenol (803 mg, 4.51 mmol), potassium carbonate (959 mg, 6.94 mmol), copper(II) oxide (690 mg, 8.67 mmol) and pyridine (4 ml) was refluxed for 10 hours. The reaction mixture was cooled to room temperature and filtered through Celite. The filtrate was diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=10:1) to give the title compound (512 mg, 38.5%) as a brown oil.

$^1$H-NMR ($CDCl_3$) δ: 0.93 (3H, t, J=6.9 Hz), 1.38-1.48 (4H, m), 1.79-1.88 (2H, m), 4.08 (2H, t, J=6.3 Hz), 6.97-7.00 (2H, m), 7.04-7.08 (2H, m), 7.18-7.22 (2H, m), 7.50 (1H, d, J=2.4 Hz).

(3) Preparation of the Intermediate 363(3).

The title compound was obtained in the same manner as the Example 125(2) using the following starting materials.

Starting materials: the intermediate 363(2); Yield: 95.6% (red oil).

$^1$H-NMR ($CDCl_3$) δ: 0.94 (3H, t, J=6.9 Hz), 1.40-1.46 (4H, m), 1.76-1.85 (2H, m), 3.86 (2H, brs), 3.97 (2H, t, J=6.3 Hz), 6.35 (1H, dd, J=2.7, 8.7 Hz), 6.42 (1H, d, J=2.7 Hz), 6.72 (1H, d, J=8.7 Hz), 6.92-6.95 (2H, m), 7.11-7.14 (2H, m).

(4) Preparation of the Intermediate 363(4).

The title compound was obtained in the same manner as the Example 123(1) using the following starting materials.

Starting materials: the intermediate 363(3) and 4-phenylbutyl bromide; Yield: 64.3% (clear colorless oil).

$^1$H-NMR ($CDCl_3$) δ: 0.92 (3H, t, J=6.9 Hz), 1.36-1.83 (10H, m), 2.67-2.72 (2H, m), 3.13-3.20 (2H, m), 3.89-3.96 (2H, m), 4.07 (1H, brs), 6.26 (1H, dd, J=2.7, 8.7 Hz), 6.30 (1H, d, J=2.7 Hz), 6.67 (1H, d, J=8.7 Hz), 6.92-6.95 (2H, m), 7.10-7.34 (7H, m).

(5) Preparation of the Intermediate 363(5).

The title compound was obtained in the same manner as the Example 123(2) using the following starting materials.

Starting materials: the intermediate 363(4) and methyl chloroglyoxylate; Yield: 71.6% (orange oil).

$^1$H-NMR ($CDCl_3$) δ: 0.92 (3H, t, J=6.9 Hz), 1.37-1.46 (4H, m), 1.55-1.64 (4H, m), 1.72-1.78 (2H, m), 2.56-2.61 (2H, m), 3.50-3.59 (4H, m), 3.92-4.00 (3H, m), 6.86-6.92 (3H, m), 7.00 (1H, dd, J=3.0, 9.0 Hz), 7.09-7.18 (5H, m), 7.22-7.27 (3H, m).

(6) Preparation of the Compound 363.

The title compound was obtained in the same manner as the Example 126(4) using the following starting material.

Starting material: the intermediate 363(5); Yield: 52.9% (yellow oil).

This compound was obtained as a mixture of the rotational isomers.

Major isomer: $^1$H-NMR (DMSO-$d_6$) δ: 0.88 (3H, t, J=6.6 Hz), 1.05-1.11 (2H, m), 1.24-1.52 (6H, m), 1.62-1.70 (2H, m), 2.86-2.93 (2H, m), 3.52-3.61 (2H, m), 3.95-3.99 (2H, m), 6.93-7.13 (8H, m), 7.18-7.22 (2H, m), 7.28-7.32 (2H, m).

Minor isomer: $^1$H-NMR (DMSO-$d_6$) δ: 0.88 (3H, t, J=6.6 Hz), 1.05-1.11 (2H, m), 1.24-1.52 (6H, m), 1.62-1.70 (2H, m), 2.86-2.93 (2H, m), 3.40-3.99 (4H, m), 6.72-6.78 (1H, m), 6.93-7.13 (7H, m), 7.18-7.22 (2H, m), 7.28-7.32 (2H, m).

Example 364

Preparation of the Compound 364

(1) Preparation of the Intermediate 364(1).

The title compound was obtained in the same manner as the Example 185(2) using the following starting materials.

Starting materials: the intermediate 188(1) and 1-nonanol; Yield: 96.7% (orange solid).

$^1$H-NMR ($CDCl_3$) δ: 0.88 (3H, t, J=6.9 Hz), 1.26-1.41 (10H, m), 1.45-1.52 (2H, m), 1.82-1.89 (2H, m), 4.14 (2H, t, J=6.6 Hz), 7.15 (1H, d, J=9.0 Hz), 7.29-7.32 (2H, m), 7.54-7.59 (2H, m), 7.70 (1H, dd, J=2.4, 9.0 Hz), 8.02 (1H, d, J=2.4 Hz).

(2) Preparation of the Intermediate 364(2).

The title compound was obtained in the same manner as the Example 125(2) using the following starting material.

Starting material: the intermediate 364(1); Yield: 98.4% (yellow solid).

$^1$H-NMR ($CDCl_3$) δ: 0.89 (3H, t, J=7.2 Hz), 1.25-1.50 (12H, m), 1.79-1.88 (2H, m), 3.89 (2H, brs), 4.02 (2H, t, J=6.6 Hz), 6.83 (1H, d, J=8.4 Hz), 6.88-6.93 (2H, m), 7.21-7.24 (2H, m), 7.50-7.55 (2H, m).

(3) Preparation of the Intermediate 364(3).

The title compound was obtained in the same manner as the Example 123(1) using the following starting materials.

Starting materials: the intermediate 364(2) and 4-phenylbutyl bromide; Yield: 78.5% (clear yellow oil).

$^1$H-NMR ($CDCl_3$) δ: 0.86-0.91 (3H, m), 1.24-1.89 (20H, m), 2.61-2.71 (2H, m), 3.99-4.03 (2H, m), 4.28 (1H, brs), 6.72-6.79 (3H, m), 7.10-7.32 (7H, m), 7.52-7.55 (2H, m).

(4) Preparation of the Intermediate 364(4).

The title compound was obtained in the same manner as the Example 123(2) using the following starting materials.

Starting materials: the intermediate 364(3) and methyl chloroglyoxylate; Yield: 73.5% (clear colorless oil).

$^1$H-NMR ($CDCl_3$) δ: 0.88 (3H, t, J=6.9 Hz), 1.26-1.49 (12H, m), 1.57-1.66 (4H, m), 1.70-1.81 (2H, m), 2.57-2.63 (2H, m), 3.50-3.59 (4H, m), 3.82-4.06 (3H, m), 6.98 (1H, d, J=8.7 Hz), 7.09-7.15 (3H, m), 7.19-7.29 (4H, m), 7.31 (1H, d, J=2.1 Hz), 7.47-7.51 (3H, m).

(5) Preparation of the Compound 364.

The title compound was obtained in the same manner as the Example 126(4) using the following starting material.

Starting material: the intermediate 364(4); Yield: 34.7% (white solid).

This compound was obtained as a mixture of the rotational isomers.

Major isomer: $^1$H-NMR (DMSO-$d_6$) δ: 0.82-0.85 (3H, m), 1.24-1.49 (16H, m), 1.67-1.74 (2H, m), 2.44-2.50 (2H, m), 3.15-3.26 (1H, m), 3.97-4.02 (3H, m), 7.06-7.20 (6H, m), 7.40-7.43 (2H, m), 7.49-7.52 (1H, m), 7.64-7.70 (3H, m).

Minor isomer: $^1$H-NMR (DMSO-$d_6$) δ: 0.82-0.85 (3H, m), 1.24-1.49 (16H, m), 1.67-1.74 (2H, m), 2.44-2.50 (2H, m), 3.15-3.26 (1H, m), 3.61-3.72 (1H, m), 3.97-4.02 (2H, m), 7.06-7.20 (5H, m), 7.30 (1H, d, J=2.1 Hz), 7.40-7.43 (2H, m), 7.48-7.51 (2H, m), 7.55 (1H, dd, J=2.1, 8.4 Hz), 7.64-7.70 (1H, m).

Example 365

Preparation of the Compound 365

(1) Preparation of the Intermediate 365(1).

The title compound was obtained in the same manner as the Example 185(2) using the following starting materials.

Starting materials: the intermediate 188(1) and 1-decanol; Yield: 66.2% (orange solid).

$^1$H-NMR ($CDCl_3$) δ: 0.89 (3H, t, J=6.9 Hz), 1.28-1.41 (12H, m), 1.45-1.52 (2H, m), 1.82-1.89 (2H, m), 4.15 (2H, t, J=6.6 Hz), 7.15 (1H, d, J=9.0 Hz), 7.29-7.32 (2H, m), 7.54-7.59 (2H, m), 7.70 (1H, dd, J=2.4, 9.0 Hz), 8.02 (1H, d, J=2.4 Hz).

(2) Preparation of the Intermediate 365(2).

The title compound was obtained in the same manner as the Example 125(2) using the following starting material.

Starting material: the intermediate 356(1); Yield: 98.1% (yellow solid).

$^1$H-NMR ($CDCl_3$) δ: 0.89 (3H, t, J=7.2 Hz), 1.25-1.55 (14H, m), 1.79-1.88 (2H, m), 3.89 (2H, brs), 4.02 (2H, t, J=6.6 Hz), 6.83 (1H, d, J=8.4 Hz), 6.88-6.93 (2H, m), 7.21-7.24 (2H, m), 7.50-7.55 (2H, m).

(3) Preparation of the Intermediate 365(3).

The title compound was obtained in the same manner as the Example 123(1) using the following starting materials.

Starting materials: the intermediate 365(2) and 4-phenylbutyl bromide; Yield: 74.3% (clear yellow oil).

$^1$H-NMR ($CDCl_3$) δ: 0.86-0.91 (3H, m), 1.24-1.89 (22H, m), 2.61-2.71 (2H, m), 3.99-4.03 (2H, m), 4.27 (1H, brs), 6.72-6.79 (3H, m), 7.10-7.32 (7H, m), 7.52-7.55 (2H, m).

(4) Preparation of the Intermediate 365(4).

The title compound was obtained in the same manner as the Example 123(2) using the following starting materials.

Starting materials: the intermediate 365(3) and methyl chloroglyoxylate; Yield: 84.5% (clear colorless oil).

$^1$H-NMR ($CDCl_3$) δ: 0.88 (3H, t, J=6.9 Hz), 1.26-1.49 (14H, m), 1.57-1.66 (4H, m), 1.70-1.81 (2H, m), 2.57-2.63 (2H, m), 3.50-3.59 (4H, m), 3.82-4.06 (3H, m), 6.98 (1H, d, J=8.7 Hz), 7.09-7.15 (3H, m), 7.19-7.29 (4H, m), 7.31 (1H, d, J=2.1 Hz), 7.47-7.51 (3H, m).

(5) Preparation of the Compound 365.

The title compound was obtained in the same manner as the Example 126(4) using the following starting material.

Starting material: the intermediate 365(4); Yield: 79.7% (white solid).

This compound was obtained as a mixture of the rotational isomers.

Major isomer: $^1$H-NMR (DMSO-$d_6$) δ: 0.82-0.85 (3H, m), 1.24-1.49 (18H, m), 1.67-1.74 (2H, m), 2.44-2.50 (2H, m), 3.15-3.26 (1H, m), 3.97-4.02 (3H, m), 7.06-7.20 (6H, m), 7.40-7.43 (2H, m), 7.49-7.52 (1H, m), 7.64-7.70 (3H, m).

Minor isomer: $^1$H-NMR (DMSO-$d_6$) δ: 0.82-0.85 (3H, m), 1.24-1.49 (18H, m), 1.67-1.74 (2H, m), 2.44-2.50 (2H, m), 3.15-3.26 (1H, m), 3.61-3.72 (1H, m), 3.97-4.02 (2H, m), 7.06-7.20 (5H, m), 7.30 (1H, d, J=2.1 Hz), 7.40-7.43 (2H, m), 7.48-7.51 (2H, m), 7.55 (1H, dd, J=2.1, 8.4 Hz), 7.64-7.70 (1H, m).

Example 366

Preparation of the Compound 366

(1) Preparation of the Intermediate 366(1).

The title compound was obtained in the same manner as the Example 123(1) using the following starting materials.

Starting materials: the intermediate 194(2) and 1-chloropentane; Yield: 45.5% (clear yellow oil).

$^1$H-NMR ($CDCl_3$) δ: 0.91-0.96 (6H, m), 1.28-1.46 (8H, m), 1.65-1.76 (2H, m), 1.79-1.89 (2H, m), 3.17-3.25 (2H, m), 4.00-4.29 (3H, m), 6.77-6.80 (2H, m), 7.17-7.25 (3H, m), 7.54-7.57 (2H, m).

(2) Preparation of the Intermediate 366(2).

The title compound was obtained in the same manner as the Example 123(2) using the following starting materials.

Starting materials: the intermediate 366(1) and methyl chloroglyoxylate; Yield: 60.3% (clear colorless oil).

$^1$H-NMR ($CDCl_3$) δ: 0.86 (3H, t, J=6.9 Hz), 0.94 (3H, t, J=6.9 Hz), 1.28-1.46 (8H, m), 1.53-1.59 (2H, m), 1.79-1.89 (2H, m), 3.48-3.56 (4H, m), 3.92-4.06 (3H, m), 6.99 (1H, d, J=8.7 Hz), 7.26-7.29 (2H, m), 7.36 (1H, d, J=2.1 Hz), 7.48-7.53 (3H, m).

(3) Preparation of the Compound 366.

The title compound was obtained in the same manner as the Example 126(4) using the following starting material.

Starting material: the intermediate 366(2); Yield: 97.0% (white solid).

This compound was obtained as a mixture of the rotational isomers.

Major isomer: $^1$H-NMR (DMSO-$d_6$) δ: 0.77-0.81 (3H, m), 0.90 (3H, t, J=6.9 Hz), 1.14-1.20 (6H, m), 1.31-1.42 (4H, m), 2.44-2.50 (2H, m), 3.22-3.26 (2H, m), 3.99-4.03 (2H, m), 7.08 (1H, d, J=8.4 Hz), 7.40-7.43 (2H, m), 7.46-7.56 (2H, m), 7.66-7.69 (2H, m).

Minor isomer: $^1$H-NMR (DMSO-$d_6$) δ: 0.77-0.81 (3H, m), 0.90 (3H, t, J=6.9 Hz), 1.14-1.20 (6H, m), 1.31-1.42 (4H, m), 2.44-2.50 (2H, m), 3.53-3.57 (1H, m), 3.99-4.03 (3H, m), 7.14 (1H, d, J=8.4 Hz), 7.30 (1H, d, J=2.7 Hz), 7.40-7.43 (2H, m), 7.46-7.56 (1H, m), 7.66-7.72 (2H, m).

Example 367

Preparation of the Compound 367

(1) Preparation of the Intermediate 367(1).

The title compound was obtained in the same manner as the Example 123(3) using the following starting materials.

Starting materials: 4-bromo-2-fluoro-1-nitrobenzene and 4-(trifluoromethoxy)phenylboronic acid; Yield: 99.2% (orange solid).

$^1$H-NMR ($CDCl_3$) δ: 7.34-7.37 (2H, m), 7.45-7.50 (2H, m), 7.61-7.65 (2H, m), 8.14-8.20 (1H, m).

(2) Preparation of the Intermediate 367(2).

The title compound was obtained in the same manner as the Example 185(2) using the following starting materials.

Starting materials: the intermediate 367(1) and 1-pentanol; Yield: 97.4% (yellow solid).

$^1$H-NMR ($CDCl_3$) δ: 0.94 (3H, t, J=7.2 Hz), 1.39-1.51 (4H, m), 1.82-1.92 (2H, m), 4.17 (2H, t, J=6.6 Hz), 7.16 (1H, dd, J=1.8, 8.4 Hz), 7.19 (1H, d, J=1.8 Hz), 7.31-7.35 (2H, m), 7.58-7.62 (2H, m), 7.93 (1H, d, J=8.4 Hz).

(3) Preparation of the Intermediate 367(3).

The title compound was obtained in the same manner as the Example 125(2) using the following starting material.

Starting material: the intermediate 367(2); Yield: 94.9% (yellow solid).

$^1$H-NMR ($CDCl_3$) δ: 0.94 (3H, t, J=7.2 Hz), 1.37-1.51 (4H, m), 1.82-1.89 (2H, m), 3.89 (2H, brs), 4.06 (2H, t, J=6.6 Hz), 6.77 (1H, d, J=8.1 Hz), 6.97-7.01 (2H, m), 7.21-7.25 (2H, m), 7.50-7.54 (2H, m).

(4) Preparation of the Intermediate 367(4).

The title compound was obtained in the same manner as the Example 123(1) using the following starting materials.

Starting materials: the intermediate 367(3) and 4-phenylbutyl bromide; Yield: 40.4% (white solid).

$^1$H-NMR ($CDCl_3$) δ: 0.94 (3H, t, J=7.2 Hz), 1.36-1.55 (4H, m), 1.70-1.86 (6H, m), 2.68 (2H, t, J=7.2 Hz), 3.17-3.23 (2H, m), 4.04 (2H, t, J=6.6 Hz), 4.27-4.31 (1H, m), 6.63 (1H, d, J=8.1 Hz), 6.94 (1H, d, J=1.8 Hz), 7.07 (1H, dd, J=1.8, 8.1 Hz), 7.16-7.32 (7H, m), 7.50-7.55 (2H, m).

(5) Preparation of the Intermediate 367(5).

The title compound was obtained in the same manner as the Example 123(2) using the following starting materials.

Starting materials: the intermediate 367(4) and methyl chloroglyoxylate; Yield: 98.4% (clear colorless oil).

$^1$H-NMR ($CDCl_3$) δ: 0.93 (3H, t, J=7.2 Hz), 1.36-1.55 (4H, m), 1.57-1.65 (4H, m), 1.70-1.86 (2H, m), 2.59-2.62 (2H, m), 3.51-3.61 (4H, m), 3.98-4.04 (3H, m), 7.05-7.19 (6H, m), 7.22-7.31 (4H, m), 7.55-7.60 (2H, m).

(6) Preparation of the Compound 367.

The title compound was obtained in the same manner as the Example 126(4) using the following starting material.

Starting material: the intermediate 367(5); Yield: 89.0% (white solid).

This compound was obtained as a mixture of the rotational isomers.

Major isomer: $^1$H-NMR (DMSO-$d_6$) δ: 0.87-0.91 (3H, m), 1.32-1.54 (8H, m), 1.67-1.76 (2H, m), 2.44-2.50 (2H, m), 3.15-3.26 (2H, m), 4.00-4.11 (2H, m), 7.08-7.29 (8H, m), 7.43-7.46 (2H, m), 7.79-7.82 (2H, m).

Minor isomer: $^1$H-NMR (DMSO-$d_6$) δ: 0.87-0.91 (3H, m), 1.32-1.54 (8H, m), 1.67-1.76 (2H, m), 2.44-2.50 (2H, m), 3.60-3.67 (1H, m), 4.00-4.11 (3H, m), 7.08-7.29 (8H, m), 7.43-7.46 (2H, m), 7.81-7.84 (2H, m).

Example 368

Preparation of the Compound 368

(1) Preparation of the Intermediate 368(1).

The title compound was obtained in the same manner as the Example 185(2) using the following starting materials.

Starting materials: the intermediate 188(1) and cyclohexanol; Yield: 98% (pale brown oil).

$^1$H-NMR ($CDCl_3$) δ: 1.36-1.63 (4H, m), 1.64-1.77 (2H, m), 1.77-1.90 (2H, m), 1.90-2.02 (2H, m), 4.44-4.55 (1H, m), 7.16 (1H, d, J=9.0 Hz), 7.27-7.33 (2H, m), 7.53-7.59 (2H, m), 7.66 (1H, dd, J=2.7, 9.0 Hz), 7.98 (1H, d, J=2.7 Hz).

(2) Preparation of the Intermediate 368(2).

The title compound was obtained in the same manner as the Example 125(2) using the following starting material.

Starting material: the intermediate 368(1); Yield: 86% (white solid).

$^1$H-NMR ($CDCl_3$) δ: 1.30-1.66 (6H, m), 1.75-1.87 (2H, m), 1.94-2.10 (2H, m), 3.89 (2H, brs), 4.22-4.35 (1H, m), 6.82-6.94 (3H, m), 7.19-7.25 (2H, m), 7.48-7.56 (2H, m).

(3) Preparation of the Intermediate 368(3).

The title compound was obtained in the same manner as the Example 123(1) using the following starting materials.

Starting materials: the intermediate 368(2) and 4-phenylbutyl bromide; Yield: 43% (colorless oil).

$^1$H-NMR ($CDCl_3$) δ: 1.28-1.47 (2H, m), 1.50-1.65 (4H, m), 1.67-1.85 (6H, m), 1.95-2.08 (2H, m), 2.68 (2H, t, J=6.6 Hz), 3.20 (2H, t, J=6.6 Hz), 4.21-4.30 (1H, m), 4.31 (1H, brs), 6.72-6.85 (3H, m), 7.14-7.32 (7H, m), 7.50-7.57 (2H, m).

(4) Preparation of the Intermediate 368(4).

The title compound was obtained in the same manner as the Example 123(2) using the following starting materials.

Starting materials: the intermediate 368(3) and methyl chloroglyoxylate; Yield: 66% (colorless oil).

$^1$H-NMR ($CDCl_3$) δ: 1.28-1.73 (10H, m), 1.73-1.87 (2H, m), 1.87-2.01 (2H, m), 2.51-2.67 (2H, m), 3.47-3.62 (1H, m), 3.53 (3H, s), 3.96-4.09 (1H, m), 4.29-4.40 (1H, m), 6.98 (1H, d, J=8.4 Hz), 7.08-7.30 (7H, m), 7.31 (1H, d, J=2.4 Hz), 7.43-7.51 (3H, m).

(5) Preparation of the Compound 368.

The title compound was obtained in the same manner as the Example 126(4) using the following starting material.

Starting material: the intermediate 368(4); Yield: 68% (white solid).

This compound was obtained as a mixture of the rotational isomers.

Major isomer: $^1$H-NMR (DMSO-$d_6$) δ: 1.19-1.60 (10H, m), 1.60-1.77 (2H, m), 1.77-1.94 (2H, m), 3.20-3.50 (2H, m), 3.73-3.99 (2H, m), 4.33-4.50 (1H, m), 7.03-7.22 (6H, m), 7.33-7.49 (3H, m), 7.53-7.60 (2H, m), 7.63-7.71 (1H, m), 13.74 (1H, brs).

Minor isomer: $^1$H-NMR (DMSO-$d_6$) δ: 1.19-1.60 (10H, m), 1.60-1.77 (2H, m), 1.77-1.94 (2H, m), 3.20-3.50 (2H, m), 3.57-3.69 (2H, m), 4.33-4.50 (1H, m), 7.03-7.22 (6H, m), 7.33-7.49 (3H, m), 7.53-7.60 (2H, m), 7.63-7.71 (1H, m), 13.74 (1H, brs).

Example 369

Preparation of the Compound 369

(1) Preparation of the Intermediate 369(1).

The title compound was obtained in the same manner as the Example 185(2) using the following starting materials.

Starting materials: the intermediate 188(1) and 3-pentanol; Yield: 93% (yellow oil).

$^1$H-NMR ($CDCl_3$) δ: 1.00 (6H, t, J=7.5 Hz), 1.71-1.83 (4H, m), 4.34 (1H, quint, J=6.0 Hz), 7.13 (1H, d, J=9.0 Hz), 7.26-7.33 (2H, m), 7.51-7.59 (2H, m), 7.66 (1H, dd, J=2.4, 9.0 Hz), 7.97 (1H, d, J=2.4 Hz).

(2) Preparation of the Intermediate 369(2).

The title compound was obtained in the same manner as the Example 125(2) using the following starting material.

Starting material: the intermediate 369(1); Yield: 91% (pale brown solid).

$^1$H-NMR ($CDCl_3$) δ: 0.99 (6H, t, J=7.5 Hz), 1.67-1.79 (4H, m), 3.90 (2H, brs), 4.18 (1H, quint, J=6.0 Hz), 6.83 (1H, d, J=8.7 Hz), 6.88 (1H, dd, J=2.1, 8.7 Hz), 6.92 (1H, d, J=2.1 Hz), 7.19-7.25 (2H, m), 7.48-7.55 (2H, m).

(3) Preparation of the Intermediate 369(3).

The title compound was obtained in the same manner as the Example 123(1) using the following starting materials.

Starting materials: the intermediate 369(2) and 4-phenylbutyl bromide; Yield: 64% (colorless oil).

$^1$H-NMR ($CDCl_3$) δ: 0.97 (6H, t, J=7.8 Hz), 1.63-1.82 (8H, m), 2.68 (2H, t, J=7.2 Hz), 3.15-3.27 (2H, m), 4.16 (1H, quint, J=5.7 Hz), 4.28-4.37 (1H, m), 6.72-6.83 (3H, m), 7.10-7.34 (7H, m), 7.51-7.57 (2H, m).

(4) Preparation of the Intermediate 369(4).

The title compound was obtained in the same manner as the Example 123(2) using the following starting materials.

Starting materials: the intermediate 369(3) and methyl chloroglyoxylate; Yield: 78% (colorless oil).

$^1$H-NMR ($CDCl_3$) δ: 0.95 (3H, t, J=7.8 Hz), 0.96 (3H, t, J=7.8 Hz), 1.58-1.77 (8H, m), 2.51-2.71 (2H, m), 3.32-3.50 (2H, m), 3.52 (3H, s), 4.05-4.30 (1H, m), 6.95 (1H, d, J=9.0 Hz), 7.07-7.28 (7H, m), 7.30 (1H, d, J=2.4 Hz), 7.44-7.52 (3H, m).

(5) Preparation of the Compound 369.

The title compound was obtained in the same manner as the Example 126(4) using the following starting material.

Starting material: the intermediate 369(4); Yield: 95% (colorless oil).

This compound was obtained as a mixture of the rotational isomers.

Major isomer: $^1$H-NMR (DMSO-$d_6$) δ: 0.90 (6H, t, J=7.5 Hz), 1.38-1.72 (8H, m), 2.47-2.63 (2H, m), 3.31-3.48 (1H, m), 3.88-4.02 (1H, m), 4.34-4.45 (1H, m), 7.07-7.25 (6H, m), 7.40-7.49 (3H, m), 7.57-7.72 (3H, m), 13.66 (1H, brs).

Minor isomer: $^1$H-NMR (DMSO-$d_6$) δ: 0.90 (6H, t, J=7.5 Hz), 1.38-1.72 (8H, m), 2.47-2.63 (2H, m), 3.61 (1H, brs), 3.88-4.02 (1H, m), 4.28-4.43 (1H, m), 7.07-7.25 (6H, m), 7.40-7.49 (3H, m), 7.57-7.72 (3H, m), 13.66 (1H, brs).

Example 370

Preparation of the Compound 370

(1) Preparation of the Intermediate 370(1).

The title compound was obtained in the same manner as the Example 208(1) using the following starting materials.

Starting materials: the intermediate 188(1) and piperidine; Yield: 93.9% (orange solid).

$^1$H-NMR ($CDCl_3$) δ: 1.56-1.68 (2H, m), 1.68-1.81 (4H, m), 3.00-3.14 (4H, m), 7.17 (1H, d, J=8.4 Hz), 7.23-7.34 (2H, m), 7.50-7.60 (2H, m), 7.63 (1H, dd, J=2.1. 8.4 Hz), 7.96 (1H, d, J=2.1 Hz).

(2) Preparation of the Intermediate 370(2).

The title compound was obtained in the same manner as the Example 125(2) using the following starting material.

Starting material: the intermediate 370(1); Yield: 80.3% (white solid).

$^1$H-NMR ($CDCl_3$) δ: 1.50-1.66 (2H, m), 1.66-1.79 (4H, m), 2.78-2.96 (4H, m), 4.05 (2H, s), 6.88-6.96 (2H, m), 7.04 (1H, d, J=9.0 Hz), 7.17-7.30 (2H, m), 7.49-7.59 (2H, m).

(3) Preparation of the Intermediate 370(3).

The title compound was obtained in the same manner as the Example 123(1) using the following starting materials.

Starting materials: the intermediate 370(2) and 4-phenylbutyl bromide; Yield: 35.3% (colorless oil).

This compound was obtained as a mixture of the rotational isomers.

Major isomer: $^1$H-NMR ($CDCl_3$) δ: 1.40-1.92 (10H, m), 2.52-2.98 (6H, m), 3.12-3.25 (2H, m), 4.61-4.80 (1H, m), 6.72 (1H, d, J=2.1 Hz), 6.83 (1H, dd, J=2.1, 8.1 Hz), 7.02 (1H, d, J=8.1 Hz), 7.12-7.36 (7H, m), 7.50-7.61 (2H, m).

Minor isomer: $^1$H-NMR ($CDCl_3$) δ: 1.40-1.92 (10H, m), 2.52-2.98 (6H, m), 3.24-3.34 (2H, m), 4.12-4.24 (1H, m), 6.72 (1H, d, J=2.1 Hz), 6.83 (1H, dd, J=2.1, 8.1 Hz), 7.02 (1H, d, J=8.1 Hz), 7.12-7.36 (7H, m), 7.50-7.61 (2H, m).

(4) Preparation of the Intermediate 370(4).

The title compound was obtained in the same manner as the Example 123(2) using the following starting materials.

Starting materials: the intermediate 370(3) and methyl chloroglyoxylate; Yield: 74.3% (colorless oil).

This compound was obtained as a mixture of the rotational isomers.

Major isomer: $^1$H-NMR ($CDCl_3$) δ: 1.44-1.83 (10H, m), 2.48-2.68 (2H, m), 2.76-2.93 (2H, m), 3.05-3.22 (2H, m), 3.54-3.74 (4H, m), 4.18-4.34 (1H, m), 7.06-7.15 (4H, m), 7.15-7.23 (3H, m), 7.23-7.32 (2H, m), 7.42-7.54 (3H, m).

Minor isomer: $^1$H-NMR ($CDCl_3$) δ: 1.44-1.83 (10H, m), 2.48-2.68 (2H, m), 2.76-2.93 (2H, m), 3.05-3.22 (2H, m), 3.54-3.74 (4H, m), 3.86-3.95 (1H, m), 7.06-7.15 (4H, m), 7.15-7.23 (3H, m), 7.23-7.32 (2H, m), 7.42-7.54 (3H, m).

(5) Preparation of the Compound 370.

The title compound was obtained in the same manner as the Example 126(4) using the following starting material.

Starting material: the intermediate 370(4); Yield: 93.8% (white solid).

This compound was obtained as a mixture of the rotational isomers.

Major isomer: $^1$H-NMR (DMSO-$d_6$) δ 1.10-1.80 (10H, m), 2.30-2.58 (2H, m), 2.60-2.76 (2H, m), 3.16-3.64 (3H, m), 3.92-4.12 (1H, m), 6.96-7.22 (6H, m), 7.36-7.55 (4H, m), 7.59-7.70 (2H, m).

Minor isomer: $^1$H-NMR (DMSO-$d_6$) δ 1.10-1.80 (10H, m), 2.30-2.58 (2H, m), 2.95-3.18 (2H, m), 3.16-3.64 (3H, m), 3.68-3.85 (1H, m), 6.96-7.22 (6H, m), 7.36-7.55 (4H, m), 7.59-7.70 (2H, m).

Example 371

Preparation of the Compound 371

(1) Preparation of the Intermediate 371(1).

A mixture of 4-chloro-2-nitrobenzaldehyde (1.856 g, 10.00 mmol), 4-(trifluoromethoxy)phenylboronic acid (3.089 g, 15.00 mmol), palladium(II) acetate (112 mg, 0.50 mmol), 2-(di-tert-butylphosphino)biphenyl (298 mg, 1.00 mmol), potassium fluoride (1.743 g, 30.00 mmol) and tetrahydrofuran (10 ml) was stirred at 70° C. for 30 minutes. The reaction mixture was cooled to room temperature, and the solvent was evaporated under reduced pressure. The residue was diluted with ethyl acetate, and filtered through Celite. The residue obtained by concentration of the filtrate under reduced pressure was purified by column chromatography on silica gel (n-hexane:ethyl acetate=10:1) to give the title compound (2.542 mg, 82%) as a yellow solid.

$^1$H-NMR ($CDCl_3$) δ: 7.37-7.41 (2H, m), 7.67-7.73 (2H, m), 7.95-7.99 (1H, m), 8.07 (1H, d, J=8.1 Hz), 8.29 (1H, d, J=1.2 Hz), 10.46 (1H, s).

(2) Preparation of the Intermediate 371(2).

A mixture of the intermediate 371(1) (934 mg, 3.00 mmol), potassium carbonate (539 mg, 3.9 mmol), hexyltriphenylphosphonium bromide (1346 mg, 3.15 mmol), water (60 μl), sodium hydroxide (100 mg, 2.5 mmol) and 1,4-dioxane (4 ml) was refluxed for 1.5 hours. The reaction mixture was cooled to room temperature, and filtered. The residue obtained by concentration of the filtrate under reduced pressure was purified by column chromatography on silica gel (n-hexane:ethyl acetate=15:1) to give the title compound (1.01 g, 89%) as a yellow liquid. This compound was obtained as a mixture of the geometric isomers.

E isomer: $^1$H-NMR ($CDCl_3$) δ: 0.83-0.95 (3H, m), 1.22-1.57 (6H, m), 2.09-2.33 (2H, m), 6.31 (1H, dd, J=6.9, 15.6 Hz), 6.86 (1H, d, J=15.6 Hz), 7.30-7.77 (6H, m), 8.05-8.19 (1H, m).

Z isomer: $^1$H-NMR ($CDCl_3$) δ: 0.83-0.95 (3H, m), 1.22-1.57 (6H, m), 2.09-2.33 (2H, m), 5.87 (1H, dd, J=7.5, 11.7 Hz), 6.71 (1H, d, J=11.7 Hz), 7.30-7.77 (6H, m), 8.05-8.19 (1H, m).

(3) Preparation of the Intermediate 371(3).

The title compound was obtained in the same manner as the Example 125(2) using the following starting material.

Starting material: the intermediate 371(2); Yield: 94% (white solid).

$^1$H-NMR ($CDCl_3$) δ: 0.85-0.92 (3H, m), 1.23-1.40 (8H, m), 1.59-1.70 (2H, m), 2.49-2.55 (2H, m), 3.65 (2H, brs), 6.86 (1H, d, J=1.5 Hz), 6.92 (1H, dd, J=1.5, 7.8 Hz), 7.11 (1H, d, J=7.8 Hz), 7.21-7.26 (2H, m), 7.51-7.58 (2H, m).

(4) Preparation of the Intermediate 371(4).

The title compound was obtained in the same manner as the Example 123(1) using the following starting materials.

Starting materials: the intermediate 371(3) and 4-phenylbutyl bromide; Yield: 56% (pale yellow oil).

$^1$H-NMR ($CDCl_3$) δ: 0.86-0.92 (3H, m), 1.23-1.81 (14H, m), 2.43-2.49 (2H, m), 2.65-2.72 (2H, m), 3.20-3.26 (2H, m), 3.61 (1H, brs), 6.74 (1H, d, J=1.5 Hz), 6.84 (1H, dd, J=1.5, 7.8 Hz), 7.10 (1H, d, J=7.8 Hz), 7.13-7.31 (7H, m), 7.51-7.60 (2H, m).

(5) Preparation of the Intermediate 371(5).

The title compound was obtained in the same manner as the Example 123(2) using the following starting materials.

Starting materials: the intermediate 371(4) and methyl chloroglyoxylate; Yield: 80% (colorless oil).

$^1$H-NMR ($CDCl_3$) δ: 0.86-0.92 (3H, m), 1.23-1.73 (14H, m), 2.54-2.64 (4H, m), 3.05-3.18 (1H, m), 3.49 (3H, s), 4.25-4.30 (1H, m), 7.09-7.32 (8H, m), 7.39 (1H, d, J=7.8 Hz), 7.48-7.55 (3H, m).

(6) Preparation of the Compound 371.

The title compound was obtained in the same manner as the Example 126(4) using the following starting material.

Starting material: the intermediate 371(5); Yield: 57% (white solid).

$^1$H-NMR (DMSO-$d_6$) δ: 0.39-0.88 (3H, m), 1.18-1.60 (14H, m), 2.41-2.59 (4H, m), 2.95-4.22 (2H, m), 7.06-7.22 (5H, m), 7.31-7.49 (4H, m), 7.54-7.60 (1H, m), 7.67-7.77 (2H, m).

Example 372

Preparation of the Compound 372

(1) Preparation of the Intermediate 372(1).

m-Chloroperbenzoic acid (3.24 g, 12.194 mmol) was added to a solution of 5-bromo-3-nitrosalicylaldehyde (2.00 g, 8.129 mmol) in dichloromethane (5 ml), and the mixture was stirred at room temperature for 2 hours. A saturated aqueous solution of sodium hydrogen sulfite was added to the reaction mixture, and the mixture was extracted with ethyl acetate. The organic layer was washed with a saturated aqueous solution of sodium hydrogen carbonate and saturated brine, and dried over anhydrous sodium sulfate. Methanol (15 ml) and catalytic amount of concentrated hydrochloric acid were added to the residue obtained by evaporation of the solvent under reduced pressure, and the mixture was stirred at room temperature for 1 hour. The residue obtained by evaporation of the solvent under reduced pressure was purified by column chromatography on silica gel (n-hexane:ethyl acetate=2:1) to give the title compound (420 mg, 22%) as a white solid.

$^1$H-NMR ($CDCl_3$) δ: 7.37 (1H, d, J=2.1 Hz), 7.80 (1H, d, J=2.1 Hz).

(2) Preparation of the Intermediate 372(2).

The title compound was obtained in the same manner as the Example 354(2) using the following starting materials.

Starting materials: the intermediate 372(1) and 1-chloropentane; Yield: 35.4% (clear yellow oil).

$^1$H-NMR ($CDCl_3$) δ: 0.90-1.05 (6H, m), 1.35-1.80 (12H, m), 3.99-4.11 (4H, m), 7.17 (1H, d, J=2.1 Hz), 7.43 (1H, d, J=2.1 Hz).

(3) Preparation of the Intermediate 372(3).

The title compound was obtained in the same manner as the Example 123(3) using the following starting materials.

Starting materials: the intermediate 372(2) and 4-(trifluoromethoxy)phenylboronic acid; Yield: 76.8% (clear yellow oil).

$^1$H-NMR ($CDCl_3$) δ: 0.91-0.98 (6H, m), 1.35-1.57 (8H, m), 1.73-1.88 (4H, m), 4.08 (2H, t, J=6.6 Hz), 4.18 (2H, t, J=6.6 Hz), 7.21 (1H, d, J=2.1 Hz), 7.28-7.32 (2H, m), 7.46 (1H, d, J=2.1 Hz), 7.53-7.57 (2H, m).

(4) Preparation of the Intermediate 372(4).

The title compound was obtained in the same manner as the Example 125(2) using the following starting material.

Starting material: the intermediate 372(3); Yield: 68.2% (brown oil).

$^1$H-NMR ($CDCl_3$) δ: 0.91-0.98 (6H, m), 1.35-1.53 (8H, m), 1.75-1.88 (4H, m), 3.91 (2H, brs), 4.00-4.04 (4H, m), 6.48 (1H, d, J=2.1 Hz), 6.54 (1H, d, J=2.1 Hz), 7.21-7.24 (2H, m), 7.49-7.54 (2H, m).

(5) Preparation of the Intermediate 372(5).

The title compound was obtained in the same manner as the Example 123(1) using the following starting materials.

Starting materials: the intermediate 372(4) and 4-phenylbutyl bromide; Yield: 60.6% (clear colorless oil).

$^1$H-NMR ($CDCl_3$) δ: 0.91-0.98 (6H, m), 1.35-1.49 (10H, m), 1.75-1.88 (6H, m), 2.62-2.71 (2H, m), 3.39-3.46 (2H, m), 3.98-4.06 (4H, m), 4.30-4.38 (1H, m), 6.41-6.44 (2H, m), 7.16-7.32 (7H, m), 7.51-7.55 (2H, m).

(6) Preparation of the Intermediate 372(6).

The title compound was obtained in the same manner as the Example 123(2) using the following starting materials.

Starting materials: the intermediate 372(5) and methyl chloroglyoxylate; Yield: 73.8% (clear colorless oil).

$^1$H-NMR ($CDCl_3$) δ: 0.91-0.98 (6H, m), 1.35-1.89 (16H, m), 2.52-2.61 (2H, m), 3.48-3.62 (4H, m), 4.00-4.28 (5H, m), 6.84 (1H, d, J=2.1 Hz), 7.05 (1H, d, J=2.1 Hz), 7.09-7.15 (3H, m), 7.18-7.23 (2H, m), 7.26-7.29 (2H, m), 7.45-7.48 (2H, m).

(7) Preparation of the Compound 372.

The title compound was obtained in the same manner as the Example 126(4) using the following starting material.

Starting material: the intermediate 372(6); Yield: 13.3% (clear yellow oil).

This compound was obtained as a mixture of the rotational isomers.

Major isomer: $^1$H-NMR (DMSO-$d_6$) δ: 0.87-0.93 (6H, m), 1.32-1.49 (12H, m), 1.62-1.76 (4H, m), 2.44-2.50 (2H, m), 3.15-3.26 (2H, m), 4.00-4.11 (4H, m), 7.05-7.20 (7H, m), 7.42-7.45 (2H, m), 7.66-7.69 (2H, m).

Minor isomer: $^1$H-NMR (DMSO-$d_6$) δ: 0.87-0.91 (6H, m), 1.32-1.54 (12H, m), 1.67-1.76 (4H, m), 2.44-2.50 (2H, m), 3.60-3.67 (1H, m), 4.00-4.11 (5H, m), 7.05-7.20 (7H, m), 7.42-7.45 (2H, m), 7.71-7.74 (2H, m).

Example 373

Preparation of the Compound 373

(1) Preparation of the Intermediate 373(1).

The title compound was obtained in the same manner as the Example 185(2) using the following starting materials.

Starting materials: the intermediate 188(1) and potassium tert-butoxide; Yield: 57.3% (yellow solid).

$^1$H-NMR ($CDCl_3$) δ: 1.46 (9H, s), 7.21-7.36 (3H, m), 7.52-7.61 (2H, m), 7.64 (1H, dd, J=2.4, 8.4 Hz), 7.90 (1H, d, J=2.4 Hz).

(2) Preparation of the Intermediate 373(2).

The title compound was obtained in the same manner as the Example 125(2) using the following starting material.

Starting material: the intermediate 373(1); Yield: 75.1% (white solid).

$^1$H-NMR ($CDCl_3$) δ: 1.43 (9H, s), 3.86 (2H, brs), 6.82 (1H, dd, J=2.4, 8.4 Hz), 6.90 (1H, d, J=2.4 Hz), 7.00 (1H, d, J=8.4 Hz), 7.17-7.27 (2H, m), 7.46-7.57 (2H, m).

(3) Preparation of the Intermediate 373(3).

The title compound was obtained in the same manner as the Example 123(1) using the following starting materials.

Starting materials: the intermediate 373(2) and 4-phenylbutyl bromide; Yield: 50.6% (pale yellow oil).

This compound was obtained as a mixture of the rotational isomers.

Major isomer: $^1$H-NMR ($CDCl_3$) δ: 1.42 (9H, s), 1.63-1.85 (4H, m), 2.55-2.75 (2H, m), 3.10-3.25 (2H, m), 4.24-4.34 (1H, m), 6.70-6.78 (2H, m), 6.95-7.02 (1H, m), 7.09-7.34 (7H, m), 7.51-7.60 (2H, m).

Minor isomer: $^1$H-NMR ($CDCl_3$) δ: 1.42 (9H, s), 1.63-1.85 (4H, m), 2.55-2.75 (2H, m), 3.10-3.25 (2H, m), 4.14-4.23 (1H, m), 6.70-6.78 (2H, m), 6.95-7.02 (1H, m), 7.09-7.34 (7H, m), 7.51-7.60 (2H, m).

(4) Preparation of the Intermediate 373(4).

The title compound was obtained in the same manner as the Example 123(2) using the following starting materials.

Starting materials: the intermediate 373(3) and methyl chloroglyoxylate; Yield: 56.6% (colorless oil).

$^1$H-NMR ($CDCl_3$) δ: 1.47 (9H, s), 1.55-1.75 (4H, m), 2.47-2.72 (2H, m), 3.47-3.66 (4H, m), 3.97-4.18 (1H, m), 7.04-7.38 (9H, m), 7.42 (1H, dd, J=2.4, 8.4 Hz), 7.45-7.57 (2H, m).

(5) Preparation of the Compound 373.

The title compound was obtained in the same manner as the Example 126(4) using the following starting material.

Starting material: the intermediate 373(4); Yield: 100% (white solid).

This compound was obtained as a mixture of the rotational isomers.

Major isomer: $^1$H-NMR (DMSO-$d_6$) δ: 1.35-1.66 (13H, m), 2.40-2.67 (2H, m), 3.41-3.60 (1H, m), 3.82-4.02 (1H, m), 7.06-7.25 (5H, m), 7.30 (1H, d, J=8.7 Hz), 7.40-7.53 (3H, m), 7.59 (1H, dd, J=2.4, 8.7 Hz), 7.65-7.78 (2H, m), 13.70 (1H, brs).

Minor isomer: $^1$H-NMR (DMSO-$d_6$) δ: 1.35-1.66 (13H, m), 2.40-2.67 (2H, m), 3.60-3.71 (1H, m), 3.82-4.02 (1H, m), 7.06-7.25 (5H, m), 7.30 (1H, d, J=8.7 Hz), 7.40-7.53 (3H, m), 7.59 (1H, dd, J=2.4, 8.7 Hz), 7.65-7.78 (2H, m), 13.70 (1H, brs).

Example 374

Preparation of the Compound 374

(1) Preparation of the Intermediate 374(1).

The title compound was obtained in the same manner as the Example 123(1) using the following starting materials.

Starting materials: the intermediate 194(2) and 4-phenoxybutyl bromide; Yield: 29.6% (white solid).

$^1$H-NMR ($CDCl_3$) δ: 0.94 (3H, t, J=7.2 Hz), 1.30-1.56 (4H, m), 1.75-2.02 (6H, m), 3.20-3.38 (2H, m), 3.92-4.13 (4H, m), 4.26-4.42 (1H, m), 6.74-6.86 (3H, m), 6.86-6.99 (3H, m), 7.18-7.34 (4H, m), 7.49-7.60 (2H, m).

(2) Preparation of the Intermediate 374(2).

The title compound was obtained in the same manner as the Example 123(2) using the following starting materials.

Starting materials: the intermediate 374(1) and methyl chloroglyoxylate; Yield: 80.5% (colorless oil).

$^1$H-NMR ($CDCl_3$) δ: 0.92 (3H, t, J=7.2 Hz), 1.28-1.52 (4H, m), 1.66-1.93 (6H, m), 3.53 (3H, s), 3.56-3.72 (1H, m), 3.86-4.14 (5H, m), 6.76-6.86 (2H, m), 6.86-6.95 (1H, m), 7.00 (1H, d, J=8.4 Hz), 7.16-7.32 (4H, m), 7.39 (1H, d, J=2.1 Hz), 7.45-7.58 (3H, m).

(3) Preparation of the Compound 374.

The title compound was obtained in the same manner as the Example 126(4) using the following starting material.

Starting material: the intermediate 374(2); Yield: 71.9% (colorless oil).

$^1$H-NMR (DMSO-$d_6$) δ: 0.87 (3H, t, J=6.9 Hz), 1.22-1.48 (4H, m), 1.48-1.84 (7H, m), 3.80-4.10 (5H, m), 6.76-6.93 (3H, m), 7.11-7.28 (3H, m), 7.35-7.48 (2H, m), 7.52-7.65 (2H, m), 7.65-7.78 (2H, m).

Example 375

Preparation of the Compound 375

(1) Preparation of the Intermediate 375(1).

The title compound was obtained in the same manner as the Example 185(2) using the following starting materials.

Starting materials: the intermediate 188(1) and 1-pentadecanol; Yield: 63% (yellow oil).

$^1$H-NMR ($CDCl_3$) δ: 0.88 (3H, t, J=6.9 Hz), 1.98-1.40 (22H, m), 1.42-1.64 (2H, m), 1.80-1.92 (2H, m), 4.14 (2H, t, J=6.6 Hz), 7.14 (1H, d, J=8.7 Hz), 7.26-7.34 (2H, m), 7.53-7.59 (2H, m), 7.69 (1H, dd, J=2.4, 8.7 Hz), 8.02 (1H, d, J=2.4 Hz).

(2) Preparation of the Intermediate 375(2).

The title compound was obtained in the same manner as the Example 125(2) using the following starting material.

Starting material: the intermediate 375(1); Yield: 94% (gray solid).

$^1$H-NMR ($CDCl_3$) δ: 0.88 (3H, t, J=6.6 Hz), 1.20-1.40 (22H, m), 1.42-1.64 (2H, m), 1.75-1.88 (2H, m), 3.89 (2H, brs), 4.03 (2H, t, J=6.6 Hz), 6.80-6.95 (3H, m), 7.19-7.26 (2H, m), 7.48-7.57 (2H, m).

(3) Preparation of the Intermediate 375(3).

The title compound was obtained in the same manner as the Example 123(1) using the following starting materials.

Starting materials: the intermediate 375(2) and 4-phenylbutyl bromide; Yield: 75% (gray solid).

$^1$H-NMR ($CDCl_3$) δ: 0.88 (3H, t, J=6.6 Hz), 1.20-1.53 (24H, m), 1.72-1.95 (6H, m), 2.52-2.75 (2H, m), 3.16-3.23 (2H, m), 4.01 (2H, t, J=6.6 Hz), 4.27 (1H, brs), 6.70-6.82 (3H, m), 7.17-7.25 (7H, m), 7.49-7.59 (2H, m).

(4) Preparation of the Intermediate 375(4).

The title compound was obtained in the same manner as the Example 123(2) using the following starting materials.

Starting materials: the intermediate 375(3) and methyl chloroglyoxylate; Yield: 84% (colorless oil).

$^1$H-NMR ($CDCl_3$) δ: 0.88 (3H, t, J=6.6 Hz), 1.20-1.50 (24H, m), 1.52-1.85 (6H, m), 2.53-2.65 (2H, m), 3.47-3.60 (2H, m), 3.53 (3H, s), 3.88-4.07 (2H, m), 6.99 (1H, d, J=8.4 Hz), 7.06-7.30 (6H, m), 7.31 (1H, d, J=2.4 Hz), 7.45-7.53 (4H, m).

(5) Preparation of the Compound 375.

The title compound was obtained in the same manner as the Example 126(4) using the following starting material.

Starting material: the intermediate 375(4); Yield: 64% (colorless oil).

$^1$H-NMR ($CDCl_3$) δ: 0.88 (3H, t, J=6.6 Hz), 1.16-1.42 (24H, m), 1.52-1.74 (6H, m), 2.50-2.63 (2H, m), 3.69-3.82 (2H, m), 3.88-3.99 (2H, m), 6.90-6.98 (1H, m), 7.03-7.34 (7H, m), 7.40-7.54 (4H, m).

Example 376

Preparation of the Compound 376

(1) Preparation of the Intermediate 376(1).

The title compound was obtained in the same manner as the Example 185(2) using the following starting materials.

Starting materials: 4-bromo-2-fluoronitrobenzene and 1-pentanol; Yield: 50% (yellow oil).

$^1$H-NMR ($CDCl_3$) δ: 0.94 (3H, t, J=7.1 Hz), 1.35-1.50 (4H, m), 1.80-1.88 (2H, m), 4.09 (2H, t, J=6.5 Hz), 7.15 (1H, dd, J=2.0, 8.6 Hz), 7.22 (1H, d, J=2.0 Hz), 7.73 (1H, d, J=8.6 Hz).

(2) Preparation of the Intermediate 376(2).

Iron (1.13 g) and concentrated hydrochloric acid (6 ml) were added to a solution of the intermediate 376(1) (1.94 g, 6.73 mmol) in methanol (36 ml), and the mixture was refluxed for 2.5 hours. The reaction mixture was cooled to room temperature, and diluted with chloroform (150 ml). The organic layer was washed with a 5% aqueous solution of sodium hydrogen carbonate, and dried over anhydrous sodium sulfate. The residue obtained by evaporation of the solvent under reduced pressure was purified by column chromatography on silica gel (n-hexane:chloroform=2:1) to give the title compound (938 mg, 54%) as a brown oil.

$^1$H-NMR ($CDCl_3$) δ: 0.94 (3H, t, J=7.1 Hz), 1.37-1.47 (4H, m), 1.78-1.84 (2H, m), 3.78 (2H, brs), 3.96 (2H, t, J=6.4 Hz), 6.58 (1H, d, J=8.4 Hz), 6.87 (1H, s), 6.88 (1H, dd, J=2.0, 8.4 Hz).

(3) Preparation of the Intermediate 376(3).

The title compound was obtained in the same manner as the Example 123(1) using the following starting materials.

Starting materials: the intermediate 376(2) and 4-phenylbutyl bromide; Yield: 68% (yellow oil).

$^1$H-NMR ($CDCl_3$) δ: 0.92 (3H, t, J=7.1 Hz), 1.36-1.45 (4H, m), 1.67-1.83 (6H, m), 2.66 (2H, t, J=7.2 Hz), 3.10 (2H, brs), 3.94 (2H, t, J=6.6 Hz), 4.14 (1H, brs), 6.42 (1H, d, J=8.4 Hz), 6.82 (1H, d, J=2.2 Hz), 6.94 (1H, dd, J=2.0, 8.4 Hz), 7.15-7.21 (3H, m), 7.25-7.31 (2H, m).

(4) Preparation of the Intermediate 376(4).

The title compound was obtained in the same manner as the Example 123(2) using the following starting materials.

Starting materials: the intermediate 376(3) and methyl chloroglyoxylate; Yield: 90% (colorless syrup).

$^1$H-NMR ($CDCl_3$) δ: 0.92 (3H, t, J=7.0 Hz), 1.33-1.44 (3H, m), 1.51-1.68 (5H, m), 1.71-1.82 (2H, m), 2.52-2.63 (2H, m), 3.43-3.55 (1H, m), 3.56 (3H, s), 3.86-3.98 (3H, m), 6.94 (1H, d, J=8.8 Hz), 7.01-7.05 (2H, m), 7.09-7.28 (5H, m).

(5) Preparation of the Intermediate 376(5).

The title compound was obtained in the same manner as the Example 123(3) using the following starting materials.

Starting materials: the intermediate 376(4) and 3-methyphenylboronic acid; Yield: 79% (colorless syrup).

$^1$H-NMR ($CDCl_3$) δ: 0.93 (3H, t, J=7.1 Hz), 1.32-1.50 (4H, m), 1.55-1.70 (4H, m), 1.76-1.85 (2H, m), 2.43 (3H, s), 2.61 (2H, t, J=7.3 Hz), 3.48-3.61 (1H, m), 3.54 (3H, s), 3.93-4.07 (3H, m), 7.07-7.28 (9H, m), 7.33-7.39 (3H, m).

(6) Preparation of the Compound 376.

The title compound was obtained in the same manner as the Example 126(4) using the following starting material.

Starting material: the intermediate 376(5); Yield: 95% (colorless syrup).

$^1$H-NMR ($CDCl_3$) δ: 0.91 (3H, t, J=7.1 Hz), 1.32-1.42 (4H, m), 1.58-1.82 (6H, m), 2.43 (3H, s), 2.61 (2H, t, J=7.3 Hz), 3.70-3.81 (2H, m), 3.99 (2H, t, J=6.6 Hz), 7.07 (1H, s), 7.09-7.28 (8H, m), 7.31-7.39 (3H, m).

Example 377

Preparation of the Compound 377

(1) Preparation of the Intermediate 377(1).

The title compound was obtained in the same manner as the Example 123(3) using the following starting materials.

Starting materials: the intermediate 376(4) and 3-(trifluoromethyl)phenylboronic acid; Yield: 70% (colorless syrup).

$^1$H-NMR ($CDCl_3$) δ: 0.93 (3H, t, J=7.1 Hz), 1.32-1.50 (4H, m), 1.55-1.72 (4H, m), 1.76-1.87 (2H, m), 2.57-2.65 (2H, m), 3.53-3.63 (1H, m), 3.57 (3H, s), 3.92-4.08 (3H, m), 7.07-7.28 (8H, m), 7.53-7.67 (2H, m), 7.74 (1H, d, J=7.5 Hz), 7.80 (1H, brs).

(2) Preparation of the Compound 377.

The title compound was obtained in the same manner as the Example 126(4) using the following starting material.

Starting material: the intermediate 377(1); Yield: 91% (colorless syrup).

$^1$H-NMR ($CDCl_3$) δ: 0.93 (3H, t, J=6.9 Hz), 1.32-1.42 (4H, m), 1.58-1.78 (6H, m), 2.60 (2H, t, J=7.0 Hz), 3.77 (2H, t, J=6.8 Hz), 3.99 (2H, t, J=6.5 Hz), 7.05 (1H, brs), 7.09-7.27 (7H, m), 7.53-7.65 (2H, m), 7.74 (1H, d, J=7.5 Hz), 7.80 (1H, brs).

Example 378

Preparation of the Compound 378

(1) Preparation of the Intermediate 378(1).

The title compound was obtained in the same manner as the Example 185(2) using the following starting materials.

Starting materials: 4-bromo-1-fluoro-2-nitrobenzene and 1-pentanol; Yield: 68.6% (clear brown oil).

$^1$H-NMR ($CDCl_3$) δ: 0.93 (3H, t, J=7.2 Hz), 1.35-1.55 (4H, m), 1.79-1.86 (2H, m), 4.08 (2H, t, J=6.3 Hz), 6.96 (1H, d, J=9.0 Hz), 7.60 (1H, dd, J=2.4, 9.0 Hz), 7.95 (1H, d, J=2.4 Hz).

(2) Preparation of the Intermediate 378(2).

The title compound was obtained in the same manner as the Example 125(2) using the following starting material.

Starting material: the intermediate 378(1); Yield: 99.5% (brown solid).

$^1$H-NMR ($CDCl_3$) δ: 0.93 (3H, t, J=7.2 Hz), 1.32-1.45 (4H, m), 1.76-1.81 (2H, m), 3.95 (2H, t, J=6.6 Hz), 4.31 (2H, brs), 6.62 (1H, d, J=8.4 Hz), 6.81 (1H, dd, J=2.4, 8.4 Hz), 6.87 (1H, d, J=2.4 Hz).

(3) Preparation of the Intermediate 378(3).

The title compound was obtained in the same manner as the Example 123(1) using the following starting materials.

Starting materials: the intermediate 378(2) and 4-phenylbutyl bromide; Yield: 58.8% (brown oil).

$^1$H-NMR ($CDCl_3$) δ: 0.90-0.94 (3H, m), 1.38-1.45 (4H, m), 1.68-1.81 (6H, m), 2.67 (2H, t, J=7.2 Hz), 3.10 (2H, t, J=6.0 Hz), 3.93 (2H, t, J=6.6 Hz), 4.19-4.27 (1H, m), 6.56 (1H, d, J=8.4 Hz), 6.64 (1H, d, J=2.1 Hz), 6.70 (1H, dd, J=2.1, 8.4 Hz), 7.16-7.31 (5H, m).

(4) Preparation of the Intermediate 378(4).

The title compound was obtained in the same manner as the Example 123(2) using the following starting materials.

Starting materials: the intermediate 378(3) and methyl chloroglyoxylate; Yield: 54.5% (white solid).

$^1$H-NMR ($CDCl_3$) δ: 0.92 (3H, t, J=7.2 Hz), 1.35-1.41 (4H, m), 1.55-1.62 (4H, m), 1.71-1.79 (2H, m), 2.58-2.63 (2H, m), 3.51-3.62 (4H, m), 3.86-3.96 (3H, m), 6.79 (1H, d, J=8.7 Hz), 7.11-7.29 (6H, m), 7.40 (1H, dd, J=2.7, 8.7 Hz).

(5) Preparation of the Intermediate 378(5).

The title compound was obtained in the same manner as the Example 123(3) using the following starting materials.

Starting materials: the intermediate 378(4) and 3-(trifluoromethyl)phenylboronic acid; Yield: 77% (colorless syrup).

$^1$H-NMR ($CDCl_3$) δ: 0.93 (3H, t, J=7.1 Hz), 1.32-1.50 (4H, m), 1.55-1.72 (4H, m), 1.75-1.86 (2H, m), 2.56-2.64 (2H, m), 3.52-3.64 (1H, m), 3.55 (3H, s), 3.94-4.05 (3H, m), 7.01 (1H, d, J=8.6 Hz), 7.08-7.25 (5H, m), 7.36 (1H, d, J=2.2 Hz), 7.51-7.67 (4H, m), 7.72 (1H, brs).

(6) Preparation of the Compound 378.

The title compound was obtained in the same manner as the Example 126(4) using the following starting material.

Starting material: the intermediate 378(5); Yield: 99% (colorless syrup).

$^1$H-NMR ($CDCl_3$) δ: 0.91 (3H, t, J=7.1 Hz), 1.30-1.42 (4H, m), 1.57-1.78 (6H, m), 2.60 (2H, t, J=7.1 Hz), 3.73-3.83 (2H, m), 3.97 (2H, t, J=6.6 Hz), 6.98 (1H, d J=8.6 Hz), 7.07-7.25 (5H, m), 7.35 (1H, d, J=2.4 Hz), 7.49-7.60 (3H, m), 7.67 (1H, d, J=7.1 Hz), 7.75 (1H, s).

Example 379

Preparation of the Compound 379

(1) Preparation of the Intermediate 379(1).

The title compound was obtained in the same manner as the Example 123(3) using the following starting materials.

Starting materials: the intermediate 378(4) and 3-methyphenylboronic acid; Yield: 71% (colorless syrup).

$^1$H-NMR ($CDCl_3$) δ: 0.93 (3H, t, J=7.1 Hz), 1.32-1.50 (4H, m), 1.58-1.68 (4H, m), 1.74-1.85 (2H, m), 2.42 (3H, s), 2.60 (2H, t, J=6.4 Hz), 3.52-3.62 (1H, m), 3.53 (3H, s), 3.95-4.06 (3H, m), 6.97 (1H, d, J=8.6 Hz), 7.08-7.34 (9H, m), 7.35 (1H, d, J=2.4 Hz), 7.52 (1H, dd, J=2.4, 8.6 Hz).

(2) Preparation of the Compound 379.

The title compound was obtained in the same manner as the Example 126(4) using the following starting material.

Starting material: the intermediate 379(1); Yield: 95% (colorless syrup).

$^1$H-NMR ($CDCl_3$) δ: 0.90 (3H, t, J=6.4 Hz), 1.28-1.42 (4H, m), 1.58-1.77 (6H, m), 2.41 (3H, s), 2.59 (2H, t, J=6.9 Hz), 3.77 (2H, t, J=6.8 Hz), 3.94 (2H, t, J=6.6 Hz), 6.94 (1H, d, J=8.6 Hz), 7.07-7.37 (10H, m), 7.50 (1H, dd, J=2.2, 8.4 Hz).

Example 380

Preparation of the Compound 380

(1) Preparation of the Intermediate 380(1).

The title compound was obtained in the same manner as the Example 185(2) using the following starting materials.

Starting materials: the intermediate 367(1) and 1-nonanol; Yield: 66% (brown oil).

$^1$H-NMR ($CDCl_3$) δ: 0.88 (3H, t, J=6.9 Hz), 1.20-1.58 (12H, m), 1.82-1.94 (2H, m), 4.17 (2H, t, J=6.6 Hz), 7.13-7.22 (2H, m), 7.30-7.37 (2H, m), 7.56-7.64 (2H, m), 7.93 (1H, d, J=8.1 Hz).

(2) Preparation of the Intermediate 380(2).

The title compound was obtained in the same manner as the Example 125(2) using the following starting material.

Starting material: the intermediate 380(1); Yield: 98% (pale brown solid).

$^1$H-NMR ($CDCl_3$) δ: 0.80-0.93 (3H, m), 1.18-1.55 (12H, m), 1.74-1.89 (2H, m), 3.38 (2H, brs), 3.97-4.08 (2H, m), 6.71-6.80 (1H, m), 6.92-7.03 (2H, m), 7.16-7.27 (2H, m), 7.45-7.55 (2H, m).

(3) Preparation of the Intermediate 380(3).

The title compound was obtained in the same manner as the Example 123(1) using the following starting materials.

Starting materials: the intermediate 380(2) and 4-phenylbutyl bromide; Yield: 77% (pale brown solid).

$^1$H-NMR ($CDCl_3$) δ: 0.82-0.94 (3H, m), 1.18-1.88 (18H, m), 2.54-2.73 (2H, m), 3.11-3.25 (2H, m), 3.98-4.08 (2H, m), 4.29 (1H, brs), 6.63 (1H, d, J=8.1 Hz), 6.91-7.33 (9H, m), 7.48-7.59 (2H, m).

(4) Preparation of the Intermediate 380(4).

The title compound was obtained in the same manner as the Example 123(2) using the following starting materials.

Starting materials: the intermediate 380(3) and methyl chloroglyoxylate; Yield: 70% (pale brown oil).

$^1$H-NMR ($CDCl_3$) δ: 0.84-0.93 (3H, m), 1.20-1.53 (12H, m), 1.53-1.74 (4H, m), 1.75-1.86 (2H, m), 2.56-2.65 (2H, m), 3.52-3.63 (2H, m), 3.56 (3H, s), 3.94-4.08 (2H, m), 7.04-7.20 (6H, m), 7.20-7.33 (4H, m), 7.55-7.62 (2H, m).

(5) Preparation of the Compound 380.

The title compound was obtained in the same manner as the Example 126(4) using the following starting material.

Starting material: the intermediate 380(4); Yield: 95% (pale brown oil).

$^1$H-NMR ($CDCl_3$) δ: 0.84-0.92 (3H, m), 1.20-1.45 (12H, m), 1.52-1.78 (6H, m), 2.56-2.65 (2H, m), 3.68-3.89 (2H, m), 3.94-4.08 (2H, m), 6.76 (1H, d, J=2.1 Hz), 6.81 (1H, dd, J=2.1, 8.1 Hz), 7.08-7.30 (8H, m), 7.50-7.60 (2H, m).

Example 381

Preparation of the Compound 381

(1) Preparation of the Intermediate 381(1).

The title compound was obtained in the same manner as the Example 185(2) using the following starting materials.

Starting materials: the intermediate 188(1) and 5,5,5-trifluoropentan-1-ol; Yield: 86% (pale yellow syrup).

$^1$H-NMR ($CDCl_3$) δ: 1.74-1.87 (2H, m), 1.88-2.03 (2H, m), 2.13-2.30 (2H, m), 4.18 (2H, t, J=5.9 Hz), 7.14 (1H, d, J=8.8 Hz), 7.31 (2H, d, J=7.9 Hz), 7.57 (2H, d, J=8.8 Hz), 7.71 (1H, dd, J=2.4, 8.8 Hz), 8.05 (1H, d, J=2.4 Hz).

(2) Preparation of the Intermediate 381(2).

The title compound was obtained in the same manner as the Example 125(2) using the following starting material.

Starting material: the intermediate 381(1); Yield: 75% (white solid).

$^1$H-NMR ($CDCl_3$) δ: 1.77-1.87 (2H, m), 1.87-1.98 (2H, m), 2.12-2.27 (2H, m), 3.88 (2H, brs), 4.06 (2H, t, J=6.0 Hz), 6.83 (1H, d, J=8.2 Hz), 6.88-6.94 (2H, m), 7.23 (2H, d, J=8.8 Hz), 7.52 (2H, d, J=8.8 Hz).

(3) Preparation of the Intermediate 381(3).

The title compound was obtained in the same manner as the Example 123(1) using the following starting materials.

Starting materials: the intermediate 381(2) and 4-phenylbutyl bromide; Yield: 100% (colorless oil).

$^1$H-NMR ($CDCl_3$) δ: 1.78-1.85 (6H, m), 1.85-1.97 (2H, m), 2.19-2.26 (2H, m), 2.68 (2H, t, J=7.1 Hz), 3.21 (2H, brs), 4.05 (2H, t, J=6.0 Hz), 4.21 (1H, brs), 6.74-6.81 (3H, m), 7.16-7.32 (7H, m), 7.54 (2H, d, J=8.6 Hz).

(4) Preparation of the Intermediate 381(4).

The title compound was obtained in the same manner as the Example 123(2) using the following starting materials.

Starting materials: the intermediate 381(3) and methyl chloroglyoxylate; Yield: 56% (colorless syrup).

$^1$H-NMR ($CDCl_3$) δ: 1.57-1.83 (6H, m), 1.83-1.93 (2H, m), 2.07-2.24 (2H, m), 2.61 (2H, t, J=7.1 Hz), 3.46-3.58 (1H, m), 3.53 (3H, s), 3.96-4.80 (3H, m), 6.99 (1H, d, J=8.7 Hz), 7.09-7.30 (7H, m), 7.32 (1H, d, J=2.2 Hz), 7.47-7.53 (3H, m).

(5) Preparation of the Compound 381.

The title compound was obtained in the same manner as the Example 126(4) using the following starting material.

Starting material: the intermediate 381(4); Yield: 100% (colorless syrup).

$^1$H-NMR ($CDCl_3$) δ: 1.59-1.74 (6H, m), 1.74-1.87 (2H, m), 2.02-2.18 (2H, m), 2.60 (2H, t, J=7.1 Hz), 3.68-3.85 (2H, m), 3.99 (2H, t, J=6.0 Hz), 6.96 (1H, d, J=8.6 Hz), 7.08-7.28 (7H, m), 7.32 (1H, d, J=2.2 Hz), 7.46-7.53 (3H, m).

Example 382

Preparation of the Compound 382

(1) Preparation of the Intermediate 382(1).

The title compound was obtained in the same manner as the Example 123(1) using the following starting materials.

Starting materials: the intermediate 194(2) and 4-(4-fluorophenyl)butyl bromide; Yield: 45% (pale brown oil).

$^1$H-NMR ($CDCl_3$) δ: 0.93 (3H, t, J=6.9 Hz), 1.33-1.52 (4H, m), 1.65-1.88 (6H, m), 2.65 (2H, t, J=6.9 Hz), 3.21 (2H, brs), 4.02 (2H, t, J=6.6 Hz), 4.27 (1H, brs), 6.72-6.85 (3H, m), 6.92-7.00 (2H, m), 7.10-7.17 (2H, m), 7.20-7.27 (2H, m), 7.51-7.58 (2H, m).

(2) Preparation of the Intermediate 382(2).

The title compound was obtained in the same manner as the Example 123(2) using the following starting materials.

Starting materials: the intermediate 382(1) and methyl chloroglyoxylate; Yield: 68% (colorless oil).

$^1$H-NMR ($CDCl_3$) δ: 0.93 (3H, t, J=6.9 Hz), 1.30-1.50 (4H, m), 1.50-1.70 (4H, m), 1.74-1.85 (2H, m), 2.52-2.64 (2H, m), 3.48-3.62 (5H, m), 3.94-4.06 (2H, m), 6.72-6.85 (3H, m), 6.92-7.00 (2H, m), 7.10-7.17 (2H, m), 7.20-7.27 (2H, m), 7.51-7.58 (2H, m).

(3) Preparation of the Compound 382.

The title compound was obtained in the same manner as the Example 126(4) using the following starting material.

Starting material: the intermediate 382(2); Yield: 74% (colorless oil).

$^1$H-NMR ($CDCl_3$) δ: 0.83-0.97 (3H, m), 1.24-1.43 (4H, m), 1.50-1.78 (6H, m), 2.50-2.62 (2H, m), 3.70-3.84 (2H, m), 3.95 (2H, t, J=6.3 Hz), 6.84-7.09 (5H, m), 7.20-7.33 (3H, m), 7.42-7.54 (3H, m).

Example 383

Preparation of the Compound 383

(1) Preparation of the Intermediate 383(1).

The title compound was obtained in the same manner as the Example 185(2) using the following starting materials.

Starting materials: the intermediate 188(1) and 2-(trifluoromethyl)ethanol; Yield: 76.7% (pale yellow solid).

$^1$H-NMR ($CDCl_3$) δ: 2.69-2.84 (2H, m), 4.39 (2H, t, J=6.6 Hz), 7.18 (1H, d, J=8.8 Hz), 7.31-7.34 (2H, m), 7.56-7.61 (2H, m), 7.75 (1H, dd, J=2.4, 8.6 Hz), 8.06 (1H, d, J=2.4 Hz).

(2) Preparation of the Intermediate 383(2).

The title compound was obtained in the same manner as the Example 125(2) using the following starting material.

Starting material: the intermediate 383(1); Yield: 93.1% (gray solid).

$^1$H-NMR ($CDCl_3$) δ: 2.62-2.77 (2H, m), 3.91 (2H, brs), 4.30 (2H, t, J=6.2 Hz), 6.85 (1H, d, J=8.1 Hz), 6.90-6.95 (2H, m), 7.23-7.28 (2H, m), 7.51-7.56 (2H, m).

(3) Preparation of the Intermediate 383(3).

The title compound was obtained in the same manner as the Example 123(1) using the following starting materials.

Starting materials: the intermediate 383(2) and 4-phenylbutyl bromide; Yield: 58.0% (colorless oil).

$^1$H-NMR ($CDCl_3$) δ: 1.69-1.80 (4H, m), 2.56-2.72 (4H, m), 3.20 (1H, brs), 4.18-4.29 (4H, m), 6.75-6.81 (3H, m), 7.23-7.31 (7H, m), 7.52-7.57 (2H, m).

(4) Preparation of the Intermediate 383(4).

The title compound was obtained in the same manner as the Example 123(2) using the following starting materials.

Starting materials: the intermediate 383(3) and methyl chloroglyoxylate; Yield: 83.0% (colorless oil).

$^1$H-NMR ($CDCl_3$) δ: 1.53-1.73 (4H, m), 2.53-2.75 (4H, m), 3.47-3.58 (1H, m), 3.54 (3H, s), 3.98-4.35 (3H, m), 7.01 (1H, d, J=8.6 Hz), 7.11-7.34 (8H, m), 7.47-7.55 (3H, m).

(5) Preparation of the Compound 383.

The title compound was obtained in the same manner as the Example 126(4) using the following starting material.

Starting material: the intermediate 383(4); Yield: 63.6% (colorless solid).

$^1$H-NMR ($CDCl_3$) δ: 1.60-1.70 (4H, m), 2.49-2.65 (4H, m), 3.70-3.85 (2H, m), 4.17-4.26 (2H, m), 6.98 (1H, d, J=8.6 Hz), 7.10-7.32 (8H, m), 7.49-7.54 (3H, m).

Example 384

Preparation of the Compound 384

(1) Preparation of the Intermediate 384(1).

The title compound was obtained in the same manner as the Example 123(1) using the following starting materials.

Starting materials: the intermediate 194(2) and 4-(4-chlorophenyl)butyl bromide; Yield: 54% (pale brown oil).

$^1$H-NMR ($CDCl_3$) δ: 0.93 (3H, t, J=6.9 Hz), 1.33-1.52 (4H, m), 1.65-1.88 (6H, m), 2.65 (2H, t, J=6.9 Hz), 3.21 (2H, brs), 4.02 (2H, t, J=6.6 Hz), 4.27 (1H, brs), 6.71-6.83 (3H, m), 6.99-7.27 (6H, m), 7.50-7.57 (2H, m).

(2) Preparation of the Intermediate 384(2).

The title compound was obtained in the same manner as the Example 123(2) using the following starting materials.

Starting materials: the intermediate 384(1) and methyl chloroglyoxylate; Yield: 48% (colorless oil).

$^1$H-NMR ($CDCl_3$) δ: 0.93 (3H, t, J=6.9 Hz), 1.30-1.48 (4H, m), 1.51-1.68 (4H, m), 1.73-1.84 (2H, m), 2.52-2.64 (2H, m), 3.48-3.62 (5H, m), 3.92-4.07 (2H, m), 6.96-7.06 (3H, m), 7.16-7.21 (2H, m), 7.26-7.33 (3H, m), 7.46-7.53 (3H, m).

(3) Preparation of the Compound 384.

The title compound was obtained in the same manner as the Example 126(4) using the following starting material.

Starting material: the intermediate 384(2); Yield: 67% (colorless oil).

$^1$H-NMR ($CDCl_3$) δ: 0.84-0.95 (3H, m), 1.26-1.41 (4H, m), 1.50-1.78 (6H, m), 2.50-2.59 (2H, m), 3.70-3.82 (2H, m), 3.94 (2H, t, J=6.6 Hz), 6.92-7.04 (3H, m), 7.12-7.32 (5H, m), 7.42-7.54 (3H, m).

Example 385

Preparation of the Compound 385

(1) Preparation of the Intermediate 385(1).

The title compound was obtained in the same manner as the Example 185(2) using the following starting materials.

Starting materials: the intermediate 367(1) and 1-pentadecanol; Yield: 66% (pale yellow solid).

$^1$H-NMR ($CDCl_3$) δ: 0.88 (3H, t, J=6.9 Hz), 1.18-1.40 (22H, m), 1.40-1.59 (2H, m), 1.80-1.93 (2H, m), 4.12 (2H, t, J=6.6 Hz), 7.12-7.20 (2H, m), 7.30-7.37 (2H, m), 7.55-7.64 (2H, m), 7.93 (1H, d, J=8.1 Hz).

(2) Preparation of the Intermediate 385(2).

The title compound was obtained in the same manner as the Example 125(2) using the following starting material.

Starting material: the intermediate 385(1); Yield: 40% (white solid).

$^1$H-NMR ($CDCl_3$) δ: 0.88 (3H, t, J=6.6 Hz), 1.18-1.40 (22H, m), 1.41-1.59 (2H, m), 1.76-1.90 (2H, m), 3.89 (2H, brs), 4.05 (2H, t, J=6.6 Hz), 6.77 (1H, d, J=8.1 Hz), 6.95-7.20 (2H, m), 7.19-7.27 (2H, m), 7.48-7.56 (2H, m).

(3) Preparation of the Intermediate 385(3).

The title compound was obtained in the same manner as the Example 123(1) using the following starting materials.

Starting materials: the intermediate 385(2) and 4-phenylbutyl bromide; Yield: 74% (brown oil).

$^1$H-NMR ($CDCl_3$) δ: 0.88 (3H, t, J=6.6 Hz), 1.20-1.53 (24H, m), 1.65-1.89 (6H, m), 2.63-2.72 (2H, m), 3.15-3.25 (2H, m), 4.04 (2H, t, J=6.6 Hz), 4.30 (1H, brs), 6.63 (1H, d, J=8.4 Hz), 6.94 (1H, d, J=2.1 Hz), 7.07 (1H, dd, J=2.1, 8.4 Hz), 7.11-7.33 (7H, m), 7.50-7.57 (2H, m).

(4) Preparation of the Intermediate 385(4).

The title compound was obtained in the same manner as the Example 123(2) using the following starting materials.

Starting materials: the intermediate 385(3) and methyl chloroglyoxylate; Yield: 66% (pale brown oil).

$^1$H-NMR ($CDCl_3$) δ: 0.82-0.93 (3H, m), 1.20-1.50 (24H, m), 1.52-1.85 (6H, m), 2.55-2.66 (2H, m), 3.48-3.62 (2H, m), 3.56 (3H, s), 3.88-4.07 (2H, m), 7.01-7.20 (6H, m), 7.21-7.34 (4H, m), 7.50-7.57 (2H, m).

(5) Preparation of the Compound 385.

The title compound was obtained in the same manner as the Example 126(4) using the following starting material.

Starting material: the intermediate 385(4); Yield: 57% (colorless oil).

$^1$H-NMR ($CDCl_3$) δ: 0.88 (3H, t, J=6.6 Hz), 1.10-1.45 (24H, m), 1.51-1.80 (6H, m), 2.53-2.65 (2H, m), 3.70-3.83 (2H, m), 3.97 (2H, t, J=6.6 Hz), 7.03 (1H, d, J=1.5 Hz), 7.06-7.34 (9H, m), 7.52-7.54 (2H, m).

Example 386

Preparation of the Compound 386

(1) Preparation of the Intermediate 386(1).

The title compound was obtained in the same manner as the Example 185(2) using the following starting materials.

Starting materials: the intermediate 367(1) and 1-heptanol; Yield: 71% (brown oil).

$^1$H-NMR ($CDCl_3$) δ: 0.83-0.94 (3H, m), 1.20-1.56 (8H, m), 1.81-1.94 (2H, m), 4.12 (2H, t, J=6.3 Hz), 7.13-7.20 (2H, m), 7.30-7.37 (2H, m), 7.57-7.64 (2H, m), 7.93 (1H, d, J=8.1 Hz).

(2) Preparation of the Intermediate 386(2).

The title compound was obtained in the same manner as the Example 125(2) using the following starting material.

Starting material: the intermediate 386(1); Yield: 82% (white solid).

$^1$H-NMR ($CDCl_3$) δ: 0.90 (3H, t, J=6.6 Hz), 1.23-1.56 (8H, m), 1.78-1.90 (2H, m), 3.89 (2H, s), 4.05 (2H, t, J=6.3 Hz), 6.77 (1H, d, J=7.8 Hz), 6.93-7.04 (2H, m), 7.18-7.28 (2H, m), 7.47-7.56 (2H, m).

(3) Preparation of the Intermediate 386(3).

The title compound was obtained in the same manner as the Example 123(1) using the following starting materials.

Starting materials: the intermediate 386(2) and 4-phenylbutyl bromide; Yield: 75% (pale brown solid).

$^1$H-NMR ($CDCl_3$) δ: 0.85-0.94 (3H, m), 1.20-1.95 (14H, m), 2.57-2.73 (2H, m), 3.10-3.25 (2H, m), 4.04 (2H, t, J=6.6 Hz), 4.29 (1H, brs), 6.63 (1H, d, J=8.1 Hz), 6.94 (1H, d, J=2.1 Hz), 7.07 (1H, dd, J=2.1, 8.1 Hz), 7.13-7.33 (7H, m), 7.48-7.56 (2H, m).

(4) Preparation of the Intermediate 386(4).

The title compound was obtained in the same manner as the Example 123(2) using the following starting materials.

Starting materials: the intermediate 386(3) and methyl chloroglyoxylate; Yield: 64% (pale yellow oil).

$^1$H-NMR ($CDCl_3$) δ: 0.85-0.94 (3H, m), 1.20-1.87 (14H, m), 2.57-2.67 (2H, m), 3.50-3.64 (2H, m), 3.56 (3H, s), 3.90-4.09 (2H, m), 7.02-7.20 (6H, m), 7.21-7.35 (4H, m), 7.54-7.62 (2H, m).

(5) Preparation of the Compound 386.

The title compound was obtained in the same manner as the Example 126(4) using the following starting material.

Starting material: the intermediate 386(4); Yield: 67% (colorless oil).

$^1$H-NMR ($CDCl_3$) δ: 0.81-0.97 (3H, m), 1.20-1.47 (8H, m), 1.55-1.79 (6H, m), 2.55-2.66 (2H, m), 3.73-3.83 (2H, m), 3.98 (2H, t, J=6.6 Hz), 7.00-7.34 (10H, m), 7.52-7.62 (2H, m).

Example 387

Preparation of the Compound 387

(1) Preparation of the Intermediate 387(1).

The title compound was obtained in the same manner as the Example 185(2) using the following starting materials.

Starting materials: the intermediate 211(1) and 1-nonanol; Yield: 68% (brown oil).

$^1$H-NMR ($CDCl_3$) δ: 0.84-0.92 (3H, m), 1.20-1.44 (12H, m), 1.71-1.83 (2H, m), 4.09 (2H, t, J=6.6 Hz), 7.00-7.06 (1H, m), 7.23-7.32 (2H, m), 7.53-7.60 (2H, m), 8.20-8.27 (2H, m).

(2) Preparation of the Intermediate 387(2).

The title compound was obtained in the same manner as the Example 125(2) using the following starting material.

Starting material: the intermediate 387(1); Yield: 40% (brown oil).

$^1$H-NMR ($CDCl_3$) δ: 0.84-0.92 (3H, m), 1.20-1.45 (12H, m), 1.57-1.70 (2H, m), 3.48 (2H, brs), 3.82 (2H, t, J=6.6 Hz), 6.63-6.70 (2H, m), 6.82 (1H, d, J=8.4 Hz), 7.17-7.25 (2H, m), 7.51-7.58 (2H, m).

(3) Preparation of the Intermediate 387(3).

The title compound was obtained in the same manner as the Example 123(1) using the following starting materials.

Starting materials: the intermediate 387(2) and 4-phenylbutyl bromide; Yield: 61% (brown oil).

$^1$H-NMR ($CDCl_3$) δ: 0.83-0.92 (3H, m), 1.20-1.35 (12H, m), 1.53-1.85 (6H, m), 2.67 (2H, t, J=6.6 Hz), 3.11 (2H, t,

J=6.6 Hz), 3.39 (1H, brs), 3.81 (2H, t, J=6.6 Hz), 6.53-6.60 (2H, m), 6.81-6.90 (1H, m), 7.14-7.33 (7H, m), 7.51-7.58 (2H, m).

(4) Preparation of the Intermediate 387(4).

The title compound was obtained in the same manner as the Example 123(2) using the following starting materials.

Starting materials: the intermediate 387(3) and methyl chloroglyoxylate; Yield: 83% (colorless oil).

$^1$H-NMR ($CDCl_3$) δ: 0.83-0.92 (3H, m), 1.20-1.42 (12H, m), 1.53-1.85 (6H, m), 2.61 (2H, t, J=6.6 Hz), 3.57 (3H, s), 3.77 (2H, t, J=6.6 Hz), 3.97 (2H, t, J=6.6 Hz), 6.88-6.95 (1H, m), 7.05-7.19 (5H, m), 7.19-7.28 (4H, m), 7.46-7.55 (2H, m).

(5) Preparation of the Compound 387.

The title compound was obtained in the same manner as the Example 126(4) using the following starting material.

Starting material: the intermediate 387(4); Yield: 77% (colorless oil).

$^1$H-NMR ($CDCl_3$) δ: 0.83-0.92 (3H, m), 1.20-1.42 (12H, m), 1.53-1.85 (6H, m), 2.60 (2H, t, J=6.6 Hz), 3.75 (2H, t, J=6.6 Hz), 3.96 (2H, t, J=6.6 Hz), 7.02-7.28 (10H, m), 7.45-7.54 (2H, m).

Example 388

Preparation of the Compound 388

(1) Preparation of the Intermediate 388(1).

The title compound was obtained in the same manner as the Example 354(2) using the following starting materials.

Starting materials: 2-chloro-5-nitrophenol and 1-bromononane; Yield: 98% (colorless oil).

$^1$H-NMR ($CDCl_3$) δ: 0.85-0.93 (3H, m), 1.20-1.59 (12H, m), 1.82-1.95 (2H, m), 4.12 (2H, t, J=6.6 Hz), 7.47-7.54 (1H, m), 7.73-7.82 (2H, m).

(2) Preparation of the Intermediate 388(2).

The title compound was obtained in the same manner as the Example 371(1) using the following starting materials.

Starting materials: the intermediate 388(1) and 4-(trifluoromethoxy)phenylboronic acid; Yield: 76% (pale yellow oil).

$^1$H-NMR ($CDCl_3$) δ: 0.85-0.93 (3H, m), 1.20-1.44 (12H, m), 1.71-1.84 (2H, m), 4.08 (2H, t, J=6.6 Hz), 7.24-7.33 (2H, m), 7.44 (1H, d, J=8.1 Hz), 7.53-7.61 (2H, m), 7.83 (1H, d, J=2.1 Hz), 7.90 (1H, dd, J=2.1, 8.1 Hz).

(3) Preparation of the Intermediate 388(3).

The title compound was obtained in the same manner as the Example 125(2) using the following starting material.

Starting material: the intermediate 388(2); Yield: 71% (pale yellow oil).

$^1$H-NMR ($CDCl_3$) δ: 0.85-0.93 (3H, m), 1.20-1.42 (12H, m), 1.65-1.77 (2H, m), 3.73 (2H, brs), 3.90 (2H, t, J=6.6 Hz), 6.31 (1H, d, J=1.8 Hz), 6.34 (1H, dd, J=1.8, 8.1 Hz), 7.00 (1H, d, J=8.1 Hz), 7.14-7.22 (2H, m), 7.48-7.55 (2H, m).

(4) Preparation of the Intermediate 388(4).

The title compound was obtained in the same manner as the Example 123(2) using the following starting materials.

Starting materials: the intermediate 388(3) and methyl chloroglyoxylate; Yield: 100% (white solid).

$^1$H-NMR ($CDCl_3$) δ: 0.85-0.93 (3H, m), 1.20-1.42 (12H, m), 1.68-1.79 (2H, m), 3.95-4.03 (5H, m), 7.12 (1H, dd, J=2.1, 8.4 Hz), 7.20-7.26 (2H, m), 7.30 (1H, d, J=8.4 Hz), 7.51-7.59 (3H, m), 8.89 (1H, s).

(5) Preparation of the Intermediate 388(5).

The title compound was obtained in the same manner as the Example 125(4) using the following starting materials.

Starting materials: the intermediate 388(4) and 4-(tert-butyl)benzyl bromide; Yield: 23% (colorless oil).

$^1$H-NMR ($CDCl_3$) δ: 0.85-0.93 (3H, m), 1.20-1.39 (21H, m), 1.58-1.70 (2H, m), 3.61 (3H, s), 3.73 (2H, t, J=6.3 Hz), 4.93 (2H, s), 6.55 (1H, d, J=1.8 Hz), 6.76 (1H, dd, J=1.8, 8.1 Hz), 7.15-7.27 (5H, m), 7.30-7.37 (2H, m), 7.47-7.56 (2H, m).

(6) Preparation of the Compound 388.

The title compound was obtained in the same manner as the Example 126(4) using the following starting material.

Starting material: the intermediate 388(5); Yield: 90% (colorless oil).

$^1$H-NMR ($CDCl_3$) δ: 0.83-0.94 (3H, m), 1.20-1.35 (21H, m), 1.56-1.68 (2H, m), 3.71 (2H, t, J=6.3 Hz), 4.91 (2H, s), 6.50 (1H, d, J=1.8 Hz), 6.75 (1H, dd, J=1.8, 8.1 Hz), 7.15-7.27 (5H, m), 7.30-7.37 (2H, m), 7.48-7.56 (2H, m).

Example 389

Preparation of the Compound 389

(1) Preparation of the Intermediate 389(1).

The title compound was obtained in the same manner as the Example 123(1) using the following starting materials.

Starting materials: the intermediate 388(3) and 4-phenylbutyl bromide; Yield: 28% (brown oil).

$^1$H-NMR ($CDCl_3$) δ: 0.85-0.93 (3H, m), 1.20-1.42 (12H, m), 1.61-1.83 (6H, m), 2.68 (2H, t, J=7.5 Hz), 3.16 (2H, t, J=6.9 Hz), 3.69 (1H, s), 3.90 (2H, t, J=6.6 Hz), 6.19 (1H, d, J=1.8 Hz), 6.25 (1H, dd, J=1.8, 8.1 Hz), 7.12 (1H, d, J=8.1 Hz), 7.14-7.34 (7H, m), 7.48-7.55 (2H, m).

(2) Preparation of the Intermediate 389(2).

The title compound was obtained in the same manner as the Example 123(2) using the following starting materials.

Starting materials: the intermediate 389(1) and methyl chloroglyoxylate; Yield: 90% (colorless oil).

$^1$H-NMR ($CDCl_3$) δ: 0.84-0.92 (3H, m), 1.19-1.42 (12H, m), 1.59-1.77 (6H, m), 2.63 (2H, t, J=6.6 Hz), 3.60 (3H, s), 3.77-3.94 (4H, m), 6.76 (1H, d, J=2.1 Hz), 6.81 (1H, dd, J=2.1, 7.8 Hz), 7.10-7.32 (8H, m), 7.50-7.58 (2H, m).

(3) Preparation of the Compound 389.

The title compound was obtained in the same manner as the Example 126(4) using the following starting material.

Starting material: the intermediate 389(2); Yield: 79% (colorless oil).

$^1$H-NMR ($CDCl_3$) δ: 0.83-0.92 (3H, m), 1.18-1.40 (12H, m), 1.53-1.73 (6H, m), 2.51-2.65 (2H, m), 3.70-3.90 (4H, m), 6.67-6.79 (2H, m), 7.02-7.27 (8H, m), 7.50-7.58 (2H, m).

Example 390

Preparation of the Compound 390

(1) Preparation of the Intermediate 390(1).

The title compound was obtained in the same manner as the Example 123(3) using the following starting materials.

Starting materials: the intermediate 378(4) and 4-(trifluoromethyl)phenylboronic acid; Yield: 59% (colorless oil).

$^1$H-NMR ($CDCl_3$) δ: 0.84-0.97 (3H, m), 1.22-1.51 (4H, m), 1.52-1.74 (4H, m), 1.74-1.87 (2H, m), 2.53-2.67 (2H, m), 3.48-3.62 (5H, m), 3.94-4.08 (2H, m), 7.01 (1H, d, J=8.4 Hz), 7.06-7.25 (5H, m), 7.38 (1H, d, J=1.8 Hz), 7.55 (1H, dd, J=1.8, 8.4 Hz), 7.55-7.62 (2H, m), 7.65-7.72 (2H, m).

(2) Preparation of the Compound 390.

The title compound was obtained in the same manner as the Example 126(4) using the following starting material.

Starting material: the intermediate 390(1); Yield: 88% (white solid).

$^1$H-NMR ($CDCl_3$) δ: 0.85-0.97 (3H, m), 1.22-1.49 (4H, m), 1.52-1.88 (6H, m), 2.53-2.67 (2H, m), 3.70-3.88 (2H, m), 3.91-4.08 (2H, m), 6.98 (1H, d, J=8.4 Hz), 7.05-7.28 (5H, m), 7.33-7.39 (1H, m), 7.47-7.72 (5H, m).

Example 391

Preparation of the Compound 391

(1) Preparation of the Intermediate 391(1).

The title compound was obtained in the same manner as the Example 123(3) using the following starting materials.

Starting materials: the intermediate 378(4) and 3-(trifluoromethoxy)phenylboronic acid; Yield: 39% (pale brown oil).

$^1$H-NMR ($CDCl_3$) δ: 0.84-0.97 (3H, m), 1.22-1.50 (4H, m), 1.52-1.74 (4H, m), 1.73-1.87 (2H, m), 2.53-2.67 (2H, m), 3.49-3.63 (5H, m), 3.94-4.08 (2H, m), 7.00 (1H, d, J=8.7 Hz), 7.07-7.25 (5H, m), 7.30-7.35 (2H, m), 7.37-7.49 (3H, m), 7.51 (1H, dd, J=2.1, 8.7 Hz).

(2) Preparation of the Compound 391.

The title compound was obtained in the same manner as the Example 126(4) using the following starting material.

Starting material: the intermediate 391(1); Yield: 83% (colorless oil).

$^1$H-NMR ($CDCl_3$) δ: 0.84-0.96 (3H, m), 1.22-1.43 (4H, m), 1.51-1.79 (6H, m), 2.53-2.64 (2H, m), 3.70-3.85 (2H, m), 3.89-4.00 (2H, m), 6.96 (1H, d, J=8.4 Hz), 7.05-7.26 (6H, m), 7.30-7.37 (2H, m), 7.38-7.46 (2H, m), 7.51 (1H, dd, J=2.1, 8.4 Hz).

Example 392

Preparation of the Compound 392

(1) Preparation of the Intermediate 392(1).

The title compound was obtained in the same manner as the Example 123(3) using the following starting materials.

Starting materials: the intermediate 376(4) and 4-(trifluoromethyl)phenylboronic acid; Yield: 95% (colorless oil).

$^1$H-NMR ($CDCl_3$) δ: 0.84-0.97 (3H, m), 1.23-1.50 (4H, m), 1.52-1.74 (4H, m), 1.74-1.87 (2H, m), 2.54-2.67 (2H, m), 3.50-3.64 (5H, m), 3.91-4.09 (2H, m), 7.07-7.29 (8H, m), 7.62-7.75 (4H, m).

(2) Preparation of the Compound 392.

The title compound was obtained in the same manner as the Example 126(4) using the following starting material.

Starting material: the intermediate 392(1); Yield: 73% (colorless oil).

$^1$H-NMR ($CDCl_3$) δ: 0.86-0.96 (3H, m), 1.26-1.46 (4H, m), 1.55-1.80 (6H, m), 2.56-2.67 (2H, m), 3.70-3.88 (2H, m), 3.94-4.05 (2H, m), 7.05-7.29 (8H, m), 7.62-7.75 (4H, m).

Example 393

Preparation of the Compound 393

(1) Preparation of the Intermediate 393(1).

The title compound was obtained in the same manner as the Example 123(3) using the following starting materials.

Starting materials: the intermediate 376(4) and 3-(trifluoromethoxy)phenylboronic acid; Yield: 90% (colorless oil).

$^1$H-NMR ($CDCl_3$) δ: 0.84-0.97 (3H, m), 1.23-1.50 (4H, m), 1.52-1.74 (4H, m), 1.74-1.87 (2H, m), 2.53-2.67 (2H, m), 3.50-3.65 (5H, m), 3.96-4.08 (2H, m), 7.04-7.20 (5H, m), 7.20-7.36 (4H, m), 7.38-7.43 (1H, m), 7.45-7.52 (2H, m).

(2) Preparation of the Compound 393.

The title compound was obtained in the same manner as the Example 126(4) using the following starting material.

Starting material: the intermediate 393(1); Yield: 86% (colorless oil).

$^1$H-NMR ($CDCl_3$) δ: 0.84-0.97 (3H, m), 1.33-1.45 (4H, m), 1.52-1.83 (6H, m), 2.54-2.67 (2H, m), 3.66-3.87 (2H, m), 3.94-4.08 (2H, m), 7.02-7.20 (9H, m), 7.37-7.55 (3H, m).

Example 394

Preparation of the Compound 394

(1) Preparation of the Intermediate 394(1).

The title compound was obtained in the same manner as the Example 185(2) using the following starting materials.

Starting materials: the intermediate 211(1) and 1-heptanol; Yield: 94% (pale yellow oil).

$^1$H-NMR ($CDCl_3$) δ: 0.80-0.94 (3H, m), 1.16-1.47 (8H, m), 1.68-1.83 (2H, m), 4.02-4.14 (2H, m), 6.96-7.05 (1H, m), 7.20-7.31 (2H, m), 7.50-7.59 (2H, m), 8.15-8.28 (2H, m).

(2) Preparation of the Intermediate 394(2).

The title compound was obtained in the same manner as the Example 125(2) using the following starting material.

Starting material: the intermediate 394(1); Yield: 42% (pale yellow oil).

$^1$H-NMR ($CDCl_3$) δ: 0.83-0.92 (3H, m), 1.18-1.38 (8H, m), 1.55-1.69 (2H, m), 3.49 (2H, brs), 3.82 (2H, t, J=6.3 Hz), 6.62-6.70 (2H, m), 6.80-6.86 (1H, m), 7.17-7.25 (2H, m), 7.50-7.57 (2H, m).

(3) Preparation of the Intermediate 394(3).

The title compound was obtained in the same manner as the Example 123(1) using the following starting materials.

Starting materials: the intermediate 394(2) and 4-phenylbutyl bromide; Yield: 59% (pale yellow oil).

$^1$H-NMR ($CDCl_3$) δ: 0.83-0.92 (3H, m), 1.17-1.38 (8H, m), 1.51-1.79 (6H, m), 2.61-2.70 (2H, m), 3.07-3.17 (2H, m), 3.39 (1H, brs), 3.81 (2H, t, J=6.3 Hz), 6.53-6.60 (2H, m), 6.82-6.89 (1H, m), 7.13-7.32 (7H, m), 7.50-7.57 (2H, m).

(4) Preparation of the Intermediate 394(4).

The title compound was obtained in the same manner as the Example 123(2) using the following starting materials.

Starting materials: the intermediate 394(3) and methyl chloroglyoxylate; Yield: 93% (colorless oil).

$^1$H-NMR ($CDCl_3$) δ: 0.83-0.92 (3H, m), 1.19-1.43 (8H, m), 1.51-1.79 (6H, m), 2.56-2.66 (2H, m), 3.57 (3H, s), 3.73-3.80 (2H, m), 3.97 (2H, t, J=6.3 Hz), 6.91 (1H, d, J=8.4 Hz), 7.07-7.19 (5H, m), 7.19-7.29 (4H, m), 7.47-7.54 (2H, m).

(5) Preparation of the Compound 394.

The title compound was obtained in the same manner as the Example 126(4) using the following starting material.

Starting material: the intermediate 394(4); Yield: 82% (colorless oil).

$^1$H-NMR ($CDCl_3$) δ: 0.83-0.92 (3H, m), 1.18-1.43 (8H, m), 1.50-1.79 (6H, m), 2.52-2.65 (2H, m), 3.69-3.80 (2H, m), 3.96 (2H, t, J=6.3 Hz), 6.91 (1H, d, J=8.4 Hz), 7.07-7.19 (5H, m), 7.19-7.29 (4H, m), 7.47-7.54 (2H, m).

Example 401

Preparation of the Compound 401

(1) Preparation of the Intermediate 401(1).

The title compound was obtained in the same manner as the Example 2(1) using the following starting materials.

Starting materials: methyl 5-bromosalicylate and benzyl bromide; Yield: 99% (colorless oil).

$^1$H-NMR ($CDCl_3$) δ: 3.90 (3H, s), 5.17 (2H, s), 6.89 (1H, d, J=9.0 Hz), 7.32-7.54 (6H, m), 7.93 (1H, d, J=2.7 Hz).

(2) Preparation of the Intermediate 401(2).

The title compound was obtained in the same manner as the Example 1(2) using the following starting materials.

Starting materials: the intermediate 401(1) and 4-(trifluoromethoxy)phenylboronic acid; Yield: 54% (white solid).

$^1$H-NMR ($CDCl_3$) δ: 3.94 (3H, s), 5.24 (2H, s), 7.09 (1H, d, J=8.7 Hz), 7.24-7.44 (5H, m), 7.47-7.53 (2H, m), 7.53-7.59 (2H, m), 7.62 (1H, dd, J=2.4, 8.7 Hz), 8.03 (1H, d, J=2.4 Hz).

(3) Preparation of the Compound 401.

The title compound was obtained in the same manner as the Example 12(4) using the following starting material.

Starting material: the intermediate 401(2); Yield: 91% (white solid).

$^1$H-NMR (DMSO-$d_6$) δ: 5.35 (2H, s), 7.22 (1H, d, J=8.7 Hz), 7.27-7.32 (2H, m), 7.41-7.50 (5H, m), 7.56-7.64 (2H, m), 7.75 (1H, dd, J=2.4, 8.4 Hz), 8.43 (1H, d, J=2.4 Hz), 10.78 (1H, brs).

Example 403

Preparation of the Compound 403

(1) Preparation of the Intermediate 403(1).

The title compound was obtained in the same manner as the Example 2(1) using the following starting materials.

Starting materials: 2,5-dihydroxybenzaldehyde and 4-(trifluoromethoxy)benzyl bromide; Yield: 71% (white solid).

$^1$H-NMR ($CDCl_3$) δ: 5.05 (2H, s), 5.16 (2H, s), 7.00 (1H, d, J=9.0 Hz), 7.17-7.27 (5H, m), 7.43-7.48 (5H, m), 10.50 (1H, s).

(2) Preparation of the Compound 403.

The title compound was obtained in the same manner as the Example 2(3) using the following starting materials.

Starting materials: the intermediate 403(1) and malonic acid; Yield: 79% (white solid).

$^1$H-NMR ($CDCl_3$) δ: 5.04 (2H, s), 5.11 (2H, s), 6.49 (1H, d, J=15.9 Hz), 6.88 (1H, d, J=8.7 Hz), 6.96 (1H, dd, J=3.0, 8.7 Hz), 7.17 (1H, d, J=3.0 Hz), 7.23-7.28 (4H, m), 7.42-7.48 (4H, m), 8.13 (1H, d, J=15.9 Hz).

Example 404

Preparation of the Compound 404

The title compound was obtained in the same manner as the Example 3 using the following starting material.

Starting material: the compound 403; Yield: 39% (white solid).

$^1$H-NMR ($CDCl_3$) δ: 2.68 (2H, t, J=7.8 Hz), 2.98 (2H, t, J=7.8 Hz), 4.99 (2H, s), 5.04 (2H, s), 6.75 (1H, dd, J=3.0, 8.7 Hz), 6.80 (1H, d, J=8.7 Hz), 6.86 (1H, d, J=3.0 Hz), 7.22-7.26 (4H, m), 7.43-7.46 (4H, m).

Example 405

Preparation of the Compound 405

(1) Preparation of the Intermediate 405(1).

The title compound was obtained in the same manner as the Example 2(1) using the following starting materials.

Starting materials: the intermediate 18(1) and 1-chlorobutane; Yield: 97% (brown oil).

$^1$H-NMR ($CDCl_3$) δ: 1.01 (3H, t, J=7.5 Hz), 1.51-1.59 (2H, m), 1.84-1.89 (2H, m), 4.14 (2H, t, J=6.3 Hz), 7.07 (1H, d, J=8.7 Hz), 7.27 (2H, d, J=8.1 Hz), 7.56-7.59 (2H, m), 7.74 (1H, dd, J=2.7, 8.7 Hz), 8.04 (1H, d, J=2.7 Hz), 10.55 (1H, s).

(2) Preparation of the Compound 405.

The title compound was obtained in the same manner as the Example 2(3) using the following starting material.

Starting material: the intermediate 405(1) and malonic acid; Yield: 74% (white solid).

$^1$H-NMR ($CDCl_3$) δ: 1.02 (3H, t, J=7.2 Hz), 1.52-1.59 (2H, m), 1.86-1.95 (2H, m), 4.10 (2H, t, J=6.6 Hz), 6.64 (1H, d, J=16.2 Hz), 7.00 (1H, d, J=8.4 Hz), 7.28 (2H, d, J=7.8 Hz), 7.55-7.58 (3H, m), 7.71 (1H, d, J=2.4 Hz), 8.13 (1H, d, J=16.2 Hz).

Example 406

Preparation of the Compound 406

(1) Preparation of the Intermediate 406(1).

The title compound was obtained in the same manner as the Example 2(1) using the following starting materials.

Starting materials: the intermediate 18(1) and 1-chloropentane; Yield: 91% (brown oil).

$^1$H-NMR ($CDCl_3$) δ: 0.96 (3H, t, J=7.2 Hz), 1.38-1.55 (4H, m), 1.84-1.93 (2H, m), 4.13 (2H, t, J=6.6 Hz), 7.07 (1H, d, J=8.7 Hz), 7.27 (2H, d, J=7.8 Hz), 7.56-7.59 (2H, m), 7.74 (1H, dd, J=2.4, 8.7 Hz), 8.04 (1H, d, J=2.4 Hz), 10.56 (1H, s).

(2) Preparation of the Compound 406.

The title compound was obtained in the same manner as the Example 2(3) using the following starting materials.

Starting materials: the intermediate 406(1) and malonic acid; Yield: 67% (white solid).

$^1$H-NMR ($CDCl_3$) δ: 0.97 (3H, t, J=7.2 Hz), 1.39-1.53 (4H, m), 1.86-1.95 (2H, m), 4.10 (2H, t, J=6.6 Hz), 6.65 (1H, d, J=16.2 Hz), 7.00 (1H, d, J=8.4 Hz), 7.28 (2H, d, J=8.7 Hz), 7.52-7.58 (3H, m), 7.71 (1H, d, J=2.4 Hz), 8.13 (1H, d, J=16.2 Hz).

Example 407

Preparation of the Compound 407

The title compound was obtained in the same manner as the Example 3 using the following starting material.

Starting material: the compound 405; Yield: 77% (white solid).

$^1$H-NMR ($CDCl_3$) δ: 0.99 (3H, t, J=7.2 Hz), 1.45-1.56 (2H, m), 1.76-1.86 (2H, m), 2.71 (2H, t, J=7.8 Hz), 3.01 (2H, t, J=7.8 Hz), 4.02 (2H, t, J=6.3 Hz), 6.90 (1H, d, J=9.0 Hz), 7.24 (2H, d, J=8.7 Hz), 7.35-7.39 (2H, m), 7.51-7.54 (2H, m).

Example 408

Preparation of the Compound 408

The title compound was obtained in the same manner as the Example 3 using the following starting material.

Starting material: the compound 406; Yield: 75% (white solid).

$^1$H-NMR ($CDCl_3$) δ: 0.94 (3H, t, J=6.9 Hz), 1.36-1.52 (4H, m), 1.78-1.88 (2H, m), 2.72 (2H, t, J=7.8 Hz), 3.01 (2H, t,

J=7.8 Hz), 4.01 (2H, t, J=6.3 Hz), 6.89 (1H, d, J=9.0 Hz), 7.24 (2H, d, J=8.7 Hz), 7.35-7.39 (2H, m), 7.50-7.55 (2H, m).

Example 409

Preparation of the Compound 409

(1) Preparation of the Intermediate 409(1).

The title compound was obtained in the same manner as the Example 2(1) using the following starting materials.

Starting materials: 3,5-dihydroxybenzaldehyde and 4-(tert-butyl)benzyl bromide; Yield: 21% (pale yellow solid).

$^1$H-NMR ($CDCl_3$) δ: 1.33 (9H, s), 5.05 (2H, s), 5.51 (1H, brs), 6.74-6.76 (1H, m), 6.96-6.98 (1H, m), 7.08-7.09 (1H, m), 7.34-7.44 (4H, m), 9.87 (1H, s).

(2) Preparation of the Intermediate 409(2).

The title compound was obtained in the same manner as the Example 89(2) using the following starting materials.

Starting materials: the intermediate 409(1) and 4-(trifluoromethoxy)phenylboronic acid; Yield: 93% (yellow oil).

$^1$H-NMR ($CDCl_3$) δ: 1.33 (9H, m), 5.06 (2H, s), 6.86-6.87 (1H, m), 7.02-7.09 (3H, m), 7.20-7.26 (3H, m), 7.33-7.44 (4H, m), 9.90 (1H, s).

(3) Preparation of the Compound 409.

The title compound was obtained in the same manner as the Example 2(3) using the following starting materials.

Starting materials: the intermediate 409(2) and malonic acid; Yield: 84% (colorless oil).

$^1$H-NMR ($CDCl_3$) δ: 1.33 (9H, s), 5.02 (2H, s), 6.37 (1H, d, J=15.9 Hz), 6.65-6.67 (1H, m), 6.78 (1H, brs), 6.92 (1H, brs), 7.00-7.03 (2H, m), 7.18-7.22 (2H, m), 7.32-7.43 (4H, m), 7.67 (1H, d, J=15.9 Hz).

Example 410

Preparation of the Compound 410

The title compound was obtained in the same manner as the Example 3 using the following starting material.

Starting material: the compound 409; Yield: 97% (colorless oil).

$^1$H-NMR ($CDCl_3$) δ: 1.32 (9H, s), 2.65 (2H, t, J=7.7 Hz), 2.89 (2H, t, J=7.7 Hz), 4.95 (2H, s), 6.46-6.47 (2H, m), 6.61 (1H, brs), 6.95-7.00 (2H, m), 7.14-7.18 (2H, m), 7.30-7.41 (4H, m).

Example 411

Preparation of the Compound 411

(1) Preparation of the Intermediate 411(1).

The title compound was obtained in the same manner as the Example 2(1) using the following starting materials.

Starting materials: 5-nitrosalicylaldehyde and 4-(tert-butyl)benzyl bromide; Yield: 92% (yellow solid).

$^1$H-NMR ($CDCl_3$): δ 1.34 (9H, s), 5.29 (2H, s), 7.19 (1H, d, J=9.2 Hz), 7.36-7.48 (4H, m), 8.41 (1H, dd, J=2.9, 9.2 Hz), 8.72 (1H, d, J=2.9 Hz), 10.51 (1H, s).

(2) Preparation of the Intermediate 411(2).

The title compound was obtained in the same manner as the Example 26(1) using the following starting materials.

Starting materials: the intermediate 411(1); Yield: 81% (yellow solid).

$^1$H-NMR ($CDCl_3$) δ: 1.32 (3H, t, J=7.1 Hz), 1.33 (9H, s), 4.27 (2H, q, J=7.1 Hz), 5.25 (2H, s), 6.62 (1H, d, J=16.1 Hz), 7.04 (1H, d, J=9.1 Hz), 7.33-7.47 (4H, m), 8.02 (1H, d, J=16.1 Hz), 8.20 (1H, dd, J=2.7, 9.1 Hz), 8.44 (1H, d, J=2.7 Hz).

(3) Preparation of the Intermediate 411(3).

The title compound was obtained in the same manner as the Example 3 using the following starting material.

Starting material: the intermediate 411(2); Yield: 86% (brown oil).

$^1$H-NMR ($CDCl_3$) δ: 1.23 (3H, t, J=7.1 Hz), 1.33 (9H, s), 2.60 (2H, t, J=7.8 Hz), 2.92 (2H, t, J=7.8 Hz), 3.38 (2H, brs), 4.11 (2H, q, J=7.1 Hz), 4.97 (2H, s), 6.51 (1H, dd, J=2.9, 8.4 Hz), 6.57 (1H, d, J=2.9 Hz), 6.74 (1H, d, J=8.4 Hz), 7.33-7.41 (4H, m).

(4) Preparation of the Intermediate 411(4).

Triethylamine (0.265 ml, 1.901 mmol) was added dropwise to a mixture of the intermediate 411(3) (561 mg, 1.579 mmol), 4-(trifluoromethoxy)benzoyl chloride (0.300 ml, 1.903 mmol) and dichloromethane (3.0 ml) at 0° C., and the mixture was stirred at room temperature for 1.5 hours. The reaction mixture was diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=3:1) to give the title compound (0.669 g, 78%) as a white solid.

$^1$H-NMR ($CDCl_3$) δ: 1.22 (3H, t, J=7.1 Hz), 1.34 (9H, s), 2.65 (2H, t, J=7.7 Hz), 3.00 (2H, t, J=7.7 Hz), 4.11 (2H, q, J=7.1 Hz), 5.07 (2H, s), 6.89-6.92 (1H, m), 7.29-7.43 (7H, m), 7.50-7.54 (1H, m), 7.72 (1H, brs), 7.88-7.91 (2H, m).

(5) Preparation of the Compound 411.

The title compound was obtained in the same manner as the Example 12(4) using the following starting material.

Starting material: the intermediate 411(4); Yield: 71% (white solid).

$^1$H-NMR (DMSO-$d_6$) δ: 1.29 (9H, s), 2.49-2.54 (2H, m), 2.80-2.85 (2H, m), 5.09 (2H, s), 7.02-7.05 (1H, m), 7.37-7.44 (4H, m), 7.51-7.60 (4H, m), 8.05-8.08 (2H, m), 10.20 (1H, s), 12.15 (1H, brs).

Example 412

Preparation of the Compound 412

(1) Preparation of the Intermediate 412(1).

A mixture of the intermediate 411(3) (625 mg, 1.758 mmol), 4-(trifluoromethoxy)phenylboronic acid (724 mg, 3.517 mmol), anhydrous copper(II) acetate (319 mg, 1.759 mmol), triethylamine (0.490 ml, 3.515 mmol) and dichloromethane (9 ml) was stirred at room temperature for 4 days. The reaction mixture was filtered through Celite. After the filtrate was washed with a 5% aqueous solution of ammonia and saturated brine, the organic layer was dried over anhydrous sodium sulfate. The residue obtained by evaporation of the solvent under reduced pressure was purified by column chromatography on silica gel (n-hexane:ethyl acetate=2:1) to give the title compound (399 mg, 44%) as a brown oil.

$^1$H-NMR ($CDCl_3$) δ: 1.21 (3H, t, J=7.1 Hz), 1.34 (9H, s), 2.63 (2H, t, J=7.7 Hz), 2.97 (2H, t, J=7.7 Hz), 4.10 (2H, q, J=7.1 Hz), 5.04 (2H, s), 5.49 (1H, brs), 6.83-6.87 (3H, m), 6.92-7.08 (4H, m), 7.35-7.44 (4H, m).

(2) Preparation of the Compound 412.

The title compound was obtained in the same manner as the Example 12(4) using the following starting material.

Starting material: the intermediate 412(1); Yield: 65% (brown solid).

$^1$H-NMR (DMSO-$d_6$) δ: 1.29 (9H, s), 2.49-2.53 (2H, m), 2.77-2.82 (2H, m), 5.05 (2H, s), 6.90-7.00 (5H, m), 7.12-7.15 (2H, m), 7.36-7.44 (4H, m), 8.06 (1H, s), 12.12 (1H, brs).

Example 413

Preparation of the Compound 413

(1) Preparation of the Intermediate 413(1).

The title compound was obtained in the same manner as the Example 2(1) using the following starting materials.

Starting materials: 4-hydroxybenzaldehyde and 4-(trifluoromethoxy)benzyl bromide acid; Yield: 92% (white solid).

$^1$H-NMR ($CDCl_3$) δ: 5.14 (2H, s), 7.06-7.09 (2H, m), 7.24-7.27 (2H, m), 7.45-7.48 (2H, m), 7.84-7.88 (2H, m), 9.90 (1H, s).

(2) Preparation of the Intermediate 413(2).

The title compound was obtained in the same manner as the Example 95(2) using the following starting material.

Starting material: the intermediate 413(1); Yield: 65% (yellow solid).

$^1$H-NMR ($CDCl_3$) δ: 4.99 (2H, s), 6.74-6.78 (2H, m), 6.83-6.86 (2H, m), 7.22 (2H, d, J=8.0 Hz), 7.42-7.46 (2H, m).

(3) Preparation of the Intermediate 413(3).

The title compound was obtained in the same manner as the Example 83(2) using the following starting material.

Starting material: the intermediate 413(2); Yield: 57% (pale yellow solid).

$^1$H-NMR ($CDCl_3$) δ: 5.05 (2H, s), 6.95 (1H, d, J=9.0 Hz), 7.07 (1H, d, J=3.0 Hz), 7.21 (1H, dd, J=3.0, 9.0 Hz), 7.24 (2H, d, J=7.5 Hz), 7.44-7.47 (2H, m), 9.84 (1H, s), 10.68 (1H, s).

(4) Preparation of the Intermediate 413(4).

The title compound was obtained in the same manner as the Example 2(1) using the following starting materials.

Starting materials: the intermediate 413(3) and 4-(tert-butyl)benzyl bromide; Yield: 79% (white solid).

$^1$H-NMR ($CDCl_3$) δ: 1.33 (9H, s), 5.04 (2H, s), 5.12 (2H, s), 7.04 (1H, d, J=9.0 Hz), 7.18 (1H, dd, J=3.0, 9.0 Hz), 7.22-7.26 (2H, m), 7.36 (2H, d, J=8.5 Hz), 7.41-7.47 (5H, m), 10.50 (1H, s).

(5) Preparation of the Compound 413.

The title compound was obtained in the same manner as the Example 2(3) using the following starting materials.

Starting materials: the intermediate 413(4) and malonic acid; Yield: 78% (white solid).

$^1$H-NMR ($CDCl_3$) δ: 1.33 (9H, s), 5.03 (2H, s), 5.08 (2H, s), 6.49 (1H, d, J=16.0 Hz), 6.90-6.98 (2H, m), 7.16 (1H, d, J=2.5 Hz), 7.22-7.26 (2H, m), 7.33-7.36 (2H, m), 7.39-7.47 (4H, m), 8.13 (1H, d, J=16.0 Hz).

Example 414

Preparation of the Compound 414

The title compound was obtained in the same manner as the Example 3 using the following starting material.

Starting material: the compound 413; Yield: 84% (white solid).

$^1$H-NMR ($CDCl_3$) δ: 1.32 (9H, s), 2.68 (2H, t, J=7.5 Hz), 2.97 (2H, t, J=7.5 Hz), 4.98 (2H, s), 5.00 (2H, s), 6.75 (1H, dd, J=3.0, 9.0 Hz), 6.84 (1H, d, J=9.0 Hz), 6.85 (1H, d, J=3.0 Hz), 7.22 (2H, d, J=8.0 Hz), 7.32-7.46 (6H, m).

Example 415

Preparation of the Compound 415

(1) Preparation of the Intermediate 415(1).

Triethylamine (0.120 ml, 0.861 mmol) was added dropwise to a mixture of the intermediate 411(3) (237 mg, 0.667 mmol), 4-(trifluoromethoxy)benzenesulfonyl chloride and dichloromethane (1.5 ml) at 0° C., and the mixture was stirred at room temperature for 15 hours. The reaction mixture was diluted with water, and extracted with ethyl acetate. The organic layer was washed with a saturated aqueous solution of sodium hydrogen carbonate and saturated brine, and dried over anhydrous sodium sulfate. The residue obtained by evaporation of the solvent under reduced pressure was purified by column chromatography on silica gel (n-hexane:ethyl acetate=3:1) to give the title compound (306 mg, 79%) as a pale pink solid.

$^1$H-NMR ($CDCl_3$) δ: 1.21 (3H, t, J=7.1 Hz), 1.33 (9H, s), 2.53 (2H, t, J=7.5 Hz), 2.89 (2H, t, J=7.5 Hz), 4.08 (2H, q, J=7.1 Hz), 5.01 (2H, s), 6.39 (1H, brs), 6.77-6.90 (3H, m), 7.23-7.27 (2H, m), 7.31-7.42 (4H, m), 7.72-7.75 (2H, m).

(2) Preparation of the Compound 415.

The title compound was obtained in the same manner as the Example 12(4) using the following starting material.

Starting material: the intermediate 415(1); Yield: 37% (white solid).

$^1$H-NMR (DMSO-$d_6$) δ: 1.27 (9H, s), 2.38 (2H, t, J=7.6 Hz), 2.70 (2H, t, J=7.6 Hz), 4.99 (2H, s), 6.81-6.93 (3H, m), 7.32-7.41 (4H, m), 7.52-7.55 (2H, m), 7.78-7.82 (2H, m), 9.99 (1H, s), 12.10 (1H, s).

Example 416

Preparation of the Compound 416

(1) Preparation of the Intermediate 416(1).

A mixture of the intermediate 411(3) (1.157 g, 3.255 mmol), iodomethane (0.250 ml, 4.016 mmol), potassium carbonate (555 mg, 4.016 mmol) and dimethylformamide (6.5 ml) was stirred at 40° C. for 20 hours. The reaction mixture was diluted with water, and extracted with ethyl acetate. The organic layer was washed saturated brine, and dried over anhydrous sodium sulfate. The residue obtained by evaporation of the solvent under reduced pressure was purified by column chromatography on silica gel (n-hexane:ethyl acetate=3:1) to give the title compound (352 mg, 29%) as a brown oil.

$^1$H-NMR ($CDCl_3$) δ: 1.23 (3H, t, J=7.1 Hz), 1.33 (9H, s), 2.61 (2H, t, J=7.8 Hz), 2.79 (3H, s), 2.95 (2H, t, J=7.8 Hz), 3.43 (1H, brs), 4.11 (2H, q, J=7.1 Hz), 4.98 (2H, s), 6.44 (1H, dd, J=2.9, 8.6 Hz), 6.51 (1H, d, J=2.9 Hz), 6.80 (1H, d, J=8.6 Hz), 7.34-7.42 (4H, m).

(2) Preparation of the Intermediate 416(2).

The title compound was obtained in the same manner as the Example 411(4) using the following starting materials.

Starting materials: the intermediate 416(1) and 4-(trifluoromethoxy)benzoyl chloride; Yield: 49% (brown oil).

$^1$H-NMR ($CDCl_3$) δ: 1.22 (3H, t, J=7.1 Hz), 1.33 (9H, s), 2.47 (2H, t, J=7.6 Hz), 2.87 (2H, t, J=7.6 Hz), 3.44 (3H, s), 4.08 (2H, q, J=7.1 Hz), 4.99 (2H, s), 6.72-6.89 (3H, m), 6.99-7.02 (2H, m), 7.29-7.42 (6H, m).

(3) Preparation of the Compound 416.

The title compound was obtained in the same manner as the Example 12(4) using the following starting material.

Starting material: the intermediate 416(2); Yield: 71% (white solid).

$^1$H-NMR ($CDCl_3$) δ: 1.33 (9H, s), 2.54 (2H, t, J=7.4 Hz), 2.87 (2H, t, J=7.4 Hz), 3.43 (3H, s), 4.99 (2H, s), 6.71-6.89 (3H, m), 6.99-7.02 (2H, m), 7.28-7.41 (6H, m).

Example 417

Preparation of the Compound 417

(1) Preparation of the Intermediate 417(1).

The title compound was obtained in the same manner as the Example 412(1) using the following starting materials.

Starting materials: the intermediate 416(1) and 4-(trifluoromethoxy)phenylboronic acid; Yield: 39% (brown oil).

$^1$H-NMR ($CDCl_3$) δ: 1.20 (3H, t, J=7.1 Hz), 1.34 (9H, s), 2.63 (2H, t, J=7.7 Hz), 2.97 (2H, t, J=7.7 Hz), 3.23 (3H, s), 4.08 (2H, q, J=7.1 Hz), 5.06 (2H, s), 6.67-6.71 (2H, m), 6.88-7.03 (5H, m), 7.36-7.44 (4H, m).

(2) Preparation of the Compound 417.

The title compound was obtained in the same manner as the Example 12(4) using the following starting material.

Starting material: the intermediate 417(1); Yield: 79% (white solid).

$^1$H-NMR ($CDCl_3$) δ: 1.34 (9H, s), 2.69 (2H, t, J=7.6 Hz), 2.97 (2H, t, J=7.6 Hz), 3.23 (3H, s), 5.06 (2H, s), 6.68-6.71 (2H, m), 6.89-7.04 (5H, m), 7.35-7.44 (4H, m).

Example 418

Preparation of the Compound 418

(1) Preparation of the Intermediate 418(1).

A mixture of 1-bromo-4-(trifluoromethoxy)benzene (711 mg, 2.95 mmol), 1-(tert-buthoxycarbonyl)piperadine (500 mg, 2.68 mmol), sodium tert-butoxide (515 mg, 5.36 mmol), tris(dibenzylideneacetone)dipalladium(0) (245 mg, 0.26 mmol), 2,2'-bis(diphenylphosphino)-1,1'-binaphthyl (333 mg, 0.53 mmol) and toluene (10 ml) was stirred at 100° C. for 4 hours. After the reaction mixture was filtered, the residue obtained by concentration of the filtrate was purified by column chromatography on silica gel (n-hexane:ethyl acetate=4:1) to give the title compound (1.03 g, 100%) as a yellow solid.

$^1$H-NMR ($CDCl_3$) δ: 1.49 (9H, s), 3.11 (4H, t, J=5.1 Hz), 3.58 (4H, t, J=5.1 Hz), 6.87-6.91 (2H, m), 7.10-7.14 (2H, m).

(2) Preparation of the Intermediate 418(2).

A mixture of the intermediate 418(1) (1.03 g, 2.97 mmol), ethyl acetate (10 ml) and 4 N hydrochloric acid-ethyl acetate (10 ml) was stirred at room temperature for 1 hour. The precipitated solid was collected by filtration to give the title compound (773 mg, 92%) as a white solid.

$^1$H-NMR (DMSO-$d_6$) δ: 3.21 (4H, brs), 3.37-3.40 (4H, m), 7.07 (2H, d, J=9.3 Hz), 7.25 (2H, d, J=9.3 Hz), 9.13 (1H, brs).

(3) Preparation of the Intermediate 418(3).

The title compound was obtained in the same manner as the Example 418(1) using the following starting materials.

Starting materials: the intermediate 4(1) and the intermediate 418(2); Yield: 13% (orange solid).

$^1$H-NMR ($CDCl_3$) δ: 1.34 (9H, s), 3.27-3.33 (8H, m), 5.13 (2H, s), 6.93-6.96 (2H, m), 7.03-7.06 (1H, m), 7.13-7.16 (2H, m), 7.20-7.27 (2H, m), 7.35-7.38 (2H, m), 7.41-7.45 (2H, m), 10.53 (1H, s).

(4) Preparation of the Compound 418.

The title compound was obtained in the same manner as the Example 2(3) using the following starting materials.

Starting materials: the intermediate 418(3) and malonic acid; Yield: 60% (yellow solid).

$^1$H-NMR ($CDCl_3$) δ: 1.33 (9H, s), 3.23-3.27 (4H, m), 3.32-3.35 (4H, m), 5.10 (2H, s), 6.54 (1H, d, J=16.2 Hz), 6.92-7.04 (4H, m), 7.13-7.18 (3H, m), 7.34-7.43 (4H, m), 8.14 (1H, d, J=16.2 Hz).

Example 419

Preparation of the Compound 419

The title compound was obtained in the same manner as the Example 3 using the following starting material.

Starting material: the compound 418; Yield: 56% (white solid).

$^1$H-NMR (DMSO-$d_6$) δ: 1.28 (9H, s), 2.80 (2H, t, J=7.8 Hz), 3.13-3.15 (4H, m), 3.27-3.32 (6H, m), 5.02 (2H, s), 6.78 (1H, dd, J=2.7, 9.0 Hz), 6.88-6.94 (2H, m), 7.06 (2H, d, J=8.7 Hz), 7.21 (2H, d, J=8.7 Hz), 7.34-7.42 (4H, m), 12.12 (1H, brs).

Example 420

Preparation of the Compound 420

Sodium hydroxide (183 mg, 4.584 mg) was added to a mixture of the intermediate 6(3) (238 mg, 0.573 mmol), 1,1,1-trichloro-2-methyl-2-propanol (203 mg, 1.146 mmol) and acetone (3 ml) at 0° C., and the mixture was stirred at room temperature for 2 hours. The reaction mixture was cooled to 0° C., acidified by addition of 2 N hydrochloric acid, and extracted with ethyl acetate. The organic layer was washed with a saturated aqueous solution of sodium hydrogen carbonate and saturated brine, and dried over anhydrous sodium sulfate. The residue obtained by evaporation of the solvent under reduced pressure was washed with a mixture of n-hexane and diisopropyl ether to give the title compound (105 mg, 37%) as a white solid.

$^1$H-NMR ($CDCl_3$) δ: 1.29 (9H, s), 1.48 (6H, s), 5.13 (2H, s), 6.72-6.79 (2H, m), 6.96 (1H, d, J=7.8 Hz), 7.36-7.46 (6H, m), 7.61 (2H, d, J=8.7 Hz).

Example 421

Preparation of the Compound 421

(1) Preparation of the Intermediate 421(1).

The title compound was obtained in the same manner as the Example 2(1) using the following starting materials.

Starting materials: methyl 5-iodosalicylate and 4-(tert-butyl)benzyl bromide; Yield: 88% (white solid).

$^1$H-NMR ($CDCl_3$) δ: 1.32 (9H, s), 3.90 (3H, s), 5.13 (2H, s), 6.79 (1H, d, J=9.0 Hz), 7.35-7.44 (4H, m), 7.69 (1H, dd, J=2.5, 9.0 Hz), 8.09 (1H, d, J=2.5 Hz).

(2) Preparation of the Intermediate 421(2).

The title compound was obtained in the same manner as the Example 1(2) using the following starting material.

Starting material: the intermediate 421(1); Yield: 54% (white solid).

$^1$H-NMR ($CDCl_3$) δ: 1.33 (9H, s), 3.94 (3H, s), 5.21 (2H, s), 7.11 (1H, d, J=8.7 Hz), 7.24-7.31 (2H, m), 7.38-7.48 (4H, m), 7.53-7.60 (2H, m), 7.63 (1H, dd, J=2.4, 8.7 Hz), 8.03 (1H, d, J=2.4 Hz).

(3) Preparation of the Compound 421.

The title compound was obtained in the same manner as the Example 12(4) using the following starting material.

Starting material: the intermediate 421(2); Yield: 99% (white solid).

$^1$H-NMR (DMSO-$d_6$) δ: 1.27 (9H, s), 5.18 (2H, s), 7.23 (1H, d, J=8.7 Hz), 7.35-7.46 (6H, m), 7.67-7.78 (3H, m), 7.80 (1H, d, J=2.4 Hz).

Example 422

Preparation of the Compound 422

A 1.65 M solution of n-Butyllithium in hexane (345 μL, 0.570 mmol) was added dropwise to a solution of the compound 12 (130 mg, 0.285 mmol) in anhydrous tetrahydrofuran (2 ml) at −78° C., and the mixture was stirred for 30 minutes. A small portion of trifluoroacetic acid was added to the reaction mixture, and the mixture was left at room temperature. The reaction mixture was diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=3:1) to give the title compound (35 mg, 24%) as a pale yellow oil.

$^1$H-NMR ($CDCl_3$) δ: 0.83 (3H, t, J=6.9 Hz), 1.23-1.38 (11H, m), 1.50-1.70 (4H, m), 2.80-3.00 (3H, m), 6.87 (1H, d, J=8.4 Hz), 6.91 (2H, m), 7.21-7.28 (2H, m), 7.31 (1H, dd, J=2.1, 8.4 Hz), 7.34-7.38 (2H, m), 7.41 (1H, d, J=2.1 Hz), 7.50-7.54 (2H, m).

Example 423

Preparation of the Compound 423

(1) Preparation of the Intermediate 423(1).

The title compound was obtained in the same manner as the Example 1(2) using the following starting materials.

Starting materials: 5-bromo-2-fluoro-1-nitrobenzene and 4-(trifluoromethoxy)phenylboronic acid; Yield: 99% (brown oil).

1H-NMR ($CDCl_3$) δ: 7.33-7.43 (3H, m), 7.57-7.62 (2H, m), 7.79-7.84 (1H, m), 8.23 (1H, dd, J=2.4, 6.9 Hz).

(2) Preparation of the Intermediate 423(2).

The title compound was obtained in the same manner as the Example 12(2) using the following starting materials.

Starting materials: the intermediate 423(1) and 4-(tert-butyl)phenol; Yield: 100% (whitish-pink solid).

$^1$H-NMR ($CDCl_3$) δ: 1.34 (9H, s), 7.01-7.04 (2H, m), 7.08 (1H, d, J=8.4 Hz), 7.30-7.34 (2H, m), 7.40-7.43 (2H, m), 7.56-7.59 (2H, m), 7.65 (1H, dd, J=2.4, 8.4 Hz), 8.13 (1H, d, J=2.4 Hz).

(3) Preparation of the Intermediate 423(3).

The title compound was obtained in the same manner as the Example 3 using the following starting material.

Starting material: the intermediate 423(2); Yield: 100% (white solid).

$^1$H-NMR ($CDCl_3$) δ: 1.32 (9H, s), 3.91 (2H, brs), 6.85-7.00 (5H, m), 7.24-7.26 (2H, m), 7.33-7.36 (2H, m), 7.53-7.56 (2H, m).

(4) Preparation of the Intermediate 423(4).

The title compound was obtained in the same manner as the Example 416(1) using the following starting materials.

Starting materials: the intermediate 423(3) and ethyl 2-bromohexanoate; Yield: 34% (pale yellow oil).

$^1$H-NMR ($CDCl_3$) δ: 0.85-0.91 (3H, m), 1.22-1.56 (16H, m), 1.74-1.89 (2H, m), 4.08-4.24 (3H, m), 4.73 (1H, brs), 6.79-6.89 (3H, m), 6.96-7.02 (2H, m), 7.23-7.27 (2H, m), 7.33-7.38 (2H, m), 7.51-7.56 (2H, m).

(5) Preparation of the Compound 423.

The title compound was obtained in the same manner as the Example 12(4) using the following starting material.

Starting material: the intermediate 423(4); Yield: 53% (white solid).

$^1$H-NMR (DMSO-$d_6$) δ: 0.78-0.83 (3H, m), 1.23-1.28 (13H, m), 1.52-1.57 (2H, m), 4.21-4.23 (1H, m), 5.10 (1H, brs), 6.83-6.96 (5H, m), 7.36-7.45 (4H, m), 7.70-7.74 (2H, m).

Example 424

Preparation of the Compound 424

(1) Preparation of the Intermediate 424(1).

The title compound was obtained in the same manner as the Example 2(1) using the following starting materials.

Starting materials: the intermediate 301(2) and 1-chloropentane; Yield: 76% (yellow oil).

$^1$H-NMR ($CDCl_3$) δ: 0.88-0.95 (9H, m), 1.31-1.49 (12H, m), 1.78-1.87 (6H, m), 4.04 (4H, t, J=6.6 Hz), 4.20 (2H, t, J=6.9 Hz), 4.65 (2H, s), 6.69 (2H, s), 7.25-7.27 (2H, m), 7.51-7.55 (2H, m).

(2) Preparation of the Compound 424.

The title compound was obtained in the same manner as the Example 12(4) using the following starting material.

Starting material: the intermediate 424(1); Yield: 23% (white solid).

$^1$H-NMR (DMSO-$d_6$) δ: 0.89 (6H, t, J=6.9 Hz), 1.31-1.42 (8H, m), 1.68-1.74 (4H, m), 4.01-4.08 (6H, m), 6.86 (2H, s), 7.39-7.41 (2H, m), 7.75-7.78 (2H, m).

Example 425

Preparation of the Compound 425

(1) Preparation of the Intermediate 425(1).

The title compound was obtained in the same manner as the Example 2(1) using the following starting materials.

Starting materials: the intermediate 301(2) and 1-chloroheptane; Yield: 100% (yellow oil).

$^1$H-NMR ($CDCl_3$) δ: 0.88-0.95 (9H, m), 1.31-1.49 (24H, m), 1.78-1.87 (6H, m), 4.04 (4H, t, J=6.6 Hz), 4.20 (2H, t, J=6.9 Hz), 4.65 (2H, s), 6.69 (2H, s), 7.25-7.27 (2H, m), 7.51-7.55 (2H, m).

(2) Preparation of the Compound 425.

The title compound was obtained in the same manner as the Example 12(4) using the following starting material.

Starting material: the intermediate 425(1); Yield: 23% (white solid).

$^1$H-NMR (DMSO-$d_6$) δ: 0.86 (6H, t, J=6.9 Hz), 1.28-1.38 (16H, m), 1.67-1.74 (4H, m), 4.01-4.08 (6H, m), 6.86 (2H, s), 7.39-7.41 (2H, m), 7.75-7.78 (2H, m).

Example 426

Preparation of the Compound 426

(1) Preparation of the Intermediate 426(1).

The title compound was obtained in the same manner as the Example 1(2) using the following starting materials.

Starting materials: 1-bromo-3,5-dimethoxybenzene and 4-(trifluoromethoxy)phenylboronic acid; Yield: 95% (pale brown oil).

$^1$H-NMR ($CDCl_3$) δ: 3.85 (6H, s), 6.48 (1H, t, J=2.4 Hz), 6.68 (2H, d, J=2.4 Hz), 7.20-7.33 (2H, m), 7.52-7.64 (2H, m).

(2) Preparation of the Intermediate 426(2).

The title compound was obtained in the same manner as the Example 83(1) using the following starting material.

Starting material: the intermediate 426(1); Yield: 94% (white solid).

$^1$H-NMR ($CDCl_3$) δ: 5.04 (2H, s), 6.36 (1H, t, J=2.1 Hz), 6.60 (2H, d, J=2.1 Hz), 7.20-7.31 (2H, m), 7.50-7.58 (2H, m).

(3) Preparation of the Intermediate 426(3).

The title compound was obtained in the same manner as the Example 2(1) using the following starting materials.

Starting materials: the intermediate 426(2) and ethyl 2-bromohexanoate; Yield: 24% (pale brown oil).

$^1$H-NMR ($CDCl_3$) δ: 0.93 (3H, t, J=7.2 Hz), 1.26 (3H, t, J=7.2 Hz), 1.30-1.62 (4H, m), 1.86-2.04 (2H, m), 4.24 (2H, q, J=7.2 Hz), 4.58-4.67 (2H, m), 6.38 (1H, t, J=2.1 Hz), 6.60-6.70 (2H, m), 7.20-7.30 (2H, m), 7.47-7.58 (2H, m).

(4) Preparation of the Intermediate 426(4).

The title compound was obtained in the same manner as the Example 89(2) using the following starting materials.

Starting materials: the intermediate 426(3) and 4-(tert-butyl)phenylboronic acid; Yield: 6% (colorless oil).

$^1$H-NMR ($CDCl_3$) δ: 0.92 (3H, t, J=7.2 Hz), 1.18-1.62 (16H, m), 1.84-2.04 (2H, m), 4.21 (2H, q, J=7.2 Hz), 4.55-4.65 (1H, m), 6.47-6.54 (1H, m), 6.75-6.85 (2H, m), 6.93-7.03 (2H, m), 7.20-7.30 (2H, m), 7.31-7.40 (2H, m), 7.45-7.58 (2H, m).

(5) Preparation of the Compound 426.

The title compound was obtained in the same manner as the Example 12(4) using the following starting material.

Starting material: the intermediate 426(4); Yield: 85% (colorless oil).

$^1$H-NMR ($CDCl_3$) δ: 0.91 (3H, t, J=7.2 Hz), 1.20-1.62 (13H, m), 1.90-2.06 (2H, m), 4.68 (1H, t, J=6.0 Hz), 6.50-6.58 (1H, m), 6.75-6.84 (2H, m), 6.93-7.02 (2H, m), 7.18-7.28 (2H, m), 7.31-7.40 (2H, m), 7.45-7.54 (2H, m).

Example 427

Preparation of the Compound 427

(1) Preparation of the Intermediate 427(1).

The title compound was obtained in the same manner as the Example 89(2) using the following starting materials.

Starting materials: the intermediate 426(2) and 4-(tert-butyl)phenylboronic acid; Yield: 24% (brown oil).

$^1$H-NMR ($CDCl_3$) δ: 1.33 (9H, s), 5.14 (1H, s), 6.43-6.49 (1H, m), 6.71-6.77 (1H, m), 6.77-6.82 (1H, m), 6.95-7.04 (2H, m), 7.20-7.30 (2H, m), 7.32-7.41 (2H, m), 7.48-7.57 (2H, m).

(2) Preparation of the Intermediate 427(2).

The title compound was obtained in the same manner as the Example 105(2) using the following starting materials.

Starting materials: the intermediate 427(1) and ethyl bromoacetate; Yield: 65% (pale yellow oil).

$^1$H-NMR ($CDCl_3$) δ: 1.29 (3H, t, J=7.2 Hz), 1.33 (9H, s), 4.27 (2H, q, J=7.2 Hz), 4.62 (2H, s), 6.51-6.56 (1H, m), 6.78-6.86 (2H, m), 6.94-7.02 (2H, m), 7.21-7.30 (2H, m), 7.32-7.40 (2H, m), 7.48-7.57 (2H, m).

(3) Preparation of the Compound 427.

The title compound was obtained in the same manner as the Example 12(4) using the following starting material.

Starting material: the intermediate 427(2); Yield: 100% (white solid).

$^1$H-NMR ($CDCl_3$) δ: 1.33 (9H, s), 4.70 (2H, s), 6.52-6.59 (1H, m), 6.78-6.86 (2H, m), 6.94-7.03 (2H, m), 7.21-7.30 (2H, m), 7.32-7.42 (2H, m), 7.48-7.58 (2H, m).

Example 428

Preparation of the Compound 428

(1) Preparation of the Intermediate 428(1).

The title compound was obtained in the same manner as the Example 416(1) using the following starting materials.

Starting materials: the intermediate 423(3) and 1-chlorobutane; Yield: 16% (pale yellow solid).

$^1$H-NMR ($CDCl_3$) δ: 0.94 (3H, t, J=7.5 Hz), 1.23-1.47 (11H, m), 1.56-2.04 (2H, m), 3.20 (2H, t, J=6.6 Hz), 4.25 (1H, brs), 6.74-6.78 (1H, m), 6.84-6.88 (2H, m), 6.93-6.99 (2H, m), 7.24-7.27 (2H, m), 7.31-7.37 (2H, m), 7.55-7.61 (2H, m).

(2) Preparation of the Intermediate 428(2).

The title compound was obtained in the same manner as the Example 416(1) using the following starting materials.

Starting materials: the intermediate 428(1) and ethyl bromoacetate; Yield: 39% (colorless oil).

$^1$H-NMR ($CDCl_3$) δ: 0.84 (3H, t, J=7.5 Hz), 1.16 (3H, t, J=7.2 Hz), 1.16-1.26 (2H, m), 1.31 (9H, s), 1.43-1.54 (2H, m), 3.29-3.35 (2H, m), 4.02-4.10 (4H, m), 6.84-6.89 (2H, m), 6.95 (1H, d, J=8.4 Hz), 7.06 (1H, dd, J=2.1, 8.4 Hz), 7.23-7.33 (5H, m), 7.54-7.60 (2H, m).

(3) Preparation of the Compound 428.

The title compound was obtained in the same manner as the Example 12(4) using the following starting material.

Starting material: the intermediate 428(2); Yield: 42% (white solid).

$^1$H-NMR (DMSO-$d_6$) δ: 0.77 (3H, t, J=7.2 Hz), 1.05-1.17 (2H, m), 1.27 (9H, s), 1.35-1.48 (2H, m), 3.26-3.33 (2H, m), 4.00 (2H, s), 6.82-6.86 (2H, m), 6.92 (1H, d, J=8.1 Hz), 7.12-7.16 (1H, m), 7.22-7.24 (1H, m), 7.32-7.36 (2H, m), 7.42-7.46 (2H, m), 7.71-7.74 (2H, m), 12.33 (1H, brs).

Example 429

Preparation of the Compound 429

(1) Preparation of the Intermediate 429(1).

The title compound was obtained in the same manner as the Example 2(1) using the following starting materials.

Starting materials: 5-bromosalicylaldehyde and 1-bromohexane; Yield: 100% (colorless oil).

$^1$H-NMR ($CDCl_3$) δ: 0.91 (3H, t, J=7.0 Hz), 1.28-1.42 (4H, m), 1.42-1.54 (2H, m), 1.79-1.89 (2H, m), 4.06 (2H, t, J=6.4 Hz), 6.88 (1H, d, J=9.0 Hz), 7.60 (1H, dd, J=2.7, 8.9 Hz), 7.92 (1H, d, J=2.6 Hz), 10.42 (1H, s).

(2) Preparation of the Intermediate 429(2).

The title compound was obtained in the same manner as the Example 1(2) using the following starting materials.

Starting materials: the intermediate 429(1) and 4-(trifluoromethoxy)phenylboronic acid; Yield: 81% (white solid).

$^1$H-NMR ($CDCl_3$) δ: 0.92 (3H, t, J=7.0 Hz), 1.32-1.42 (4H, m), 1.45-1.57 (2H, m), 1.83-1.93 (2H, m), 4.13 (2H, t, J=6.4 Hz), 7.07 (1H, d, J=8.8 Hz), 7.25-7.30 (2H, m), 7.58 (2H, d, J=8.8 Hz), 7.74 (1H, dd, J=2.6, 8.6 Hz), 8.04 (1H, d, J=2.6 Hz), 10.55 (1H, s).

(3) Preparation of the Intermediate 429(3).

The title compound was obtained in the same manner as the Example 95(2) using the following starting material.

Starting material: the intermediate 429(2); Yield: 69% (colorless oil).

$^1$H-NMR ($CDCl_3$) δ: 0.92 (3H, t, J=7.1 Hz), 1.32-1.42 (4H, m), 1.42-1.54 (2H, m), 1.78-1.89 (2H, m), 4.08 (2H, t, J=6.6 Hz), 5.71 (1H, s), 6.90 (1H, d, J=8.4 Hz), 7.03 (1H, dd, J=2.4, 8.4 Hz), 7.15 (1H, d, J=2.2 Hz), 7.22-7.27 (2H, m), 7.54 (2H, d, J=8.4 Hz).

(4) Preparation of the Intermediate 429(4).

The title compound was obtained in the same manner as the Example 105(2) using the following starting materials.

Starting materials: the intermediate 429(3) and ethyl 2-bromooctanoate; Yield: 77% (colorless oil).

$^1$H-NMR ($CDCl_3$) δ: 0.86-0.95 (6H, m), 1.24 (3H, t, J=7.1 Hz), 1.28-2.03 (14H, m), 3.97-4.07 (2H, m), 4.16-4.26 (2H, m), 4.68 (1H, t, J=6.3 Hz), 6.95 (1H, d, J=9.0 Hz), 7.13-7.18 (2H, m), 7.24 (2H, d, J=8.8 Hz), 7.50 (2H, d, J=8.8 Hz).

(5) Preparation of the Compound 429.

The title compound was obtained in the same manner as the Example 12(4) using the following starting material.

Starting material: the intermediate 429(4); Yield: 95% (white solid).

$^1$H-NMR ($CDCl_3$) δ: 0.82-0.98 (6H, m), 1.25-1.69 (14H, m), 1.81-1.92 (2H, m), 2.00-2.09 (2H, m), 4.07 (2H, t, J=6.7 Hz), 4.62 (1H, t, J=5.7 Hz), 6.99 (1H, d, J=8.4 Hz), 7.17-7.30 (4H, m), 7.50 (2H, d, J=8.6 Hz).

Example 430

Preparation of the Compound 430

(1) Preparation of the Intermediate 430(1).

The title compound was obtained in the same manner as the Example 2(1) using the following starting materials.

Starting materials: 4-bromosalicylaldehyde and 1-bromohexane; Yield: 92% (pale yellow solid).

$^1$H-NMR ($CDCl_3$) δ: 0.90-0.95 (3H, m), 1.33-1.39 (4H, m), 1.45-1.53 (2H, m), 1.82-1.91 (2H, m), 4.08 (2H, t, J=6.4 Hz), 7.16 (1H, s), 7.18-7.19 (1H, m), 7.70 (1H, dd, J=0.6, 7.9 Hz), 10.44 (1H, d, J=0.6 Hz).

(2) Preparation of the Intermediate 430(2).

The title compound was obtained in the same manner as the Example 1(2) using the following starting materials.

Starting materials: the intermediate 430(1) and 4-(trifluoromethoxy)phenylboronic acid; Yield: 93% (colorless oil).

$^1$H-NMR ($CDCl_3$) δ: 0.88-0.94 (3H, m), 1.33-1.40 (4H, m), 1.47-1.56 (2H, m), 1.84-1.93 (2H, m), 4.16 (2H, t, J=6.4 Hz), 7.11 (1H, d, J=1.3 Hz), 7.18-7.21 (1H, m), 7.30-7.34 (2H, m), 7.60-7.65 (2H, m), 7.91 (1H, d, J=7.9 Hz), 10.53 (1H, d, J=0.7 Hz).

(3) Preparation of the Intermediate 430(3).

The title compound was obtained in the same manner as the Example 95(2) using the following starting material.

Starting material: the intermediate 430(2); Yield: 81% (pink solid).

$^1$H-NMR ($CDCl_3$) δ: 0.90-0.94 (3H, m), 1.33-1.41 (4H, m), 1.44-1.53 (2H, m), 1.81-1.90 (2H, m), 4.11 (2H, t, J=6.6 Hz), 5.69 (1H, s), 6.98-7.08 (3H, m), 7.24-7.27 (2H, m), 7.51-7.56 (2H, m).

(4) Preparation of the Intermediate 430(4).

The title compound was obtained in the same manner as the Example 105(2) using the following starting materials.

Starting materials: the intermediate 430(3) and ethyl 2-bromooctanoate; Yield: 83% (colorless oil).

$^1$H-NMR ($CDCl_3$) δ: 0.87-0.94 (6H, m), 1.27 (3H, t, J=7.1 Hz), 1.27-1.38 (10H, m), 1.38-1.61 (4H, m), 1.79-2.05 (4H, m), 3.99-4.12 (2H, m), 4.17-4.28 (2H, m), 4.63-4.67 (1H, m), 6.94 (1H, d, J=8.2 Hz), 7.01-7.07 (2H, m), 7.24-7.27 (2H, m), 7.51-7.56 (2H, m).

(5) Preparation of the Compound 430.

The title compound was obtained in the same manner as the Example 12(4) using the following starting material.

Starting material: the intermediate 430(4); Yield: 87% (colorless solid).

$^1$H-NMR ($CDCl_3$) δ: 0.88-0.94 (6H, m), 1.24-1.52 (12H, m), 1.58-1.65 (2H, m), 1.83-1.93 (2H, m), 2.01-2.09 (2H, m), 4.08-4.12 (2H, m), 4.60 (1H, t, J=5.5 Hz), 7.04-7.11 (3H, m), 7.27-7.30 (2H, m), 7.52-7.57 (2H, m).

Example 431

Preparation of the Compound 431

(1) Preparation of the Intermediate 431(1).

The title compound was obtained in the same manner as the Example 12(2) using the following starting materials.

Starting materials: 2-fluoro-5-nitrobenzaldehyde and 4-(tert-butyl)phenol; Yield: 97% (white solid).

$^1$H-NMR ($CDCl_3$) δ: 1.37 (9H, s), 6.93 (1H, d, J=9.0 Hz), 7.06-7.16 (2H, m), 7.47-7.52 (2H, m), 8.30 (1H, dd, J=3.0, 9.0 Hz), 8.79 (1H, d, J=3.0 Hz), 10.60 (1H, s).

(2) Preparation of the Intermediate 431(2).

A mixture of the intermediate 431(1) (620 mg, 2.07 mmol), ethylene glycol (141 mg, 2.27 mmol), p-toluenesulfonic acid monohydrate (5 mg) and toluene (5 ml) was refluxed for 5 hours. The reaction mixture was cooled to room temperature, diluted with water, and extracted with ethyl acetate. The organic layer was washed with water and saturated brine, and dried over anhydrous sodium sulfate. The solvent was evaporated under reduced pressure to give the title compound (730 mg, 100%) as a yellow oil $^1$H-NMR ($CDCl_3$) δ: 1.34 (9H, s), 4.08-4.10 (2H, m), 4.20-4.22 (2H, m), 6.26 (1H, s), 6.83 (1H, d, J=9.0 Hz), 7.00-7.04 (2H, m), 7.41-7.44 (2H, m), 8.12 (1H, dd, J=2.7, 9.0 Hz), 8.52 (1H, d, J=2.7 Hz).

(3) Preparation of the Intermediate 431(3).

The title compound was obtained in the same manner as the Example 3 using the following starting material.

Starting material: the intermediate 431(2); Yield: 97% (white solid).

$^1$H-NMR ($CDCl_3$) δ: 1.29 (9H, s), 3.62 (2H, brs), 3.96-3.99 (2H, m), 4.10-4.12 (2H, m), 5.99 (1H, s), 6.64 (1H, dd, J=3.0, 9.0 Hz), 6.78 (1H, d, J=9.0 Hz), 6.84-6.88 (2H, m), 6.95 (1H, d, J=3.0 Hz), 7.26-7.29 (2H, m).

(4) Preparation of the Intermediate 431(4).

The title compound was obtained in the same manner as the Example 412(1) using the following starting materials.

Starting materials: the intermediate 431(3) and 4-(trifluoromethoxy)phenylboronic acid; Yield: 24% (brown oil).

$^1$H-NMR ($CDCl_3$) δ: 1.31 (9H, s), 3.97-4.00 (2H, m), 4.10-4.13 (2H, m), 5.68 (1H, s), 6.08 (1H, s), 6.86 (1H, d, J=9.0 Hz), 6.91-6.96 (4H, m), 7.03-7.12 (3H, m), 7.30-7.34 (3H, m).

(5) Preparation of the Intermediate 431(5).

A mixture of the intermediate 431(4) (220 mg, 0.465 mmol), pyridinium p-toluenesulfonate (35 mg, 0.139 mmol), acetone (10 ml) and water (2 ml) was stirred at 70° C. for 1 hour. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was washed with n-hexane to give the title compound (155 mg, 77%) as a yellow solid.

$^1$H-NMR ($CDCl_3$) δ: 1.33 (9H, s), 5.72 (1H, s), 6.91-7.01 (5H, m), 7.11-7.14 (2H, m), 7.23-7.26 (1H, m), 7.36-7.39 (2H, m), 7.59 (1H, d, J=3.0 Hz), 10.42 (1H, s).

(6) Preparation of the Compound 431.

The title compound was obtained in the same manner as the Example 2(3) using the following starting materials.

Starting materials: the intermediate 431(5) and malonic acid; Yield: 91% (yellow solid).

$^1$H-NMR ($CDCl_3$) δ: 1.32 (9H, s), 6.49 (1H, d, J=15.9 Hz), 6.87 (1H, d, J=8.7 Hz), 6.90-6.93 (2H, m), 6.96-6.99 (2H, m), 7.05 (1H, dd, J=2.7, 8.7 Hz), 7.11-7.15 (2H, m), 7.33-7.36 (3H, m), 8.02 (1H, d, J=15.9 Hz).

Example 432

Preparation of the Compound 432

The title compound was obtained in the same manner as the Example 3 using the following starting material.

Starting material: the compound 431; Yield: 83% (whitish-pink solid).

$^1$H-NMR (DMSO-$d_6$) δ: 1.26 (9H, s), 2.19 (2H, t, J=7.2 Hz), 2.65 (2H, t, J=7.2 Hz), 6.76-6.80 (3H, m), 6.92 (1H, dd, J=2.7, 8.7 Hz), 7.05-7.09 (3H, m), 7.16-7.19 (2H, m), 7.30-7.35 (2H, m), 8.28 (1H, s).

Example 433

Preparation of the Compound 433

(1) Preparation of the Intermediate 433(1).

The title compound was obtained in the same manner as the Example 2(1) using the following starting materials.

Starting materials: 4-bromo-2-nitrophenol and 4-phenylbutyl bromide; Yield: 82% (yellow oil).

$^1$H-NMR ($CDCl_3$) δ: 1.73-1.95 (4H, m), 2.61-2.77 (2H, m), 4.02-4.12 (2H, m), 6.92 (1H, d, J=9.0 Hz), 7.12-7.24 (3H, m), 7.23-7.36 (2H, m), 7.59 (1H, dd, J=2.4, 9.0 Hz), 7.95 (1H, d, J=2.4 Hz).

(2) Preparation of the Intermediate 433(2).

The title compound was obtained in the same manner as the Example 1(2) using the following starting materials.

Starting materials: the intermediate 433(1) and 4-(trifluoromethoxy)phenylboronic acid; Yield: 86% (yellow oil).

$^1$H-NMR ($CDCl_3$) δ: 1.78-1.98 (4H, m), 2.63-2.78 (2H, m), 4.10-4.20 (2H, m), 7.11 (1H, d, J=8.7 Hz), 7.15-7.25 (3H, m), 7.25-7.38 (4H, m), 7.51-7.62 (2H, m), 7.68 (1H, dd, J=2.4, 8.7 Hz), 8.02 (1H, d, J=2.4 Hz).

(3) Preparation of the Intermediate 433(3).

The title compound was obtained in the same manner as the Example 3 using the following starting material.

Starting material: the intermediate 433(2); Yield: 97% (green oil).

$^1$H-NMR ($CDCl_3$) δ: 1.72-1.96 (4H, m), 2.62-2.77 (2H, m), 3.69 (2H, brs), 3.94-4.10 (2H, m), 6.76-6.84 (1H, m), 6.84-6.94 (2H, m), 7.14-7.35 (7H, m), 7.44-7.55 (2H, m).

(4) Preparation of the Intermediate 433(4).

The title compound was obtained in the same manner as the Example 416(1) using the following starting materials.

Starting materials: the intermediate 433(3) and 1-iodobutane; Yield: 38% (pale yellow oil).

$^1$H-NMR ($CDCl_3$) δ: 0.96 (3H, t, J=7.5 Hz), 1.36-1.56 (2H, m), 1.59-1.73 (2H, m), 1.74-1.95 (4H, m), 2.70 (2H, t, J=6.9 Hz), 3.18 (2H, t, J=6.9 Hz), 4.03 (2H, d, J=6.0 Hz), 4.24 (1H, brs), 6.72-6.84 (3H, m), 7.14-7.36 (7H, m), 7.50-7.60 (2H, m).

(5) Preparation of the Intermediate 433(5).

The title compound was obtained in the same manner as the Example 416(1) using the following starting materials.

Starting materials: the intermediate 433(4) and ethyl bromoacetate; Yield: 63% (pale yellow oil).

This compound was obtained as a mixture of the rotational isomers.

Major isomer: $^1$H-NMR ($CDCl_3$) δ: 0.90 (3H, t, J=7.2 Hz), 1.10-1.45 (5H, m), 1.45-1.70 (2H, m), 1.74-1.97 (4H, m), 2.62-2.78 (2H, m), 3.23-3.38 (2H, m), 3.95-4.18 (6H, m), 6.80-6.92 (2H, m), 7.04-7.13 (1H, m), 7.08 (1H, dd, J=2.4, 8.4 Hz), 7.13-7.37 (6H, m), 7.46-7.60 (2H, m).

Minor isomer: $^1$H-NMR ($CDCl_3$) δ: 0.90 (3H, t, J=7.2 Hz), 1.10-1.45 (5H, m), 1.45-1.70 (2H, m), 1.74-1.97 (4H, m), 2.62-2.78 (2H, m), 3.23-3.38 (2H, m), 3.95-4.32 (6H, m), 6.80-6.92 (2H, m), 7.04-7.13 (1H, m), 7.08 (1H, dd, J=2.4, 8.4 Hz), 7.13-7.37 (6H, m), 7.46-7.60 (2H, m).

(6) Preparation of the Compound 433.

The title compound was obtained in the same manner as the Example 12(4) using the following starting material.

Starting material: the intermediate 433(5); Yield: 36% (pale yellow oil).

$^1$H-NMR ($CDCl_3$) δ: 0.89 (3H, t, J=7.2 Hz), 1.21-1.42 (2H, m), 1.42-1.58 (2H, m), 1.72-2.00 (4H, m), 2.71 (2H, t, J=7.5 Hz), 3.12 (2H, t, J=7.5 Hz), 3.66 (2H, s), 4.06 (2H, t, J=6.6 Hz), 6.91-6.99 (1H, m), 7.14-7.36 (9H, m), 7.46-7.57 (2H, m).

Example 434

Preparation of the Compound 434

A mixture of the intermediate 110(1) (118 mg, 0.285 mmol), sodium chlorite (38.0 mg, 0.427 mmol), acetonitrile (3 ml) and water (0.3 ml) was stirred at room temperature for 18 hours. The reaction mixture was diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=1:1) to give the title compound (45.0 mg, 37%) as a white solid.

$^1$H-NMR ($CDCl_3$) δ: 1.35 (9H, s), 7.02 (1H, d, J=2.1 Hz), 7.07-7.14 (2H, m), 7.22-7.30 (2H, m), 7.39 (1H, dd, J=2.1, 8.1 Hz), 7.42-7.52 (4H, m), 8.30 (1H, d, J=8.1 Hz).

Example 435

Preparation of the Compound 435

(1) Preparation of the Intermediate 435(1).

The title compound was obtained in the same manner as the Example 416(1) using the following starting materials.

Starting materials: the intermediate 423(3) and 1-iodopropane; Yield: 63% (brown oil).

$^1$H-NMR ($CDCl_3$) δ: 0.97 (3H, t, J=7.5 Hz), 1.32 (9H, s), 1.58-1.76 (2H, m), 3.04-3.28 (2H, m), 4.29 (1H, brs), 6.76 (1H, dd, J=2.1, 8.1 Hz), 6.82-6.91 (2H, m), 6.92-7.01 (2H, m), 7.20-7.30 (2H, m), 7.30-7.40 (2H, m), 7.52-7.63 (2H, m).

(2) Preparation of the Intermediate 435(2).

The title compound was obtained in the same manner as the Example 416(1) using the following starting materials.

Starting materials: the intermediate 435(1) and ethyl bromoacetate; Yield: 15% (brown oil).

$^1$H-NMR ($CDCl_3$) δ: 0.77 (3H, t, J=7.2 Hz), 1.15 (3H, t, J=7.2 Hz), 1.31 (9H, s), 1.44-1.62 (2H, m), 3.20-3.35 (2H, m), 3.96-4.16 (4H, m), 6.81-6.92 (2H, m), 6.95 (1H, d, J=8.4 Hz), 7.05 (1H, dd, J=2.1, 8.4 Hz), 7.21-7.35 (5H, m), 7.51-7.61 (2H, m).

(3) Preparation of the Compound 435.

The title compound was obtained in the same manner as the Example 12(4) using the following starting material.

Starting material: the intermediate 435(2); Yield: 100% (brown oil).

$^1$H-NMR ($CDCl_3$) δ: 0.70-0.86 (3H, m), 1.29 (9H, s), 1.38-1.56 (2H, m), 2.96-3.15 (2H, m), 3.75 (2H, s), 6.80-6.98 (3H, m), 7.05-7.16 (1H, m), 7.19-7.40 (5H, m), 7.44-7.56 (2H, m).

Example 436

Preparation of the Compound 436

(1) Preparation of the Intermediate 436(1).

The title compound was obtained in the same manner as the Example 95(2) using the following starting material.

Starting material: the intermediate 335(1); Yield: 86% (pale yellow oil).

$^1$H-NMR ($CDCl_3$) δ: 1.34 (9H, s), 5.68 (1H, s), 6.83-6.85 (1H, m), 7.10-7.32 (8H, m), 7.44-7.49 (2H, m).

(2) Preparation of the Intermediate 436(2).

The title compound was obtained in the same manner as the Example 105(2) using the following starting materials.

Starting materials: the intermediate 436(1) and ethyl bromoacetate; Yield: 90% (colorless oil).

$^1$H-NMR ($CDCl_3$) δ: 1.27 (3H, t, J=7.0 Hz), 1.31 (9H, s), 4.24 (2H, q, J=7.0 Hz), 4.73 (2H, s), 6.75-6.79 (1H, m), 7.02 (1H, d, J=8.6 Hz), 7.10-7.28 (7H, m), 7.45-7.50 (2H, m).

(3) Preparation of the Compound 436.

The title compound was obtained in the same manner as the Example 12(4) using the following starting material.

Starting material: the intermediate 436(2); Yield: 98% (colorless oil).

$^1$H-NMR ($CDCl_3$) δ: 1.31 (9H, s), 4.74 (2H, s), 6.76-6.79 (1H, m), 7.07 (1H, d, J=8.4 Hz), 7.13-7.56 (2H, m), 7.20-7.30 (5H, m), 7.45-7.50 (2H, m).

Example 437

Preparation of the Compound 437

(1) Preparation of the Intermediate 437(1).

The title compound was obtained in the same manner as the Example 12(2) using the following starting materials.

Starting materials: the intermediate 12(1) and 3-(tert-butyl)phenol; Yield: 96% (pale yellow solid).

$^1$H-NMR ($CDCl_3$) δ: 1.34 (9H, s), 6.89-6.92 (1H, m), 6.97 (1H, d, J=8.6 Hz), 7.18-7.19 (1H, m), 7.24-7.38 (4H, m), 7.58-7.63 (2H, m), 7.69 (1H, dd, J=2.6, 8.6 Hz), 8.14 (1H, d, J=2.2 Hz), 10.61 (1H, s).

(2) Preparation of the Compound 437.

The title compound was obtained in the same manner as the Example 2(3) using the following starting materials.

Starting materials: the intermediate 437(2) and malonic acid; Yield: 95% (white solid).

$^1$H-NMR ($CDCl_3$) δ: 1.33 (9H, s), 6.67 (1H, d, J=16.2 Hz), 6.80-6.85 (1H, m), 6.91 (1H, d, J=8.6 Hz), 7.13-7.15 (1H, m), 7.22-7.34 (4H, m), 7.48 (1H, dd, J=2.2, 8.6 Hz), 7.56-7.60 (2H, m), 7.80 (1H, d, J=2.2 Hz), 8.19 (1H, d, J=16.2 Hz).

Example 438

Preparation of the Compound 438

The title compound was obtained in the same manner as the Example 3 using the following starting material.

Starting material: the compound 437; Yield: 99% (white solid).

$^1$H-NMR ($CDCl_3$) δ: 1.32 (9H, s), 2.77 (2H, t, J=7.7 Hz), 3.08 (2H, t, J=7.7 Hz), 6.75-6.79 (1H, m), 6.88 (1H, d, J=8.4 Hz), 7.09-7.10 (1H, m), 7.14-7.17 (1H, m), 7.24-7.29 (3H, m), 7.34 (1H, dd, J=2.2, 8.4 Hz), 7.47 (1H, d, J=2.2 Hz), 7.53-7.58 (2H, m).

Example 439

Preparation of the Compound 439

(1) Preparation of the Intermediate 439(1).

The title compound was obtained in the same manner as the Example 95(2) using the following starting material.

Starting material: the intermediate 437(1); Yield: 94% (yellow oil).

$^1$H-NMR ($CDCl_3$) δ: 1.33 (9H, s), 5.70 (1H, s), 6.83-6.86 (1H, m), 6.92 (1H, d, J=8.4 Hz), 7.02 (1H, dd, J=2.2, 8.2 Hz), 7.15-7.16 (1H, m), 7.18-7.21 (1H, m), 7.25-7.32 (4H, m), 7.55-7.59 (2H, m).

(2) Preparation of the Intermediate 439(2).

The title compound was obtained in the same manner as the Example 105(2) using the following starting materials.

Starting materials: the intermediate 439(1) and ethyl bromoacetate; Yield: 86% (colorless oil).

$^1$H-NMR ($CDCl_3$) δ: 1.26 (3H, t, J=7.1 Hz), 1.32 (9H, s), 4.24 (2H, q, J=7.1 Hz), 4.75 (2H, s), 6.77-6.81 (1H, m), 7.00 (1H, d, J=8.6 Hz), 7.11-7.17 (4H, m), 7.22-7.30 (3H, m), 7.52-7.57 (2H, m).

(3) Preparation of the Compound 439.

The title compound was obtained in the same manner as the Example 12(4) using the following starting material.

Starting material: the intermediate 439(2); Yield: 98% (colorless oil).

$^1$H-NMR ($CDCl_3$) δ: 1.31 (9H, s), 4.77 (2H, s), 6.77-6.81 (1H, m), 7.02-7.05 (1H, m), 7.13-7.23 (7H, m), 7.53-7.57 (2H, m).

Example 440

Preparation of the Compound 440

(1) Preparation of the Intermediate 440(1).

The title compound was obtained in the same manner as the Example 1(2) using the following starting materials.

Starting materials: the intermediate 315(2) and 4-(pentyloxy)phenylboronic acid; Yield: 86% (colorless oil).

$^1$H-NMR ($CDCl_3$) δ: 0.93 (3H, t, J=6.9 Hz), 1.26 (3H, t, J=7.2 Hz), 1.30 (9H, s), 1.33-1.51 (4H, m), 1.73-1.85 (2H, m), 3.96 (2H, t, J=6.6 Hz), 4.22 (2H, q, J=7.2 Hz), 4.69 (2H, s), 6.87-6.98 (4H, m), 7.01 (1H, d, J=8.4 Hz), 7.18 (1H, d, J=2.4 Hz), 7.25 (1H, dd, J=2.4, 8.4 Hz), 7.27-7.34 (2H, m), 7.36-7.43 (2H, m).

(2) Preparation of the Compound 440.

The title compound was obtained in the same manner as the Example 12(4) using the following starting material.

Starting material: the intermediate 440(1); Yield: 56% (white solid).

$^1$H-NMR ($CDCl_3$) δ: 0.93 (3H, t, J=6.9 Hz), 1.31 (9H, s), 1.33-1.50 (4H, m), 1.73-1.85 (2H, m), 3.97 (2H, t, J=6.6 Hz), 4.69 (2H, s), 6.90-6.99 (4H, m), 7.06 (1H, d, J=8.4 Hz), 7.21 (1H, d, J=2.4 Hz), 7.29 (1H, dd, J=2.4, 8.4 Hz), 7.31-7.38 (2H, m), 7.37-7.43 (2H, m).

Example 441

Preparation of the Compound 441

(1) Preparation of the Intermediate 441(1).

The title compound was obtained in the same manner as the Example 1(2) using the following starting materials.

Starting materials: the intermediate 315(2) and 4-(isopropyl)phenylboronic acid; Yield: 52% (colorless oil).

$^1$H-NMR ($CDCl_3$) δ: 1.25 (6H, d, J=6.9 Hz), 1.26 (3H, t, J=7.2 Hz), 1.30 (9H, s), 2.91 (1H, sept, J=6.9 Hz), 4.22 (2H, q, J=7.2 Hz), 4.70 (2H, s), 6.87-6.98 (2H, m), 7.01 (1H, d, J=8.4 Hz), 7.16-7.34 (6H, m), 7.35-7.45 (2H, m).

(2) Preparation of the Compound 441.

The title compound was obtained in the same manner as the Example 12(4) using the following starting material.

Starting material: the intermediate 441(1); Yield: 90% (white solid).

$^1$H-NMR ($CDCl_3$) δ: 1.26 (6H, d, J=6.9 Hz), 1.30 (9H, s), 2.92 (1H, sept, J=6.9 Hz), 4.73 (2H, s), 6.90-7.00 (2H, m), 7.05 (1H, d, J=8.4 Hz), 7.20-7.29 (4H, m), 7.29-7.36 (2H, m), 7.36-7.46 (2H, m).

Example 442

Preparation of the Compound 442

(1) Preparation of the Intermediate 442(1).

The title compound was obtained in the same manner as the Example 1(2) using the following starting materials.

Starting materials: 4-bromo-2-fluoro-1-nitrobenzene and 4-(trifluoromethoxy)phenylboronic acid; Yield: 91% (yellow solid).

$^1$H-NMR ($CDCl_3$) δ: 7.31-7.41 (2H, m), 7.43-7.53 (2H, m), 7.58-7.68 (2H, m), 8.18 (1H, t, J=8.4 Hz).

(2) Preparation of the Intermediate 442(2).

The title compound was obtained in the same manner as the Example 12(2) using the following starting materials.

Starting materials: the intermediate 442(1) and 4-(tert-butyl)phenol; Yield: 95% (white solid).

$^1$H-NMR ($CDCl_3$) δ: 1.33 (9H, s), 6.98-7.06 (2H, m), 7.18 (1H, d, J=2.1 Hz), 7.24-7.32 (2H, m), 7.34 (1H, dd, J=2.1, 8.4 Hz), 7.37-7.44 (2H, m), 7.46-7.55 (2H, m), 8.05 (1H, d, J=8.4 Hz).

(3) Preparation of the Intermediate 442(3).

The title compound was obtained in the same manner as the Example 3 using the following starting material.

Starting material: the intermediate 442(2); Yield: 92% (brown oil).

$^1$H-NMR ($CDCl_3$) δ: 1.31 (9H, s), 3.91 (2H, brs), 6.88 (1H, d, J=8.1 Hz), 6.91-6.98 (2H, m), 7.11 (1H, d, J=1.8 Hz), 7.16-7.25 (3H, m), 7.30-7.38 (2H, m), 7.44-7.51 (2H, m).

(4) Preparation of the Intermediate 442(4).

The title compound was obtained in the same manner as the Example 416(1) using the following starting materials.

Starting materials: the intermediate 442(3) and ethyl bromoacetate; Yield: 33% (pale yellow oil).

$^1$H-NMR ($CDCl_3$) δ: 1.20-1.38 (12H, m), 3.98 (2H, d, J=5.4 Hz), 4.23 (2H, q, J=7.2 Hz), 4.86-4.98 (1H, m), 6.67 (1H, d, J=8.4 Hz), 6.93-7.02 (2H, m), 7.09 (1H, d, J=2.1 Hz), 7.14-7.28 (3H, m), 7.29-7.38 (2H, m), 7.41-7.50 (2H, m).

(5) Preparation of the Compound 442.

The title compound was obtained in the same manner as the Example 12(4) using the following starting material.

Starting material: the intermediate 442(4); Yield: 87% (white solid).

$^1$H-NMR (DMSO-$d_6$) δ: 1.26 (9H, s), 3.91 (2H, s), 5.58 (1H, brs), 6.72 (1H, d, J=8.4 Hz), 6.85-6.96 (2H, m), 7.16 (1H, d, J=1.8 Hz), 7.26-7.43 (5H, m), 7.58-7.69 (2H, m), 12.70 (1H, brs).

Example 443

Preparation of the Compound 443

(1) Preparation of the Intermediate 443(1).

The title compound was obtained in the same manner as the Example 1(2) using the following starting materials.

Starting materials: the intermediate 315(2) and 4-butylphenylboronic acid; Yield: 89% (colorless oil).

$^1$H-NMR ($CDCl_3$) δ: 0.93 (3H, t, J=7.2 Hz), 1.26 (3H, t, J=7.2 Hz), 1.30 (9H, s), 1.31-1.34 (2H, m), 1.54-1.65 (2H, m), 2.61 (2H, t, J=7.5 Hz), 4.22 (2H, q, J=7.2 Hz), 4.70 (2H, s), 6.93-6.98 (2H, m), 7.02 (1H, d, J=8.4 Hz), 7.18-7.22 (3H, m), 7.27-7.34 (3H, m), 7.37-7.41 (2H, m).

(2) Preparation of the Compound 443.

The title compound was obtained in the same manner as the Example 12(4) using the following starting material.

Starting material: the intermediate 443(1); Yield: 82% (white solid).

$^1$H-NMR (DMSO-$d_6$) δ: 0.989 (3H, t, J=6.9 Hz), 1.26 (9H, s), 1.29-1.36 (2H, m), 1.50-1.60 (2H, m), 2.58 (2H, t, J=7.5 Hz), 4.74 (2H, s), 6.87 (2H, d, J=8.7 Hz), 7.10 (1H, d, J=8.7 Hz), 7.22 (2H, d, J=8.1 Hz), 7.26 (1H, d, J=2.1 Hz), 7.33 (2H, d, J=8.7 Hz), 7.43 (1H, dd, J=2.1, 8.7 Hz), 7.48 (2H, d, J=8.7 Hz), 13.06 (1H, brs).

Example 444

Preparation of the Compound 444

(1) Preparation of the Intermediate 444(1).

The title compound was obtained in the same manner as the Example 1(2) using the following starting materials.

Starting materials: the intermediate 315(2) and 4-methyphenylboronic acid; Yield: 57% (colorless oil).

$^1$H-NMR ($CDCl_3$) δ: 1.26 (3H, t, J=7.2 Hz), 1.30 (9H, s), 2.36 (3H, s), 4.22 (2H, q, J=7.2 Hz), 4.70 (2H, s), 6.92-6.98 (2H, m), 7.02 (1H, d, J=8.4 Hz), 7.18-7.22 (3H, m), 7.25-7.39 (5H, m).

(2) Preparation of the Compound 444.

The title compound was obtained in the same manner as the Example 12(4) using the following starting material.

Starting material: the intermediate 444(1); Yield: 83% (white solid).

$^1$H-NMR (DMSO-$d_6$) δ: 1.26 (9H, s), 2.31 (3H, s), 4.74 (2H, s), 6.85-6.89 (2H, m), 7.11 (1H, d, J=8.7 Hz), 7.21 (2H, d, J=8.1 Hz), 7.27 (1H, d, J=2.4 Hz), 7.30-7.34 (2H, m), 7.41-67.49 (3H, m), 13.03 (1H, brs).

Example 445

Preparation of the Compound 445

(1) Preparation of the Intermediate 445(1).

The title compound was obtained in the same manner as the Example 1(2) using the following starting materials.

Starting materials: the intermediate 315(2) and 4-methoxyphenylboronic acid; Yield: 80% (colorless oil).

$^1$H-NMR ($CDCl_3$) δ: 1.26 (3H, t, J=7.2 Hz), 1.30 (9H, s), 3.82 (3H, s), 4.22 (2H, q, J=7.2 Hz), 4.70 (2H, s), 6.89-6.98 (4H, m), 7.01 (1H, d, J=8.1 Hz), 7.19 (1H, d, J=2.1 Hz), 7.25 (1H, dd, J=2.1, 8.1 Hz), 7.29-7.34 (2H, m), 7.39-7.44 (2H, m).

(2) Preparation of the Compound 445.

The title compound was obtained in the same manner as the Example 12(4) using the following starting material.

Starting material: the intermediate 445(1); Yield: 89% (white solid).

$^1$H-NMR (DMSO-$d_6$) δ: 1.26 (9H, s), 3.76 (3H, s), 4.73 (2H, s), 6.86 (2H, d, J=8.4 Hz), 6.96 (2H, d, J=8.7 Hz), 7.09 (1H, d, J=8.4 Hz), 7.24 (1H, d, J=2.4 Hz), 7.33 (2H, d, J=8.7 Hz), 7.39 (1H, dd, J=2.4, 8.7 Hz), 7.52 (2H, d, J=8.7 Hz), 13.03 (1H, brs).

Example 446

Preparation of the Compound 446

(1) Preparation of the Intermediate 446(1).

The title compound was obtained in the same manner as the Example 1(2) using the following starting materials.

Starting materials: the intermediate 315(2) and 4-(tert-butyl)phenylboronic acid; Yield: 66% (colorless oil).

$^1$H-NMR ($CDCl_3$) δ: 1.25 (3H, t, J=7.2 Hz), 1.30 (9H, s), 1.32 (9H, s), 4.22 (2H, q, J=7.2 Hz), 4.70 (2H, s), 6.91-6.98 (2H, m), 7.02 (1H, d, J=8.4 Hz), 7.22 (1H, d, J=2.4 Hz), 7.23-7.34 (3H, m), 7.35-7.44 (4H, m).

(2) Preparation of the Compound 446.

The title compound was obtained in the same manner as the Example 12(4) using the following starting material.

Starting material: the intermediate 446(1); Yield: 99% (white solid).

$^1$H-NMR ($CDCl_3$) δ: 1.31 (9H, s), 1.34 (9H, s), 4.71 (2H, s), 6.92-7.00 (2H, m), 7.07 (1H, d, J=8.4 Hz), 7.24 (1H, d, J=2.4 Hz), 7.29-7.38 (3H, m), 7.40-7.44 (4H, m).

Example 447

Preparation of the Compound 447

(1) Preparation of the Intermediate 447(1).

The title compound was obtained in the same manner as the Example 2(1) using the following starting materials.

Starting materials: 4-bromophenol and 3-bromopentane; Yield: 71% (colorless oil).

$^1$H-NMR ($CDCl_3$) δ: 0.94 (6H, t, J=7.5 Hz), 1.60-1.73 (4H, m), 4.06 (1H, quint, J=6.0 Hz), 6.73-6.82 (2H, m), 7.31-7.38 (2H, m).

(2) Preparation of the Intermediate 447(2).

A 1.6 M solution of n-Butyllithium in hexane (1.91 ml, 3.05 mmol) was added dropwise to a solution of the intermediate 447(1) (742 mg, 3.05 mmol) in anhydrous tetrahydrofuran (10 ml) at −78° C. After the reaction mixture was allowed to warm to −30° C., triisopropyl borate (0.73 ml, 3.20 mmol) was added to the reaction mixture, followed by stirring at room temperature for 1 hour. 2 N hydrochloric acid was added to the reaction mixture, and the mixture was extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=1:1) to give the title compound (381 mg, 60%) as a white solid.

$^1$H-NMR ($CDCl_3$) δ: 0.99 (6H, t, J=7.5 Hz), 1.63-1.79 (4H, m), 4.25 (1H, quint, J=6.0 Hz), 6.95-7.04 (2H, m), 8.11-8.18 (2H, m).

(3) Preparation of the Intermediate 447(3).

The title compound was obtained in the same manner as the Example 1(2) using the following starting materials.

Starting materials: the intermediates 315 (2) and 447 (2); Yield: 81% (colorless oil).

$^1$H-NMR ($CDCl_3$) δ: 0.95 (6H, t, J=7.5 Hz), 1.26 (3H, t, J=7.2 Hz), 1.30 (9H, s), 1.61-1.74 (4H, m), 4.11 (1H, quint, J=5.7 Hz), 4.22 (2H, q, J=7.2 Hz), 4.70 (2H, s), 6.96-6.99 (4H, m), 7.01 (1H, d, J=8.4 Hz), 7.18 (1H, d, J=2.4 Hz), 7.24 (1H, dd, J=2.4, 8.4 Hz), 7.28-7.35 (2H, m), 7.35-7.42 (2H, m).

(4) Preparation of the Compound 447.

The title compound was obtained in the same manner as the Example 12(4) using the following starting material.

Starting material: the intermediate 447(3); Yield: 80% (white solid).

$^1$H-NMR ($CDCl_3$) δ: 0.96 (6H, t, J=7.5 Hz), 1.31 (9H, s), 1.61-1.74 (4H, m), 4.12 (1H, quint, J=5.7 Hz), 4.69 (2H, s), 6.89-6.99 (4H, m), 7.06 (1H, d, J=8.4 Hz), 7.20 (1H, d, J=2.4 Hz), 7.27 (1H, dd, J=2.4, 8.4 Hz), 7.32-7.36 (2H, m), 7.36-7.42 (2H, m).

Example 448

Preparation of the Compound 448

(1) Preparation of the Intermediate 448(1).

The title compound was obtained in the same manner as the Example 1(2) using the following starting materials.

Starting materials: the intermediate 315(2) and 4-(methylthio)phenylboronic acid; Yield: 94% (colorless oil).

$^1$H-NMR ($CDCl_3$) δ: 1.26 (3H, t, J=7.2 Hz), 1.30 (9H, s), 2.49 (3H, s), 4.22 (2H, q, J=7.2 Hz), 4.70 (2H, s), 6.91-6.98

(2H, m), 7.02 (1H, d, J=8.4 Hz), 7.21 (1H, d, J=2.4 Hz), 7.23-7.35 (5H, m), 7.36-7.44 (2H, m).

(2) Preparation of the Compound 448.

The title compound was obtained in the same manner as the Example 12(4) using the following starting material.

Starting material: the intermediate 448(1); Yield: 79% (white solid).

$^1$H-NMR ($CDCl_3$) δ: 1.31 (9H, s), 2.50 (3H, s), 4.71 (2H, s), 6.92-6.98 (2H, m), 7.07 (1H, d, J=8.4 Hz), 7.22 (1H, d, J=2.4 Hz), 7.24-7.38 (5H, m), 7.37-7.45 (2H, m).

Example 449

Preparation of the Compound 449

(1) Preparation of the Intermediate 449(1).

A mixture of the intermediate 448(1) (206 mg, 0.457 mmol), m-chloroperbenzoic acid (819 mg, 2.29 mmol) and chloroform (5 ml) was stirred at room temperature for 1 hour. A saturated aqueous solution of sodium hydrogen carbonate was added to the reaction mixture, and the mixture was extracted with ethyl acetate. The organic layer was dried over anhydrous sodium sulfate. The residue obtained by evaporation of the solvent under reduced pressure was purified by column chromatography on silica gel (n-hexane:ethyl acetate=1:1) to give the title compound (195 mg, 88%) as a colorless oil.

$^1$H-NMR ($CDCl_3$) δ: 1.27 (3H, t, J=7.2 Hz), 1.30 (9H, s), 3.06 (3H, s), 4.24 (2H, q, J=7.2 Hz), 4.74 (2H, s), 6.91-7.00 (2H, m), 7.02 (1H, d, J=8.4 Hz), 7.25 (1H, d, J=2.4 Hz), 7.30-7.38 (3H, m), 7.63-7.69 (2H, m), 7.92-7.99 (2H, m).

(2) Preparation of the Compound 449.

The title compound was obtained in the same manner as the Example 12(4) using the following starting material.

Starting material: the intermediate 449(1); Yield: 82% (white solid).

$^1$H-NMR ($CDCl_3$) δ: 1.31 (9H, s), 3.07 (3H, s), 4.75 (2H, s), 6.92-7.00 (2H, m), 7.11 (1H, d, J=8.4 Hz), 7.26 (1H, d, J=2.4 Hz), 7.32-7.40 (3H, m), 7.64-7.70 (2H, m), 7.93-8.00 (2H, m).

Example 450

Preparation of the Compound 450

(1) Preparation of the Intermediate 450(1).

The title compound was obtained in the same manner as the Example 12(3) using the following starting materials.

Starting materials: the intermediate 110(1) and bis(2,2,2-trifluoroethyl)(methoxycarbonylmethyl)phosphonate; Yield: 50% (colorless oil).

$^1$H-NMR ($CDCl_3$) δ: 1.31 (9H, s), 3.72 (3H, s), 6.01 (1H, d, J=12.3 Hz), 6.90-6.97 (2H, m), 6.97-7.11 (1H, m), 7.20-7.27 (2H, m), 7.30-7.37 (4H, m), 7.49-7.57 (2H, m), 7.81 (1H, d, J=7.8 Hz).

(2) Preparation of the Compound 450.

The title compound was obtained in the same manner as the Example 12(4) using the following starting material.

Starting material: the intermediate 450(1); Yield: 90% (white solid).

$^1$H-NMR ($CDCl_3$) δ: 1.31 (9H, s), 6.03 (1H, d, J=12.3 Hz), 6.91-6.98 (2H, m), 7.07 (1H, d, J=1.8 Hz), 7.20-7.39 (6H, m), 7.46-7.55 (2H, m), 7.80 (1H, d, J=8.1 Hz).

Example 451

Preparation of the Compound 451

(1) Preparation of the Intermediate 451(1).

The title compound was obtained in the same manner as the Example 105(2) using the following starting materials.

Starting materials: the intermediate 308(1) and ethyl bromoacetate; Yield: 95% (white solid).

$^1$H-NMR ($CDCl_3$) δ: 1.24 (3H, t, J=7.2 Hz), 1.33 (9H, s), 4.20 (2H, q, J=7.2 Hz), 4.66 (2H, s), 5.10 (2H, s), 6.55-6.64 (2H, m), 6.90-6.97 (3H, m), 7.11-7.18 (2H, m), 7.38-7.42 (4H, m).

(2) Preparation of the Compound 451.

The title compound was obtained in the same manner as the Example 12(4) using the following starting material.

Starting material: the intermediate 451(1); Yield: 99% (white solid).

$^1$H-NMR ($CDCl_3$) δ: 1.33 (9H, s), 4.66 (2H, s), 5.10 (2H, s), 6.64-6.74 (2H, m), 6.92-6.99 (3H, m), 7.12-7.19 (2H, m), 7.32-7.46 (4H, m).

Example 452

Preparation of the Compound 452

(1) Preparation of the Intermediate 452(1).

The title compound was obtained in the same manner as the Example 105(2) using the following starting materials.

Starting materials: the intermediate 309(2) and ethyl bromoacetate; Yield: 97% (white solid).

$^1$H-NMR ($CDCl_3$) δ: 1.24 (3H, t, J=7.2 Hz), 1.75-1.94 (4H, m), 2.70 (2H, t, J=7.2 Hz), 4.02 (2H, t, J=6.0 Hz), 4.20 (2H, q, J=7.2 Hz), 4.63 (2H, s), 6.55-6.65 (2H, m), 6.85 (1H, d, J=8.1 Hz), 6.89-6.97 (2H, m), 7.10-7.34 (7H, m).

(2) Preparation of the Compound 452.

The title compound was obtained in the same manner as the Example 12(4) using the following starting material.

Starting material: the intermediate 452(1); Yield: 86% (white solid).

$^1$H-NMR ($CDCl_3$) δ: 1.73-1.95 (4H, m), 2.70 (2H, t, J=7.2 Hz), 4.04 (2H, t, J=6.0 Hz), 4.64 (2H, s), 6.55-6.64 (2H, m), 6.85-6.98 (3H, m), 7.12-7.34 (7H, m).

Example 453

Preparation of the Compound 453

(1) Preparation of the Intermediate 453(1).

The title compound was obtained in the same manner as the Example 12(2) using the following starting materials.

Starting materials: 5-bromo-2-fluorobenzaldehyde and 4-(tert-butyl)phenol; Yield: 90% (pale brown solid).

$^1$H-NMR ($CDCl_3$) δ: 1.35 (9H, s), 6.79 (1H, d, J=8.8 Hz), 6.97-7.02 (2H, m), 7.39-7.44 (2H, m), 7.56 (1H, dd, J=2.6, 8.8 Hz), 8.02 (1H, d, J=2.6 Hz), 10.45 (1H, s).

(2) Preparation of the Intermediate 453(2).

The title compound was obtained in the same manner as the Example 95(2) using the following starting material.

Starting material: the intermediate 453(1); Yield: 69% (pale yellow solid).

$^1$H-NMR ($CDCl_3$) δ: 1.30 (9H, s), 5.63 (1H, s), 6.71 (1H, d, J=8.6 Hz), 6.88-6.95 (3H, m), 7.17 (1H, d, J=2.2 Hz), 7.31-7.36 (2H, m).

(3) Preparation of the Intermediate 453(3).

The title compound was obtained in the same manner as the Example 105(2) using the following starting materials.

Starting materials: the intermediate 453(2) and ethyl bromoacetate; Yield: 94% (pale yellow oil).

$^1$H-NMR ($CDCl_3$) δ: 1.27 (3H, t, J=7.1 Hz), 1.31 (9H, s), 4.23 (2H, q, J=7.1 Hz), 4.66 (2H, s), 6.82-6.85 (1H, m), 6.88-6.93 (2H, m), 7.06-7.10 (2H, m), 7.29-7.34 (2H, m).

(4) Preparation of the Intermediate 453(4).

The title compound was obtained in the same manner as the Example 1(2) using the following starting materials.

Starting materials: the intermediate 453(3) and 4-(tert-butyl)phenylboronic acid; Yield: 26% (colorless oil).

$^1$H-NMR ($CDCl_3$) δ: 1.25 (3H, t, J=7.0 Hz), 1.31 (9H, s), 1.36 (9H, s), 4.22 (2H, q, J=7.0 Hz), 4.73 (2H, s), 6.93-7.02 (3H, m), 7.16-7.19 (2H, m), 7.30-7.35 (2H, m), 7.43-7.50 (4H, m).

(5) Preparation of the Compound 453.

The title compound was obtained in the same manner as the Example 12(4) using the following starting material.

Starting material: the intermediate 453(4); Yield: 77% (white solid).

$^1$H-NMR ($CDCl_3$) δ: 1.32 (9H, s), 1.36 (9H, s), 4.73 (2H, s), 6.94-6.99 (2H, m), 7.05 (1H, d, J=8.2 Hz), 7.22-7.26 (2H, m), 7.33-7.39 (2H, m), 7.48 (4H, brs).

Example 454

Preparation of the Compound 454

(1) Preparation of the Intermediate 454(1).

The title compound was obtained in the same manner as the Example 1(2) using the following starting materials.

Starting materials: the intermediate 453(3) and 4-(n-pentyloxy)phenylboronic acid; Yield: 78% (colorless oil).

$^1$H-NMR ($CDCl_3$) δ: 0.95 (3H, t, J=7.1 Hz), 1.25 (3H, t, J=7.1 Hz), 1.31 (9H, s), 1.34-1.52 (4H, m), 1.77-1.86 (2H, m), 4.00 (2H, t, J=6.4 Hz), 4.22 (2H, q, J=7.1 Hz), 4.73 (2H, s), 6.92-7.02 (5H, m), 7.13-7.16 (2H, m), 7.30-7.35 (2H, m), 7.43-7.48 (2H, m).

(2) Preparation of the Compound 454.

The title compound was obtained in the same manner as the Example 12(4) using the following starting material.

Starting material: the intermediate 454(1); Yield: 68% (white solid).

$^1$H-NMR ($CDCl_3$) δ: 0.95 (3H, t, J=7.0 Hz), 1.31 (9H, s), 1.32-1.52 (4H, m), 1.77-1.86 (2H, m), 4.00 (2H, t, J=6.6 Hz), 4.73 (2H, s), 6.93-6.99 (4H, m), 7.02-7.05 (1H, m), 7.18-7.22 (2H, m), 7.32-7.37 (2H, m), 7.43-7.48 (2H, m).

Example 455

Preparation of the Compound 455

(1) Preparation of the Intermediate 455(1).

The title compound was obtained in the same manner as the Example 1(2) using the following starting materials.

Starting materials: the intermediate 315(2) and 2,5-dichlorophenylboronic acid; Yield: 82% (colorless oil).

$^1$H-NMR ($CDCl_3$) δ: 1.27 (3H, t, J=7.2 Hz), 1.30 (9H, s), 4.24 (2H, q, J=7.2 Hz), 4.73 (2H, s), 6.94-6.98 (2H, m), 7.00 (1H, d, J=8.4 Hz), 7.08 (1H, d, J=2.1 Hz), 7.12 (1H, dd, J=2.1, 8.4 Hz), 7.21 (1H, dd, J=2.4, 8.4 Hz), 7.29 (1H, d, J=2.4 Hz), 7.31-7.38 (2H, m), 7.35 (1H, d, J=8.4 Hz).

(2) Preparation of the Compound 455.

The title compound was obtained in the same manner as the Example 12(4) using the following starting material.

Starting material: the intermediate 455(1); Yield: 61% (white solid).

$^1$H-NMR (DMSO-$d_6$) δ: 1.26 (9H, s), 4.79 (2H, s), 6.86-6.92 (2H, m), 7.09 (1H, d, J=2.1 Hz), 7.12 (1H, d, J=8.4 Hz), 7.23 (1H, dd, J=2.1, 8.4 Hz), 7.32-7.38 (2H, m), 7.44 (1H, dd, J=2.7, 8.4 Hz), 7.48 (1H, d, J=2.7 Hz), 7.56 (1H, d, J=8.4 Hz), 13.01 (1H, brs).

Example 456

Preparation of the Compound 456

(1) Preparation of the Intermediate 456(1).

The title compound was obtained in the same manner as the Example 1(2) using the following starting materials.

Starting materials: the intermediate 315(2) and 2-(trifluoromethoxy)phenylboronic acid; Yield: 77% (colorless oil).

$^1$H-NMR ($CDCl_3$) δ: 1.26 (3H, t, J=7.2 Hz), 1.30 (9H, s), 4.24 (2H, q, J=7.2 Hz), 4.73 (2H, s), 6.93-6.98 (2H, m), 7.01 (1H, d, J=8.4 Hz), 7.11 (1H, d, J=2.1 Hz), 7.15 (1H, dd, J=2.1, 8.4 Hz), 7.28-7.38 (6H, m).

(2) Preparation of the Compound 456.

The title compound was obtained in the same manner as the Example 12(4) using the following starting material.

Starting material: the intermediate 456(1); Yield: 100% (white solid).

$^1$H-NMR (DMSO-$d_6$) δ: 1.26 (9H, s), 4.77 (2H, s), 6.85-6.90 (2H, m), 7.07 (1H, d, J=2.1 Hz), 7.13 (1H, d, J=8.4 Hz), 7.23 (1H, dd, J=2.1, 8.4 Hz), 7.31-7.40 (2H, m), 7.43-7.53 (4H, m), 13.12 (1H, brs).

Example 457

Preparation of the Compound 457

(1) Preparation of the Intermediate 457(1).

The title compound was obtained in the same manner as the Example 1(2) using the following starting materials.

Starting materials: the intermediate 315(2) and 4-chlorophenylboronic acid; Yield: 77% (colorless oil).

$^1$H-NMR ($CDCl_3$) δ: 1.26 (3H, t, J=7.2 Hz), 1.31 (9H, s), 4.23 (2H, q, J=7.2 Hz), 4.71 (2H, s), 6.92-6.97 (2H, m), 7.02 (1H, d, J=8.7 Hz), 7.19 (1H, d, J=2.4 Hz), 7.26 (1H, dd, J=2.4, 8.7 Hz), 7.29-7.42 (6H, m).

(2) Preparation of the Compound 457.

The title compound was obtained in the same manner as the Example 12(4) using the following starting material.

Starting material: the intermediate 457(1); Yield: 86% (white solid).

$^1$H-NMR (DMSO-$d_6$) δ: 1.26 (9H, s), 4.76 (2H, s), 6.85-6.89 (2H, m), 7.13 (1H, d, J=8.7 Hz), 7.30-7.34 (3H, m), 7.44-7.50 (3H, m), 7.61-7.66 (2H, m), 13.05 (1H, brs).

Example 458

Preparation of the Compound 458

(1) Preparation of the Intermediate 458(1).

The title compound was obtained in the same manner as the Example 1(2) using the following starting materials.

Starting materials: the intermediate 315(2) and phenylboronic acid; Yield: 52% (colorless oil).

$^1$H-NMR ($CDCl_3$) δ: 1.26 (3H, t, J=7.2 Hz), 1.31 (9H, s), 4.23 (2H, q, J=7.2 Hz), 4.71 (2H, s), 6.93-6.98 (2H, m), 7.03 (1H, d, J=8.7 Hz), 7.24 (1H, d, J=2.1 Hz), 7.29-7.41 (6H, m), 7.46-7.50 (2H, m).

(2) Preparation of the Compound 458.

The title compound was obtained in the same manner as the Example 12(4) using the following starting material.

Starting material: the intermediate 458(1); Yield: 94% (white solid).

$^1$H-NMR (DMSO-$d_6$) δ: 1.26 (9H, s), 4.76 (2H, s), 6.87 (2H, d, J=9.0 Hz), 7.13 (1H, d, J=8.7 Hz), 7.30-7.48 (7H, m), 7.58 (2H, d, J=7.5 Hz), 13.04 (1H, brs).

Example 459

Preparation of the Compound 459

(1) Preparation of the Intermediate 459(1).

The title compound was obtained in the same manner as the Example 1(2) using the following starting materials.

Starting materials: the intermediate 315(2) and 4-fluorophenylboronic acid; Yield: 76% (colorless oil).

$^1$H-NMR ($CDCl_3$) δ: 1.26 (3H, t, J=7.2 Hz), 1.31 (9H, s), 4.23 (2H, q, J=7.2 Hz), 4.71 (2H, s), 6.93-6.97 (2H, m), 7.02 (1H, d, J=8.7 Hz), 7.04-7.10 (2H, m), 7.18 (1H, d, J=2.4 Hz), 7.23 (1H, dd, J=2.4, 8.7 Hz), 7.29-7.35 (2H, m), 7.41-7.45 (2H, m).

(2) Preparation of the Compound 459.

The title compound was obtained in the same manner as the Example 12(4) using the following starting material.

Starting material: the intermediate 459(1); Yield: 90% (white solid).

$^1$H-NMR (DMSO-$d_6$) δ: 1.26 (9H, s), 4.76 (2H, s), 6.87 (2H, d, J=9.0 Hz), 7.12 (1H, d, J=8.7 Hz), 7.20-7.26 (2H, m), 7.30 (1H, d, J=2.4 Hz), 7.33 (2H, d, J=9.0 Hz), 7.45 (1H, dd, J=2.4, 8.7 Hz), 7.61-7.65 (2H, m), 13.05 (1H, brs).

Example 460

Preparation of the Compound 460

(1) Preparation of the Intermediate 1(2).

The title compound was obtained in the same manner as the Example 1(2) using the following starting materials.

Starting materials: the intermediate 315(2) and 4-(isopropoxy)phenylboronic acid; Yield: 60% (colorless oil).

$^1$H-NMR ($CDCl_3$) δ: 1.26 (3H, t, J=7.2 Hz), 1.30 (9H, s), 1.34 (6H, d, J=6.0 Hz), 4.22 (2H, q, J=7.2 Hz), 4.55 (1H, sept, J=6.0 Hz), 4.70 (2H, s), 6.87-6.92 (2H, m), 6.93-6.97 (2H, m), 7.01 (1H, d, J=8.4 Hz), 7.19 (1H, d, J=2.4 Hz), 7.24 (1H, dd, J=2.4, 8.4 Hz), 7.29-7.34 (2H, m), 7.37-7.41 (2H, m).

(2) Preparation of the Compound 460.

The title compound was obtained in the same manner as the Example 12(4) using the following starting material.

Starting material: the intermediate 460(1); Yield: 90% (white solid).

$^1$H-NMR (DMSO-$d_6$) δ: 1.256 (9H, s), 1.261 (6H, d, J=6.0 Hz), 4.62 (1H, sept, J=6.0 Hz), 4.74 (2H, s), 6.84-6.89 (2H, m), 6.92-6.96 (2H, m), 7.09 (1H, d, J=8.7 Hz), 7.23 (1H, d, J=2.4 Hz), 7.30-7.35 (2H, m), 7.39 (1H, dd, J=2.4, 8.7 Hz), 7.45-7.50 (2H, m).

Example 461

Preparation of the Compound 461

(1) Preparation of the Intermediate 461(1).

The title compound was obtained in the same manner as the Example 12(2) using the following starting materials.

Starting materials: the intermediate 333(1) and p-butoxyphenol; Yield: 100% (yellow oil).

$^1$H-NMR ($CDCl_3$) δ: 0.99 (3H, t, J=7.2 Hz), 1.50-1.57 (2H, m), 1.75-1.83 (2H, m), 3.97 (2H, t, J=6.6 Hz), 6.92-6.95 (3H, m), 7.05-7.08 (2H, m), 7.23-7.27 (2H, m), 7.29-7.33 (1H, m), 7.47-7.50 (2H, m), 7.99 (1H, d, J=8.1 Hz), 10.59 (1H, d, J=0.9 Hz).

(2) Preparation of the Intermediate 461(2).

The title compound was obtained in the same manner as the Example 2(3) using the following starting materials.

Starting materials: the intermediate 461(1) and malonic acid; Yield: 100% (white solid).

$^1$H-NMR ($CDCl_3$) δ: 0.99 (3H, t, J=7.2 Hz), 1.47-1.55 (2H, m), 1.75-1.83 (2H, m), 3.96 (2H, t, J=6.6 Hz), 6.64 (1H, d, J=16.2 Hz), 6.89-7.02 (5H, m), 7.22-7.28 (3H, m), 7.45-7.50 (2H, m), 7.69 (1H, d, J=8.4 Hz), 8.18 (1H, d, J=16.2 Hz).

(3) Preparation of the Compound 461.

The title compound was obtained in the same manner as the Example 3 using the following starting material.

Starting material: the intermediate 461(2); Yield: 34% (white solid).

$^1$H-NMR (DMSO-$d_6$) δ: 0.93 (3H, t, J=7.2 Hz), 1.39-1.46 (2H, m), 1.63-1.73 (2H, m), 2.57 (2H, t, J=7.5 Hz), 2.88 (2H, t, J=7.5 Hz), 3.93 (2H, t, J=6.6 Hz), 6.92-6.99 (5H, m), 7.34-7.42 (4H, m), 7.62-7.65 (2H, m), 12.17 (1H, brs).

Example 462

Preparation of the Compound 462

(1) Preparation of the Intermediate 462(1).

The title compound was obtained in the same manner as the Example 12(2) using the following starting materials.

Starting materials: the intermediate 333(1) and 4-(tert-butyl)thiophenol; Yield: 93% (pale yellow solid).

$^1$H-NMR ($CDCl_3$) δ: 1.34 (9H, s), 7.20-7.29 (3H, m), 7.36-7.46 (6H, m), 7.49 (1H, dd, J=1.8, 8.1 Hz), 7.94 (1H, d, J=8.1 Hz), 10.42 (1H, s).

(2) Preparation of the Compound 462.

The title compound was obtained in the same manner as the Example 2(3) using the following starting materials.

Starting materials: the intermediate 462(1) and malonic acid; Yield: 93% (white solid).

$^1$H-NMR ($CDCl_3$) δ: 1.30 (9H, s), 6.43 (1H, d, J=15.9 Hz), 7.22-7.41 (6H, m), 7.46-7.55 (4H, m), 7.73 (1H, d, J=8.1 Hz), 8.42 (1H, d, J=15.9 Hz).

Example 463

Preparation of the Compound 463

(1) Preparation of the Intermediate 463(1).

The title compound was obtained in the same manner as the Example 12(2) using the following starting materials.

Starting materials: 4-bromo-2-fluorobenzaldehyde and phenol; Yield: 88% (white solid).

$^1$H-NMR ($CDCl_3$) δ: 7.01 (1H, d, J=1.8 Hz), 7.06-7.14 (2H, m), 7.21-7.29 (1H, m), 7.31 (1H, ddd, J=1.2, 2.1, 8.4 Hz), 7.40-7.48 (2H, m), 7.79 (1H, d, J=8.4 Hz), 10.48 (1H, d, J=0.9 Hz).

(2) Preparation of the Intermediate 463(2).

The title compound was obtained in the same manner as the Example 1(2) using the following starting materials.

Starting materials: the intermediate 463(1) and phenylboronic acid; Yield: 95% (pale yellow solid).

$^1$H-NMR ($CDCl_3$) δ: 7.08-7.15 (3H, m), 7.15-7.24 (1H, m), 7.42-7.55 (8H, m), 8.01 (1H, d, J=8.1 Hz), 10.53 (1H, d, J=0.6 Hz).

(3) Preparation of the Compound 463.

The title compound was obtained in the same manner as the Example 2(3) using the following starting materials.

Starting materials: the intermediate 463(2) and malonic acid; Yield: 100% (white solid).

$^1$H-NMR ($CDCl_3$) δ: 6.61 (1H, d, J=16.2 Hz), 7.02-7.19 (4H, m), 7.29-7.45 (6H, m), 7.47-7.54 (2H, m), 7.73 (1H, d, J=8.1 Hz), 8.13 (1H, d, J=16.2 Hz).

Example 464

Preparation of the Compound 464

The title compound was obtained in the same manner as the Example 3 using the following starting material.

Starting material: the compound 463; Yield: 50% (white solid).

$^1$H-NMR ($CDCl_3$) δ: 2.73 (2H, t, J=7.5 Hz), 3.02 (2H, t, J=7.5 Hz), 6.96-7.03 (2H, m), 7.04-7.13 (2H, m), 7.27-7.43 (7H, m), 7.44-7.52 (2H, m).

Example 465

Preparation of the Compound 465

(1) Preparation of the Intermediate 465(1).

The title compound was obtained in the same manner as the Example 12(2) using the following starting materials.

Starting materials: 4-bromo-2-fluorobenzaldehyde and 3-(tert-butyl)phenol; Yield: 87% (pale yellow oil).

$^1$H-NMR ($CDCl_3$) δ: 1.34 (9H, s), 6.87 (1H, ddd, J=1.2, 2.4, 7.8 Hz), 7.01 (1H, d, J=1.8 Hz), 7.14 (1H, t, J=2.4 Hz), 7.25-7.40 (3H, m), 7.79 (1H, d, J=8.4 Hz), 10.50 (1H, d, J=0.6 Hz).

(2) Preparation of the Intermediate 465(2).

The title compound was obtained in the same manner as the Example 1(2) using the following starting materials.

Starting materials: the intermediate 465(1) and 4-(tert-butyl)phenylboronic acid; Yield: 98% (pale yellow oil).

$^1$H-NMR ($CDCl_3$) δ: 1.33 (9H, s), 1.34 (9H, s), 6.88 (1H, ddd, J=1.2, 2.4, 7.8 Hz), 7.10 (1H, d, J=1.8 Hz), 7.16-7.36 (3H, m), 7.36-7.48 (5H, m), 7.99 (1H, d, J=8.4 Hz), 10.54 (1H, d, J=0.6 Hz).

(3) Preparation of the Intermediate 465(3).

The title compound was obtained in the same manner as the Example 95(2) using the following starting material.

Starting material: the intermediate 465(2); Yield: 94% (pale brown oil).

$^1$H-NMR ($CDCl_3$) δ: 1.32 (18H, s), 5.61 (1H, s), 6.77-6.91 (2H, m), 7.07-7.19 (3H, m), 7.20-7.31 (3H, m), 7.32-7.42 (3H, m).

(4) Preparation of the Intermediate 465(4).

The title compound was obtained in the same manner as the Example 105(2) using the following starting materials.

Starting materials: the intermediate 465(3) and ethyl bromoacetate; Yield: 38% (pale yellow oil).

$^1$H-NMR ($CDCl_3$) δ: 1.26 (3H, t, J=7.2 Hz), 1.31 (9H, s), 1.33 (9H, s), 4.22 (2H, q, J=7.2 Hz), 4.71 (2H, s), 6.77 (1H, ddd, J=0.9, 2.7, 8.1 Hz), 7.01 (1H, d, J=8.4 Hz), 7.07-7.13 (1H, m), 7.13-7.17 (1H, m), 7.18-7.25 (2H, m), 7.29 (1H, dd, J=2.1, 8.4 Hz), 7.38-7.43 (4H, m).

(5) Preparation of the Compound 465.

The title compound was obtained in the same manner as the Example 12(4) using the following starting material.

Starting material: the intermediate 465(4); Yield: 81% (white solid).

$^1$H-NMR ($CDCl_3$) δ: 1.31 (9H, s), 1.34 (9H, s), 4.71 (2H, s), 6.77 (1H, ddd, J=0.9, 2.7, 8.1 Hz), 7.06 (1H, d, J=8.4 Hz), 7.11-7.19 (2H, m), 7.20-7.29 (2H, m), 7.33 (1H, dd, J=2.1, 8.4 Hz), 7.40-7.44 (4H, m).

Example 466

Preparation of the Compound 466

(1) Preparation of the Intermediate 466(1).

The title compound was obtained in the same manner as the Example 1(2) using the following starting materials.

Starting materials: the intermediate 79(1) and 2-(trifluoromethoxy)phenylboronic acid; Yield: 94% (pale yellow solid).

$^1$H-NMR ($CDCl_3$) δ: 1.34 (9H, s), 7.02-7.07 (3H, m), 7.24-7.27 (1H, m), 7.31-7.44 (6H, m), 8.00 (1H, d, J=8.1 Hz), 10.58 (1H, d, J=0.7 Hz).

(2) Preparation of the Compound 466.

The title compound was obtained in the same manner as the Example 2(3) using the following starting materials.

Starting materials: the intermediate 466(1) and malonic acid; Yield: 94% (white solid).

$^1$H-NMR ($CDCl_3$) δ: 1.34 (9H, s), 6.65 (1H, d, J=16.2 Hz), 6.97-7.03 (3H, m), 7.22 (1H, dd, J=1.5, 8.1 Hz), 7.29-7.42 (6H, m), 7.72 (1H, d, J=8.1 Hz), 8.17 (1H, d, J=16.2 Hz).

Example 467

Preparation of the Compound 467

The title compound was obtained in the same manner as the Example 3 using the following starting material.

Starting material: the compound 466; Yield: 83% (white solid).

$^1$H-NMR ($CDCl_3$) δ: 1.31 (9H, s), 2.76 (2H, t, J=7.3 Hz), 3.05 (2H, t, J=7.3 Hz), 6.91-6.93 (2H, m), 6.99 (1H, d, J=1.7 Hz), 7.15 (1H, dd, J=1.7, 7.7 Hz), 7.28-7.38 (7H, m).

Example 468

Preparation of the Compound 468

(1) Preparation of the Intermediate 468(1).

The title compound was obtained in the same manner as the Example 1(2) using the following starting materials.

Starting materials: the intermediate 315(2) and 4-hydroxyphenylboronic acid; Yield: 56% (white solid).

$^1$H-NMR ($CDCl_3$) δ: 1.26 (3H, t, J=7.2 Hz), 1.30 (9H, s), 4.23 (2H, q, J=7.2 Hz), 4.70 (2H, s), 5.22 (1H, brs), 6.81-6.86 (2H, m), 6.92-6.97 (2H, m), 7.00 (1H, d, J=8.4 Hz), 7.17 (1H, d, J=2.1 Hz), 7.21 (1H, dd, J=2.1, 8.4 Hz), 7.28-7.36 (4H, m).

(2) Preparation of the Intermediate 468(2).

The title compound was obtained in the same manner as the Example 2(1) using the following starting materials.

Starting materials: the intermediate 468(1) and 1-iodobutane; Yield: 82% (white solid).

$^1$H-NMR ($CDCl_3$) δ: 0.97 (3H, t, J=7.2 Hz), 1.26 (3H, t, J=7.2 Hz), 1.30 (9H, s), 1.43-1.55 (2H, m), 1.72-1.82 (2H, m), 3.97 (2H, t, J=6.6 Hz), 4.22 (2H, q, J=7.2 Hz), 4.70 (2H, s), 6.88-6.97 (4H, m), 7.01 (1H, d, J=8.7 Hz), 7.19 (1H, d, J=2.1 Hz), 7.25 (1H, dd, J=2.1, 8.7 Hz), 7.29-7.34 (2H, m), 7.37-7.42 (2H, m).

(3) Preparation of the Compound 468.

The title compound was obtained in the same manner as the Example 12(4) using the following starting material.

Starting material: the intermediate 468(2); Yield: 84% (white solid).

$^1$H-NMR (DMSO-$d_6$) δ: 0.93 (3H, t, J=7.5 Hz), 1.26 (9H, s), 1.43 (2H, sext, J=7.5 Hz), 1.72 (2H, quint, J=6.6 Hz), 3.97 (2H, t, J=6.6 Hz), 4.73 (2H, s), 6.85-6.89 (2H, m), 6.93-6.97 (2H, m), 7.09 (1H, d, J=8.4 Hz), 7.23 (1H, d, J=2.1 Hz), 7.30-7.35 (2H, m), 7.39 (1H, dd, J=2.1, 8.4 Hz), 7.48-7.51 (2H, m), 13.03 (1H, brs).

Example 469

Preparation of the Compound 469

(1) Preparation of the Intermediate 469(1).

The title compound was obtained in the same manner as the Example 1(2) using the following starting materials.

Starting materials: the intermediate 79(1) and 2-naphthaleneboronic acid; Yield: 92% (pale yellow solid).

$^1$H-NMR ($CDCl_3$) δ: 1.34 (9H, s), 7.04-7.09 (2H, m), 7.27 (1H, d, J=1.8 Hz), 7.39-7.44 (2H, m), 7.48-7.56 (3H, m), 7.63 (1H, dd, J=1.8, 8.4 Hz), 7.82-7.91 (3H, m), 7.98 (1H, d, J=4.8 Hz), 8.05 (1H, d, J=8.1 Hz), 10.54 (1H, s).

(2) Preparation of the Compound 469.

The title compound was obtained in the same manner as the Example 2(3) using the following starting materials.

Starting materials: the intermediate 469(1) and malonic acid; Yield: 96% (white solid).

$^1$H-NMR (DMSO-$d_6$) δ: 1.27 (9H, s), 6.69 (1H, d, J=16.2 Hz), 6.94-6.98 (2H, m), 7.39-7.43 (3H, m), 7.51-7.57 (2H, m), 7.72-7.83 (3H, m), 7.97-8.01 (3H, m), 8.07 (1H, d, J=8.1 Hz), 8.26 (1H, s), 12.51 (1H, brs).

Example 470

Preparation of the Compound 470

The title compound was obtained in the same manner as the Example 3 using the following starting material.

Starting material: the compound 469; Yield: 89% (white solid).

$^1$H-NMR (DMSO-$d_6$) δ: 1.27 (9H, s), 2.57 (2H, t, J=7.8 Hz), 2.85 (2H, t, J=7.8 Hz), 6.90-6.93 (2H, m), 7.32 (1H, d, J=1.8 Hz), 7.37-7.40 (2H, m), 7.48-7.55 (3H, m), 7.56 (1H, dd, J=1.8, 8.1 Hz), 7.75 (1H, dd, J=1.8, 8.4 Hz), 7.90-7.98 (3H, m), 8.16 (1H, s), 12.24 (1H, brs).

Example 471

Preparation of the Compound 471

(1) Preparation of the Intermediate 471(1).

The title compound was obtained in the same manner as the Example 1(2) using the following starting materials.

Starting materials: the intermediate 315(2) and 4-cyanophenylboronic acid; Yield: 90% (colorless oil).

$^1$H-NMR ($CDCl_3$) δ: 1.27 (3H, t, J=7.2 Hz), 1.31 (9H, s), 4.24 (2H, q, J=7.2 Hz), 4.74 (2H, s), 6.93-6.98 (2H, m), 7.4 (1H, d, J=8.7 Hz), 7.24 (1H, d, J=2.4 Hz), 7.30-7.36 (3H, m), 7.56-7.58 (2H, m), 7.66-7.68 (2H, m).

(2) Preparation of the Compound 471.

The title compound was obtained in the same manner as the Example 12(4) using the following starting material.

Starting material: the intermediate 471(1); Yield: 77% (white solid).

$^1$H-NMR (DMSO-$d_6$) δ: 1.25 (9H, s), 4.79 (2H, s), 6.85-6.90 (2H, m), 7.17 (1H, d, J=8.4 Hz), 7.31-7.34 (2H, m), 7.45 (1H, d, J=2.4 Hz), 7.59 (1H, dd, J=2.4, 8.4 Hz), 7.81-7.88 (4H, m), 13.12 (1H, brs).

Example 472

Preparation of the Compound 472

(1) Preparation of the Intermediate 472(1).

The title compound was obtained in the same manner as the Example 12(2) using the following starting materials.

Starting materials: the intermediate 333(1) and m-butoxyphenol; Yield: 72% (yellow oil).

$^1$H-NMR ($CDCl_3$) δ: 0.96 (3H, t, J=7.2 Hz), 1.44-1.54 (2H, m), 1.72-1.80 (2H, m), 3.95 (2H, t, J=6.6 Hz), 6.65-6.75 (3H, m), 7.11 (1H, d, J=1.5 Hz), 7.25-7.31 (3H, m), 7.37-7.40 (1H, m), 7.51-7.56 (2H, m), 8.01 (1H, d, J=8.1 Hz), 10.51 (1H, s).

(2) Preparation of the Intermediate 472(2).

The title compound was obtained in the same manner as the Example 2(3) using the following starting materials.

Starting materials: the intermediate 472(1) and malonic acid; Yield: 75% (whitish-pink solid).

$^1$H-NMR ($CDCl_3$) δ: 0.96 (3H, t, J=7.2 Hz), 1.41-1.54 (2H, m), 1.71-1.80 (2H, m), 3.94 (2H, t, J=6.6 Hz), 6.58-6.63 (3H, m), 6.68-6.71 (1H, m), 7.09 (1H, d, J=1.5 Hz), 7.21-7.27 (3H, m), 7.34 (1H, dd, J=1.5, 8.1 Hz), 7.49-7.53 (2H, m), 7.72 (1H, d, J=8.1 Hz), 8.11 (1H, d, J=15.9 Hz).

(3) Preparation of the Compound 472.

The title compound was obtained in the same manner as the Example 3 using the following starting material.

Starting material: the intermediate 472(2); Yield: 80% (white solid).

$^1$H-NMR (DMSO-$d_6$) δ: 0.90 (3H, t, J=7.2 Hz), 1.36-1.45 (2H, m), 1.61-1.70 (2H, m), 2.54 (2H, t, J=7.8 Hz), 2.82 (2H, t, J=7.8 Hz), 3.93 (2H, t, J=6.6 Hz), 6.47-6.54 (2H, m), 6.67 (1H, dd, J=2.1, 8.4 Hz), 7.18-7.27 (2H, m), 7.39-7.46 (4H, m), 7.70-7.73 (2H, m), 12.19 (1H, s).

Example 473

Preparation of the Compound 473

(1) Preparation of the Intermediate 473(1).

The title compound was obtained in the same manner as the Example 12(2) using the following starting materials.

Starting materials: the intermediate 333(1) and 4-(tert-butoxy)phenol; Yield: 85% (yellowish-white solid).

$^1$H-NMR ($CDCl_3$) δ: 1.36 (9H, s), 7.00-7.07 (5H, m), 7.24-7.28 (2H, m), 7.33-7.37 (1H, m), 7.48-7.53 (2H, m), 8.00 (1H, d, J=8.1 Hz), 10.56 (1H, s).

(2) Preparation of the Intermediate 473(2).

The title compound was obtained in the same manner as the Example 2(3) using the following starting materials.

Starting materials: the intermediate 473(1) and malonic acid; Yield: 86% (white solid).

$^1$H-NMR ($CDCl_3$) δ: 1.35 (9H, s), 6.63 (1H, d, J=15.9 Hz), 6.98-7.00 (5H, m), 7.23-7.28 (2H, m), 7.30 (1H, dd, J=1.8, 8.4 Hz), 7.47-7.50 (2H, m), 7.70 (1H, d, J=8.4 Hz), 8.15 (1H, d, J=15.9 Hz), 10.56 (1H, s).

(3) Preparation of the Compound 473.

The title compound was obtained in the same manner as the Example 3 using the following starting material.

Starting material: the intermediate 473(2); Yield: 88% (white solid).

$^1$H-NMR (DMSO-d$_6$) δ: 1.26 (9H, s), 2.53 (2H, t, J=7.8 Hz), 2.85 (2H, t, J=7.8 Hz), 6.90-6.99 (4H, m), 7.10-7.12 (1H, m), 7.39-7.43 (4H, m), 7.67-7.70 (2H, m), 12.25 (1H, s).

Example 474

Preparation of the Compound 474

(1) Preparation of the Intermediate 474(1).

The title compound was obtained in the same manner as the Example 12(2) using the following starting materials.

Starting materials: the intermediate 333(1) and 4-trifluoromethylphenol; Yield: 67% (white solid).

$^1$H-NMR ($CDCl_3$) δ: 7.15-7.19 (2H, m), 7.26-7.40 (3H, m), 7.48-7.52 (1H, m), 7.55-7.58 (2H, m), 7.65-7.68 (2H, m), 8.06 (1H, d, J=8.1 Hz), 10.44 (1H, s).

(2) Preparation of the Intermediate 474(2).

The title compound was obtained in the same manner as the Example 2(3) using the following starting materials.

Starting materials: the intermediate 474(1) and malonic acid; Yield: 95% (white solid).

$^1$H-NMR ($CDCl_3$) δ: 6.58 (1H, d, J=15.9 Hz), 7.08-7.11 (2H, m), 7.15 (1H, d, J=1.8 Hz), 7.26-7.33 (2H, m), 7.44 (1H, dd, J=1.8, 8.1 Hz), 7.52-7.56 (2H, m), 7.60-7.63 (2H, m), 7.78 (1H, d, J=8.1 Hz), 8.02 (1H, d, J=15.9 Hz).

(3) Preparation of the Compound 474.

The title compound was obtained in the same manner as the Example 3 using the following starting material.

Starting material: the intermediate 474(2); Yield: 37% (white solid).

$^1$H-NMR (DMSO-d$_6$) δ: 2.53 (2H, t, J=7.8 Hz), 2.79 (2H, t, J=7.8 Hz), 7.11-7.13 (2H, m), 7.38-7.59 (5H, m), 7.72-7.80 (4H, m), 12.21 (1H, s).

Example 475

Preparation of the Compound 475

(1) Preparation of the Intermediate 475(1).

The title compound was obtained in the same manner as the Example 12(2) using the following starting materials.

Starting materials: the intermediate 333(1) and 4-(tert-pentyl)phenol; Yield: 100% (yellow oil).

$^1$H-NMR ($CDCl_3$) δ: 0.70 (3H, t, J=7.2 Hz), 1.31 (6H, s), 1.65 (2H, q, J=7.2 Hz), 7.03-7.08 (3H, m), 7.22-7.28 (2H, m), 7.33-7.37 (3H, m), 7.50-7.54 (2H, m), 8.01 (1H, d, J=7.8 Hz), 10.54 (1H, s).

(2) Preparation of the Intermediate 475(2).

The title compound was obtained in the same manner as the Example 2(3) using the following starting materials.

Starting materials: the intermediate 475(1) and malonic acid; Yield: 93% (white solid).

$^1$H-NMR ($CDCl_3$) δ: 0.70 (3H, t, J=7.2 Hz), 1.29 (6H, s), 1.64 (2H, q, J=7.2 Hz), 6.63 (1H, d, J=15.9 Hz), 6.97-7.00 (2H, m), 7.06 (1H, d, J=1.8 Hz), 7.23-7.27 (2H, m), 7.31-7.33 (3H, m), 7.48-7.52 (2H, m), 7.72 (1H, d, J=8.1 Hz), 8.15 (1H, d, J=15.9 Hz).

(3) Preparation of the Compound 475.

The title compound was obtained in the same manner as the Example 3 using the following starting material.

Starting material: the intermediate 475(2); Yield: 78% (white solid).

$^1$H-NMR (DMSO-d$_6$) δ: 0.62 (3H, t, J=7.2 Hz), 1.23 (6H, s), 1.58 (2H, q, J=7.2 Hz), 2.54 (2H, t, J=7.8 Hz), 2.84 (2H, t, J=7.8 Hz), 6.90-6.92 (2H, m), 7.15 (1H, s), 7.30-7.33 (2H, m), 7.39-7.44 (4H, m), 7.68-7.72 (2H, m), 12.18 (1H, s).

Example 476

Preparation of the Compound 476

(1) Preparation of the Intermediate 476(1).

The title compound was obtained in the same manner as the Example 12(2) using the following starting materials.

Starting materials: the intermediate 333(1) and 2-naphthol; Yield: 80% (yellow solid).

$^1$H-NMR ($CDCl_3$) δ: 7.11 (1H, d, J=1.5 Hz), 7.22-7.26 (2H, m), 7.34 (1H, dd, J=2.4, 8.7 Hz), 7.40-7.54 (6H, m), 7.74-7.77 (1H, m), 7.86-7.89 (1H, m), 7.92 (1H, d, J=8.7 Hz), 8.06 (1H, d, J=8.1 Hz), 10.58 (1H, d, J=0.9 Hz).

(2) Preparation of the Intermediate 476(2).

The title compound was obtained in the same manner as the Example 2(3) using the following starting materials.

Starting materials: the intermediate 476(1) and malonic acid; Yield: 84% (white solid).

$^1$H-NMR ($CDCl_3$) δ: 6.65 (1H, d, J=16.2 Hz), 7.10 (1H, d, J=2.1 Hz), 7.22-7.24 (2H, m), 7.30 (1H, dd, J=2.1, 8.7 Hz), 7.36-7.51 (6H, m), 7.72-7.78 (2H, m), 7.83-7.90 (2H, m), 8.17 (1H, d, J=16.2 Hz).

(3) Preparation of the Compound 476.

The title compound was obtained in the same manner as the Example 3 using the following starting material.

Starting material: the intermediate 476(2); Yield: 68% (white solid).

$^1$H-NMR (DMSO-d$_6$) δ: 2.58 (2H, t, J=7.8 Hz), 2.88 (2H, t, J=7.8 Hz), 7.26-7.51 (9H, m), 7.71-7.74 (2H, m), 7.79-7.82 (1H, m), 7.90-7.93 (1H, m), 7.98 (1H, d, J=9.0 Hz), 12.22 (1H, s).

Example 477

Preparation of the Compound 477

(1) Preparation of the Intermediate 477(1).

The title compound was obtained in the same manner as the Example 12(2) using the following starting materials.

Starting materials: 4-bromo-2-fluorobenzaldehyde and 4-(trifluoromethoxy)phenol; Yield: 91% (yellow solid).

$^1$H-NMR ($CDCl_3$) δ: 7.03 (1H, d, J=1.8 Hz), 7.08-7.15 (2H, m), 7.26-7.33 (2H, m), 7.36 (1H, ddd, J=0.6, 1.8, 8.4 Hz), 7.81 (1H, d, J=8.4 Hz), 10.44 (1H, d, J=0.6 Hz).

(2) Preparation of the Intermediate 477(2).

The title compound was obtained in the same manner as the Example 1(2) using the following starting materials.

Starting materials: the intermediate 477(1) and 4-(trifluoromethoxy)phenylboronic acid; Yield: 98% (pale yellow solid).

$^1$H-NMR ($CDCl_3$) δ: 7.07-7.18 (3H, m), 7.21-7.34 (4H, m), 7.44 (1H, ddd, J=0.9, 1.8, 8.4 Hz), 7.50-7.59 (2H, m), 8.03 (1H, d, J=8.4 Hz), 10.48 (1H, d, J=0.9 Hz).

(3) Preparation of the Compound 477.

The title compound was obtained in the same manner as the Example 2(3) using the following starting materials.

Starting materials: the intermediate 477(2) and malonic acid; Yield: 89% (white solid).

$^1$H-NMR ($CDCl_3$) δ: 6.60 (1H, d, J=16.2 Hz), 7.02-7.12 (3H, m), 7.18-7.32 (4H, m), 7.38 (1H, dd, J=1.8, 8.4 Hz), 7.50-7.59 (2H, m), 7.75 (1H, d, J=8.4 Hz), 8.10 (1H, d, J=16.2 Hz).

Example 478

Preparation of the Compound 478

(1) Preparation of the Intermediate 478(1).

The title compound was obtained in the same manner as the Example 1(2) using the following starting materials.

Starting materials: the intermediate 477(1) and 4-(tert-butyl)phenylboronic acid; Yield: 98% (pale yellow oil).

$^1$H-NMR ($CDCl_3$) δ: 1.34 (9H, s), 7.09-7.16 (3H, m), 7.21-7.29 (2H, m), 7.43-7.51 (5H, m), 8.01 (1H, d, J=8.4 Hz), 10.47 (1H, s).

(2) Preparation of the Compound 478.

The title compound was obtained in the same manner as the Example 2(3) using the following starting materials.

Starting materials: the intermediate 478(1) and malonic acid; Yield: 77% (white solid).

$^1$H-NMR ($CDCl_3$) δ: 1.34 (9H, s), 6.58 (1H, d, J=16.2 Hz), 7.02-7.09 (2H, m), 7.11 (1H, d, J=1.5 Hz), 7.16-7.27 (2H, m), 7.40-7.50 (5H, m), 7.73 (1H, d, J=8.4 Hz), 8.09 (1H, d, J=16.2 Hz).

Example 479

Preparation of the Compound 479

The title compound was obtained in the same manner as the Example 3 using the following starting material.

Starting material: the compound 477; Yield: 88% (white solid).

$^1$H-NMR ($CDCl_3$) δ: 2.73 (2H, t, J=7.2 Hz), 3.01 (2H, t, J=7.2 Hz), 6.92-7.03 (2H, m), 7.06 (1H, d, J=1.8 Hz), 7.15-7.28 (4H, m), 7.29 (1H, dd, J=1.8, 7.8 Hz), 7.38 (1H, d, J=7.8 Hz), 7.45-7.55 (2H, m).

Example 480

Preparation of the Compound 480

The title compound was obtained in the same manner as the Example 3 using the following starting material.

Starting material: the compound 478; Yield: 91% (white solid).

$^1$H-NMR ($CDCl_3$) δ: 1.33 (9H, s), 2.72 (2H, t, J=7.2 Hz), 2.99 (2H, t, J=7.2 Hz), 6.94-7.02 (2H, m), 7.09 (1H, brs), 7.12-7.20 (2H, m), 7.30-7.36 (2H, m), 7.40-7.47 (4H, m).

Example 481

Preparation of the Compound 481

(1) Preparation of the Intermediate 481(1).

The title compound was obtained in the same manner as the Example 12(2) using the following starting materials.

Starting materials: 4-bromo-2-fluorobenzaldehyde and 4-butylphenol; Yield: 90% (white solid).

$^1$H-NMR ($CDCl_3$) δ: 0.95 (3H, t, J=7.2 Hz), 1.31-1.44 (2H, m), 1.57-1.69 (2H, m), 2.60-2.69 (2H, m), 6.95-7.05 (3H, m), 7.20-7.27 (2H, m), 7.28 (1H, ddd, J=0.9, 1.8, 8.4 Hz), 7.78 (1H, d, J=8.4 Hz), 10.49 (1H, d, J=0.9 Hz).

(2) Preparation of the Intermediate 481(2).

The title compound was obtained in the same manner as the Example 1(2) using the following starting materials.

Starting materials: the intermediate 481(1) and 4-(trifluoromethoxy)phenylboronic acid; Yield: 90% (pale yellow oil).

$^1$H-NMR ($CDCl_3$) δ: 0.94 (3H, t, J=7.2 Hz), 1.30-1.44 (2H, m), 1.55-1.68 (2H, m), 2.58-2.67 (2H, m), 7.00-7.06 (3H, m), 7.18-7.30 (4H, m), 7.35 (1H, ddd, J=0.9, 1.8, 8.4 Hz), 7.46-7.55 (2H, m), 7.99 (1H, d, J=8.4 Hz), 10.55 (1H, d, J=0.9 Hz).

(3) Preparation of the Intermediate 481(3).

The title compound was obtained in the same manner as the Example 95(2) using the following starting material.

Starting material: the intermediate 481(2); Yield: 88% (pale brown oil).

$^1$H-NMR ($CDCl_3$) δ: 0.93 (3H, t, J=7.2 Hz), 1.30-1.44 (2H, m), 1.52-1.67 (2H, m), 2.55-2.65 (2H, m), 5.67 (1H, s), 6.94-7.02 (2H, m), 7.05 (1H, d, J=2.4 Hz), 7.10 (1H, d, J=8.4 Hz), 7.13-7.26 (5H, m), 7.40-7.49 (2H, m).

(4) Preparation of the Intermediate 481(4).

The title compound was obtained in the same manner as the Example 105(2) using the following starting materials.

Starting materials: the intermediate 481(3) and ethyl bromoacetate; Yield: 65% (colorless oil).

$^1$H-NMR ($CDCl_3$) δ: 0.92 (3H, t, J=7.2 Hz), 1.27 (3H, t, J=7.2 Hz), 1.28-1.44 (2H, m), 1.52-1.65 (2H, m), 2.54-2.62 (2H, m), 4.23 (2H, q, J=7.2 Hz), 4.72 (2H, s), 6.90-6.98 (2H, m), 7.02 (1H, d, J=8.4 Hz), 7.09-7.17 (2H, m), 7.16 (1H, d, J=1.8 Hz), 7.19-7.29 (3H, m), 7.44-7.50 (2H, m).

(5) Preparation of the Compound 481.

The title compound was obtained in the same manner as the Example 12(4) using the following starting material.

Starting material: the intermediate 481(4); Yield: 81% (white solid).

$^1$H-NMR ($CDCl_3$) δ: 0.92 (3H, t, J=7.2 Hz), 1.28-1.44 (2H, m), 1.52-1.65 (2H, m), 2.54-2.62 (2H, m), 4.72 (2H, s), 6.90-6.98 (2H, m), 7.02 (1H, d, J=8.4 Hz), 7.09-7.17 (2H, m), 7.16 (1H, d, J=1.8 Hz), 7.19-7.29 (3H, m), 7.44-7.50 (2H, m).

Example 482

Preparation of the Compound 482

(1) Preparation of the Intermediate 482(1).

The title compound was obtained in the same manner as the Example 2(1) using the following starting materials.

Starting materials: the intermediate 18(1) and methyl 4-chloro-2-methylbutyrate; Yield: 81% (pale yellow solid).

$^1$H-NMR ($CDCl_3$) δ: 1.29 (3H, d, J=7.2 Hz), 1.92-2.08 (1H, m), 2.22-2.38 (1H, m), 2.71-2.86 (1H, m), 3.70 (3H, s), 4.10-4.28 (2H, m), 7.07 (1H, d, J=8.7 Hz), 7.24-7.34 (2H, m), 7.54-7.64 (2H, m), 7.75 (1H, dd, J=2.4, 8.7 Hz), 8.04 (1H, d, J=2.4 Hz), 10.52 (1H, s).

(2) Preparation of the Intermediate 482(2).

The title compound was obtained in the same manner as the Example 95(2) using the following starting material.

Starting material: the intermediate 482(1); Yield: 92% (yellow solid).

$^1$H-NMR ($CDCl_3$) δ: 1.27 (3H, d, J=7.2 Hz), 1.92-2.10 (1H, m), 2.16-2.33 (1H, m), 2.66-2.83 (1H, m), 3.72 (3H, s), 4.12 (2H, t, J=6.0 Hz), 6.03 (1H, brs), 6.89 (1H, d, J=8.4 Hz), 7.01 (1H, dd, J=2.4, 8.4 Hz), 7.15 (1H, d, J=2.4 Hz), 7.19-7.30 (2H, m), 7.48-7.59 (2H, m).

(3) Preparation of the Intermediate 482(3).

The title compound was obtained in the same manner as the Example 2(1) using the following starting materials.

Starting materials: the intermediate 482(2) and p-(tert-butyl)benzyl bromide; Yield: 67% (colorless oil).

$^1$H-NMR ($CDCl_3$) δ: 1.25 (3H, d, J=7.2 Hz), 1.33 (9H, s), 1.84-2.02 (1H, m), 2.16-2.34 (1H, m), 2.73-2.91 (1H, m), 3.67 (3H, s), 4.02-4.18 (2H, m), 5.13 (2H, s), 6.96 (1H, d, J=8.1 Hz), 7.06-7.14 (2H, m), 7.19-7.28 (2H, m), 7.37-7.44 (4H, m), 7.44-7.53 (2H, m).

(4) Preparation of the Compound 482.

The title compound was obtained in the same manner as the Example 12(4) using the following starting material.

Starting material: the intermediate 482(3); Yield: 87% (white solid).

$^1$H-NMR ($CDCl_3$) δ: 1.23 (3H, d, J=6.9 Hz), 1.30 (9H, s), 1.82-2.00 (1H, m), 2.14-2.30 (1H, m), 2.69-2.86 (1H, m), 4.00-4.17 (1H, m), 5.11 (2H, s), 6.92 (1H, d, J=8.1 Hz), 7.04 (1H, dd, J=2.1, 8.1 Hz), 7.08 (1H, d, J=2.1 Hz), 7.15-7.24 (2H, m), 7.32-7.47 (6H, m).

Example 483

Preparation of the Compound 483

(1) Preparation of the Intermediate 483(1).

The title compound was obtained in the same manner as the Example 1(2) using the following starting materials.

Starting materials: the intermediate 79(1) and 2,5-dichlorophenylboronic acid; Yield: 95% (pale yellow solid).

$^1$H-NMR ($CDCl_3$) δ: 1.33 (9H, s), 6.98 (1H, d, J=1.5 Hz), 7.02-7.07 (2H, m), 7.18-7.21 (1H, m), 7.25-7.29 (2H, m), 7.36-7.42 (3H, m), 8.00 (1H, d, J=7.8 Hz), 10.56 (1H, s).

(2) Preparation of the Compound 483.

The title compound was obtained in the same manner as the Example 2(3) using the following starting materials.

Starting materials: the intermediate 483(1) and malonic acid. Yield: 84% (white solid).

$^1$H-NMR (DMSO-$d_6$) δ: 1.27 (9H, s), 6.69 (1H, d, J=16.2 Hz), 6.97-6.99 (3H, m), 7.29 (1H, d, J=8.1 Hz), 7.41-7.60 (5H, m), 7.83 (1H, d, J=16.2 Hz), 8.01 (1H, d, J=8.1 Hz), 12.53 (1H, brs).

Example 484

Preparation of the Compound 484

The title compound was obtained in the same manner as the Example 3 using the following starting material.

Starting material: the compound 483; Yield: 100% (white solid).

$^1$H-NMR (DMSO-$d_6$) δ: 1.26 (9H, s), 2.57 (2H, t, J=7.5 Hz), 2.87 (2H, t, J=7.5 Hz), 6.87-6.94 (3H, m), 7.18 (1H, d, J=7.5 Hz), 7.37-7.46 (5H, m), 7.56 (1H, d, J=8.4 Hz), 12.22 (1H, brs).

Example 485

Preparation of the Compound 485

(1) Preparation of the Intermediate 485(1).

The title compound was obtained in the same manner as the Example 1(2) using the following starting materials.

Starting materials: the intermediate 315(2) and 3-nitrophenylboronic acid; Yield: 55% (colorless oil).

$^1$H-NMR ($CDCl_3$) δ: 1.27 (3H, t, J=7.2 Hz), 1.31 (9H, s), 4.24 (2H, q, J=7.2 Hz), 4.74 (2H, s), 6.93-6.98 (2H, m), 7.06 (1H, d, J=8.7 Hz), 7.27 (1H, d, J=2.4 Hz), 7.31-7.37 (3H, m), 7.55 (1H, t, J=7.8 Hz), 7.78-7.81 (1H, m), 8.13-8.16 (1H, m), 8.33-8.36 (1H, m).

(2) Preparation of the Compound 485.

The title compound was obtained in the same manner as the Example 12(4) using the following starting material.

Starting material: the intermediate 485(1); Yield: 66% (white solid).

$^1$H-NMR (DMSO-$d_6$) δ: 1.26 (9H, s), 4.80 (2H, s), 6.86-6.90 (2H, m), 7.19 (1H, d, J=8.7 Hz), 7.31-7.35 (2H, m), 7.50 (1H, d, J=2.1 Hz), 7.61 (1H, dd, J=2.1, 8.7 Hz), 7.70 (1H, t, J=8.1 Hz), 8.08-8.18 (2H, m), 8.37 (1H, t, J=2.1 Hz), 13.12 (1H, brs).

Example 486

Preparation of the Compound 486

(1) Preparation of the Intermediate 486(1).

The title compound was obtained in the same manner as the Example 1(2) using the following starting materials.

Starting materials: the intermediate 315(2) and 3-aminophenylboronic acid; Yield: 53% (colorless oil).

$^1$H-NMR ($CDCl_3$) δ: 1.26 (3H, t, J=7.2 Hz), 1.31 (9H, s), 3.71 (2H, brs), 4.22 (2H, q, J=7.2 Hz), 4.71 (2H, s), 6.61-6.64 (1H, m), 6.79 (1H, t, J=1.8 Hz), 6.86-6.90 (1H, m), 6.92-6.97 (2H, m), 7.00 (1H, d, J=8.1 Hz), 7.15 (1H, d, J=7.8 Hz), 7.19-7.21 (1H, m), 7.27-7.34 (3H, m).

(2) Preparation of the Compound 486.

The title compound was obtained in the same manner as the Example 12(4) using the following starting material.

Starting material: the intermediate 486(1); Yield: 77% (white solid).

$^1$H-NMR (DMSO-$d_6$) δ: 1.26 (9H, s), 4.74 (2H, s), 6.48-6.51 (1H, m), 6.67-6.73 (2H, m), 6.85-6.89 (2H, m), 7.04 (1H, d, J=7.8 Hz), 7.09 (1H, d, J=8.4 Hz), 7.14 (1H, d, J=2.1 Hz), 7.32-7.35 (3H, m).

Example 487

Preparation of the Compound 487

(1) Preparation of the Intermediate 487(1).

The title compound was obtained in the same manner as the Example 1(2) using the following starting materials.

Starting materials: 4-bromo-2-methoxybenzaldehyde and 4-(trifluoromethoxy)phenylboronic acid; Yield: 100% (white solid).

$^1$H-NMR ($CDCl_3$) δ: 4.01 (3H, s), 7.13 (1H, d, J=1.2 Hz), 7.18-7.26 (1H, m), 7.29-7.38 (2H, m), 7.58-7.70 (2H, m), 7.91 (1H, d, J=7.8 Hz), 10.49 (1H, s).

(2) Preparation of the Intermediate 487(2).

The title compound was obtained in the same manner as the Example 83(1) using the following starting material.

Starting material: the intermediate 487(1); Yield: 48% (white solid).

$^1$H-NMR ($CDCl_3$) δ: 7.18 (1H, d, J=1.8 Hz), 7.22 (1H, dd, J=1.8, 8.1 Hz), 7.29-7.37 (2H, m), 7.61-7.69 (3H, m), 9.94 (1H, s), 11.14 (1H, s).

(3) Preparation of the Intermediate 487(3).

The title compound was obtained in the same manner as the Example 2(1) using the following starting materials.

Starting materials: the intermediate 487(2) and benzyl 3-bromopropyl ether; Yield: 90% (colorless oil).

$^1$H-NMR ($CDCl_3$) δ: 2.10-2.26 (2H, m), 3.70 (2H, t, J=6.0 Hz), 4.29 (2H, t, J=6.0 Hz), 4.54 (2H, s), 7.14 (1H, d, J=1.2 Hz), 7.16-7.38 (8H, m), 7.58-7.68 (2H, m), 7.90 (1H, d, J=7.8 Hz), 10.44 (1H, s).

(4) Preparation of the Compound 487.

The title compound was obtained in the same manner as the Example 2(3) using the following starting materials.

Starting materials: the intermediate 487(3) and malonic acid; Yield: 89% (white solid).

$^1$H-NMR ($CDCl_3$) δ: 2.13-2.27 (2H, m), 3.73 (2H, t, J=6.0 Hz), 4.26 (2H, t, J=6.0 Hz), 4.54 (2H, s), 6.58 (1H, d, J=15.9 Hz), 7.11 (1H, d, J=1.5 Hz), 7.17 (1H, d, J=1.5, 7.8 Hz), 7.21-7.38 (8H, m), 7.55-7.66 (2H, m), 8.08 (1H, d, J=15.9 Hz).

Example 488

Preparation of the Compound 488

The title compound was obtained in the same manner as the Example 3 using the following starting material.

Starting material: the compound 487; Yield: 93% (white solid).

$^1$H-NMR ($CDCl_3$) δ: 2.08-2.21 (2H, m), 2.67 (3H, t, J=7.8 Hz), 2.95 (2H, t, J=7.8 Hz), 3.70 (2H, t, J=6.3 Hz), 4.18 (2H, t, J=6.3 Hz), 4.54 (2H, s), 7.01 (1H, d, J=1.5 Hz), 7.06 (1H, dd, J=1.5, 7.5 Hz), 7.20-7.36 (8H, m), 7.52-7.61 (2H, m).

Example 489

Preparation of the Compound 489

(1) Preparation of the Intermediate 489(1).

The title compound was obtained in the same manner as the Example 2(1) using the following starting materials.

Starting materials: the intermediate 487(2) and 3-chloropropyl phenyl sulfide; Yield: 87% (yellow solid).

$^1$H-NMR ($CDCl_3$) δ: 2.13-2.30 (2H, m), 3.17 (2H, t, J=6.9 Hz), 4.27 (2H, t, J=6.0 Hz), 7.08 (1H, d, J=1.5 Hz), 7.12-7.41 (8H, m), 7.55-7.64 (2H, m), 7.89 (1H, d, J=7.8 Hz), 10.49 (1H, s).

(2) Preparation of the Compound 489.

The title compound was obtained in the same manner as the Example 2(3) using the following starting materials.

Starting materials: the intermediate 489(1) and malonic acid; Yield: 93% (pale yellow solid).

$^1$H-NMR ($CDCl_3$) δ: 2.16-2.29 (2H, m), 3.19 (2H, t, J=6.9 Hz), 4.24 (2H, t, J=6.0 Hz), 6.58 (1H, d, J=16.2 Hz), 7.05 (1H, d, J=1.5 Hz), 7.12-7.22 (2H, m), 7.22-7.34 (4H, m), 7.34-7.42 (2H, m), 7.54-7.66 (3H, m), 8.12 (1H, d, J=16.2 Hz).

Example 490

Preparation of the Compound 490

(1) Preparation of the Intermediate 490(1).

The title compound was obtained in the same manner as the Example 12(2) using the following starting materials.

Starting materials: 4-bromo-2-fluorobenzaldehyde and 2-(isopropyl)phenol; Yield: 59% (pale brown oil).

$^1$H-NMR ($CDCl_3$) δ: 1.23 (6H, d, J=7.2 Hz), 3.18 (1H, sept, J=7.2 Hz), 6.87 (1H, d, J=1.8 Hz), 6.92-6.99 (1H, m), 7.22-7.30 (3H, m), 7.38-7.44 (1H, m), 7.79 (1H, d, J=8.4 Hz), 10.56 (1H, d, J=0.6 Hz).

(2) Preparation of the Intermediate 490(2).

The title compound was obtained in the same manner as the Example 1(2) using the following starting materials.

Starting materials: the intermediate 490(1) and 4-(trifluoromethoxy)phenylboronic acid; Yield: 99% (pale yellow oil).

$^1$H-NMR ($CDCl_3$) δ: 1.26 (6H, d, J=7.2 Hz), 3.30 (1H, sept, J=7.2 Hz), 6.88 (1H, d, J=1.8 Hz), 6.92-7.02 (1H, m), 7.19-7.30 (5H, m), 7.38-7.52 (3H, m), 8.01 (1H, d, J=8.4 Hz), 10.62 (1H, d, J=0.6 Hz).

(3) Preparation of the Compound 490.

The title compound was obtained in the same manner as the Example 2(3) using the following starting materials.

Starting materials: the intermediate 490(2) and malonic acid; Yield: 70% (white solid).

$^1$H-NMR ($CDCl_3$) δ: 1.26 (6H, d, J=7.2 Hz), 3.29 (1H, sept, J=7.2 Hz), 6.66 (1H, d, J=15.9 Hz), 6.87 (1H, d, J=1.8 Hz), 6.87-6.93 (2H, m), 7.14-7.32 (4H, m), 7.36-7.50 (3H, m), 7.72 (1H, d, J=8.4 Hz), 8.21 (1H, d, J=15.9 Hz).

Example 491

Preparation of the Compound 491

The title compound was obtained in the same manner as the Example 3 using the following starting material.

Starting material: the compound 490; Yield: 40% (white solid).

$^1$H-NMR ($CDCl_3$) δ: 1.27 (6H, d, J=7.2 Hz), 2.78 (2H, t, J=7.2 Hz), 3.09 (2H, t, J=7.2 Hz), 3.29 (1H, sept, J=7.2 Hz), 6.80-6.85 (2H, m), 6.86 (1H, d, J=1.8 Hz), 7.09-7.24 (4H, m), 7.32-7.39 (2H, m), 7.40-7.47 (2H, m).

Example 492

Preparation of the Compound 492

(1) Preparation of the Intermediate 492(1).

The title compound was obtained in the same manner as the Example 12(2) using the following starting materials.

Starting materials: 4-bromo-2-fluorobenzaldehyde and 4-(benzyloxy)phenol; Yield: 97% (white solid).

$^1$H-NMR ($CDCl_3$) δ: 5.09 (2H, s), 6.93 (1H, d, J=1.8 Hz), 7.04 (4H, s), 7.22-7.28 (1H, m), 7.31-7.48 (5H, m), 7.77 (1H, d, J=8.4 Hz), 10.51 (1H, d, J=0.6 Hz).

(2) Preparation of the Intermediate 492(2).

The title compound was obtained in the same manner as the Example 1(2) using the following starting materials.

Starting materials: the intermediate 492(1) and 4-(trifluoromethoxy)phenylboronic acid; Yield: 73% (white solid).

$^1$H-NMR ($CDCl_3$) δ: 5.08 (2H, s), 6.96 (1H, d, J=1.8 Hz), 6.98-7.10 (4H, m), 7.22-7.28 (2H, m), 7.30-7.53 (8H, m), 7.99 (1H, d, J=8.4 Hz), 10.58 (1H, d, J=0.9 Hz).

(3) Preparation of the Intermediate 492(3).

The title compound was obtained in the same manner as the Example 95(2) using the following starting material.

Starting material: the intermediate 492(2); Yield: 66% (white solid).

$^1$H-NMR ($CDCl_3$) δ: 5.06 (2H, s), 5.70 (1H, s), 6.94-7.12 (6H, m), 7.14-7.24 (3H, m), 7.30-7.49 (7H, m).

(4) Preparation of the Intermediate 492(4).

The title compound was obtained in the same manner as the Example 105(2) using the following starting materials.

Starting materials: the intermediate 492(3) and ethyl bromoacetate; Yield: 92% (white solid).

$^1$H-NMR ($CDCl_3$) δ: 1.28 (3H, t, J=7.2 Hz), 4.24 (2H, q, J=7.2 Hz), 4.73 (2H, s), 5.04 (2H, s), 6.92-7.04 (5H, m), 7.08 (1H, d, J=1.8 Hz), 7.17-7.25 (3H, m), 7.30-7.49 (7H, m).

(5) Preparation of the Compound 492.

The title compound was obtained in the same manner as the Example 12(4) using the following starting material.

Starting material: the intermediate 492(4); Yield: 90% (white solid).

$^1$H-NMR (DMSO-d$_6$) δ: 4.77 (2H, s), 5.06 (2H, s), 6.92-7.04 (4H, m), 7.13 (1H, d, J=8.1 Hz), 7.21 (1H, d, J=2.4 Hz), 7.28-7.49 (8H, m), 7.63-7.69 (2H, m), 13.06 (1H, brs).

Example 493

Preparation of the Compound 493

The title compound was obtained in the same manner as the Example 3 using the following starting material.

Starting material: the compound 492; Yield: 93% (white solid).

$^1$H-NMR (CDCl$_3$) δ: 4.76 (2H, s), 6.76-6.86 (2H, m), 6.90-6.99 (2H, m), 7.01-7.10 (2H, m), 7.17-7.28 (4H, m), 7.41-7.49 (2H, m).

Example 494

Preparation of the Compound 494

(1) Preparation of the Intermediate 494(1).

The title compound was obtained in the same manner as the Example 12(2) using the following starting materials.

Starting materials: 4-bromo-2-fluorobenzaldehyde and 3,5-dimethylphenol; Yield: 92% (pale yellow solid).

$^1$H-NMR (CDCl$_3$) δ: 2.34 (6H, s), 6.70 (2H, s), 6.88 (1H, s), 7.00 (1H, d, J=1.8 Hz), 7.29 (1H, dd, J=1.8, 8.1 Hz), 7.78 (1H, d, J=8.1 Hz), 10.46 (1H, d, J=0.6 Hz).

(2) Preparation of the Intermediate 494(2).

The title compound was obtained in the same manner as the Example 1(2) using the following starting materials.

Starting materials: the intermediate 494(1) and 4-(tert-butyl)phenylboronic acid; Yield: 91% (pale yellow oil).

$^1$H-NMR (CDCl$_3$) δ: $^1$H-NMR (CDCl$_3$) δ: 1.34 (9H, s), 2.31 (6H, s), 6.71 (2H, s), 6.81 (1H, s), 7.10 (1H, d, J=1.8 Hz), 7.50 (1H, dd, J=1.8, 8.1 Hz), 7.35-7.50 (4H, m), 7.98 (1H, d, J=8.1 Hz), 10.46 (1H, d, J=0.6 Hz).

(3) Preparation of the Compound 494.

The title compound was obtained in the same manner as the Example 2(3) using the following starting materials.

Starting materials: the intermediate 494(2) and malonic acid; Yield: 85% (white solid).

$^1$H-NMR (DMSO-d$_6$) δ: 1.29 (9H, s), 2.25 (6H, s), 6.60-6.80 (5H, m), 7.15 (1H, d, J=1.8 Hz), 7.42-7.50 (2H, m), 7.51-7.59 (2H, m), 7.76 (1H, d, J=16.2 Hz), 7.96 (1H, d, J=8.1 Hz), 12.42 (1H, brs).

Example 495

Preparation of the Compound 495

(1) Preparation of the Intermediate 495(1).

The title compound was obtained in the same manner as the Example 1(2) using the following starting materials.

Starting materials: the intermediate 79(1) and 4-(tert-butyl)phenylboronic acid; Yield: 94% (pale yellow solid).

$^1$H-NMR (CDCl$_3$) δ: 1.33 (9H, s), 1.34 (9H, s), 7.01-7.06 (2H, m), 7.12 (1H, d, J=1.7 Hz), 7.38-7.45 (7H, m), 7.98 (1H, d, J=8.1 Hz), 10.52 (1H, d, J=0.7 Hz).

(2) Preparation of the Compound 495.

The title compound was obtained in the same manner as the Example 2(3) using the following starting materials.

Starting materials: the intermediate 495(1) and malonic acid; Yield: 95% (white solid).

$^1$H-NMR (CDCl$_3$) δ: 1.33 (18H, s), 6.60 (1H, d, J=16.1 Hz), 6.95-7.00 (2H, m), 7.22 (1H, d, J=1.8 Hz), 7.33-7.39 (3H, m), 7.41-7.47 (4H, m), 7.69 (1H, d, J=8.2 Hz), 8.13 (1H, d, J=16.1 Hz).

Example 496

Preparation of the Compound 496

(1) Preparation of the Intermediate 496(1).

The title compound was obtained in the same manner as the Example 1(2) using the following starting materials.

Starting materials: the intermediate 79(1) and 3,5-methyphenylboronic acid; Yield: 72% (pale yellow solid).

$^1$H-NMR (CDCl$_3$) δ: 1.33 (9H, s), 2.34 (6H, s), 7.00-7.05 (3H, m), 7.10-7.15 (3H, m), 7.37-7.42 (3H, m), 7.98 (1H, d, J=7.1 Hz), 10.50 (1H, d, J=0.7 Hz).

(2) Preparation of the Compound 496.

The title compound was obtained in the same manner as the Example 2(3) using the following starting materials.

Starting materials: the intermediate 496(1) and malonic acid; Yield: 94% (white solid).

$^1$H-NMR (CDCl$_3$) δ: 1.33 (9H, s), 2.35 (6H, s), 6.61 (1H, d, J=16.1 Hz), 6.95-7.01 (3H, m), 7.09-7.16 (3H, m), 7.34-7.39 (3H, m), 7.70 (1H, d, J=8.1 Hz), 8.13 (1H, d, J=16.1 Hz).

Example 497

Preparation of the Compound 497

The title compound was obtained in the same manner as the Example 3 using the following starting material.

Starting material: the compound 495; Yield: 95% (white solid).

$^1$H-NMR (CDCl$_3$) δ: 1.31 (9H, s), 1.33 (9H, s), 2.74 (2H, t, J=7.5 Hz), 3.02 (2H, t, J=7.5 Hz), 6.89-6.94 (2H, m), 7.08 (1H, d, J=1.7 Hz), 7.26-7.35 (4H, m), 7.38-7.45 (4H, m).

Example 498

Preparation of the Compound 498

The title compound was obtained in the same manner as the Example 3 using the following starting material.

Starting material: the compound 496; Yield: 96% (white solid).

$^1$H-NMR (CDCl$_3$) δ: 1.31 (9H, s), 2.33 (6H, s), 2.73 (2H, t, J=7.3 Hz), 3.01 (2H, t, J=7.3 Hz), 6.88-6.93 (2H, m), 6.95 (1H, brs), 7.10 (3H, brs), 7.26-7.34 (4H, m).

Example 499

Preparation of the Compound 499

The title compound was obtained in the same manner as the Example 3 using the following starting material.

Starting material: the compound 494; Yield: 83% (white solid).

$^1$H-NMR (CDCl$_3$) δ: 1.30 (9H, s), 2.27 (6H, s), 2.72 (2H, t, J=7.2 Hz), 2.97 (2H, t, J=7.2 Hz), 6.60 (2H, s), 6.71 (1H, s), 7.08 (1H, d, J=1.5 Hz), 7.24-7.34 (2H, m), 7.37-7.48 (4H, m).

Example 500

Preparation of the Compound 500

(1) Preparation of the Intermediate 500(1).

The title compound was obtained in the same manner as the Example 2(1) using the following starting materials.

Starting materials: the intermediate 487(2) and (1-bromoethyl)benzene; Yield: 84% (white solid).

$^1$H-NMR ($CDCl_3$) δ: 1.75 (3H, d, J=6.6 Hz), 5.51 (1H, q, J=6.6 Hz), 6.99 (1H, d, J=1.5 Hz), 7.10-7.17 (1H, m), 7.21-7.48 (9H, m), 7.88 (1H, d, J=8.1 Hz), 10.66 (1H, s).

(2) Preparation of the Compound 500.

The title compound was obtained in the same manner as the Example 2(3) using the following starting materials.

Starting materials: the intermediate 500(1) and malonic acid; Yield: 81% (white solid).

$^1$H-NMR ($CDCl_3$) δ: 1.76 (3H, d, J=6.3 Hz), 5.47 (1H, q, J=6.3 Hz), 6.67 (1H, d, J=16.2 Hz), 6.93 (1H, d, J=1.8 Hz), 7.09 (1H, dd, J=1.8, 8.1 Hz), 7.19-7.33 (3H, m), 7.33-7.46 (6H, m), 7.59 (1H, d, J=8.1 Hz), 8.24 (1H, d, J=16.2 Hz).

Example 501

Preparation of the Compound 501

The title compound was obtained in the same manner as the Example 3 using the following starting material.

Starting material: the compound 500; Yield: 68% (white solid).

$^1$H-NMR ($CDCl_3$) δ: 1.67 (3H, d, J=6.3 Hz), 2.78 (2H, t, J=7.5 Hz), 3.08 (2H, t, J=7.5 Hz), 5.39 (1H, q, J=6.3 Hz), 6.85 (1H, d, J=1.5 Hz), 6.98 (1H, dd, J=1.5, 7.8 Hz), 7.14-7.43 (10H, m).

Example 502

Preparation of the Compound 502

(1) Preparation of the Intermediate 502(1).

The title compound was obtained in the same manner as the Example 447(2) using the following starting materials.

Starting materials: 1-bromo-4-(tert-butoxy)benzene and trimethyl borate; Yield: 32% (white solid).

$^1$H-NMR (DMSO-$d_6$) δ: 1.31 (9H, s), 6.96 (2H, d, J=8.4 Hz), 7.78 (2H, d, J=8.4 Hz).

(2) Preparation of the Intermediate 502(2).

The title compound was obtained in the same manner as the Example 1(2) using the following starting materials.

Starting materials: the intermediates 502(1) and 315 (2); Yield: 62% (colorless oil).

$^1$H-NMR ($CDCl_3$) δ: 1.26 (3H, t, J=7.24 Hz), 1.31 (9H, s), 1.35 (9H, s), 4.22 (2H, q, J=7.2 Hz), 4.70 (2H, s), 6.92-6.96 (2H, m), 6.97-7.02 (2H, m), 7.01 (1H, d, J=8.1 Hz), 7.22 (1H, d, J=2.4 Hz), 7.25-7.33 (3H, m), 7.35-7.41 (2H, m).

(3) Preparation of the Compound 502.

The title compound was obtained in the same manner as the Example 12(4) using the following starting material.

Starting material: the intermediate 502(2); Yield: 80% (white solid).

$^1$H-NMR (DMSO-$d_6$) δ: 1.26 (9H, s), 1.30 (9H, s), 4.74 (2H, s), 6.87 (2H, d, J=8.7 Hz), 6.99 (2H, d, J=8.4 Hz), 7.10 (1H, d, J=8.4 Hz), 7.26 (1H, d, J=2.4 Hz), 7.32 (2H, d, J=8.7 Hz), 7.40-7.45 (1H, m), 7.49 (2H, d, J=8.4 Hz), 13.04 (1H, brs).

Example 503

Preparation of the Compound 503

(1) Preparation of the Intermediate 503(1).

The title compound was obtained in the same manner as the Example 1(2) using the following starting materials.

Starting materials: the intermediate 79(1) and 3-(trifluoromethoxy)phenylboronic acid; Yield: 90% (pale yellow solid).

$^1$H-NMR ($CDCl_3$) δ: 1.34 (9H, s), 7.02-7.09 (3H, m), 7.22-7.27 (1H, m), 7.33-7.48 (6H, m), 8.02 (1H, d, J=8.1 Hz), 10.54 (1H, d, J=0.7 Hz).

(2) Preparation of the Compound 503.

The title compound was obtained in the same manner as the Example 2(3) using the following starting materials.

Starting materials: the intermediate 503(1) and malonic acid; Yield: 90% (pale yellow solid).

$^1$H-NMR ($CDCl_3$) δ: 1.34 (9H, s), 6.62 (1H, d, J=16.1 Hz), 6.97-7.02 (2H, m), 7.09 (1H, d, J=1.8 Hz), 7.19-7.24 (1H, m), 7.31-7.44 (6H, m), 7.74 (1H, d, J=8.2 Hz), 8.14 (1H, d, J=16.1 Hz).

Example 504

Preparation of the Compound 504

The title compound was obtained in the same manner as the Example 3 using the following starting material.

Starting material: the compound 503; Yield: 91% (white solid).

$^1$H-NMR ($CDCl_3$) δ: 1.32 (9H, s), 2.75 (2H, t, J=7.3 Hz), 3.04 (2H, t, J=7.3 Hz), 6.90-6.95 (2H, m), 7.07 (1H, d, J=1.7 Hz), 7.14-7.18 (1H, m), 7.24-7.27 (1H, m), 7.32-7.41 (6H, m).

Example 505

Preparation of the Compound 505

(1) Preparation of the Intermediate 505(1).

The title compound was obtained in the same manner as the Example 1(2) using the following starting materials.

Starting materials: the intermediate 314(3) and 4-butylphenylboronic acid; Yield: 84% (colorless oil).

$^1$H-NMR ($CDCl_3$) δ: 0.95 (3H, t, J=7.2 Hz), 1.25 (3H, t, J=7.2 Hz), 1.30-1.47 (2H, m), 1.32 (9H, s), 1.55-1.69 (2H, m), 2.61-2.70 (2H, m), 4.22 (2H, q, J=7.2 Hz), 4.73 (2H, s), 6.93-7.04 (3H, m), 7.13-7.20 (2H, m), 7.21-7.29 (2H, m), 7.30-7.37 (2H, m), 7.43-7.48 (2H, m).

(2) Preparation of the Compound 505.

The title compound was obtained in the same manner as the Example 12(4) using the following starting material.

Starting material: the intermediate 505(1); Yield: 91% (pale yellow oil).

$^1$H-NMR ($CDCl_3$) δ: 0.94 (3H, t, J=7.2 Hz), 1.31 (9H, s), 1.32-1.46 (2H, m), 1.56-1.69 (2H, m), 2.61-2.70 (2H, m), 4.74 (2H, s), 6.93-7.04 (3H, m), 7.13-7.20 (2H, m), 7.21-7.29 (2H, m), 7.30-7.37 (2H, m), 7.43-7.48 (2H, m).

Example 506

Preparation of the Compound 506

(1) Preparation of the Intermediate 506(1).

The title compound was obtained in the same manner as the Example 2(1) using the following starting materials.

Starting materials: the intermediate 487(2) and α-bromo-diphenylmethane; Yield: 62% (yellow oil).

$^1$H-NMR ($CDCl_3$) δ: 6.41 (1H, s), 7.11 (1H, d, J=1.5 Hz), 7.14-7.55 (14H, m), 7.60-7.68 (1H, m), 7.92 (1H, d, J=8.1 Hz), 10.67 (1H, s).

(2) Preparation of the Compound 506.

The title compound was obtained in the same manner as the Example 2(3) using the following starting materials.

Starting materials: the intermediate 506(1) and malonic acid; Yield: 24% (white solid).

$^1$H-NMR ($CDCl_3$) δ: 6.38 (1H, s), 6.61 (1H, d, J=16.2 Hz), 7.07 (1H, d, J=1.8 Hz), 7.14 (1H, dd, J=1.8, 8.4 Hz), 7.18-7.55 (14H, m), 7.63 (1H, d, J=8.1 Hz), 8.26 (1H, d, J=16.2 Hz), 10.75 (1H, brs).

Example 507

Preparation of the Compound 507

The title compound was obtained in the same manner as the Example 3 using the following starting material.

Starting material: the compound 506; Yield: 52% (white solid).

$^1$H-NMR ($CDCl_3$) δ: 2.77 (2H, d, J=7.8 Hz), 3.11 (2H, d, J=7.8 Hz), 6.31 (1H, s), 6.94-7.00 (1H, m), 7.00-7.06 (1H, m), 7.15-7.41 (11H, m), 7.41-7.51 (4H, m), 11.26 (1H, brs).

Example 508

Preparation of the Compound 508

The title compound was obtained in the same manner as the Example 3 using the following starting material.

Starting material: the compound 489; Yield: 30% (white solid).

$^1$H-NMR ($CDCl_3$) δ: 2.08-2.27 (2H, m), 2.70 (2H, t, J=7.5 Hz), 2.99 (2H, t, J=7.5 Hz), 3.16 (2H, t, J=6.9 Hz), 4.16 (2H, t, J=6.9 Hz), 6.97 (1H, d, J=1.5 Hz), 7.06 (1H, dd, J=1.5, 7.8 Hz), 7.12-7.43 (8H, m), 7.50-7.63 (2H, m), 10.70 (1H, brs).

Example 509

Preparation of the Compound 509

(1) Preparation of the Intermediate 509(1).

The title compound was obtained in the same manner as the Example 12(2) using the following starting materials.

Starting materials: the intermediate 333(1) and 4-isopropylphenol; Yield: 84% (colorless oil).

$^1$H-NMR ($CDCl_3$) δ: 1.27 (6H, d, J=6.9 Hz), 2.83-3.02 (1H, m), 7.00-7.10 (3H, m), 7.20-7.31 (4H, m), 7.31-7.40 (1H, m), 7.46-7.56 (2H, m), 8.01 (1H, d, J=8.4 Hz), 10.54 (1H, s).

(2) Preparation of the Compound 509.

The title compound was obtained in the same manner as the Example 2(3) using the following starting materials.

Starting materials: the intermediate 509(1) and malonic acid; Yield: 73% (white solid).

$^1$H-NMR ($CDCl_3$) δ: 1.26 (6H, d, J=6.9 Hz), 2.83-3.02 (1H, m), 6.63 (1H, d, J=16.2 Hz), 6.87-7.01 (2H, m), 7.06 (1H, d, J=1.8 Hz), 7.09-7.35 (5H, m), 7.46-7.55 (2H, m), 7.72 (1H, d, J=8.1 Hz), 8.15 (1H, d, J=16.2 Hz).

Example 510

Preparation of the Compound 510

The title compound was obtained in the same manner as the Example 3 using the following starting material.

Starting material: the compound 509; Yield: 82% (white solid).

$^1$H-NMR ($CDCl_3$) δ: 1.25 (6H, d, J=6.9 Hz), 2.75 (2H, t, J=7.8 Hz), 2.81-2.97 (1H, m), 3.04 (2H, t, J=7.8 Hz), 6.88-6.96 (2H, m), 7.04 (1H, d, J=1.8 Hz), 7.14-7.31 (5H, m), 7.35 (1H, d, J=7.8 Hz), 7.44-7.52 (2H, m), 9.90 (1H, brs).

Example 511

Preparation of the Compound 511

(1) Preparation of the Intermediate 511(1).

The title compound was obtained in the same manner as the Example 12(2) using the following starting materials.

Starting materials: the intermediate 333(1) and 4-butylphenol; Yield: 45% (yellow oil).

$^1$H-NMR ($CDCl_3$) δ: 0.94 (3H, t, J=7.2 Hz), 1.26-1.45 (2H, m), 1.52-1.72 (2H, m), 2.63 (2H, t, J=7.2 Hz), 6.98-7.11 (3H, m), 7.16-7.42 (5H, m), 7.45-7.59 (2H, m), 8.00 (1H, d, J=8.1 Hz), 10.54 (1H, s).

(2) Preparation of the Compound 511.

The title compound was obtained in the same manner as the Example 2(3) using the following starting materials.

Starting materials: the intermediate 511(1) and malonic acid; Yield: 58% (white solid).

$^1$H-NMR ($CDCl_3$) δ: 0.94 (3H, t, J=7.2 Hz), 1.29-1.45 (2H, m), 1.53-1.69 (2H, m), 2.61 (2H, t, J=7.8 Hz), 6.63 (1H, d, J=16.2 Hz), 6.72-7.01 (2H, m), 7.03 (1H, d, J=1.5 Hz), 7.13-7.36 (5H, m), 7.44-7.55 (2H, m), 7.71 (1H, d, J=8.1 Hz), 8.15 (1H, d, J=16.2 Hz).

Example 512

Preparation of the Compound 512

The title compound was obtained in the same manner as the Example 3 using the following starting material.

Starting material: the compound 511; Yield: 59% (white solid).

$^1$H-NMR ($CDCl_3$) δ: 0.93 (3H, t, J=7.5 Hz), 1.28-1.44 (2H, m), 1.52-1.66 (2H, m), 2.59 (2H, t, J=7.8 Hz), 2.75 (2H, t, J=7.8 Hz), 3.04 (2H, t, J=7.8 Hz), 6.84-6.95 (2H, m), 7.02 (1H, d, J=2.1 Hz), 7.09-7.17 (2H, m), 7.17-7.28 (3H, m), 7.35 (1H, d, J=8.1 Hz), 7.42-7.52 (2H, m), 10.02 (1H, brs).

Example 513

Preparation of the Compound 513

(1) Preparation of the Intermediate 513(1).

The title compound was obtained in the same manner as the Example 95(2) using the following starting material.

Starting material: the intermediate 490(2); Yield: 90% (brown oil).

$^1$H-NMR ($CDCl_3$) δ: 1.27 (6H, d, J=6.6 Hz), 3.34 (1H, sept, J=6.6 Hz), 5.70 (1H, s), 6.87 (1H, d, J=2.1 Hz), 6.88-6.95 (1H, m), 7.11 (1H, d, J=8.4 Hz), 7.15-7.24 (5H, m), 7.35-7.44 (3H, m).

(2) Preparation of the Intermediate 513(2).

The title compound was obtained in the same manner as the Example 105(2) using the following starting materials.

Starting materials: the intermediate 513(1) and ethyl bromoacetate; Yield: 95% (colorless oil).

$^1$H-NMR ($CDCl_3$) δ: 1.27 (3H, t, J=7.2 Hz), 1.28 (6H, d, J=6.6 Hz), 3.42 (1H, sept, J=6.6 Hz), 4.23 (2H, q, J=7.2 Hz), 4.73 (2H, s), 6.80-6.87 (1H, m), 7.00-7.14 (4H, m), 7.17-7.25 (3H, m), 7.31-7.38 (1H, m), 7.41-7.47 (2H, m).

(3) Preparation of the Compound 513.

The title compound was obtained in the same manner as the Example 12(4) using the following starting material.

Starting material: the intermediate 513(2); Yield: 60% (colorless oil).

$^1$H-NMR ($CDCl_3$) δ: 1.28 (6H, d, J=6.6 Hz), 3.39 (1H, sept, J=6.6 Hz), 4.76 (2H, s), 6.80-6.86 (1H, m), 7.00-7.16 (4H, m), 7.18-7.27 (3H, m), 7.32-7.39 (1H, m), 7.41-7.47 (2H, m).

Example 514

Preparation of the Compound 514

(1) Preparation of the Intermediate 514(1).

The title compound was obtained in the same manner as the Example 1(2) using the following starting materials.

Starting materials: the intermediate 465(1) and 3-(trifluoromethoxy)phenylboronic acid; Yield: 87% (pale yellow oil).

$^1$H-NMR ($CDCl_3$) δ: 1.34 (9H, s), 6.87-6.90 (1H, m), 7.08 (1H, d, J=1.5 Hz), 7.20-7.27 (3H, m), 7.31-7.47 (5H, m), 8.02 (1H, d, J=8.4 Hz), 10.56 (1H, s).

(2) Preparation of the Compound 514.

The title compound was obtained in the same manner as the Example 2(3) using the following starting materials.

Starting materials: the intermediate 514(1) and malonic acid; Yield: 98% (white solid).

$^1$H-NMR (DMSO-$d_6$) δ: 1.28 (9H, s), 6.69 (1H, d, J=16.2 Hz), 6.77 (1H, ddd, J=1.2, 2.4, 8.1 Hz), 7.17-7.41 (5H, m), 7.56-7.71 (4H, m), 7.82 (1H, d, J=16.2 Hz), 8.03 (1H, d, J=8.1 Hz), 12.49 (1H, brs).

Example 515

Preparation of the Compound 515

The title compound was obtained in the same manner as the Example 3 using the following starting material.

Starting material: the compound 514; Yield: 98% (white solid).

$^1$H-NMR (DMSO-$d_6$) δ: 1.27 (9H, s), 2.55 (2H, t, J=7.5 Hz), 2.86 (2H, t, J=7.5 Hz), 6.69-6.74 (1H, m), 7.09-7.17 (3H, m), 7.28 (1H, d, J=8.1 Hz), 7.32-7.35 (1H, m), 7.44-7.50 (2H, m), 7.53-7.64 (3H, m), 12.00 (1H, brs).

Example 516

Preparation of the Compound 516

(1) Preparation of the Intermediate 516(1).

The title compound was obtained in the same manner as the Example 12(2) using the following starting materials.

Starting materials: the intermediate 333(1) and 4-isopropylbenzenethiol; Yield: 87% (pale yellow solid).

$^1$H-NMR ($CDCl_3$) δ: 1.27 (6H, d, J=6.9 Hz), 2.88-3.02 (1H, m), 7.20-7.30 (5H, m), 7.40-7.51 (5H, m), 7.94 (1H, d, J=8.1 Hz), 10.41 (1H, s).

(2) Preparation of the Compound 516.

The title compound was obtained in the same manner as the Example 2(3) using the following starting materials.

Starting materials: the intermediate 516(1) and malonic acid; Yield: 67% (pale yellow solid).

$^1$H-NMR ($CDCl_3$) δ: 1.24 (6H, d, J=6.9 Hz), 2.90 (1H, sept, J=6.9 Hz), 6.44 (1H, d, J=15.9 Hz), 7.18-7.31 (6H, m), 7.46-7.52 (4H, m), 7.73 (1H, d, J=8.4 Hz), 8.42 (1H, d, J=15.9 Hz).

Example 517

Preparation of the Compound 517

The title compound was obtained in the same manner as the Example 3 using the following starting material.

Starting material: the compound 462; Yield: 40% (white solid).

$^1$H-NMR ($CDCl_3$) δ: 1.30 (9H, s), 2.72 (2H, t, J=7.8 Hz), 3.16 (2H, t, J=7.8 Hz), 7.19-7.25 (4H, m), 7.30-7.49 (7H, m).

Example 518

Preparation of the Compound 518

(1) Preparation of the Intermediate 518(1).

The title compound was obtained in the same manner as the Example 1(2) using the following starting materials.

Starting materials: the intermediate 79(1) and 4-(isopropyl)phenylboronic Acid; Yield: 100% (pale yellow oil).

$^1$H-NMR ($CDCl_3$) δ: 1.26 (6H, d, J=6.6 Hz), 1.34 (9H, s), 2.93 (1H, sept, J=6.6 Hz), 7.01-7.06 (2H, m), 7.11 (1H, d, J=1.5 Hz), 7.29 (2H, d, J=8.4 Hz), 7.37-7.46 (5H, m), 7.98 (1H, d, J=8.1 Hz), 10.52 (1H, s).

(2) Preparation of the Compound 518.

The title compound was obtained in the same manner as the Example 2(3) using the following starting materials.

Starting materials: the intermediate 518(1) and malonic acid; Yield: 92% (white solid).

$^1$H-NMR (DMSO-$d_6$) δ: 1.20 (6H, d, J=6.9 Hz), 1.27 (9H, s), 2.90 (1H, sept, J=6.6 Hz), 6.64 (1H, d, J=16.0 Hz), 6.94-6.98 (2H, m), 7.18 (1H, d, J=1.8 Hz), 7.30 (2H, d, J=8.1 Hz), 7.38-7.42 (2H, m), 7.50-7.58 (3H, m), 7.80 (1H, d, J=16.0 Hz), 7.98 (1H, d, J=8.1 Hz), 12.46 (1H, brs).

Example 519

Preparation of the Compound 519

The title compound was obtained in the same manner as the Example 3 using the following starting material.

Starting material: the compound 518; Yield: 81% (white solid).

$^1$H-NMR (DMSO-$d_6$) δ: 1.20 (6H, d, J=6.9 Hz), 1.27 (9H, s), 2.54 (2H, t, J=7.2 Hz), 2.83 (2H, t, J=7.2 Hz), 2.90 (1H, sept, J=6.9 Hz), 6.88-6.92 (2H, m), 7.06-7.10 (1H, m), 7.28 (2H, d, J=8.4 Hz), 7.36-7.43 (4H, m), 7.47 (2H, d, J=8.4 Hz), 12.19 (1H, brs).

Example 520

Preparation of the Compound 520

(1) Preparation of the Intermediate 520(1).

The title compound was obtained in the same manner as the Example 1(2) using the following starting materials.

Starting materials: 4-bromo-2-fluorobenzaldehyde and 4-isopropylphenylboronic acid; Yield: 100% (white solid).

$^1$H-NMR ($CDCl_3$) δ: 1.30 (6H, d, J=6.9 Hz), 2.98 (1H, sept, J=6.9 Hz), 7.32-7.43 (3H, m), 7.47-7.52 (1H, m), 7.53-7.58 (2H, m), 7.92 (1H, t, J=7.8 Hz), 10.38 (1H, s).

(2) Preparation of the Intermediate 520(2).

The title compound was obtained in the same manner as the Example 12(2) using the following starting materials.

Starting materials: the intermediate 520(1) and 4-(tert-butyl)benzenethiol; Yield: 86% (pale yellow oil).

$^1$H-NMR ($CDCl_3$) δ: 1.26 (6H, d, J=6.9 Hz), 1.34 (9H, m), 2.93 (1H, sept, J=6.9 Hz), 7.23-7.30 (3H, m), 7.36-7.44 (6H, m), 7.52 (1H, dd, J=1.8, 7.8 Hz), 7.92 (1H, d, J=7.8 Hz), 10.41 (1H, s).

(3) Preparation of the Compound 520.

The title compound was obtained in the same manner as the Example 2(3) using the following starting materials.

Starting materials: the intermediate 520(2) and malonic acid; Yield: 80% (pale yellow solid).

$^1$H-NMR ($CDCl_3$) δ: 1.27 (6H, d, J=7.2 Hz), 1.30 (9H, m), 2.94 (1H, sept, J=7.2 Hz), 6.42 (1H, d, J=15.9 Hz), 7.24-7.35 (6H, m), 7.44 (2H, d, J=8.4 Hz), 7.52 (1H, dd, J=1.8, 8.1 Hz), 7.56 (1H, d, J=1.8 Hz), 7.72 (1H, d, J=8.1 Hz), 8.43 (1H, d, J=15.9 Hz).

Example 521

Preparation of the Compound 521

(1) Preparation of the Intermediate 521(1).

The title compound was obtained in the same manner as the Example 1(2) using the following starting materials.

Starting materials: the intermediates 79(1) and 447(1); Yield: 88% (yellow oil).

$^1$H-NMR ($CDCl_3$) δ: 0.95 (6H, t, J=7.2 Hz), 1.34 (9H, s), 1.62-1.75 (4H, m), 4.09-4.20 (1H, m), 6.88-6.98 (2H, m), 6.98-7.06 (2H, m), 7.08 (1H, d, J=1.8 Hz), 7.32-7.51 (5H, m), 7.97 (1H, d, J=7.8 Hz), 10.50 (1H, s).

(2) Preparation of the Compound 521.

The title compound was obtained in the same manner as the Example 2(3) using the following starting materials.

Starting materials: the intermediate 521(1) and malonic acid; Yield: 81% (pale yellow solid).

$^1$H-NMR ($CDCl_3$) δ: 0.95 (6H, t, J=7.5 Hz), 1.33 (9H, s), 1.61-1.74 (4H, m), 4.07-4.19 (1H, m), 6.59 (1H, d, J=16.2 Hz), 6.86-7.02 (4H, m), 7.08 (1H, d, J=1.8 Hz), 7.28-7.48 (5H, m), 7.68 (1H, d, J=8.4 Hz), 8.13 (1H, d, J=16.2 Hz).

Example 522

Preparation of the Compound 522

The title compound was obtained in the same manner as the Example 3 using the following starting material.

Starting material: the compound 521; Yield: 85% (white solid).

$^1$H-NMR ($CDCl_3$) δ: 0.95 (6H, t, J=7.5 Hz), 1.31 (9H, s), 1.61-1.74 (4H, m), 2.73 (2H, t, J=7.8 Hz), 3.01 (2H, t, J=7.8 Hz), 4.04-4.18 (1H, m), 6.85-6.96 (4H, m), 7.06 (1H, d, J=1.5 Hz), 7.23 (1H, dd, J=1.5, 8.1 Hz), 7.27-7.36 (3H, m), 7.38-7.44 (2H, m).

Example 523

Preparation of the Compound 523

(1) Preparation of the Intermediate 523(1).

The title compound was obtained in the same manner as the Example 75(1) using the following starting materials.

Starting materials: the intermediate 333(1) and 4-butoxyphenol; Yield: 88% (yellow oil).

$^1$H-NMR ($CDCl_3$) δ: 0.99 (3H, t, J=7.2 Hz), 1.40-1.59 (2H, m), 1.70-1.85 (2H, m), 3.97 (2H, t, J=6.3 Hz), 6.89-7.00 (3H m), 7.02-7.12 (2H, m), 7.20-7.37 (3H, m), 7.44-7.54 (2H, m), 7.99 (1H, d, J=8.1 Hz), 10.58 (1H, s).

(2) Preparation of the Intermediate 523(2).

The title compound was obtained in the same manner as the Example 95(2) using the following starting material.

Starting material: the intermediate 523(1); Yield: 71% (white solid).

$^1$H-NMR ($CDCl_3$) δ: 0.98 (3H, t, J=6.9 Hz), 1.40-1.58 (2H, m), 1.70-1.84 (2H, m), 3.94 (2H, t, J=6.6 Hz), 5.78 (1H, s), 6.84-6.93 (2H m), 6.95-7.05 (2H, m), 7.09 (1H, d, J=8.1 Hz), 7.14-7.24 (3H, m), 7.38-7.46 (2H, m).

(3) Preparation of the Intermediate 523(3).

The title compound was obtained in the same manner as the Example 105(2) using the following starting materials.

Starting materials: the intermediate 523(2) and ethyl bromoacetate; Yield: 96% (colorless oil).

$^1$H-NMR ($CDCl_3$) δ: 0.97 (3H, t, J=7.2 Hz), 1.27 (3H, t, J=7.2 Hz), 1.40-1.57 (2H, m), 1.68-1.83 (2H, m), 3.93 (2H, t, J=7.2 Hz), 4.24 (2H, q, J=7.2 Hz), 4.73 (2H, s), 6.82-6.92 (2H m), 6.95-7.05 (3H, m), 7.07 (1H, d, J=2.4 Hz), 7.15-7.26 (3H, m), 7.40-7.50 (2H, m).

(4) Preparation of the Compound 523.

The title compound was obtained in the same manner as the Example 12(4) using the following starting material.

Starting material: the intermediate 523(3); Yield: 55% (white solid).

$^1$H-NMR ($CDCl_3$) δ: 0.97 (3H, t, J=7.5 Hz), 1.40-1.58 (2H, m), 1.67-1.83 (2H, m), 3.93 (2H, t, J=6.6 Hz), 4.71 (2H, s), 6.80-6.92 (2H m), 6.93-7.10 (4H, m), 7.14-7.30 (3H, m), 7.37-7.49 (2H, m).

Example 524

Preparation of the Compound 524

(1) Preparation of the Intermediate 524(1).

The title compound was obtained in the same manner as the Example 95(2) using the following starting material.

Starting material: the intermediate 514(1); Yield: 100% (pale yellow oil).

$^1$H-NMR ($CDCl_3$) δ: 1.33 (9H, s), 5.75 (1H, brs), 6.81-6.85 (1H, m), 7.10-7.20 (5H, m), 7.24-7.31 (3H, m), 7.35-7.41 (2H, m).

(2) Preparation of the Intermediate 524(2).

The title compound was obtained in the same manner as the Example 105(2) using the following starting materials.

Starting materials: the intermediate 524(1) and ethyl bromoacetate; Yield: 100% (pale yellow oil).

$^1$H-NMR ($CDCl_3$) δ: 1.27 (3H, t, J=7.2 Hz), 1.32 (9H, s), 4.24 (2H, q, J=7.2 Hz), 4.73 (2H, s), 6.77 (1H, ddd, J=1.2, 2.4, 8.1 Hz), 7.02 (1H, t, J=8.4 Hz), 7.04-7.16 (3H, m), 7.21-7.31 (4H, m), 7.37-7.43 (2H, m).

(3) Preparation of the Compound 524.

The title compound was obtained in the same manner as the Example 12(4) using the following starting material.

Starting material: the intermediate 524(2); Yield: 62% (white solid).

$^1$H-NMR (DMSO-$d_6$) δ: 1.26 (9H, s), 4.78 (2H, s), 6.60-6.72 (1H, m), 7.05-7.25 (4H, m), 7.28-7.35 (1H, m), 7.42 (1H, d, J=2.4 Hz), 7.51-7.59 (3H, m), 7.62-7.69 (1H, m), 13.09 (1H, brs).

Example 525

Preparation of the Compound 525

(1) Preparation of the Intermediate 525(1).

The title compound was obtained in the same manner as the Example 95(2) using the following starting material.

Starting material: the intermediate 463(1); Yield: 89% (brown oil).

$^1$H-NMR ($CDCl_3$) δ: 5.62 (1H, s), 6.94-6.98 (2H, m), 7.05-7.09 (2H, m), 7.16 (1H, dd, J=2.2, 8.6 Hz), 7.20-7.23 (1H, m), 7.37-7.44 (2H, m).

(2) Preparation of the Intermediate 525(2).

The title compound was obtained in the same manner as the Example 105(2) using the following starting materials.

Starting materials: the intermediate 525(1) and ethyl bromoacetate; Yield: 90% (colorless oil).

$^1$H-NMR ($CDCl_3$) δ: 1.26 (3H, t, J=7.1 Hz), 4.21 (2H, q, J=7.1 Hz), 4.65 (2H, s), 6.83 (1H, d, J=8.8 Hz), 6.98-7.02 (2H, m), 7.06-7.13 (2H, m), 7.18 (1H, dd, J=2.4, 8.6 Hz), 7.37-7.44 (2H, m).

(3) Preparation of the Intermediate 525(3).

The title compound was obtained in the same manner as the Example 1(2) using the following starting materials.

Starting materials: the intermediate 525(2) and phenylboronic acid; Yield: 68% (pale yellow oil).

$^1$H-NMR ($CDCl_3$) δ: 1.27 (3H, t, J=7.1 Hz), 4.23 (2H, q, J=7.1 Hz), 4.70 (2H, s), 6.97-7.90 (4H, m), 7.25-7.42 (7H, m), 7.47-7.51 (2H, m).

(4) Preparation of the Compound 525.

The title compound was obtained in the same manner as the Example 12(4) using the following starting material.

Starting material: the intermediate 525(3); Yield: 78% (pale yellow solid).

$^1$H-NMR ($CDCl_3$) δ: 4.73 (2H, s), 6.99-7.14 (4H, m), 7.27-7.44 (7H, m), 7.48-7.52 (2H, m).

Example 526

Preparation of the Compound 526

(1) Preparation of the Intermediate 526(1).

The title compound was obtained in the same manner as the Example 1(2) using the following starting materials.

Starting materials: the intermediate 525(2) and 4-(trifluoromethoxy)phenylboronic acid; Yield: 63% (pale yellow oil).

$^1$H-NMR ($CDCl_3$) δ: 1.27 (3H, t, J=7.1 Hz), 4.23 (2H, q, J=7.1 Hz), 4.71 (2H, s), 6.97-7.11 (4H, m), 7.20-7.36 (6H, m), 7.46-7.51 (2H, m).

(2) Preparation of the Compound 526.

The title compound was obtained in the same manner as the Example 12(4) using the following starting material.

Starting material: the intermediate 526(1); Yield: 82% (white solid).

$^1$H-NMR ($CDCl_3$) δ: 4.74 (2H, s), 6.99-7.15 (4H, m), 7.22-7.39 (6H, m), 7.48-7.52 (2H, m).

Example 527

Preparation of the Compound 527

(1) Preparation of the Intermediate 527(1).

A mixture of the intermediate 110(1) (300 mg, 0.723 mmol), (methoxymethyl)triphenylphosphonium chloride (545 mg, 1.59 mmol), potassium tert-butoxide (162 mg, 1.45 mmol) and anhydrous N,N-dimethylformamide (3 ml) was stirred at 60° C. for 1 hour. A saturated aqueous solution of ammonium chloride and water were added to the reaction mixture, and the mixture was extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=5:1) to give the title compound (320 mg, 100%) as a colorless oil. This compound was obtained as a mixture of the geometric isomers.

$^1$H-NMR ($CDCl_3$) δ: [1.30 (s), 1.31 (s), 9H in total], [3.65 (s), 3.81 (s), 3H in total], [5.59 (d, J=6.9 Hz), 5.99 (d, J=12.9 Hz), 1H in total], [6.19 (d, J=7.2 Hz), 6.85-6.95 (m), 7.07-7.04 (m), 7.18-7.38 (m), 7.44 (d, J=8.1 Hz), 7.47-7.56 (m), 8.21 (d, J=8.1 Hz), 12H in total].

(2) Preparation of the Intermediate 527(2).

A mixture of the intermediate 527(1) (320 mg, 0.723 mmol), 2 N hydrochloric acid (2 ml) and tetrahydrofuran (4 ml) was refluxed for 6 hours. The reaction mixture was cooled to room temperature, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=5:1) to give the title compound (176 mg, 57%) as a colorless oil.

$^1$H-NMR ($CDCl_3$) δ: 1.37 (9H, s), 3.79 (2H, d, J=1.5 Hz), 6.88-6.97 (2H, m), 7.09-7.02 (1H, m), 7.20-7.28 (2H, m), 7.28-7.39 (4H, m), 7.44-7.55 (2H, m), 9.80 (1H, t, J=1.5 Hz).

(3) Preparation of the Intermediate 527(3).

The title compound was obtained in the same manner as the Example 26(1) using the following starting materials.

Starting materials: the intermediate 527(2) and triethyl phosphonoacetate; Yield: 87% (colorless oil).

$^1$H-NMR ($CDCl_3$) δ: 1.27 (3H, t, J=7.2 Hz), 1.32 (9H, s), 3.59 (2H, d, J=6.9 Hz), 4.17 (2H, q, J=7.2 Hz), 5.83 (1H, d, J=15.6 Hz), 6.87-6.95 (2H, m), 7.07-7.11 (1H, m), 7.11 (1H, d, J=6.9, 15.6 Hz), 7.21-7.30 (4H, m), 7.30-7.39 (2H, m), 7.46-7.54 (2H, m).

(4) Preparation of the Intermediate 527(4).

The title compound was obtained in the same manner as the Example 3 using the following starting material.

Starting material: the intermediate 527(3); Yield: 98% (colorless oil).

$^1$H-NMR ($CDCl_3$) δ: 1.23 (3H, t, J=7.2 Hz), 1.32 (9H, s), 2.00 (2H, quint, J=7.5 Hz), 2.35 (2H, t, J=7.5 Hz), 2.73 (2H, t, J=7.5 Hz), 4.11 (2H, q, J=7.2 Hz), 6.87-6.94 (2H, m), 7.06-7.10 (1H, m), 7.20-7.28 (2H, m), 7.30-7.38 (4H, m), 7.47-7.54 (2H, m).

(5) Preparation of the Compound 527.

The title compound was obtained in the same manner as the Example 12(4) using the following starting material.

Starting material: the intermediate 527(4); Yield: 89% (colorless oil).

$^1$H-NMR ($CDCl_3$) δ: 1.31 (9H, s), 2.00 (2H, quint, J=7.5 Hz), 2.40 (2H, t, J=7.5 Hz), 2.75 (2H, t, J=7.5 Hz), 6.87-6.94 (2H, m), 7.07 (1H, d, J=2.1 Hz), 7.20-7.28 (3H, m), 7.29-7.38 (3H, m), 7.46-7.53 (2H, m).

Example 528

Preparation of the Compound 528

(1) Preparation of the Intermediate 528(1).

The title compound was obtained in the same manner as the Example 12(2) using the following starting materials.

Starting materials: the intermediate 333(1) and thiophenol; Yield: 100% (pale yellow oil).

$^1$H-NMR ($CDCl_3$) δ: 7.22-7.29 (3H, m), 7.37-7.53 (8H, m), 7.96 (1H, d, J=7.8 Hz), 10.42 (1H, s).

(2) Preparation of the Compound 528.

The title compound was obtained in the same manner as the Example 2(3) using the following starting materials.

Starting materials: the intermediate 528(1) and malonic acid; Yield: 94% (yellow solid).

$^1$H-NMR (DMSO-$d_6$) δ: 6.61 (1H, d, J=15.9 Hz), 7.24-7.47 (7H, m), 7.71 (1H, d, J=1.8 Hz), 7.76-7.80 (3H, m), 8.05 (1H, d, J=8.1 Hz), 8.07 (1H, d, J=15.9 Hz), 12.57 (1H, brs).

Example 529

Preparation of the Compound 529

(1) Preparation of the Intermediate 529(1).

The title compound was obtained in the same manner as the Example 12(3) using the following starting materials.

Starting materials: the intermediate 462(1) and bis(2,2,2-trifluoroethyl)(methoxycarbonylmethyl)phosphonate; Yield: 100% (pale yellow oil).

$^1$H-NMR ($CDCl_3$) δ: 1.29 (9H, s), 3.66 (3H, s), 5.98 (1H, d, J=12.3 Hz), 7.21-7.33 (7H, m), 7.42-7.53 (4H, m), 7.61 (1H, d, J=7.8 Hz).

(2) Preparation of the Compound 529.

The title compound was obtained in the same manner as the Example 12(4) using the following starting material.

Starting material: the intermediate 529(1); Yield: 91% (white solid).

$^1$H-NMR (DMSO-$d_6$) δ: 1.25 (9H, s), 6.49 (1H, d, J=12.3 Hz), 7.19 (1H, d, J=12.3 Hz), 7.24-7.27 (2H, m), 7.37-7.49 (5H, m), 7.56-7.65 (2H, m), 7.69-7.72 (2H, m), 12.48 (1H, brs).

Example 530

Preparation of the Compound 530

(1) Preparation of the Intermediate 530(1).

A mixture of methyl methylsulfinylmethyl sulfide (115 mg, 0.929 mmol) and sodium hydroxide was stirred at 70° C. for 30 minutes, and the intermediate 462(1) (200 mg, 0.465 mmol) was added to the mixture, followed by refluxing for 1.5 hours. The reaction mixture was diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=1:1) to give the title compound (0.172 g, 69%) as a white solid.

$^1$H-NMR ($CDCl_3$) δ: 1.28 (9H, s), 2.12 (3H, s), 2.58 (3H, s) 7.19-7.36 (6H, m), 7.50-7.60 (3H, m), 7.62 (1H, d, J=2.1 Hz), 7.95 (1H, d, J=8.1 Hz), 8.04 (1H, s).

(2) Preparation of the Intermediate 530(2).

A solution of the intermediate 530(1) (0.172 g, 0.320 mmol) in a 2 N solution of hydrochloric acid-ethanol (5 ml) was refluxed for 7 hours. The reaction mixture was diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=10:1) to give the title compound (0.031 g, 20%) as a white solid.

$^1$H-NMR ($CDCl_3$) δ: 1.23 (3H, t, J=7.2 Hz), 1.28 (9H, s), 3.88 (2H, s), 4.12 (2H, q, J=7.2 Hz), 7.13-7.21 (2H, m), 7.21-7.34 (4H, m), 7.40 (1H, d, J=7.8 Hz), 7.44-7.55 (3H, m), 7.58 (1H, d, J=1.8 Hz).

(3) Preparation of the Compound 530.

The title compound was obtained in the same manner as the Example 12(4) using the following starting material.

Starting material: the intermediate 530(2); Yield: 100% (colorless oil).

$^1$H-NMR ($CDCl_3$) δ: 1.28 (9H, s), 3.93 (2H, s), 7.14-7.34 (6H, m), 7.39 (1H, d, J=7.8 Hz), 7.44-7.54 (3H, m), 7.57 (1H, d, J=2.1 Hz).

Example 531

Preparation of the Compound 531

(1) Preparation of the Intermediate 531(1).

The title compound was obtained in the same manner as the Example 431(2) using the following starting material.

Starting material: the intermediate 79(1); Yield: 100% (pale yellow solid).

$^1$H-NMR ($CDCl_3$) δ: 1.33 (9H, s), 3.99-4.04 (2H, m), 4.12-4.17 (2H, m), 6.13 (1H, s), 6.93-6.98 (2H, m), 7.16-7.28 (2H, m), 7.34-7.39 (2H, m), 7.48 (1H, d, J=8.4 Hz).

(2) Preparation of the Intermediate 531(2).

The title compound was obtained in the same manner as the Example 418(1) using the following starting materials.

Starting materials: the intermediate 531(1) and 4-(trifluoromethoxy)aniline; Yield: 83% (brown oil).

$^1$H-NMR ($CDCl_3$) δ: 1.31 (9H, s), 3.98-4.07 (2H, m), 4.13-4.18 (2H, m), 5.75 (1H, brs), 6.10 (1H, s), 6.47 (1H, d, J=2.4 Hz), 6.79 (1H, dd, J=2.4, 8.1 Hz), 6.91-6.99 (4H, m), 7.02-7.04 (2H, m), 7.31-7.35 (2H, m), 7.50 (1H, d, J=8.4 Hz).

(3) Preparation of the Intermediate 531(3).

The title compound was obtained in the same manner as the Example 431(5) using the following starting material.

Starting material: the intermediate 531(2); Yield: 68% (white solid).

$^1$H-NMR ($CDCl_3$) δ: 1.38 (9H, s), 6.13 (1H, brs), 6.30 (1H, d, J=2.1 Hz), 6.69 (1H, dd, J=1.5, 8.7 Hz), 6.98-7.03 (2H, m), 7.07-7.15 (4H, m), 7.37-7.41 (2H, m), 7.83 (1H, d, J=8.7 Hz), 10.30 (1H, s).

(4) Preparation of the Compound 531.

The title compound was obtained in the same manner as the Example 2(3) using the following starting materials.

Starting materials: the intermediate 531(3) and malonic acid; Yield: 97% (pale brown solid).

$^1$H-NMR (DMSO-$d_6$) δ: 1.28 (9H, s), 6.39 (1H, d, J=16.2 Hz), 6.42 (1H, d, J=3.0 Hz), 6.85 (1H, dd, J=2.4, 8.4 Hz), 7.00 (2H, d, J=9.0 Hz), 7.12 (2H, d, J=9.0 Hz), 7.22 (2H, d, J=9.0 Hz), 7.44 (2H, d, J=9.0 Hz), 7.72 (1H, d, J=98.4 Hz), 7.76 (1H, d, J=16.2 Hz), 8.84 (1H, s), 12.16 (1H, brs).

Example 532

Preparation of the Compound 532

The title compound was obtained in the same manner as the Example 3 using the following starting material.

Starting material: the compound 531; Yield: 80% (pale brown solid).

$^1$H-NMR (DMSO-d$_6$) δ: 1.27 (9H, s), 2.48 (2H, t, J=7.2 Hz), 2.75 (2H, t, J=7.2 Hz), 6.45 (1H, d, J=2.1 Hz), 6.81 (1H, dd, J=2.1, 8.4 Hz), 6.84-6.94 (2H, m), 7.00-7.05 (2H, m), 7.13-7.19 (3H, m), 7.36-7.41 (2H, m), 8.35 (1H, s).

Example 533

Preparation of the Compound 533

(1) Preparation of the Intermediate 533(1).

A mixture of the intermediate 6313(3) (1.11 g, 2.77 mmol), n-butyryl chloride (0.347 ml, 3.32 mmol), sodium hydrogen carbonate (698 mg, 8.31 mmol), dichloromethane (5 ml) and water (5 ml) was stirred at room temperature for 1 hour. The reaction mixture was diluted with water, and extracted with chloroform. The organic layer was washed with saturated brine, and dried over anhydrous sodium sulfate. The residue obtained by evaporation of the solvent under reduced pressure was washed with a mixture of n-hexane and diisopropyl ether to give the title compound (1.17 g, 90%) as a white solid.

$^1$H-NMR (CDCl$_3$) δ: 0.98 (3H, t, J=7.5 Hz), 1.33 (9H, s), 1.65-1.79 (2H, m), 2.32-2.39 (2H, m), 6.95-7.02 (2H, m), 7.06 (1H, d, J=2.1 Hz), 7.19-7.25 (2H, m), 7.31 (1H, dd, J=2.1, 8.4 Hz), 7.35-7.42 (2H, m), 7.44-7.51 (2H, m), 7.77 (1H, brs), 8.55 (1H, d, J=8.4 Hz).

(2) Preparation of the Intermediate 533(2).

A solution of the intermediate 533(1) (1.17 g, 2.49 mmol) in anhydrous tetrahydrofuran (2 ml) was added dropwise to a suspension of lithium aluminium hydride (283 mg, 7.47 mmol) in anhydrous tetrahydrofuran (5 ml), and the mixture was refluxed for 3 hours. The reaction mixture was cooled to 0° C., followed by addition of 2 N hydrochloric acid, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=3:1) to give the title compound (1.13 g, 99%) as a brown oil.

$^1$H-NMR (CDCl$_3$) δ: 0.93 (3H, t, J=7.5 Hz), 1.31 (9H, s), 1.32-1.47 (2H, m), 1.53-1.68 (2H, m), 3.13-3.24 (2H, m), 4.35 (1H, brs), 6.78 (1H, d, J=8.4 Hz), 6.90-6.98 (2H, m), 7.07 (1H, d, J=1.8 Hz), 7.15-7.22 (2H, m), 7.25 (1H, dd, J=1.8, 8.4 Hz), 7.30-7.36 (2H, m), 7.42-7.50 (2H, m).

(3) Preparation of the Intermediate 533(3).

The title compound was obtained in the same manner as the Example 416(1) using the following starting materials.

Starting materials: the intermediate 533(2) and ethyl iodoacetate; Yield: 82% (brown oil).

$^1$H-NMR (CDCl$_3$) δ: 0.83 (3H, t, J=7.5 Hz), 1.17 (3H, t, J=7.2 Hz), 1.23-1.34 (2H, m), 1.30 (9H, s), 1.41-1.53 (2H, m), 3.25-3.33 (2H, m), 4.06 (2H, q, J=7.2 Hz), 4.08 (2H, s), 6.81-6.88 (2H, m), 7.12-7.32 (7H, m), 7.45-7.53 (2H, m).

(4) Preparation of the Compound 533.

The title compound was obtained in the same manner as the Example 12(4) using the following starting material.

Starting material: the intermediate 533(3); Yield: 82% (white solid).

$^1$H-NMR (CDCl$_3$) δ: 0.89 (3H, t, J=7.2 Hz), 1.24-1.38 (2H, m), 1.32 (9H, s), 1.44-1.57 (2H, m), 3.12-3.20 (2H, m), 3.81 (2H, s), 6.90-6.97 (2H, m), 7.12 (1H, d, J=1.8 Hz), 7.21-7.31 (4H, m), 7.32-7.39 (2H, m), 7.44-7.51 (2H, m).

Example 534

Preparation of the Compound 534

(1) Preparation of the Intermediate 534(1).

A mixture of the intermediate 442(3) (1.11 g, 2.77 mmol), di-tert-butyl dicarbonate (1.81 g, 8.31 nmol), a 4 N solution of sodium hydroxide (5 ml) and tetrahydrofuran (5 ml) was refluxed for 6 hours. 2 N hydrochloric acid was added to the reaction mixture, and the mixture was extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=3:1) to give the title compound (1.24 g, 89%) as a brown oil.

$^1$H-NMR (CDCl$_3$) δ: 1.33 (9H, s), 1.53 (9H, s), 6.95-7.02 (2H, m), 7.05 (1H, d, J=2.1 Hz), 7.16 (1H, brs), 7.18-7.25 (2H, m), 7.29 (1H, dd, J=1.8, 8.4 Hz), 7.34-7.41 (2H, m), 7.42-7.50 (2H, m), 8.27 (1H, d, J=8.4 Hz).

(2) Preparation of the Intermediate 534(2).

The title compound was obtained in the same manner as the Example 533(2) using the following starting material.

Starting material: the intermediate 534(1); Yield: 23% (white solid).

$^1$H-NMR (CDCl$_3$) δ: 1.31 (9H, s), 2.90 (3H, d, J=4.8 Hz), 4.32 (1H, q, J=4.5 Hz), 6.78 (1H, d, J=8.4 Hz), 6.90-6.96 (2H, m), 7.09 (1H, d, J=1.8 Hz), 7.15-7.23 (2H, m), 7.27-7.36 (3H, m), 7.43-7.50 (2H, m).

(3) Preparation of the Intermediate 534(3).

The title compound was obtained in the same manner as the Example 416(1) using the following starting materials.

Starting materials: the intermediate 534(2) and ethyl iodoacetate; Yield: 59% (colorless oil).

$^1$H-NMR (CDCl$_3$) δ: 1.17 (3H, t, J=7.2 Hz), 1.30 (9H, s), 3.03 (3H, s), 4.07 (2H, q, J=7.2 Hz), 4.12 (2H, s), 6.85-6.92 (2H, m), 7.09 (1H, d, J=2.1 Hz), 7.11 (1H, d, J=7.8 Hz), 7.16-7.23 (2H, m), 7.25-7.35 (3H, m), 7.43-7.50 (2H, m).

(4) Preparation of the Compound 534.

The title compound was obtained in the same manner as the Example 12(4) using the following starting material.

Starting material: the intermediate 534(3); Yield: 60% (white solid).

$^1$H-NMR (CDCl$_3$) δ: 1.32 (9H, s), 2.94 (3H, s), 3.85 (2H, s), 6.91-6.98 (2H, m), 7.12 (1H, d, J=2.1 Hz), 7.18-7.32 (4H, m), 7.32-7.39 (2H, m), 7.44-7.50 (2H, m).

Example 535

Preparation of the Compound 535

(1) Preparation of the Intermediate 535(1).

The title compound was obtained in the same manner as the Example 12(3) using the following starting materials.

Starting materials: the intermediate 531(3) and bis(2,2,2-trifluoroethyl)(methoxycarbonylmethyl)phosphonate; Yield: 100% (yellow solid).

$^1$H-NMR (CDCl$_3$) δ: 1.31 (9H, s), 3.72 (3H, s), 5.84 (1H, brs), 5.85 (1H, d, J=12.6 Hz), 6.44 (1H, d, J=2.1 Hz), 6.74 (1H, dd, J=2.1, 8.7 Hz), 6.90-6.95 (2H, m), 7.01-7.10 (4H, m), 7.17 (1H, d, J=12.6 Hz), 7.31-7.36 (2H, m), 7.90 (1H, d, J=8.7 Hz).

(2) Preparation of the Compound 535.

The title compound was obtained in the same manner as the Example 12(4) using the following starting material.

Starting material: the intermediate 535(1); Yield: 87% (yellow solid).

$^1$H-NMR (DMSO-$d_6$) δ: 1.27 (9H, s), 5.81 (1H, d, J=12.9 Hz), 6.41 (1H, d, J=2.1 Hz), 6.80 (1H, dd, J=2.1, 8.4 Hz), 6.95-7.02 (3H, m), 7.09-7.12 (2H, m), 7.20 (2H, d, J=8.7 Hz), 7.40-7.44 (2H, m), 7.82 (1H, d, J=8.4 Hz), 8.70 (1H, s), 12.33 (1H, brs).

Example 536

Preparation of the Compound 536

(1) Preparation of the Intermediate 536(1).

The title compound was obtained in the same manner as the Example 418(1) using the following starting materials.

Starting materials: the intermediate 315(2) and 4-(trifluoromethoxy)aniline; Yield: 33% (pale yellow oil).

$^1$H-NMR ($CDCl_3$) δ: 1.25 (3H, t, J=6.9 Hz), 1.30 (9H, s), 4.21 (2H, q, J=6.9 Hz), 4.63 (2H, s), 5.63 (1H, brs), 6.67 (1H, d, J=2.7 Hz), 6.77 (1H, dd, J=2.7, 8.7 Hz), 6.86-6.96 (5H, m), 7.03 (2H, d, J=9.0 Hz), 7.29-7.34 (2H, m).

(2) Preparation of the Compound 536.

The title compound was obtained in the same manner as the Example 12(4) using the following starting material.

Starting material: the intermediate 536(1); Yield: 89.0% (white solid).

$^1$H-NMR (DMSO-$d_6$) δ: 1.26 (9H, s), 4.63 (2H, s), 6.62 (1H, d, J=2.7 Hz), 6.83-6.99 (6H, m), 7.14 (2H, d, J=8.4 Hz), 7.34-7.38 (2H, m), 8.18 (1H, s), 12.96 (1H, brs).

Example 537

Preparation of the Compound 537

(1) Preparation of the Intermediate 537(1).

The title compound was obtained in the same manner as the Example 105(2) using the following starting materials.

Starting materials: the intermediate 312(1) and ethyl bromoacetate; Yield: 54% (colorless oil).

$^1$H-NMR ($CDCl_3$) δ: 1.20 (3H, t, J=7.2 Hz), 1.32 (9H, s), 4.16 (2H, q, J=7.2 Hz), 4.62 (2H, s), 6.63-6.70 (1H, m), 6.89-6.99 (5H, m), 7.00-7.07 (1H, m), 7.13-7.22 (2H, m), 7.32-7.40 (2H, m).

(2) Preparation of the Compound 537.

The title compound was obtained in the same manner as the Example 12(4) using the following starting material.

Starting material: the intermediate 537(1); Yield: 69% (colorless oil).

$^1$H-NMR ($CDCl_3$) δ: 1.32 (9H, s), 4.66 (2H, s), 6.70-6.77 (1H, m), 6.89-6.98 (5H, m), 7.02-7.09 (1H, m), 7.12-7.22 (2H, m), 7.32-7.41 (2H, m).

Example 538

Preparation of the Compound 538

(1) Preparation of the Intermediate 538(1).

The title compound was obtained in the same manner as the Example 2(1) using the following starting materials.

Starting materials: the intermediate 95(3) and benzyl bromide; Yield: 83% (pale yellow oil).

$^1$H-NMR ($CDCl_3$) δ: 5.20 (2H, s), 6.91-6.98 (2H, m), 7.07 (1H, d, J=9.0 Hz), 7.13-7.20 (2H, m), 7.24 (1H, dd, J=3.0, 9.0 Hz), 7.35-7.48 (5H, m), 7.50 (1H, d, J=3.0 Hz), 10.51 (1H, s).

(2) Preparation of the Intermediate 538(2).

The title compound was obtained in the same manner as the Example 95(2) using the following starting material.

Starting material: the intermediate 538(1); Yield: 53% (pale yellow oil).

$^1$H-NMR ($CDCl_3$) δ: 5.09 (2H, s), 6.82-6.90 (2H, m), 6.64-7.04 (4H, m), 7.14-7.20 (2H, m), 7.30-7.42 (4H, m), 8.25 (1H, s).

(3) Preparation of the Intermediate 538(3).

The title compound was obtained in the same manner as the Example 89(2) using the following starting materials.

Starting materials: the intermediate 538(2) and 4-(tert-butyl)phenylboronic acid; Yield: 50% (colorless oil).

$^1$H-NMR ($CDCl_3$) δ: 1.31 (9H, s), 5.08 (2H, s), 6.68-6.76 (2H, m), 6.87-7.04 (8H, m), 7.10-7.18 (2H, m), 7.17-7.42 (4H, m).

(4) Preparation of the Intermediate 538(4).

The title compound was obtained in the same manner as the Example 3 using the following starting material.

Starting material: the intermediate 538(3); Yield: 50% (colorless oil).

$^1$H-NMR ($CDCl_3$) δ: 1.31 (9H, s), 5.49 (1H, s), 6.61 (1H, d, J=2.7 Hz), 6.69 (1H, dd, J=2.7, 8.4 Hz), 6.85-6.94 (2H, m), 6.94-7.00 (2H, m), 7.02 (1H, d, J=8.4 Hz), 7.08-7.16 (2H, m), 7.30-7.39 (2H, m).

(5) Preparation of the Intermediate 538(5).

The title compound was obtained in the same manner as the Example 105(2) using the following starting materials.

Starting materials: the intermediate 538(4) and ethyl bromoacetate; Yield: 99% (white solid).

$^1$H-NMR ($CDCl_3$) δ: 1.27 (3H, t, J=7.2 Hz), 1.31 (9H, s), 4.23 (2H, q, J=7.2 Hz), 4.67 (2H, s), 6.64-6.73 (2H, m), 6.90-7.02 (5H, m), 7.10-7.20 (2H, m), 7.29-7.37 (2H, m).

(6) Preparation of the Compound 538.

The title compound was obtained in the same manner as the Example 12(4) using the following starting material.

Starting material: the intermediate 538(5); Yield: 81% (colorless oil).

$^1$H-NMR ($CDCl_3$) δ: 1.29 (9H, s), 4.70 (2H, s), 6.63-6.72 (2H, m), 6.91-6.99 (4H, m), 7.01 (1H, d, J=8.4 Hz), 7.11-7.19 (2H, m), 7.30-7.37 (2H, m).

Example 539

Preparation of the Compound 539

The title compound was obtained in the same manner as the Example 416(1) using the following starting materials.

Starting materials: the compound 6 (3) and methyl bromoacetate; Yield: 47% (white solid).

$^1$H-NMR ($CDCl_3$) δ: 1.34 (9H, s), 4.04 (2H, s), 5.11 (2H, s), 6.68 (1H, d, J=1.5 Hz), 6.90-6.97 (2H, m), 7.21-7.28 (2H, m), 7.37-7.56 (6H, m).

Example 540

Preparation of the Compound 540

(1) Preparation of the Intermediate 540(1).

The title compound was obtained in the same manner as the Example 12(2) using the following starting materials.

Starting materials: the intermediates 12(1) and 67 (3); Yield: 11% (pale yellow solid).

$^1$H-NMR ($CDCl_3$) δ: 1.21 (3H, d, J=7.2 Hz), 1.37 (9H, s), 2.70 (2H, t, J=7.5 Hz), 3.07 (2H, t, J=7.5 Hz), 4.11 (2H, q, J=7.2 Hz), 6.95 (1H, d, J=8.4 Hz), 7.02 (1H, d, J=8.4 Hz), 7.27-7.32 (2H, m), 7.43-7.63 (8H, m), 7.70 (1H, dd, J=2.4, 8.7 Hz), 8.15 (1H, d, J=2.4 Hz).

(2) Preparation of the Intermediate 540(2).

The title compound was obtained in the same manner as the Example 26(1) using the following starting materials.

Starting materials: the intermediate 540(1) and triethyl phosphonoacetate; Yield: 11% (white solid).

$^1$H-NMR ($CDCl_3$) δ: 1.21 (3H, d, J=6.9 Hz), 1.34 (3H, d, J=7.2 Hz), 1.37 (9H, s), 2.70 (2H, t, J=7.5 Hz), 3.06 (2H, t, J=7.5 Hz), 4.11 (2H, q, J=7.2 Hz), 4.27 (2H, q, J=6.9 Hz), 6.66 (1H, d, J=16.2 Hz), 6.86-6.94 (2H, m), 7.25-7.45 (2H, m), 7.41-7.60 (9H, m), 7.80 (1H, d, J=2.1 Hz), 8.09 (1H, d, J=16.2 Hz).

(3) Preparation of the Compound 540.

The title compound was obtained in the same manner as the Example 12(4) using the following starting material.

Starting material: the intermediate 540(2); Yield: 86% (white solid).

$^1$H-NMR (DMSO-$d_6$) δ: 1.32 (9H, s), 2.60 (2H, t, J=7.8 Hz), 2.92 (2H, t, J=7.8 Hz), 6.85 (1H, d, J=16.2 Hz), 6.87-6.96 (2H, m), 7.44-7.61 (7H, m), 7.66 (1H, d, J=2.4 Hz), 7.73 (1H, dd, J=2.4, 8.7 Hz), 7.86-7.91 (2H, m), 7.92 (1H, d, J=16.2 Hz), 8.21 (1H, d, J=2.4 Hz), 12.32 (2H, brs).

Example 541

Preparation of the Compound 541

The title compound was obtained in the same manner as the Example 3 using the following starting material.

Starting material: the compound 540; Yield: 77% (white solid).

$^1$H-NMR (DMSO-$d_6$) δ: 1.32 (9H, s), 2.59-2.67 (4H, m), 2.91-3.00 (4H, m), 6.82-6.88 (2H, m), 7.42-7.69 (10H, m), 7.75-7.80 (2H, m), 12.17 (2H, brs).

Example 542

Preparation of the Compound 542

(1) Preparation of the Intermediate 542(1).

The title compound was obtained in the same manner as the Example 12(2) using the following starting materials.

Starting materials: the intermediate 12(1) and 5-(tert-butyl)-2-hydroxybenzaldehyde; Yield: 59% (pale brown solid).

$^1$H-NMR ($CDCl_3$) δ: 1.37 (9H, s), 6.98 (1H, d, J=8.4 Hz), 7.00 (1H, d, J=8.4 Hz), 7.26-7.37 (2H, m), 7.56-7.69 (3H, m), 7.73 (1H, dd, J=2.4, 8.4 Hz), 8.02 (1H, d, J=2.4 Hz), 8.17 (1H, d, J=2.4 Hz), 10.47 (1H, s), 10.58 (1H, s).

(2) Preparation of the Intermediate 542(2).

The title compound was obtained in the same manner as the Example 2(3) using the following starting materials.

Starting materials: the intermediate 542(1) and malonic acid; Yield: 82% (white solid).

$^1$H-NMR ($CDCl_3$) δ: 1.25 (9H, s), 3.74 (2H, t, J=4.5 Hz), 3.97 (2H, s), 4.14 (2H, t, J=4.5 Hz), 7.23 (1H, d, J=8.4 Hz), 6.88-6.92 (3H, m), 7.21-7.25 (2H, m), 7.50-7.54 (2H, m).

(3) Preparation of the Compound 542.

The title compound was obtained in the same manner as the Example 3 using the following starting material.

Starting material: the intermediate 542(2); Yield: 80% (white solid).

$^1$H-NMR (DMSO-$d_6$) δ: 1.29 (9H, s), 2.53 (2H, t, J=8.1 Hz), 2.62 (2H, t, J=8.1 Hz), 2.84 (2H, t, J=8.1 Hz), 2.96 (2H, t, J=8.1 Hz), 6.70 (1H, d, J=8.4 Hz), 6.75 (1H, d, J=8.4 Hz), 7.24 (1H, dd, J=2.4, 8.4 Hz), 7.34-7.54 (4H, m), 7.64 (1H, d, J=2.4 Hz), 7.70-7.82 (2H, m), 12.15 (2H, brs).

Example 543

Preparation of the Compound 543

(1) Preparation of the Intermediate 543(1).

The title compound was obtained in the same manner as the Example 2(1) using the following starting materials.

Starting materials: the intermediate 18(1) and 1-bromo-5-chloropentane; Yield: 33% (pale yellow solid).

$^1$H-NMR ($CDCl_3$) δ: 1.70-1.85 (2H, m), 1.93-2.09 (4H, m), 4.20 (4H, t, J=6.0 Hz), 7.08 (2H, d, J=8.5 Hz), 7.24-7.33 (4H, m), 7.54-7.62 (4H, m), 7.75 (2H, dd, J=2.5, 8.5 Hz), 8.04 (2H, d, J=2.5 Hz), 10.55 (2H, s).

(2) Preparation of the Compound 543.

The title compound was obtained in the same manner as the Example 2(3) using the following starting materials.

Starting materials: the intermediate 543(1) and malonic acid; Yield: 74% (white solid).

$^1$H-NMR (DMSO-$d_6$) δ: 1.58-1.75 (2H, m), 1.83-1.99 (4H, m), 4.17 (4H, t, J=6.0 Hz), 6.73 (2H, d, J=16.0 Hz), 7.20 (2H, d, J=8.5 Hz), 7.37-7.46 (4H, m), 7.70 (2H, dd, J=2.5, 8.5 Hz), 7.80-7.86 (4H, m), 7.89 (2H, d, J=16.0 Hz), 8.00 (2H, d, J=2.5 Hz), 12.32 (2H, brs).

Example 544

Preparation of the Compound 544

The title compound was obtained in the same manner as the Example 3 using the following starting material.

Starting material: the compound 543; Yield: 66% (white solid).

$^1$H-NMR (DMSO-$d_6$) δ: 1.59-1.73 (2H, m), 1.78-1.93 (4H, m), 2.54 (4H, t, J=7.5 Hz), 2.86 (4H, t, J=7.5 Hz), 4.07 (4H, t, J=6.0 Hz), 7.05 (2H, d, J=8.5 Hz), 7.36-7.43 (4H, m), 7.44-7.51 (4H, m), 7.67-7.75 (4H, m), 12.06 (2H, brs).

Example 545

Preparation of the Compound 545

(1) Preparation of the Intermediate 545(1).

The title compound was obtained in the same manner as the Example 95(2) using the following starting material.

Starting material: the intermediate 542(1); Yield: 37% (yellow solid).

$^1$H-NMR ($CDCl_3$) δ: 1.28 (9H, s), 6.18 (2H, brs), 6.78-6.92 (3H, m), 6.96 (1H, dd, J=2.1, 8.7 Hz), 7.08 (1H, d, J=2.1 Hz), 7.18-7.30 (3H, m), 7.44-7.56 (2H, m).

(2) Preparation of the Intermediate 545(2).

The title compound was obtained in the same manner as the Example 105(2) using the following starting material.

Starting material: the intermediate 545(1); Yield: 55% (colorless oil).

$^1$H-NMR ($CDCl_3$) δ: 1.24 (3H, t, J=7.2 Hz), 1.27 (3H, t, J=7.2 Hz), 1.31 (9H, s), 4.15-4.32 (4H, m), 4.71 (2H, s), 4.80 (2H, s), 6.84-6.96 (2H, m), 6.96-7.05 (2H, m) 7.05-7.16 (1H, m), 7.19 (1H, d, J=2.1 Hz), 7.22-7.30 (2H, m), 7.46-7.58 (2H, m).

(3) Preparation of the Compound 545.

The title compound was obtained in the same manner as the Example 12(4) using the following starting material.

Starting material: the intermediate 545(2); Yield: 60% (white solid).

$^1$H-NMR (DMSO-$d_6$) δ: 1.30 (9H, s), 4.19 (2H, s), 4.31 (2H, s), 6.95 (1H, dd, J=1.8, 8.4 Hz), 6.99-7.10 (2H, m), 7.12 (1H, d, J=1.8 Hz), 7.19 (1H, dd, J=1.8, 8.4 Hz), 7.34-7.39 (1H, m), 7.39-7.50 (2H, m), 7.75-7.86 (2H, m).

Example 546

Preparation of the Compound 546

The title compound was obtained in the same manner as the Example 12(4) using the following starting material.

Starting material: the compound 301 (3); Yield: 17% (colorless oil).

$^1$H-NMR (DMSO-$d_6$) δ: 1.29 (9H, s), 4.25 (2H, s), 5.15 (2H, s), 6.70 (1H, d, J=2.1 Hz), 6.82 (1H, d, J=2.1 Hz), 7.38-7.46 (6H, m), 7.69-7.72 (2H, m).

Example 547

Preparation of the Compound 547

(1) Preparation of the Intermediate 547(1).

A mixture of 4-bromo-2-fluorobenzoic acid (2.000 g, 9.132 mmol), concentrated sulfuric acid (2 ml) and methanol (20 ml) was refluxed for 2 hours. After the reaction mixture was cooled to room temperature, water was added to the residue obtained by evaporation of the solvent under reduced pressure, and the mixture was extracted with ethyl acetate. The organic layer was washed with saturated brine, and dried over anhydrous sodium sulfate. The residue obtained by evaporation of the solvent under reduced pressure was recrystallized from methanol to give the title compound (1.906 g, 90%) as a white solid.

$^1$H-NMR ($CDCl_3$) δ: 3.93 (3H, s), 7.31-7.40 (2H, m), 7.83 (1H, t, J=8.4 Hz).

(2) Preparation of the Intermediate 547(2).

The title compound was obtained in the same manner as the Example 1(2) using the following starting materials.

Starting materials: the intermediate 547(1) and 4-(trifluoromethoxy)phenylboronic acid; Yield: 96% (white solid).

$^1$H-NMR ($CDCl_3$) δ: 3.96 (3H, s), 7.28-7.38 (3H, m), 7.41 (1H, dd, J=2.1, 7.8 Hz), 7.58-7.67 (2H, m), 8.02 (1H, t, J=7.8 Hz).

(3) Preparation of the Intermediate 547(3).

The title compound was obtained in the same manner as the Example 12(2) using the following starting materials.

Starting materials: the intermediate 547(2) and 4-tert-butylbenzenethiol; Yield: 8% (white solid).

$^1$H-NMR ($CDCl_3$) δ: 1.36 (9H, s), 3.98 (3H, s), 6.88 (1H, d, J=1.5 Hz), 7.11-7.20 (2H, m), 7.22-7.44 (3H, m), 7.44-7.52 (4H, m), 8.05 (1H, d, J=7.8 Hz).

(4) Preparation of the Compound 547.

The title compound was obtained in the same manner as the Example 12(4) using the following starting material.

Starting material: the intermediate 547(3); Yield: 100% (white solid).

$^1$H-NMR ($CDCl_3$) δ: 1.37 (9H, s), 6.91 (1H, d, J=1.8 Hz), 7.14-7.21 (2H, m), 7.29-7.37 (3H, m), 7.47-7.59 (4H, m), 8.18 (1H, d, J=8.1 Hz).

Example 548

Preparation of the Compound 548

(1) Preparation of the Intermediate 548(1).

The title compound was obtained in the same manner as the Example 1(2) using the following starting materials.

Starting materials: 4-bromo-2-fluorobenzonitrile and 4-(trifluoromethoxy)phenylboronic acid; Yield: 98% (white solid).

$^1$H-NMR ($CDCl_3$) δ: 7.23 (2H, m), 7.41 (1H, dd, J=1.5, 9.9 Hz), 7.46 (1H, dd, J=1.5, 8.1 Hz), 7.57-7.68 (2H, m), 7.71 (1H, dd, J=6.6, 8.1 Hz).

(2) Preparation of the Intermediate 548(2).

The title compound was obtained in the same manner as the Example 12(2) using the following starting materials.

Starting materials: the intermediate 548(1) and 4-tert-butylbenzenethiol; Yield: 85% (white solid).

$^1$H-NMR ($CDCl_3$) δ: 1.34 (9H, s), 7.21-7.29 (3H, m), 7.38-7.50 (7H, m), 7.70 (1H, d, J=8.1 Hz).

(3) Preparation of the Intermediate 548(3).

The title compound was obtained in the same manner as the Example 530(1) using the following starting materials.

Starting materials: the intermediate 548(2) and methyl (methylsulfinyl)methyl sulfide; Yield: 40% (yellow solid).

$^1$H-NMR ($CDCl_3$) δ: 1.30 (9H, s), 2.39 (3H, s), 2.53 (3H, s) 5.45 (2H, brs), 7.17-7.55 (11H, m).

(4) Preparation of the Intermediate 548(4).

A mixture of the intermediate 548(3) (154 mg, 0.279 mmol), copper(II) chloride dihydrate (48 mg, 0.279 mmol) and ethanol (4 ml) was stirred at room temperature for 16 hours. The reaction mixture was diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=10:1) to give the title compound (8 mg, 6%) as a yellow solid.

$^1$H-NMR ($CDCl_3$) δ: 1.35 (9H, s), 1.42 (3H, t, J=7.2 Hz), 4.44 (2H, q, J=7.2 Hz), 7.12 (1H, d, J=1.8 Hz), 7.17-7.24 (2H, m), 7.33-7.44 (3H, m), 7.46 (4H, s), 7.89 (1H, d, J=8.4 Hz).

(5) Preparation of the Compound 548.

The title compound was obtained in the same manner as the Example 12(4) using the following starting material.

Starting material: the intermediate 548(4); Yield: 100% (yellow solid).

$^1$H-NMR ($CDCl_3$) δ: 1.36 (9H, s), 7.06 (1H, d, J=1.5 Hz), 7.14-7.24 (2H, m), 7.30-7.38 (2H, m), 7.41 (1H, dd, J=1.5, 8.1 Hz), 7.49 (4H, s), 8.54 (1H, d, J=8.1 Hz).

Example 549

Preparation of the Compound 549

(1) Preparation of the Intermediate 549(1).

A mixture of the intermediate 18(1) (3.00 g, 10.6 mmol), tert-butyldimethylchlorosilane (1.76 g, 11.7 mmol), imidazole (0.941 g, 13.8 mmol) and dichloromethane (50 ml) was stirred at 0° C. for 18 hours. The reaction mixture was diluted with water, and extracted with dichloromethane. The organic layer was washed saturated brine, and dried over anhydrous sodium sulfate. The residue obtained by evaporation of the solvent under reduced pressure was purified by column chromatography on silica gel (n-hexane:ethyl acetate=10:1) to give the title compound (3.26 g, 77%) as a colorless oil.

$^1$H-NMR ($CDCl_3$) δ: 0.32 (6H, s), 1.05 (9H, s), 6.97 (1H, d, J=8.4 Hz), 7.22-7.33 (2H, m), 7.52-7.62 (2H, m), 7.66 (1H, dd, J=2.7, 8.4 Hz), 8.02 (1H, d, J=2.4 Hz), 10.51 (1H, s).

(2) Preparation of the Intermediate 549(2).

A solution of n-butyllithium in hexane (2.50 ml, 4.00 mmol) was added dropwise to a solution of 1-bromo-4-(tert-butyl)benzene (1.28 g, 6.00 mmol) in anhydrous tetrahydrofuran (10 ml) at −78° C., and the mixture was stirred for 30 minutes. A solution of the intermediate 549(1) (793 mg, 2.00 mmol) in anhydrous tetrahydrofuran (1 ml) was added dropwise to the reaction mixture at −78° C., and the mixture was stirred for 1 hours. A saturated aqueous solution of ammonium chloride and water were added to the reaction mixture, and the mixture was extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=5:1) to give the title compound (1.01 g, 95%) as a colorless oil.

$^1$H-NMR ($CDCl_3$) δ: 0.23 (6H, s), 0.90 (9H, s), 1.29 (9H, s), 2.67 (1H, d, J=5.4 Hz), 6.10 (1H, d, J=5.4 Hz), 6.89 (1H, d, J=8.4 Hz), 7.20-7.40 (6H, m), 7.49-7.58 (4H, m).

(3) Preparation of the Intermediate 549(3).

A mixture of the intermediate 549(2) (2.47 g, 4.65 mmol), pyridinium dichromate (2.62 g, 9.30 mmol), silica gel (10 g) and chloroform (40 ml) was refluxed for 3 hours. The reaction mixture was filtered, and the residue obtained by concentration of the filtrate under reduced pressure was purified by column chromatography on silica gel (n-hexane:ethyl acetate=10:1) to give the title compound (2.36 g, 96%) as a pale yellow oil.

$^1$H-NMR ($CDCl_3$) δ: 0.08 (6H, s), 0.64 (9H, s), 1.33 (9H, s), 6.94 (1H, d, J=8.4 Hz), 7.22-7.29 (3H, m), 7.41-7.49 (2H, m), 7.53-7.62 (3H, m), 7.75-7.83 (2H, m).

(4) Preparation of the Intermediate 549(4).

A solution of tetrabutylammonium fluoride in tetrahydrofuran (5.35 ml, 5.35 mmol) was added to a solution of the intermediate 549(3) (2.36 g, 4.46 mmol) in tetrahydrofuran (5 ml) at 0° C., and the mixture was stirred for 1 hour. 2 N hydrochloric acid and water were added to the reaction mixture, and the mixture was extracted with ethyl acetate. The organic layer was washed with saturated brine, and dried over anhydrous sodium sulfate. The residue obtained by evaporation of the solvent under reduced pressure was washed with a mixture of n-hexane and diisopropyl ether to give the title compound (2.36 g, 62%) as a white solid.

$^1$H-NMR ($CDCl_3$) δ: 1.38 (9H, s), 7.17 (1H, d, J=8.4 Hz), 7.21-7.29 (2H, m), 7.42-7.52 (2H, m), 7.52-7.58 (2H, m), 7.66-7.75 (3H, m), 7.83 (1H, d, J=2.4 Hz), 12.06 (1H, s).

(5) Preparation of the Intermediate 549(5).

The title compound was obtained in the same manner as the Example 105(2) using the following starting materials.

Starting materials: the intermediate 549(4) and ethyl bromoacetate; Yield: 98% (colorless oil).

$^1$H-NMR ($CDCl_3$) δ: 1.24 (3H, t, J=7.2 Hz), 1.34 (9H, s), 4.20 (2H, q, J=7.2 Hz), 4.61 (2H, s), 6.94 (1H, d, J=8.4 Hz), 7.21-7.30 (2H, m), 7.43-7.50 (2H, m), 7.51-7.59 (3H, m), 7.61 (1H, dd, J=2.4, 8.4 Hz), 7.82-7.89 (2H, m).

(6) Preparation of the Compound 549.

The title compound was obtained in the same manner as the Example 12(4) using the following starting material.

Starting material: the intermediate 549(5); Yield: 82% (white solid).

$^1$H-NMR ($CDCl_3$) δ: 1.37 (9H, s), 4.85 (2H, s), 7.20 (1H, d, J=8.4 Hz), 7.24-7.31 (2H, m), 7.49-7.57 (4H, m), 7.62 (1H, d, J=2.4 Hz), 7.73 (1H, dd, J=2.4, 8.4 Hz), 7.84-7.90 (2H, m).

Example 550

Preparation of the Compound 550

A mixture of the intermediate 549(300 mg, 0.635 mmol), 10% palladium on activated carbon (34 mg, 5 mol %), 2 N hydrochloric acid (0.1 ml) and methanol (5 ml) was stirred for 18 hours under hydrogen atmosphere. The reaction mixture was filtered. The residue obtained by concentration of the filtrate under reduced pressure was purified by column chromatography on silica gel (n-hexane:ethyl acetate=1:1) to give the title compound (64 mg, 22%) as a white solid.

$^1$H-NMR ($CDCl_3$) δ: 1.29 (9H, s), 4.07 (2H, s), 4.68 (2H, s), 6.85 (1H, d, J=8.4 Hz), 7.15-7.28 (4H, m), 7.28-7.34 (2H, m), 7.35-7.42 (2H, m), 7.48-7.55 (2H, m).

Example 551

Preparation of the Compound 551

(1) Preparation of the Intermediate 551(1).

A mixture of 4-(tert-butyl)benzyl bromide (1.01 ml, 5.50 mmol), triphenylphosphine (1.31 g, 5.00 mmol) and anhydrous tetrahydrofuran was refluxed for 3 hours. The reaction mixture was cooled to room temperature. The precipitated solid was collected by filtration, and washed with diethyl ether to give the title compound (2.31 g, 94%) as a white solid.

$^1$H-NMR ($CDCl_3$) δ: 1.23 (9H, s), 5.35 (2H, d, J=14.1 Hz), 6.98-7.04 (2H, m), 7.10-7.20 (2H, m), 7.54-7.83 (15H, m).

(2) Preparation of the Intermediate 551(2).

The title compound was obtained in the same manner as the Example 26(1) using the following starting materials.

Starting materials: the intermediates 549(1) and 551(1); Yield: 64% (pale yellow oil).

This compound was obtained as a mixture of the geometric isomers.

$^1$H-NMR ($CDCl_3$) δ: [0.26 (s), 0.27 (s), 6H in total], [1.02 (s), 1.09 (s), 9H in total], [1.31 (s), 1.32 (s), 9H in total], [6.60-6.73 (m), 6.85-6.93 (m), 7.22-7.53 (m), 7.57-7.64 (m), 7.78 (d, J=2.4 Hz), 13H in total].

(3) Preparation of the Intermediate 551(3).

The title compound was obtained in the same manner as the Example 3 using the following starting material.

Starting material: the intermediate 551(2); Yield: 83% (white solid).

$^1$H-NMR ($CDCl_3$) δ: 0.29 (6H, s), 1.06 (9H, s), 1.32 (9H, s), 2.83-2.98 (4H, m), 6.87 (1H, d, J=8.4 Hz), 7.09-7.17 (2H, m), 7.17-7.36 (6H, m), 7.43-7.50 (2H, m).

(4) Preparation of the Intermediate 551(4).

The title compound was obtained in the same manner as the Example 549(4) using the following starting material.

Starting material: the intermediate 551(3); Yield: 95% (colorless oil).

$^1$H-NMR ($CDCl_3$) δ: 1.32 (9H, s), 2.87-3.03 (4H, m), 4.70-4.73 (1H, m), 6.83 (1H, d, J=8.4 Hz), 7.11-7.18 (2H, m), 7.18-7.36 (6H, m), 7.43-7.50 (2H, m).

(5) Preparation of the Intermediate 551(5).

The title compound was obtained in the same manner as the Example 105(2) using the following starting materials.

Starting materials: the intermediate 551(4) and ethyl bromoacetate; Yield: 64% (colorless oil).

$^1$H-NMR ($CDCl_3$) δ: 1.32 (9H, s), 1.33 (3H, t, J=7.2 Hz), 2.88-3.07 (4H, m), 4.29 (2H, q, J=7.2 Hz), 4.65 (2H, s), 6.79 (1H, d, J=8.4 Hz), 7.11-7.18 (2H, m), 7.18-7.36 (6H, m), 7.42-7.49 (2H, m).

(6) Preparation of the Compound 551.

The title compound was obtained in the same manner as the Example 12(4) using the following starting material.

Starting material: the intermediate 551(5); Yield: 88% (white solid).

$^1$H-NMR ($CDCl_3$) δ: 1.31 (9H, s), 2.87-3.07 (4H, m), 4.66 (2H, s), 6.82 (1H, d, J=8.4 Hz), 7.08-7.14 (2H, m), 7.20-7.33 (5H, m), 7.34 (1H, dd, J=2.4, 8.4 Hz), 7.42-7.49 (2H, m).

Example 601

Preparation of the Compound 601

(1) Preparation of the Intermediate 601(1).

The title compound was obtained in the same manner as the Example 123(1) using the following starting materials.

Starting materials: 4-bromo-2-fluoroaniline and benzyl bromide; Yield: 80% (pale yellow oil).

$^1$H-NMR ($CDCl_3$) δ: 4.29 (1H, s), 4.34 (2H, s), 6.48-6.54 (1H, m), 7.02-7.39 (7H, m).

(2) Preparation of the Intermediate 601(2).

The title compound was obtained in the same manner as the Example 123(3) using the following starting materials.

Starting materials: the intermediate 601(1) and 4-(trifluoromethoxy)phenylboronic acid; Yield: 83% (pale yellow solid).

$^1$H-NMR ($CDCl_3$) δ: 4.39 (1H, s), 4.41 (2H, s), 6.67-6.75 (1H, m), 7.15-7.51 (11H, m).

(3) Preparation of the Intermediate 601(3).

The title compound was obtained in the same manner as the Example 219(1) using the following starting materials.

Starting materials: the intermediate 601(2) and succinic acid monoethyl ester chloride; Yield: 88% (pale yellow solid).

$^1$H-NMR ($CDCl_3$) δ: 1.25 (3H, t, J=7.2 Hz), 2.31-2.82 (4H, m), 4.14 (2H, q, J=7.2 Hz), 4.54 (1H, d, J=14.4 Hz), 5.27 (1H, d, J=14.4 Hz), 7.03-7.10 (1H, m), 7.19-7.34 (9H, m), 7.52-7.58 (2H, m).

(4) Preparation of the Compound 601.

The title compound was obtained in the same manner as the Example 126(4) using the following starting material.

Starting material: the intermediate 601(3); Yield: 53% (white solid).

$^1$H-NMR ($CDCl_3$) δ: 2.25-2.65 (4H, m), 4.55 (1H, d, J=14.1 Hz), 5.04 (1H, d, J=14.4 Hz), 7.01-7.21 (10H, m), 7.40 (2H, d, J=8.7 Hz).

Example 602

Preparation of the Compound 602

(1) Preparation of the Intermediate 602(1).

The title compound was obtained in the same manner as the Example 219(1) using the following starting materials.

Starting materials: the intermediate 601(2) and ethyl malonyl chloride; Yield: 43% (pale yellow oil).

$^1$H-NMR ($CDCl_3$) δ: 1.26 (3H, t, J=6.9 Hz), 3.28 (2H, s), 4.14 (2H, q, J=7.2 Hz), 4.51 (1H, d, J=14.4 Hz), 5.35 (1H, d, J=14.4 Hz), 7.22-7.35 (10H, m), 7.51-7.56 (2H, m).

(2) Preparation of the Compound 602.

The title compound was obtained in the same manner as the Example 126(4) using the following starting material.

Starting material: the intermediate 602(1); Yield: 13% (white solid).

$^1$H-NMR ($CDCl_3$) δ: 3.20 (2H, s), 4.58 (2H, s), 7.03-7.30 (10H, m), 7.41 (2H, d, J=9.0 Hz).

Example 603

Preparation of the Compound 603

(1) Preparation of the Intermediate 603(1).

The title compound was obtained in the same manner as the Example 123(1) using the following starting materials.

Starting materials: 4-bromobenzylamine hydrochloride and 4-(tert-butyl)benzyl bromide; Yield: 48% (colorless oil).

$^1$H-NMR ($CDCl_3$) δ: 1.32 (9H, s), 3.75 (2H, s), 3.76 (2H, s), 7.20-7.49 (8H, m).

(2) Preparation of the Intermediate 603(2).

The title compound was obtained in the same manner as the Example 123(2) using the following starting materials.

Starting materials: the intermediate 603(1) and methyl chloroglyoxylate; Yield: 93% (colorless oil).

This compound was obtained as a mixture of the rotational isomers.

$^1$H-NMR ($CDCl_3$) δ: [1.31 (s), 1.32 (s), 9H in total], [3.87 (s), 3.88 (s), 3H in total], [4.28 (s), 4.29 (s), 2H in total], [4.44 (s), 4.45 (s), 2H in total], [7.06-7.19 (m), 7.32-7.41 (m), 7.42-7.51 (m), 8H in total].

(3) Preparation of the Intermediate 603(3).

The title compound was obtained in the same manner as the Example 123(3) using the following starting materials.

Starting materials: the intermediate 603(2) and 4-(trifluoromethoxy)phenylboronic acid; Yield: 82% (pale brown oil).

This compound was obtained as a mixture of the rotational isomers.

$^1$H-NMR ($CDCl_3$) δ: [1.32 (s), 1.33 (s), 9H in total], [3.89 (s), 3.89 (s), 3H in total]. [4.34 (s), 4.38 (s), 2H in total], [4.50 (s), 4.54 (s), 2H in total], [7.06-7.66 (m), 7.06-7.66 (m) 12H in total].

(4) Preparation of the Compound 603.

The title compound was obtained in the same manner as the Example 126(4) using the following starting material.

Starting material: the intermediate 603(3); Yield: 85% (white solid).

This compound was obtained as a mixture of the rotational isomers.

$^1$H-NMR (DMSO-$d_6$) δ: 1.26 (9H, m), 1.26 (9H, m), 4.27 (2H, m), 4.32 (2H, m), 4.40 (2H, m), 4.44 (2H, m), 7.10-7.18 (2H, m), 7.10-7.18 (2H, m), 7.26-7.38 (4H, m), 7.26-7.38 (4H, m), 7.41-7.50 (2H, m), 7.41-7.50 (2H, m), 7.73-7.83 (4H, m), 7.73-7.83 (4H, m).

Example 604

Preparation of the Compound 604

(1) Preparation of the Intermediate 604(1).

The title compound was obtained in the same manner as the Example 123(1) using the following starting materials.

Starting materials: 4-bromoaniline and 4-(tert-butyl)benzyl bromide; Yield: 32% (white solid).

$^1$H-NMR ($CDCl_3$) δ: 1.32 (9H, s), 4.05 (1H, s), 4.25 (2H, d, J=3.3 Hz), 6.49-6.52 (2H, m), 7.21-7.39 (6H, m).

(2) Preparation of the Intermediate 604(2).

The title compound was obtained in the same manner as the Example 123(3) using the following starting materials.

Starting materials: the intermediate 604(1) and 4-(trifluoromethoxy)phenylboronic acid; Yield: 22% (pale yellow solid).

$^1$H-NMR ($CDCl_3$) δ: 1.33 (9H, s), 4.12 (1H, brs), 4.34 (2H, s), 6.68-6.74 (2H, m), 7.17-7.26 (2H, m), 7.30-7.42 (6H, m), 7.50-7.55 (2H, m).

(3) Preparation of the Intermediate 604(3).

The title compound was obtained in the same manner as the Example 219(1) using the following starting materials.

Starting materials: the intermediate 604(2) and ethyl glutaryl chloride; Yield: 100% (pale yellow solid).

$^1$H-NMR ($CDCl_3$) δ: 1.29 (9H, s), 1.30 (3H, t, J=7.2 Hz), 1.70-2.48 (6H, m), 4.06 (2H, q, J=7.2 Hz), 4.87 (2H, s), 7.05-7.17 (4H, m), 7.26-7.42 (4H, m), 7.50-7.60 (4H, m).

(4) Preparation of the Compound 604.

The title compound was obtained in the same manner as the Example 126(4) using the following starting material.

Starting material: the intermediate 604(3); Yield: 23% (pale yellow oil).

$^1$H-NMR ($CDCl_3$) δ: 1.30 (9H, s), 1.90-2.00 (2H, m), 2.17 (2H, t, J=7.2 Hz), 2.33 (2H, t, J=7.2 Hz), 4.87 (2H, s), 7.05-7.17 (4H, m), 7.27-7.31 (4H, m), 7.49-7.61 (4H, m).

Example 605

Preparation of the Compound 605

(1) Preparation of the Intermediate 605(1).

The title compound was obtained in the same manner as the Example 125(4) using the following starting materials.

Starting materials: the intermediate 604(2) and methyl bromoacetate; Yield: 67% (pale yellow oil).

$^1$H-NMR ($CDCl_3$) δ: 1.31 (9H, s), 3.76 (3H, s), 4.13 (2H, s), 4.66 (2H, s), 6.73-6.79 (2H, m), 7.20-7.25 (4H, m), 7.34-7.45 (4H, m), 7.49-7.54 (2H, m).

(2) Preparation of the Compound 605.

The title compound was obtained in the same manner as the Example 126(4) using the following starting material.

Starting material: the intermediate 605(1); Yield: 63% (white solid).

$^1$H-NMR (DMSO-$d_6$) δ: 1.26 (9H, s), 4.22 (2H, s), 4.61 (2H, s), 6.63-6.72 (2H, m), 7.18-7.52 (8H, m), 7.61-7.71 (2H, m).

Example 606

Preparation of the Compound 606

(1) Preparation of the Intermediate 606(1).

The title compound was obtained in the same manner as the Example 132(1) using the following starting materials.

Starting materials: 4-(trifluoromethoxy)phenol and 4-fluoro-1-nitrobenzene; Yield: 100% (yellow oil).

$^1$H-NMR ($CDCl_3$) δ: 7.02-7.06 (2H, m), 7.10-7.14 (2H, m), 7.26-7.31 (2H, m), 8.21-8.25 (2H, m).

(2) Preparation of the Intermediate 606(2).

The title compound was obtained in the same manner as the Example 125(2) using the following starting material.

Starting material: the intermediate 606(1); Yield: 93% (yellow oil).

$^1$H-NMR ($CDCl_3$) δ: 3.61 (2H, brs), 6.67-6.70 (2H, m), 6.85-6.88 (2H, m), 6.89-6.92 (2H, m), 7.12 (2H, t, J=9.0 Hz).

(3) Preparation of the Intermediate 606(3).

The title compound was obtained in the same manner as the Example 123(1) using the following starting materials.

Starting materials: the intermediate 606(2) and 4-(tert-butyl)benzyl bromide; Yield: 56% (yellow oil).

$^1$H-NMR ($CDCl_3$) δ: 1.33 (9H, s), 3.94 (1H, brs), 4.28 (2H, s), 6.23-6.66 (2H, m), 6.88-6.92 (4H, m), 7.09-7.13 (2H, m), 7.30-7.33 (2H, m), 7.37-7.40 (2H, m).

(4) Preparation of the Intermediate 606(4).

The title compound was obtained in the same manner as the Example 125(4) using the following starting materials.

Starting materials: the intermediate 606(3) and methyl bromoacetate; Yield: 73% (colorless oil).

$^1$H-NMR ($CDCl_3$) δ: 1.33 (9H, s), 3.75 (3H, s), 4.08 (2H, s), 4.61 (2H, s), 6.66-6.70 (2H, m), 6.88-6.94 (4H, m), 7.09-7.13 (2H, m), 7.20-7.29 (2H, m), 7.35-7.38 (2H, m).

(5) Preparation of the Compound 606.

The title compound was obtained in the same manner as the Example 126(4) using the following starting material.

Starting material: the intermediate 606(4); Yield: 30% (brown oil).

$^1$H-NMR ($CDCl_3$) δ: 1.32 (9H, s), 4.11 (2H, s), 4.59 (2H, s), 6.69-6.72 (2H, m), 6.88-6.94 (4H, m), 7.09-7.13 (2H, m), 7.20-7.23 (2H, m), 7.35-7.38 (2H, m).

Example 607

Preparation of the Compound 607

(1) Preparation of the Intermediate 607(1).

The title compound was obtained in the same manner as the Example 125(4) using the following starting materials.

Starting materials: the intermediate 604(1) and ethyl 3-bromopropionate; Yield: 14% (colorless oil).

$^1$H-NMR ($CDCl_3$) δ: 1.21-1.32 (12H, m), 2.62 (2H, t, J=7.8 Hz), 3.73 (2H, t, J=7.8 Hz), 4.10 (2H, q, J=6.9 Hz), 4.51 (2H, s), 6.56-6.59 (2H, m), 7.08-7.11 (2H, m), 7.24-7.33 (4H, m).

(2) Preparation of the Intermediate 607(2).

The title compound was obtained in the same manner as the Example 123(3) using the following starting materials.

Starting materials: the intermediate 607(1) and 4-(trifluoromethoxy)phenylboronic acid; Yield: 58% (colorless oil).

$^1$H-NMR ($CDCl_3$) δ: 1.22-1.31 (12H, m), 2.68 (2H, t, J=7.2 Hz), 3.81 (2H, t, J=7.2 Hz), 4.41 (2H, q, J=7.2 Hz), 4.59 (2H, s), 6.77-6.80 (2H, m), 7.15 (2H, d, J=8.4 Hz), 7.21 (2H, d, J=8.4 Hz), 7.32-7.35 (2H, m), 7.40-7.43 (2H, m), 7.50-7.53 (2H, m).

(3) Preparation of the Compound 607.

The title compound was obtained in the same manner as the Example 126(4) using the following starting material.

Starting material: the intermediate 607(2); Yield: 89% (white solid).

$^1$H-NMR ($CDCl_3$) δ: 1.31 (9H, s), 2.73 (2H, t, J=7.8 Hz), 3.79 (2H, t, J=7.8 Hz), 4.57 (2H, s), 6.80-6.84 (2H, m), 7.14-7.17 (2H, m), 7.20-7.24 (2H, m), 7.32-7.35 (2H, m), 7.41-7.45 (2H, m), 7.51-7.53 (2H, m).

Example 608

Preparation of the Compound 608

(1) Preparation of the Intermediate 608(1).

The title compound was obtained in the same manner as the Example 219(1) using the following starting materials.

Starting materials: the intermediate 604(2) and ethyl malonyl chloride; Yield: 52% (colorless oil).

$^1$H-NMR ($CDCl_3$) δ: 1.24 (3H, t, J=7.2 Hz), 1.30 (9H, s), 3.27 (2H, s), 4.14 (2H, q, J=7.2 Hz), 4.92 (2H, s), 7.10-7.21 (4H, m), 7.26-7.33 (4H, m), 7.48-7.59 (4H, m).

(2) Preparation of the Compound 608.

The title compound was obtained in the same manner as the Example 126(4) using the following starting material.

Starting material: the intermediate 608(1); Yield: 65% (white solid).

$^1$H-NMR ($CDCl_3$) δ: 1.21 (9H, s), 3.23 (2H, s), 4.93 (2H, s), 7.06 (2H, d, J=8.4 Hz), 7.13 (2H, d, J=8.1 Hz), 7.18-7.26 (4H, m), 7.32 (2H, d, J=7.8 Hz), 7.37 (2H, d, J=8.4 Hz).

Example 609

Preparation of the Compound 609

(1) Preparation of the Intermediate 609(1).

The title compound was obtained in the same manner as the Example 219(1) using the following starting materials.

Starting materials: the intermediate 604(2) and ethyl succinyl chloride; Yield: 23% (pale yellow oil).

$^1$H-NMR ($CDCl_3$) δ: 1.25 (3H, t, J=6.9 Hz), 1.29 (9H, s), 2.41 (2H, t, J=6.9 Hz), 2.65 (2H, t, J=6.9 Hz), 4.13 (2H, q, J=6.9 Hz), 4.88 (2H, s), 7.12-7.18 (4H, m), 7.26-7.31 (4H, m), 7.49-7.60 (4H, m).

(2) Preparation of the Compound 609.

The title compound was obtained in the same manner as the Example 126(4) using the following starting material.

Starting material: the intermediate 609(1); Yield: 49% (white solid).

$^1$H-NMR ($CDCl_3$) δ: 1.28 (9H, s), 2.27 (2H, t, J=6.0 Hz), 2.66 (2H, t, J=6.0 Hz), 4.87 (2H, s), 7.09-7.15 (4H, m), 7.25-7.30 (4H, m), 7.51 (2H, d, J=8.1 Hz), 7.56 (2H, d, J=8.7 Hz).

Example 610

Preparation of the Compound 610

(1) Preparation of the Intermediate 610(1).

The title compound was obtained in the same manner as the Example 157(2) using the following starting materials.

Starting materials: the intermediate 153(2) and 1-bromo-4-(tert-butyl)benzene; Yield: 73% (pale yellow oil).

$^1$H-NMR ($CDCl_3$) δ: 1.30 (9H, s), 5.48 (1H, s), 6.88-7.12 (8H, m), 7.15-7.32 (4H, m).

(2) Preparation of the Intermediate 610(2).

The title compound was obtained in the same manner as the Example 123(1) using the following starting materials.

Starting materials: the intermediate 610(1) and methyl bromoacetate; Yield: 98% (pale yellow oil).

$^1$H-NMR ($CDCl_3$) δ: 1.30 (9H, s), 3.68 (3H, s), 4.42 (2H, s), 6.87-6.95 (3H, m), 6.97-7.04 (5H, m), 7.13-7.28 (4H, m).

(3) Preparation of the Compound 610.

The title compound was obtained in the same manner as the Example 126(4) using the following starting material.

Starting material: the intermediate 610(2); Yield: 87% (white solid).

$^1$H-NMR (DMSO-$d_6$) δ: 1.26 (9H, s), 4.59 (2H, s), 6.72-6.80 (2H, m), 6.97-7.35 (10H, m), 12.91 (1H, brs).

Example 611

Preparation of the Compound 611

(1) Preparation of the Intermediate 611(1).

The title compound was obtained in the same manner as the Example 123(2) using the following starting materials.

Starting materials: aniline and methyl chloroglyoxylate; Yield: 67% (white solid).

H-NMR ($CDCl_3$) δ: 3.98 (3H, s), 7.20 (1H, t, J=7.5 Hz), 7.39 (2H, t, J=7.5 Hz), 7.64 (2H, d, J=7.5 Hz), 8.87 (1H, brs).

(2) Preparation of the Intermediate 611(2).

The title compound was obtained in the same manner as the Example 125(4) using the following starting materials.

Starting materials: the intermediate 611(1) and 4-bromobenzyl bromide; Yield: 48% (colorless oil).

$^1$H-NMR ($CDCl_3$) δ: 3.54 (3H, s), 4.90 (2H, s), 7.00-7.17 (4H, m), 7.28-7.38 (3H, m), 7.38-7.47 (2H, m).

(3) Preparation of the Intermediate 611(3).

The title compound was obtained in the same manner as the Example 123(3) using the following starting materials.

Starting materials: the intermediate 611(2) and 4-(trifluoromethoxy)phenylboronic acid; Yield: 71% (yellow oil).

$^1$H-NMR ($CDCl_3$) δ: 3.55 (3H, s), 4.99 (2H, s), 7.05-7.15 (2H, m), 7.22-7.39 (7H, m), 7.44-7.52 (2H, m), 7.53-7.61 (2H, m).

(4) Preparation of the Compound 611.

The title compound was obtained in the same manner as the Example 126(4) using the following starting material.

Starting material: the intermediate 611(3); Yield: 90% (white solid).

$^1$H-NMR (DMSO-$d_6$) δ: 4.93 (2H, s), 7.02-7.68 (11H, m), 7.75 (2H, d, J=8.5 Hz).

Example 612

Preparation of the Compound 612

(1) Preparation of the Intermediate 612(1).

The title compound was obtained in the same manner as the Example 123(2) using the following starting materials.

Starting materials: 4-(tert-butyl)aniline and methyl chloroglyoxylate; Yield: 99% (white solid).

$^1$H-NMR ($CDCl_3$) δ: 1.32 (9H, s), 3.98 (3H, s), 7.37-7.44 (2H, m), 7.53-7.60 (2H, m), 8.81 (1H, brs).

(2) Preparation of the Intermediate 612(2).

The title compound was obtained in the same manner as the Example 125(4) using the following starting materials.

Starting materials: the intermediate 612(1) and 4-bromomethylbiphenyl; Yield: 45% (white solid).

$^1$H-NMR ($CDCl_3$) δ: 1.28 (9H, s), 3.55 (3H, s), 4.96 (2H s), 6.98-7.06 (2H, m), 7.28-7.39 (5H, m), 7.39-7.48 (2H, m), 7.48-7.63 (4H, m).

(3) Preparation of the Compound 612.

The title compound was obtained in the same manner as the Example 126(4) using the following starting material.

Starting material: the intermediate 612(2); Yield: 93% (white solid).

$^1$H-NMR ($CDCl_3$) δ: 1.23 (9H, s), 4.99 (2H, s), 7.03-7.78 (13H, m).

Example 613

Preparation of the Compound 613

(1) Preparation of the Intermediate 613(1).

The title compound was obtained in the same manner as the Example 125(4) using the following starting materials.

Starting materials: the intermediate 612(1) and 4-bromobenzyl bromide; Yield: 89% (white solid).

$^1$H-NMR ($CDCl_3$) δ: 1.28 (9H, s), 3.53 (3H, s), 4.86 (2H s), 7.12 (2H, d, J=8.5 Hz), 7.31 (2H, d, J=8.5 Hz), 7.42 (2H, d, J=8.5 Hz), 7.96 (2H, d, J=8.5 Hz).

(2) Preparation of the Intermediate 613(2).

The title compound was obtained in the same manner as the Example 123(3) using the following starting materials.

Starting materials: the intermediate 613(1) and 4-(trifluoromethoxy)phenylboronic acid; Yield: 23% (white solid).

$^1$H-NMR ($CDCl_3$) δ: 1.29 (9H, s), 3.55 (3H, s), 4.97 (2H, s), 6.97-7.07 (2H, m), 7.23-7.39 (6H, m), 7.50 (2H, d, J=8.2 Hz), 7.54-7.63 (2H, m).

(3) Preparation of the Compound 613.

The title compound was obtained in the same manner as the Example 126(4) using the following starting material.

Starting material: the intermediate 613(2); Yield: 62% (white solid).

$^1$H-NMR (DMSO-$d_6$) δ: 1.23 (9H, s), 4.90 (2H, s), 7.06-7.53 (8H, m), 7.53-7.68 (2H, m), 7.70-7.84 (2H, m).

Example 614

Preparation of the Compound 614

(1) Preparation of the Intermediate 614(1).

The title compound was obtained in the same manner as the Example 123(2) using the following starting materials.

Starting materials: the intermediate 2,6-dichloroaniline and methyl chloroglyoxylate; Yield: 94% (white solid).

$^1$H-NMR ($CDCl_3$) δ: 4.01 (3H, s), 7.25 (1H, t, J=8.0 Hz), 7.41 (2H, d, J=8.0 Hz), 8.59 (1H, brs).

(2) Preparation of the Intermediate 614(2).

The title compound was obtained in the same manner as the Example 125(4) using the following starting materials.

Starting materials: the intermediate 614(1) and 4-bromobenzyl bromide; Yield: 71% (white solid).

$^1$H-NMR ($CDCl_3$) δ: 3.65 (3H, s), 4.89 (2H, s), 7.07-7.16 (2H, m), 7.18-7.27 (1H, m), 7.29-7.40 (4H, m).

(3) Preparation of the Intermediate 614(3).

The title compound was obtained in the same manner as the Example 123(3) using the following starting materials.

Starting materials: the intermediate 614(2) and 4-(trifluoromethoxy)phenylboronic acid; Yield: 11% (colorless oil).

$^1$H-NMR ($CDCl_3$) δ: 3.65 (3H, s), 4.99 (2H, s), 7.15-7.38 (7H, m), 7.38-7.49 (2H, m), 7.51-7.63 (2H, m).

(4) Preparation of the Compound 614.

The title compound was obtained in the same manner as the Example 126(4) using the following starting material.

Starting material: the intermediate 614(3); Yield: 94% (white solid).

$^1$H-NMR (DMSO-$d_6$) δ: 4.82 (2H, s), 7.23-7.66 (9H, m), 7.70-7.87 (2H, m).

Example 615

Preparation of the Compound 615

(1) Preparation of the Intermediate 615(1).

The title compound was obtained in the same manner as the Example 123(2) using the following starting materials.

Starting materials: 4-(trifluoromethoxy)aniline and methyl chloroglyoxylate; Yield: 86% (white solid).

$^1$H-NMR ($CDCl_3$) δ: 3.99 (3H, s), 7.21-7.31 (2H, m), 7.65-7.75 (2H, m), 8.91 (1H, brs).

(2) Preparation of the Intermediate 615(2).

The title compound was obtained in the same manner as the Example 125(4) using the following starting materials.

Starting materials: the intermediate 615(1) and 4-bromobenzyl bromide; Yield: 73% (white solid).

$^1$H-NMR ($CDCl_3$) δ: 3.57 (3H, s), 4.88 (2H, s), 7.03-7.14 (4H, m), 7.14-7.22 (2H, m), 7.38-7.50 (2H, m).

(3) Preparation of the Intermediate 615(3).

The title compound was obtained in the same manner as the Example 123(3) using the following starting materials.

Starting materials: the intermediate 615(2) and 4-(tert-butyl)phenylboronic acid; Yield: 29% (colorless oil).

$^1$H-NMR ($CDCl_3$) δ: 1.36 (9H, s), 3.57 (3H, s), 4.96 (2H, s), 7.06-7.23 (4H, m), 7.23-7.33 (2H, m), 7.42-7.49 (2H, m), 7.49-7.60 (4H, m).

(4) Preparation of the Compound 615.

The title compound was obtained in the same manner as the Example 126(4) using the following starting material.

Starting material: the intermediate 615(3); Yield: 42% (white solid).

$^1$H-NMR (DMSO-$d_6$) δ: 1.30 (9H, s), 4.94 (2H, s), 7.15-7.50 (8H, m), 7.50-7.67 (4H, m).

Example 616

Preparation of the Compound 616

(1) Preparation of the Intermediate 616(1).

The title compound was obtained in the same manner as the Example 185(2) using the following starting materials.

Starting materials: the intermediate 1-fluoro-4-nitrobenzene and 4-(trifluoromethoxy)benzyl alcohol; Yield: 85% (white solid).

$^1$H-NMR ($CDCl_3$) δ: 5.16 (2H, s), 7.00-7.07 (2H, m), 7.24-7.31 (2H, m), 7.44-7.51 (2H, m), 8.19-8.26 (2H, m).

(2) Preparation of the Intermediate 616(2).

The title compound was obtained in the same manner as the Example 125(2) using the following starting material.

Starting material: the intermediate 616(1); Yield: 97% (gray solid).

$^1$H-NMR ($CDCl_3$) δ: 3.47 (2H, brs), 4.98 (2H, s), 6.62-6.68 (2H, m), 6.76-6.84 (2H, m), 7.19-7.25 (2H, m), 7.41-7.48 (2H, m).

(3) Preparation of the Intermediate 616(3).

The title compound was obtained in the same manner as the Example 125(3) using the following starting materials.

Starting materials: the intermediate 616(2) and methyl chloroglyoxylate; Yield: 93% (white solid).

$^1$H-NMR ($CDCl_3$) δ: 3.97 (3H, s), 5.06 (2H, s), 6.93-7.00 (2H, m), 7.21-7.28 (2H, m), 7.43-7.49 (2H, m), 7.54-7.61 (2H, m), 8.78 (1H, brs).

(4) Preparation of the Intermediate 616(4).

The title compound was obtained in the same manner as the Example 125(4) using the following starting materials.

Starting materials: the intermediate 616(3) and 4-(tert-butyl)benzyl bromide; Yield: 71% (white solid).

$^1$H-NMR ($CDCl_3$) δ: 1.30 (9H, s), 3.54 (3H, s), 4.86 (2H, s), 5.01 (2H, s), 6.83-6.90 (2H, m), 6.96-7.03 (2H, m), 7.11-7.17 (2H, m), 7.20-7.27 (2H, m), 7.28-7.33 (2H, m), 7.41-7.47 (2H, m).

(5) Preparation of the Compound 616.

The title compound was obtained in the same manner as the Example 126(4) using the following starting material.

Starting material: the intermediate 616(4); Yield: 95% (white solid).

$^1$H-NMR (DMSO-$d_6$) δ: 1.23 (9H, s), 4.82 (2H, s), 5.07 (2H, s), 6.94-7.01 (2H, m), 7.05-7.15 (4H, m), 7.26-7.42 (4H, m), 7.51-7.59 (2H, m), 13.87 (1H, brs).

Example 617

Preparation of the Compound 617

(1) Preparation of the Intermediate 617(1).

Phosphoryl chloride (0.931 ml, 9.90 mmol) was added dropwise to a solution of 4-nitrobenzoic acid (1.50 g, 9.00 mmol) in anhydrous tetrahydrofuran (5 ml) at 0° C., and the mixture was stirred for 30 minutes. Then 4-(trifluoromethoxy)aniline (1.75 g, 9.90 mmol) and pyridine (0.801 g, 9.90 mmol) were added to the mixture at 0° C., and the mixture was stirred at room temperature for 1 hour. 2 N hydrochloric acid was added to the reaction mixture, and the mixture was extracted with ethyl acetate. The organic layer was washed with a saturated aqueous solution of sodium hydrogen carbonate and saturated brine, and dried over anhydrous sodium sulfate. The residue obtained by evaporation of the solvent under reduced pressure was washed with diisopropyl ether to give the title compound (1.41 g, 48%) as a white solid.

$^1$H-NMR ($CDCl_3$) δ: 7.22-7.30 (2H, m), 7.65-7.73 (2H, m), 7.89 (1H, brs), 8.01-8.07 (2H, m), 8.33-8.39 (2H, m).

(2) Preparation of the Intermediate 617(2).

The title compound was obtained in the same manner as the Example 125(2) using the following starting material.

Starting material: the intermediate 617(1); Yield: 94% (white solid).

$^1$H-NMR ($CDCl_3$) δ: 5.81 (2H, brs), 6.57-6.64 (2H, m), 7.28-7.35 (2H, m), 7.69-7.75 (2H, m), 7.83-7.90 (2H, m), 9.95 (1H, brs).

(3) Preparation of the Intermediate 617(3).

The title compound was obtained in the same manner as the Example 123(1) using the following starting materials.

Starting materials: the intermediate 617(2) and 4-(tert-butyl)benzyl bromide; Yield: 68% (white solid).

$^1$H-NMR ($CDCl_3$) δ: 1.33 (9H, s), 4.36 (2H, s), 4.48 (1H, brs), 6.62-6.69 (2H, m), 7.16-7.23 (2H, m), 7.28-7.44 (4H, m), 7.60-7.76 (5H, m).

(4) Preparation of the Intermediate 617(4).

The title compound was obtained in the same manner as the Example 125(3) using the following starting materials.

Starting materials: the intermediate 617(3) and methyl chloroglyoxylate; Yield: 81% (white solid).

$^1$H-NMR ($CDCl_3$) δ: 1.29 (9H, s), 3.61 (3H, s), 4.96 (2H, s), 7.11-7.17 (2H, m), 7.19-7.28 (4H, m), 7.28-7.34 (2H, m), 7.62-7.68 (2H, m), 7.78 (1H, brs), 7.80-7.87 (2H, m).

(5) Preparation of the Compound 617.

The title compound was obtained in the same manner as the Example 126(4) using the following starting material.

Starting material: the intermediate 617(4); Yield: 95% (white solid).

$^1$H-NMR (DMSO-$d_6$) δ: 1.24 (9H, s), 4.99 (2H, s), 7.11-7.18 (2H, m), 7.30-7.44 (6H, m), 7.81-7.98 (4H, m), 10.48 (1H, brs), 14.21 (1H, brs).

Example 618

Preparation of the Compound 618

(1) Preparation of the Intermediate 618(1).

The intermediate 617(4) (372 mg, 0.703 mmol) was added to a suspension of sodium hydride (18.5 mg, 0.773 mmol) in N,N-dimethylformamide (5 ml) at 0° C., and the mixture was stirred for 30 minutes. Then iodomethane (0.087 ml, 1.41 mmol) was added to the mixture, and the mixture was stirred at room temperature for 1 hour. 2N hydrochloric acid was added to the reaction mixture, and the mixture was extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=1:1) to give the title compound (343 mg, 90%) as a white solid.

$^1$H-NMR ($CDCl_3$) δ: 1.28 (9H, s), 3.45 (3H, s), 3.47 (3H, s), 4.84 (2H, s), 6.87-6.95 (2H, m), 6.99-7.12 (6H, m), 7.20-7.29 (4H, m).

(2) Preparation of the Compound 618.

The title compound was obtained in the same manner as the Example 126(4) using the following starting material.

Starting material: the intermediate 618(1); Yield: 95% (white solid).

$^1$H-NMR (DMSO-$d_6$) δ: 1.24 (9H, s), 3.35 (3H, s), 4.83 (2H, s), 6.93-7.01 (2H, m), 7.04-7.12 (2H, m), 7.14-7.40 (8H, m), 13.97 (1H, brs).

Example 619

Preparation of the Compound 619

(1) Preparation of the Intermediate 619(1).

The title compound was obtained in the same manner as the Example 185(2) using the following starting materials.

Starting materials: the intermediate 4-(trifluoromethoxy) benzyl alcohol and 1,3-dinitrobenzene; Yield: 59% (yellow oil).

$^1$H-NMR ($CDCl_3$) δ: 5.14 (2H, s), 7.25-7.31 (3H, m), 7.46 (1H, t, J=8.1 Hz), 7.47-7.50 (2H, m), 7.82 (1H, t, J=2.4 Hz), 7.85-7.88 (1H, m).

(2) Preparation of the Intermediate 619(2).

The title compound was obtained in the same manner as the Example 125(2) using the following starting material.

Starting material: the intermediate 619(1); Yield: 97% (pale brown solid).

$^1$H-NMR ($CDCl_3$) δ: 3.67 (2H, brs), 5.02 (2H, s), 6.29-6.41 (3H, m), 7.02-7.11 (1H, m), 7.19-7.25 (2H, m), 7.42-7.48 (2H, m).

(3) Preparation of the Intermediate 619(3).

The title compound was obtained in the same manner as the Example 125(3) using the following starting materials.

Starting materials: the intermediate 619(2) and methyl chloroglyoxylate; Yield: 77% (white solid).

$^1$H-NMR ($CDCl_3$) δ: 3.98 (3H, s), 5.08 (2H, s), 6.80 (1H, ddd, J=0.9, 2.4, 8.4 Hz), 7.09 (1H, ddd, J=0.9, 2.4, 8.4 Hz), 7.20-7.27 (2H, m), 7.28 (1H, t, J=8.4 Hz), 7.45-7.51 (2H, m), 7.52 (1H, t, J=2.4 Hz), 8.83 (1H, brs).

(4) Preparation of the Intermediate 619(4).

The title compound was obtained in the same manner as the Example 125(4) using the following starting materials.

Starting materials: the intermediate 619(3) and 4-(tert-butyl)benzyl bromide; Yield: 94% (white solid).

$^1$H-NMR ($CDCl_3$) δ: 1.29 (9H, s), 3.55 (3H, s), 4.89 (2H, s), 4.92 (2H, s), 6.65 (1H, t, J=2.4 Hz), 6.71 (1H, ddd, J=0.9, 2.4, 7.8 Hz), 6.91 (1H, ddd, J=0.9, 2.4, 7.8 Hz), 7.12-7.18 (2H, m), 7.19-7.26 (3H, m), 7.28-7.34 (2H, m), 7.36-7.43 (2H, m).

(5) Preparation of the Compound 619.

The title compound was obtained in the same manner as the Example 126(4) using the following starting material.

Starting material: the intermediate 619(4); Yield: 80% (white solid).

$^1$H-NMR (DMSO-$d_6$) δ: 1.24 (9H, s), 4.91 (2H, s), 5.08 (2H, s), 6.78 (1H, ddd, J=0.9, 2.1, 7.8 Hz), 6.92 (1H, t, J=2.1 Hz), 6.97 (1H, ddd, J=0.9, 2.1, 8.1 Hz), 7.05-7.13 (2H, m), 7.25-7.35 (3H, m), 7.36-7.43 (2H, m), 7.51-7.59 (2H, m), 14.03 (1H, brs).

Example 620

Preparation of the Compound 620

(1) Preparation of the Intermediate 620(1).

The title compound was obtained in the same manner as the Example 185(2) using the following starting materials.

Starting materials: 1-fluoro-2-nitrobenzene and 4-(trifluoromethoxy)benzyl alcohol; Yield: 80% (pale yellow solid).

$^1$H-NMR ($CDCl_3$) δ: 5.23 (2H, s), 7.03-7.14 (2H, m), 7.22-7.29 (2H, m), 7.48-7.57 (3H, m), 7.88 (1H, dd, J=1.5, 8.1 Hz).

(2) Preparation of the Intermediate 620(2).

The title compound was obtained in the same manner as the Example 125(2) using the following starting material.

Starting material: the intermediate 620(1); Yield: 100% (pale brown solid).

$^1$H-NMR ($CDCl_3$) δ: 3.82 (2H, brs), 5.08 (2H, s), 6.67-6.87 (4H, m), 7.20-7.27 (2H, m), 7.44-7.50 (2H, m).

(3) Preparation of the Intermediate 620(3).

The title compound was obtained in the same manner as the Example 125(3) using the following starting materials.

Starting materials: the intermediate 620(2) and methyl chloroglyoxylate; Yield: 92% (white solid).

$^1$H-NMR ($CDCl_3$) δ: 3.96 (3H, s), 5.18 (2H, s), 6.96 (1H, dd, J=1.8, 7.8 Hz), 7.04 (1H, dt, J=1.8, 7.8 Hz), 7.13 (1H, dt, J=1.8, 7.8 Hz), 7.24-7.31 (2H, m), 7.45-7.51 (2H, m), 8.43 (1H, dd, J=1.5, 7.8 Hz), 9.56 (1H, brs).

(4) Preparation of the Intermediate 620(4).

The title compound was obtained in the same manner as the Example 125(4) using the following starting materials.

Starting materials: the intermediate 620(3) and 4-(tert-butyl)benzyl bromide; Yield: 94% (colorless oil).

$^1$H-NMR ($CDCl_3$) δ: 1.25 (9H, s), 3.51 (3H, s), 4.52 (1H, d, J=14.4 Hz), 4.95 (1H, d, J=12.0 Hz), 5.03 (1H, d, J=12.0 Hz), 5.19 (1H, d, J=14.4 Hz), 6.83-7.00 (3H, m), 7.09-7.14 (2H, m), 7.19-7.30 (5H, m), 7.37-7.43 (2H, m).

(5) Preparation of the Compound 620.

The title compound was obtained in the same manner as the Example 126(4) using the following starting material.

Starting material: the intermediate 620(4); Yield: 88% (white solid).

$^1$H-NMR (DMSO-$d_6$) δ: 1.20 (9H, s), 4.43 (1H, d, J=15.0 Hz), 5.06 (1H, d, J=15.0 Hz), 5.13 (2H, s), 6.88 (1H, dt, J=0.9, 7.5 Hz), 7.01 (1H, dd, J=1.8, 7.8 Hz), 7.04-7.14 (3H, m), 7.18-7.32 (3H, m), 7.34-7.42 (2H, m), 7.51-7.57 (2H, m), 13.71 (1H, brs).

Example 621

Preparation of the Compound 621

(1) Preparation of the Intermediate 621(1).

The title compound was obtained in the same manner as the Example 132(1) using the following starting materials.

Starting materials: 1-fluoro-4-nitrobenzene and 4-(trifluoromethoxy)thiophenol; Yield: 92% (pale yellow oil).

$^1$H-NMR ($CDCl_3$) δ: 7.18-7.24 (2H, m), 7.27-7.32 (2H, m), 7.54-7.60 (2H, m), 8.08-8.13 (2H, m).

(2) Preparation of the Intermediate 621(2).

The title compound was obtained in the same manner as the Example 376(2) using the following starting material.

Starting material: the intermediate 621(1); Yield: 65% (pale yellow oil).

$^1$H-NMR ($CDCl_3$) δ: 3.86 (2H, brs), 6.65-6.72 (2H, m), 7.01-7.13 (4H, m), 7.28-7.34 (2H, m).

(3) Preparation of the Intermediate 621(3).

The title compound was obtained in the same manner as the Example 125(3) using the following starting materials.

Starting materials: the intermediate 621(2) and methyl chloroglyoxylate; Yield: 92% (pale yellow solid).

$^1$H-NMR (DMSO-$d_6$) δ: 3.86 (3H, s), 7.29-7.38 (4H, m), 7.43-7.49 (2H, m), 7.80-7.86 (2H, m), 10.99 (1H, brs).

(4) Preparation of the Intermediate 621(4).

The title compound was obtained in the same manner as the Example 125(4) using the following starting materials.

Starting materials: the intermediate 621(3) and 4-(tert-butyl)benzyl bromide; Yield: 98% (colorless oil).

$^1$H-NMR ($CDCl_3$) δ: 1.29 (9H, s), 3.58 (3H, s), 4.89 (2H, s), 6.97-7.04 (2H, m), 7.11-7.22 (6H, m), 7.28-7.33 (2H, m), 7.34-7.39 (2H, m).

(5) Preparation of the Compound 621.

The title compound was obtained in the same manner as the Example 126(4) using the following starting material.

Starting material: the intermediate 621(4); Yield: 83% (white solid).

$^1$H-NMR (DMSO-$d_6$) δ: 1.22 (9H, s), 4.88 (2H, s), 7.06-7.13 (2H, m), 7.17-7.24 (2H, m), 7.25-7.35 (4H, m), 7.35-7.46 (4H, m), 14.11 (1H, brs).

Example 622

Preparation of the Compound 622

(1) Preparation of the Intermediate 622(1).

The title compound was obtained in the same manner as the Example 354(2) using the following starting materials.

Starting materials: 4-nitrobenzcatechin and 4-(trifluoromethoxy)benzyl bromide; Yield: 92% (yellow solid).

$^1$H-NMR ($CDCl_3$) δ: 5.20 (2H, s), 5.24 (2H, s), 6.97 (1H, d, J=8.7 Hz), 7.23-7.26 (4H, m), 7.45-7.51 (4H, m), 7.84 (1H, d, J=2.4 Hz), 7.90 (1H, dd, J=2.4, 8.7 Hz).

(2) Preparation of the Intermediate 622(2).

The title compound was obtained in the same manner as the Example 125(2) using the following starting material.

Starting material: the intermediate 622(1); Yield: 68% (white solid).

$^1$H-NMR ($CDCl_3$) δ: 5.01 (2H, s), 5.07 (2H, s), 6.23 (1H, dd, J=2.7, 8.4 Hz), 6.34 (1H, d, J=2.7 Hz), 6.78 (1H, d, J=8.4 Hz), 7.16-7.26 (4H, m), 7.41-7.46 (4H, m).

(3) Preparation of the Intermediate 622(3).

The title compound was obtained in the same manner as the Example 123(2) using the following starting materials.

Starting materials: the intermediate 622(2) and methyl chloroglyoxylate; Yield: 98% (white solid).

$^1$H-NMR ($CDCl_3$) δ: 3.97 (3H, s), 5.12 (2H, s), 5.16 (2H, s), 6.90 (1H, d, J=8.7 Hz), 6.99 (1H, dd, J=2.7, 8.7 Hz), 7.19-7.23 (4H, m), 7.42-7.50 (4H, m), 7.57 (1H, d, J=2.7 Hz), 8.76 (1H, brs).

(4) Preparation of the Intermediate 622(4).

The title compound was obtained in the same manner as the Example 123(1) using the following starting materials.

Starting materials: the intermediate 622(3) and 4-(tert-butyl)benzyl bromide; Yield: 72% (yellow oil).

$^1$H-NMR ($CDCl_3$) δ: 1.29 (9H, s), 3.48 (3H, s), 4.82 (2H, s), 4.91 (2H, s), 5.09 (2H, s), 6.57 (1H, d, J=2.4 Hz), 6.64 (1H, dd, J=2.4, 8.4 Hz), 6.80 (1H, d, J=8.4 Hz), 7.10-7.13 (2H, m), 7.21-7.22 (4H, m), 7.29-7.32 (2H, m), 7.34-7.37 (2H, m), 7.39-7.43 (2H, m).

(5) Preparation of the Compound 622.

The title compound was obtained in the same manner as the Example 126(4) using the following starting material.

Starting material: the intermediate 622(4); Yield: 39% (white solid).

$^1$H-NMR (DMSO-d$_6$) δ: 1.23 (9H, s), 3.48 (2H, s), 5.03 (2H, s), 5.07 (2H, s), 6.75-6.78 (1H, m), 6.90-6.93 (1H, m), 7.02-7.05 (2H, m), 7.20-7.27 (3H, m), 7.34-7.37 (4H, m), 7.51-7.54 (4H, m).

Example 623

Preparation of the Compound 623

(1) Preparation of the Intermediate 623(1).

The title compound was obtained in the same manner as the Example 123(1) using the following starting materials.

Starting materials: the intermediate 622(3) and iodomethane; Yield: 100% (colorless oil).

$^1$H-NMR (CDCl$_3$) δ: 3.28 (3H, s), 3.51 (3H, s), 5.11 (2H, s), 5.13 (2H, s), 6.76-6.83 (2H, m), 6.89 (1H, d, J=8.7 Hz), 7.21-7.24 (4H, m), 7.43-7.74 (4H, m).

(2) Preparation of the Compound 623.

The title compound was obtained in the same manner as the Example 126(4) using the following starting material.

Starting material: the intermediate 623(1); Yield: 79% (white solid).

$^1$H-NMR (DMSO-d$_6$) δ: 3.11 (3H, s), 5.11 (2H, s), 5.13 (2H, s), 6.85-6.87 (1H, m), 6.99-7.02 (1H, m), 7.14-7.16 (1H, m), 7.35-7.39 (4H, m), 7.54-7.60 (4H, m).

Example 624

Preparation of the Compound 624

The title compound was obtained in the same manner as the Example 126(4) using the following starting material.

Starting material: the compound 622 (3); Yield: 99% (white solid).

$^1$H-NMR (DMSO-d$_6$) δ: 5.10 (2H, s), 5.11 (2H, s), 6.98 (1H, d, J=9.0 Hz), 7.34-7.39 (5H, m), 7.53-7.64 (5H, m), 10.07 (1H, brs).

Example 625

Preparation of the Compound 625

(1) Preparation of the Intermediate 625(1).

The title compound was obtained in the same manner as the Example 354(2) using the following starting materials.

Starting materials: 2-methyl-5-nitrophenol and 4-(trifluoromethoxy)benzyl bromide; Yield: 96% (white solid).

$^1$H-NMR (CDCl$_3$) δ: 2.36 (3H, s), 5.16 (2H, s), 7.22-7.32 (3H, m), 7.46-7.54 (2H, m), 7.70-7.84 (2H, m).

(2) Preparation of the Intermediate 625(2).

The title compound was obtained in the same manner as the Example 125(2) using the following starting material.

Starting material: the intermediate 625(1); Yield: 100% (gray solid).

$^1$H-NMR (CDCl$_3$) δ: 2.17 (3H, s), 3.55 (2H, brs), 5.02 (2H, s), 6.23-6.28 (2H, m), 6.90-6.97 (1H, m), 7.19-7.26 (2H, m), 7.43-7.50 (2H, m).

(3) Preparation of the Intermediate 625(3).

The title compound was obtained in the same manner as the Example 125(3) using the following starting materials.

Starting materials: the intermediate 625(2) and methyl chloroglyoxylate; Yield: 97% (white solid).

$^1$H-NMR (CDCl$_3$) δ: 2.26 (3H, s), 3.98 (3H, s), 5.10 (2H, s), 6.91 (1H, dd, J=1.8, 7.8 Hz), 7.13 (1H, d, J=7.8 Hz), 7.20-7.27 (2H, m), 7.46-7.53 (2H, m), 7.55 (1H, d, J=1.8 Hz), 8.80 (1H, brs).

(4) Preparation of the Intermediate 625(4).

The title compound was obtained in the same manner as the Example 125(4) using the following starting materials.

Starting materials: the intermediate 625(3) and 4-(tert-butyl)benzyl bromide; Yield: 92% (colorless oil).

$^1$H-NMR (CDCl$_3$) δ: 1.29 (9H, s), 2.23 (3H, s), 3.53 (3H, s), 4.84 (2H, s), 4.86 (2H, s), 6.48 (1H, d, J=2.1 Hz), 6.62 (1H, dd, J=2.1, 7.5 Hz), 7.06 (1H, d, J=7.5 Hz), 7.11-7.17 (2H, m), 7.19-7.25 (2H, m), 7.28-7.34 (2H, m), 7.35-7.40 (2H, m).

(5) Preparation of the Compound 625.

The title compound was obtained in the same manner as the Example 126(4) using the following starting material.

Starting material: the intermediate 625(4); Yield: 97% (white solid).

$^1$H-NMR (DMSO-d$_6$) δ: 1.23 (9H, s), 2.14 (3H, s), 4.88 (2H, s), 5.06 (2H, s), 6.65 (1H, dd, J=1.8, 8.1 Hz), 6.94 (1H, d, J=1.5 Hz), 7.02-7.09 (2H, m), 7.11 (1H, d, J=8.1 Hz), 7.27-7.32 (2H, m), 7.36-7.43 (2H, m), 7.52-7.59 (2H, m), 13.12 (1H, brs).

Example 626

Preparation of the Compound 626

(1) Preparation of the Intermediate 626(1).

The title compound was obtained in the same manner as the Example 157(2) using the following starting materials.

Starting materials: the intermediate 126(2) and 4-(trifluoromethoxy)aniline; Yield: 93% (brown oil).

$^1$H-NMR (CDCl$_3$) δ: 1.30 (9H, s), 3.58 (3H, s), 4.86 (2H, s), 5.90 (1H, s), 6.85-6.99 (4H, m), 6.99-7.09 (2H, m), 7.09-7.22 (4H, m), 7.27-7.36 (2H, m).

(2) Preparation of the Compound 626.

The title compound was obtained in the same manner as the Example 126(4) using the following starting material.

Starting material: the intermediate 626(1); Yield: 84% (pale brown solid).

$^1$H-NMR (DMSO-d$_6$) δ: 1.24 (9H, s), 4.62-4.90 (2H, m), 6.83-7.00 (2H, m), 7.00-7.38 (10H, m), 8.23-8.40 (1H, m).

Example 627

Preparation of the Compound 627

(1) Preparation of the Intermediate 627(1).

The title compound was obtained in the same manner as the Example 208(1) using the following starting materials.

Starting materials: 1-fluoro-4-nitrobenzene and 1-phenylpiperazine; Yield: 92% (yellow solid).

$^1$H-NMR (CDCl$_3$) δ: 3.31-3.42 (4H, m), 3.53-3.66 (4H, m), 6.81-7.03 (5H, m), 7.24-7.35 (2H, m), 8.11-8.20 (2H, m).

(2) Preparation of the Intermediate 627(2).

The title compound was obtained in the same manner as the Example 125(2) using the following starting material.

Starting material: the intermediate 627(1); Yield: 100% (gray solid).

$^1$H-NMR (CDCl$_3$) δ: 3.16-3.23 (4H, m), 3.31-3.37 (4H, m), 3.44 (2H, brs), 6.65-6.71 (2H, m), 6.84-6.92 (3H, m), 6.95-7.02 (2H, m), 7.27-7.33 (2H, m).

(3) Preparation of the Intermediate 627(3).

The title compound was obtained in the same manner as the Example 125(3) using the following starting materials.

Starting materials: the intermediate 627(2) and methyl chloroglyoxylate; Yield: 99% (yellow solid).

$^1$H-NMR ($CDCl_3$) δ: 3.34 (8H, brs), 3.97 (3H, s), 6.86-7.02 (5H, m), 7.26-7.34 (2H, m), 7.53-7.60 (2H, m), 8.76 (1H, brs).

(4) Preparation of the Intermediate 627(4).

The title compound was obtained in the same manner as the Example 125(4) using the following starting materials.

Starting materials: the intermediate 627(3) and 4-(tert-butyl)benzyl bromide; Yield: 77% (white solid).

$^1$H-NMR ($CDCl_3$) δ: 1.30 (9H, s), 3.33 (8H, brs), 3.57 (3H, s), 4.85 (2H, s), 6.80-7.03 (7H, m), 7.13-7.19 (2H, m), 7.26-7.33 (4H, m).

(5) Preparation of the Compound 627.

The title compound was obtained in the same manner as the Example 126(4) using the following starting material.

Starting material: the intermediate 627(4); Yield: 94% (white solid).

$^1$H-NMR (DMSO-$d_6$) δ: 1.25 (9H, s), 3.19-3.35 (8H, m), 4.82 (2H, s), 6.77-7.08 (7H, m), 7.09-7.15 (2H, m), 7.19-7.27 (2H, m), 7.30-7.37 (2H, m), 13.80 (1H, brs).

Example 628

Preparation of the Compound 628

(1) Preparation of the Intermediate 628(1).

The title compound was obtained in the same manner as the Example 208(1) using the following starting materials.

Starting materials: 1-fluoro-4-nitrobenzene and 1-[4-(trifluoromethoxy)phenyl]piperazine; Yield: 91% (yellow solid).

$^1$H-NMR ($CDCl_3$) δ: 3.31-3.38 (4H, m), 3.56-3.63 (4H, m), 6.85-6.97 (4H, m), 7.12-7.19 (2H, m), 8.13-8.19 (2H, m).

(2) Preparation of the Intermediate 628(2).

The title compound was obtained in the same manner as the Example 125(2) using the following starting material.

Starting material: the intermediate 628(1); Yield: 97% (pale brown solid).

$^1$H-NMR ($CDCl_3$) δ: 3.14-3.24 (4H, m), 3.29-3.37 (4H, m), 3.55 (2H, brs), 6.63-6.73 (2H, m), 6.84-7.00 (4H, m), 7.09-7.17 (2H, m).

(3) Preparation of the Intermediate 628(3).

The title compound was obtained in the same manner as the Example 125(3) using the following starting materials.

Starting materials: the intermediate 628(2) and methyl chloroglyoxylate; Yield: 98% (white solid).

$^1$H-NMR (DMSO-$d_6$) δ: 3.22-3.34 (8H, m), 3.84 (3H, s), 6.97-7.03 (2H, m), 7.04-7.11 (2H, m), 7.19-7.26 (2H, m), 7.59-7.66 (2H, m), 10.64 (1H, brs).

(4) Preparation of the Intermediate 628(4).

The title compound was obtained in the same manner as the Example 125(4) using the following starting materials.

Starting materials: the intermediate 628(3) and 4-(tert-butyl)benzyl bromide; Yield: 72% (white solid).

$^1$H-NMR ($CDCl_3$) δ: 1.30 (9H, s), 3.26-3.39 (8H, m), 3.57 (3H, s), 4.85 (2H, s), 6.80-6.87 (2H, m), 6.91-7.01 (4H, m), 7.11-7.20 (4H, m), 7.28-7.33 (2H, m).

(5) Preparation of the Compound 628.

The title compound was obtained in the same manner as the Example 126(4) using the following starting material.

Starting material: the intermediate 628(4); Yield: 95% (white solid).

$^1$H-NMR (DMSO-$d_6$) δ: 1.25 (9H, s), 3.22-3.31 (8H, m), 4.81 (2H, s), 6.91-6.98 (2H, m), 7.00-7.15 (6H, m), 7.18-7.25 (2H, m), 7.31-7.37 (2H, m), 13.80 (1H, brs).

Example 629

Preparation of the Compound 629

(1) Preparation of the Intermediate 629(1).

The title compound was obtained in the same manner as the Example 354(2) using the following starting materials.

Starting materials: 2-chloro-5-nitrophenol and 4-(trifluoromethoxy)benzyl bromide; Yield: 98% (white solid).

$^1$H-NMR ($CDCl_3$) δ: 5.23 (2H, s), 7.24-7.31 (2H, m), 7.50-7.58 (3H, m), 7.80-7.87 (2H, m).

(2) Preparation of the Intermediate 629(2).

The title compound was obtained in the same manner as the Example 376(2) using the following starting material.

Starting material: the intermediate 629(1); Yield: 46% (pale brown solid).

$^1$H-NMR ($CDCl_3$) δ: 3.68 (2H, brs), 5.08 (2H, s), 6.26 (1H, dd, J=2.4, 8.1 Hz), 6.30 (1H, d, J=2.4 Hz), 7.13 (1H, d, J=8.1 Hz), 7.21-7.27 (2H, m), 7.46-7.52 (2H, m).

(3) Preparation of the Intermediate 629(3).

The title compound was obtained in the same manner as the Example 125(3) using the following starting materials.

Starting materials: the intermediate 629(2) and methyl chloroglyoxylate; Yield: 93% (white solid).

$^1$H-NMR ($CDCl_3$) δ: 3.99 (3H, s), 5.18 (2H, s), 6.94 (1H, dd, J=2.4, 8.4 Hz), 7.21-7.28 (2H, m), 7.36 (1H, d, J=8.4 Hz), 7.50-7.56 (2H, m), 7.72 (1H, d, J=2.4 Hz), 8.82 (1H, brs).

(4) Preparation of the Intermediate 629(4).

The title compound was obtained in the same manner as the Example 125(4) using the following starting materials.

Starting materials: the intermediate 629(3) and 4-(tert-butyl)benzyl bromide; Yield: 92% (colorless oil).

$^1$H-NMR ($CDCl_3$) δ: 1.29 (9H, s), 3.54 (3H, s), 4.85 (2H, s), 4.91 (2H, s), 6.57 (1H, d, J=2.1 Hz), 6.66 (1H, dd, J=2.1, 8.1 Hz), 7.09-7.14 (2H, m), 7.21-7.26 (2H, m), 7.29-7.35 (3H, m), 7.38-7.44 (2H, m).

(5) Preparation of the Compound 629.

The title compound was obtained in the same manner as the Example 126(4) using the following starting material.

Starting material: the intermediate 629(4); Yield: 98% (white solid).

$^1$H-NMR (DMSO-$d_6$) δ: 1.23 (9H, s), 4.94 (2H, s), 5.19 (2H, s), 6.77 (1H, d, J=2.1, 8.1 Hz), 7.08 (1H, d, J=8.4 Hz), 7.24 (1H, d, J=2.1 Hz), 7.28-7.34 (2H, m), 7.38-7.47 (4H, m), 7.55-7.63 (2H, m), 14.02 (1H, brs).

Example 630

Preparation of the Compound 630

(1) Preparation of the Intermediate 630(1).

The title compound was obtained in the same manner as the Example 354(2) using the following starting materials.

Starting materials: 4-nitrothiophenol and 4-(trifluoromethoxy)benzyl bromide; Yield: 86% (pale yellow solid).

$^1$H-NMR ($CDCl_3$) δ: 4.24 (2H, s), 7.15-7.21 (2H, m), 7.30-7.35 (2H, m), 7.38-7.44 (2H, m), 8.09-8.14 (2H, m).

(2) Preparation of the Intermediate 630(2).

The title compound was obtained in the same manner as the Example 376(2) using the following starting material.

Starting material: the intermediate 630(1); Yield: 82% (white solid).

$^1$H-NMR ($CDCl_3$) δ: 3.76 (2H, brs), 3.90 (2H, s), 6.53-6.59 (2H, m), 7.05-7.19 (6H, m).

(3) Preparation of the Intermediate 630(3).

The title compound was obtained in the same manner as the Example 125(3) using the following starting materials.

Starting materials: the intermediate 630(2) and methyl chloroglyoxylate; Yield: 98% (white solid).

$^1$H-NMR ($CDCl_3$) δ: 3.98 (3H, s), 4.07 (2H, s), 7.08-7.15 (2H, m), 7.24-7.32 (4H, m), 7.52-7.58 (2H, m), 8.82 (1H, brs).

(4) Preparation of the Intermediate 630(4).

The title compound was obtained in the same manner as the Example 125(4) using the following starting materials.

Starting materials: the intermediate 630(3) and 4-(tert-butyl)benzyl bromide; Yield: 95% (colorless oil).

$^1$H-NMR ($CDCl_3$) δ: 1.29 (9H, s), 3.53 (3H, s), 4.08 (2H, s), 4.87 (2H, s), 6.92-6.99 (2H, m), 7.09-7.15 (4H, m), 7.16-7.21 (2H, m), 7.23-7.32 (4H, m).

(5) Preparation of the Compound 630.

The title compound was obtained in the same manner as the Example 126(4) using the following starting material.

Starting material: the intermediate 630(4); Yield: 95% (white solid).

$^1$H-NMR (DMSO-$d_6$) δ: 1.24 (9H, s), 4.27 (2H, s), 4.86 (2H, s), 7.05-7.16 (4H, m), 7.24-7.36 (6H, m), 7.40-7.47 (2H, m), 13.99 (1H, brs).

Example 631

Preparation of the Compound 631

(1) Preparation of the Intermediate 631(1).

The title compound was obtained in the same manner as the Example 132(1) using the following starting materials.

Starting materials: 1-fluoro-2-nitrobenzene and 4-(trifluoromethoxy)thiophenol; Yield: 91% (yellow oil).

$^1$H-NMR ($CDCl_3$) δ: 6.86 (1H, dd, J=1.2, 8.1 Hz), 7.22-7.42 (4H, m), 7.59-7.66 (2H, m), 8.24 (1H, dd, J=1.5, 8.1 Hz).

(2) Preparation of the Intermediate 631(2).

The title compound was obtained in the same manner as the Example 376(2) using the following starting material.

Starting material: the intermediate 631(1); Yield: 79% (colorless oil).

$^1$H-NMR ($CDCl_3$) δ: 4.31 (2H, brs), 6.73-6.83 (2H, m), 7.02-7.12 (4H, m), 7.23-7.30 (1H, m), 7.45 (1H, dd, J=1.5, 7.5 Hz).

(3) Preparation of the Intermediate 631(3).

The title compound was obtained in the same manner as the Example 125(3) using the following starting materials.

Starting materials: the intermediate 631(2) and methyl chloroglyoxylate; Yield: 96% (colorless oil).

$^1$H-NMR ($CDCl_3$) δ: 3.93 (3H, s), 7.06-7.28 (5H, m), 7.47-7.55 (1H, m), 7.66 (1H, dd, J=1.8, 7.8 Hz), 8.53 (1H, dd, J=1.5, 8.1 Hz), 9.99 (1H, brs).

(4) Preparation of the Intermediate 631(4).

The title compound was obtained in the same manner as the Example 125(4) using the following starting materials.

Starting materials: the intermediate 631(3) and 4-(tert-butyl)benzyl bromide; Yield: 91% (colorless oil).

This compound was obtained as a mixture of the rotational isomers.

Major isomer: $^1$H-NMR ($CDCl_3$) δ: 1.29 (9H, s), 3.55 (3H, s), 4.28 (1H, d, J=14.4 Hz), 5.48 (1H, d, J=14.4 Hz), 6.81-6.87 (1H, m), 7.05-7.25 (7H, m), 7.26-7.32 (2H, m), 7.40-7.46 (2H, m).

Minor isomer: $^1$H-NMR ($CDCl_3$) δ: 1.29 (9H, s), 3.55 (3H, s), 4.67 (1H, d, J=15.6 Hz), 4.91 (1H, d, J=15.0 Hz), 6.81-6.87 (1H, m), 7.05-7.25 (7H, m), 7.26-7.32 (2H, m), 7.40-7.46 (2H, m).

(5) Preparation of the Compound 631.

The title compound was obtained in the same manner as the Example 126(4) using the following starting material.

Starting material: the intermediate 631(4); Yield: 97% (white solid).

This compound was obtained as a mixture of the rotational isomers.

Major isomer: $^1$H-NMR (DMSO-$d_6$) δ: 1.24 (9H, s), 4.30 (1H, d, J=14.7 Hz), 5.28 (1H, d, J=14.7 Hz), 6.96-7.17 (4H, m), 7.18-7.50 (8H, m), 13.96 (1H, brs).

Minor isomer: $^1$H-NMR (DMSO-$d_6$) δ: 1.20 (9H, s), 4.74 (1H, d, J=15.3 Hz), 4.95 (1H, d, J=15.3 Hz), 6.96-7.17 (4H, m), 7.18-7.50 (8H, m), 13.96 (1H, brs).

Example 632

Preparation of the Compound 632

(1) Preparation of the Intermediate 632(1).

The title compound was obtained in the same manner as the Example 125(3) using the following starting materials.

Starting materials: 2-aminobiphenyl and methyl chloroglyoxylate; Yield: 88% (pale purple solid).

$^1$H-NMR ($CDCl_3$) δ: 3.88 (3H, s), 7.22-7.55 (8H, m), 8.46 (1H, dd, J=2.1, 8.1 Hz), 9.08 (1H, brs).

(2) Preparation of the Intermediate 632(2).

The title compound was obtained in the same manner as the Example 123(1) using the following starting materials.

Starting materials: the intermediate 632(1) and 4-bromobenzyl bromide; Yield: 100% (pale purple oil).

$^1$H-NMR ($CDCl_3$) δ: 3.38 (1H, d, J=14.7 Hz), 3.64 (3H, s), 5.10 (1H, d, J=14.7 Hz), 6.75-6.79 (1H, m), 6.86-6.91 (2H, m), 7.14-7.21 (1H, m), 7.28-7.33 (2H, m), 7.38-7.52 (5H, m), 7.57-7.61 (2H, m).

(3) Preparation of the Intermediate 632(3).

The title compound was obtained in the same manner as the Example 123(3) using the following starting materials.

Starting materials: the intermediate 632(2) and 4-(trifluoromethoxy)phenylboronic acid; Yield: 52% (pale yellow oil).

$^1$H-NMR ($CDCl_3$) δ: 3.49 (1H, d, J=14.1 Hz), 3.64 (3H, s), 5.20 (1H, d, J=14.1 Hz), 6.82-6.86 (1H, m), 7.08-7.12 (2H, m), 7.14-7.21 (1H, m), 7.23-7.29 (2H, m), 7.37-7.55 (9H, m), 7.59-7.64 (2H, m).

(4) Preparation of the Compound 632.

The title compound was obtained in the same manner as the Example 126(4) using the following starting material.

Starting material: the intermediate 632(3); Yield: 86% (white solid).

$^1$H-NMR ($CDCl_3$) δ: 3.40 (1H, d, J=14.7 Hz), 5.01 (1H, d, J=14.7 Hz), 6.97-7.00 (1H, m), 7.08 (2H, d, J=8.4 Hz), 7.27-7.34 (1H, m), 7.38-7.58 (9H, m), 7.66-7.69 (2H, m), 7.71-7.75 (2H, m).

Example 633

Preparation of the Compound 633

(1) Preparation of the Intermediate 633(1).

The title compound was obtained in the same manner as the Example 354(2) using the following starting materials.

Starting materials: the intermediate 354(1) and ethyl 7-bromoheptanoate; Yield: 70% (yellow solid).

$^1$H-NMR ($CDCl_3$) δ: 1.26 (3H, t, J=7.2 Hz), 1.41-1.46 (2H, m), 1.49-1.56 (2H, m), 1.62-1.68 (2H, m), 1.70-1.92 (2H, m), 2.32 (2H, t, J=7.2 Hz), 4.10-4.67 (4H, m), 6.97-7.00 (2H, m), 7.04-7.08 (2H, m), 7.18-7.22 (2H, m), 7.50 (1H, d, J=2.4 Hz).

(2) Preparation of the Intermediate 633(2).

The title compound was obtained in the same manner as the Example 125(2) using the following starting material.

Starting material: the intermediate 633(1); Yield: 99% (white solid).

$^1$H-NMR ($CDCl_3$) δ: 1.26 (3H, t, J=7.2 Hz), 1.36-1.56 (4H, m), 1.62-1.68 (2H, m), 1.70-1.90 (2H, m), 2.32 (2H, t, J=7.2 Hz), 3.89 (2H, brs), 4.03 (2H, t, J=6.6 Hz), 4.13 (2H, q, J=7.2 Hz), 6.86 (1H, d, J=8.1 Hz), 6.90-6.92 (2H, m), 7.21-7.25 (2H, m), 7.50-7.55 (2H, m).

(3) Preparation of the Intermediate 633(3).

The title compound was obtained in the same manner as the Example 123(1) using the following starting materials.

Starting materials: the intermediate 633(2) and 4-phenylbutyl bromide; Yield: 42% (colorless oil).

$^1$H-NMR ($CDCl_3$) δ: 1.26 (3H, t, J=7.2 Hz), 1.42-1.90 (12H, m), 2.32 (2H, t, J=7.2 Hz), 2.66-2.69 (2H, m), 3.19-3.22 (2H, m), 3.99-4.04 (2H, m), 4.10-4.14 (2H, m), 4.26 (1H, brs), 6.73-6.79 (3H, m), 7.18-7.30 (7H, m), 7.52-7.55 (2H, m).

(4) Preparation of the Intermediate 633(4).

The title compound was obtained in the same manner as the Example 125(3) using the following starting materials.

Starting materials: the intermediate 633(3) and methyl chloroglyoxylate; Yield: 92% (colorless oil).

$^1$H-NMR ($CDCl_3$) δ: 1.25 (3H, t, J=7.2 Hz), 1.38-1.82 (12H, m), 2.31 (2H, t, J=7.2 Hz), 2.56-2.67 (2H, m), 3.48-3.54 (4H, m), 3.99-4.04 (3H, m), 4.13 (2H, q, J=7.2 Hz), 6.98 (1H, d, J=8.7 Hz), 7.10-7.15 (3H, m), 7.19-7.29 (4H, m), 7.32 (1H, d, J=2.4 Hz), 7.47-7.51 (3H, m).

(5) Preparation of the Compound 633.

The title compound was obtained in the same manner as the Example 126(4) using the following starting material.

Starting material: the intermediate 633(4); Yield: 18% (colorless oil).

This compound was obtained as a mixture of the rotational isomers.

Major isomer: $^1$H-NMR (DMSO-$d_6$) δ: 1.30-1.59 (10H, m), 1.66-1.70 (2H, m), 2.20 (2H, t, J=7.5 Hz), 2.49-2.57 (2H, m), 3.40-3.53 (1H, m), 3.85-3.91 (1H, m), 3.96-4.10 (2H, m), 7.10-7.13 (3H, m), 7.17-7.21 (3H, m), 7.43-7.48 (3H, m), 7.65-7.71 (3H, m).

Minor isomer: $^1$H-NMR (DMSO-$d_6$) δ: 1.30-1.59 (10H, m), 1.66-1.70 (2H, m), 2.20 (2H, t, J=7.5 Hz), 2.49-2.57 (2H, m), 3.57-3.65 (1H, m), 3.96-4.10 (3H, m), 7.08-7.13 (3H, m), 7.17-7.22 (3H, m), 7.43-7.48 (3H, m), 7.68-7.76 (3H, m).

Example 634

Preparation of the Compound 634

(1) Preparation of the Intermediate 634(1).

The title compound was obtained in the same manner as the Example 185(2) using the following starting materials.

Starting materials: the intermediate 188(1) and 2-adamantanol; Yield: 74% (yellow solid).

$^1$H-NMR ($CDCl_3$) δ: 1.52-1.59 (2H, m), 1.77-1.82 (4H, m), 1.90-1.98 (4H, m), 2.15-2.23 (4H, m), 4.63-4.65 (1H, m), 7.15 (1H, d, J=9.0 Hz), 7.29-7.32 (2H, m), 7.54-7.59 (2H, m), 7.70 (1H, dd, J=2.4, 8.7 Hz), 8.02 (1H, d, J=2.4 Hz).

(2) Preparation of the Intermediate 634(2).

The title compound was obtained in the same manner as the Example 125(2) using the following starting material.

Starting material: the intermediate 634(1); Yield: 66% (white solid).

$^1$H-NMR ($CDCl_3$) δ: 1.52-1.59 (2H, m), 1.77-1.82 (4H, m), 1.90-1.98 (4H, m), 2.15-2.23 (4H, m), 3.94 (2H, brs), 4.47-4.49 (1H, m), 6.83 (1H, d, J=8.4 Hz), 6.87 (1H, dd, J=2.1, 8.4 Hz), 6.94 (1H, d, J=2.1 Hz), 7.21-7.25 (2H, m), 7.50-7.54 (2H, m).

(3) Preparation of the Intermediate 634(3).

The title compound was obtained in the same manner as the Example 123(1) using the following starting materials.

Starting materials: the intermediate 634(2) and 4-phenylbutyl bromide; Yield: 83% (white solid).

$^1$H-NMR ($CDCl_3$) δ: 1.52-1.59 (2H, m), 1.70-1.98 (12H, m), 2.15-2.23 (4H, m), 2.65-2.72 (2H, m), 3.19-3.27 (2H, m), 4.38 (1H, brs), 4.47-4.49 (1H, m), 6.76-6.78 (3H, m), 7.10-7.31 (7H, m), 7.52-7.56 (2H, m).

(4) Preparation of the Intermediate 634(4).

The title compound was obtained in the same manner as the Example 125(3) using the following starting materials.

Starting materials: the intermediate 634(3) and methyl chloroglyoxylate; Yield: 81% (colorless oil).

$^1$H-NMR ($CDCl_3$) δ: 1.52-1.98 (14H, m), 2.15-2.23 (4H, m), 2.57-2.64 (2H, m), 3.43-3.53 (4H, m), 4.16-4.24 (1H, m), 4.46-4.48 (1H, m), 6.96 (1H, d, J=8.7 Hz), 7.10-7.15 (3H, m), 7.19-7.23 (4H, m), 7.31 (1H, d, J=2.4 Hz), 7.44-7.49 (3H, m).

(5) Preparation of the Compound 634.

The title compound was obtained in the same manner as the Example 126(4) using the following starting material.

Starting material: the intermediate 634(4); Yield: 70% (yellow oil).

This compound was obtained as a mixture of the rotational isomers.

Major isomer: $^1$H-NMR (DMSO-$d_6$) δ: 1.37-1.50 (6H, m), 1.70-1.91 (8H, m), 2.06-2.21 (4H, m), 2.44-2.50 (2H, m), 3.22-3.26 (1H, m), 4.09-4.12 (1H, m), 4.53-4.56 (1H, m), 7.06-7.20 (6H, m), 7.40-7.43 (3H, m), 7.49-7.52 (1H, m), 7.62-7.65 (2H, m).

Minor isomer: $^1$H-NMR (DMSO-$d_6$) δ: 1.37-1.50 (6H, m), 1.70-1.91 (8H, m), 2.06-2.21 (4H, m), 2.44-2.50 (2H, m), 3.22-3.26 (1H, m), 3.66-3.68 (1H, m), 4.53-4.56 (1H, m), 7.02-7.20 (5H, m), 7.30 (1H, d, J=2.4 Hz), 7.40-7.51 (4H, m), 7.64-7.70 (2H, m).

Example 635

Preparation of the Compound 635

(1) Preparation of the Intermediate 635(1).

The title compound was obtained in the same manner as the Example 132(1) using the following starting materials.

Starting materials: 4-bromo-2-fluoro-1-nitrobenzene and 4-(tert-butyl)phenol; Yield: 100% (pale yellow oil).

$^1$H-NMR ($CDCl_3$) δ: 1.34 (9H, s), 6.97-7.02 (2H, m), 7.12 (1H, d, J=1.8 Hz), 7.28 (1H, dd, J=1.8, 8.7 Hz), 7.40-7.44 (2H, m), 7.83 (1H, d, J=8.7 Hz).

(2) Preparation of the Intermediate 635(2).

The title compound was obtained in the same manner as the Example 123(3) using the following starting materials.

Starting materials: the intermediate 635(1) and 4-(trifluoromethoxy)phenylboronic acid; Yield: 76% (yellow oil).

$^1$H-NMR ($CDCl_3$) δ: 1.33 (9H, s), 7.00-7.04 (2H, m), 7.18 (1H, d, J=1.8 Hz), 7.26-7.30 (2H, m), 7.34 (1H, dd, J=1.8, 8.4 Hz), 7.38-7.42 (2H, m), 7.49-7.53 (2H, m), 8.05 (1H, d, J=8.4 Hz).

(3) Preparation of the Intermediate 635(3).

The title compound was obtained in the same manner as the Example 125(2) using the following starting material.

Starting material: the intermediate 635(2); Yield: 52% (gray solid).

$^1$H-NMR ($CDCl_3$) δ: 1.31 (9H, s), 3.91 (2H, brs), 6.88 (1H, d, J=8.1 Hz), 6.91-6.97 (2H, m), 7.11 (1H, d, J=2.1 Hz), 7.17-7.22 (3H, m), 7.30-7.36 (2H, m), 7.44-7.50 (2H, m).

(4) Preparation of the Intermediate 635(4).

The title compound was obtained in the same manner as the Example 123(1) using the following starting materials.

Starting materials: the intermediate 635(3) and 4-phenylbutyl bromide; Yield: 45% (pale yellow oil).

$^1$H-NMR ($CDCl_3$) δ: 1.31 (9H, s), 1.62-2.05 (4H, m), 2.64 (2H, d, J=7.2 Hz), 3.14-3.25 (2H, m), 4.26 (1H, brs), 6.76 (1H, d, J=8.4 Hz), 6.91-6.96 (2H, m), 7.07 (1H, d, J=2.1 Hz), 7.14-7.35 (10H, m), 7.43-7.49 (2H, m).

(5) Preparation of the Intermediate 635(5).

The title compound was obtained in the same manner as the Example 125(3) using the following starting materials.

Starting materials: the intermediate 635(4) and methyl chloroglyoxylate; Yield: 63% (colorless oil).

$^1$H-NMR ($CDCl_3$) δ: 1.33 (9H, s), 1.65-1.68 (4H, m), 2.58-2.62 (2H, m), 3.63 (3H, s), 3.64-3.70 (1H, m), 3.99-4.04 (1H, m), 6.94-7.00 (2H, m), 7.05 (1H, d, J=2.1 Hz), 6.99-7.29 (9H, m), 7.34-7.40 (2H, m), 7.44-7.50 (2H, m).

(6) Preparation of the Compound 635.

The title compound was obtained in the same manner as the Example 126(4) using the following starting material.

Starting material: the intermediate 635(5); Yield: 85% (white solid).

$^1$H-NMR (DMSO-$d_6$) δ: 1.28 (9H, s), 1.45-1.60 (4H, m), 2.49-2.54 (2H, m), 3.48-3.95 (2H, m), 6.95-7.26 (8H, m), 7.38-7.47 (6H, m), 7.65-7.73 (2H, m).

Example 636

Preparation of the Compound 636

(1) Preparation of the Intermediate 636(1).

The title compound was obtained in the same manner as the Example 132(1) using the following starting materials.

Starting materials: the intermediate 188(1) and 4-(tert-butyl)phenol; Yield: 100% (whitish-pink solid).

$^1$H-NMR ($CDCl_3$) δ: 1.34 (9H, s), 7.01-7.04 (2H, m), 7.08 (1H, d, J=8.4 Hz), 7.30-7.34 (2H, m), 7.40-7.43 (2H, m), 7.56-7.59 (2H, m), 7.65 (1H, dd, J=2.4, 8.4 Hz), 8.13 (1H, d, J=2.4 Hz).

(2) Preparation of the Intermediate 636(2).

The title compound was obtained in the same manner as the Example 125(2) using the following starting material.

Starting material: the intermediate 636(1); Yield: 100% (white solid).

$^1$H-NMR ($CDCl_3$) δ: 1.32 (9H, s), 3.91 (2H, brs), 6.85-7.00 (5H, m), 7.24-7.26 (2H, m), 7.33-7.36 (2H, m), 7.53-7.56 (2H, m).

(3) Preparation of the Intermediate 636(3).

The title compound was obtained in the same manner as the Example 123(1) using the following starting materials.

Starting materials: the intermediate 636(2) and 4-phenylbutyl bromide; Yield: 57% (colorless oil).

$^1$H-NMR ($CDCl_3$) δ: 1.32 (9H, s), 1.66-1.90 (4H, m), 2.62-2.67 (2H, m), 3.21-3.23 (2H, m), 4.22-4.28 (1H, m), 6.74-6.87 (3H, m), 6.93-6.97 (2H, m), 7.14-7.35 (9H, m), 7.54-7.60 (2H, m).

(4) Preparation of the Intermediate 636(4).

The title compound was obtained in the same manner as the Example 125(3) using the following starting materials.

Starting materials: the intermediate 636(3) and methyl chloroglyoxylate; Yield: 42% (colorless oil).

$^1$H-NMR ($CDCl_3$) δ: 1.33 (9H, s), 1.66-1.70 (4H, m), 2.59-2.62 (2H, m), 3.60-3.71 (4H, m), 4.02-4.10 (1H, m), 6.92 (1H, d, J=8.4 Hz), 6.95-6.99 (2H, m), 7.08-7.24 (5H, m), 7.27-7.30 (2H, m), 7.37-7.44 (4H, m), 7.48-7.51 (2H, m).

(5) Preparation of the Compound 636.

The title compound was obtained in the same manner as the Example 126(4) using the following starting material.

Starting material: the intermediate 636(4); Yield: 84% (white solid).

This compound was obtained as a mixture of the rotational isomers.

Major isomer: $^1$H-NMR (DMSO-$d_6$) δ: 1.29 (9H, s), 1.48-1.54 (4H, m), 2.44-2.50 (2H, m), 3.15-3.26 (2H, m), 6.82 (1H, d, J=8.4 Hz), 7.08-7.20 (7H, m), 7.37-7.52 (6H, m), 7.62-7.69 (2H, m).

Minor isomer: $^1$H-NMR (DMSO-$d_6$) δ: 1.29 (9H, s), 1.48-1.54 (4H, m), 2.44-2.50 (2H, m), 3.15-3.26 (1H, m), 3.64-3.68 (1H, m), 6.87 (1H, d, J=8.4 Hz), 6.94-6.97 (2H, m), 7.08-7.20 (5H, m), 7.37-7.55 (6H, m), 7.62-7.75 (2H, m).

Example 637

Preparation of the Compound 637

(1) Preparation of the Intermediate 637(1).

The title compound was obtained in the same manner as the Example 185(2) using the following starting materials.

Starting materials: the intermediate 188(1) and 4-(butyl)cyclohexanol; Yield: 98% (pale brown oil).

This compound was obtained as a mixture of the geometric isomers (2:1).

Major isomer: $^1$H-NMR ($CDCl_3$) δ: 0.82-1.64 (15H, m), 1.80-2.23 (3H, m), 4.26-4.39 (1H, m), 7.17 (1H, d, J=6.0 Hz), 7.27-7.32 (2H, m), 7.52-7.58 (2H, m), 7.66 (1H, dd, J=2.7, 8.7 Hz), 7.99 (1H, d, J=2.7 Hz).

Minor isomer: $^1$H-NMR ($CDCl_3$) δ: 0.82-1.64 (15H, m), 1.80-2.23 (3H, m), 4.71-4.78 (1H, m), 7.14 (1H, d, J=6.0 Hz), 7.27-7.32 (2H, m), 7.52-7.58 (2H, m), 7.66 (1H, dd, J=2.7, 8.7 Hz), 8.01 (1H, d, J=2.7 Hz).

(2) Preparation of the Intermediate 637(2).

The title compound was obtained in the same manner as the Example 125(2) using the following starting material.

Starting material: the intermediate 637(1); Yield: 86% (white solid).

This compound was obtained as a mixture of the geometric isomers (3:1).

Major isomer: $^1$H-NMR ($CDCl_3$) δ: 0.84-1.66 (15H, m), 1.80-2.25 (3H, m), 3.87 (2H, brs), 4.10-4.23 (1H, m), 6.82-6.96 (3H, m), 7.19-7.25 (2H, m), 7.48-7.55 (2H, m).

Minor isomer: $^1$H-NMR ($CDCl_3$) δ: 0.84-1.66 (15H, m), 1.80-2.25 (3H, m), 3.87 (2H, brs), 4.61-4.64 (1H, m), 6.82-6.96 (3H, m), 7.19-7.25 (2H, m), 7.48-7.55 (2H, m).

(3) Preparation of the Intermediate 637(3).

The title compound was obtained in the same manner as the Example 123(1) using the following starting materials.

Starting materials: the intermediate 637(2) and 4-phenylbutyl bromide; Yield: 43% (colorless oil).

This compound was obtained as a mixture of the geometric isomers (3:1).

Major isomer: $^1$H-NMR ($CDCl_3$) δ: 0.83-2.24 (22H, m), 2.55-2.73 (2H, m), 3.09-3.28 (2H, m), 4.08-4.20 (1H, m), 4.24-4.32 (1H, m), 6.71-6.86 (3H, m), 7.10-7.34 (7H, m), 7.50-7.58 (2H, m).

Minor isomer: $^1$H-NMR ($CDCl_3$) δ: 0.83-2.24 (22H, m), 2.55-2.73 (2H, m), 3.09-3.28 (2H, m), 4.29-4.35 (1H, m), 4.53-4.60 (1H, m), 6.71-6.86 (3H, m), 7.10-7.34 (7H, m), 7.50-7.58 (2H, m).

(4) Preparation of the Intermediate 637(4).

The title compound was obtained in the same manner as the Example 125(3) using the following starting materials.

Starting materials: the intermediate 637(3) and methyl chloroglyoxylate; Yield: 66% (colorless oil).

This compound was obtained as a mixture of the geometric isomers (3:1).

Major isomer: $^1$H-NMR ($CDCl_3$) δ: 0.83-2.18 (22H, m), 2.54-2.65 (2H, m), 3.45-3.62 (1H, m), 3.53 (3H, s), 3.87-4.02 (1H, m), 4.13-4.28 (1H, m), 6.98 (1H, d, J=8.7 Hz), 7.08-7.30 (8H, m), 7.31 (1H, d, J=2.4 Hz), 7.44-7.52 (2H, m).

Minor isomer: $^1$H-NMR ($CDCl_3$) δ: 0.83-2.18 (22H, m), 2.54-2.65 (2H, m), 3.45-3.62 (1H, m), 3.52 (3H, s), 4.07-4.21 (1H, m), 4.55-4.62 (1H, m), 6.97 (1H, d, J=8.7 Hz), 7.08-7.31 (9H, m), 7.44-7.52 (2H, m).

(5) Preparation of the Compound 637.

The title compound was obtained in the same manner as the Example 126(4) using the following starting material.

Starting material: the intermediate 637(4); Yield: 68% (white solid).

This compound was obtained as a mixture of the geometric isomers (3:1).

Major isomer: $^1$H-NMR (DMSO-$d_6$) δ: 0.80-2.04 (22H, m), 2.44-2.59 (2H, m), 3.43-3.58 (1H, m), 3.74-3.86 (1H, m), 4.26-4.40 (1H, m), 7.04-7.24 (6H, m), 7.38-7.47 (3H, m), 7.57-7.72 (3H, m), 13.49 (1H, brs).

Minor isomer: $^1$H-NMR (DMSO-$d_6$) δ: 0.80-2.04 (22H, m), 2.44-2.59 (2H, m), 3.43-3.58 (1H, m), 3.87-3.99 (1H, m), 4.62-4.69 (1H, m), 7.04-7.24 (6H, m), 7.38-7.47 (3H, m), 7.57-7.72 (3H, m), 13.49 (1H, brs).

Example 638

Preparation of the Compound 638

(1) Preparation of the Intermediate 638(1).

The title compound was obtained in the same manner as the Example 132(1) using the following starting materials.

Starting materials: the intermediate 188(1) and phenol; Yield: 92% (brown solid).

$^1$H-NMR ($CDCl_3$) δ: 7.05-7.15 (3H, m), 7.18-7.26 (1H, m), 7.28-7.37 (2H, m), 7.37-7.46 (2H, m), 7.55-7.63 (2H, m), 7.67 (1H, dd, J=2.4, 8.4 Hz), 8.14 (1H, d, J=2.4 Hz).

(2) Preparation of the Intermediate 638(2).

The title compound was obtained in the same manner as the Example 125(2) using the following starting material.

Starting material: the intermediate 638(1); Yield: 91% (pale yellow oil).

$^1$H-NMR ($CDCl_3$) δ: 3.91 (2H, s), 6.84-6.96 (2H, m), 6.98-7.14 (4H, m), 7.21-7.30 (2H, m), 7.30-7.39 (2H, m), 7.51-7.60 (2H, m).

(3) Preparation of the Intermediate 638(3).

The title compound was obtained in the same manner as the Example 123(1) using the following starting materials.

Starting materials: the intermediate 638(2) and 4-phenylbutyl bromide; Yield: 49% (yellow oil).

$^1$H-NMR ($CDCl_3$) δ: 1.60-1.79 (4H, m), 2.57-2.72 (2H, m), 3.14-3.28 (2H, m), 4.17-4.26 (1H, m), 6.77 (1H, dd, J=2.7, 8.4 Hz), 6.82-6.91 (2H, m), 6.98-7.38 (12H, m), 7.52-7.61 (2H, m).

(4) Preparation of the Intermediate 638(4).

The title compound was obtained in the same manner as the Example 123(2) using the following starting materials.

Starting materials: the intermediate 638(3) and methyl chloroglyoxylate; Yield: 73% (colorless oil).

$^1$H-NMR ($CDCl_3$) δ: 1.58-1.75 (4H, m), 2.50-2.70 (2H, m), 3.54-3.73 (4H, m), 3.97-4.13 (1H, m), 6.92 (1H, d, J=8.4 Hz), 7.01-7.34 (10H, m), 7.34-7.46 (4H, m), 7.46-7.54 (2H, m).

(5) Preparation of the Compound 638.

The title compound was obtained in the same manner as the Example 126(4) using the following starting material.

Starting material: the intermediate 638(4); Yield: 94% (white solid).

$^1$H-NMR ($CDCl_3$) δ: 1.28-1.60 (4H, m), 2.24-2.47 (2H, m), 3.30-3.54 (1H, m), 3.56-3.80 (1H, m), 6.58-7.50 (17H, m).

Example 639

Preparation of the Compound 639

(1) Preparation of the Intermediate 639(1).

The title compound was obtained in the same manner as the Example 185(2) using the following starting materials.

Starting materials: the intermediate 188(1) and l-menthol; Yield: 66% (brown oil).

$^1$H-NMR ($CDCl_3$) δ: 0.77 (3H, d, J=6.9 Hz), 0.83-1.36 (9H, m), 1.42-1.84 (4H, m), 2.12-2.32 (2H, m), 4.25 (1H, td, J=3.9, 10.5 Hz), 7.16 (1H, d, J=8.7 Hz), 7.24-7.35 (2H, m), 7.50-7.61 (2H, m), 7.66 (1H, dd, J=2.7, 8.7 Hz), 7.97 (1H, d, J=2.7 Hz).

(2) Preparation of the Intermediate 639(2).

The title compound was obtained in the same manner as the Example 125(2) using the following starting material.

Starting material: the intermediate 639(1); Yield: 91% (pale yellow oil).

$^1$H-NMR ($CDCl_3$) δ: 0.75-1.36 (11H, m), 1.36-1.64 (3H, m), 1.67-1.82 (2H, m), 2.14-2.33 (2H, m), 3.88 (2H, s), 4.02-4.20 (1H, m), 6.80-6.97 (3H, m), 7.16-7.30 (2H, m), 7.46-7.58 (2H, m).

(3) Preparation of the Intermediate 639(3).

The title compound was obtained in the same manner as the Example 123(1) using the following starting materials.

Starting materials: the intermediate 639(2) and 4-phenylbutyl bromide; Yield: 59% (brown oil).

$^1$H-NMR ($CDCl_3$) δ: 0.70-1.30 (11H, m), 1.36-1.65 (3H, m), 1.65-1.95 (6H, m), 2.08-2.28 (2H, m), 2.53-2.74 (2H, m), 3.02-3.32 (2H, m), 4.02-4.16 (1H, m), 4.24-4.38 (1H, m), 6.72-6.86 (2H, m), 7.05-7.35 (8H, m), 7.46-7.59 (2H, m).

(4) Preparation of the Intermediate 639(4).

The title compound was obtained in the same manner as the Example 123(2) using the following starting materials.

Starting materials: the intermediate 639(3) and methyl chloroglyoxylate; Yield: 72% (colorless oil).

$^1$H-NMR ($CDCl_3$) δ: 0.71-0.86 (2H, m), 0.86-1.32 (9H, m), 1.32-1.88 (9H, m), 2.00-2.30 (2H, m), 2.48-2.72 (2H, m), 3.30-3.45 (1H, m), 3.45-3.64 (3H, m), 4.05-4.29 (2H, m), 6.98-7.07 (1H, m), 7.07-7.17 (3H, m), 7.17-7.39 (5H, m), 7.43-7.57 (3H, m).

(5) Preparation of the Compound 639.

The title compound was obtained in the same manner as the Example 126(4) using the following starting material.

Starting material: the intermediate 639(4); Yield: 55% (white solid).

$^1$H-NMR ($CDCl_3$) δ: 0.48-1.18 (12H, m), 1.30-1.82 (8H, m), 1.90-2.20 (2H, m), 2.36-2.68 (2H, m), 3.42-3.64 (1H, m), 3.74-3.96 (1H, m), 4.00-4.20 (1H, m), 6.86-7.32 (9H, m), 7.32-7.58 (3H, m).

Example 640

Preparation of the Compound 640

(1) Preparation of the Intermediate 640(1).

The title compound was obtained in the same manner as the Example 123(1) using the following starting materials.

Starting materials: the intermediate 226(1) and ethyl bromoacetate; Yield: 56% (pale yellow oil).

$^1$H-NMR ($CDCl_3$) δ: 0.93 (3H, t, J=7.2 Hz), 1.21 (3H, t, J=6.9 Hz), 1.30-1.87 (10H, m), 2.58-2.64 (2H, m), 3.31-3.36 (2H, m), 3.99 (2H, t, J=6.6 Hz), 4.04 (2H, s), 4.11 (2H, t, J=7.2 Hz), 6.88 (1H, d, J=8.4 Hz), 7.09 (1H, dd, J=2.4, 8.4 Hz), 7.11-7.16 (3H, m), 7.17 (1H, d, J=2.4 Hz), 7.21-7.28 (4H, m), 7.47-7.52 (2H, m).

(2) Preparation of the Compound 640.

The title compound was obtained in the same manner as the Example 126(4) using the following starting material.

Starting material: the intermediate 640(1); Yield: 60% (colorless oil).

$^1$H-NMR ($CDCl_3$) δ: 0.94 (3H, t, J=6.9 Hz), 1.33-1.71 (8H, m), 1.80-1.88 (2H, m), 2.59 (2H, t, J=7.5 Hz), 3.13 (2H, t, J=7.2 Hz), 3.64 (2H, s), 4.04 (2H, t, J=6.9 Hz), 6.97 (1H, d, J=8.4 Hz), 7.08-7.32 (9H, m), 7.45-7.51 (2H, m).

Example 641

Preparation of the Compound 641

(1) Preparation of the Intermediate 641(1).

The title compound was obtained in the same manner as the Example 123(1) using the following starting materials.

Starting materials: 3-bromoaniline and ethyl 2-bromohexanoate; Yield: 48% (colorless oil).

$^1$H-NMR ($CDCl_3$) δ: 0.88-0.94 (3H, m), 1.24-1.36 (7H, m), 1.70-1.82 (2H, m), 3.99-4.25 (4H, m), 6.50-6.55 (1H, m), 6.75 (1H, t, J=1.8 Hz), 6.81-6.86 (1H, m), 7.01 (1H, t, J=8.1 Hz).

(2) Preparation of the Intermediate 641(2).

The title compound was obtained in the same manner as the Example 123(1) using the following starting materials.

Starting materials: the intermediate 641(1) and 4-(tert-butyl)benzyl bromide; Yield: 57% (colorless oil).

$^1$H-NMR ($CDCl_3$) δ: 0.82 (3H, t, J=7.2 Hz), 1.19-1.37 (16H, m), 1.71-2.12 (2H, m), 4.11 (2H, q, J=7.2 Hz), 4.30-4.33 (1H, m), 4.49-4.62 (2H, m), 6.65-6.68 (1H, m), 6.83-6.86 (1H, m), 6.95 (1H, t, J=2.4 Hz), 6.99 (1H, t, J=8.4 Hz), 7.16-7.29 (2H, m), 7.29-7.32 (2H, m).

(3) Preparation of the Intermediate 641(3).

The title compound was obtained in the same manner as the Example 123(3) using the following starting materials.

Starting materials: the intermediate 641(2) and 4-(trifluoromethoxy)phenylboronic acid; Yield: 73% (yellow oil).

$^1$H-NMR ($CDCl_3$) δ: 0.83 (3H, t, J=7.2 Hz), 1.19-1.37 (16H, m), 1.71-2.12 (2H, m), 4.13 (2H, q, J=7.2 Hz), 4.30-4.33 (1H, m), 4.49-4.62 (2H, m), 6.78-6.83 (1H, m), 6.89-6.94 (2H, m), 7.19-7.34 (7H, m), 7.40-7.45 (2H, m).

(4) Preparation of the Compound 641.

The title compound was obtained in the same manner as the Example 126(4) using the following starting material.

Starting material: the intermediate 641(3); Yield: 81% (colorless oil).

$^1$H-NMR (DMSO-$d_6$) δ: 0.78 (3H, t, J=7.2 Hz), 1.11-1.40 (13H, m), 1.74-1.98 (2H, m), 4.44-4.62 (3H, m), 6.70-6.75 (1H, m), 6.89-6.94 (2H, m), 7.17-7.27 (3H, m), 7.31-7.36 (2H, m), 7.37-7.40 (2H, m), 7.57-7.60 (2H, m).

Example 642

Preparation of the Compound 642

(1) Preparation of the Intermediate 642(1).

The title compound was obtained in the same manner as the Example 123(1) using the following starting materials.

Starting materials: 4-bromoaniline and ethyl 2-bromohexanoate; Yield: 36% (yellow oil).

$^1$H-NMR ($CDCl_3$) δ: 0.90 (3H, t, J=7.2 Hz), 1.25 (3H, t, J=7.2 Hz), 1.33-1.41 (4H, m), 1.71-1.81 (2H, m), 3.97-4.01 (1H, m), 4.10-4.22 (3H, m), 6.48-6.51 (2H, m), 7.22-7.26 (2H, m).

(2) Preparation of the Intermediate 642(2).

The title compound was obtained in the same manner as the Example 123(1) using the following starting materials.

Starting materials: the intermediate 642(1) and 4-(tert-butyl)benzyl bromide; Yield: 72% (colorless oil).

$^1$H-NMR ($CDCl_3$) δ: 0.83 (3H, t, J=7.2 Hz), 1.21 (3H, t, J=7.2 Hz), 1.25-1.36 (13H, m), 1.75-2.00 (2H, m), 4.11 (2H, q, J=7.2 Hz), 4.31 (1H, t, J=7.2 Hz), 4.43-4.63 (2H, m), 6.63-6.67 (2H, m), 7.15-7.31 (6H, m).

(3) Preparation of the Intermediate 642(3).

The title compound was obtained in the same manner as the Example 123(3) using the following starting materials.

Starting materials: the intermediate 642(2) and 4-(trifluoromethoxy)phenylboronic acid; Yield: 85% (yellow oil).

$^1$H-NMR ($CDCl_3$) δ: 0.83 (3H, t, J=7.2 Hz), 1.22-1.43 (16H, m), 1.78-1.90 (1H, m), 1.95-2.07 (1H, m), 4.08-4.18 (2H, m), 4.43 (1H, t, J=7.5 Hz), 4.52-4.72 (2H, m), 6.83-6.86 (2H, m), 7.19-7.26 (4H, m), 7.31-7.40 (4H, m), 7.50-7.55 (2H, m).

(4) Preparation of the Compound 642.

The title compound was obtained in the same manner as the Example 126(4) using the following starting material.

Starting material: the intermediate 642(3); Yield: 34% (yellowish-white solid).

$^1$H-NMR (DMSO-$d_6$) δ: 0.79 (3H, t, J=7.2 Hz), 1.15-1.40 (13H, m), 1.74-1.78 (1H, m), 1.90-1.96 (1H, m), 4.48-4.53 (3H, m), 6.80-6.83 (2H, m), 7.22-7.25 (2H, m), 7.31-7.36 (4H, m), 7.45-7.48 (2H, m), 7.64-7.67 (2H, m), 12.72 (1H, s).

Example 643

Preparation of the Compound 643

(1) Preparation of the Intermediate 643(1).

The title compound was obtained in the same manner as the Example 123(1) using the following starting materials.

Starting materials: the intermediate 367(4) and ethyl bromoacetate; Yield: 77% (pale brown oil).

$^1$H-NMR ($CDCl_3$) δ: 0.93 (3H, t, J=6.9 Hz), 1.23 (3H, t, J=7.2 Hz), 1.34-1.49 (4H, m), 1.58-1.72 (4H, m), 1.82 (2H, quint, J=6.9 Hz), 2.62 (2H, t, J=7.2 Hz), 3.32 (2H, t, J=6.9 Hz), 4.01 (2H, t, J=6.6 Hz), 4.06 (2H, s), 4.13 (2H, q, J=7.2 Hz), 7.00-7.28 (10H, m), 7.51-7.57 (2H, m).

(2) Preparation of the Compound 643.

The title compound was obtained in the same manner as the Example 126(4) using the following starting material.

Starting material: the intermediate 643(1); Yield: 82% (pale yellow oil).

$^1$H-NMR ($CDCl_3$) δ: 0.94 (3H, t, J=6.6 Hz), 1.34-1.95 (10H, m), 2.60 (2H, t, J=7.2 Hz), 3.13 (2H, t, J=7.5 Hz), 3.65 (2H, s), 4.06 (2H, t, J=6.6 Hz), 7.05-7.30 (10H, m), 7.51-7.58 (2H, m).

Example 644

Preparation of the Compound 644

(1) Preparation of the Intermediate 644(1).

The title compound was obtained in the same manner as the Example 123(1) using the following starting materials.

Starting materials: the intermediate 351(3) and ethyl bromoacetate; Yield: 58% (white solid).

$^1$H-NMR ($CDCl_3$) δ: 1.19 (3H, t, J=7.2 Hz), 1.23 (9H, s), 1.58-1.76 (4H, m), 2.61 (2H, t, J=6.9 Hz), 3.40 (2H, t, J=6.9 Hz), 3.72 (2H, t, J=5.7 Hz), 4.09 (2H, t, J=7.2 Hz), 4.13 (2H, t, J=5.7 Hz), 4.13 (2H, s), 6.91 (1H, d, J=8.4 Hz), 7.07-7.62 (11H, m).

(2) Preparation of the Compound 644.

The title compound was obtained in the same manner as the Example 126(4) using the following starting material.

Starting material: the intermediate 644(1); Yield: 46% (colorless oil).

$^1$H-NMR ($CDCl_3$) δ: 1.22 (9H, s), 1.53-1.71 (4H, m), 2.59 (2H, t, J=7.2 Hz), 3.15 (2H, t, J=7.5 Hz), 3.71 (2H, s), 3.72 (2H, t, J=5.4 Hz), 4.14 (2H, t, J=5.1 Hz), 6.98 (1H, d, J=8.1 Hz), 7.10-7.52 (11H, m).

Example 645

Preparation of the Compound 645

(1) Preparation of the Intermediate 645(1).

The title compound was obtained in the same manner as the Example 123(3) using the following starting materials.

Starting materials: 5-bromosalicylaldehyde and 4-(trifluoromethoxy)phenylboronic acid; Yield: 78% (yellow solid).

$^1$H-NMR ($CDCl_3$) δ: 7.09 (1H, d, J=8.1 Hz), 7.30 (2H, d, J=7.8 Hz), 7.54-7.59 (2H, m), 7.72-7.76 (2H, m), 9.98 (1H, s), 11.03 (1H, s).

(2) Preparation of the Intermediate 645(2).

The title compound was obtained in the same manner as the Example 354(2) using the following starting material.

Starting material: the intermediate 645(1); Yield: 83% (colorless oil).

$^1$H-NMR ($CDCl_3$) δ: 0.96 (3H, t, J=7.5 Hz), 1.37-1.55 (4H, m), 1.83-1.91 (2H, m), 4.13 (2H, t, J=6.3 Hz), 7.06 (1H, d, J=8.4 Hz), 7.25-7.29 (2H, m), 7.55-7.59 (2H, m), 7.73 (1H, dd, J=2.4, 8.4 Hz), 8.04 (1H, d, J=2.4 Hz), 10.55 (1H, s).

(3) Preparation of the Intermediate 645(3).

A mixture of the intermediate 645(2) (875 mg, 2.484 mmol), 4-(tert-butyl)aniline (408 mg, 2.732 mmol), sodium triacetoxyborohydride (790 mg, 3.726 mmol), acetic acid (164 mg, 2.732 mmol) and dichloromethane (7 ml) was stirred at room temperature for 4 hours. The reaction mixture was diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=15:1) to give the title compound (1.21 g, 100%) as a colorless oil.

$^1$H-NMR ($CDCl_3$) δ: 0.94 (3H, t, J=7.2 Hz), 1.27 (9H, s), 1.35-1.51 (4H, m), 1.80-1.86 (2H, m), 4.05 (2H, t, J=6.3 Hz), 4.11 (1H, s), 4.38 (2H, s), 6.61-6.67 (2H, m), 6.93 (1H, d, J=8.4 Hz), 7.17-7.26 (4H, m), 7.40 (1H, dd, J=2.4, 8.4 Hz), 7.47-7.52 (2H, m), 7.53 (1H, d, J=2.4 Hz).

(4) Preparation of the Intermediate 645(4).

The title compound was obtained in the same manner as the Example 125(3) using the following starting materials.

Starting materials: the intermediate 645(3) and methyl chloroglyoxylate; Yield: 89% (pale brown oil).

$^1$H-NMR ($CDCl_3$) δ: 0.86-0.96 (3H, m), 1.22-1.41 (13H, m), 1.55-1.68 (2H, m), 3.54 (3H, s), 3.82 (2H, t, J=6.6 Hz), 5.04 (2H, s), 6.84 (1H, d, J=8.4 Hz), 6.99-7.08 (2H, m), 7.18-7.33 (4H, m), 7.40 (1H, dd, J=2.4, 8.4 Hz), 7.45-7.55 (3H, m).

(5) Preparation of the Compound 645.

The title compound was obtained in the same manner as the Example 126(4) using the following starting material.

Starting material: the intermediate 645(4); Yield: 98% (white solid).

$^1$H-NMR (DMSO-$d_6$) δ: 0.83-0.94 (3H, m), 1.14-1.46 (13H, m), 1.58-1.73 (2H, m), 3.80-4.07 (2H, m), 4.79 (2H, s), 6.90-7.08 (1H, m), 7.08-7.35 (4H, m), 7.35-7.56 (3H, m), 7.56-7.77 (3H, m).

Example 646

Preparation of the Compound 646

(1) Preparation of the Intermediate 646(1).

The title compound was obtained in the same manner as the Example 354(2) using the following starting materials.

Starting materials: the intermediate 354(1) and ethyl 9-bromononanoate; Yield: 100% (yellow oil).

$^1$H-NMR ($CDCl_3$) δ: 1.23-1.28 (3H, m), 1.30-1.36 (6H, m), 1.48-1.52 (2H, m), 1.60-1.65 (2H, m), 1.80-1.85 (2H, m), 2.26-2.32 (2H, m), 4.10-4.14 (4H, m), 7.16 (1H, d, J=8.7 Hz), 7.28-7.33 (2H, m), 7.54-7.58 (2H, m), 7.77 (1H, dd, J=2.7, 8.7 Hz), 8.02 (1H, d, J=2.7 Hz).

(2) Preparation of the Intermediate 646(2).

The title compound was obtained in the same manner as the Example 125(2) using the following starting material.

Starting material: the intermediate 646(1); Yield: 92% (white solid).

$^1$H-NMR ($CDCl_3$) δ: 1.23-1.28 (3H, m), 1.30-1.36 (6H, m), 1.48-1.52 (2H, m), 1.60-1.65 (2H, m), 1.80-1.85 (2H, m), 2.26-2.32 (2H, m), 3.89 (2H, brs), 4.03 (2H, t, J=6.6 Hz), 4.12 (2H, q, J=7.2 Hz), 6.83 (1H, d, J=8.4 Hz), 6.88-6.94 (2H, m), 7.21-7.24 (2H, m), 7.50-7.54 (2H, m).

(3) Preparation of the Intermediate 646(3).

The title compound was obtained in the same manner as the Example 123(1) using the following starting materials.

Starting materials: the intermediate 646(2) and 4-phenylbutyl bromide; Yield: 67% (colorless oil).

$^1$H-NMR ($CDCl_3$) δ: 1.23-1.28 (3H, m), 1.30-1.85 (16H, m), 2.26-2.32 (2H, m), 2.68 (2H, t, J=7.2 Hz), 3.18-3.24 (2H, m), 4.03 (2H, t, J=6.6 Hz), 4.12 (2H, q, J=7.2 Hz), 4.25-4.29 (1H, m), 6.73-6.80 (3H, m), 7.18-7.30 (7H, m), 7.52-7.55 (2H, m).

(4) Preparation of the Intermediate 646(4).

The title compound was obtained in the same manner as the Example 125(3) using the following starting materials.

Starting materials: the intermediate 646(3) and methyl chloroglyoxylate; Yield: 78% (colorless oil).

$^1$H-NMR ($CDCl_3$) δ: 1.23-1.28 (3H, m), 1.30-1.85 (16H, m), 2.29 (2H, t, J=7.2 Hz), 2.57-2.63 (2H, m), 3.48-3.58 (4H, m), 3.97-4.09 (3H, m), 4.12 (2H, q, J=7.2 Hz), 6.98 (1H, d, J=8.4 Hz), 7.10-7.15 (3H, m), 7.19-7.28 (4H, m), 7.31 (1H, d, J=2.4 Hz), 7.46-7.51 (3H, m).

(5) Preparation of the Compound 646.

The title compound was obtained in the same manner as the Example 126(4) using the following starting material.

Starting material: the intermediate 646(4); Yield: 29% (white solid).

This compound was obtained as a mixture of the rotational isomers.

Major isomer: $^1$H-NMR (DMSO-$d_6$) δ: 1.27-1.54 (14H, m), 1.67-1.74 (2H, m), 2.10-2.16 (2H, m), 2.48-2.51 (2H, m), 3.19-4.01 (4H, m), 7.07-7.20 (6H, m), 7.40-7.43 (2H, m), 7.48-7.54 (2H, m), 7.64-7.67 (2H, m), 12.52 (1H, brs).

Minor isomer: $^1$H-NMR (DMSO-$d_6$) δ: 1.27-1.54 (14H, m), 1.67-1.74 (2H, m), 2.10-2.16 (2H, m), 2.48-2.51 (2H, m), 3.19-4.01 (4H, m), 7.07-7.20 (5H, m), 7.30 (1H, d, J=2.1 Hz), 7.40-7.43 (2H, m), 7.48-7.59 (2H, m), 7.68-7.71 (2H, m), 12.52 (1H, brs).

Example 647

Preparation of the Compound 647

(1) Preparation of the Intermediate 647(1).

The title compound was obtained in the same manner as the Example 123(1) using the following starting materials.

Starting materials: the intermediate 645(3) and ethyl bromoacetate; Yield: 51% (pale yellow oil).

$^1$H-NMR ($CDCl_3$) δ: 0.94 (3H, t, J=6.6 Hz), 1.24 (3H, t, J=7.2 Hz), 1.26 (9H, s), 1.30-1.59 (4H, m), 1.76-1.89 (2H, m), 4.03 (2H, t, J=6.6 Hz), 4.12 (2H, s), 4.21 (2H, q, J=7.2 Hz), 4.66 (2H, s), 6.58-6.69 (2H, m), 6.93 (1H, d, J=8.1 Hz), 7.13-7.27 (4H, m), 7.40 (1H, dd, J=2.4, 8.1 Hz), 7.43-7.54 (3H, m).

(2) Preparation of the Compound 647.

The title compound was obtained in the same manner as the Example 126(4) using the following starting material.

Starting material: the intermediate 647(1); Yield: 87% (white solid).

$^1$H-NMR (DMSO-$d_6$) δ: 0.91 (3H, t, J=7.2 Hz), 1.16 (9H, s), 1.28-1.53 (4H, m), 1.70-1.85 (2H, m), 3.85 (2H, s), 4.08 (2H, t, J=6.3 Hz), 4.51 (2H, s), 6.40 (2H, d, J=8.7 Hz), 6.98-7.14 (3H, m), 7.32 (2H, d, J=8.7 Hz), 7.50 (1H, dd, J=2.4, 8.4 Hz), 7.60-7.72 (2H, m), 7.79 (1H, d, J=2.4 Hz).

Example 648

Preparation of the Compound 648

(1) Preparation of the Intermediate 648(1).

The title compound was obtained in the same manner as the Example 354(2) using the following starting materials.

Starting materials: 4-bromo-2-hydroxybenzonitrile and 1-chloropentane; Yield: 100% (colorless oil).

$^1$H-NMR ($CDCl_3$) δ: 0.94 (3H, t, J=7.2 Hz), 1.36-1.53 (4H, m), 1.86 (2H, quint, J=6.6 Hz), 4.06 (2H, t, J=6.6 Hz), 7.11-7.15 (2H, m), 7.40 (1H, d, J=7.8 Hz).

(2) Preparation of the Intermediate 648(2).

The title compound was obtained in the same manner as the Example 123(3) using the following starting materials.

Starting materials: the intermediate 648(1) and 4-(trifluoromethoxy)phenylboronic acid; Yield: 95% (white solid).

$^1$H-NMR ($CDCl_3$) δ: 0.95 (3H, t, J=6.9 Hz), 1.35-1.56 (4H, m), 1.89 (2H, quint, J=6.3 Hz), 4.14 (2H, t, J=6.3 Hz), 7.09-7.17 (2H, m), 7.32 (2H, d, J=8.4 Hz), 7.58-7.61 (3H, m).

(3) Preparation of the Intermediate 648(3).

A solution of the intermediate 648(2) (500 mg, 1.43 mmol) in anhydrous tetrahydrofuran (2 ml) was added dropwise to a suspension of lithium aluminium hydride (163 mg, 4.29 mmol) in anhydrous tetrahydrofuran (3 ml) under reflux, and the mixture was stirred for 40 minutes. The reaction mixture was cooled to 0° C., followed by addition of 2 N hydrochloric acid, and extracted with ethyl acetate. The organic layer was washed with saturated brine, and dried over anhydrous sodium sulfate. The solvent was evaporated under reduced pressure to give the title compound (520 mg, 100%) as a pale brown oil.

$^1$H-NMR ($CDCl_3$) δ: 0.95 (3H, t, J=7.5 Hz), 1.34-1.54 (4H, m), 1.81-1.90 (4H, m), 3.87 (2H, s), 4.06 (2H, t, J=6.6 Hz), 7.01 (1H, d, J=1.8 Hz), 7.08 (1H, dd, J=1.8, 7.5 Hz), 7.26-7.30 (3H, m), 7.55-7.60 (2H, m).

(4) Preparation of the Intermediate 648(4).

The title compound was obtained in the same manner as the Example 157(2) using the following starting materials.

Starting materials: the intermediate 648(3) and 1-bromo-4-(tert-butyl)benzene; Yield: 42% (colorless oil).

$^1$H-NMR ($CDCl_3$) δ: 0.93 (3H, t, J=7.5 Hz), 1.27 (9H, s), 1.30-1.53 (4H, m), 1.78-1.92 (3H, m), 4.07 (2H, t, J=6.6 Hz), 4.37 (2H, s), 6.06-6.65 (2H, m), 7.02-7.40 (7H, m), 7.47-7.59 (2H, m).

(5) Preparation of the Intermediate 648(5).

The title compound was obtained in the same manner as the Example 125(3) using the following starting materials.

Starting materials: the intermediate 648(4) and methyl chloroglyoxylate; Yield: 69% (colorless oil).

$^1$H-NMR ($CDCl_3$) δ: 0.91 (3H, t, J=6.9 Hz), 1.27 (9H, s), 1.31-1.39 (4H, m), 1.56-1.70 (2H, m), 3.54 (3H, s), 3.84 (2H, t, J=6.6 Hz), 5.03 (2H, s), 6.93 (1H, d, J=1.8 Hz), 7.04-7.11 (3H, m), 7.25-7.32 (4H, m), 7.42 (1H, d, J=8.1 Hz), 7.54-7.59 (2H, m).

(6) Preparation of the Compound 648.

The title compound was obtained in the same manner as the Example 126(4) using the following starting material.

Starting material: the intermediate 648(5); Yield: 89% (solid).

$^1$H-NMR (DMSO-$d_6$) δ: 0.87 (3H, t, J=6.9 Hz), 1.23 (9H, s), 1.26-1.35 (4H, m), 1.52-1.70 (2H, m), 3.95 (2H, t, J=6.3 Hz), 4.85 (2H, s), 7.16-7.23 (4H, m), 7.32-7.36 (3H, m), 7.43 (2H, d, J=8.4 Hz), 7.79 (2H, d, J=8.4 Hz), 14.01 (1H, brs).

Example 649

Preparation of the Compound 649

(1) Preparation of the Intermediate 649(1).

The title compound was obtained in the same manner as the Example 123(1) using the following starting materials.

Starting materials: the intermediate 648(4) and ethyl bromoacetate; Yield: 70% (pale yellow oil).

$^1$H-NMR ($CDCl_3$) δ: 0.94 (3H, t, J=6.9 Hz), 1.23 (3H, t, J=6.6 Hz), 1.27 (9H, s), 1.34-1.50 (4H, m), 1.84 (2H, quint, J=6.9 Hz), 4.07 (2H, t, J=6.6 Hz), 4.12 (2H, s), 4.23 (2H, q, J=6.9 Hz), 4.65 (2H, s), 6.58-6.63 (2H, m), 7.03-7.06 (2H, m), 7.20-7.32 (5H, m), 7.55-7.61 (2H, m).

(2) Preparation of the Compound 649.

The title compound was obtained in the same manner as the Example 126(4) using the following starting material.

Starting material: the intermediate 649(1); Yield: 94% (white solid).

$^1$H-NMR (DMSO-$d_6$) δ: 0.91 (3H, t, J=7.5 Hz), 1.20 (9H, s), 1.34-1.48 (4H, m), 1.79 (2H, quint, J=6.9 Hz), 4.08-4.21 (4H, m), 4.52 (2H, s), 6.47 (2H, d, J=9.0 Hz), 7.12-7.25 (5H, m), 7.43 (2H, d, J=9.0 Hz), 7.79 (2H, d, J=9.0 Hz), 12.58 (1H, brs).

Example 650

Preparation of the Compound 650

(1) Preparation of the Intermediate 650(1).

The title compound was obtained in the same manner as the Example 354(2) using the following starting materials.

Starting materials: 2-chloro-5-nitrophenol and 1-bromoheptane; Yield: 98% (pale yellow oil).

$^1$H-NMR ($CDCl_3$) δ: 0.84-0.95 (3H, m), 1.33-1.56 (8H, m), 1.80-1.96 (2H, m), 4.12 (2H, t, J=6.3 Hz), 7.47-7.55 (1H, m), 7.74-7.82 (2H, m).

(2) Preparation of the Intermediate 650(2).

The title compound was obtained in the same manner as the Example 371(1) using the following starting materials.

Starting materials: the intermediate 650(1) and 4-(trifluoromethoxy)phenylboronic acid; Yield: 80% (colorless oil).

$^1$H-NMR ($CDCl_3$) δ: 0.84-0.92 (3H, m), 1.20-1.44 (8H, m), 1.71-1.83 (2H, m), 4.02-4.13 (2H, m), 7.20-7.35 (2H, m), 7.44 (1H, d, J=8.4 Hz), 7.53-7.60 (2H, m), 7.81 (1H, d, J=2.1 Hz), 7.90 (1H, dd, J=2.1, 8.4 Hz).

(3) Preparation of the Intermediate 650(3).

The title compound was obtained in the same manner as the Example 125(2) using the following starting material.

Starting material: the intermediate 650(2); Yield: 46% (purple oil).

$^1$H-NMR ($CDCl_3$) δ: 0.83-0.93 (3H, m), 1.20-1.43 (8H, m), 1.64-1.77 (2H, m), 3.74 (2H, brs), 3.91 (2H, t, J=6.6 Hz), 6.31 (1H, d, J=2.4 Hz), 6.35 (1H, dd, J=2.4, 8.1 Hz), 7.10 (1H, d, J=8.1 Hz), 7.15-7.22 (2H, m), 7.48-7.55 (2H, m).

(4) Preparation of the Intermediate 650(4).

The title compound was obtained in the same manner as the Example 123(1) using the following starting materials.

Starting materials: the intermediate 650(3) and 4-phenylbutyl bromide; Yield: 55% (brown oil).

$^1$H-NMR ($CDCl_3$) δ: 0.83-0.93 (3H, m), 1.20-1.43 (8H, m), 1.61-1.84 (6H, m), 2.68 (2H, t, J=6.9 Hz), 3.16 (2H, t, J=6.9 Hz), 3.69 (1H, brs), 3.94 (2H, t, J=6.6 Hz), 6.19 (1H, d, J=1.8 Hz), 6.25 (1H, dd, J=1.8, 8.4 Hz), 7.12 (1H, d, J=8.4 Hz), 7.14-7.34 (7H, m), 7.48-7.55 (2H, m).

(5) Preparation of the Intermediate 650(5).

The title compound was obtained in the same manner as the Example 125(3) using the following starting materials.

Starting materials: the intermediate 650(4) and methyl chloroglyoxylate; Yield: 93% (colorless oil).

$^1$H-NMR ($CDCl_3$) δ: 0.83-0.93 (3H, m), 1.20-1.43 (8H, m), 1.59-1.80 (6H, m), 2.63 (2H, t, J=6.9 Hz), 3.56-3.64 (1H, m), 3.60 (3H, s), 3.80-3.88 (1H, m), 3.91 (2H, t, J=6.6 Hz), 6.75 (1H, d, J=1.8 Hz), 6.81 (1H, dd, J=1.8, 8.4 Hz), 7.10-7.31 (8H, m), 7.51-7.59 (2H, m).

(6) Preparation of the Compound 650.

The title compound was obtained in the same manner as the Example 126(4) using the following starting material.

Starting material: the intermediate 650(5); Yield: 93% (colorless oil).

$^1$H-NMR ($CDCl_3$) δ: 0.82-0.92 (3H, m), 1.17-1.38 (8H, m), 1.51-1.71 (6H, m), 2.52-2.63 (2H, m), 3.70-3.89 (4H, m), 6.65-6.78 (2H, m), 7.03-7.27 (8H, m), 7.43-7.53 (2H, m).

Example 651

Preparation of the Compound 651

(1) Preparation of the Intermediate 651(1).

The title compound was obtained in the same manner as the Example 185(2) using the following starting materials.

Starting materials: the intermediate 188(1) and sodium methoxide; Yield: 81% (white solid).

$^1$H-NMR ($CDCl_3$) δ: 4.01 (3H, s), 7.18 (1H, d, J=9.0 Hz), 7.28-7.33 (2H, m), 7.54-7.58 (2H, m), 7.74 (1H, dd, J=2.7, 9.0 Hz), 8.05 (1H, d, J=2.7 Hz).

(2) Preparation of the Intermediate 651(2).

The title compound was obtained in the same manner as the Example 125(2) using the following starting material.

Starting material: the intermediate 651(1); Yield: 97% (white solid).

$^1$H-NMR ($CDCl_3$) δ: 3.89 (5H, brs), 6.83-6.96 (3H, m), 7.22-7.25 (2H, m), 7.50-7.54 (2H, m).

(3) Preparation of the Intermediate 651(3).

The title compound was obtained in the same manner as the Example 123(1) using the following starting materials.

Starting materials: the intermediate 651(2) and 4-phenylbutyl bromide; Yield: 25% (white solid).

$^1$H-NMR ($CDCl_3$) δ: 1.74-1.77 (4H, m), 2.64-2.70 (2H, m), 3.18-3.23 (2H, m), 3.88 (3H, s), 4.22-4.27 (1H, m), 6.73-6.82 (3H, m), 7.19-7.28 (7H, m), 7.53-7.56 (2H, m).

(4) Preparation of the Intermediate 651(4).

The title compound was obtained in the same manner as the Example 125(3) using the following starting materials.

Starting materials: the intermediate 651(3) and methyl chloroglyoxylate; Yield: 100% (white solid).

$^1$H-NMR ($CDCl_3$) δ: 1.58-1.70 (4H, m), 2.57-2.63 (2H, m), 3.49-3.58 (4H, m), 3.88 (3H, s), 3.97-4.07 (1H, m), 7.00 (1H, d, J=8.7 Hz), 7.10-7.16 (3H, m), 7.20-7.32 (5H, m), 7.47-7.54 (3H, m).

(5) Preparation of the Compound 651.

The title compound was obtained in the same manner as the Example 126(4) using the following starting material.

Starting material: the intermediate 651(4); Yield: 88% (white solid).

This compound was obtained as a mixture of the rotational isomers.

Major isomer: $^1$H-NMR (DMSO-$d_6$) δ: 1.35-1.52 (4H, m), 3.33 (3H, s), 3.56-3.85 (4H, m), 7.07-7.20 (6H, m), 7.40-7.44 (2H, m), 7.48-7.54 (2H, m), 7.62-7.67 (2H, m).

Minor isomer: $^1$H-NMR (DMSO-$d_6$) δ: 1.35-1.52 (4H, m), 3.33 (3H, s), 3.56-3.85 (4H, m), 7.07-7.20 (5H, m), 7.27 (1H, d, J=2.1 Hz), 7.40-7.44 (2H, m), 7.48-7.60 (2H, m), 7.68-7.71 (2H, m).

Example 652

Preparation of the Compound 652

(1) Preparation of the Intermediate 652(1).

The title compound was obtained in the same manner as the Example 185(2) using the following starting materials.

Starting materials: the intermediate 367(1) and 1-hexanol; Yield: 100% (yellow solid).

$^1$H-NMR ($CDCl_3$) δ: 0.89-0.94 (3H, m), 1.32-1.38 (4H, m), 1.49-1.56 (2H, m), 1.84-1.90 (2H, m), 4.17 (2H, t, J=6.6 Hz), 7.15-7.19 (2H, m), 7.32-7.35 (2H, m), 7.56-7.62 (2H, m), 7.94 (1H, d, J=8.4 Hz).

(2) Preparation of the Intermediate 652(2).

The title compound was obtained in the same manner as the Example 125(2) using the following starting material.

Starting material: the intermediate 652(1); Yield: 89% (white solid).

$^1$H-NMR ($CDCl_3$) δ: 0.89-0.94 (3H, m), 1.32-1.38 (4H, m), 1.49-1.56 (2H, m), 1.80-1.89 (2H, m), 3.90 (2H, brs), 4.06 (2H, t, J=6.6 Hz), 6.77 (1H, d, J=7.8 Hz), 6.97-7.01 (2H, m), 7.22-7.25 (2H, m), 7.50-7.55 (2H, m).

(3) Preparation of the Intermediate 652(3).

The title compound was obtained in the same manner as the Example 123(1) using the following starting materials.

Starting materials: the intermediate 652(2) and 4-phenylbutyl bromide; Yield: 91% (yellow solid).

$^1$H-NMR ($CDCl_3$) δ: 0.89-0.94 (3H, m), 1.32-1.52 (8H, m), 1.75-1.89 (4H, m), 2.68-2.73 (2H, m), 3.17-3.24 (2H, m), 4.06 (2H, t, J=6.6 Hz), 4.26-4.32 (1H, m), 6.64 (1H, d, J=8.4 Hz), 6.95 (1H, d, J=2.7 Hz), 7.07 (1H, dd, J=2.7, 8.4 Hz), 7.18-7.31 (7H, m), 7.50-7.55 (2H, m).

(4) Preparation of the Intermediate 652(4).

The title compound was obtained in the same manner as the Example 125(3) using the following starting materials.

Starting materials: the intermediate 652(3) and methyl chloroglyoxylate; Yield: 69% (colorless oil).

$^1$H-NMR ($CDCl_3$) δ: 0.89-0.94 (3H, m), 1.32-1.52 (6H, m), 1.75-1.89 (6H, m), 2.58-2.65 (2H, m), 3.54-3.60 (4H, m), 3.98-4.16 (3H, m), 7.07-7.18 (6H, m), 7.21-7.31 (4H, m), 7.58-7.61 (2H, m).

(5) Preparation of the Compound 652.

The title compound was obtained in the same manner as the Example 126(4) using the following starting material.

Starting material: the intermediate 652(4); Yield: 96% (white solid).

This compound was obtained as a mixture of the rotational isomers.

Major isomer: $^1$H-NMR (DMSO-$d_6$) δ: 0.84-0.88 (3H, m), 1.28-1.52 (10H, m), 1.66-1.75 (2H, m), 2.48-2.52 (2H, m), 3.62-4.08 (4H, m), 7.10-7.23 (8H, m), 7.43-7.46 (2H, m), 7.79-7.82 (2H, m).

Minor isomer: $^1$H-NMR (DMSO-$d_6$) δ: 0.84-0.88 (3H, m), 1.28-1.52 (10H, m), 1.66-1.75 (2H, m), 2.48-2.52 (2H, m), 3.12-4.08 (4H, m), 7.07-7.29 (8H, m), 7.43-7.46 (2H, m), 7.81-7.84 (2H, m).

Example 653

Preparation of the Compound 653

(1) Preparation of the Intermediate 653(1).

The title compound was obtained in the same manner as the Example 185(2) using the following starting materials.

Starting materials: the intermediate 367(1) and 1-octanol; Yield: 83% (yellow solid).

$^1$H-NMR ($CDCl_3$) δ: 0.89-0.94 (3H, m), 1.32-1.38 (8H, m), 1.49-1.56 (2H, m), 1.84-1.90 (2H, m), 4.17 (2H, t, J=6.6 Hz), 7.15-7.19 (2H, m), 7.32-7.35 (2H, m), 7.56-7.62 (2H, m), 7.94 (1H, d, J=8.4 Hz).

(2) Preparation of the Intermediate 653(2).

The title compound was obtained in the same manner as the Example 125(2) using the following starting material.

Starting material: the intermediate 653(1); Yield: 96% (white solid).

$^1$H-NMR ($CDCl_3$) δ: 0.89-0.94 (3H, m), 1.32-1.56 (10H, m), 1.80-1.89 (2H, m), 3.89 (2H, brs), 4.05 (2H, t, J=6.6 Hz), 6.77 (1H, d, J=7.8 Hz), 6.97-7.01 (2H, m), 7.22-7.25 (2H, m), 7.50-7.55 (2H, m).

(3) Preparation of the Intermediate 653(3).

The title compound was obtained in the same manner as the Example 123(1) using the following starting materials.

Starting materials: the intermediate 653(2) and 4-phenylbutyl bromide; Yield: 57% (white solid).

$^1$H-NMR ($CDCl_3$) δ: 0.89-0.94 (3H, m), 1.32-1.52 (12H, m), 1.75-1.89 (4H, m), 2.68-2.73 (2H, m), 3.17-3.24 (2H, m), 4.06 (2H, t, J=6.6 Hz), 4.26-4.32 (1H, m), 6.64 (1H, d, J=8.4 Hz), 6.95 (1H, d, J=2.7 Hz), 7.07 (1H, dd, J=2.7, 8.4 Hz), 7.18-7.31 (7H, m), 7.50-7.55 (2H, m).

(4) Preparation of the Intermediate 653(4).

The title compound was obtained in the same manner as the Example 125(3) using the following starting materials.

Starting materials: the intermediate 653(3) and methyl chloroglyoxylate; Yield: 100% (colorless oil).

$^1$H-NMR ($CDCl_3$) δ: 0.89-0.94 (3H, m), 1.32-1.52 (10H, m), 1.75-1.89 (6H, m), 2.58-2.65 (2H, m), 3.54-3.60 (4H, m), 3.98-4.16 (3H, m), 7.06-7.18 (6H, m), 7.21-7.31 (4H, m), 7.57-7.60 (2H, m).

(5) Preparation of the Compound 653.

The title compound was obtained in the same manner as the Example 126(4) using the following starting material.

Starting material: the intermediate 653(4); Yield: 64% (white solid).

This compound was obtained as a mixture of the rotational isomers.

Major isomer: $^1$H-NMR (DMSO-$d_6$) δ: 0.84-0.88 (3H, m), 1.23-1.52 (14H, m), 1.66-1.75 (2H, m), 2.48-2.52 (2H, m), 3.62-4.08 (4H, m), 7.10-7.23 (8H, m), 7.43-7.46 (2H, m), 7.79-7.82 (2H, m).

Minor isomer: $^1$H-NMR (DMSO-$d_6$) δ: 0.84-0.88 (3H, m), 1.23-1.52 (14H, m), 1.66-1.75 (2H, m), 2.48-2.52 (2H, m), 3.12-4.08 (4H, m), 7.07-7.29 (8H, m), 7.43-7.46 (2H, m), 7.81-7.84 (2H, m).

Example 654

Preparation of the Compound 654

(1) Preparation of the Intermediate 654(1).

The title compound was obtained in the same manner as the Example 371(1) using the following starting materials.

Starting materials: 2-chloro-5-nitrophenol and 4-(trifluoromethoxy)phenylboronic acid; Yield: 7% (yellow solid).

$^1$H-NMR ($CDCl_3$) δ: 5.58 (1H, s), 7.36-7.42 (3H, m), 7.53-7.57 (2H, m), 7.84-7.90 (2H, m).

(2) Preparation of the Intermediate 654(2).

The title compound was obtained in the same manner as the Example 354(2) using the following starting materials.

Starting materials: the intermediate 654(1) and 1-chloropentane; Yield: 75% (yellow solid).

$^1$H-NMR ($CDCl_3$) δ: 0.87-0.92 (3H, m), 1.32-1.38 (4H, m), 1.75-1.81 (2H, m), 4.08 (2H, t, J=6.6 Hz), 7.27-7.30 (2H, m), 7.44 (1H, d, J=8.7 Hz), 7.57-7.60 (2H, m), 7.81 (1H, d, J=2.1 Hz), 7.90 (1H, dd, J=2.1, 8.7 Hz).

(3) Preparation of the Intermediate 654(3).

The title compound was obtained in the same manner as the Example 125(2) using the following starting material.

Starting material: the intermediate 654(2); Yield: 100% (colorless oil).

$^1$H-NMR ($CDCl_3$) δ: 0.88 (3H, t, J=6.9 Hz), 1.32-1.38 (4H, m), 1.69-1.74 (2H, m), 3.73 (2H, brs), 3.90 (2H, t, J=6.6 Hz), 6.30-6.36 (2H, m), 7.10 (1H, d, J=7.8 Hz), 7.17-7.21 (2H, m), 7.50-7.53 (2H, m).

(4) Preparation of the Intermediate 654(4).

The title compound was obtained in the same manner as the Example 125(3) using the following starting materials.

Starting materials: the intermediate 654(3) and methyl chloroglyoxylate; Yield: 67% (white solid).

$^1$H-NMR ($CDCl_3$) δ: 0.88 (3H, t, J=6.9 Hz), 1.30-1.38 (4H, m), 1.69-1.78 (2H, m), 3.98-4.02 (5H, m), 7.11 (1H, dd, J=2.1, 8.4 Hz), 7.21-7.25 (2H, m), 7.30 (1H, d, J=8.4 Hz), 7.53-7.56 (3H, m), 8.89 (1H, brs).

(5) Preparation of the Intermediate 654(5).

The title compound was obtained in the same manner as the Example 123(1) using the following starting materials.

Starting materials: the intermediate 654(4) and 4-phenylbutyl bromide; Yield: 85% (yellow oil).

$^1$H-NMR ($CDCl_3$) δ: 0.88 (3H, t, J=6.9 Hz), 1.30-1.38 (4H, m), 1.65-1.75 (6H, m), 2.61-2.65 (2H, m), 3.61 (3H, s), 3.81-3.92 (4H, m), 6.76 (1H, d, J=2.1 Hz), 6.82 (1H, dd, J=2.1, 8.4 Hz), 7.13-7.29 (8H, m), 7.53-7.56 (2H, m).

(6) Preparation of the Compound 654.

The title compound was obtained in the same manner as the Example 126(4) using the following starting material.

Starting material: the intermediate 654(5); Yield: 82% (white solid).

$^1$H-NMR (DMSO-$d_6$) δ: 0.83 (3H, t, J=6.9 Hz), 1.21-1.31 (4H, m), 1.40-1.51 (4H, m), 1.62-1.66 (2H, m), 2.50-2.54 (2H, m), 3.71 (2H, t, J=6.6 Hz), 3.92 (2H, t, J=6.0 Hz), 6.90-6.94 (1H, m), 7.08-7.15 (4H, m), 7.20-7.25 (3H, m), 7.38-7.41 (2H, m), 7.60-7.63 (2H, m).

Example 655

Preparation of the Compound 655

(1) Preparation of the Intermediate 655(1).

The title compound was obtained in the same manner as the Example 123(1) using the following starting materials.

Starting materials: the intermediate 194(2) and benzyl 3-bromopropyl ether; Yield: 60% (pale yellow oil).

$^1$H-NMR ($CDCl_3$) δ: 0.93 (3H, t, J=7.2 Hz), 1.34-1.50 (4H, m), 1.80 (2H, quint, J=7.2 Hz), 2.00 (2H, quint, J=6.0 Hz), 3.35 (2H, t, J=6.6 Hz), 3.63 (2H, t, J=5.7 Hz), 4.00 (2H, t, J=6.9 Hz), 4.53 (2H, s), 6.79-6.82 (3H, m), 7.20-7.36 (7H, m), 7.52-7.58 (2H, m).

(2) Preparation of the Intermediate 655(2).

The title compound was obtained in the same manner as the Example 125(3) using the following starting materials.

Starting materials: the intermediate 655(1) and methyl chloroglyoxylate; Yield: 99% (pale yellow oil).

$^1$H-NMR ($CDCl_3$) δ: 0.86-0.95 (3H, m), 1.23-1.48 (4H, m), 1.77-1.95 (4H, m), 3.53-3.57 (5H, m), 3.97-4.14 (4H, m), 4.44 (2H, s), 6.98 (1H, d, J=8.4 Hz), 7.23-7.30 (7H, m), 7.37 (1H, d, J=2.4 Hz), 7.45-7.50 (3H, m).

(3) Preparation of the Compound 655.

The title compound was obtained in the same manner as the Example 126(4) using the following starting material.

Starting material: the intermediate 655(2); Yield: 61% (white solid).

This compound was obtained as a mixture of the rotational isomers.

Major isomer: $^1$H-NMR (DMSO-$d_6$) δ: 0.85-0.91 (3H, m), 1.24-1.46 (4H, m), 1.60-1.79 (4H, m), 3.34-4.09 (6H, m), 4.32-4.34 (2H, m), 7.09 (1H, d, J=8.4 Hz), 7.20-7.72 (11H, m).

Minor isomer: $^1$H-NMR (DMSO-$d_6$) δ: 0.85-0.91 (3H, m), 1.24-1.46 (4H, m), 1.60-1.79 (4H, m), 3.34-4.09 (6H, m), 4.32-4.34 (2H, m), 7.16 (1H, d, J=8.7 Hz), 7.20-7.72 (11H, m).

Example 656

Preparation of the Compound 656

(1) Preparation of the Intermediate 656(1).

The title compound was obtained in the same manner as the Example 185(2) using the following starting materials.

Starting materials: the intermediate 188(1) and 3-cyclohexyl-1-propanol; Yield: 79% (orange solid).

$^1$H-NMR ($CDCl_3$) δ: 0.88-0.99 (2H, m), 1.16-1.40 (6H, m), 1.63-1.92 (7H, m), 4.13 (2H, t, J=6.6 Hz), 7.15 (1H, d, J=8.7 Hz), 7.28-7.32 (2H, m), 7.55-7.58 (2H, m), 7.70 (1H, dd, J=2.4, 8.7 Hz), 8.03 (1H, d, J=2.4 Hz).

(2) Preparation of the Intermediate 656(2).

The title compound was obtained in the same manner as the Example 125(2) using the following starting material.

Starting material: the intermediate 656(1); Yield: 88% (white solid).

$^1$H-NMR ($CDCl_3$) δ: 0.88-0.99 (2H, m), 1.16-1.40 (6H, m), 1.63-1.92 (7H, m), 3.88 (2H, brs), 4.01 (2H, t, J=6.6 Hz), 6.83 (1H, d, J=7.8 Hz), 6.88-6.93 (2H, m), 7.22-7.25 (2H, m), 7.50-7.55 (2H, m).

(3) Preparation of the Intermediate 656(3).

The title compound was obtained in the same manner as the Example 123(1) using the following starting materials.

Starting materials: the intermediate 656(2) and 4-phenylbutyl bromide; Yield: 51% (white solid).

$^1$H-NMR ($CDCl_3$) δ: 0.88-0.99 (2H, m), 1.16-1.40 (6H, m), 1.63-1.92 (11H, m), 2.69 (2H, t, J=7.2 Hz), 3.20-3.24 (2H, m), 4.00 (2H, t, J=6.6 Hz), 4.26-4.28 (1H, m), 6.73-6.80 (3H, m), 7.19-7.31 (7H, m), 7.52-7.57 (2H, m).

(4) Preparation of the Intermediate 656(4).

The title compound was obtained in the same manner as the Example 125(3) using the following starting materials.

Starting materials: the intermediate 656(3) and methyl chloroglyoxylate; Yield: 100% (colorless oil).

$^1$H-NMR ($CDCl_3$) δ: 0.88-0.99 (2H, m), 1.16-1.36 (6H, m), 1.63-1.85 (11H, m), 2.57-2.63 (2H, m), 3.54-3.61 (4H, m), 3.94-4.05 (3H, m), 6.98 (1H, d, J=8.4 Hz), 7.10-7.16 (3H, m), 7.20-7.32 (5H, m), 7.47-7.51 (3H, m).

(5) Preparation of the Compound 656.

The title compound was obtained in the same manner as the Example 126(4) using the following starting material.

Starting material: the intermediate 656(4); Yield: 99% (white solid).

This compound was obtained as a mixture of the rotational isomers.

Major isomer: $^1$H-NMR (DMSO-$d_6$) δ 0.83-0.93 (2H, m), 1.15-1.73 (17H, m), 2.57-2.63 (2H, m), 3.58-3.63 (1H, m), 3.96-4.05 (3H, m), 7.06-7.20 (6H, m), 7.40-7.44 (2H, m), 7.48-7.57 (2H, m), 7.63-7.67 (2H, m).

Minor isomer: $^1$H-NMR (DMSO-$d_6$) δ: 0.83-0.93 (2H, m), 1.15-1.73 (17H, m), 2.57-2.63 (2H, m), 3.10-3.28 (1H, m), 3.96-4.05 (3H, m), 7.06-7.20 (5H, m), 7.26-7.29 (1H, m), 7.40-7.44 (2H, m), 7.48-7.57 (2H, m), 7.67-7.70 (2H, m).

Example 657

Preparation of the Compound 657

(1) Preparation of the Intermediate 657(1).

The title compound was obtained in the same manner as the Example 354(2) using the following starting materials.

Starting materials: the intermediate 354(1) and 3-phenoxypropyl bromide; Yield: 80% (yellow oil).

$^1$H-NMR ($CDCl_3$) δ: 2.26-2.41 (2H, m), 4.22 (2H, t, J=6.0 Hz), 4.36 (2H, t, J=6.0 Hz), 6.88-7.00 (3H, m), 7.19 (1H, d, J=8.7 Hz), 7.24-7.36 (4H, m), 7.50-7.60 (2H, m), 7.70 (1H, dd, J=2.4, 8.4 Hz), 8.04 (1H, d, J=2.4 Hz).

(2) Preparation of the Intermediate 657(2).

The title compound was obtained in the same manner as the Example 125(2) using the following starting material.

Starting material: the intermediate 657(1); Yield: 57% (yellow solid).

$^1$H-NMR ($CDCl_3$) δ: 2.24-2.40 (2H, m), 3.88 (2H, s), 4.18 (2H, t, J=6.0 Hz), 4.25 (2H, t, J=6.0 Hz), 6.83-7.00 (6H, m), 7.18-7.34 (4H, m), 7.47-7.56 (2H, m).

(3) Preparation of the Intermediate 657(3).

The title compound was obtained in the same manner as the Example 123(1) using the following starting materials.

Starting materials: the intermediate 657(2) and iodopentane; Yield: 23% (white solid).

$^1$H-NMR ($CDCl_3$) δ: 0.83-1.00 (3H, m), 1.28-1.48 (4H, m), 1.58-1.74 (2H, m), 2.24-2.40 (2H, m), 3.16 (2H, t, J=6.9 Hz), 4.17 (2H, t, J=6.3 Hz), 4.20-4.32 (3H, m), 6.72-6.87 (3H, m), 6.87-7.01 (3H, m), 7.19-7.35 (4H, m), 7.50-7.60 (2H, m).

(4) Preparation of the Intermediate 657(4).

The title compound was obtained in the same manner as the Example 125(3) using the following starting materials.

Starting materials: the intermediate 657(3) and methyl chloroglyoxylate; Yield: 100% (colorless oil).

$^1$H-NMR ($CDCl_3$) δ: 0.75-0.94 (3H, m), 1.11-1.40 (4H, m), 1.42-1.64 (2H, m), 2.22-2.39 (2H, m), 3.38-3.56 (4H, m), 3.85-4.00 (1H, m), 4.08-4.34 (4H, m), 6.88-6.98 (3H, m), 7.05 (1H, d, J=8.4 Hz), 7.22-7.34 (4H, m), 7.37 (1H, d, J=2.4 Hz), 7.47-7.58 (3H, m).

(5) Preparation of the Compound 657.

The title compound was obtained in the same manner as the Example 126(4) using the following starting material.

Starting material: the intermediate 657(4); Yield: 80% (pale yellow oil).

$^1$H-NMR ($CDCl_3$) δ: 0.59-0.83 (3H, m), 0.83-1.20 (4H, m), 1.20-1.56 (2H, m), 1.80-2.16 (2H, m), 3.15-4.18 (6H, m), 6.60-6.99 (4H, m), 7.00-7.30 (6H, m), 7.30-7.54 (2H, m).

Example 658

Preparation of the Compound 658

(1) Preparation of the Intermediate 658(1).

The title compound was obtained in the same manner as the Example 185(2) using the following starting materials.

Starting materials: the intermediate 188(1) and cyclopentanol; Yield: 70% (orange solid).

$^1$H-NMR ($CDCl_3$) δ: 1.64-1.97 (8H, m), 4.93-4.98 (1H, m), 7.15 (1H, d, J=8.7 Hz), 7.28-7.32 (2H, m), 7.55-7.58 (2H, m), 7.68 (1H, dd, J=2.4, 8.7 Hz), 8.00 (1H, d, J=2.4 Hz).

(2) Preparation of the Intermediate 658(2).

The title compound was obtained in the same manner as the Example 125(2) using the following starting material.

Starting material: the intermediate 658(1); Yield: 87% (white solid).

$^1$H-NMR ($CDCl_3$) δ: 1.64-1.97 (8H, m), 3.88 (2H, brs), 4.80-4.86 (1H, m), 6.83 (1H, d, J=7.8 Hz), 6.87-6.92 (2H, m), 7.22-7.25 (2H, m), 7.50-7.55 (2H, m).

(3) Preparation of the Intermediate 658(3).

The title compound was obtained in the same manner as the Example 123(1) using the following starting materials.

Starting materials: the intermediate 658(2) and 4-phenylbutyl bromide; Yield: 89% (yellow oil).

$^1$H-NMR ($CDCl_3$) δ: 1.64-1.97 (12H, m), 2.69 (2H, t, J=7.2 Hz), 3.20-3.24 (2H, m), 4.23 (1H, brs), 4.80-4.86 (1H, m), 6.73-6.80 (3H, m), 7.19-7.31 (7H, m), 7.52-7.57 (2H, m).

(4) Preparation of the Intermediate 658(4).

The title compound was obtained in the same manner as the Example 125(3) using the following starting materials.

Starting materials: the intermediate 658(3) and methyl chloroglyoxylate; Yield: 75% (colorless oil).

$^1$H-NMR ($CDCl_3$) δ: 1.57-1.91 (12H, m), 2.57-2.62 (2H, m), 3.50-3.59 (4H, m), 3.89-4.02 (1H, m), 4.79-4.86 (1H, m), 6.97 (1H, d, J=8.7 Hz), 7.10-7.16 (3H, m), 7.20-7.32 (5H, m), 7.47-7.51 (3H, m).

(5) Preparation of the Compound 658.

The title compound was obtained in the same manner as the Example 126(4) using the following starting material.

Starting material: the intermediate 658(4); Yield: 90% (white solid).

This compound was obtained as a mixture of the rotational isomers.

Major isomer: $^1$H-NMR (DMSO-$d_6$) δ: 1.33-1.88 (12H, m), 2.57-2.62 (2H, m), 3.10-4.11 (2H, m), 4.86-4.93 (1H, m), 7.04-7.17 (6H, m), 7.40-7.43 (2H, m), 7.48-7.55 (2H, m), 7.63-7.67 (2H, m).

Minor isomer: $^1$H-NMR (DMSO-$d_6$) δ: 1.33-1.88 (12H, m), 2.57-2.62 (2H, m), 3.10-4.11 (2H, m), 4.86-4.93 (1H, m), 7.04-7.17 (5H, m), 7.27-7.29 (1H, m), 7.40-7.43 (2H, m), 7.48-7.55 (2H, m), 7.67-7.70 (2H, m).

Example 659

Preparation of the Compound 659

(1) Preparation of the Intermediate 659(1).

The title compound was obtained in the same manner as the Example 185(2) using the following starting materials.

Starting materials: the intermediate 188(1) and cycloheptanol; Yield: 72% (white solid).

$^1$H-NMR ($CDCl_3$) δ: 1.48-2.09 (12H, m), 4.60-4.69 (1H, m), 7.11 (1H, d, J=8.7 Hz), 7.28-7.32 (2H, m), 7.54-7.58 (2H, m), 7.67 (1H, dd, J=2.4, 8.7 Hz), 7.98 (1H, d, J=2.4 Hz).

(2) Preparation of the Intermediate 659(2).

The title compound was obtained in the same manner as the Example 125(2) using the following starting material.

Starting material: the intermediate 659(1); Yield: 81% (white solid).

$^1$H-NMR ($CDCl_3$) δ: 1.48-1.90 (10H, m), 2.03-2.08 (2H, m), 3.88 (2H, brs), 4.44-4.48 (1H, m), 6.81 (1H, d, J=8.1 Hz), 6.87-6.93 (2H, m), 7.22-7.25 (2H, m), 7.50-7.55 (2H, m).

(3) Preparation of the Intermediate 659(3).

The title compound was obtained in the same manner as the Example 123(1) using the following starting materials.

Starting materials: the intermediate 659(2) and 4-phenylbutyl bromide; Yield: 72% (yellow oil).

$^1$H-NMR ($CDCl_3$) δ: 1.48-1.90 (14H, m), 2.03-2.08 (2H, m), 2.69 (2H, t, J=7.2 Hz), 3.15-3.21 (2H, m), 4.30 (1H, brs), 4.41-4.49 (1H, m), 6.73-6.80 (3H, m), 7.19-7.31 (7H, m), 7.52-7.57 (2H, m).

(4) Preparation of the Intermediate 659(4).

The title compound was obtained in the same manner as the Example 125(3) using the following starting materials.

Starting materials: the intermediate 659(3) and methyl chloroglyoxylate; Yield: 80% (colorless oil).

$^1$H-NMR ($CDCl_3$) δ: 1.48-1.85 (14H, m), 1.95-2.05 (2H, m), 2.57-2.62 (2H, m), 3.50-3.59 (4H, m), 3.98-4.05 (1H, m), 4.48-4.51 (1H, m), 6.92 (1H, d, J=8.4 Hz), 7.10-7.16 (3H, m), 7.20-7.22 (2H, m), 7.24-7.28 (2H, m), 7.32 (1H, d, J=2.4 Hz), 7.45-7.50 (3H, m).

(5) Preparation of the Compound 659.

The title compound was obtained in the same manner as the Example 126(4) using the following starting material.

Starting material: the intermediate 659(4); Yield: 67% (white solid).

This compound was obtained as a mixture of the rotational isomers.

Major isomer: $^1$H-NMR (DMSO-$d_6$) δ: 1.33-1.73 (14H, m), 1.89-2.01 (2H, m), 2.57-2.62 (2H, m), 3.21-3.97 (2H, m), 4.52-4.63 (1H, m), 7.03-7.20 (6H, m), 7.40-7.43 (2H, m), 7.48-7.55 (2H, m), 7.63-7.67 (2H, m).

Minor isomer: $^1$H-NMR (DMSO-$d_6$) δ: 1.33-1.73 (14H, m), 1.89-2.01 (2H, m), 2.57-2.62 (2H, m), 3.21-3.97 (2H, m), 4.52-4.63 (1H, m), 7.03-7.20 (5H, m), 7.28-7.29 (1H, m), 7.40-7.43 (2H, m), 7.48-7.55 (2H, m), 7.67-7.69 (2H, m).

Example 660

Preparation of the Compound 660

(1) Preparation of the Intermediate 660(1).

The title compound was obtained in the same manner as the Example 125(4) using the following starting materials.

Starting materials: the intermediate 125(3) and methyl 4-(bromomethyl)benzoate; Yield: 63% (white solid).

$^1$H-NMR ($CDCl_3$) δ: 3.60 (3H, s), 3.91 (3H, s), 5.03 (2H, s), 7.09-7.17 (2H, m), 7.24-7.37 (4H, m), 7.47-7.59 (4H, m), 7.93-8.02 (2H, m).

(2) Preparation of the Compound 660.

The title compound was obtained in the same manner as the Example 126(4) using the following starting material.

Starting material: the intermediate 660(1); Yield: 67% (pale yellow solid).

$^1$H-NMR ($CDCl_3$) δ: 5.04 (2H, s), 7.00-7.62 (10H, m), 7.93-8.02 (2H, m).

Example 661

Preparation of the Compound 661

(1) Preparation of the Intermediate 661(1).

The title compound was obtained in the same manner as the Example 125(4) using the following starting materials.

Starting materials: the intermediate 125(3) and 2-(bromomethyl)naphthalene; Yield: 86% (colorless oil).

$^1$H-NMR ($CDCl_3$) δ: 3.60 (3H, s), 5.15 (2H, s), 7.11-7.17 (2H, m), 7.22-7.30 (2H, m), 7.40-7.57 (7H, m), 7.54-7.88 (3H, m), 7.66 (1H, s).

(2) Preparation of the Compound 661.

The title compound was obtained in the same manner as the Example 126(4) using the following starting material.

Starting material: the intermediate 661(1); Yield: 90% (white solid).

$^1$H-NMR ($CDCl_3$) δ: 5.13 (2H, s), 7.07-7.14 (2H, m), 7.22-7.30 (2H, m), 7.35-7.57 (7H, m), 7.63 (1H, brs), 7.70-7.89 (3H, m).

Example 662

Preparation of the Compound 662

(1) Preparation of the Intermediate 662(1).

The title compound was obtained in the same manner as the Example 354(2) using the following starting materials.

Starting materials: the intermediate 354(1) and 3,5-dimethylbenzyl bromide; Yield: 96% (yellow solid).

$^1$H-NMR ($CDCl_3$) δ: 2.34 (6H, s), 5.22 (2H, s), 6.98 (1H, s), 7.08 (2H, s), 7.19 (1H, d, J=8.7 Hz), 7.28-7.32 (2H, m), 7.54-7.58 (2H, m), 7.68 (1H, dd, J=2.4, 8.7 Hz), 8.06 (1H, d, J=2.4 Hz).

(2) Preparation of the Intermediate 662(2).

The title compound was obtained in the same manner as the Example 125(2) using the following starting material.

Starting material: the intermediate 662(1); Yield: 63% (white solid).

$^1$H-NMR ($CDCl_3$) δ: 2.32 (6H, s), 3.94 (2H, brs), 5.05 (2H, s), 6.90-6.94 (3H, m), 6.99 (1H, s), 7.07 (2H, s), 7.21-7.25 (2H, m), 7.50-7.54 (2H, m).

(3) Preparation of the Intermediate 662(3).

The title compound was obtained in the same manner as the Example 123(1) using the following starting materials.

Starting materials: the intermediate 662(2) and 4-phenylbutyl bromide; Yield: 25% (white solid).

$^1$H-NMR ($CDCl_3$) δ: 1.46-1.58 (2H, m), 1.70-1.79 (2H, m), 2.33 (6H, s), 2.65-2.69 (2H, m), 3.18-3.23 (2H, m), 4.31-4.35 (1H, m), 5.03 (2H, s), 6.75-6.81 (2H, m), 6.88 (1H, d, J=8.4 Hz), 6.99 (1H, s), 7.05 (2H, s), 7.16-7.29 (7H, m), 7.52-7.56 (2H, m).

(4) Preparation of the Intermediate 662(4).

The title compound was obtained in the same manner as the Example 125(3) using the following starting materials.

Starting materials: the intermediate 662(3) and methyl chloroglyoxylate; Yield: 100% (colorless oil).

$^1$H-NMR ($CDCl_3$) δ: 1.56-1.68 (4H, m), 2.33 (6H, s), 2.50-2.61 (2H, m), 3.50-3.59 (4H, m), 4.01-4.11 (1H, m), 5.09 (2H, s), 6.97 (1H, s), 7.02-7.15 (4H, m), 7.18-7.23 (2H, m), 7.26-7.29 (2H, m), 7.32 (1H, d, J=2.4 Hz), 7.45-7.50 (5H, m).

(5) Preparation of the Compound 662.

The title compound was obtained in the same manner as the Example 126(4) using the following starting material.

Starting material: the intermediate 662(4); Yield: 98% (white solid).

This compound was obtained as a mixture of the rotational isomers.

Major isomer: $^1$H-NMR (DMSO-$d_6$) δ: 1.37-1.48 (4H, m), 2.26 (6H, s), 2.48-2.52 (2H, m), 3.20-4.04 (2H, m), 5.11 (2H, s), 6.94 (1H, s), 7.03-7.19 (8H, m), 7.41-7.44 (2H, m), 7.47-7.51 (2H, m), 7.63-7.66 (2H, m).

Minor isomer: $^1$H-NMR (DMSO-$d_6$) δ: 1.37-1.48 (4H, m), 2.26 (6H, s), 2.48-2.52 (2H, m), 3.20-4.04 (2H, m), 5.11 (2H, s), 6.91 (1H, s), 7.03-7.19 (7H, m), 7.32 (1H, d, J=2.7 Hz), 7.41-7.44 (2H, m), 7.47-7.57 (2H, m), 7.68-7.71 (2H, m).

Example 663

Preparation of the Compound 663

(1) Preparation of the Intermediate 663(1).

The title compound was obtained in the same manner as the Example 253(1) using the following starting materials.

Starting materials: the intermediate 125(2) and cyclopentanone; Yield: 33% (white solid).

$^1$H-NMR ($CDCl_3$) δ: 1.47-1.80 (6H, m), 2.00-2.10 (2H, m), 3.79 (1H, brs), 3.83 (1H, quint, J=6.0 Hz), 6.64-6.69 (2H, m), 7.21-7.25 (2H, m), 7.36-7.41 (2H, m), 7.50-7.55 (2H, m).

(2) Preparation of the Intermediate 663(2).

The title compound was obtained in the same manner as the Example 123(2) using the following starting materials.

Starting materials: the intermediate 663(1) and methyl chloroglyoxylate; Yield: 79% (pale yellow oil).

$^1$H-NMR ($CDCl_3$) δ: 1.43-1.62 (6H, m), 1.95-2.05 (2H, m), 3.51 (3H, s), 4.80-4.92 (1H, m), 7.27-7.33 (4H, m), 7.56-7.63 (4H, m).

(3) Preparation of the Compound 663.

The title compound was obtained in the same manner as the Example 126(4) using the following starting material.

Starting material: the intermediate 663(2); Yield: 86% (white solid).

$^1$H-NMR (DMSO-$d_6$) δ: 1.34-1.62 (6H, m), 1.83-2.01 (2H, m), 4.70 (1H, quint, J=8.4 Hz), 7.38 (2H, d, J=8.4 Hz), 7.48 (2H, d, J=8.1 Hz), 7.77 (2H, d, J=8.4 Hz), 7.84 (2H, d, J=9.0 Hz), 13.77 (1H, brs).

Example 664

Preparation of the Compound 664

(1) Preparation of the Intermediate 664(1).

The title compound was obtained in the same manner as the Example 253(1) using the following starting materials.

Starting materials: the intermediate 125(2) and cycloheptanone; Yield: 28% (pale brown solid).

$^1$H-NMR ($CDCl_3$) δ: 1.45-1.80 (10H, m), 1.99-2.07 (2H, m), 3.37-3.54 (1H, m), 3.76 (1H, brs), 6.58-6.65 (2H, m), 7.18-7.23 (2H, m), 7.36-7.40 (2H, m), 7.46-7.53 (2H, m).

(2) Preparation of the Intermediate 664(2).

The title compound was obtained in the same manner as the Example 123(2) using the following starting materials.

Starting materials: the intermediate 664(1) and methyl chloroglyoxylate; Yield: 77% (pale yellow oil).

$^1$H-NMR ($CDCl_3$) δ: 1.36-1.70 (10H, m), 1.99-2.05 (2H, m), 3.50 (3H, s), 4.50-4.63 (1H, m), 7.27-7.32 (4H, m), 7.54-7.63 (4H, m).

(3) Preparation of the Compound 664.

The title compound was obtained in the same manner as the Example 126(4) using the following starting material.

Starting material: the intermediate 664(2); Yield: 77% (white solid).

$^1$H-NMR (DMSO-$d_6$) δ: 1.38-1.63 (10H, m), 1.88-2.02 (2H, m), 4.35-4.50 (1H, m), 7.38 (2H, d, J=8.4 Hz), 7.48 (2H, d, J=7.8 Hz), 7.76 (2H, d, J=8.4 Hz), 7.84 (2H, d, J=9.0 Hz), 13.74 (1H, brs).

Example 665

Preparation of the Compound 665

(1) Preparation of the Intermediate 665(1).

The title compound and the geometric isomer (the intermediate 666(1)) were obtained in the same manner as the Example 253(1) using the following starting materials.

Starting materials: the intermediate 125(2) and 4-(tert-butyl)cyclohexanone; Yield: 39% (white solid).

$^1$H-NMR ($CDCl_3$) δ: 0.87 (9H, s), 1.05-1.27 (4H, m), 1.51-1.64 (3H, m), 1.97-2.02 (2H, m), 3.66-3.74 (1H, m), 3.95 (1H, brs), 6.66-6.70 (2H, m), 7.20-7.25 (2H, m), 7.37-7.41 (2H, m), 7.50-7.54 (2H, m).

(2) Preparation of the Intermediate 665(2).

The title compound was obtained in the same manner as the Example 123(2) using the following starting materials.

Starting materials: the intermediate 665(1) and methyl chloroglyoxylate; Yield: 98% (white solid).

$^1$H-NMR ($CDCl_3$) δ: 0.81 (9H, s), 1.14-1.39 (5H, m), 1.75-1.91 (2H, m), 1.92-2.20 (2H, m), 3.50 (3H, s), 4.41-4.49 (1H, m), 7.25-7.32 (4H, m), 7.53-7.63 (4H, m).

(3) Preparation of the Compound 665.

The title compound was obtained in the same manner as the Example 126(4) using the following starting material.

Starting material: the intermediate 665(2); Yield: 98% (white solid).

$^1$H-NMR (DMSO-$d_6$) δ: 0.64 (9H, s), 0.73-0.98 (3H, m), 1.25-1.36 (2H, m), 1.58-1.69 (2H, m), 2.01-2.05 (2H, m), 4.40-4.60 (1H, m), 7.46-7.49 (4H, m), 7.76 (2H, d, J=8.1 Hz), 7.82 (2H, d, J=9.0 Hz), 13.66 (1H, brs).

Example 666

Preparation of the Compound 666

(1) Preparation of the Intermediate 666(1).

The title compound and the geometric isomer (the intermediate 665(1)) were obtained in the same manner as the Example 253(1) using the following starting materials.

Starting materials: the intermediate 125(2) and 4-(tert-butyl)cyclohexanone; Yield: 20% (white solid).

$^1$H-NMR (CDCl$_3$) δ: 0.88 (9H, s), 1.04-1.23 (5H, m), 1.83-1.86 (2H, m), 2.18-2.22 (2H, m), 3.16-3.28 (1H, m), 3.61 (1H, brs), 6.62-6.67 (2H, m), 7.20-7.23 (2H, m), 7.35-7.40 (2H, m), 7.47-7.54 (2H, m).

(2) Preparation of the Intermediate 666(2).

The title compound was obtained in the same manner as the Example 123(2) using the following starting materials.

Starting materials: the intermediate 666(1) and methyl chloroglyoxylate; Yield: 98% (white solid).

$^1$H-NMR (CDCl$_3$) δ: 0.69 (9H, s), 0.81-1.09 (3H, m), 1.41-1.47 (2H, m), 1.66-1.77 (2H, m), 2.05-2.12 (2H, m), 3.49 (3H, s), 4.60-4.72 (1H, m), 7.31 (2H, d, J=8.1 Hz), 7.39 (2H, d, J=8.4 Hz), 7.55-7.62 (4H, m).

(3) Preparation of the Compound 666.

The title compound was obtained in the same manner as the Example 126(4) using the following starting material.

Starting material: the intermediate 666(2); Yield: 90% (white solid).

$^1$H-NMR (DMSO-d$_6$) δ: 0.78 (9H, s), 1.08-1.24 (5H, m), 1.68-1.99 (4H, m), 3.98-4.23 (1H, m), 7.35 (2H, d, J=8.4 Hz), 7.48 (2H, d, J=8.1 Hz), 7.75 (2H, d, J=8.4 Hz), 7.78-7.85 (2H, m), 13.72 (1H, brs).

Example 667

Preparation of the Compound 667

(1) Preparation of the Intermediate 667(1).

The title compound and the geometric isomer (the intermediate 668(1)) were obtained in the same manner as the Example 253(1) using the following starting materials.

Starting materials: the intermediate 125(2) and 4-methylcyclohexanone; Yield: 24% (white solid).

$^1$H-NMR (CDCl$_3$) δ: 0.94 (3H, d, J=6.3 Hz), 1.18-1.30 (2H, m), 1.55-1.83 (7H, m), 3.57-3.62 (1H, m), 3.89 (1H, brs), 6.64-6.68 (2H, m), 7.20-7.23 (2H, m), 7.36-7.40 (2H, m), 7.49-7.54 (2H, m).

(2) Preparation of the Intermediate 667(2).

The title compound was obtained in the same manner as the Example 123(2) using the following starting materials.

Starting materials: the intermediate 667(1) and methyl chloroglyoxylate; Yield: 100% (colorless oil).

$^1$H-NMR (CDCl$_3$) δ: 0.80 (3H, d, J=7.2 Hz), 1.45-1.56 (4H, m), 1.58-1.74 (4H, m), 1.84-1.99 (1H, m), 3.50 (3H, s), 4.41-4.52 (1H, m), 7.25-7.33 (4H, m), 7.55-7.65 (4H, m).

(3) Preparation of the Compound 667.

The title compound was obtained in the same manner as the Example 126(4) using the following starting material.

Starting material: the intermediate 667(2); Yield: 89% (white solid).

$^1$H-NMR (DMSO-d$_6$) δ: 0.75 (3H, d, J=6.9 Hz), 1.34-1.83 (9H, m), 4.15-4.35 (1H, m), 7.38 (2H, d, J=8.1 Hz), 7.47 (2H, d, J=8.7 Hz), 7.77 (2H, d, J=8.1 Hz), 7.85 (2H, d, J=8.7 Hz), 13.70 (1H, brs).

Example 668

Preparation of the Compound 668

(1) Preparation of the Intermediate 668(1).

The title compound and the geometric isomer (the intermediate 667(1)) were obtained in the same manner as the Example 253(1) using the following starting materials.

Starting materials: the intermediate 125(2) and 4-methylcyclohexanone; Yield: 45% (white solid).

$^1$H-NMR (CDCl$_3$) δ: 0.93 (3H, d, J=6.6 Hz), 1.00-1.21 (4H, m), 1.30-1.46 (1H, m), 1.75-1.78 (2H, m), 2.11-2.15 (2H, m), 3.17-3.25 (1H, m), 3.60 (1H, brs), 6.61-6.66 (2H, m), 7.20-7.25 (2H, m), 7.36-7.39 (2H, m), 7.49-7.54 (2H, m).

(2) Preparation of the Intermediate 668(2).

The title compound was obtained in the same manner as the Example 123(2) using the following starting materials.

Starting materials: the intermediate 668(1) and methyl chloroglyoxylate; Yield: 100% (colorless oil).

$^1$H-NMR (CDCl$_3$) δ: 0.86 (3H, d, J=6.0 Hz), 1.07-1.33 (5H, m), 1.72-1.76 (2H, m), 1.90-1.94 (2H, m), 3.50 (3H, s), 4.41-4.60 (1H, m), 7.24-7.32 (4H, m), 7.54-7.63 (4H, m).

(3) Preparation of the Compound 668.

The title compound was obtained in the same manner as the Example 126(4) using the following starting material.

Starting material: the intermediate 668(2); Yield: 89% (white solid).

$^1$H-NMR (DMSO-d$_6$) δ: 0.83 (3H, d, J=6.0 Hz), 1.05-1.28 (5H, m), 1.68-1.85 (4H, m), 4.19-4.40 (1H, m), 7.35 (2H, d, J=8.4 Hz), 7.48 (2H, d, J=8.4 Hz), 7.75 (2H, d, J=8.4 Hz), 7.82-7.85 (2H, m), 13.67 (1H, brs).

Example 669

Preparation of the Compound 669

(1) Preparation of the Intermediate 669(1).

The title compound was obtained in the same manner as the Example 123(1) using the following starting materials.

Starting materials: the intermediate 125(2) and 1-iododecane; Yield: 86% (white solid).

$^1$H-NMR (CDCl$_3$) δ: 0.84-0.95 (3H, m), 1.23-1.49 (14H, m), 1.52-1.70 (2H, m), 3.14 (2H, t, J=7.2 Hz), 3.74 (1H, brs), 6.62-6.71 (2H, m), 7.18-7.28 (2H, m), 7.35-7.43 (2H, m), 7.48-7.57 (2H, m).

(2) Preparation of the Intermediate 669(2).

The title compound was obtained in the same manner as the Example 125(3) using the following starting materials.

Starting materials: the intermediate 669(1) and methyl chloroglyoxylate; Yield: 71% (colorless oil).

$^1$H-NMR (CDCl$_3$) δ: 0.83-0.93 (3H, m), 1.14-1.42 (14H, m), 1.50-1.65 (2H, m), 3.58 (3H, s), 3.75-3.85 (2H, m), 6.62-6.71 (2H, m), 7.18-7.28 (2H, m), 7.35-7.43 (2H, m), 7.48-7.57 (2H, m).

(3) Preparation of the Compound 669.

The title compound was obtained in the same manner as the Example 126(4) using the following starting material.

Starting material: the intermediate 669(2); Yield: 86% (pale yellow oil).

$^1$H-NMR (CDCl$_3$) δ: 0.82-0.92 (3H, m), 1.17-1.37 (14H, m), 1.50-1.65 (2H, m), 3.72-3.82 (2H, m), 7.20-7.33 (4H, m), 7.53-7.62 (4H, m).

Example 670

Preparation of the Compound 670

(1) Preparation of the Intermediate 670(1).

A solution of 4-(2,5-dimethylphenyl)butyric acid (271 mg, 1.410 mmol) in anhydrous tetrahydrofuran (1 ml) was added dropwise to a suspension of lithium aluminium hydride (58 mg, 1.410 mmol) in anhydrous tetrahydrofuran (2 ml) at 0°

C., and the mixture was stirred at room temperature for 1 hour. The reaction mixture was cooled to 0° C., diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=5:1) to give the title compound (150 mg, 60%) as a colorless oil.

$^1$H-NMR (CDCl$_3$) δ: 1.58-1.67 (4H, m), 2.26 (3H, s), 2.29 (3H, s), 2.54-2.62 (2H, m), 3.63-3.71 (2H, m), 6.88-6.95 (2H, m), 6.99-7.04 (1H, m).

(2) Preparation of the Intermediate 670(2).

A mixture of the intermediate 670(1) (150 mg, 0.841 mmol), triphenylphosphine (331 mg, 1.262 mmol), tetrabromomethane (474 mg, 1.430 mmol) and dichloromethane (3 ml) was stirred at room temperature for 2 hours. The reaction mixture was diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=1:1) to give the title compound (174 mg, 86%) as a clear colorless oil.

$^1$H-NMR (CDCl$_3$) δ: 1.68-1.77 (2H, m), 1.89-1.97 (2H, m), 2.26 (3H, s), 2.29 (3H, s), 2.56-2.61 (2H, m), 3.44 (2H, t, J=6.9 Hz), 6.90-6.95 (2H, m), 7.01-7.05 (1H, m).

(3) Preparation of the Intermediate 670(3).

The title compound was obtained in the same manner as the Example 123(1) using the following starting materials.

Starting materials: the intermediates 670 (2) and 194 (2); Yield: 61% (white solid).

$^1$H-NMR (CDCl$_3$) δ: 0.93 (3H, t, J=6.9 Hz), 1.38-1.51 (4H, m), 1.68-1.88 (6H, m), 2.26 (3H, s), 2.28 (3H, s), 2.60-2.65 (2H, m), 3.20-3.26 (2H, m), 4.02 (2H, t, J=6.6 Hz), 4.29 (1H, brs), 6.74-6.81 (3H, m), 6.88-6.98 (2H, m), 7.01-7.05 (1H, m), 7.22-7.26 (2H, m), 7.52-7.57 (2H, m).

(4) Preparation of the Intermediate 670(4).

The title compound was obtained in the same manner as the Example 125(3) using the following starting materials.

Starting materials: the intermediate 670(3) and methyl chloroglyoxylate; Yield: 82% (colorless oil).

$^1$H-NMR (CDCl$_3$) δ: 0.86-0.95 (3H, m), 1.23-1.85 (10H, m), 2.20 (3H, s), 2.23 (3H, s), 2.51-2.57 (2H, m), 3.50-3.60 (1H, m), 3.53 (3H, s), 3.95-4.08 (3H, m), 6.85-7.01 (4H, m), 7.26-7.29 (2H, m), 7.34 (1H, d, J=2.1 Hz), 7.48-7.52 (3H, m).

(5) Preparation of the Compound 670.

The title compound was obtained in the same manner as the Example 126(4) using the following starting material.

Starting material: the intermediate 670(4); Yield: 70% (colorless oil).

$^1$H-NMR (DMSO-d$_6$) δ: 0.83-0.92 (3H, m), 1.24-1.73 (10H, m), 2.10-2.16 (6H, m), 2.38-2.50 (2H, m), 3.15-4.03 (4H, m), 6.65-6.94 (3H, m), 7.06-7.18 (1H, m), 7.30-7.72 (6H, m).

Example 671

Preparation of the Compound 671

(1) Preparation of the Intermediate 671(1).

The title compound was obtained in the same manner as the Example 123(3) using the following starting materials.

Starting materials: 1-bromo-4-nitrobenzene and 2-naphthaleneboronic acid; Yield: 99% (white solid).

$^1$H-NMR (CDCl$_3$) δ: 7.53-7.59 (2H, m), 7.75 (1H, dd, J=1.8, 8.4 Hz), 7.84-8.03 (5H, m), 8.10 (1H, d, J=1.8 Hz), 8.31-8.39 (2H, m).

(2) Preparation of the Intermediate 671(2).

The title compound was obtained in the same manner as the Example 125(2) using the following starting material.

Starting material: the intermediate 671(1); Yield: 100% (white solid).

$^1$H-NMR (CDCl$_3$) δ: 3.71 (2H, brs), 6.77-6.82 (2H, m), 7.40-7.60 (4H, m), 7.70 (1H, dd, J=1.8, 8.4 Hz), 7.80-7.90 (3H, m), 7.97 (1H, d, J=1.8 Hz).

(3) Preparation of the Intermediate 671(3).

The title compound was obtained in the same manner as the Example 123(1) using the following starting materials.

Starting materials: the intermediate 671(2) and 4-phenylbutyl bromide; Yield: 15% (brown oil).

$^1$H-NMR (CDCl$_3$) δ: 1.63-1.83 (4H, m), 2.68 (2H, t, J=7.5 Hz), 3.20 (2H, t, J=7.5 Hz), 3.72 (1H, brs), 6.67-6.74 (2H, m), 7.15-7.34 (5H, m), 7.37-7.50 (2H, m), 7.53-7.61 (2H, m), 7.71 (1H, dd, J=1.8, 8.4 Hz), 7.79-7.88 (3H, m), 7.94-7.98 (1H, m).

(4) Preparation of the Intermediate 671(4).

The title compound was obtained in the same manner as the Example 125(3) using the following starting materials.

Starting materials: the intermediate 671(3) and methyl chloroglyoxylate; Yield: 60% (pale yellow oil).

$^1$H-NMR (CDCl$_3$) δ: 1.58-1.74 (4H, m), 2.63 (2H, t, J=7.5 Hz), 3.59 (3H, s), 3.86 (2H, t, J=7.5 Hz), 7.11-7.33 (7H, m), 7.47-7.57 (2H, m), 7.67-7.76 (3H, m), 7.85-7.97 (3H, m), 8.02-8.05 (1H, m).

(5) Preparation of the Compound 671.

The title compound was obtained in the same manner as the Example 126(4) using the following starting material.

Starting material: the intermediate 671(4); Yield: 78% (pale yellow oil).

$^1$H-NMR (CDCl$_3$) δ: 1.60-1.74 (4H, m), 2.57-2.67 (2H, m), 3.79-3.88 (2H, m), 7.10-7.31 (7H, m), 7.47-7.57 (2H, m), 7.67-7.76 (3H, m), 7.85-7.97 (3H, m), 8.02-8.05 (1H, m).

Example 672

Preparation of the Compound 672

(1) Preparation of the Intermediate 672(1).

The title compound was obtained in the same manner as the Example 123(3) using the following starting materials.

Starting materials: the intermediate 359(4) and 3,5-dimethyphenylboronic acid; Yield: 80% (colorless oil).

$^1$H-NMR (CDCl$_3$) δ: 0.93 (3H, t, J=6.9 Hz), 1.30-1.49 (4H, m), 1.57-1.69 (4H, m), 1.71-1.86 (2H, m), 2.37 (6H, s), 2.55-2.65 (2H, m), 3.53 (3H, s), 3.86-4.05 (3H, m), 4.70-4.79 (1H, m), 6.44-6.48 (2H, m), 6.54-6.59 (1H, m), 6.92-7.00 (2H, m), 7.08-7.17 (3H, m), 7.17-7.29 (1H, m), 7.35 (1H, d, J=2.4 Hz), 7.51 (1H, dd, J=2.4, 8.7 Hz).

(2) Preparation of the Compound 672.

The title compound was obtained in the same manner as the Example 126(4) using the following starting material.

Starting material: the intermediate 672(1); Yield: 11% (pale yellow oil).

$^1$H-NMR (CDCl$_3$) δ: 0.84-0.94 (3H, m), 1.12-1.45 (4H, m), 1.50-1.78 (6H, m), 2.35 (6H, s), 2.48-2.63 (2H, m), 3.76 (2H, brs), 3.85-4.00 (2H, m), 6.88-7.00 (2H, m), 7.04-7.38 (7H, m), 7.43-7.52 (2H, m).

Example 673

Preparation of the Compound 673

(1) Preparation of the Intermediate 673(1).

The title compound was obtained in the same manner as the Example 208(1) using the following starting materials.

Starting materials: the intermediate 211(1) and pyrrolidine; Yield: 94% (yellow solid).

$^1$H-NMR ($CDCl_3$) δ: 1.81-1.90 (4H, m), 3.00-3.09 (4H, m), 6.75 (1H, d, J=9.0 Hz), 7.21-7.30 (2H, m), 7.35-7.42 (2H, m), 8.02 (1H, d, J=2.7 Hz), 8.11 (1H, dd, J=2.7, 9.0 Hz).

(2) Preparation of the Intermediate 673(2).

The title compound was obtained in the same manner as the Example 125(2) using the following starting material.

Starting material: the intermediate 673(1); Yield: 100% (pale green oil).

$^1$H-NMR ($CDCl_3$) δ: 1.67-1.77 (4H, m), 2.73-2.83 (4H, m), 3.42 (2H, brs), 6.59 (1H, d, J=2.4 Hz), 6.65 (1H, dd, J=2.4, 8.4 Hz), 6.82 (1H, d, J=8.4 Hz), 7.14-7.23 (2H, m), 7.47-7.56 (2H, m).

(3) Preparation of the Intermediate 673(3).

The title compound was obtained in the same manner as the Example 123(1) using the following starting materials.

Starting materials: the intermediate 673(2) and 4-phenylbutyl bromide; Yield: 45% (pale brown oil).

$^1$H-NMR ($CDCl_3$) δ: 1.55-1.79 (8H, m), 2.61-2.71 (4H, m), 2.75 (2H, brs), 3.10 (2H, brs), 3.23 (1H, brs), 6.50 (2H, brs), 6.86 (1H, brs), 7.12-7.24 (6H, m), 7.25-7.31 (1H, m), 7.48-7.57 (2H, brs).

(4) Preparation of the Intermediate 673(4).

The title compound was obtained in the same manner as the Example 125(3) using the following starting materials.

Starting materials: the intermediate 673(3) and methyl chloroglyoxylate; Yield: 90% (colorless oil).

$^1$H-NMR ($CDCl_3$) δ: 1.57-1.68 (4H, m), 1.74-1.83 (4H, m), 2.56-2.65 (2H, m), 2.86-2.95 (4H, m), 3.57 (3H, s), 3.70-3.79 (2H, m), 6.77 (1H, d, J=8.4 Hz), 6.92 (1H, d, J=2.4 Hz), 7.02 (1H, dd, J=2.4, 8.4 Hz), 7.08-7.26 (7H, m), 7.32-7.39 (2H, m).

(5) Preparation of the Compound 673.

The title compound was obtained in the same manner as the Example 126(4) using the following starting material.

Starting material: the intermediate 673(4); Yield: 92% (white solid).

$^1$H-NMR ($CDCl_3$) δ: 1.55-1.69 (4H, m), 1.72-1.84 (4H, m), 2.53-2.65 (2H, m), 2.84-2.96 (4H, m), 3.69-3.88 (2H, m), 6.79 (1H, d, J=9.0 Hz), 6.89 (1H, d, J=2.4 Hz), 7.00 (1H, dd, J=2.4, 9.0 Hz), 7.07-7.25 (7H, m), 7.33-7.44 (2H, m).

Example 674

Preparation of the Compound 674

(1) Preparation of the Intermediate 674(1).

The title compound was obtained in the same manner as the Example 208(1) using the following starting materials.

Starting materials: the intermediate 211(1) and hexamethyleneimine; Yield: 94% (yellow oil).

$^1$H-NMR ($CDCl_3$) δ: 1.49-1.66 (8H, m), 3.14-3.24 (4H, m), 6.98 (1H, d, J=9.0 Hz), 7.22-7.30 (2H, m), 7.38-7.46 (2H, m), 7.99 (1H, d, J=2.7 Hz), 8.09 (1H, dd, J=2.7, 9.0 Hz).

(2) Preparation of the Intermediate 674(2).

The title compound was obtained in the same manner as the Example 125(2) using the following starting material.

Starting material: the intermediate 674(1); Yield: 96% (white solid).

$^1$H-NMR ($CDCl_3$) δ: 1.32-1.54 (8H, m), 2.84-2.94 (4H, m), 3.44 (2H, brs), 6.58 (1H, d, J=2.4 Hz), 6.63 (1H, dd, J=2.4, 8.4 Hz), 6.99 (1H, d, J=8.4 Hz), 7.17-7.25 (2H, m), 7.48-7.58 (2H, m).

(3) Preparation of the Intermediate 674(3).

The title compound was obtained in the same manner as the Example 123(1) using the following starting materials.

Starting materials: the intermediate 674(2) and 4-phenylbutyl bromide; Yield: 80% (brown oil).

$^1$H-NMR ($CDCl_3$) δ: 1.34-1.94 (12H, m), 2.58-3.29 (9H, m), 6.42-6.59 (2H, m), 7.00-7.33 (8H, m), 7.46-7.58 (2H, m).

(4) Preparation of the Intermediate 674(4).

The title compound was obtained in the same manner as the Example 125(3) using the following starting materials.

Starting materials: the intermediate 674(3) and methyl chloroglyoxylate; Yield: 78% (colorless oil).

$^1$H-NMR ($CDCl_3$) δ: 1.40-1.72 (12H, m), 2.56-2.67 (2H, m), 2.96-3.06 (4H, m), 3.56 (3H, s), 3.71-3.78 (2H, m), 6.93-6.97 (1H, m), 7.00-7.04 (2H, m), 7.07-7.27 (7H, m), 7.40-7.48 (2H, m).

(5) Preparation of the Compound 674.

The title compound was obtained in the same manner as the Example 126(4) using the following starting material.

Starting material: the intermediate 674(4); Yield: 90% (white solid).

$^1$H-NMR ($CDCl_3$) δ: 1.40-1.72 (12H, m), 2.54-2.66 (2H, m), 2.96-3.07 (4H, m), 3.68-3.78 (2H, m), 6.91-6.96 (1H, m), 6.98-7.06 (2H, m), 7.07-7.27 (7H, m), 7.39-7.50 (2H, m).

Example 675

Preparation of the Compound 675

(1) Preparation of the Intermediate 675(1).

The title compound was obtained in the same manner as the Example 208(1) using the following starting materials.

Starting materials: the intermediate 211(1) and thiomorpholine; Yield: 100% (yellow solid).

$^1$H-NMR ($CDCl_3$) δ: 2.50-2.57 (4H, m), 3.18-3.27 (4H, m), 7.07 (1H, d, J=9.0 Hz), 7.30-7.37 (2H, m), 7.57-7.65 (2H, m), 8.08 (1H, d, J=2.7 Hz), 8.17 (1H, dd, J=2.7, 9.0 Hz).

(2) Preparation of the Intermediate 675(2).

The title compound was obtained in the same manner as the Example 376(2) using the following starting material.

Starting material: the intermediate 675(1); Yield: 66% (white solid).

$^1$H-NMR ($CDCl_3$) δ: 2.42-2.54 (4H, m), 2.93-3.03 (4H, m), 3.57 (2H, brs), 6.58-6.69 (2H, m), 6.90-6.95 (1H, m), 7.17-7.27 (2H, m), 7.48-7.60 (2H, m).

(3) Preparation of the Intermediate 675(3).

The title compound was obtained in the same manner as the Example 123(1) using the following starting materials.

Starting materials: the intermediate 675(2) and 4-phenylbutyl bromide; Yield: 46% (brown oil).

$^1$H-NMR ($CDCl_3$) δ: 1.59-1.80 (4H, m), 2.44-2.53 (4H, m), 2.66 (2H, t, J=6.9 Hz), 2.93-3.02 (4H, m), 3.07-3.17 (2H, m), 3.51 (1H, brs), 6.47-6.59 (2H, m), 6.94 (1H, d, J=8.4 Hz), 7.14-7.32 (7H, m), 7.53-7.59 (2H, m).

(4) Preparation of the Intermediate 675(4).

The title compound was obtained in the same manner as the Example 125(3) using the following starting materials.

Starting materials: the intermediate 675(3) and methyl chloroglyoxylate; Yield: 100% (colorless oil).

$^1$H-NMR ($CDCl_3$) δ: 1.56-1.72 (4H, m), 2.48-2.55 (4H, m), 2.61 (2H, t, J=6.9 Hz), 3.05-3.12 (4H, m), 3.57 (3H, s), 3.77 (2H, t, J=6.9 Hz), 6.96-7.20 (6H, m), 7.20-7.32 (4H, m), 7.52-7.58 (2H, m).

(5) Preparation of the Compound 675.

The title compound was obtained in the same manner as the Example 126(4) using the following starting material.

Starting material: the intermediate 675(4); Yield: 90% (white solid).

$^1$H-NMR ($CDCl_3$) δ: 1.56-1.74 (4H, m), 2.47-2.55 (4H, m), 2.56-2.66 (2H, m), 3.04-3.13 (4H, m), 3.72-3.81 (2H, m), 6.96-7.20 (6H, m), 7.20-7.31 (4H, m), 7.52-7.60 (2H, m).

Example 676

Preparation of the Compound 676

(1) Preparation of the Intermediate 676(1).

The title compound was obtained in the same manner as the Example 354(2) using the following starting materials.

Starting materials: the intermediate 354(1) and 5-bromopentyl acetate; Yield: 93% (white solid).

$^1$H-NMR ($CDCl_3$) δ: 1.57-1.64 (2H, m), 1.70-1.77 (2H, m), 1.88-1.93 (2H, m), 2.07 (3H, s), 4.09-4.18 (4H, m), 7.15 (1H, d, J=9.0 Hz), 7.29-7.32 (2H, m), 7.54-7.58 (2H, m), 7.70 (1H, dd, J=2.4, 9.0 Hz), 8.03 (1H, d, J=2.4 Hz).

(2) Preparation of the Intermediate 676(2).

The title compound was obtained in the same manner as the Example 125(2) using the following starting material.

Starting material: the intermediate 676(1); Yield: 66% (white solid).

$^1$H-NMR ($CDCl_3$) δ: 1.54-1.61 (2H, m), 1.70-1.77 (2H, m), 1.83-1.93 (2H, m), 2.06 (3H, s), 3.89 (2H, brs), 4.03-4.13 (4H, m), 6.83 (1H, d, J=8.1 Hz), 6.88-6.93 (2H, m), 7.22-7.27 (2H, m), 7.50-7.55 (2H, m).

(3) Preparation of the Intermediate 676(3).

The title compound was obtained in the same manner as the Example 123(1) using the following starting materials.

Starting materials: the intermediate 676(2) and 4-phenylbutyl bromide; Yield: 50% (colorless oil).

$^1$H-NMR ($CDCl_3$) δ: 1.49-1.61 (2H, m), 1.70-1.90 (8H, m), 2.04 (3H, s), 2.68 (2H, t, J=7.2 Hz), 3.19-3.23 (2H, m), 4.02 (2H, t, J=6.6 Hz), 4.09 (2H, t, J=6.6 Hz), 4.26 (1H, brs), 6.74-6.79 (3H, m), 7.18-7.30 (7H, m), 7.52-7.56 (2H, m).

(4) Preparation of the Intermediate 676(4).

The title compound was obtained in the same manner as the Example 125(3) using the following starting materials.

Starting materials: the intermediate 676(3) and methyl chloroglyoxylate; Yield: 85% (colorless oil).

$^1$H-NMR ($CDCl_3$) δ: 1.49-1.88 (10H, m), 2.05 (3H, s), 2.58-2.63 (2H, m), 3.47-3.56 (4H, m), 3.95-4.11 (5H, m), 6.99 (1H, d, J=8.7 Hz), 7.10-7.16 (3H, m), 7.20-7.22 (2H, m), 7.24-7.29 (2H, m), 7.32 (1H, d, J=2.4 Hz), 7.46-7.52 (3H, m).

(5) Preparation of the Compound 676.

The title compound was obtained in the same manner as the Example 126(4) using the following starting material.

Starting material: the intermediate 676(4); Yield: 85% (white solid).

This compound was obtained as a mixture of the rotational isomers.

Major isomer: $^1$H-NMR (DMSO-$d_6$) δ: 1.43-1.60 (8H, m), 1.69-1.74 (2H, m), 2.49-2.59 (2H, m), 3.38-3.52 (3H, m), 3.84-4.10 (3H, m), 7.11-7.13 (3H, m), 7.18-7.22 (3H, m), 7.43-7.48 (3H, m), 7.65-7.71 (3H, m), 13.58 (1H, brs).

Minor isomer: $^1$H-NMR (DMSO-$d_6$) δ: 1.43-1.60 (8H, m), 1.69-1.74 (2H, m), 2.49-2.59 (2H, m), 3.38-3.62 (3H, m), 3.84-4.38 (3H, m), 7.08-7.13 (3H, m), 7.18-7.22 (3H, m), 7.43-7.48 (3H, m), 7.65-7.76 (3H, m), 13.58 (1H, brs).

Example 677

Preparation of the Compound 677

(1) Preparation of the Intermediate 677(1).

The title compound was obtained in the same manner as the Example 185(2) using the following starting materials.

Starting materials: 4-bromo-1-fluoro-2-nitrobenzene and 1-pentanol; Yield: 69% (yellow oil).

$^1$H-NMR ($CDCl_3$) δ: 0.93 (3H, t, J=7.2 Hz), 1.34-1.49 (4H, m), 1.79-1.86 (2H, m), 4.08 (2H, t, J=6.6 Hz), 6.96 (1H, d, J=9.0 Hz), 7.60 (1H, dd, J=2.7, 9.0 Hz), 7.95 (1H, d, J=2.7 Hz).

(2) Preparation of the Intermediate 677(2).

The title compound was obtained in the same manner as the Example 123(3) using the following starting materials.

Starting materials: the intermediate 677(1) and 4-methylbenzeneboronic acid; Yield: 90% (yellow solid).

$^1$H-NMR ($CDCl_3$) δ: 0.94 (3H, t, J=7.2 Hz), 1.34-1.50 (4H, m), 1.81-1.91 (2H, m), 2.40 (3H, s), 4.13 (2H, t, J=6.6 Hz), 7.12 (1H, d, J=8.7 Hz), 7.24-7.27 (2H, m), 7.43-7.47 (2H, m), 7.71 (1H, dd, J=2.4, 8.7 Hz), 8.04 (1H, d, J=2.4 Hz).

(3) Preparation of the Intermediate 677(3).

The title compound was obtained in the same manner as the Example 125(2) using the following starting material.

Starting material: the intermediate 677(2); Yield: 96% (white solid).

$^1$H-NMR ($CDCl_3$) δ: 0.94 (3H, t, J=7.2 Hz), 1.36-1.50 (4H, m), 1.81-1.91 (2H, m), 2.37 (3H, s), 3.86 (2H, brs), 4.02 (2H, t, J=6.6 Hz), 6.82 (1H, d, J=8.4 Hz), 6.91-6.96 (2H, m), 7.19-7.21 (2H, m), 7.41-7.44 (2H, m).

(4) Preparation of the Intermediate 677(4).

The title compound was obtained in the same manner as the Example 123(1) using the following starting materials.

Starting materials: the intermediate 677(3) and 4-phenylbutyl bromide; Yield: 93% (yellow oil).

$^1$H-NMR ($CDCl_3$) δ: 0.93 (3H, t, J=7.2 Hz), 1.36-1.50 (4H, m), 1.51-1.88 (6H, m), 2.37 (3H, s), 2.64-2.71 (2H, m), 3.19-3.24 (2H, m), 4.00 (2H, t, J=6.6 Hz), 4.24 (1H, brs), 6.78-6.84 (3H, m), 7.11-7.30 (7H, m), 7.43-7.46 (2H, m).

(5) Preparation of the Intermediate 677(5).

The title compound was obtained in the same manner as the Example 125(3) using the following starting materials.

Starting materials: the intermediate 677(4) and methyl chloroglyoxylate; Yield: 75% (colorless oil).

$^1$H-NMR ($CDCl_3$) δ: 0.93 (3H, t, J=7.2 Hz), 1.36-1.50 (4H, m), 1.57-1.88 (6H, m), 2.39 (3H, s), 2.56-2.64 (2H, m), 3.52-3.60 (4H, m), 3.96-4.02 (3H, m), 6.96 (1H, d, J=8.7 Hz), 7.10-7.16 (3H, m), 7.20-7.25 (4H, m), 7.33 (1H, d, J=2.4 Hz), 7.37-7.40 (2H, m), 7.51 (1H, dd, J=2.4, 8.7 Hz).

(6) Preparation of the Compound 677.

The title compound was obtained in the same manner as the Example 126(4) using the following starting material.

Starting material: the intermediate 677(5); Yield: 69% (white solid).

This compound was obtained as a mixture of the rotational isomers.

Major isomer: $^1$H-NMR (DMSO-$d_6$) δ: 0.84-0.91 (3H, m), 1.36-1.52 (8H, m), 1.65-1.74 (2H, m), 2.33 (3H, s), 2.56-2.64 (2H, m), 3.13-4.04 (4H, m), 7.07-7.25 (8H, m), 7.41-7.46 (4H, m).

Minor isomer: $^1$H-NMR (DMSO-$d_6$) δ: 0.84-0.91 (3H, m), 1.36-1.52 (8H, m), 1.65-1.74 (2H, m), 2.33 (3H, s), 2.56-2.64 (2H, m), 3.13-4.04 (4H, m), 7.02-7.25 (8H, m), 7.41-7.51 (4H, m).

Example 678

Preparation of the Compound 678

(1) Preparation of the Intermediate 678(1).

The title compound was obtained in the same manner as the Example 123(3) using the following starting materials.

Starting materials: the intermediate 677(1) and 4-isopropylbenzeneboronic acid; Yield: 100% (yellow oil).

$^1$H-NMR ($CDCl_3$) δ: 0.94 (3H, t, J=7.2 Hz), 1.29 (6H, d, J=6.9 Hz), 1.38-1.51 (4H, m), 1.81-1.90 (2H, m), 2.92-2.99 (1H, m), 4.13 (2H, t, J=6.6 Hz), 7.12 (1H, d, J=8.7 Hz), 7.30-7.34 (2H, m), 7.46-7.50 (2H, m), 7.71 (1H, dd, J=2.4, 8.7 Hz), 8.04 (1H, d, J=2.4 Hz).

(2) Preparation of the Intermediate 678(2).

The title compound was obtained in the same manner as the Example 125(2) using the following starting material.

Starting material: the intermediate 678(1); Yield: 85% (white solid).

$^1$H-NMR ($CDCl_3$) δ: 0.94 (3H, t, J=7.2 Hz), 1.28 (6H, d, J=6.9 Hz), 1.38-1.51 (4H, m), 1.79-1.88 (2H, m), 2.90-2.96 (1H, m), 3.86 (2H, brs), 4.02 (2H, t, J=6.6 Hz), 6.82 (1H, d, J=8.4 Hz), 6.91-6.96 (2H, m), 7.24-7.29 (2H, m), 7.44-7.48 (2H, m).

(3) Preparation of the Intermediate 678(3).

The title compound was obtained in the same manner as the Example 123(1) using the following starting materials.

Starting materials: the intermediate 678(2) and 4-phenylbutyl bromide; Yield: 89% (yellow oil).

$^1$H-NMR ($CDCl_3$) δ: 0.93 (3H, t, J=7.2 Hz), 1.28 (6H, d, J=6.9 Hz), 1.36-1.50 (4H, m), 1.51-1.88 (6H, m), 2.64-2.71 (2H, m), 2.92-2.99 (1H, m), 3.19-3.24 (2H, m), 4.00 (2H, t, J=6.6 Hz), 4.24 (1H, brs), 6.78-6.84 (3H, m), 7.11-7.30 (7H, m), 7.43-7.46 (2H, m).

(4) Preparation of the Intermediate 678(4).

The title compound was obtained in the same manner as the Example 125(3) using the following starting materials.

Starting materials: the intermediate 678(3) and methyl chloroglyoxylate; Yield: 79% (colorless oil).

$^1$H-NMR ($CDCl_3$) δ: 0.93 (3H, t, J=7.2 Hz), 1.28 (6H, d, J=6.9 Hz), 1.36-1.50 (4H, m), 1.51-1.88 (6H, m), 2.64-2.71 (2H, m), 2.92-2.99 (1H, m), 3.52-3.60 (4H, m), 3.96-4.02 (3H, m), 6.96 (1H, d, J=8.7 Hz), 7.10-7.16 (3H, m), 7.20-7.25 (2H, m), 7.28-7.31 (2H, m), 7.34 (1H, d, J=2.7 Hz), 7.41-7.44 (2H, m), 7.51 (1H, dd, J=2.7, 8.7 Hz).

(5) Preparation of the Compound 678.

The title compound was obtained in the same manner as the Example 126(4) using the following starting material.

Starting material: the intermediate 678(4); Yield: 62% (white solid).

This compound was obtained as a mixture of the rotational isomers.

Major isomer: $^1$H-NMR (DMSO-$d_6$) δ: 0.84-0.91 (3H, m), 1.23 (6H, d, J=6.9 Hz), 1.33-1.52 (8H, m), 1.65-1.74 (2H, m), 2.56-2.64 (2H, m), 2.87-2.96 (1H, m), 3.13-4.04 (4H, m), 7.07-7.19 (6H, m), 7.28-7.30 (2H, m), 7.44-7.49 (4H, m).

Minor isomer: $^1$H-NMR (DMSO-$d_6$) δ: 0.84-0.91 (3H, m), 1.23 (6H, d, J=6.9 Hz), 1.33-1.52 (8H, m), 1.65-1.74 (2H, m), 2.56-2.64 (2H, m), 2.87-2.96 (1H, m), 3.13-4.04 (4H, m), 7.03-7.23 (6H, m), 7.29-7.32 (2H, m), 7.44-7.51 (4H, m).

Example 679

Preparation of the Compound 679

(1) Preparation of the Intermediate 679(1).

A mixture of the intermediate 125(2) (500 mg, 1.97 mmol), 4-(tert-butyl)cyclohexanecarboxylic acid (mixture of cis- and trans-) (800 mg, 4.34 mmol), 1-ethyl-3-(3-dimethylaminopropyl)carbodiimide hydrochloride (909 mg, 4.74 mmol) and chloroform (20 ml) was stirred at room temperature for 5 hours. Water was added to the reaction mixture, and the mixture was extracted with ethyl acetate. The organic layer was washed with a saturated aqueous solution of sodium hydrogen carbonate and saturated brine, and dried over anhydrous sodium sulfate. The residue obtained by evaporation of the solvent under reduced pressure was purified by column chromatography on silica gel (n-hexane:ethyl acetate=5:1) to give the title compound (618 mg, 75%) as a white solid.

$^1$H-NMR ($CDCl_3$) δ: 0.84 (9H, s), 1.00-1.08 (2H, m), 1.21-1.42 (2H, m), 1.56-1.71 (3H, m), 2.21-2.26 (2H, m), 2.62-2.72 (1H, m), 7.25-7.28 (3H, m), 7.38 (1H, brs), 7.49-7.64 (5H, m).

(2) Preparation of the Intermediate 679(2).

A solution of the intermediate 679(1) (313 mg, 0.746 mmol) in anhydrous tetrahydrofuran (2 ml) was added dropwise to a suspension of lithium aluminium hydride (141 mg, 3.730 mmol) in anhydrous tetrahydrofuran (3 ml) under reflux, and the mixture was stirred for 2 hours. The reaction mixture was cooled to 0° C., followed by addition of 2 N hydrochloric acid, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=20:1) to give the title compound (258 mg, 85%) as a white solid.

$^1$H-NMR ($CDCl_3$) δ: 0.85 (9H, s), 0.98-1.14 (4H, m), 1.15-1.57 (3H, m), 1.84-1.86 (2H, m), 1.98-2.19 (1H, m), 3.19 (2H, d, J=7.5 Hz), 3.79 (1H, brs), 6.64-6.70 (2H, m), 7.21-7.23 (2H, m), 7.35-7.43 (2H, m), 7.50-7.55 (2H, m).

(3) Preparation of the Intermediate 679(3).

The title compound was obtained in the same manner as the Example 123(2) using the following starting materials.

Starting materials: the intermediate 679(2) and methyl chloroglyoxylate; Yield: 90% (colorless oil).

$^1$H-NMR ($CDCl_3$) δ: 0.85 (9H, s), 0.90-1.02 (1H, m), 1.19-1.33 (3H, m), 1.38-1.49 (3H, m), 1.55-1.69 (2H, m), 1.81-1.93 (1H, m), 3.58 (3H, s), 3.92 (2H, d, J=8.1 Hz), 7.27-7.32 (4H, m), 7.55-7.62 (4H, m).

(4) Preparation of the Compound 679.

The title compound was obtained in the same manner as the Example 126(4) using the following starting material.

Starting material: the intermediate 679(3); Yield: 81% (white solid).

$^1$H-NMR (DMSO-$d_6$) δ: 0.83 (9H, s), 0.90-1.02 (1H, m), 1.23-1.25 (2H, m), 1.31-1.40 (2H, m), 1.47-1.72 (5H, m), 3.87 (2H, d, J=7.5 Hz), 7.41-7.48 (4H, m), 7.75-7.84 (4H, m), 13.90 (1H, brs).

Example 680

Preparation of the Compound 680

(1) Preparation of the Intermediate 680(1).

The title compound was obtained in the same manner as the Example 679(1) using the following starting materials.

Starting materials: the intermediate 125(2) and 4-(tert-butyl)cyclohexanecarboxylic acid (mixture of cis- and trans-); Yield: 25% (white solid).

$^1$H-NMR ($CDCl_3$) δ: 0.97 (9H, s), 1.04-1.10 (3H, m), 1.44-1.72 (3H, m), 1.83-2.00 (2H, m), 2.00-2.10 (1H, m), 2.11-2.30 (1H, m), 7.25-7.28 (3H, m), 7.49-7.63 (6H, m).

(2) Preparation of the Intermediate 680(2).

The title compound was obtained in the same manner as the Example 679(2) using the following starting material.

Starting material: the intermediate 680(1); Yield: 100% (white solid).

$^1$H-NMR ($CDCl_3$) δ: 0.85 (9H, s), 0.93-1.04 (5H, m), 1.45-1.61 (1H, m), 1.78-2.05 (5H, m), 2.99 (2H, d, J=6.6 Hz), 6.65-6.70 (2H, m), 7.21-7.24 (2H, m), 7.36-7.44 (2H, m), 7.50-7.54 (2H, m).

(3) Preparation of the Intermediate 680(3).

The title compound was obtained in the same manner as the Example 123(2) using the following starting materials.

Starting materials: the intermediate 680(2) and methyl chloroglyoxylate; Yield: 92% (colorless oil).

$^1$H-NMR ($CDCl_3$) δ: 0.81 (9H, s), 0.87-1.09 (4H, m), 1.43-1.59 (2H, m), 1.71-1.92 (4H, m), 3.58 (3H, s), 3.69 (2H, d, J=7.5 Hz), 7.27-7.34 (4H, m), 7.56-7.63 (4H, m).

(4) Preparation of the Compound 680.

The title compound was obtained in the same manner as the Example 126(4) using the following starting material.

Starting material: the intermediate 680(3); Yield: 87% (yellow oil).

$^1$H-NMR (DMSO-$d_6$) δ: 0.79 (9H, s), 0.82-0.93 (4H, m), 1.25-1.40 (3H, m), 1.71-1.82 (3H, m), 3.63 (2H, d, J=7.2 Hz), 7.39-7.51 (4H, m), 7.68-7.84 (4H, m), 14.13 (1H, brs).

Example 681

Preparation of the Compound 681

(1) Preparation of the Intermediate 681(1).

The title compound was obtained in the same manner as the Example 679(1) using the following starting materials.

Starting materials: the intermediate 3-bromoaniline and 4-phenylbutyric acid; Yield: 90% (white solid).

$^1$H-NMR ($CDCl_3$) δ: 2.00-2.15 (2H, m), 2.34 (2H, t, J=7.5 Hz), 2.71 (2H, t, J=7.5 Hz), 7.06 (1H, brs), 7.12-7.43 (8H, m), 7.71-7.81 (1H, m).

(2) Preparation of the Intermediate 681(2).

The title compound was obtained in the same manner as the Example 125(4) using the following starting materials.

Starting materials: the intermediate 681(1) and ethyl bromoacetate; Yield: 40% (pale yellow oil).

$^1$H-NMR ($CDCl_3$) δ: 1.28 (3H, t, J=7.2 Hz), 1.83-1.90 (2H, m), 2.14 (2H, t, J=7.5 Hz), 2.57 (2H, t, J=7.5 Hz), 4.20 (2H, q, J=7.2 Hz), 4.32 (2H, s), 7.03-7.33 (7H, m), 7.42-7.54 (2H, m).

(3) Preparation of the Intermediate 681(3).

The title compound was obtained in the same manner as the Example 123(3) using the following starting materials.

Starting materials: the intermediate 681(2) and 4-(trifluoromethoxy)phenylboronic acid; Yield: 67% (colorless oil).

$^1$H-NMR ($CDCl_3$) δ: 1.27 (3H, t, J=7.2 Hz), 1.85-2.02 (2H, m), 2.20 (2H, t, J=7.2 Hz), 2.58 (2H, t, J=7.2 Hz), 4.21 (2H, q, J=7.2 Hz), 4.39 (2H, s), 7.03-7.35 (8H, m), 7.40-7.60 (5H, m).

(4) Preparation of the Compound 681.

The title compound was obtained in the same manner as the Example 126(4) using the following starting material.

Starting material: the intermediate 681(3); Yield: 53% (pale black solid).

$^1$H-NMR ($CDCl_3$) δ: 1.60-1.88 (2H, m), 1.88-2.20 (2H, m), 2.20-2.53 (2H, m), 4.19 (2H, s), 6.73-7.61 (13H, m), 10.05 (1H, brs).

Example 682

Preparation of the Compound 682

(1) Preparation of the Intermediate 682(1).

The title compound was obtained in the same manner as the Example 679(1) using the following starting materials.

Starting materials: the intermediate 194(2) and 4-phenylbutyric acid; Yield: 63.7% (white solid).

$^1$H-NMR ($CDCl_3$) δ: 0.95 (3H, t, J=7.2 Hz), 1.39-1.50 (4H, m), 1.81-1.89 (2H, m), 2.05-2.13 (2H, m), 2.42 (2H, t, J=7.2 Hz), 2.74 (2H, t, J=7.2 Hz), 4.07 (2H, t, J=6.6 Hz), 6.92 (1H, d, J=8.4 Hz), 7.19-7.30 (8H, m), 7.58-7.61 (2H, m), 7.78 (1H, brs), 8.69 (1H, d, J=2.1 Hz).

(2) Preparation of the Intermediate 682(2).

The title compound was obtained in the same manner as the Example 125(4) using the following starting materials.

Starting materials: the intermediate 682(1) and ethyl bromoacetate; Yield: 37% (colorless oil).

$^1$H-NMR ($CDCl_3$) δ: 0.92 (3H, t, J=6.9 Hz), 1.20-1.50 (7H, m), 1.67-2.30 (6H, m), 2.56 (2H, t, J=6.6 Hz), 3.63 (1H, d, J=17.1 Hz), 3.99 (2H, t, J=6.6 Hz), 4.08-4.30 (2H, m), 5.05 (1H, d, J=17.1 Hz), 6.99 (1H, d, J=9.0 Hz), 7.04-7.22 (5H, m), 7.22-7.33 (2H, m), 7.45-7.56 (3H, m), 7.66 (1H, d, J=2.1 Hz).

(3) Preparation of the Compound 682.

The title compound was obtained in the same manner as the Example 126(4) using the following starting material.

Starting material: the intermediate 682(2); Yield: 100% (colorless oil).

$^1$H-NMR ($CDCl_3$) δ: 0.82-0.97 (3H, m), 1.21-1.46 (4H, m), 1.62-1.92 (4H, m), 1.96-2.24 (2H, m), 2.47 (2H, t, J=7.5 Hz), 3.69 (1H, d, J=16.8 Hz), 3.85-4.02 (2H, m), 4.81 (1H, d, J=16.8 Hz), 6.90-7.24 (8H, m), 7.40-7.52 (3H, m), 7.58 (1H, d, J=2.1 Hz).

Example 683

Preparation of the Compound 683

(1) Preparation of the Intermediate 683(1).

The title compound was obtained in the same manner as the Example 123(3) using the following starting materials.

Starting materials: the intermediate 126(2) and 4-(2-calboxyethyl)phenylboronic acid; Yield: 36% (white solid).

$^1$H-NMR ($CDCl_3$) δ: 1.30 (9H, s), 2.72 (2H, t, J=7.2 Hz), 3.00 (2H, t, J=7.2 Hz), 3.57 (3H, s), 4.94 (2H, s), 7.11-7.20 (4H, m), 7.25-7.34 (4H, m), 7.47-7.54 (4H, m).

(2) Preparation of the Compound 683.

The title compound was obtained in the same manner as the Example 126(4) using the following starting material.

Starting material: the intermediate 683(1); Yield: 83% (pale yellow oil).

$^1$H-NMR (DMSO-$d_6$) δ: 1.25 (9H, s), 2.56 (2H, t, J=7.5 Hz), 2.85 (2H, t, J=7.5 Hz), 4.93 (2H, s), 7.16 (2H, d, J=8.4 Hz), 7.26-7.36 (6H, m), 7.56 (2H, d, J=8.4 Hz), 7.65 (2H, d, J=8.4 Hz).

Example 684

Preparation of the Compound 684

(1) Preparation of the Intermediate 684(1).

The title compound was obtained in the same manner as the Example 1(2) using the following starting materials.

Starting materials: the intermediate 126(2) and 4-acetylphenylboronic acid; Yield: 50% (white solid).

$^1$H-NMR ($CDCl_3$) δ: 1.30 (9H, s), 2.64 (3H, s), 3.60 (3H, s), 4.96 (2H, s), 7.19 (4H, d, J=8.1 Hz), 7.32 (2H, d, J=8.1 Hz), 7.58 (2H, d, J=8.1 Hz), 7.65 (2H, d, J=8.1 Hz), 8.03 (2H, d, J=8.1 Hz).

(2) Preparation of the Compound 684.

The title compound was obtained in the same manner as the Example 12(4) using the following starting material.

Starting material: the intermediate 684(1); Yield: 62% (pale yellow solid).

$^1$H-NMR (DMSO-$d_6$) δ: 1.24 (9H, s), 2.60 (3H, s), 4.92 (2H, s), 7.06-7.35 (4H, m), 7.39 (2H, d, J=8.5 Hz), 7.67 (2H, d, J=8.5 Hz), 7.79 (2H, d, J=8.5 Hz), 8.01 (2H, d, J=8.5 Hz).

Example 685

Preparation of the Compound 685

(1) Preparation of the Intermediate 685(1).

The title compound was obtained in the same manner as the Example 1(2) using the following starting materials.

Starting materials: the intermediate 126(2) and 4-N-(methanesulfonamide)phenylboronic acid; Yield: 30% (colorless oil).

$^1$H-NMR ($CDCl_3$) δ: 1.30 (9H, s), 3.05 (3H, s), 3.58 (3H, s), 4.94 (2H, s), 6.88 (1H, s), 7.10-7.23 (4H, m), 7.26-7.39 (4H, m), 7.45-7.62 (4H, m).

(2) Preparation of the Compound 685.

The title compound was obtained in the same manner as the Example 12(4) using the following starting material.

Starting material: the intermediate 685(1); Yield: 35% (white solid).

$^1$H-NMR (DMSO-$d_6$) δ: 1.24 (9H, s), 3.01 (3H, s), 4.91 (2H, s), 7.05-7.44 (8H, m), 7.50-7.73 (4H, m), 9.90 (1H, s).

Example 686

Preparation of the Compound 686

(1) Preparation of the Intermediate 686(1).

The title compound was obtained in the same manner as the Example 1(2) using the following starting materials.

Starting materials: the intermediate 126(2) and 4-hydroxyphenylboronic acid; Yield: 37% (white solid).

$^1$H-NMR ($CDCl_3$) δ: 1.29 (9H, s), 3.57 (3H, s), 4.94 (2H, s), 6.59 (1H, s), 6.83-6.94 (2H, m), 7.06-7.14 (2H, m), 7.15-7.24 (2H, m), 7.28-7.36 (2H, m), 7.37-7.50 (4H, m).

(2) Preparation of the Compound 686.

The title compound was obtained in the same manner as the Example 12(4) using the following starting material.

Starting material: the intermediate 686(1); Yield: 63% (white solid).

$^1$H-NMR (DMSO-$d_6$) δ: 1.24 (9H, s), 4.85 (2H, s), 6.79 (2H, d, J=8.2 Hz), 7.06-7.53 (10H, m).

Test Example 1

Human PAI-1 Inhibitory Activity

[Method]

In a 96-well multiplate (black), 1.5 μl of DMSO solution of the compound according to the present invention, which had been prepared to achieve 80-fold the test concentration (=the final concentration when fluorogenic substrate is added), was diluted with 52.5 μl of pH 7.5 Tris buffer. To this solution, 6 μl of 80 nM recombinant human PAI-1 (Molecular Innovations, Inc.) solution prepared with Tris buffer was added, and the plate was incubated for 5 minutes at room temperature. Furthermore, 30 μl of 800 IU/ml two-chain tPA (Activity Standard; American diagnostica, inc.) prepared with Tris buffer was added, and the mixed solution was incubated for 15 minutes at room temperature. Then, 30 μl of 400 μM fluorogenic substrate (Pyr-Gly-Arg-MCA; Peptide Institute, Inc.) for tPA prepared with Tris buffer was added and reacted for 30 minutes at room temperature. Every 5 minutes from the reaction start, fluorescence (excitation wavelength=360 nm, emission wavelength=465 nm) was measured using SPECTRAFLUOR (TECAN G.M.B.H.) or GENios (TECAN G.M.B.H.), and intensity of fluorescence increased by 30 minute reaction were measured. The increments of fluorescence by 30 minutes reaction in the presence or absence (tPA alone) of PAI-1 in the control wells (DMSO) were calculated respectively, and their differences ([data in the absence of PAI-1]−[data in the presence of PAI-1]) being 100% of PAI-1 activity, the inhibition rates of PAI-1 activity in the presence of the compound according to the present invention were calculated.

<Composition of pH 7.5 Tris Buffer>

50 mM Tris, 150 mM NaCl, 10 μg/ml BSA, 0.01% Tween80 (SIGMA-ALDRICH Corporation)

[Results]

In the following, inhibition rates of human PAI-1 activity are shown. "NT" on the table means that the measurement was not carried out.

TABLE 5-1

| Compound | Inhibition Rate of PAI Activity (%) Compound Concentration | | | |
|---|---|---|---|---|
| No. | 25 μM | 10 μM | 5 μM | 2.5 μM |
| 1 | NT | 31 | 18 | NT |
| 2 | NT | 31 | 35 | NT |
| 3 | NT | 68 | 35 | NT |
| 4 | NT | 78 | 84 | 39 |
| 5 | NT | 95 | 87 | 36 |
| 6 | NT | 94 | 83 | 46 |
| 7 | NT | 21 | 14 | NT |
| 8 | NT | 5 | NT | NT |
| 9 | NT | 99 | 90 | 40 |
| 10 | >99 | 65 | 32 | NT |
| 11 | 99 | 84 | 41 | NT |
| 12 | NT | 94 | 92 | 43 |
| 13 | NT | 93 | 83 | 35 |
| 14 | NT | 3 | NT | NT |
| 15 | 94 | 47 | 23 | NT |
| 16 | 96 | 46 | 23 | NT |

TABLE 5-1-continued

| Compound No. | Inhibition Rate of PAI Activity (%) Compound Concentration 25 μM | 10 μM | 5 μM | 2.5 μM |
|---|---|---|---|---|
| 17 | 97 | 67 | 37 | NT |
| 18 | 92 | 65 | 36 | NT |
| 19 | 77 | 13 | NT | NT |
| 20 | 53 | 10 | NT | NT |
| 21 | 70 | 11 | NT | NT |
| 22 | 80 | 13 | NT | NT |
| 23 | 47 | 7 | NT | NT |
| 24 | 64 | 11 | NT | NT |
| 25 | 93 | 97 | 96 | 72 |
| 26 | 25 | 9 | NT | NT |
| 27 | 92 | 29 | 5 | NT |
| 28 | 94 | 40 | 17 | NT |
| 29 | 88 | 56 | 21 | NT |
| 30 | >99 | 70 | 29 | NT |
| 31 | 89 | 49 | 21 | NT |
| 32 | 97 | 47 | 22 | NT |
| 33 | 96 | 53 | 23 | NT |
| 34 | 99 | 53 | 24 | NT |
| 35 | 95 | 57 | 28 | NT |
| 36 | 99 | 60 | 23 | NT |
| 37 | 84 | 47 | 23 | NT |
| 38 | 93 | 34 | 14 | NT |
| 39 | 94 | 56 | 25 | NT |
| 40 | >99 | 66 | 22 | NT |
| 41 | 91 | 56 | 25 | NT |
| 42 | 97 | 59 | 27 | NT |
| 43 | 94 | 66 | 29 | NT |
| 44 | 21 | 25 | 16 | NT |
| 45 | 31 | 15 | NT | NT |
| 46 | 20 | 9 | NT | NT |
| 47 | 91 | 47 | 22 | NT |
| 48 | 93 | 50 | 20 | NT |
| 49 | 97 | 66 | 30 | NT |
| 50 | 96 | 56 | 23 | NT |
| 51 | 94 | 69 | 32 | NT |
| 52 | 94 | 64 | 28 | NT |
| 53 | 74 | 32 | 19 | NT |
| 54 | 75 | 40 | 22 | NT |
| 55 | 95 | 46 | 21 | NT |
| 56 | 91 | 47 | 22 | NT |
| 57 | 82 | 53 | 24 | NT |
| 58 | 97 | 53 | 22 | NT |
| 59 | 77 | 53 | 25 | NT |
| 60 | 25 | 35 | 15 | NT |
| 61 | 97 | 48 | 21 | NT |
| 62 | 99 | 62 | 29 | NT |
| 63 | 93 | 72 | 38 | NT |
| 64 | 95 | 74 | 49 | NT |
| 65 | 93 | 72 | 42 | NT |
| 66 | >99 | 80 | 52 | NT |

TABLE 5-2

| Compound No. | Inhibition Rate of PAI-1 Activity (%) Compound Concentration 25 μM | 10 μM | 5 μM | 2.5 μM |
|---|---|---|---|---|
| 67 | 94 | 70 | 37 | NT |
| 68 | 95 | 74 | 40 | NT |
| 69 | 97 | 73 | 50 | NT |
| 70 | 95 | 71 | 47 | NT |
| 71 | 93 | 80 | 51 | 31 |
| 72 | 98 | 72 | 32 | 13 |
| 73 | >99 | 66 | 30 | 11 |
| 74 | 96 | 53 | 13 | 4 |
| 75 | 91 | 53 | 25 | 11 |
| 76 | 98 | 54 | 24 | 14 |
| 77 | 73 | 51 | 27 | 14 |
| 78 | 98 | 60 | 24 | 12 |
| 79 | 90 | 84 | 39 | 19 |
| 80 | 94 | 82 | 43 | 21 |

TABLE 5-2-continued

| Compound No. | Inhibition Rate of PAI-1 Activity (%) Compound Concentration 25 μM | 10 μM | 5 μM | 2.5 μM |
|---|---|---|---|---|
| 81 | 70 | 63 | 28 | 11 |
| 82 | 98 | 59 | 26 | 10 |
| 83 | 56 | 46 | 27 | 18 |
| 84 | 95 | 62 | 28 | 19 |
| 85 | 85 | 61 | 40 | 22 |
| 86 | 98 | 80 | 47 | 23 |
| 87 | 96 | 81 | 44 | 21 |
| 88 | 97 | 83 | 42 | 20 |
| 89 | 95 | 87 | 46 | 20 |
| 90 | 96 | 83 | 42 | 17 |
| 91 | 96 | 67 | 30 | 15 |
| 92 | 97 | 63 | 25 | 6 |
| 93 | 94 | 87 | 51 | 29 |
| 94 | 97 | 90 | 56 | 28 |
| 95 | 96 | 77 | 28 | 7 |
| 96 | 99 | 75 | 36 | 12 |
| 97 | 53 | 40 | 30 | 14 |
| 98 | 98 | 84 | 57 | 34 |
| 99 | 99 | 66 | 31 | 5 |
| 100 | 98 | 91 | 64 | 38 |
| 101 | >99 | 73 | 42 | 21 |
| 102 | 97 | 74 | 43 | 20 |
| 103 | 89 | 57 | 33 | 19 |
| 104 | 96 | 77 | 47 | 18 |
| 105 | >99 | 76 | 38 | 17 |
| 106 | 93 | 85 | 50 | 25 |
| 107 | 97 | 85 | 48 | 25 |
| 108 | 95 | 86 | 52 | 25 |
| 109 | 96 | 50 | 24 | 18 |
| 110 | 83 | 51 | 37 | 17 |
| 111 | 94 | 88 | 55 | 23 |
| 112 | 95 | 82 | 34 | 9 |
| 113 | 97 | 85 | 58 | 27 |
| 114 | 95 | 87 | 64 | 26 |
| 115 | 90 | 59 | 34 | 10 |
| 116 | 91 | 81 | 56 | 26 |
| 117 | 96 | 91 | 63 | 34 |
| 118 | 93 | 82 | 56 | 37 |
| 119 | 99 | 93 | 75 | 41 |
| 120 | 98 | 87 | 59 | 35 |
| 121 | >99 | 34 | NT | NT |
| 122 | 99 | 63 | 29 | 16 |
| 123 | NT | 62 | 27 | 15 |
| 124 | NT | 49 | 22 | 14 |
| 125 | NT | 31 | 15 | NT |
| 126 | NT | 43 | 16 | NT |
| 127 | NT | 43 | 21 | 16 |
| 128 | NT | 89 | 58 | 26 |
| 129 | NT | 95 | 75 | 43 |
| 130 | NT | 96 | 82 | 42 |
| 131 | 34 | 10 | NT | NT |
| 132 | 82 | 32 | NT | NT |

TABLE 5-3

| Compound No. | Inhibition Rate of PAI-1 Activity (%) Compound Concentration 25 μM | 10 μM | 5 μM | 2.5 μM |
|---|---|---|---|---|
| 133 | NT | 92 | 80 | 45 |
| 134 | 75 | 14 | NT | NT |
| 135 | 67 | 6 | NT | NT |
| 136 | 79 | 47 | 16 | NT |
| 137 | 61 | 5 | NT | NT |
| 138 | 61 | 4 | NT | NT |
| 139 | 66 | 59 | 25 | NT |
| 140 | 77 | 31 | 6 | NT |
| 141 | 52 | 5 | NT | NT |
| 142 | 33 | 3 | NT | NT |
| 143 | 22 | 1 | NT | NT |
| 144 | 76 | 22 | 3 | NT |

TABLE 5-3-continued

| Compound No. | Inhibition Rate of PAI-1 Activity (%) Compound Concentration 25 μM | 10 μM | 5 μM | 2.5 μM |
|---|---|---|---|---|
| 145 | 74 | 35 | 7 | NT |
| 146 | 90 | 73 | 33 | NT |
| 147 | 92 | 80 | 38 | NT |
| 148 | 98 | 55 | 17 | NT |
| 149 | 34 | 3 | NT | NT |
| 150 | 87 | 75 | 33 | NT |
| 151 | 90 | 80 | 35 | NT |
| 152 | 93 | 88 | 41 | NT |
| 153 | 93 | 54 | 20 | NT |
| 154 | 20 | 3 | NT | NT |
| 155 | 38 | 15 | 7 | NT |
| 156 | 67 | 25 | 10 | NT |
| 157 | 96 | 56 | 25 | NT |
| 158 | >99 | 61 | 26 | NT |
| 159 | 92 | 45 | 21 | NT |
| 160 | 68 | 26 | 14 | NT |
| 161 | >99 | 62 | 27 | 11 |
| 162 | >99 | 74 | 30 | 16 |
| 163 | >99 | 84 | 37 | 15 |
| 164 | 96 | 79 | 40 | 15 |
| 165 | 96 | 64 | 27 | 14 |
| 166 | 84 | 79 | 44 | 15 |
| 167 | 87 | 75 | 37 | 12 |
| 168 | NT | 94 | 63 | 29 |
| 169 | 84 | 91 | 59 | 26 |
| 170 | 94 | 73 | 38 | 18 |
| 171 | 81 | 44 | 22 | 9 |
| 172 | 94 | 89 | 58 | 30 |
| 173 | 90 | 95 | 63 | 30 |
| 174 | 91 | 92 | 61 | 26 |
| 175 | 87 | 94 | 66 | 28 |
| 176 | 91 | 94 | 65 | 32 |
| 177 | 91 | 83 | 43 | 18 |
| 178 | 88 | 88 | 56 | 23 |
| 179 | NT | 91 | 64 | 29 |
| 180 | 71 | 36 | 19 | NT |
| 181 | 31 | 11 | 10 | NT |
| 182 | 89 | 85 | 56 | 26 |
| 183 | 29 | 11 | NT | NT |
| 184 | 85 | 86 | 59 | 30 |
| 185 | 89 | 87 | 81 | 46 |
| 186 | NT | 91 | 76 | 35 |
| 187 | 88 | 92 | 75 | 40 |
| 188 | 91 | 91 | 73 | 38 |
| 189 | NT | 95 | 87 | 53 |
| 190 | 91 | 91 | 65 | 32 |
| 191 | 87 | 92 | 74 | 46 |
| 192 | 94 | 95 | 80 | 52 |
| 193 | NT | 89 | 81 | 51 |
| 194 | NT | 84 | 84 | 57 |
| 195 | 93 | 94 | 77 | 48 |
| 196 | 64 | 35 | 18 | 3 |
| 197 | 73 | 92 | 90 | 66 |
| 198 | 85 | 95 | 79 | 46 |

TABLE 5-4

| Compound No. | Inhibition Rate of PAI-1 Activity (%) Compound Concentration 25 μM | 10 μM | 5 μM | 2.5 μM |
|---|---|---|---|---|
| 199 | NT | 89 | 83 | 55 |
| 200 | 92 | 89 | 64 | 37 |
| 201 | 82 | 89 | 64 | 35 |
| 202 | 98 | 94 | 70 | 39 |
| 203 | 97 | 91 | 69 | 42 |
| 204 | >99 | 85 | 58 | 32 |
| 205 | 98 | 80 | 50 | 17 |
| 206 | 89 | 92 | 78 | 46 |
| 207 | NT | 90 | 79 | 49 |

TABLE 5-4-continued

| Compound No. | Inhibition Rate of PAI-1 Activity (%) Compound Concentration 25 μM | 10 μM | 5 μM | 2.5 μM |
|---|---|---|---|---|
| 208 | NT | 98 | 89 | 65 |
| 209 | 94 | 98 | 81 | 49 |
| 210 | 94 | 70 | 39 | 19 |
| 211 | NT | 96 | 87 | 57 |
| 212 | NT | 95 | 78 | 45 |
| 213 | NT | 84 | 93 | 71 |
| 214 | NT | 93 | 87 | 55 |
| 215 | NT | 92 | 90 | 63 |
| 216 | 84 | 88 | 75 | 43 |
| 217 | NT | 84 | 86 | 66 |
| 218 | NT | 78 | 83 | 61 |
| 219 | 86 | 58 | 33 | 4 |
| 220 | 89 | 86 | 51 | 22 |
| 221 | NT | 86 | 80 | 53 |
| 222 | NT | 91 | 74 | 40 |
| 223 | NT | 27 | 13 | NT |
| 224 | 86 | 63 | 29 | 15 |
| 225 | 88 | 50 | 27 | 12 |
| 226 | NT | 92 | 85 | 53 |
| 227 | NT | 90 | 63 | 31 |
| 228 | 95 | 71 | 45 | 22 |
| 229 | 94 | 80 | 48 | 20 |
| 230 | 92 | 95 | 75 | 51 |
| 231 | 94 | 97 | 81 | 55 |
| 232 | 96 | 82 | 52 | 24 |
| 233 | NT | 93 | 78 | 49 |
| 234 | 96 | 83 | 59 | 29 |
| 235 | 93 | 89 | 66 | 35 |
| 236 | 95 | 86 | 61 | 32 |
| 237 | NT | 92 | 75 | 48 |
| 238 | 93 | 95 | 76 | 45 |
| 239 | 98 | 80 | 43 | 20 |
| 240 | 95 | 91 | 62 | 28 |
| 241 | NT | 93 | 82 | 55 |
| 242 | NT | 94 | 88 | 69 |
| 243 | 89 | 64 | 42 | 12 |
| 244 | NT | 91 | 71 | 39 |
| 245 | NT | 97 | 93 | 68 |
| 246 | NT | 96 | 79 | 50 |
| 247 | NT | 99 | 93 | 63 |
| 248 | 96 | 89 | 60 | 32 |
| 249 | NT | 89 | 68 | 38 |
| 250 | NT | 78 | 83 | 61 |
| 251 | NT | 63 | 62 | 47 |
| 252 | 34 | 6 | 3 | 2 |
| 253 | 36 | 16 | 9 | 4 |
| 254 | 31 | 9 | 3 | 4 |
| 255 | 23 | 8 | 2 | NT |
| 404 | 84 | 31 | 14 | 10 |
| 409 | 97 | 59 | 26 | 11 |
| 410 | 98 | 71 | 37 | 21 |
| 412 | 92 | 46 | 22 | 12 |
| 413 | 84 | 66 | 38 | 31 |
| 414 | 96 | 67 | 33 | 16 |
| 417 | 98 | 79 | 44 | 25 |
| 420 | 83 | 64 | 42 | 16 |
| 539 | 65 | 34 | 14 | 5 |

TABLE 5-5

| Compound No. | Inhibition Rate of PAI-1 Activity (%) Compound Concentration 25 μM | 10 μM | 5 μM | 2.5 μM |
|---|---|---|---|---|
| 540 | 91 | 91 | 75 | 51 |
| 541 | >99 | 93 | 77 | 50 |
| 609 | >99 | 69 | 38 | 18 |
| 616 | 96 | 83 | 49 | 22 |
| 619 | 92 | 83 | 48 | 24 |

TABLE 5-5-continued

| Compound | Inhibition Rate of PAI-1 Activity (%) Compound Concentration | | | |
|---|---|---|---|---|
| No. | 25 μM | 10 μM | 5 μM | 2.5 μM |
| 620 | 95 | 77 | 41 | 21 |
| 621 | 91 | 95 | 67 | 34 |
| 622 | 88 | 72 | 44 | 26 |
| 623 | 87 | 41 | 22 | 13 |
| 625 | 91 | 92 | 59 | 24 |
| 626 | 97 | 77 | 42 | 19 |
| 629 | 88 | 92 | 62 | 29 |
| 630 | 88 | 89 | 56 | 26 |
| 631 | 86 | 86 | 58 | 22 |

TABLE 5-6

| Compound | Inhibition Rate of PAI-1 Activity (%) Compound Concentration | | | | |
|---|---|---|---|---|---|
| No. | 10 μM | 5 μM | 2.5 μM | 1 μM | 0.5 μM |
| 542 | — | 67 | 47 | 14 | 0 |
| 546 | — | 61 | 33 | 14 | 4 |
| 603 | 97 | 82 | 40 | 16 | — |

Test Example 2

Human PAI-1 Inhibitory Activity

[Method]

Except using the pH 7.4 HEPES buffer instead of the pH 7.5 Tris buffer, and the change of incubation time from 15 minutes to 10 minutes of the mixed solution added to two-chain tPA solution, tests were carried out in the same manner as the Test Example 1.

<Composition of pH 7.4 HEPES Buffer>

0.1 M HEPES, 0.1 M NaCl. 1 mM EDTA. 0.1% Polyethylene glycol 8,000 (Hampton Research Corporation), 2 mM Dimethyldecylphoshine oxide [Apo-10] (Fluka Corporation)

[Results]

In the following, inhibition rates of human PAI-1 activity are shown.

TABLE 6-1

| Compound | Inhibition Rate of PAI-1 Activity (%) Compound Concentration | | | |
|---|---|---|---|---|
| No. | 3 μM | 1 μM | 0.3 μM | 0.1 μM |
| 5 | 90 | 34 | 13 | 2 |
| 9 | 98 | 25 | 6 | 0 |
| 13 | 99 | 36 | 8 | 5 |
| 30 | 92 | 25 | 5 | 0 |
| 73 | 98 | 27 | 6 | 0 |
| 76 | 99 | 37 | 12 | 10 |
| 78 | 96 | 21 | 4 | 0 |
| 80 | >99 | 44 | 11 | 3 |
| 86 | 87 | 22 | 0 | 0 |
| 88 | 97 | 25 | 5 | 0 |
| 90 | 97 | 22 | 6 | 4 |
| 94 | 96 | 24 | 3 | 0 |
| 96 | 96 | 26 | 7 | 6 |
| 98 | 84 | 25 | 2 | 0 |
| 100 | 93 | 29 | 2 | 0 |
| 102 | 94 | 28 | 7 | 0 |
| 105 | 99 | 44 | 3 | 2 |

TABLE 6-1-continued

| Compound | Inhibition Rate of PAI-1 Activity (%) Compound Concentration | | | |
|---|---|---|---|---|
| No. | 3 μM | 1 μM | 0.3 μM | 0.1 μM |
| 106 | 97 | 39 | 8 | 0 |
| 112 | >99 | 56 | 19 | 0 |
| 113 | 73 | 26 | 6 | 0 |
| 116 | 89 | 15 | 0 | 0 |
| 117 | >99 | 46 | 7 | 2 |
| 118 | >99 | 49 | 6 | 0 |
| 129 | 86 | 19 | 3 | 1 |
| 130 | 84 | 18 | 2 | 0 |
| 139 | 97 | 30 | 3 | 0 |
| 147 | 99 | 35 | 7 | 0 |
| 168 | 99 | 33 | 0 | 0 |
| 172 | 76 | 18 | 8 | 4 |
| 174 | 96 | 26 | 0 | 0 |
| 176 | 96 | 21 | 10 | 0 |
| 179 | >99 | 68 | 19 | 1 |
| 185 | >99 | 34 | 9 | 0 |
| 186 | >99 | 22 | 9 | 0 |
| 188 | 97 | 33 | 0 | 0 |
| 189 | 97 | 60 | 2 | 4 |
| 190 | 95 | 27 | 3 | 2 |
| 192 | >99 | 35 | 1 | 0 |
| 193 | >99 | 34 | 5 | 2 |
| 194 | 98 | 63 | 7 | 0 |
| 197 | >99 | 38 | 1 | 6 |
| 198 | >99 | 33 | 8 | 11 |
| 199 | >99 | 64 | 13 | 9 |
| 206 | >99 | 66 | 13 | 3 |
| 208 | 99 | 36 | 1 | 10 |
| 211 | 96 | 43 | 16 | 9 |
| 212 | 98 | 64 | 15 | 5 |
| 213 | 98 | 48 | 10 | 0 |
| 214 | 96 | 40 | 2 | 4 |
| 215 | 95 | 54 | 18 | 7 |
| 221 | >99 | 55 | 6 | 0 |
| 222 | >99 | 45 | 3 | 0 |
| 226 | 99 | 89 | 17 | 0 |
| 227 | 98 | 41 | 7 | 0 |
| 230 | 96 | 27 | 8 | 0 |
| 231 | 98 | 34 | 6 | 0 |
| 233 | 97 | 55 | 9 | 0 |
| 238 | 87 | 21 | 0 | 0 |
| 251 | 83 | 34 | 11 | 0 |
| 301 | 97 | 96 | 25 | 15 |
| 302 | 98 | 27 | 9 | 0 |
| 303 | 94 | 87 | 13 | 0 |
| 304 | 99 | 23 | 1 | 3 |
| 305 | 88 | 54 | 9 | 6 |
| 306 | 97 | 72 | 0 | 0 |
| 307 | 91 | 22 | 1 | 0 |

TABLE 6-2

| Compound | Inhibition Rate of PAI-1 Activity (%) Compound Concentration | | | |
|---|---|---|---|---|
| No. | 3 μM | 1 μM | 0.3 μM | 0.1 μM |
| 308 | 95 | 63 | 22 | 0 |
| 309 | 91 | 66 | 17 | 1 |
| 310 | 96 | 72 | 19 | 11 |
| 311 | 97 | 77 | 11 | 0 |
| 312 | 94 | 87 | 24 | 17 |
| 313 | 93 | 52 | 3 | 1 |
| 314 | 93 | 22 | 5 | 0 |
| 315 | >99 | 60 | 16 | 13 |
| 316 | 84 | 28 | 8 | 10 |
| 317 | 94 | 79 | 16 | 14 |
| 318 | >99 | 90 | 20 | 8 |
| 319 | 70 | 17 | 9 | 0 |
| 320 | 98 | 70 | 9 | 1 |

TABLE 6-2-continued

| Compound No. | Inhibition Rate of PAI-1 Activity (%) Compound Concentration 3 μM | 1 μM | 0.3 μM | 0.1 μM |
|---|---|---|---|---|
| 321 | 94 | 86 | 15 | 3 |
| 322 | 92 | 69 | 4 | 0 |
| 323 | 82 | 91 | 16 | 19 |
| 324 | 97 | 66 | 1 | 0 |
| 325 | 91 | 85 | 5 | 11 |
| 326 | 94 | 94 | 28 | 0 |
| 327 | 95 | 94 | 15 | 0 |
| 328 | >99 | 30 | 14 | 0 |
| 329 | 98 | 28 | 11 | 6 |
| 330 | 96 | 47 | 1 | 0 |
| 331 | 98 | 83 | 1 | 2 |
| 332 | >99 | 29 | 4 | 12 |
| 333 | 91 | 28 | 10 | 4 |
| 334 | 87 | 21 | 1 | 0 |
| 335 | >99 | 80 | 8 | 4 |
| 336 | >99 | 45 | 5 | 0 |
| 337 | 97 | 19 | 8 | 2 |
| 351 | 84 | 23 | 7 | 2 |
| 352 | 90 | 72 | 4 | 0 |
| 353 | 87 | 87 | 19 | 6 |
| 354 | 89 | 91 | 10 | 5 |
| 355 | 86 | 91 | 3 | 2 |
| 356 | >99 | 53 | 13 | 7 |
| 357 | >99 | 69 | 2 | 0 |
| 358 | 98 | 55 | 10 | 0 |
| 359 | 96 | 26 | 7 | 1 |
| 360 | 92 | 35 | 8 | 5 |
| 361 | 97 | 68 | 5 | 9 |
| 362 | >99 | 61 | 18 | 11 |
| 363 | >99 | 72 | 4 | 2 |
| 364 | 92 | 97 | 94 | 41 |
| 365 | 92 | 97 | 97 | 41 |
| 366 | 96 | 46 | 24 | 8 |
| 367 | 94 | 52 | 26 | 10 |
| 368 | 85 | 95 | 22 | 0 |
| 369 | 95 | 70 | 8 | 0 |
| 370 | 97 | 66 | 0 | 0 |
| 371 | 91 | 93 | 17 | 10 |
| 372 | 93 | 97 | 27 | 2 |
| 373 | 90 | 28 | 0 | 0 |
| 374 | >99 | 57 | 16 | 5 |
| 375 | 79 | >99 | 97 | 73 |
| 376 | 95 | 62 | 15 | 6 |
| 377 | 94 | 83 | 23 | 1 |
| 378 | 91 | 80 | 7 | 20 |
| 379 | 92 | 78 | 17 | 14 |
| 380 | >99 | 97 | 96 | 76 |
| 381 | >99 | 48 | 13 | 12 |
| 382 | 97 | 84 | 12 | 13 |
| 383 | 98 | 32 | 6 | 2 |
| 384 | 95 | 91 | 11 | 0 |
| 385 | >99 | >99 | >99 | 74 |
| 386 | >99 | >99 | 18 | 5 |

TABLE 6-3

| Compound No. | Inhibition Rate of PAI-1 Activity (%) Compound Concentration 3 μM | 1 μM | 0.3 μM | 0.1 μM |
|---|---|---|---|---|
| 387 | >99 | >99 | >99 | 66 |
| 388 | >99 | >99 | >99 | 75 |
| 389 | >99 | >99 | 97 | 65 |
| 390 | 87 | 79 | 12 | 4 |
| 391 | 89 | 69 | 8 | 10 |
| 392 | >99 | 77 | 14 | 7 |
| 393 | 97 | 75 | 19 | 8 |
| 394 | >99 | 98 | 69 | 13 |
| 421 | 81 | 14 | 3 | 0 |

TABLE 6-3-continued

| Compound No. | Inhibition Rate of PAI-1 Activity (%) Compound Concentration 3 μM | 1 μM | 0.3 μM | 0.1 μM |
|---|---|---|---|---|
| 422 | >99 | 72 | 24 | 12 |
| 423 | 96 | 74 | 1 | 1 |
| 424 | >99 | 38 | 4 | 0 |
| 425 | — | >99 | 54 | 17 |
| 426 | 97 | 95 | 29 | 10 |
| 427 | 97 | 62 | 27 | 1 |
| 428 | 94 | 92 | 36 | 18 |
| 429 | 95 | 93 | 9 | 7 |
| 430 | >99 | 97 | 15 | 1 |
| 431 | >99 | 77 | 0 | 0 |
| 432 | 97 | 25 | 0 | 4 |
| 433 | 98 | 41 | 6 | 13 |
| 434 | >99 | 66 | 8 | 14 |
| 435 | 98 | 81 | 29 | 12 |
| 436 | >99 | 63 | 19 | 3 |
| 437 | 98 | 67 | 12 | 0 |
| 438 | >99 | 50 | 11 | 13 |
| 439 | >99 | 44 | 9 | 12 |
| 440 | >99 | 96 | 3 | 0 |
| 441 | 98 | 89 | 29 | 9 |
| 442 | >99 | 83 | 4 | 1 |
| 443 | >99 | 76 | 8 | 7 |
| 444 | 96 | 11 | 0 | 0 |
| 445 | 50 | 12 | 1 | 0 |
| 446 | >99 | 84 | 13 | 3 |
| 447 | >99 | 89 | 11 | 4 |
| 448 | >99 | 39 | 11 | 4 |
| 450 | 98 | 58 | 11 | 9 |
| 452 | 94 | 15 | 8 | 9 |
| 453 | >99 | 96 | 15 | 4 |
| 454 | >99 | >99 | 17 | 11 |
| 455 | 99 | 93 | 20 | 9 |
| 456 | 98 | 70 | 13 | 7 |
| 457 | >99 | 63 | 18 | 21 |
| 458 | 72 | 24 | 29 | 20 |
| 459 | 86 | 42 | 31 | 26 |
| 460 | >99 | 63 | 8 | 1 |
| 461 | 98 | 95 | 26 | 1 |
| 462 | 95 | 97 | 94 | 37 |
| 465 | 98 | 87 | 17 | 10 |
| 466 | >99 | 88 | 9 | 4 |
| 467 | >99 | 73 | 6 | 2 |
| 468 | 97 | 86 | 5 | 1 |
| 469 | >99 | 96 | 22 | 4 |
| 470 | >99 | 87 | 16 | 3 |
| 471 | 49 | 11 | 7 | 5 |
| 472 | >99 | 71 | 14 | 15 |
| 473 | >99 | 26 | 9 | 15 |
| 474 | >99 | 43 | 11 | 2 |
| 475 | >99 | 94 | 27 | 4 |
| 476 | >99 | 65 | 3 | 0 |
| 477 | >99 | 60 | 21 | 7 |
| 478 | >99 | 90 | 33 | 11 |
| 479 | >99 | 70 | 14 | 17 |
| 480 | >99 | 80 | 22 | 17 |
| 481 | >99 | 70 | 16 | 19 |
| 482 | >99 | 52 | 12 | 7 |

TABLE 6-4

| Compound No. | Inhibition Rate of PAI-1 Activity (%) Compound Concentration 3 μM | 1 μM | 0.3 μM | 0.1 μM |
|---|---|---|---|---|
| 483 | >99 | 76 | 8 | 0 |
| 484 | >99 | 73 | 7 | 0 |
| 485 | 69 | 11 | 6 | 0 |
| 487 | 98 | 26 | 3 | 0 |
| 488 | 91 | 36 | 10 | 0 |

TABLE 6-4-continued

| Compound No. | Inhibition Rate of PAI-1 Activity (%) Compound Concentration 3 μM | 1 μM | 0.3 μM | 0.1 μM |
|---|---|---|---|---|
| 489 | >99 | 69 | 14 | 12 |
| 490 | >99 | 91 | 13 | 6 |
| 491 | >99 | 66 | 10 | 6 |
| 492 | >99 | >99 | 20 | 5 |
| 494 | 92 | 87 | 24 | 9 |
| 495 | >99 | 98 | 64 | 8 |
| 496 | >99 | 85 | 9 | 4 |
| 497 | >99 | >99 | 24 | 3 |
| 498 | >99 | 44 | 4 | 1 |
| 499 | 98 | 77 | 14 | 15 |
| 500 | 80 | 25 | 14 | 19 |
| 501 | 83 | 12 | 0 | 12 |
| 502 | >99 | 53 | 1 | 3 |
| 503 | 93 | 97 | 27 | 13 |
| 504 | >99 | 91 | 26 | 13 |
| 505 | >99 | >99 | 33 | 0 |
| 506 | >99 | 78 | 9 | 2 |
| 507 | >99 | 49 | 8 | 6 |
| 508 | 98 | 48 | 9 | 18 |
| 509 | >99 | 96 | 22 | 1 |
| 510 | >99 | 84 | 8 | 0 |
| 511 | >99 | >99 | 68 | 11 |
| 512 | 98 | 96 | 41 | 18 |
| 513 | >99 | 69 | 7 | 17 |
| 514 | >99 | 96 | 22 | 21 |
| 515 | >99 | 86 | 16 | 12 |
| 516 | >99 | 98 | 39 | 16 |
| 517 | >99 | 95 | 50 | 20 |
| 518 | >99 | >99 | 54 | 14 |
| 519 | >99 | >99 | 19 | 1 |
| 520 | >99 | >99 | 72 | 14 |
| 521 | >99 | >99 | 82 | 25 |
| 522 | 98 | 98 | 71 | 33 |
| 523 | >99 | 78 | 15 | 11 |
| 524 | >99 | 75 | 2 | 0 |
| 527 | >99 | 98 | 36 | 6 |
| 528 | 97 | 51 | 12 | 8 |
| 529 | >99 | 94 | 29 | 18 |
| 530 | >99 | 93 | 21 | 17 |
| 531 | 96 | 94 | 38 | 3 |
| 532 | >99 | >99 | 59 | 12 |
| 533 | 97 | 97 | 83 | 25 |
| 534 | >99 | 84 | 21 | 13 |
| 535 | 93 | 82 | 16 | 4 |
| 536 | >99 | 87 | 12 | 1 |
| 537 | 97 | 92 | 26 | 0 |
| 538 | 98 | 87 | 12 | 0 |
| 543 | 94 | 73 | 1 | 0 |
| 544 | 92 | 56 | 3 | 0 |
| 547 | >99 | 97 | 17 | 4 |
| 548 | >99 | 95 | 16 | 0 |
| 549 | >99 | 84 | 22 | 23 |
| 550 | >99 | 81 | 2 | 0 |
| 551 | >99 | 92 | 4 | 0 |
| 632 | 97 | 31 | 9 | 0 |
| 633 | 61 | 39 | 11 | 11 |
| 634 | 92 | >99 | 37 | 17 |
| 635 | 91 | 45 | 30 | 14 |
| 636 | 81 | 72 | 21 | 2 |
| 637 | 71 | 80 | 5 | 0 |
| 638 | >99 | 57 | 15 | 5 |

TABLE 6-5

| Compound No. | Inhibition Rate of PAI-1 Activity (%) Compound Concentration 3 μM | 1 μM | 0.3 μM | 0.1 μM |
|---|---|---|---|---|
| 639 | 87 | 91 | 12 | 6 |
| 640 | 92 | 92 | 19 | 0 |
| 641 | 95 | 95 | 53 | 9 |
| 642 | 93 | 94 | 57 | 16 |
| 643 | 92 | 38 | 18 | 0 |
| 644 | 93 | 30 | 8 | 27 |
| 645 | >99 | 95 | 26 | 6 |
| 646 | 86 | 38 | 15 | 4 |
| 647 | 98 | 95 | 43 | 27 |
| 648 | 89 | 86 | 23 | 4 |
| 649 | 97 | 96 | 64 | 10 |
| 650 | >99 | >99 | 40 | 16 |
| 651 | 74 | 15 | 0 | 0 |
| 652 | >99 | >99 | 22 | 19 |
| 653 | >99 | >99 | 95 | 43 |
| 654 | >99 | >99 | 19 | 4 |
| 655 | 97 | 44 | 0 | 3 |
| 656 | 88 | 95 | 64 | 24 |
| 657 | >99 | 99 | 20 | 15 |
| 658 | >99 | 97 | 20 | 9 |
| 659 | 96 | >99 | 26 | 12 |
| 661 | >99 | 27 | 11 | 6 |
| 662 | 95 | 98 | 28 | 18 |
| 665 | >99 | 67 | 8 | 9 |
| 666 | 98 | 89 | 21 | 0 |
| 669 | >99 | >99 | 34 | 28 |
| 670 | 94 | 97 | 55 | 6 |
| 671 | 92 | 23 | 12 | 26 |
| 672 | >99 | 92 | 15 | 3 |
| 673 | >99 | >99 | 15 | 0 |
| 674 | 98 | >99 | 55 | 5 |
| 675 | >99 | 95 | 14 | 10 |
| 676 | >99 | 60 | 4 | 7 |
| 677 | 98 | 93 | 17 | 19 |
| 678 | 94 | 97 | 33 | 19 |
| 679 | >99 | 84 | 9 | 6 |
| 680 | >99 | 77 | 9 | 7 |
| 682 | 98 | 32 | 5 | 2 |

TABLE 6-6

| Compound No. | Inhibition Rate of PAI-1 Activity (%) Compound Concentration 25 μM | 10 μM | 3 μM | 1 μM |
|---|---|---|---|---|
| 401 | 53 | 17 | 15 | — |
| 405 | 95 | >99 | 63 | 14 |
| 406 | 91 | 94 | 92 | 25 |
| 407 | 98 | >99 | 41 | 14 |
| 408 | 97 | 98 | 91 | 16 |
| 411 | 94 | >99 | 89 | 21 |
| 415 | >99 | >99 | 98 | 41 |
| 416 | >99 | >99 | 54 | 26 |
| 418 | 90 | 94 | 95 | 73 |
| 419 | >99 | 98 | 93 | 41 |
| 601 | 97 | 67 | 19 | 6 |
| 602 | >99 | 78 | 18 | 9 |
| 604 | 46 | 36 | 20 | 0 |
| 605 | 96 | 96 | 92 | 48 |
| 607 | 94 | 95 | 97 | 94 |
| 608 | 95 | 95 | 59 | 11 |
| 610 | 86 | 97 | 94 | 49 |
| 611 | 81 | 45 | 13 | 5 |
| 612 | >99 | 84 | 25 | 7 |
| 613 | 94 | >99 | >99 | 38 |
| 614 | 97 | 96 | 52 | 20 |
| 615 | 95 | >99 | 98 | 43 |
| 617 | >99 | >99 | 64 | 6 |
| 618 | >99 | 78 | 24 | 0 |

TABLE 6-6-continued

| Compound | Inhibition Rate of PAI-1 Activity (%) Compound Concentration | | | |
|---|---|---|---|---|
| No. | 25 μM | 10 μM | 3 μM | 1 μM |
| 627 | >99 | 57 | 14 | 0 |
| 628 | 90 | >99 | >99 | 40 |

From the above results, concentrations of the present application compounds that inhibit 50% of the human PAI-1 activity ($IC_{50}$) were calculated. The results are shown on the following tables.

TABLE 7-1

| Compound No. | $IC_{50}$ (μM) |
|---|---|
| 5 | 1.27 |
| 9 | 1.30 |
| 13 | 1.17 |
| 30 | 1.41 |
| 73 | 1.27 |
| 76 | 1.16 |
| 78 | 1.38 |
| 80 | 1.06 |
| 86 | 1.54 |
| 88 | 1.31 |
| 90 | 1.35 |
| 94 | 1.34 |
| 96 | 1.33 |
| 98 | 1.54 |
| 100 | 1.34 |
| 102 | 1.32 |
| 105 | 1.07 |
| 106 | 1.15 |
| 112 | 0.79 |
| 113 | 1.75 |
| 116 | 1.65 |
| 117 | 1.04 |
| 118 | 1.01 |
| 129 | 1.63 |
| 130 | 1.71 |
| 139 | 1.25 |
| 147 | 1.17 |
| 168 | 1.14 |
| 172 | 1.84 |
| 174 | 1.32 |
| 176 | 1.40 |
| 179 | 0.66 |
| 185 | 1.15 |
| 186 | 1.14 |
| 188 | 1.18 |
| 189 | 0.88 |
| 190 | 1.32 |
| 192 | 1.06 |
| 193 | 1.13 |
| 194 | 0.82 |
| 197 | 1.04 |
| 198 | 1.08 |
| 199 | 0.74 |
| 206 | 0.73 |
| 208 | 1.13 |
| 221 | 0.93 |
| 222 | 1.06 |
| 226 | 0.51 |
| 227 | 1.11 |
| 230 | 1.32 |
| 231 | 1.19 |
| 233 | 0.90 |
| 238 | 1.57 |
| 251 | 1.35 |
| 301 | 0.47 |
| 302 | 1.70 |
| 303 | 0.54 |
| 304 | 1.23 |

TABLE 7-1-continued

| Compound No. | $IC_{50}$ (μM) |
|---|---|
| 305 | 0.94 |
| 306 | 0.88 |
| 307 | 1.53 |
| 308 | 0.67 |
| 309 | 0.66 |
| 310 | 0.71 |
| 311 | 0.58 |
| 312 | 0.53 |
| 313 | 0.98 |
| 314 | 1.86 |
| 315 | 0.85 |
| 316 | 1.78 |
| 317 | 0.65 |
| 318 | 0.58 |
| 319 | 2.10 |
| 320 | 0.74 |
| 321 | 0.60 |
| 322 | 0.74 |
| 323 | 0.49 |
| 324 | 0.83 |
| 325 | 0.58 |
| 326 | 0.33 |
| 327 | 0.42 |
| 328 | 1.46 |
| 329 | 1.72 |
| 330 | 1.03 |
| 331 | 0.79 |
| 332 | 1.47 |
| 333 | 1.72 |
| 334 | 1.91 |
| 335 | 0.74 |
| 336 | 1.08 |
| 337 | 2.02 |
| 351 | 1.95 |
| 352 | 0.74 |
| 353 | 0.51 |
| 354 | 0.56 |
| 355 | 0.64 |
| 356 | 0.93 |
| 357 | 0.77 |
| 358 | 0.90 |

TABLE 7-2

| Compound No. | $IC_{50}$ (μM) |
|---|---|
| 359 | 1.64 |
| 360 | 1.59 |
| 361 | 0.83 |
| 362 | 0.84 |
| 363 | 0.83 |
| 364 | 0.11 |
| 365 | 0.11 |
| 366 | 1.06 |
| 367 | 0.90 |
| 368 | 0.45 |
| 369 | 0.69 |
| 370 | 0.94 |
| 371 | 0.69 |
| 372 | 0.46 |
| 373 | 1.58 |
| 374 | 0.88 |
| 375 | <0.1 |
| 376 | 0.79 |
| 377 | 0.48 |
| 378 | 0.62 |
| 379 | 0.64 |
| 380 | <0.1 |
| 381 | 1.04 |
| 382 | 0.65 |
| 383 | 1.34 |
| 384 | 0.51 |
| 385 | <0.1 |

TABLE 7-2-continued

| Compound No. | $IC_{50}$ (μM) |
|---|---|
| 386 | 0.47 |
| 387 | <0.1 |
| 388 | <0.1 |
| 389 | <0.1 |
| 390 | 0.65 |
| 391 | 0.78 |
| 392 | 0.71 |
| 393 | 0.69 |
| 394 | 0.22 |

Test Example 3

Rat PAI-1 Inhibitory Activity

[Method]

Except using recombinant rat PAI-1 (Molecular Innovations, Inc) instead of recombinant human PAI-1, tests were carried out in the same manner as the Test Example 2.

[Results]

In the following, inhibition rates of rat PAI-1 activity are shown.

TABLE 8

| Compound | Inhibition Rate of PAI-1 Activity (%) Compound Concentration | | | |
|---|---|---|---|---|
| No. | 10 μM | 3 μM | 1 μM | 0.3 μM |
| 5 | 93 | 52 | 15 | 5 |
| 9 | 96 | 71 | 15 | 0 |
| 13 | >99 | 69 | 14 | 0 |
| 30 | 89 | 47 | 5 | 0 |
| 73 | 98 | 75 | 13 | 0 |
| 76 | 86 | 56 | 6 | 0 |
| 78 | 90 | 71 | 4 | 0 |
| 80 | 84 | 71 | 11 | 0 |
| 86 | 69 | 34 | 12 | 0 |
| 88 | 83 | 51 | 0 | 0 |
| 90 | 90 | 77 | 0 | 0 |
| 94 | 91 | 45 | 15 | 0 |
| 96 | 96 | 49 | 14 | 3 |
| 98 | 95 | 39 | 10 | 0 |
| 100 | >99 | 70 | 7 | 0 |
| 102 | 93 | 55 | 12 | 0 |
| 105 | 90 | 74 | 6 | 0 |
| 106 | >99 | 85 | 16 | 0 |
| 112 | 96 | 75 | 14 | 0 |
| 113 | 99 | 33 | 9 | 0 |
| 116 | 98 | 43 | 12 | 2 |
| 117 | 94 | 63 | 7 | 0 |
| 118 | 93 | 77 | 16 | 0 |
| 129 | 90 | 46 | 14 | 2 |
| 130 | >99 | 50 | 16 | 1 |
| 139 | 88 | 85 | 22 | 0 |
| 147 | 87 | 70 | 14 | 0 |
| 168 | 97 | 61 | 12 | 0 |
| 172 | 97 | 49 | 6 | 0 |
| 174 | 94 | 76 | 11 | 0 |
| 176 | >99 | 71 | 23 | 0 |
| 179 | >99 | >99 | 38 | 7 |
| 185 | 76 | 85 | 17 | 3 |
| 186 | 89 | 83 | 27 | 2 |
| 188 | >99 | 84 | 14 | 0 |
| 189 | >99 | 93 | 32 | 9 |
| 190 | >99 | 66 | 11 | 0 |
| 192 | 96 | 76 | 8 | 0 |
| 193 | 70 | 81 | 26 | 2 |
| 194 | >99 | 98 | 39 | 5 |
| 197 | 75 | 84 | 37 | 0 |
| 198 | 89 | 84 | 12 | 4 |

TABLE 8-continued

| Compound | Inhibition Rate of PAI-1 Activity (%) Compound Concentration | | | |
|---|---|---|---|---|
| No. | 10 μM | 3 μM | 1 μM | 0.3 μM |
| 199 | >99 | 97 | 35 | 0 |
| 206 | 88 | 90 | 29 | 3 |
| 208 | 81 | 82 | 12 | 0 |
| 211 | 87 | 78 | 17 | 4 |
| 212 | 67 | 73 | 40 | 8 |
| 213 | 78 | 90 | 26 | 8 |
| 214 | 97 | 77 | 8 | 0 |
| 215 | 97 | 84 | 16 | 2 |
| 221 | NT | 89 | 37 | 10 |
| 222 | NT | 91 | 32 | 3 |
| 226 | >99 | 92 | 49 | 9 |
| 227 | 95 | 77 | 14 | 0 |
| 230 | 94 | 83 | 13 | 0 |
| 231 | >99 | 89 | 18 | 3 |
| 233 | >99 | 93 | 20 | 4 |
| 238 | 98 | 46 | 8 | 0 |

From the above results, concentrations of the present application compounds that inhibit 50% of the rat PAI-1 activity ($IC_{50}$) were calculated. The results are shown on the following table.

TABLE 9

| Compound No. | $IC_{50}$ (μM) |
|---|---|
| 5 | 2.80 |
| 9 | 2.07 |
| 13 | 2.17 |
| 30 | 3.31 |
| 73 | 2.10 |
| 76 | 2.88 |
| 78 | 2.33 |
| 80 | 2.20 |
| 86 | 5.21 |
| 88 | 3.24 |
| 90 | 2.65 |
| 94 | 3.18 |
| 96 | 2.90 |
| 98 | 3.53 |
| 100 | 2.30 |
| 102 | 2.75 |
| 105 | 2.19 |
| 106 | 1.71 |
| 112 | 1.98 |
| 113 | 3.68 |
| 116 | 3.24 |
| 117 | 2.48 |
| 118 | 1.92 |
| 129 | 3.13 |
| 130 | 2.76 |
| 139 | 1.61 |
| 147 | 2.16 |
| 168 | 2.45 |
| 172 | 3.04 |
| 174 | 2.04 |
| 176 | 1.87 |
| 179 | 1.11 |
| 185 | 1.72 |
| 186 | 1.55 |
| 188 | 1.79 |
| 189 | 1.28 |
| 190 | 2.30 |
| 192 | 2.14 |
| 193 | 1.82 |
| 194 | 1.14 |
| 197 | 1.42 |
| 198 | 1.84 |
| 199 | 1.18 |
| 206 | 1.39 |

TABLE 9-continued

| Compound No. | $IC_{50}$ (μM) |
|---|---|
| 208 | 1.89 |
| 221 | 1.27 |
| 222 | 1.34 |
| 226 | 1.00 |
| 227 | 1.95 |
| 230 | 1.83 |
| 231 | 1.57 |
| 233 | 1.46 |
| 238 | 3.14 |

Test Example 4

Human PAI-1 Inhibitory Activity

[Method]

100 μl of tPA solution, where one-chain recombinant tPA (hereinafter referred to as tPA; American diagnostica, inc.) had been diluted with Buffer A to achieve a concentration of 10 μg/ml, was added to each well of a 96-well plate (Nunc Maxisorp), and the plate was incubated for one night at 4° C. to be coated with tPA. Then, after suction of tPA solution from the 96-well plate, the plate was rinsed successively with Buffer A and Buffer B.

To Buffer B, solutions of the compound according to the present invention dissolved with DMSO (final DMSO concentration: 0.2%) and recombinant human PAI-1 (Molecular Innovations, Inc.) were added. The mixtures were blended so that the final concentrations would be 0.1 to 3.0 μM and 50 ng/ml respectively, and were incubated for 15 minutes on ice. These mixed solutions were added to the rinsed 96-well plate at 100 μl/well, and incubated for 60 minutes at room temperature. To prepare a calibration curve, PAI-1 solutions without the compound according to the present invention (solutions where the final concentrations being 100, 50, 25, 12.5, 6.25, 3.13, or 1.56 ng/ml PAI-1) were added at 100 μl/well, and the plate was incubated for 60 minutes at room temperature, as standard.

After incubation, the reaction mixture was removed by suction, and each well was rinsed with Wash Buffer. Next, anti-human PAI-1 monoclonal antibody (PROGEN Inc.) diluted with Buffer C to be 3.0 μg/ml was added to the 96-well plate at 100 μl/well, and the plate was incubated for 1 hour at room temperature. After rinsing each well with Wash Buffer, alkaline phosphatase-labeled goat anti-mouse IgG (H+L) (Jackson ImmunoResearch, Inc.) diluted with Buffer D to be 0.12 μg/ml was added at 100 μl/well, and the plate was incubated for 1 hour at room temperature. After rinsing each well with Wash Buffer, 1.0 mg/ml p-Nitrophenyl Phosphate (SIGMA) was added to the 96-well plate at 100 μl/well to start the reaction. After 30 to 60 minutes, 25 μl of 0.5 N NaOH was added to stop the reaction, and the absorbance was measured at 405 nm using a multiplate reader (GENios; TECAN G.M.B.H.). Based on the calibration curve prepared from the standard wells, amounts of PAI-1 bound to tPA in the wells that had been treated with the compound according to the present invention were calculated, and the PAI-1 inhibition rates by the compounds according to the present invention were obtained by the following equation. [PAI-1 Inhibition Rate (%)]=[1−(amount of PAI-1 bound to tPA on the well by treatment with the compound according to the present invention)/(amount of PAI-1 bound to tPA on the well by treatment with PAI-1 solution not including the compound according to the present invention (solution having the final concentration of 50 ng/ml PAI-1)]×100

<Composition of Buffer A>

0.1 M Tris-HCl, 150 mM NaCl, pH 7.7

<Composition of Buffer B>

50 mM sodium phosphate, 0.1 M NaCl, 1 mM EDTA, pH 6.6

<Composition of Buffer C>

50 mM sodium phosphate, 100 mM NaCl, pH 7.4

<Composition of Buffer D>

0.01 M Tris-HCl, 0.25 M NaCl, pH 8.0

<Composition of Wash Buffer>

0.05% Tween 20, 0.1% BSA in Buffer A

<Composition of p-Nitrophenyl Phosphate Solution>

1 M Diethanolamine 0.5 mM $MgCl_2$, p-Nitrophenyl phosphate, pH 9.8

In the following, inhibition rates of human PAI-1 activities are shown.

TABLE 10

| Compound | Inhibition Rate of PAI-1 Activity (%) Compound Concentration | | |
|---|---|---|---|
| No. | 3 μM | 1 μM | 0.3 μM |
| 5 | 67 | 23 | 9 |
| 13 | 41 | 14 | 7 |
| 78 | 83 | 39 | 20 |
| 80 | 29 | 0 | 0 |
| 90 | 70 | 9 | 2 |
| 100 | 79 | 37 | 7 |
| 102 | 83 | 0 | 0 |
| 105 | 33 | 4 | 7 |
| 106 | 17 | 7 | 0 |
| 112 | 36 | 6 | 0 |
| 118 | 46 | 4 | 0 |
| 129 | 19 | 15 | 5 |
| 130 | 15 | 3 | 1 |
| 139 | 32 | 10 | 6 |
| 174 | 32 | 7 | 0 |
| 176 | 29 | 9 | 9 |
| 185 | 49 | 20 | 10 |
| 186 | 53 | 37 | 15 |
| 189 | 70 | 30 | 16 |
| 190 | 55 | 9 | 0 |
| 194 | 56 | 22 | 6 |
| 197 | 73 | 34 | 21 |
| 198 | 33 | 4 | 6 |
| 199 | 73 | 41 | 18 |
| 206 | 40 | 17 | 0 |
| 208 | 36 | 13 | 0 |
| 221 | 38 | 13 | 0 |
| 226 | 65 | 26 | 11 |
| 233 | 50 | 28 | 13 |

Test Example 5

Anti-Thrombotic Activity (Rat AV Shunt Model)

AV shunt model using 7-week old male Crlj: CD (SD) rats were prepared, and anti thrombotic activities when the compounds according to the present invention were administered orally were examined.

[Method]

(1) Preparation of Administering Solution of Test Compounds

Required amount of the test compounds were weighed and suspended by adding 0.5% CMC (carboxymethylcellulose)-Na solution little by little, and the solutions (10 mg/kg or 30 mg/kg solution) were prepared so that their final concentration became 2 mg/ml or 6 mg/ml using a graduated cylinder. 5 ml was prepared for 1 course.

(2) Administration

To 7-week old Crlj: CD (SD) male rats, 5 ml/kg of vehicle (0.5% CMC-Na solution) or 5 ml/kg of the administering solution of the test compound (10 mg/kg or 30 mg/kg) were administered orally for 4 days. The administration on the 4th day was carried out about 1 hour before the following perfusion start.

(3) Preparation of AV Shunt Model and Measurement of Thrombus Weight

A 6.5 cm silk thread (Matsuda Ika Kogyou; No. 1-0) was put through in an 8 cm No. 7 polyethylene tube (Hibiki), and No. 3 tubes (12.5 cm) were connected to both of the ends via No. 5 tube (1.5 cm), to prepare a catheter for shunt. On the connected part where the silk thread was through, parafilm was wrapped around to avoid blood leakage.

Rats were anesthetized with pentobarbital (50 mg/kg; intraperitoneally). Saline was filled in the above catheter, and each of the ends of the catheter was inserted in right carotid artery and left carotid artery, respectively, and blood was circulated. 30 minutes later, the catheter was pinched with forceps to stop blood flow, and tube parts where the silk thread was through were cut and removed. The silk thread was carefully removed from the tubes, remaining wet weight was weighed after removing the liquid phase with filter paper, and further subtraction of the weight of the silk thread, gave the thrombus weight.

(4) Statistical Treatment

For the thrombus weight in each group, an average value±standard error (S.E.) was calculated. For the significance test between the vehicle administered group and the compound according to the present invention administered group, Dunnett's multiple comparison was carried out (significance level 5%). For the test, the SAS System Release 8.2 (TS2M0) for Windows (Registered Trademark) (SAS Institute Inc.) and its cooperative system EXSAS Ver. 7.10 (Arm Systex Co. Ltd.) were employed.

[Results]

The results are shown in the following.

TABLE 11

| Test Compound | Dose (mg/kg/day) | Number of Examples | Thrombus Weight (mg) |
|---|---|---|---|
| Vehicle (0.5% CMC-Na) | — | 5 | 72.7 ± 2.7 |
| Compound 5 | 10 | 5 | 57.5 ± 5.0* |
| Compound 17 | 30 | 5 | 60.4 ± 3.8* |
| Compound 129 | 10 | 5 | 56.7 ± 3.8** |

*$p < 0.05$; **$p < 0.01$

The invention claimed is:

1. A compound represented by the following formula (I) or a salt thereof:

[Formula 1]

(I)

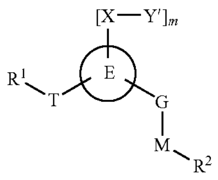

wherein:

m represents 1;

E represents the following formula (II):

[Formula 2]

(II)

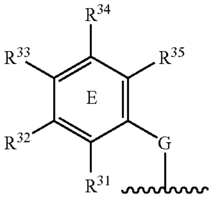

wherein $R^{35}$ represents the formula —X—Y'; and one of $R^{31}$, $R^{32}$, $R^{33}$ and $R^{34}$ represents the formula $R^1$-T-, and each of the other three independently represents a hydrogen atom or a group selected from the following substituent group γ-1;

$R^1$ represents a $C_{6-10}$ aryl group or a $C_{6-10}$ aryl group substituted with one to five groups selected from the following substituent group α-1, wherein, when the number of the substituents is two or more, each of the substituents may be the same or different;

T represents a single bond or —O—;

G represents an oxygen atom;

$R^2$ represents a $C_{6-10}$ aryl group or a $C_{6-10}$ aryl group substituted with one to five groups selected from the following substituent group β-1, wherein, when the number of the substituents is two or more, each of the substituents may be the same or different;

X represents —CH═CH—, or —$CH_2CH_2$—;

Y' represents a carboxy group; and

M represents a single bond, or the formula —$Z^2$—O— wherein, the bond at the left-hand end binds to G, and the bond at the right-hand end binds to $R^2$ in each of the formulas; and $Z^2$ represents a $C_{1-9}$ straight chain alkylene group; provided that:

when $R^{33}$ is the formula $R^1$-T-; each of $R^{31}$, $R^{32}$ and $R^{34}$ is a hydrogen atom; $R^1$ is a $C_{6-10}$ aryl group or a $C_{6-10}$ aryl group substituted with a group or groups selected from a halogen atom, a nitro group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group, an amino group and a $C_{1-6}$ alkylenedioxy group; $R^2$ is a $C_{6-10}$ aryl group or a $C_{6-10}$ aryl group substituted with a group or groups selected from a halogen atom, a nitro group, a $C_{1-6}$ alkroup, a halogenated $C_{1-6}$ alkyl group, a $C_{1-6}$ alkoxy group, a halogenated $C_{1-6}$ alkoxy group, a phenyl group and a carboxy group; and M is a single bond; then T represents is —O—;

[substituent group α-1]

a halogen atom, a cyano group, a nitro group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group, an amino group and a $C_{1-6}$ alkylenedioxy group;

[substituent group β-1]

a halogen atom, a nitro group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group, a phenyl group and a carboxy group;

[substituent group γ-1]

a halogen atom, a $C_{1-6}$ alkyl group and a $C_{1-6}$ alkoxy group.

2. A medicament comprising the compound according to claim 1 or a pharmacologically acceptable salt thereof.

3. The compound or the salt thereof according to claim 1, wherein one of $R^{31}$, $R^{32}$, $R^{33}$ and $R^{34}$ is the formula $R^1$-T-, and each of the other three is a hydrogen atom.

4. The compound or the salt thereof according to claim 3, wherein $R^{32}$ is the formula $R^1$-T-.

5. The compound or the salt thereof according to claim 1, wherein $R^1$ is a phenyl group substituted with one or two groups selected from the substituent group α-1.

6. The compound or the salt thereof according to claim 1, wherein $R^1$ is a phenyl group substituted with a group selected from a $C_{1-6}$ alkyl group, a $C_{1-6}$ alkoxy group, and a halogenated $C_{1-6}$ alkoxy group.

7. The compound or the salt thereof according to claim 1, wherein $R^1$ is a phenyl group substituted with a halogenated $C_{1-6}$ alkoxy group.

8. The compound or the salt thereof according to claim 1, wherein $R^1$ is a group selected from the group consisting of:

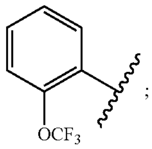 ; 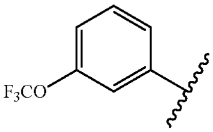 ; and

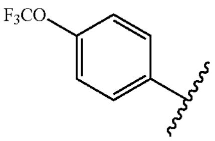 .

9. The compound or the salt thereof according to claim 1, wherein T is a single bond.

10. The compound or the salt thereof according to claim 1, wherein $R^2$ is a phenyl group substituted with one or two groups selected from the substituent group β-1.

11. The compound or the salt thereof according to claim 1, wherein $R^2$ is a phenyl group substituted with a group selected from a $C_{1-6}$ alkyl group, a halogenated $C_{1-6}$ alkyl group, a $C_{1-6}$ alkoxy group, and a halogenated $C_{1-6}$ alkoxy group.

12. The compound or the salt thereof according to claim 1, wherein $R^2$ is a group selected from the group consisting of:

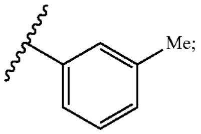 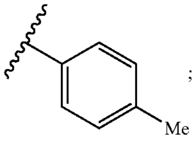 ;

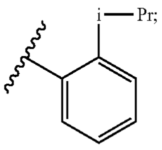 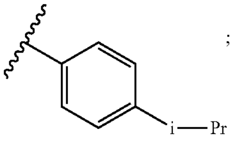 ;

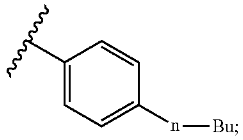 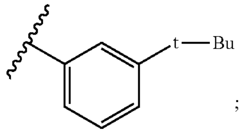 ;

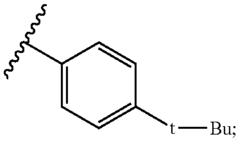 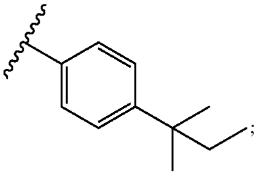

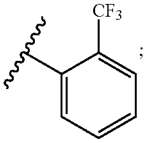 ; 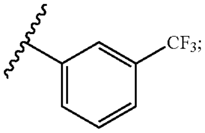

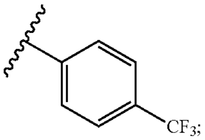 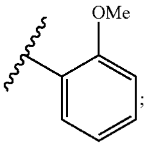

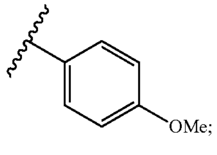 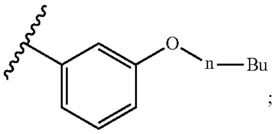 ;

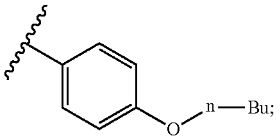 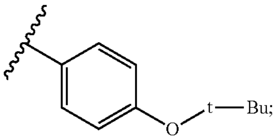

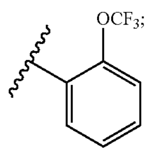 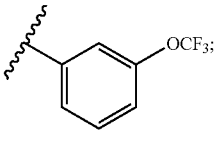 and

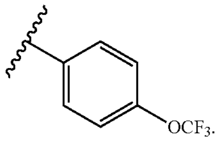

13. The compound or the salt thereof according to claim 1, wherein X is $-CH_2CH_2-$.
14. The compound or the salt thereof according to claim 1, wherein M is a single bond.
15. The compound or the salt thereof according to claim 1, wherein the compound is selected from the group consisting of:
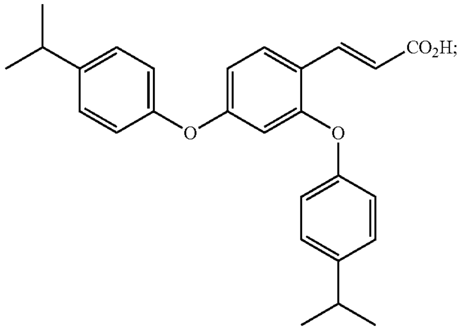
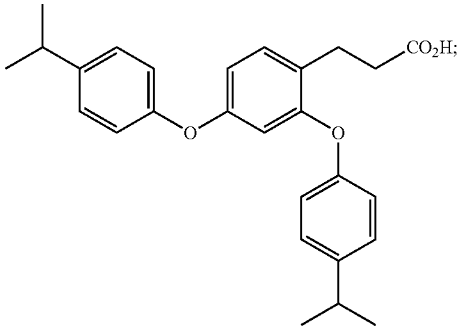
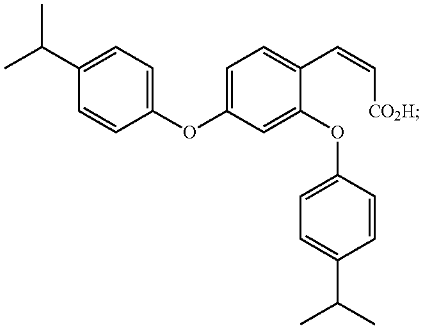
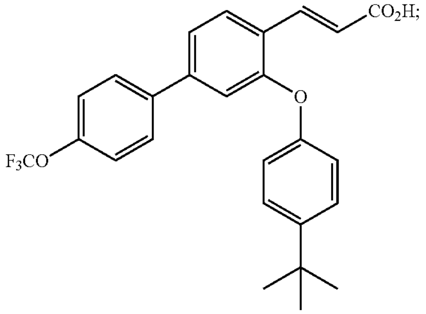
-continued
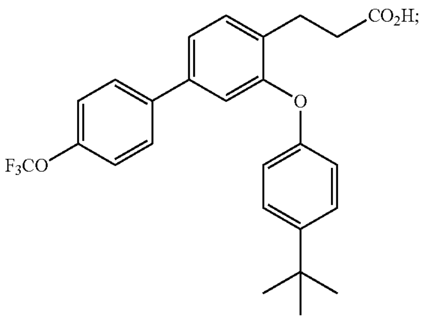
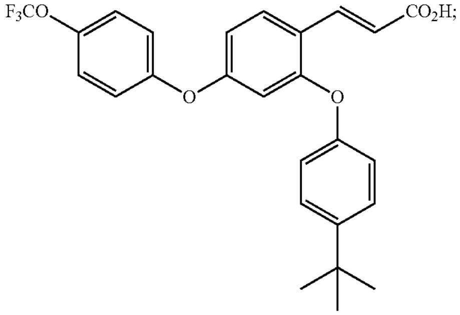
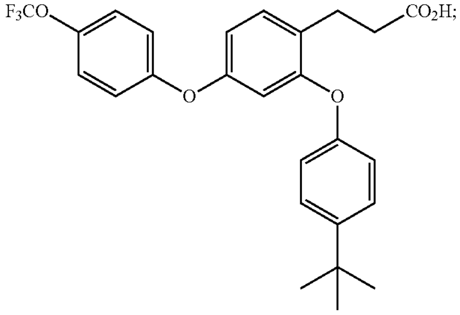
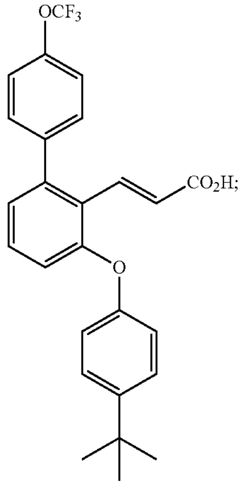
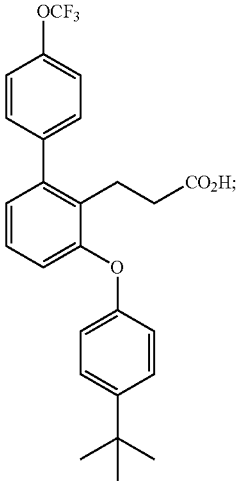

-continued
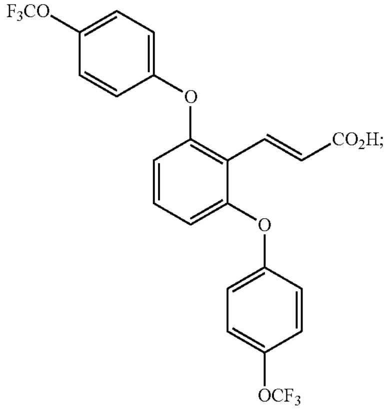
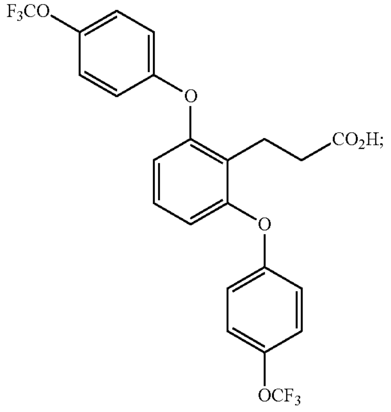
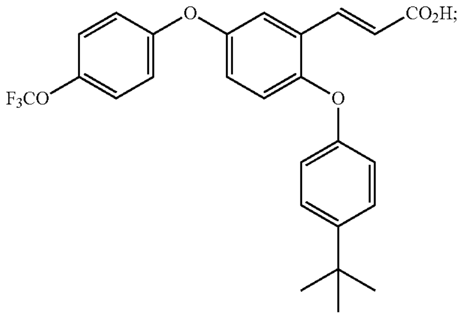
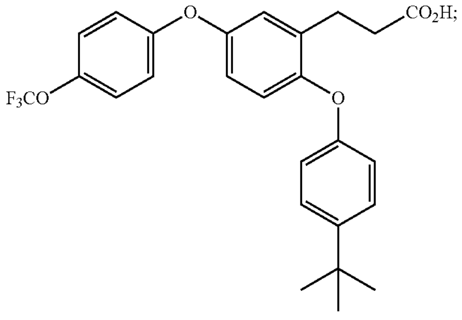
-continued
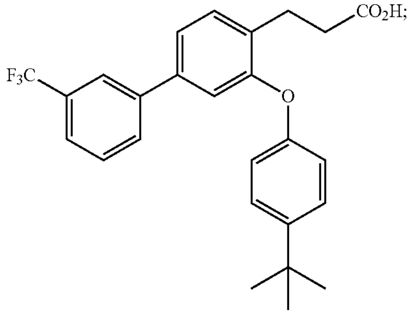
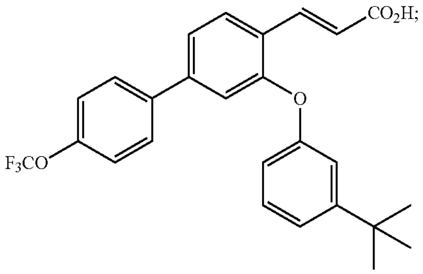
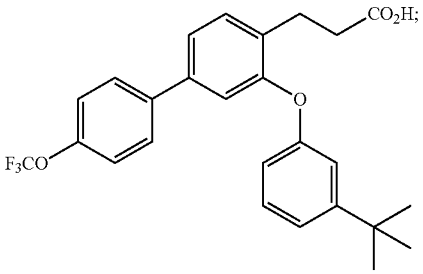
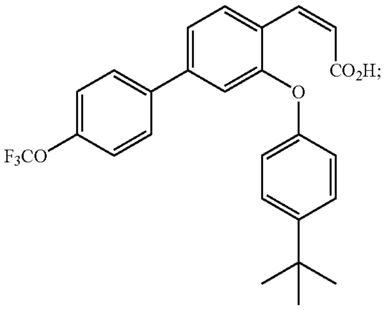
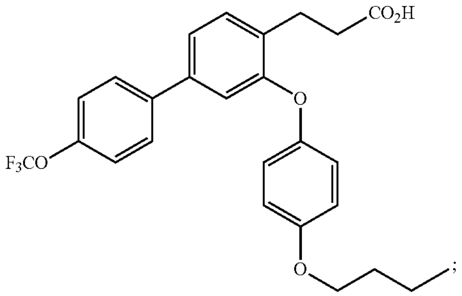
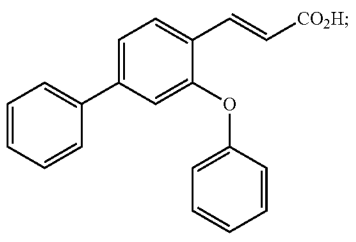

-continued
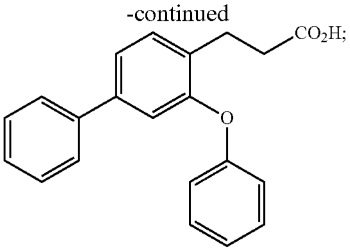
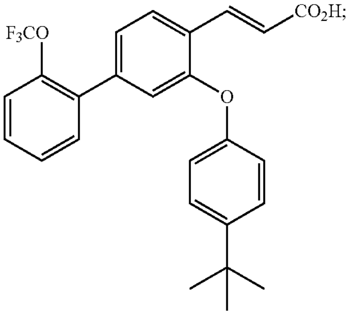
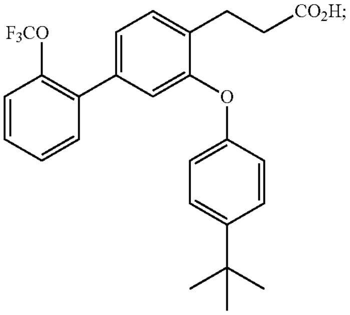
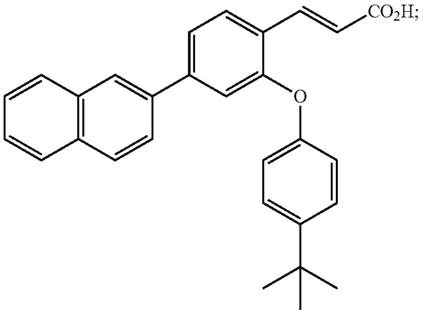
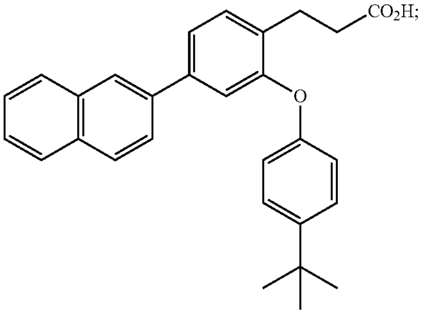
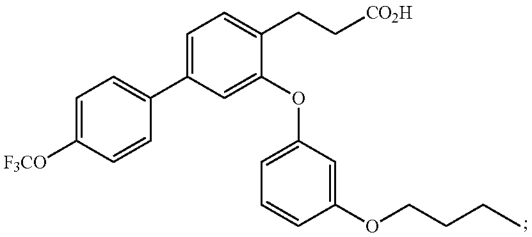
-continued
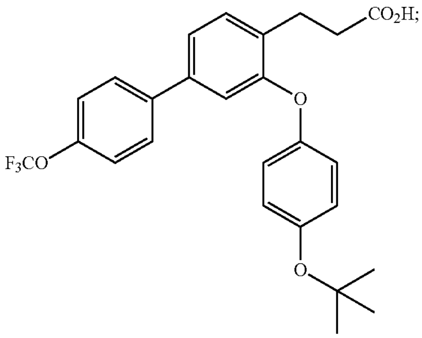
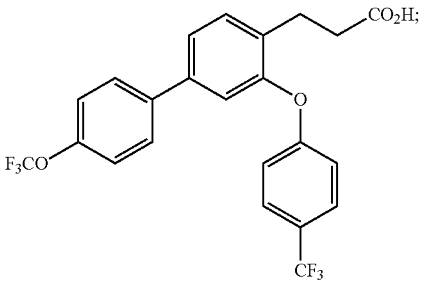
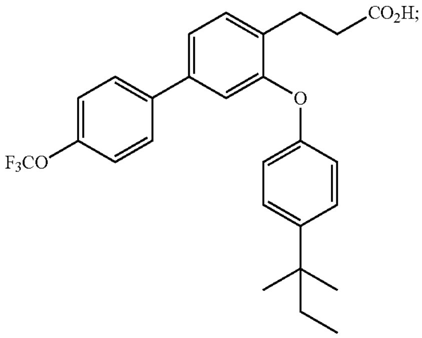
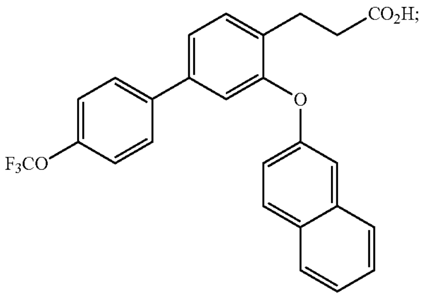
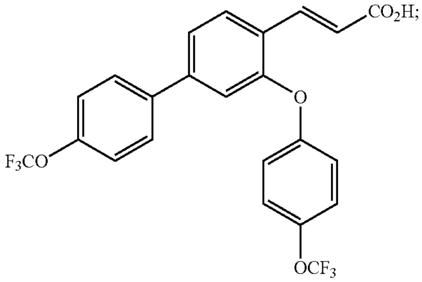

-continued
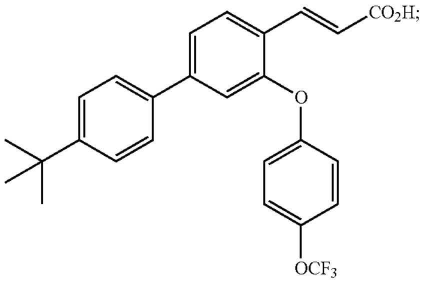
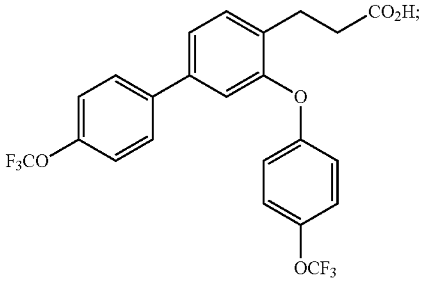
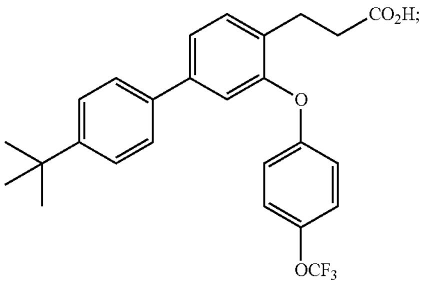
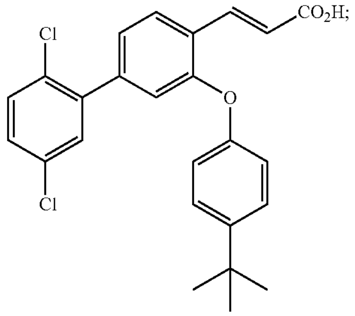
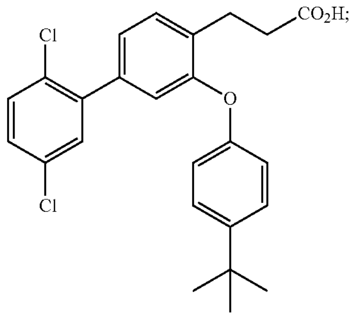
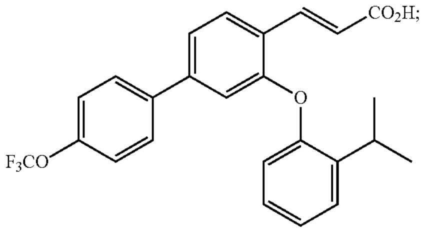
-continued
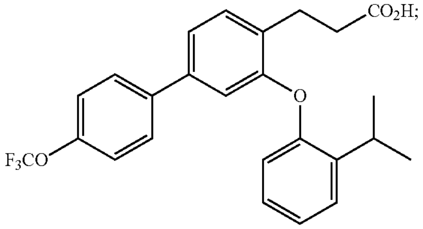
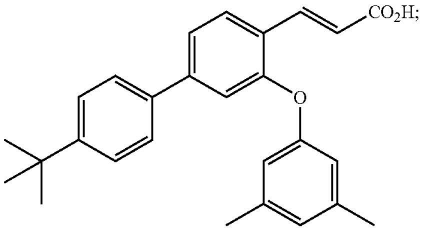
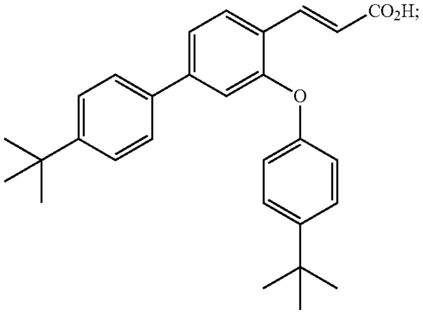
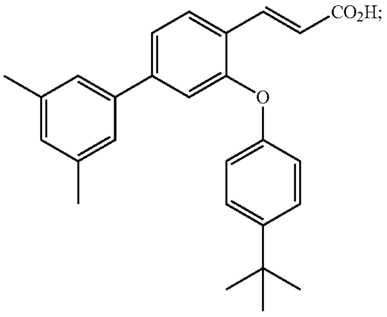
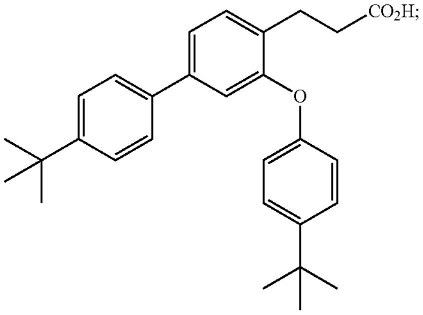
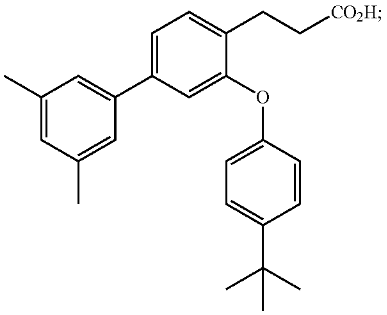

-continued
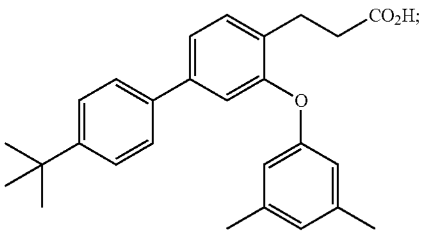
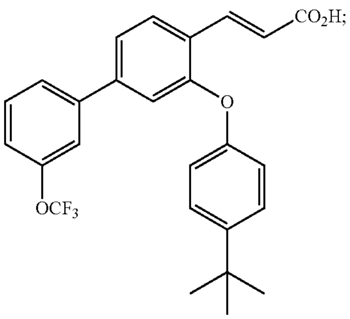
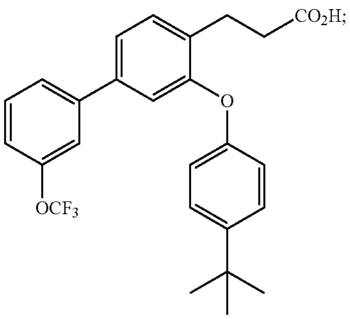
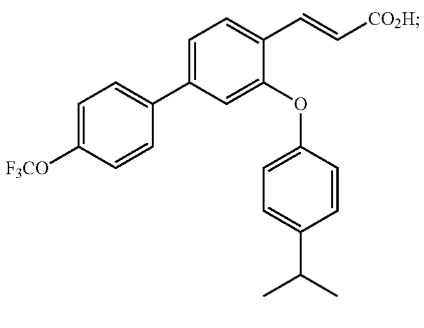
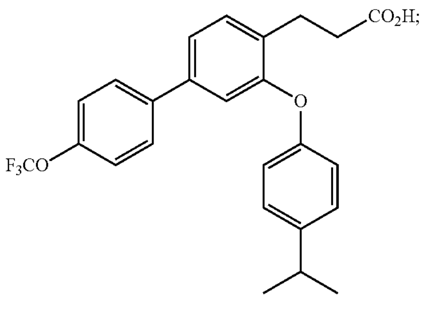
-continued
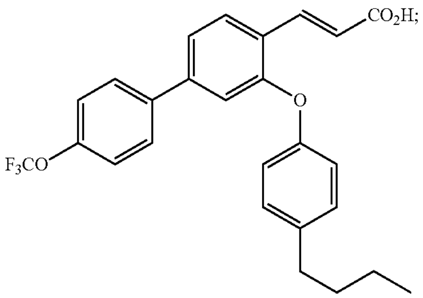
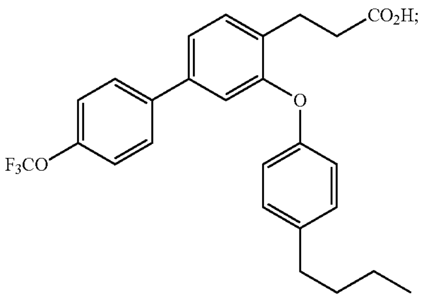
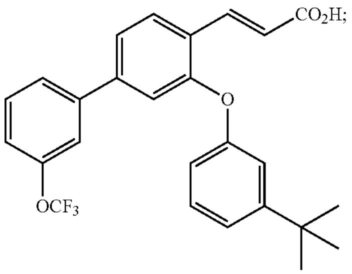
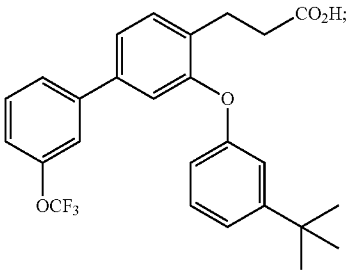
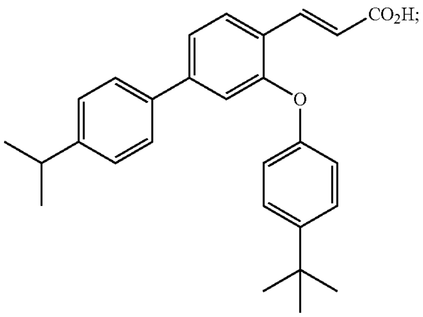

-continued
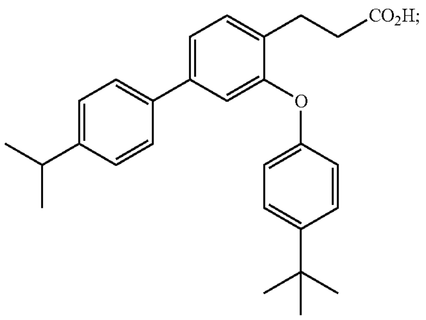
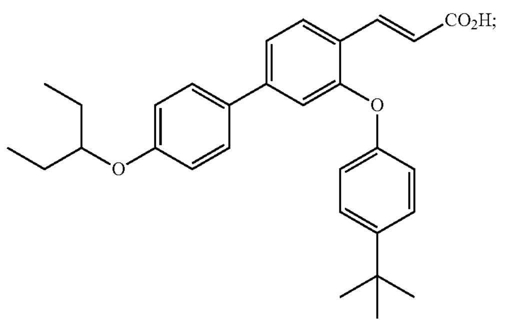
and
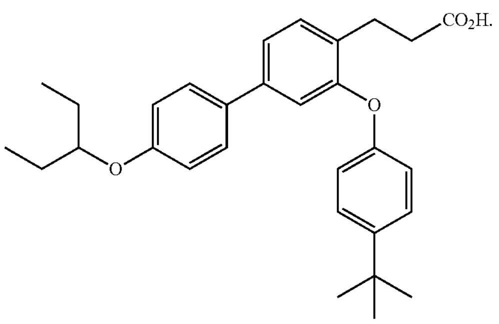
16. The compound or the salt thereof according to claim 15, wherein the compound is selected from the group consisting of:
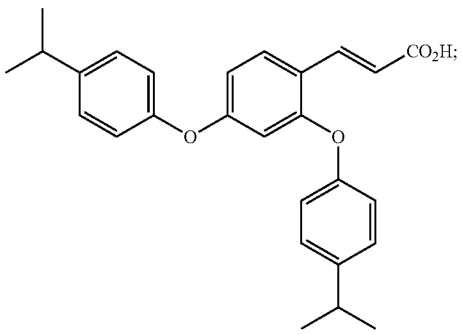
-continued
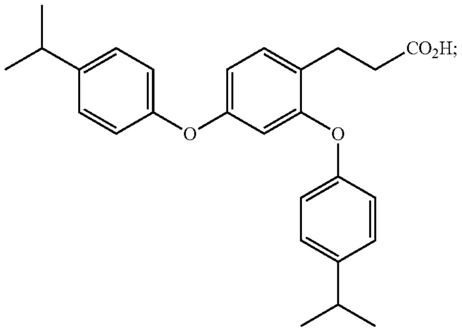
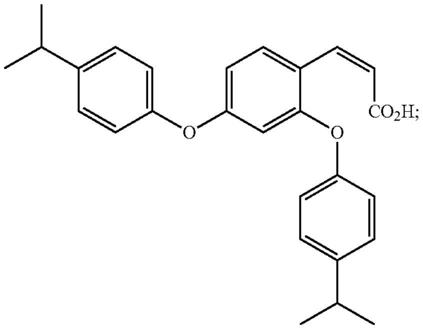
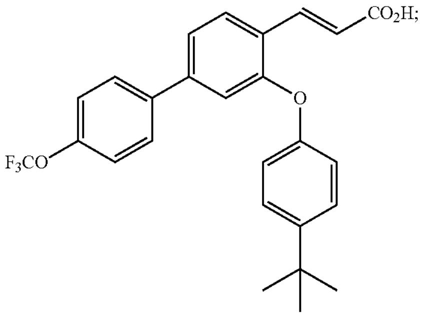
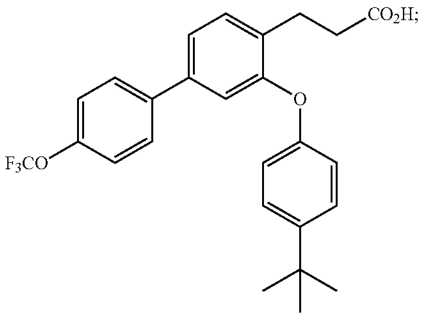
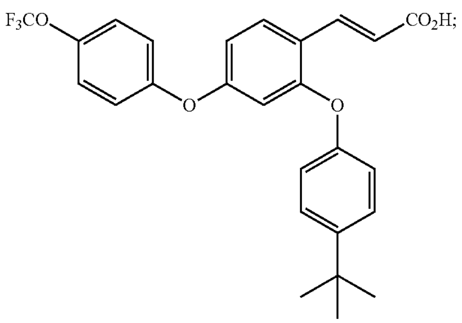

-continued
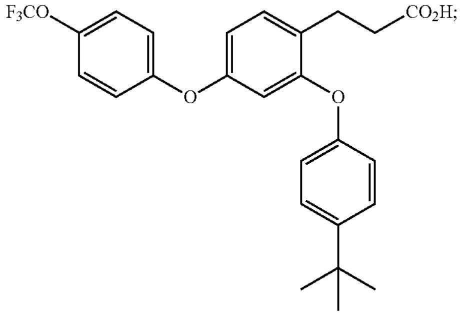
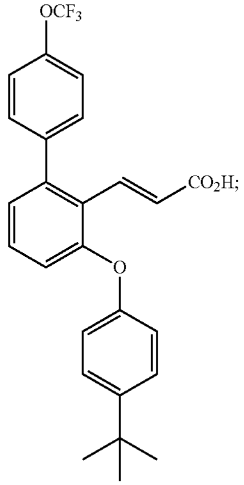
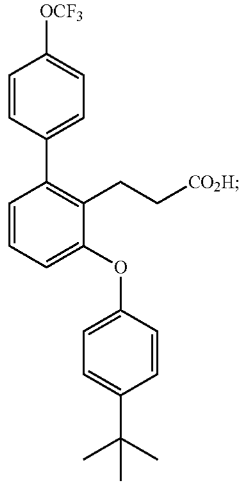
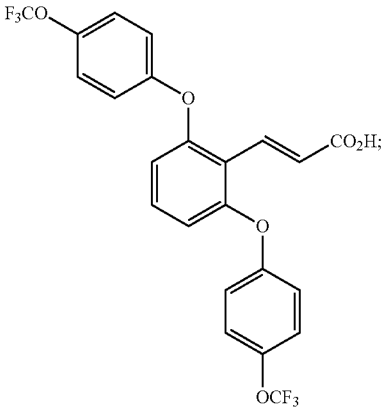
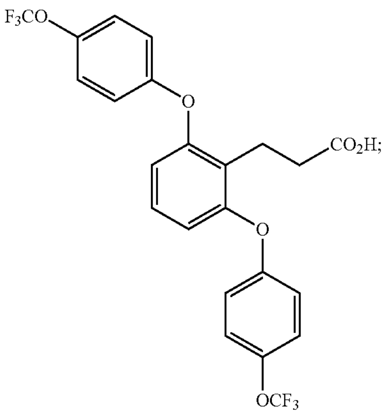
-continued
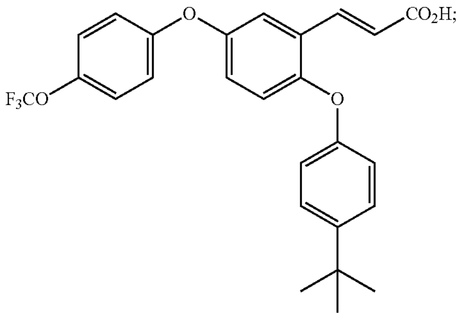
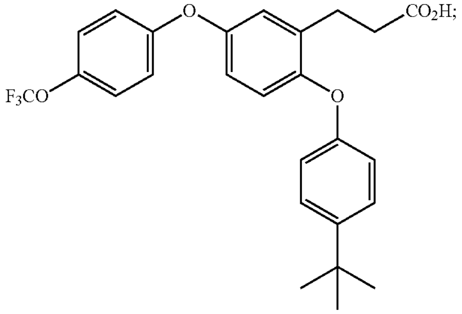
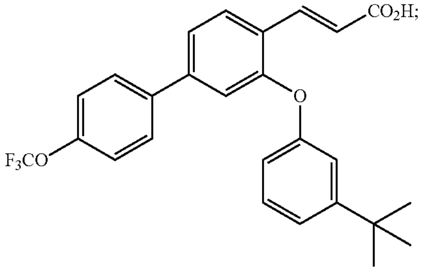
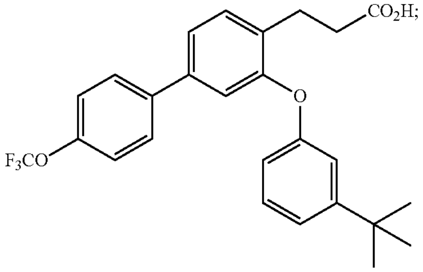
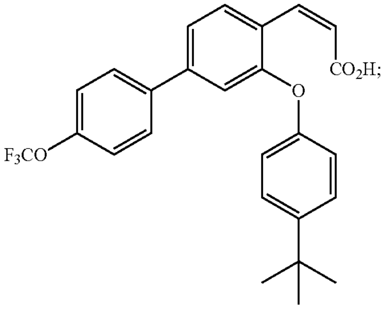

-continued
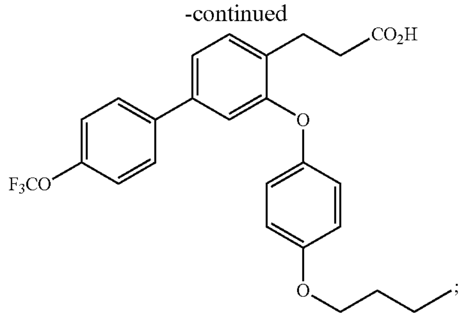
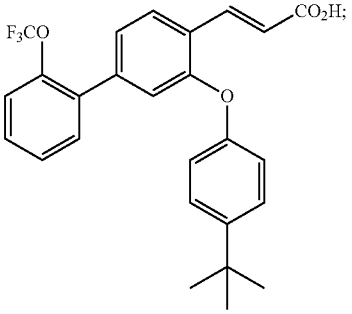
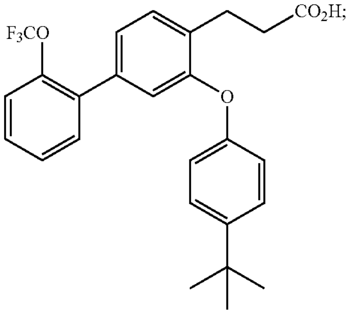
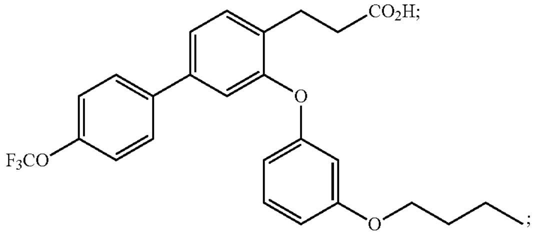
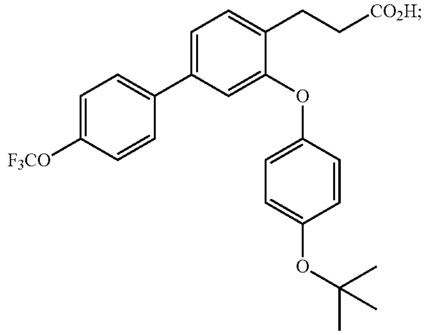
-continued
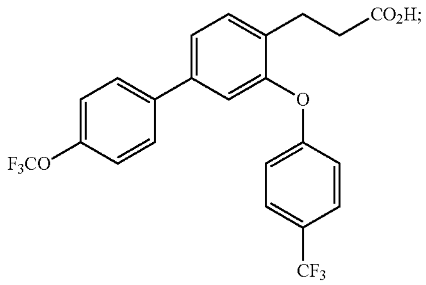
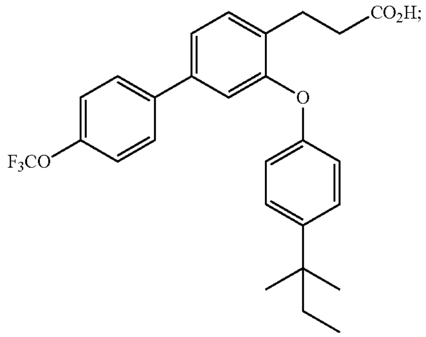
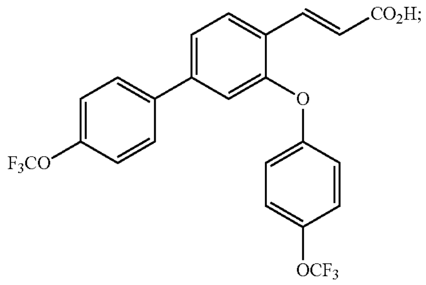
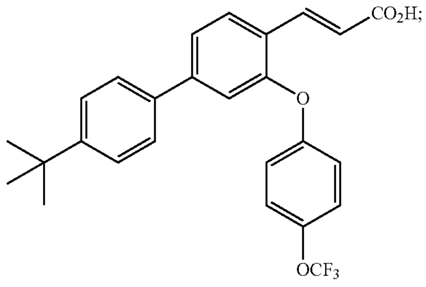
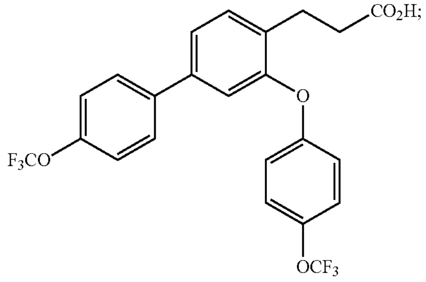

-continued
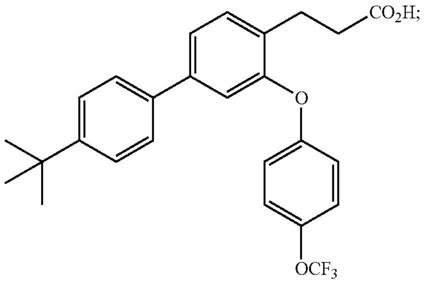
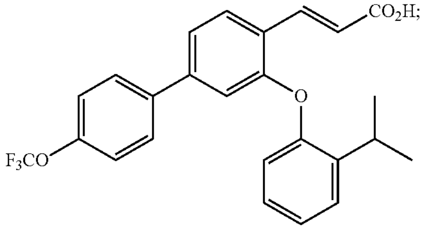
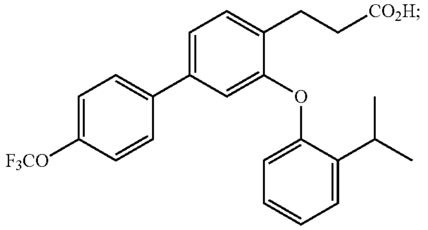
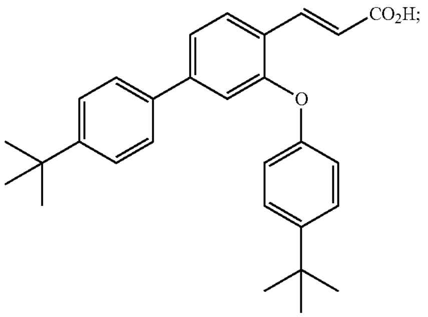
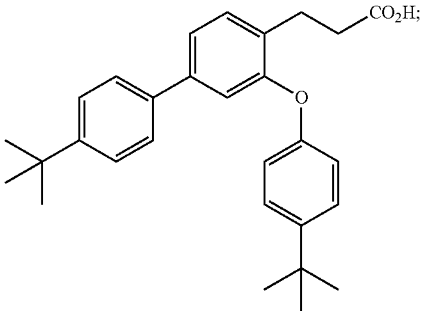
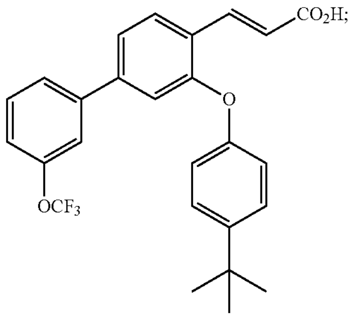
-continued
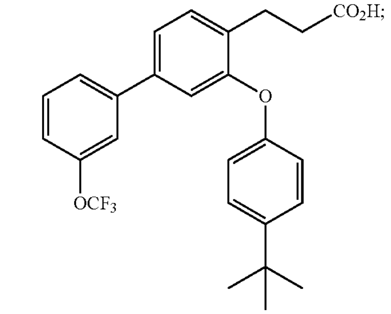
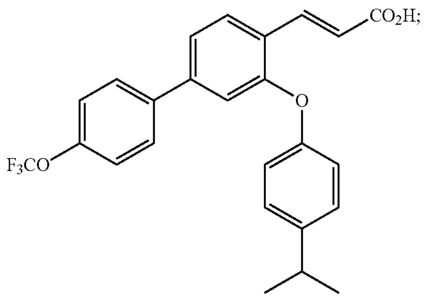
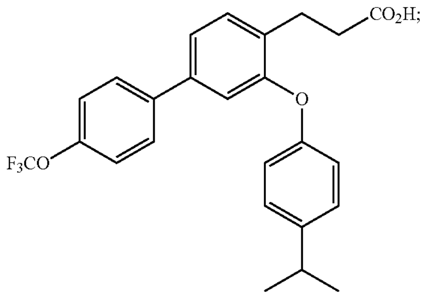
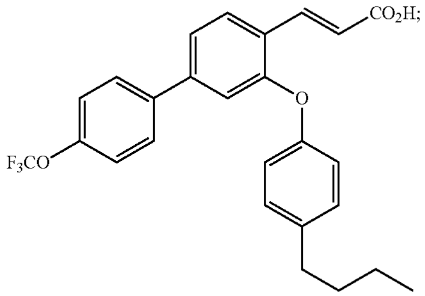
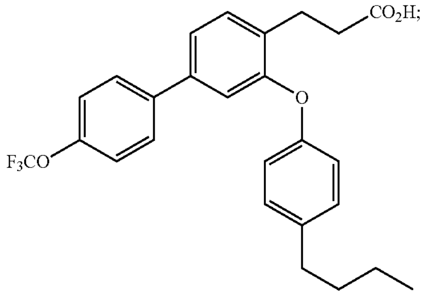

-continued
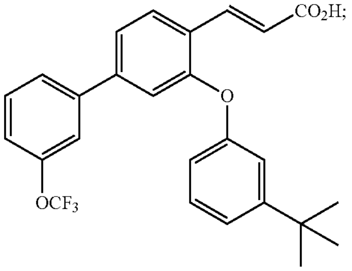
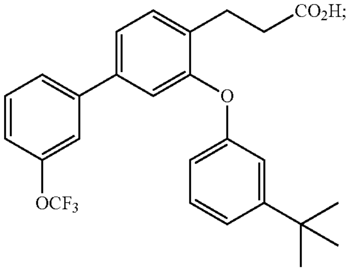
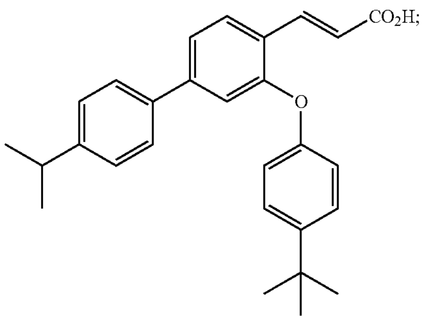
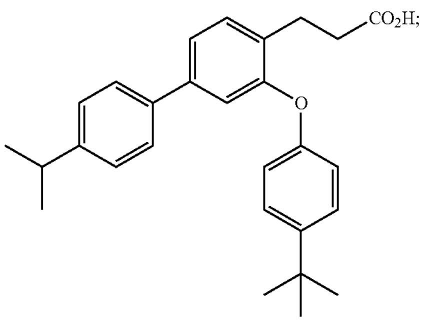
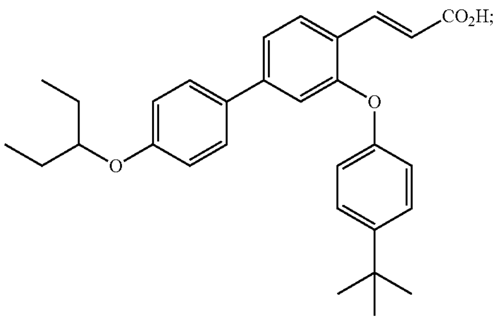
and
-continued
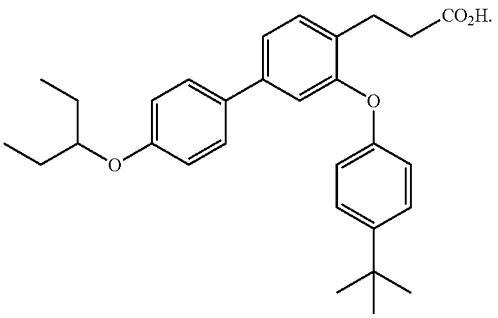
17. The compound or salt thereof according to claim 15, wherein, the compound is selected from the group consisting of:
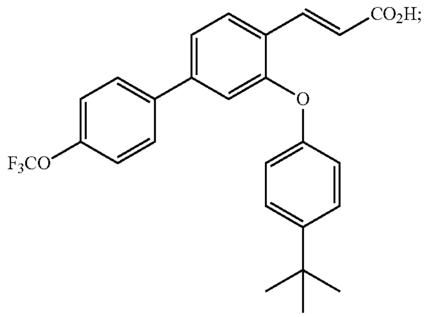
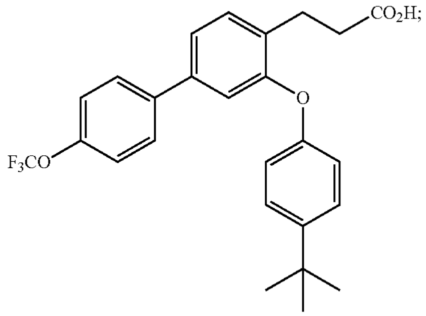
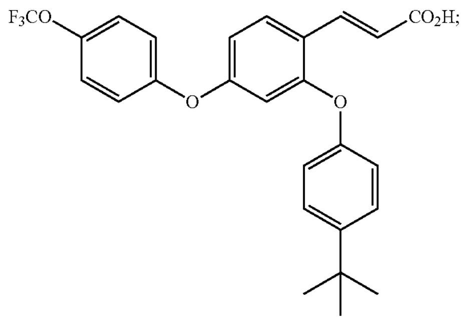

-continued
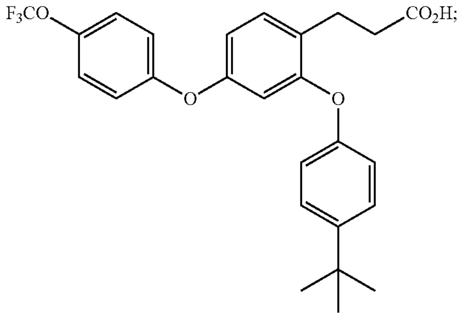
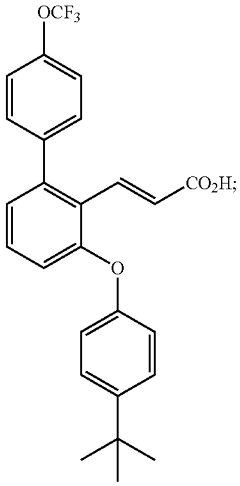
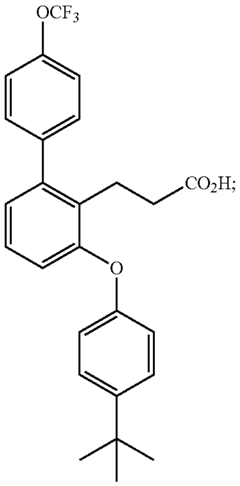
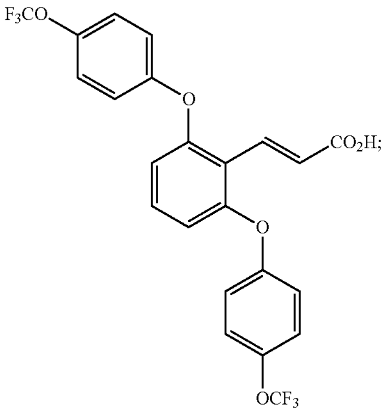
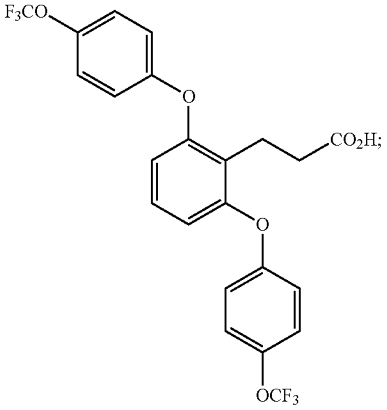
-continued
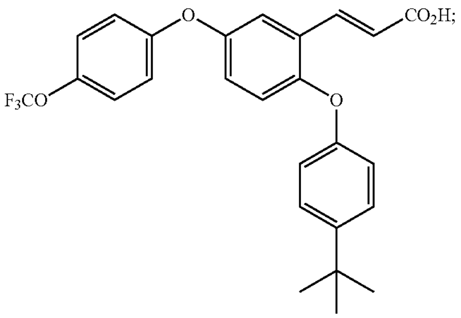
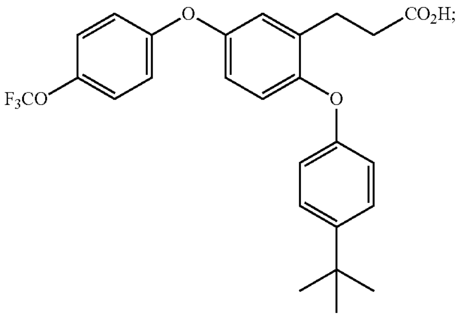
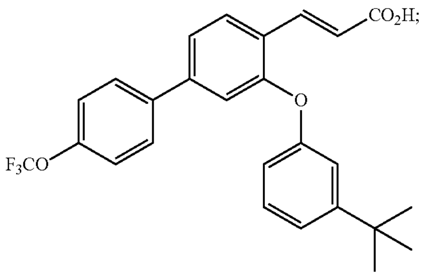
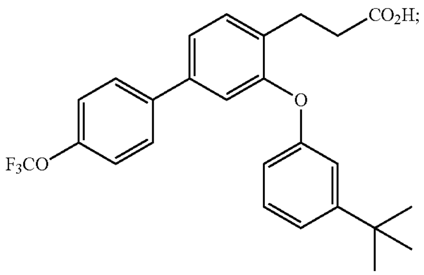
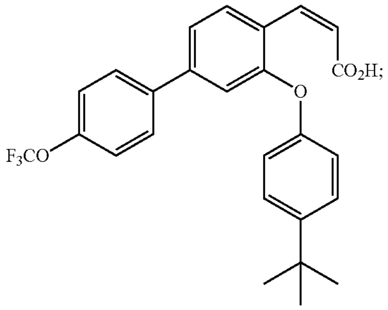

-continued
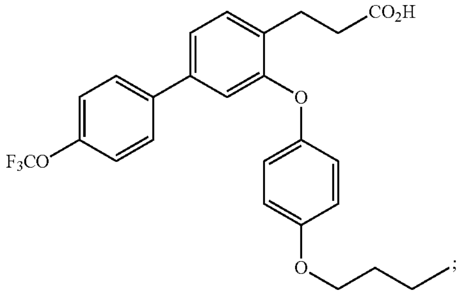
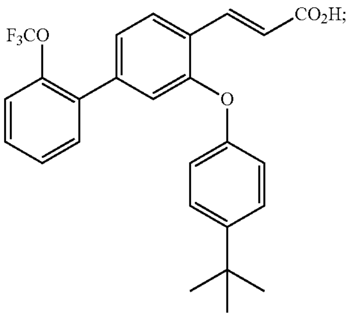
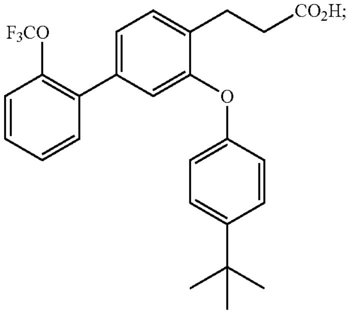
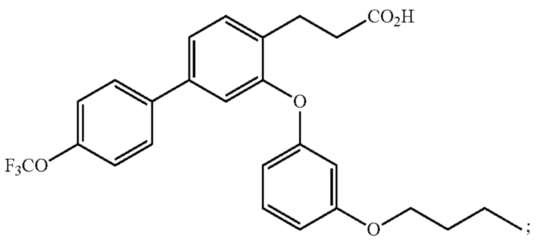
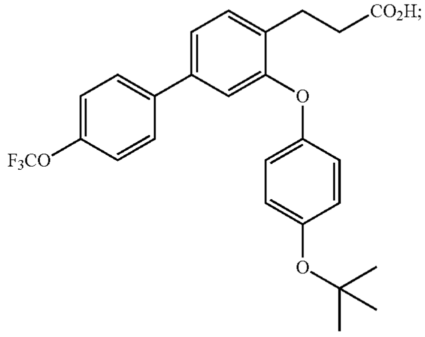
-continued
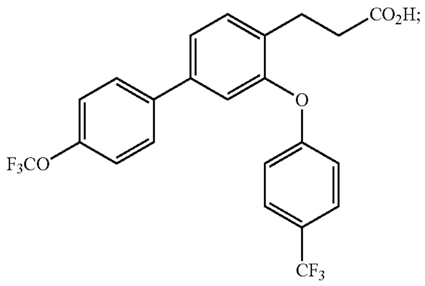
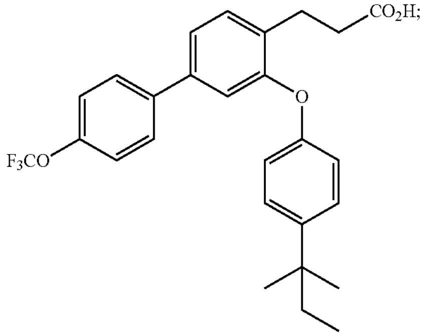
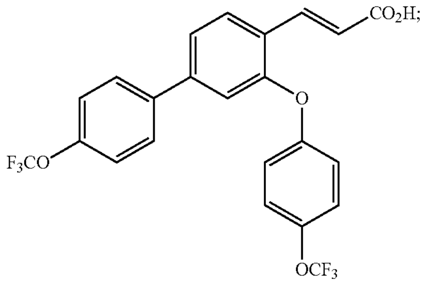
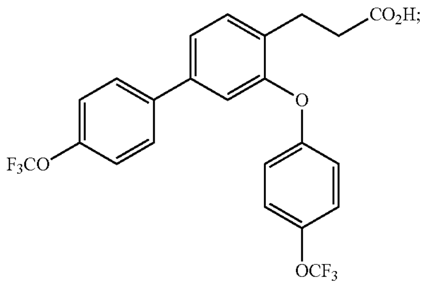
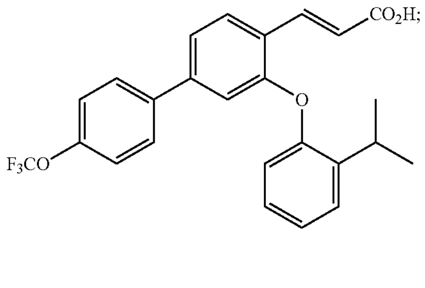
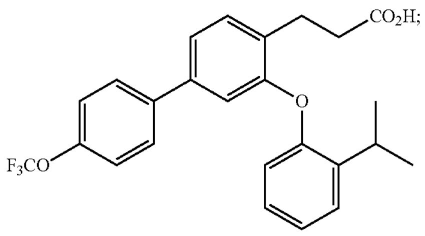

-continued
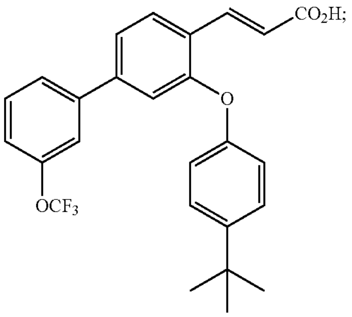
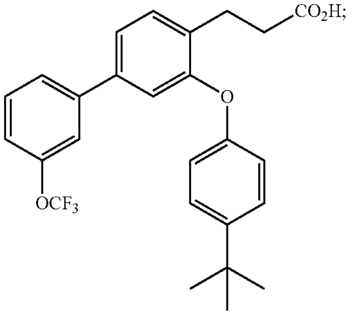
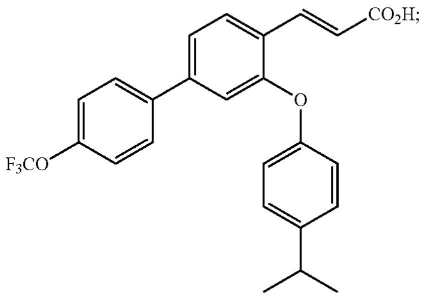
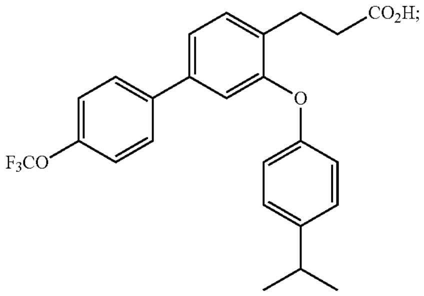
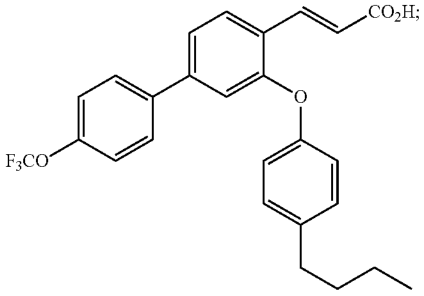
-continued
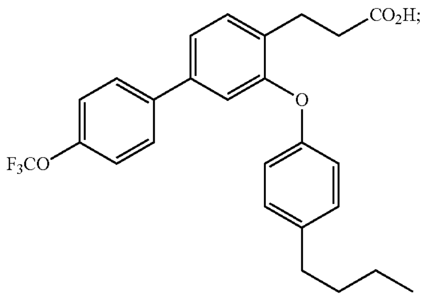
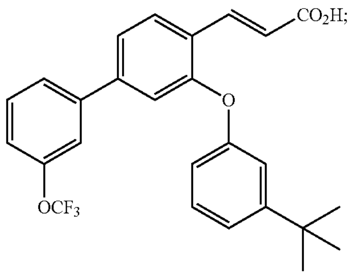
and
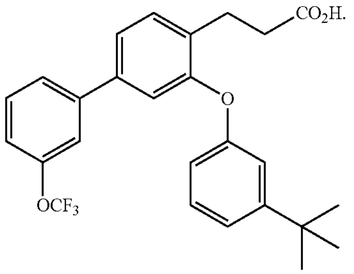
18. The compound or the salt thereof according to claim 15, wherein the compound is selected from the group consisting of:
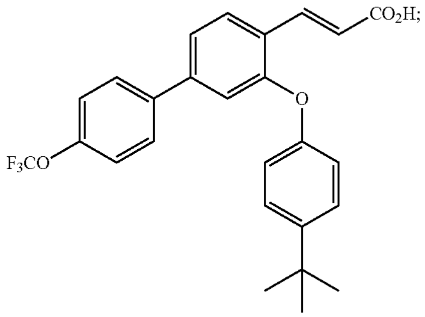
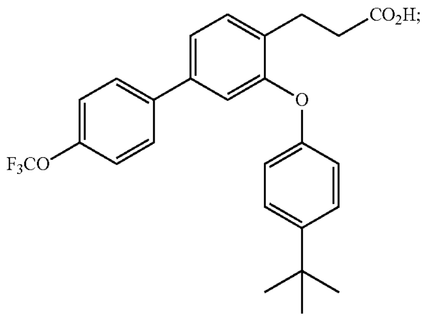

-continued
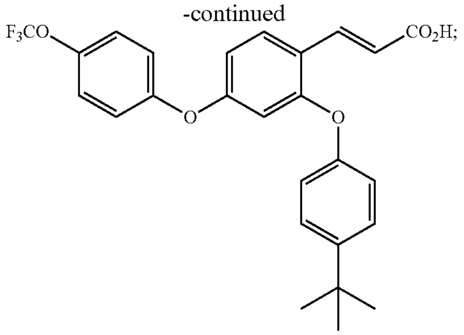
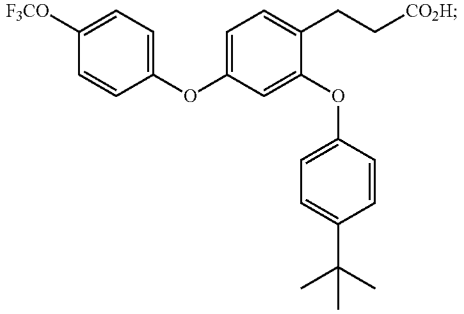
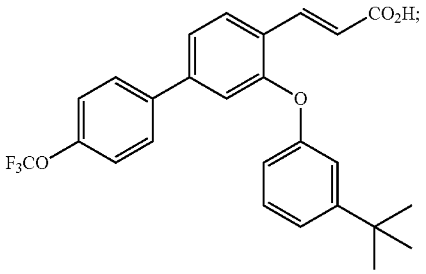
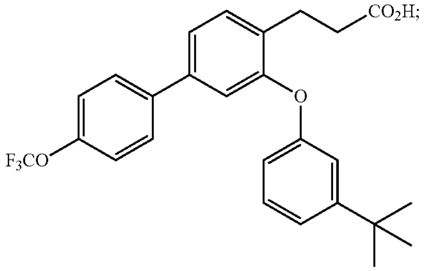
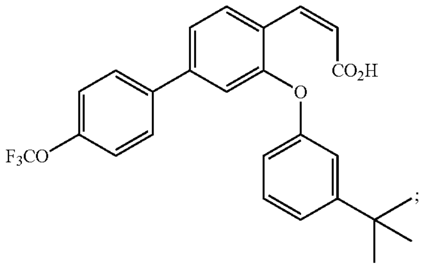
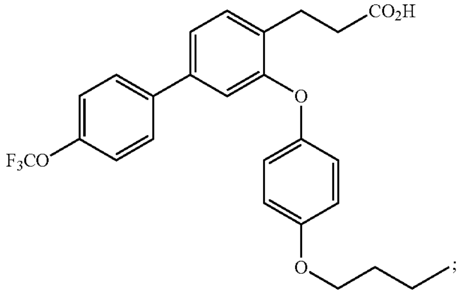
-continued
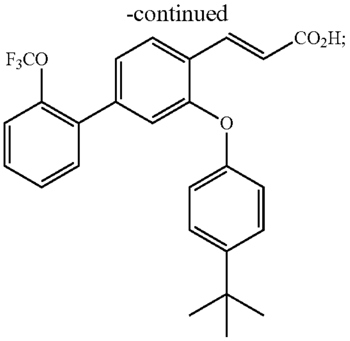
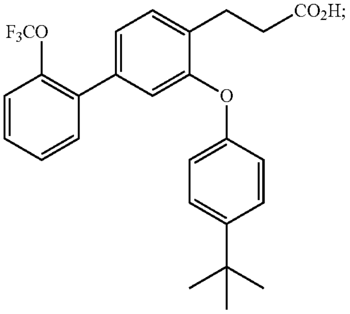
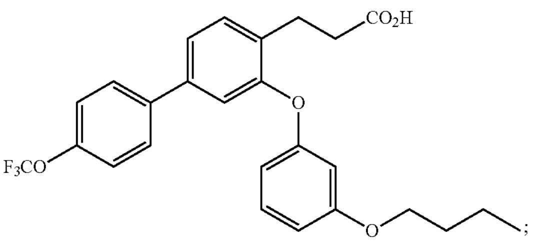
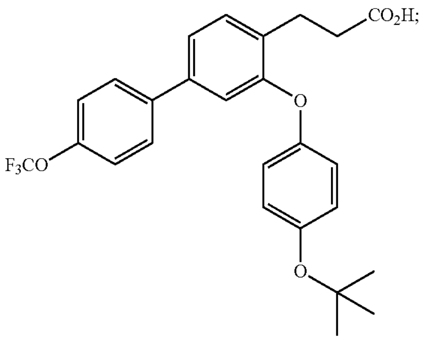
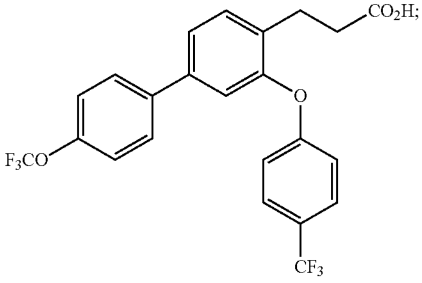

-continued
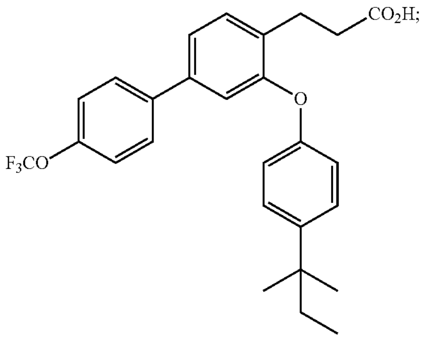
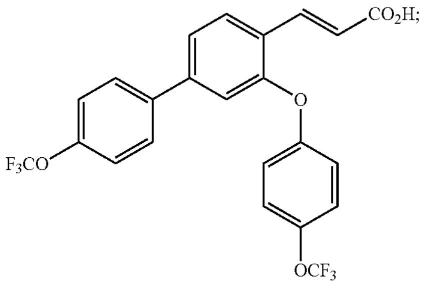
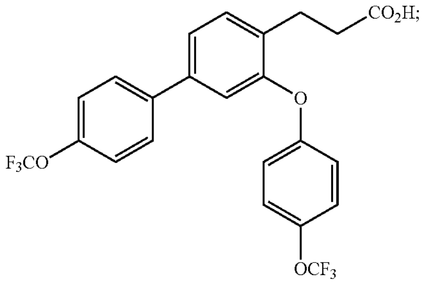
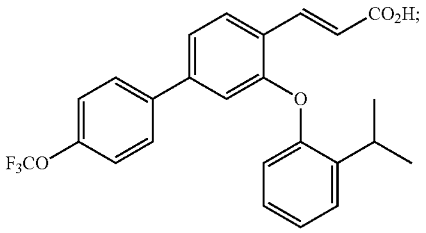
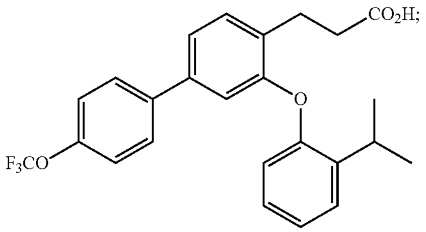
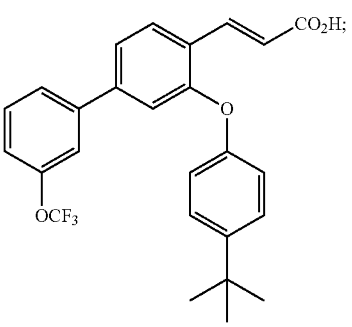
-continued
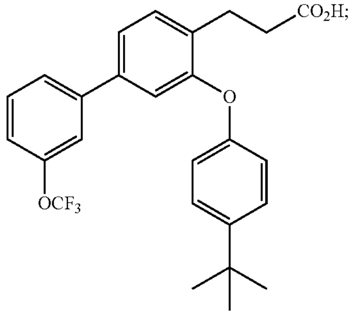
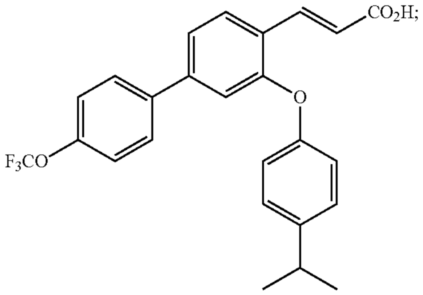
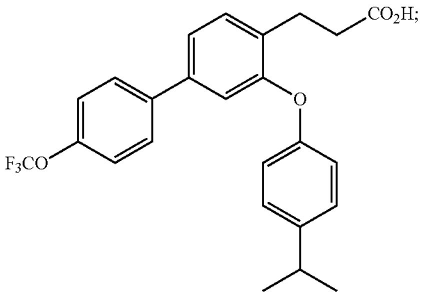
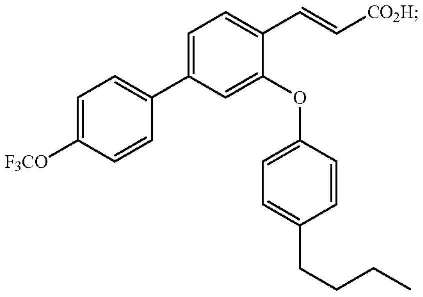
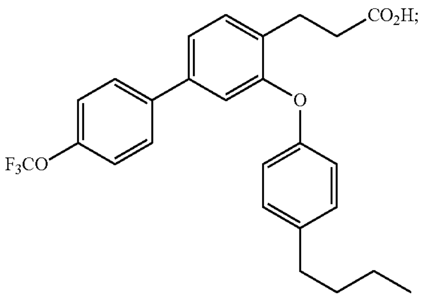

-continued
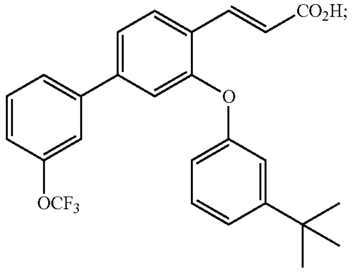
and
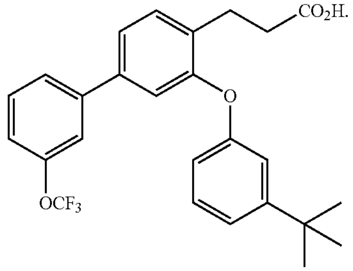
19. The compound or salt thereof according to claim 15, wherein the compound is selected from the group consisting of:
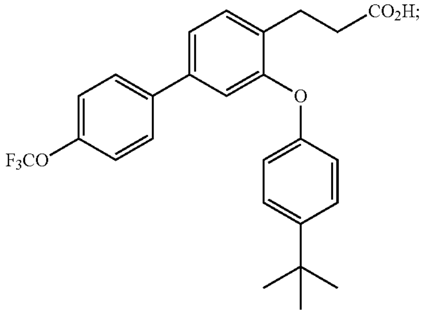
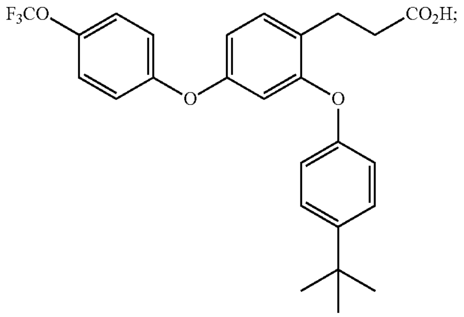
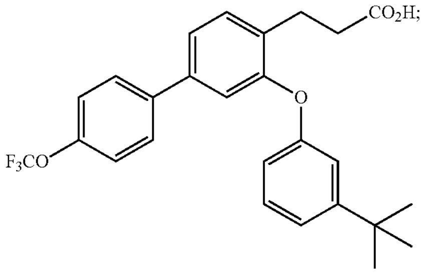
-continued
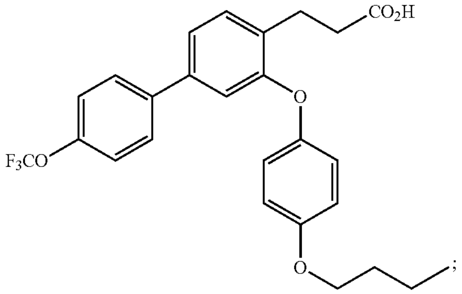
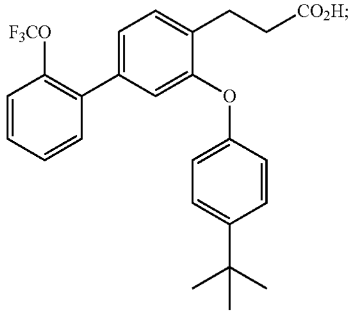
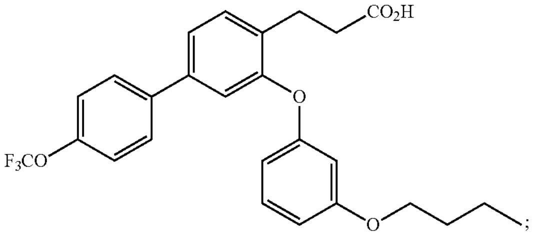
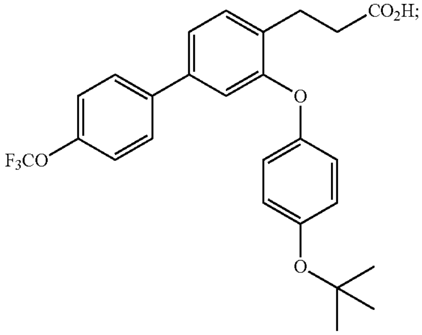
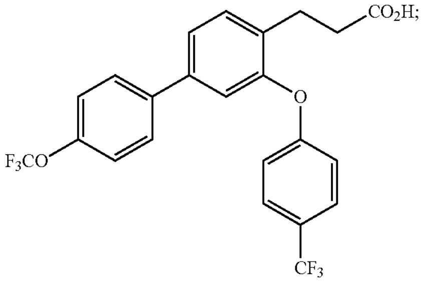

-continued
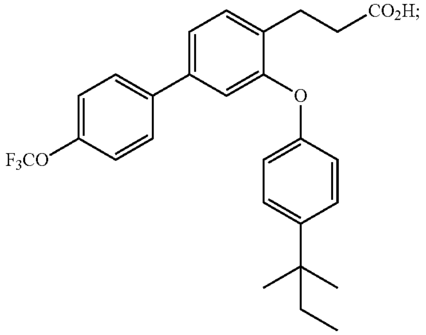
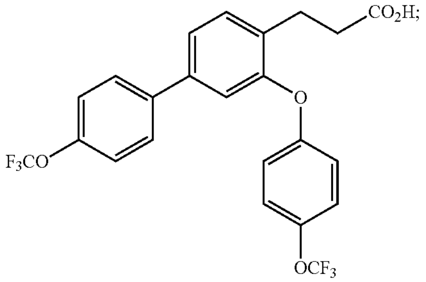
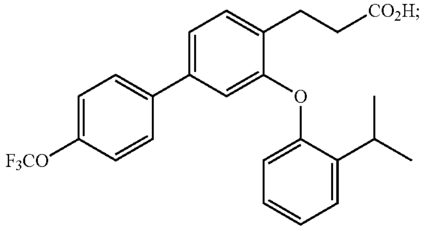
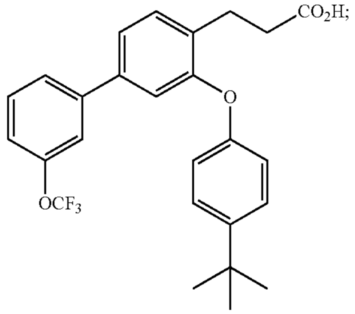
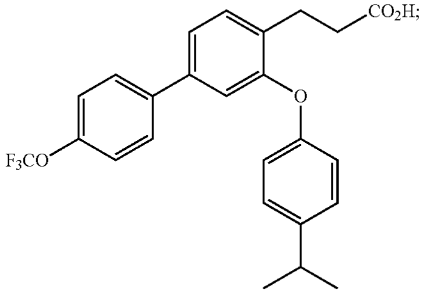
-continued
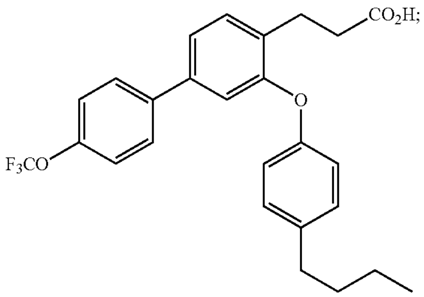
and
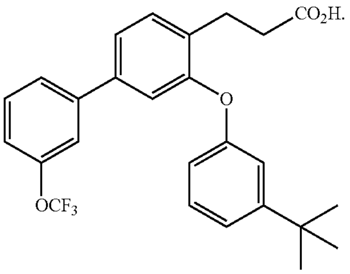
20. The compound or the salt thereof according to claim 15, wherein, the compound is selected from the group consisting of:
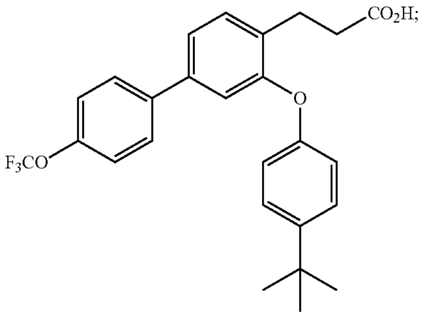
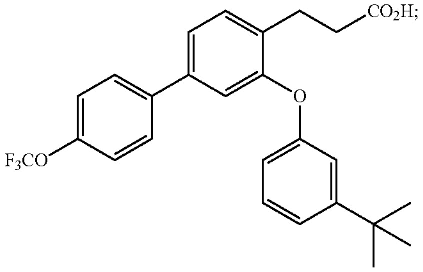
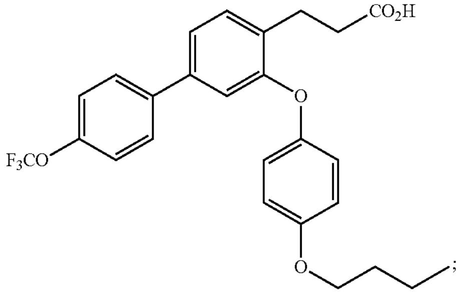

-continued
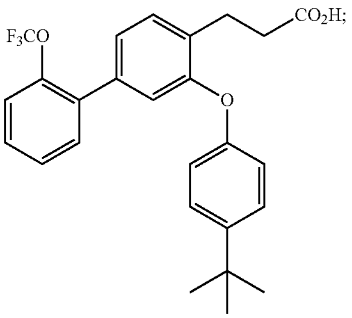
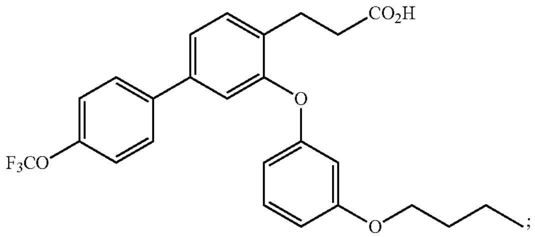
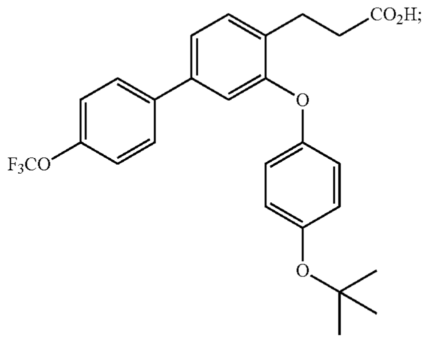
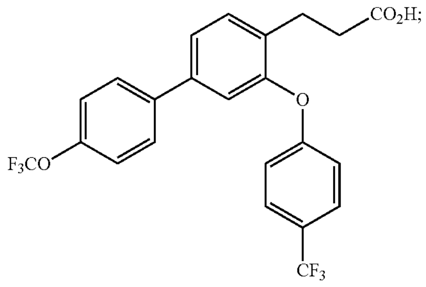
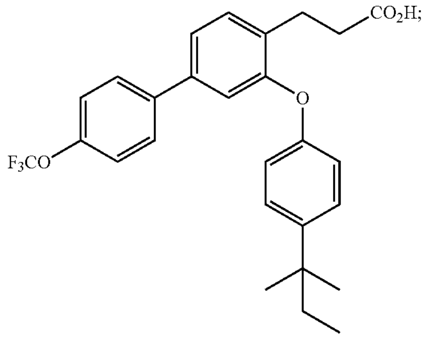
-continued
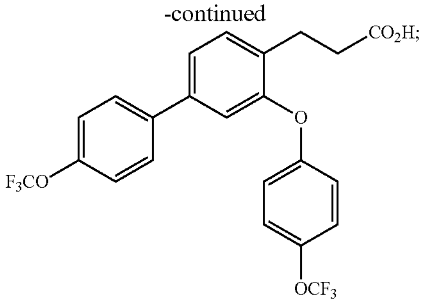
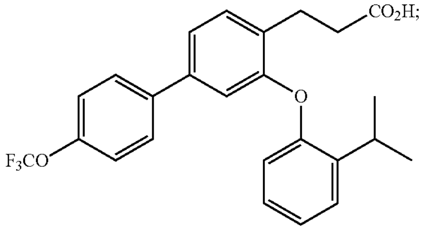
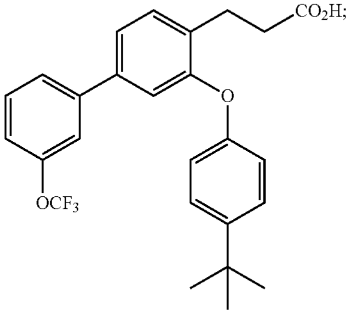
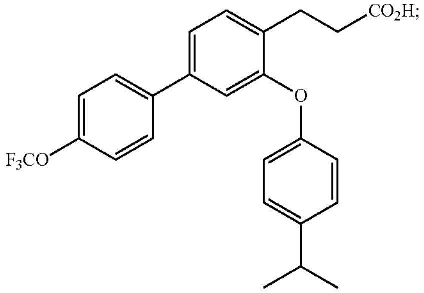
and
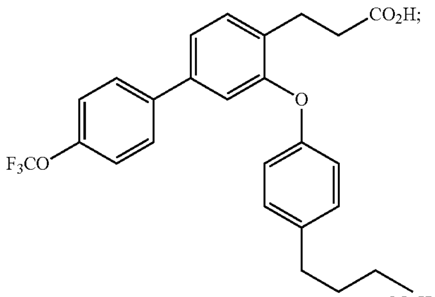
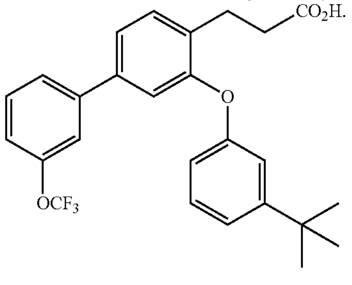
* * * * *